(12) United States Patent
Dillard et al.

(10) Patent No.: US 8,921,359 B2
(45) Date of Patent: Dec. 30, 2014

(54) INHIBITORS OF BETA-SECRETASE

(71) Applicants: Lawrence W. Dillard, Yardley, PA (US); Jing Yuan, Lansdale, PA (US); Lanqi Jia, Horsham, PA (US); Yajun Zheng, Hockessin, DE (US)

(72) Inventors: Lawrence W. Dillard, Yardley, PA (US); Jing Yuan, Lansdale, PA (US); Lanqi Jia, Horsham, PA (US); Yajun Zheng, Hockessin, DE (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 36 days.

(21) Appl. No.: 13/867,590

(22) Filed: Apr. 22, 2013

(65) Prior Publication Data
US 2013/0317014 A1 Nov. 28, 2013

Related U.S. Application Data

(62) Division of application No. 13/059,879, filed as application No. PCT/US2009/004686 on Aug. 14, 2009, now Pat. No. 8,450,308.

(60) Provisional application No. 61/189,464, filed on Aug. 19, 2008, provisional application No. 61/211,750, filed on Apr. 2, 2009.

(51) Int. Cl.
| | | |
|---|---|---|
| *A61K 31/54* | (2006.01) | |
| *A61K 31/415* | (2006.01) | |
| *A61K 31/44* | (2006.01) | |
| *A61K 31/41* | (2006.01) | |
| *A61K 31/4965* | (2006.01) | |
| *A61K 31/497* | (2006.01) | |
| *A61K 31/505* | (2006.01) | |
| *C07D 498/16* | (2006.01) | |
| *C07D 495/10* | (2006.01) | |
| *C07D 491/20* | (2006.01) | |
| *C07D 498/10* | (2006.01) | |
| *C07D 513/10* | (2006.01) | |
| *C07D 491/107* | (2006.01) | |
| *C07D 498/20* | (2006.01) | |

(52) U.S. Cl.
CPC ............ *C07D 498/20* (2013.01); *C07D 498/16* (2013.01); *C07D 495/10* (2013.01); *C07D 491/20* (2013.01); *C07D 498/10* (2013.01); *C07D 513/10* (2013.01); *C07D 491/107* (2013.01)
USPC ........ 514/227.2; 514/386; 514/278; 514/364; 514/256; 514/272; 514/383

(58) Field of Classification Search
None
See application file for complete search history.

(56) References Cited

U.S. PATENT DOCUMENTS 5,430,048 A * 7/1995 Gadwood ..................... 514/386

\* cited by examiner

*Primary Examiner* — Yong Chu
(74) *Attorney, Agent, or Firm* — McCarter & English, LLP; Steven G. Davis; Xin Zhang

(57) ABSTRACT

The present invention is directed to a compound represented by the following structural formula:

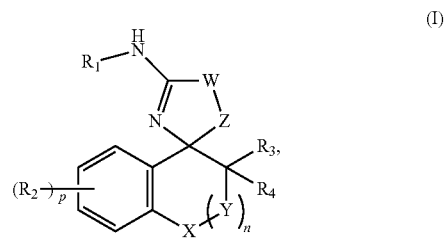

(I)

or a pharmaceutically acceptable salt thereof. Pharmaceutical composition comprising a compound represented by Structural Formula (I) and method of use of these compound for inhibiting BACE activity in a subject in need of such treatment are also described.

15 Claims, No Drawings

INHIBITORS OF BETA-SECRETASE

CROSS-REFERENCE TO RELATED APPLICATIONS

This application is a divisional application of U.S. patent application Ser. No. 13/059,879, filed May 9, 2011, which is the U.S. National Stage of PCT International Application Number PCT/US2009/004686, filed Aug. 14, 2009, which claims the benefit of U.S. Provisional Application No. 61/189,464, filed on Aug. 19, 2008, and U.S. Provisional Application No. 61/211,750 filed Apr. 2, 2009. The entire teachings of the above applications are incorporated herein by reference.

BACKGROUND OF THE INVENTION

β-Amyloid deposits and neurofibrillary tangles are two major pathologic characterizations associated with Alzheimer's disease (AD). Clinically, AD is characterized by the loss of memory, cognition, reasoning, judgment, and orientation. Also affected, as the disease progresses, are motor, sensory and linguistic abilities until global impairment of multiple cognitive functions occurs. These cognitive losses take place gradually, but typically lead to severe impairment and eventual death in 4-12 years.

β-Amyloid deposits are predominantly an aggregate of Aβ peptide, which in turn is a product of the proteolysis of amyloid precursor protein (APP). More specifically, Aβ peptide results from the cleavage of APP at the C-terminals by one or more γ-secretases, and at the N-terminus by β-secretase enzyme (BACE), also known as aspartyl protease, as part of the β-amyloidogenic pathway.

BACE activity is correlated directly to the generation of Aβ peptide from APP, and studies increasingly indicate that the inhibition of BACE inhibits the production of Aβ peptide.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders.

Recently, Amyloid-β (Aβ) has been reported to be implicated in the development of RGC apotosis in glaucoma, with evidence of caspase-3-mediated abnormal amyloid precursor protein processing, increased expression of Aβ in RGCs in experimental glaucoma and decreased vitreous Aβ levels (consistent with retinal Aβ deposition) in patients with glaucoma.

The present invention provides compounds that are BACE inhibitors and are useful as therapeutic agents in the treatment, prevention and amelioration of a disease or disorder characterized by elevated β-amyloid deposits or β-amyloid levels in a patient.

SUMMARY OF THE INVENTION

The present invention relates to compounds represented by the following Structural Formula:

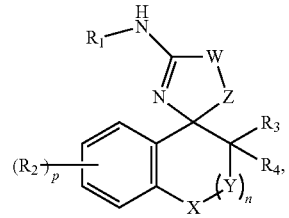

(I)

or a pharmaceutically acceptable salt thereof, wherein:

$R_1$ is —H, aryl($C_1$-$C_6$)alkyl or heteroaryl($C_1$-$C_6$)alkyl;

each $R_2$ is independently selected from a) —H, -halogen, —CN, —NO$_2$, —OR$_5$, —NR$_6$R$_7$, —S(O)$_t$R$_5$, —C(=O)OR$_5$, —C(=O)NR$_{12}$R$_{13}$, and —C(=O)R$_5$; and b) ($C_1$-$C_6$)alkyl, ($C_2$-$C_6$)alkenyl, ($C_2$-$C_6$)alkynyl, ($C_3$-$C_8$)cycloalkyl, aryl, heteroaryl, phenoxy, or benzyloxy, each optionally substituted with 1 to 3 substituents selected from the group consisting of F, —Cl, —Br, —CN, —OR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;

$R_3$ and $R_4$ are each independently —H, -halogen, —CN, —NO$_2$, —OR$_5$, —NR$_6$R$_7$, —S(O)$_t$R$_5$, —C(=O)OR$_5$, —C(=O)NR$_{12}$R$_{13}$, —C(=O)R$_5$, ($C_1$-$C_6$)alkyl, ($C_2$-$C_6$)alkenyl, ($C_2$-$C_6$)alkynyl, ($C_3$-$C_8$)cycloalkyl, aryl, or heteroaryl, wherein each ($C_1$-$C_6$)alkyl, ($C_2$-$C_6$)alkenyl, ($C_2$-$C_6$)alkynyl, ($C_3$-$C_8$)cycloalkyl, aryl, or heteroaryl is optionally substituted with 1 to 3 substituents independently selected from the group consisting of —F, —Cl, —Br, —CN, —OR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, an aryl group, and a heteroaryl group; or X is —O—, —S—, —SO—, —SO$_2$—, —CH$_2$—O—, or —O—CH$_2$—;

each Y is independently —C(R$_8$R$_9$)—;

W is —N(R$_{14}$)—, —S—, —O—;

Z is —C(=O)—, —C(=S)—, —C(=NR$_{15}$)—, —O—, —C(=O)C(R$_{16}$R$_{17}$)—, —C(=S)CR$_{16}$R$_{17}$—, —C(=NR$_{15}$)C(R$_{16}$R$_{17}$)—, —(CR$_{16}$R$_{17}$)$_m$— or —O—(CR$_{16}$R$_{17}$)—;

$R_5$ is —H, ($C_1$-$C_6$)alkyl, halo($C_1$-$C_6$)alkyl, ($C_2$-$C_6$)alkenyl, ($C_2$-$C_6$)alkynyl, ($C_1$-$C_3$)alkoxy($C_1$-$C_6$)alkyl, ($C_3$-$C_8$)cycloalkyl, ($C_3$-$C_8$)cycloalkyl($C_1$-$C_6$)alkyl, ($C_3$-$C_7$) cycloheteroalkyl, aryl, heteroaryl or benzyl, each of which is optionally substituted with 1 to 3 substituents independently selected from the group consisting of —F, —Cl, —Br, —CN, ($C_1$-$C_6$)alkyl, halo($C_1$-$C_6$)alkyl, and ($C_1$-$C_3$)alkoxy($C_1$-$C_6$)alkyl;

each $R_6$ and $R_7$ are independently —H, ($C_1$-$C_6$)alkyl, hydroxy($C_1$-$C_6$)alkyl, halo($C_1$-$C_6$)alkyl, ($C_3$-$C_8$)cycloalkyl, ($C_3$-$C_8$)cycloalkyl($C_1$-$C_6$)alkyl, each optionally substituted with —F, —Cl, —Br, —CN, ($C_1$-$C_6$)alkyl, halo($C_1$-$C_6$)alkyl or ($C_1$-$C_3$)alkoxy($C_1$-$C_6$)alkyl;

each $R_8$ and $R_9$ are independently —H, ($C_1$-$C_6$)alkyl, hydroxy($C_1$-$C_6$)alkyl, halo($C_1$-$C_6$)alkyl, ($C_2$-$C_6$)alkenyl, ($C_2$-$C_6$)alkynyl, ($C_3$-$C_{14}$)cycloalkyl, ($C_3$-$C_{13}$)cycloheteroalkyl, aryl or heteroaryl, each optionally substituted with 1 to 4 substituents independently selected from the group consisting of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl, heteroaryl, (C$_3$-C$_8$)cycloalkyl and (C$_3$-C$_8$)cycloheteroalkyl; or R$_8$ and R$_9$, together with the carbon to which they are attached, form ring A, which is a 3-14 membered monocyclic ring, 9-14 membered bicyclic ring or 9-14 membered polycyclic ring, wherein ring A is optionally substituted with 1 to 4 substituents independently selected from the group consisting of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl and heteroaryl;

R$_{11}$ is —H, (C$_1$-C$_6$)alkyl or halo(C$_1$-C$_6$)alkyl;

R$_{12}$ and R$_{13}$ are each independently —H, (C$_1$-C$_6$)alkyl, (C$_1$-C$_3$)alkoxy(C$_1$-C$_6$)alkyl, hydroxy(C$_1$-C$_6$)alkyl, cyano(C$_1$-C$_6$)alkyl, amino(C$_1$-C$_6$)alkyl, (C$_1$-C$_3$)alkylamino(C$_1$-C$_6$)alkyl, or di(C$_1$-C$_3$)alkylamino(C$_1$-C$_6$)alkyl;

or R$_{12}$ and R$_{13}$, together with the nitrogen to which they are attached, form a 3-8 membered ring optionally substituted with 1 to 3 substituents independently selected from the group consisting of F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, and (C$_1$-C$_6$)alkoxy(C$_1$-C$_3$)alkyl; wherein the 3-8 membered ring optionally contains 1 to 3 additional heteroatoms, which are independently selected from O, N, and S, wherein when the additional heteroatom is nitrogen, the nitrogen is optionally substituted with (C$_1$-C$_3$)alkyl or halo(C$_1$-C$_3$)alkyl, and when the additional heteroatom is sulfur, the sulfur is optionally mono or di-oxygenated;

R$_{14}$ is —H, (C$_1$-C$_6$)alkyl, halo(C$_1$-C$_6$)alkyl, (C$_3$-C$_8$)cycloalkyl, cycloheteroalkyl(C$_1$-C$_3$)alkyl, (C$_3$-C$_8$)cycloalkyl(C$_1$-C$_3$)alkyl, aryl(C$_1$-C$_6$)alkyl, heteroaryl(C$_1$-C$_6$)alkyl, each optionally substituted with 1 to 3 substituents independently selected from the group consisting of —F, —Cl, —Br, —CN, (C$_1$-C$_6$)alkyl, halo(C$_1$-C$_6$)alkyl and (C$_1$-C$_3$)alkoxy;

R$_{15}$ is —H or (C$_1$-C$_6$)alkyl;

R$_{16}$ and R$_{17}$ are each independently —H or (C$_1$-C$_3$)alkyl;

R$_{18}$ is —H or (C$_1$-C$_3$)alkyl;

i is 0, 1 or 2;

p is 1, 2, 3 or 4;

m is 1 or 2; and n is 1 or 2.

In another embodiment, compounds of the invention is represented by Structural Formula (I'):

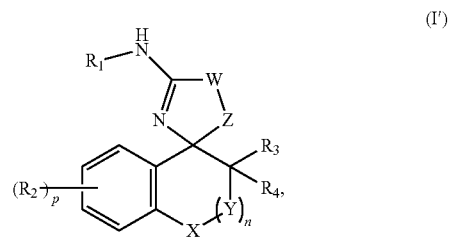

(I')

or a pharmaceutically acceptable salt thereof, wherein:

R$_1$ is R$_1$ is —H, (C$_1$-C$_6$)alkyl, aryl(C$_1$-C$_6$)alkyl, or heteroaryl(C$_1$-C$_6$)alkyl;

R$_2$ is a) —H, —F, —Cl, —Br, or —CN or b) (C$_1$-C$_6$)alkyl, (C$_2$-C$_6$)alkenyl, (C$_2$-C$_6$)alkynyl, (C$_3$-C$_8$)cycloalkyl, aryl, heteroaryl, phenoxy, or benzyloxy, each optionally substituted with 1 to 3 substituents selected from the group consisting of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy and (C$_1$-C$_6$)alkoxy(C$_1$-C$_3$)alkyl;

R$_3$ and R$_4$ are each independently —H, —F, —Br, —Cl or (C$_1$-C$_6$)alkyl;

X is —O—, —S—, —SO—, —SO$_2$—, —CH$_2$O— or —OCH$_2$—;

Y is —C(R$_8$R$_9$)—;

W is —N(R$_{14}$)—, —S—, —O—;

Z is —C(=O)—, —C(=S)—, —C(=NR$_{15}$)—, —O—, —C(=O)C(R$_{16}$R$_{17}$)—, —C(=S)C(R$_{16}$R$_{17}$)—, —C(=NR$_{15}$)C(R$_{16}$R$_{17}$)—, —N(R$_{18}$)—, or —(CR$_{16}$R$_{17}$)$_m$—;

R$_5$ is —H, (C$_4$-C$_6$)alkyl, halo(C$_1$-C$_6$)alkyl, (C$_2$-C$_6$)alkenyl, (C$_2$-C$_6$)alkynyl, (C$_1$-C$_3$)alkoxy(C$_1$-C$_6$)alkyl, (C$_3$-C$_8$)cycloalkyl, (C$_3$-C$_8$)cycloalkyl(C$_1$-C$_6$)alkyl, (C$_3$-C$_7$) cycloheteroalkyl, aryl, heteroaryl or benzyl, each of which is optionally substituted with 1 to 3 substituents independently selected from the group consisting of —F, —Cl, —Br, —CN, (C$_1$-C$_6$)alkyl, halo(C$_1$-C$_6$)alkyl, and (C$_1$-C$_3$)alkoxy(C$_1$-C$_6$)alkyl;

R$_6$ and R$_7$ are each independently —H, (C$_1$-C$_6$)alkyl, hydroxy(C$_1$-C$_6$)alkyl, halo(C$_1$-C$_6$)alkyl, (C$_3$-C$_8$)cycloalkyl, (C$_3$-C$_8$)cycloalkyl(C$_1$-C$_6$)alkyl, each optionally substituted with 1 to 3 substituents independently selected from the group consisting of —F, —Cl, —Br, —CN, (C$_1$-C$_6$)alkyl, halo(C$_1$-C$_6$)alkyl and (C$_1$-C$_3$)alkoxy(C$_1$-C$_6$)alkyl;

R$_8$ and R$_9$ are each independently —H, (C$_1$-C$_6$)alkyl, hydroxy(C$_1$-C$_6$)alkyl, halo(C$_1$-C$_6$)alkyl, (C$_2$-C$_6$)alkenyl, (C$_2$-C$_6$)alkynyl, (C$_3$-C$_8$)cycloalkyl, (C$_3$-C$_7$)cycloheteroalkyl, aryl or heteroaryl, each optionally substituted with 1 to 3 substituents independently selected from the group consisting of —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy and halo(C$_1$-C$_3$)alkoxy; or R$_8$ and R$_9$, together with the carbon to which they are attached, form a 3-8 membered ring (ring A) optionally substituted with 1 to 3 substituents independently selected from the group consisting of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-

$C_6$)alkyl, ($C_1$-$C_3$)alkoxy, halo($C_1$-$C_3$)alkoxy and ($C_1$-$C_6$)alkoxy($C_1$-$C_3$)alkyl, wherein ring A contains 0 to 3 heteroatoms, which are independently selected from O, N and S; wherein when the heteroatom is nitrogen, the nitrogen is substituted with —H, ($C_1$-$C_6$)alkyl, halo($C_1$-$C_6$)alkyl or ($C_1$-$C_3$)alkylcarbonyl, and when the heteroatom is sulfur, the sulfur is optionally mono- or di-oxygenated;

$R_{11}$ is —H, ($C_1$-$C_6$)alkyl or halo($C_1$-$C_6$)alkyl;

$R_{12}$ and $R_{13}$ are each independently —H, ($C_1$-$C_6$)alkyl, ($C_1$-$C_3$)alkoxy($C_1$-$C_6$)alkyl, hydroxy($C_1$-$C_6$)alkyl, cyano($C_1$-$C_6$)alkyl, amino($C_1$-$C_6$)alkyl, ($C_1$-$C_3$)alkylamino($C_1$-$C_6$)alkyl, or di($C_1$-$C_3$)alkylamino($C_1$-$C_6$)alkyl;

or $R_{12}$ and $R_{13}$, together with the nitrogen to which they are attached, form a 3-8 membered ring optionally substituted with 1 to 3 substituents independently selected from the group consisting of —F, —Cl, —Br, —CN, —$OR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy and ($C_1$-$C_6$)alkoxy($C_1$-$C_3$)alkyl, wherein ring A contains 0 to 3 heteroatoms, which are independently selected from O, N and S, wherein when the heteroatom is nitrogen, the nitrogens is substituted with —H, ($C_1$-$C_3$)alkyl or halo($C_1$-$C_3$)alkyl, and when the heteroatom is sulfur, the sulfurs is optionally mono or di-oxygenated;

$R_{14}$ is —H, ($C_1$-$C_6$)alkyl, halo($C_1$-$C_6$)alkyl, ($C_3$-$C_8$)cycloalkyl, cycloheteroalkyl($C_1$-$C_3$)alkyl, ($C_3$-$C_8$)cycloalkyl($C_1$-$C_3$)alkyl, aryl($C_1$-$C_6$)alkyl, heteroaryl($C_1$-$C_6$)alkyl, each optionally substituted with 1 to 3 substituents independently selected from the group consisting of —F, —Cl, —Br, —CN, ($C_1$-$C_6$)alkyl, halo($C_1$-$C_6$)alkyl and ($C_1$-$C_3$)alkoxy;

$R_{15}$ is —H or ($C_1$-$C_6$)alkyl;

$R_{16}$ and $R_{17}$ are each independently —H or ($C_1$-$C_3$)alkyl;

$R_{18}$ is —H or ($C_1$-$C_3$)alkyl;

i is 0, 1 or 2;

p is 1 or 2;

m is 1 or 2; and n is 1 or 2.

One embodiment of the invention is a pharmaceutical composition comprising a pharmaceutically acceptable carrier or diluent and a BACE inhibitor disclosed herein (e.g., a compound represented by Structural Formula (I) or (I'), or a pharmaceutically acceptable salt thereof).

Another embodiment of the invention is a method of inhibiting BACE activity in a subject in need of such treatment. The method comprises administering to the subject an effective amount of a BACE inhibitor disclosed herein (e.g., a compound represented by Structural Formula (I) or (I'), or a pharmaceutically acceptable salt thereof).

Another embodiment of the invention is a method of treating a BACE mediated disorder in a subject. The method comprises administering to the subject an effective amount of a BACE inhibitor disclosed herein (e.g., a compound represented by Structural Formula (I) or (I'), or a pharmaceutically acceptable salt thereof).

Another embodiment of the invention is a method of treating a disorder selected from the group consisting of Alzheimer's disease, cognitive impairment, Down's Syndrome, HCHWA-D, cognitive decline, senile dementia, cerebral amyloid angiopathy, degenerative dementia, other neurodegenerative disorders, and glaucoma in a subject in need of such treatment comprising administering to the subject an effective amount of a compound disclosed herein (e.g., a compound represented by Structural Formula (I) or (I') or a pharmaceutically acceptable salt thereof).

Another embodiment of the invention is the use of a BACE inhibitor disclosed herein (e.g., a compound represented by Structural Formula (I) or (I'), or a pharmaceutically acceptable salt thereof) for the manufacture of a medicament for inhibiting BACE activity in a subject.

Another embodiment of the invention is the use of a BACE inhibitor disclosed herein (e.g., a compound represented by Structural Formula (I) or (I'), or a pharmaceutically acceptable salt thereof) for the manufacture of a medicament for treating a BACE mediated disorder in a subject.

Another embodiment of the invention is the use of a compound disclosed herein (e.g., a compound represented by Structural Formula (I) or (I'), or a pharmaceutically acceptable salt thereof) for the manufacture of a medicament for treating a disorder selected from the group consisting of Alzheimer's disease, cognitive impairment, Down's Syndrome, HCHWA-D, cognitive decline, senile dementia, cerebral amyloid angiopathy, degenerative dementia, other neurodegenerative disorders, and glaucoma in a subject.

DETAILED DESCRIPTION OF THE INVENTION

The present invention is directed to compounds represented by the Structural Formula (I) or a pharmaceutically acceptable salt thereof. Values and particular values for the variables in Structural Formula I or an enantiomer, a diastereomer, a tautomer, or a pharmaceutically acceptable salt thereof are provided in the following paragraphs. It is understood that the invention encompasses all combinations of the substituent variables (i.e., $R_1$, $R_2$, $R_3$, etc.) defined herein. For Structural Formula (I):

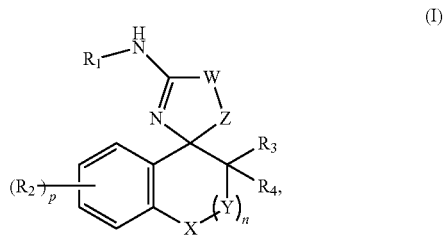

or an enantiomer, a diastereomer or a pharmaceutically acceptable salt thereof:

$R_1$ is —H, ($C_1$-$C_6$)alkyl, aryl($C_1$-$C_6$)alkyl or heteroaryl($C_1$-$C_6$)alkyl. In one embodiment $R_1$ is —H, ($C_1$-$C_6$)alkyl or benzyl. In another embodiment, $R_1$ is —H.

each $R_2$ is independently selected from a) —H, —F, —Cl, —Br, and —CN and b) ($C_1$-$C_6$)alkyl, ($C_2$-$C_6$)alkenyl, ($C_2$-$C_6$)alkynyl, ($C_3$-$C_8$)cycloalkyl, aryl, heteroaryl, phenoxy, or benzyloxy, each optionally substituted with 1 to 3 substituents independently selected from the group consisting of —F, —Cl, —Br, —CN, —$OR_5$, —$NR_6R_7$, —$S(O)_iR_5$, —$NR_{11}S(=O)_iR_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl.

In one embodiment, $R_2$ is —H, —Br, —F, —Cl, ($C_1$-$C_6$)alkyl, ($C_3$-$C_8$)cycloalkyl, aryl, heteroaryl, phenoxy, or benzyloxy, each optionally substituted with 1 to 3 substituents independently selected from the group consisting of —F, —Cl, —Br, —CN, —OR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_3$-C$_8$)cycloalkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl and heteroaryl.

In another particular embodiment, R$_2$ is —H, —Cl, —Br or —F.

In another particular embodiment, R$_2$ is (C$_1$-C$_6$)alkyl. More particularly, R$_2$ is (C$_1$-C$_3$)alkyl.

In another particular embodiment, R$_2$ is a (C$_2$-C$_6$) alkynyl optionally substituted with —F, —Cl, —Br, —CN, —OR$_5$, —SR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_3$-C$_8$)cycloalkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl or heteroaryl. More particularly, R$_2$ is a (C$_2$-C$_6$) alkynyl optionally substituted with (C$_1$-C$_6$)alkyl or (C$_3$-C$_8$)cycloalkyl.

In another particular embodiment, R$_2$ is phenyl optionally substituted with 1-3 substituents independently selected from the group consisting of —F, —Cl, —Br, —CN, —OR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_3$-C$_8$)cycloalkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl and heteroaryl. More specifically, the substituents are independently selected from the group consisting of —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy, halo(C$_1$-C$_3$)alkoxy, (C$_1$-C$_3$)alkylthio, (C$_1$-C$_3$)alkylcarbonyl and (C$_1$-C$_3$)alkoxycarbonyl.

In another particular embodiment, R$_2$ is pyridinyl, thiophenyl, pyrrolyl, pyrimidinyl, cyclohexyl, or thiazolyl, each optionally substituted with 1-3 substituents independently selected from the group consisting of —F, —Cl, —Br, —CN, —OR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_3$-C$_8$)cycloalkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl and heteroaryl. More particularly, the substituents are independently selected from the group consisting of —F, —Cl, —Br, —CN, (C$_1$-C$_3$)alkyl, a 5-6 membered aryl or heteroaryl. Even more specifically, the substituents are independently selected from the group —F, —Cl, —Br, —CN, (C$_1$-C$_3$)alkyl, pyrrolyl and imidazolyl.

In another particular embodiment, R$_2$ is phenoxy or benzyloxy, each optionally substituted with 1-3 substituents independently selected from the group consisting of —F, —Cl, —Br, —CN, —OR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_3$-C$_8$)cycloalkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl and heteroaryl. More particularly, R$_2$ is unsubstituted phenoxy or benzyloxy.

R$_3$ and R$_4$ are each independently —H, —F, —Br, —Cl or (C$_1$-C$_6$)alkyl optionally substituted with an aryl group or a heteraryl group. In a particular embodiment, R$_3$ and R$_4$ are both —H. In another particular embodiment, R$_3$ and R$_4$ are independently —H, —F or methyl. In another particular embodiment, one of R$_3$ and R$_4$ are —H, the other is a (C$_1$-C$_6$)alkyl optionally substituted with a phenyl group, where the phenyl group is optionally substituted with 1-3 substituents independently selected from the group consisting of —F, —Cl, —Br, —CN, (C$_1$-C$_3$)alkoxy, halo(C$_1$-C$_3$)alkoxy, (C$_1$-C$_6$)alkyl and halo(C$_1$-C$_6$)alkyl.

R$_5$ is —H, (C$_1$-C$_6$)alkyl, halo(C$_1$-C$_6$)alkyl, (C$_2$-C$_6$)alkenyl, (C$_2$-C$_6$)alkynyl, (C$_1$-C$_3$)alkoxy(C$_1$-C$_6$)alkyl, (C$_3$-C$_8$)cycloalkyl, (C$_3$-C$_8$)cycloalkyl(C$_1$-C$_6$)alkyl, (C$_3$-C$_7$) cycloheteroalkyl, aryl, heteroaryl, or benzyl, each of which is optionally substituted with 1 to 3 substituents independently selected from the group consisting of —F, —Cl, —Br, —CN, (C$_1$-C$_6$)alkyl, halo(C$_1$-C$_6$)alkyl, (C$_1$-C$_3$)alkoxy, halo(C$_1$-C$_3$)alkoxy and (C$_1$-C$_3$)alkoxy(C$_1$-C$_6$)alkyl. In a particular embodiment, R$_5$ is (C$_1$-C$_6$)alkyl, halo(C$_1$-C$_6$)alkyl, (C$_1$-C$_3$)alkoxy(C$_1$-C$_6$)alkyl, (C$_3$-C$_7$)cycloheteroalkyl or benzyl. In a more particular embodiment, R$_5$ is (C$_1$-C$_6$)alkyl, halo(C$_1$-C$_6$)alkyl, (C$_1$-C$_3$)alkoxy(C$_1$-C$_3$)alkyl, pyrrolidinyl or benzyl. More particular, R$_5$ is methyl, ethyl, propyl, butyl, methoxypropyl, methoxyethyl, benzyl or pyrrolidinyl.

each R$_6$ and R$_7$ are independently —H, (C$_1$-C$_6$)alkyl, hydroxy(C$_1$-C$_6$)alkyl, halo(C$_1$-C$_6$)alkyl, (C$_3$-C$_8$)cycloalkyl, (C$_3$-C$_8$)cycloalkyl(C$_1$-C$_6$)alkyl, each optionally substituted with 1 to 3 substituents independently selected from the group consisting of —F, —Cl, —Br, —CN, (C$_1$-C$_6$)alkyl, halo(C$_1$-C$_6$)alkyl and (C$_1$-C$_3$)alkoxy(C$_1$-C$_6$)alkyl. In a particular embodiment, R$_6$ and R$_7$ are each independently —H or (C$_1$-C$_6$)alkyl. In another particular embodiment, R$_6$ and R$_7$ are both —H.

In one embodiment, each R$_8$ and R$_9$ are independently —H, (C$_1$-C$_6$)alkyl, hydroxy(C$_1$-C$_6$)alkyl, halo(C$_1$-C$_6$)alkyl, (C$_2$-C$_6$)alkenyl, (C$_2$-C$_6$)alkynyl, (C$_3$-C$_{14}$) cycloalkyl, (C$_3$-C$_{13}$)cycloheteroalkyl, aryl or heteroaryl, each optionally substituted with 1 to 3 substituents independently selected from the group consisting of —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy, halo (C$_1$-C$_3$)alkoxy, (C$_3$-C$_8$) cycloalkyl and (C$_3$-C$_7$)cycloheteroalkyl.

In a particular embodiment, R$_8$ and R$_9$ are each independently —H, (C$_1$-C$_6$)alkyl, hydroxy(C$_1$-C$_6$)alkyl, (C$_3$-C$_{14}$)cycloalkyl, (C$_3$-C$_{13}$)cycloheteroalkyl, phenyl or heteraryl, each of which optionally substituted with 1 to 3 substituents independently selected from the group consisting of —F, —Cl, —Br, —CN, (C$_1$-C$_6$)alkyl, halo(C$_1$-C$_6$)alkyl, hydroxy (C$_1$-C$_6$)alkyl, (C$_1$-C$_3$)alkoxy, halo(C$_1$-C$_3$)alkoxy, (C$_3$-C$_8$)cycloalkyl, (C$_3$-C$_8$)cycloheteroalkyl, phenyloxy and benzyloxy.

In another particular embodiment, R$_8$ and R$_9$ are both —H, (C$_1$-C$_3$)alkyl or hydroxy(C$_1$-C$_3$)alkyl. More particularly, R$_8$ and R$_9$ are both —H, methyl or hydroxymethyl.

In another embodiment, one of R$_8$ and R$_9$ is —H, the other one is a (C$_1$-C$_6$)alkyl optionally substituted with 1 to 3 substituents independently selected from the group consisting of —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy, halo(C$_1$-C$_3$)alkoxy, (C$_3$-C$_8$) cycloalkyl and (C$_3$-C$_8$)cycloheteroalkyl. More particularly, substituents are selected from the group consisting of (C$_1$-C$_6$)alkyl and (C$_3$-C$_8$)cycloheteroalkyl. Even more particularly, one of R$_8$ and R$_9$ is —H, the other one is a (C$_1$-C$_3$)

alkyl optionally substituted ($C_3$-$C_8$)cycloheteroalkyl (preferrably a tetrahydrofuran or tetrahydropyran).

In another embodiment, one of $R_8$ and $R_9$ is —H, the other one is a ($C_2$-$C_6$)alkenyl optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy, ($C_3$-$C_8$) cycloalkyl and ($C_3$-$C_8$)cycloheteroalkyl. More particularly, substituents are selected from the group consisting of ($C_1$-$C_3$)alkyl and hydroxy($C_1$-$C_3$)alkyl.

In another particular embodiment, one of $R_8$ and $R_9$ is —H and the other is unsubstituted phenyl. In another particular embodiment, one of $R_8$ and $R_9$ is —H and the other is phenyl substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy, ($C_1$-$C_3$)alkylcarbonyl and ($C_1$-$C_3$)alkoxycarbonyl. More particularly, the substituents independently selected from —F, —Cl, —Br, —CN, trifluoromethyl, methoxy, trifluoromethoxy.

In another particular embodiment, one of $R_8$ and $R_9$ is —H and the other is ($C_3$-$C_{14}$)cyloalkyl (preferrably monocyclic ($C_3$-$C_8$)cycloalkyl such as cyclopentyl and cyclohexyl, or bicyclic fused ($C_9$-$C_{14}$)cycloalkyl, such as 6,7,8,9-tetrahydro-5H-benzo[7]annulene, 2,3-dihydro-1H-indene, tetrahydronaphthalene, decahydronaphthalene), ($C_3$-$C_{13}$)cycloheteroalkyl (preferrably monocyclic ($C_3$-$C_7$)cycloheteroalkyl such as tetrahydrofuran, tetrahydropyran and piperidine, or bicyclic fused or bridged ($C_8$-$C_{13}$)cycloheteroalkyl such as 5,6,7,8-tetrahydroquinoline, 5,6,7,8-tetrahydroisoquinoline, and 2-oxabicyclo[2.2.2]octane) or heteroaryl (preferrably 5-6 membered heteroaryl such as pyridinyl or thiophenyl), each optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy 5-6 membered heteroaryl (preferrably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxy. More particularly, one of $R_8$ and $R_9$ is —H and the other is unsubstituted ($C_3$-$C_8$)cyloalkyl (preferrably cyclopentyl and cyclohexyl), ($C_3$-$C_7$)cycloheteroalkyl (preferrably tetrahydrofuran or and tetrahydropyran) or heteroaryl (preferrably pyridinyl or thiophenyl). In another more particular embodiment, one of $R_8$ and $R_9$ is —H and the other is ($C_3$-$C_8$)cyloalkyl (preferrably cyclopentyl and cyclohexyl), ($C_3$-$C_7$)cycloheteroalkyl (preferrably tetrahydrofuran or and tetrahydropyran) or heteroaryl (preferrably pyridinyl or thiophenyl), each of which is optionally substituted with ($C_1$-$C_6$)alkyl, preferably methyl.

In another embodiment, $R_8$ and $R_9$, together with the carbon to which they are attached, form ring A, which is a 3-14 membered monocyclic ring, 9-14 membered bicyclic ring or 9-14 membered polycyclic ring, wherein ring A is optionally substituted with 1 to 3 substituents independently selected from the group consisting of —F, —Cl, —Br, —CN, —$OR_5$, —$NR_6R_7$, —$NR_{11}S(=O)_iR_5$, —C(=O)$OR_5$, —C(=O)$NR_{12}R_{13}$, —$NR_{11}C(=O)R_5$, —C(=S)$NR_{12}R_{13}$, —C(=O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl. In a particular embodiment, ring A is optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy, 5-6 membered heteroaryl (preferrably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxy. In a particular embodiment, ring A is a 5-7 membered monocycle ring optionally substituted with 1 to 3 substituents independently selected from the group consisting of ($C_1$-$C_6$)alkyl, halo($C_1$-$C_6$)alkyl, ($C_1$-$C_6$) alkoxy and ($C_1$-$C_3$)alkylcarbonyl, in another particular embodiment, ring A is a 9-14 membered bicyclic fused or bicyclic bridged ring optionally substituted with 1 to 3 substituents independently selected from the group consisting of ($C_1$-$C_6$)alkyl, halo($C_1$-$C_6$)alkyl, ($C_1$-$C_6$)alkoxy and ($C_1$-$C_3$) alkylcarbonyl. In another particular embodiment, ring A is selected from tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, and 2-oxabicyclo[2.2.2]octane, each optionally substituted with 1 to 3 substituents independently selected from the group consisting of ($C_1$-$C_6$)alkyl, halo($C_1$-$C_6$)alkyl, ($C_1$-$C_6$)alkoxy and ($C_1$-$C_3$)alkylcarbonyl.

$R_{11}$ is —H, ($C_1$-$C_6$)alkyl or halo($C_1$-$C_6$)alkyl. In a particular embodiment, $R_{11}$ is —H.

Each $R_{12}$ and $R_{13}$ are independently —H, ($C_1$-$C_6$)alkyl, ($C_1$-$C_3$)alkoxy($C_1$-$C_6$)alkyl, hydroxy($C_1$-$C_6$)alkyl, cyano ($C_1$-$C_6$)alkyl, amino($C_1$-$C_6$)alkyl, ($C_1$-$C_3$)alkylamino($C_1$-$C_6$)alkyl, or di($C_1$-$C_3$)alkylamino($C_1$-$C_6$)alkyl. In a particular embodiment, $R_{12}$ and $R_{13}$ are independently —H, ($C_1$-$C_6$) alkyl, ($C_1$-$C_3$)alkoxy($C_1$-$C_3$)alkyl, hydroxy($C_1$-$C_3$)alkyl, cyano($C_1$-$C_3$)alkyl, or di($C_1$-$C_3$)alkylamino($C_1$-$C_3$)alkyl. More particularly, $R_{12}$ and $R_{13}$ are independently —H, methyl, ethyl, propyl, butyl, methoxyethyl, cyanoethyl, or dimethylaminoethyl.

$R_{14}$ is —H, ($C_1$-$C_6$)alkyl, halo($C_1$-$C_6$)alkyl, ($C_3$-$C_8$)cycloalkyl, cycloheteroalkyl($C_1$-$C_3$)alkyl, ($C_3$-$C_8$)cycloalkyl ($C_1$-$C_3$)alkyl, aryl($C_1$-$C_6$)alkyl, heteroaryl($C_1$-$C_6$)alkyl, each optionally substituted with 1 to 3 substituents independently selected from the group consisting of —F, —Cl, —Br, —CN, ($C_1$-$C_6$)alkyl, halo($C_1$-$C_6$)alkyl and ($C_1$-$C_3$)alkoxy. In a particular embodiment, $R_{14}$ is ($C_1$-$C_6$)alkyl, halo($C_1$-$C_3$)alkyl, ($C_3$-$C_8$)cycloalkyl($C_1$-$C_3$)alkyl or benzyl. In another particular embodiment, $R_{14}$ is ethyl, propyl, cyclohexylmethyl, cyclopropylethyl, trifluoroethyl, or benzyl. In another particular embodiment, $R_{14}$ is methyl.

$R_{15}$ is —H or ($C_1$-$C_6$)alkyl. In a particular embodiment, $R_{15}$ is —H.

$R_{16}$ and $R_{17}$ are each independently —H or ($C_1$-$C_3$)alkyl. In a particular embodiment, $R_{16}$ and $R_{17}$ are both —H.

$R_{18}$ is —H or ($C_1$-$C_3$)alkyl. In a particular embodiment, $R_{18}$ is —H.

X is —O—, —S—, —SO—, —$SO_2$—, —$CH_2O$—, or —$OCH_2$—. In a particular embodiment, X is —O—. In another particular embodiment, X is —S—. In another particular embodiment, X is —SO—. In another particular embodiment, X is —$SO_2$—.

Y is —C($R_8R_9$)—.

W is —N($R_{14}$)—, —S—, or —O—. In a particular embodiment, W is —N($R_{14}$)—.

Z is —C(=O)—, —C(=S)—, —C(=$NR_{15}$)—, —O—, —C(=O)C($R_{16}R_{17}$)—, —C(=S)C($R_{16}R_{17}$)—, —C(=$NR_{15}$)C($R_{16}R_{17}$)—, —N($R_{18}$)—, or —(C$R_{16}R_{17})_m$—. In a particular embodiment, Z is —O—. In another particular embodiment, Z is —C(=O)—.

i is 0, 1 or 2;

p is 1 or 2. In a particular embodiment, p is 1.

m is 1 or 2.

n is 1 or 2. In a particular embodiment, n is 1.

One embodiment of the present invention is directed to compounds represented by the Structural Formula (I') or a pharmaceutically acceptable salt thereof. Values and particular values for the variables in Structural Formula (I') or an enantiomer, a diastereomer, a tautomer, or a pharmaceutically acceptable salt thereof are provided in the following paragraphs. It is understood that the invention encompasses all combinations of the substituent variables (i.e., $R^1$, $R^2$, $R^3$, etc.) defined herein. For Structural Formula (I'):

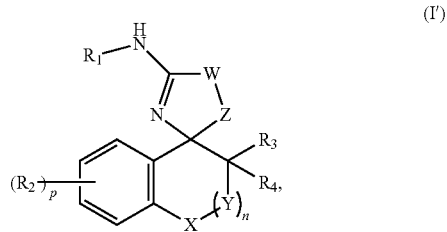

(I')

or an enantiomer, a diastereomer or a pharmaceutically acceptable salt thereof:

$R_1$ is —H, $(C_1-C_6)$alkyl, aryl$(C_1-C_6)$alkyl or heteroaryl$(C_1-C_6)$alkyl. In one embodiment $R_1$ is —H, $(C_1-C_6)$alkyl or benzyl. In another embodiment, $R_1$ is —H.

$R_2$ is a) —H, —F, —Cl, —Br, or —CN or b) $(C_1-C_6)$alkyl, $(C_2-C_6)$alkenyl, $(C_2-C_6)$alkynyl, $(C_3-C_8)$cycloalkyl, aryl, heteroaryl, phenoxy, or benzyloxy, each optionally substituted with 1 to 3 substituents independently selected from the group consisting of —F, —Cl, —Br, —CN, —$OR_5$, —$NR_6R_7$, —$S(O)_tR_5$, —$NR_{11}S(=O)_tR_5$, —$C(=O)OR_5$, —$C(=O)NR_{12}R_{13}$, —$NR_{11}C(=O)R_5$, —$C(=S)NR_{12}R_{13}$, —$C(=O)R_5$, $(C_1-C_6)$alkyl, $(C_2-C_6)$alkenyl, halo$(C_1-C_6)$alkyl, $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, $(C_1-C_3)$alkoxy, halo$(C_1-C_3)$alkoxy, $(C_1-C_6)$alkoxy$(C_1-C_3)$alkyl and aryl.

In one embodiment, $R_2$ is —H, —Br, —F, —Cl, $(C_1-C_6)$alkyl, $(C_3-C_8)$cycloalkyl, aryl, heteroaryl, phenoxy, or benzyloxy, each optionally substituted with 1 to 3 substituents independently selected from the group consisting of —F, —Cl, —Br, —CN, —$OR_5$, —$NR_6R_7$, —$S(O)_tR_5$, —$NR_{11}S(=O)_tR_5$, —$COOR_5$, —$CONR_{12}R_{13}$, —$NR_{11}C(=O)R_5$, —$C(=S)NR_{12}R_{13}$, —$COR_5$, $(C_1-C_3)$alkyl, halo$(C_1-C_3)$alkyl, $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, or $(C_1-C_6)$alkoxy$(C_1-C_3)$alkyl.

In another particular embodiment, $R_2$ is —H, —Cl, —Br or —F.

In another particular embodiment, $R_2$ is $(C_1-C_6)$alkyl. More particularly, $R_2$ is $(C_1-C_3)$alkyl.

In another particular embodiment, $R_2$ is phenyl optionally substituted with 1-3 substituents independently selected from the group consisting of —F, —Cl, —Br, —CN, —$OR_5$, —$NR_6R_7$, —$S(O)_tR_5$, —$NR_{11}S(=O)_tR_5$, —$C(=O)OR_5$, —$C(=O)NR_{12}R_{13}$, —$NR_{11}C(=O)R_5$, —$C(=S)NR_{12}R_{13}$, —$C(=O)R_5$; $(C_1-C_6)$alkyl, $(C_2-C_6)$alkenyl, halo$(C_1-C_6)$alkyl, $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, $(C_1-C_3)$alkoxy, halo$(C_1-C_3)$alkoxy and $(C_1-C_6)$alkoxy$(C_1-C_3)$alkyl.

In another particular embodiment, $R_2$ is pyridinyl, thiophenyl, pyrrolyl, pyrimidinyl or cyclohexyl, each optionally substituted with 1-3 substituents independently selected from the group consisting of —F, —Cl, —Br, —CN, —$OR_5$, —$NR_6R_7$, —$S(O)_tR_5$, —$NR_{11}S(=O)_tR_5$, —$C(=O)OR_5$, —$C(=O)NR_{12}R_{13}$, —$NR_{11}C(=O)R_5$, —$C(=S)NR_{12}R_{13}$, —$C(=O)R_5$, $(C_1-C_6)$alkyl, $(C_2-C_6)$alkenyl, halo$(C_1-C_6)$alkyl, $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, $(C_1-C_3)$alkoxy, halo$(C_1-C_3)$alkoxy, $(C_1-C_6)$alkoxy$(C_1-C_3)$alkyl and aryl. More particularly, the substituents are independently selected from the group consisting of —F, —Cl, —Br, —CN and $(C_1-C_3)$alkyl.

In another particular embodiment, $R_2$ is phenoxy or benzyloxy, each optionally substituted with 1-3 substituents independently selected from the group consisting of —F, —Cl, —Br, —CN, —$OR_5$, —$NR_6R_7$, —$S(O)_tR_5$, —$NR_{11}S(=O)_tR_5$, —$C(=O)OR_5$, —$C(=O)NR_{12}R_{13}$, —$NR_{11}C(=O)R_5$, —$C(=S)NR_{12}R_{13}$, —$C(=O)R_5$, $(C_1-C_6)$alkyl, $(C_2-C_6)$alkenyl, halo$(C_1-C_6)$alkyl, or $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, $(C_1-C_3)$alkoxy, halo$(C_1-C_3)$alkoxy, and $(C_1-C_6)$alkoxy$(C_1-C_3)$alkyl. More particularly, $R_2$ is unsubstituted phenoxy or benzyloxy.

$R_3$ and $R_4$ are each independently —H, —F, —Br, —Cl or $(C_1-C_6)$alkyl. In a particular embodiment, $R_3$ and $R_4$ are both —H. In another particular embodiment, $R_3$ and $R_4$ are independently —H, —F or methyl.

$R_5$ is —H, $(C_1-C_6)$alkyl, halo$(C_1-C_6)$alkyl, $(C_2-C_6)$alkenyl, $(C_2-C_6)$alkynyl, $(C_1-C_3)$alkoxy$(C_1-C_6)$alkyl, $(C_3-C_8)$cycloalkyl, $(C_3-C_8)$cycloalkyl$(C_1-C_6)$alkyl, $(C_3-C_7)$cycloheteroalkyl, aryl, heteroaryl, or benzyl, each of which is optionally substituted with 1 to 3 substituents independently selected from the group consisting of —F, —Cl, —Br, —CN, $(C_1-C_6)$alkyl, halo$(C_1-C_6)$alkyl, $(C_1-C_3)$alkoxy, halo$(C_1-C_3)$alkoxy and $(C_1-C_3)$alkoxy$(C_1-C_6)$alkyl. In a particular embodiment, $R_5$ is $(C_1-C_6)$alkyl, halo$(C_1-C_6)$alkyl, $(C_1-C_3)$alkoxy$(C_1-C_6)$alkyl, $(C_3-C_7)$cycloheteroalkyl or benzyl. In a more particular embodiment, $R_5$ is $(C_1-C_6)$alkyl, halo$(C_1-C_6)$alkyl, $(C_1-C_3)$alkoxy$(C_1-C_3)$alkyl, pyrrolidinyl or benzyl. More particular, $R_5$ is methyl, ethyl, propyl, butyl, methoxypropyl, methoxyethyl, benzyl or pyrrolidinyl.

$R_6$ and $R_7$ are each independently —H, $(C_1-C_6)$alkyl, hydroxy$(C_1-C_6)$alkyl, halo$(C_1-C_6)$alkyl, $(C_3-C_8)$cycloalkyl, $(C_3-C_8)$cycloalkyl$(C_1-C_6)$alkyl, each optionally substituted with 1 to 3 substituents independently selected from the group consisting of —F, —Cl, —Br, —CN, $(C_1-C_6)$alkyl, halo$(C_1-C_6)$alkyl and $(C_1-C_3)$alkoxy$(C_1-C_6)$alkyl. In a particular embodiment, $R_6$ and $R_7$ are each independently —H or $(C_1-C_6)$alkyl. In another particular embodiment, $R_6$ and $R_7$ are both —H.

In one embodiment, $R_8$ and $R_9$ are each independently —H, $(C_1-C_6)$alkyl, hydroxy$(C_1-C_6)$alkyl, halo$(C_1-C_6)$alkyl, $(C_2-C_6)$alkenyl, $(C_2-C_6)$alkynyl, $(C_3-C_8)$cycloalkyl, $(C_3-C_7)$cycloheteroalkyl, aryl or heteroaryl, each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy and halo$(C_1-C_3)$alkoxy. In a particular embodiment, $R_8$ and $R_9$ are each independently —H, $(C_1-C_6)$alkyl, hydroxy$(C_1-C_6)$alkyl, $(C_3-C_8)$cycloalkyl, $(C_3-C_7)$cycloheteroalkyl, phenyl or heteraryl, each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy and halo$(C_1-C_3)$alkoxy. In another particular embodiment, $R_8$ and $R_9$ are both —H, $(C_1-C_3)$alkyl or hydroxy$(C_1-C_3)$alkyl. More particularly, $R_8$ and $R_9$ are both —H, methyl or hydroxymethyl. In another particular embodiment, one of $R_8$ and $R_9$ is —H and the other is unsubstituted phenyl. In another particular embodiment, one of $R_8$ and $R_9$ is —H and the other is phenyl substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy and halo($C_1$-$C_3$)alkoxy. More particularly, the substituents independently selected from —F, —Cl, —Br, —CN, trifluoromethyl, methoxy, trifluoromethoxy. In another particular embodiment, one of $R_8$ and $R_9$ is —H and the other is ($C_3$-$C_8$)cyloalkyl (preferably cyclopentyl and cyclohexyl), ($C_3$-$C_7$)cycloheteroalkyl (preferrably tetrahydrofuran or and tetrahydropyran) or heteroaryl (preferrably pyridinyl or thiophenyl), each optionally substituted with 1 to 3 substitutents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy and halo($C_1$-$C_3$)alkoxy. More particularly, one of $R_8$ and $R_9$ is —H and the other is unsubstituted ($C_3$-$C_8$)cyloalkyl (preferably cyclopentyl and cyclohexyl), ($C_3$-$C_7$)cycloheteroalkyl (preferrably tetrahydrofuran or and tetrahydropyran) or heteroaryl (preferrably pyridinyl or thiophenyl). In another more particular embodiment, one of $R_8$ and $R_9$ is —H and the other is ($C_3$-$C_8$)cyloalkyl (preferably cyclopentyl and cyclohexyl), ($C_3$-$C_7$)cycloheteroalkyl (preferrably tetrahydrofuran or and tetrahydropyran) or heteroaryl (preferrably pyridinyl or thiophenyl), each of which is optionally substituted with ($C_1$-$C_6$)alkyl, preferably methyl.

In another embodiment, $R_8$ and $R_9$, together with the carbon to which they are attached, form a substituted 3-8 membered ring (ring A) optionally substituted with 1 to 3 substituents independently selected from the group consisting of —F, —Cl, —Br, —CN, —$OR_5$, —$NR_6R_7$, —S(O)$_i R_5$, —$NR_{11}$S(=O)$_i R_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy and ($C_1$-$C_6$)alkoxy($C_1$-$C_3$)alkyl; wherein ring A contains 0 to 3 heteroatoms, which are selected from O, N, S; wherein when the heteroatom is nitrogen, the nitrogen is substituted with —H, ($C_1$-$C_6$)alkyl, halo($C_1$-$C_6$)alkyl or ($C_1$-$C_3$)alkylcarbonyl, and when the heteroatom is sulfur, the sulfur is optionally mono- or di-oxygenated. In a particular embodiment, ring A is optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy and halo($C_1$-$C_3$)alkoxy. In a particular embodiment, ring A is tetrahydrofuran, tetrahydropyran, cyclopentane, cyclohexane, cycloheptane, oxepane, 1,3-dioxane, or piperidine, each optionally substituted with 1 to 3 substituents independently selected from the group consisting of ($C_1$-$C_6$)alkyl, halo($C_1$-$C_6$)alkyl and ($C_1$-$C_3$)alkylcarbonyl.

$R_{11}$ is —H, ($C_1$-$C_6$)alkyl or halo($C_1$-$C_6$)alkyl. In a particular embodiment, $R_{11}$ is —H.

$R_{12}$ and $R_{13}$ are each independently —H, ($C_1$-$C_6$)alkyl, ($C_1$-$C_3$)alkoxy($C_1$-$C_6$)alkyl, hydroxy($C_1$-$C_6$)alkyl, cyano($C_1$-$C_6$)alkyl, amino($C_1$-$C_6$)alkyl, ($C_1$-$C_3$)alkylamino($C_1$-$C_6$)alkyl, or di($C_1$-$C_3$)alkylamino($C_1$-$C_6$)alkyl. In a particular embodiment, $R_{12}$ and $R_{13}$ are independently —H, ($C_1$-$C_6$)alkyl, ($C_1$-$C_3$)alkoxy($C_1$-$C_3$)alkyl, hydroxy($C_1$-$C_3$)alkyl, cyano($C_1$-$C_3$)alkyl, or di($C_1$-$C_3$)alkylamino($C_1$-$C_3$)alkyl. More particularly, $R_{12}$ and $R_{13}$ are independently —H, methyl, ethyl, propyl, butyl, methoxyethyl, cyanoethyl, or dimethylaminoethyl.

$R_{14}$ is —H, ($C_1$-$C_6$)alkyl, halo($C_1$-$C_6$)alkyl, ($C_3$-$C_8$)cycloalkyl, cycloheteroalkyl($C_1$-$C_3$)alkyl, ($C_3$-$C_8$)cycloalkyl($C_1$-$C_3$)alkyl, aryl($C_1$-$C_6$)alkyl, heteroaryl($C_1$-$C_6$)alkyl, each optionally substituted with 1 to 3 substituents independently selected from the group consisting of —F, —Cl, —Br, —CN, ($C_1$-$C_6$)alkyl, halo($C_1$-$C_6$)alkyl and ($C_1$-$C_3$)alkoxy. In a particular embodiment, $R_{14}$ is ($C_1$-$C_6$)alkyl, halo($C_1$-$C_3$)alkyl, ($C_3$-$C_8$)cycloalkyl($C_1$-$C_3$)alkyl or benzyl. In another particular embodiment, $R_{14}$ is ethyl, propyl, cyclohexylmethyl, cyclopropylethyl, trifluoroethyl, or benzyl. In another particular embodiment, $R_{14}$ is methyl.

$R_{15}$ is —H or ($C_1$-$C_6$)alkyl. In a particular embodiment, $R_{15}$ is —H.

$R_{16}$ and $R_{17}$ are each independently —H or ($C_1$-$C_3$)alkyl. In a particular embodiment, $R_{16}$ and $R_{17}$ are both —H.

$R_{18}$ is —H or ($C_1$-$C_3$)alkyl. In a particular embodiment, $R_{18}$ is —H.

X is —O—, —S—, —SO—, —$SO_2$—, —$CH_2O$—, or —$OCH_2$—. In a particular embodiment, X is —O—. In another particular embodiment, X is —S—. In another particular embodiment, X is —SO—. In another particular embodiment, X is —$SO_2$—.

Y is —C($R_8R_9$)—.

W is —N($R_{14}$)—, —S—, or —O—. In a particular embodiment, W is —N($R_{14}$)—.

Z is —C(=O)—, —C(=S)—, —C(=$NR_{15}$)—, —O—, —C(=O)C($R_{16}R_{17}$)—, —C(=S)C($R_{16}R_{17}$)—, —C(=$NR_{15}$)C($R_{16}R_{17}$)—, —N($R_{18}$)—, or —(C$R_{16}R_{17}$)$_m$—. In a particular embodiment, Z is —O—. In another particular embodiment, Z is —C(=O)—.

i is 0, 1 or 2;
p is 1 or 2. In a particular embodiment, p is 1.
m is 1 or 2.
n is 1 or 2. In a particular embodiment, n is 1.

In a $1^{st}$ specific embodiment, the compound of the present invention is represented by Structural Formula (II):

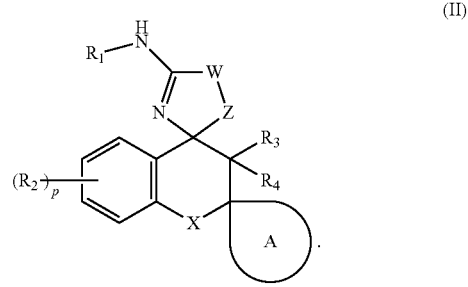

Ring A is an optionally substituted 3-14 membered monocyclic ring, 9-14 membered bicyclic ring or 9-14 membered polycyclic ring. Values and particular values for the remainder of the variables in Structural Formula (II) are as described above for Structural Formula (I). Ring A is optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxy.

Alternatively, Ring A is an optionally substituted 3-8 membered ring containing 0 to 3 heteroatoms, which are independently selected from O, N and S; wherein when the heteroatom is nitrogen, the nitrogen is substituted with —H, ($C_1$-$C_6$)alkyl, halo($C_1$-$C_6$)alkyl or ($C_1$-$C_3$)alkylcarbonyl, and when the heteroatom is sulfur, the sulfur is optionally mono- or di-oxygenated. Values and particular values for the remainder of the variables in Structural Formula (II) are as described above for Structural Formula (I'). Ring A is optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy and halo($C_1$-$C_3$)alkoxy.

In a $2^{nd}$ specific embodiment, the compound of the present invention is represented by the following Structural Formulas:

(III)
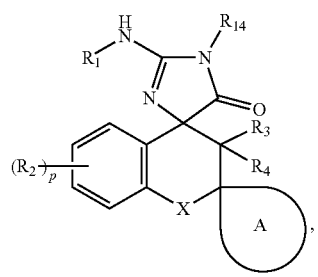

(IV)
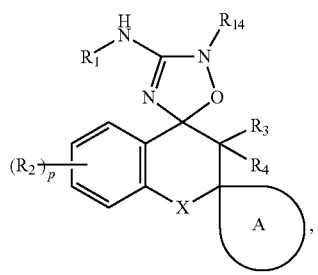

(V)
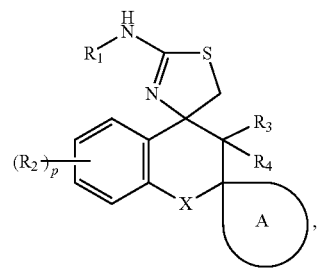

(XIV)
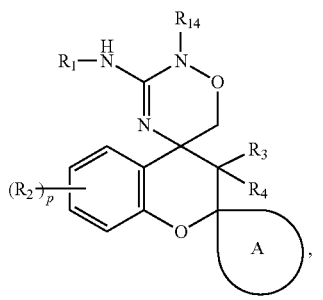

(VI)
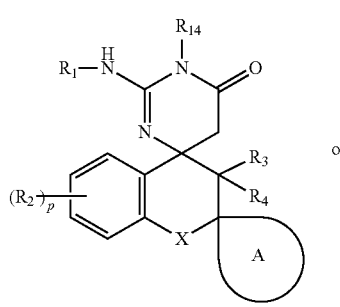

or (VII)
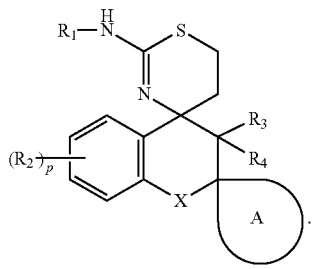

Values and particular values for Structural Formulas (III), (IV), (V), (VI), (VII) and (XIV) are as described above for Structural Formula (II) in the $1^{st}$ specific embodiment. More specifically, $R_2$ is independently —H, —F, —Cl or —Br and p is 2.

In a $3^{rd}$ specific embodiment, the compound of the present invention is represented by the following Structural Formulas:

(IIIa)
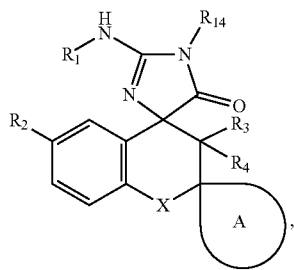

(IVa)
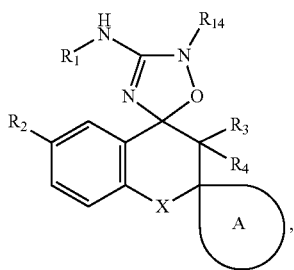

(Va)
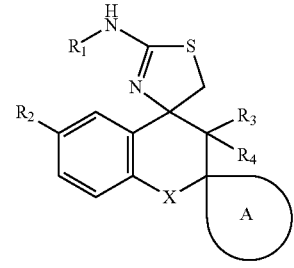

(XIVa)
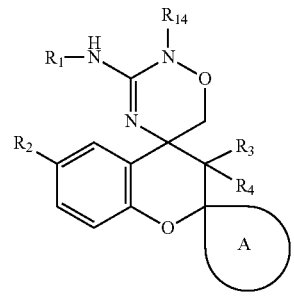

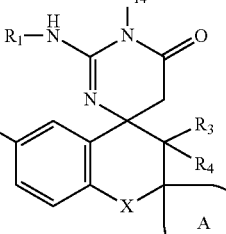

(VIa)

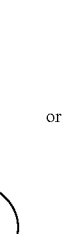

(VIIa)

Values and particular values for Structural Formulas (IIIa), (IVa), (Va), (VIa), (VIIa) and (XIVa) are as described above for Structural Formula (II).

In a more specific embodiment, for compounds of Structural Formulas (IIIa)-(VIIa) and (XIVa), X is —O—, and the values and specific values of the remainder of the variable are as described in the 3$^{rd}$ specific embodiment.

In another more specific embodiment, for compounds of Structural Formulas (IIIa)-(VIa) and (XIVa), X is —S—, and the values and specific values of the remainder of the variable are as described above in the 3$^{rd}$ specific embodiment.

In another more specific embodiment, for compounds of Structural Formulas (IIIa)-(VIIa) and (XIVa), X is —SO—, and the values and specific values of the remainder of the variable are as described above in the 3$^{rd}$ specific embodiment.

In another more specific embodiment, for compounds of Structural Formulas (IIIa)-(VIIa) and (XIVa), X is —SO$_2$—, and the values and specific values of the remainder of the variable are as described above in the 3$^{rd}$ specific embodiment.

In a 4$^{th}$ specific embodiment, for compounds of Structural Formulas (IIIa)-(VIIa) and (XIVa), R$_2$ is —H, —Cl, —Br, —F or (C$_1$-C$_6$)alkyl, and the values and specific values of the remainder of the variable are as described above in the 3$^{rd}$ specific embodiment.

In a more specific embodiment, for compounds of Structural Formulas (IIIa)-(VIIa) and (XIVa), R$_2$ is —H, —Cl, —Br, —F or (C$_1$-C$_6$)alkyl and X is —O—. Values and specific values of the remainder of the variable are as described above in the 4$^{th}$ specific embodiment.

In another more specific embodiment, for compounds of Structural Formulas (IIIa)-(VIIa) and (XIVa), R$_2$ is —H, —Cl, —Br, —F or (C$_1$-C$_6$)alkyl and X is —S—. Values and specific values of the remainder of the variable are as described above in the 4$^{th}$ specific embodiment.

In another more specific embodiment, for compounds of Structural Formulas (IIIa)-(VIIa) and (XIVa), R$_2$ is —H, —Cl, —Br, —F or (C$_1$-C$_6$)alkyl and X is —SO—. Values and specific values of the remainder of the variable are as described above in the 4$^{th}$ specific embodiment.

In another more specific embodiment, for compounds of Structural Formulas (IIa)-(VIa) and (XIVa), R$_2$ is —H, —Cl, —Br, —F or (C$_1$-C$_6$)alkyl and X is —SO$_2$—. Values and specific values of the remainder of the variable are as described above in the 4$^{th}$ specific embodiment.

In another more specific embodiment, for compounds of Structural Formulas (IIa)-(VIa) and (XIVa), ring A a 5-7 membered monocyclic ring containing 0 to 2 heteratoms independently selected from O, S and N, wherein ring A is optionally substituted with 1 to 3 substituents independently selected from the group consisting of (C$_1$-C$_6$)alkyl, halo(C$_1$-C$_6$)alkyl, (C$_1$-C$_6$)alkoxy, (C$_1$-C$_3$)alkylcarbonyl, 5-6 membered heteroaryl (preferrably pyridine or pyrimidine), phenyl, phenoxy and benzoxy, wherein the phenyl, phenoxy and benzoxy are each optionally substituted with —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy or halo(C$_1$-C$_3$)alkoxy. Values and specific values for the remainder of the variables in Structural Formulas (IIa)-(VIa) and (XIVa) are as described above in the 4$^{th}$ specific embodiment. In a even more specific embodiment, X is —O—. In another even more specific embodiment, X is —O—; R$_3$ and R$_4$ are —H; and R$_1$ is —H.

In another more embodiment, for compounds of Structural Formulas (IIa)-(VIa) and (XIVa), ring A is a 9-14 membered bicyclic fused or bicyclic bridged ring containing 0 to 2 heteratoms independently selected from O, S and N, wherein ring A is optionally substituted with 1 to 3 substituents independently selected from the group consisting of (C$_1$-C$_6$)alkyl, halo(C$_1$-C$_6$)alkyl, (C$_1$-C$_6$)alkoxy, (C$_1$-C$_3$)alkylcarbonyl, 5-6 membered heteroaryl (preferrably pyridine or pyrimidine), phenyl, phenoxy and benzoxy, wherein the phenyl, phenoxy and benzoxy are each optionally substituted with —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy or halo(C$_1$-C$_3$)alkoxy. Values and specific values for the remainder of the variables in Structural Formulas (IIa)-(VIa) are as described above in the 4$^{th}$ specific embodiment. In a even more specific embodiment, X is —O—. In another even more specific embodiment, X is —O—; R$_3$ and R$_4$ are —H; and R$_1$ is —H.

In another more specific embodiment, for compounds of Structural Formulas (IIa)-(VIa) and (XIVa), ring A is selected from tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, and 2-oxabicyclo[2.2.2]octane, each optionally substituted with 1 to 3 substituents independently selected from the group consisting of (C$_1$-C$_6$)alkyl, halo(C$_1$-C$_6$)alkyl, (C$_1$-C$_6$)alkoxy, C$_3$)alkylcarbonyl, 5-6 membered heteroaryl (preferrably pyridine or pyrimidine), phenyl, phenoxy and benzoxy, wherein the phenyl, phenoxy and benzoxy are each optionally substituted with —F, —Cl, —Br, —CN, (C$_1$-C$_6$)alkyl, halo (C$_1$-C$_6$)alkyl, hydroxy(C$_1$-C$_6$)alkyl, (C$_1$-C$_3$)alkoxy or halo (C$_1$-C$_3$)alkoxy. Values and specific values for the remainder of the variables in Structural Formulas (IIa)-(VIa) are as described above in the 4$^{th}$ specific embodiment. In a even more specific embodiment, X is —O—. In another even more specific embodiment, X is —O—; R$_3$ and R$_4$ are —H; and R$_1$ is —H.

In another more specific embodiment, for compounds of Structural Formulas (IIIa), (IVa), (VIa), and (XIVa), R$_{14}$ is (C$_1$-C$_6$)alkyl, halo(C$_1$-C$_3$)alkyl, (C$_3$-C$_8$)cycloalkyl(C$_1$-C$_3$)alkyl or benzyl. Values and specific values for the remainder of the variables in Structural Formulas (IIIa), (IVa), (VIa), and (XIVa), are as described above in the 4$^{th}$ specific embodiment. In an even more specific embodiment, X is —O—. In another even more specific embodiment, X is —O—; and $R_{14}$ is ethyl, propyl, cyclohexylmethyl, cyclopropylethyl, trifluoroethyl, or benzyl. In another even more specific embodiment, X is —O—; and $R_{14}$ is methyl.

In another more specific embodiment, for compounds of Structural Formulas (IIIa), (IVa), (VIa) and (XIVa), $R_{14}$ is ($C_1$-$C_6$)alkyl, halo($C_1$-$C_3$)alkyl, ($C_3$-$C_8$)cycloalkyl($C_1$-$C_3$) alkyl or benzyl; and ring A is selected from tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, and 2-oxabicyclo[2.2.2]octane, each optionally substituted with 1 to 3 substituents independently selected from the group consisting of ($C_1$-$C_6$) alkyl, halo($C_1$-$C_6$)alkyl, ($C_1$-$C_6$)alkoxy, ($C_1$-$C_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxy. Values and specific values for the remainder of the variables in Structural Formulas (IIIa), (IVa), (VIa) and (XIVa), are as described above in the 4$^{th}$ specific embodiment. In an even more specific embodiment, X is —O—. In another even more specific embodiment, X is —O—; $R_{14}$ is ethyl, propyl, cyclohexylmethyl, cyclopropylethyl, trifluoroethyl, or benzyl; and ring A is unsubstituted tetrahydrofuran, tetrahydropyran, cyclopentane, cyclohexane, cycloheptane, oxepane, 1,3-dioxane, or piperidine. In another even more specific embodiment, X is —O—; $R_{14}$ is methyl; and ring A is unsubstituted tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane.

In a 5$^{th}$ specific embodiment, for compounds of Structural Formulas (IIIa)-(VIIa) and (XIVa), $R_2$ is ($C_3$-$C_8$)cycloalkyl, ($C_3$-$C_8$)cycloheteroalkyl, heteroaryl, phenoxy or benzyloxy, each of which is optionally substituted with 1 to 3 substituents independently selected from the group consisting of —F, —Cl, —Br, —CN, —$OR_5$, —$SR_5$, —$NR_6R_7$, —S(O)$_rR_5$, —$NR_{11}$S(=O)$_rR_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_3$-$C_8$)cycloalkyl, ($C_2$-$C_6$)alkenyl, halo($C_1$-$C_6$) alkyl, ($C_1$-$C_3$)alkylsulfonylaminoalkyl, hydroxy($C_1$-$C_6$) alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy ($C_1$-$C_3$)alkyl, aryl and heteroaryl. Values and specific values of the remainder of the variable are as described in the 3$^{rd}$ specific embodiment. More specifically, $R_2$ is cyclohexyl, pyrrolidinyl, pyridinyl, pyrimidinyl, thiophenyl or thiazolyl. Even more specifically, the substituents are independently selected from —F, —Cl, —Br, —CN, hydroxy($C_1$-$C_6$)alkyl, cyano($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, phenyl and 5-6 membered heteroaryl (preferably pyridine or pyrimidine).

In a more specific embodiment, for compounds of Structural Formulas (IIIa)-(VIIa) and (XIVa), X is —O—, and the values and specific values of the remainder of the variable are as described in the 5$^{th}$ specific embodiment.

In another more specific embodiment, for compounds of Structural Formulas (IIIa)-(VIIa) and (XIVa), X is —S—, and the values and specific values of the remainder of the variable are as described in the 5$^{th}$ specific embodiment.

In another more specific embodiment, for compounds of Structural Formulas (IIIa)-(VIIa) and (XIVa), X is —SO—, and the values and specific values of the remainder of the variable are as described in the 5$^{th}$ specific embodiment.

In another more specific embodiment, for compounds of Structural Formulas (IIIa)-(VIIa) and (XIVa), X is —$SO_2$—, and the values and specific values of the remainder of the variable are as described in the 5$^{th}$ specific embodiment.

In another more specific embodiment, for compounds of Structural Formulas (IIa)-(VIa) and (XIVa), ring A a 5-7 membered monocyclic ring containing 0 to 2 heteroatoms independently selected from O, S and N, wherein ring A is optionally substituted with 1 to 3 substituents independently selected from the group consisting of ($C_1$-$C_6$)alkyl, halo($C_1$-$C_6$)alkyl, ($C_1$-$C_6$)alkoxy, ($C_1$-$C_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$) alkyl, ($C_1$-$C_3$)alkoxy or halo($C_1$-$C_3$)alkoxy. Values and specific values for the remainder of the variables in Structural Formulas (IIa)-(VIa) and (XIVa) are as described above in the 5$^{th}$ specific embodiment. In a even more specific embodiment, X is —O—. In another even more specific embodiment, X is —O—; $R_3$ and $R_4$ are —H; and $R_1$ is —H.

In another more embodiment, for compounds of Structural Formulas (IIa)-(VIa) and (XIVa), ring A is a 9-14 membered bicyclic fused or bicyclic bridged ring containing 0 to 2 heteroatoms independently selected from O, S and N, wherein ring A is optionally substituted with 1 to 3 substituents independently selected from the group consisting of ($C_1$-$C_6$)alkyl, halo($C_1$-$C_6$)alkyl, ($C_1$-$C_6$)alkoxy, ($C_1$-$C_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxy. Values and specific values for the remainder of the variables in Structural Formulas (IIa)-(VIa) are as described above in the 5$^{th}$ specific embodiment. In a even more specific embodiment, X is —O—. In another even more specific embodiment, X is —O—; $R_3$ and $R_4$ are —H; and $R_1$ is —H.

In another more specific embodiment, for compounds of Structural Formulas (IIIa)-(VIIa) and (XIVa), ring A is selected from tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, and 2-oxabicyclo[2.2.2]octane, each optionally substituted with 1 to 3 substituents independently selected from the group consisting of ($C_1$-$C_6$)alkyl, halo($C_1$-$C_6$)alkyl, ($C_1$-$C_6$)alkoxy, ($C_1$-$C_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$) alkyl, ($C_1$-$C_3$)alkoxy or halo($C_1$-$C_3$)alkoxy. Values and specific values for the remainder of the variables in Structural Formulas (IIIa)-(VIIa) are as described above in the 5$^{th}$ specific embodiment. In an even more specific embodiment, X is —O—. In another even more specific embodiment, X is —O—; $R_3$ and $R_4$ are —H; and $R_1$ is —H.

In another more specific embodiment, for compounds of Structural Formulas (Ina), (IVa), (VIa) and (XIVa), $R_{14}$ is ($C_1$-$C_6$)alkyl, halo($C_1$-$C_3$)alkyl, ($C_3$-$C_8$)cycloalkyl($C_1$-$C_3$) alkyl or benzyl. Values and specific values for the remainder of the variables in Structural Formulas (Ina), (IVa) and (VIa) are as described above in the 5$^{th}$ specific embodiment. In an even more specific embodiment, X is —O—. In another even more specific embodiment, X is —O—; and R$_{14}$ is methyl, ethyl, propyl, cyclohexylmethyl, cyclopropylethyl, trifluoroethyl, or benzyl; R$_3$ and R$_4$ are —H; and R$_1$ is —H.

In another more specific embodiment, for compounds of Structural Formulas (IIIa), (IVa), (VIa) and (XIVa), R$_{14}$ is (C$_1$-C$_6$)alkyl, halo(C$_1$-C$_3$)alkyl, (C$_3$-C$_8$)cycloalkyl(C$_1$-C$_3$)alkyl or benzyl; and ring A is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substituents independently selected from the group consisting of (C$_1$-C$_6$)alkyl, halo(C$_1$-C$_6$)alkyl, (C$_1$-C$_6$)alkoxy and (C$_1$-C$_3$)alkylcarbonyl. Values and specific values for the remainder of the variables in Structural Formulas (IIIa), (IVa), (VIa) and (XIVa) are as described above in the 5$^{th}$ specific embodiment. In an even more specific embodiment, X is —O—. In another even more specific embodiment, X is —O—; R$_{14}$ is methyl, ethyl, propyl, cyclohexylmethyl, cyclopropylethyl, trifluoroethyl, or benzyl; ring A is unsubstituted tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane; R$_3$ and R$_4$ are —H; and R$_1$ is —H.

In a 6$^{th}$ specific embodiment, for compounds of Structural Formulas (IIIa)-(VIIa), R$_2$ is aryl and values and specific values for the remainder of the variables are as described above in the 3$^{rd}$ specific embodiment. More specifically, R$_2$ is phenyl.

In a more specific embodiment, for compounds of Structural Formulas (IIIa)-(VIIa) and (XIVa), X is —O—, and values and specific values for the remainder of the variables are as described above in the 6$^{th}$ specific embodiment.

In another more specific embodiment, for compounds of Structural Formulas (IIIa)-(VIIa) and (XIVa), X is —S—, and values and specific values for the remainder of the variables are as described above in the 6$^{th}$ specific embodiment.

In another more specific embodiment, for compounds of Structural Formulas (IIIa)-(VIIa) and (XIVa), X is —SO—, and values and specific values for the remainder of the variables are as described above in the 6$^{th}$ specific embodiment.

In another more specific embodiment, for compounds of Structural Formulas (IIIa)-(VIIa) and (XIVa), X is —SO$_2$—, and values and specific values for the remainder of the variables are as described above in the 6$^{th}$ specific embodiment.

In another more specific embodiment, for compounds of Structural Formulas (IIIa)-(VIIa) and (XIVa), ring A is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substituents independently selected from the group consisting of (C$_1$-C$_6$)alkyl, halo(C$_1$-C$_6$)alkyl, (C$_1$-C$_6$)alkoxy, (C$_1$-C$_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy or halo(C$_1$-C$_3$)alkoxy. Values and specific values for the remainder of the variables in Structural Formulas (IIIa)-(VIIa) and (XIVa) are as described above in the 6$^{th}$ specific embodiment. In an even more specific embodiment, X is —O—. In another even more specific embodiment, X is —O—; R$_3$ and R$_4$ are —H; and R$_1$ is —H.

In another more specific embodiment, for compounds of Structural Formulas (IIIa), (IVa), (VIa) and (XIVa), R$_{14}$ is (C$_1$-C$_6$)alkyl, halo(C$_1$-C$_3$)alkyl, (C$_3$-C$_8$)cycloalkyl(C$_1$-C$_3$)alkyl or benzyl. Values and specific values for the remainder of the variables in Structural Formulas (IIIa), (IVa), (VIa) and (XIVa), are as described above in the 6$^{th}$ specific embodiment. In an even more specific embodiment, X is —O—. In another even more specific embodiment, X is —O—; and R$_{14}$ is methyl, ethyl, propyl, cyclohexylmethyl, cyclopropylethyl, trifluoroethyl, or benzyl; R$_3$ and R$_4$ are —H; and R$_1$ is —H.

In another more specific embodiment, for compounds of Structural Formulas (IIIa), (IVa), (VIa) and (XIVa), R$_{14}$ is (C$_1$-C$_6$)alkyl, halo(C$_1$-C$_3$)alkyl, (C$_3$-C$_8$)cycloalkyl(C$_1$-C$_3$)alkyl or benzyl; and ring A is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substituents independently selected from the group consisting of (C$_1$-C$_6$)alkyl, halo(C$_1$-C$_6$)alkyl, (C$_1$-C$_6$)alkoxy, (C$_1$-C$_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy or halo(C$_1$-C$_3$)alkoxy. Values and specific values for the remainder of the variables in Structural Formulas (IIIa), (IVa), (VIa) and (XIVa), are as described above in the 6$^{th}$ specific embodiment. In an even more specific embodiment, X is —O—. In another even more specific embodiment, X is —O—; R$_{14}$ is methyl, ethyl, propyl, cyclohexylmethyl, cyclopropylethyl, trifluoroethyl, or benzyl; ring A is unsubstituted tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, tetrahydroisoquinoline, or 2-oxabicyclo[2.2.2]octane; R$_3$ and R$_4$ are —H; and R$_1$ is —H.

In a 7$^{th}$ specific embodiment, the compounds of the present invention are represented by the following Structural Formulas:

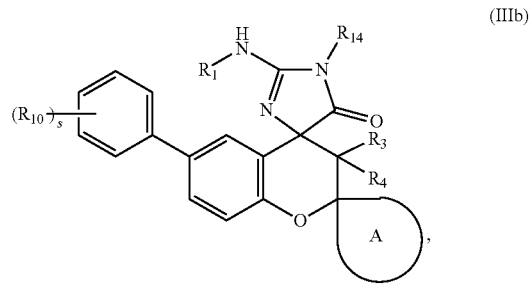

(IIIb)

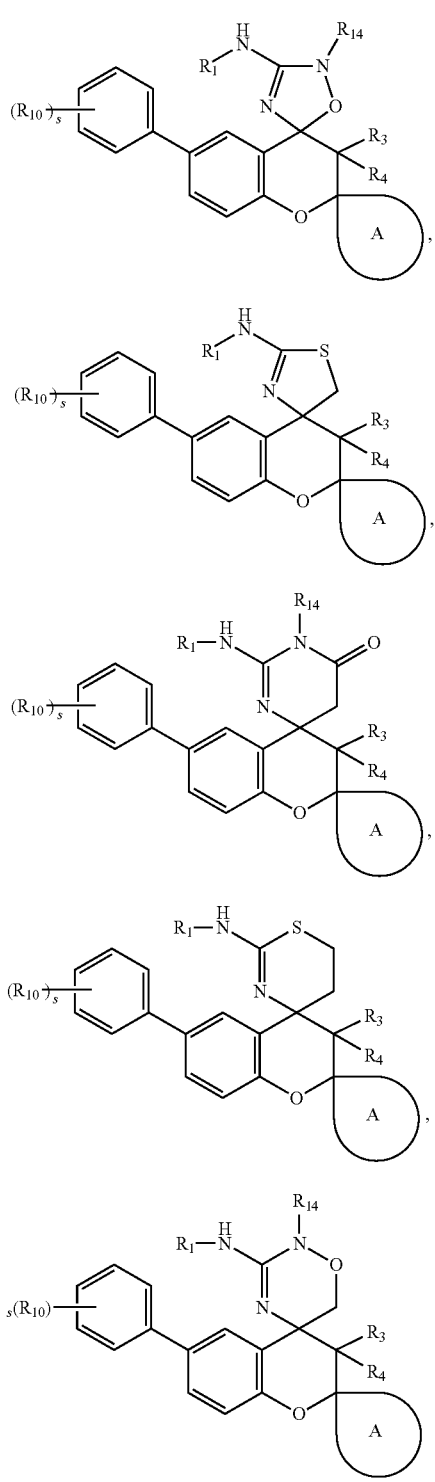

$R_{10}$ is —F, —Cl, —Br, —CN, —OR$_5$, —NR$_6$R$_7$, —S(O)$_1$R$_5$, —NR$_{11}$S(=O)$_1$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_6$)alkoxy(C$_1$-C$_3$)alkyl, aryl or heteroaryl, s is 0, 1, 2 or 3. Values and specific values for the remainder of the variables in Structural Formulas (IIIb)-(VIIb) and (XIVb) are as described above for Structural Formula (II).

In a more specific embodiment, for compounds of Structural Formulas (IIb)-(VIb) and (XIVb), ring A a 5-7 membered monocyclic ring containing 0 to 2 heteroatoms independently selected from O, S and N, wherein ring A is optionally substituted with 1 to 3 substituents independently selected from the group consisting of (C$_1$-C$_6$)alkyl, halo(C$_1$-C$_6$)alkyl, (C$_1$-C$_6$)alkoxy, (C$_1$-C$_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy or halo(C$_1$-C$_3$)alkoxy. Values and specific values for the remainder of the variables in Structural Formulas (IIb)-(VIb) and (XIVb) are as described above in the 7$^{th}$ specific embodiment. In a even more specific embodiment, R$_3$ and R$_4$ are —H; and R$_1$ is —H.

In another more embodiment, for compounds of Structural Formulas (IIb)-(VIb) and (XIVb), ring A is a 9-14 membered bicyclic fused or bicyclic bridged ring containing 0 to 2 heteroatoms independently selected from O, S and N, wherein ring A is optionally substituted with 1 to 3 substituents independently selected from the group consisting of (C$_1$-C$_6$)alkyl, halo(C$_1$-C$_6$)alkyl, (C$_1$-C$_6$)alkoxy, (C$_1$-C$_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy or halo(C$_1$-C$_3$)alkoxy. Values and specific values for the remainder of the variables in Structural Formulas (IIb)-(VIb) and (XIVb) are as described above in the 7$^{th}$ specific embodiment. In a even more specific embodiment, R$_3$ and R$_4$ are —H; and R$_1$ is —H.

In another more specific embodiment, for compounds of Structural Formulas (IIIb)-(VIIb) and (XIVb), ring A is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substituents independently selected from the group consisting of (C$_1$-C$_6$)alkyl, halo(C$_1$-C$_6$)alkyl, (C$_1$-C$_6$)alkoxy, (C$_1$-C$_3$)alkylcarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy or halo(C$_1$-C$_3$)alkoxy. Values and specific values for the remainder of the variables in Structural Formulas (IIIb)-(VIIb) and (XIVb) are as described above in the 7$^{th}$ specific embodiment. Even more specifically, R$_3$ and R$_4$ are —H.

In a more specific embodiment, for compounds of Structural Formulas (IIIb), (IVb), (VIb) and (XIVb), R$_{14}$ is (C$_1$-C$_6$)alkyl, halo(C$_1$-C$_3$)alkyl, (C$_3$-C$_8$)cycloalkyl(C$_1$-C$_3$)alkyl or benzyl. Values and specific values for the remainder of the variables in Structural Formulas (IIIb), (IVb), (VIb) and (XIVb), are as described above in the 7$^{th}$ specific embodiment. Even more specifically, R$_{14}$ is methyl.

In another more specific embodiment, for compounds of Structural Formulas (IVb), (IVb), (VIb) and (XIVb), R$_{14}$ is (C$_1$-C$_6$)alkyl, halo(C$_1$-C$_3$)alkyl, (C$_3$-C$_8$)cycloalkyl(C$_1$-C$_3$) alkyl or benzyl; and ring A is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substituents independently selected from the group consisting of $(C_1-C_6)$alkyl, halo$(C_1-C_6)$alkyl, $(C_1-C_6)$alkoxy, $(C_1-C_3)$alkylcarbonyl, 5-6 membered heteroaryl (preferrably pyridine or pyrimidine), phenyl, phenoxy and benzoxy are each optionally substituted with —F, —Cl, —Br, —CN, $(C_1-C_6)$alkyl, halo$(C_1-C_6)$alkyl, hydroxy$(C_1-C_6)$alkyl, $(C_1-C_3)$alkoxy or halo$(C_1-C_3)$alkoxy. Values and specific values for the remainder of the variables in Structural Formulas (IIIb), (IVb), (VIb) and (XIVb) are as described above in the $7^{th}$ specific embodiment. Even more specifically, $R_{14}$ is methyl, $R_1$ is —H, and ring A is unsubstituted tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane.

In an $8^{th}$ specific embodiment, for compounds of Structural Formulas (IIIb)-(VIIb) and (XIVb), the values for the variables are defined as the following:

$R_{10}$ is —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$; $(C_1-C_6)$alkyl, $(C_2-C_6)$alkenyl, halo$(C_1-C_6)$alkyl, $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, or $(C_1-C_6)$alkoxy$(C_1-C_3)$alkyl;

s is 0, 1 or 2;

ring A is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-M-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substituents independently selected from the group consisting of $(C_1-C_6)$alkyl, halo$(C_1-C_6)$alkyl, $(C_1-C_6)$alkoxy, $(C_1-C_3)$alkylcarbonyl, 5-6 membered heteroaryl (preferrably pyridine or pyrimidine), phenyl, phenoxy and benzoxy, wherein the phenyl, phenoxy and benzoxy are each optionally substituted with —F, —Cl, —Br, —CN, $(C_1-C_6)$alkyl, halo$(C_1-C_6)$alkyl, hydroxy$(C_1-C_6)$alkyl, $(C_1-C_3)$alkoxy or halo$(C_1-C_3)$alkoxy;

$R_1$ is —H;

$R_3$ and $R_4$ are —H;

$R_5$ is $(C_1-C_6)$alkyl or $(C_1-C_3)$alkoxy$(C_1-C_3)$alkyl;

$R_6$ and $R_7$ are —H;

$R_{11}$ is —H;

$R_{12}$ and $R_{13}$ are independently —H, $(C_1-C_6)$alkyl, $(C_1-C_3)$alkoxy$(C_1-C_3)$alkyl, hydroxy$(C_1-C_3)$alkyl, cyano$(C_1-C_3)$alkyl, or di$(C_1-C_3)$alkylamino$(C_1-C_3)$alkyl;

$R_{14}$ is $(C_1-C_6)$alkyl, halo$(C_1-C_3)$alkyl, $(C_3-C_8)$cycloalkyl$(C_1-C_3)$alkyl or benzyl; and i is 0, 1, or 2.

In a more specific embodiment, for compounds of Structural Formulas (IIIb)-(VIIb) and (XIVb), $R_{10}$ is —F, —Cl, —Br, —CN, —CF$_3$, or —OR$_5$; and $R_{14}$ is methyl. Values and specific values for the remainder of the variables are as described above in the $8^{th}$ specific embodiment.

In a $9^{th}$ specific embodiment, the compounds of the present invention are represented by the following Structural Formulas:

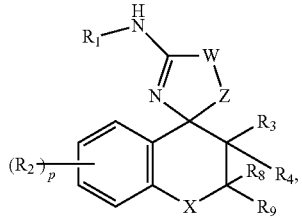
(VIII)

wherein $R_8$ and $R_9$ are each independently —H, $(C_1-C_6)$alkyl, hydroxy$(C_1-C_6)$alkyl, halo$(C_1-C_6)$alkyl, $(C_2-C_6)$alkenyl, $(C_2-C_6)$alkynyl, $(C_3-C_{14})$ cycloalkyl, $(C_3-C_{13})$cycloheteroalkyl, aryl or heteroaryl, each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy, aryl, heteroaryl, $(C_3-C_8)$ cycloalkyl and $(C_3-C_7)$ cycloheteroalkyl. Values and specific values for the remainder of the variables are as described above for Structural Formula (I).

Alternatively, for compounds represented by Structural Formula (VIII), $R_8$ and $R_9$ are each independently —H, $(C_1-C_6)$alkyl, hydroxy$(C_1-C_6)$alkyl, halo$(C_1-C_6)$alkyl, $(C_2-C_6)$alkenyl, $(C_2-C_6)$alkynyl, $(C_3-C_8)$ cycloalkyl, $(C_3-C_7)$cycloheteroalkyl, aryl or heteroaryl, each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy and halo$(C_1-C_3)$alkoxy. Values and specific values for the remainder of the variables are as described above for Structural Formula (I').

In a $10^{th}$ specific embodiment, the compounds of the present invention are represented by the following Structural Formulas:

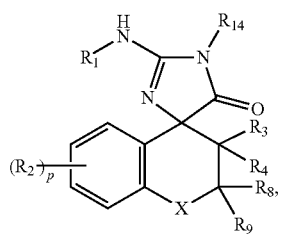
(IX)

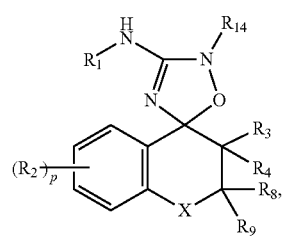
(X)

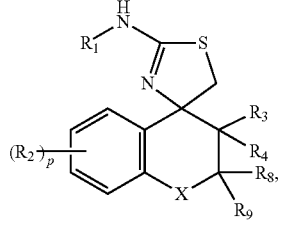
(XI)

(XV)
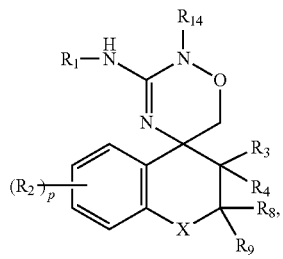

(XII)
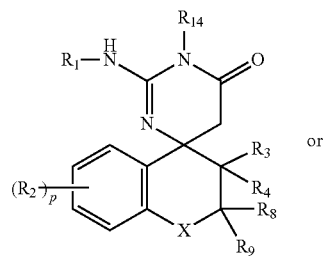

or (XIII)
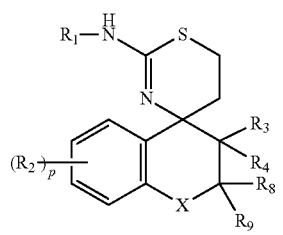

Values and specific values for variables for Structural Formulas (IX)-(XIII) and (XV) are as described above for Structural Formula (VIII) in the 9th specific embodiment. In a more specific embodiment, X is —O—. In another more specific embodiment, X is —O—, $R_2$ is independently —H, —F, —Cl or —Br and p is 2.

In an 11th specific embodiment, compounds of the present invention are represented by the following Structural Formulas:

(IXa)
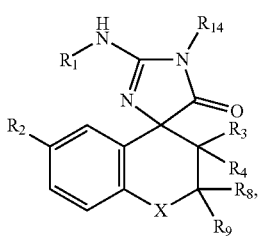

(Xa)
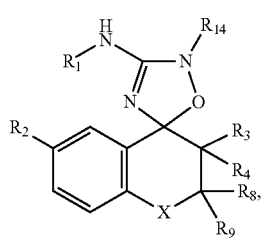

(XIa)
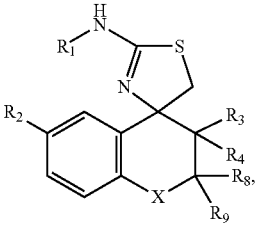

(XVa)
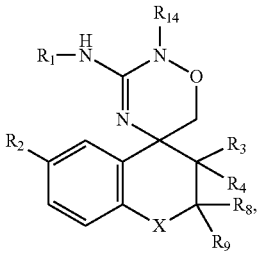

(XIIa)
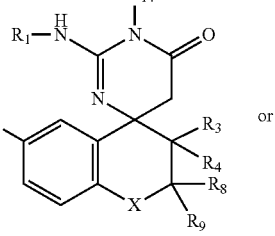

or (XIIIa)
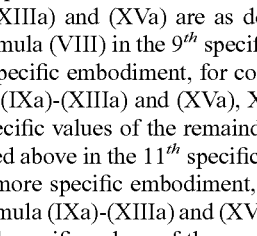

Values and specific values for variables for Structural Formulas (IXa)-(XIIIa) and (XVa) are as described above for Structural Formula (VIII) in the 9th specific embodiment In a more specific embodiment, for compounds of Structural Formula (IXa)-(XIIIa) and (XVa), X is —O— and the values and specific values of the remainder of the variables are as described above in the 11th specific embodiment.

In another more specific embodiment, for compounds of Structural Formula (IXa)-(XIIIa) and (XVa), X is —S—, and the values and specific values of the remainder of the variables are as described above in the 11th specific embodiment.

In another more specific embodiment, for compounds of Structural Formula (IXa)-(XIIIa) and (XVa), X is —SO—, and the values and specific values of the remainder of the variables are as described in the 11th specific embodiment.

In another more specific embodiment, for compounds of Structural Formula (IXa)-(XIIIa) and (XVa), X is —SO$_2$—, and the values and specific values of the remainder of the variables are as described in the 11th specific embodiment.

In a 12th specific embodiment, for compounds of Structural Formula (IXa)-(XIIIa) and (XVa), $R_2$ is —H, —Cl, —Br, —F or $(C_1$-$C_6)$alkyl, and the values and specific values of the remainder of the variable are as described above in the 11th specific embodiment.

In a more specific embodiment, for compounds of Structural Formula (IXa)-(XIIIa) and (XVa), X is —O—, and the values and specific values of the remainder of the variable are as described above in the 12$^{th}$ specific embodiment.

In another more specific embodiment, for compounds of Structural Formula (IXa)-(XIIIa) and (XVa), X is —S—, and the values and specific values of the remainder of the variable are as described above in the 12$^{th}$ specific embodiment.

In another more specific embodiment, for compounds of Structural Formula (IXa)-(XIIIa) and (XVa), X is —SO—, and the values and specific values of the remainder of the variable are as described above in the 12$^{th}$ specific embodiment.

In another more specific embodiment, for compounds of Structural Formula (IXa)-(XIIIa) and (XVa), X is —SO$_2$—, and the values and specific values of the remainder of the variable are as described above in the 12$^{th}$ specific embodiment.

In another more specific embodiment, for compounds of Structural Formula (IXa)-(XIIIa) and (XVa), $R_8$ and $R_9$ are each independently —H, $(C_1-C_6)$alkyl, $(C_2-C_6)$alkenyl, hydroxy$(C_1-C_6)$alkyl, $(C_3-C_8)$ cycloalkyl, $(C_3-C_7)$cycloheteroalkyl, phenyl or heteraryl, each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$ alkoxy, aryl, heteroaryl, $(C_3-C_8)$ cycloalkyl and $(C_3-C_7)$cycloheteroalkyl. Values and specific values of the remainder of the variables are as described above in the 12$^{th}$ specific embodiment. In an even more specific embodiment, X is —O—.

In another more specific embodiment, for compounds of Structural Formula (IXa)-(XIIIa) and (XVa), $R_8$ and $R_9$ are both —H, $(C_1-C_3)$alkyl or hydroxy$(C_1-C_3)$alkyl. Values and specific values of the remainder of the variables are as described above in the 12$^{th}$ specific embodiment. In an even more specific embodiment, X is —O—. In another even more specific embodiment, X is —O—, and $R_8$ and $R_9$ are —H, methyl or hydroxymethyl.

In another more specific embodiment, for compounds of Structural Formula (IXa)-(XIIIa) and (XVa), one of $R_8$ and $R_9$ is —H, the other one is a $(C_1-C_6)$alkyl optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo $(C_1-C_3)$alkoxy, $(C_3-C_8)$ cycloalkyl and $(C_3-C_8)$cycloheteroalkyl. More particularly, substituents are selected from the group consisting of $(C_1-C_6)$alkyl and $(C_3-C_8)$cycloheteroalkyl. Values and specific values of the remainder of the variables are as described above in the 12$^{th}$ specific embodiment. More particularly, X is —O—. Even more particularly, one of $R_8$ and $R_9$ is —H, the other one is a $(C_1-C_3)$alkyl optionally substituted $(C_3-C_8)$cycloheteroalkyl (preferably a tetrahydrofuran and tetrahydropyran) and X is —O—.

In another more specific embodiment, for compounds of Structural Formula (IXa)-(XIIIa) and (XVa), one of $R_8$ and $R_9$ is —H, the other one is a $(C_2-C_6)$alkenyl optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo $(C_1-C_3)$alkoxy, $(C_3-C_8)$ cycloalkyl and $(C_3-C_8)$cycloheteroalkyl. Values and specific values of the remainder of the variables are as described above in the 12$^{th}$ specific embodiment. More particularly, X is —O—. Even more particularly, substituents are selected from the group consisting of $(C_1-C_3)$ alkyl and hydroxy$(C_1-C_3)$alkyl.

In another more specific embodiment, for compounds of Structural Formula (IXa)-(XIIIa) and (XVa), one of $R_8$ and $R_9$ is —H and the other is unsubstituted phenyl. Values and specific values of the remainder of the variables are as described above in the 12$^{th}$ specific embodiment. In an even more specific embodiment, X is —O—.

In another more specific embodiment, for compounds of Structural Formula (IXa)-(XIIIa) and (XVa), one of $R_8$ and $R_9$ is —H and the other is phenyl substituted with 1 to 3 substitutents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy, $(C_1-C_3)$alkylcarbonyl and $(C_1-C_3)$alkoxycarbonyl. Values and specific values of the remainder of the variables are as described above in the 12$^{th}$ specific embodiment. In an even more specific embodiment, X is —O—. In another even more specific embodiment, X is —O—; and one of $R_8$ and $R_9$ is —H and the other is phenyl substituted with 1 to 3 substitutents independently selected from the group consisting independently selected from —F, —Cl, —Br, —CN, trifluoromethyl, methoxy, trifluoromethoxy, ethoxy, acetyl, ethoxycarbonyl and hydroxymethyl.

In another particular embodiment, for compounds of Structural Formula (IXa)-(XIIIa) and (XVa), one of $R_8$ and $R_9$ is —H and the other is monocylic $(C_3-C_8)$cyloalkyl (such as cyclopentyl and cyclohexyl), bicyclic fused $(C_9-C_{14})$cycloalkyl (such as 6,7,8,9-tetrahydro-5H-benzo[7]annulene, hydro-1H-indene, tetrahydronaphthalene, decahydronaphthalene), monocylic $(C_3-C_7)$cycloheteroalkyl (such as tetrahydrofuran, tetrahydropyran and piperidine), bicyclic fused or bicyclic bridged $(C_8-C_{13})$cycloheteroalkyl (such as 5,6,7,8-tetrahydroquinoline, 5,6,7,8-tetrahydroisoquinoline, and 2-oxabicyclo[2.2.2]octane) or heteroaryl (preferably 5-6 membered heteroaryl such as pyridinyl or thiophenyl), each optionally substituted with 1 to 3 substitutents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, $(C_1-C_6)$ alkyl, halo$(C_1-C_6)$alkyl, hydroxy$(C_1-C_6)$alkyl, $(C_1-C_3)$ alkoxy or halo$(C_1-C_3)$alkoxy. Values and specific values of the remainder of the variables are as described above in the 12$^{th}$ specific embodiment. In an even more specific embodiment, X is —O—. In another even more specific embodiment, X is —O—; and one of $R_8$ and $R_9$ is —H and the other is monocylic $(C_3-C_8)$cyloalkyl (such as cyclopentyl and cyclohexyl), bicyclic fused $(C_9-C_{14})$cycloalkyl (such as 6,7,8,9-tetrahydro-5H-benzo[7]annulene, 2,3-dihydro-1H-indene, tetrahydronaphthalene, decahydronaphthalene), monocylic $(C_3-C_7)$cycloheteroalkyl (such as tetrahydrofuran, tetrahydropyran and piperidine), bicyclic fused or bicyclic bridged $(C_8-C_{13})$cycloheteroalkyl (such as 5,6,7,8-tetrahydroquinoline, 5,6,7,8-tetrahydroisoquinoline, and 2-oxabicyclo[2.2.2]octane) or heteroaryl (preferably 5-6 membered heteroaryl such as pyridinyl or thiophenyl), each optionally substituted with 1 to 3 substitutents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo $(C_1-C_3)$alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, $(C_1-C_6)$alkyl, halo$(C_1-C_6)$ alkyl, hydroxy$(C_1-C_6)$alkyl, $(C_1-C_3)$alkoxy or halo$(C_1-C_3)$ alkoxy. In another even more specific embodiment, X is —O—; one of $R_8$ and $R_9$ is —H and the other is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substitutents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, $(C_1-C_6)$alkyl, halo$(C_1-C_6)$alkyl, hydroxy$(C_1-C_6)$alkyl, $(C_1-C_3)$alkoxy or halo$(C_1-C_3)$alkoxy.

In another particular embodiment, for compounds of Structural Formula (IXa)-(XIIIa), one of $R_8$ and $R_9$ is —H and the other is $(C_3-C_8)$cyloalkyl (preferably cyclopentyl and cyclohexyl), $(C_3-C_7)$cycloheteroalkyl (preferably tetrahydrofuran or and tetrahydropyran) or heteroaryl (preferably pyridinyl or thiophenyl), each optionally substituted with 1 to 3 substitutents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy and halo$(C_1-C_3)$alkoxy. Values and specific values of the remainder of the variables are as described above in the $12^{th}$ specific embodiment. In an even more specific embodiment, X is —O—. In another even more specific embodiment, X is —O—; and one of $R_8$ and $R_9$ is —H and the other is $(C_3-C_8)$cyloalkyl (preferably cyclopentyl and cyclohexyl), $(C_3-C_7)$cycloheteroalkyl (preferably tetrahydrofuran or and tetrahydropyran) or heteroaryl (preferably pyridinyl or thiophenyl), each optionally substituted with 1 to 3 $(C_1-C_6)$alkyl.

In a $13^{th}$ specific embodiment, for compounds of Structural Formula (IXa)-(XIIIa) and (XVa), $R_2$ is $(C_3-C_8)$cycloalkyl, $(C_3-C_8)$cycloheteroalkyl, heteroaryl, phenoxy or benzyloxy, each of which is optionally substituted with 1 to 3 substituents independently selected from the group consisting of —F, —Cl, —Br, —CN, —$OR_5$, —$SR_5$, —$NR_6R_7$, —$S(O)_iR_5$, —$NR_{11}S(=O)_iR_5$, —$C(=O)OR_5$, —$C(=O)NR_{12}R_{13}$, —$NR_{11}C(=O)R_5$, —$C(=S)NR_{12}R_{13}$, —$C(=O)R_5$, $(C_1-C_6)$alkyl, $(C_3-C_8)$cycloalkyl, $(C_2-C_6)$alkenyl, halo$(C_1-C_6)$alkyl, $(C_1-C_3)$alkylsulfonylaminoalkyl, hydroxy$(C_1-C_6)$alkyl, cyano$(C_1-C_6)$alkyl, $(C_1-C_3)$alkylcarbonylamino$(C_1-C_6)$alkyl, $(C_1-C_3)$alkoxy, halo$(C_1-C_3)$alkoxyl, $(C_1-C_3)$alkoxy$(C_1-C_3)$alkyl, aryl and heteroaryl. Values and specific values of the remainder of the variable are as described in the $11^{th}$ specific embodiment. Even more specifically, $R_2$ is cyclohexyl, pyrrolidinyl, pyridinyl, pyrimidinyl, thiophenyl or thiazolyl. Even more specifically, the substituents are independently selected from —F, —Cl, —Br, —CN, hydroxy$(C_1-C_6)$alkyl, cyano$(C_1-C_6)$alkyl, $(C_1-C_3)$alkoxy, halo$(C_1-C_3)$alkoxy, $(C_1-C_6)$alkoxy$(C_1-C_3)$alkyl, phenyl and 5-6 membered heteroaryl.

In a more specific embodiment, for compounds of Structural Formula (IXa)-(XIIIa) and (XVa), X is —O—, and the values and specific values of the remainder of the variable are as described in the $13^{th}$ specific embodiment.

In another more specific embodiment, for compounds of Structural Formula (IXa)-(XIIIa) and (XVa), X is —S—, and the values and specific values of the remainder of the variable are as described above in the $13^{th}$ specific embodiment.

In another more specific embodiment, for compounds of Structural Formula (IXa)-(XIIIa) and (XVa), X is —SO—, and the values and specific values of the remainder of the variable are as described above in the $13^{th}$ specific embodiment.

In another more specific embodiment, for compounds of Structural Formula (IXa)-(XIIIa) and (XVa), X is —$SO_2$—, and the values and specific values of the remainder of the variable are as described above in the $13^{th}$ specific embodiment.

In another more specific embodiment, for compounds of Structural Formula (IXa)-(XIIIa) and (XVa), $R_8$ and $R_9$ are each independently —H, $(C_1-C_6)$alkyl, $(C_2-C_6)$alkenyl, hydroxy$(C_1-C_6)$alkyl, $(C_3-C_{14})$ cycloalkyl, $(C_3-C_{13})$cycloheteroalkyl, phenyl or heteraryl, each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo $(C_1-C_3)$alkoxy, aryl, heteroaryl, $(C_3-C_8)$ cycloalkyl and $(C_3-C_7)$cycloheteroalkyl. Values and specific values of the remainder of the variables are as described above in the $13^{th}$ specific embodiment. Even more specifically, X is —O—.

In another more specific embodiment, for compounds of Structural Formula (IXa)-(XIIIa), $R_8$ and $R_9$ are both —H, $(C_1-C_3)$alkyl or hydroxy$(C_1-C_3)$alkyl. Values and specific values of the remainder of the variables are as described above in the $13^{th}$ specific embodiment. In an even more specific embodiment, X is —O—. In another even more specific embodiment, X is —O—; and $R_8$ and $R_9$ are —H, methyl or hydroxymethyl.

In another more specific embodiment, for compounds of Structural Formula (IXa)-(XIIIa) and (XVa), one of $R_8$ and $R_9$ is —H, the other one is a $(C_1-C_6)$alkyl optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo $(C_1-C_3)$alkoxy, $(C_3-C_8)$ cycloalkyl and $(C_3-C_8)$cycloheteroalkyl. More particularly, substituents are selected from the group consisting of $(C_1-C_6)$alkyl and $(C_3-C_8)$cycloheteroalkyl. Values and specific values of the remainder of the variables are as described above in the $13^{th}$ specific embodiment. More particularly, X is —O—. Even more particularly, one of $R_8$ and $R_9$ is —H, the other one is a $(C_1-C_3)$alkyl optionally substituted $(C_3-C_8)$cycloheteroalkyl (preferably a tetrahydrofuran and tetrahydropyran) and X is —O—.

In another more specific embodiment, for compounds of Structural Formula (IXa)-(XIIIa) and (XVa), one of $R_8$ and $R_9$ is —H, the other one is a $(C_2-C_6)$alkenyl optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo $(C_1-C_3)$alkoxy, $(C_3-C_8)$ cycloalkyl and $(C_3-C_8)$cycloheteroalkyl. Values and specific values of the remainder of the variables are as described above in the $13^{th}$ specific embodiment. More particularly, X is —O—. Even more particularly, substituents are selected from the group consisting of $(C_1-C_3)$ alkyl and hydroxy$(C_1-C_3)$alkyl.

In another more specific embodiment, for compounds of Structural Formula (IXa)-(XIIIa) and (XVa), one of $R_8$ and $R_9$ is —H and the other is unsubstituted phenyl. Values and specific values of the remainder of the variables are as described above in the $13^{th}$ specific embodiment. Even more specifically, X is —O—.

In another specific embodiment, for compounds of Structural Formula (IXa)-(XIIIa) and (XVa), one of $R_8$ and $R_9$ is —H and the other is phenyl substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy, $(C_1-C_3)$alkylcarbonyl and $(C_1-C_3)$alkoxycarbonyl. Values and specific values of the remainder of the variables are as described above in the $13^{th}$ specific embodiment. In an even more specific embodiment, X is —O—. In another even more specific embodiment, X is —O—; and one of $R_8$ and $R_9$ is —H and the other is phenyl substituted with 1 to 3 substitutents independently selected from the group consisting of —F, —Cl, —Br, —CN, trifluoromethyl, methoxy, trifluoromethoxy, ethoxy, acetyl, ethoxycarbonyl and hydroxymethyl.

In another specific embodiment, for compounds of Structural Formula (IXa)-(XIIIa) and (XVa), one of $R_8$ and $R_9$ is —H and the other is monocylic $(C_3-C_8)$cyloalkyl (such as cyclopentyl and cyclohexyl), bicyclic fused $(C_9-C_{14})$cycloalkyl (such as 6,7,8,9-tetrahydro-5H-benzo[7]annulene, 2,3-dihydro-1H-indene, tetrahydronaphthalene, decahydronaphthalene), monocylic $(C_3-C_7)$cycloheteroalkyl (such as tetrahydrofuran, tetrahydropyran and piperidine), bicyclic fused or bicyclic bridged $(C_8-C_{13})$cycloheteroalkyl (such as 5,6,7,8-tetrahydroquinoline, 5,6,7,8-tetrahydroisoquinoline, and 2-oxabicyclo[2.2.2]octane) or heteroaryl (preferably 5-6 membered heteroaryl such as pyridinyl or thiophenyl), each optionally substituted with 1 to 3 substitutents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, $(C_1-C_6)$ alkyl, halo$(C_1-C_6)$alkyl, hydroxy$(C_1-C_6)$alkyl, $(C_1-C_3)$ alkoxy or halo$(C_1-C_3)$alkoxy. Values and specific values of the remainder of the variables are as described above in the $13^{th}$ specific embodiment. In an even more specific embodiment, X is —O—. In another even more specific embodiment, X is —O—; and one of $R_8$ and $R_9$ is —H and the other is monocylic $(C_3-C_8)$cyloalkyl (such as cyclopentyl and cyclohexyl), bicyclic fused $(C_9-C_{14})$cycloalkyl (such as 6,7,8,9-tetrahydro-5H-benzo[7]annulene, 2,3-dihydro-1H-indene, tetrahydronaphthalene, decahydronaphthalene), monocylic $(C_3-C_7)$cycloheteroalkyl (such as tetrahydrofuran, tetrahydropyran and piperidine), bicyclic fused or bicyclic bridged $(C_8-C_{13})$cycloheteroalkyl (such as 5,6,7,8-tetrahydroquinoline, 5,6,7,8-tetrahydroisoquinoline, and 2-oxabicyclo[2.2.2] octane) or heteroaryl (preferably 5-6 membered heteroaryl such as pyridinyl or thiophenyl), each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo $(C_1-C_3)$alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, $(C_1-C_6)$alkyl, halo$(C_1-C_6)$ alkyl, hydroxy$(C_1-C_6)$alkyl, $(C_1-C_3)$alkoxy or halo$(C_1-C_3)$ alkoxy. In another even more specific embodiment, X is —O—; one of $R_8$ and $R_9$ is —H and the other is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substitutents independently selected from the group consisting of —F, —Cl, —Br, —CN, $(C_1-C_6)$alkyl, halo$(C_1-C_6)$ alkyl, hydroxy$(C_1-C_6)$alkyl, $(C_1-C_3)$alkoxy, halo$(C_1-C_3)$ alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, $(C_1-C_6)$alkyl, halo$(C_1-C_6)$alkyl, hydroxy$(C_1-C_6)$alkyl, $(C_1-C_3)$alkoxy or halo$(C_1-C_3)$alkoxyl.

In another specific embodiment, for compounds of Structural Formula (IXa)-(XIIIa), one of $R_8$ and $R_9$ is —H and the other is $(C_3-C_8)$cyloalkyl (preferably cyclopentyl and cyclohexyl), $(C_3-C_7)$cycloheteroalkyl (preferably tetrahydrofuran or and tetrahydropyran) or heteroaryl (preferably pyridinyl or thiophenyl), each optionally substituted with 1 to 3 substitutents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy and halo$(C_1-C_3)$ alkoxy. Values and specific values of the remainder of the variables are as described above in the $13^{th}$ specific embodiment. In an even more specific embodiment, X is —O—. In another even more specific embodiment, X is —O—; and one of $R_8$ and $R_9$ is —H and the other is $(C_3-C_8)$cyloalkyl (preferably cyclopentyl and cyclohexyl), $(C_3-C_7)$cycloheteroalkyl (preferably tetrahydrofuran or and tetrahydropyran) or heteroaryl (preferably pyridinyl or thiophenyl), each optionally substituted with 1 to 3 $(C_1-C_6)$alkyl.

In a $14^{th}$ specific embodiment, for compounds of Structural Formula (IXa)-(XIIIa) and (XVa), $R_2$ is aryl and the values and specific values of the remainder of the variable are as described in the $11^{th}$ specific embodiment. More specifically, $R_2$ is phenyl. In another more specific embodiment, $R_2$ is indolinyl or benzoimidazole (connected through the benzene ring).

In a more specific embodiment, for compounds of Structural Formula (IXa)-(XIIIa) and (XVa), X is —O—, and the values and specific values of the remainder of the variable are as described above in the $14^{th}$ specific embodiment.

In another more specific embodiment, for compounds of Structural Formula (IXa)-(XIIIa) and (XVa), X is —S—, and the values and specific values of the remainder of the variable are as described above in the $14^{th}$ specific embodiment.

In another more specific embodiment, for compounds of Structural Formula (IXa)-(XIIIa) and (XVa), X is —SO—, and the values and specific values of the remainder of the variable are as described above in the $14^{th}$ specific embodiment.

In a more specific embodiment, for compounds of Structural Formula (IXa)-(XIIIa) and (XVa), X is —SO$_2$—, and the values and specific values of the remainder of the variable are as described above in the $14^{th}$ specific embodiment.

In another more specific embodiment, for compounds of Structural Formula (IXa)-(XIIIa) and (XVa), $R_8$ and $R_9$ are each independently —H, $(C_1-C_6)$alkyl, $(C_2-C_6)$alkenyl, hydroxy$(C_1-C_6)$alkyl, $(C_3-C_{14})$ cycloalkyl, $(C_3-C_{13})$cycloheteroalkyl, phenyl or heteraryl, each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo $(C_1-C_3)$alkoxy, aryl, heteroaryl, $(C_3-C_8)$ cycloalkyl and $(C_3-C_7)$cycloheteroalkyl. Values and specific values of the remainder of the variables are as described above in the $14^{th}$ specific embodiment. Even more specifically, X is —O—.

In another more specific embodiment, for compounds of Structural Formula (IXa)-(XIIIa) and (XVa), $R_8$ and $R_9$ are both —H, $(C_1-C_3)$alkyl or hydroxy$(C_1-C_3)$alkyl. Values and specific values of the remainder of the variables are as described above in the $14^{th}$ specific embodiment. In an even more specific embodiment, X is —O—. In another even more specific embodiment, X is —O—; and $R_8$ and $R_9$ are —H, methyl or hydroxymethyl.

In another more specific embodiment, for compounds of Structural Formula (IXa)-(XIIIa) and (XVa), one of $R_8$ and $R_9$ is —H, the other one is a $(C_1-C_6)$alkyl optionally substituted with 1 to 3 substituents independently selected from the group consisting of —F, —Cl, —Br, —CN, $(C_1-C_6)$alkyl, halo($C_1$-$C_6$)alkyl, hydroxy($C_1$-$C_6$)alkyl, ($C_1$-$C_3$)alkoxy, halo($C_1$-$C_3$)alkoxy, ($C_3$-$C_8$) cycloalkyl and ($C_3$-$C_8$)cycloheteroalkyl. More particularly, substituents are selected from the group consisting of ($C_1$-$C_6$)alkyl and ($C_3$-$C_8$)cycloheteroalkyl. Values and specific values of the remainder of the variables are as described above in the 14$^{th}$ specific embodiment. More particularly, X is —O—. Even more particularly, one of $R_8$ and $R_9$ is —H, the other one is a ($C_1$-$C_3$)alkyl optionally substituted ($C_3$-$C_8$)cycloheteroalkyl (preferably a tetrahydrofuran and tetrahydropyran) and X is —O—.

In another more specific embodiment, for compounds of Structural Formula (IXa)-(XIIIa) and (XVa), one of $R_8$ and $R_9$ is —H, the other one is a ($C_2$-$C_6$)alkenyl optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy, ($C_3$-$C_8$) cycloalkyl and ($C_3$-$C_8$)cycloheteroalkyl. Values and specific values of the remainder of the variables are as described above in the 14$^{th}$ specific embodiment. More particularly, X is —O—. Even more particularly, substituents are selected from the group consisting of ($C_1$-$C_3$)alkyl and hydroxy($C_1$-$C_3$)alkyl.

In another more specific embodiment, for compounds of Structural Formula (IXa)-(XIIIa)) and (XVa), one of $R_8$ and $R_9$ is —H and the other is unsubstituted phenyl. Values and specific values of the remainder of the variables are as described above in the 14$^{th}$ specific embodiment. Even more specifically, X is —O—.

In another specific embodiment, for compounds of Structural Formula (IXa)-(XIIIa) and (XVa), one of $R_8$ and $R_9$ is —H and the other is phenyl substituted with 1 to 3 substitutents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy, ($C_1$-$C_3$)alkylcarbonyl and ($C_1$-$C_3$)alkoxycarbonyl. Values and specific values of the remainder of the variables are as described above in the 14$^{th}$ specific embodiment. In an even more specific embodiment, X is —O—. In another even more specific embodiment, X is —O—; and one of $R_8$ and $R_9$ is —H and the other is phenyl substituted with 1 to 3 substitutents independently selected from the group consisting of —F, —Cl, —Br, —CN, trifluoromethyl, methoxy, trifluoromethoxy, ethoxy, acetyl, ethoxycarbonyl and hydroxymethyl.

In another specific embodiment, for compounds of Structural Formula (IXa)-(XIIIa) and (XVa), one of $R_8$ and $R_9$ is —H and the other is monocylic ($C_3$-$C_8$)cyloalkyl (such as cyclopentyl and cyclohexyl), bicyclic fused ($C_9$-$C_{14}$)cycloalkyl (such as 6,7,8,9-tetrahydro-5H-benzo[7]annulene, 2,3-dihydro-1H-indene, tetrahydronaphthalene, decahydronaphthalene), monocylic ($C_3$-$C_7$)cycloheteroalkyl (such as tetrahydrofuran, tetrahydropyran and piperidine), bicyclic fused or bridged ($C_8$-$C_{13}$)cycloheteroalkyl (such as 5,6,7,8-tetrahydroquinoline, 5,6,7,8-tetrahydroisoquinoline, and 2-oxabicyclo[2.2.2]octane) or heteroaryl (preferably 5-6 membered heteroaryl such as pyridinyl or thiophenyl), each optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxy. Values and specific values of the remainder of the variables are as described above in the 14$^{th}$ specific embodiment. In an even more specific embodiment, X is —O—. In another even more specific embodiment, X is —O—; and one of $R_8$ and $R_9$ is —H and the other is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxyl.

In another specific embodiment, for compounds of Structural Formula (IXa)-(XIIIa), one of $R_8$ and $R_9$ is —H and the other is ($C_3$-$C_8$)cyloalkyl (preferably cyclopentyl and cyclohexyl), ($C_3$-$C_7$)cycloheteroalkyl (preferably tetrahydrofuran or and tetrahydropyran) or heteroaryl (preferably pyridinyl or thiophenyl), each optionally substituted with 1 to 3 substitutents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy and halo($C_1$-$C_3$)alkoxy. Values and specific values of the remainder of the variables are as described above in the 14$^{th}$ specific embodiment. In an even more specific embodiment, X is —O—. In another even more specific embodiment, X is —O—; and one of $R_8$ and $R_9$ is —H and the other is ($C_3$-$C_8$)cyloalkyl (preferably cyclopentyl and cyclohexyl), ($C_3$-$C_7$)cycloheteroalkyl (preferably tetrahydrofuran or and tetrahydropyran) or heteroaryl (preferably pyridinyl or thiophenyl), each optionally substituted with 1 to 3 ($C_1$-$C_6$)alkyl.

In a 15$^{th}$ specific embodiment, the compounds of the present invention are represented by the following Structural Formulas:

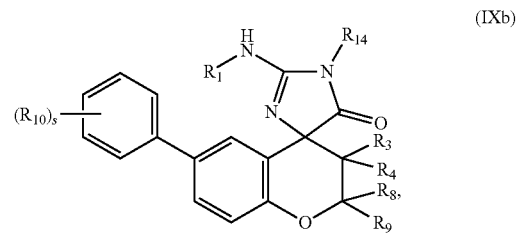

(IXb)

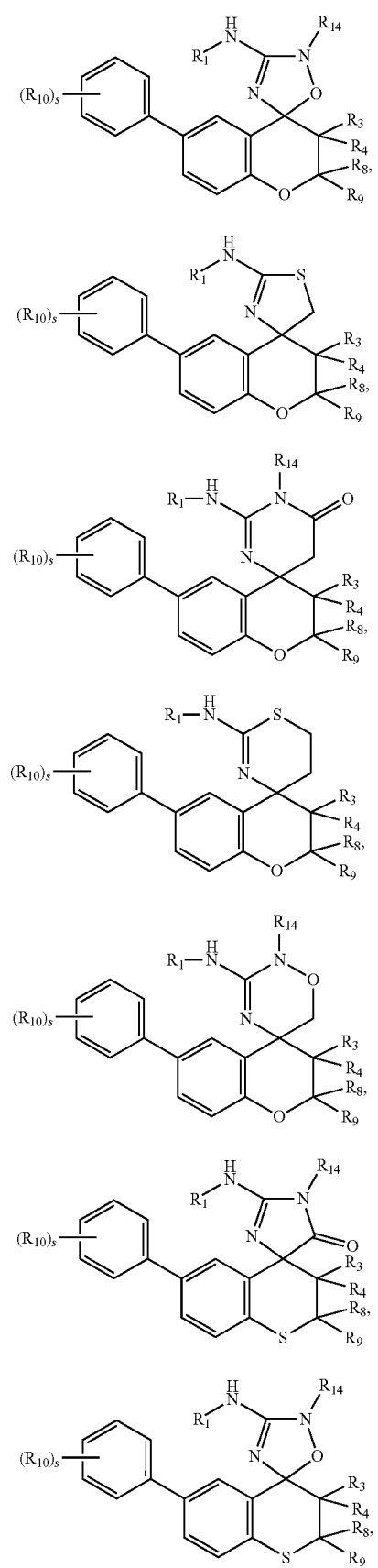
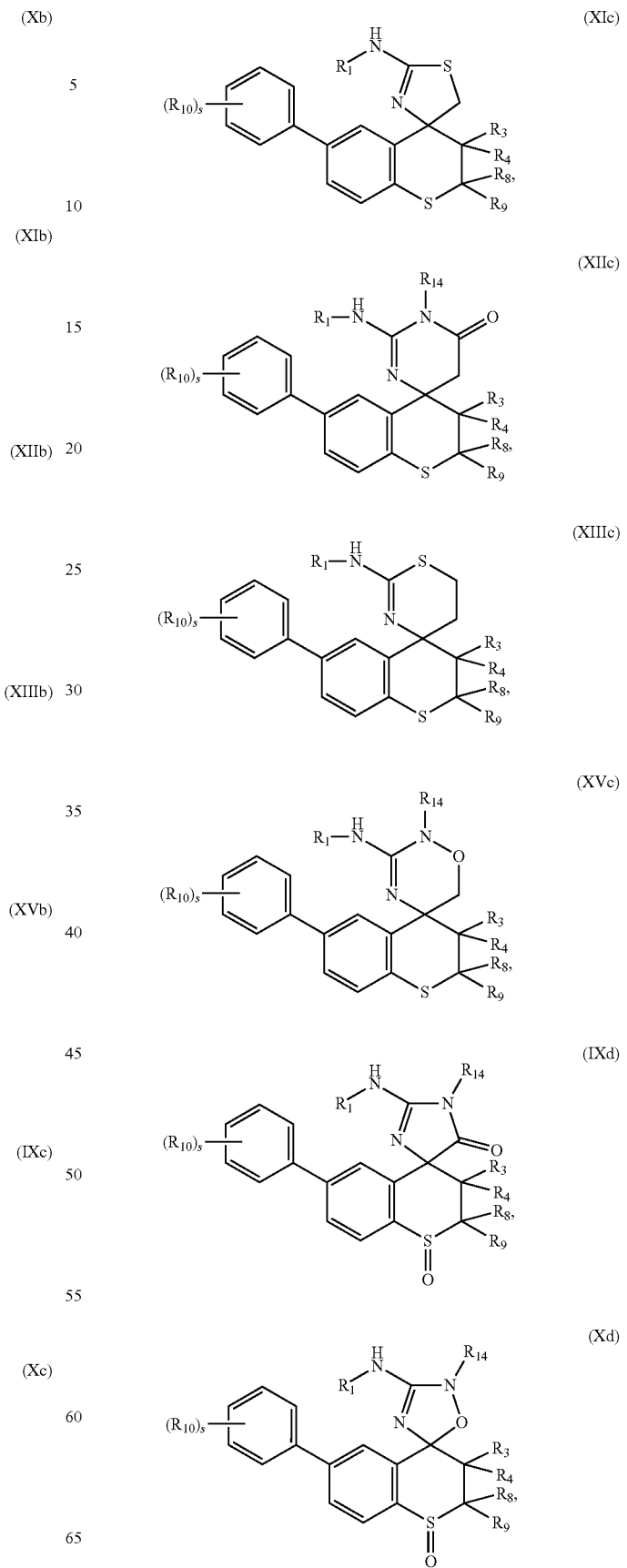

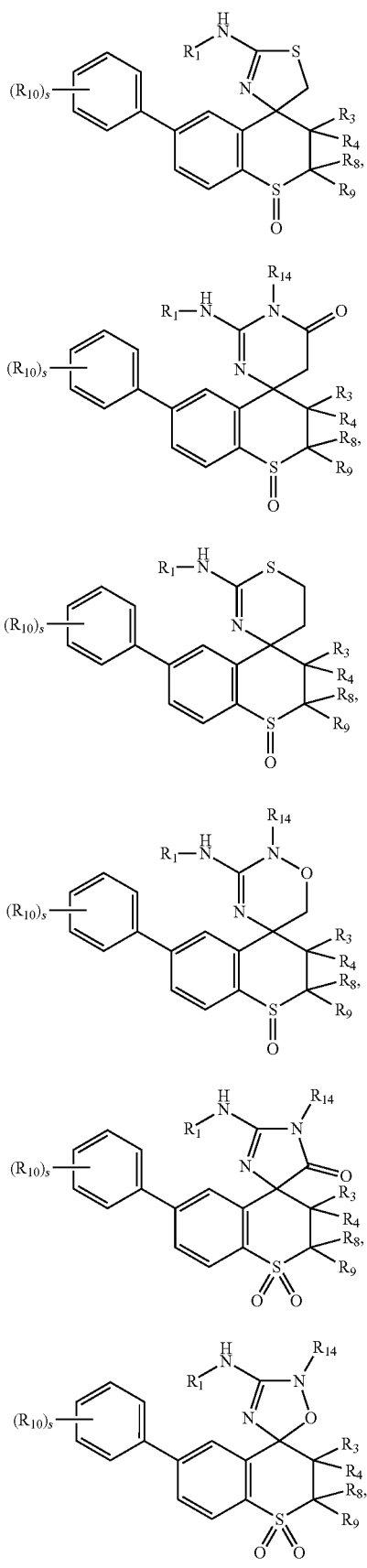
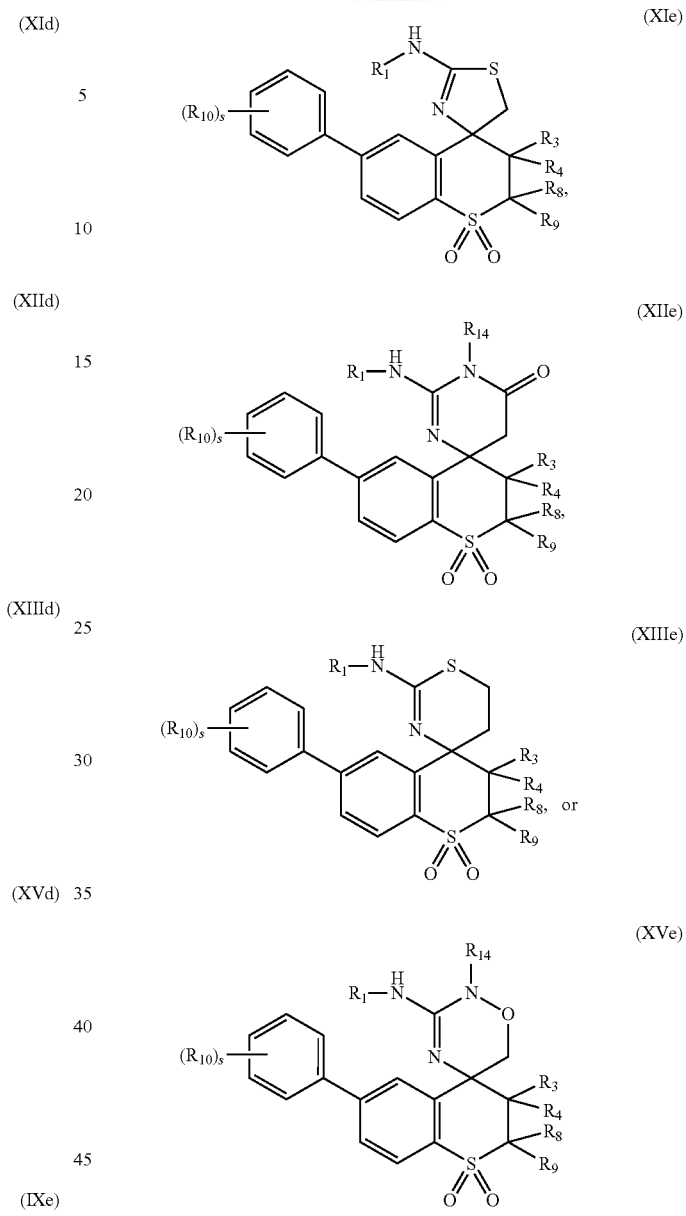

wherein $R_{10}$ is —F, —Cl, —Br, —CN, —$OR_5$, —$NR_6R_7$, —$S(O)_iR_5$, —$NR_{11}S(=O)_iR_5$, —$C(=O)OR_5$, —$C(=O)NR_{12}R_{13}$, —$NR_{11}C(=O)R_5$, —$C(=S)NR_{12}R_{13}$, —$C(=O)R_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_6$)alkoxy($C_1$-$C_3$)alkyl, aryl or heteroaryl; and s is 0, 1, 2 or 3. Values and specific values for the remainder of the variables for Structural Formulas (IXb)-(XIIIb), (XVb), (XVc), (IXd)-(XIIId), (XVd), (IXe)-(XIIIe) and (XVe), are as described above in the 11$^{th}$ specific embodiment In a more specific embodiment, for compounds of Structural Formulas (IXb)-(XIIIb), (XVb), (IXc)-(XIIIc), (XVc), (IXd)-(XIIId), (XVd), (IXe)-(XIIIe) and (XVe), $R_8$ and $R_9$ are each independently —H, ($C_1$-$C_6$)alkyl, ($C_2$-$C_6$)alkenyl, hydroxy($C_1$-$C_6$)alkyl, ($C_3$-$C_{14}$) cycloalkyl, ($C_3$-$C_{13}$)cycloheteroalkyl, phenyl or heteraryl, each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy, aryl, heteroaryl, $(C_3-C_{14})$ cycloalkyl and $(C_3-C_{13})$cycloheteroalkyl. Values and specific values of the remainder of the variables are as described above in the 15$^{th}$ specific embodiment.

In another more specific embodiment, for compounds of Structural Formulas (IXb)-(XIIIb), (XVb), (IXc)-(XIIIc), (XVc), (IXd)-(XIIId), (XVd), (IXe)-(XIIIe) and (XVe), $R_8$ and $R_9$ are both —H, $(C_1-C_3)$alkyl or hydroxy$(C_1-C_3)$alkyl. More specifically, $R_8$ and $R_9$ are —H, methyl or hydroxymethyl. Values and specific values of the remainder of the variables are as described above in the 15$^{th}$ specific embodiment.

In another more specific embodiment, for compounds of Structural Formulas (IXb)-(XIIIb), (XVb), (IXc)-(XIIIc), (XVc), (IXd)-(XIIId), (XVd), (IXe)-(XIIIe) and (XVe), one of $R_8$ and $R_9$ is —H, the other one is a $(C_1-C_6)$alkyl optionally substituted with 1 to 3 substituents independently selected from the group consisting of —F, —Cl, —Br, —CN, $(C_1-C_6)$ alkyl, halo$(C_1-C_6)$alkyl, hydroxy$(C_1-C_6)$alkyl, $(C_1-C_3)$ alkoxy, halo$(C_1-C_3)$alkoxy, $(C_3-C_8)$ cycloalkyl and $(C_3-C_8)$ cycloheteroalkyl. More particularly, substituents are selected from the group consisting of $(C_1-C_6)$alkyl and $(C_3-C_8)$cycloheteroalkyl. Values and specific values of the remainder of the variables are as described above in the 15$^{th}$ specific embodiment. Even more particularly, one of $R_8$ and $R_9$ is —H, the other one is a $(C_1-C_3)$alkyl optionally substituted $(C_3-C_8)$ cycloheteroalkyl (preferably a tetrahydrofuran and tetrahydropyran).

In another more specific embodiment, for compounds of Structural Formulas (IXb)-(XIIIb), (XVb), (IXc)-(XIIIc), (XVc), (IXd)-(XIIId), (XVd), (IXe)-(XIIIe) and (XVe), one of $R_8$ and $R_9$ is —H, the other one is a $(C_2-C_6)$alkenyl optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy, $(C_3-C_8)$ cycloalkyl and $(C_3-C_8)$cycloheteroalkyl. Values and specific values of the remainder of the variables are as described above in the 15$^{th}$ specific embodiment. Even more particularly, substituents are selected from the group consisting of $(C_1-C_3)$alkyl and hydroxy$(C_1-C_3)$alkyl.

In another more specific embodiment, for compounds of Structural Formula (IXb)-(XIIIb), (XVb), (IXc)-(XIIIc), (XVc), (IXd)-(XIIId), (XVd), (IXe)-(XIIIe) and (XVe), one of $R_8$ and $R_9$ is —H and the other is unsubstituted phenyl. Values and specific values of the remainder of the variables are as described above in the 15$^{th}$ specific embodiment.

In another specific embodiment, for compounds of Structural Formulas (IXb(IXb)-(XIIIb), (XVb), (IXc)-(XIIIc), (XVc), (IXd)-(XIIId), (XVd), (IXe)-(XIIIe) and (XVe), one of $R_8$ and $R_9$ is —H and the other is phenyl substituted with 1 to 3 substituents independently selected from the group consisting of —F, —Cl, —Br, —CN, $(C_1-C_6)$alkyl, halo$(C_1-C_6)$ alkyl, hydroxy$(C_1-C_6)$alkyl, $(C_1-C_3)$alkoxy, halo$(C_1-C_3)$ alkoxy, $(C_1-C_3)$alkylcarbonyl and $(C_1-C_3)$alkoxycarbonyl. More specifically, the substituents are independently selected from —F, —Cl, —Br, —CN, trifluoromethyl, methoxy, trifluoromethoxy, ethoxy, acetyl, ethoxycarbonyl and hydroxymethyl. Values and specific values of the remainder of the variables are as described above in the 15$^{th}$ specific embodiment.

In another specific embodiment, for compounds of Structural Formulas (IXb)-(XIIIb), (XVb), (IXc)-(XIIIc), (XVc), (IXd)-(XIIId), (XVd), (IXe)-(XIIIe) and (XVe), one of $R_8$ and $R_9$ is —H and the other is monocylic $(C_3-C_8)$cyloalkyl (such as cyclopentyl and cyclohexyl), bicyclic fused $(C_9-C_{14})$cycloalkyl (such as 6,7,8,9-tetrahydro-5H-benzo[7]annulene, 2,3-dihydro-1H-indene, tetrahydronaphthalene, decahydronaphthalene), monocylic $(C_3-C_7)$cycloheteroalkyl (such as tetrahydrofuran, tetrahydropyran and piperidine), bicyclic fused or bicyclic bridged $(C_8-C_{13})$cycloheteroalkyl (such as 5,6,7,8-tetrahydroquinoline, 5,6,7,8-tetrahydroisoquinoline, and 2-oxabicyclo[2.2.2]octane) or heteroaryl (preferably 5-6 membered heteroaryl such as pyridinyl or thiophenyl), each optionally substituted with 1 to 3 substituents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy, halo$(C_1-C_3)$alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, $(C_1-C_6)$ alkyl, halo$(C_1-C_6)$alkyl, hydroxy$(C_1-C_6)$alkyl, $(C_1-C_3)$ alkoxy or halo$(C_1-C_3)$alkoxy. Values and specific values of the remainder of the variables are as described above in the 15$^{th}$ specific embodiment. In another even more specific embodiment, one of $R_8$ and $R_9$ is —H and the other is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substituents independently selected from the group consisting of —F, —Cl, —Br, —CN, $(C_1-C_6)$alkyl, halo$(C_1-C_6)$ alkyl, hydroxy$(C_1-C_6)$alkyl, $(C_1-C_3)$alkoxy, halo$(C_1-C_3)$ alkoxy 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, $(C_1-C_6)$alkyl, halo$(C_1-C_6)$alkyl, hydroxy$(C_1-C_6)$alkyl, $(C_1-C_3)$alkoxy or halo$(C_1-C_3)$alkoxyl. Values and specific values for the remainder of the variables are as described above in the specific embodiment.

In another specific embodiment, for compounds of Structural Formulas (IXb)-(XIIIb), (IXc)-(XIIIc), (IXd)-(XIIId) and (IXe)-(XIIIe), one of $R_8$ and $R_9$ is —H and the other is $(C_3-C_8)$cyloalkyl (preferably cyclopentyl and cyclohexyl), $(C_3-C_7)$cycloheteroalkyl (preferably tetrahydrofuran or and tetrahydropyran) or heteroaryl (preferably pyridinyl or thiophenyl), each optionally substituted with 1 to 3 substitutents independently selected from the group consisting of —F, —Cl, —Br, —CN, $(C_1-C_6)$alkyl, halo$(C_1-C_6)$alkyl, hydroxy$(C_1-C_6)$alkyl, $(C_1-C_3)$alkoxy and halo$(C_1-C_3)$ alkoxy. More specifically, the substitutents $(C_1-C_6)$alkyl. Values and specific values of the remainder of the variables are as described above in the 15$^{th}$ specific embodiment.

In a 16$^{th}$ specific embodiment, for compounds of Structural Formulas (IXb)-(XIIIb), (XVb), (IXc)-(XIIIc), (XVc), (IXd)-(XIIId), (XVd), (IXe)-(XIIIe) and (XVe), the variables are as defined below:

$R_{10}$ is —F, —Cl, —Br, —CN, —OR$_5$, —NR$_6$R$_7$, —S(O)$_t$R$_5$, —NR$_{11}$S(=O)$_t$R$_5$, —COOR$_5$, —CONR$_{12}$R$_{13}$, —NR$_{11}$C(=O)R$_5$, —C(=S)NR$_{12}$R$_{13}$, —COR$_5$; $(C_2-C_6)$ alkenyl, halo$(C_1-C_6)$alkyl, or $(C_1-C_3)$alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, or ($C_1$-$C_6$)alkoxy($C_1$-$C_3$)alkyl;

s is 0, 1 or 2;

one of $R_8$ and $R_9$ is —H, the other is selected from the group consisting of phenyl, tetrahydrofuran, tetrahydropyran, cyclopentane, cyclohexane, cycloheptane, oxepane, 1,3-dioxane, piperidine, 6,7,8,9-tetrahydro-5H-benzo[7]annulene, tetrahydronaphthalene, decahydronaphthalene, 5,6,7,8-tetrahydroquinoline, 5,6,7,8-tetrahydroisoquinoline, or 2-oxabicyclo[2.2.2]octane, each optionally substituted with 1 to 3 substitutents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy, ($C_1$-$C_3$)alkylcarbonyl and ($C_1$-$C_3$)alkoxycarbonyl, 5-6 membered heteroaryl (preferably pyridine or pyrimidine), phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxyl;

$R_1$ is —H;

$R_3$ and $R_4$ are independently selected from the group consisting of —H, —F, —Cl, —Br and ($C_1$-$C_3$)alkyl;

$R_5$ is ($C_1$-$C_6$)alkyl, ($C_1$-$C_3$)alkoxy($C_1$-$C_3$)alkyl or pyrrolidinyl;

$R_6$ and $R_7$ are —H;

$R_{11}$ is —H;

$R_{12}$ and $R_{13}$ are independently —H, ($C_1$-$C_6$)alkyl, ($C_1$-$C_3$)alkoxy($C_1$-$C_3$)alkyl, hydroxy($C_1$-$C_3$)alkyl, cyano($C_1$-$C_3$)alkyl, or di($C_1$-$C_3$)alkylamino($C_1$-$C_3$)alkyl;

$R_{14}$ is ($C_1$-$C_6$)alkyl, halo($C_1$-$C_3$)alkyl, ($C_3$-$C_8$)cycloalkyl ($C_1$-$C_3$)alkyl or benzyl; and i is 0, 1, or 2.

In a more specific embodiment, for compounds of Structural Formulas (IXb)-(XIIIb), (XVb), (XVc), (IXd)-(XIIId), (XVd), (IXe)-(XIIIe) and (XVe), $R_{10}$ is —CN, —F, —Cl, or —Br; and the remainder of the variables are as described above in the 16$^{th}$ specific embodiment.

In another more specific embodiment, for compounds of Structural Formulas (IXb)-(XIIIb), (XVb), (IXc)-(XIIIc), (XVc), (IXd)-(XIIId), (XVd), (IXe)-(XIIIe) and (XVe), one of $R_8$ and $R_9$ is —H, the other is phenyl, tetrahydropyran, tetrahydropyran, cyclopentane, cyclohexane, cycloheptane, oxepane, 1,3-dioxane, piperidine, 6,7,8,9-tetrahydro-5H-benzo[7]annulene, 2, dihydro-1H-indene, tetrahydronaphthalene, decahydronaphthalene, 5,6,7,8-tetrahydroquinoline, 5,6,7,8-tetrahydroisoquinoline, or 2-oxabicyclo[2.2.2]octane, each of which is unsubstituted; and the remainder of the variables are as described above in the 16$^{th}$ specific embodiment In another embodiment of the present invention, the compounds are listed in the following table:

| COMPOUND NO. | STRUCTURE |
|---|---|
| 1 | 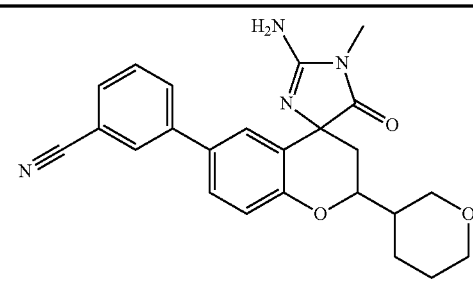 |
| 2 | 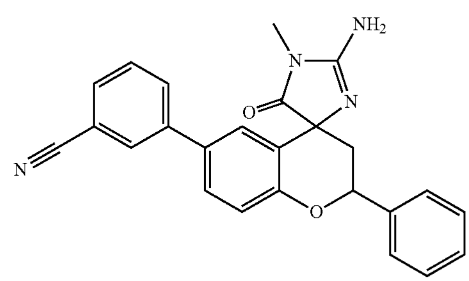 [SMILES: CN1C(=O)C2(CC(c3ccccc3)Oc3ccc(-c4cccc(C#N)c4)cc32)N=C1N] |
| 2A | 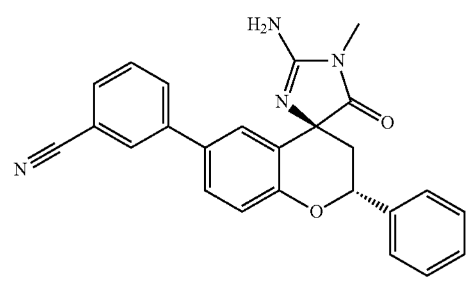 [SMILES: CN1C(=O)[C@@]2(C[C@H](c3ccccc3)Oc3ccc(-c4cccc(C#N)c4)cc32)N=C1N] |

-continued
| COMPOUND NO. | STRUCTURE |
|---|---|
| 2B | 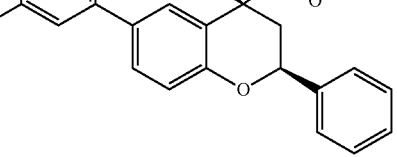 |
| 3 | 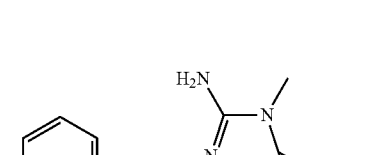 |
| 4 | 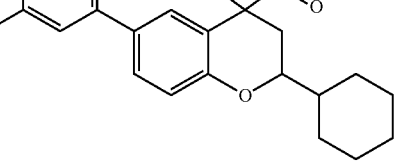 |
| 5 | 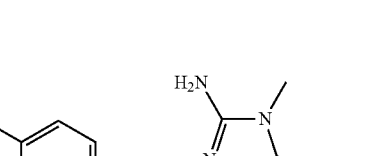 |
| 6 | 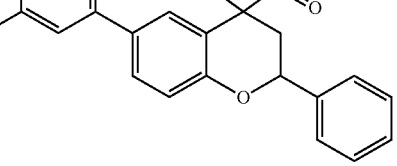 |

-continued

| COMPOUND NO. | STRUCTURE |
|---|---|
| 7 | 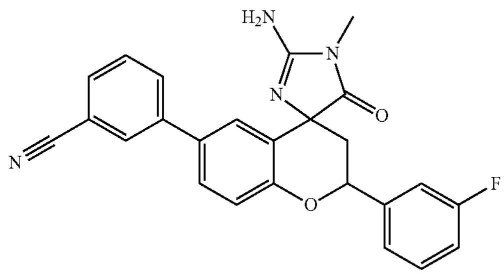 [SMILES: CN1C(=O)C2(CC(c3cccc(F)c3)Oc3ccc(-c4cccc(C#N)c4)cc32)N=C1N] |
| 8A | 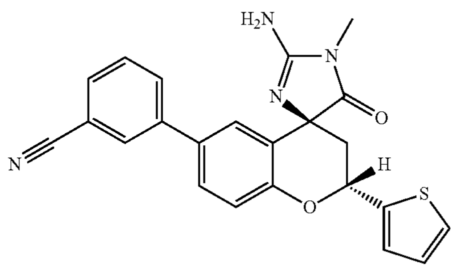 [SMILES: CN1C(=O)[C@@]2(C[C@H](c3cccs3)Oc3ccc(-c4cccc(C#N)c4)cc32)N=C1N] |
| 8B | 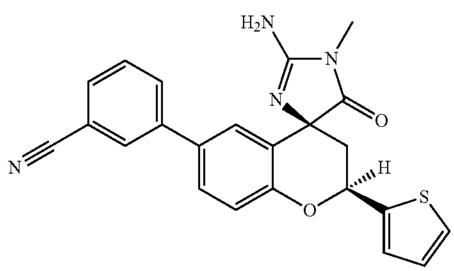 [SMILES: CN1C(=O)[C@@]2(C[C@@H](c3cccs3)Oc3ccc(-c4cccc(C#N)c4)cc32)N=C1N] |
| 9 | 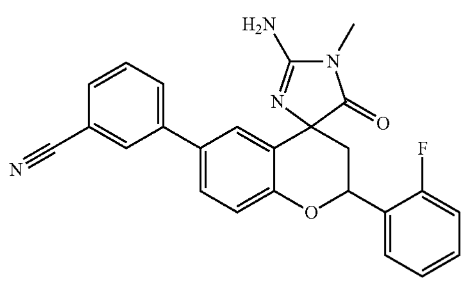 [SMILES: CN1C(=O)C2(CC(c3ccccc3F)Oc3ccc(-c4cccc(C#N)c4)cc32)N=C1N] |
| 10 | 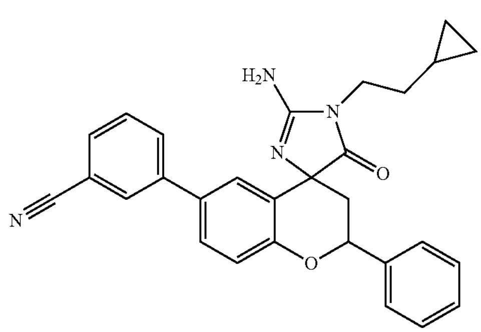 [SMILES: N#Cc1cccc(-c2ccc3c(c2)C2(CC(c4ccccc4)O3)N=C(N)N(CCC3CC3)C2=O)c1] |

-continued

| COMPOUND NO. | STRUCTURE |
|---|---|
| 11 | 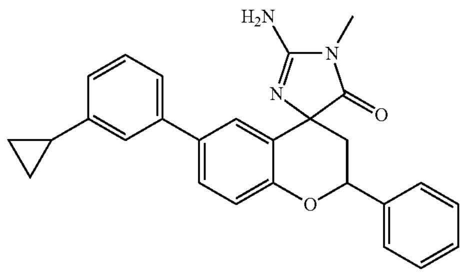 [SMILES: CN1C(=O)C2(CC(c3ccccc3)Oc3ccc(-c4cccc(C5CC5)c4)cc32)N=C1N] |
| 12 | 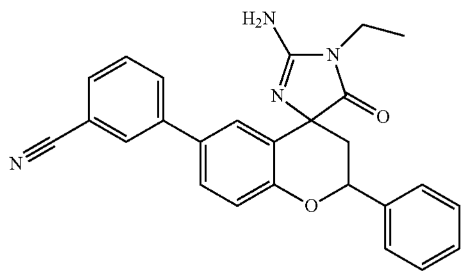 [SMILES: CCN1C(=O)C2(CC(c3ccccc3)Oc3ccc(-c4cccc(C#N)c4)cc32)N=C1N] |
| 13 | 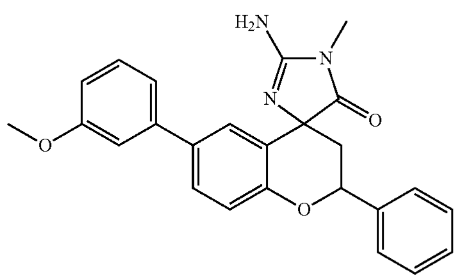 [SMILES: COc1cccc(-c2ccc3c(c2)C2(CC(c4ccccc4)O3)N=C(N)N(C)C2=O)c1] |
| 14 | 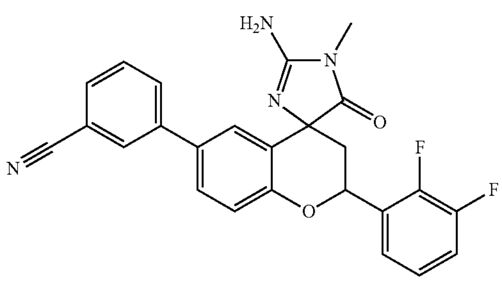 [SMILES: CN1C(=O)C2(CC(c3cccc(F)c3F)Oc3ccc(-c4cccc(C#N)c4)cc32)N=C1N] |
| 15 | 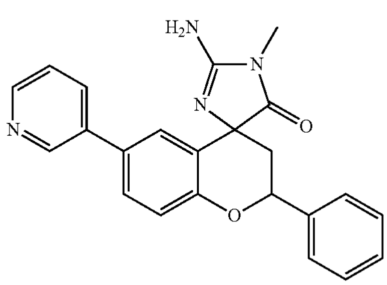 [SMILES: CN1C(=O)C2(CC(c3ccccc3)Oc3ccc(-c4cccnc4)cc32)N=C1N] |

-continued

| COMPOUND NO. | STRUCTURE |
|---|---|
| 16 | 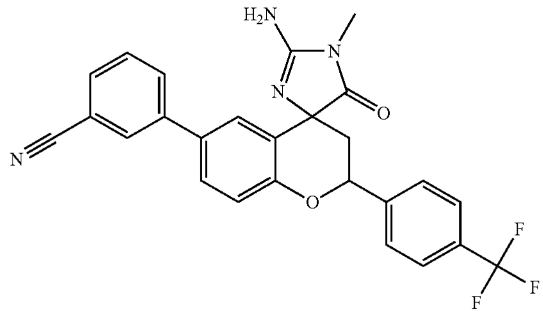 [SMILES: CN1C(=O)C2(CC(c3ccc(C(F)(F)F)cc3)Oc3ccc(-c4cccc(C#N)c4)cc32)N=C1N] |
| 17 | 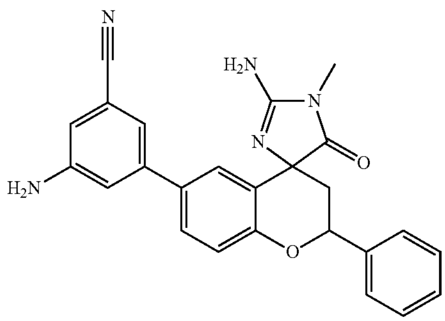 [SMILES: CN1C(=O)C2(CC(c3ccccc3)Oc3ccc(-c4cc(N)cc(C#N)c4)cc32)N=C1N] |
| 18 | 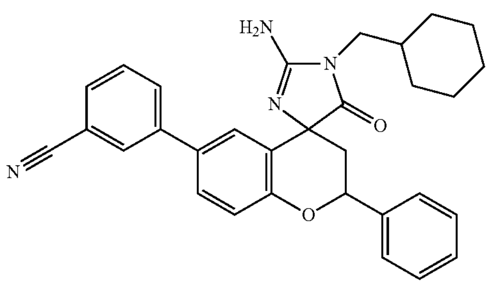 [SMILES: N#Cc1cccc(-c2ccc3c(c2)C2(CC(c4ccccc4)O3)N=C(N)N(CC3CCCCC3)C2=O)c1] |
| 19 | 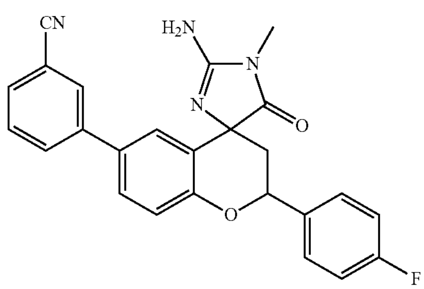 [SMILES: CN1C(=O)C2(CC(c3ccc(F)cc3)Oc3ccc(-c4cccc(C#N)c4)cc32)N=C1N] |
| 19A | 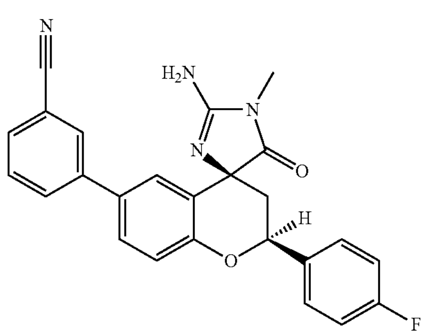 [SMILES: CN1C(=O)[C@@]2(C[C@@H](c3ccc(F)cc3)Oc3ccc(-c4cccc(C#N)c4)cc32)N=C1N] |

-continued

| COMPOUND NO. | STRUCTURE |
|---|---|
| 20 | 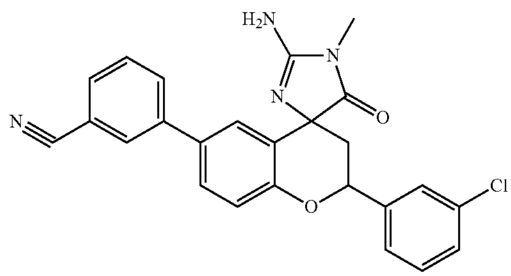 [SMILES: CN1C(=O)C2(CC(c3cccc(Cl)c3)Oc3ccc(-c4cccc(C#N)c4)cc32)N=C1N] |
| 21 | 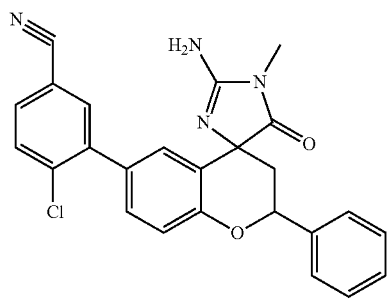 [SMILES: CN1C(=O)C2(CC(c3ccccc3)Oc3ccc(-c4cc(C#N)ccc4Cl)cc32)N=C1N] |
| 22 | 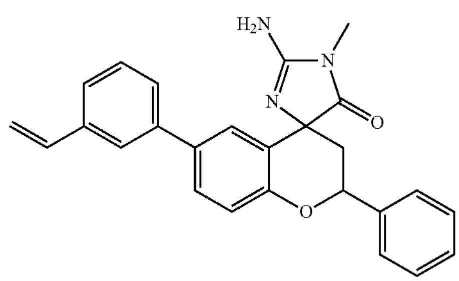 [SMILES: C=Cc1cccc(-c2ccc3c(c2)C2(CC(c4ccccc4)O3)N=C(N)N(C)C2=O)c1] |
| 23 | 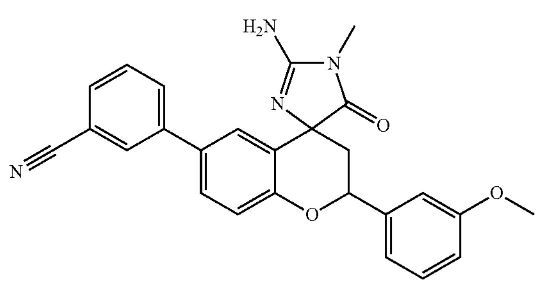 [SMILES: COc1cccc(C2CC3(N=C(N)N(C)C3=O)c3cc(-c4cccc(C#N)c4)ccc3O2)c1] |
| 24 | 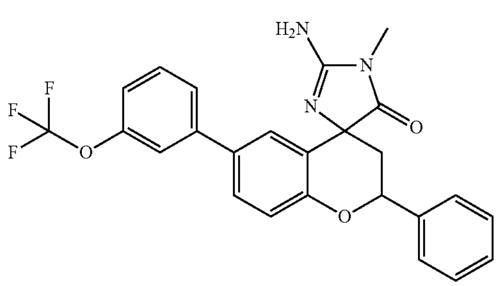 [SMILES: CN1C(=O)C2(CC(c3ccccc3)Oc3ccc(-c4cccc(OC(F)(F)F)c4)cc32)N=C1N] |

-continued

| COMPOUND NO. | STRUCTURE |
|---|---|
| 25A | 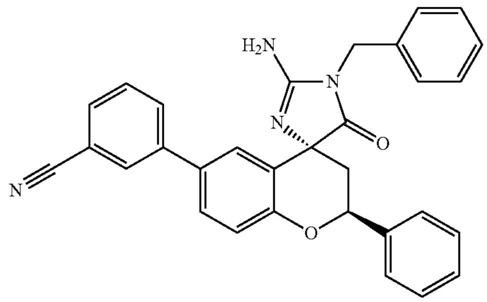 [SMILES: N#Cc1cccc(-c2ccc3c(c2)[C@@]2(C[C@@H](c4ccccc4)O3)N=C(N)N(Cc3ccccc3)C2=O)c1] |
| 25B | 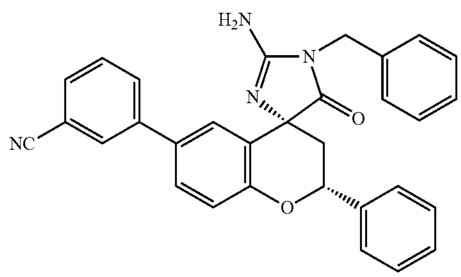 [SMILES: N#Cc1cccc(-c2ccc3c(c2)[C@@]2(C[C@H](c4ccccc4)O3)N=C(N)N(Cc3ccccc3)C2=O)c1] |
| 26 | 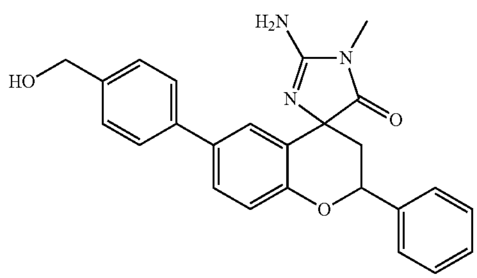 [SMILES: CN1C(=O)C2(CC(c3ccccc3)Oc3ccc(-c4ccc(CO)cc4)cc32)N=C1N] |
| 27 | 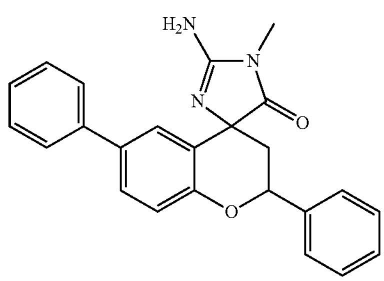 [SMILES: CN1C(=O)C2(CC(c3ccccc3)Oc3ccc(-c4ccccc4)cc32)N=C1N] |
| 28 | 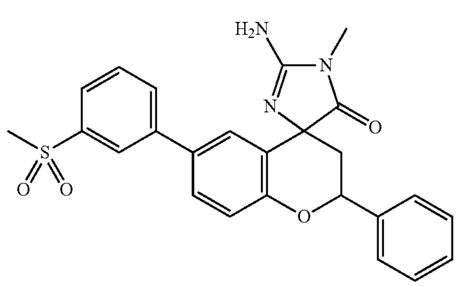 [SMILES: CN1C(=O)C2(CC(c3ccccc3)Oc3ccc(-c4cccc(S(C)(=O)=O)c4)cc32)N=C1N] |

-continued
| COMPOUND NO. | STRUCTURE |
|---|---|
| 29 | 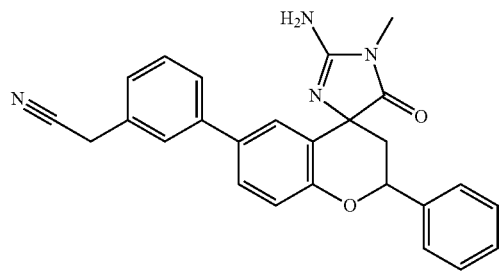 [SMILES: CN1C(=O)C2(CC(c3ccccc3)Oc3ccc(-c4cccc(CC#N)c4)cc32)N=C1N] |
| 30 | 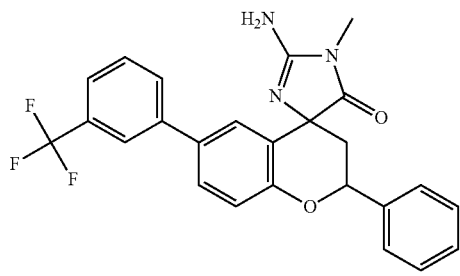 [SMILES: CN1C(=O)C2(CC(c3ccccc3)Oc3ccc(-c4cccc(C(F)(F)F)c4)cc32)N=C1N] |
| 31 | 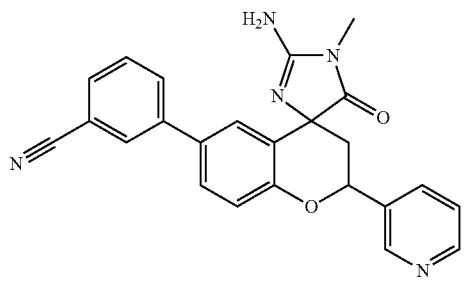 [SMILES: CN1C(=O)C2(CC(c3cccnc3)Oc3ccc(-c4cccc(C#N)c4)cc32)N=C1N] |
| 32 | 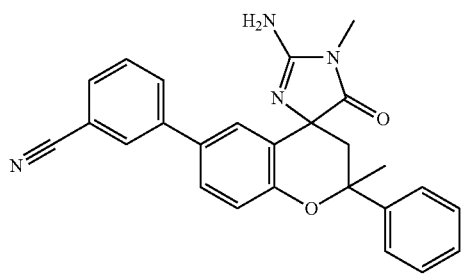 [SMILES: CN1C(=O)C2(CC(C)(c3ccccc3)Oc3ccc(-c4cccc(C#N)c4)cc32)N=C1N] |
| 33 | 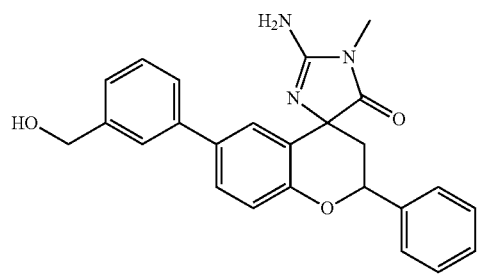 [SMILES: CN1C(=O)C2(CC(c3ccccc3)Oc3ccc(-c4cccc(CO)c4)cc32)N=C1N] |

-continued
| COMPOUND NO. | STRUCTURE |
|---|---|
| 34 | 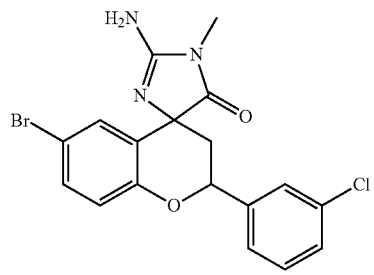 [SMILES: CN1C(=O)C2(CC(c3cccc(Cl)c3)Oc3ccc(Br)cc32)N=C1N] |
| 35 | 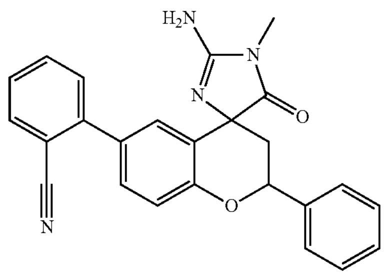 [SMILES: CN1C(=O)C2(CC(c3ccccc3)Oc3ccc(-c4ccccc4C#N)cc32)N=C1N] |
| 36 | 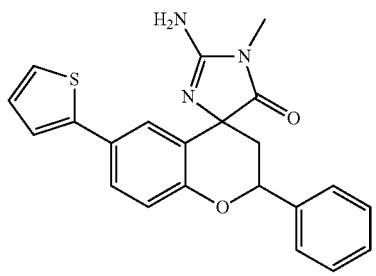 [SMILES: CN1C(=O)C2(CC(c3ccccc3)Oc3ccc(-c4cccs4)cc32)N=C1N] |
| 37 | 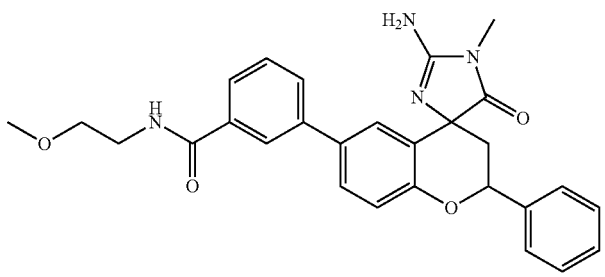 |
| 38 | 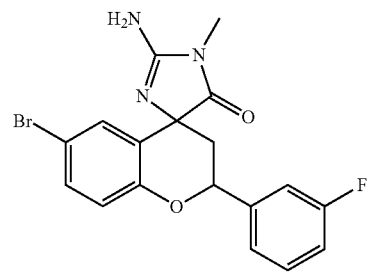 [SMILES: CN1C(=O)C2(CC(c3cccc(F)c3)Oc3ccc(Br)cc32)N=C1N] |

-continued
| COMPOUND NO. | STRUCTURE |
|---|---|
| 39 | 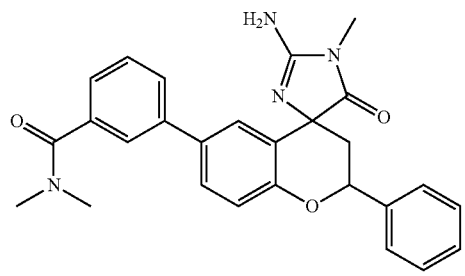 [SMILES: CN(C)C(=O)c1cccc(-c2ccc3c(c2)C2(CC(c4ccccc4)O3)N=C(N)N(C)C2=O)c1] |
| 40 | 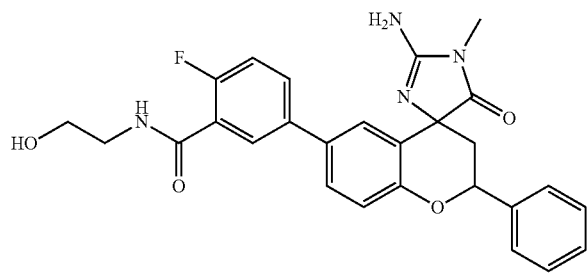 [SMILES: CN1C(=O)C2(CC(c3ccccc3)Oc3ccc(-c4ccc(F)c(C(=O)NCCO)c4)cc32)N=C1N] |
| 41 | 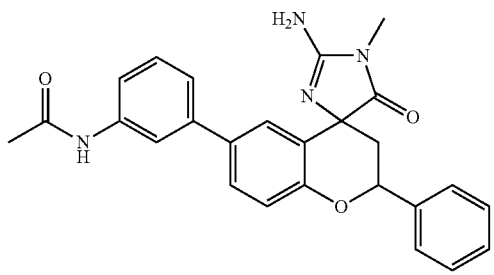 [SMILES: CC(=O)Nc1cccc(-c2ccc3c(c2)C2(CC(c4ccccc4)O3)N=C(N)N(C)C2=O)c1] |
| 42 | 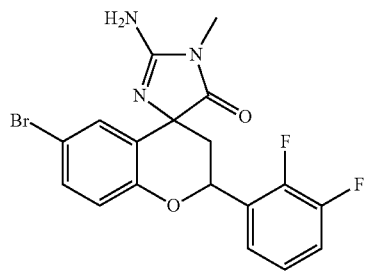 [SMILES: CN1C(=O)C2(CC(c3cccc(F)c3F)Oc3ccc(Br)cc32)N=C1N] |
| 43 | 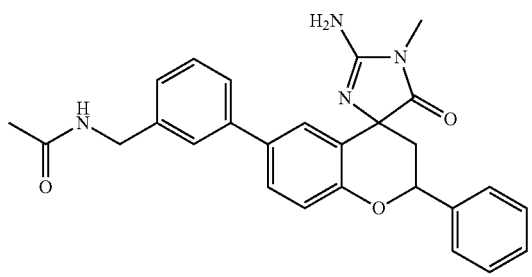 [SMILES: CC(=O)NCc1cccc(-c2ccc3c(c2)C2(CC(c4ccccc4)O3)N=C(N)N(C)C2=O)c1] |

| COMPOUND NO. | STRUCTURE |
|---|---|
| 44 | 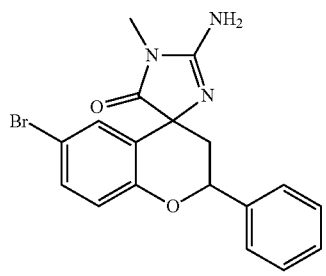 [SMILES: CN1C(=O)C2(CC(c3ccccc3)Oc3ccc(Br)cc32)N=C1N] |
| 44A | 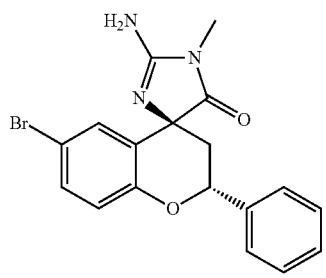 [SMILES: CN1C(=O)[C@@]2(C[C@H](c3ccccc3)Oc3ccc(Br)cc32)N=C1N] |
| 44B | 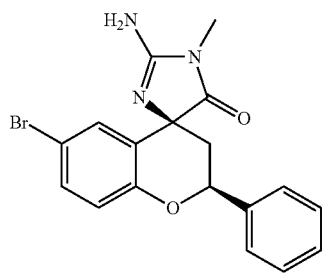 [SMILES: CN1C(=O)[C@@]2(C[C@@H](c3ccccc3)Oc3ccc(Br)cc32)N=C1N] |
| 45 | 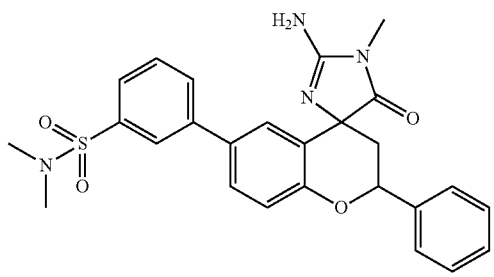 [SMILES: CN1C(=O)C2(CC(c3ccccc3)Oc3ccc(-c4cccc(S(=O)(=O)N(C)C)c4)cc32)N=C1N] |
| 46 | 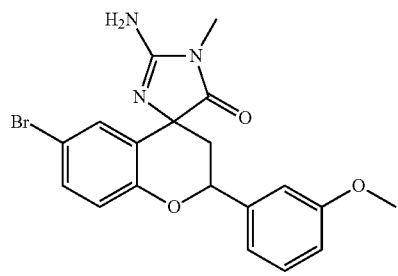 [SMILES: COc1cccc(C2CC3(N=C(N)N(C)C3=O)c3cc(Br)ccc3O2)c1] |

-continued
| COMPOUND NO. | STRUCTURE |
|---|---|
| 47 | 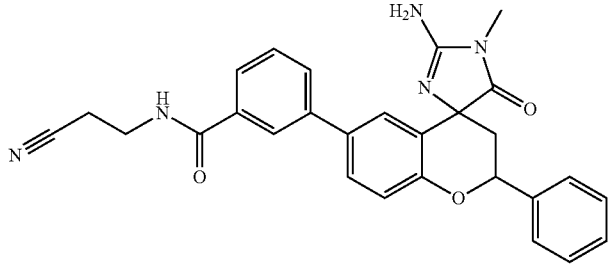 [SMILES: CN1C(=O)C2(CC(c3ccccc3)Oc3ccc(-c4cccc(C(=O)NCCC#N)c4)cc32)N=C1N] |
| 48 | 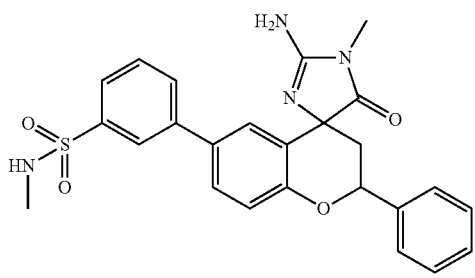 [SMILES: CNS(=O)(=O)c1cccc(-c2ccc3c(c2)C2(CC(c4ccccc4)O3)N=C(N)N(C)C2=O)c1] |
| 49 | 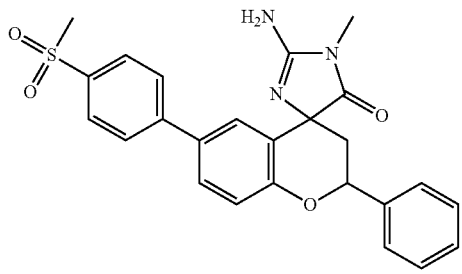 [SMILES: CN1C(=O)C2(CC(c3ccccc3)Oc3ccc(-c4ccc(S(C)(=O)=O)cc4)cc32)N=C1N] |
| 50 | 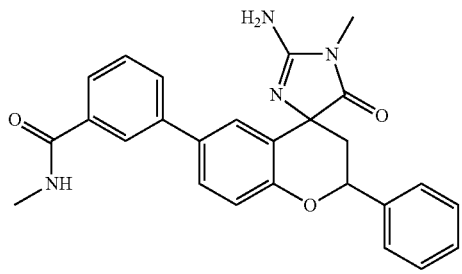 [SMILES: CNC(=O)c1cccc(-c2ccc3c(c2)C2(CC(c4ccccc4)O3)N=C(N)N(C)C2=O)c1] |
| 51A | 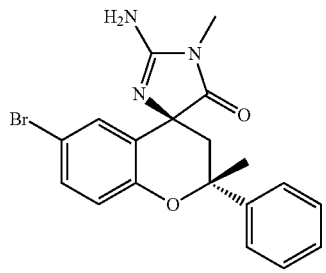 [SMILES: CN1C(=O)[C@@]2(C[C@](C)(c3ccccc3)Oc3ccc(Br)cc32)N=C1N] |

-continued
| COMPOUND NO. | STRUCTURE |
| --- | --- |
| 51B | 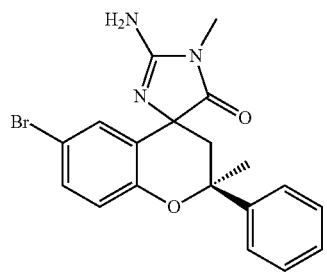 [SMILES: CN1C(=O)C2(C[C@@](C)(c3ccccc3)Oc3ccc(Br)cc32)N=C1N] |
| 52 | 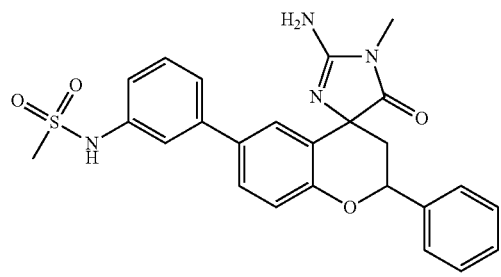 [SMILES: CN1C(=O)C2(CC(c3ccccc3)Oc3ccc(-c4cccc(NS(C)(=O)=O)c4)cc32)N=C1N] |
| 53 | 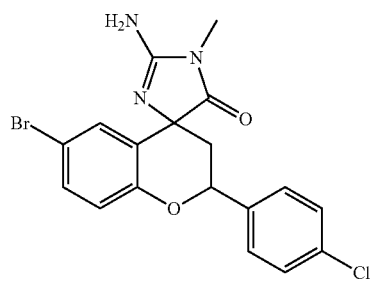 [SMILES: CN1C(=O)C2(CC(c3ccc(Cl)cc3)Oc3ccc(Br)cc32)N=C1N] |
| 54 | 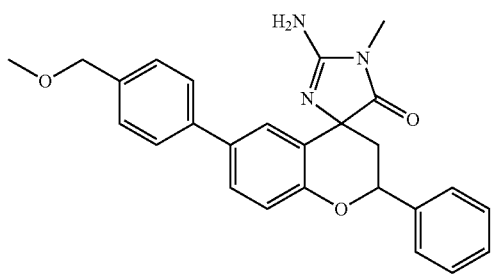 [SMILES: COCc1ccc(-c2ccc3c(c2)C2(CC(c4ccccc4)O3)N=C(N)N(C)C2=O)cc1] |
| 55A | 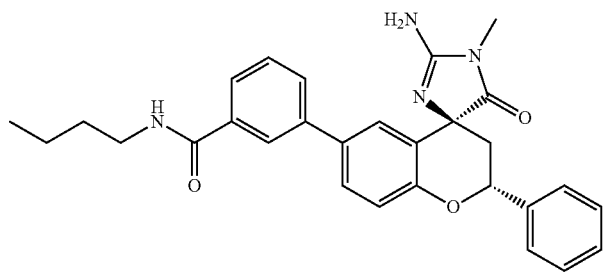 [SMILES: CCCCNC(=O)c1cccc(-c2ccc3c(c2)[C@]2(C[C@H](c4ccccc4)O3)N=C(N)N(C)C2=O)c1] |

-continued
| COMPOUND NO. | STRUCTURE |
|---|---|
| 55B | 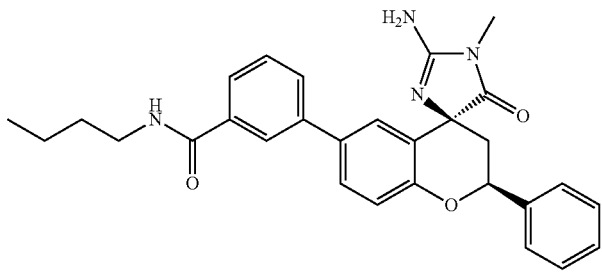 [SMILES: CCCCNC(=O)c1cccc(-c2ccc3c(c2)[C@]2(C[C@@H](c4ccccc4)O3)N=C(N)N(C)C2=O)c1] |
| 56 | 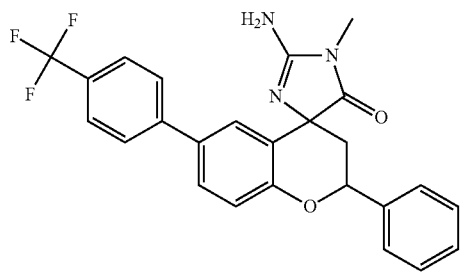 [SMILES: CN1C(=O)C2(CC(c3ccccc3)Oc3ccc(-c4ccc(C(F)(F)F)cc4)cc32)N=C1N] |
| 57 | 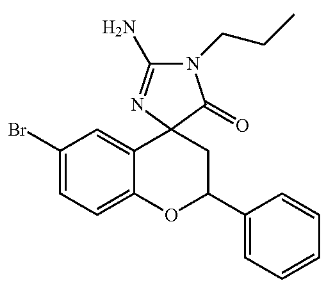 [SMILES: CCCN1C(=O)C2(CC(c3ccccc3)Oc3ccc(Br)cc32)N=C1N] |
| 57A | 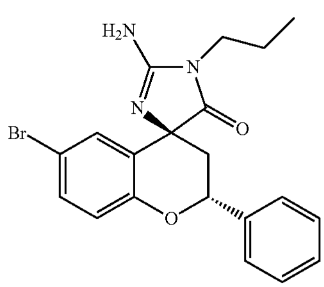 [SMILES: CCCN1C(=O)[C@@]2(C[C@H](c3ccccc3)Oc3ccc(Br)cc32)N=C1N] |
| 58 | 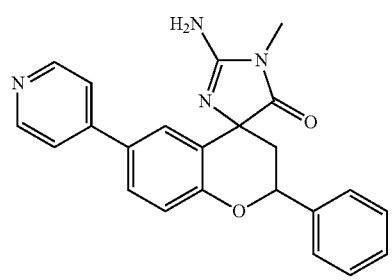 [SMILES: CN1C(=O)C2(CC(c3ccccc3)Oc3ccc(-c4ccncc4)cc32)N=C1N] |

-continued
| COMPOUND NO. | STRUCTURE |
|---|---|
| 59 | 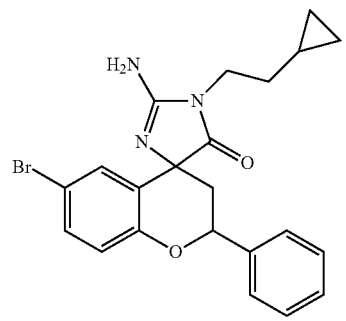 [SMILES: NC1=NC2(CC(c3ccccc3)Oc3ccc(Br)cc32)C(=O)N1CCC1CC1] |
| 60 | 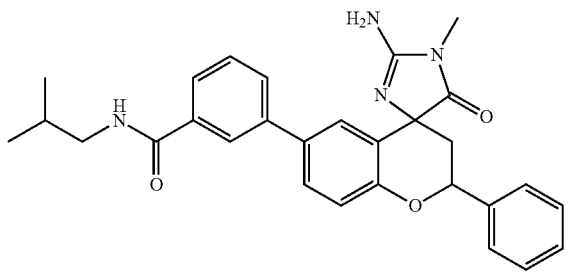 [SMILES: CC(C)CNC(=O)c1cccc(-c2ccc3c(c2)C2(CC(c4ccccc4)O3)N=C(N)N(C)C2=O)c1] |
| 61 | 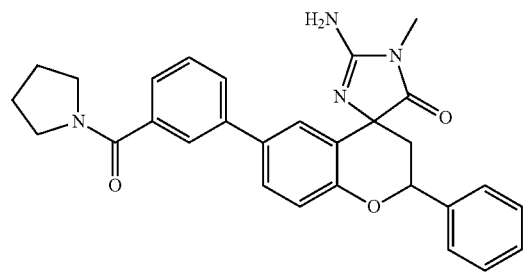 [SMILES: CN1C(=O)C2(CC(c3ccccc3)Oc3ccc(-c4cccc(C(=O)N5CCCC5)c4)cc32)N=C1N] |
| 62 | 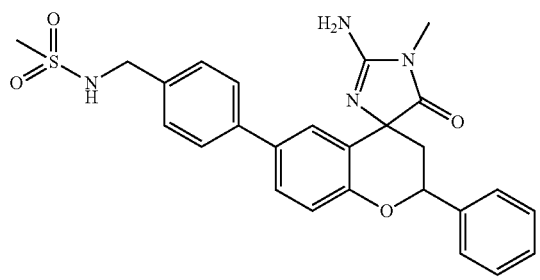 [SMILES: CN1C(=O)C2(CC(c3ccccc3)Oc3ccc(-c4ccc(CNS(C)(=O)=O)cc4)cc32)N=C1N] |
| 63 | 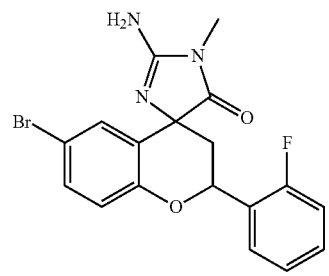 [SMILES: CN1C(=O)C2(CC(c3ccccc3F)Oc3ccc(Br)cc32)N=C1N] |

-continued
| COMPOUND NO. | STRUCTURE |
|---|---|
| 64 | 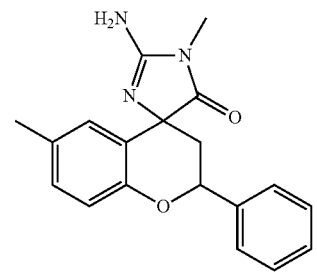 [SMILES: Cc1ccc2c(c1)C1(CC(c3ccccc3)O2)N=C(N)N(C)C1=O] |
| 65 | 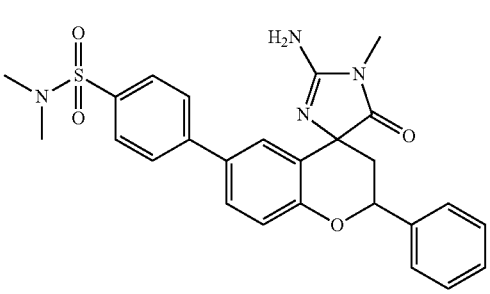 [SMILES: CN1C(=O)C2(CC(c3ccccc3)Oc3ccc(-c4ccc(S(=O)(=O)N(C)C)cc4)cc32)N=C1N] |
| 66 | 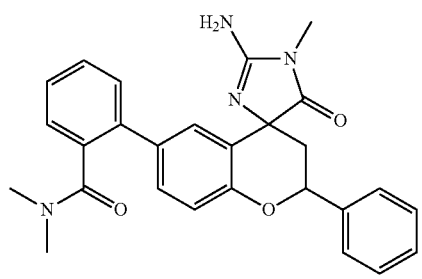 [SMILES: CN(C)C(=O)c1ccccc1-c1ccc2c(c1)C1(CC(c3ccccc3)O2)N=C(N)N(C)C1=O] |
| 67 | 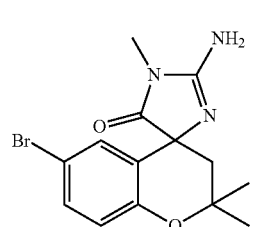 |
| 68 | 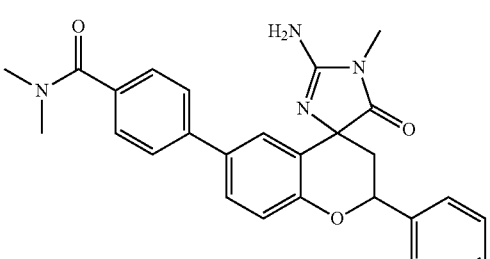 |

-continued

| COMPOUND NO. | STRUCTURE |
|---|---|
| 69 | 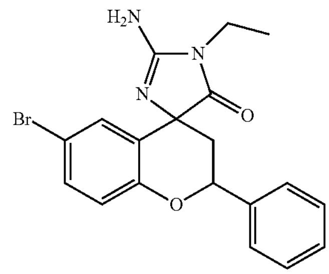 [SMILES: CCN1C(=O)C2(CC(c3ccccc3)Oc3ccc(Br)cc32)N=C1N] |
| 70 | 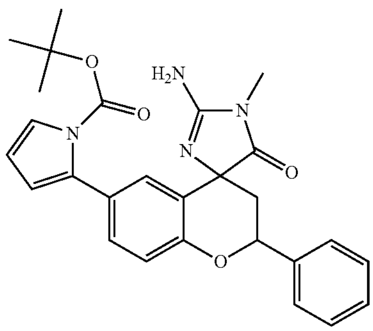 [SMILES: CN1C(=O)C2(CC(c3ccccc3)Oc3ccc(-c4cccn4C(=O)OC(C)(C)C)cc32)N=C1N] |
| 71 | 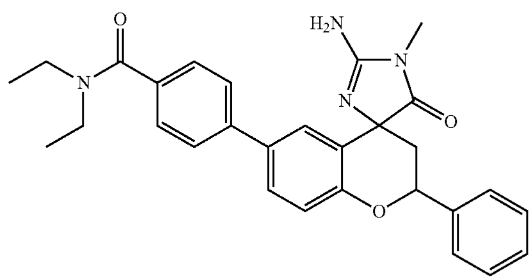 [SMILES: CCN(CC)C(=O)c1ccc(-c2ccc3c(c2)C2(CC(c4ccccc4)O3)N=C(N)N(C)C2=O)cc1] |
| 72 | 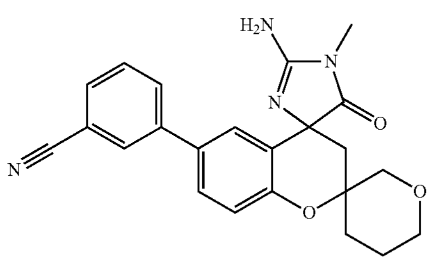 |
| 72A | 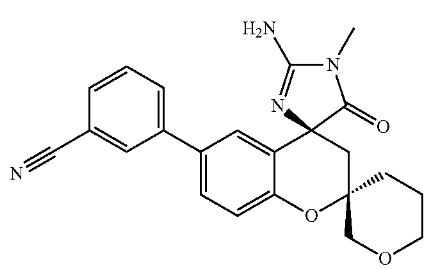 [SMILES: CN1C(=O)[C@@]2(C[C@]3(CCCOC3)Oc3ccc(-c4cccc(C#N)c4)cc32)N=C1N] |

-continued

| COMPOUND NO. | STRUCTURE |
|---|---|
| 72B | 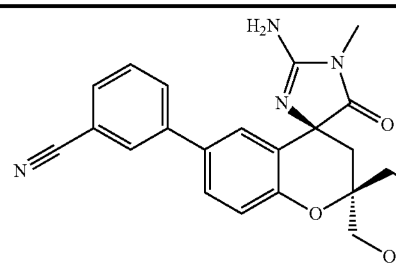 |
| 73 | 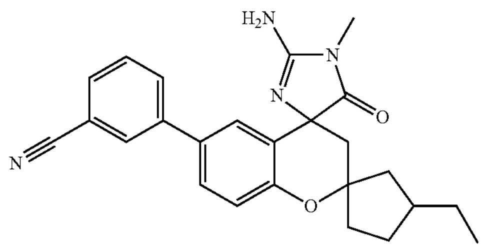 [SMILES: CCC1CCC2(C1)CC1(N=C(N)N(C)C1=O)c1cc(-c3cccc(C#N)c3)ccc1O2] |
| 74 | 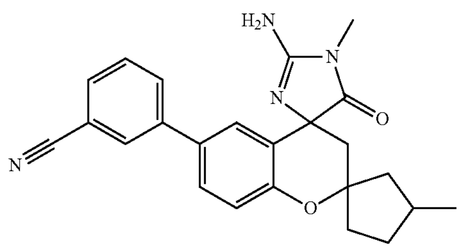 [SMILES: CC1CCC2(C1)CC1(N=C(N)N(C)C1=O)c1cc(-c3cccc(C#N)c3)ccc1O2] |
| 75 | 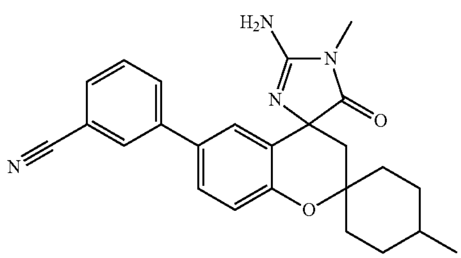 [SMILES: CC1CCC2(CC1)CC1(N=C(N)N(C)C1=O)c1cc(-c3cccc(C#N)c3)ccc1O2] |
| 76 | 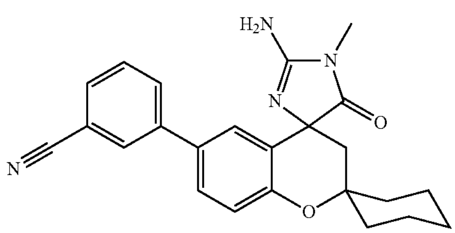 [SMILES: CN1C(=O)C2(CC3(CCCCC3)Oc3ccc(-c4cccc(C#N)c4)cc32)N=C1N] |
| 77 | 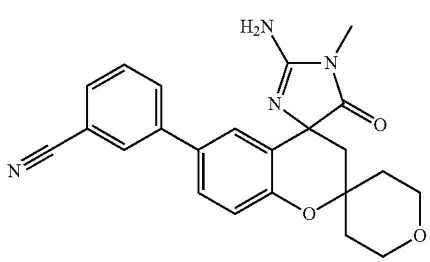 [SMILES: CN1C(=O)C2(CC3(CCOCC3)Oc3ccc(-c4cccc(C#N)c4)cc32)N=C1N] |

-continued

| COMPOUND NO. | STRUCTURE |
|---|---|
| 78 | 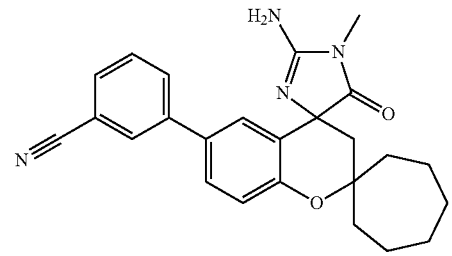 [SMILES: CN1C(=O)C2(CC3(CCCCCC3)Oc3ccc(-c4cccc(C#N)c4)cc32)N=C1N] |
| 79 | 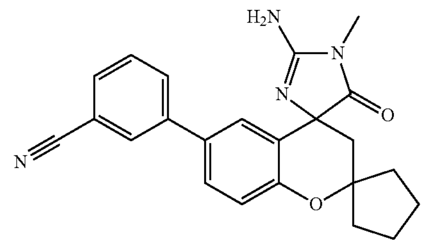 [SMILES: CN1C(=O)C2(CC3(CCCC3)Oc3ccc(-c4cccc(C#N)c4)cc32)N=C1N] |
| 80 | 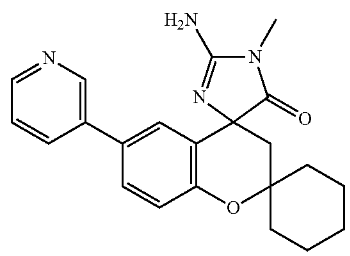 [SMILES: CN1C(=O)C2(CC3(CCCCC3)Oc3ccc(-c4cccnc4)cc32)N=C1N] |
| 81 | 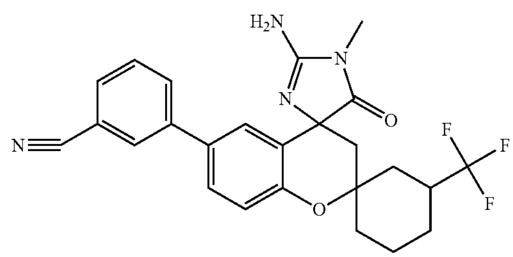 [SMILES: CN1C(=O)C2(CC3(CCCC(C(F)(F)F)C3)Oc3ccc(-c4cccc(C#N)c4)cc32)N=C1N] |
| 82 | 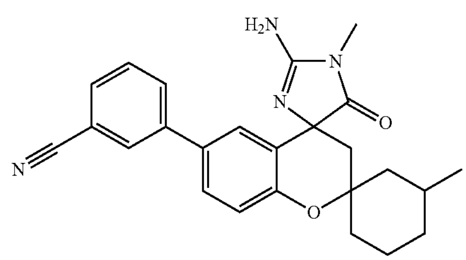 [SMILES: CC1CCCC2(C1)CC1(N=C(N)N(C)C1=O)c1cc(-c3cccc(C#N)c3)ccc1O2] |
| 83 | 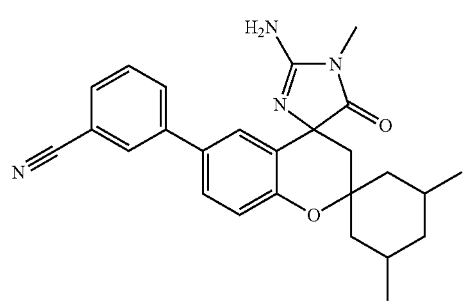 [SMILES: CC1CC(C)CC2(C1)CC1(N=C(N)N(C)C1=O)c1cc(-c3cccc(C#N)c3)ccc1O2] |

| COMPOUND NO. | STRUCTURE |
|---|---|
| 84 | 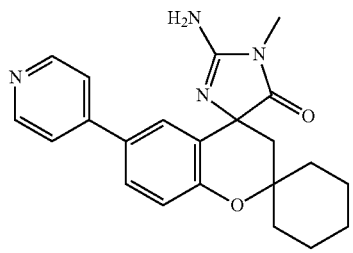 [SMILES: CN1C(=O)C2(CC3(CCCCC3)Oc3ccc(-c4ccncc4)cc32)N=C1N] |
| 85 | 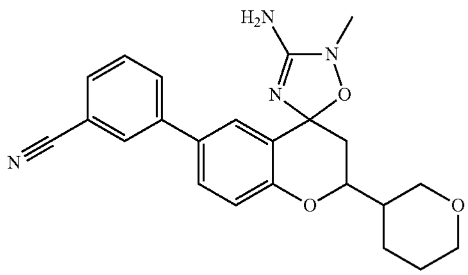 [SMILES: CN1OC2(CC(C3CCCOC3)Oc3ccc(-c4cccc(C#N)c4)cc32)N=C1N] |
| 86 | 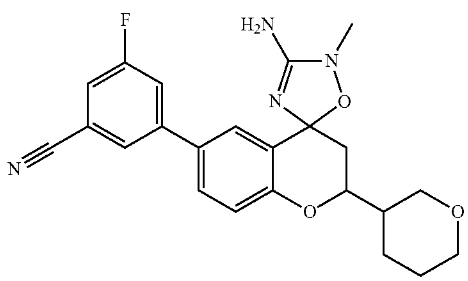 [SMILES: CN1OC2(CC(C3CCCOC3)Oc3ccc(-c4cc(F)cc(C#N)c4)cc32)N=C1N] |
| 87 | 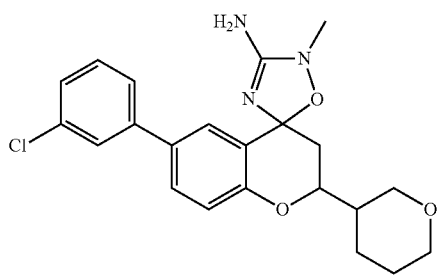 [SMILES: CN1OC2(CC(C3CCCOC3)Oc3ccc(-c4cccc(Cl)c4)cc32)N=C1N] |
| 88 | 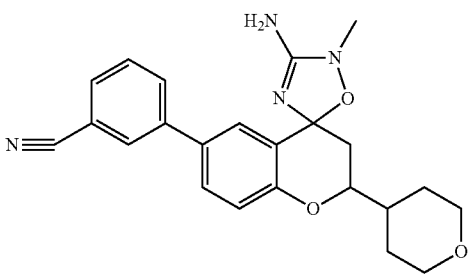 [SMILES: CN1OC2(CC(C3CCOCC3)Oc3ccc(-c4cccc(C#N)c4)cc32)N=C1N] |

| COMPOUND NO. | STRUCTURE |
|---|---|
| 89A | 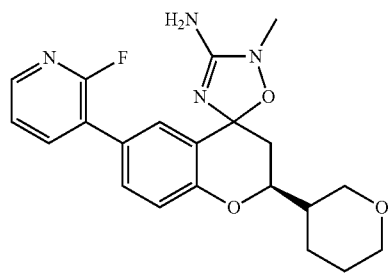 [SMILES: CN1OC2(C[C@@H](C3CCCOC3)Oc3ccc(-c4cccnc4F)cc32)N=C1N] |
| 89B | 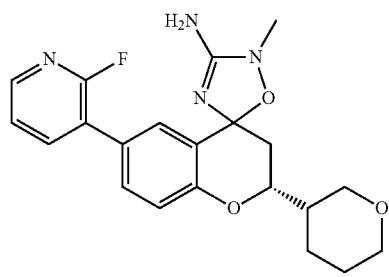 |
| 90 | 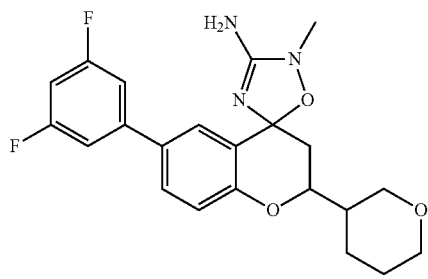 [SMILES: CN1OC2(CC(C3CCCOC3)Oc3ccc(-c4cc(F)cc(F)c4)cc32)N=C1N] |
| 91 | 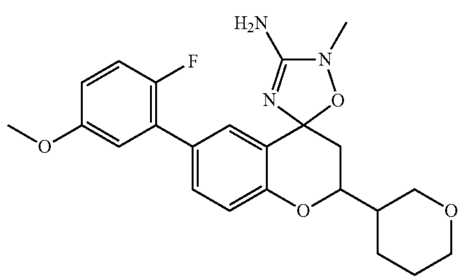 [SMILES: COc1ccc(F)c(-c2ccc3c(c2)C2(CC(C4CCCOC4)O3)N=C(N)N(C)O2)c1] |
| 92 | 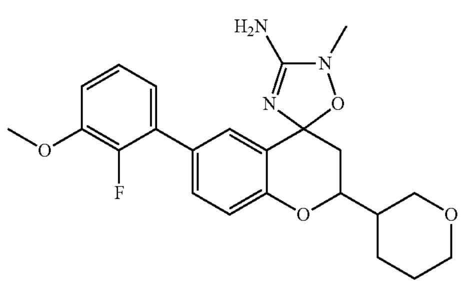 [SMILES: COc1cccc(-c2ccc3c(c2)C2(CC(C4CCCOC4)O3)N=C(N)N(C)O2)c1F] |

| COMPOUND NO. | STRUCTURE |
|---|---|
| 93 | 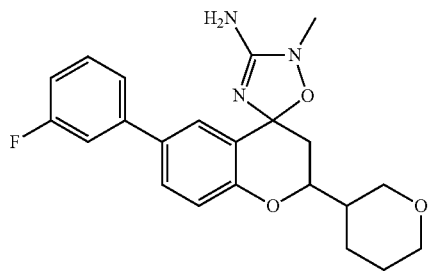 [SMILES: CN1OC2(CC(C3CCCOC3)Oc3ccc(-c4cccc(F)c4)cc32)N=C1N] |
| 94 | 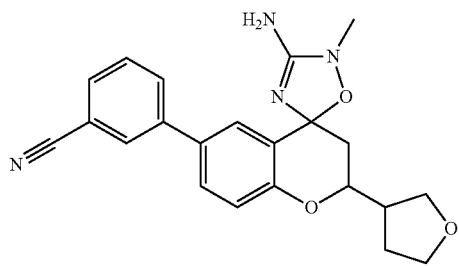 [SMILES: CN1OC2(CC(C3CCOC3)Oc3ccc(-c4cccc(C#N)c4)cc32)N=C1N] |
| 95 | 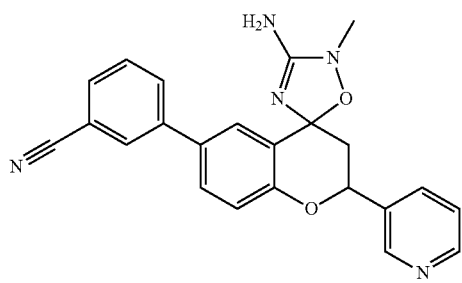 [SMILES: CN1OC2(CC(c3cccnc3)Oc3ccc(-c4cccc(C#N)c4)cc32)N=C1N] |
| 96 | 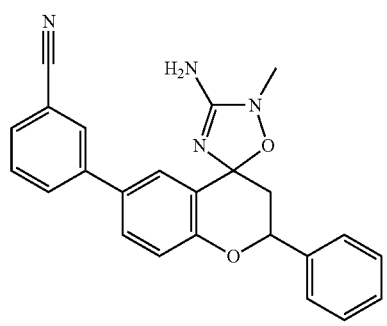 [SMILES: CN1OC2(CC(c3ccccc3)Oc3ccc(-c4cccc(C#N)c4)cc32)N=C1N] |
| 97 | 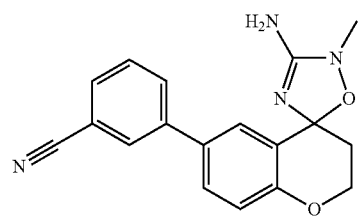 [SMILES: CN1OC2(CCOc3ccc(-c4cccc(C#N)c4)cc32)N=C1N] |

-continued

| COMPOUND NO. | STRUCTURE |
|---|---|
| 98 | 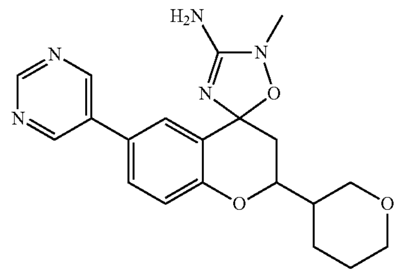 [SMILES: CN1OC2(CC(C3CCCOC3)Oc3ccc(-c4cncnc4)cc32)N=C1N] |
| 99 | 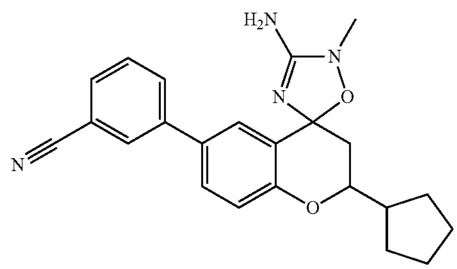 [SMILES: CN1OC2(CC(C3CCCC3)Oc3ccc(-c4cccc(C#N)c4)cc32)N=C1N] |
| 100 | 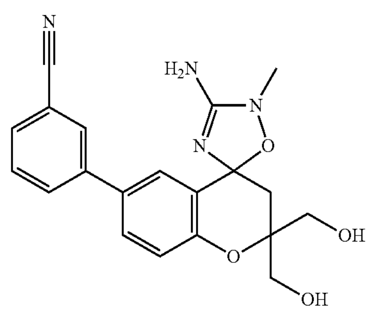 [SMILES: CN1OC2(CC(CO)(CO)Oc3ccc(-c4cccc(C#N)c4)cc32)N=C1N] |
| 101 | 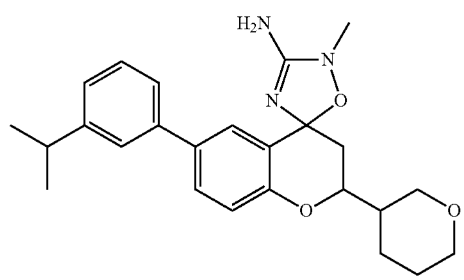 [SMILES: CC(C)c1cccc(-c2ccc3c(c2)C2(CC(C4CCCOC4)O3)N=C(N)N(C)O2)c1] |
| 102 | 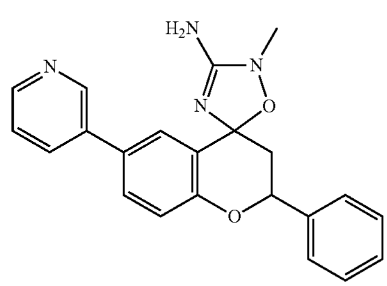 [SMILES: CN1OC2(CC(c3ccccc3)Oc3ccc(-c4cccnc4)cc32)N=C1N] |

| COMPOUND NO. | STRUCTURE |
|---|---|
| 103 | 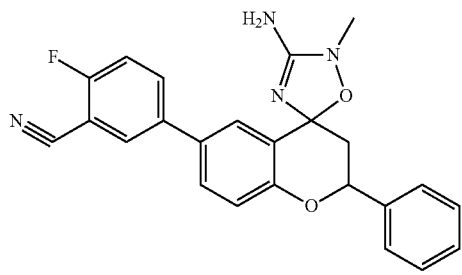 [SMILES: CN1OC2(CC(c3ccccc3)Oc3ccc(-c4ccc(F)c(C#N)c4)cc32)N=C1N] |
| 104 | 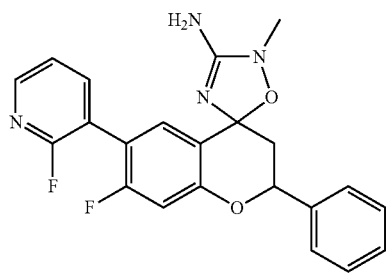 [SMILES: CN1OC2(CC(c3ccccc3)Oc3cc(F)c(-c4cccnc4F)cc32)N=C1N] |
| 105 | 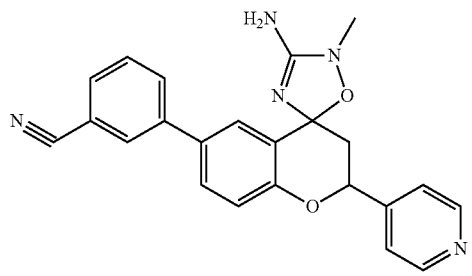 [SMILES: CN1OC2(CC(c3ccncc3)Oc3ccc(-c4cccc(C#N)c4)cc32)N=C1N] |
| 106 | 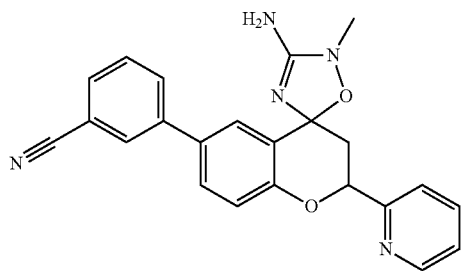 [SMILES: CN1OC2(CC(c3ccccn3)Oc3ccc(-c4cccc(C#N)c4)cc32)N=C1N] |
| 107 | 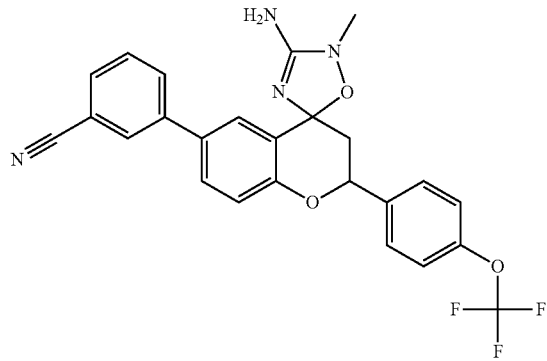 [SMILES: CN1OC2(CC(c3ccc(OC(F)(F)F)cc3)Oc3ccc(-c4cccc(C#N)c4)cc32)N=C1N] |

-continued

| COMPOUND NO. | STRUCTURE |
|---|---|
| 108 | 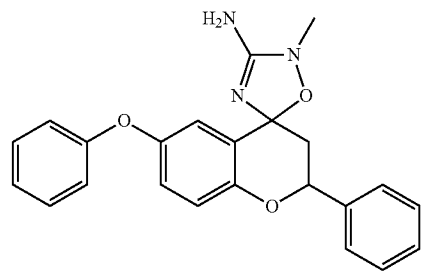 [SMILES: CN1OC2(CC(c3ccccc3)Oc3ccc(Oc4ccccc4)cc32)N=C1N] |
| 109 | 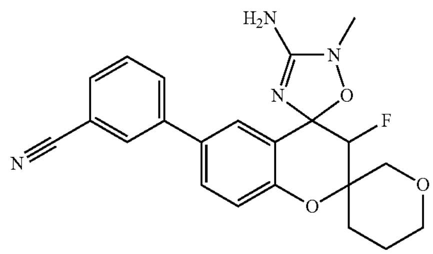 |
| 110 | 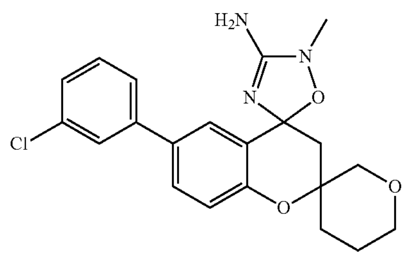 [SMILES: CN1OC2(CC3(CCCOC3)Oc3ccc(-c4cccc(Cl)c4)cc32)N=C1N] |
| 111 | 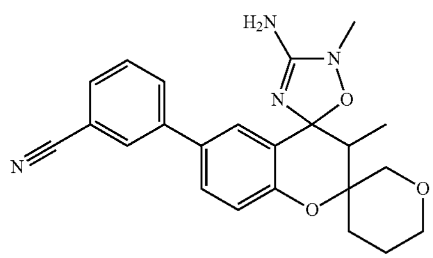 [SMILES: CC1C2(CCCOC2)Oc2ccc(-c3cccc(C#N)c3)cc2C12N=C(N)N(C)O2] |
| 112 | 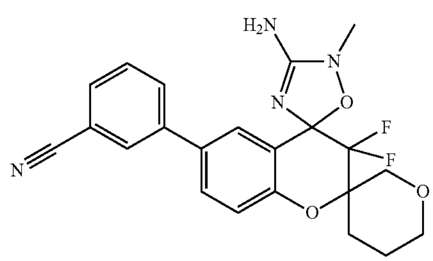 [SMILES: CN1OC2(N=C1N)c1cc(-c3cccc(C#N)c3)ccc1OC1(CCCOC1)C2(F)F] |
| 113A | 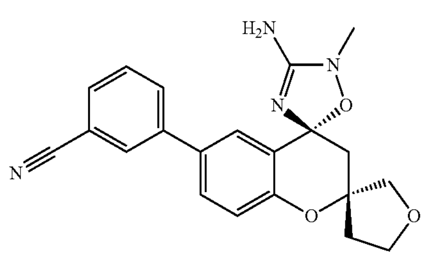 [SMILES: CN1O[C@@]2(C[C@@]3(CCOC3)Oc3ccc(-c4cccc(C#N)c4)cc32)N=C1N] |

-continued

| COMPOUND NO. | STRUCTURE |
|---|---|
| 113B | 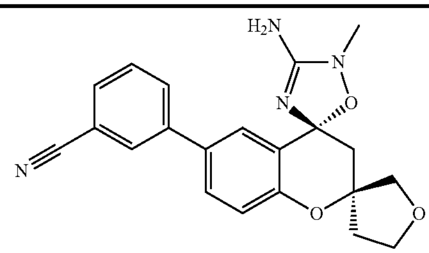 |
| 114 | 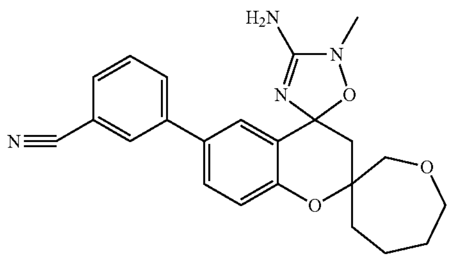 [SMILES: CN1OC2(CC3(CCCCOC3)Oc3ccc(-c4cccc(C#N)c4)cc32)N=C1N] |
| 115 | 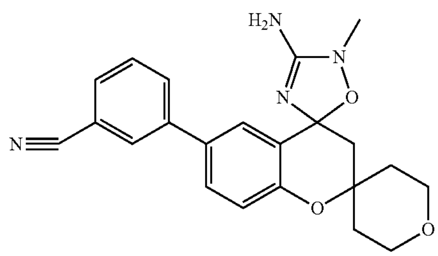 [SMILES: CN1OC2(CC3(CCOCC3)Oc3ccc(-c4cccc(C#N)c4)cc32)N=C1N] |
| 116 | 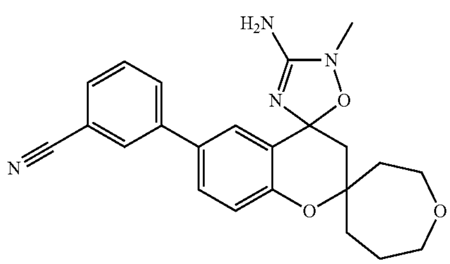 [SMILES: CN1OC2(CC3(CCCOCC3)Oc3ccc(-c4cccc(C#N)c4)cc32)N=C1N] |
| 117 | 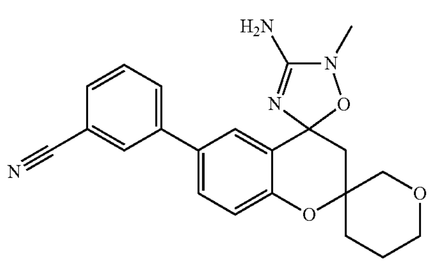 [SMILES: CN1OC2(CC3(CCCOC3)Oc3ccc(-c4cccc(C#N)c4)cc32)N=C1N] |
| 118 | 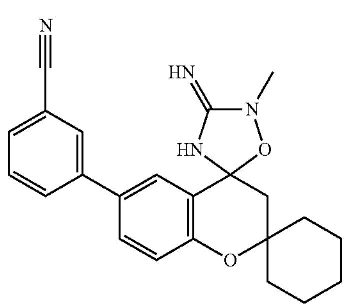 [SMILES: CN1OC2(CC3(CCCCC3)Oc3ccc(-c4cccc(C#N)c4)cc32)NC1=N] |

-continued
| COMPOUND NO. | STRUCTURE |
|---|---|
| 119 | 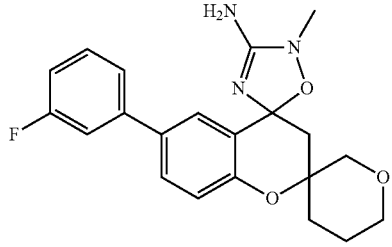 [SMILES: CN1OC2(CC3(CCCOC3)Oc3ccc(-c4cccc(F)c4)cc32)N=C1N] |
| 120 | 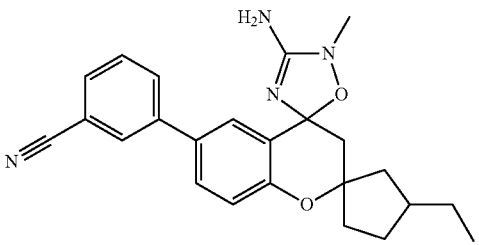 [SMILES: CCC1CCC2(C1)CC1(N=C(N)N(C)O1)c1cc(-c3cccc(C#N)c3)ccc1O2] |
| 121 | 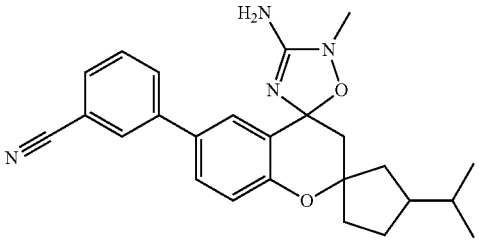 [SMILES: CC(C)C1CCC2(C1)CC1(N=C(N)N(C)O1)c1cc(-c3cccc(C#N)c3)ccc1O2] |
| 122 | 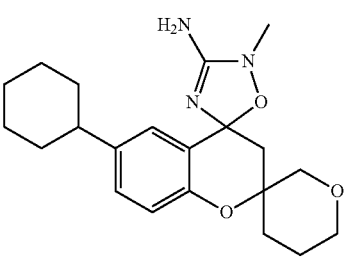 [SMILES: CN1OC2(CC3(CCCOC3)Oc3ccc(C4CCCCC4)cc32)N=C1N] |
| 123 | 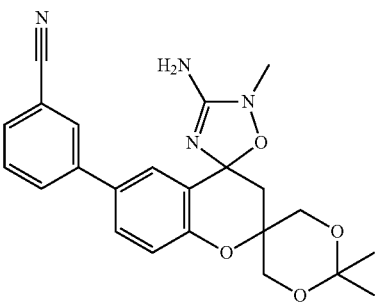 [SMILES: CN1OC2(CC3(COC(C)(C)OC3)Oc3ccc(-c4cccc(C#N)c4)cc32)N=C1N] |
| 124 | 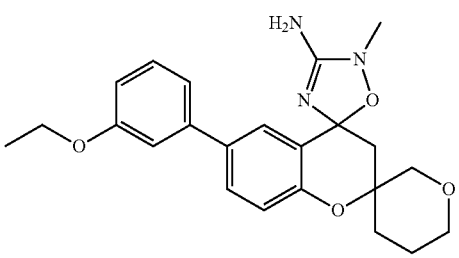 [SMILES: CCOc1cccc(-c2ccc3c(c2)C2(CC4(CCCOC4)O3)N=C(N)N(C)O2)c1] |

| COMPOUND NO. | STRUCTURE |
|---|---|
| 125 | 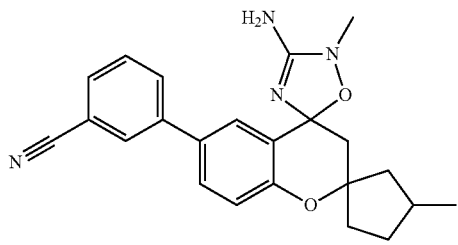 [SMILES: CC1CCC2(C1)CC1(N=C(N)N(C)O1)c1cc(-c3cccc(C#N)c3)ccc1O2] |
| 126 | 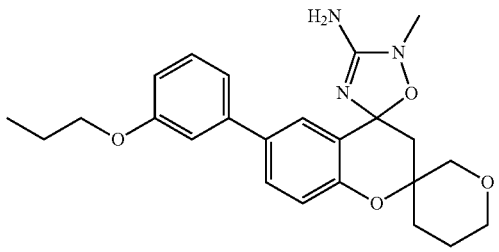 [SMILES: CCCOc1cccc(-c2ccc3c(c2)C2(CC4(CCCOC4)O3)N=C(N)N(C)O2)c1] |
| 127A | 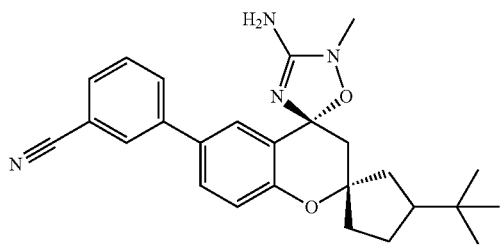 |
| 127B | 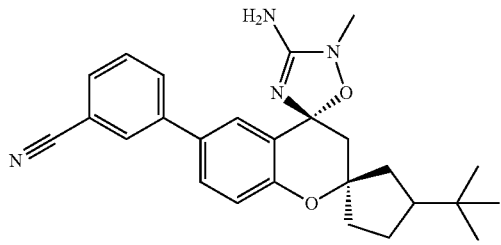 |
| 128 | 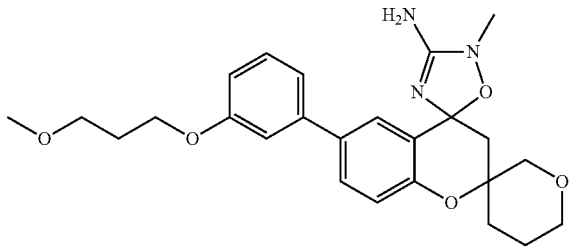 [SMILES: COCCCOc1cccc(-c2ccc3c(c2)C2(CC4(CCCOC4)O3)N=C(N)N(C)O2)c1] |
| 129 | 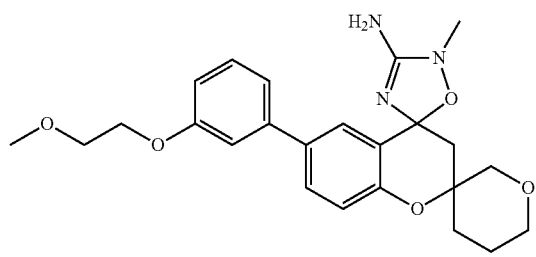 [SMILES: COCCOc1cccc(-c2ccc3c(c2)C2(CC4(CCCOC4)O3)N=C(N)N(C)O2)c1] |

-continued

| COMPOUND NO. | STRUCTURE |
|---|---|
| 130 | (structure) |
| 131 | (structure) |
| 132 | (structure) |
| 133 | (structure) |
| 134 | (structure) |
| 135A | (structure) |

-continued

| COMPOUND NO. | STRUCTURE |
|---|---|
| 135B | 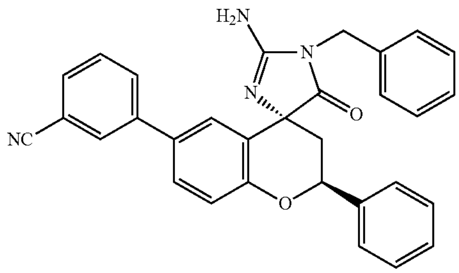 [SMILES: N#Cc1cccc(-c2ccc3c(c2)[C@@]2(C[C@@H](c4ccccc4)O3)N=C(N)N(Cc3ccccc3)C2=O)c1] |
| 136 | 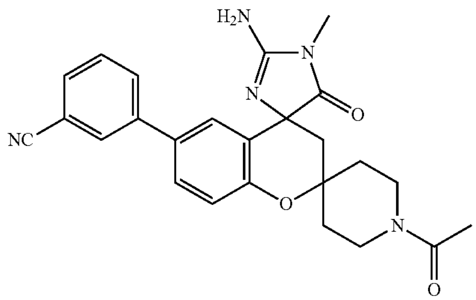 [SMILES: CC(=O)N1CCC2(CC1)CC1(N=C(N)N(C)C1=O)c1cc(-c3cccc(C#N)c3)ccc1O2] |
| 137 | 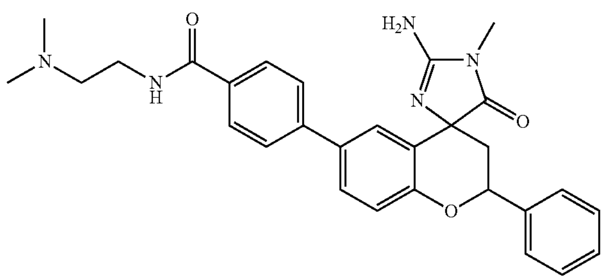 [SMILES: CN(C)CCNC(=O)c1ccc(-c2ccc3c(c2)C2(CC(c4ccccc4)O3)N=C(N)N(C)C2=O)cc1] |
| 138 | 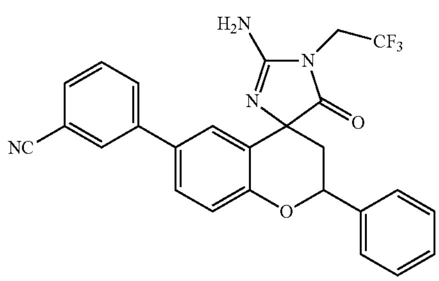 [SMILES: N#Cc1cccc(-c2ccc3c(c2)C2(CC(c4ccccc4)O3)N=C(N)N(CC(F)(F)F)C2=O)c1] |
| 139 | 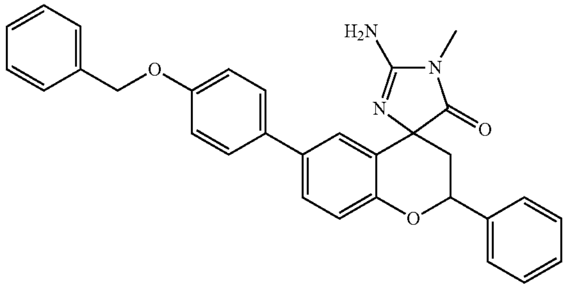 [SMILES: CN1C(=O)C2(CC(c3ccccc3)Oc3ccc(-c4ccc(OCc5ccccc5)cc4)cc32)N=C1N] |

-continued
| COMPOUND NO. | STRUCTURE |
|---|---|
| 140 | 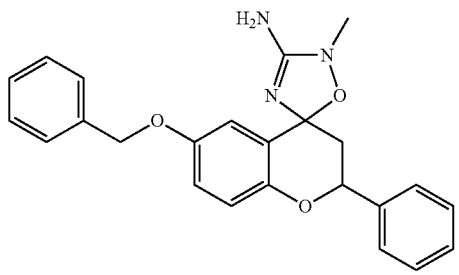 [SMILES: CN1OC2(CC(c3ccccc3)Oc3ccc(OCc4ccccc4)cc32)N=C1N] |
| 141 | 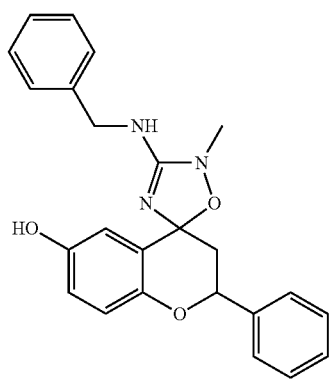 [SMILES: CN1OC2(CC(c3ccccc3)Oc3ccc(O)cc32)N=C1NCc1ccccc1] |
| 142 | 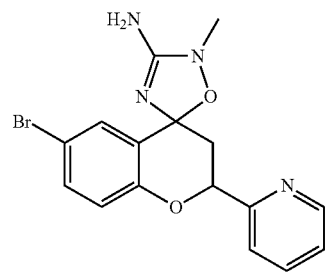 [SMILES: CN1OC2(CC(c3ccccn3)Oc3ccc(Br)cc32)N=C1N] |
| 143 | 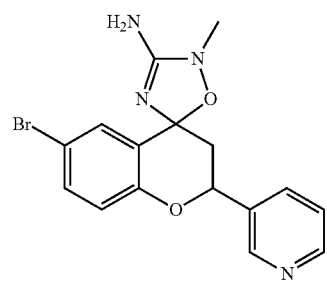 [SMILES: CN1OC2(CC(c3cccnc3)Oc3ccc(Br)cc32)N=C1N] |
| 144 | 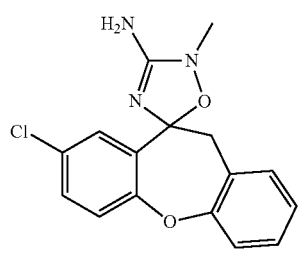 [SMILES: CN1OC2(Cc3ccccc3Oc3ccc(Cl)cc32)N=C1N] |

-continued
| COMPOUND NO. | STRUCTURE |
|---|---|
| 145 | 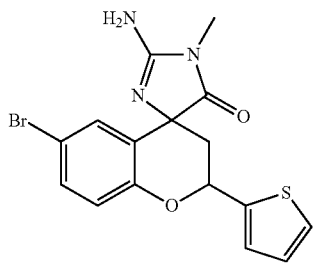 |
| 146 | 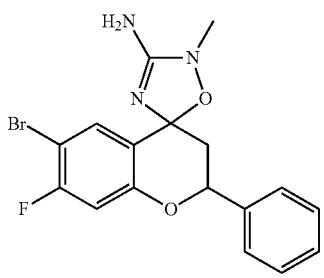 [SMILES: CN1OC2(CC(c3ccccc3)Oc3cc(F)c(Br)cc32)N=C1N] |
| 147 | 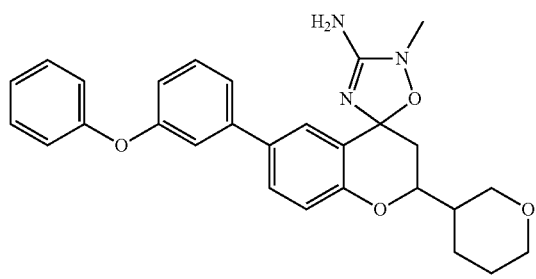 [SMILES: CN1OC2(CC(C3CCCOC3)Oc3ccc(-c4cccc(Oc5ccccc5)c4)cc32)N=C1N] |
| 148 | 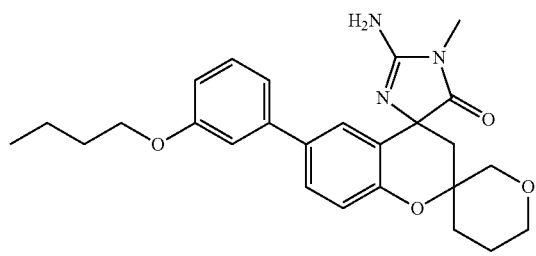 [SMILES: CCCCOc1cccc(-c2ccc3c(c2)C2(CC4(CCCOC4)O3)N=C(N)N(C)C2=O)c1] |
| 150 | 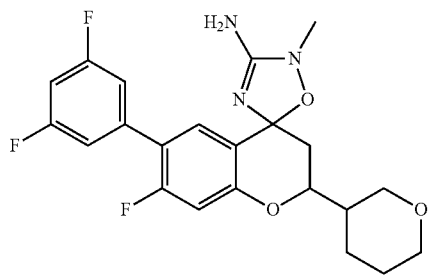 [SMILES: CN1OC2(CC(C3CCCOC3)Oc3cc(F)c(-c4cc(F)cc(F)c4)cc32)N=C1N] |

| COMPOUND NO. | STRUCTURE |
|---|---|
| 151A | 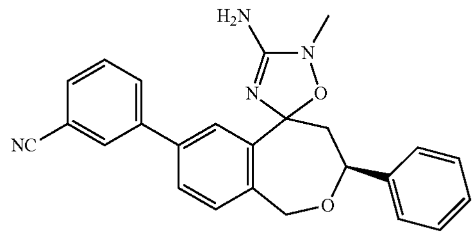 [SMILES: CN1OC2(C[C@@H](c3ccccc3)OCc3ccc(-c4cccc(C#N)c4)cc32)N=C1N] |
| 151B | 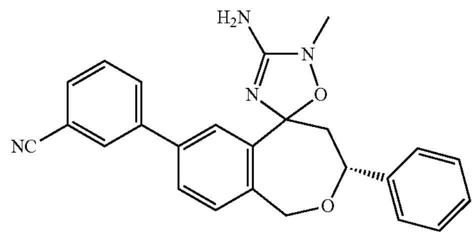 |
| 152 | 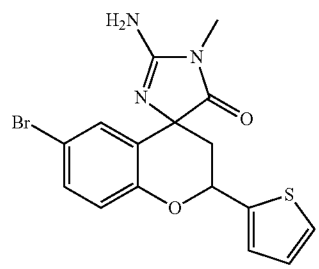 [SMILES: CN1C(=O)C2(CC(c3cccs3)Oc3ccc(Br)cc32)N=C1N] |
| 153 | 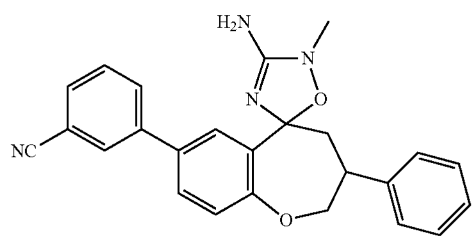 [SMILES: CN1OC2(CC(c3ccccc3)COc3ccc(-c4cccc(C#N)c4)cc32)N=C1N] |
| 154 | 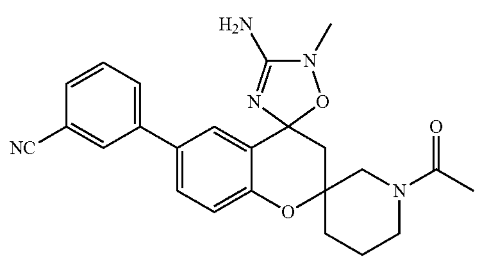 [SMILES: CC(=O)N1CCCC2(C1)CC1(N=C(N)N(C)O1)c1cc(-c3cccc(C#N)c3)ccc1O2] |
| 155 | 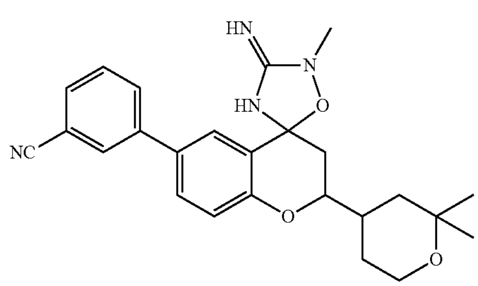 [SMILES: CN1OC2(CC(C3CCOC(C)(C)C3)Oc3ccc(-c4cccc(C#N)c4)cc32)NC1=N] |

-continued

| COMPOUND NO. | STRUCTURE |
|---|---|
| 156 | 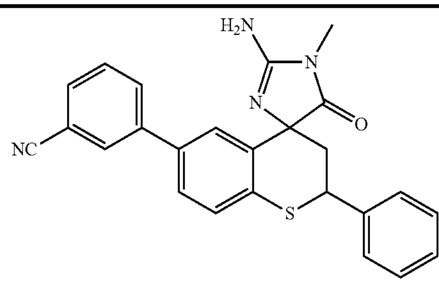 |
| 157 | 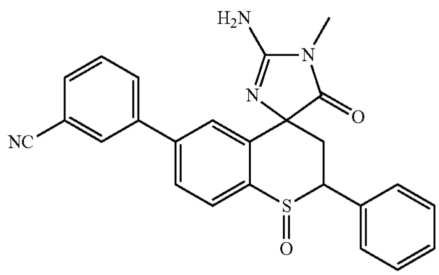 [SMILES: CN1C(=O)C2(CC(c3ccccc3)S(=O)c3ccc(-c4cccc(C#N)c4)cc32)N=C1N] |
| 158 | 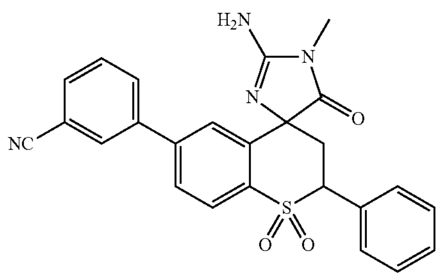 [SMILES: CN1C(=O)C2(CC(c3ccccc3)S(=O)(=O)c3ccc(-c4cccc(C#N)c4)cc32)N=C1N] |
| 159A | 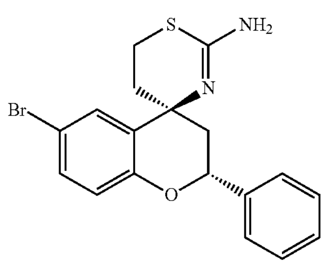 [SMILES: NC1=N[C@@]2(CCS1)C[C@H](c1ccccc1)Oc1ccc(Br)cc12] |
| 159B | 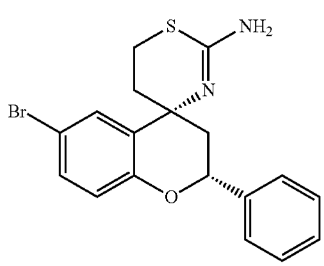 [SMILES: NC1=N[C@]2(CCS1)C[C@H](c1ccccc1)Oc1ccc(Br)cc12] |
| 160 | 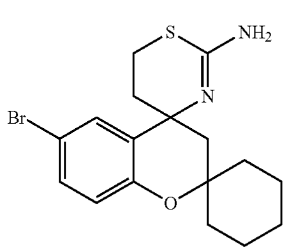 [SMILES: NC1=NC2(CCS1)CC1(CCCCC1)Oc1ccc(Br)cc12] |

-continued
| COMPOUND NO. | STRUCTURE |
|---|---|
| 161 | 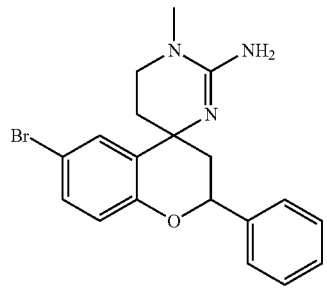 [SMILES: CN1CCC2(CC(c3ccccc3)Oc3ccc(Br)cc32)N=C1N] |
| 162 | 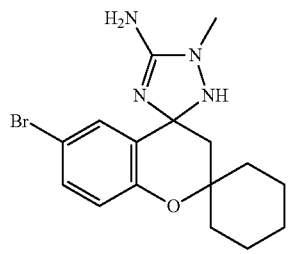 [SMILES: CN1NC2(CC3(CCCCC3)Oc3ccc(Br)cc32)N=C1N] |
| 163 | 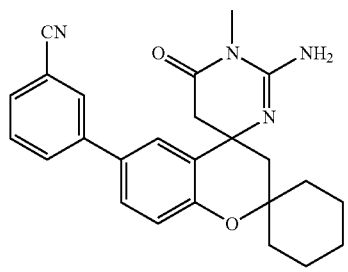 [SMILES: CN1C(=O)CC2(CC3(CCCCC3)Oc3ccc(-c4cccc(C#N)c4)cc32)N=C1N] |
| 164 | 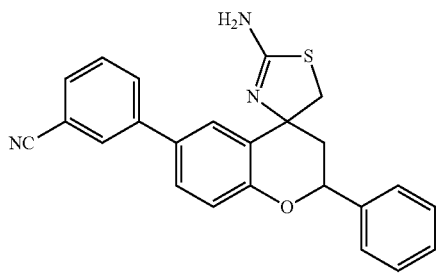 [SMILES: N#Cc1cccc(-c2ccc3c(c2)C2(CSC(N)=N2)CC(c2ccccc2)O3)c1] |
| 165 | 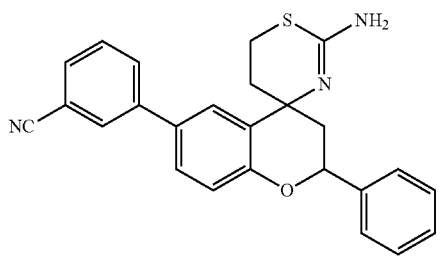 [SMILES: N#Cc1cccc(-c2ccc3c(c2)C2(CCSC(N)=N2)CC(c2ccccc2)O3)c1] |

-continued
| COMPOUND NO. | STRUCTURE |
|---|---|
| 166 | 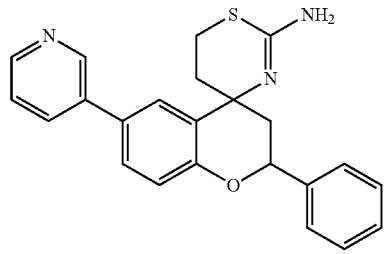 [SMILES: NC1=NC2(CCS1)CC(c1ccccc1)Oc1ccc(-c3cccnc3)cc12] |
| 167 | 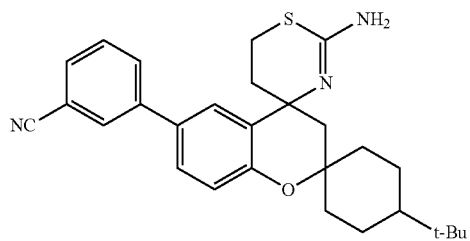 [SMILES: CC(C)(C)C1CCC2(CC1)CC1(CCSC(N)=N1)c1cc(-c3cccc(C#N)c3)ccc1O2] |
| 168 | 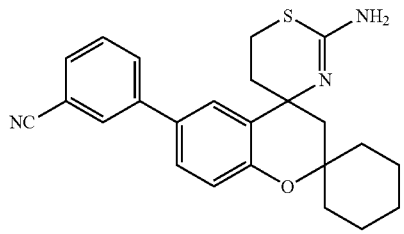 [SMILES: N#Cc1cccc(-c2ccc3c(c2)C2(CCSC(N)=N2)CC2(CCCCC2)O3)c1] |
| 169 | 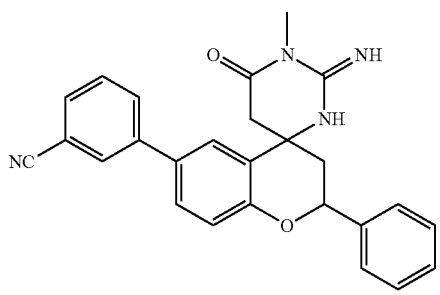 [SMILES: CN1C(=N)NC2(CC1=O)CC(c1ccccc1)Oc1ccc(-c3cccc(C#N)c3)cc12] |
| 170 | 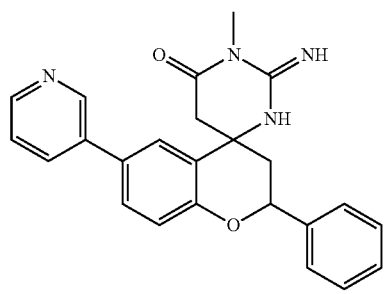 [SMILES: CN1C(=N)NC2(CC1=O)CC(c1ccccc1)Oc1ccc(-c3cccnc3)cc12] |

-continued
| COMPOUND NO. | STRUCTURE |
|---|---|
| 171 | 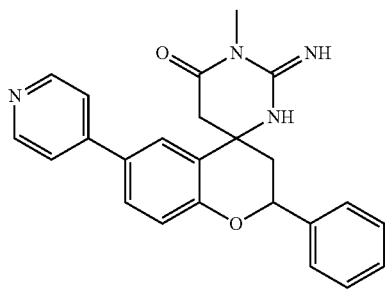 [SMILES: CN1C(=N)NC2(CC1=O)CC(c1ccccc1)Oc1ccc(-c3ccncc3)cc12] |
| 172 | 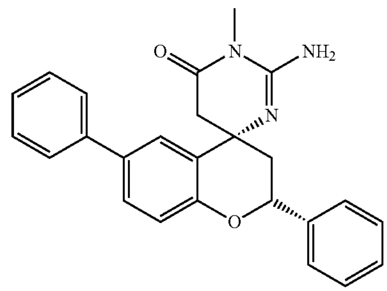 |
| 173 | 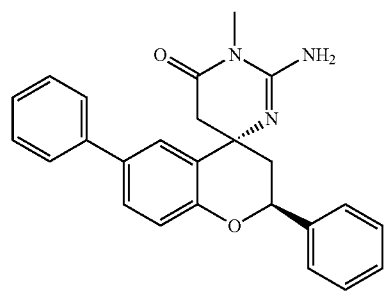 [SMILES: CN1C(=O)C[C@]2(C[C@@H](c3ccccc3)Oc3ccc(-c4ccccc4)cc32)N=C1N] |
| 174 | 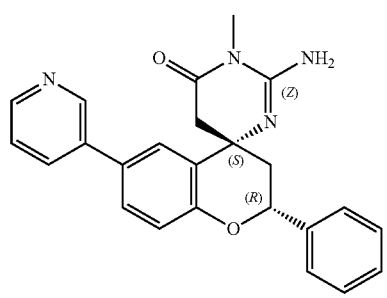 |
| 175 | 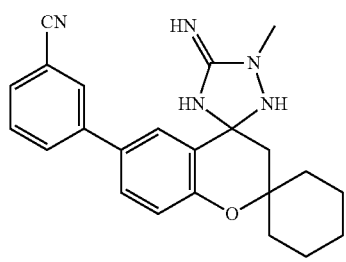 [SMILES: CN1NC2(CC3(CCCCC3)Oc3ccc(-c4cccc(C#N)c4)cc32)NC1=N] |

-continued
| COMPOUND NO. | STRUCTURE |
|---|---|
| 176 | 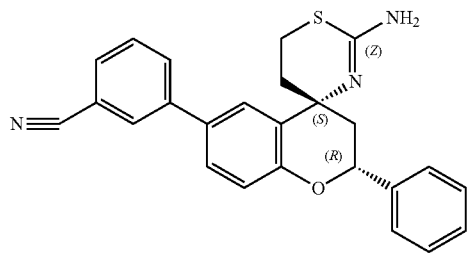 |
| 177 | 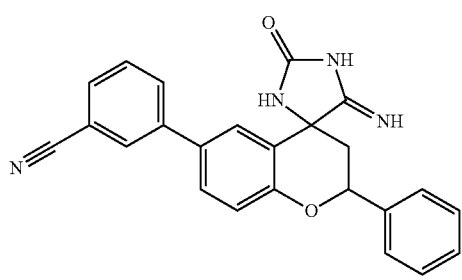 [SMILES: N#Cc1cccc(-c2ccc3c(c2)C2(CC(c4ccccc4)O3)NC(=O)NC2=N)c1] |
| 178 | 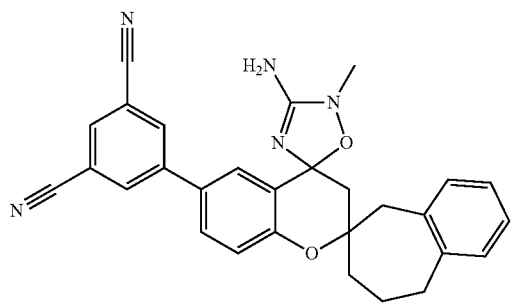 [SMILES: CN1OC2(CC3(CCCc4ccccc4C3)Oc3ccc(-c4cc(C#N)cc(C#N)c4)cc32)N=C1N] |
| 179 | 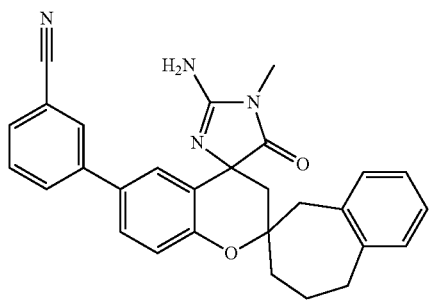 [SMILES: CN1C(=O)C2(CC3(CCCc4ccccc4C3)Oc3ccc(-c4cccc(C#N)c4)cc32)N=C1N] |
| 180 | 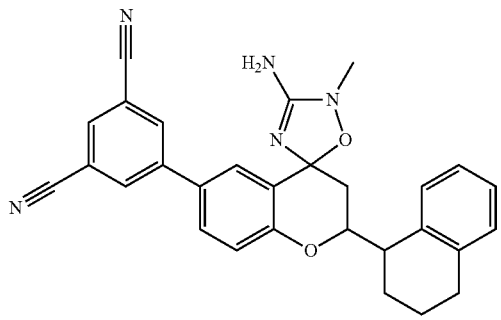 [SMILES: CN1OC2(CC(C3CCCc4ccccc43)Oc3ccc(-c4cc(C#N)cc(C#N)c4)cc32)N=C1N] |

-continued
| COMPOUND NO. | STRUCTURE |
|---|---|
| 181 | 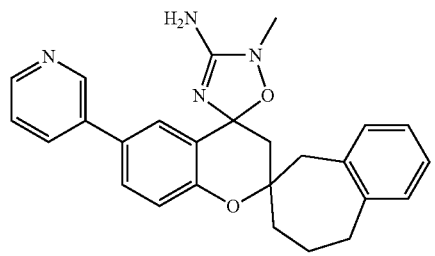 [SMILES: CN1OC2(CC3(CCCc4ccccc4C3)Oc3ccc(-c4cccnc4)cc32)N=C1N] |
| 182 | 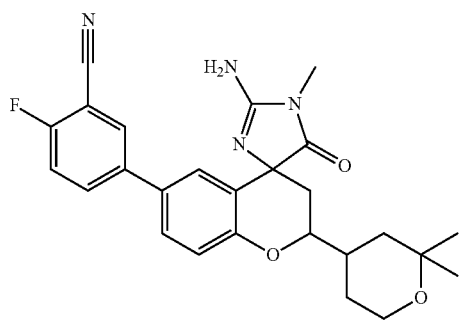 [SMILES: CN1C(=O)C2(CC(C3CCOC(C)(C)C3)Oc3ccc(-c4ccc(F)c(C#N)c4)cc32)N=C1N] |
| 183 | 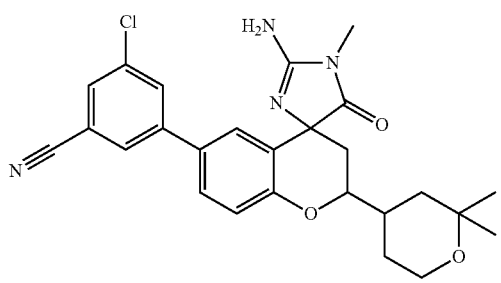 [SMILES: CN1C(=O)C2(CC(C3CCOC(C)(C)C3)Oc3ccc(-c4cc(Cl)cc(C#N)c4)cc32)N=C1N] |
| 184 | 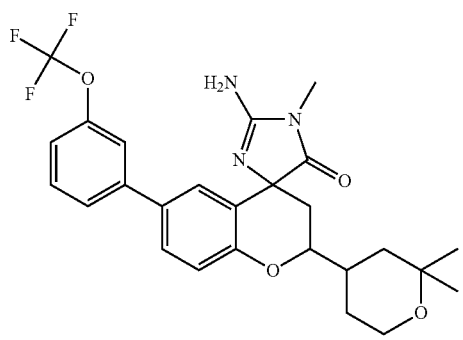 [SMILES: CN1C(=O)C2(CC(C3CCOC(C)(C)C3)Oc3ccc(-c4cccc(OC(F)(F)F)c4)cc32)N=C1N] |
| 185 | 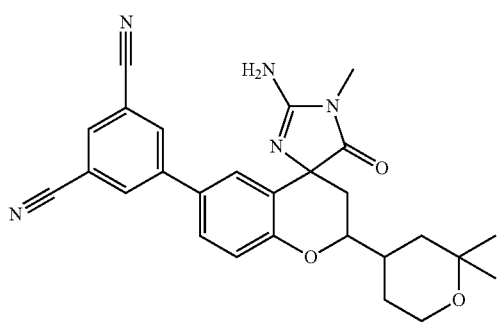 [SMILES: CN1C(=O)C2(CC(C3CCOC(C)(C)C3)Oc3ccc(-c4cc(C#N)cc(C#N)c4)cc32)N=C1N] |

-continued
| COMPOUND NO. | STRUCTURE |
|---|---|
| 186 | 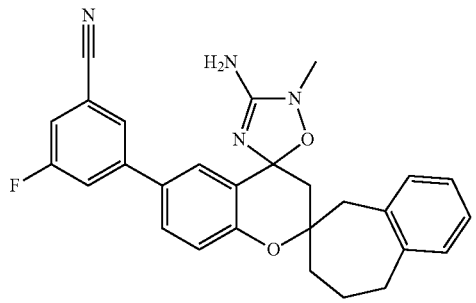 [SMILES: CN1OC2(CC3(CCCc4ccccc4C3)Oc3ccc(-c4cc(F)cc(C#N)c4)cc32)N=C1N] |
| 187 | 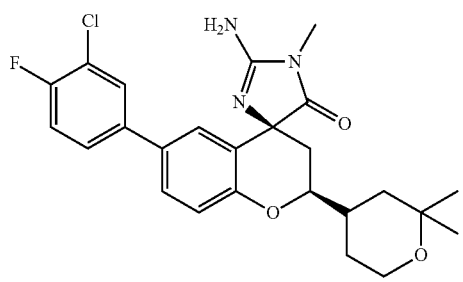 [SMILES: CN1C(=O)[C@@]2(C[C@@H](C3CCOC(C)(C)C3)Oc3ccc(-c4ccc(F)c(Cl)c4)cc32)N=C1N] |
| 188 | 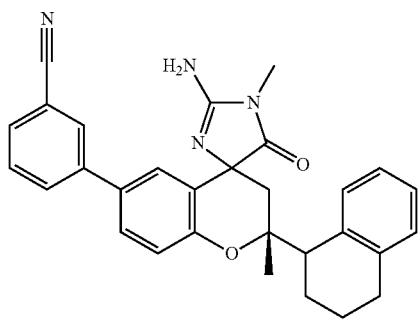 |
| 189 | 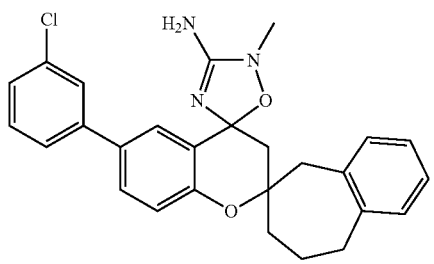 [SMILES: CN1OC2(CC3(CCCc4ccccc4C3)Oc3ccc(-c4cccc(Cl)c4)cc32)N=C1N] |
| 190 | 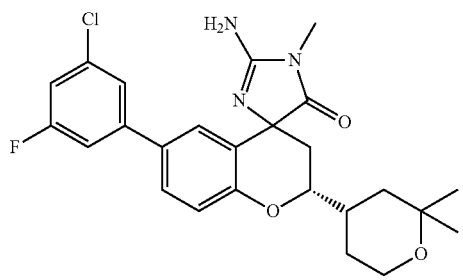 [SMILES: CN1C(=O)C2(C[C@H](C3CCOC(C)(C)C3)Oc3ccc(-c4cc(F)cc(Cl)c4)cc32)N=C1N] |

-continued
| COMPOUND NO. | STRUCTURE |
|---|---|
| 191 | 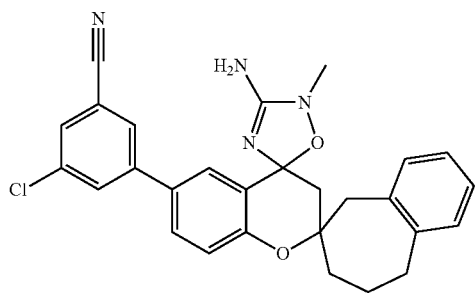 [SMILES: CN1OC2(CC3(CCCc4ccccc4C3)Oc3ccc(-c4cc(Cl)cc(C#N)c4)cc32)N=C1N] |
| 192 | 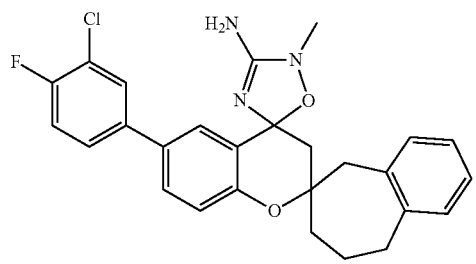 [SMILES: CN1OC2(CC3(CCCc4ccccc4C3)Oc3ccc(-c4ccc(F)c(Cl)c4)cc32)N=C1N] |
| 193 | 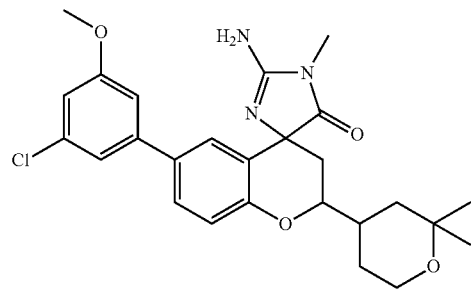 [SMILES: COc1cc(Cl)cc(-c2ccc3c(c2)C2(CC(C4CCOC(C)(C)C4)O3)N=C(N)N(C)C2=O)c1] |
| 194 | 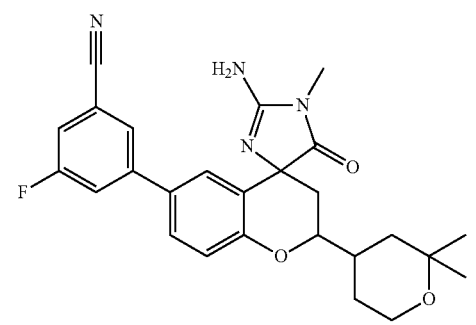 [SMILES: CN1C(=O)C2(CC(C3CCOC(C)(C)C3)Oc3ccc(-c4cc(F)cc(C#N)c4)cc32)N=C1N] |
| 195 | 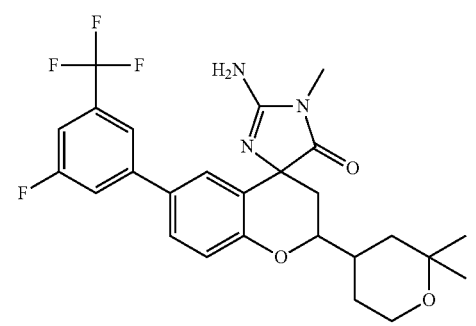 [SMILES: CN1C(=O)C2(CC(C3CCOC(C)(C)C3)Oc3ccc(-c4cc(F)cc(C(F)(F)F)c4)cc32)N=C1N] |

| COMPOUND NO. | STRUCTURE |
|---|---|
| 196 | 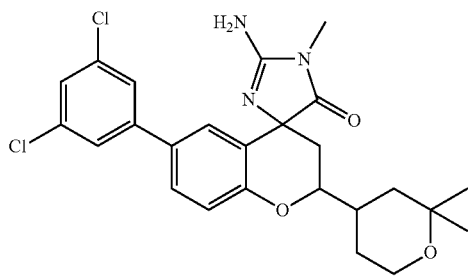 [SMILES: CN1C(=O)C2(CC(C3CCOC(C)(C)C3)Oc3ccc(-c4cc(Cl)cc(Cl)c4)cc32)N=C1N] |
| 197 | 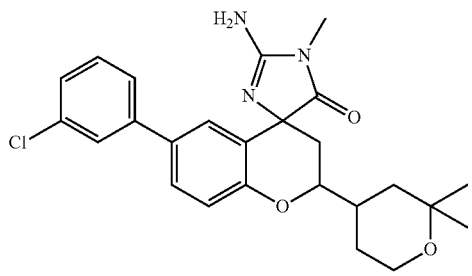 [SMILES: CN1C(=O)C2(CC(C3CCOC(C)(C)C3)Oc3ccc(-c4cccc(Cl)c4)cc32)N=C1N] |
| 198 | 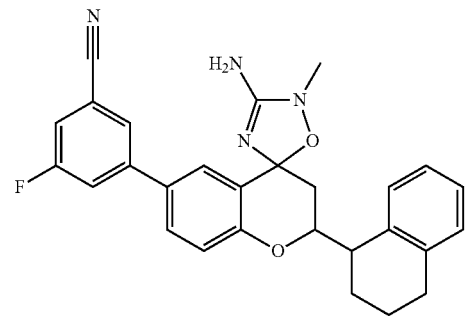 [SMILES: CN1OC2(CC(C3CCCc4ccccc43)Oc3ccc(-c4cc(F)cc(C#N)c4)cc32)N=C1N] |
| 199 | 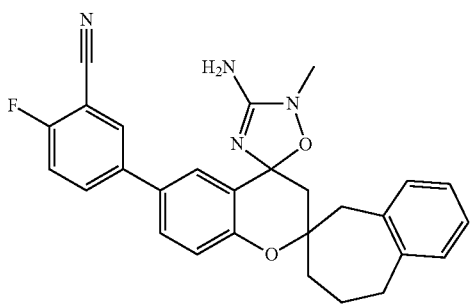 [SMILES: CN1OC2(CC3(CCCc4ccccc4C3)Oc3ccc(-c4ccc(F)c(C#N)c4)cc32)N=C1N] |
| 200 | 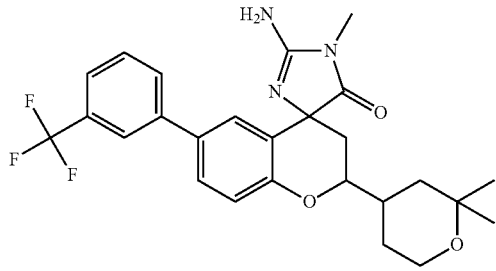 [SMILES: CN1C(=O)C2(CC(C3CCOC(C)(C)C3)Oc3ccc(-c4cccc(C(F)(F)F)c4)cc32)N=C1N] |

| COMPOUND NO. | STRUCTURE |
|---|---|
| 201 | 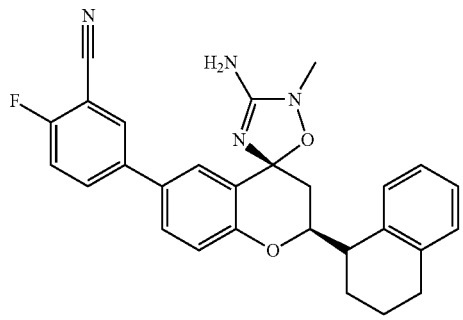 [SMILES: CN1O[C@@]2(C[C@@H](C3CCCc4ccccc43)Oc3ccc(-c4ccc(F)c(C#N)c4)cc32)N=C1N] |
| 202 | 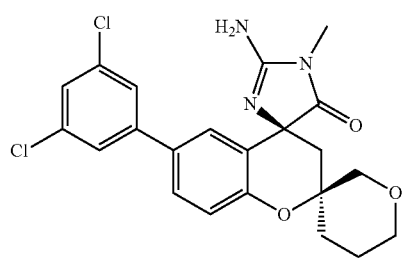 [SMILES: CN1C(=O)[C@@]2(C[C@]3(CCCOC3)Oc3ccc(-c4cc(Cl)cc(Cl)c4)cc32)N=C1N] |
| 203 | 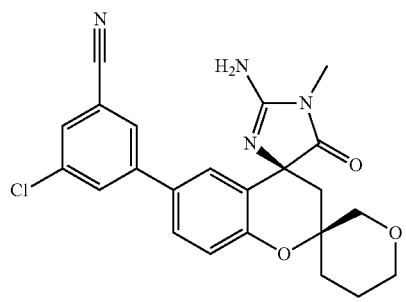 [SMILES: CN1C(=O)[C@@]2(C[C@]3(CCCOC3)Oc3ccc(-c4cc(Cl)cc(C#N)c4)cc32)N=C1N] |
| 204 | 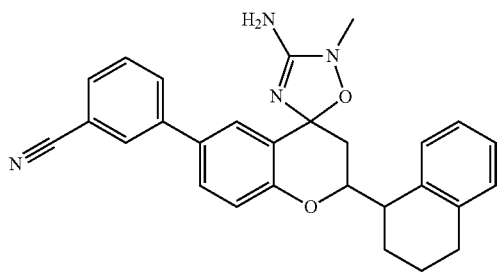 [SMILES: CN1OC2(CC(C3CCCc4ccccc43)Oc3ccc(-c4cccc(C#N)c4)cc32)N=C1N] |
| 205 | 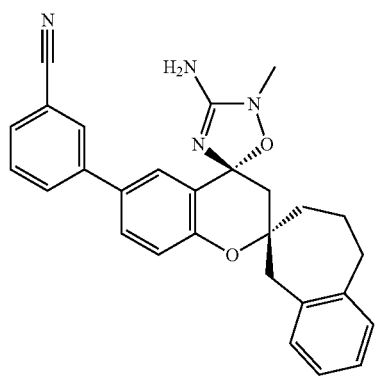 [SMILES: CN1O[C@@]2(C[C@]3(CCCc4ccccc4C3)Oc3ccc(-c4cccc(C#N)c4)cc32)N=C1N] |

-continued
| COMPOUND NO. | STRUCTURE |
|---|---|
| 206 | 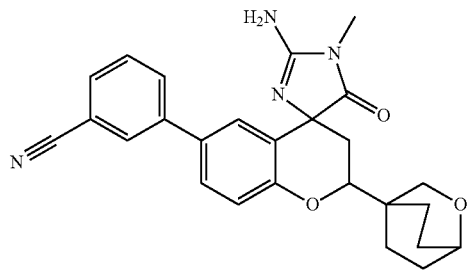 [SMILES: CN1C(=O)C2(CC(C34CCC(CC3)OC4)Oc3ccc(-c4cccc(C#N)c4)cc32)N=C1N] |
| 207 | 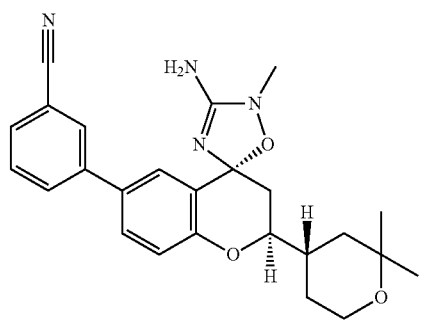 [SMILES: CN1O[C@@]2(C[C@@H]([C@H]3CCOC(C)(C)C3)Oc3ccc(-c4cccc(C#N)c4)cc32)N=C1N] |
| 208 | 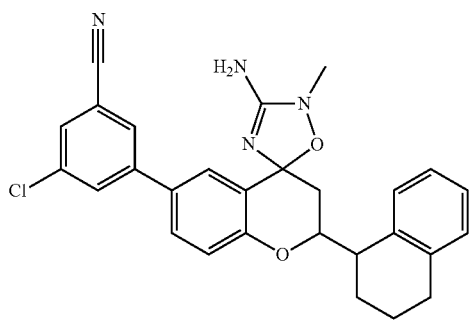 [SMILES: CN1OC2(CC(C3CCCc4ccccc43)Oc3ccc(-c4cc(Cl)cc(C#N)c4)cc32)N=C1N] |
| 209 | 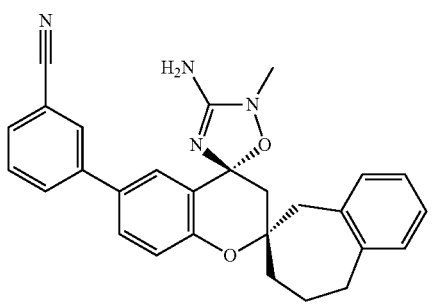 [SMILES: CN1O[C@@]2(C[C@@]3(CCCc4ccccc4C3)Oc3ccc(-c4cccc(C#N)c4)cc32)N=C1N] |
| 210 | 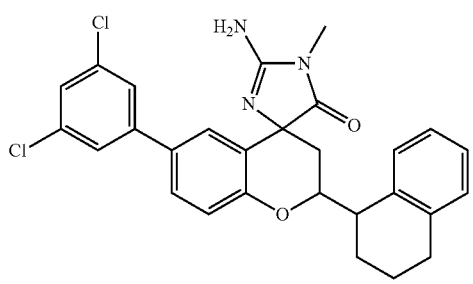 [SMILES: CN1C(=O)C2(CC(C3CCCc4ccccc43)Oc3ccc(-c4cc(Cl)cc(Cl)c4)cc32)N=C1N] |

131
-continued
| COMPOUND NO. | STRUCTURE |
|---|---|
| 211 | 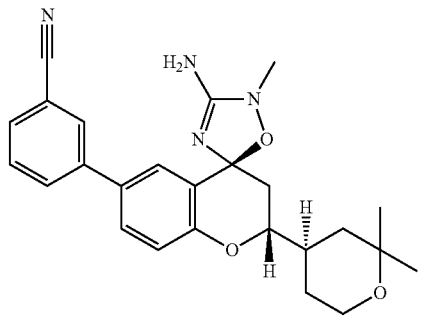 [SMILES: CN1O[C@]2(C[C@H]([C@@H]3CCOC(C)(C)C3)Oc3ccc(-c4cccc(C#N)c4)cc32)N=C1N] |
| 212 | 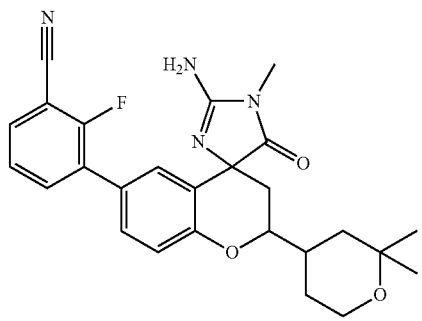 [SMILES: CN1C(=O)C2(CC(C3CCOC(C)(C)C3)Oc3ccc(-c4cccc(C#N)c4F)cc32)N=C1N] |
| 213 | 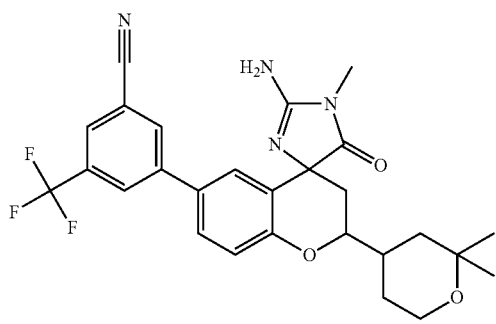 [SMILES: CN1C(=O)C2(CC(C3CCOC(C)(C)C3)Oc3ccc(-c4cc(C#N)cc(C(F)(F)F)c4)cc32)N=C1N] |
| 214 | 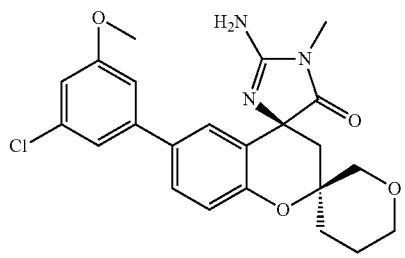 [SMILES: COc1cc(Cl)cc(-c2ccc3c(c2)[C@]2(C[C@]4(CCCOC4)O3)N=C(N)N(C)C2=O)c1] |
| 215 | 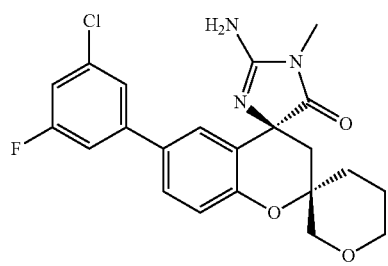 [SMILES: CN1C(=O)[C@@]2(C[C@]3(CCCOC3)Oc3ccc(-c4cc(F)cc(Cl)c4)cc32)N=C1N] |
132

| COMPOUND NO. | STRUCTURE |
| --- | --- |
| 216 | 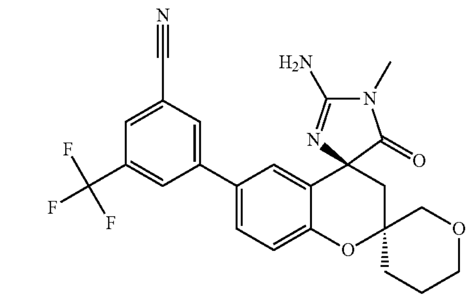 [SMILES: CN1C(=O)[C@@]2(C[C@]3(CCCOC3)Oc3ccc(-c4cc(C#N)cc(C(F)(F)F)c4)cc32)N=C1N] |
| 217 | 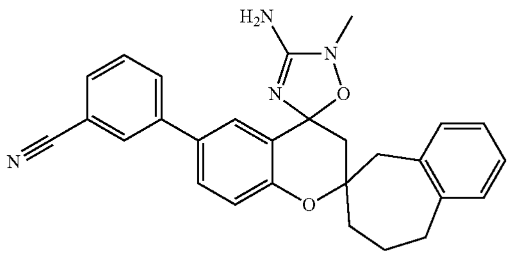 [SMILES: CN1OC2(CC3(CCCc4ccccc4C3)Oc3ccc(-c4cccc(C#N)c4)cc32)N=C1N] |
| 218 | 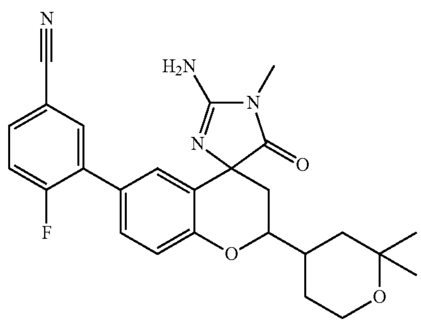 |
| 219 | 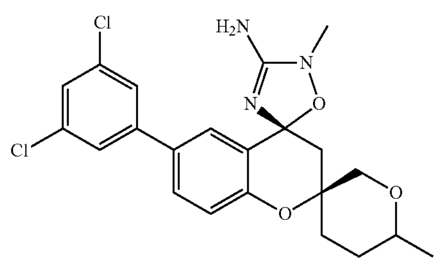 |
| 220 | 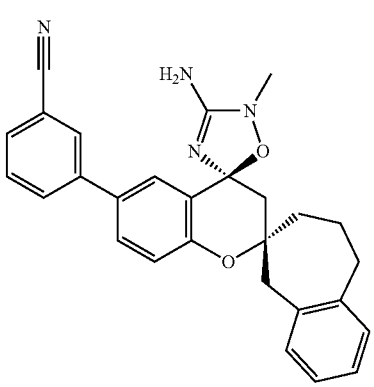 [SMILES: CN1O[C@]2(C[C@]3(CCCc4ccccc4C3)Oc3ccc(-c4cccc(C#N)c4)cc32)N=C1N] |

-continued
| COMPOUND NO. | STRUCTURE |
|---|---|
| 221 | 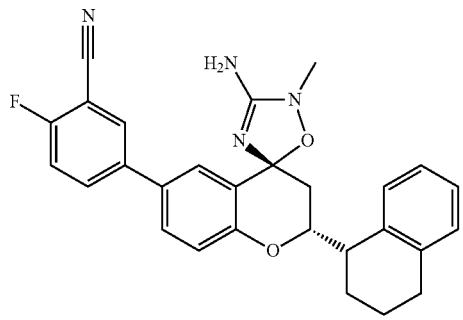 [SMILES: CN1O[C@@]2(C[C@H](C3CCCc4ccccc43)Oc3ccc(-c4ccc(F)c(C#N)c4)cc32)N=C1N] |
| 222 | 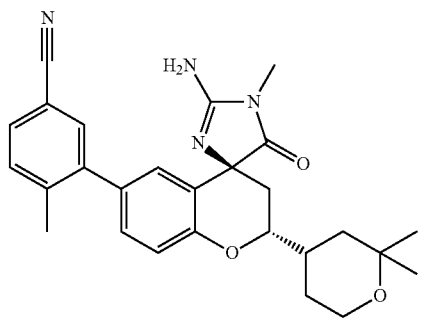 [SMILES: Cc1ccc(C#N)cc1-c1ccc2c(c1)[C@]1(C[C@H](C3CCOC(C)(C)C3)O2)N=C(N)N(C)C1=O] |
| 223 | 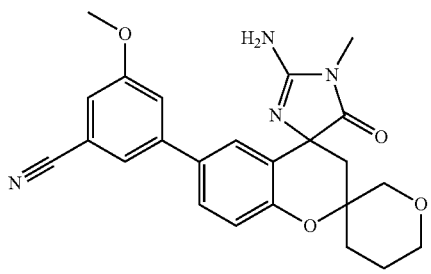 [SMILES: COc1cc(C#N)cc(-c2ccc3c(c2)C2(CC4(CCCOC4)O3)N=C(N)N(C)C2=O)c1] |
| 224 | 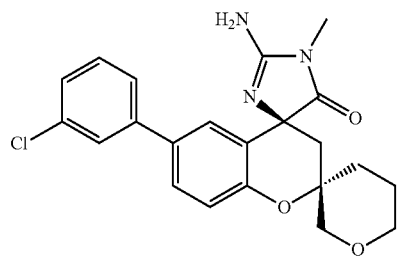 [SMILES: CN1C(=O)[C@@]2(C[C@]3(CCCOC3)Oc3ccc(-c4cccc(Cl)c4)cc32)N=C1N] |
| 225 | 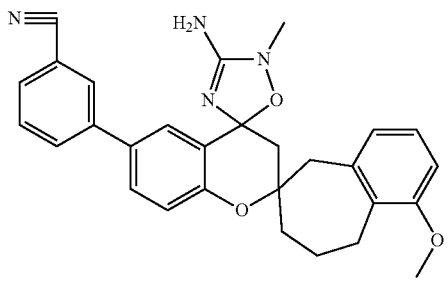 [SMILES: COc1cccc2c1CCCC1(C2)CC2(N=C(N)N(C)O2)c2cc(-c3cccc(C#N)c3)ccc2O1] |

| COMPOUND NO. | STRUCTURE |
|---|---|
| 226 | 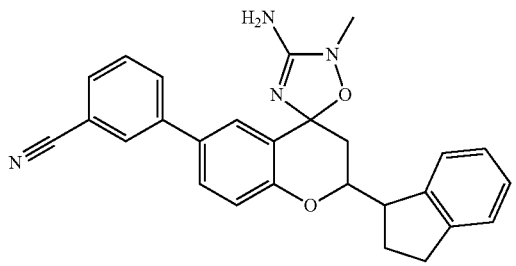 [SMILES: CN1OC2(CC(C3CCc4ccccc43)Oc3ccc(-c4cccc(C#N)c4)cc32)N=C1N] |
| 227 | 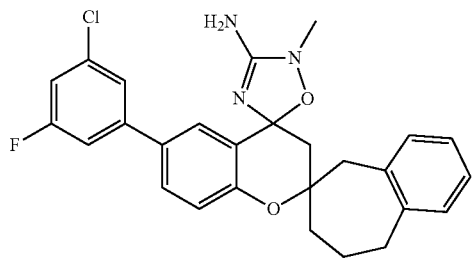 [SMILES: CN1OC2(CC3(CCCc4ccccc4C3)Oc3ccc(-c4cc(F)cc(Cl)c4)cc32)N=C1N] |
| 228 | 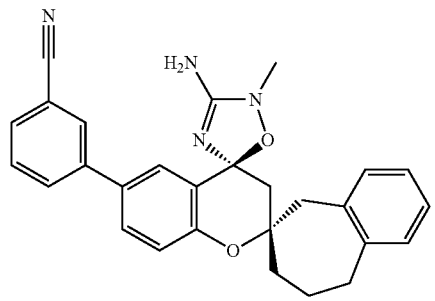 [SMILES: CN1O[C@]2(C[C@@]3(CCCc4ccccc4C3)Oc3ccc(-c4cccc(C#N)c4)cc32)N=C1N] |
| 229 | 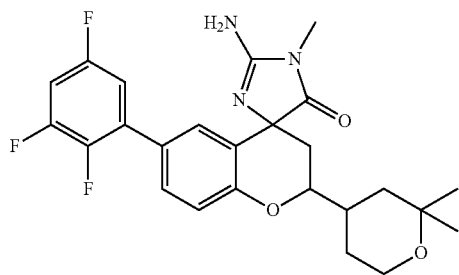 [SMILES: CN1C(=O)C2(CC(C3CCOC(C)(C)C3)Oc3ccc(-c4cc(F)cc(F)c4F)cc32)N=C1N] |
| 230 | 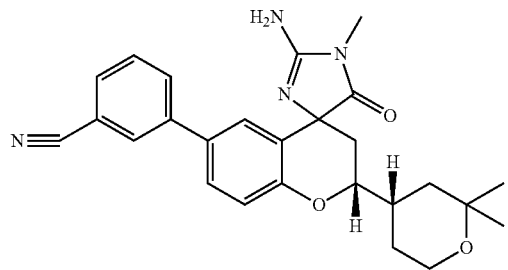 [SMILES: CN1C(=O)C2(C[C@H]([C@H]3CCOC(C)(C)C3)Oc3ccc(-c4cccc(C#N)c4)cc32)N=C1N] |

| COMPOUND NO. | STRUCTURE |
|---|---|
| 231 | 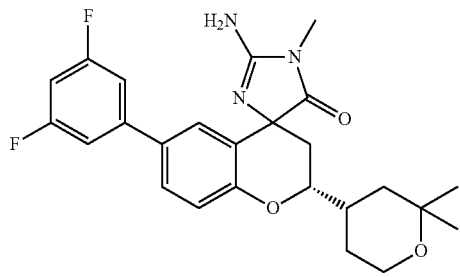 [SMILES: CN1C(=O)C2(C[C@H](C3CCOC(C)(C)C3)Oc3ccc(-c4cc(F)cc(F)c4)cc32)N=C1N] |
| 232 | 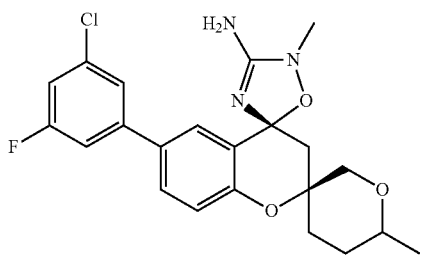 |
| 233 | 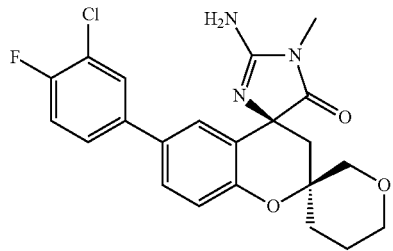 [SMILES: CN1C(=O)[C@@]2(C[C@]3(CCCOC3)Oc3ccc(-c4ccc(F)c(Cl)c4)cc32)N=C1N] |
| 234 | 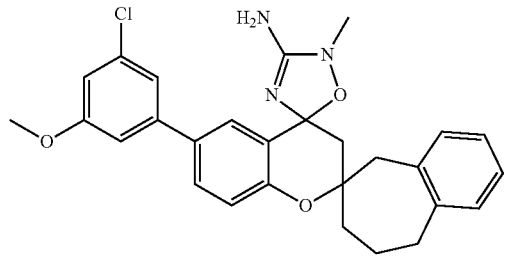 [SMILES: COc1cc(Cl)cc(-c2ccc3c(c2)C2(CC4(CCCc5ccccc5C4)O3)N=C(N)N(C)O2)c1] |
| 235 | 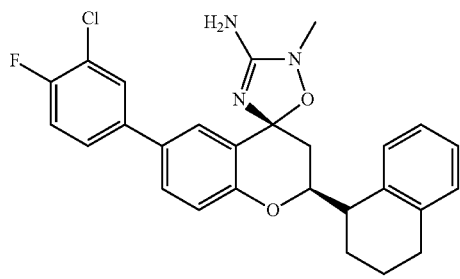 [SMILES: CN1O[C@@]2(C[C@@H](C3CCCc4ccccc43)Oc3ccc(-c4ccc(F)c(Cl)c4)cc32)N=C1N] |

| COMPOUND NO. | STRUCTURE |
|---|---|
| 236 | 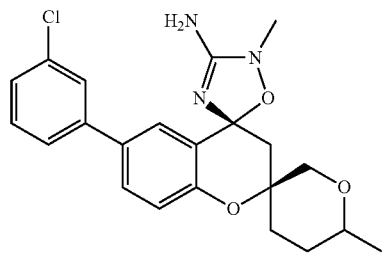 |
| 237 | 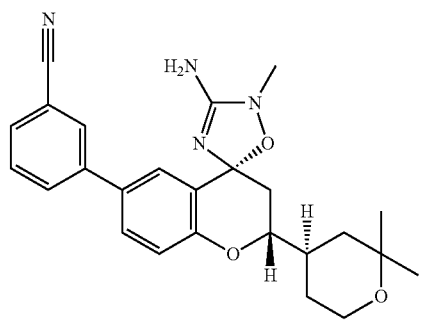 [SMILES: CN1O[C@@]2(C[C@H]([C@@H]3CCOC(C)(C)C3)Oc3ccc(-c4cccc(C#N)c4)cc32)N=C1N] |
| 238 | 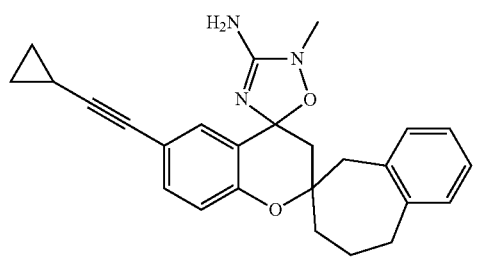 [SMILES: CN1OC2(CC3(CCCc4ccccc4C3)Oc3ccc(C#CC4CC4)cc32)N=C1N] |
| 239 | 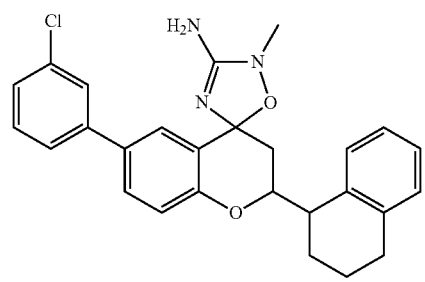 [SMILES: CN1OC2(CC(C3CCCc4ccccc43)Oc3ccc(-c4cccc(Cl)c4)cc32)N=C1N] |
| 240 | 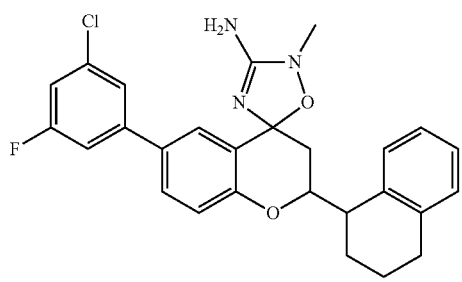 [SMILES: CN1OC2(CC(C3CCCc4ccccc43)Oc3ccc(-c4cc(F)cc(Cl)c4)cc32)N=C1N] |

| COMPOUND NO. | STRUCTURE |
|---|---|
| 241 | 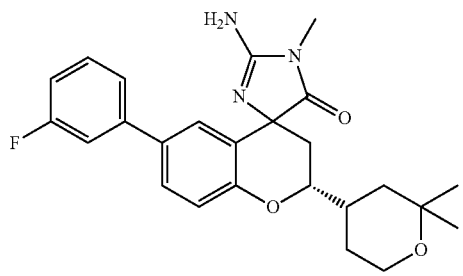 [SMILES: CN1C(=O)C2(C[C@H](C3CCOC(C)(C)C3)Oc3ccc(-c4cccc(F)c4)cc32)N=C1N] |
| 242 | 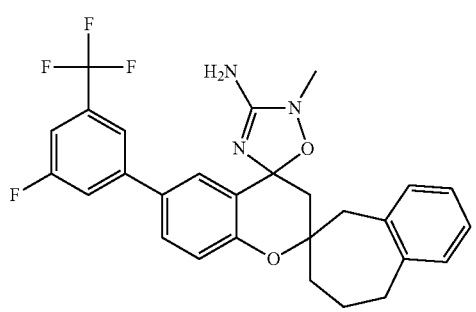 [SMILES: CN1OC2(CC3(CCCc4ccccc4C3)Oc3ccc(-c4cc(F)cc(C(F)(F)F)c4)cc32)N=C1N] |
| 243 | 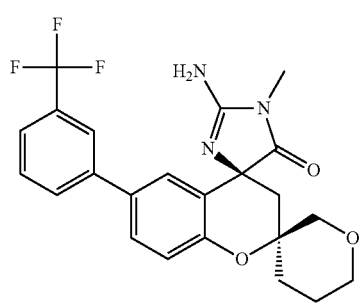 [SMILES: CN1C(=O)[C@@]2(C[C@]3(CCCOC3)Oc3ccc(-c4cccc(C(F)(F)F)c4)cc32)N=C1N] |
| 244 | 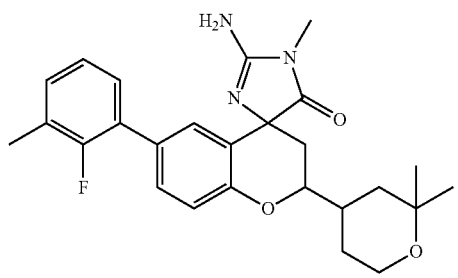 |
| 245 | 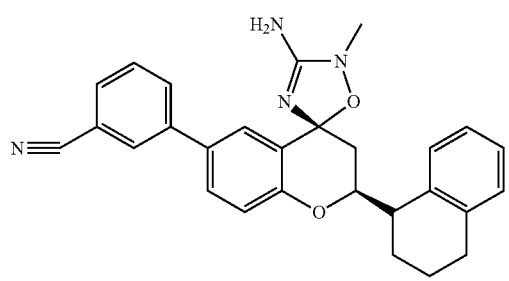 [SMILES: CN1O[C@@]2(C[C@@H](C3CCCc4ccccc43)Oc3ccc(-c4cccc(C#N)c4)cc32)N=C1N] |

US 8,921,359 B2
145    146
-continued
| COMPOUND NO. | STRUCTURE |
|---|---|
| 246 | 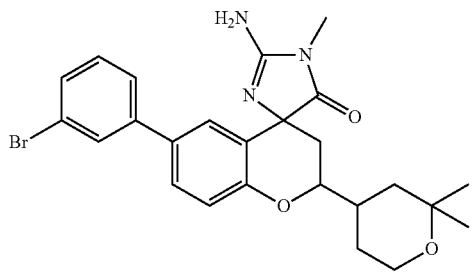 |
| 247 | 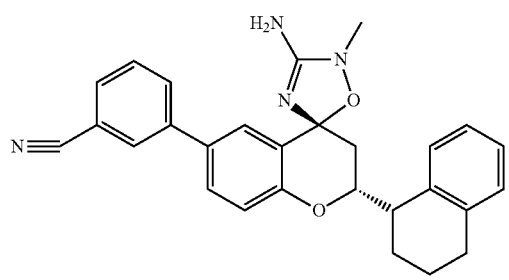 [SMILES: CN1O[C@@]2(C[C@H](C3CCCc4ccccc43)Oc3ccc(-c4cccc(C#N)c4)cc32)N=C1N] |
| 248 | 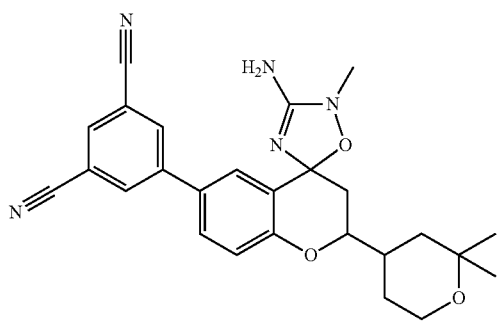 [SMILES: CN1OC2(CC(C3CCOC(C)(C)C3)Oc3ccc(-c4cc(C#N)cc(C#N)c4)cc32)N=C1N] |
| 249 | 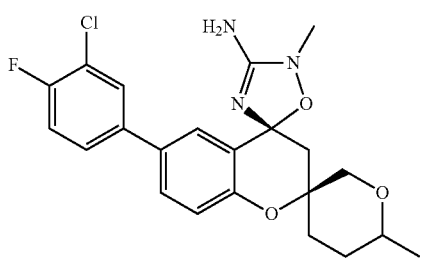 |
| 250 | 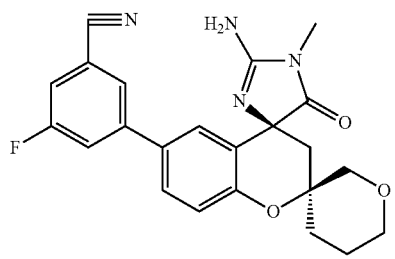 [SMILES: CN1C(=O)[C@@]2(C[C@]3(CCCOC3)Oc3ccc(-c4cc(F)cc(C#N)c4)cc32)N=C1N] |

-continued
| COMPOUND NO. | STRUCTURE |
|---|---|
| 251 | 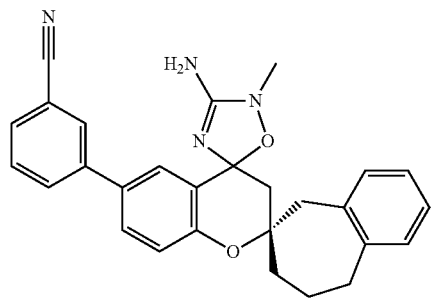 [SMILES: CN1OC2(C[C@@]3(CCCc4ccccc4C3)Oc3ccc(-c4cccc(C#N)c4)cc32)N=C1N] |
| 252 | 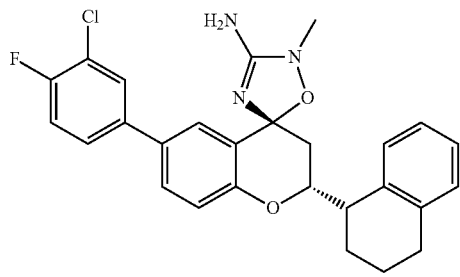 [SMILES: CN1O[C@@]2(C[C@H](C3CCCc4ccccc43)Oc3ccc(-c4ccc(F)c(Cl)c4)cc32)N=C1N] |
| 253 | 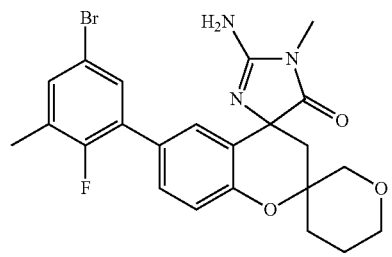 [SMILES: Cc1cc(Br)cc(-c2ccc3c(c2)C2(CC4(CCCOC4)O3)N=C(N)N(C)C2=O)c1F] |
| 254 | 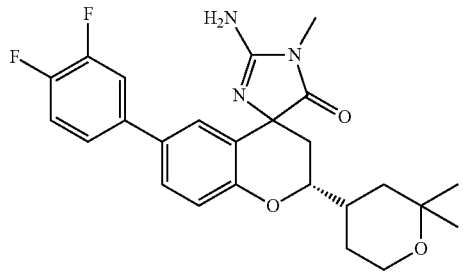 [SMILES: CN1C(=O)C2(C[C@H](C3CCOC(C)(C)C3)Oc3ccc(-c4ccc(F)c(F)c4)cc32)N=C1N] |
| 255 | 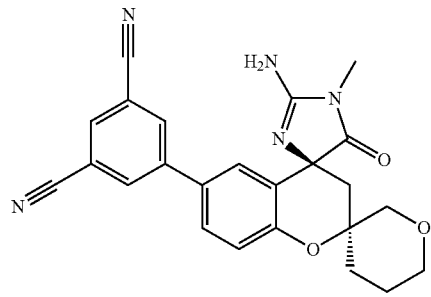 [SMILES: CN1C(=O)[C@@]2(C[C@]3(CCCOC3)Oc3ccc(-c4cc(C#N)cc(C#N)c4)cc32)N=C1N] |

| COMPOUND NO. | STRUCTURE |
|---|---|
| 256 | 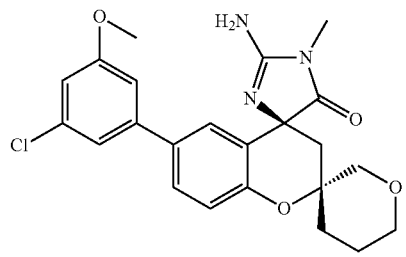 [SMILES: COc1cc(Cl)cc(-c2ccc3c(c2)[C@]2(C[C@@]4(CCCOC4)O3)N=C(N)N(C)C2=O)c1] |
| 257 | 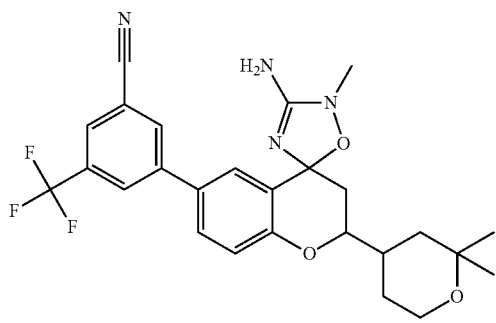 [SMILES: CN1OC2(CC(C3CCOC(C)(C)C3)Oc3ccc(-c4cc(C#N)cc(C(F)(F)F)c4)cc32)N=C1N] |
| 258 | 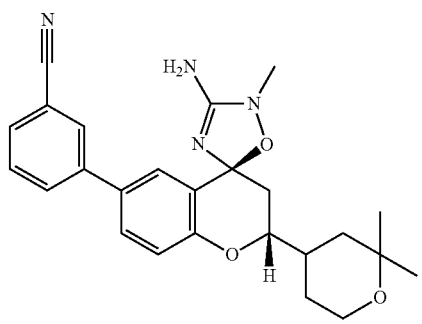 [SMILES: CN1O[C@]2(C[C@H](C3CCOC(C)(C)C3)Oc3ccc(-c4cccc(C#N)c4)cc32)N=C1N] |
| 259 | 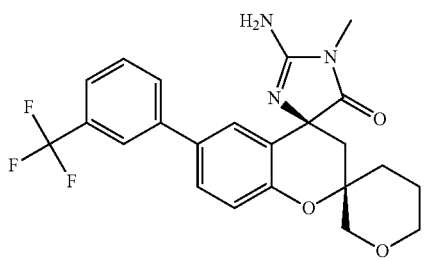 [SMILES: CN1C(=O)[C@@]2(C[C@]3(CCCOC3)Oc3ccc(-c4cccc(C(F)(F)F)c4)cc32)N=C1N] |
| 260 | 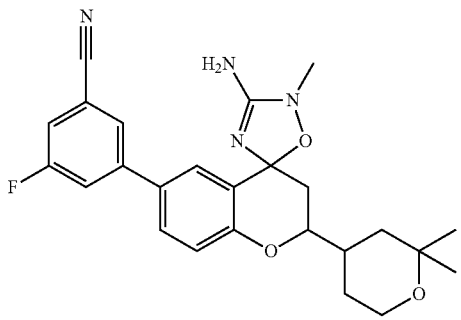 [SMILES: CN1OC2(CC(C3CCOC(C)(C)C3)Oc3ccc(-c4cc(F)cc(C#N)c4)cc32)N=C1N] |

| COMPOUND NO. | STRUCTURE |
|---|---|
| 261 | 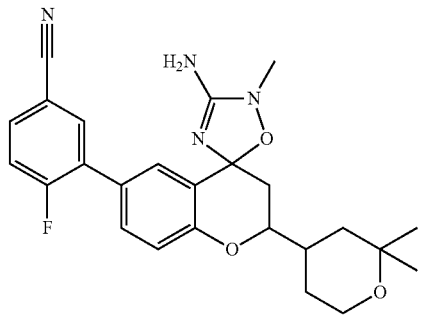 |
| 262 | 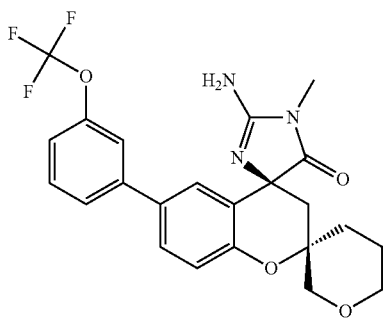 [SMILES: CN1C(=O)[C@@]2(C[C@]3(CCCOC3)Oc3ccc(-c4cccc(OC(F)(F)F)c4)cc32)N=C1N] |
| 263 | 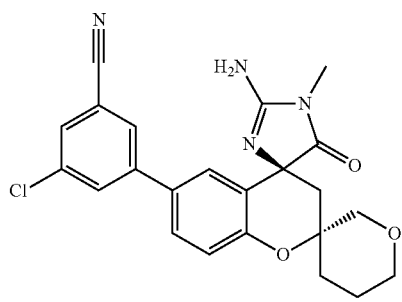 [SMILES: CN1C(=O)[C@@]2(C[C@@]3(CCCOC3)Oc3ccc(-c4cc(Cl)cc(C#N)c4)cc32)N=C1N] |
| 264 | 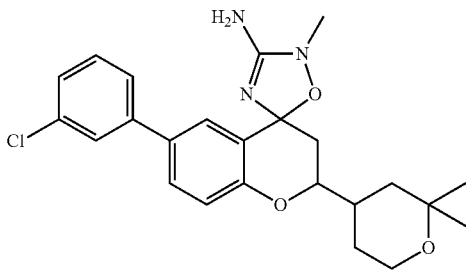 [SMILES: CN1OC2(CC(C3CCOC(C)(C)C3)Oc3ccc(-c4cccc(Cl)c4)cc32)N=C1N] |
| 265 | 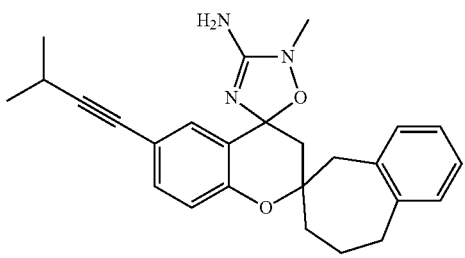 [SMILES: CC(C)C#Cc1ccc2c(c1)C1(CC3(CCCc4ccccc4C3)O2)N=C(N)N(C)O1] |

-continued
| COMPOUND NO. | STRUCTURE |
|---|---|
| 266 | 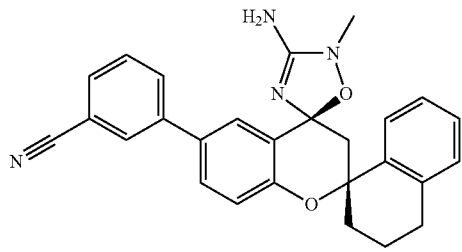 [SMILES: CN1O[C@]2(C[C@@]3(CCCc4ccccc43)Oc3ccc(-c4cccc(C#N)c4)cc32)N=C1N] |
| 267 | 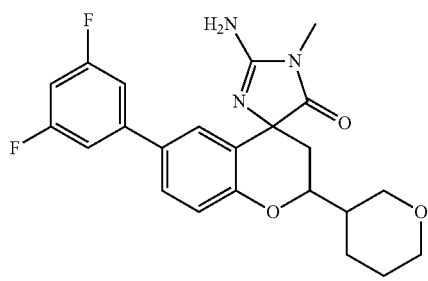 [SMILES: CN1C(=O)C2(CC(C3CCCOC3)Oc3ccc(-c4cc(F)cc(F)c4)cc32)N=C1N] |
| 268 | 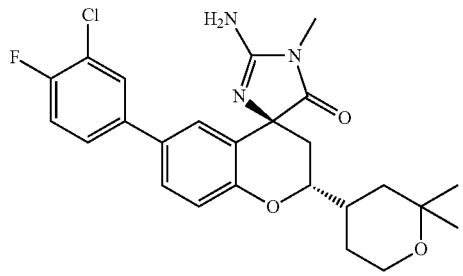 [SMILES: CN1C(=O)[C@@]2(C[C@H](C3CCOC(C)(C)C3)Oc3ccc(-c4ccc(F)c(Cl)c4)cc32)N=C1N] |
| 269 | 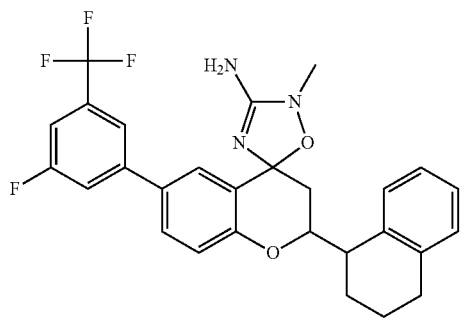 [SMILES: CN1OC2(CC(C3CCCc4ccccc43)Oc3ccc(-c4cc(F)cc(C(F)(F)F)c4)cc32)N=C1N] |
| 270 | 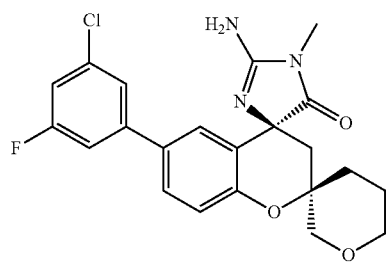 [SMILES: CN1C(=O)[C@@]2(C[C@@]3(CCCOC3)Oc3ccc(-c4cc(F)cc(Cl)c4)cc32)N=C1N] |

| COMPOUND NO. | STRUCTURE |
|---|---|
| 271 | 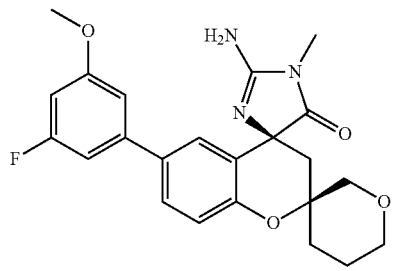 [SMILES: COc1cc(F)cc(-c2ccc3c(c2)[C@]2(C[C@]4(CCCOC4)O3)N=C(N)N(C)C2=O)c1] |
| 272 | 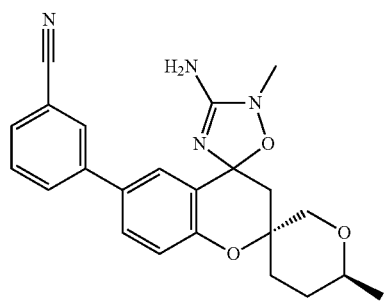 [SMILES: C[C@H]1CC[C@]2(CO1)CC1(N=C(N)N(C)O1)c1cc(-c3cccc(C#N)c3)ccc1O2] |
| 273 | 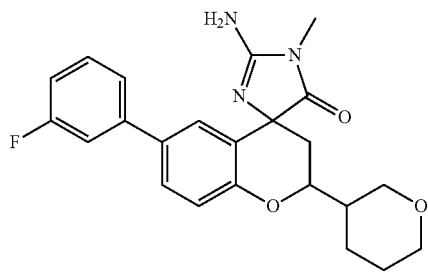 [SMILES: CN1C(=O)C2(CC(C3CCCOC3)Oc3ccc(-c4cccc(F)c4)cc32)N=C1N] |
| 274 | 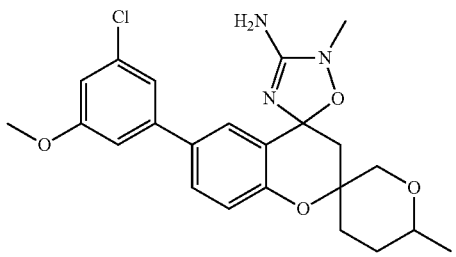 |
| 275 | 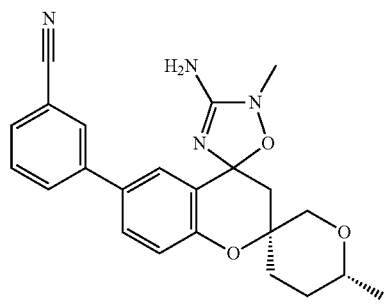 [SMILES: C[C@@H]1CC[C@@]2(CO1)CC1(N=C(N)N(C)O1)c1cc(-c3cccc(C#N)c3)ccc1O2] |

| COMPOUND NO. | STRUCTURE |
|---|---|
| 276 | 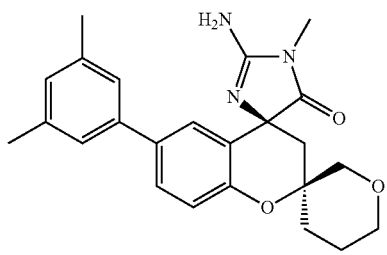 [SMILES: Cc1cc(C)cc(-c2ccc3c(c2)[C@]2(C[C@]4(CCCOC4)O3)N=C(N)N(C)C2=O)c1] |
| 277 | 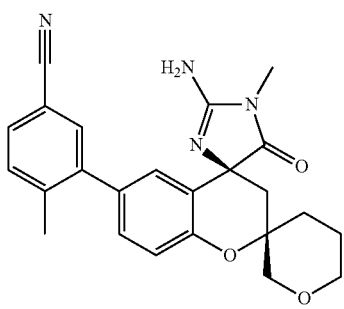 [SMILES: Cc1ccc(C#N)cc1-c1ccc2c(c1)[C@]1(C[C@]3(CCCOC3)O2)N=C(N)N(C)C1=O] |
| 278 | 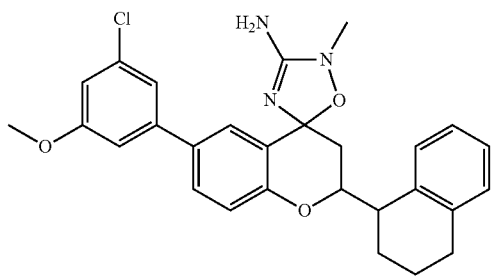 [SMILES: COc1cc(Cl)cc(-c2ccc3c(c2)C2(CC(C4CCCc5ccccc54)O3)N=C(N)N(C)O2)c1] |
| 279 | 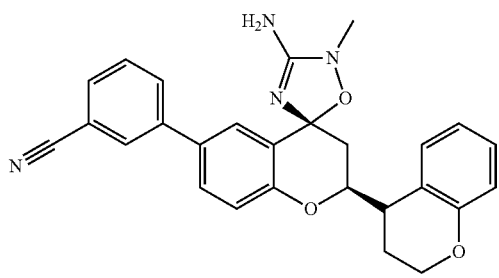 [SMILES: CN1O[C@@]2(C[C@@H](C3CCOc4ccccc43)Oc3ccc(-c4cccc(C#N)c4)cc32)N=C1N] |
| 280 | 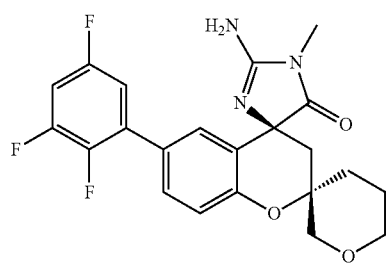 [SMILES: CN1C(=O)[C@@]2(C[C@]3(CCCOC3)Oc3ccc(-c4cc(F)cc(F)c4F)cc32)N=C1N] |

-continued
| COMPOUND NO. | STRUCTURE |
|---|---|
| 281 | 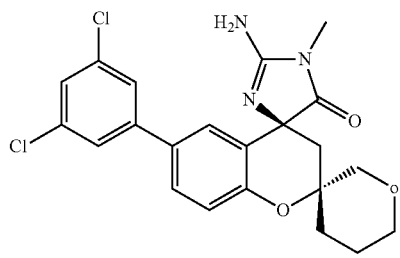 |
| 282 | 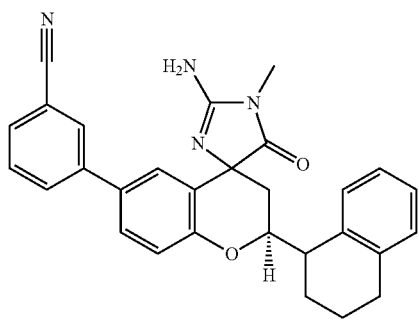 [SMILES: CN1C(=O)C2(C[C@@H](C3CCCc4ccccc43)Oc3ccc(-c4cccc(C#N)c4)cc32)N=C1N] |
| 283 | 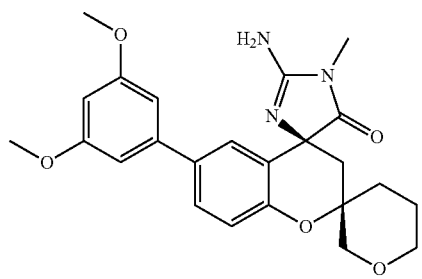 [SMILES: COc1cc(OC)cc(-c2ccc3c(c2)[C@]2(C[C@]4(CCCOC4)O3)N=C(N)N(C)C2=O)c1] |
| 284 | 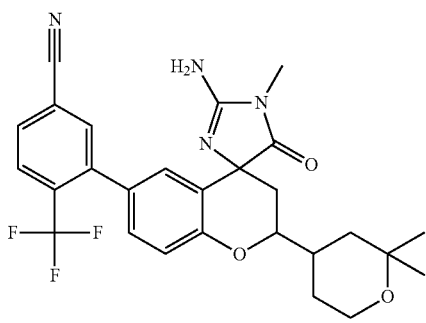 [SMILES: CN1C(=O)C2(CC(C3CCOC(C)(C)C3)Oc3ccc(-c4cc(C#N)ccc4C(F)(F)F)cc32)N=C1N] |
| 285 | 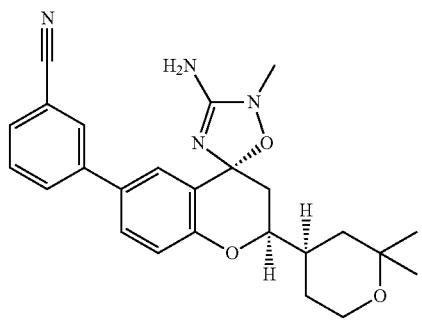 [SMILES: CN1O[C@@]2(C[C@@H]([C@@H]3CCOC(C)(C)C3)Oc3ccc(-c4cccc(C#N)c4)cc32)N=C1N] |

-continued
| COMPOUND NO. | STRUCTURE |
|---|---|
| 286 | 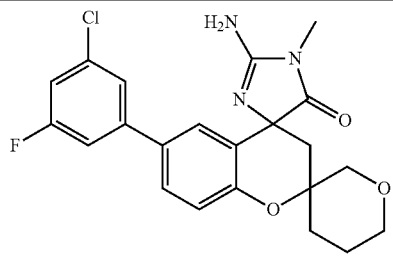 |
| 287 | 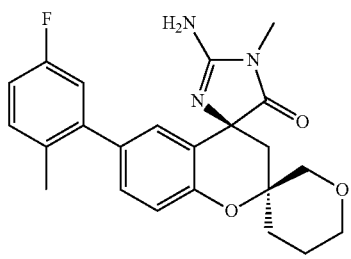 [SMILES: Cc1ccc(F)cc1-c1ccc2c(c1)[C@]1(C[C@]3(CCCOC3)O2)N=C(N)N(C)C1=O] |
| 288 | 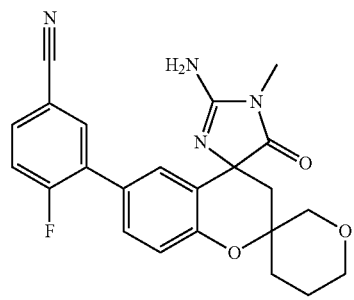 |
| 289 | 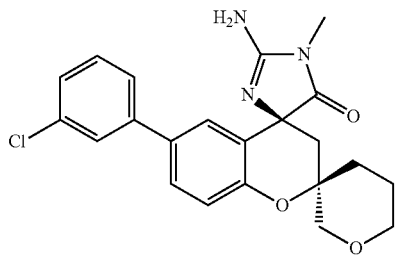 [SMILES: CN1C(=O)[C@@]2(C[C@@]3(CCCOC3)Oc3ccc(-c4cccc(Cl)c4)cc32)N=C1N] |
| 290 | 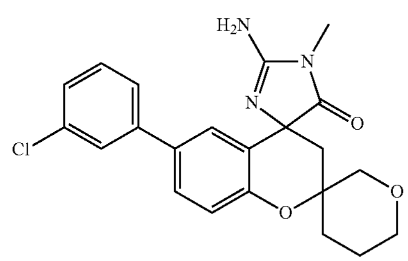 [SMILES: CN1C(=O)C2(CC3(CCCOC3)Oc3ccc(-c4cccc(Cl)c4)cc32)N=C1N] |
| 291 | 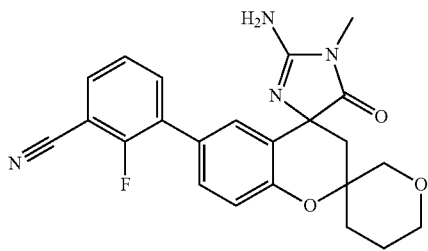 [SMILES: CN1C(=O)C2(CC3(CCCOC3)Oc3ccc(-c4cccc(C#N)c4F)cc32)N=C1N] |

-continued
| COMPOUND NO. | STRUCTURE |
|---|---|
| 292 | 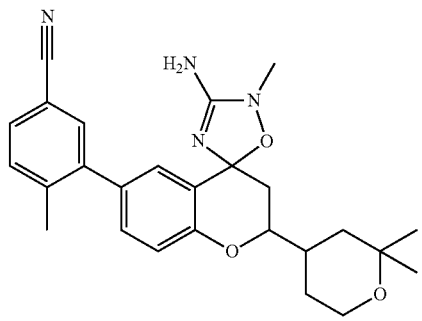 [SMILES: Cc1ccc(C#N)cc1-c1ccc2c(c1)C1(CC(C3CCOC(C)(C)C3)O2)N=C(N)N(C)O1] |
| 293 | 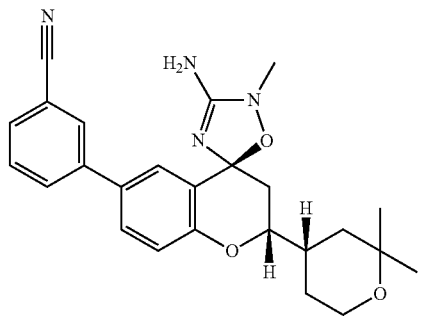 [SMILES: CN1O[C@]2(C[C@H]([C@H]3CCOC(C)(C)C3)Oc3ccc(-c4cccc(C#N)c4)cc32)N=C1N] |
| 294 | 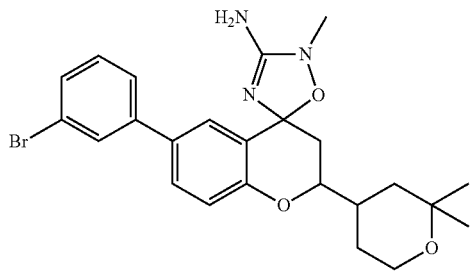 |
| 295 | 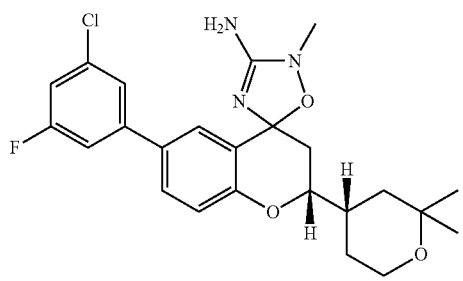 [SMILES: CN1OC2(C[C@H]([C@H]3CCOC(C)(C)C3)Oc3ccc(-c4cc(F)cc(Cl)c4)cc32)N=C1N] |
| 296 | 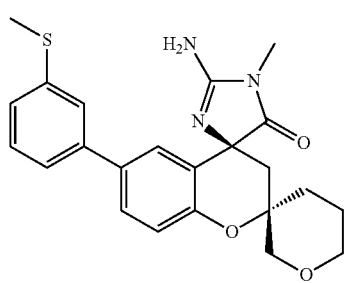 [SMILES: CSc1cccc(-c2ccc3c(c2)[C@]2(C[C@]4(CCCOC4)O3)N=C(N)N(C)C2=O)c1] |

| COMPOUND NO. | STRUCTURE |
|---|---|
| 297 | 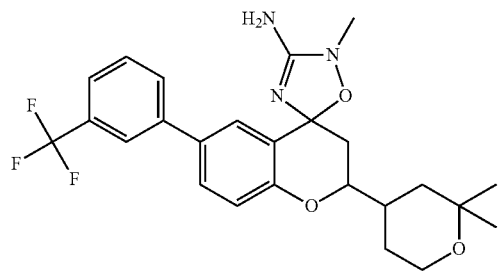 [SMILES: CN1OC2(CC(C3CCOC(C)(C)C3)Oc3ccc(-c4cccc(C(F)(F)F)c4)cc32)N=C1N] |
| 298 | 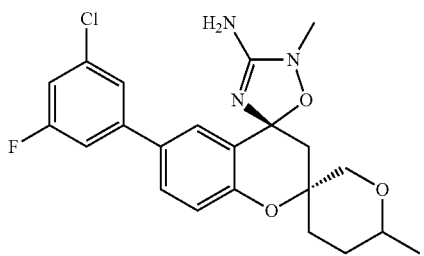 |
| 299 | 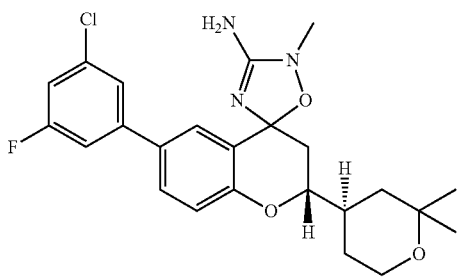 [SMILES: CN1OC2(C[C@H]([C@@H]3CCOC(C)(C)C3)Oc3ccc(-c4cc(F)cc(Cl)c4)cc32)N=C1N] |
| 300 | 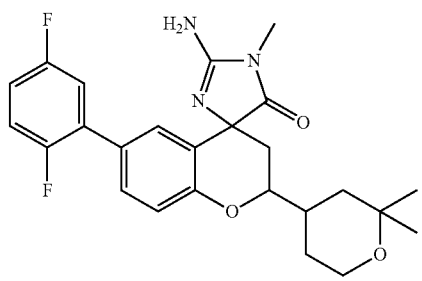 [SMILES: CN1C(=O)C2(CC(C3CCOC(C)(C)C3)Oc3ccc(-c4cc(F)ccc4F)cc32)N=C1N] |
| 301 | 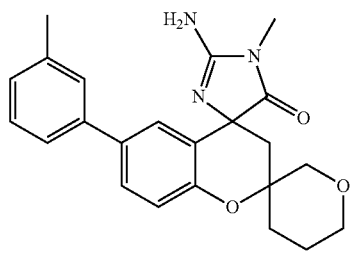 [SMILES: Cc1cccc(-c2ccc3c(c2)C2(CC4(CCCOC4)O3)N=C(N)N(C)C2=O)c1] |

-continued
| COMPOUND NO. | STRUCTURE |
|---|---|
| 302 | 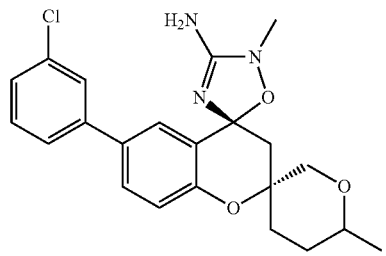 |
| 303 | 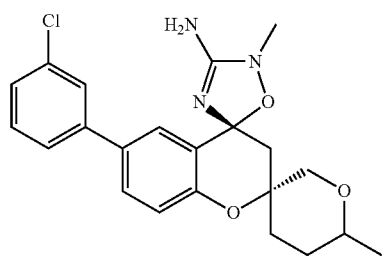 |
| 304 | 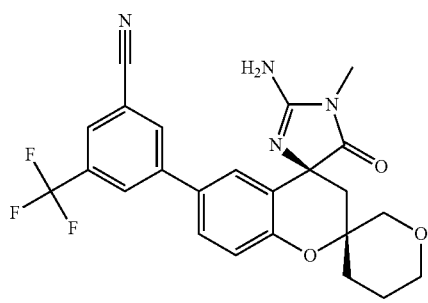 [SMILES: CN1C(=O)[C@@]2(C[C@@]3(CCCOC3)Oc3ccc(-c4cc(C#N)cc(C(F)(F)F)c4)cc32)N=C1N] |
| 305 | 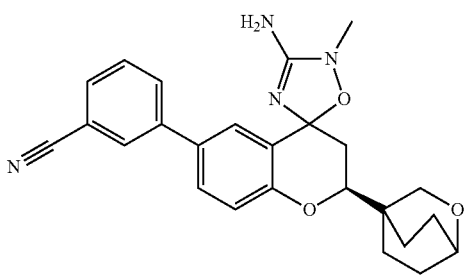 [SMILES: CN1OC2(C[C@@H](C34CCC(CC3)OC4)Oc3ccc(-c4cccc(C#N)c4)cc32)N=C1N] |
| 306 | 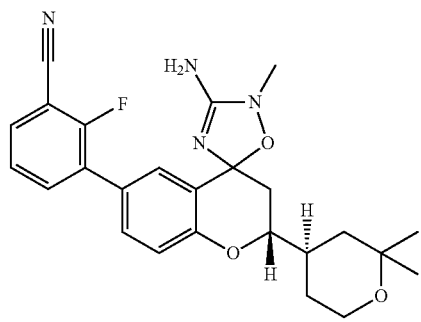 [SMILES: CN1OC2(C[C@H]([C@@H]3CCOC(C)(C)C3)Oc3ccc(-c4cccc(C#N)c4F)cc32)N=C1N] |

| COMPOUND NO. | STRUCTURE |
|---|---|
| 307 | 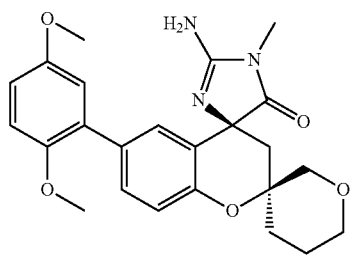 [SMILES: COc1ccc(OC)c(-c2ccc3c(c2)[C@]2(C[C@]4(CCCOC4)O3)N=C(N)N(C)C2=O)c1] |
| 308 | 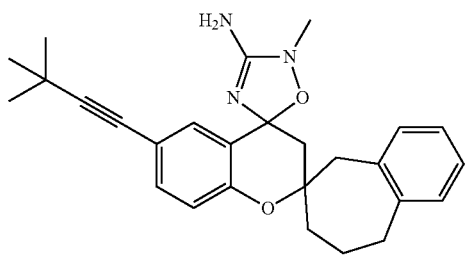 [SMILES: CN1OC2(CC3(CCCc4ccccc4C3)Oc3ccc(C#CC(C)(C)C)cc32)N=C1N] |
| 309 | 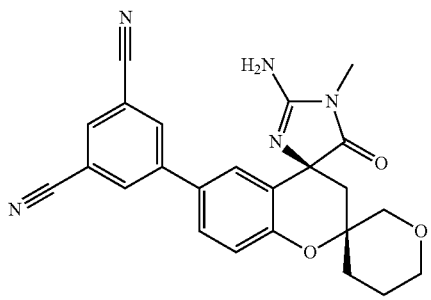 [SMILES: CN1C(=O)[C@@]2(C[C@@]3(CCCOC3)Oc3ccc(-c4cc(C#N)cc(C#N)c4)cc32)N=C1N] |
| 310 | 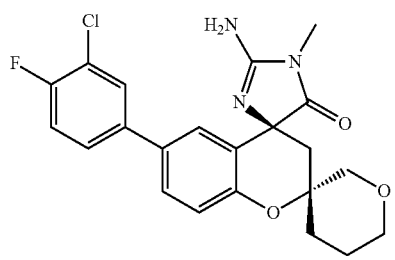 [SMILES: CN1C(=O)[C@@]2(C[C@@]3(CCCOC3)Oc3ccc(-c4ccc(F)c(Cl)c4)cc32)N=C1N] |
| 311 | 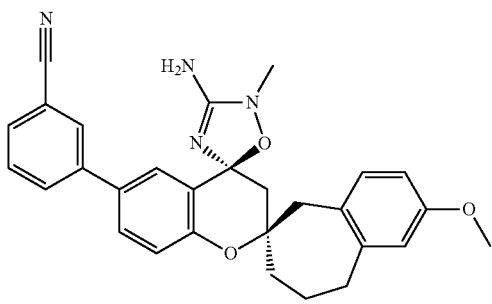 [SMILES: COc1ccc2c(c1)CCC[C@@]1(C2)C[C@@]2(N=C(N)N(C)O2)c2cc(-c3cccc(C#N)c3)ccc2O1] |

US 8,921,359 B2
171                                                                 172
-continued
| COMPOUND NO. | STRUCTURE |
|---|---|
| 312 | 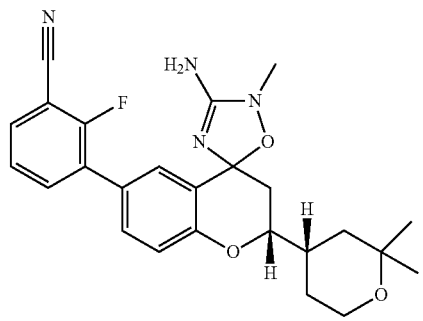 [SMILES: CN1OC2(C[C@H]([C@H]3CCOC(C)(C)C3)Oc3ccc(-c4cccc(C#N)c4F)cc32)N=C1N] |
| 313 | 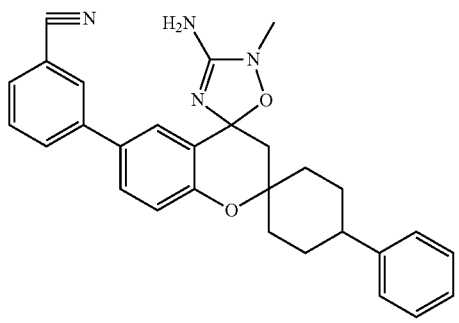 [SMILES: CN1OC2(CC3(CCC(c4ccccc4)CC3)Oc3ccc(-c4cccc(C#N)c4)cc32)N=C1N] |
| 314 | 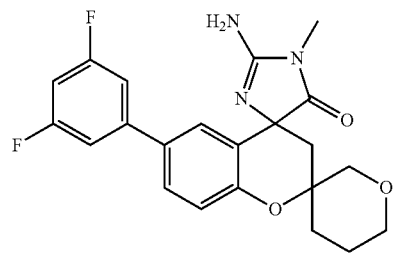 [SMILES: CN1C(=O)C2(CC3(CCCOC3)Oc3ccc(-c4cc(F)cc(F)c4)cc32)N=C1N] |
| 315 | 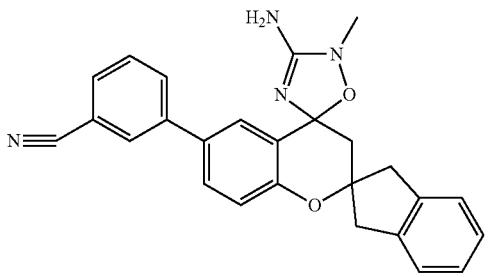 [SMILES: CN1OC2(CC3(Cc4ccccc4C3)Oc3ccc(-c4cccc(C#N)c4)cc32)N=C1N] |
| 316 | 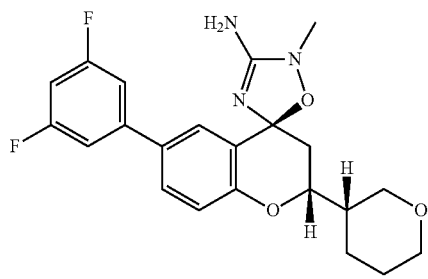 [SMILES: CN1O[C@]2(C[C@H]([C@H]3CCCOC3)Oc3ccc(-c4cc(F)cc(F)c4)cc32)N=C1N] |

-continued
| COMPOUND NO. | STRUCTURE |
|---|---|
| 317 | 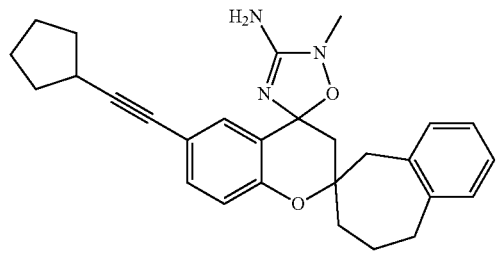 [SMILES: CN1OC2(CC3(CCCc4ccccc4C3)Oc3ccc(C#CC4CCCC4)cc32)N=C1N] |
| 318 | 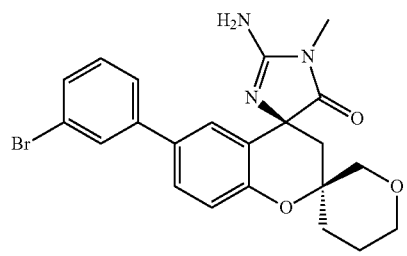 [SMILES: CN1C(=O)[C@@]2(C[C@]3(CCCOC3)Oc3ccc(-c4cccc(Br)c4)cc32)N=C1N] |
| 319 | 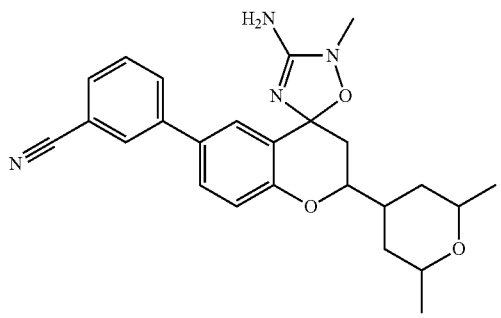 [SMILES: CC1CC(C2CC3(N=C(N)N(C)O3)c3cc(-c4cccc(C#N)c4)ccc3O2)CC(C)O1] |
| 320 | 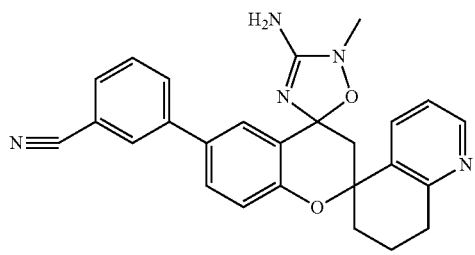 [SMILES: CN1OC2(CC3(CCCc4ncccc43)Oc3ccc(-c4cccc(C#N)c4)cc32)N=C1N] |
| 321 | 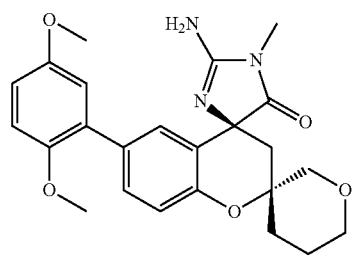 [SMILES: COc1ccc(OC)c(-c2ccc3c(c2)[C@]2(C[C@@]4(CCCOC4)O3)N=C(N)N(C)C2=O)c1] |

-continued
| COMPOUND NO. | STRUCTURE |
|---|---|
| 322 | 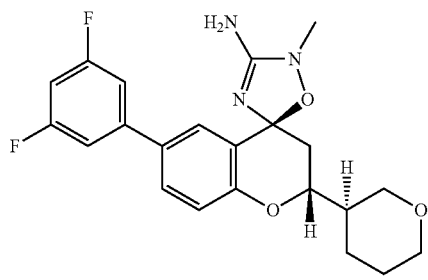 [SMILES: CN1O[C@]2(C[C@H]([C@@H]3CCCOC3)Oc3ccc(-c4cc(F)cc(F)c4)cc32)N=C1N] |
| 323 | 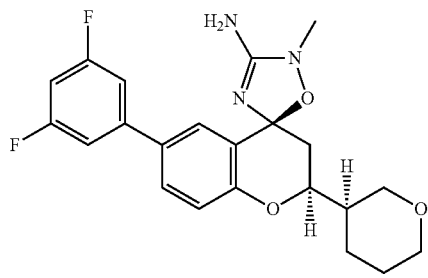 [SMILES: CN1O[C@]2(C[C@@H]([C@@H]3CCCOC3)Oc3ccc(-c4cc(F)cc(F)c4)cc32)N=C1N] |
| 324 | 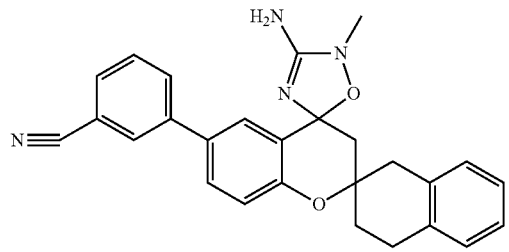 [SMILES: CN1OC2(CC3(CCc4ccccc4C3)Oc3ccc(-c4cccc(C#N)c4)cc32)N=C1N] |
| 325 | 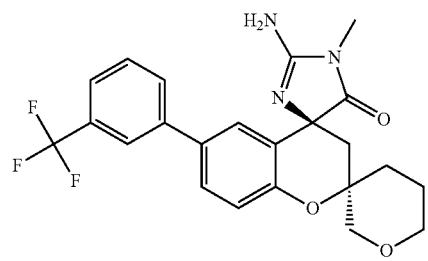 [SMILES: CN1C(=O)[C@@]2(C[C@@]3(CCCOC3)Oc3ccc(-c4cccc(C(F)(F)F)c4)cc32)N=C1N] |
| 326 | 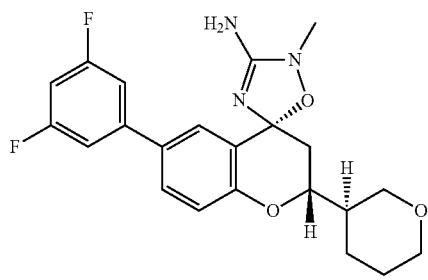 [SMILES: CN1O[C@@]2(C[C@H]([C@@H]3CCCOC3)Oc3ccc(-c4cc(F)cc(F)c4)cc32)N=C1N] |

-continued
| COMPOUND NO. | STRUCTURE |
|---|---|
| 327 | 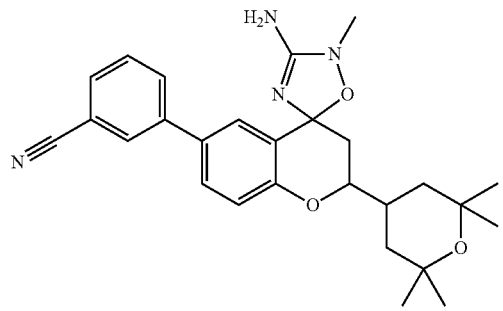 [SMILES: CN1OC2(CC(C3CC(C)(C)OC(C)(C)C3)Oc3ccc(-c4cccc(C#N)c4)cc32)N=C1N] |
| 328 | 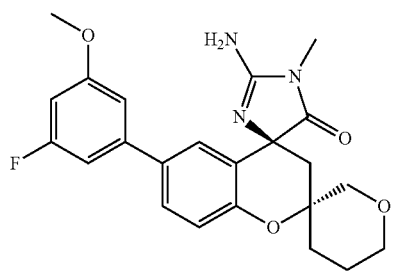 [SMILES: COc1cc(F)cc(-c2ccc3c(c2)[C@]2(C[C@@]4(CCCOC4)O3)N=C(N)N(C)C2=O)c1] |
| 329 | 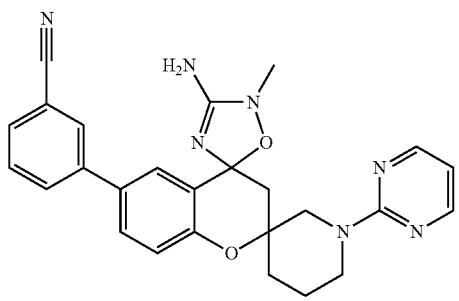 [SMILES: CN1OC2(CC3(CCCN(c4ncccn4)C3)Oc3ccc(-c4cccc(C#N)c4)cc32)N=C1N] |
| 330 | 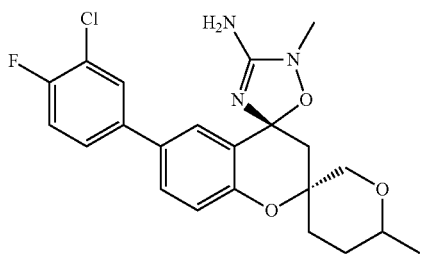 |
| 331 | 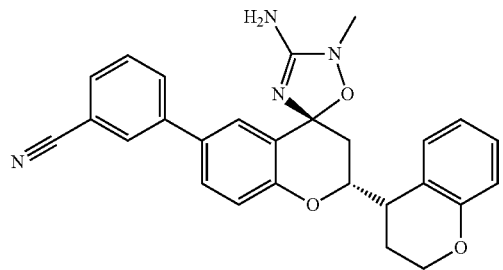 [SMILES: CN1O[C@@]2(C[C@H](C3CCOc4ccccc43)Oc3ccc(-c4cccc(C#N)c4)cc32)N=C1N] |

| COMPOUND NO. | STRUCTURE |
|---|---|
| 332 | 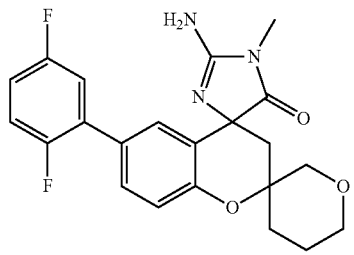 [SMILES: CN1C(=O)C2(CC3(CCCOC3)Oc3ccc(-c4cc(F)ccc4F)cc32)N=C1N] |
| 333 | 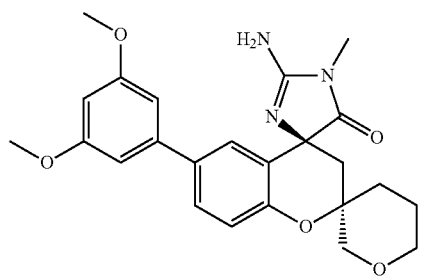 [SMILES: COc1cc(OC)cc(-c2ccc3c(c2)[C@]2(C[C@@]4(CCCOC4)O3)N=C(N)N(C)C2=O)c1] |
| 334 | 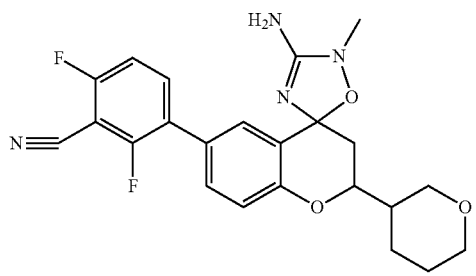 [SMILES: CN1OC2(CC(C3CCCOC3)Oc3ccc(-c4ccc(F)c(C#N)c4F)cc32)N=C1N] |
| 335 | 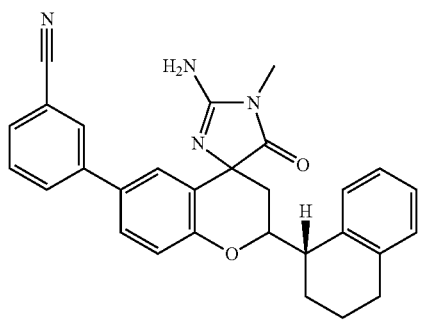 [SMILES: CN1C(=O)C2(CC([C@H]3CCCc4ccccc43)Oc3ccc(-c4cccc(C#N)c4)cc32)N=C1N] |
| 336 | 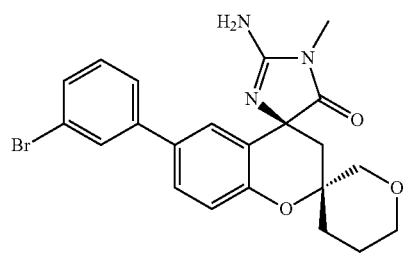 [SMILES: CN1C(=O)[C@@]2(C[C@@]3(CCCOC3)Oc3ccc(-c4cccc(Br)c4)cc32)N=C1N] |

| COMPOUND NO. | STRUCTURE |
|---|---|
| 337 | 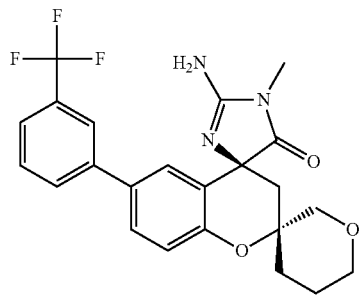 [SMILES: CN1C(=O)[C@@]2(C[C@@]3(CCCOC3)Oc3ccc(-c4cccc(C(F)(F)F)c4)cc32)N=C1N] |
| 338 | 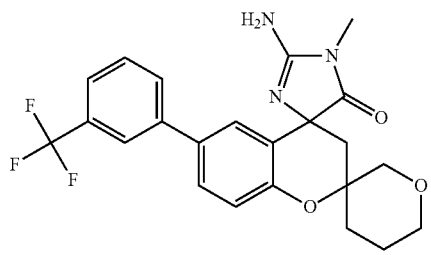 [SMILES: CN1C(=O)C2(CC3(CCCOC3)Oc3ccc(-c4cccc(C(F)(F)F)c4)cc32)N=C1N] |
| 339 | 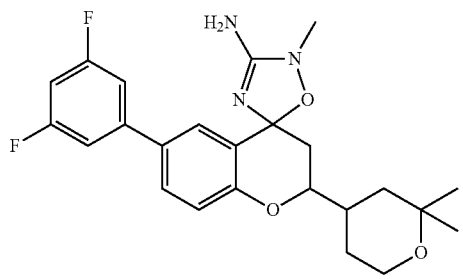 [SMILES: CN1OC2(CC(C3CCOC(C)(C)C3)Oc3ccc(-c4cc(F)cc(F)c4)cc32)N=C1N] |
| 340 | 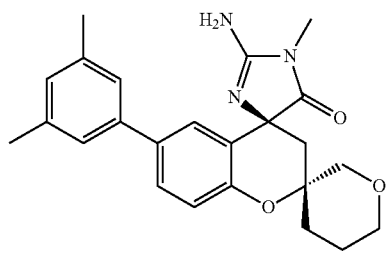 [SMILES: Cc1cc(C)cc(-c2ccc3c(c2)[C@]2(C[C@@]4(CCCOC4)O3)N=C(N)N(C)C2=O)c1] |
| 341 | 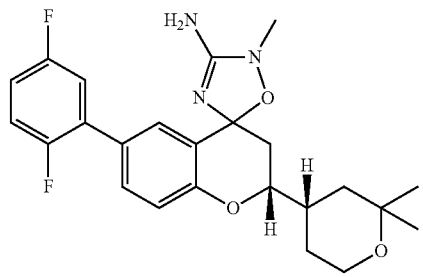 [SMILES: CN1OC2(C[C@H]([C@H]3CCOC(C)(C)C3)Oc3ccc(-c4cc(F)ccc4F)cc32)N=C1N] |

| COMPOUND NO. | STRUCTURE |
|---|---|
| 342 | 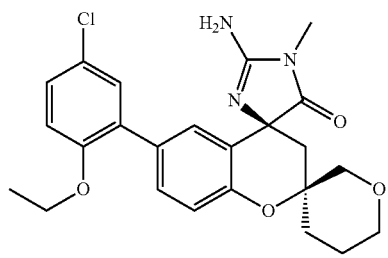 [SMILES: CCOc1ccc(Cl)cc1-c1ccc2c(c1)[C@]1(C[C@]3(CCCOC3)O2)N=C(N)N(C)C1=O] |
| 343 | 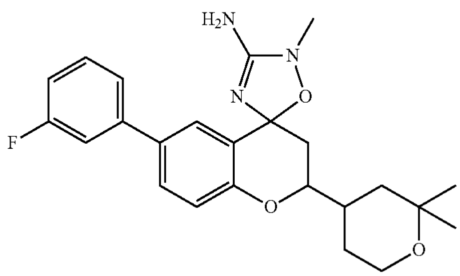 [SMILES: CN1OC2(CC(C3CCOC(C)(C)C3)Oc3ccc(-c4cccc(F)c4)cc32)N=C1N] |
| 344 | 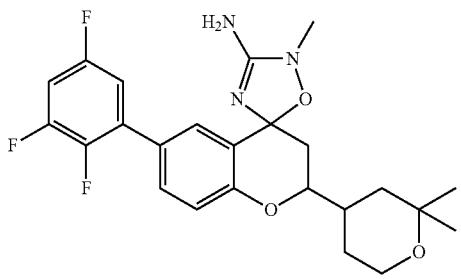 [SMILES: CN1OC2(CC(C3CCOC(C)(C)C3)Oc3ccc(-c4cc(F)cc(F)c4F)cc32)N=C1N] |
| 345 | 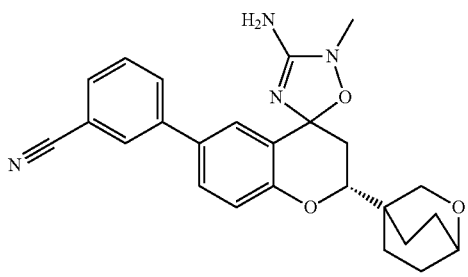 [SMILES: CN1OC2(C[C@H](C34CCC(CC3)OC4)Oc3ccc(-c4cccc(C#N)c4)cc32)N=C1N] |
| 346 | 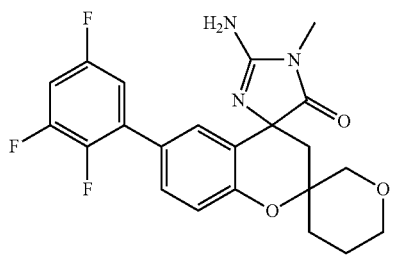 [SMILES: CN1C(=O)C2(CC3(CCCOC3)Oc3ccc(-c4cc(F)cc(F)c4F)cc32)N=C1N] |

-continued
| COMPOUND NO. | STRUCTURE |
|---|---|
| 347 | 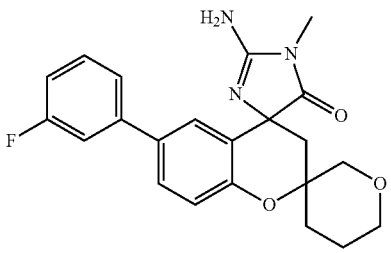 [SMILES: CN1C(=O)C2(CC3(CCCOC3)Oc3ccc(-c4cccc(F)c4)cc32)N=C1N] |
| 348 | 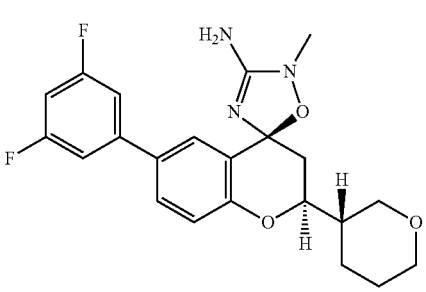 [SMILES: CN1O[C@]2(C[C@@H]([C@H]3CCCOC3)Oc3ccc(-c4cc(F)cc(F)c4)cc32)N=C1N] |
| 349 | 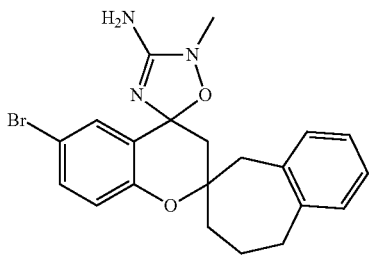 [SMILES: CN1OC2(CC3(CCCc4ccccc4C3)Oc3ccc(Br)cc32)N=C1N] |
| 350 | 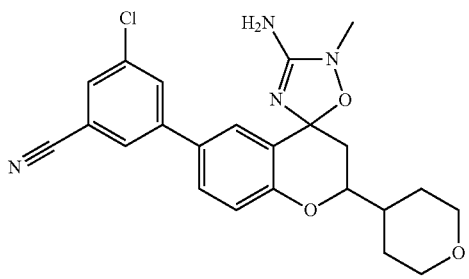 [SMILES: CN1OC2(CC(C3CCOCC3)Oc3ccc(-c4cc(Cl)cc(C#N)c4)cc32)N=C1N] |
| 351 | 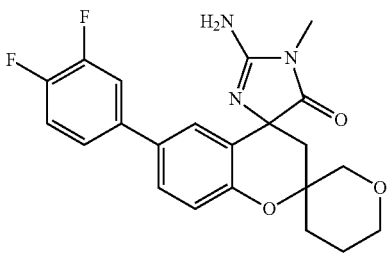 [SMILES: CN1C(=O)C2(CC3(CCCOC3)Oc3ccc(-c4ccc(F)c(F)c4)cc32)N=C1N] |

| COMPOUND NO. | STRUCTURE |
|---|---|
| 352 | 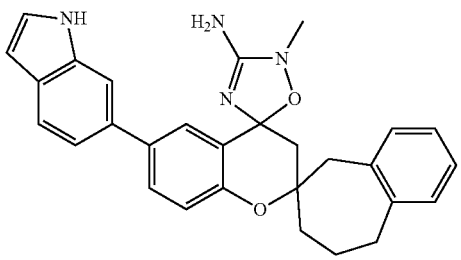 [SMILES: CN1OC2(CC3(CCCc4ccccc4C3)Oc3ccc(-c4ccc5cc[nH]c5c4)cc32)N=C1N] |
| 353 | 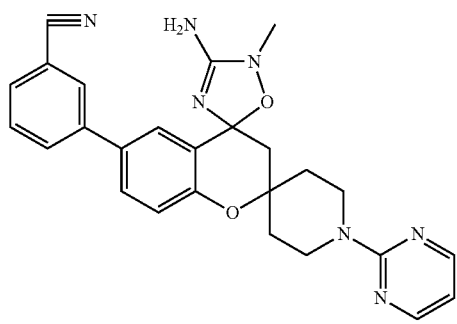 [SMILES: CN1OC2(CC3(CCN(c4ncccn4)CC3)Oc3ccc(-c4cccc(C#N)c4)cc32)N=C1N] |
| 354 | 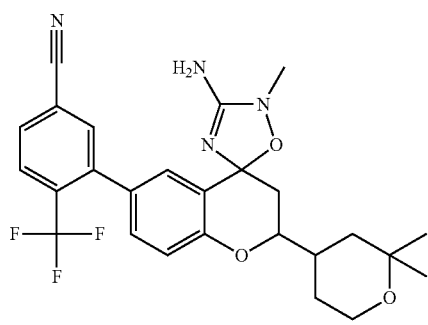 [SMILES: CN1OC2(CC(C3CCOC(C)(C)C3)Oc3ccc(-c4cc(C#N)ccc4C(F)(F)F)cc32)N=C1N] |
| 355 | 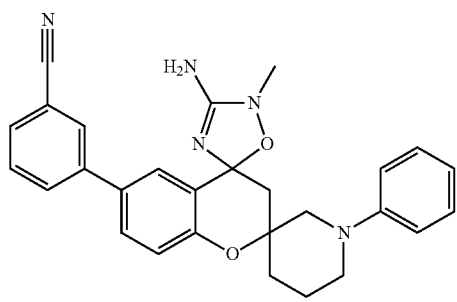 |
| 356 | 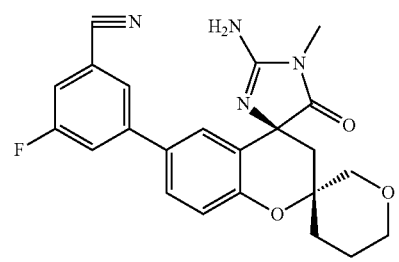 [SMILES: CN1C(=O)[C@@]2(C[C@@]3(CCCOC3)Oc3ccc(-c4cc(F)cc(C#N)c4)cc32)N=C1N] |

| COMPOUND NO. | STRUCTURE |
|---|---|
| 357 | 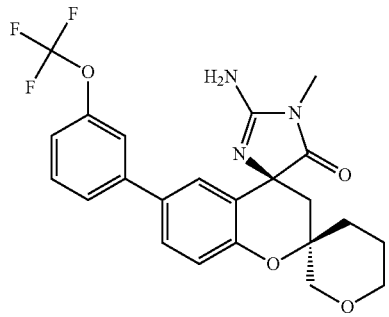 [SMILES: CN1C(=O)[C@@]2(C[C@@]3(CCCOC3)Oc3ccc(-c4cccc(OC(F)(F)F)c4)cc32)N=C1N] |
| 358 | 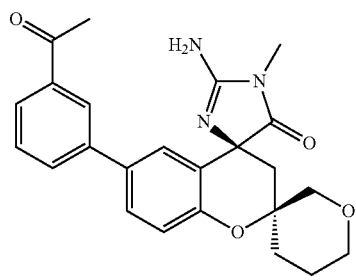 [SMILES: CC(=O)c1cccc(-c2ccc3c(c2)[C@]2(C[C@]4(CCCOC4)O3)N=C(N)N(C)C2=O)c1] |
| 359 | 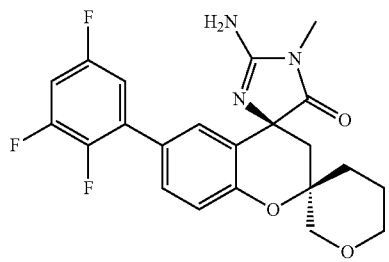 |
| 360 | 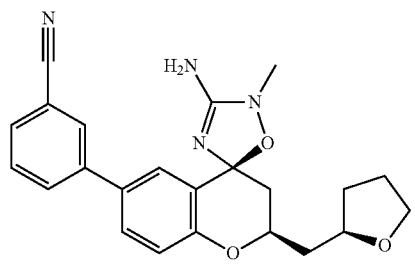 [SMILES: CN1O[C@]2(C[C@@H](C[C@H]3CCCO3)Oc3ccc(-c4cccc(C#N)c4)cc32)N=C1N] |
| 361 | 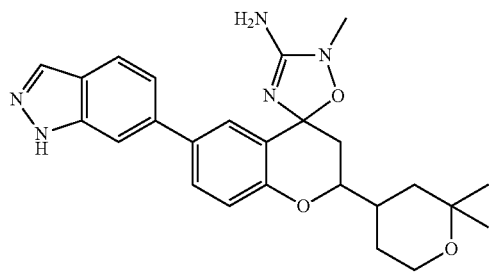 [SMILES: CN1OC2(CC(C3CCOC(C)(C)C3)Oc3ccc(-c4ccc5cn[nH]c5c4)cc32)N=C1N] |

| COMPOUND NO. | STRUCTURE |
|---|---|
| 362 | 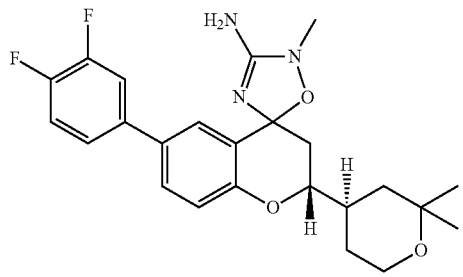 [SMILES: CN1OC2(C[C@H]([C@@H]3CCOC(C)(C)C3)Oc3ccc(-c4ccc(F)c(F)c4)cc32)N=C1N] |
| 363 | 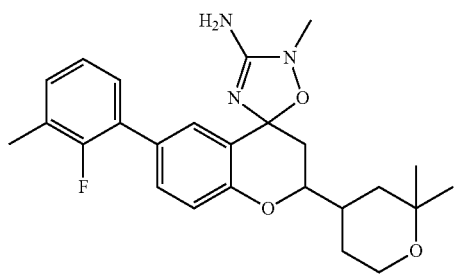 |
| 364 | 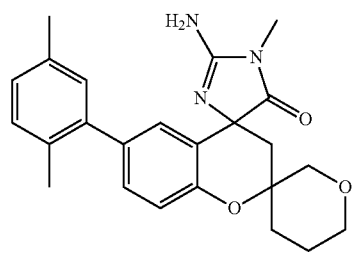 [SMILES: Cc1ccc(C)c(-c2ccc3c(c2)C2(CC4(CCCOC4)O3)N=C(N)N(C)C2=O)c1] |
| 365 | 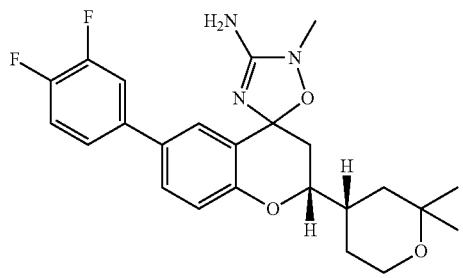 [SMILES: CN1OC2(C[C@H]([C@H]3CCOC(C)(C)C3)Oc3ccc(-c4ccc(F)c(F)c4)cc32)N=C1N] |
| 366 | 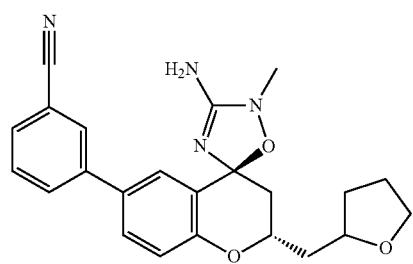 [SMILES: CN1O[C@]2(C[C@H](CC3CCCO3)Oc3ccc(-c4cccc(C#N)c4)cc32)N=C1N] |

US 8,921,359 B2
-continued
| COMPOUND NO. | STRUCTURE |
|---|---|
| 367 | 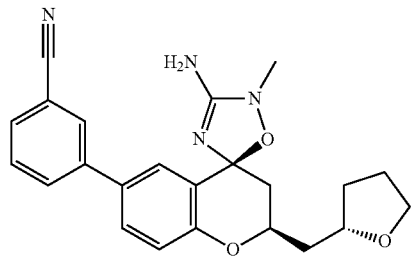 [SMILES: CN1O[C@]2(C[C@@H](C[C@@H]3CCCO3)Oc3ccc(-c4cccc(C#N)c4)cc32)N=C1N] |
| 368 | 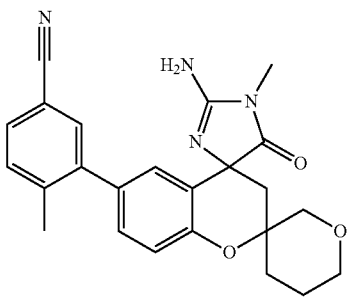 |
| 369 | 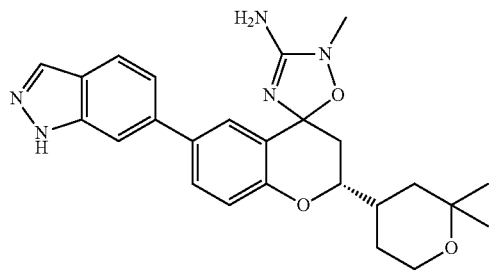 [SMILES: CN1OC2(C[C@H](C3CCOC(C)(C)C3)Oc3ccc(-c4ccc5cn[nH]c5c4)cc32)N=C1N] |
| 370 | 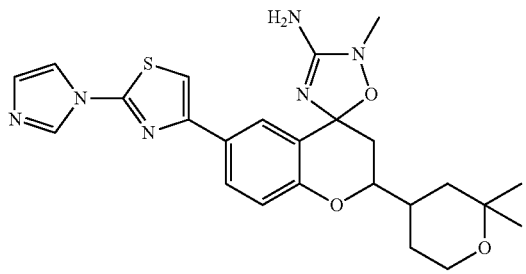 [SMILES: CN1OC2(CC(C3CCOC(C)(C)C3)Oc3ccc(-c4csc(-n5ccnc5)n4)cc32)N=C1N] |
| 371 | 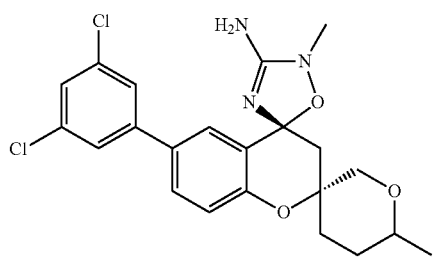 |

| COMPOUND NO. | STRUCTURE |
|---|---|
| 372 | 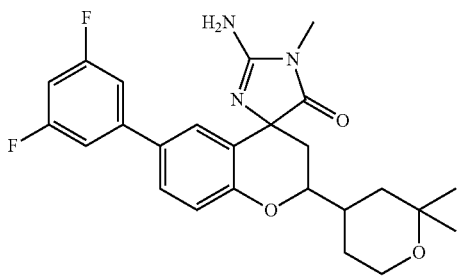 [SMILES: CN1C(=O)C2(CC(C3CCOC(C)(C)C3)Oc3ccc(-c4cc(F)cc(F)c4)cc32)N=C1N] |
| 373 | 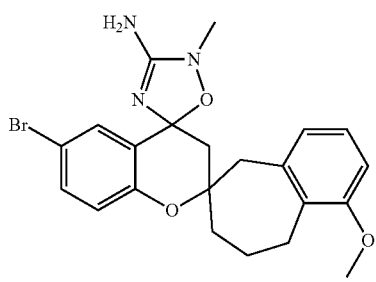 [SMILES: COc1cccc2c1CCCC1(C2)CC2(N=C(N)N(C)O2)c2cc(Br)ccc2O1] |
| 374 | 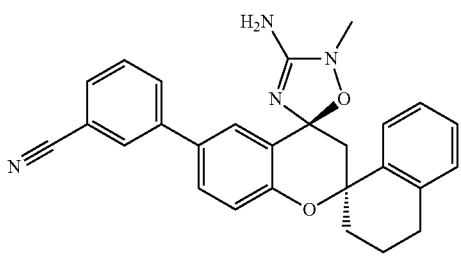 [SMILES: CN1O[C@]2(C[C@]3(CCCc4ccccc43)Oc3ccc(-c4cccc(C#N)c4)cc32)N=C1N] |
| 375 | 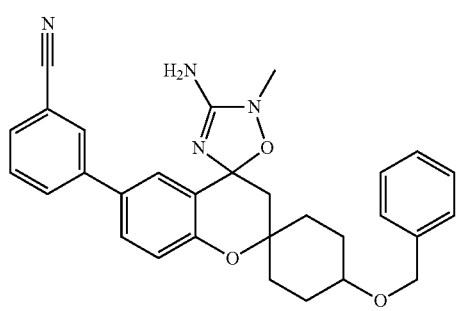 [SMILES: CN1OC2(CC3(CCC(OCc4ccccc4)CC3)Oc3ccc(-c4cccc(C#N)c4)cc32)N=C1N] |
| 376 | 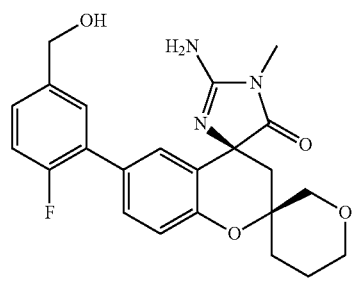 [SMILES: CN1C(=O)[C@@]2(C[C@]3(CCCOC3)Oc3ccc(-c4cc(CO)ccc4F)cc32)N=C1N] |

| COMPOUND NO. | STRUCTURE |
|---|---|
| 377 | 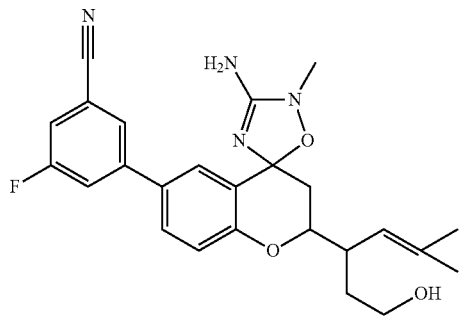 [SMILES: CC(C)=CC(CCO)C1CC2(N=C(N)N(C)O2)c2cc(-c3cc(F)cc(C#N)c3)ccc2O1] |
| 378 | 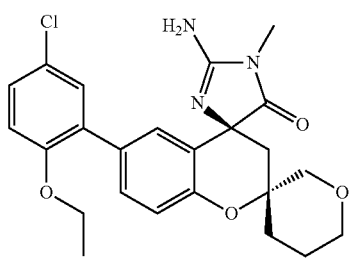 [SMILES: CCOc1ccc(Cl)cc1-c1ccc2c(c1)[C@]1(C[C@@]3(CCCOC3)O2)N=C(N)N(C)C1=O] |
| 379 | 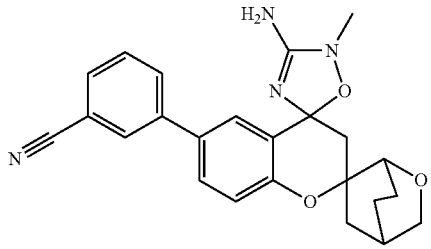 [SMILES: CN1OC2(CC3(CC4CCC3OC4)Oc3ccc(-c4cccc(C#N)c4)cc32)N=C1N] |
| 380 | 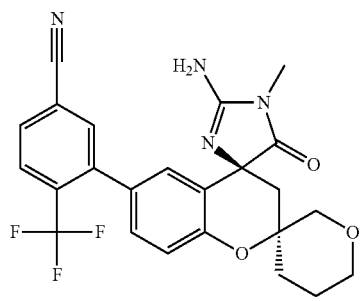 [SMILES: CN1C(=O)[C@@]2(C[C@]3(CCCOC3)Oc3ccc(-c4cc(C#N)ccc4C(F)(F)F)cc32)N=C1N] |
| 381 | 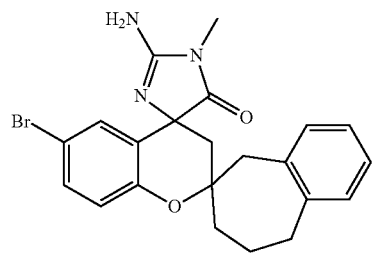 [SMILES: CN1C(=O)C2(CC3(CCCc4ccccc4C3)Oc3ccc(Br)cc32)N=C1N] |

-continued
| COMPOUND NO. | STRUCTURE |
|---|---|
| 382 | 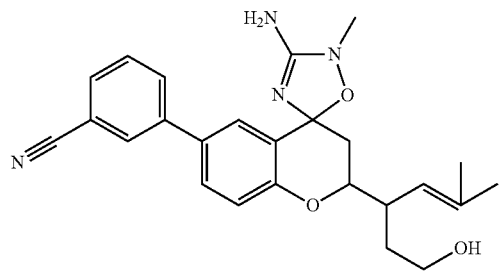 [SMILES: CC(C)=CC(CCO)C1CC2(N=C(N)N(C)O2)c2cc(-c3cccc(C#N)c3)ccc2O1] |
| 383 | 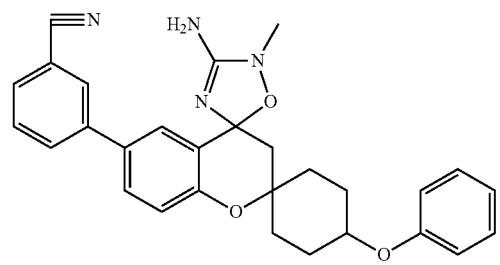 [SMILES: CN1OC2(CC3(CCC(Oc4ccccc4)CC3)Oc3ccc(-c4cccc(C#N)c4)cc32)N=C1N] |
| 384 | 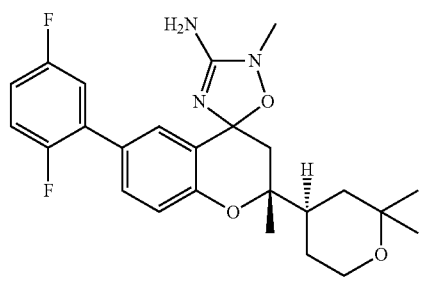 [SMILES: CN1OC2(C[C@](C)([C@@H]3CCOC(C)(C)C3)Oc3ccc(-c4cc(F)ccc4F)cc32)N=C1N] |
| 385 | 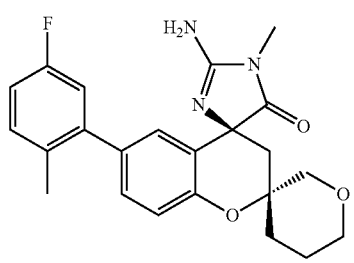 [SMILES: Cc1ccc(F)cc1-c1ccc2c(c1)[C@]1(C[C@@]3(CCCOC3)O2)N=C(N)N(C)C1=O] |
| 386 | 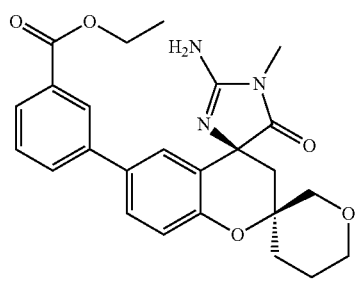 [SMILES: CCOC(=O)c1cccc(-c2ccc3c(c2)[C@]2(C[C@]4(CCCOC4)O3)N=C(N)N(C)C2=O)c1] |

| COMPOUND NO. | STRUCTURE |
|---|---|
| 387 | 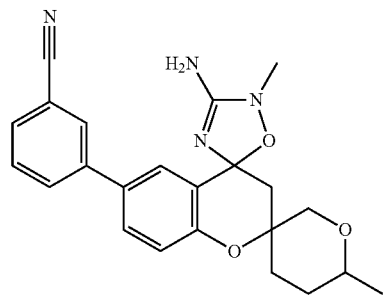 [SMILES: CC1CCC2(CO1)CC1(N=C(N)N(C)O1)c1cc(-c3cccc(C#N)c3)ccc1O2] |
| 388 | 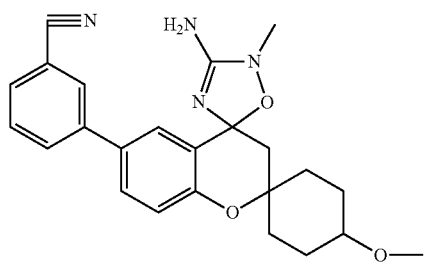 [SMILES: COC1CCC2(CC1)CC1(N=C(N)N(C)O1)c1cc(-c3cccc(C#N)c3)ccc1O2] |
| 389 | 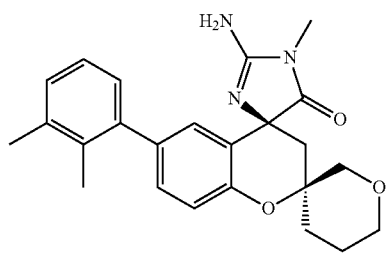 [SMILES: Cc1cccc(-c2ccc3c(c2)[C@]2(C[C@]4(CCCOC4)O3)N=C(N)N(C)C2=O)c1C] |
| 390 | 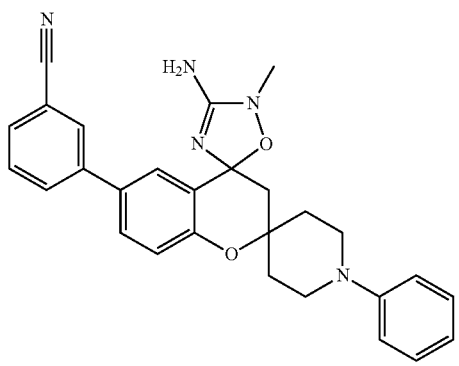 [SMILES: CN1OC2(CC3(CCN(c4ccccc4)CC3)Oc3ccc(-c4cccc(C#N)c4)cc32)N=C1N] |
| 391 | 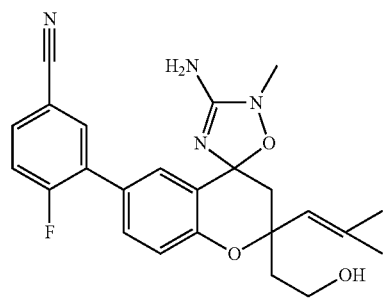 [SMILES: CC(C)=CC1(CCO)CC2(N=C(N)N(C)O2)c2cc(-c3cc(C#N)ccc3F)ccc2O1] |

-continued
| COMPOUND NO. | STRUCTURE |
|---|---|
| 392 | 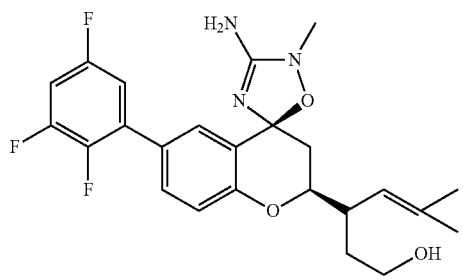 |
| 393 | 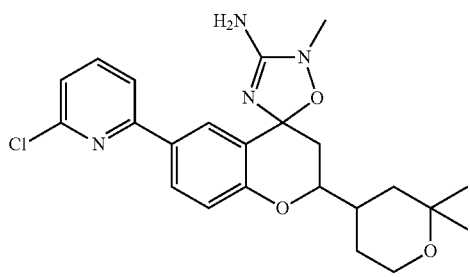 [SMILES: CN1OC2(CC(C3CCOC(C)(C)C3)Oc3ccc(-c4cccc(Cl)n4)cc32)N=C1N] |
| 394 | 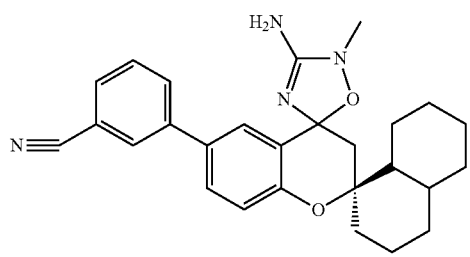 |
| 395 | 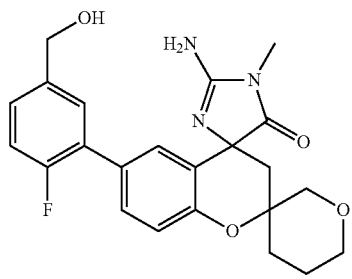 [SMILES: CN1C(=O)C2(CC3(CCCOC3)Oc3ccc(-c4cc(CO)ccc4F)cc32)N=C1N] |
| 396 | 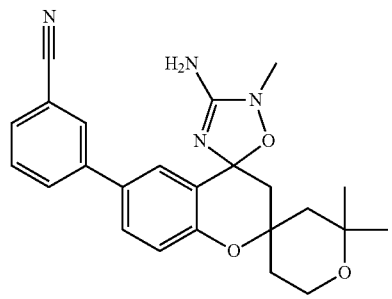 [SMILES: CN1OC2(CC3(CCOC(C)(C)C3)Oc3ccc(-c4cccc(C#N)c4)cc32)N=C1N] |

| COMPOUND NO. | STRUCTURE |
|---|---|
| 397 | 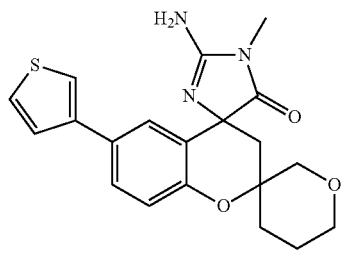 [SMILES: CN1C(=O)C2(CC3(CCCOC3)Oc3ccc(-c4ccsc4)cc32)N=C1N] |
| 398 | 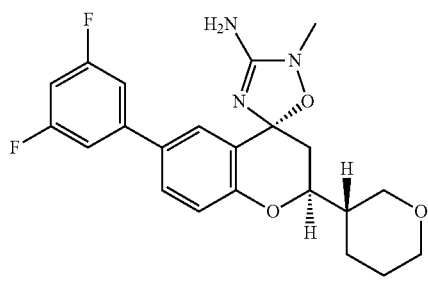 [SMILES: CN1O[C@@]2(C[C@@H]([C@H]3CCCOC3)Oc3ccc(-c4cc(F)cc(F)c4)cc32)N=C1N] |
| 399 | 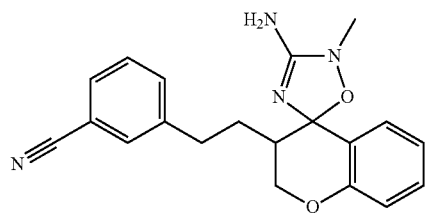 [SMILES: CN1OC2(N=C1N)c1ccccc1OCC2CCc1cccc(C#N)c1] |
| 400 | 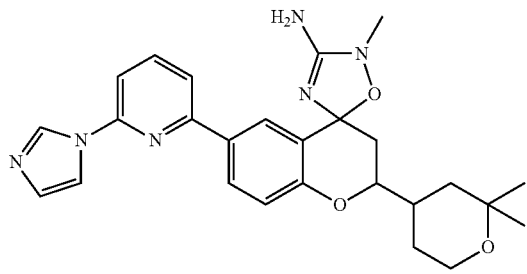 [SMILES: CN1OC2(CC(C3CCOC(C)(C)C3)Oc3ccc(-c4cccc(-n5ccnc5)n4)cc32)N=C1N] |
| 401 | 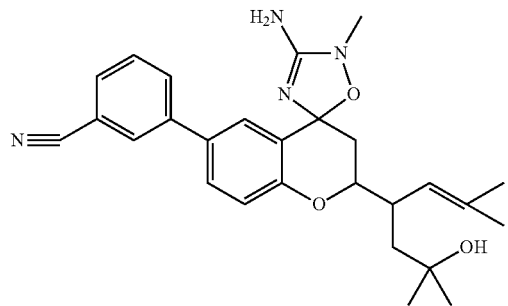 [SMILES: CC(C)=CC(CC(C)(C)O)C1CC2(N=C(N)N(C)O2)c2cc(-c3cccc(C#N)c3)ccc2O1] |

| COMPOUND NO. | STRUCTURE |
|---|---|
| 402 | 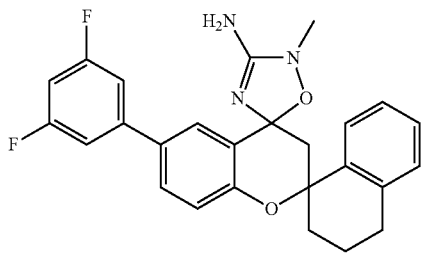 [SMILES: CN1OC2(CC3(CCCc4ccccc43)Oc3ccc(-c4cc(F)cc(F)c4)cc32)N=C1N] |
| 403 | 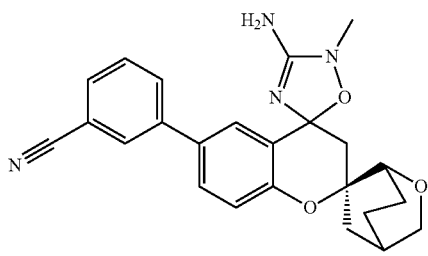 [SMILES: CN1OC2(C[C@]3(CC4CCC3OC4)Oc3ccc(-c4cccc(C#N)c4)cc32)N=C1N] |
| 404 | 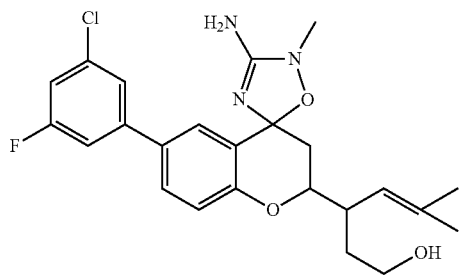 [SMILES: CC(C)=CC(CCO)C1CC2(N=C(N)N(C)O2)c2cc(-c3cc(F)cc(Cl)c3)ccc2O1] |
| 405 | 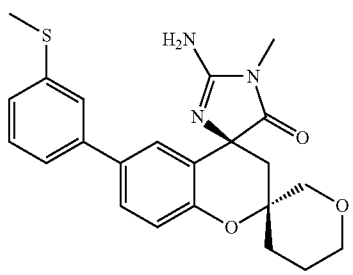 [SMILES: CSc1cccc(-c2ccc3c(c2)[C@]2(C[C@@]4(CCCOC4)O3)N=C(N)N(C)C2=O)c1] |
| 406 | 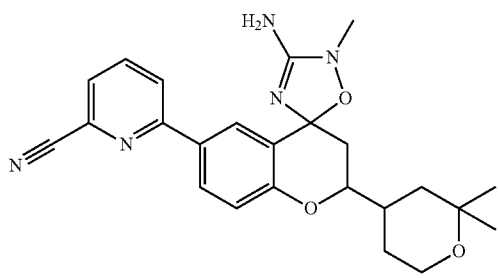 [SMILES: CN1OC2(CC(C3CCOC(C)(C)C3)Oc3ccc(-c4cccc(C#N)n4)cc32)N=C1N] |

| COMPOUND NO. | STRUCTURE |
|---|---|
| 407 | 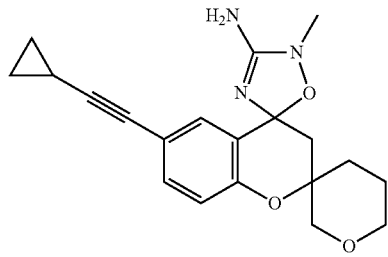 [SMILES: CN1OC2(CC3(CCCOC3)Oc3ccc(C#CC4CC4)cc32)N=C1N] |
| 408 | 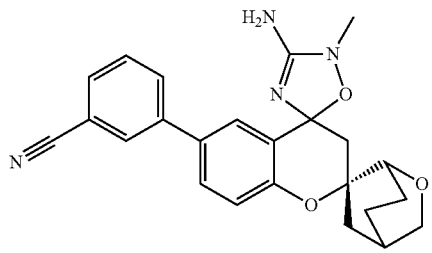 [SMILES: CN1OC2(C[C@@]3(CC4CCC3OC4)Oc3ccc(-c4cccc(C#N)c4)cc32)N=C1N] |
| 409 | 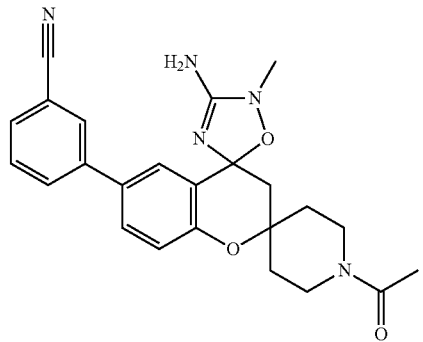 [SMILES: CC(=O)N1CCC2(CC1)CC1(N=C(N)N(C)O1)c1cc(-c3cccc(C#N)c3)ccc1O2] |
| 410 | 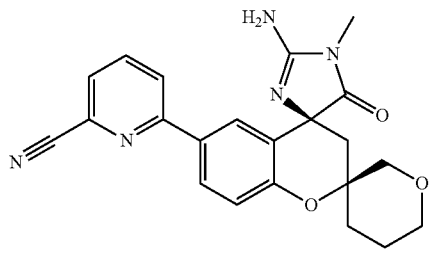 [SMILES: CN1C(=O)[C@@]2(C[C@]3(CCCOC3)Oc3ccc(-c4cccc(C#N)n4)cc32)N=C1N] |
| 411 | 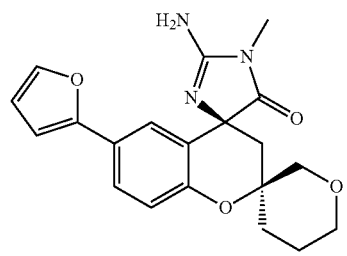 [SMILES: CN1C(=O)[C@@]2(C[C@]3(CCCOC3)Oc3ccc(-c4ccco4)cc32)N=C1N] |

| COMPOUND NO. | STRUCTURE |
|---|---|
| 412 | 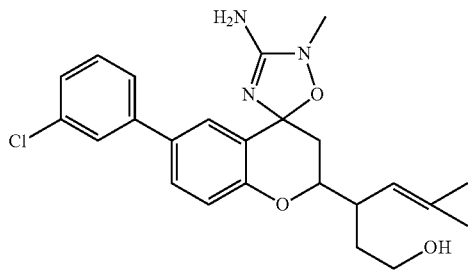 [SMILES: CC(C)=CC(CCO)C1CC2(N=C(N)N(C)O2)c2cc(-c3cccc(Cl)c3)ccc2O1] |
| 413 | 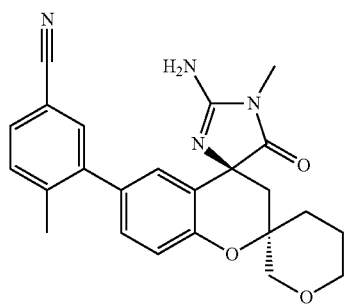 [SMILES: Cc1ccc(C#N)cc1-c1ccc2c(c1)[C@]1(C[C@@]3(CCCOC3)O2)N=C(N)N(C)C1=O] |
| 414 | 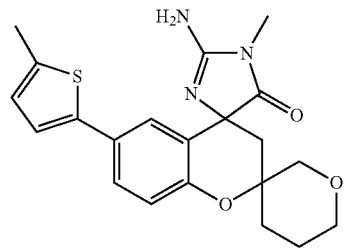 [SMILES: Cc1ccc(-c2ccc3c(c2)C2(CC4(CCCOC4)O3)N=C(N)N(C)C2=O)s1] |
| 415 | 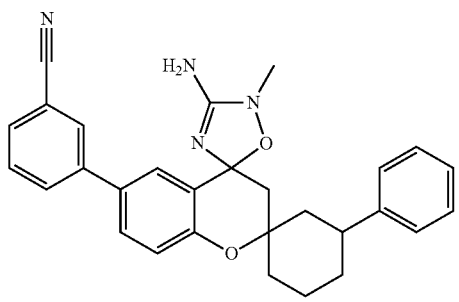 [SMILES: CN1OC2(CC3(CCCC(c4ccccc4)C3)Oc3ccc(-c4cccc(C#N)c4)cc32)N=C1N] |
| 416 | 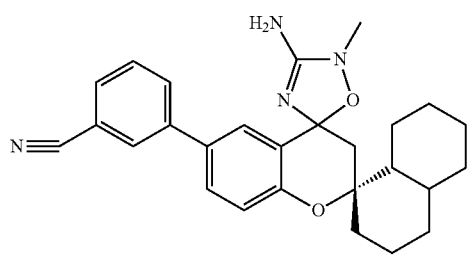 |

| COMPOUND NO. | STRUCTURE |
|---|---|
| 417 | 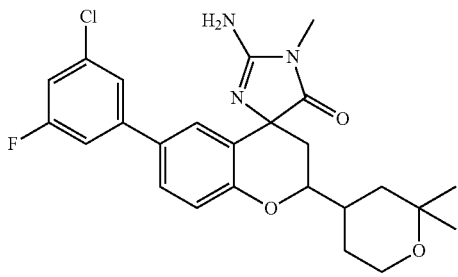 |
| 418 | 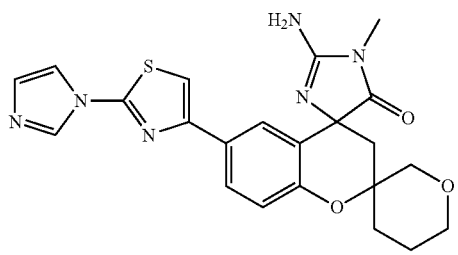 [SMILES: CN1C(=O)C2(CC3(CCCOC3)Oc3ccc(-c4csc(-n5ccnc5)n4)cc32)N=C1N] |
| 419 | 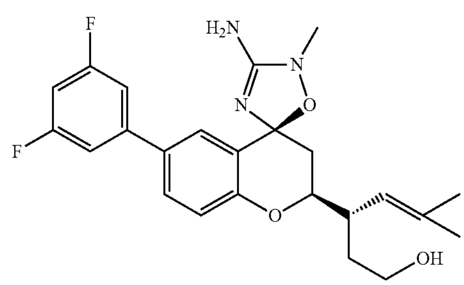 [SMILES: CC(C)=C[C@H](CCO)[C@@H]1C[C@@]2(N=C(N)N(C)O2)c2cc(-c3cc(F)cc(F)c3)ccc2O1] |
| 420 | 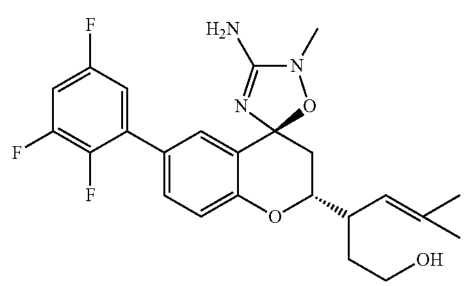 |
| 421 | 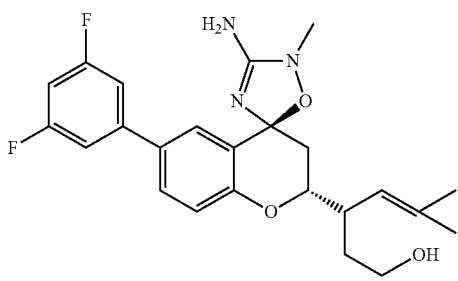 [SMILES: CC(C)=CC(CCO)[C@H]1C[C@@]2(N=C(N)N(C)O2)c2cc(-c3cc(F)cc(F)c3)ccc2O1] |

| COMPOUND NO. | STRUCTURE |
|---|---|
| 422 | 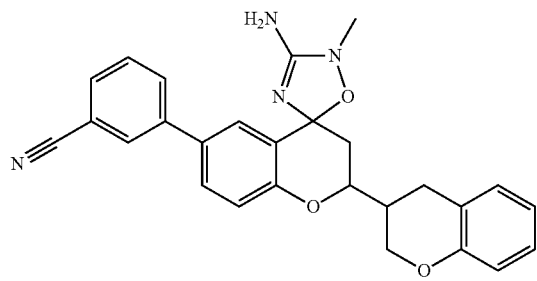 [SMILES: CN1OC2(CC(C3COc4ccccc4C3)Oc3ccc(-c4cccc(C#N)c4)cc32)N=C1N] |
| 423 | 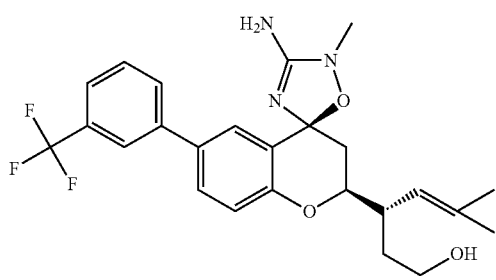 [SMILES: CC(C)=C[C@H](CCO)[C@@H]1C[C@@]2(N=C(N)N(C)O2)c2cc(-c3cccc(C(F)(F)F)c3)ccc2O1] |
| 424 | 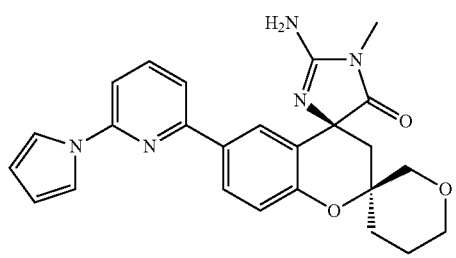 [SMILES: CN1C(=O)[C@@]2(C[C@]3(CCCOC3)Oc3ccc(-c4cccc(-n5cccc5)n4)cc32)N=C1N] |
| 425 | 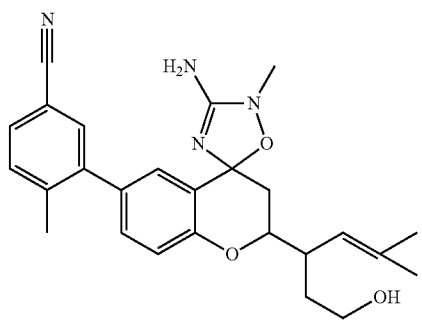 [SMILES: CC(C)=CC(CCO)C1CC2(N=C(N)N(C)O2)c2cc(-c3cc(C#N)ccc3C)ccc2O1] |
| 426 | 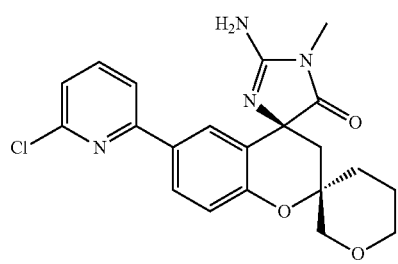 [SMILES: CN1C(=O)[C@@]2(C[C@]3(CCCOC3)Oc3ccc(-c4cccc(Cl)n4)cc32)N=C1N] |

| COMPOUND NO. | STRUCTURE |
|---|---|
| 427 | 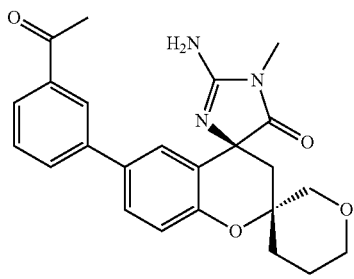 [SMILES: CC(=O)c1cccc(-c2ccc3c(c2)[C@]2(C[C@@]4(CCCOC4)O3)N=C(N)N(C)C2=O)c1] |
| 428 | 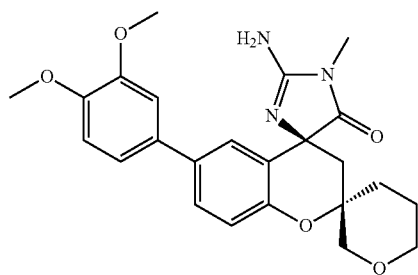 [SMILES: COc1ccc(-c2ccc3c(c2)[C@]2(C[C@]4(CCCOC4)O3)N=C(N)N(C)C2=O)cc1OC] |
| 429 | 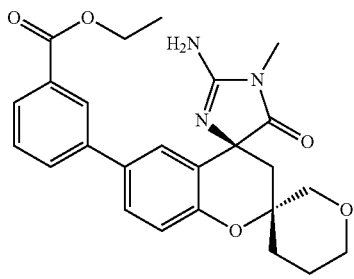 [SMILES: CCOC(=O)c1cccc(-c2ccc3c(c2)[C@]2(C[C@@]4(CCCOC4)O3)N=C(N)N(C)C2=O)c1] |
| 430 | 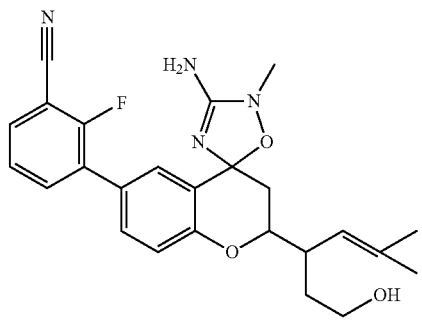 [SMILES: CC(C)=CC(CCO)C1CC2(N=C(N)N(C)O2)c2cc(-c3cccc(C#N)c3F)ccc2O1] |
| 431 | 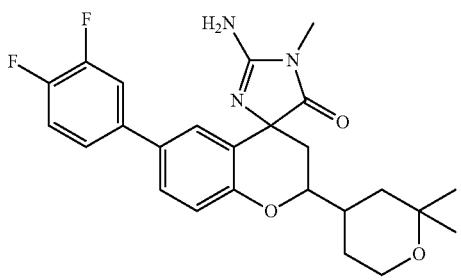 [SMILES: CN1C(=O)C2(CC(C3CCOC(C)(C)C3)Oc3ccc(-c4ccc(F)c(F)c4)cc32)N=C1N] |

| COMPOUND NO. | STRUCTURE |
|---|---|
| 432 | 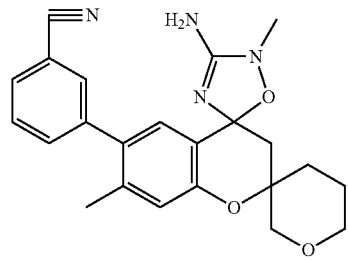 [SMILES: Cc1cc2c(cc1-c1cccc(C#N)c1)C1(CC3(CCCOC3)O2)N=C(N)N(C)O1] |
| 433 | 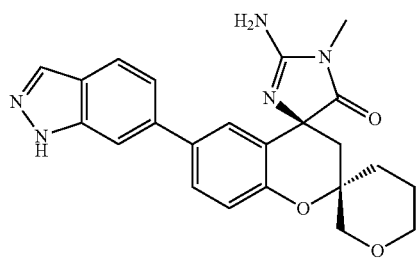 [SMILES: CN1C(=O)[C@@]2(C[C@]3(CCCOC3)Oc3ccc(-c4ccc5cn[nH]c5c4)cc32)N=C1N] |
| 434 | 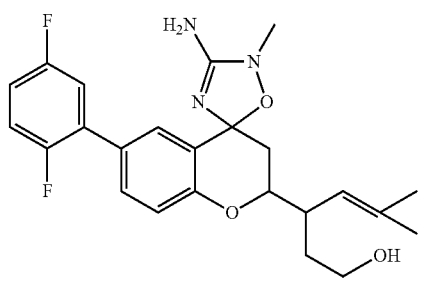 [SMILES: CC(C)=CC(CCO)C1CC2(N=C(N)N(C)O2)c2cc(-c3cc(F)ccc3F)ccc2O1] |
| 435 | 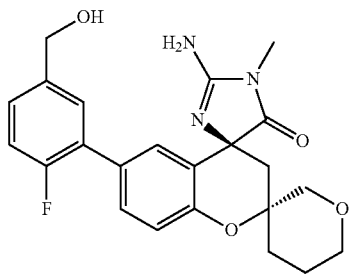 [SMILES: CN1C(=O)[C@@]2(C[C@@]3(CCCOC3)Oc3ccc(-c4cc(CO)ccc4F)cc32)N=C1N] |
| 436 | 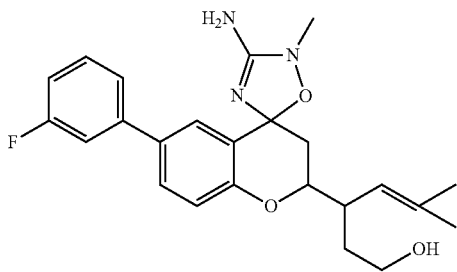 [SMILES: CC(C)=CC(CCO)C1CC2(N=C(N)N(C)O2)c2cc(-c3cccc(F)c3)ccc2O1] |

-continued
| COMPOUND NO. | STRUCTURE |
|---|---|
| 437 | 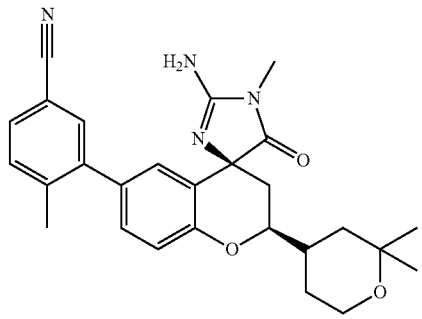 [SMILES: Cc1ccc(C#N)cc1-c1ccc2c(c1)[C@]1(C[C@@H](C3CCOC(C)(C)C3)O2)N=C(N)N(C)C1=O] |
| 438 | 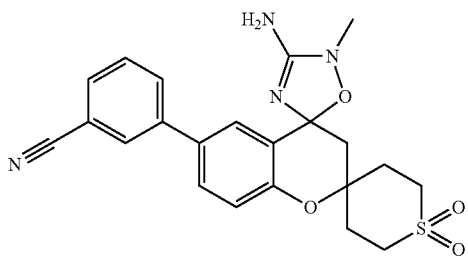 [SMILES: CN1OC2(CC3(CCS(=O)(=O)CC3)Oc3ccc(-c4cccc(C#N)c4)cc32)N=C1N] |
| 439 | 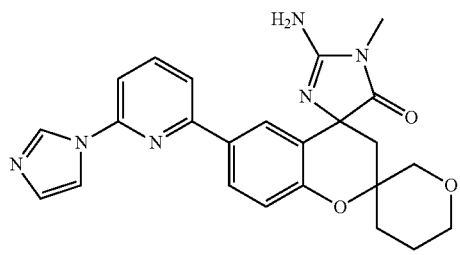 [SMILES: CN1C(=O)C2(CC3(CCCOC3)Oc3ccc(-c4cccc(-n5ccnc5)n4)cc32)N=C1N] |
| 440 | 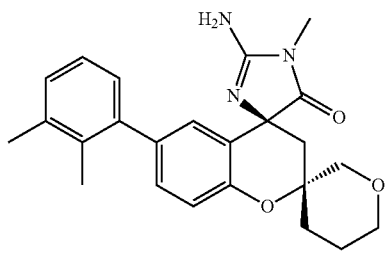 [SMILES: Cc1cccc(-c2ccc3c(c2)[C@]2(C[C@@]4(CCCOC4)O3)N=C(N)N(C)C2=O)c1C] |
| 441 | 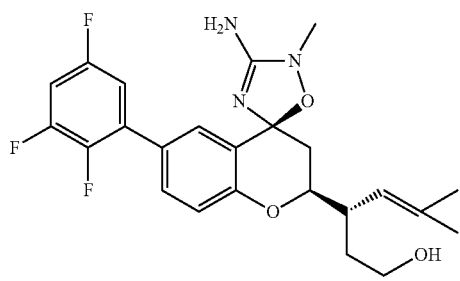 [SMILES: CC(C)=C[C@H](CCO)[C@@H]1C[C@@]2(N=C(N)N(C)O2)c2cc(-c3cc(F)cc(F)c3F)ccc2O1] |

US 8,921,359 B2
-continued
| COMPOUND NO. | STRUCTURE |
|---|---|
| 442 | 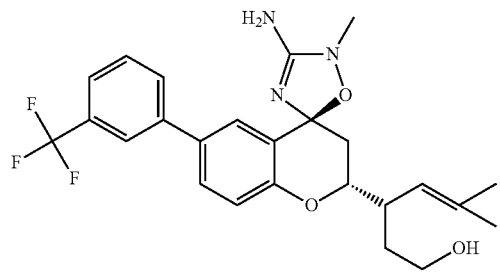 [SMILES: CC(C)=CC(CCO)[C@H]1C[C@@]2(N=C(N)N(C)O2)c2cc(-c3cccc(C(F)(F)F)c3)ccc2O1] |
| 443 | 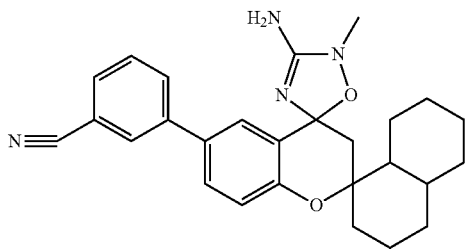 [SMILES: CN1OC2(CC3(CCCC4CCCCC43)Oc3ccc(-c4cccc(C#N)c4)cc32)N=C1N] |
| 444 | 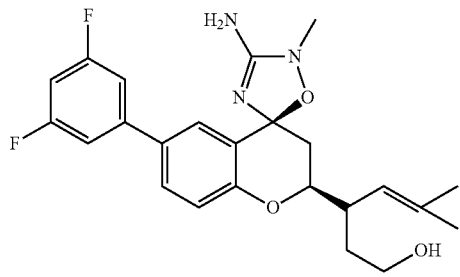 |
| 445 | 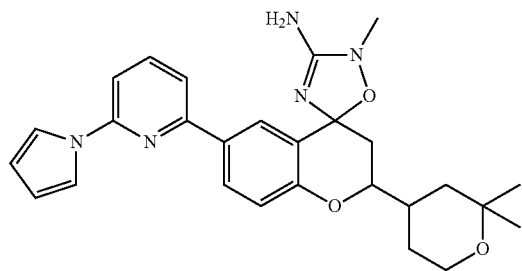 [SMILES: CN1OC2(CC(C3CCOC(C)(C)C3)Oc3ccc(-c4cccc(-n5cccc5)n4)cc32)N=C1N] |
| 446 | 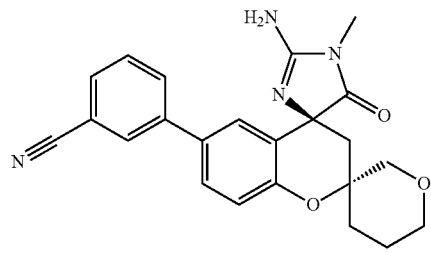 [SMILES: CN1C(=O)[C@@]2(C[C@@]3(CCCOC3)Oc3ccc(-c4cccc(C#N)c4)cc32)N=C1N] |

| COMPOUND NO. | STRUCTURE |
|---|---|
| 447 | 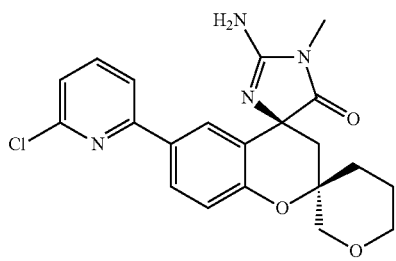 [SMILES: CN1C(=O)[C@@]2(C[C@@]3(CCCOC3)Oc3ccc(-c4cccc(Cl)n4)cc32)N=C1N] |
| 448 | 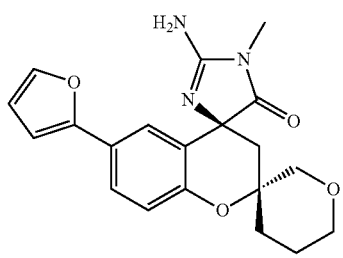 [SMILES: CN1C(=O)[C@@]2(C[C@@]3(CCCOC3)Oc3ccc(-c4ccco4)cc32)N=C1N] |
| 449 | 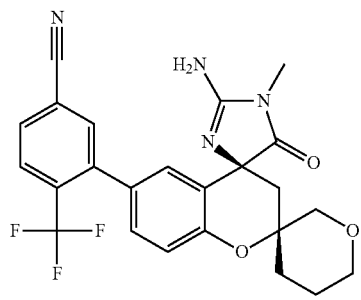 [SMILES: CN1C(=O)[C@@]2(C[C@@]3(CCCOC3)Oc3ccc(-c4cc(C#N)ccc4C(F)(F)F)cc32)N=C1N] |
| 450 | 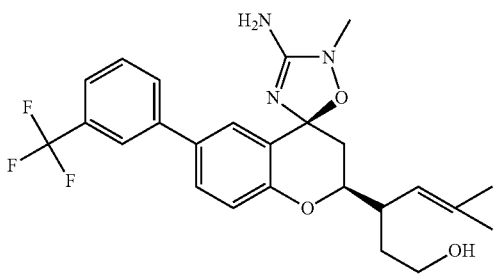 |
| 451 | 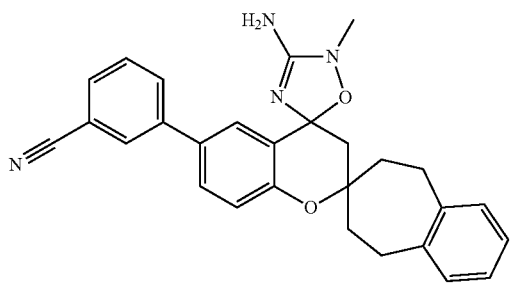 [SMILES: CN1OC2(CC3(CCc4ccccc4CC3)Oc3ccc(-c4cccc(C#N)c4)cc32)N=C1N] |

| COMPOUND NO. | STRUCTURE |
|---|---|
| 452 | 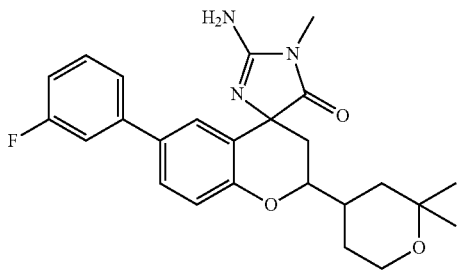 [SMILES: CN1C(=O)C2(CC(C3CCOC(C)(C)C3)Oc3ccc(-c4cccc(F)c4)cc32)N=C1N] |
| 453 | 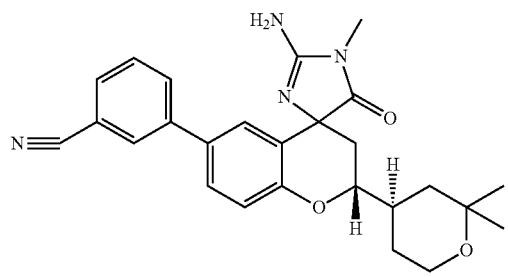 [SMILES: CN1C(=O)C2(C[C@H]([C@@H]3CCOC(C)(C)C3)Oc3ccc(-c4cccc(C#N)c4)cc32)N=C1N] |
| 454 | 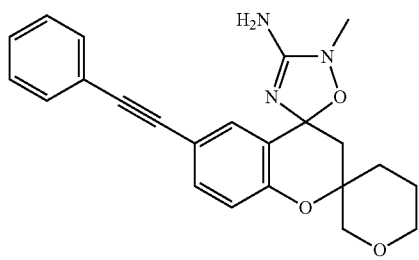 [SMILES: CN1OC2(CC3(CCCOC3)Oc3ccc(C#Cc4ccccc4)cc32)N=C1N] |
| 455 | 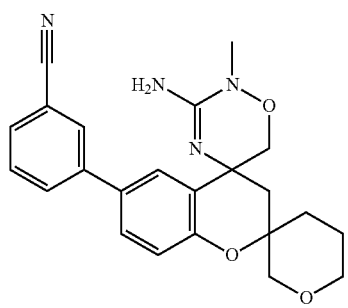 [SMILES: CN1OCC2(CC3(CCCOC3)Oc3ccc(-c4cccc(C#N)c4)cc32)N=C1N] |
| 456 | 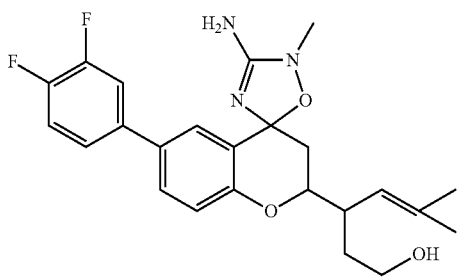 [SMILES: CC(C)=CC(CCO)C1CC2(N=C(N)N(C)O2)c2cc(-c3ccc(F)c(F)c3)ccc2O1] |

| COMPOUND NO. | STRUCTURE |
|---|---|
| 457 | 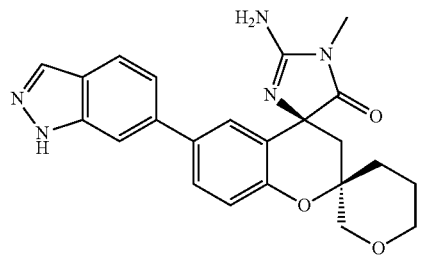 [SMILES: CN1C(=O)[C@@]2(C[C@@]3(CCCOC3)Oc3ccc(-c4ccc5cn[nH]c5c4)cc32)N=C1N] |
| 458 | 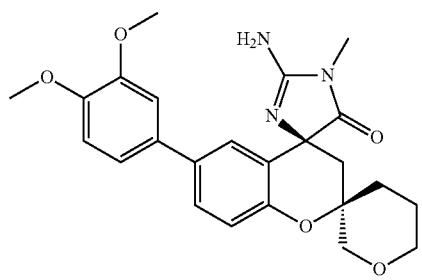 [SMILES: COc1ccc(-c2ccc3c(c2)[C@]2(C[C@@]4(CCCOC4)O3)N=C(N)N(C)C2=O)cc1OC] |
| 459 | 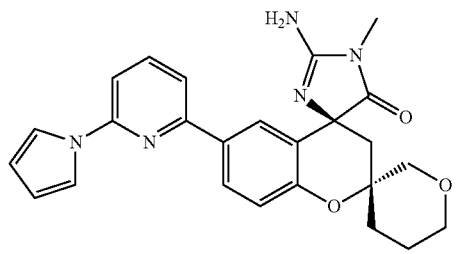 [SMILES: CN1C(=O)[C@@]2(C[C@@]3(CCCOC3)Oc3ccc(-c4cccc(-n5cccc5)n4)cc32)N=C1N] |
| 460 | 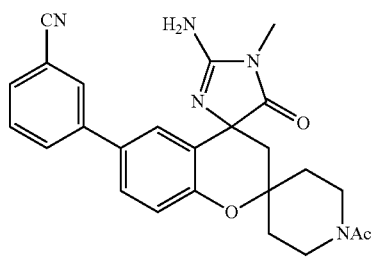 |
| 461 | 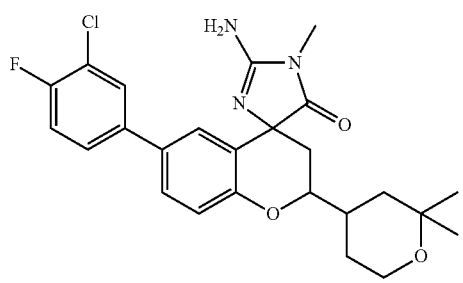 [SMILES: CN1C(=O)C2(CC(C3CCOC(C)(C)C3)Oc3ccc(-c4ccc(F)c(Cl)c4)cc32)N=C1N] |

US 8,921,359 B2
231
232
-continued
| COMPOUND NO. | STRUCTURE |
|---|---|
| 462 | 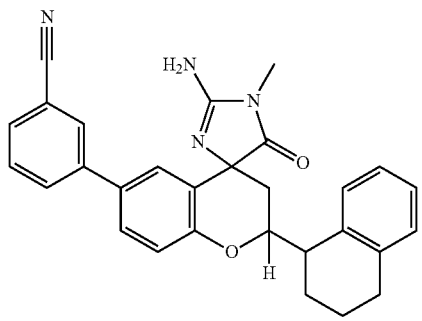 [SMILES: CN1C(=O)C2(CC(C3CCCc4ccccc43)Oc3ccc(-c4cccc(C#N)c4)cc32)N=C1N] |
| 463 | 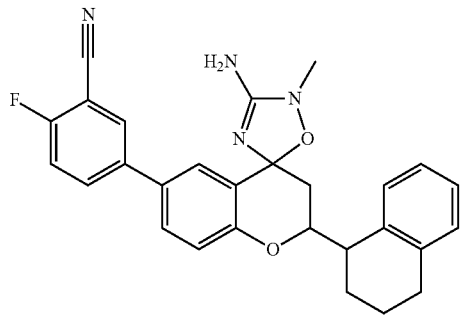 [SMILES: CN1OC2(CC(C3CCCc4ccccc43)Oc3ccc(-c4ccc(F)c(C#N)c4)cc32)N=C1N] |
| 464 | 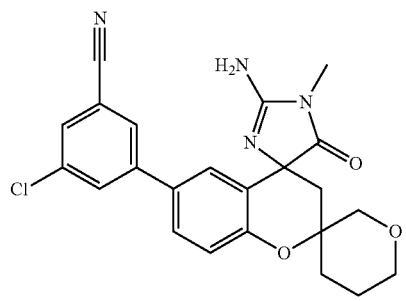 [SMILES: CN1C(=O)C2(CC3(CCCOC3)Oc3ccc(-c4cc(Cl)cc(C#N)c4)cc32)N=C1N] |
| 465 | 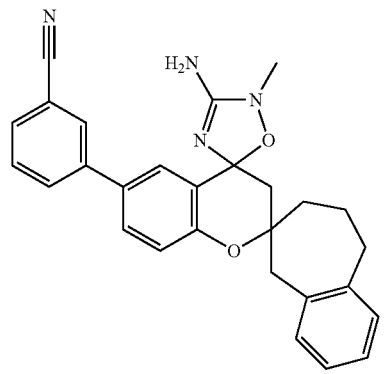 [SMILES: CN1OC2(CC3(CCCc4ccccc4C3)Oc3ccc(-c4cccc(C#N)c4)cc32)N=C1N] |

| COMPOUND NO. | STRUCTURE |
|---|---|
| 466 | 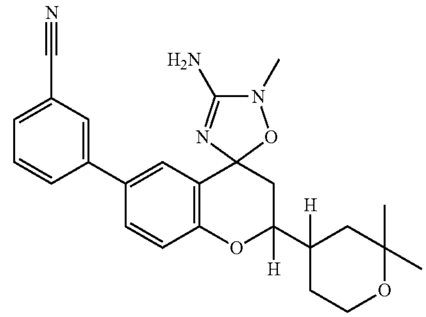 [SMILES: CN1OC2(CC(C3CCOC(C)(C)C3)Oc3ccc(-c4cccc(C#N)c4)cc32)N=C1N] |
| 467 | 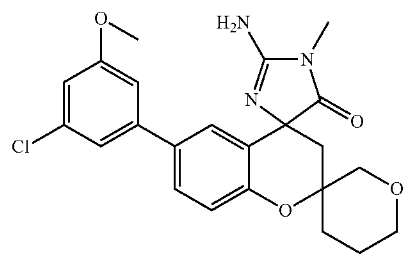 [SMILES: COc1cc(Cl)cc(-c2ccc3c(c2)C2(CC4(CCCOC4)O3)N=C(N)N(C)C2=O)c1] |
| 468 | 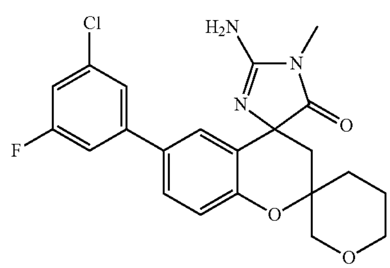 [SMILES: CN1C(=O)C2(CC3(CCCOC3)Oc3ccc(-c4cc(F)cc(Cl)c4)cc32)N=C1N] |
| 469 | 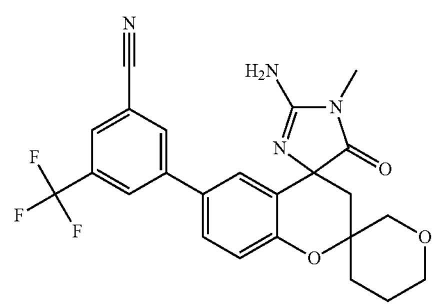 [SMILES: CN1C(=O)C2(CC3(CCCOC3)Oc3ccc(-c4cc(C#N)cc(C(F)(F)F)c4)cc32)N=C1N] |
| 470 | 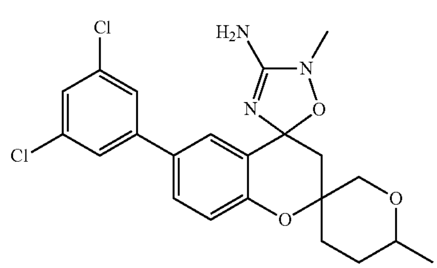 [SMILES: CC1CCC2(CO1)CC1(N=C(N)N(C)O1)c1cc(-c3cc(Cl)cc(Cl)c3)ccc1O2] |

| COMPOUND NO. | STRUCTURE |
|---|---|
| 471 | 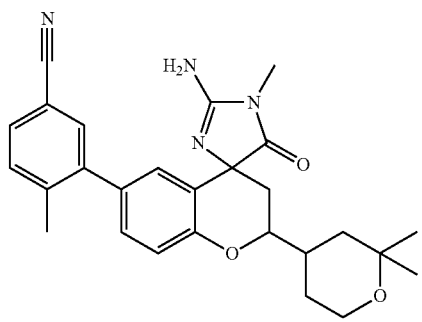 [SMILES: Cc1ccc(C#N)cc1-c1ccc2c(c1)C1(CC(C3CCOC(C)(C)C3)O2)N=C(N)N(C)C1=O] |
| 472 | 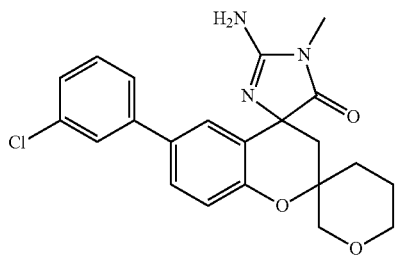 [SMILES: CN1C(=O)C2(CC3(CCCOC3)Oc3ccc(-c4cccc(Cl)c4)cc32)N=C1N] |
| 473 | 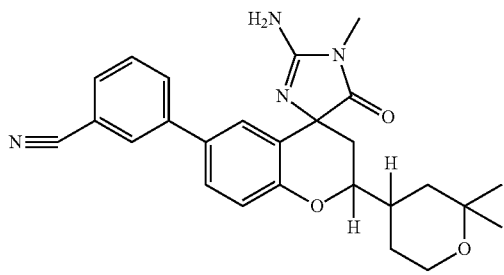 [SMILES: CN1C(=O)C2(CC(C3CCOC(C)(C)C3)Oc3ccc(-c4cccc(C#N)c4)cc32)N=C1N] |
| 474 | 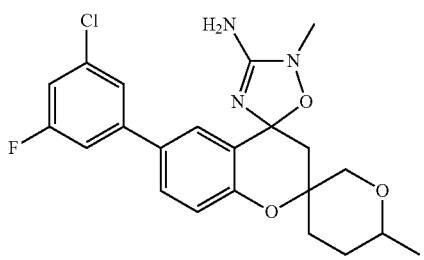 [SMILES: CC1CCC2(CO1)CC1(N=C(N)N(C)O1)c1cc(-c3cc(F)cc(Cl)c3)ccc1O2] |
| 475 | 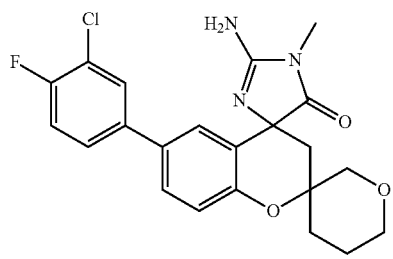 [SMILES: CN1C(=O)C2(CC3(CCCOC3)Oc3ccc(-c4ccc(F)c(Cl)c4)cc32)N=C1N] |

-continued
| COMPOUND NO. | STRUCTURE |
|---|---|
| 476 | 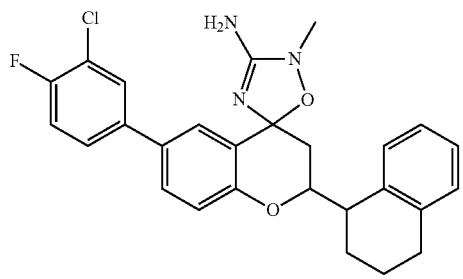 [SMILES: CN1OC2(CC(C3CCCc4ccccc43)Oc3ccc(-c4ccc(F)c(Cl)c4)cc32)N=C1N] |
| 477 | 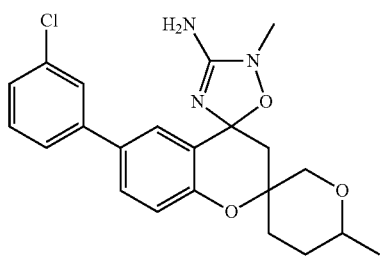 [SMILES: CC1CCC2(CO1)CC1(N=C(N)N(C)O1)c1cc(-c3cccc(Cl)c3)ccc1O2] |
| 478 | 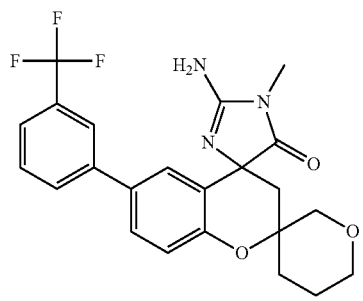 [SMILES: CN1C(=O)C2(CC3(CCCOC3)Oc3ccc(-c4cccc(C(F)(F)F)c4)cc32)N=C1N] |
| 479 | 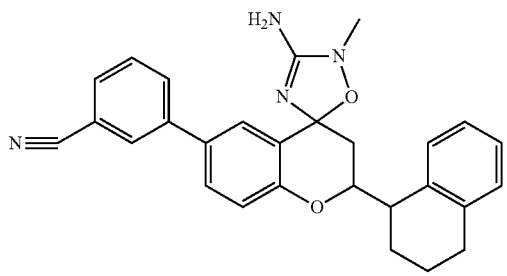 [SMILES: CN1OC2(CC(C3CCCc4ccccc43)Oc3ccc(-c4cccc(C#N)c4)cc32)N=C1N] |
| 480 | 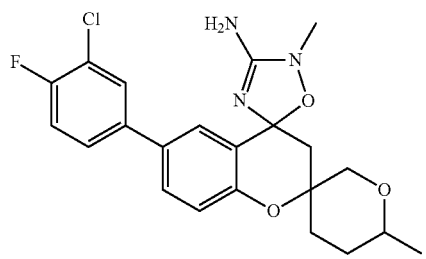 [SMILES: CC1CCC2(CO1)CC1(N=C(N)N(C)O1)c1cc(-c3ccc(F)c(Cl)c3)ccc1O2] |

-continued

| COMPOUND NO. | STRUCTURE |
|---|---|
| 481 | 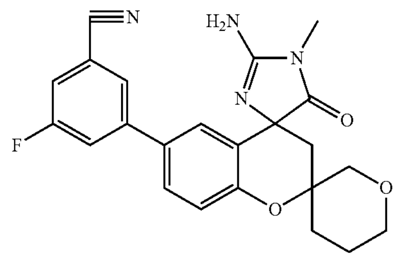 [SMILES: CN1C(=O)C2(CC3(CCCOC3)Oc3ccc(-c4cc(F)cc(C#N)c4)cc32)N=C1N] |
| 482 | 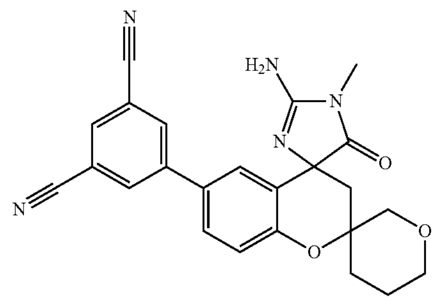 [SMILES: CN1C(=O)C2(CC3(CCCOC3)Oc3ccc(-c4cc(C#N)cc(C#N)c4)cc32)N=C1N] |
| 483 | 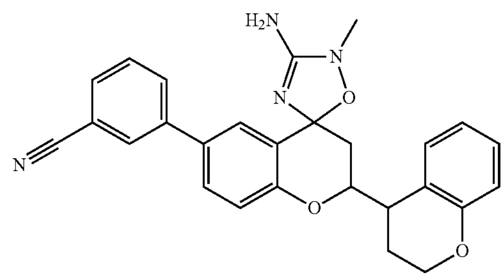 [SMILES: CN1OC2(CC(C3CCOc4ccccc43)Oc3ccc(-c4cccc(C#N)c4)cc32)N=C1N] |
| 484 | 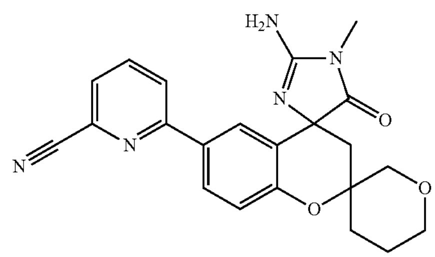 [SMILES: CN1C(=O)C2(CC3(CCCOC3)Oc3ccc(-c4cccc(C#N)n4)cc32)N=C1N] |
| 485 | 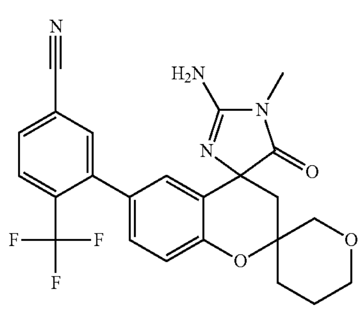 [SMILES: CN1C(=O)C2(CC3(CCCOC3)Oc3ccc(-c4cc(C#N)ccc4C(F)(F)F)cc32)N=C1N] |

-continued

| COMPOUND NO. | STRUCTURE |
|---|---|
| 486 | 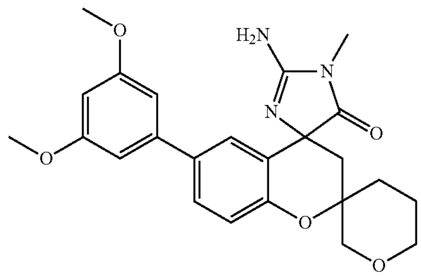 [SMILES: COc1cc(OC)cc(-c2ccc3c(c2)C2(CC4(CCCOC4)O3)N=C(N)N(C)C2=O)c1] |
| 487 | 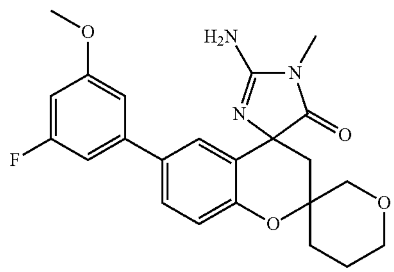 [SMILES: COc1cc(F)cc(-c2ccc3c(c2)C2(CC4(CCCOC4)O3)N=C(N)N(C)C2=O)c1] |
| 488 | 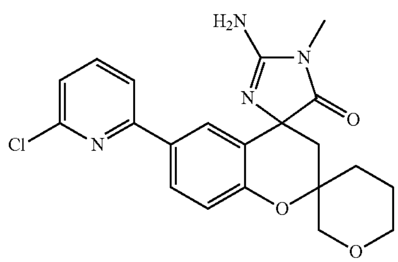 [SMILES: CN1C(=O)C2(CC3(CCCOC3)Oc3ccc(-c4cccc(Cl)n4)cc32)N=C1N] |
| 489 | 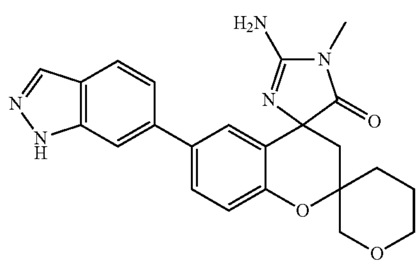 [SMILES: CN1C(=O)C2(CC3(CCCOC3)Oc3ccc(-c4ccc5cn[nH]c5c4)cc32)N=C1N] |
| 490 | 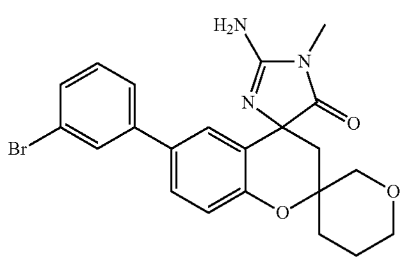 |
| 491 | 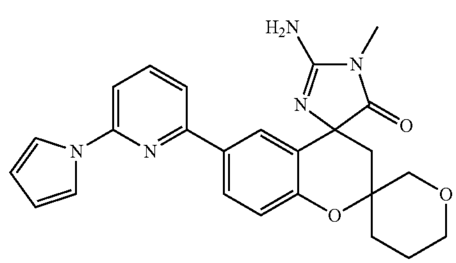 [SMILES: CN1C(=O)C2(CC3(CCCOC3)Oc3ccc(-c4cccc(-n5cccc5)n4)cc32)N=C1N] |

| COMPOUND NO. | STRUCTURE |
|---|---|
| 492 | 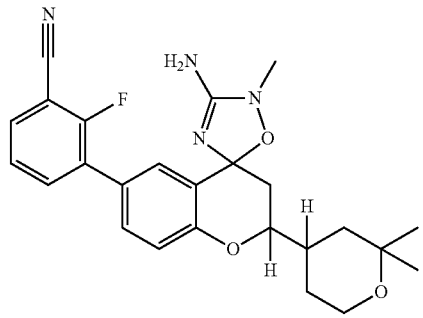 [SMILES: CN1OC2(CC(C3CCOC(C)(C)C3)Oc3ccc(-c4cccc(C#N)c4F)cc32)N=C1N] |
| 493 | 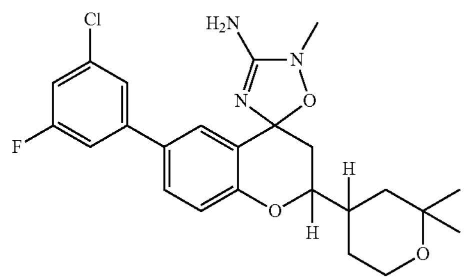 [SMILES: CN1OC2(CC(C3CCOC(C)(C)C3)Oc3ccc(-c4cc(F)cc(Cl)c4)cc32)N=C1N] |
| 494 | 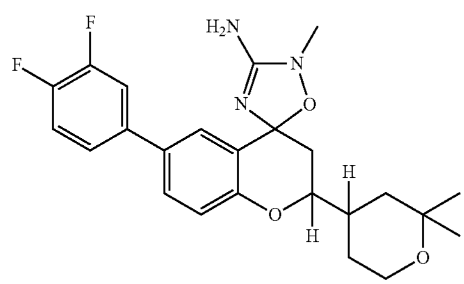 [SMILES: CN1OC2(CC(C3CCOC(C)(C)C3)Oc3ccc(-c4ccc(F)c(F)c4)cc32)N=C1N] |
| 495 | 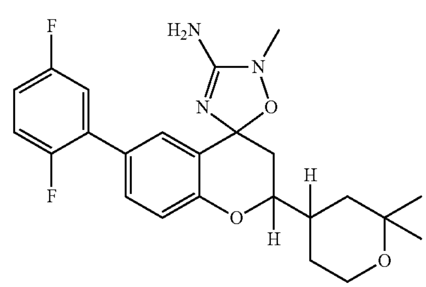 [SMILES: CN1OC2(CC(C3CCOC(C)(C)C3)Oc3ccc(-c4cc(F)ccc4F)cc32)N=C1N] |
| 496 | 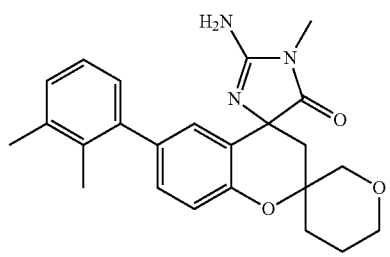 [SMILES: Cc1cccc(-c2ccc3c(c2)C2(CC4(CCCOC4)O3)N=C(N)N(C)C2=O)c1C] |

| COMPOUND NO. | STRUCTURE |
|---|---|
| 497 | 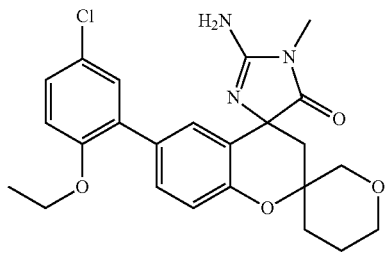 [SMILES: CCOc1ccc(Cl)cc1-c1ccc2c(c1)C1(CC3(CCCOC3)O2)N=C(N)N(C)C1=O] |
| 498 | 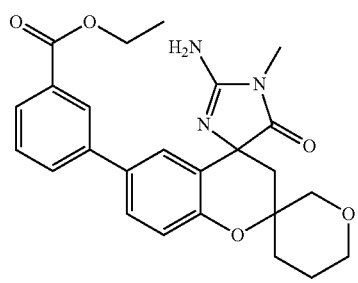 [SMILES: CCOC(=O)c1cccc(-c2ccc3c(c2)C2(CC4(CCCOC4)O3)N=C(N)N(C)C2=O)c1] |
| 499 | 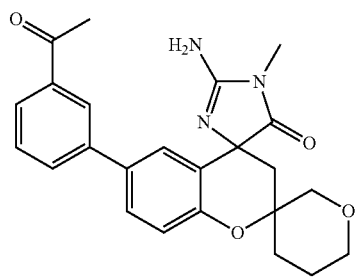 [SMILES: CC(=O)c1cccc(-c2ccc3c(c2)C2(CC4(CCCOC4)O3)N=C(N)N(C)C2=O)c1] |
| 500 | 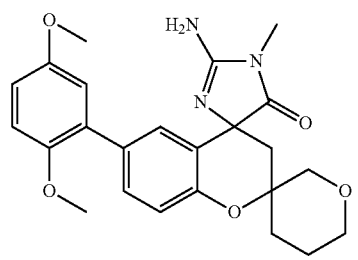 [SMILES: COc1ccc(OC)c(-c2ccc3c(c2)C2(CC4(CCCOC4)O3)N=C(N)N(C)C2=O)c1] |
| 501 | 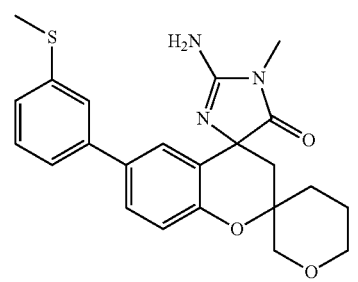 [SMILES: CSc1cccc(-c2ccc3c(c2)C2(CC4(CCCOC4)O3)N=C(N)N(C)C2=O)c1] |

-continued
| COMPOUND NO. | STRUCTURE |
|---|---|
| 502 | 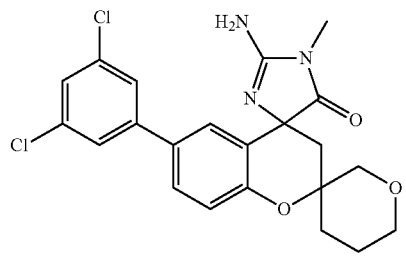 [SMILES: CN1C(=O)C2(CC3(CCCOC3)Oc3ccc(-c4cc(Cl)cc(Cl)c4)cc32)N=C1N] |
| 503 | 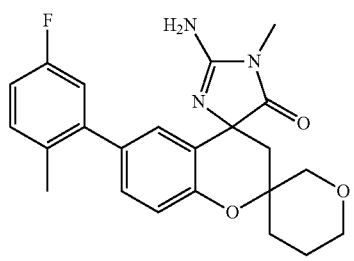 [SMILES: Cc1ccc(F)cc1-c1ccc2c(c1)C1(CC3(CCCOC3)O2)N=C(N)N(C)C1=O] |
| 504 | 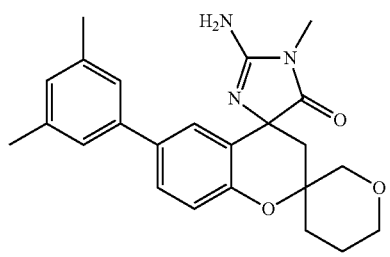 [SMILES: Cc1cc(C)cc(-c2ccc3c(c2)C2(CC4(CCCOC4)O3)N=C(N)N(C)C2=O)c1] |
| 505 | 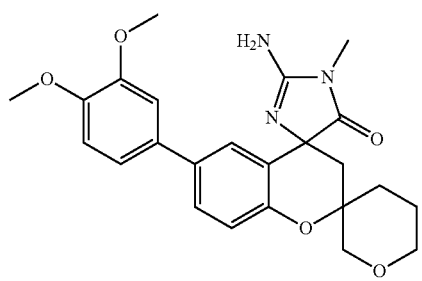 [SMILES: COc1ccc(-c2ccc3c(c2)C2(CC4(CCCOC4)O3)N=C(N)N(C)C2=O)cc1OC] |
| 506 | 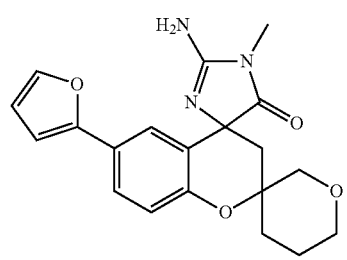 [SMILES: CN1C(=O)C2(CC3(CCCOC3)Oc3ccc(-c4ccco4)cc32)N=C1N] |

| COMPOUND NO. | STRUCTURE |
|---|---|
| 507 | 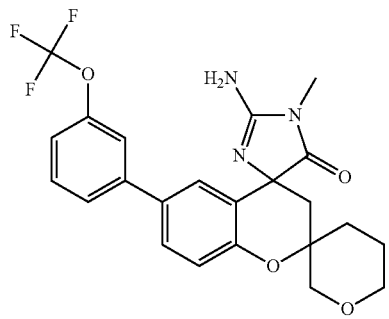 [SMILES: CN1C(=O)C2(CC3(CCCOC3)Oc3ccc(-c4cccc(OC(F)(F)F)c4)cc32)N=C1N] |
| 508 | 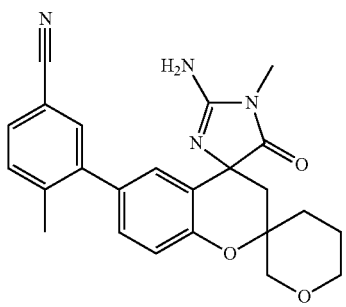 [SMILES: Cc1ccc(C#N)cc1-c1ccc2c(c1)C1(CC3(CCCOC3)O2)N=C(N)N(C)C1=O] |
| 509 | 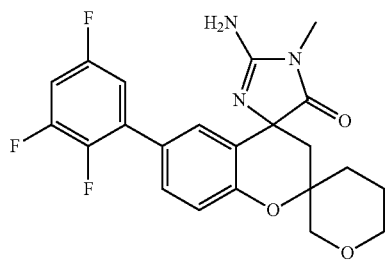 [SMILES: CN1C(=O)C2(CC3(CCCOC3)Oc3ccc(-c4cc(F)cc(F)c4F)cc32)N=C1N] |
| 510 | 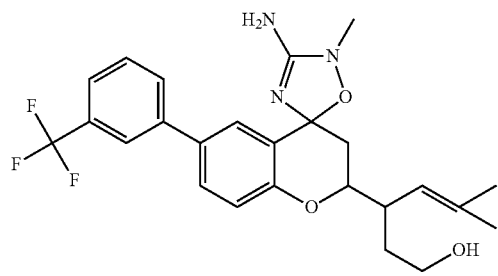 [SMILES: CC(C)=CC(CCO)C1CC2(N=C(N)N(C)O2)c2cc(-c3cccc(C(F)(F)F)c3)ccc2O1] |
| 511 | 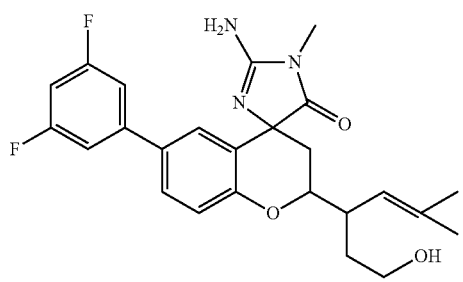 [SMILES: CC(C)=CC(CCO)C1CC2(N=C(N)N(C)C2=O)c2cc(-c3cc(F)cc(F)c3)ccc2O1] |

| COMPOUND NO. | STRUCTURE |
|---|---|
| 512 | 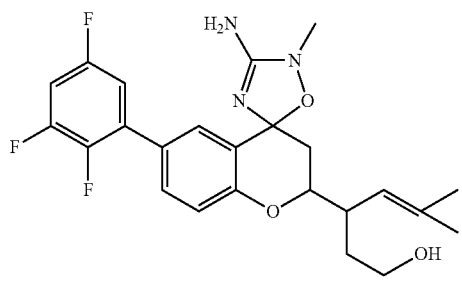 [SMILES: CC(C)=CC(CCO)C1CC2(N=C(N)N(C)O2)c2cc(-c3cc(F)cc(F)c3F)ccc2O1] |
| 513 | 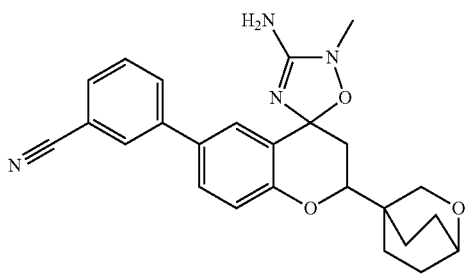 [SMILES: CN1OC2(CC(C34CCC(CC3)OC4)Oc3ccc(-c4cccc(C#N)c4)cc32)N=C1N] |
| 514 | 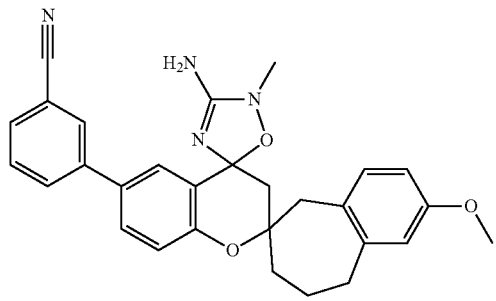 [SMILES: COc1ccc2c(c1)CCCC1(C2)CC2(N=C(N)N(C)O2)c2cc(-c3cccc(C#N)c3)ccc2O1] |
| 515 | 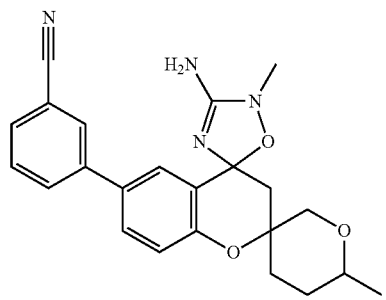 [SMILES: CC1CCC2(CO1)CC1(N=C(N)N(C)O1)c1cc(-c3cccc(C#N)c3)ccc1O2] |
| 516 | 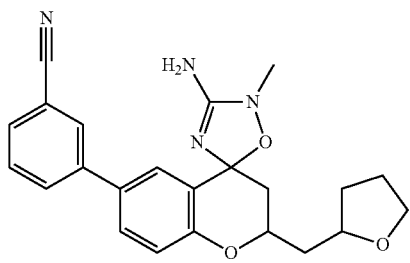 [SMILES: CN1OC2(CC(CC3CCCO3)Oc3ccc(-c4cccc(C#N)c4)cc32)N=C1N] |

| COMPOUND NO. | STRUCTURE |
|---|---|
| 517 | 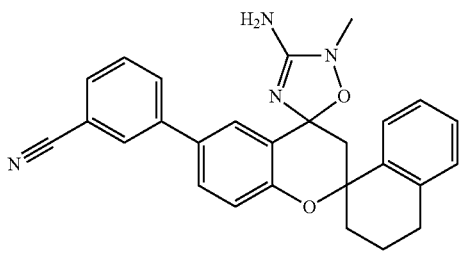 [SMILES: CN1OC2(CC3(CCCc4ccccc43)Oc3ccc(-c4cccc(C#N)c4)cc32)N=C1N] |
| 518 | 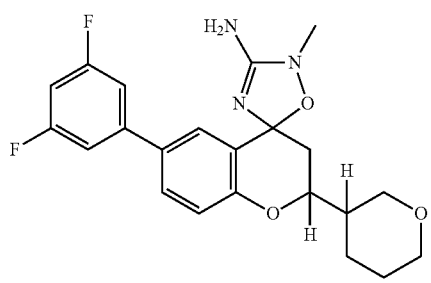 [SMILES: CN1OC2(CC(C3CCCOC3)Oc3ccc(-c4cc(F)cc(F)c4)cc32)N=C1N] |
| 519 | 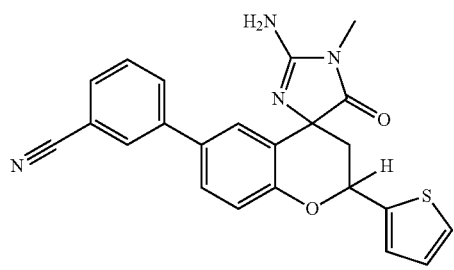 [SMILES: CN1C(=O)C2(CC(c3cccs3)Oc3ccc(-c4cccc(C#N)c4)cc32)N=C1N] |
| 520 | 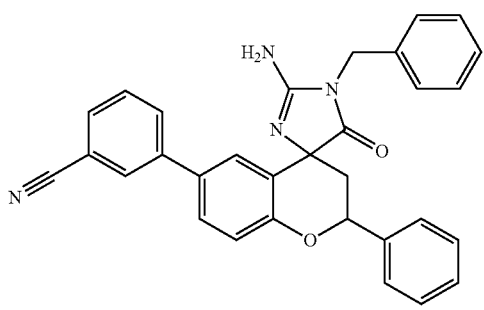 [SMILES: N#Cc1cccc(-c2ccc3c(c2)C2(CC(c4ccccc4)O3)N=C(N)N(Cc3ccccc3)C2=O)c1] |
| 521 | 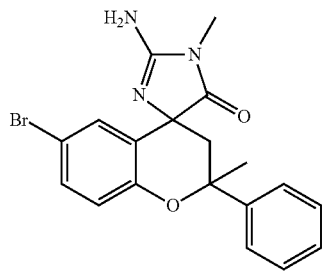 [SMILES: CN1C(=O)C2(CC(C)(c3ccccc3)Oc3ccc(Br)cc32)N=C1N] |

-continued

| COMPOUND NO. | STRUCTURE |
|---|---|
| 522 | 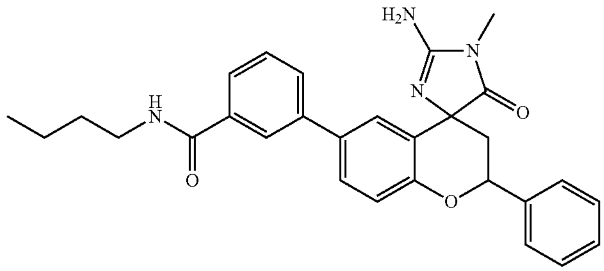 |
| 523 | 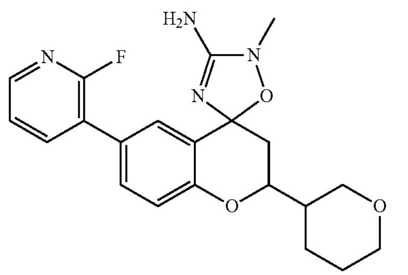 [SMILES: CN1OC2(CC(C3CCCOC3)Oc3ccc(-c4cccnc4F)cc32)N=C1N] |
| 524 | 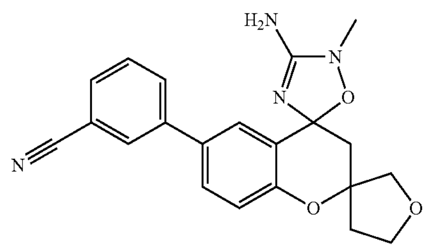 [SMILES: CN1OC2(CC3(CCOC3)Oc3ccc(-c4cccc(C#N)c4)cc32)N=C1N] |
| 525 | 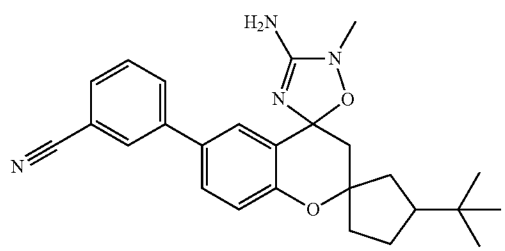 [SMILES: CN1OC2(CC3(CCC(C(C)(C)C)C3)Oc3ccc(-c4cccc(C#N)c4)cc32)N=C1N] |
| 526 | 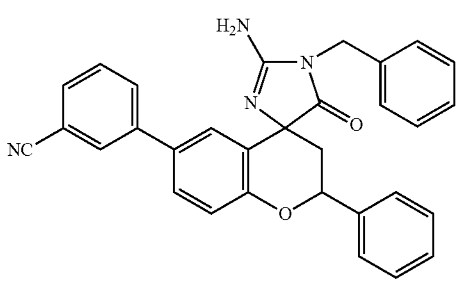 [SMILES: N#Cc1cccc(-c2ccc3c(c2)C2(CC(c4ccccc4)O3)N=C(N)N(Cc3ccccc3)C2=O)c1] |
| 527 | 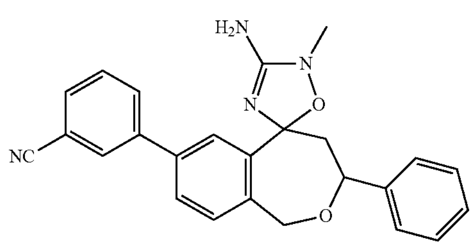 [SMILES: CN1OC2(CC(c3ccccc3)OCc3ccc(-c4cccc(C#N)c4)cc32)N=C1N] |

| COMPOUND NO. | STRUCTURE |
|---|---|
| 528 | 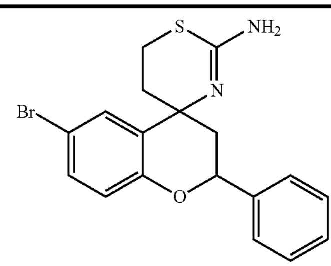 |
| 529 | 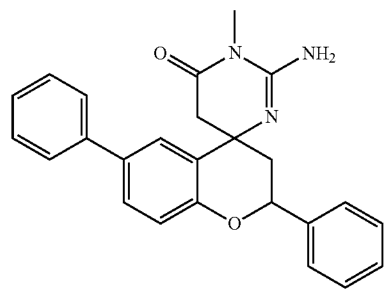 [SMILES: CN1C(=O)CC2(CC(c3ccccc3)Oc3ccc(-c4ccccc4)cc32)N=C1N] |
| 530 | 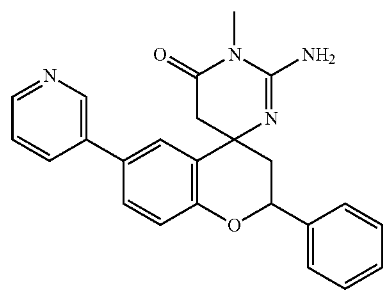 [SMILES: CN1C(=O)CC2(CC(c3ccccc3)Oc3ccc(-c4cccnc4)cc32)N=C1N] |
| 531 | 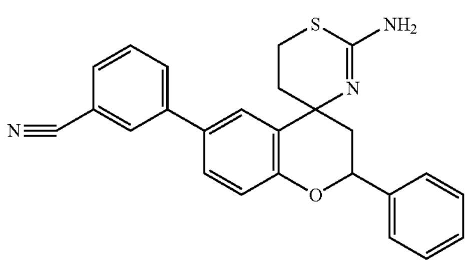 [SMILES: N#Cc1cccc(-c2ccc3c(c2)C2(CCSC(N)=N2)CC(c2ccccc2)O3)c1] |

Also included in the present invention are all possible stereoisomers of compounds 1-531 depicted above.

When any variable (e.g., aryl, heterocyclyl, $R^1$, $R^2$, etc.) occurs more than once in a compound, its definition on each occurrence is independent of any other occurrence.

"Alkyl" means a saturated aliphatic branched or straight-chain monovalent hydrocarbon radical having the specified number of carbon atoms. Thus, "$(C_1-C_6)$alkyl" means a radical having from 1-6 carbon atoms in a linear or branched arrangement. "$(C_1-C_6)$alkyl" includes methyl, ethyl, propyl, butyl, pentyl, and hexyl. Also included within the definition of "alkyl" are those alkyl groups that are optionally substituted. Suitable substitutions include, but are not limited to, -halogen, —OH, —CN, alkoxy, amino, cycloalkyl, aryl, heteroaryl, or aryloxy.

"Alkenyl" means branched or straight-chain monovalent hydrocarbon radical containing at least one double bond and having specified number of carbon atoms. Alkenyl may be mono or polyunsaturated, and may exist in the E or Z configuration. Thus, "$(C_2-C_6)$alkenyl" means a radical having from 2-6 carbon atoms in a linear or branched arrangement.

"Alkynyl" means branched or straight-chain monovalent hydrocarbon radical containing at least one triple bond and having specified number of carbon atoms. Thus, "$(C_2-C_6)$alkynyl" means a radical having from 2-6 carbon atoms in a linear or branched arrangement.

"Cycloalkyl" means a saturated aliphatic cyclic hydrocarbon radical having the specified number of carbon atoms. It can be monocyclic, bicyclic, polycyclic (e.g., tricyclic), fused, bridged, or spiro. For example, monocyclic $(C_3-C_8)$ cycloalkyl means a radical having from 3-8 carbon atoms arranged in a ring. Monocyclic $(C_3-C_8)$cycloalkyl includes cyclopropyl, cyclobutyl, cyclopentyl, cyclohexyl, cycloheptyl and cyclooctane.

Monocyclic ring systems have a single ring structure. They include saturated or unsaturated aliphatic cyclic hydrocarbon rings or aromatic hydrocarbon ring having the specified number of carbon atoms. The monocyclic ring system can optionally contain 1 to 3 heteroatoms in the ring structure and each heteroatom is independently selected from the group consisting O, N and S. When the heteroatom is N, it can be substituted with —H, alkyl, cycloalkyl, cycloalkylalkyl, aryl, arylalkyl, heteroaryl, heteroarylalkyl (preferably, —H, ($C_1$-$C_6$) alkyl, halo($C_1$-$C_6$)alkyl or ($C_1$-$C_3$)alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —S(O)$_2$—). Examples of monocyclic ring system include, but are not limited to, cyclopropyl, cyclobutyl, cyclopentyl, cyclohexyl, cycloheptyl, cyclooctane, azetidine, pyrrolidine, piperidine, piperazine, hexahydropyrimidine, tetrahydrofuran, tetrahydropyran, oxepane, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine, tetrahydro-2H-1,2-thiazine 1,1-dioxide, and isothiazolidine 1,1-dioxide, tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one.

Bicyclic ring systems have two rings that have at least one ring atom in common Bicyclic ring systems include fused, bridged and spiro ring systems. The two rings can both be aliphatic (e.g., cycloalkyl or cycloheteroalkyl), both be aromatic (e.g., aryl or heteroaryl), or a combination thereof. The bicyclic ring systems can optionally contain 1 to 3 heteroatoms in the ring structure and each heteroatom is independently selected from the group consisting O, N and S. When the heteroatom is N, it can be substituted with H, alkyl, cycloalkyl, cycloalkylalkyl, aryl, arylalkyl, heteroaryl, heteroarylalkyl (preferably, —H, ($C_1$-$C_6$)alkyl, halo($C_1$-$C_6$) alkyl or ($C_1$-$C_3$)alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —S(O)$_2$—).

A fused bicyclic ring system has two rings which have two adjacent ring atoms in common. The two rings can both be aliphatic (e.g., cycloalkyl or cycloheteroalkyl), both be aromatic (e.g., aryl or heteroaryl), or a combination thereof. For example, the first ring can be monocyclic cycloalkyl or monocyclic cycloheteroalkyl, and the second ring can a cycloalkyl, partially unsaturated carbocycle, aryl, heteroaryl or a monocyclic cycloheteroalkyl. For example, the second ring can be a ($C_3$-$C_6$)cycloalkyl, such as cyclopropyl, cyclobutyl, cyclopentyl and cyclohexyl. Alternatively, the second ring can be an aryl ring, e.g., phenyl. Examples of fused bicyclic ring systems include, but not limited to, 6,7,8,9-tetrahydro-5H-benzo[7]annulene, 2,3-dihydro-1H-indene, octahydro-1H-indene, tetrahydronaphthalene, decahydronaphthalene, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, 3-azabicyclo[3.2.0]heptane, 5,6,7,8-tetrahydroquinoline and 5,6,7,8-tetrahydroisoquinoline and 2,3,4,5-tetrahydrobenzo[b]oxepine.

A Spiro bicyclic ring system has two rings which have only one ring atom in common. The two rings can both be aliphatic (e.g., cycloalkyl or cycloheteroalkyl), both be aromatic (e.g., aryl or heteroaryl), or a combination thereof. For example, the first ring can be a monocyclic cycloalkyl or a monocyclic cycloheteroalkyl and the second ring can be a cycloalkyl, partially unsaturated carbocycle, aryl, heteroaryl or a monocyclic cycloheteroalkyl. Examples of spiral bicyclic ring system include, but are not limited to, spiro[2.2]pentane, spiro[2.3]hexane, spiro[3.3]heptane, spiro[2.4]heptane, spiro[3.4]octane, spiro[2.5]octane, azaspiro[4.4]nonane, 7-azaspiro[4.4]nonane, azasprio[4.5]decane, 8-azaspiro[4.5]decane, azaspiro[5.5]undecane, 3-azaspiro[5.5]undecane and 3,9-diazaspiro[5.5]undecane.

A bridged bicyclic ring system has two rings which have three or more adjacent ring atoms in common. The two rings can both be aliphatic (e.g., cycloalkyl or cycloheteroalkyl), both be aromatic (e.g., aryl or heteroaryl), or a combination thereof. For example, the first ring can be a monocyclic cycloalkyl or a monocyclic cycloheteroalkyl and the other ring is a cycloalkyl, partially unsaturated carbocycle, aryl, heteroaryl or a monocyclic cycloheteroalkyl. Examples of bridged bicyclic ring system include, but are not limited to, bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane bicyclo[3.3.3]undecane, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane and 2-oxabicyclo[2.2.2]octane.

Polycyclic ring systems have more than two rings (e.g., three rings resulting in a tricyclic ring system) and adjacent rings have at least one ring atom in common. Polycyclic ring systems include fused, bridged and spiro ring systems. A fused polycyclic ring system has at least two rings that have two adjacent ring atoms in common A spiro polycyclic ring system has at least two rings that have only one ring atom in common. A bridged polycyclic ring system has at least two rings that have three or more adjacent ring atoms in common. Examples of polycyclic ring system include, but not limited to, tricyclo[3.3.1.0$^{3,7}$]nonane (noradamantane) and tricyclo[3.3.1.1$^{3,7}$]decane (adamantane) and 2,3-dihydro-1H-phenalene.

"Cycloheteroalkyl" means a saturated 4-12 membered ring containing 1 to 4 heteroatoms, which may be the same or different, selected from N, O or S and optionally containing one or more double bonds. It can be monocyclic, bicyclic, polycyclic (e.g. tricyclic), fused, bridged, or spiro.

When the heteroatom is N, it can be substituted with H, alkyl, cycloalkyl, cycloalkylalkyl, aryl, arylalkyl, heteroaryl, heteroarylalkyl (preferably, —H, ($C_1$-$C_6$)alkyl, halo($C_1$-$C_6$) alkyl or ($C_1$-$C_3$)alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —S(O)$_2$—).

Haloalkyl and halocycloalkyl include mono, poly, and perhaloalkyl groups where the halogens are independently selected from fluorine, chlorine, and bromine "Heteroaryl" means a monovalent heteroaromatic monocyclic or polycyclic ring radical. Heteroaryl rings are 5- and 6-membered aromatic heterocyclic rings containing 1 to 4 heteroatoms independently selected from N, O, and S, and include, but are not limited to furan, thiophene, pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, and tetrazole. Bicyclic heteroaryl rings are bicyclo[4.4.0] and bicyclo[4.3.0] fused ring systems containing 1 to 4 heteroatoms independently selected from N, O, and S, and include indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, and pteridine.

"Alkoxy" means an alkyl radical attached through an oxygen linking atom. "$(C_1-C_4)$-alkoxy" includes methoxy, ethoxy, propoxy, and butoxy.

"Aromatic" means an unsaturated cycloalkyl ring system.

"Aryl" means an aromatic monocyclic, or polycyclic carbocyclic ring system. Aryl systems include, but limited to, phenyl, naphthalenyl, fluorenyl, indenyl, azulenyl, and anthracenyl.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Halogen" used herein refers to fluorine, chlorine, bromine, or iodine.

"Carbocycle" means 3-14 membered saturated or unsaturated aliphatic cyclic hydrocarbon ring.

"Cycloalkene" a unsaturated and non-aromatic aliphatic cyclic hydrocarbon radical having the specified number of carbon atoms. It can be monocyclic, bicyclic, tricyclic, fused, bridged, or spiro. Thus, $(C_3-C_8)$cycloalkene means a radical having from 3-8 carbon atoms arranged in a ring. $(C_3-C_8)$ cycloalkene includes cyclobutene, cyclopentene, cyclohexene, cycloheptene and cyclooctene.

Ring A is a 3-14 membered monocyclic ring system, 9-14 membered bicyclic ring system or 9-14 membered polycyclic ring system. The rings of the bicyclic and polycyclic ring systems can be fused, bridged or spiral. Ring A can be aromatic (e.g., aryl or heteroaryl) or aliphatic (saturated or unsaturated), provided that when Ring A is a monocyclic ring, it can only be aliphatic. For example, ring A can be a carbocycle such as a cycloalkene (e.g., cyclopentene, cyclohexene, cycloheptene or cyclooctene), a cycloalkane ring or a cycloheteroalkane ring as defined above. Ring A can optionally contain 1 to 3 heteroatoms each independently selected from O, S and N. When the heteroatom is N, it can be substituted with H, alkyl, cycloalkyl, cycloalkylalkyl, aryl, arylalkyl, heteroaryl, heteroarylalkyl (preferably, —H, $(C_1-C_6)$alkyl, halo$(C_1-C_6)$alkyl or $(C_1-C_3)$alkylcarbonyl), each of which can be optionally substituted with halogen, hydroxy, alkoxy, haloalkyl, alkyl, etc. When the heteroatom is S, it can be optionally mono- or di-oxygenated (i.e. —S(O)— or —S(O)$_2$—).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl) amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

It may be necessary and/or desirable during synthesis to protect sensitive or reactive groups on any of the molecules concerned. Representative conventional protecting groups are described in T. W. Greene and P. G. M. Wuts "Protective Groups in Organic Synthesis" John Wiley & Sons, Inc., New York 1999. Protecting groups may be added and removed using methods well known in the art.

The invention also includes various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Certain of the compounds of the present invention may exist in various stereoisomeric or tautomeric forms. Stereoisomers are compounds which differ only in their spatial arrangement. The invention encompasses all such forms, including compounds in the form of essentially pure entiomers, racemic mixtures and tautomers, which includes forms not depicted structurally. When a disclosed compound is named or depicted by structure without indicating stereochemistry, it is understood that the name or structure encompasses all possible stereoisomers, tautomers, geometric isomers or a combination thereof.

Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S, a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

Atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. A mixture of "cis" and "trans" species is designated "cis/trans".

The point at which a group or moiety is attached to the remainder of the compound or another group or moiety can be indicated by "⁓" which represents "⋯", "▬" or "-".

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of the compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention are BACE inhibitors for treating, preventing or ameliorating disorders or diseases characterized by elevated β-amyloid deposits or β-amyloid levels in a subject. Such diseases or disorders include, but not limited to, Alzheimer's disease, Trisomy 21 (Down's Syndrome), Hereditary Cerebral Hemorrhage with Amyloidosis of the Dutch-type (HCHWA-D), other neurodegenerative disorders and glaucoma. Accordingly, the present invention provides methods for modulating BACE and treating, preventing or ameliorating Alzheimer's disease, Trisomy 21 (Down's Syndrome), Hereditary Cerebral Hemorrhage with Amyloidosis of the Dutch-type (HCHWA-D) and other neurodegenerative disorders. Such methods comprises administering to a patient suffering from, suspected of suffering from or being susceptible to the disease or disorder an effective amount of the compound of Structural Formula (I) or a pharmaceutically acceptable salt thereof.

The present invention also provides a method for the treatment of a disorder related to or associated with excessive BACE activity in a patient in need thereof which comprises administering to said patient an effective amount of the compound of Structural Formula (I) or a pharmaceutically acceptable salt thereof. Representative disorders include Alzheimer's disease, cognitive impairment, Down's Syndrome, HCHWA-D, cognitive decline, senile dementia, cerebral amyloid angiopathy, degenerative dementia, other neurodegenerative disorders, and glaucoma. Certain of these diseases are characterized by production of β-amyloid deposits or neurofibrillary tangles.

The present invention also provides methods for inhibiting the activity of BACE, comprising administering to a subject and/or contacting a receptor thereof with an effective amount of at least one compound of Structural Formula (I) or a pharmaceutically acceptable salt thereof.

The present invention also provides methods of ameliorating β-amyloid deposits in a subject, comprising administering to said subject an effective amount of at least one compound of Structural Formula (I) or a pharmaceutically acceptable salt thereof.

The present invention also provides methods of treating a disorder selected from the group consisting of Alzheimer's disease, cognitive impairment, Down's Syndrome, HCHWA-D, cognitive decline, senile dementia, cerebral amyloid angiopathy, degenerative dementia, other neurodegenerative disorders, and glaucoma in a subject in need of such treatment comprising administering to the subject an effective amount of a compound of Structural Formula (I) or a pharmaceutically acceptable salt thereof. In one embodiment, the disorder is Alzheimer's disease. In another embodiment, the disorder is glaucoma.

A pharmaceutical composition of the invention may, alternatively or in addition to a compound of Formula I or any formula of the invention described herein, comprise a pharmaceutically acceptable salt of a compound of Formula I or a prodrug or pharmaceutically active metabolite of such a compound or salt and one or more pharmaceutically acceptable carriers therefor.

The compositions of the invention are BACE inhibitors. Said compositions can contain compounds having a mean inhibition constant ($IC_{50}$) against BACE of between about 50 µM to about 0.01 nM; between about 10 µM to about 0.01 nM; between about 5 µM to about 0.01 nM; between about 1 µM to about 0.01 nM; between about 500 nM to about 0.01 nM; between about 100 nM to about 0.01 nM; between about 50 nM to about 0.01 nM; or between about 5 nM to about 0.01 nM.

The invention includes a therapeutic method for treating or ameliorating an BACE mediated disorder in a subject in need thereof comprising administering to a subject in need thereof an effective amount of a compound of Formula I or any other formulas of the invention described herein, or the enantiomers, diastereomers, or salts thereof or composition thereof.

Administration methods include administering an effective amount (i.e., an effective amount) of a compound or composition of the invention at different times during the course of therapy or concurrently in a combination form. The methods of the invention include all known therapeutic treatment regimens.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

"Prodrug" means a pharmaceutically acceptable form of an effective derivative of a compound (or a salt thereof) of the invention, wherein the prodrug may be: 1) a relatively active precursor which converts in vivo to a compound of the invention; 2) a relatively inactive precursor which converts in vivo to a compound of the invention; or 3) a relatively less active component of the compound that contributes to therapeutic activity after becoming available in vivo (i.e., as a metabolite). See "Design of Prodrugs", ed. H. Bundgaard, Elsevier, 1985.

"Metabolite" means a pharmaceutically acceptable form of a metabolic derivative of a compound (or a salt thereof) of the invention, wherein the derivative is an active compound that contributes to therapeutic activity after becoming available in vivo.

"Effective amount" means that amount of active compound agent that elicits the desired biological response in a subject. Such response includes alleviation of the symptoms of the disease or disorder being treated. The effective amount of a compound of the invention in such a therapeutic method is from about 0.01 mg/kg/day to about 1000 mg/kg/day, from about 0.1 mg/kg/day to about 100 mg/kg/day, from about 0.5 mg/kg/day to about 50 mg/kg/day, or from about 1 mg/kg/day to 10 mg/kg/day.

"Pharmaceutically acceptable carrier" means compounds and compositions that are of sufficient purity and quality for use in the formulation of a composition of the invention and that, when appropriately administered to an animal or human, do not produce an adverse reaction.

"BACE mediated disorder or disease" includes disorders or diseases associated with the elevated expression or overexpression of BACE and conditions that accompany such diseases.

An embodiment of the invention includes administering β-secretase inhibiting compound of Formula I or any formula of the invention described herein or a composition thereof in a combination therapy with one or more additional agents for the treatment of Alzheimer's disease. Additional agents include, but are not limited to: cholinesterase inhibitors, such as donepezil, rivastigmine, and galantamine; memantine; tacrine; antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone.

Combination therapy includes co-administration of the compound of the invention and said other agent, sequential administration of the compound and the other agent, administration of a composition containing the compound and the other agent, or simultaneous administration of separate compositions containing of the compound and the other agent.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound of Formula I may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

Compounds of the invention may also be administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

Methods of Preparation

In cases where the synthetic intermediates and final products of Formula I described below contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not usually described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

| Abbreviation | Meaning |
| --- | --- |
| AcCl | acetyl chloride |
| $AlCl_3$ | aluminum chloride |
| Ar | argon |
| $B_2H_6$ | diborane |
| Boc | tert-butoxy carbonyl or t-butoxy carbonyl |
| borax | sodium borate |
| brine | saturated aqueous NaCl |
| $CH_2N_2$ | carbodiimide |
| $CH_3CN$ | acetonitrile |

General Synthetic Schemes

| Abbreviation | Meaning |
| --- | --- |
| $Cs_2CO_3$ | cesium carbonate |
| $CuBr-SMe_2$ | cuprous bromide methylsulfide complex |
| CuI | cuprous iodide |
| DCM or $CH_2Cl_2$ | methylene chloride |
| DIBAL-H | diisobutylaluminum hydride |
| DMAP | 4-(dimethylamino)pyridine |
| EtI | ethyl iodide |
| Et | ethyl |
| $Et_2O$ | ethyl ether |
| EtOAc, EA | ethyl acetate |
| EtOH | ethanol |
| $Et_3O^+BF_4^-$ | triethyloxonium tetrafluoroborate |
| h, hr | hour |
| HCl | hydrochloric acid |
| $H_2O$ | water |
| $H_2O_2$ | hydrogen peroxide |
| $HCONH_2$ | formamide |
| HMPA | hexamethylphosphoric triamide |
| HMPT | hexamethylphosphorous triamide |
| HPLC | high performance liquid chromatography |
| $K_2CO_3$ | potassium carbonate |
| KCN | potassium cyanide |
| Lawesson's reagent | 2,4-bis(4-methoxyphenyl)-1,3,2,4-dithiadiphosphetane 2,4-disulfide |
| min | minute |
| MeOH | methanol |
| MeI | methyl iodide |
| Me | methyl |
| MeNHOH | methylhydroxylamine |
| MTBA | 4-(methylthio)benzoic acid |
| $Me_2S$ | methyl sulfide |
| NaOH | sodium hydroxid |
| NaOMe | sodium methoxide |
| $Na_2S_2O_3$ | sodium thiosulfate |
| $Na_2SO_4$ | sodium sulfate |
| $NH_4OH$ | ammonium hydroxide |
| $(NH_4)_2CO_3$ | ammonium carbonate |
| $NH_4I$ | ammonium iodide |
| $Na_2CO_3$ | sodium carbonate |
| $NaHCO_3$ | sodium bicarbonate |
| NaH | sodium hydride |
| $PdCl_2dppf$ | [1,1-bis(diphenylphosphino)ferrocene]dichloropalladium (II) |
| $Pd(OH)_2$ | palladium hydroxide |
| $Pd(PPh_3)_2Cl_2$ | bis(triphenylphosphine)palladium (II) dichloride |
| $Pd(PPh_3)_4$ | tetrakis(triphenylphosphine)palladium(0) |
| PrBr | propyl bromide |
| $PBr_3$ | phosphorous tribromide |
| PCC | pyridinium chlorochromate |
| PE | petroleum ether |
| PPA | polyphosphoric acid |
| $PPh_3$ | triphenyl phosphine |
| Selectfluor™ | 1-chloromethyl-4-fluoro-1,4-diazoniabicyclo[2.2.2]octane bis(tetrafluoroborate) |
| $SOCl_2$ | thionyl chloride |
| TFA | trifluoroacetic acid |
| THF | tetrahydrofuran |
| TLC | thin layer chromatography |
| $TiCl_4$ | titanium chloride |

Compounds of the invention can be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic schemes.

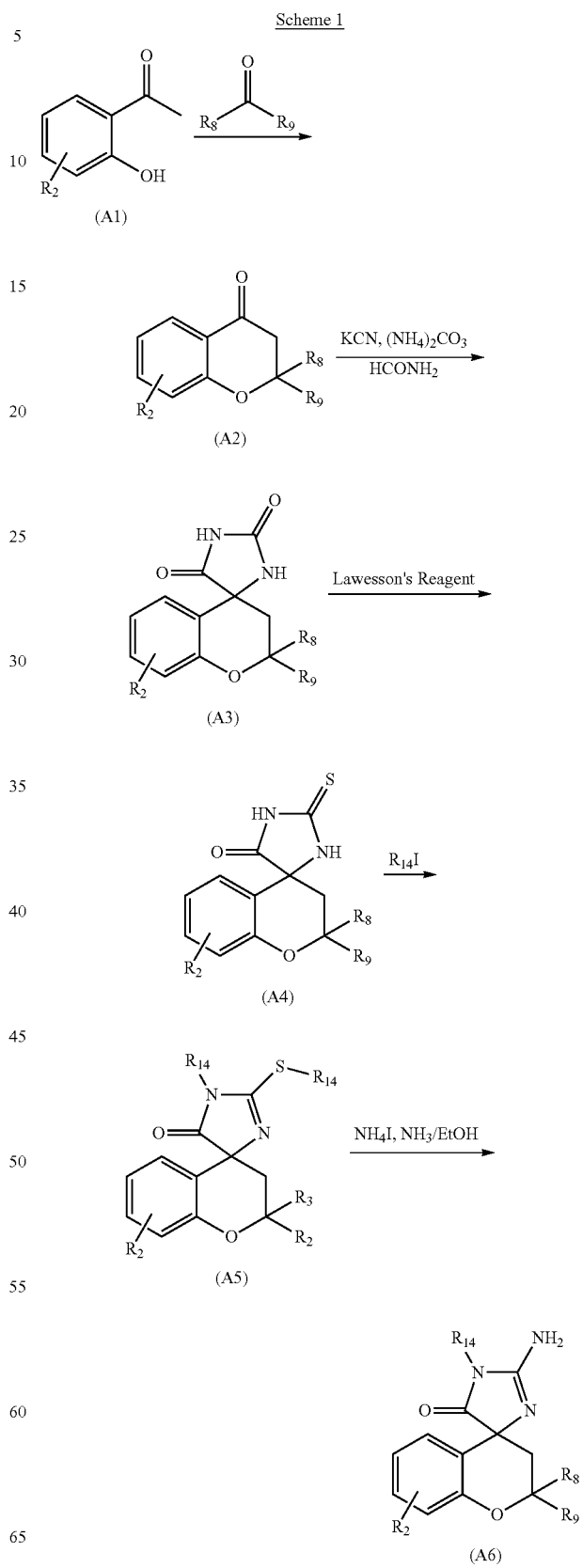

Scheme 2
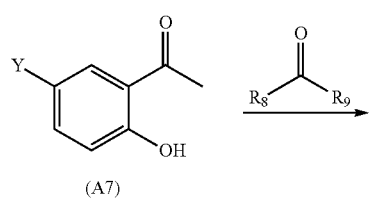
(A7)
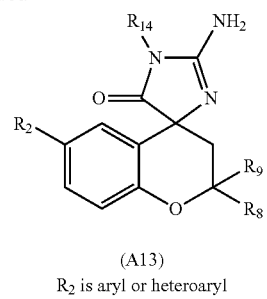
(A13)
R2 is aryl or heteroaryl
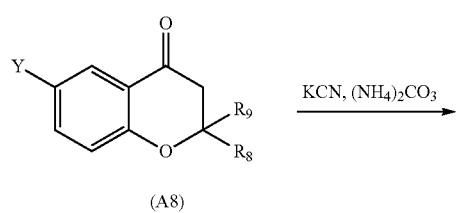
(A8)
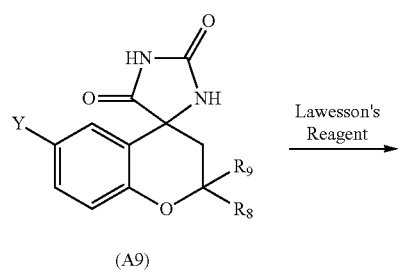
(A9)
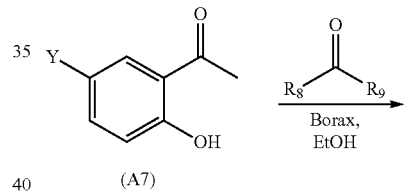
(A7)
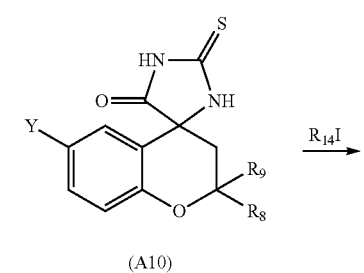
(A10)
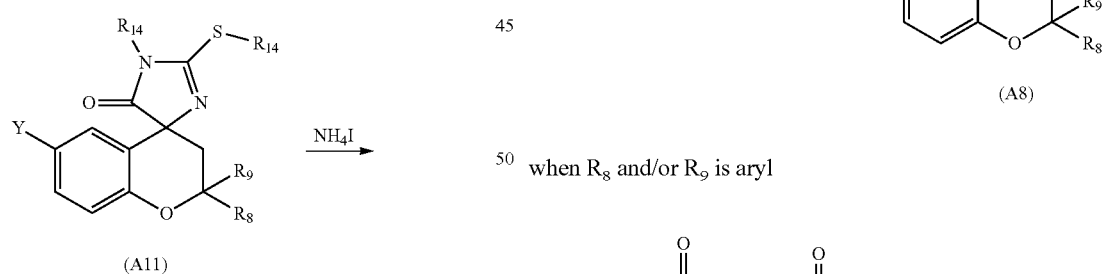
when R8 and/or R9 is not aryl
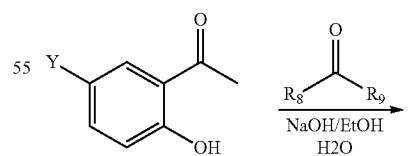
(A7)
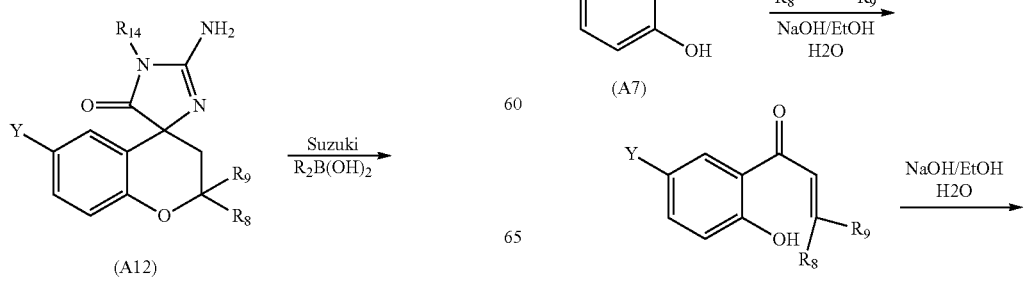
when R8 and/or R9 is aryl
(A11)
(A12)

-continued

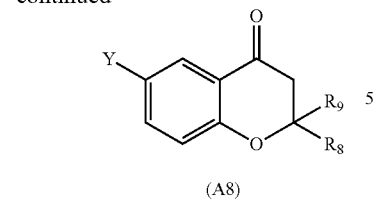

(A8)

Scheme 3

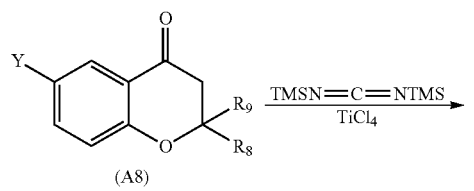

(A8)

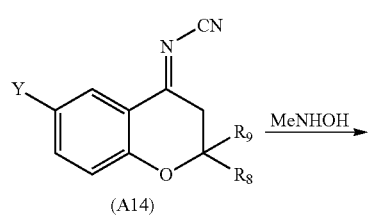

(A14)

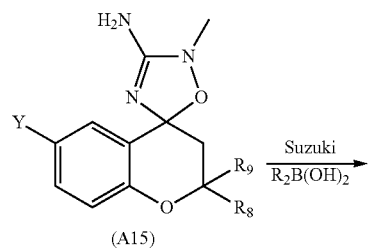

(A15)

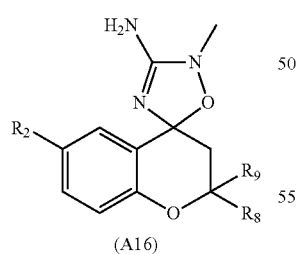

(A16)

R₂ is aryl or heteroaryl

While this invention has been particularly shown and described with references to example embodiments thereof, it will be understood by those skilled in the art that various changes in form and details may be made therein without departing from the scope of the invention encompassed by the appended claims.

EXEMPLIFICATION

Example 1

3-(2'-amino-1'-methyl-5'-oxo-2-(tetrahydro-2H-pyran-3-yl)-1',5'-dihydrospiro[chroman-4,4'-imidazole]-6-yl)benzonitrile (Compound 1)

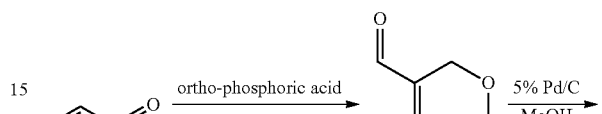

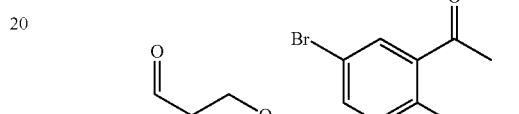

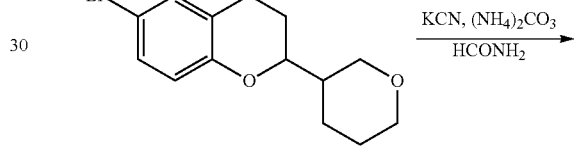

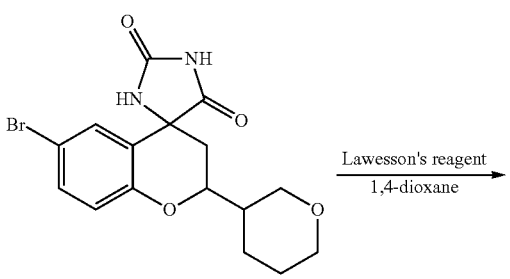

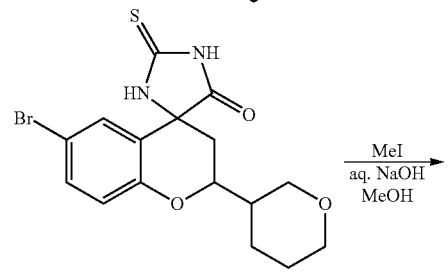

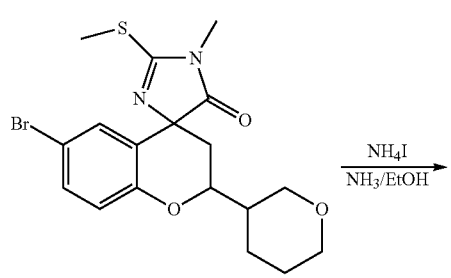

-continued

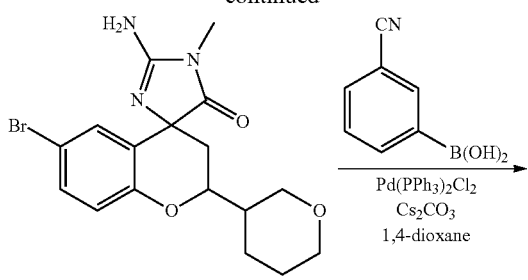

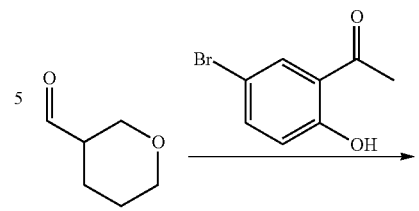

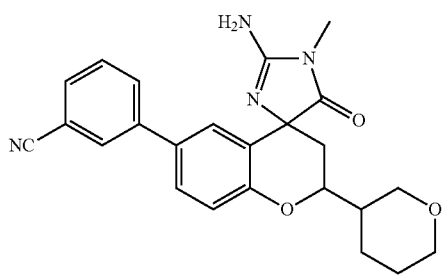 [SMILES: CN1C(=O)C2(CC(C3CCCOC3)Oc3ccc(-c4cccc(C#N)c4)cc32)N=C1N]

Experimental Data:

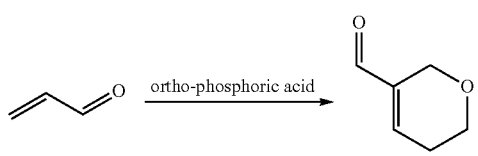

Step 1. 5,6-dihydro-2H-pyran-3-carbaldehyde 140 g of water, 186 g of CH$_2$Cl$_2$, H$_3$PO$_4$ (34 g) was added to the acrylaldehyde (62 g, 1.1 mol) and the mixture was stirred at 80° C. overnight. The organic layer was separated and the upper aqueous layer was extracted with 100 mL of CH$_2$Cl$_2$. Distillation of the organic phase gave 5,6-dihydro-2H-pyran-3-carbaldehyde (25 g, 40%). $^1$H-NMR (CDCl$_3$): 2.41 (d, 2H), 2.69 (t, 1H), 3.74 (t, 4H), 3.90 (t, 1H), 4.31 (s, 2H), 6.81 (m, 1H), 9.46 (s, 1H).

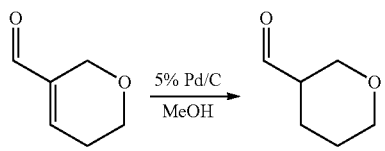 [SMILES: "MeOH" ; O=CC1=CCCOC1 ; O=CC1CCCOC1]

Step 2. tetrahydro-2H-pyran-3-carbaldehyde 5,6-Dihydro-2H-pyran-3-carbaldehyde (20 g, 178.6 mmol) was dissolved in MeOH (150 mL). Pd/C (1 g, 5%) was added and the mixture was reacted at room temperature under H$_2$ at 50 Psi. The mixture was concentrated in vacuo to give tetrahydro-2H-pyran-3-carbaldehyde (20 g, 100%). $^1$H-NMR (CDCl$_3$): 2.40 (t, 2H), 3.74 (t, 2H), 4.27 (m, 2H), 6.89 (m, 1H), 9.36 (t, 1H).

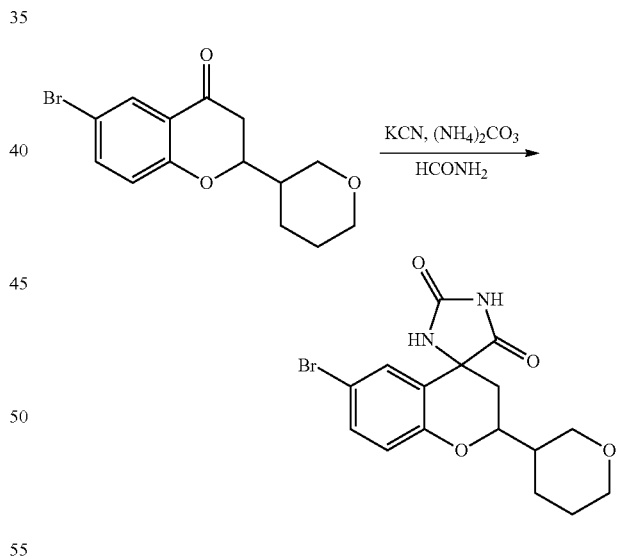

Step 3. 6-bromo-2-(tetrahydro-2H-pyran-3-yl)chroman-4-one

A mixture of 1-(5-bromo-2-hydroxy-phenyl)-ethanone (19.45 g, 90.9 mmol), tetrahydro-2H-pyran-3-carbaldehyde (10 g, 90.9 mmol) and borax (34.6 g, 90.9 mmol) in ethanol (120 mL) and H$_2$O (200 mL) was refluxed for one day. The reaction mixture was cooled, diluted with an equal volume of H$_2$O and extracted with ethyl acetate. The organic layer was dried over anhydrous Na$_2$SO$_4$, filtered, and evaporated to give 6-bromo-2-(tetrahydro-2H-pyran-3-yl)chroman-4-one (4 g, 15%). $^1$H-NMR (CDCl$_3$): 1.30 (m, 2H), 1.48 (m, 5H), 1.64 (m, 4H), 1.94 (d, 2H), 6.86 (d, 1H), 7.51 (dd, 1H), 7.92 (d, 1H).

Step 4. 6-bromo-2-(tetrahydro-2H-pyran-3-yl)spiro[chroman-4,4'-imidazolidine]-2',5'-dione A glass pressure tube was charged with a mixture 6-bromo-2-(tetrahydro-2H-pyran-3-yl)chroman-4-one (4 g, 13.03 mmol), KCN (1.7 g, 26.06 mmol), and (NH$_4$)$_2$CO$_3$ (9.4 g, 97.7 mmol). Formamide (30 mL) was added to fill the tube nearly completely. The mixture was heated at 80° C. for 2 days. The reaction mixture was then cooled and poured over ice. Acidification with concentrated HCl gave a precipitate which was filtered, washed twice with water, and then redissolved in ethyl acetate, dried over Na$_2$SO$_4$, and filtered. The filtrate was concentrated in vacuo to give the residue, which was purified by column to give 6-bromo-2-(tetrahydro-2H-pyran-3-yl)spiro[chroman-4,4'-imidazolidine]-2',5'-dione (1.5 g, 30%). $^1$H-NMR (MeOD): 1.20 (s, 1H), 1.42 (s, 1H), 1.65 (m, 2H), 1.89 (m, 2H), 2.01 (m, 1H), 2.19 (m, 1H), 3.40 (m, 2H), 3.85 (m, 2H), 4.10 (m, 1H), 6.79 (d, 1H), 7.23 (s, 1H), 7.33 (t, 1H).

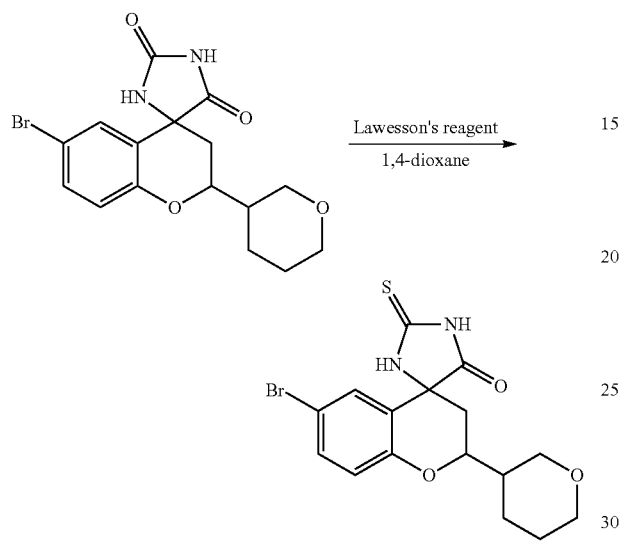

Step 5. 6-bromo-2-(tetrahydro-2H-pyran-3-yl)-2'-thioxospiro[chroman-4,4'-imidazolidin]-5'-one A suspension of 6-bromo-2-(tetrahydro-2H-pyran-3-yl)spiro[chroman-4,4'-imidazolidine]-2',5'-dione (300 mg, 0.79 mmol) and Lawesson's Reagent (319 mg, 0.79 mmol) in dry 1,4-dioxane (4 mL) was heated at 120° C. for 30 minutes in microwave. The mixture was concentrated in vacuo and the residue was purified by preparative TLC to give 6-bromo-2-(tetrahydro-2H-pyran-3-yl)-2'-thioxospiro[chroman-4,4'-imidazolidin]-5'-one (120 mg, 40%).

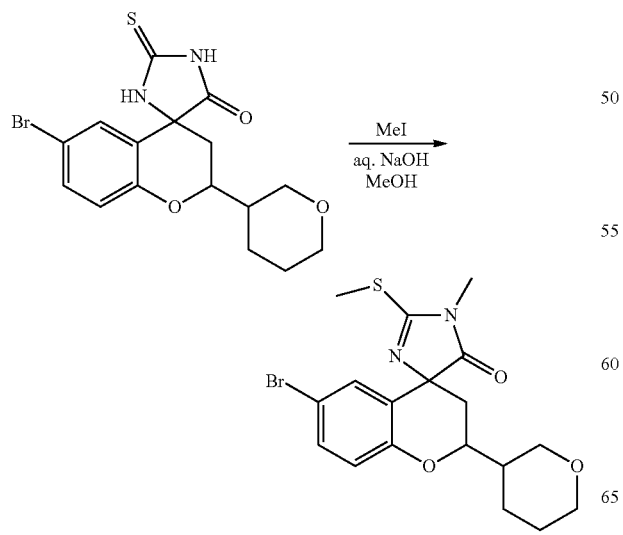

Step 6. 6-bromo-1'-methyl-2'-(methylthio)-2-(tetrahydro-2H-pyran-3-yl)spiro[chroman-4,4'-imidazol]-5'(1'H)-one To a solution of 6-bromo-2-(tetrahydro-2H-pyran-3-yl)-2'-thioxospiro[chroman-4,4'-imidazo-lidin]-5'-one (120 mg, 0.3 mmol) in MeOH (16 mL) was added a solution of NaOH (0.6 N, 1.2 mL) and MeI (0.3 mL). The reaction mixture was heated at 60° C. for 10 minutes in microwave. The mixture was concentrated in vacuo to give the residue, which was purified by preparative TLC to give 6-bromo-1'-methyl-2'-(methylthio)-2-(tetrahydro-2H-pyran-3-yl)spiro[chroman-4,4'-imidazol]-5'(1'H)-one (20 mg, 100%).

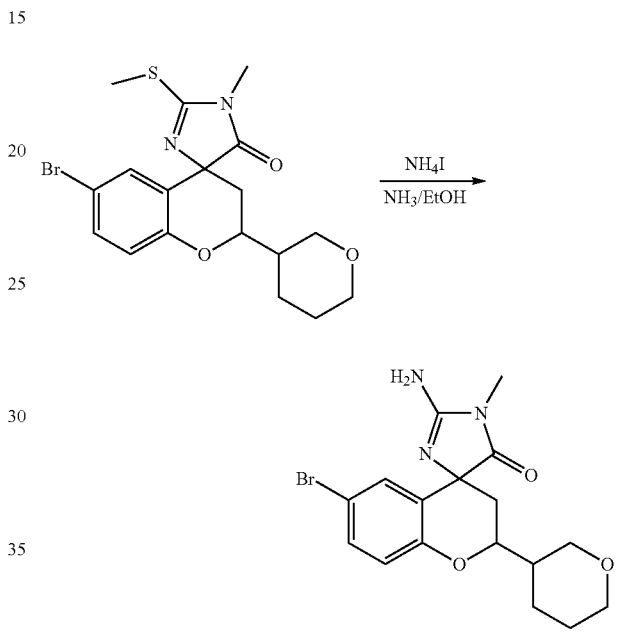

Step 7. 2'-amino-6-bromo-1'-methyl-2-(tetrahydro-2H-pyran-3-yl)spiro[chroman-4,4'-imidazol]-5'(1'H)-one A solution of 6-bromo-1'-methyl-2'-(methylthio)-2-(tetrahydro-2H-pyran-3-yl)spiro[c-hroman-4,4'-imidazol]-5'(1'H)-one (20 mg, 0.047 mmol), NH$_4$I (54.5 mg, 0.37 mmol) in a solution of NH$_3$/EtOH (2 mL, 8 N) was heated at 120° C. in a tube in a microwave reactor for 3 h. After cooling, the mixture was concentrated in vacuo to give 2'-amino-6-bromo-1'-methyl-2-(tetrahydro-2H-pyran-3-yl)spiro[chroman-4,4'-imidazol]-5'(1'H)-one (20 mg, 100%).

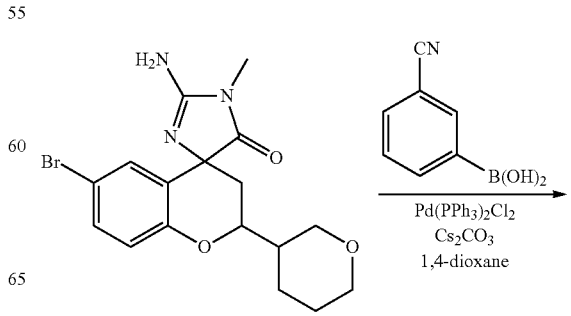

-continued

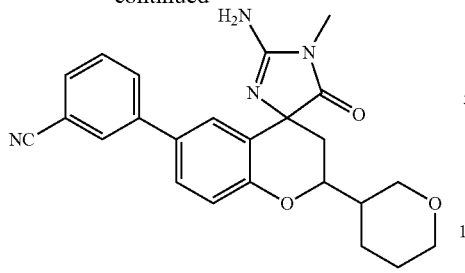

Step 8. 3-(2'-amino-1'-methyl-5'-oxo-2-(tetrahydro-2H-pyran-3-yl)-1',5'-dihydrospiro[chroman-4,4'-imidazole]-6-yl)benzonitrile (Compound 1)

Pd(PPh$_3$)$_2$Cl$_2$ (10 mg) in a 10 mL tube under Ar was treated sequentially with 2'-amino-6-bromo-1'-methyl-2-(tetrahydro-2H-pyran-3-yl)spiro[chroman-4,4'-imidazol]-5'(1'H)-one (20 mg, mmol) in 1,4-dioxane (1 mL), Cs$_2$CO$_3$ (2 N, 0.3 mL) and 3-cyanophenylboronic acid (29 mg, 0.197 mmol). The mixture was heated under microwave at 120° C. for 30 minutes. Then the reaction mixture was concentrated in vacuo to give the residue, which was purified by preparative TLC and then by preparative HPLC to give pure 3-(2'-amino-1'-methyl-5'-oxo-2-(tetrahydro-2H-pyran-3-yl)-1',5'-dihydrospiro[chroman-4,4'-imidazole]-6-yl)benzonitrile (2.51 mg, 10%). $^1$H-NMR (MeOD): 1.69 (t, 2H), 1.91 (m, 2H), 2.18 (t, 1H), 2.41 (d, 1H), 3.08 (t, 2H), 3.24 (s, 3H), 3.49 (m, 2H), 3.88 (dd, 2H), 4.40 (m, 1H), 7.05 (d, 1H), 7.50 (m, 1H), 7.61 (m, 3H), 7.86 (t, 1H), 7.94 (d, 1H).

Example 2

3-(2'-amino-1'-methyl-5'-oxo-2-phenyl-1',5'-dihydrospiro[chroman-4,4'-imidazole]-6-yl)benzonitrile (Compound 2)

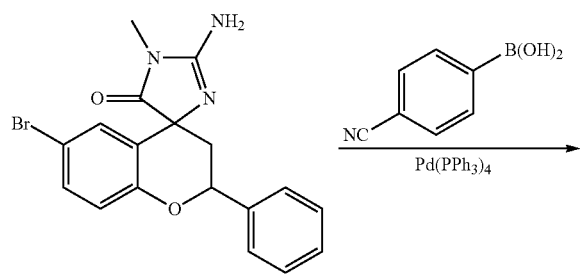

Pd(PPh$_3$)$_4$ (28 mg, 0.073 mmol) in a 10 mL flask under Ar was treated sequentially with 2'-amino-6-bromo-1'-methyl-2-phenylspiro[chroman-4,4'-imidazol]-5'(1'H)-one (28 mg, 0.073 mmol) in toluene (4.4 mL), Na$_2$CO$_3$ (2 N, 2.2 mL) and 4-cyanophenylboronic acid (12.9 mg, 0.088 mmol). The mixture was refluxed under Ar for 3-5 h. The reaction mixture was concentrated in vacuo to give the residue, which was purified by preparative TLC followed by preparative HPLC to give pure 3-(2'-amino-1'-methyl-5'-oxo-2-phenyl-1',5'-dihydrospiro[chroman-4,4'-imidazole]-6-yl)benzonitrile (2.58 mg, 9%). $^1$H-NMR (CDCl$_3$): 0.92 (m, 1H), 1.07 (m, 1H), 1.75 (s, 3H), 4.32 (d, 1H), 5.62 (d, 1H), 5.82-5.98 (m, 5H), 6.06 (m, 2H), 6.15 (m, 2H), 6.47 (d, 1H), 6.46 (s, 1H).

Example 2a

Synthesis of Compound 2a

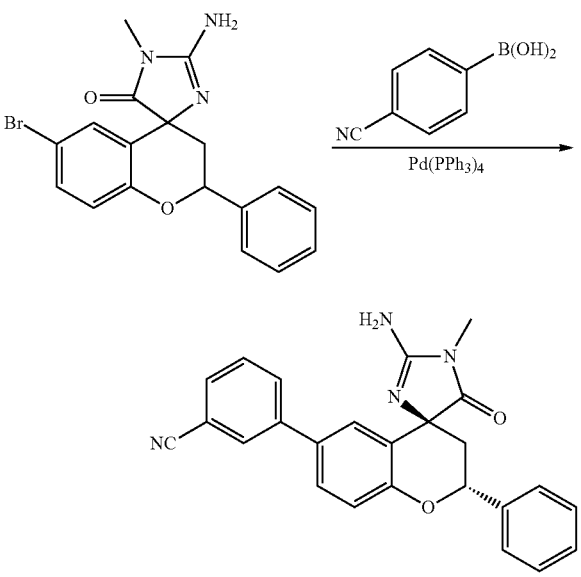

Pd(PPh$_3$)$_4$ (60 mg, 0.052 mmol) in a 100 mL flask under Ar was treated sequentially with 2'-amino-6-bromo-1'-methyl-2-phenylspiro[chroman-4,4'-imidazol]-5'(1'H)-one (100 mg, 0.26 mmol) in toluene (15.6 mL), Na$_2$CO$_3$ (2 N, 7.8 mL), and 4-cyanophenylboronic acid (76.5 mg, 0.52 mmol). The mixture was refluxed under Ar for 3-5 h. The reaction mixture was concentrated in vacuo to give a residue, which was purified by preparative TLC followed by preparative HPLC to give pure 3-(2'-amino-1'-methyl-5'-oxo-2-phenyl-1',5'-dihydrospiro[chroman-4,4'-imidazole]-6-yl)benzonitrile (31 mg, 29%) as a racemic product. $^1$H-NMR (CDCl$_3$): 2.18 (m, 1H), 2.29 (t, 1H), 3.13 (s, 3H), 5.90 (d, 1H), 7.05 (d, 1H), 7.25 (m, 1H), 7.34 (m, 1H), 7.38 (m, 2H), 7.45 (m, 2H), 7.50-7.64 (m, 3H), 7.82-7.87 (m, 2H).

Example 3

3-(2'-amino-2-cyclohexy-1'-methyl-5'-oxo-1',5'-dihydrospiro[chroman-4,4'-imidazole]-6-yl)benzonitrile (Compound 3)

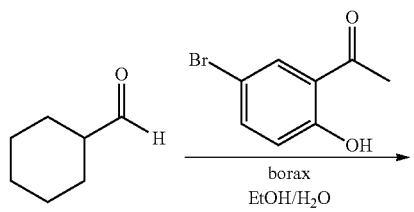

-continued

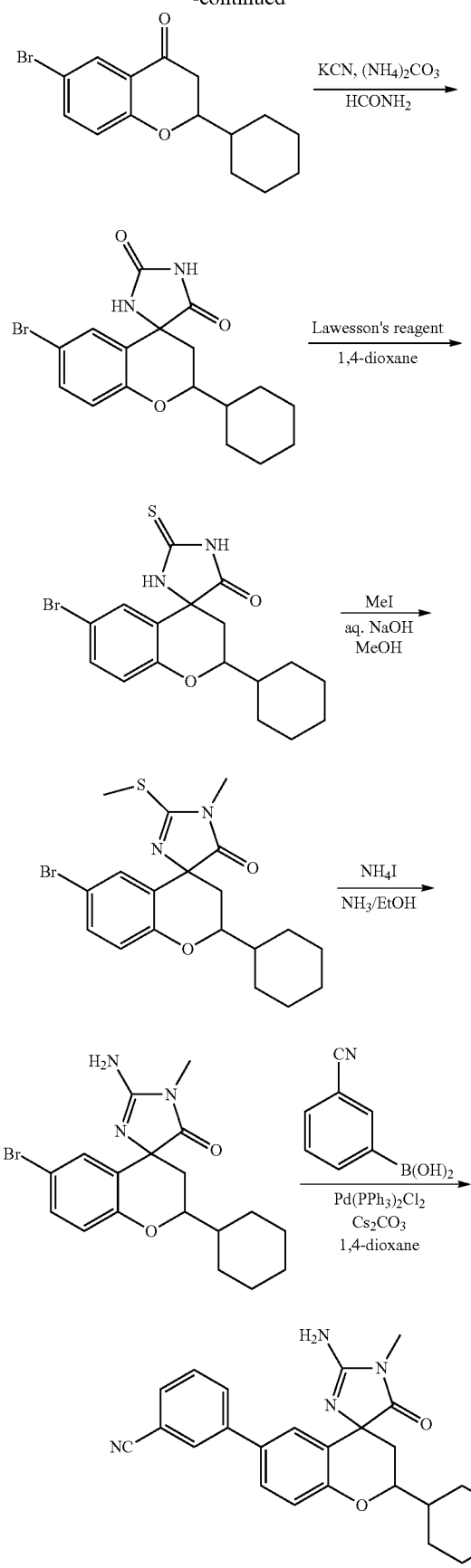

Experimental Data:

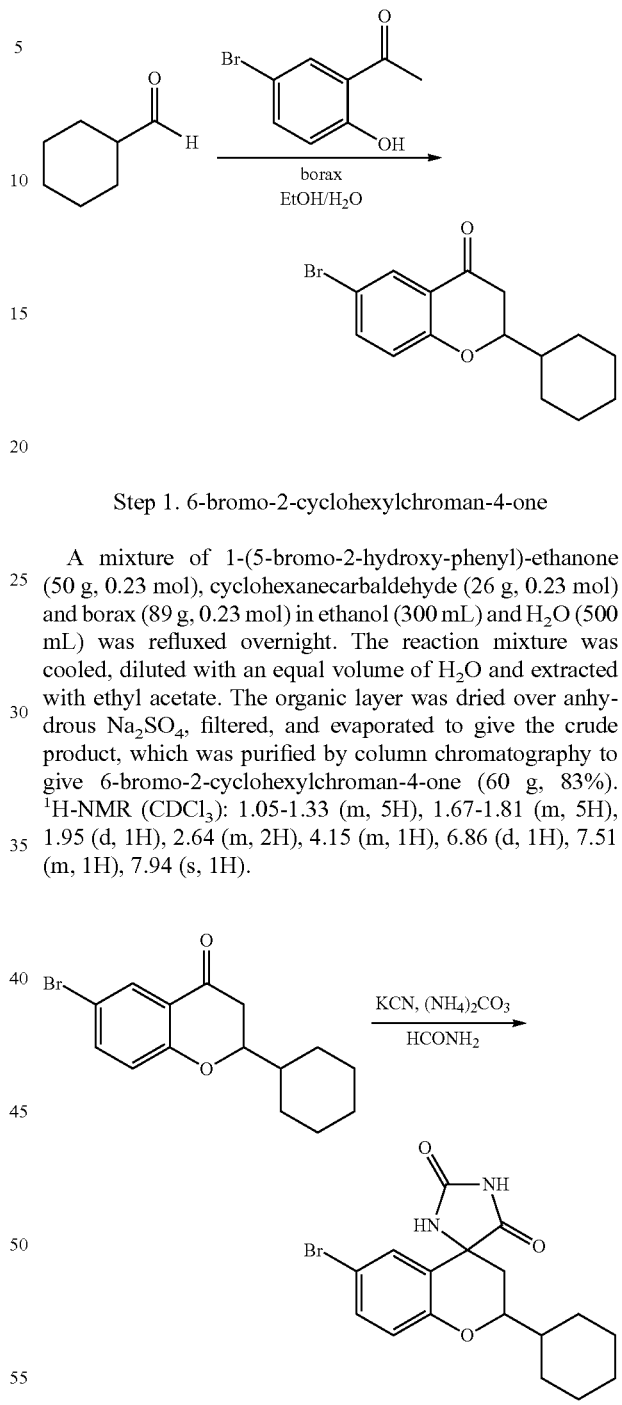

Step 1. 6-bromo-2-cyclohexylchroman-4-one

A mixture of 1-(5-bromo-2-hydroxy-phenyl)-ethanone (50 g, 0.23 mol), cyclohexanecarbaldehyde (26 g, 0.23 mol) and borax (89 g, 0.23 mol) in ethanol (300 mL) and $H_2O$ (500 mL) was refluxed overnight. The reaction mixture was cooled, diluted with an equal volume of $H_2O$ and extracted with ethyl acetate. The organic layer was dried over anhydrous $Na_2SO_4$, filtered, and evaporated to give the crude product, which was purified by column chromatography to give 6-bromo-2-cyclohexylchroman-4-one (60 g, 83%). $^1$H-NMR (CDCl$_3$): 1.05-1.33 (m, 5H), 1.67-1.81 (m, 5H), 1.95 (d, 1H), 2.64 (m, 2H), 4.15 (m, 1H), 6.86 (d, 1H), 7.51 (m, 1H), 7.94 (s, 1H).

Step 2. 6-bromo-2-cyclohexylspiro[chroman-4,4'-imidazolidine]-2',5'-dione

A mixture of 6-bromo-2-cyclohexylchroman-4-one (1.5 g, 5 mmol), KCN (0.63 g, 10 mmol), $(NH_4)_2CO_3$ (3.6 g, 37.5 mmol) in $HCONH_2$ (30 mL) were added to fill a 40 mL CEM microwave test tube nearly completely. The mixture was heated at 70° C. for 4 hrs. The reaction mixture was then cooled and poured over ice water. Acidification with concentrated HCl was performed to give a precipitate which was filtered, washed twice with water, and then dissolved in ethyl acetate, dried over Na₂SO₄, and filtered. The filtrate was concentrated in vacuo to give the residue, which was purified by column chromatography to give 6-bromo-2-cyclohexyl-spiro[chroman-4,4'-imidazolidine]-2',5'-dione (0.75 g, 42%). ¹H-NMR (CDCl₃): 1.11-1.30 (m, 5H), 1.74 (m, 2H), 1.83 (m, 2H) 1.97 (m, 2H), 2.04 (d, 1H), 2.25 (d, 1H), 4.59 (m, 1H), 5.56 (s, 1H), 6.78 (d, 1H), 7.30 (m, 2H), 7.82 (s, 1H).

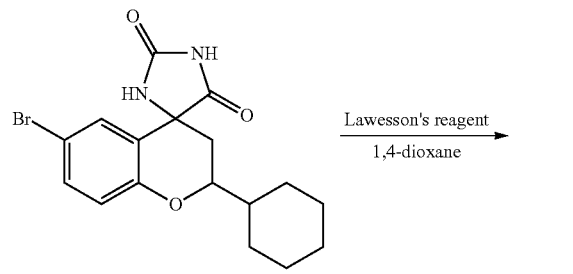

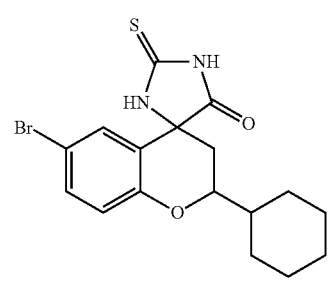

Step 3. 6-bromo-2-cyclohexyl-2'-thioxospiro[chroman-4,4'-imidazolidin]-5'-one A suspension of 6-bromo-2-cyclohexylspiro[chroman-4,4'-imidazolidine]-2',5'-dione (400 mg, 1.06 mmol) and Lawesson's Reagent (427 mg, 1.06 mmol) in dry 1,4-dioxane (6 mL) was heated at 120° C. in a 10 mL CEM microwave test tube for 30 minutes. The mixture was concentrated in vacuo and the residue was purified by preparative TLC to give 6-bromo-2-cyclohexyl-2'-thioxospiro[chroman-4,4'-imidazolidin]-5'-one (280 mg, 67%). ¹H-NMR (CDCl₃): 0.78-0.92 (m, 2H), 1.13 (m, 1H), 1.17-1.31 (m, 3H), 1.71 (m, 2H), 1.78 (m, 2H), 1.94 (d, 1H), 2.05 (t, 1H), 2.61 (d, 1H), 4.91 (m, 1H), 6.78 (d, 1H), 7.04 (s, 1H), 7.13 (s, 1H), 7.32 (d, 1H), 9.33 (s, 1H).

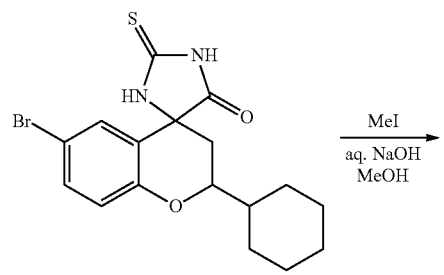

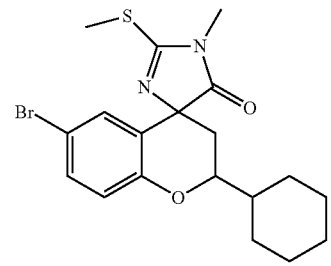

Step 4. 6-bromo-2-cyclohexyl-1'-methyl-2'-(methylthio)spiro[chroman-4,4'-imidazol]-5'(1'H)-one A mixture of 6-bromo-2-cyclohexyl-2'-thioxospiro[chroman-4,4'-imidazolidin]-5'-one (57×5 mg, 0.75 mmol), NaOH solution (0.6 N, 0.7×5 mL), CH₃I (0.2×5 mL) in methanol (4×5 mL) was heated at 60° C. in a 10 mL CEM test tube for 10 minutes. The reaction mixture was concentrated to give the residue, which was purified by column chromatography to give 6-bromo-2-cyclohexyl-1'-methyl-2'-(methylthio)spiro[chroman-4,4'-imidazol]-5'(1'H)-one (170 mg, 56%).

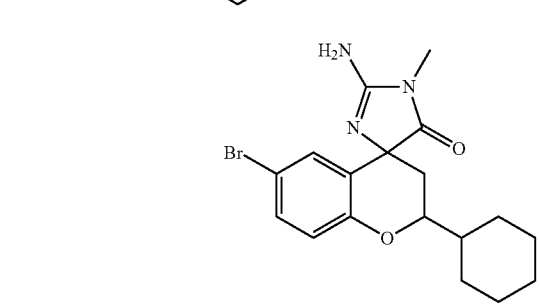

Step 5. 2'-amino-6-bromo-2-cyclohexy-1'-methyl-spiro[chroman-4,4'-imidazol]-5'(1'H)-one A solution of 6-bromo-2-cyclohexyl-1'-methyl-2'-(methylthio)spiro[chroman-4,4'-imidazol]-5'(1'H)-one (170 mg, 0.40 mmol), NH₄I (117 mg, 0.80 mmol) in a solution of NH₃/EtOH (10 mL, 1.5 N) was heated at 120° C. in a 40 mL test tube under microwave reactor for 3 hrs. After cooling, the mixture was concentrated in vacuo to give the residue, which was purified by preparative TLC to afford 2'-amino-6-bromo-2-cyclohexy-1'-methylspiro[chroman-4,4'-imidazol]-5'(1'H)-one (90 mg, 57%).

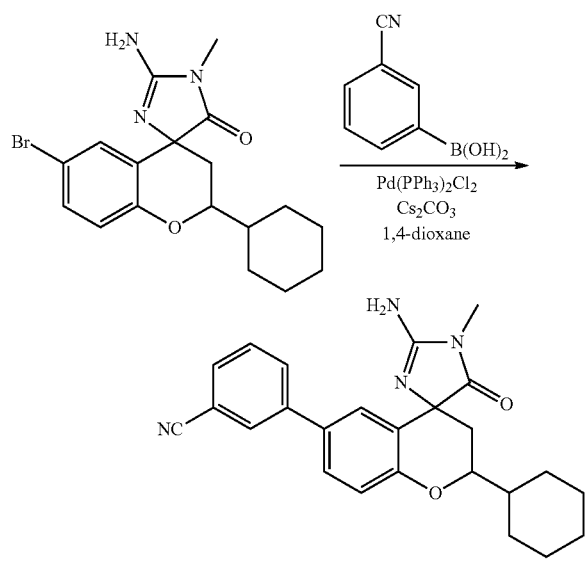

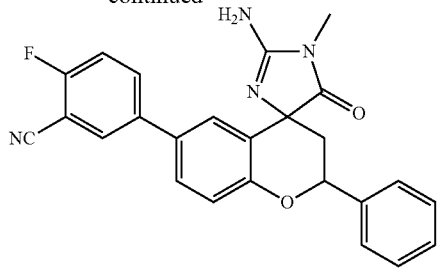

Step 6. 3-(2'-amino-2-cyclohexy-1'-methyl-5'-oxo-1', 5'-dihydrospiro[chroman-4,4'-imidazole]-6-yl)benzonitrile A mixture of 2'-amino-6-bromo-2-cyclohexy-1'-methyl-spiro[chroman-4,4'-imidazol]-5'(1'H)-one (30 mg, 0.08 mmol), 3-cyanophenylboronic acid (23 mg, 0.15 mmol), Pd(PPh₃)₂Cl₂ (20 mg), aqueous cesium carbonate solution (2 M, 0.5 mL) in dry 1,4-dioxane (1 mL) was heated at 120° C. under microwave for 35 minutes. The reaction mixture was concentrated to give the residue, which was purified by preparative TLC and preparative HPLC to give 3-(2'-amino-2-cyclohexy-1'-methyl-5'-oxo-1',5'-dihydrospiro[chroman-4, 4'-imidazole]-6-yl)benzonitrile (18.2 mg, 56%). $^{1}$H-NMR (MeOD): 1.22-1.39 (m, 4H), 1.69-1.86 (m, 4H), 2.01 (s, 1H), 2.13-2.24 (m, 1H), 2.28-2.46 (m, 1H), 3.12 (s, 1H), 3.27-3.36 (m, 3H), 4.63 (m, 1H), 7.06 (m, 1H), 7.49 (s, 1H), 7.57-7.76 (m, 3H), 7.86 (t, 1H), 7.94 (d, 1H).

Example 4

5-(2'-amino-1'-methyl-5'-oxo-2-phenyl-1',5'-dihydrospiro[chroman-4,4'-imidazole]-6-yl)-2-fluorobenzonitrile (Compound 4)

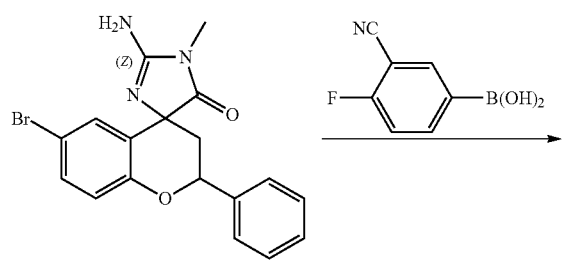

-continued

Pd(PPh₃)₂Cl₂ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs₂CO₃ (2 N, 0.3 mL) and 3-cyano-4-fluorophenylboronic acid (17 mg, 0.104 mmol). The mixture was heated under Ar at 120° C. under microwave for 30 min. The reaction mixture was concentrated in vacuo to give the residue, which was purified by preparative HPLC twice to give pure 5-(2'-amino-1'-methyl-5'-oxo-2-phenyl-1',5'-dihydrospiro[chroman-4,4'-imidazole]-6-yl)-2-fluorobenzonitrile (7 mg, 32%). $^{1}$H-NMR (MeOD): 2.15 (m, 1H), 2.29 (t, 1H), 3.12 & 3.18 (s, 3H), 5.30 & 5.89 (m, 1H), 7.03 (m, 1H), 7.21 (m, 1H), 7.31-7.50 (m, 6H), 7.85 (m, 2H).

Example 5

5-(2'-amino-1'-methyl-5'-oxo-2-phenyl-1',5'-dihydrospiro[chroman-4,4'-imidazole]-6-yl)nicotinonitrile (Compound 5)

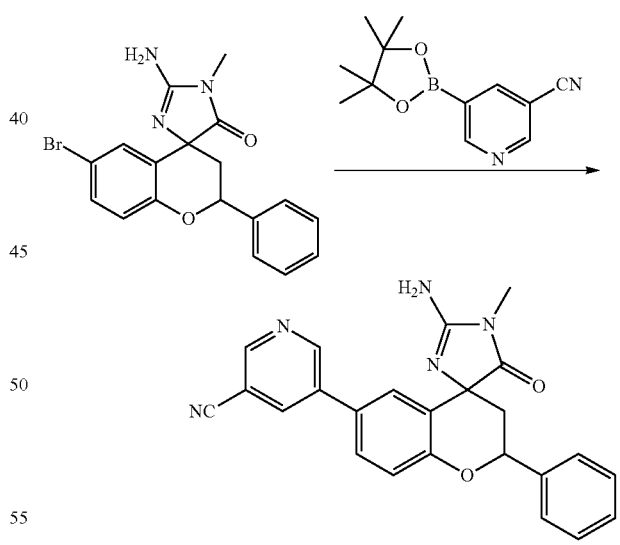

Pd(PPh₃)₂Cl₂ (10 mg) in a 10 mL tube under Ar was treated sequentially with 2'-amino-6-bromo-1'-(cyclohexylmethyl)-2-phenylspiro[chroman-4,4'-imidazol]-5'(1'H)-one (20 mg, 0.052 mmol) in 1,4-dioxane (1 mL), Cs₂CO₃ (2 N, 0.3 mL) and 5-(4,4,5,5-tetramethyl-[1,3,2]dioxaborolan-2-yl)-nicotinonitrile (24 mg, 0.104 mmol). The mixture was heated at 120° C. in a microwave reactor for 0.5 h. The reaction mixture was concentrated in vacuo to give the residue, which was purified by preparative TLC to give pure 5-(2'-amino-1'-methyl-5'-oxo-2-phenyl-1',5'-dihydrospiro[chroman-4,4'-imidazole]-6-yl)nicotinonitrile (6.27 mg, 30%). $^1$H-NMR (MeOD): 2.04 (d, 1H), 2.20 (m, 1H), 3.06 (m, 3H), 5.24 (d, 0.3H), 5.82 (d, 0.7H), 7.01 (m, 1H), 7.36 (m, 6H), 7.50 (m, 1H), 8.29 (m, 1H), 8.70 (m, 1H), 8.89 (m, 1H).

Example 6

Synthesis of Compound 8a and 8b

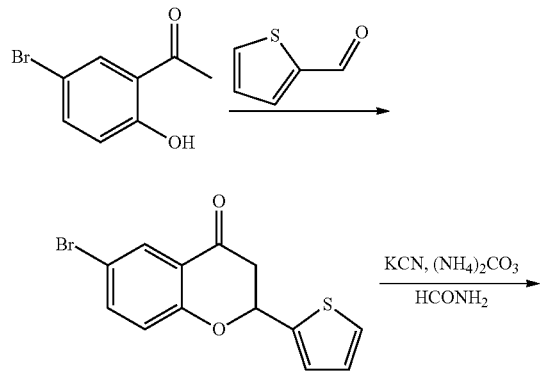

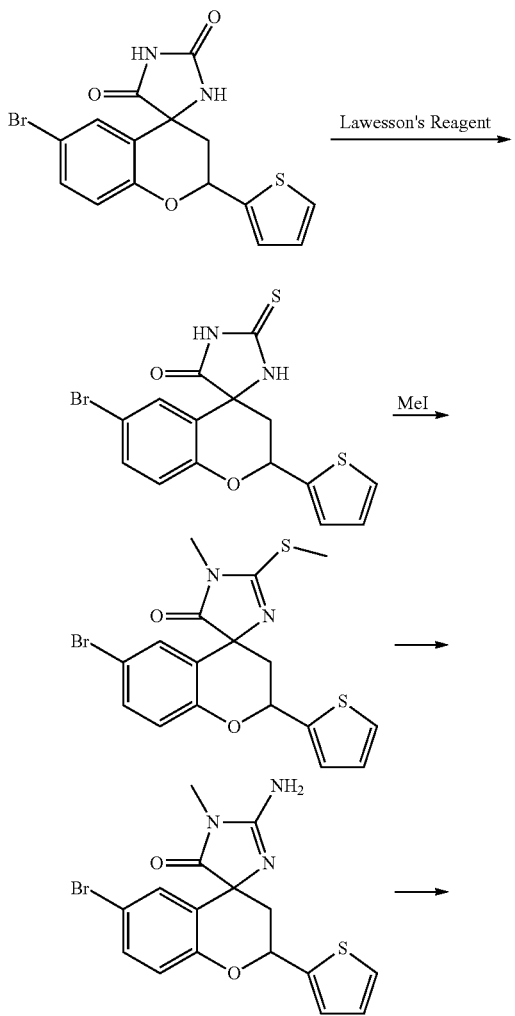

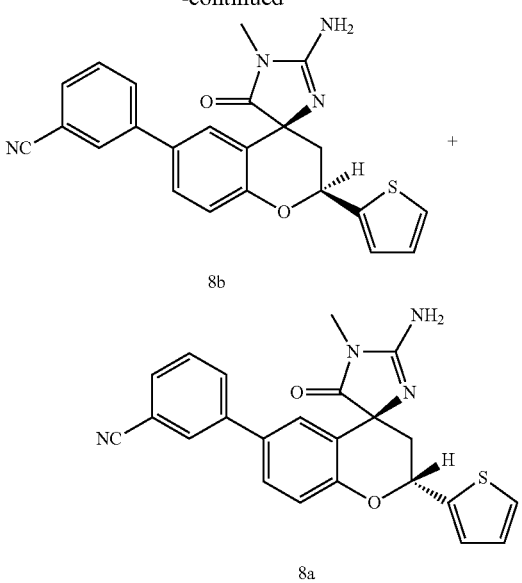

Experimental Data:

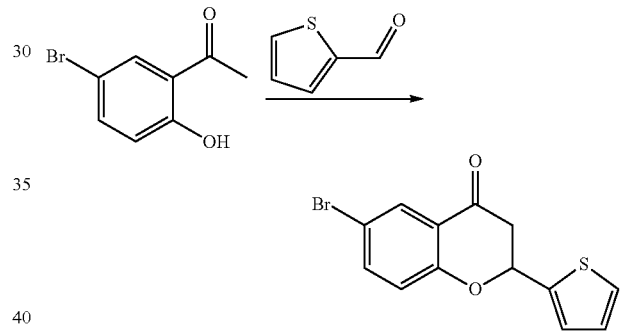

Step 1. 6-bromo-2-thiophen-2-yl-chroman-4-one

A mixture of 1-(5-bromo-2-hydroxy-phenyl)-ethanone (20 g, 0.093 mol), thiophene-2-carbaldehyde (10.46 g, 0.093 mol) and borax (35.4 g, 0.093 mol) in ethanol (120 mL) and H$_2$O (200 mL) was refluxed for one day. The reaction mixture was cooled, diluted with an equal volume of H$_2$O and extracted with ethyl acetate. The organic layer was dried over anhydrous Na$_2$SO$_4$, filtered, and evaporated to give 6-bromo-2-thiophen-2-yl-chroman-4-one (16 g, 50%). $^1$H-NMR (CDCl$_3$): 3.01 (m, 1H), 3.10 (m, 1H), 5.75 (dd, 1H), 6.94 (d, 1H), 7.02 (t, 1H), 7.05 (d, 1H), 7.32 (d, 1H), 7.54 (dd, 1H), 8.00 (d, 1H).

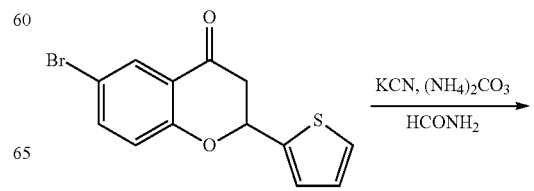

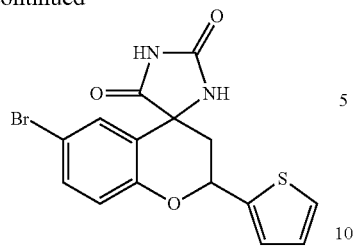

Step 2. 6-bromo-2-(thiophen-2-yl)spiro[chroman-4,4'-imidazolidine]-2',5'-dione A glass pressure tube was charged with a mixture of 6-bromo-2-thiophen-2-yl-chroman-4-one (1.5 g, 48.7 mmol), KCN (0.63 g, 97.4 mmol), and (NH₄)₂CO₃ (3.27 g, 34.1 mmol). Formamide (30 mL) and DMF (10 mL) were added to fill the tube nearly completely. The mixture was heated at 70° C. for 2 h with microwave. The reaction mixture was then cooled and poured over ice. Acidification with concentrated HCl gave a precipitate which was filtered, washed twice with water, and then dissolved in ethyl acetate, dried over Na₂SO₄, and filtered. The filtrate was concentrated in vacuo to give the residue, which was purified by column to give 6-bromo-2-(thiophen-2-yl)spiro[chroman-4,4'-imidazolidine]-2',5'-dione (150 mg, 8%).

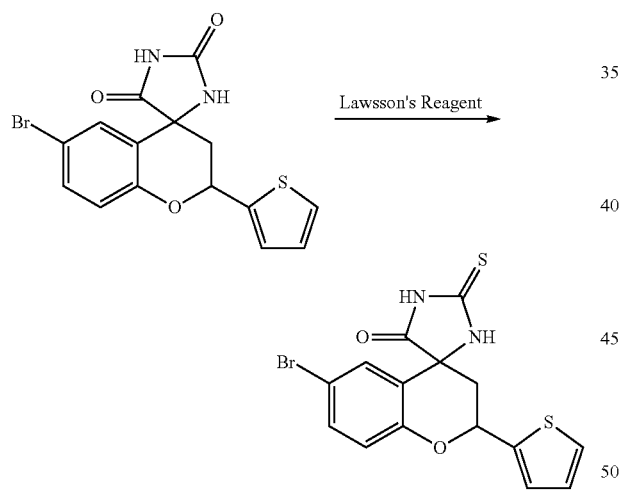

Step 3. 6-bromo-2-(thiophen-2-yl)-2'-thioxospiro[chroman-4,4'-imidazolidin]-5'-one A suspension of 6-bromo-2-(thiophen-2-yl)spiro[chroman-4,4'-imidazolidine]-2',5'-dione (135 mg, 0.357 mmol) and Lawesson's Reagent (144.3 mg, 0.357 mmol) in anhydrous 1,4-dioxane (4 mL) was heated under reflux for 24 h. The mixture was concentrated in vacuo and the residue was purified by preparative TLC to give 6-bromo-2-(thiophen-2-yl)-2'-thioxospiro[chroman-4,4'-imidazolidin]-5'-one (100 mg, 80%). ¹H-NMR (CDCl₃): 2.41 (m, 1H), 2.55 (dd, 1H), 6.04 (dd, 1H), 6.80 (d, 1H), 6.94 (t, 1H), 7.12 (d, 1H), 7.33 (m, 3H).

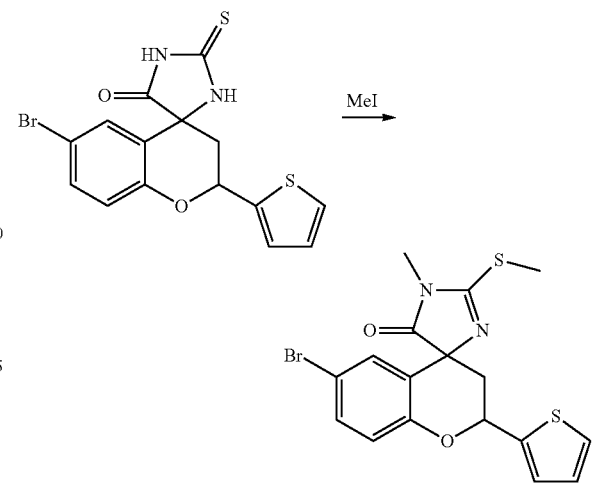

Step 4. 6-bromo-1'-methyl-2'-(methylthio)-2-(thiophen-2-yl)spiro[chroman-4,4'-imidazol]-5'(1'H)-one To a solution of 6-bromo-2-(thiophen-2-yl)-2'-thioxospiro[chroman-4,4'-imidazo-lidin]-5'-one (100 mg, 0.254 mmol) in MeOH (6 mL) was added a solution of NaOH (20.32 mg, 0.508 mmol) in H₂O (1 mL). After stirring for 10 minutes, MeI (544.4 mg, 3.81 mmol) was added. The reaction mixture was heated under reflux for 2 h. The mixture was concentrated in vacuo to give the residue, which was purified by preparative TLC to give 6-bromo-1'-methyl-2'-(methylthio)-2-(thiophen-2-yl)spiro[chroman-4,4'-imidazol]-5'(1'H)-one (20 mg, 20%). ¹H-NMR (CDCl₃): 2.22 (d, 1H), 2.41 (t, 1H), 2.74 (s, 3H), 3.02 (s, 3H), 6.12 (d, 1H), 6.80 (d, 1H), 6.94 (m, 2H), 7.31 (m, 1H), 7.33 (m, 2H).

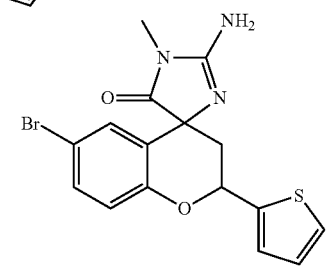

Step 5. 2'-amino-6-bromo-1'-methyl-2-(thiophen-2-yl)spiro[chroman-4,4'-imidazol]-5'(1'H)-one A solution of 6-bromo-1'-methyl-2'-(methylthio)-2-(thiophen-2-yl)spiro[chroman-4,4'-imidazol]-5'(1'H)-one (20 mg, 0.047 mmol), NH₄I (13.7 mg, 0.094 mmol) in a solution of NH₃/EtOH (2 mL, 2 N) was heated at 110° C. in a tube in a microwave reactor for 2-2.5 h. After cooling, the mixture was concentrated in vacuum to give the residue, which was purified by preparative TLC to afford 2'-amino-6-bromo-1'-methyl-2-(thiophen-2-yl)spiro[chroman-4,4'-imidazol]-5'(1'H)-one (5 mg, 20%). ¹H-NMR (CDCl₃): 2.52 (m, 2H), 3.14 (s, 3H), 6.12 (d, 1H), 6.94 (d, 1H), 7.02 (t, 1H), 7.14 (d, 1H), 7.43 (t, 3H).

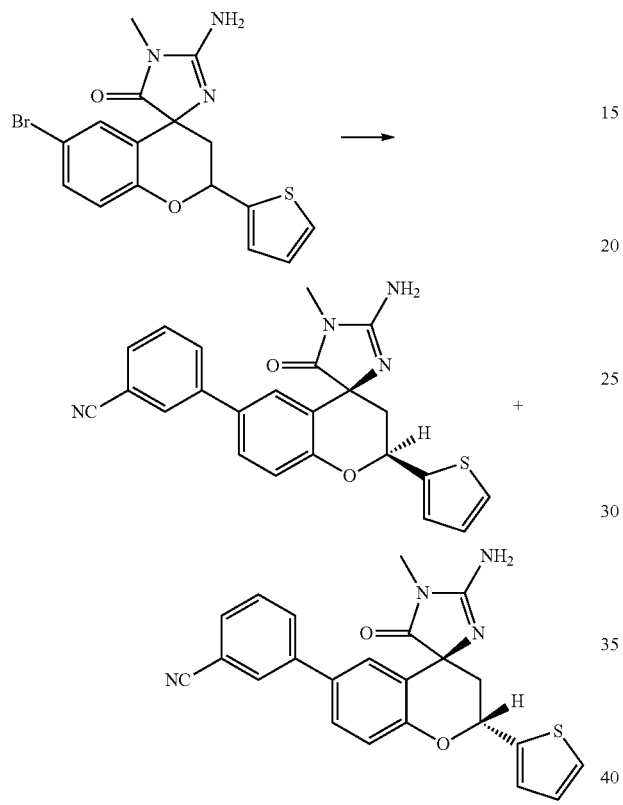

Step 6. 3-((2S,4S)-2'-amino-1'-methyl-5'-oxo-2-(thiophen-2-yl)-1',5'-dihydrospiro[chrom-an-4,4'-imidazole]-6-yl)benzonitrile Pd(PPh₃)₂Cl₂ (20 mg) in a 10 mL of flask under Ar was treated sequentially with 2'-amino-6-bromo-1'-methyl-2-(thiophen-2-yl)spiro[chroman-4,4'-imidazol]-5'(1'H)-one (46 mg, 0.117 mmol) in 1,4-dioxane (5 mL), Cs₂CO₃ (2 N, 0.5 mL) and 4-cyanophenylboronic acid (34.5 mg, 0.23 mmol). The mixture was refluxed under Ar for 2 h. The reaction mixture was concentrated in vacuo to give the residue, which was purified by preparative TLC followed by preparative HPLC to give pure 3-((2S,4S)-2'-amino-1'-methyl-5'-oxo-2-(thiophen-2-yl)-1',5'-dihydrospiro[chroman-4,4'-imidazole]-6-yl)benzonitrile (Compound 8a, 1.35 mg, 1%). ¹H-NMR (CDCl₃): 442-069-3B: 2.30 (d, 1H), 2.49 (d, 1H), 3.01 (d, 3H), 5.81 (dd, 1H), 6.95 (t, 1H), 7.00 (m, 2H), 7.05 (s, 1H), 7.30 (d, 1H), 7.40 (d, 1H), 7.49 (d, 1H), 7.51 (t, 1H), 7.61 (t, 2H), and 3-((2R,4S)-2'-Amino-1'-methyl-5'-oxo-2-(thiophen-2-yl)-1',5'-dihydrospiro[chroman-4,4'-imidazole]-6-yl)-benzonitrile (Compound 8b, 1.10 mg, 1%). ¹H-NMR (CDCl₃): 2.40 (d, 1H), 2.63 (t, 1H), 3.31 (s, 3H), 6.12 (d, 1H), 6.95 (t, 1H), 7.00 (d, 1H), 7.05 (m, 2H), 7.30 (d, 1H), 7.48 (m, 2H), 7.54 (d, 1H), 7.68 (t, 2H).

Example 7

3-(2'-amino-2-(2-fluorophenyl)-1'-methyl-5'-oxo-1',5'-dihydrospiro[chroman-4,4'-imidazole]-6-yl)benzonitrile (Compound 9)

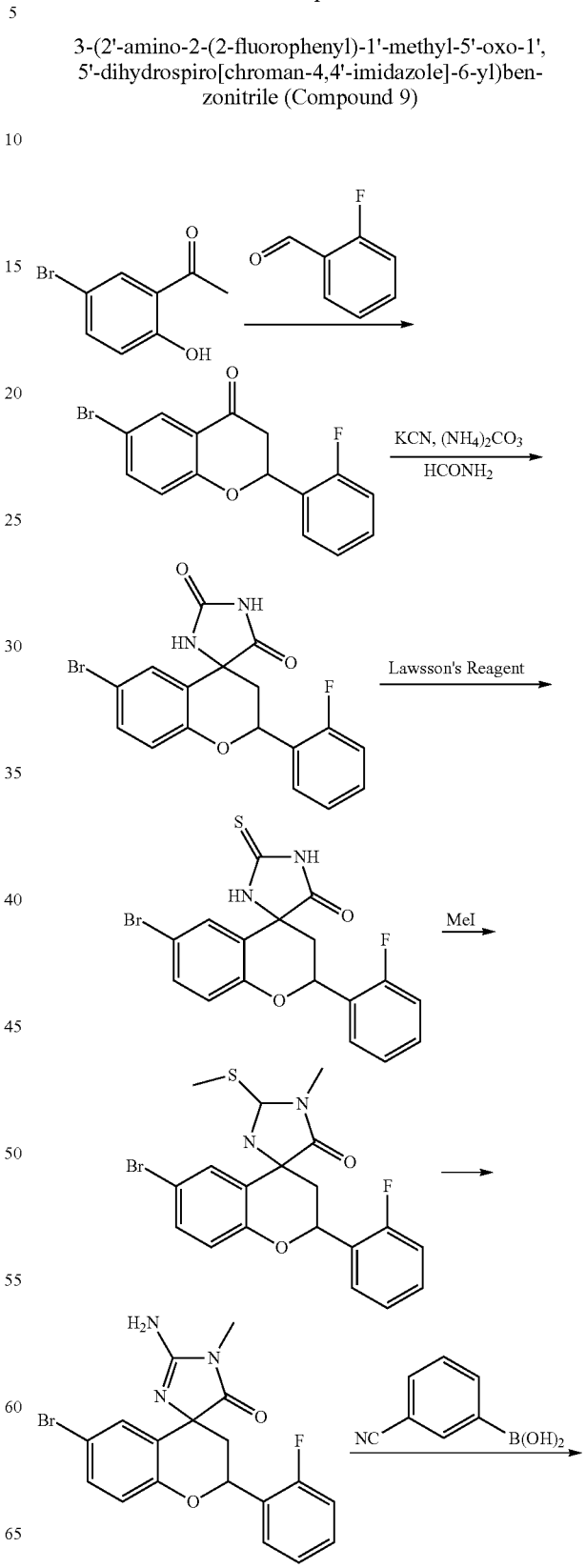

-continued

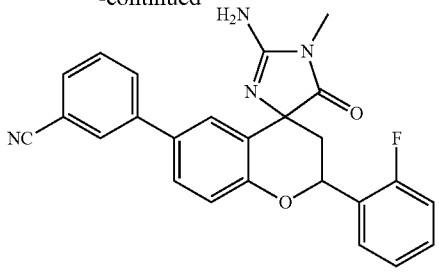

Step 1

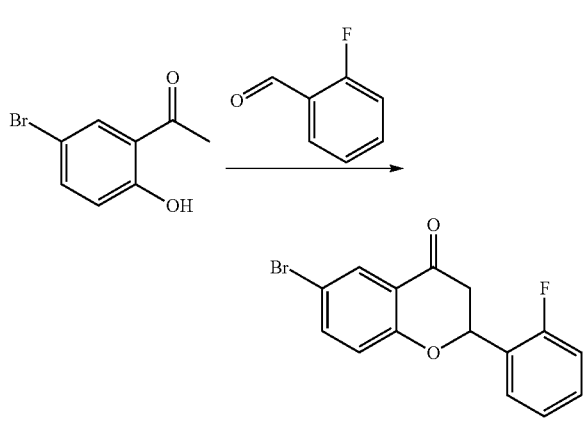

A mixture of 1-(5-bromo-2-hydroxy-phenyl)-ethanone (15 g, 70.1 mmol), 2-fluorobenzaldehyde (8.7 g, 70.1 mmol), and borax (26.7 g, 70.1 mmol) in ethanol (90 mL) and H$_2$O (150 mL) was refluxed for one day. The reaction mixture was cooled, diluted with an equal volume of H$_2$O, and extracted with ether. The ether was dried over anhydrous Na$_2$SO$_4$, filtered, and evaporated to give 6-bromo-2-(2-fluorophenyl) chroman-4-one (15 g, 50%). $^1$HNMR (CDCl$_3$): 2.8 (d, 1H), 3.0 (t, 1H), 5.7 (d, 1H), 6.7 (d, 1H), 6.9 (t, 1H), 7.2 (m, 2H), 7.3 (m, 2H), 7.5 (m, 2H), 7.9 (t, 1H), 8.1 (d, 1H).

Step 2

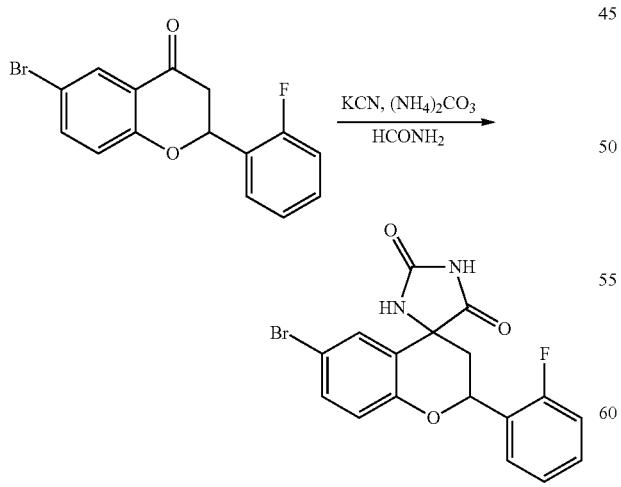

A steel bomb was charged with a mixture of 6-bromo-2-(2-fluorophenyl)chroman-4-one (2 g, 6.25 mmol), KCN (0.82 g, 12.5 mmol), and (NH$_4$)$_2$CO$_3$ (4.5 g, 46.87 mmol). Formamide (25 mL) is added to fill the steel bomb nearly completely. The mixture was heated at 70° C. for 48 h then at 110° C. for another 8 h. The reaction mixture was then cooled and poured over ice. Acidification with concentrated HCl yielded a precipitate which was filtered, washed twice with water, and then dissolved in ethyl acetate, dried over Na$_2$SO$_4$, and filtered. The filtrate was concentrated in vacuo to give a residue, which was purified by column to give 6-bromo-2-(2-fluorophenyl)spiro[chroman-4,4'-imidazolidine]-2',5'-dione (250 mg, 10%). $^1$H-NMR (CDCl$_3$): 2.3 (t, 1H), 2.5 (d, 1H), 5.6 (s, 1H), 6.2 (d, 1H), 6.9 (t, 1H), 7.1 (t, 1H), 7.2 (t, 1H), 7.4 (m, 3H), 7.6 (t, 1H), 7.9 (s, 1H).

Step 3

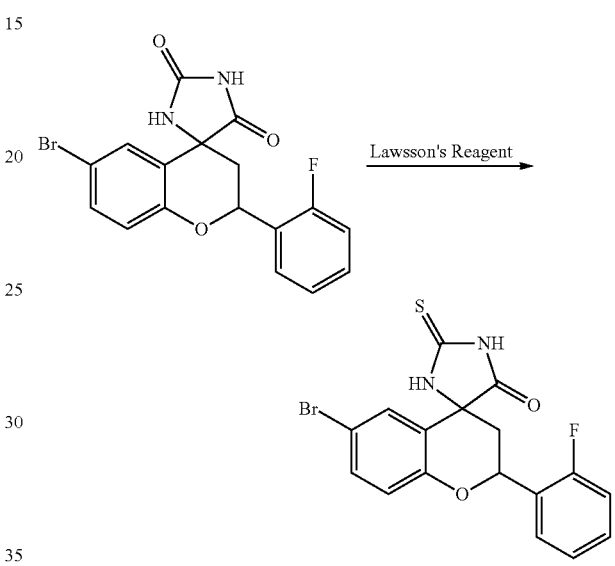

A suspension of 6-bromo-2-(2-fluorophenyl)spiro[chroman-4,4'-imidazolidine]-2',5'-dione (250 mg, 0.64 mmol) and Lawesson's Reagent (259 mg, 0.64 mmol) in dry 1,4-dioxane (20 mL) was refluxed for 24 h. The mixture was concentrated in vacuo and the residue was purified by preparative TLC to give 6-bromo-2-(2-fluorophenyl)-2'-thioxospiro[chroman-4,4'-imidazolidin]-5'-one (180 mg, 67%).

Step 4

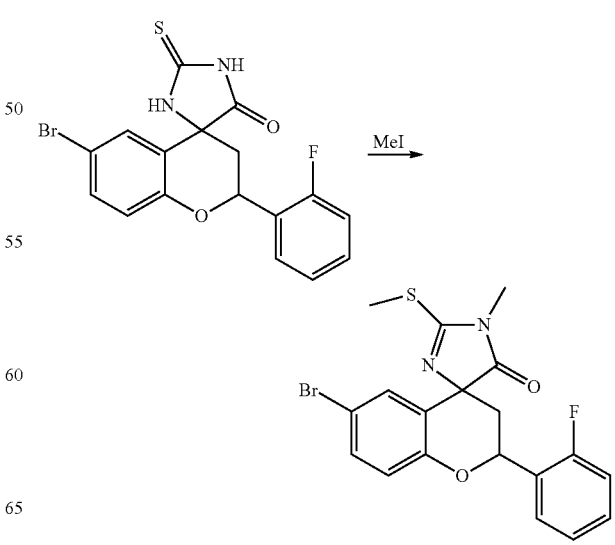

To a solution of 6-bromo-2-(2-fluorophenyl)-2'-thioxospiro[chroman-4,4'-imidazolidin]-5'-one (180 mg, 0.443 mmol) in MeOH (10 mL) was added a solution of NaOH (35.46 mg, 0.887 mmol) in H₂O (2 mL). After stirring for 10 min, MeI (951 mg, 6.65 mmol) was added. The reaction mixture was refluxed for 2 h. The mixture was concentrated in vacuo to give a residue, which as purified by preparative TLC to give 6-bromo-2-(2-fluorophenyl)-1'-methyl-2'-(methylthio)spiro[chroman-4,4'-imidazol]-5'(1'H)-one (80 mg, 41%).

Step 5

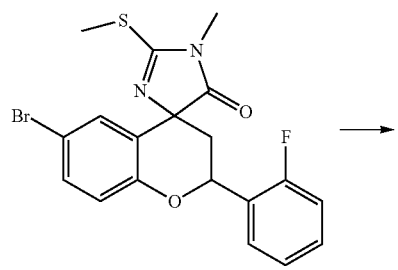

A solution of 6-bromo-2-(2-fluorophenyl)-1'-methyl-2'-(methylthio)spiro[chroman-4,4'-imidazol]-5'(1'H)-one (80 mg, 0.183 mmol) and NH₄I (53.21 mg, 0.367 mmol) in a solution of NH₃/EtOH (2 mL, 1.5 N) was heated at 110° C. in a tube under microwave reactor for 3 h. After cooling, the mixture was concentrated in vacuo to give a residue, which was purified by preparative TLC to afford 2'-amino-6-bromo-2-(2-fluorophenyl)-1'-methylspiro[chroman-4,4'-imidazol]-5'(1'H)-one (52 mg, 70%). ¹H-NMR (MeOD): 2.15 (d, 1H), 2.25 (d, 1H), 3.20 (s, 3H), 6.15 (d, 1H), 6.78 (d, 1H), 6.99 (t, 1H), 7.05 (s, 1H), 7.15 (t, 1H), 7.25 (d, 2H), 7.50 (t, 1H).

Step 6

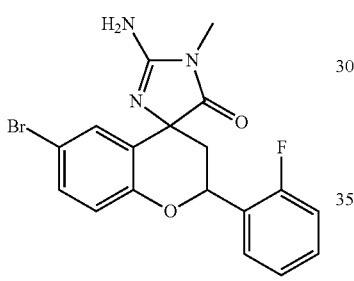

-continued

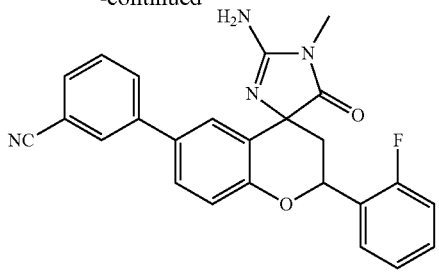

Pd(PPh₃)₄ (3.84 mg, 0.1 mmol) was added to the solution of 2'-amino-6-bromo-2-(2-fluorophenyl)-1'-methylspiro[chroman-4,4'-imidazol]-5'(1'H)-one (42 mg, 0.1 mmol) and 3-cyanophenylboronic acid (18.3 mg, 0.12 mmol) in dimethyl-benzene (6.6 mL) and an aqueous solution of Na₂CO₃ (2 M, 0.23 mL). The mixture was heated at 90° C. in an oil bath overnight. The mixture was concentrated to give the crude product which was purified by prepared HPLC to give the desired product 3-(2'-amino-2-(2-fluorophenyl)-1'-methyl-5'-oxo-1',5'-dihydrospiro[chroman-4,4'-imidazole]-6-yl)benzonitrile (2.2 mg, 0.5%). ¹H-NMR (MeOD): 2.5 (d, 1H), 3.30 (t, 1H), 3.5 (s, 3H), 6.35 (d, 1H), 7.2 (t, 2H), 7.3 (d, 2H), 7.65 (t, 3H), 7.75 (s, 2H), 7.85 (d, 2H).

Example 8

2'-amino-6-(3-cyclopropylphenyl)-1'-methyl-2-phenylspiro[chroman-4,4'-imidazol]-5'(1'H)-one (Compound 11)

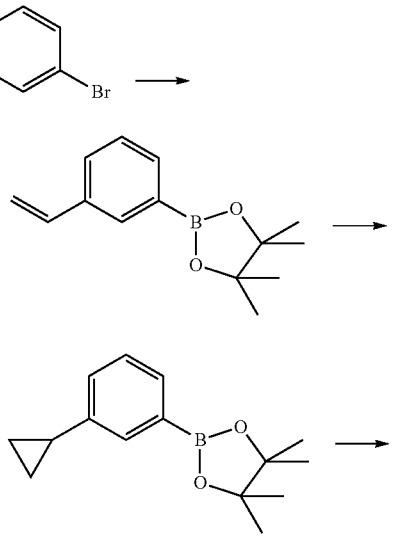

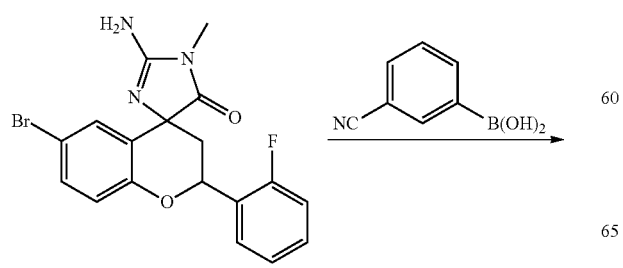

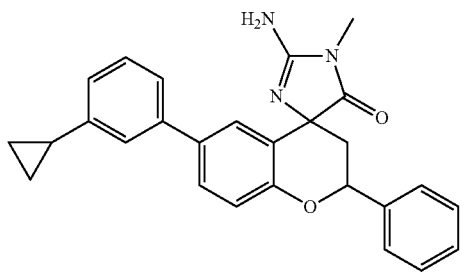

Experimental Data:

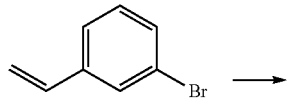

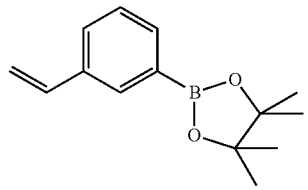

Step 1. 4,4,5,5-tetramethyl-2-(3-vinylphenyl)-1,3,2-dioxaborolane

1-Bromo-3-vinylbenzene (1 g, 5.5 mmol), bis(pinacolaco) (1.5 g, 6 mmol), K₂CO₃ (2.3 g, 16.5 mol) and Pd(PPh₃)₂Cl₂ (0.3 g 0.33 mol) were dissolved in dioxane (5 ml). The mixture was flushed with argon for 30 minutes, and then refluxed for 12 hour. The mixture was cooled to room temperature, extracted with ethyl acetate, washed with brine, dried over Na₂SO₄ and concentrated in vacuo to give 4,4,5,5-tetramethyl-2-(3-vinylphenyl)-1,3,2-dioxaborolane (500 mg, 16%).

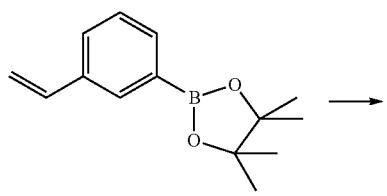

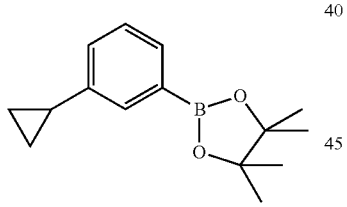

Step 2. 2-(3-cyclopropylphenyl)-4,4,5,5-tetramethyl-1,3,2-dioxaborolane

To a solution of Zn(C₂H₅)₂ (1 M, 6 mL) in DCM (1 mL) was added trifluoro-acetic acid (0.46 ml, 6 mmol) in DCM (1 mL) very slowly under N₂ in ice bath. The mixture was stirred for 20 minutes. CH₂I₂ (1.61 g, 6 mmol) in DCM (1 mL) was added to the mixture. After stirring for 20 minutes, 4,4,5,5-tetramethyl-2-(3-vinylphenyl)-1,3,2-dioxaborolane (690 mg, 3 mmol) in DCM (1 mL) was added. The mixture was stirred at room temperature for 2 hour. the mixture was quenched by NH₄Cl solution, extracted with DCM 3 times, washed with brine, filtered and concentrated to give the residue, which was purified preparative TLC and HPLC to give 2-(3-cyclopropylphenyl)-4,4,5,5-tetramethyl-1,3,2-dioxaborolane (70 mg, 10%).

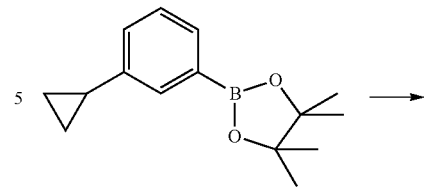

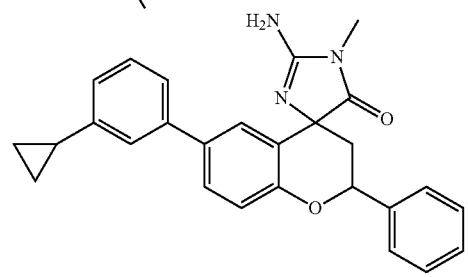

Step 3. 2'-amino-6-(3-cyclopropylphenyl)-1'-methyl-2-phenylspiro[chroman-4,4'-imidazol]-5'(1'H)-one Pd(PPh₃)₂Cl₂ (5 mg, 0.01 mmol) in a 10 mL of flask under Ar was treated sequentially with 2'-amino-6-bromo-1'-methyl-2-phenylspiro[chroman-4,4'-imidazol]-5'(1'H)-one (110 mg, 0.29 mmol) in 1,4-dioxane (5.0 mL), Cs₂CO₃ (2 N, 1 mL) and 2-(3-cyclopropylphenyl)-4,4,5,5-tetramethyl-1,3,2-dioxaborolane (70 mg, 0.29 mmol) The mixture was refluxed for 2 hour. The reaction mixture was concentrated in vacuo to give the residue, which was purified by preparative TLC and HPLC to give 2'-amino-6-(3-cyclopropylphenyl)-1'-methyl-2-phenylspiro[chroman-4,4'-imidazol]-5'(1'H)-one (3.6 mg, 3%). ¹H-NMR (MeOD): 0.71 (m, 1H), 0.98 (m, 1H), 1.97 (m, 1H), 2.31 (m, 1H), 2.65 (m, 0.8H), 2.75 (m, 0.2H), 3.32 (m, 3H), 5.24 (m, 0.2H), 5.86 (m, 0.8H), 6.99 (m, 1H), 7.12 (m, 2H), 7.23 (m, 2H), 7.28 (m, 2H), 7.46 (m, 6H).

Example 9

3-(2'-amino-1'-ethyl-5'-oxo-2-phenyl-1',5'-dihydrospiro[chroman-4,4'-imidazole]-6-yl)benzonitrile (Compound 12)

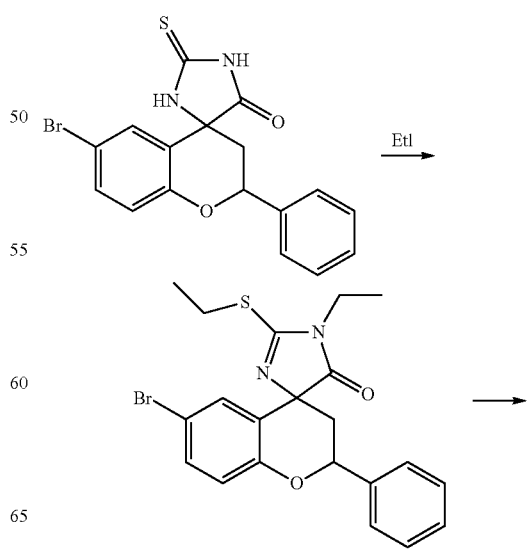

-continued

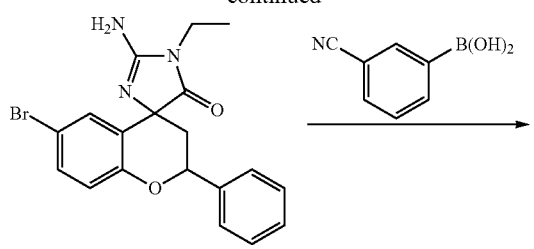

Step 1

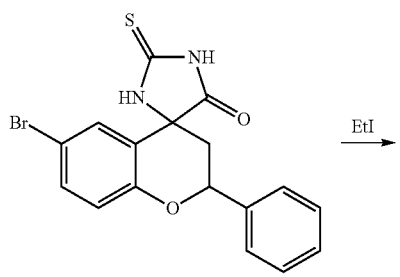

To a mixture of 6-bromo-2-phenyl-2'-thioxospiro[chroman-4,4'-imidazolidin]-5'-one (250 mg, 0.64 mmol) and K₂CO₃ (356 mg, 2.6 mmol) in CH₃CN (8 mL) was added EtI (402 mg, 2.6 mmol). The reaction mixture refluxed for 2 h. The mixture was filtered, and the filtrate was concentrated to give a residue, which was purified by preparative TLC to give 6-bromo-1'-ethyl-2'-(ethylthio)-2-phenylspiro[chroman-4,4'-imidazol]-5'(1'H)-one (195 mg, 69%).

Step 2

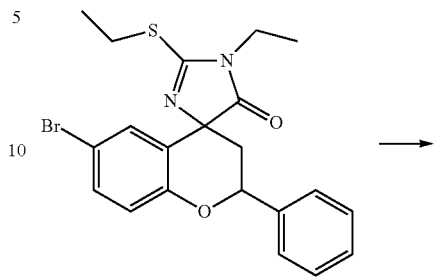

A solution of 6-bromo-1'-ethyl-2'-(ethylthio)-2-phenylspiro[chroman-4,4'-imidazol]-5'(1'H)-one (195 mg, 0.44 mmol) and NH₄I (128 mg, 0.88 mmol) in a solution of NH₃/EtOH (5 mL, 1.5 N) was heated at 110° C. in a tube in a microwave reactor for 2-2.5 h. After cooling, the mixture was concentrated in vacuo to give a residue, which was purified by preparative TLC to afford 2'-amino-6-bromo-1'-ethyl-2-phenylspiro[chroman-4,4'-imidazol]-5'(1'H)-one (42 mg, 24%).
¹H-NMR (MeOD): 1.12 (m, 3H), 1.98 (m, 1H), 3.16 (m, 1H), 3.54 (m, 2H), 5.75 (m, 1H), 6.77 (m, 1H), 6.95 (m, 1H), 7.23 (m, 2H), 7.33 (m, 4H).

Step 3

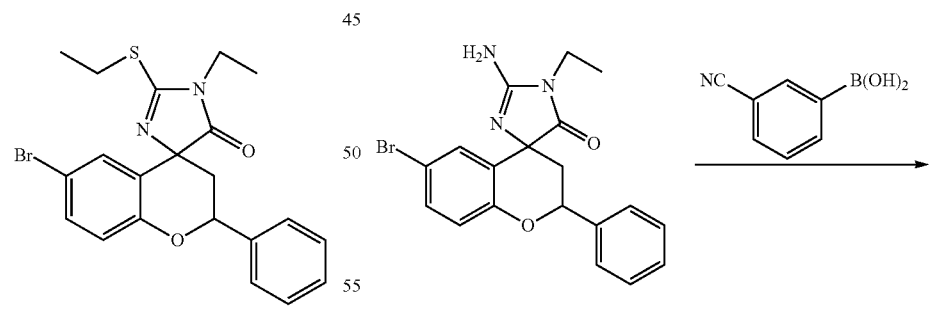

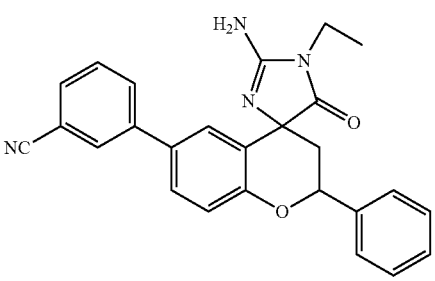

301

Pd(PPh$_3$)$_4$ (40 mg, 0.10 mmol) in a 10 mL flask under Ar was treated sequentially with 2'-amino-6-bromo-1'-ethyl-2-phenylspiro[chroman-4,4'-imidazol]-5'(1'H)-one (42 mg, 0.10 mmol) in toluene (5 mL), Na$_2$CO$_3$ (2 N, 2 mL), and 4-cyanophenylboronic acid (31 mg, 0.21 mmol). The mixture refluxed under Ar overnight. The reaction mixture was concentrated in vacuo to give a residue, which was purified by preparative TLC followed by preparative HPLC to give pure 3-(2'-amino-1'-ethyl-5'-oxo-2-phenyl-1',5'-dihydrospiro [chroman-4,4'-imidazole]-6-yl)benzonitrile (1.76 mg, 3%). $^1$H-NMR (MeOD): 1.31 (m, 3H), 2.55 (m, 2H), 3.84 (m, 2H), 5.26 (m, 1H), 5.86 (m, 1H), 7.14 (m, 1H), 7.47 (m, 6H), 7.59 (m, 1H), 7.28 (m, 2H), 7.90 (m, 2H).

Example 10

2'-amino-6-(3-methoxyphenyl)-1'-methyl-2-phenyl-spiro[chroman-4,4'-imidazol]-5'(1'H)-one (Compound 13)

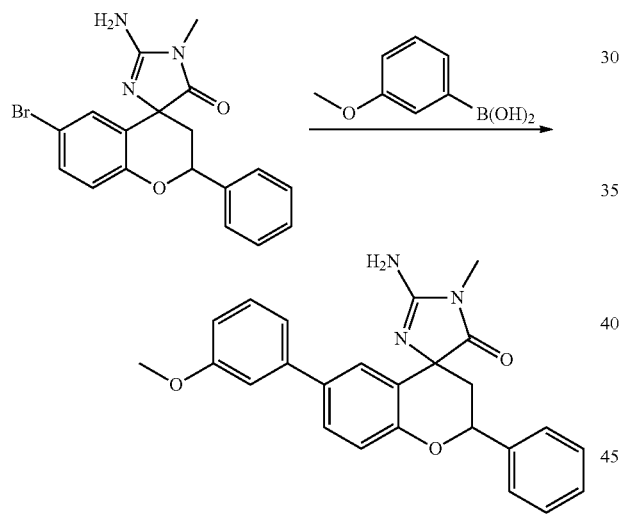

Pd(PPh$_3$)$_2$Cl$_2$ (5 mg, 0.01 mmol) in a 10 mL of flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-methoxyphenylboronic acid (16 mg, 0.104 mmol). The mixture was heated under 120° C. under Ar using microwave for 30 minutes. The reaction mixture was concentrated in vacuo to give the residue, which was purified preparative TLC and HPLC to give 2'-amino-6-(3-methoxyphenyl)-1'-methyl-2-phenylspiro[chroman-4,4'-imidazol]-5'(1'H)-one (1.69 mg, 8%). $^1$H-NMR (MeOD): 2.05 (m, 1H), 2.21 (m, 1H), 3.06 (m, 3H), 3.72 (s, 3H), 5.19 (m, 0.3H), 5.81 (m, 0.7H), 6.76 (m, 1H), 6.91 (m, 2H), 6.97 (m, 1H), 7.08 (m, 1H), 7.21 (m, 1H), 7.26 (m, 1H), 7.33 (m, 2H), 7.39 (m, 2H), 7.57 (m, 1H).

302

Example 11

3-(2'-amino-2-(2,3-difluorophenyl)-1'-methyl-5'-oxo-1',5'-dihydrospiro[chroman-4,4'-imidazole]-6-yl)benzonitrile (Compound 14)

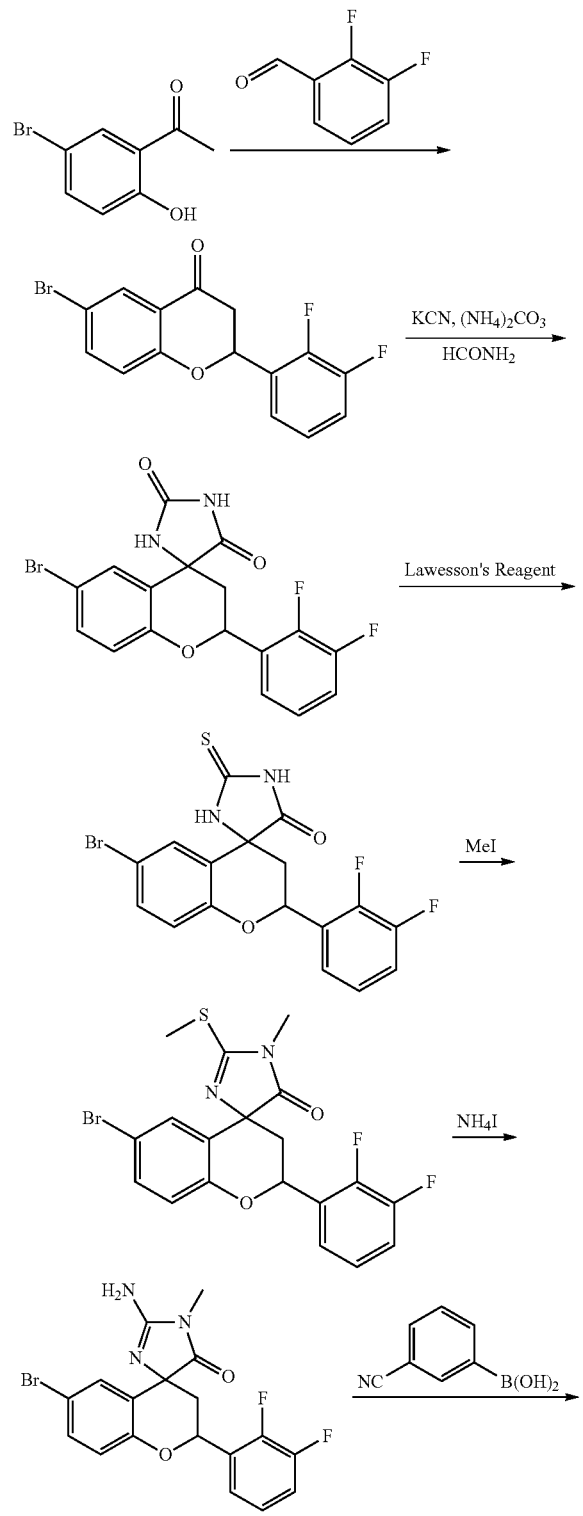

-continued

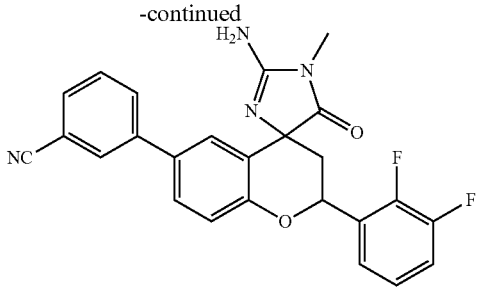

Experimental Data:

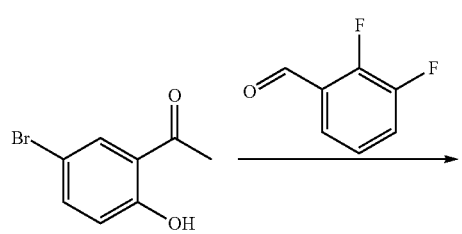

Step 1. 6-bromo-2-(3-fluorophenyl)chroman-4-one

A mixture of 1-(5-bromo-2-hydroxy-phenyl)-ethanone (22.6 g, 0.11 mol), 2,3-difluoro-benzaldehyde (15 g, 0.11 mol) and borax (40.2 g, 0.11 mol) in ethanol (140 mL) and H$_2$O (234 mL) was refluxed for one day. The reaction mixture was cooled, diluted with an equal volume of H$_2$O and extracted with ethyl acetate. The organic layer was dried over anhydrous Na$_2$SO$_4$, filtered, and evaporated to give 6-bromo-2-(3-fluorophenyl)chroman-4-one (5.3 g, 15%). $^1$H-NMR (CDCl$_3$): 2.95 (d, 1H), 3.05 (t, 3H), 5.75 (d, 1H), 6.97 (d, 1H), 7.20 (m, 2H), 7.35 (m, 1H), 7.60 (d, 1H), 8.05 (s, 1H).

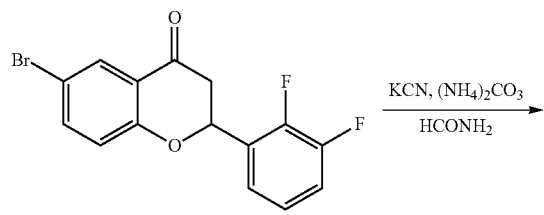

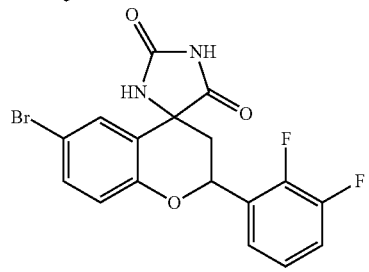

Step 2. 6-bromo-2-(2,3-difluorophenyl)spiro[chroman-4,4'-imidazolidine]-2',5'-dione A mixture of 6-bromo-2-(2,3-difluorophenyl)chroman-4-one (1.49 g, 4.4 mmol), KCN (0.57 g, 8.8 mmol), (NH$_4$)$_2$CO$_3$ (2.96 g, 30.8 mmol) in HCONH$_2$ (30 mL) and DMF (5 mL) was added to fill a 40 mL CEM microwave test tube nearly completely. The mixture was heated at 70° C. for 2 hrs. The reaction mixture was then cooled and poured over ice water. Acidification with concentrated HCl was performed to give a precipitate which was filtered, washed twice with water, and then dissolved in ethyl acetate, dried over Na$_2$SO$_4$, and filtered. The filtrate was concentrated in vacuo to give the residue, which was purified by column chromatography to give 6-bromo-2-(2,3-difluorophenyl)spiro[chroman-4,4'-imidazolidine]-2',5'-dione (235 mg, 13%). $^1$H-NMR (CDCl$_3$): 2.34 (t, 1H), 2.54 (d, 1H), 5.50 (s, 1H), 6.18 (d, 1H), 6.91 (m, 1H), 7.16 (m, 3H), 7.28 (m, 1H), 7.39 (m, 2H), 7.70 (s, 1H).

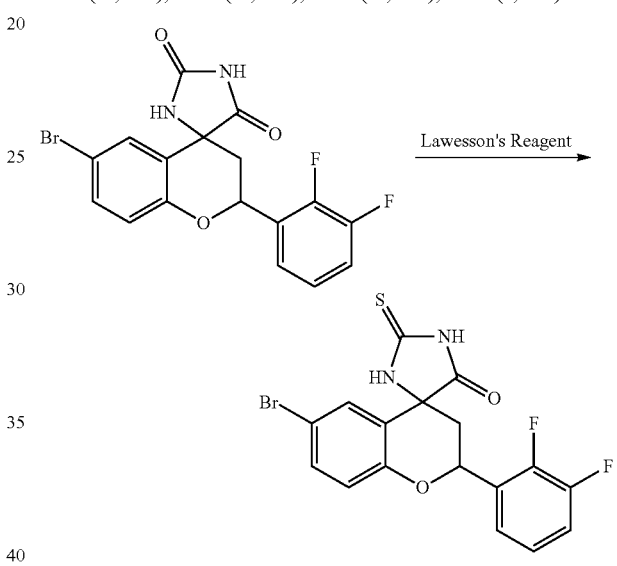

Step 3. 6-bromo-2-(2,3-difluorophenyl)-2'-thioxospiro[chroman-4,4'-imidazolidine]-5'-one A suspension of 6-bromo-2-(2,3-difluorophenyl)spiro[chroman-4,4'-imidazolidine]-2',5'-dione (212 mg, 0.52 mmol) and Lawesson's Reagent (201 mg, 0.52 mmol) in dry m-xylene (4.5 mL) was heated at 150° C. in a 10 mL CEM microwave test tube for 25 minutes. The mixture was concentrated in vacuo and the residue was purified by preparative TLC to give 6-bromo-2-(2,3-difluorophenyl)-2'-thioxospiro[chroman-4,4'-imidazolidine]-5'-one (163 mg, 74%). $^1$H-NMR (CDCl$_3$): 2.33 (t, 3H), 2.54 (d, 1H), 5.36 (s, 1H), 6.17 (d, 1H), 6.91 (d, 1H), 7.17 (m, 3H), 7.30 (m, 2H), 7.46 (s, 1H).

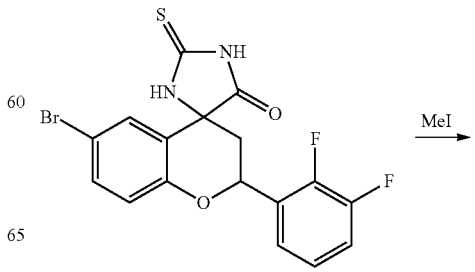

-continued

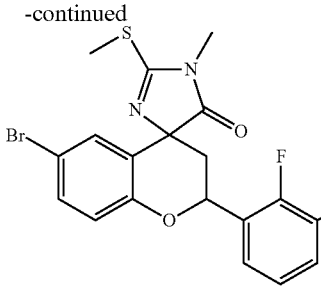

Step 4. 6-bromo-2-(2,3-difluorophenyl)-1'-methyl-2'-(methylthio)spiro[chroman-4,4'-imidazol]-5'(1'H)-one To a solution of 6-bromo-2-(2,3-difluorophenyl)-2'-thioxospiro[chroman-4,4'-imidazolidine]-5'-one (173 mg, 0.41 mmol) in MeOH (5 mL) was added a solution of NaOH (41 mg, 1.02 mmol) in $H_2O$ (1 mL). After stirring for 10 minutes, MeI (0.87 g, 6.12 mmol) was added. The reaction mixture was heated under reflux for 2 h. The mixture was concentrated in vacuo to give the residue, which was purified by preparative TLC to give 6-bromo-2-(2,3-difluorophenyl)-1'-methyl-2'-(methylthio)spiro[chroman-4,4'-imidazol]-5'(1'H)-one (63 mg, 16%). $^1$H-NMR (CDCl$_3$): 2.06 (d, 1H), 2.47 (t, 1H), 2.58 (s, 3H), 3.12 (s, 3H), 6.23 (d, 1H), 6.86 (m, 2H), 7.14 (m, 2H), 7.31 (m, 2H).

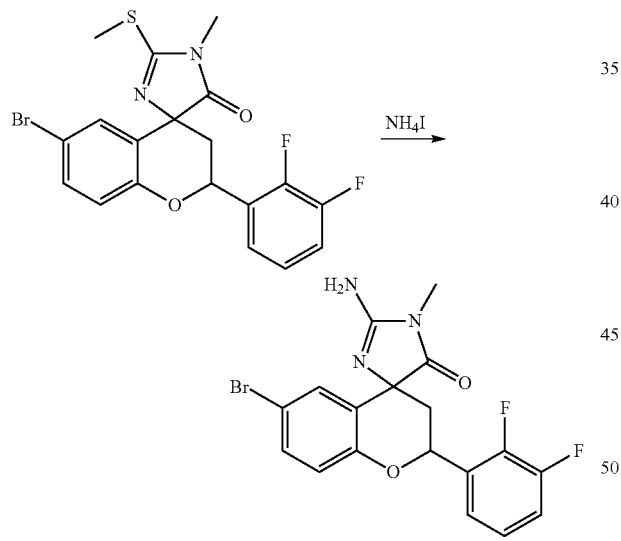

Step 5. 2'-amino-6-bromo-2-(2,3-difluorophenyl)-1'-methylspiro[chroman-4,4'-imidazol]-5'(1'H)-one A solution of 6-bromo-2-(2,3-difluorophenyl)-1'-methyl-2'-(methylthio)spiro[chroman-4,4'-imidazol]-5'(1'H)-one (63 mg, 0.14 mmol), NH$_4$I (60.6 mg, 0.42 mmol) in a solution of NH$_3$/EtOH (3 mL, 1.5 N) was heated at 110° C. in a tube under microwave reactor for 3 hrs. After cooling, the mixture was concentrated in vacuo to give the residue, which was purified by preparative TLC to afford 2'-amino-6-bromo-2-(2,3-difluorophenyl)-1'-methylspiro[chroman-4,4'-imidazol]-5'(1'H)-one (35 mg, 60%). $^1$H-NMR (CDCl$_3$): 2.31 (d, 1H), 2.45 (t, 1H), 3.27 (s, 3H), 6.12 (d, 1H), 6.87 (m, 1H), 7.09 (m, 3H), 7.34 (m, 2H), 7.45 (m, 1H).

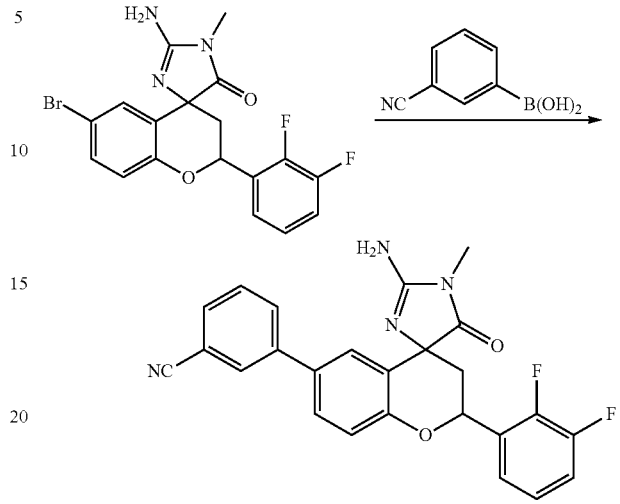

Step 6. 3-(2'-amino-2-(2,3-difluorophenyl)-1'-methyl-5'-oxo-1',5'-dihydrospiro[chroman-4,4'-imidazole]-6-yl)benzonitrile A mixture of 2'-amino-6-bromo-2-(2,3-difluorophenyl)-1'-methylspiro[chroman-4,4'-imidazol]-5'(1'H)-one (25 mg, 0.05 mmol), 3-cyanophenylboronic acid (19.7 mg, 0.104 mmol), Pd(PPh$_3$)$_2$Cl$_2$ (10 mg, 50%), aqueous cesium carbonate solution (2 M, 0.3 mL) in dry 1,4-dioxane (1 mL) was heated at 120° C. under microwave reactor for 30 minutes. The mixture was concentrated to give the residue, which was purified by preparative TLC to give 3-(2'-amino-2-(2,3-difluorophenyl)-1'-methyl-5'-oxo-1',5'-dihydrospiro[chroman-4,4'-imidazole]-6-yl)benzonitrile (7.02 mg, 27%). $^1$H-NMR (CDCl$_3$): 2.20 (m, 2H), 3.12 (s, 3H), 6.25 (d, 1H), 6.77 (d, 1H), 7.13 (m, 3H), 7.29 (m, 1H), 7.34 (d, 1H), 7.43 (m, 1H), 7.48 (m, 2H), 7.51 (m, 1H), 7.61 (d, 1H), 7.68 (s, 1H), 7.78 (d, 1H).

Example 12

2'-amino-1'-methyl-2-phenyl-6-(pyridin-3-yl)spiro[chroman-4,4'-imidazol]-5'(1'H)-one Compound 15

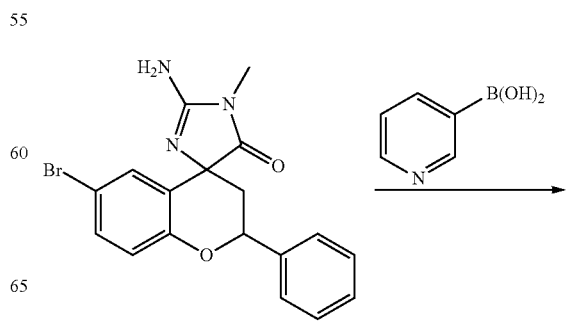

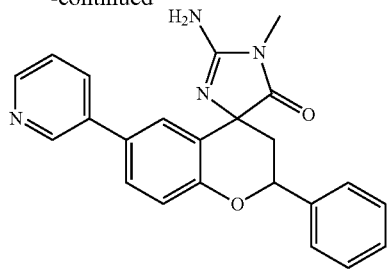

Pd(PPh$_3$)$_2$Cl$_2$ (10 mg) in a 10 mL tube under Ar was treated sequentially with 2'-amino-6-bromo-1'-methyl-2-phenyl-spiro[chroman-4,4'-imidazol]-5'(1'H)-one (20 mg, 0.052 mmol) in 1,4-dioxane (1 mL), Cs$_2$CO$_3$ (2 N, 0.3 mL) and pyridin-3-ylboronic acid (13 mg, 0.1 mmol). The mixture was heated under microwave at 120° C. for 30 min. The reaction mixture was concentrated in vacuo to give the residue, which was purified by preparative TLC to give pure 2'-amino-1'-methyl-2-phenyl-6-(pyridin-3-yl)spiro[chroman-4,4'-imidazol]-5'(1'H)-one (18 mg, 80%). $^1$H-NMR (MeOD): 2.39 (t, 1H), 2.52 (dd, 1H), 3.28 (s, 3H), 5.80 (d, 1H), 7.10 (d, 1H), 7.31 (m, 2H), 7.35 (m, 2H), 7.39 (m, 3H), 7.51 (s, 1H), 7.61 (m, 2H), 8.19 (d, 1H).

Example 13

3-amino-5-(2'-amino-1'-methyl-5'-oxo-2-phenyl-1',5'-dihydrospiro[chroman-4,4'-imidazole]-6-yl)benzonitrile Compound 17

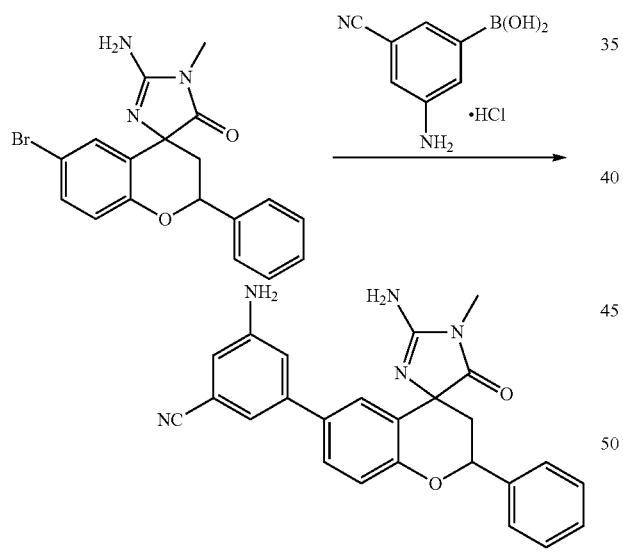

Pd(PPh$_3$)$_2$Cl$_2$ (10 mg) in a 10 mL tube under Ar was treated sequentially with 2'-amino-6-bromo-1'-(cyclohexylmethyl)-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-amino-5-cyanophenylboronic acid hydrochloride (21 mg, 0.104 mmol). The mixture was heated at 120° C. under microwave reactor for 0.5 h. The reaction mixture was concentrated in vacuo to give the residue, which was purified by preparative TLC followed by preparative HPLC to give pure β-amino-5-(2'-amino-1'-methyl-5'-oxo-2-phenyl-1',5'-dihydrospiro[chroman-4,4'-imidazole]-6-yl)benzonitrile (3.53 mg, 16%). $^1$H-NMR (MeOD): 2.44 (m, 1H), 2.60 (m, 1H), 5.24 (d, 0.3H), 5.85 (d, 0.7H), 6.91 (m, 1H), 7.14 (m, 3H), 7.48 (m, 6H), 7.60 (m, 1H).

Example 14

3-(2'-amino-1'-(cyclohexylmethyl)-5'-oxo-2-phenyl-1',5'-dihydrospiro[chroman-4,4'-imidazole]-6-yl)benzonitrile (Compound 18)

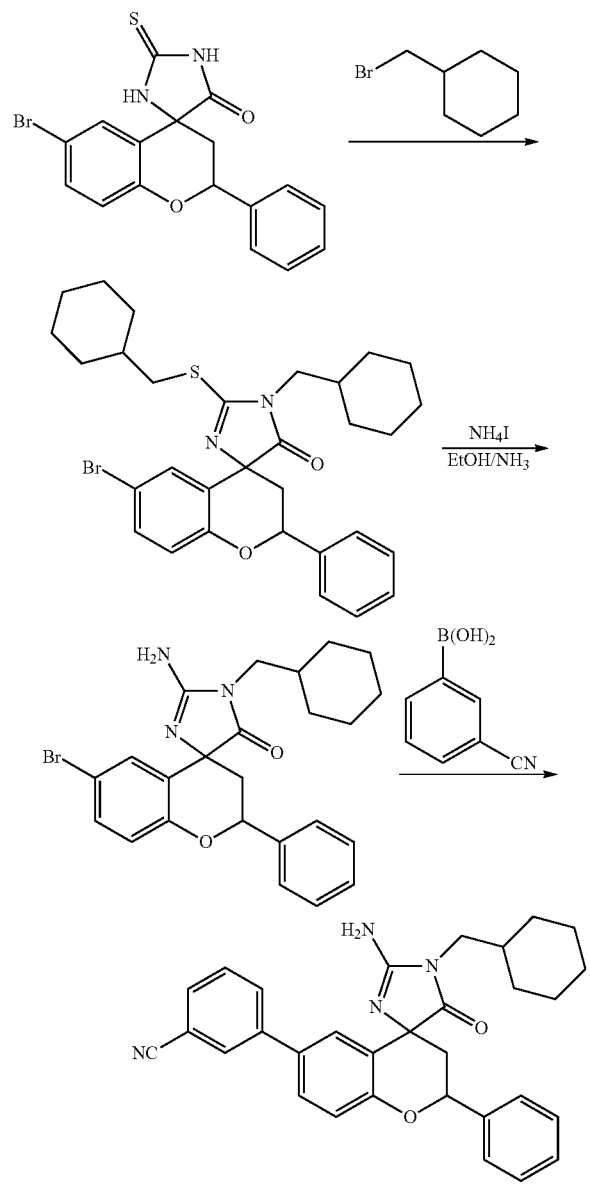

Experimental Data:

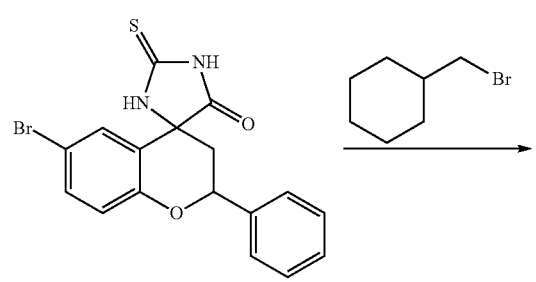

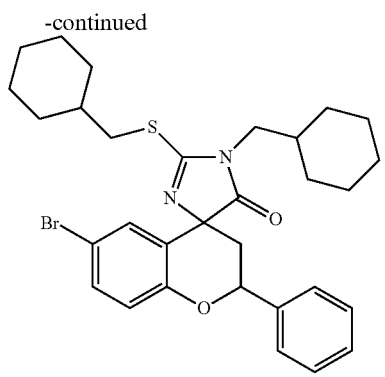

Step 1. 6-bromo-1'-(cyclohexylmethyl)-2'-(cyclohexylmethylthio)-2-phenylspirochroman-4,4'-imidazol]-5'(1'H)-one A mixture of 6-bromo-2-phenyl-2'-thioxospiro[chroman-4,4'-imidazolidin]-5'-one (180 mg, 0.464 mmol), excess bromomethyl-cyclohexane (327 mg, 1.856 mmol) and solid $K_2CO_3$ (256 mg, 1.856 mmol) in $CH_3CN$ (10 mL) was stirred for 4 hours at 60° C. The mixture was filtered and the filtrate was concentrated. The crude product was purified by preparative TLC (71 mg, 26%).

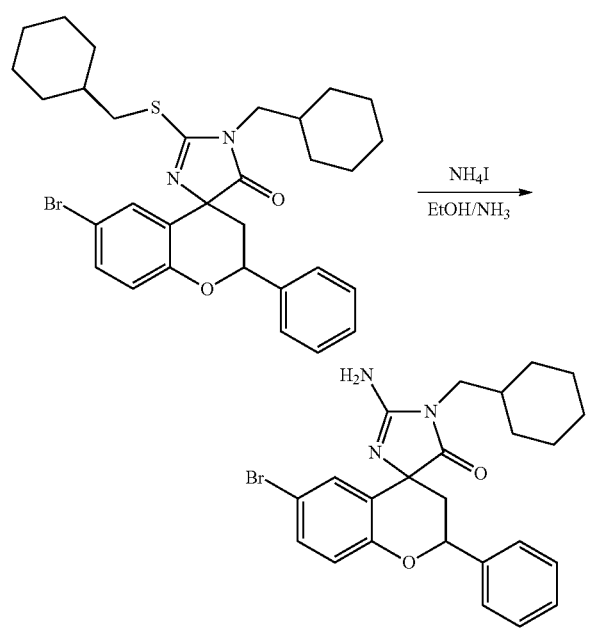

Step 2. 2'-amino-6-bromo-1'-(cyclohexylmethyl)-2-phenylspiro[chroman-4,4'-imidazol]-5'(1'H)-one A solution of 6-bromo-1'-(cyclohexylmethyl)-2'-(cyclohexylmethylthio)-2-phenylspiro chroman-4,4'-imidazol]-5' (1'H)-one (70 mg, 0.293 mmol), $NH_4I$ (85 mg, 0.586 mmol) in a solution of $NH_3$/EtOH (3 mL, 1.5 N) was heated at 120° C. in a tube under microwave reactor for 2 h. After cooling, the mixture was concentrated in vacuum to give the residue, which was purified by preparative TLC to afford 2'-amino-6-bromo-1'-(cyclohexylmethyl)-phenylspiro[chroman-4,4'-imidazol]-5'(1'H)-one (30 mg, 54%).

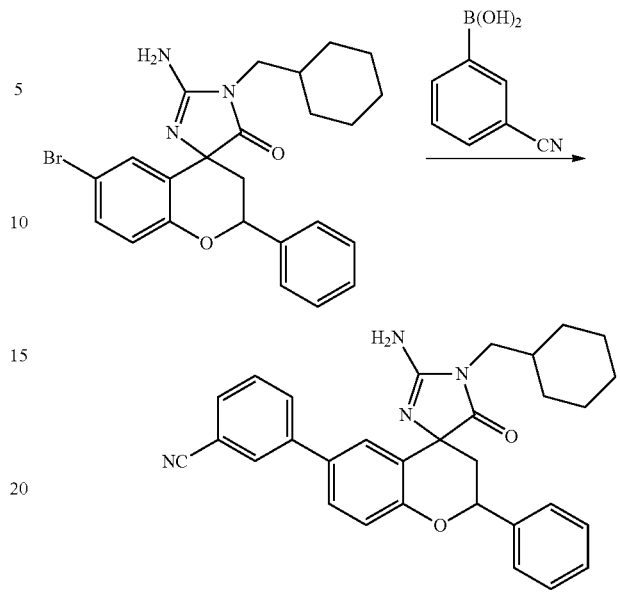

Step 3. 3-(2'-amino-1'-(cyclohexylmethyl)-5'-oxo-2-phenyl-1',5'-dihydrospiro[chroman-4,4'-imidazole]-6-yl)benzonitrile $Pd(PPh_3)_2Cl_2$ (10 mg, 0.014 mmol) in a 10 mL tube under Ar was treated sequentially with 2'-amino-6-bromo-1'-(cyclohexylmethyl)-2-phenylspiro[chroman-4,4'-imidazol]-5' (1'H)-one (30 mg, 0.064 mmol) in 1,4-dioxane (1.5 mL), $Cs_2CO_3$ (2 N, 0.5 mL) and 3-cyanophenylboronic acid (19 mg, 0.128 mmol). The mixture was heated at 120° C. under microwave reactor for 0.5 h. The reaction mixture was concentrated in vacuo to give the residue, which was purified by preparative TLC followed by preparative HPLC to give pure 3-(2'-amino-1'-(cyclohexylmethyl)-5'-oxo-2-phenyl-1',5'-dihydrospiro[chroman-4,4'-imidazole]-6-yl)benzonitrile (9.74 mg, 31%). $^1$H-NMR (MeOD): 1.02 (m, 5H), 1.62 (m, 6H), 2.03 (m, 1H), 2.24 (m, 1H), 3.30 (m, 1H), 3.44 (m, 1H), 5.91 (m, 1H), 6.97 (m, 1H), 7.16 (m, 1H), 7.25 (m, 1H), 7.35 (m, 3H), 7.46 (m, 2H), 7.56 (m, 1H), 7.71 (m, 2H)

Example 15

3-(2'-amino-2-(4-fluorophenyl)-1'-methyl-5'-oxo-1',5'-dihydrospiro[chrom-an-4,4'-imidazole]-6-yl)benzonitrile (Compound 19 and 19a)

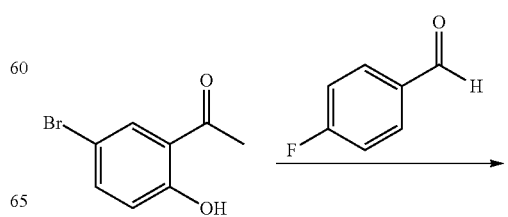

311

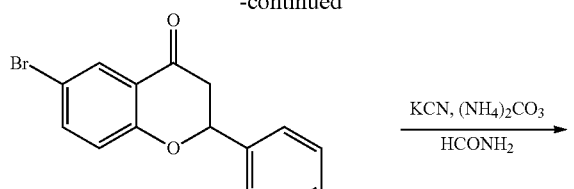

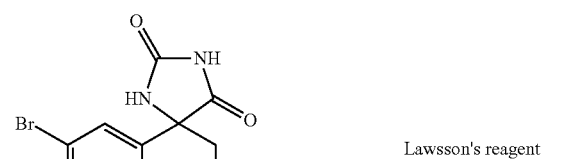

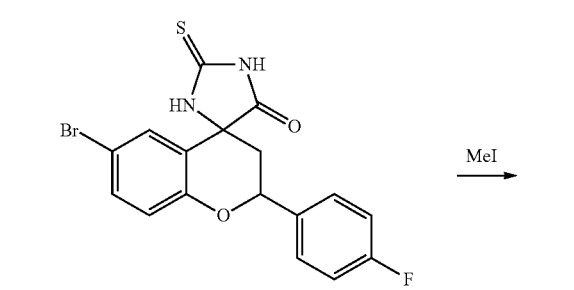

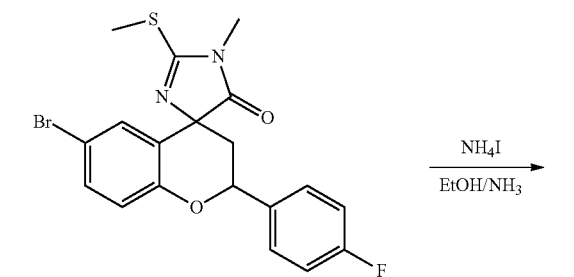

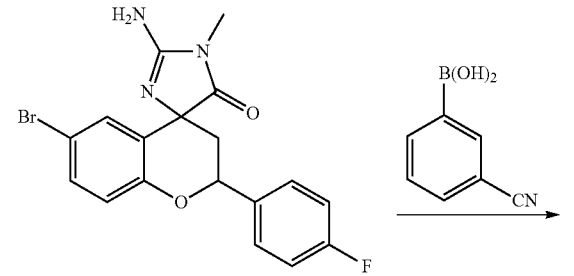

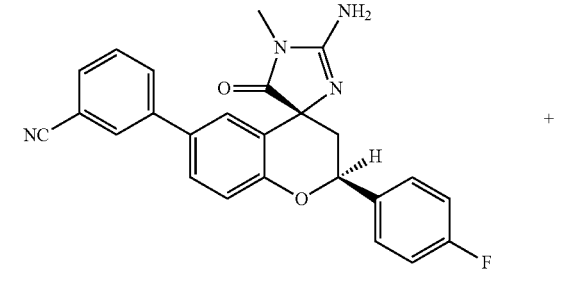

312

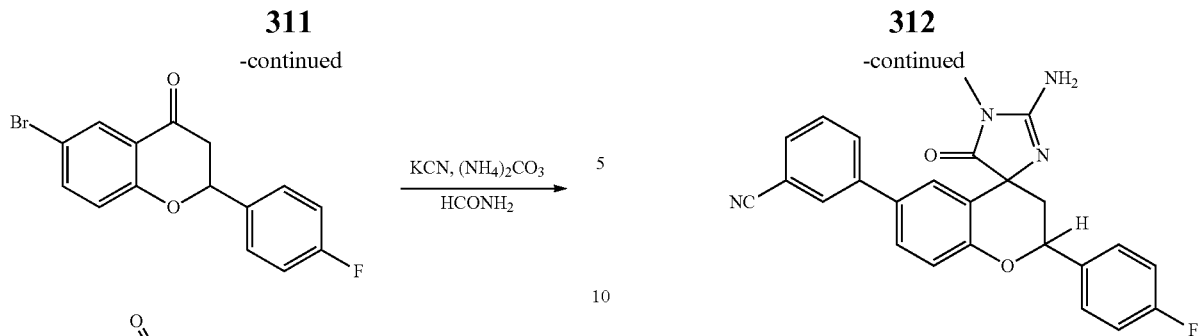

Experimental Data:

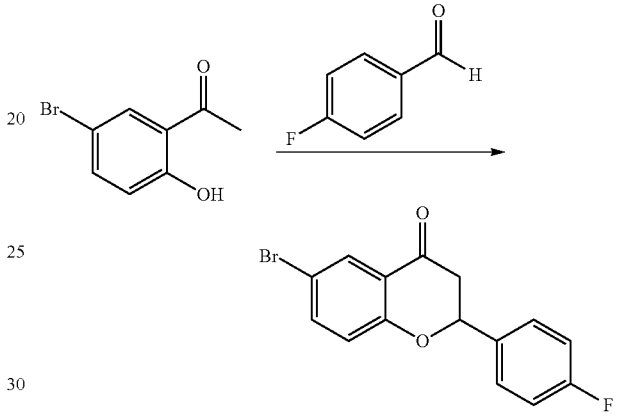

Step 1. 6-Bromo-2-(4-fluoro-phenyl)-chroman-4-one

A mixture of 1-(5-bromo-2-hydroxy-phenyl)-ethanone (30 g, 0.14 mol), 4-fluoro-benzaldehy-de (19.3 g, 0.14 mol) and borax (53.34 g, 0.14 mol) in ethanol (180 mL) and $H_2O$ (300 mL) was refluxed for one day. The reaction mixture was cooled, diluted with an equal volume of $H_2O$ and extracted with ethyl acetate. The organic layer was dried over anhydrous $Na_2SO_4$, filtered, and evaporated to give 6-bromo-2-(4-fluoro-phenyl)-chroman-4-one (10 g, 20%). $^1$H-NMR ($CDCl_3$): 2.81 (dd, 1H), 2.99 (t, 1H), 5.49 (dd, 1H), 6.87 (d, 1H), 7.04 (t, 2H), 7.38 (t, 2H), 7.51 (dd, 1H), 7.94 (d, 1H).

313

Step 2. 6-bromo-2-(4-fluorophenyl)spiro[chroman-4,4'-imidazolidine]-2',5'-dione A glass pressure tube was charged with a mixture of 6-bromo-2-(4-fluoro-phenyl)-chroman-4-one (1.5 g, 4.7 mmol), KCN (0.6 g, 9.4 mmol), and $(NH_4)_2CO_3$ (3.16 g, 32.9 mmol). Formamide (40 mL) was added to fill the tube nearly completely. The mixture was heated at 70° C. for 2 h with microwave. The reaction mixture was then cooled and poured over ice. Acidification with concentrated HCl gave a precipitate which was filtered, washed twice with water, and then redissolved in ethyl acetate, dried over $Na_2SO_4$ and filtered. The filtrate was concentrated in vacuo to give the residue, which was purified by column to give 6-bromo-2-(4-fluorophenyl)spiro[chroman-4,4'-imidazolidine]-2',5'-dione (300 mg, 20%). $^1$H-NMR (MeOD): 2.19 (m, 1H), 2.23 (m, 1H), 5.76 (dd, 1H), 6.78 (d, 1H), 7.00 (t, 2H), 726 (t, 2H), 7.37 (m, 2H).

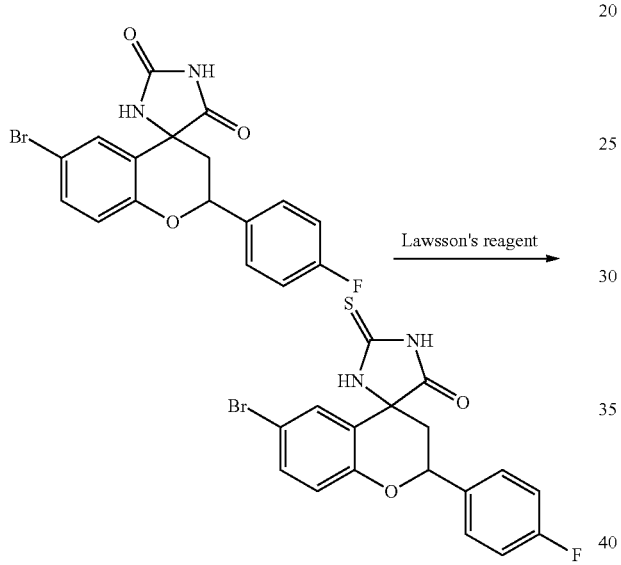

Step 3. 6-bromo-2-(4-fluorophenyl)-2'-thioxospiro[chroman-4,4'-imidazolidin]-5'-one A suspension of 6-bromo-2-(4-fluorophenyl)spiro[chroman-4,4'-imidazolidine]-2',5'-dione (300 mg, 0.77 mmol) and Lawesson's Reagent (310 mg, 0.77 mmol) in dry 1,4-dioxane (4 mL) was heated at 120° C. for 30 min with microwave. The mixture was concentrated in vacuo and the residue was purified by preparative TLC to give 6-bromo-2-(4-fluorophenyl)-2'-thioxospiro[chroman-4,4'-imidazolidin]-5'-one (160 mg, 50%).

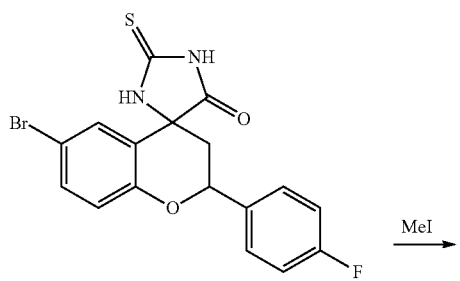

314

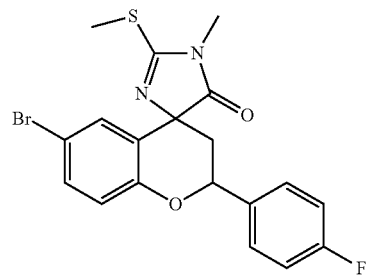

Step 4. 6-bromo-2-(4-fluorophenyl)-1'-methyl-2'-(methylthio)spiro-[chroman-4,4'-imidazol]-5'(1'H)-one To a solution of 6-bromo-2-(4-fluorophenyl)-2'-thioxospiro[chroman-4,4'-imidazolidin]-5'-one (160 mg, 0.39 mmol) in MeOH (16 mL) was added a solution of NaOH (0.6 N, 1.6 mL) and MeI (0.3 mL). The reaction mixture was heated at 60° C. for 10 min with microwave. The mixture was concentrated in vacuo to give the residue, which was purified by preparative TLC to give 6-bromo-2-(4-fluorophenyl)-F-methyl-2'-(methylthio)-spiro[chroman-4,4'-imidazol]-5' (1'H)-one (80 mg, 50%).

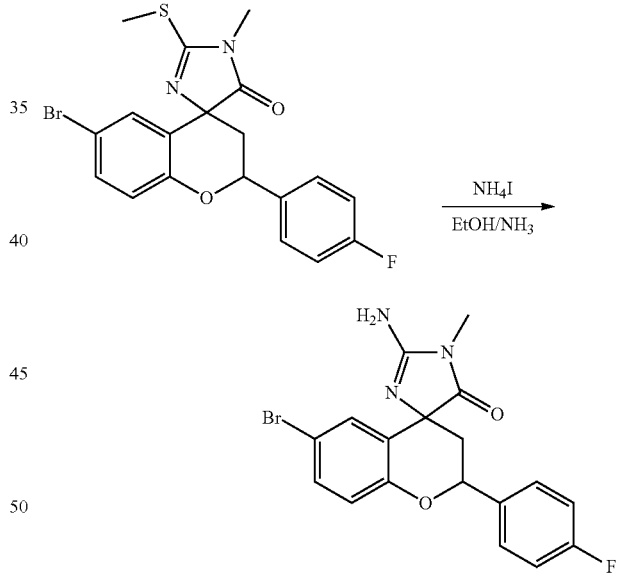

Step 5. 2'-amino-6-bromo-(4-fluorophenyl)-1'-methylspiro[chroman-4,4'-imidazol]-5'(1-'H)-one A solution of 6-bromo-2-(4-fluorophenyl)-1'-methyl-2'-(methylthio)spiro[chroma-4,4'-imi-zol]-5'(1'H)-one (80 mg, 0.184 mmol), $NH_4I$ (214 mg, 1.47 mmol) in a solution of $NH_3$/EtOH (2 mL, 8 N) was heated at 120° C. in a tube under microwave reactor for 3 h. After cooling, the mixture was concentrated in vacuum to give 2'-amino-6-bromo-(4-fluorophenyl)-1'-methylspiro[chroman-4,4'-imidazol]-5'(1'H)-one (40 mg, 50%).

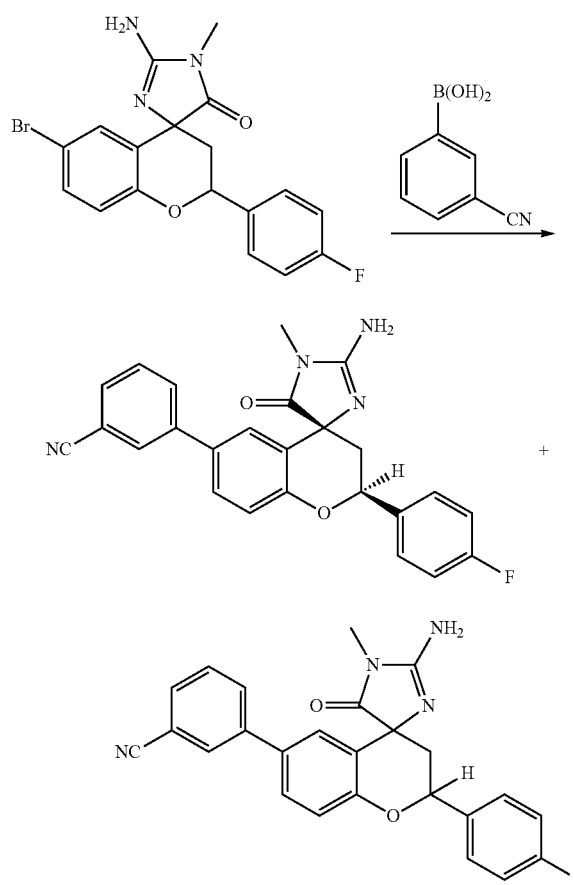

Step 6. 3-((2S,4S)-2'-amino-2-(4-fluorophenyl)-1'-methyl-5'-oxo-1',5'-dihydrospiro[chroman-4,4'-imidazole]-6-yl)benzonitrile (6 mg, 10%) and 3-(2'-amino-2-(4-fluorophenyl)-1'-methyl-5'-oxo-1',5'-dihydrospiro[chrom-an-4,4'-imidazole]-6-yl)benzonitrile (19)

Pd(PPh$_3$)$_2$Cl$_2$ (10 mg) in a 10 mL of tube under Ar$_2$ was treated sequentially with 2'-amino-6-bromo-2-(4-fluorophenyl)-1'-methylspiro[chroman-4,4'-imidazol]-5'(1'H)-one (40 mg, 0.099 mmol) in 1,4-dioxane (1 mL), Cs$_2$CO$_3$ (2 N, 0.3 mL) and 3-cyanophenylboronic acid (29 mg, 0.197 mmol). The mixture was heated under microwave at 120° C. for 30 min. The reaction mixture was concentrated in vacuo to give the residue, which was purified by preparative TLC and then by preparative HPLC to give pure 3-((2S,4S)-2'-amino-2-(4-fluorophenyl)-1'-methyl-5'-oxo-1',5'-dihydrospiro[chroman-4,4'-imidazole]-6-yl)benzonitrile (19a) (6 mg, 10%), $^1$H-NMR (MeOD): 2.41 (t, 1H), 2.60 (t, 1H), 3.10 (s, 3H), 5.83 (d, 1H), 7.16 (m, 3H), 7.52 (m, 2H), 7.60 (m, 2H), 7.69 (m, 2H), 7.90 (m, 1H), 7.99 (d, 1H), and 3-(2'-amino-2-(4-fluorophenyl)-1'-methyl-5'-oxo-1',5'-dihydrospiro[chrom-an-4,4'-imidazole]-6-yl)benzonitrile (19) (4 mg, 8%), $^1$H-NMR (MeOD): 2.42 (t, 1H), 2.60 (t, 1H), 3.20 (s, 3H), 5.87 (d, 1H), 7.19 (m, 3H), 7.45 (m, 2H), 7.51 (m, 1H), 7.54 (m, 1H), 7.64 (m, 2H), 7.90 (t, 1H), 7.99 (d, 1H).

Example 16

3-(2'-amino-2-(3-chlorophenyl)-1'-methyl-5'-oxo-1',5'-dihydrospiro[chroman-4,4'-imidazole]-6-yl)benzonitrile (Compound 20)

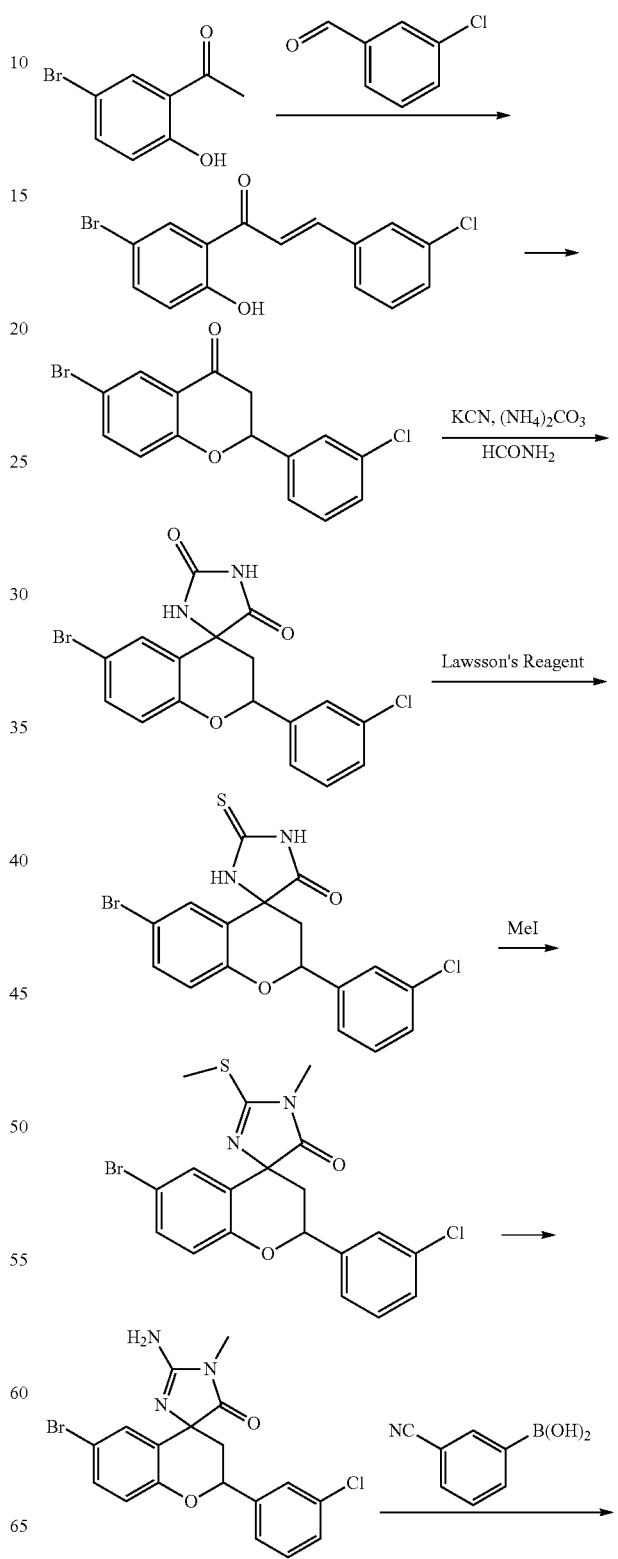

-continued

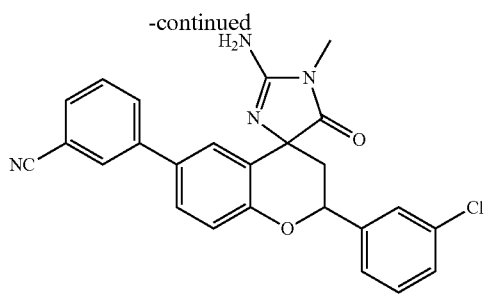

Step 1

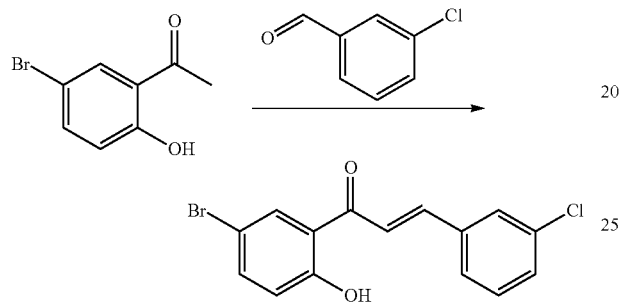

In a bottle 1-(5-bromo-2-hydroxyphenyl)ethanone (25 g, 0.02 mol), 3-chlorobenzaldehyde (16.35 g, 0.12 mol), EtOH (96%, 144 mL), and NaOH (42.1 g, 1.06 mol) were combined. The mixture was stirred vigorously for 0.5 h. 2-Methoxy-2-methylpropane was added and the mixture was filtered. The filtrate was poured into HCl (1 N, 800 mL) and filtered. The combined solid was dried to give 1-(5-bromo-2-hydroxyphenyl)-3-(3-chlorophenyl)prop-2-en-1-one (23.47 g, 60%). $^1$H-NMR (CDCl$_3$): 6.88 (d, 1H), 4.35 (m, 2H), 7.49 (m, 3H), 7.61 (s, 1H), 7.80 (m, 1H), 7.93 (m, 1H), 12.56 (s, 1H).

Step 2

1-(5-Bromo-2-hydroxyphenyl)-3-(3-chlorophenyl)prop-2-en-1-one (23 g, 68 mmol) was dissolved in H$_2$O (513 mL) and EtOH (171 mL). Then NaOH (2.74 g, 68 mmol) was added. The mixture was stirred overnight and filtered. The solid was dissolved in EtOAc and washed with H$_2$O twice. The organic layer was dried and filtered. The filtrate was concentrated to give 6-bromo-2-(3-chlorophenyl)chroman-4-one (18.82 g, 82%). $^1$H-NMR (CDCl$_3$): 2.87 (m, 1H), 3.02 (m, 1H), 5.44 (m, 1H), 6.96 (d, 1H), 7.31 (m, 1H), 7.37 (m, 2H), 7.48 (s, 1H), 7.58 (m, 1H), 8.02 (d, 1H).

Step 3

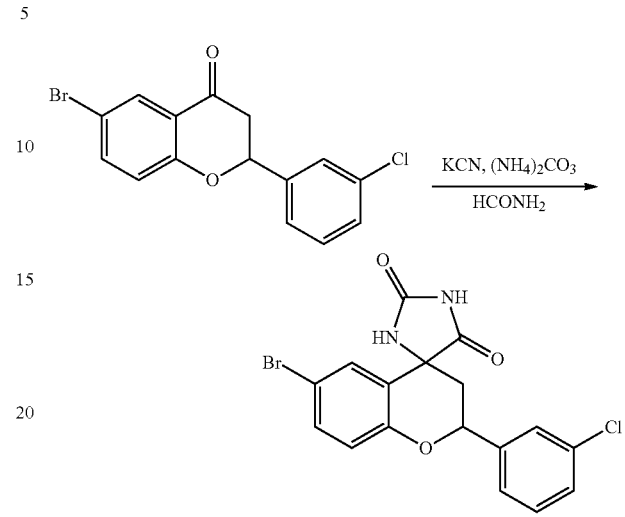

In a steel bomb, a mixture of 6-bromo-2-(3-chlorophenyl)chroman-4-one (7 g, 21 mmol), KCN (2.71 g, 42 mmol), and (NH$_4$)$_2$CO$_3$ (15 g, 156 mmol) in formamide (60 mL) was heated and stirred at 70° C. for 24 h and then heated at 110° C. for 2 days. The mixture was poured into ice/water. Concentrated HCl was added till pH=1. The mixture is filtered to afford a solid, and the filtrate was extracted with CH$_2$Cl$_2$. The organic layer was concentrated to give a residue, which was combined with the solid above. The combined solid was purified through column chromatography to give 6-bromo-2-(3-chlorophenyl)spiro[chroman-4,4'-imidazolidine]-2',5'-dione (470 mg, 5%). $^1$H-NMR (CDCl$_3$): 2.20 (m, 1H), 2.28 (m, 1H), 5.76 (m, 1H), 6.82 (m, 1H), 7.27 (m, 5H), 7.39 (m, 1H).

Step 4

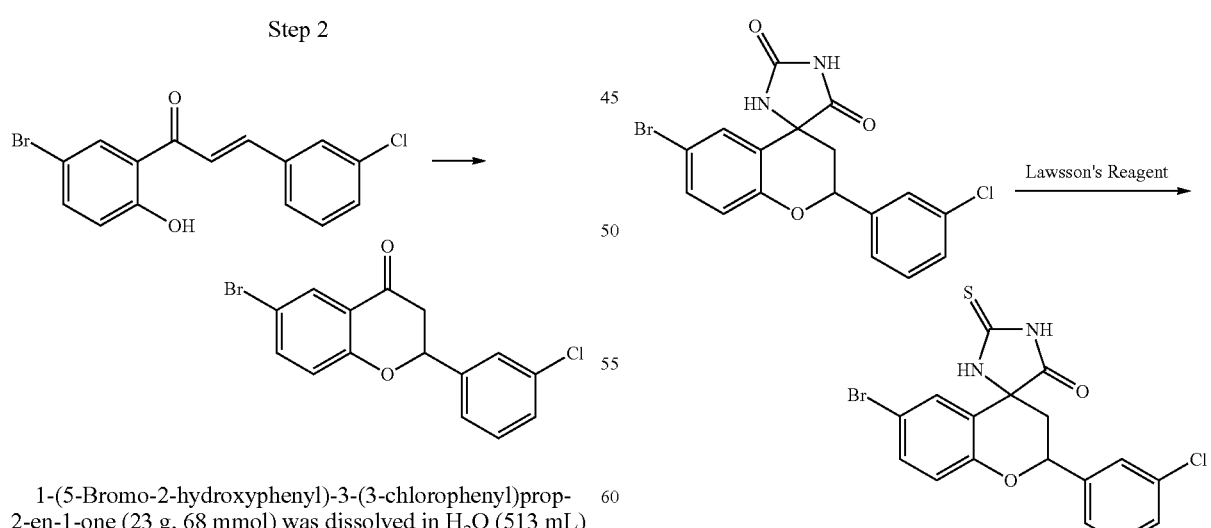

A mixture of 6-bromo-2-(3-chlorophenyl)spiro[chroman-4,4'-imidazolidine]-2',5'-dione (470 mg, 1.16 mmol) and Lawesson's Reagent (468 mg, 1.16 mmol) in 1,4-dioxane (16 mL) was stirred at 110° C. overnight. The solvent was removed in vacuo and the residue was purified by preparative TLC to give 6-bromo-2-(3-chlorophenyl)-2'-thioxospiro[chroman-4,4'-imidazolidin]-5'-one (350 mg, 71%).

Step 5

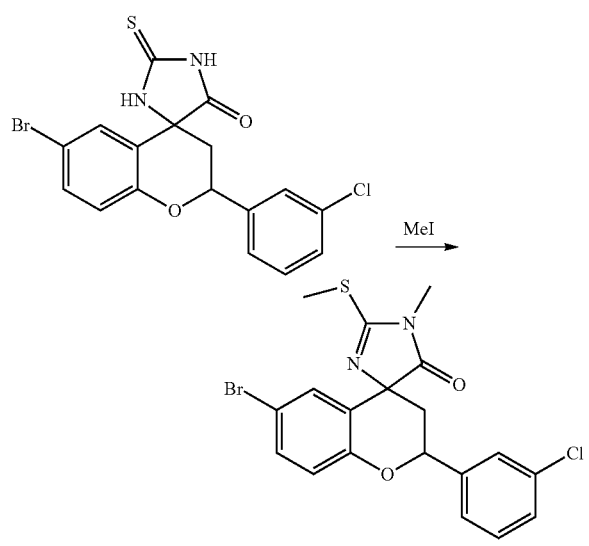

To a mixture of 6-bromo-2-(3-chlorophenyl)-2'-thioxospiro[chroman-4,4'-imidazolidin]-5'-one (250 mg, 0.6 mmol) and K$_2$CO$_3$ (327 mg, 2.4 mmol) in CH$_3$CN (6 mL) was added MeI (339 mg, 2.4 mmol). The reaction mixture was heated under reflux for 2 h. The mixture was filtered, and the filtrate was concentrated to give a residue, which was purified by preparative TLC to give 6-bromo-2-(3-chlorophenyl)-1'-methyl-2'-(methylthio)spiro chroman-4,4'-imidazol]-5' (1'H)-one (100 mg, 37%). $^1$H-NMR (CDCl$_3$): 1.92 (m, 1H), 2.41 (m, 1H), 2.56 (s, 3H), 3.07 (s, 3H), 5.80 (m, 1H), 6.80 (m, 2H), 7.26 (m, 4H), 7.39 (m, 1H).

Step 6

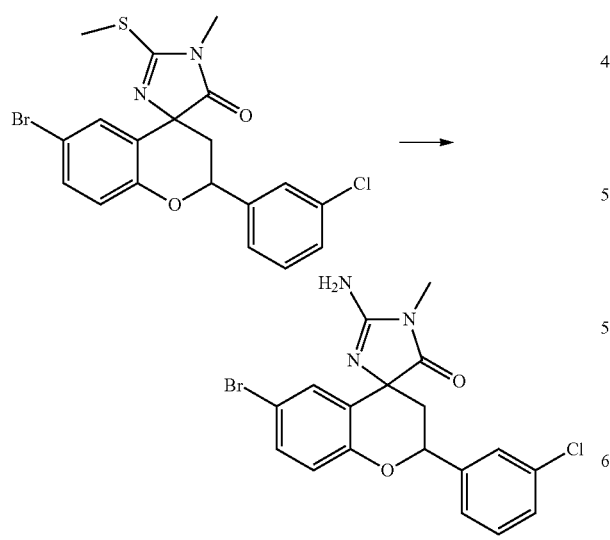

A solution of 6-bromo-2-(3-chlorophenyl)-1'-methyl-2'-(methylthio)spiro[chroman-4,4'-imidazol]-5'(1'H)-one (100 mg, 0.22 mmol) and NH$_4$I (64 mg, 0.44 mmol) in a solution of NH$_3$/EtOH (4 mL, 1.5 N) was heated at 110° C. in a tube under microwave reactor for 2-2.5 h. After cooling, the mixture was concentrated in vacuo to give a residue, which was purified by preparative TLC to afford 2'-amino-6-bromo-2-(3-chlorophenyl)-1'-methylspiro[chroman-4,4'-imidazol]-5'(1'H)-one (42 mg, 46%).

$^1$H-NMR (MeOD): 2.12 (m, 2H), 3.06 (s, 3H), 5.80 (m, 1H), 6.83 (m, 1H), 7.03 (m, 1H), 7.27 (m, 4H), 7.40 (m, 1H).

Step 7

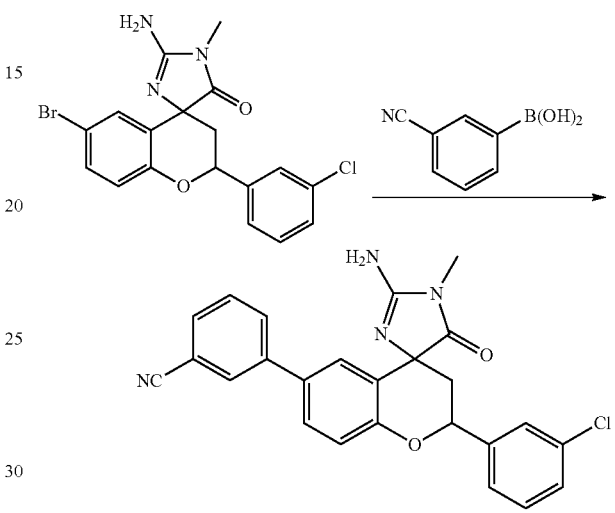

Pd(PPh$_3$)$_4$ (27 mg, 0.072 mmol) in a 10 mL flask under Ar was treated sequentially with 2'-amino-6-bromo-2-(3-chlorophenyl)-1'-methylspiro[chroman-4,4'-imidazol]-5'(1'H)-one (30 mg, 0.072 mmol) in toluene (5 mL), Na$_2$CO$_3$ (2 N, 2 mL), and 4-cyanophenylboronic acid (12.9 mg, 0.088 mmol). The mixture was refluxed under Ar overnight. The reaction mixture was concentrated in vacuo to give a residue, which was purified by preparative TLC followed by preparative HPLC to give pure 3-(2'-amino-2-(3-chlorophenyl)-1'-methyl-5'-oxo-1',5'-dihydrospiro[chroman-4,4'-imidazole]-6-yl)benzonitrile (1.03 mg, 3%). $^1$H-NMR (MeOD): 2.63 (m, 2H), 3.22 (s, 3H), 5.34 (m, 1H), 7.18 (m, 1H), 7.41 (m, 3H), 7.54 (m, 2H), 7.10 (m, 1H), 7.17 (m, 2H), 7.89 (m, 1H), 7.98 (m, 1H).

Example 17

3-(2'-amino-1'-methyl-5'-oxo-2-phenyl-1',5'-dihydrospiro[chroman-4,4'-imidazole]-6-yl)-4-chlorobenzonitrile (Compound 21)

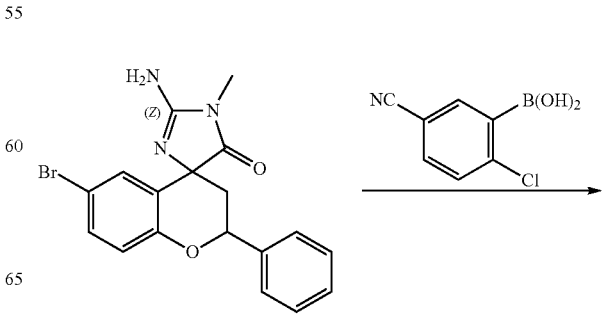

3H), 5.85 (d, 1H), 6.14 (m, 1H), 6.23 (m, 1H), 7.05 (m, 1H), 7.16 (m, 1H), 7.32 (m, 2H), 7.49 (m, 5H).

Example 19

3-(2'-amino-2-(3-methoxyphenyl)-1'-methyl-5'-oxo-1',5'-dihydrospiro[chroman-4,4'-imidazole]-6-yl)benzonitrile (Compound 23)

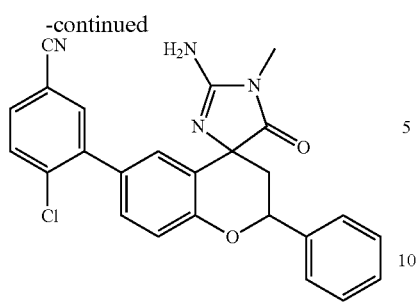

Pd(PPh$_3$)$_2$Cl$_2$ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 2-chloro-5-cyanophenylboronic acid (18.9 mg, 0.104 mmol). The mixture was heated at 120° C. under Ar under microwave for 30 min. The reaction mixture was concentrated in vacuo to give the residue, which was purified preparative HPLC twice to give pure 3-(2'-amino-1'-methyl-5'-oxo-2-phenyl-1',5'-dihydrospiro[chroman-4,4'-imidazole]-6-yl)-4-chlorobenzonitrile (4.2 mg, 18%). $^1$H-NMR (MeOD): 2.38 (m, 1H), 2.52 (m, 1H), 3.15 (s, 3H), 5.18 & 5.76 (m, 1H), 7.03 & 7.18 (m, 1H), 7.26-7.64 (m, 10H).

Example 18

2'-amino-1'-methyl-2-phenyl-6-(3-vinylphenyl)spiro[chroman-4,4'-imidazol]-5'(1'H)-one (Compound 22)

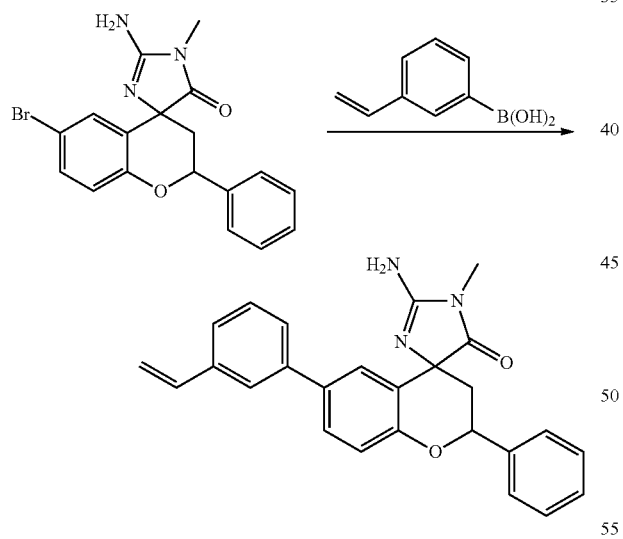

Pd(PPh$_3$)$_2$Cl$_2$ (15 mg) in a 10 mL tube under Ar was treated sequentially with 2'-amino-6-bromo-1'-methyl-2-phenyl-spiro[chroman-4,4'-imidazol]-5'(1'H)-one (50 mg, 0.13 mmol) in 1,4-dioxane (2 mL), Cs$_2$CO$_3$ (2 N, 0.6 mL) and 3-vinylphenylboronic acid (29 mg, 0.19 mmol). The mixture was heated at 120° C. under microwave reactor for 0.5 h. The reaction mixture was concentrated in vacuo to give the residue, which was purified by preparative TLC to give pure 2'-amino-1'-methyl-2-phenyl-6-(3-vinylphenyl)spiro[chroman-4,4'-imidazol]-5'(1'H)-one (3 mg, 6%). $^1$H-NMR (MeOD): 1.40 (s, 9H), 2.44 (m, 1H), 2.61 (m, 1H), 3.25 (s,

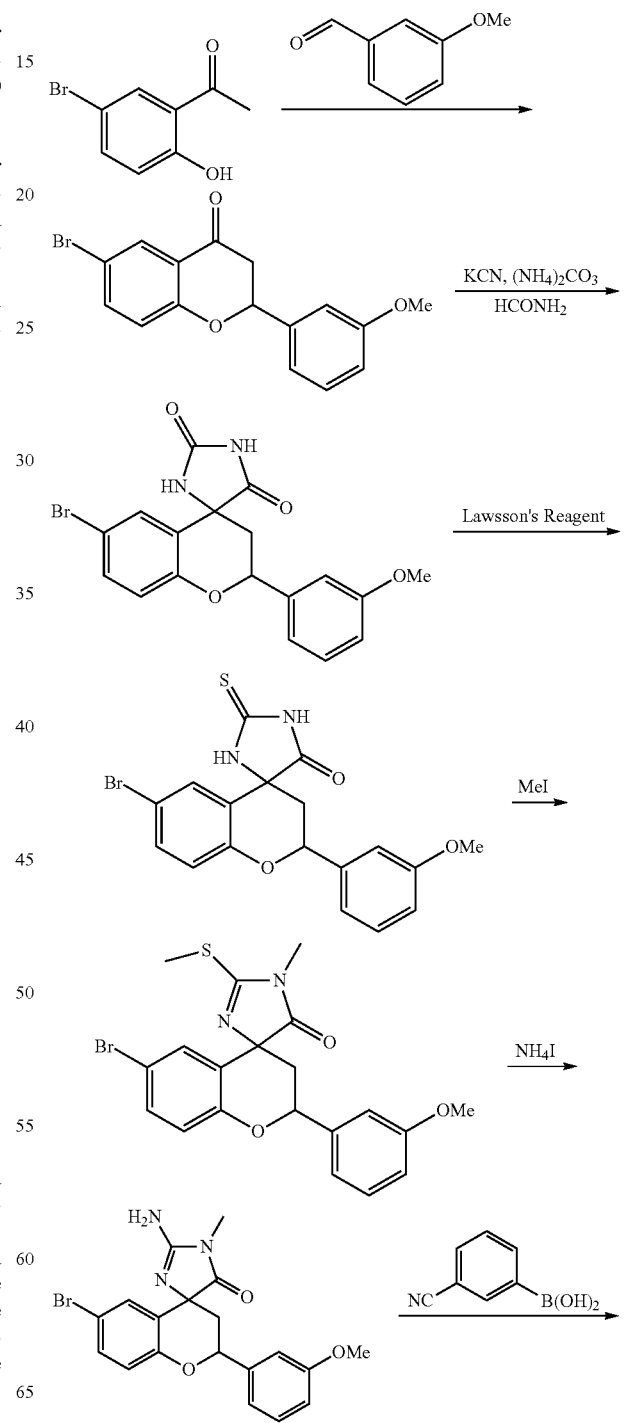

323

-continued

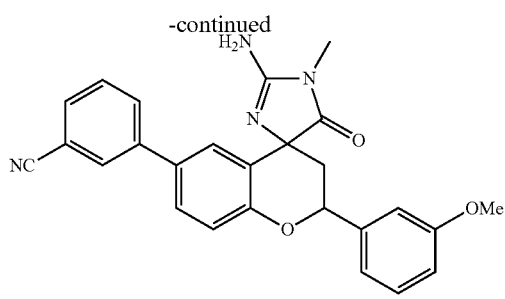

Experimental Data:

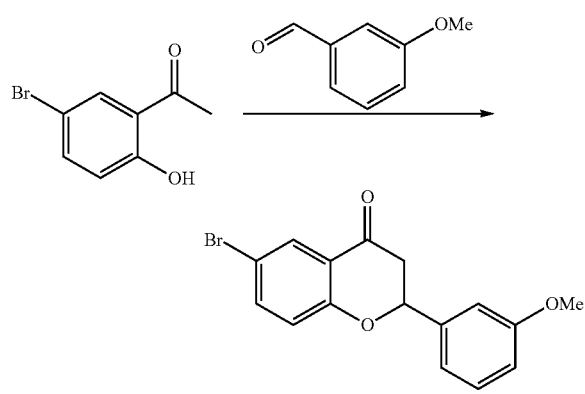

Step 1.
6-bromo-2-(3-methoxyphenyl)chroman-4-one

A mixture of 1-(5-bromo-2-hydroxy-phenyl)-ethanone (18 g, 84.1 mmol), 3-methoxy-benzaldehyde (11.4 g, 84.1 mmol) and borax (32 g, 84.1 mmol) in ethanol (112 mL) and H$_2$O (187 mL) was refluxed for one day. The reaction mixture was cooled, diluted with an equal volume of H$_2$O and extracted with ether. The ether was dried over anhydrous Na$_2$SO$_4$, filtered, and evaporated to give 6-bromo-2-(3-methoxyphenyl)chroman-4-one (10 g, 36%). $^1$H-NMR (CDCl$_3$): 2.71 (d, 1H), 2.99 (t, 1H), 3.75 (s, 3H), 5.38 (d, 1H), 6.90 (m, 4H), 7.27 (t, 1H), 7.51 (d, 1H), 7.95 (s, 1H).

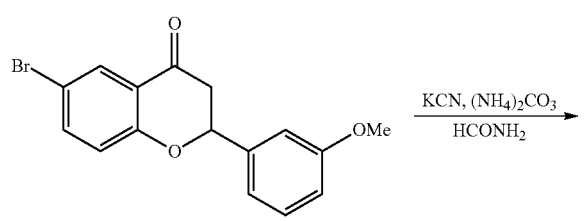

324

Step 2. 6-bromo-2-(3-methoxyphenyl)spiro[chroman-4,4'-imidazolidine]-2',5'-dione A steel bomb was charged with a mixture of 6-bromo-2-(3-methoxyphenyl) chroman-4-one (3.3 g, 9.94 mmol), KCN (1.29 g, 20 mmol), and (NH$_4$)$_2$CO$_3$ (7.15 g, 75 mmol). Formamide (25 mL) was added to fill the steel bomb nearly completely. The mixture was heated at 70° C. for 48 h then at 110° C. for another 4 h. The reaction mixture was then cooled and poured over ice. Acidification with concentrated HCl gave a precipitate which was filtered, washed twice with water, and then dissolved in ethyl acetate, dried over Na$_2$SO$_4$, and filtered. The filtrate was concentrated in vacuo to give the residue, which was purified by column to give 6-bromo-2-(3-methoxyphenyl)spiro[chroman-4,4'-imidazolidine]-2',5'-dione (1.3 g, 32%). $^1$H-NMR (CDCl$_3$): 2.21 (t, 1H), 2.40 (d, 1H), 3.41 (s, 3H), 5.74 (d, 1H), 6.81 (d, 2H), 6.90 (t, 2H), 7.25 (m, 3H), 7.89 (s, 1H).

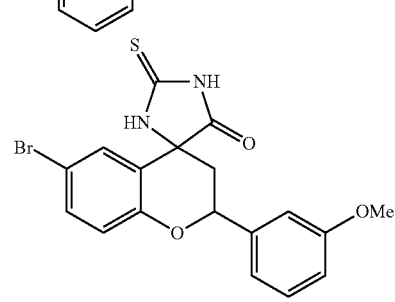

Step 3. 6-bromo-2-(3-methoxyphenyl)-2'-thioxospiro[chroman-4,4'-imidazolidin]-5'-one A suspension of 6-bromo-2-(3-methoxyphenyl)spiro[chroman-4,4'-imidazolidine]-2',5'-dione (250 mg, 0.64 mmol) and Lawsson's Reagent (250 mg, 0.62 mmol) in dry 1,4-dioxane (20 mL) was refluxed for 24 h. The mixture was concentrated in vacuo and the residue was purified by preparative TLC to give 6-bromo-2-(3-methoxyphenyl)-2'-thioxospiro[chroman-4,4'-imidazolidin]-5'-one (100 mg, 45%).

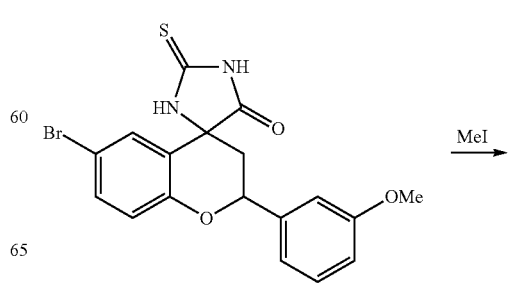

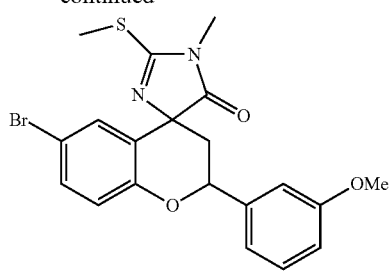

Step 4. 6-bromo-2-(3-methoxyphenyl)-1'-methyl-2'-(methylthio)spiro[chroman-4,4'-imidazol]-5'(1'H)-one To a solution of 6-bromo-2-(3-methoxyphenyl)-2'-thioxospiro[chroman-4,4'-imidazolidin]-5'-one (100 mg, 0.24 mmol) in MeOH (5 mL) was added a solution of NaOH (19.14 mg, 0.48 mmol) in H₂O (1 mL). After stirring for 10 min, MeI (515 mg, 3.6 mmol) was added. The reaction mixture was refluxed for 2 h. The mixture was concentrated in vacuo to give the residue, which was purified by preparative TLC to give 6-bromo-2-(3-methoxyphenyl)-1'-methyl-2'-(methylthio)spiro[chroman-4,4'-imidazol]-5'(1'H)-one (65 mg, 60%).

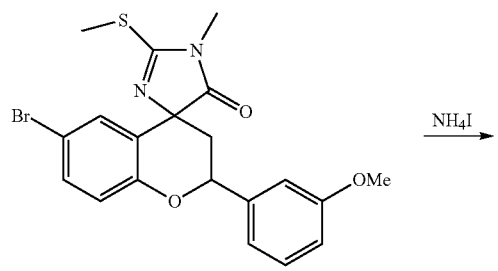

Step 5. 2'-amino-6-bromo-2-(3-methoxyphenyl)-1'-methylspiro[chroman-4,4'-imidazol]-5'(1'H)-one A solution of 6-bromo-2-(3-methoxyphenyl)-1'-methyl-2'-(methylthio)spiro[chroman-4,4'-imidazol]-5'(1'H)-one (65 mg, 0.146 mmol), NH₄I (42.26 mg, 0.3 mmol) in a solution of NH₃/EtOH (2 mL, 8 N) was heated at 120° C. in a tube under microwave reactor for 2 h. After cooling, the mixture was concentrated in vacuum to give 2'-amino-6-bromo-2-(3-methoxyphenyl)-1'-methylspiro[chroman-4,4'-imidazol]-5'(1'H)-one (46 mg, 80%).

Step 6. 3-(2'-amino-2-(3-methoxyphenyl)-1'-methyl-5'-oxo-1',5'-dihydrospiro[chroman-4,4'-imidazole]-6-yl)benzonitrile Pd(PPh₃)₂Cl₂ (20 mg) in a 10 mL flask under Ar was treated sequentially with 2'-amino-6-bromo-2-(3-methoxyphenyl)-1'-methylspiro[chroman-4,4'-imidazol]-5'(1'H)-one (46 mg, 0.11 mmol) in 1,4-dioxane (5 mL), Cs₂CO₃ (2 N, 0.5 mL) and 4-cyanophenylboronic acid (32.6 mg, 0.22 mmol). The mixture was refluxed under Ar for 2 h. The reaction mixture was concentrated in vacuo to give the residue, which was purified by preparative TLC followed by preparative HPLC to give pure 3-(2'-amino-2-(3-methoxyphenyl)-1'-methyl-5'-oxo-1',5'-dihydrospiro[chroman-4,4'-imidazole]-6-yl)benzonitrile (10 mg, 20%). ¹H-NMR (CDCl₃): 2.26 (m, 1H), 2.48 (m, 1H), 3.72 (s, 3H), 5.62 (m, 1H), 6.79 (m, 3H), 6.94 (d, 1H), 7.12 (d, 1H), 7.20 (s, 1H), 7.29 (m, 1H), 7.36 (m, 1H), 7.41 (t, 1H), 7.61 (d, 2H).

Example 20

2'-amino-1'-methyl-2-phenyl-6-(3-(trifluoromethoxy)phenyl)spiro[chroman-4,4'-imidazol]-5'(1'H)-one (Compound 24)

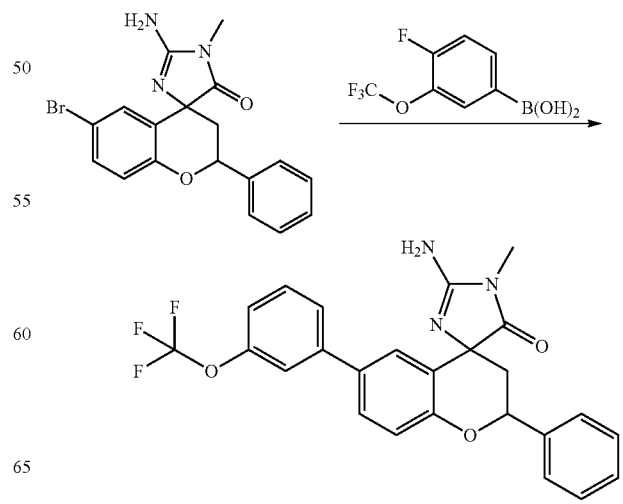

Pd(PPh$_3$)$_2$Cl$_2$ (10 mg) in a 10 mL tube under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 4-fluoro-3-(trifluoromethoxy)phenylboronic acid (20 mg, 0.106 mmol). The mixture was heated at 120° C. under microwave reactor for 0.5 h. The reaction mixture was concentrated in vacuo to give the residue, which was purified by preparative TLC to give pure 2'-amino-1'-methyl-2-phenyl-6-(3-(trifluoromethoxy)phenyl)spiro[chroman-4,4'-imidazol]-5'(1'H)-one (3.32 mg, 14%). $^1$H-NMR (MeOD): 2.23 (m, 2H), 3.10 (s, 3H), 5.80 (d, 1H), 6.98 (m, 1H), 7.13 (m, 1H), 7.26 (m, 2H), 7.34 (m, 3H), 7.38 (m, 3H), 7.46 (m, 2H).

Example 21

3-((2S,4R)-2'-amino-1'-benzyl-5'-oxo-2-phenyl-1',5'-dihydrospiro[chroman-4,4'-imidazole]-6-yl)benzonitrile (Compound 25a) and 3-((2R,4R)-2'-amino-1'-benzyl-5'-oxo-2-phenyl-1',5'-dihydrospiro[chroman-4,4'-imidazole]-6-yl)benzonitrile (Compound 25b)

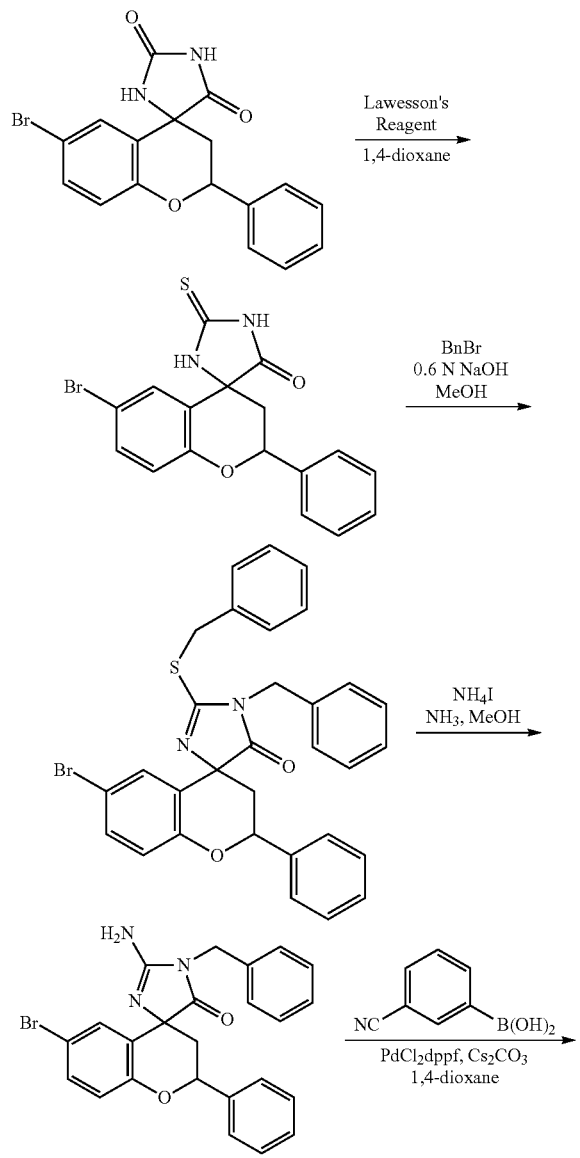

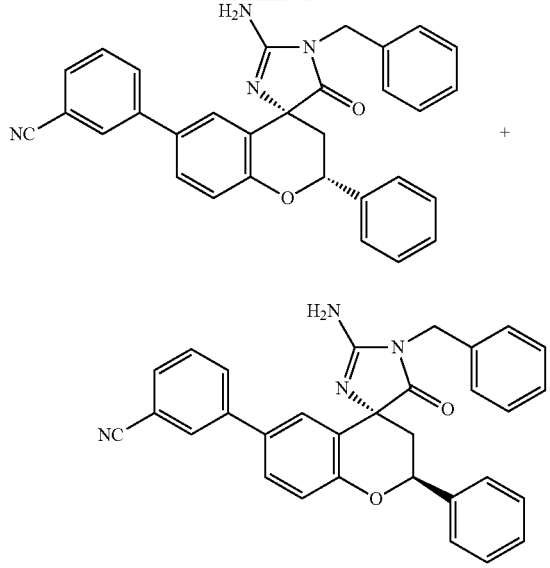

Step 1

To a solution of 6-bromo-2-phenylspiro[chroman-4,4'-imidazolidine]-2',5'-dione (440 mg, 1.18 mmol) in 1,4-dioxane (3.6 mL) in a 10 mL CEM microwave test tube was added Lawesson's reagent (477 mg, 1.18 mmol). The resulting mixture was heated in a CEM microwave reactor at 110° C. for 40 min and then cooled to room temperature. The solvent was removed in vacuo, and the residue was purified by flash chromatography to give 6-bromo-2-phenyl-2'-thioxospiro[chroman-4,4'-imidazolidin]-5'-one (238 mg, 52%). MS m/z 389 (M+H$^+$).

Step 2

To a solution of 6-bromo-2-phenyl-2'-thioxospiro[chroman-4,4'-imidazolidin]-5'-one (110 mg, 0.28 mmol) in MeOH (5 mL) in a 10 mL CEM microwave test tube was added a 0.6 N NaOH aqueous solution (1.0 mL). After stirring at room temperature for 10 min, MeI (158 mg, 1.08 mmol) was added, and the reaction was stirred at room temperature for 2 hrs. Upon removing the solvent in vacuo, the residue was purified by flash chromatography to give 1'-benzyl-2'-(benzylthio)-6-bromo-2-phenylspiro[chroman-4,4'-imidazol]-5'(1'H)-one (63.3 mg, 39%). MS m/z 569 (M+H$^+$).

Step 3

To a solution of 1'-benzyl-2'-(benzylthio)-6-bromo-2-phenylspiro[chroman-4,4'-imidazol]-5'(1'H)-one (60 mg, 0.10 mmol) in MeOH/EtOH (1:1, 2 mL) in a 10 mL CEM microwave test tube was added NH$_4$I (50 mg, 0.34 mmol) and NH$_3$/MeOH (7 N, 2 mL). The resulting mixture was heated in a CEM microwave reactor at 120° C. for 60 min. The cooled mixture was concentrated in vacuo and the residue was purified by reversed phase HPLC to give 2'-amino-1'-benzyl-6-bromo-2-phenylspiro[chroman-4,4'-imidazol]-5'(1'H)-one (17.3 mg, 34%) as a TFA salt. MS m/z 462 (M+H$^+$).

Step 4

To a solution of 2'-amino-1'-benzyl-6-bromo-2-phenylspiro[chroman-4,4'-imidazol]-5'(1'H)-one (17.3 mg, 0.04 mmol) in 1,4-dioxane (1.5 mL) was added $Cs_2CO_3$ (excess), 3-cyanophenylboronic acid (excess), and catalytical amount of $PdCl_2$dppf. After degassing, the resulting mixture was heated in a CEM microwave reactor at 130° C. for 30 min Solvent was removed in vacuo and the residue was purified by reverse phase HPLC to give 3-((2R,4R)-2'-amino-1'-benzyl-5'-oxo-2-phenyl-1',5'-dihydrospiro[chroman-4,4'-imidazole]-6-yl)benzonitrile (6.0 mg, 33%) as a TFA salt (25b) and 3-((2S,4R)-2'-amino-1'-benzyl-5'-oxo-2-phenyl-1',5'-dihydrospiro[chroman-4,4'-imidazole]-6-yl)benzonitrile (0.86 mg, 4.8%) as a TFA salt. (25a). $^1$H NMR (400 MHz, $CD_3OD$): 7.84-7.60 (m, 4H), 7.74-7.24 (m, 12H), 7.12 (d, 1H), 5.92 (d, 1H), 4.62 (s, 2H), 2.60 (d, 1H), 2.42 (d, 1H); MS m/z 485 (M+H$^+$) (25b). $^1$H NMR (400 MHz, $CD_3OD$): 7.74-7.36 (m, 16H), 7.16 (d, 1H), 5.24 (d, 1H), 5.08, 5.00 (two d, 2H), 2.64 (d, 1H), 2.56 (d, 1H); MS m/z 485 (M+H$^+$) (25a).

Example 22

2'-amino-6-(4-(hydroxymethyl)phenyl)-1'-methyl-2-phenylspiro[chroman-4,4'-imidazol]-5'(1'H)-one (Compound 26)

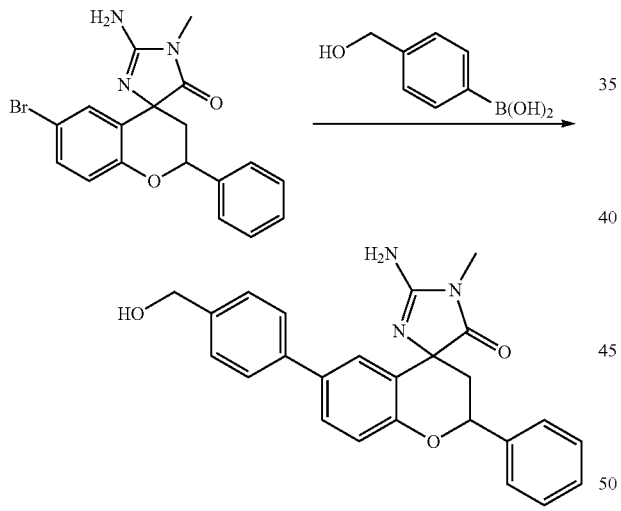

$Pd(PPh_3)_2Cl_2$ (5 mg, 0.007 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), $Cs_2CO_3$ (2 N, 0.3 mL) and 4-(hydroxymethyl)phenylboronic acid (17 mg, 0.104 mmol). The mixture was heated at 120° C. under Ar in a microwave reactor for 30 minutes. The reaction mixture was concentrated in vacuo to give the residue, which was purified by preparative TLC and HPLC to give 2'-amino-6-(4-(hydroxymethyl)phenyl)-F-methyl-2-phenylspiro[chroman-4,4'-imidazol]-5'(1'H)-one (1.16 mg, 5%). $^1$H-NMR (MeOD): 2.42 (m, 1H), 2.57 (m, 1H), 3.31 (m, 3H), 4.15 (s, 2H), 5.83 (m, 1H), 7.09 (m, 1H), 7.28 (m, 1H), 7.38 (m, 4H), 7.47 (m, 3H), 7.56 (m, 1H), 7.61 (m, 1H).

Example 23

2'-amino-1'-methyl-2,6-diphenylspiro-[chroman-4,4'-imidazol]-5'(1'H)-one (Compound 27)

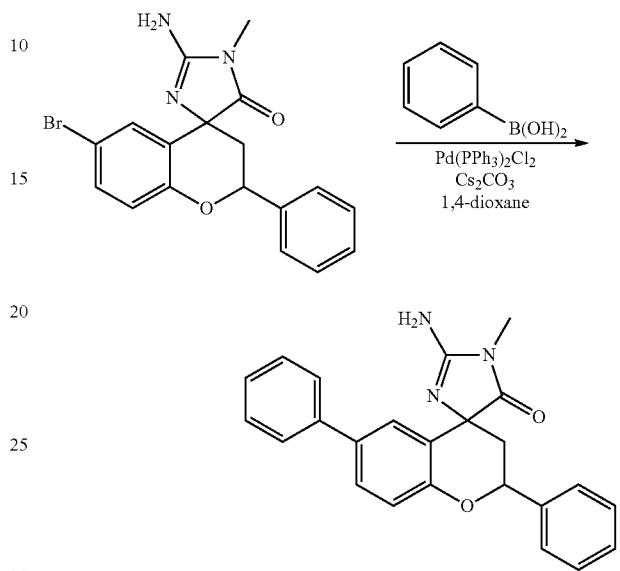

$Pd(PPh_3)_2Cl_2$ (10 mg) in a 10 mL tube under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), $Cs_2CO_3$ (2 N, 0.3 mL) and phenylboronic acid (16 mg, 0.1 mmol). The mixture was heated under microwave at 120° C. for 30 minutes. The reaction mixture was concentrated in vacuo to give the residue, which was purified by preparative TLC and then by preparative HPLC to give pure 2'-amino-1'-methyl-2,6-diphenylspiro-[chroman-4,4'-imidazol]-5'(1'H)-one (1.55 mg, 5%). $^1$H-NMR (MeOD): 2.42 (m, 1H), 2.61 (m, 1H), 3.27 (s, 3H), 5.83 (d, 1H), 7.10 (d, 1H), 7.29 (m, 1H), 7.40 (m, 5H), 7.59 (m, 5H).

Example 24

2'-amino-1'-methyl-6-(3-(methylsulfonyl)phenyl)-2-phenylspiro[chroman-4,4'-imidazol]-5'(1'H)-one (Compound 28)

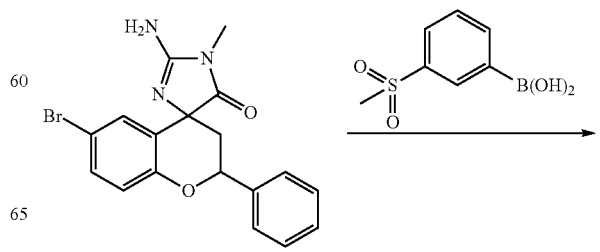

-continued

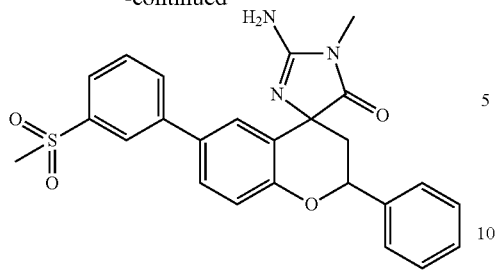

Pd(PPh$_3$)$_2$Cl$_2$ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(methylsulfonyl)phenylboronic acid (20.8 mg, 0.104 mmol). The mixture was heated at 120° C. under Ar in a microwave reactor for 30 minutes. The reaction mixture was concentrated in vacuo to give the residue, which was purified by preparative TLC to give 2'-amino-1'-methyl-6-(3-(methylsulfonyl)phenyl)-2-phenylspiro[chroman-4,4'-imidazol]-5'(1'H)-one (16.89 mg, 70%). $^1$H-NMR (MeOD): 2.01 (m, 1H), 2.31 (m, 1H), 3.14 (m, 3H), 3.21 (m, 3H), 5.22 (m, 0.2H), 5.83 (m, 0.7H), 6.89 (m, 1H), 7.18 (m, 1H), 7.23 (m, 1H), 7.32 (m, 2H), 7.39 (m, 2H), 7.45 (m, 1H), 7.57 (m, 1H), 7.76 (m, 2H), 7.96 (m, 1H).

Example 25

2-(3-(2'-amino-1'-methyl-5'-oxo-2-phenyl-1',5'-dihydrospiro[chroman-4,4'-imidazole]-6-yl)phenyl)acetonitrile (Compound 29)

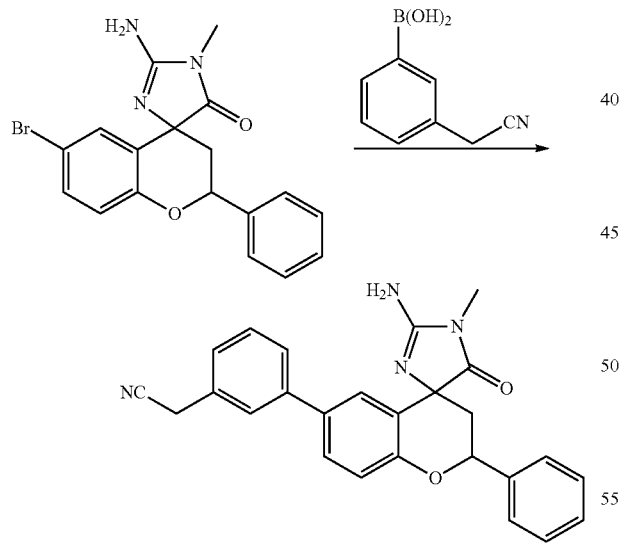

Pd(PPh$_3$)$_2$Cl$_2$ (10 mg, 0.014 mmol) in a 10 mL tube under Ar was treated sequentially with 2'-amino-6-bromo-1'-(cyclohexylmethyl)-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(cyanomethyl)phenylboronic acid (16.7 mg, 0.104 mmol). The mixture was heated at 120° C. in a microwave reactor for 0.5 h. The reaction mixture was concentrated in vacuo to give the residue, which was purified by preparative TLC followed by preparative HPLC to give pure 2-(3-(2'-amino-1'-methyl-5'-oxo-2-phenyl-1',5'-dihydrospiro[chroman-4,4'-imidazole]-6-yl)phenyl)acetonitrile (5.25 mg, 24%). $^1$H-NMR (MeOD): 2.04 (m, 1H), 2.21 (m, 1H), 3.08 (d, 3H), 3.85 (s, 2H), 5.21 (d, 0.2H), 5.81 (d, 0.8H), 6.94 (d, 1H), 7.11 (m, 1H), 7.24 (m, 2H), 7.35 (m, 3H), 7.39 (m, 5H).

Example 26

2'-amino-1'-methyl-2-phenyl-6-(3-(trifluoromethyl) phenyl)spiro[chroman-4,4'-imidazol]-5'(1'H)-one (Compound 30)

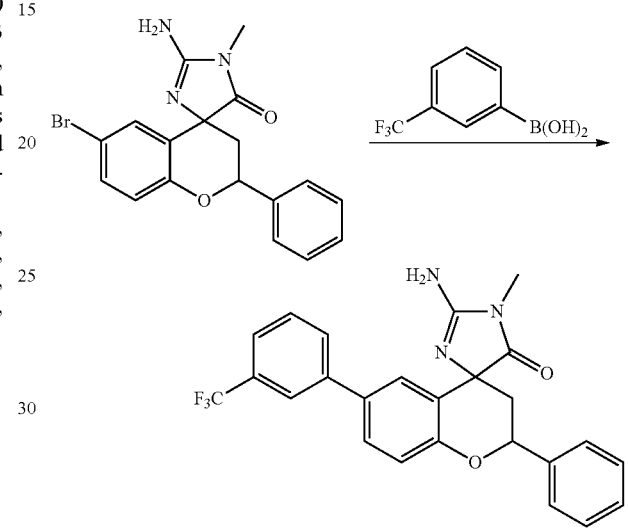

Pd(PPh$_3$)$_2$Cl$_2$ (10 mg) in a 10 mL CEM test tube under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(trifluoromethyl)phenylboronic acid (19.7 mg, 0.1 mmol). The mixture was heated under microwave at 120° C. for 30 minutes. The reaction mixture was concentrated in vacuo to give the residue, which was purified by preparative TLC and preparative HPLC to give pure 2'-amino-1'-methyl-2-phenyl-6-(3-(trifluoromethyl)phenyl)spiro[chroman-4,4'-imidazol]-5'(1'H)-one (4.31 mg, 18%). $^1$H-NMR (CDCl$_3$): 1.95 (d, 1H), 2.66 (t, 1H), 3.16 (d, 3H), 5.97 (d, 1H), 6.96 (s, 1H), 7.06 (m, 2H), 7.20 (s, 1H), 7.38 (m, 3H), 7.44 (m, 3H), 7.53 (m, 1H), 7.62 (m, 1H), 7.70 (s, 1H).

Example 27

3-(2'-amino-1',2-dimethyl-5'-oxo-2-phenyl-1',5'-dihydrospiro[chroman-4,4'-imidazole]-6-yl)benzonitrile (Compound 32)

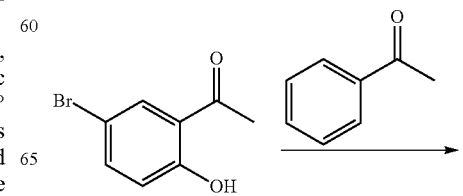

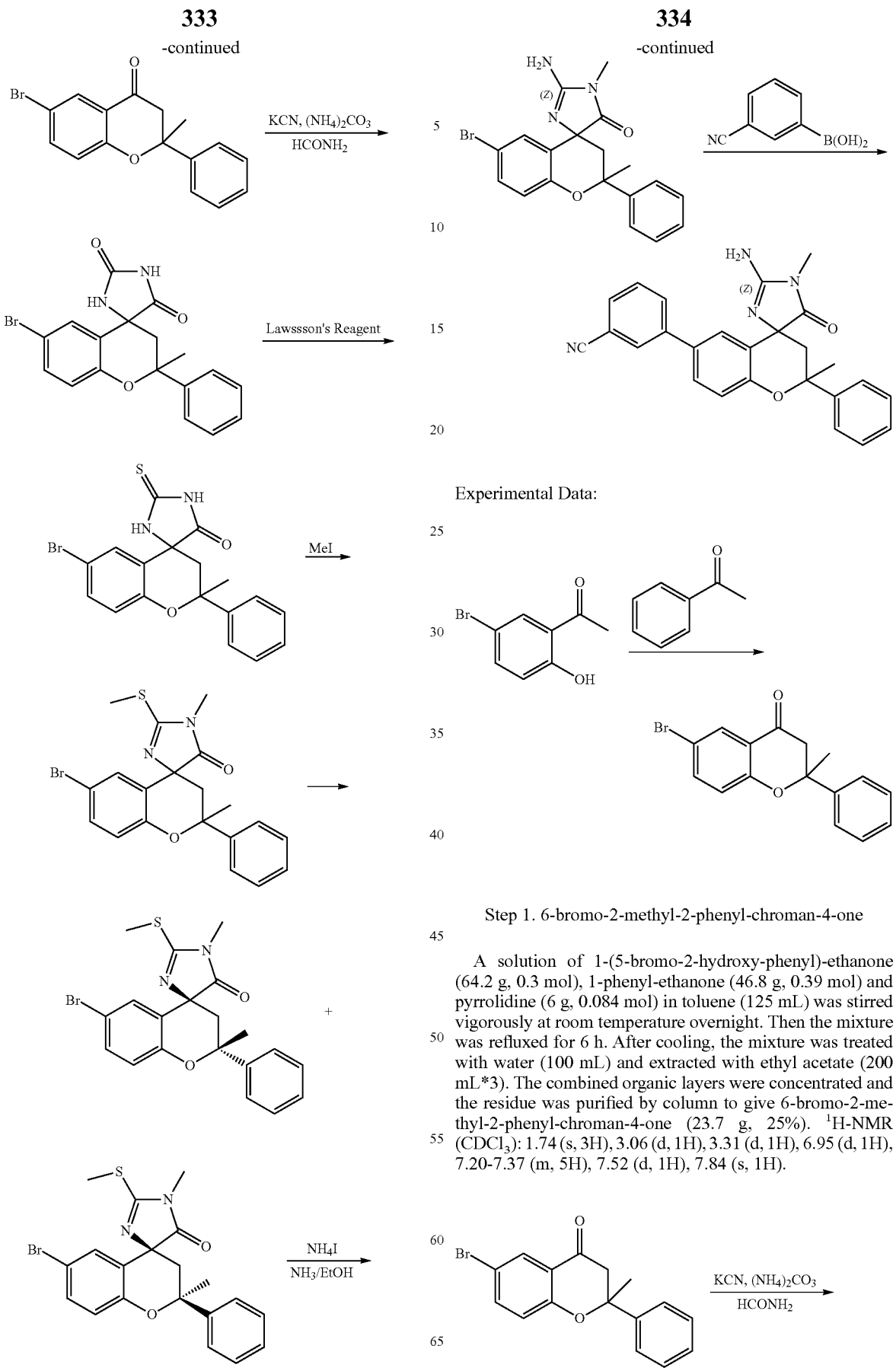

Experimental Data:

Step 1. 6-bromo-2-methyl-2-phenyl-chroman-4-one

A solution of 1-(5-bromo-2-hydroxy-phenyl)-ethanone (64.2 g, 0.3 mol), 1-phenyl-ethanone (46.8 g, 0.39 mol) and pyrrolidine (6 g, 0.084 mol) in toluene (125 mL) was stirred vigorously at room temperature overnight. Then the mixture was refluxed for 6 h. After cooling, the mixture was treated with water (100 mL) and extracted with ethyl acetate (200 mL*3). The combined organic layers were concentrated and the residue was purified by column to give 6-bromo-2-methyl-2-phenyl-chroman-4-one (23.7 g, 25%). $^1$H-NMR (CDCl$_3$): 1.74 (s, 3H), 3.06 (d, 1H), 3.31 (d, 1H), 6.95 (d, 1H), 7.20-7.37 (m, 5H), 7.52 (d, 1H), 7.84 (s, 1H).

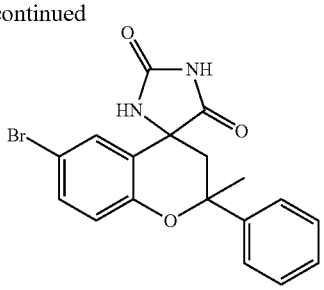

Step 2. 6-bromo-2-methyl-2-phenylspiro[chroman-4, 4'-imidazolidine]-2',5'-dione A steel pressure tube was charged with a mixture of 6-bromo-2-methyl-2-phenyl-chroman-4-one (6.2 g, 19.6 mmol), KCN (2.55 g, 39.2 mmol), and (NH$_4$)$_2$CO$_3$ (14.1 g, 147 mmol). Formamide (70 mL) was added to fill the pressure tube nearly completely. The mixture was heated at 70° C. for 48 h then at 110° C. for another 24 h. The reaction mixture was then cooled and poured over ice. After acidification with concentrated HCl, the mixture was extracted with ethyl acetate (150 mL*3). The combined organic layers were dried over Na$_2$SO$_4$ and filtered. The filtrate was concentrated in vacuo to give the residue, which was purified by column to give 6-bromo-2-methyl-2-phenylspiro[chroman-4,4'-imidazolidine]-2',5'-dione (3 g, 40%). $^1$H-NMR (CDCl$_3$): 1.76 (s, 3H), 2.77 (m, 1H), 2.85 (m, 1H), 4.48 (s, 1H), 7.05 (m, 2H), 7.21-7.54 (m, 6H), 8.55 (s, 1H).

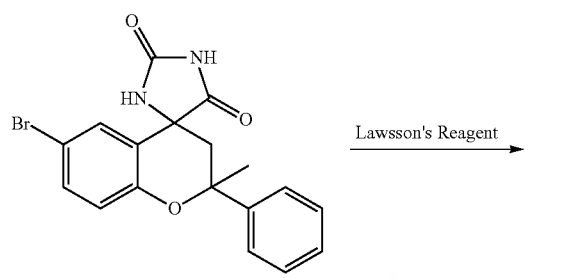

Lawsson's Reagent →

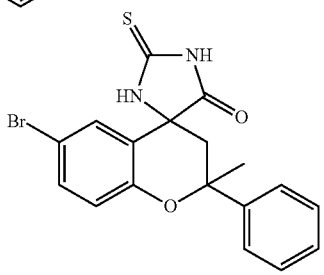

Step 3. 6-bromo-2-methyl-2-phenyl-2'-thioxospiro[chroman-4,4'-imidazolidin]-5'-one A suspension of 6-bromo-2-methyl-2-phenylspiro[chroman-4,4'-imidazolidine]-2',5'-dione (1.16 g, 3 mmol) and Lawesson's Reagent (1.21 g, 3 mmol) in dry 1,4-dioxane (24 mL) was refluxed for 24 h. The mixture was concentrated in vacuo and the residue was purified by column to give 6-bromo-2-methyl-2-phenyl-2'-thioxospiro[chroman-4,4'-imidazolidin]-5'-one (748 mg, 61%). $^1$H-NMR (CDCl$_3$): 1.75 (s, 3H), 3.78 (m, 2H), 5.79 (s, 1H), 6.94 (m, 1H), 7.14 (m, 1H), 7.22 (m, 1H), 7.26-7.53 (m, 5H), 8.39 (s, 1H).

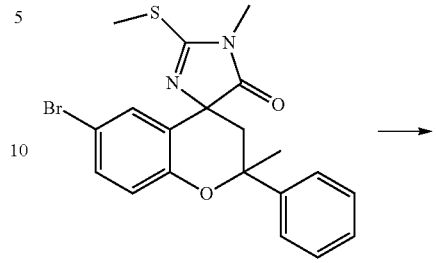

Step 4. (2R,4S)-6-bromo-1',2-dimethyl-2'-(methylthio)-2-phenylspiro[chroman-4,4'-imidazol]-5'(1'H)-one & (2S,4S)-6-Bromo-1',2-dimethyl-2'-(methylthio)-2-phenylspiro[chroman-4,4'-imidazol]-5'(1'H)-one To a solution of 6-bromo-2-phenyl-2'-thioxospiro[chroman-4,4'-imidazolidin]-5'-one (748 mg, 1.86 mmol) in MeOH (22 mL) was added a solution of NaOH (149 mg, 3.72 mmol) in H$_2$O (4.5 mL). After stirring for 10 minutes, MeI (2.11 g, 149 mmol) was added. The reaction mixture was refluxed for 2 h. The mixture was concentrated in vacuo to give the residue, which was purified by preparative TLC to give (2R,4S)-6-bromo-1',2-dimethyl-2'-(methylthio)-2-phenylspiro[chroman-4,4'-imidazol]-5'(1'H)-one (29 mg, total yield 36%) and (2S,4S)-6-bromo-1',2-dimethyl-2'-(methylthio)-2-phenylspiro[chroman-4,4'-imidazol]-5'(1'H)-one (263 mg, total yield 36%).

(2R,4S)-6-Bromo-1',2-dimethyl-2'-(methylthio)-2-phenylspiro[chroman-4,4'-imidazol]-5'(1'H)-one: $^1$H-NMR: 1.75 (s, 3H), 1.99 (m, 1H), 2.47 (d, 1H), 2.53 (s, 3H), 3.07 (s, 3H), 6.70 (d, 1H), 6.84 (d, 1H), 7.18-7.33 (m, 4H), 7.49 (d, 2H).

(2S,4S)-6-Bromo-1',2-dimethyl-2'-(methylthio)-2-phenylspiro[chroman-4,4'-imidazol]-5'(1'H)-one: $^1$H-NMR: 1.61 (s, 3H), 2.10 (s, 3H), 2.82-2.95 (m, 2H), 3.28 (s, 3H), 6.82-6.98 (m, 2H), 7.12-7.46 (m, 5H), 7.72 (m, 1H).

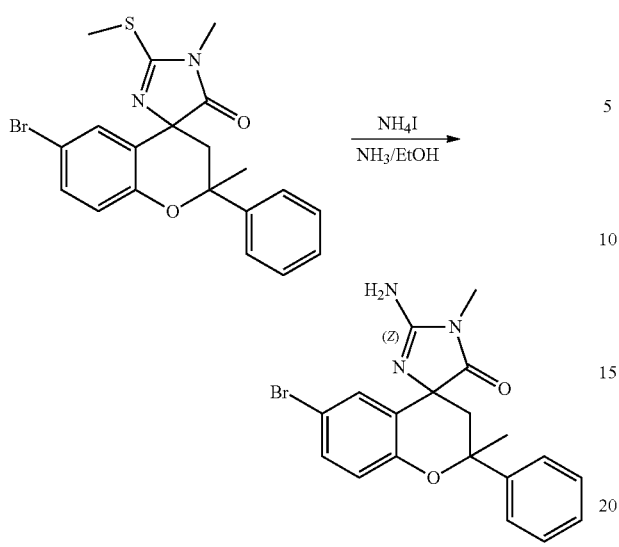

Step 5. 2'-amino-6-bromo-1',2-dimethyl-2-phenyl-spiro[chroman-4,4'-imidazol]-5'(1'H)-one A solution of 6-bromo-1',2-dimethyl-2'-(methylthio)-2-phenylspiro[chroman-4,4'-imidazol]-5'(1'H)-one (292 mg, 0.667 mmol), NH$_4$I (245.7 mg, 1.668 mmol) in a solution of NH$_3$/EtOH (30 mL, 5 N) was heated at 110° C. in a CEM tube in a microwave reactor for 4 h. After cooling, the mixture was concentrated in vacuum to give the residue, which was purified by preparative TLC to afford 2'-amino-6-bromo-1',2-dimethyl-2-phenylspiro[chroman-4,4'-imidazol]-5'(1'H)-one (45 mg, 18%). $^1$H-NMR (MeOD): 1.63 (s, 3H), 1.77 (s, 3H), 2.74 (d, 2H), 6.75 (d, 1H), 7.06 (d, 1H), 7.22 (m, 1H), 7.31 (m, 3H), 7.45 (m, 2H).

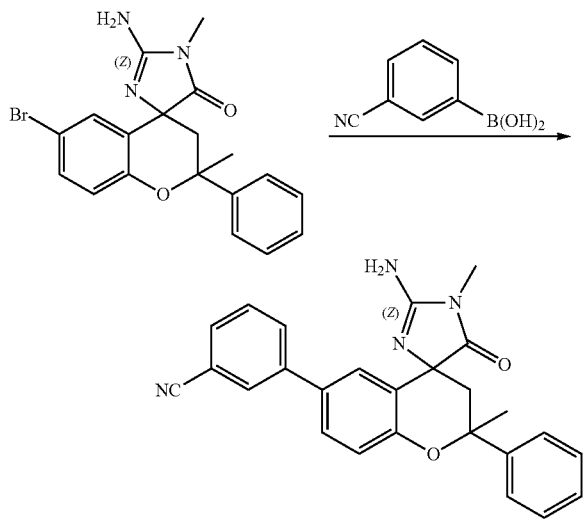

Step 6. 3-(2'-amino-1',2-dimethyl-5'-oxo-2-phenyl-1',5'-dihydrospiro[chroman-4,4'-imidazole]-6-yl)benzonitrile Pd(PPh$_3$)$_2$Cl$_2$ (14 mg, 0.01 mmol) in a 10 mL flask under Ar was treated sequentially with 2'-amino-6-bromo-1',2-dimethyl-2-phenylspiro[chroman-4,4'-imidazol]-5'(1'H)-one (45 mg, 0.113 mmol) in 1,4-dioxane (2 mL), Cs$_2$CO$_3$ (2 N, 0.45 mL) and 4-cyanophenylboronic acid (33 mg, 0.226 mmol). The mixture was refluxed under Ar in a microwave reactor for 2 h. The reaction mixture was concentrated in vacuo to give the residue, which was purified preparative HPLC twice to give pure 3-(2'-amino-1',2-dimethyl-5'-oxo-2-phenyl-1',5'-dihydrospiro[chroman-4,4'-imidazole]-6-yl)benzonitrile (17 mg, 36%). $^1$H-NMR (CDCl$_3$): 1.78 (s, 3H), 1.97 (s, 3H), 2.60 (d, 1H), 2.85 (d, 1H), 6.84 & 6.93 (s, 1H), 7.23 (m, 2H), 7.31 (m, 4H), 7.48 (m, 2H), 7.52 (m, 2H), 7.62 (m, 1H), 7.67 (m, 1H), 11.51 (brs, 1H).

Example 28

2'-amino-6-(3-(hydroxymethyl)phenyl)-1'-methyl-2-phenylspiro[chroman-4,4'-imidazol]-5'(1'H)-one
(Compound 33)

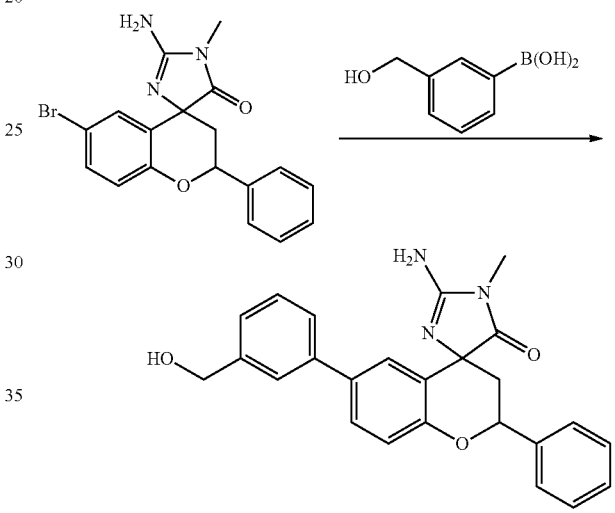

Pd(PPh$_3$)$_2$Cl$_2$ (10 mg) in a 10 mL tube under Ar was treated sequentially with 2'-amino-6-bromo-1'-methyl-2-phenylspiro[chroman-4,4'-imidazol]-5'(1'H)-one (20 mg, 0.05 mmol) in 1,4-dioxane (1 mL), Cs$_2$CO$_3$ (2 N, 0.3 mL) and 3-(hydroxymethyl)phenylboronic acid (15 mg, 0.1 mmol). The mixture was heated in a microwave reactor at 120° C. for 30 min. The reaction mixture was concentrated in vacuo to give the residue, which was purified by preparative TLC to give pure 2'-amino-6-(3-(hydroxymethyl)phenyl)-1'-methyl-2-phenylspi-ro[chroman-4,4'-imidazol]-5'(1'H)-one (1.3 mg, 5%). $^1$H-NMR (MeOD): 2.05 (t, 1H), 2.21 (t, 1H), 3.07 (s, 3H), 4.50 (s, 1H), 5.81 (d, 1H), 6.94 (d, 1H), 7.11 (s, 1H), 7.19 (d, 1H), 7.30 (m, 4H), 7.41 (m, 4H).

Example 29

2'-amino-6-bromo-2-(3-chlorophenyl)-1'-methylspiro[chroman-4,4'-imidazol]-5'(1'H)-one (Compound 34)

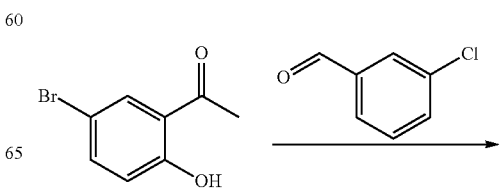

340

Step 1

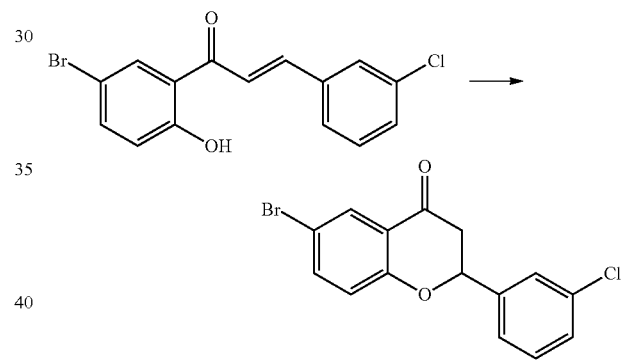

In a bottle, 1-(5-bromo-2-hydroxyphenyl)ethanone (25 g, 0.02 mol), 3-chlorobenzaldehyde (16.35 g, 0.12 mol), EtOH (96%, 144 mL) and NaOH (42.1 g, 1.06 mol) were combined. The mixture was stirred vigorously for 0.5 h. 2-Methoxy-2-methylpropane (300 mL) was added and the mixture was filtered. The filtrate was poured into HCl (1 N, 800 mL) and filtered to give 1-(5-bromo-2-hydroxyphenyl)-3-(3-chlorophenyl)prop-2-en-1-one (23.47 g, 60%). $^1$H-NMR (CDCl$_3$): 6.88 (d, 1H), 4.35 (m, 2H), 7.49 (m, 3H), 7.61 (s, 1H), 7.80 (m, 1H), 7.93 (m, 1H), 12.56 (s, 1H).

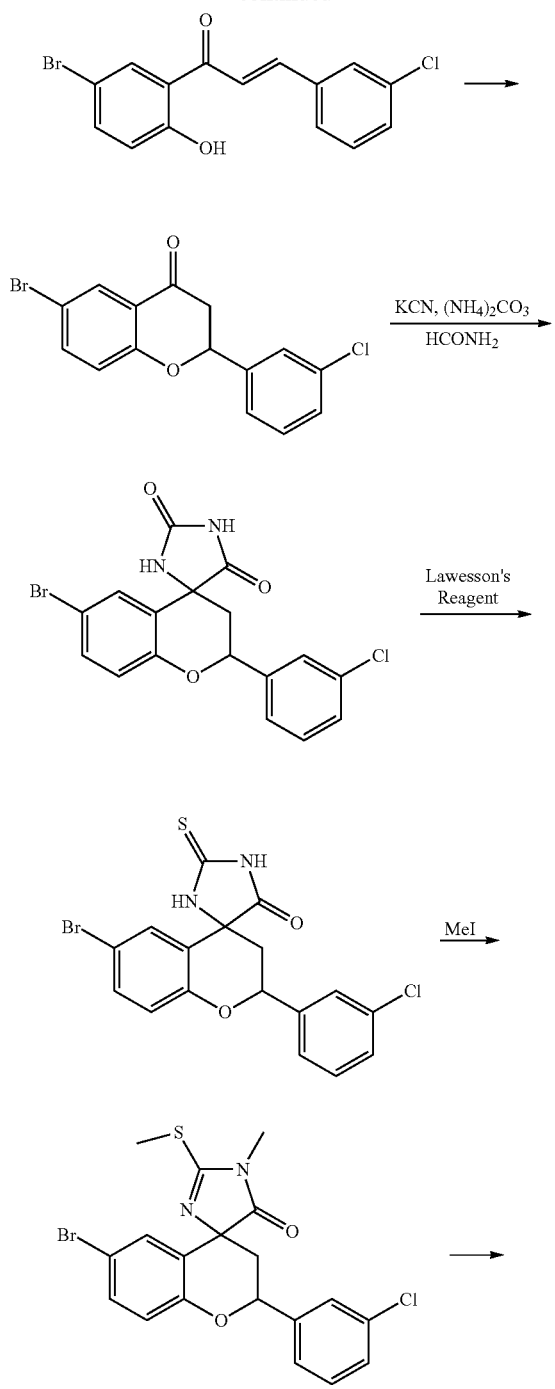

1-(5-Bromo-2-hydroxyphenyl)-3-(3-chlorophenyl)prop-2-en-1-one (23 g, 68 mmol) was dissolved in H$_2$O (513 mL) and EtOH (171 mL). Then NaOH (2.74 g, 68 mmol) was added. The mixture was stirred overnight and filtered to give a solid cake. The cake was dissolved in EtOAc and washed with H$_2$O twice. The organic layer was dried and filtered. The filtrate was concentrated to give 6-bromo-2-(3-chlorophenyl)chroman-4-one (18.82 g, 82%). $^1$H-NMR (CDCl$_3$): 2.87 (m, 1H), 3.02 (m, 1H), 5.44 (m, 1H), 6.96 (d, 1H), 7.31 (m, 1H), 7.37 (m, 2H), 7.48 (s, 1H), 7.58 (m, 1H), 8.02 (d, 1H).

Step 2

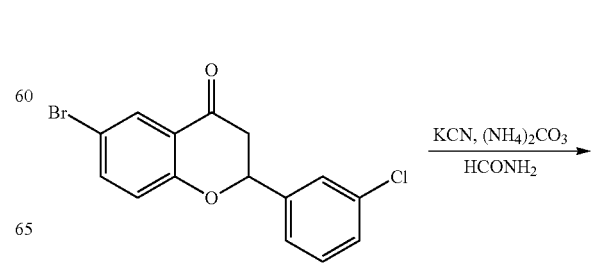

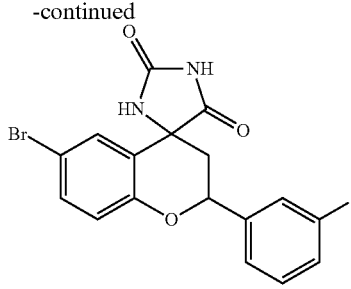

In a steel bomb, a mixture of 6-bromo-2-(3-chlorophenyl) chroman-4-one (7 g, 21 mmol), KCN (2.71 g, 42 mmol) and (NH$_4$)$_2$CO$_3$ (15 g, 156 mmol) in formamide (60 mL) was heated and stirred at 70° C. for 24 h and then at 110° C. for 2 days. The mixture was poured into ice/water. Concentrated HCl was added till pH=1. The mixture was filtered to yield a solid cake. The filtrate was extracted with CH$_2$Cl$_2$. The organic layer was concentrated to give a residue, which was combined with the cake above. The solid was purified by column chromatography to give 6-bromo-2-(3-chlorophenyl) spiro[chroman-4,4'-imidazolidine]-2',5'-dione (470 mg, 5%).
$^1$H-NMR (CDCl$_3$): 2.20 (m, 1H), 2.28 (m, 1H), 5.76 (m, 1H), 6.82 (m, 1H), 7.27 (m, 5H), 7.39 (m, 1H).

Step 3

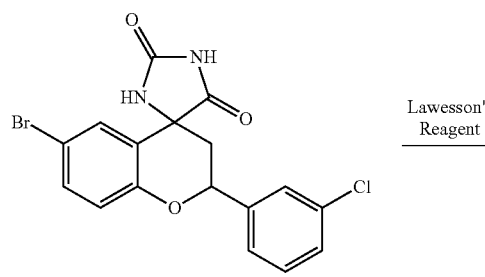

A mixture of 6-bromo-2-(3-chlorophenyl)spiro[chroman-4,4'-imidazolidine]-2',5'-dione (470 mg, 1.16 mmol) and Lawesson's Reagent (468 mg, 1.16 mmol) in 1,4-dioxane (16 mL) was stirred at 110° C. overnight. The solvent was removed in vacuo and the residue was purified by preparative TLC to give 6-bromo-2-(3-chlorophenyl)-2'-thioxospiro [chroman-4,4'-imidazolidin]-5'-one (350 mg, 71%).

Step 4

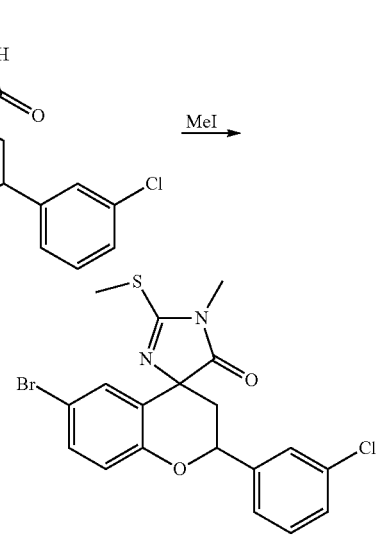

To a mixture of 6-bromo-2-(3-chlorophenyl)-2'-thioxospiro[chroman-4,4'-imidazolidin]-5'-one (250 mg, 0.6 mmol) and K$_2$CO$_3$ (327 mg, 2.4 mmol) in CH$_3$CN (6 mL) was added MeI (339 mg, 2.4 mmol). The reaction mixture was refluxed for 2 h. The mixture was filtered, and the filtrate was concentrated to give a residue which was purified by preparative TLC to give 6-bromo-2-(3-chlorophenyl)-1'-methyl-2'-(methylthio)spiro chroman-4,4'-imidazol]-5'(1'H)-one (100 mg, 37%).
$^1$H-NMR (CDCl$_3$): 1.92 (m, 1H), 2.41 (m, 1H), 2.56 (s, 3H), 3.07 (s, 3H), 5.80 (m, 1H0, 6.80 (m, 2H), 7.26 (m, 4H), 7.39 (m, 1H).

Step 5

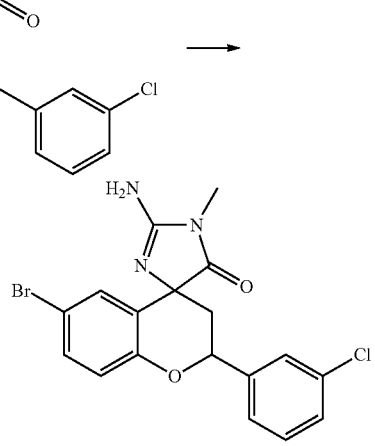

A solution of 6-bromo-2-(3-chlorophenyl)-1'-methyl-2'-(methylthio)spiro chroman-4,4'-imidazol]-5'(1'H)-one (100 mg, 0.22 mmol), NH₄I (64 mg, 0.44 mmol) in a solution of NH₃/EtOH (4 mL, 1.5 N) was heated at 110° C. in a tube in a microwave reactor for 2-2.5 h. After cooling, the mixture was concentrated in vacuo to give a residue which was purified by preparative TLC to afford 2'-amino-6-bromo-2-(3-chlorophenyl)-1'-methylspiro[chroman-4,4'-imidazol]-5'(1'H)-one (42 mg, 46%). ¹H-NMR (MeOD): 2.12 (m, 2H), 3.06 (s, 3H), 5.80 (m, 1H), 6.83 (m, 1H0, 7.03 (m, 1H), 7.27 (m, 4H), 7.40 (m, 1H).

Example 30

2-(2'-amino-1'-methyl-5'-oxo-2-phenyl-1',5'-dihydrospiro[chroman-4,4'-imidazole]-6-yl)benzonitrile (Compound 35)

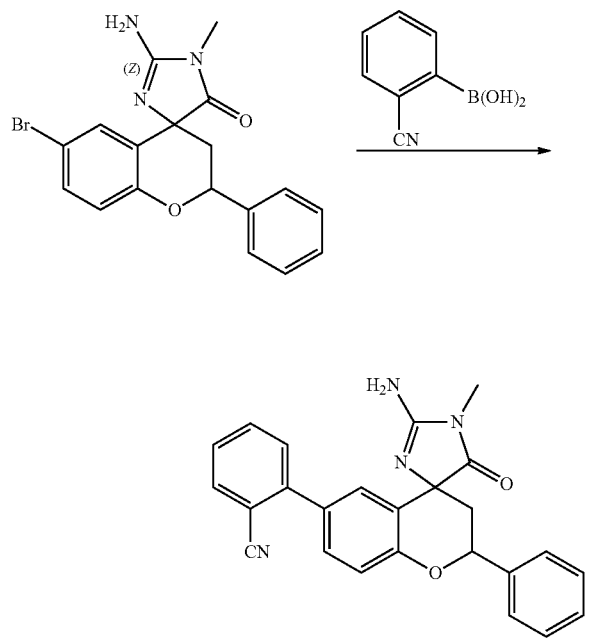

Pd(PPh₃)₂Cl₂ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs₂CO₃ (2 N, 0.3 mL) and 2-cyanophenylboronic acid (15.3 mg, 0.104 mmol). The mixture was heated at 120° C. under Ar in a microwave reactor for 30 min. The reaction mixture was concentrated in vacuo to give the residue, which was purified by preparative HPLC twice to give pure 2-(2'-amino-1'-methyl-5'-oxo-2-phenyl-1',5'-dihydrospiro[chroman-4,4'-imidazole]-6-yl)benzonitrile (2.83 mg, 13%). ¹H-NMR (MeOD): 2.48-2.60 (m, 2H), 3.33 (s, 3H), 5.26 & 5.88 (m, 1H), 7.17 (m, 1H), 7.37-7.60 (m, 9H), 7.70 (m, 1H), 7.81 (m, 1H).

Example 31

2'-amino-1'-methyl-2-phenyl-6-(thiophen-2-yl)spiro[chroman-4,4'-imidazol]-5'(1'H)-one (Compound 36)

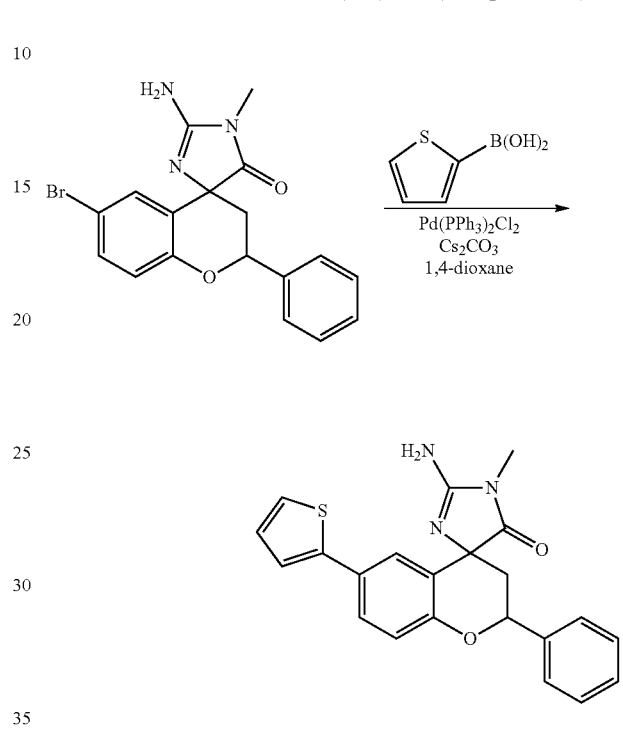

A mixture of 2'-amino-6-bromo-1'-methyl-2-phenylspiro[chroman-4,4'-imidazol]-5'(1'H)-one (21 mg, 0.05 mmol), thiophen-2-ylboronic acid (14 mg, 0.1 mmol), Cs₂CO₃ solution (2 M, 0.5 mL) and Pd(PPh₃)₂Cl₂ (10 mg) in 1,4-dioxane (1 mL) was stirred in a microwave test tube under Ar at 120° C. for 35 minutes. The reaction mixture was concentrated in vacuo to give the residue, which was purified by preparative TLC to give 2'-amino-1'-methyl-2-phenyl-6-(thiophen-2-yl)spiro[chroman-4,4'-imidazol]-5'-(1'H)-one (0.87 mg, 4%). ¹H-NMR (MeOD): 2.45-2.54 (M, 1H), 2.60-2.63 (m, 1H), 3.32 (s, 3H), 5.88 (d, 1H), 7.06-7.14 (m, 2H), 7.33-7.39 (m, 2H), 7.41-7.50 (m, 3H), 7.51-7.64 (m, 4H).

Example 32

5-(2'-amino-1'-methyl-5'-oxo-2-phenyl-1',5'-dihydrospiro[chroman-4,4'-imidazole]-6-yl)-2-fluorobenzonitrile (Compound 37)

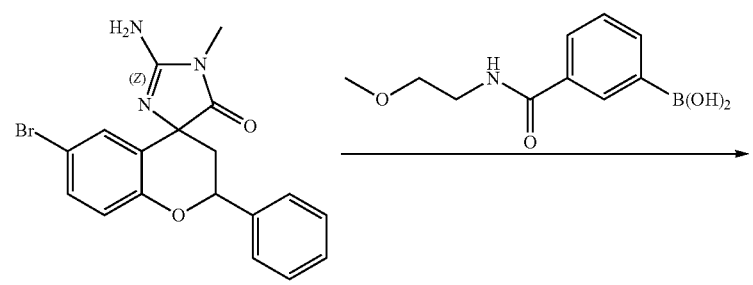

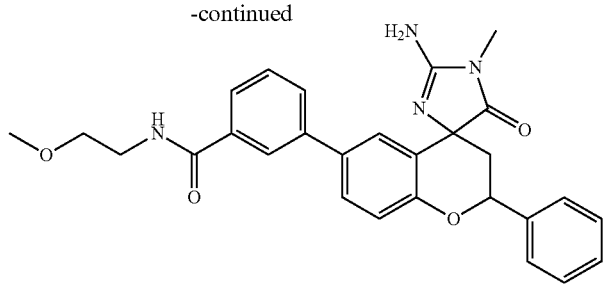

Pd(PPh$_3$)$_2$Cl$_2$ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(2-methoxyethylcarbamoyl)phenylboronic acid (23.2 mg, 0.104 mmol). The mixture was heated at 120° C. under Ar in a microwave reactor for 30 min. The reaction mixture was concentrated in vacuo to give the residue, which was purified by preparative HPLC twice to give pure 5-(2'-amino-1'-methyl-5'-oxo-2-phenyl-1',5'-dihydrospiro[chroman-4,4'-imidazole]-6-yl)-2-fluorobenzonitrile (9.38 mg, 37%). $^1$H-NMR (MeOD): 2.38 (m, 1H), 2.55 (m, 1H), 3.24 (s, 3H), 3.39 (s, 3H), 3.50 (s, 4H), 5.15 & 5.76 (m, 1H), 7.04 (m, 1H), 7.32 (m, 3H), 7.40 (m, 4H), 7.55-7.67 (m, 3H), 7.94 (m, 1H).

Example 33

2'-amino-6-bromo-2-(3-fluorophenyl)-1'-methylspiro[chroman-4,4'-imidazol]-5'(1'H)-one (Compound 38)

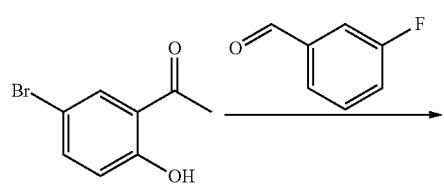

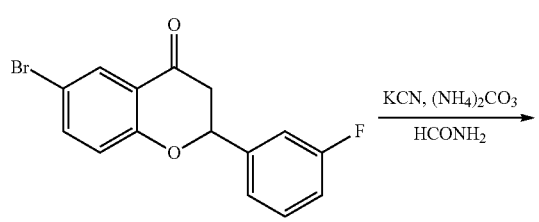

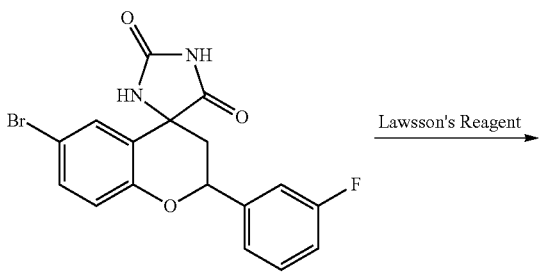

Step 1

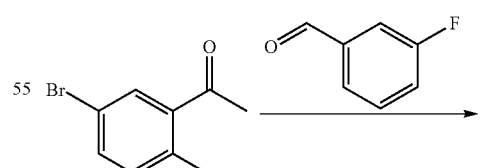

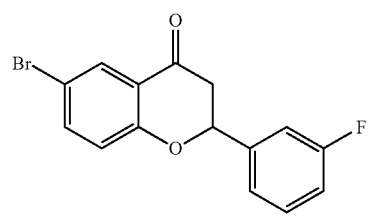

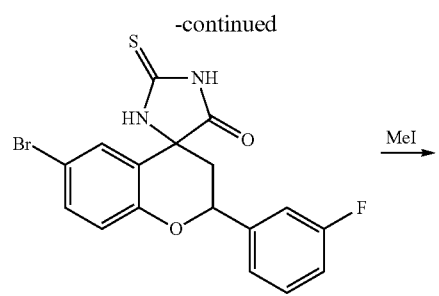

A mixture of 1-(5-bromo-2-hydroxy-phenyl)-ethanone (15 g, 0.07 mol), 3-fluorobenzaldehyde (8.7 g, 0.07 mol) and borax (26.7 g, 0.07 mol) in ethanol (90 mL) and H₂O (150 mL) was refluxed for one day. The reaction mixture was cooled, diluted with an equal volume of H₂O, and extracted with ethyl acetate. The organic layer was dried over anhydrous Na₂SO₄, filtered, and evaporated to give 6-bromo-2-(3-fluorophenyl)chroman-4-one (8.3 g, 37%). ¹H-NMR (CDCl₃): 2.93 (d, 1H), 3.03 (m, 1H), 5.47 (d, 1H), 7.06 (d, 1H), 7.11 (m, 1H), 7.22 (m, 2H), 7.40 (m, 1H), 7.57 (d, 1H), 8.04 (s, 1H).

Step 2

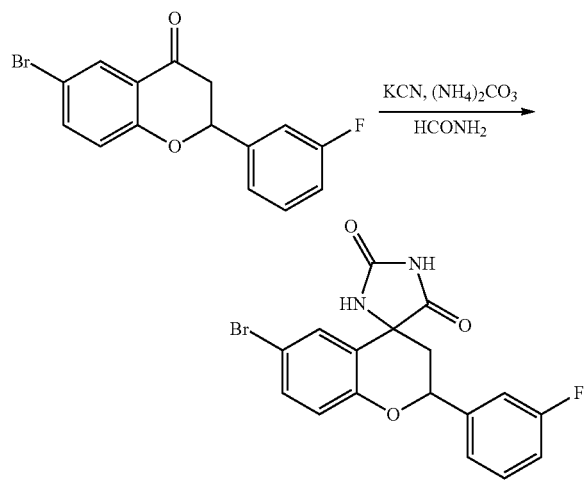

A steel bomb was charged with a mixture of 6-bromo-2-(3-fluorophenyl)chroman-4-one (3.2 g, 0.01 mol), potassium cyanide (1.95 g, 0.03 mmol), and (NH₄)₂CO₃ (7.2 g, 0.075 mmol). Formamide (20 mL) was added to fill the steel bomb nearly completely. The mixture was heated at 70° C. for 48 h then at 110° C. for another 8 h. The reaction mixture was then cooled and poured over ice. Acidification with concentrated HCl was performed to give a precipitate which is filtered, washed twice with water, and then dissolved in ethyl acetate, dried over Na₂SO₄, and filtered. The filtrate was concentrated in vacuo to give a residue, which was purified by preparative TLC to give 6-bromo-2-(3-fluorophenyl)spiro[chroman-4,4'-imidazolidine]-2',5'-dione (0.31 g, 8%). ¹H-NMR (CDCl₃): 2.27 (t, 1H), 2.48 (d, 1H), 5.53 (s, 1H), 5.88 (d, 1H), 6.89 (d, 1H), 7.08 (m, 1H), 7.18 (m, 2H), 7.38 (m, 3H), 7.78 (s, 1H).

Step 3

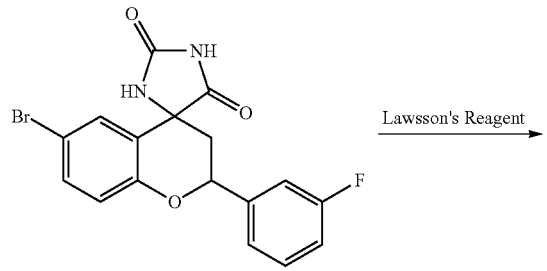

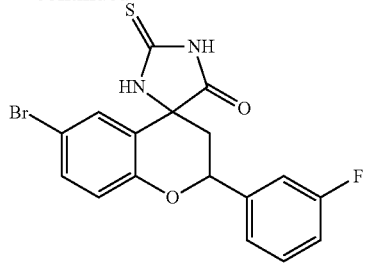

A suspension of 6-bromo-2-(3-fluorophenyl)spiro[chroman-4,4'-imidazolidine]-2',5'-dione (300 mg, 0.77 mmol) and Lawesson's reagent (312 mg, 0.77 mmol) in dry 1,4-dioxane (10 mL) was refluxed for 24 h. The mixture was concentrated in vacuo and the residue was purified by preparative TLC to give 6-bromo-2-(3-fluorophenyl)-2'-thioxospiro[chroman-4,4'-imidazolidine]-5'-one (35 mg, 17%).

Step 4

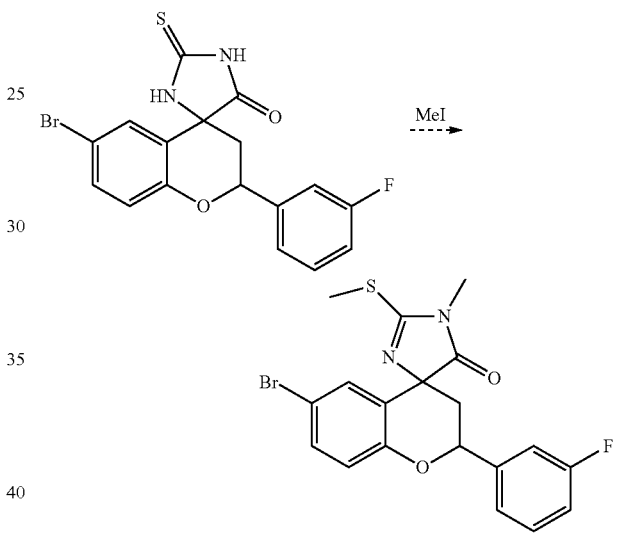

To a solution of 6-bromo-2-(3-fluorophenyl)-2'-thioxospiro[chroman-4,4'-imidazolidine]-5'-one (264 mg, 0.65 mmol) in MeOH (10 mL) was added a solution of NaOH (65 mg, 1.63 mmol) in H₂O (2 mL). After stirring for 10 minutes, MeI (1.4 g, 9.75 mmol) was added. The reaction mixture was heated under reflux for 2 h. The mixture was concentrated in vacuo to give a residue, which was purified by preparative TLC to give 6-bromo-2-(3-fluorophenyl)-1'-methyl-2'-(methylthio)spiro[chroman-4,4'-imidazol]-5'(1'H)-one (80 mg, 28%).

Step 5

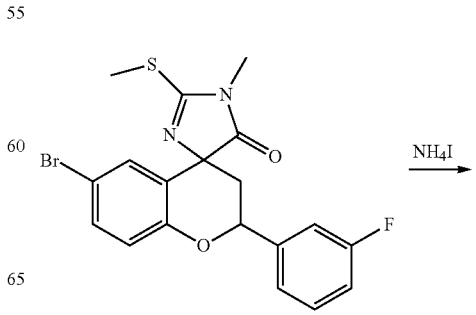

-continued

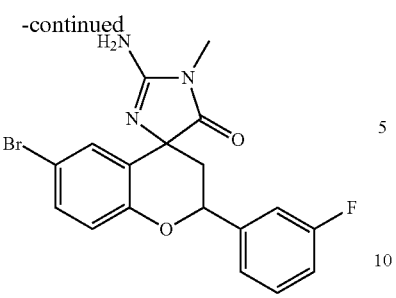

A solution of 6-bromo-2-(3-fluorophenyl)-1'-methyl-2'-(methylthio)spiro[chroman-4,4'-imidazol]-5'(1'H)-one (80 mg, 0.18 mmol) and NH$_4$I (52 mg, 0.36 mmol) in NH$_3$/EtOH (4 mL, 1.5 N) was heated at 110° C. in a tube in a microwave reactor for 2-2.5 h. After cooling, the mixture was concentrated in vacuo to give a residue, which was purified by preparative TLC and then by preparative HPLC to afford 2'-amino-6-bromo-2-(3-fluorophenyl)-1'-methylspiro[chroman-4,4'-imidazol]-5'(1'H)-one (36 mg, 50%). $^1$H-NMR (MeOD): 2.16 (m, 2H), 3.12 (s, 3H), 5.87 (d, 1H), 6.90 (d, 1H), 7.08 (m, 2H), 7.25 (m, 2H), 7.33 (d, 1H), 7.41 (m, 1H).

Example 34

3-(2'-amino-1'-methyl-5'-oxo-2-phenyl-1',5'-dihydrospiro[chroman-4,4'-imidazole]-6-yl)-N,N-dimethylbenzamide (Compound 39)

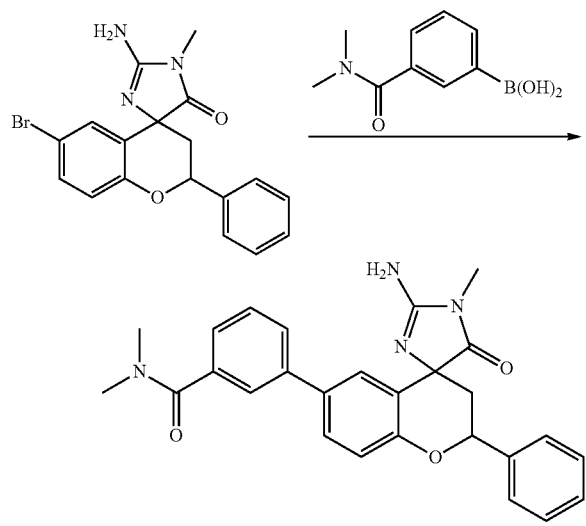

Pd(PPh$_3$)$_2$Cl$_2$ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(dimethylcarbamoyl)phenylboronic acid (20 mg, 0.104 mmol). The mixture was heated at 120° C. under Ar in a microwave reactor for 30 minutes. The reaction mixture was concentrated in vacuo to give the residue, which was purified by preparative TLC to give 3-(2'-amino-1'-methyl-5'-oxo-2-phenyl-1',5'-dihydrospiro[chroman-4,4'-imidazole]-6-yl)-N,N-dimethylbenzamide (1.44 mg, 6%). $^1$H-NMR (MeOD): 2.44 (m, 1H), 2.62 (m, 1H), 3.14 (s, 3H), 3.13 (s, 1H), 5.24 (m, 0.3H), 5.88 (m, 0.7H), 7.15 (m, 1H), 7.41 (m, 3H), 7.45 (m, 1H), 7.53 (m, 4H), 7.18 (m, 3H).

Example 35

5-(2'-amino-1'-methyl-5'-oxo-2-phenyl-1',5'-dihydrospiro[chroman-4,4'-imidazole]-6-yl)-2-fluoro-N-(2-hydroxyethyl)benzamide (Compound 40)

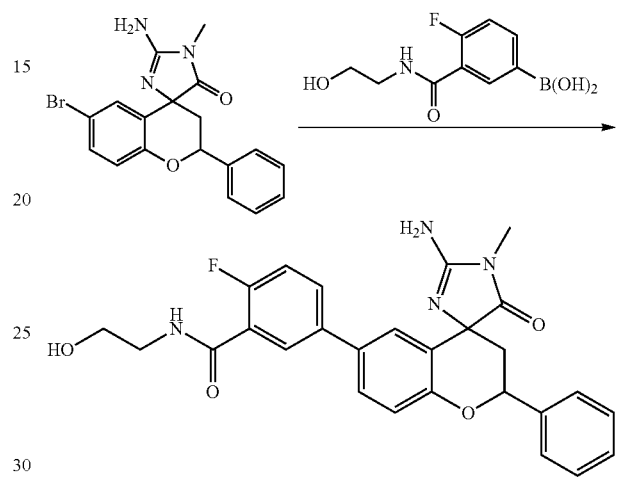

Pd(PPh$_3$)$_2$Cl$_2$ (10 mg) in a 10 mL tube under Ar was treated sequentially with 2'-amino-6-bromo-1'-methyl-2-phenyl-spiro[chroman-4,4'-imidazol]-5'(1'H)-one (20 mg, 0.052 mmol) in 1,4-dioxane (1 mL), Cs$_2$CO$_3$ (2 N, 0.3 mL) and 4-fluoro-3-(2-hydroxyethylcarbamoyl)phenylboronic acid (23 mg, 0.106 mmol). The mixture was heated at 120° C. in a microwave reactor for 0.5 h. The reaction mixture was concentrated in vacuo to give the residue, which was purified by preparative TLC to give pure 5-(2'-amino-1'-methyl-5'-oxo-2-phenyl-1',5'-dihydrospiro[chroman-4,4'-imidazole]-6-yl)-2-fluoro-N-(2-hydroxyethyl)benzamide (3.1 mg, 12%). $^1$H-NMR (MeOD): 2.48 (m, 1H), 2.61 (m, 1H), 3.34 (s, 3H), 3.57 (m, 2H), 3.72 (m, 2H), 5.27 (d, 0.3H), 5.89 (d, 0.8H), 7.18 (m, 1H), 7.30 (m, 1H), 7.45 (m, 1H), 7.52 (m, 4H), 7.67 (m, 1H), 7.79 (m, 1H), 8.01 (m, 1H), 8.32 (m, 1H).

Example 36

N-(3-(2'-amino-1'-methyl-5'-oxo-2-phenyl-1',5'-dihydrospiro[chroman-4,4'-imidazole]-6-yl)phenyl)acetamide (Compound 41)

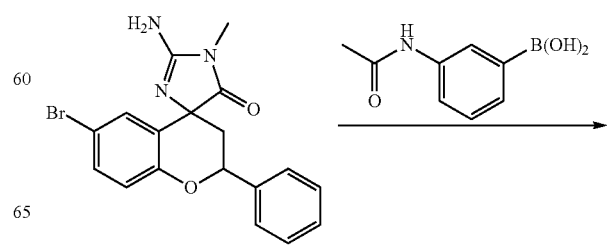

-continued

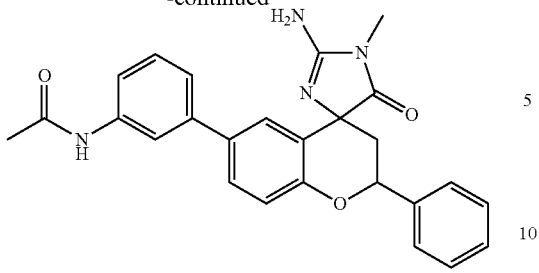

Pd(PPh$_3$)$_2$Cl$_2$ (10 mg) in a 10 mL tube under Ar was treated sequentially with 2'-amino-6-bromo-1'-methyl-2-phenyl-spiro[chroman-4,4'-imidazol]-5'(1'H')-one (20 mg, 0.052 mmol) in 1,4-dioxane (1 mL), Cs$_2$CO$_3$ (2 N, 0.3 mL) and 3-acetamidophenylboronic acid (17.9 mg, 0.1 mmol). The mixture was heated at 120° C. in a microwave reactor for 30 min. The reaction mixture was concentrated in vacuo to give the residue, which was purified by preparative TLC to give pure N-(3-(2'-amino-1'-methyl-5'-oxo-2-phenyl-1',5'-dihydrospir-o[chroman-4,4'-imidazole]-6-yl)phenyl)acetamide (5.8 mg, 20%). $^1$H-NMR (MeOD): 2.03 (s, 3H), 2.21 (t, 1H), 2.41 (t, 1H), 3.07 (s, 3H), 5.81 (d, 1H), 6.92 (d, 1H), 7.12 (t, 1H), 7.21 (t, 2H), 7.33 (t, 2H), 7.49 (m, 4H), 7.59 (d, 1H).

Example 37

N-(3-(2'-amino-1'-methyl-5'-oxo-2-phenyl-1',5'-dihydrospiro[chroman-4,4'-imidazole]-6-yl)benzyl)acetamide (Compound 43)

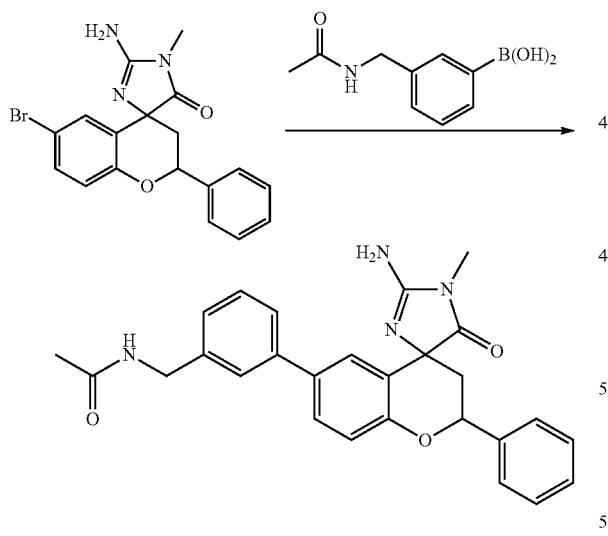

Pd(PPh$_3$)$_2$Cl$_2$ (10 mg) in a 10 mL CEM test tube under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(acetamidomethyl)phenylboronic acid (19.3 mg, 0.1 mmol). The mixture was heated in a microwave reactor at 120° C. for 30 minutes. The reaction mixture was concentrated in vacuo to give the residue, which was purified by preparative TLC to give pure N-(3-(2'-amino-1'-methyl-5'-oxo-2-phenyl-1',5'-dihydrospiro-[chroman-4,4'-imidazole]-6-yl)benzyl)acetamide (2.5 mg, 11%). $^1$H-NMR (MeOD): 2.01 (s, 3H), 2.16 (d, 1H), 2.32 (t, 1H), 3.17 (s, 3H), 4.40 (s, 2H), 5.92 (d, 1H), 7.03 (d, 1H), 7.23 (d, 2H), 7.36 (m, 2H), 7.41 (t, 4H), 7.48 (m, 3H).

Example 38

2'-amino-6-bromo-1'-methyl-2-phenylspiro[chroman-4,4'-imidazol]-5'(1'H)-one (Compound 44)

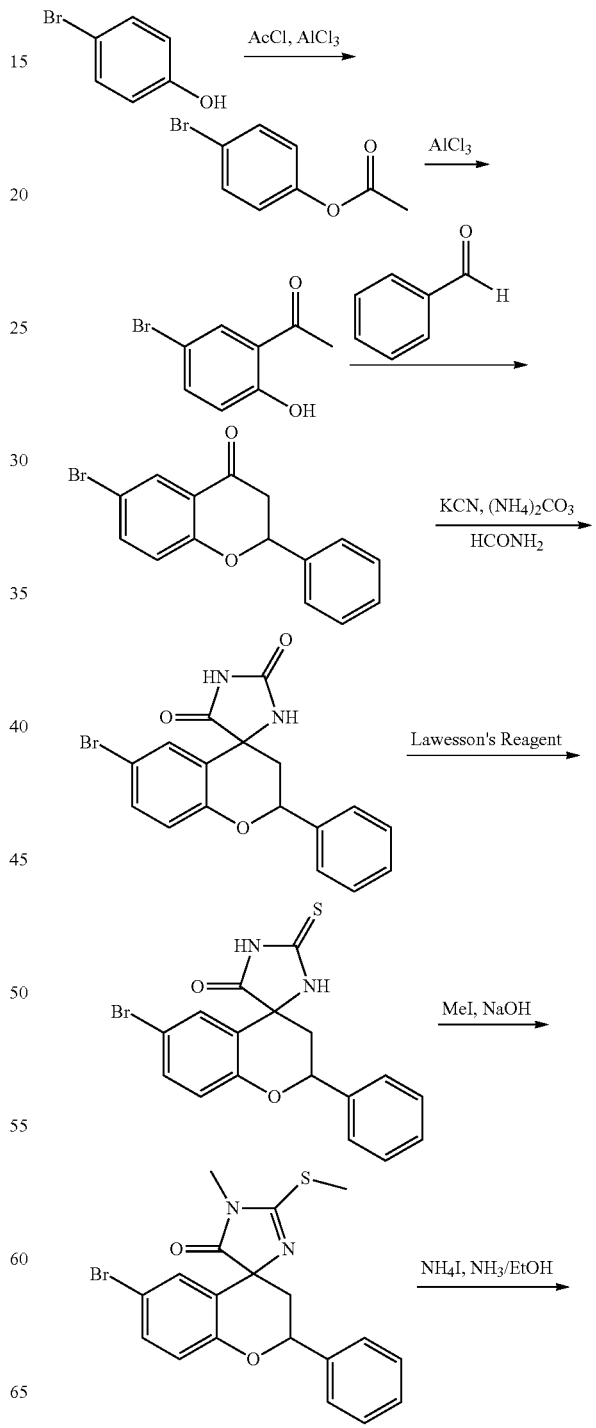

-continued

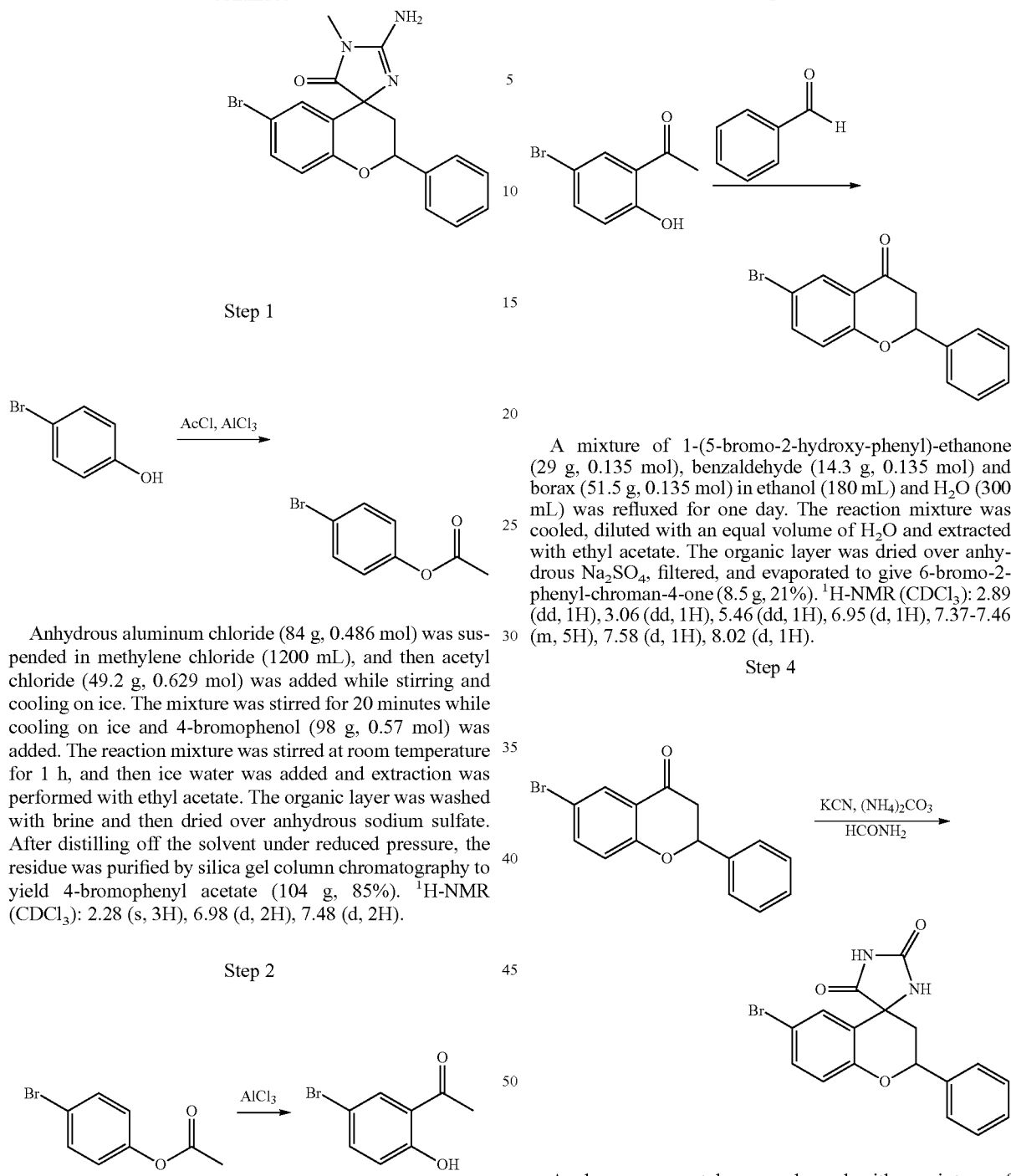

Step 1

Anhydrous aluminum chloride (84 g, 0.486 mol) was suspended in methylene chloride (1200 mL), and then acetyl chloride (49.2 g, 0.629 mol) was added while stirring and cooling on ice. The mixture was stirred for 20 minutes while cooling on ice and 4-bromophenol (98 g, 0.57 mol) was added. The reaction mixture was stirred at room temperature for 1 h, and then ice water was added and extraction was performed with ethyl acetate. The organic layer was washed with brine and then dried over anhydrous sodium sulfate. After distilling off the solvent under reduced pressure, the residue was purified by silica gel column chromatography to yield 4-bromophenyl acetate (104 g, 85%). $^1$H-NMR (CDCl$_3$): 2.28 (s, 3H), 6.98 (d, 2H), 7.48 (d, 2H).

Step 2

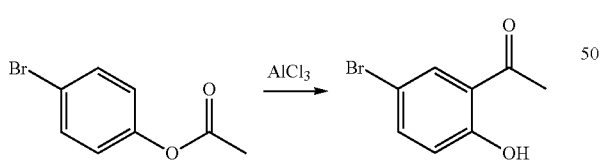

A mixture of 4-bromophenyl acetate (104 g, 0.484 mol) and anhydrous aluminum chloride (130.5 g, 0.968 mol) was stirred at 120-140° C. for 20 minutes. The reaction mixture was cooled to 60-80° C. Ice water was added and extraction was performed with ethyl acetate. The organic layer was washed with brine and dried over anhydrous sodium sulfate. After distilling off the solvent under reduced pressure, the residue was purified by silica gel column chromatography to yield 1-(5-bromo-2-hydroxy-phenyl)-ethanone (101 g, 98%). $^1$H-NMR (CDCl$_3$): 2.60 (s, 3H), 6.87 (d, 1H), 7.53 (dd, 1H), 7.81 (s, 1H), 12.12 (s, 1H).

Step 3

A mixture of 1-(5-bromo-2-hydroxy-phenyl)-ethanone (29 g, 0.135 mol), benzaldehyde (14.3 g, 0.135 mol) and borax (51.5 g, 0.135 mol) in ethanol (180 mL) and H$_2$O (300 mL) was refluxed for one day. The reaction mixture was cooled, diluted with an equal volume of H$_2$O and extracted with ethyl acetate. The organic layer was dried over anhydrous Na$_2$SO$_4$, filtered, and evaporated to give 6-bromo-2-phenyl-chroman-4-one (8.5 g, 21%). $^1$H-NMR (CDCl$_3$): 2.89 (dd, 1H), 3.06 (dd, 1H), 5.46 (dd, 1H), 6.95 (d, 1H), 7.37-7.46 (m, 5H), 7.58 (d, 1H), 8.02 (d, 1H).

Step 4

A glass pressure tube was charged with a mixture of 6-bromo-2-phenyl-chroman-4-one (7.6 g, 25 mmol), KCN (3.25 g, 50 mmol), and (NH$_4$)$_2$CO$_3$ (18 g, 187.5 mmol). Formamide (80 mL) was added to fill the pressure tube nearly completely. The mixture was heated at 70° C. for 24 h then at 110° C. for another 48 h. The reaction mixture was then cooled and poured over ice. Acidification with concentrated HCl yielded a precipitate which was filtered, washed twice with water, and then dissolved in ethyl acetate, dried over Na$_2$SO$_4$, and filtered. The filtrate was concentrated in vacuo to give a residue, which was purified by column to give 6-bromo-2-phenylspiro[chroman-4,4'-imidazolidine]-2',5'-dione (466 mg, 5%). $^1$H-NMR (MeOD): 2.28 (t, 1H), 2.43 (dd, 1H), 5.83 (d, 1H), 6.90 (d, 1H), 7.33-7.45 (m, 7H).

Step 5

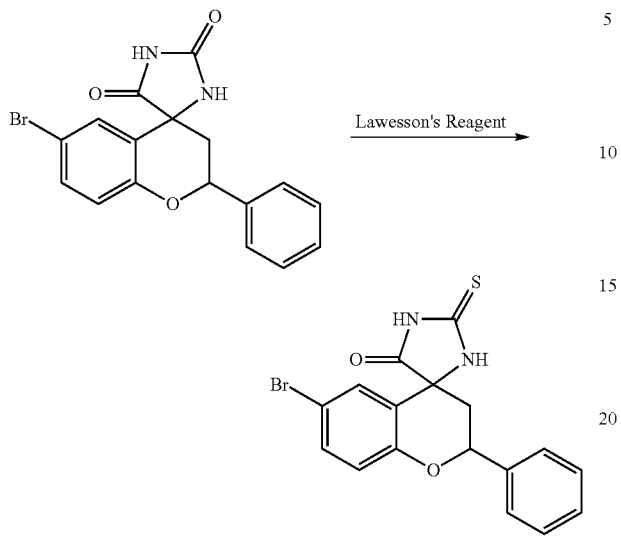

A suspension of 6-bromo-2-phenylspiro[chroman-4,4'-imidazolidine]-2',5'-dione (186 mg, 0.5 mmol) and Lawesson's Reagent (202 mg, 0.5 mmol) in dry 1,4-dioxane (8 mL) was refluxed for 24 h. The mixture was concentrated in vacuo and the residue was purified by preparative TLC to give 6-bromo-2-phenyl-2'-thioxospiro[chroman-4,4'-imidazolidin]-5'-one (115 mg, 62%). $^1$H-NMR (CDCl$_3$): 2.35 (t, 1H), 2.49 (dd, 1H), 5.83 (d, 1H), 6.90 (d, 1H), 7.36-7.45 (m, 7H).

Step 6

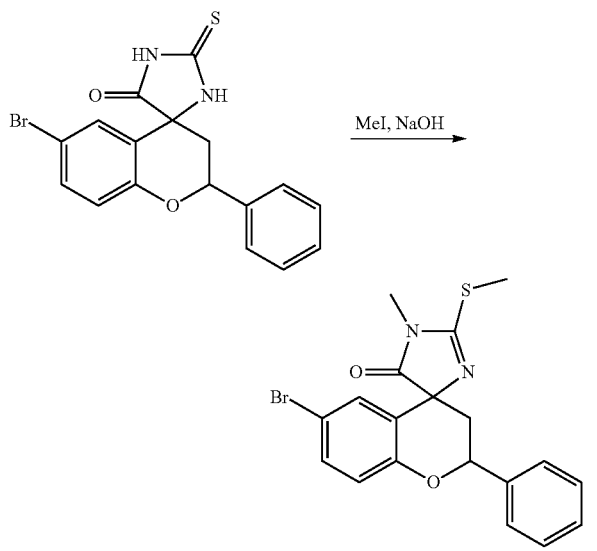

To a solution of 6-bromo-2-phenyl-2'-thioxospiro[chroman-4,4'-imidazolidin]-5'-one (115 mg, 0.298 mmol) in MeOH (5 mL) was added a solution of NaOH (24 mg, 0.608 mmol) in H$_2$O (1 mL). After stirring for 10 minutes, MeI (176 mg, 1.236 mmol) was added. The reaction mixture was refluxed for 2 h. And then MeI (500 mg, 3.52 mmol) was added and the reaction mixture was refluxed for another 2 h. The mixture was concentrated in vacuo to give a residue, which was purified by preparative TLC to give 6-bromo-1'-methyl-2'-(methylthio)-2-phenylspiro[chroman-4,4'-imidazol]-5'(1'H)-one (59 mg, 48%).

Step 7

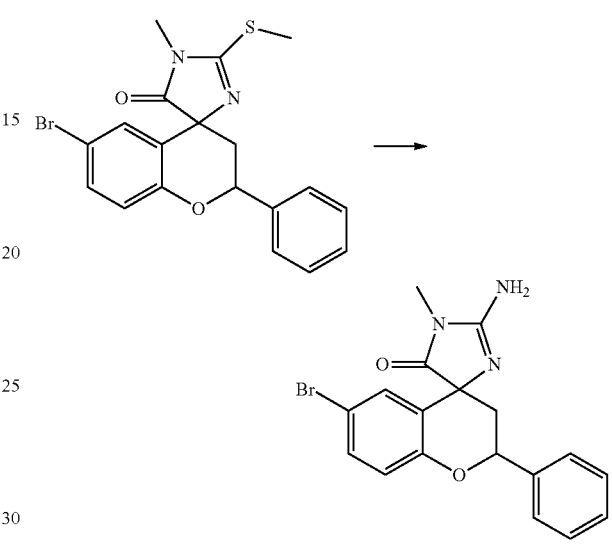

A solution of 6-bromo-1'-methyl-2'-(methylthio)-2-phenylspiro[chroman-4,4'-imidazol]-5'(1'H)-one (59 mg, 0.142 mmol), NH$_4$I (41.5 mg, 0.286 mmol) in a solution of NH$_3$/EtOH (4 mL, 1.5 N) was heated at 110° C. in a tube in a microwave reactor for 2-2.5 h. After cooling, the mixture was concentrated in vacuo to give a residue, which was purified by preparative TLC to afford 2'-amino-6-bromo-1'-methyl-2-phenylspiro[chroman-4,4'-imidazol]-5'(1'H)-one (21 mg, 38%). $^1$H-NMR (MeOD): 2.04 (d, 1H), 2.15 (dd, 1H), 4.51 (m, 1H), 5.75 (d, 1H), 6.78 (m, 1H), 6.99 (d, 1H), 7.20-7.26 (m, 2H), 7.26-7.35 (m, 4H).

Example 38a

Cis-2'-amino-6-bromo-1'-methyl-2-phenylspiro[chroman-4,4'-imidazol]-5'(1'H)-one (Compound 44b) and Trans-2'-amino-6-bromo-1'-methyl-2-phenylspiro[chroman-4,4'-imidazol]-5'(1'H)-one (Compound 44a)

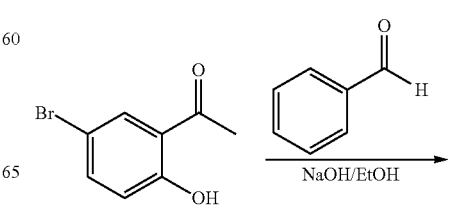

357
-continued

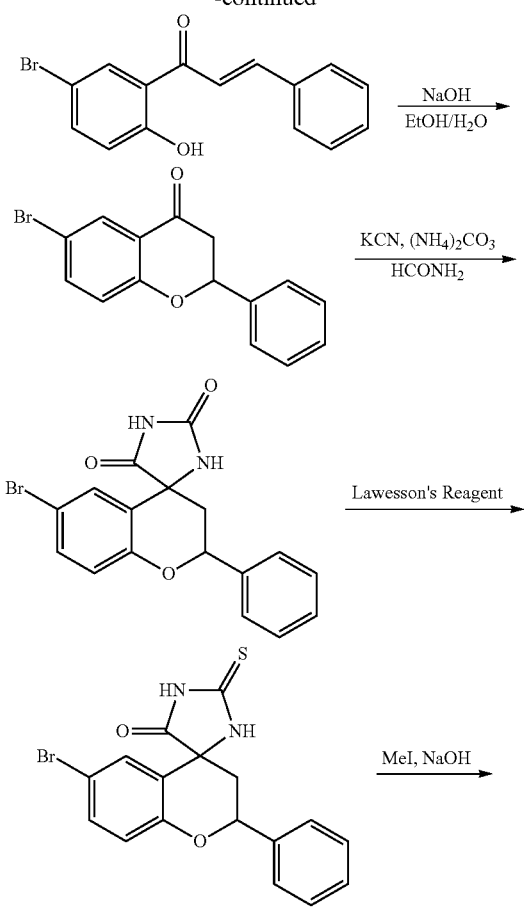

358

Step 1

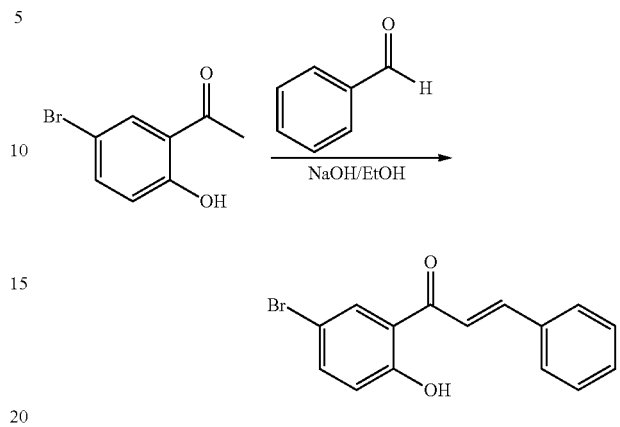

A mixture of 4-bromophenyl acetate (64.2 g, 0.3 mol), benzaldehyde (31.8 g, 0.3 mol), 96% EtOH (370 mL), and NaOH (108 g) was stirred vigorously for 0.5-1 h, during which time, the reaction solidified. After standing for 3 h, the reaction mixture was triturated with MTBA (400 mL), and the solid was filtered and then dissolved in 600 mL of ethyl acetate. The organic layers was separated, dried over $Na_2SO_4$, filtered, and concentrated to give 1-(5-bromo-2-hydroxy-phenyl)-3-phenyl-propenone (55 g, 61%. $^1$H-NMR ($CDCl_3$): 6.86 (m, 1H), 7.38 (m, 3H), 7.49 (m, 2H), 7.61 (m, 2H), 7.93 (t, 2H), 12.66 (s, 1H).

Step 2

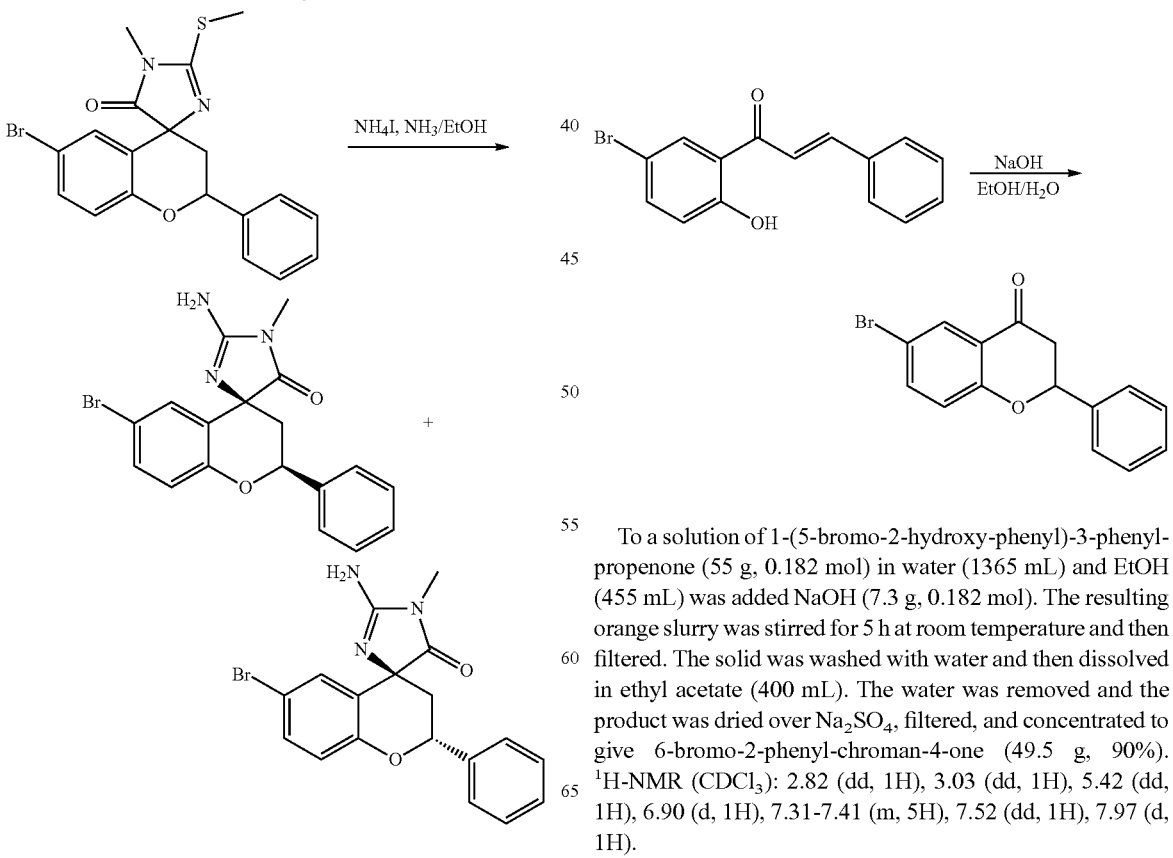

To a solution of 1-(5-bromo-2-hydroxy-phenyl)-3-phenyl-propenone (55 g, 0.182 mol) in water (1365 mL) and EtOH (455 mL) was added NaOH (7.3 g, 0.182 mol). The resulting orange slurry was stirred for 5 h at room temperature and then filtered. The solid was washed with water and then dissolved in ethyl acetate (400 mL). The water was removed and the product was dried over $Na_2SO_4$, filtered, and concentrated to give 6-bromo-2-phenyl-chroman-4-one (49.5 g, 90%). $^1$H-NMR ($CDCl_3$): 2.82 (dd, 1H), 3.03 (dd, 1H), 5.42 (dd, 1H), 6.90 (d, 1H), 7.31-7.41 (m, 5H), 7.52 (dd, 1H), 7.97 (d, 1H).

Step 3

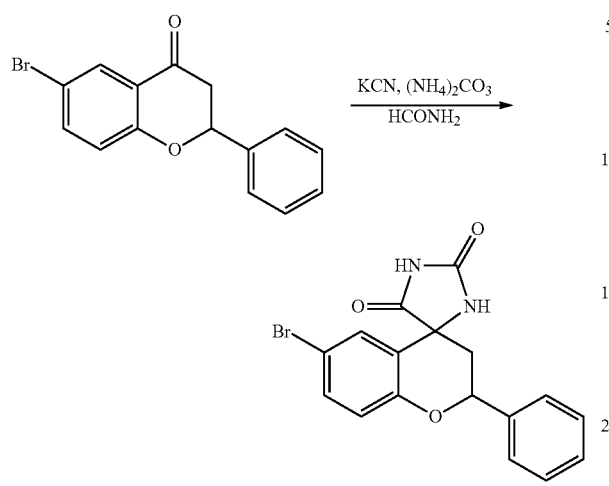

A glass pressure tube was charged with a mixture of 6-bromo-2-phenyl-chroman-4-one (15.1 g, 50 mmol), KCN (6.5 g, 100 mmol), and (NH$_4$)$_2$CO$_3$ (36 g, 375 mmol). Formamide (80 mL) was added to fill the pressure tube nearly completely. The mixture was heated at 70° C. for 24 h then at 110° C. for another 48 h. The reaction mixture was then cooled and poured over ice. Acidification with concentrated HCl yielded a precipitate which was filtered, washed twice with water, dissolved in ethyl acetate, dried over Na$_2$SO$_4$, and filtered. The filtrate was concentrated in vacuo to give a residue, which was purified by column to give 6-bromo-2-phenylspiro[chroman-4,4'-imidazolidine]-2',5'-dione (2.4 g, 13%). $^1$H-NMR (CDCl$_3$): 2.28 (t, 1H), 2.43 (dd, 1H), 5.66 (m, 1H), 5.82 (d, 1H), 6.86 (d, 1H), 7.33-7.41 (m, 7H), 8.03 (m, 1H).

Step 4

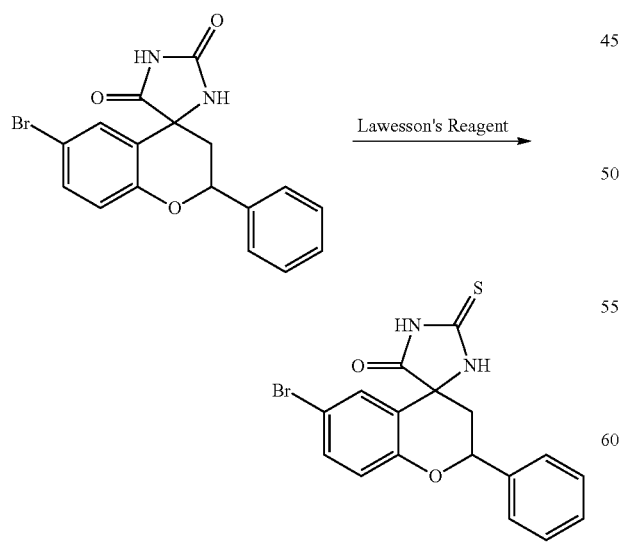

A suspension of 6-bromo-2-phenylspiro[chroman-4,4'-imidazolidine]-2',5'-dione (1.12 g, 3 mmol) and Lawesson's Reagent (1.21 g, 3 mmol) in dry 1,4-dioxane (25 mL) was refluxed for 24 h. The mixture was concentrated in vacuo and the residue was purified by preparative TLC to give 6-bromo-2-phenyl-2'-thioxospiro[chroman-4,4'-imidazolidin]-5'-one (780 mg, 67%). $^1$H-NMR (CDCl$_3$): 2.26 (dd, 1H), 2.43 (dd, 1H), 5.76 (dd, 1H), 6.84 (m, 2H), 7.32-7.36 (m, 6H), 8.22 (m, 1H).

Step 5

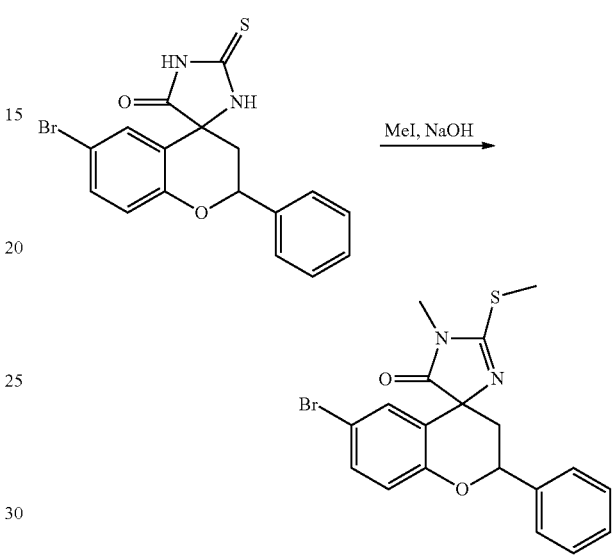

To a solution of 6-bromo-2-phenyl-2'-thioxospiro[chroman-4,4'-imidazolidin]-5'-one (580.5 mg, 1.5 mmol) in MeOH (10 mL) was added a solution of NaOH (120 mg, 3 mmol) in H$_2$O (2 mL). After stirring for 10 min, MeI (3.2 g, 225 mmol) was added. The reaction mixture was refluxed for 2 h. Then MeI (3.2 mg, 225 mmol) was added and the reaction was refluxed for another 2 h. The mixture was concentrated in vacuo to give a residue, which was purified by preparative TLC to give 6-bromo-1'-methyl-2'-(methylthio)-2-phenyl-spiro[chroman-4,4'-imidazol]-5'(1'H)-one (380 mg, 61%).

Step 6

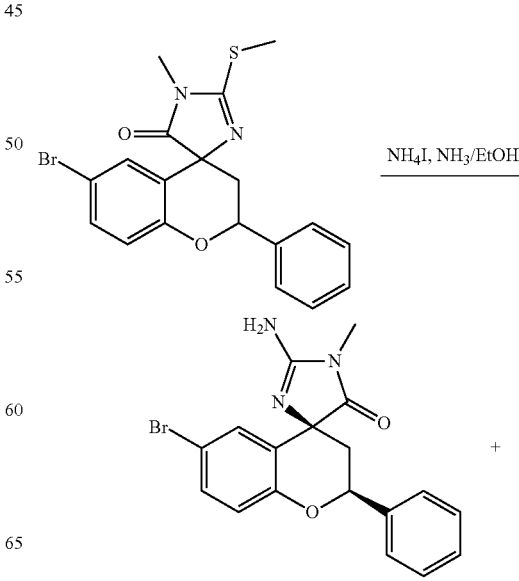

(m, 1H), 2.71 (s, 6H), 3.29 (s, 3H), 5.28 (d, 0.3H), 5.89 (d, 0.7H), 7.19 (m, 1H), 7.47 (m, 6H), 7.69 (m, 2H), 7.75 (m, 1H), 7.93 (m, 2H).

Example 40

2'-amino-6-bromo-2-(3-methoxyphenyl)-1'-methyl-spiro[chroman-4,4'-imidazol]-5'(1'H)-one (Compound 46)

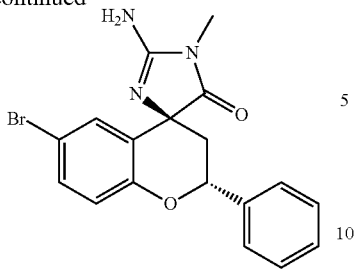

A solution of 6-bromo-1'-methyl-2'-(methylthio)-2-phenylspiro[chroman-4,4'-imidazol]-5'(1'H)-one (380 mg, 0.913 mmol), and NH₄I (265 mg, 1.83 mmol) in a solution of NH₃/EtOH (8 mL, 1.5 N) was heated at 110° C. in a CEM tube in a microwave reactor for 2 h. After cooling, the mixture was concentrated in vacuo to give a residue, which was purified by preparative TLC to afford 2'-amino-6-bromo-1'-methyl-2-phenylspiro[chroman-4,4'-imidazol]-5'(1'H)-one with two isomers: cis isomer (21 mg, 38%) and trans isomer (25 mg, 45%).

(cis): ¹H-NMR (MeOD): 2.05 (t, 1H), 2.25 (t, 1H), 3.13 (s, 3H), 5.86 (d, 1H), 6.87 (d, 1H), 7.09 (m, 1H), 7.31-7.35 (m, 2H), 7.36-7.48 (m, 4H).

(trans): ¹H-NMR (MeOD): 2.12 (m, 1H), 2.25 (t, 1H), 3.14&3.20 (s, 3H), 5.87 (d, 1H), 6.88 (d, 1H), 7.11 (m, 1H), 7.32-7.36 (m, 2H), 7.38-7.48 (m, 4H).

Example 39

3-(2'-amino-1'-methyl-5'-oxo-2-phenyl-1',5'-dihydrospiro[chroman-4,4'-imidazole]-6-yl)-N,N-dimethylbenzenesulfonamide (Compound 45)

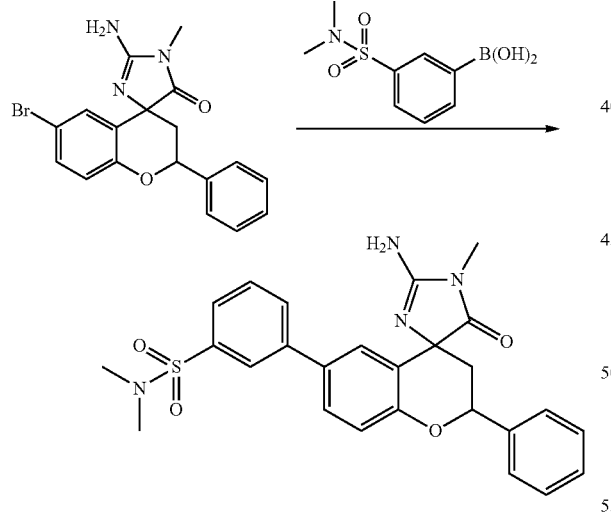

Pd(PPh₃)₂Cl₂ (10 mg) in a 10 mL tube under Ar was treated sequentially with 2'-amino-6-bromo-1'-(cyclohexylmethyl)-2-phenylspiro[chroman-4,4'-imidazol]-5'(1'H)-one (20 mg, 0.052 mmol) in 1,4-dioxane (1 mL), Cs₂CO₃ (2 N, 0.3 mL) and 3-(N,N-dimethylsulfamoyl)phenylboronic acid (24 mg, 0.104 mmol). The mixture was heated at 120° C. in a microwave reactor for 0.5 h. The reaction mixture was concentrated in vacuo to give the residue, which was purified by preparative TLC followed by preparative HPLC to give pure 3-(2'-amino-1'-methyl-5'-oxo-2-phenyl-1',5'-dihydrospiro[chroman-4,4'-imidazole]-6-yl)-N,N-dimethylbenzenesulfonamide (1.7 mg, 7%). ¹H-NMR (MeOD): 2.47 (m, 1H), 2.62

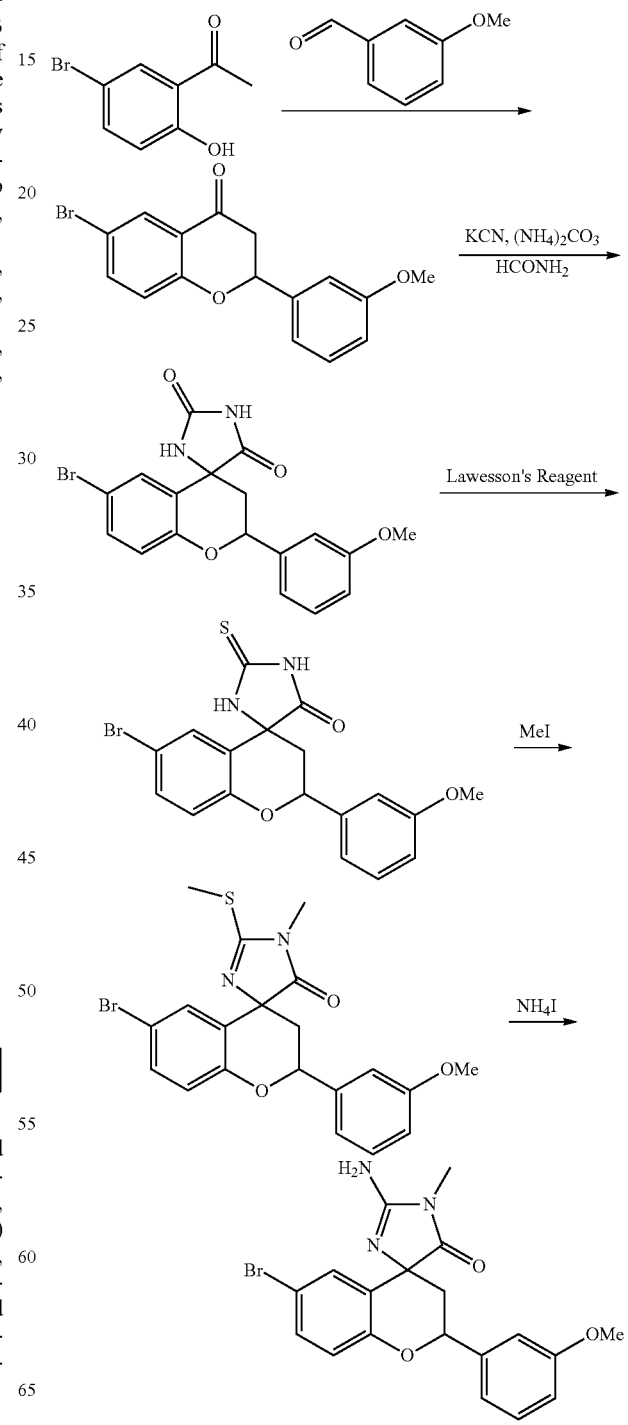

Step 1

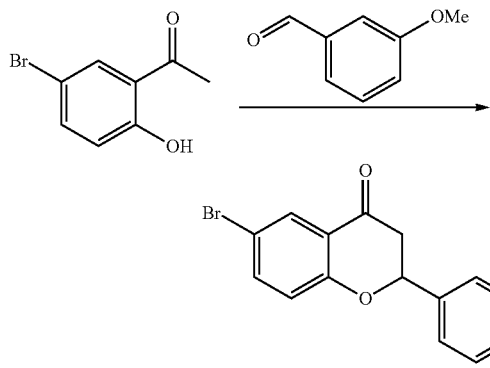

A mixture of 1-(5-bromo-2-hydroxy-phenyl)-ethanone (18 g, 84.1 mmol), 3-methoxy-benzaldehyde (11.4 g, 84.1 mol), and borax (51.5 g, 0.135 mol) in ethanol (112 mL) and $H_2O$ (187 mL) was refluxed for one day. The reaction mixture was cooled, diluted with an equal volume of $H_2O$, and extracted with ether. The ether was dried over anhydrous $Na_2SO_4$, filtered, and evaporated to give 6-bromo-2-(3-methoxy-phenyl)-chroman-4-one (5 g, 18%). $^1$H-NMR ($CDCl_3$): 2.89 (d, 1H), 3.04 (t, 1H), 3.81 (s, 3H), 5.43 (d, 2H), 6.96 (m, 3H), 7.32 (m, 1H), 7.58 (m, 1H), 8.01 (s, 1H)

Step 2

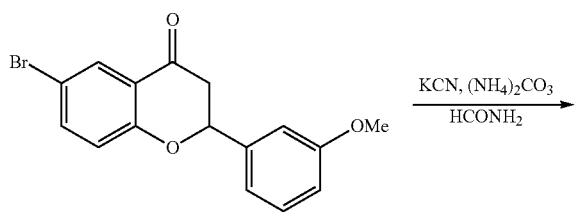

A steel bomb was charged with a mixture of 6-bromo-2-(3-methoxyphenyl)chroman-4-one (2 g, 6 mmol), KCN (770 mg, 12 mmol), and $(NH_4)_2CO_3$ (4 g, 42 mmol). Formamide (20 mL) was added to fill the pressure tube nearly completely. The mixture was heated at 70° C. for 72 h then at 110° C. for another 5 h. The reaction mixture was then cooled and poured over ice. Acidification with concentrated HCl yielded a precipitate which was filtered, washed twice with water, and then dissolved in ethyl acetate, dried over $Na_2SO_4$, and filtered. The filtrate was concentrated in vacuo to give a residue, which is purified by column to give 6-bromo-2-(3-methoxyphenyl)spiro[chroman-4,4'-imidazolidine]-2',5'-dione (534 mg, 22%). $^1$H-NMR (MeOD): 2.26 (d, 1H), 2.37 (t, 1H), 3.79 (s, 3H), 5.80 (d, 1H), 6.88 (m, 2H), 7.00 (m, 2H), 7.44 (m, 2H).

Step 3

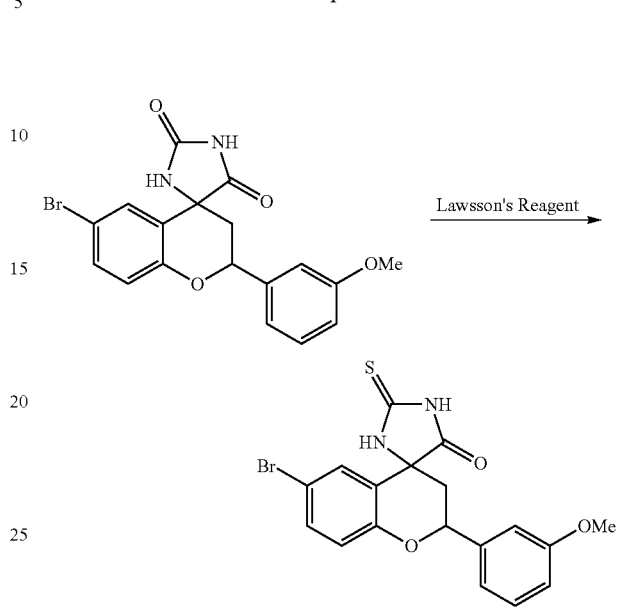

A suspension of 6-bromo-2-(3-methoxyphenyl)spiro[chroman-4,4'-imidazolidine]-2',5'-dione (273 mg, 0.679 mmol) and Lawesson's Reagent (274 mg, 0.629 mmol) in dry 1,4-dioxane (10 mL) was refluxed for 24 h. The mixture was concentrated in vacuo and the residue was purified by preparative TLC to give 6-bromo-2-(3-methoxyphenyl)-2'-thioxospiro[chroman-4,4'-imidazolidin]-5'-one (200 mg, 71%).

$^1$H-NMR ($CDCl_3$): 2.24 (m, 1H), 2.41 (m, 1H), 3.76 (s, 3H), 5.72 (m, 1H), 6.88 (m, 4H), 7.31 (m, 1H), 8.24 (m, 1H).

Step 4

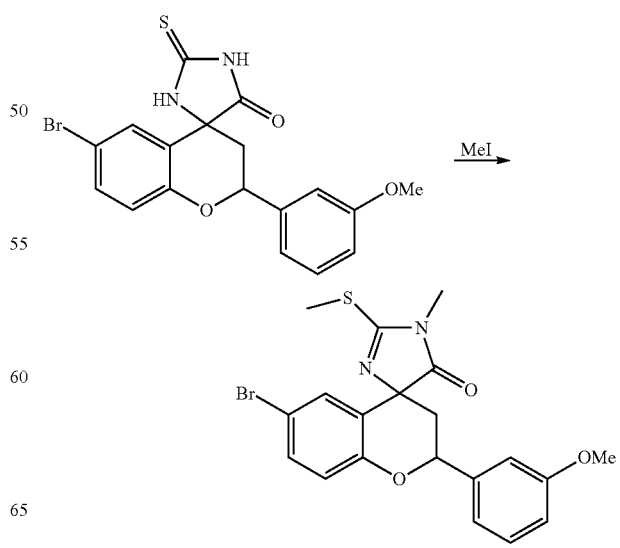

To a solution of 6-bromo-2-(3-methoxyphenyl)-2'-thioxospiro[chroman-4,4'-imidazolidin]-5'-one (50 mg, 0.12 mmol) in MeOH (5 mL) was added a solution of NaOH (9.5 mg) in H₂O (1 mL). After stirring for 10 minutes, MeI (171 mg) was added. The reaction mixture was refluxed for 2 h. The mixture was concentrated in vacuo to give a residue, which was purified by preparative TLC to give 6-bromo-2-(3-methoxyphenyl)-1'-methyl-2'-(methylthio)spiro[chroman-4,4'-imidazol]-5'(1'H)-one (13 mg, 21%).

Step 5

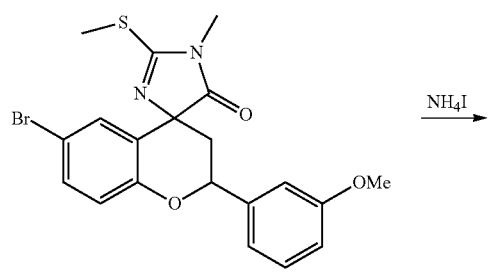

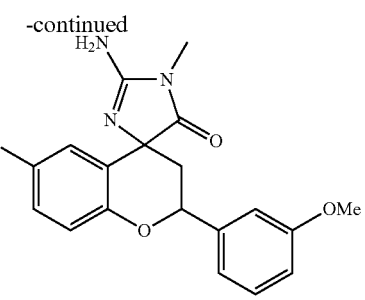

A solution of 6-bromo-2-(3-methoxyphenyl)-1'-methyl-2'-(methylthio)spiro[chroman-4,4'-imidazol]-5'(1'H)-one (13 mg) and NH₄I (10 mg) in a solution of NH₃/EtOH (2 mL, 1.5 N) was heated at 110° C. in a tube in a microwave reactor for 2-2.5 h. After cooling, the mixture was concentrated in vacuo to give a residue, which was purified by preparative TLC to afford 2'-amino-6-bromo-2-(3-methoxyphenyl)-1'-methylspiro[chroman-4,4'-imidazol]-5'(1'H)-one (2.17 mg, 22%).

¹H-NMR (MeOD): 2.00 (d, 1H), 2.13 (m, 1H), 3.03 (s, 3H), 3.70 (s, 3H), 5.70 (m, 1H), 6.77 (m, 2H), 6.89 (m, 2H), 7.00 (m, 1H), 7.21 (m, 2H).

Example 41

3-(2'-amino-1'-methyl-5'-oxo-2-phenyl-1',5'-dihydrospiro[chroman-4,4'-imidazole]-6-yl)-N-(2-cyanoethyl)benzamide (Compound 47)

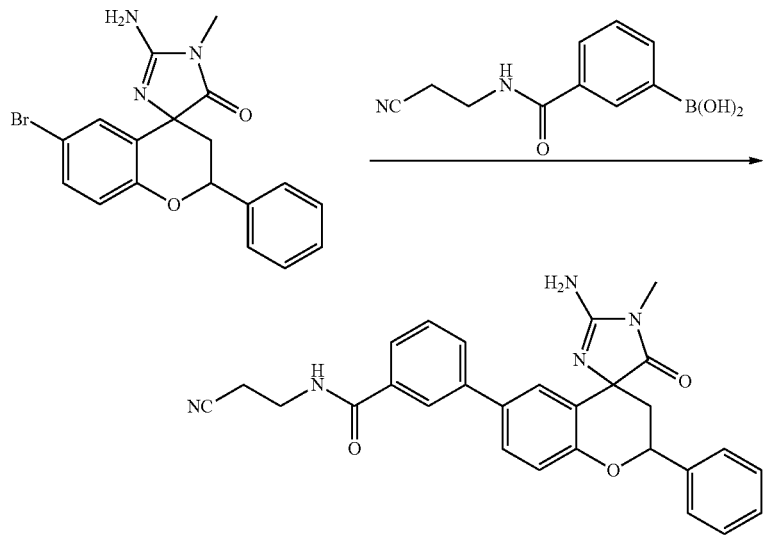

Pd(PPh₃)₂Cl₂ (10 mg) in a 10 mL CEM test tube under Ar was treated sequentially with 2'-amino-6-bromo-1'-methyl-2-phenylspiro[chroman-4,4'-imidazol]-5'(1'H)-one (20 mg, 0.05 mmol) in 1,4-dioxane (1 mL), Cs₂CO₃ (2 N, 0.3 mL) and 3-(2-cyanoethyl-carbamoyl)phenylboronic acid (22 mg, 0.1 mmol). The mixture was heated in a microwave reactor at 120° C. for 30 mins. The reaction mixture was concentrated in vacuo to give the residue, which was purified by preparative TLC to give pure 3-(2'-amino-1'-methyl-5'-oxo-2-phenyl-1',5'-dihydrospiro[chroman-4,4'-imidazole]-6-yl)-N-(2-cyanoethyl)benzamide (1.96 mg, 8%). ¹H-NMR (MeOD): 2.52 (m, 1H), 2.64 (m, 1H), 2.83 (t, 2H), 3.35 (s, 3H), 3.68 (t, 2H), 5.86 (d, 1H), 7.18 (d, 1H), 7.43 (m, 3H), 7.55 (m, 3H), 7.57 (d, 1H), 7.71 (d, 1H), 7.79 (m, 2H), 8.05 (s, 1H).

Example 42

3-(2'-amino-1'-methyl-5'-oxo-2-phenyl-1',5'-dihydrospiro[chroman-4,4'-imidazole]-6-yl)-N-methylbenzenesulfonamide (Compound 48)

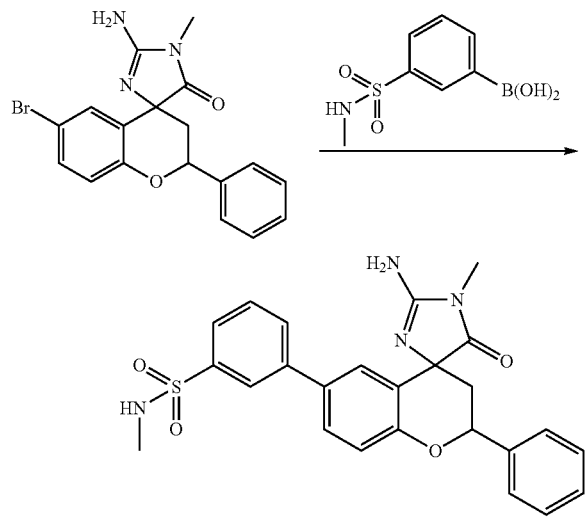

Pd(PPh$_3$)$_2$Cl$_2$ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(N-methylsulfamoyl)phenylboronic acid (23 mg, 0.104 mmol). The mixture was heated at 120° C. under Ar in microwave reactor for 30 minutes. The reaction mixture was concentrated in vacuo to give the residue, which was purified by preparative TLC to give 3-(2'-amino-1'-methyl-5'-oxo-2-phenyl-1',5'-dihydrospiro[chroman-4,4'-imidazole]-6-yl)-N-methylbenzenesulfonamide (5.88 mg, 24%). $^1$H-NMR (MeOD): 2.16 (m, 1H), 2.22 (m, 1H), 2.41 (m, 3H), 3.15 (m, 3H), 5.21 (m, 0.2H), 5.83 (m, 0.8H), 6.98 (m, 1H), 7.16 (m, 1H), 7.25 (m, 1H), 7.32 (m, 2H), 7.38 (m, 2H), 7.42 (m, 1H), 7.51 (m, 1H), 7.66 (m, 2H), 7.86 (m, 1H).

Example 43

2'-amino-1'-methyl-6-(4-(methylsulfonyl)phenyl)-2-phenylspir-o[chroman-4,4'-imidazol]-5'(1'H)-one (Compound 49)

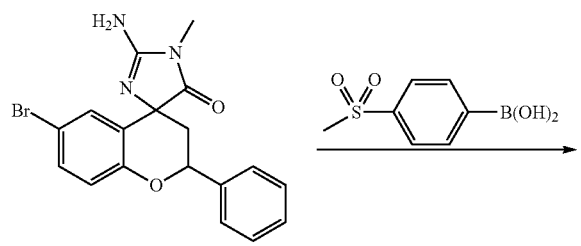

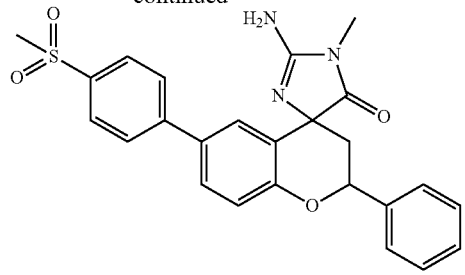

Pd(PPh$_3$)$_2$Cl$_2$ (10 mg) in a 10 mL tube under Ar was treated sequentially with 2'-amino-6-bromo-1'-methyl-2-phenyl-spiro[chroman-4,4'-imidazol]-5'(1'H)-one (20 mg, 0.052 mmol) in 1,4-dioxane (1 mL), Cs$_2$CO$_3$ (2 N, 0.3 mL) and 4-(methylsulfonyl)phenylboronic acid (20.8 mg, 0.1 mmol). The mixture was heated in a microwave reactor at 120° C. for 30 min. The reaction mixture was concentrated in vacuo to give the residue, which was purified by preparative TLC to give pure 2'-amino-1'-methyl-6-(4-(methylsulfonyl)phenyl)-2-phenylspir-o[chroman-4,4'-imidazol]-5'(1'H)-one (18 mg, 80%). $^1$H-NMR (CDCl$_3$+MeOD): 2.07 (dd, 1H), 2.41 (t, 1H), 3.01 (s, 3H), 3.12 (s, 3H), 5.25 (d, 0.5H), 5.89 (d, 1H), 6.90 (d, 1H), 7.31 (s, 2H), 7.32 (t, 2H), 7.39 (d, 3H), 7.60 (t, 2H), 7.87 (d, 2H).

Example 44

3-(2'-amino-1'-methyl-5'-oxo-2-phenyl-1',5'-dihydrospiro[chroman-4,4'-imidazole]-6-yl)-N-methylbenzamide (Compound 50)

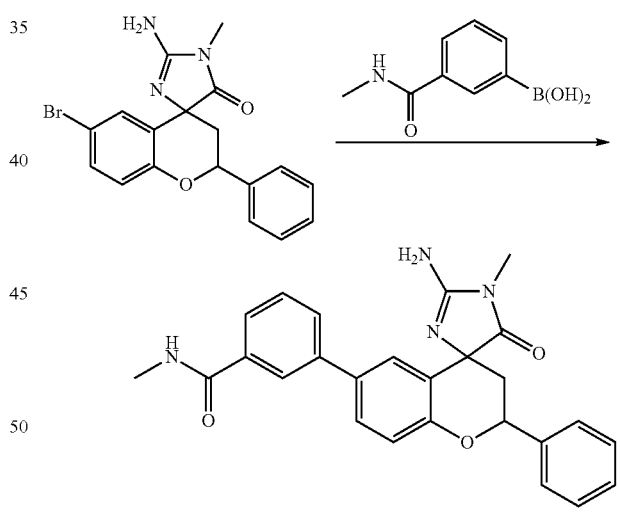

Pd(PPh$_3$)$_2$Cl$_2$ (10 mg) in a 10 mL CEM test tube under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(methylcarbamoyl)phenylboronic acid (18.6 mg, 0.104 mmol). The mixture was heated in a microwave reactor at 120° C. for 30 minutes. The reaction mixture was concentrated in vacuo to give the residue, which was purified by preparative TLC and preparative HPLC to give pure 3-(2'-amino-1'-methyl-5'-oxo-2-phenyl-1',5'-dihydrospiro[chroman-4,4'-imidazole]-6-yl)-N-methylbenzamide (0.96 mg, 4%). $^1$H-NMR (CDCl$_3$): 2.36 (d, 1H), 2.57 (t, 1H), 2.73 (s, 3H), 2.97 (s, 3H), 5.87 (d, 1H), 7.11 (m, 2H), 7.45 (m, 8H), 7.51 (m, 1H), 7.60 (s, 1H), 7.78 (s, 1H).

Example 45

N-(3-(2'-amino-1'-methyl-5'-oxo-2-phenyl-1',5'-dihydrospiro[chroman-4,4'-imidazole]-6-yl)phenyl)methanesulfonamide (Compound 52)

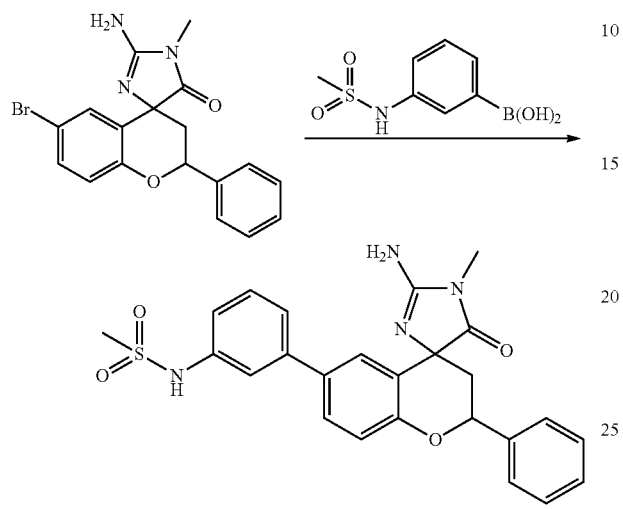

Pd(PPh$_3$)$_2$Cl$_2$ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 3-(methylsulfonamido)phenylboronic acid (22 mg, 0.104 mmol). The mixture was heated at 120° C. under Ar in a microwave reactor for 30 minutes. The reaction mixture was concentrated in vacuo to give the residue, which was purified by preparative TLC and HPLC to give N-(3-(2'-amino-1'-methyl-5'-oxo-2-phenyl-1',5'-dihydrospiro[chroman-4,4'-imidazole]-6-yl)phenyl)methanesulfonamide (0.91 mg, 4%). $^1$H-NMR (MeOD): 2.46 (m, 1H), 2.62 (m, 1H), 2.97 (s, 3H), 3.29 (s, 3H), 5.86 (m, 1H), 6.94 (m, 2H), 7.13 (m, 1H), 7.18 (m, 1H), 7.41 (m, 6H), 7.62 (m, 1H), 7.81 (m, 1H).

Example 46

2'-amino-6-bromo-2-(4-chlorophenyl)-1'-methylspiro[chroman-4,4'-imidazol]-5'(1'H)-one (Compound 53)

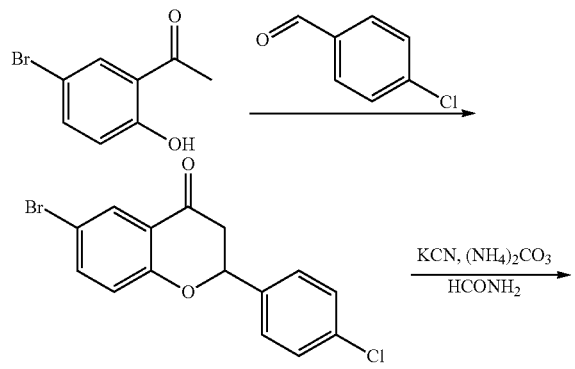

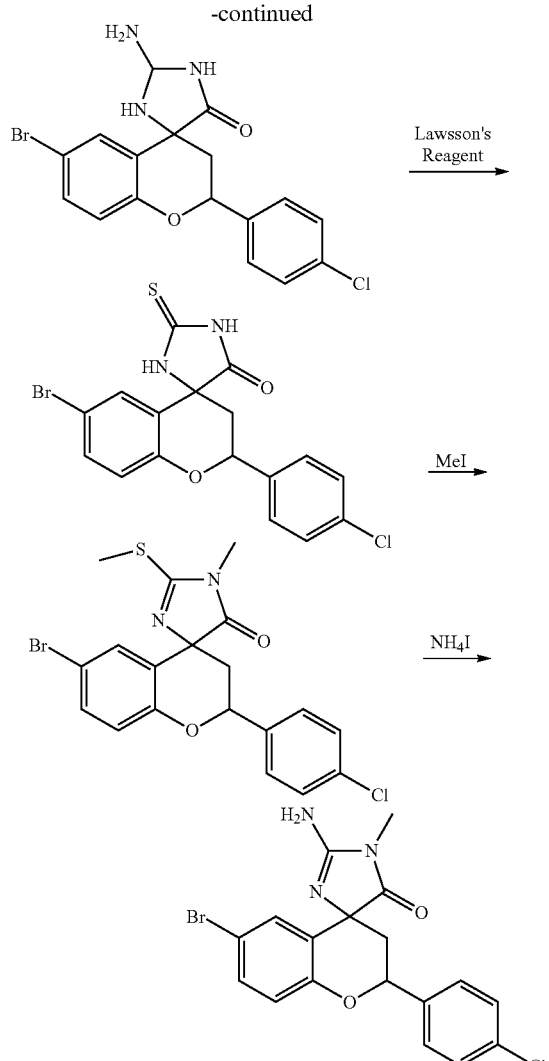

Step 1

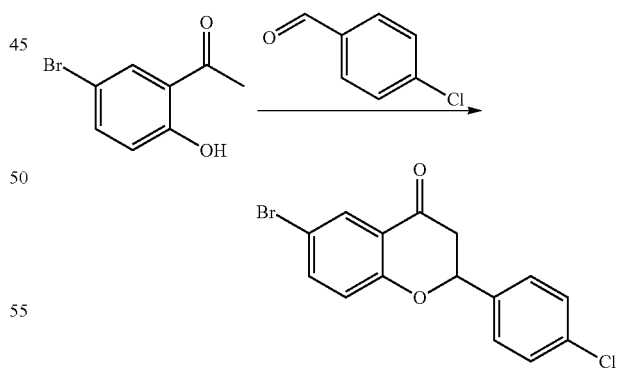

A mixture of 1-(5-bromo-2-hydroxy-phenyl)-ethanone (6 g, 28 mmol), 4-chloro-benzaldehyde (3.92 g, 28 mmol), and borax (10H$_2$O, 10.67 g, 28 mmol) in H$_2$O (60 mL) and EtOH (36 mL) was stirred at 110° C. overnight. The mixture was filtered to give a solid cake. The cake was dissolved in EtOAc and filtered. The filtrate was dried, filtered, and concentrated to give 6-bromo-2-(4-chloro-phenyl)-chroman-4-one (8.43 g, 89%). $^1$H-NMR (CDCl$_3$): 2.88 (m, 1H), 3.04 (m, 1H), 5.44 (m, 1H), 6.94 (m, 1H), 7.39 (m, 4H), 7.57 (m, 1H), 8.02 (m, 1H).

Step 2

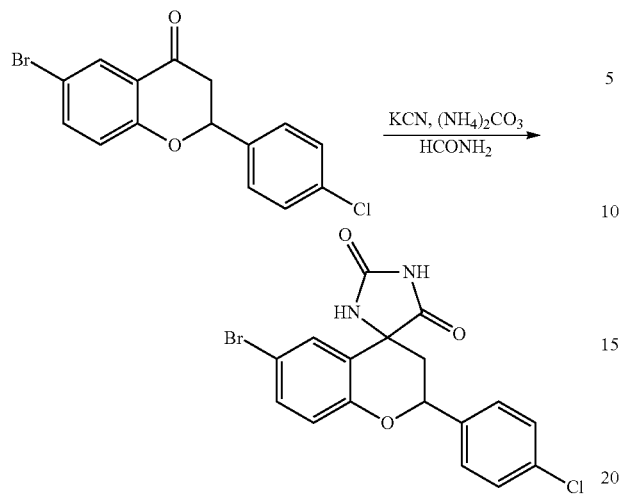

In a steel bomb, a mixture of 6-bromo-2-(4-chlorophenyl) chroman-4-one (4 g, 12 mmol), KCN (1.54 g, 24 mmol), and (NH$_4$)$_2$CO$_3$ (8.6 g, 90 mmol) in formamide (40 mL) was heated and stirred at 70° C. for 24 h and then at 110° C. for 2 days. The mixture was poured into ice/water. Concentrated HCl was added until pH=1. The mixture was filtered to give a solid cake and the filtrate was extracted with CH$_2$Cl$_2$. The organic layer was concentrated to give a residue, which was combined with the cake above. The solid was purified by column chromatography to give 6-bromo-2-(4-chlorophenyl) spiro[chroman-4,4'-imidazolidine]-2',5'-dione (600 mg, 12%).

Step 3

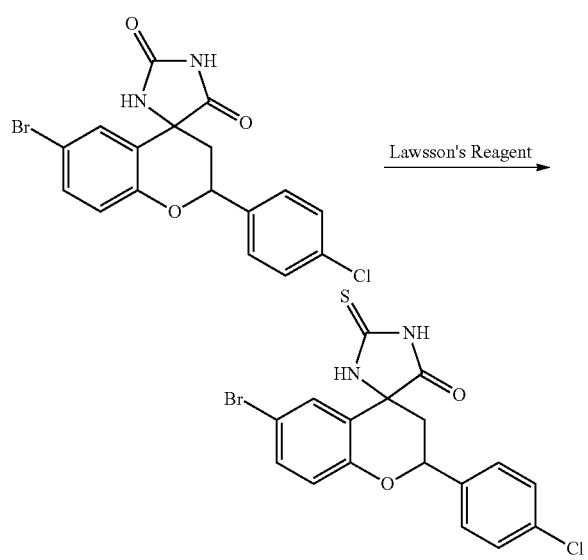

A mixture of 6-bromo-2-(4-chlorophenyl)spiro[chroman-4,4'-imidazolidine]-2',5'-dione (600 mg, 1.48 mmol) and Lawesson's Reagent (596 mg, 1.48 mmol) in 1,4-dioxane (25 mL) was stirred at 110° C. overnight. The solvent was removed in vacuo and the residue was purified by preparative TLC to give 6-bromo-2-(4-chlorophenyl)-2'-thioxospiro [chroman-4,4'-imidazolidin]-5'-one (450 mg, 69%).

$^1$H-NMR (MeOD): 2.24 (m, 1H), 2.45 (m, 1H), 6.82 (m, 1H), 6.91 (m, 1H), 7.20 (m, 1H), 7.44 (m, 5H).

Step 4

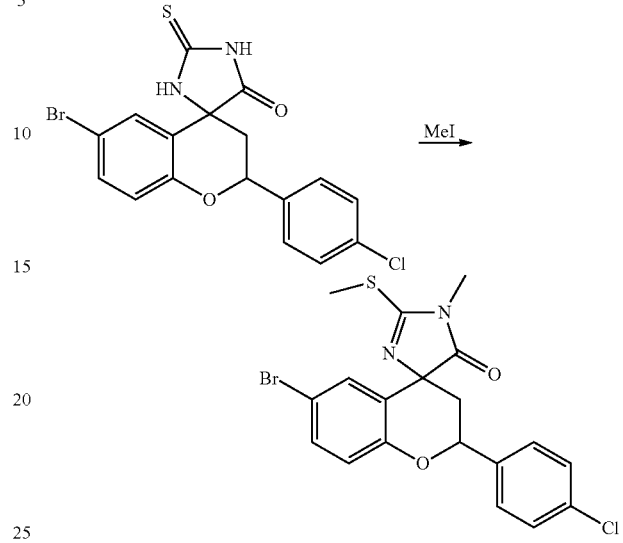

To a mixture of 6-bromo-2-(4-chlorophenyl)-2'-thioxospiro[chroman-4,4'-imidazolidin]-5'-one (450 mg, 1.07 mmol) and K$_2$CO$_3$ (588 mg, 4.27 mmol) in CH$_3$CN (10 mL) was added MeI (610 mg, 4.27 mmol). The reaction mixture was refluxed for 2 h. The mixture was filtered, and the filtrate was concentrated to give a residue, which was purified by preparative TLC to give 6-bromo-2-(4-chlorophenyl)-1'-methyl-2'-(methylthio)spiro[chroman-4,4'-imidazol]-5'(1'H)-one (325 mg, 37%). $^1$H-NMR (CDCl$_3$): 1.89 (m, 1H), 2.41 (m, 1H), 2.56 (t, 3H), 3.17 (m, 3H), 5.81 (m, 1H), 6.79 (m, 2H), 7.23 (m, 1H), 7.43 (m, 4H).

Step 5

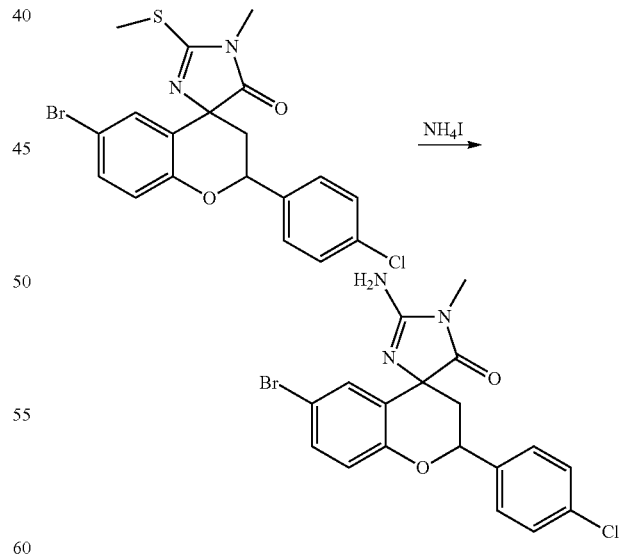

A solution of 6-bromo-2-(4-chlorophenyl)-1'-methyl-2'-(methylthio)spiro[chroman-4,4'-imidazol]-5'(1'H)-one (300 mg, 0.67 mmol) and NH$_4$I (194 mg, 1.33 mmol) in NH$_3$/EtOH (5 mL, 1.5 N) was heated at 110° C. in a tube in a microwave reactor for 2-2.5 h. After cooling, the mixture was concentrated in vacuo to give a residue, which was purified by preparative TLC to afford 2'-amino-6-bromo-2-(4-chlorophenyl)-1'-methylspiro[chroman-4,4'-imidazol]-5'(1'H)-one (35 mg, 12%). ¹H-NMR (MeOD): 2.19 (m, 1H), 2.41 (m, 1H), 3.11 (m, 3H), 5.15 (m, 0.5H), 5.38 (m, 0.5H), 6.78 (m, 1H), 6.82 (m, 0.5H), 7.02 (m, 0.5H), 7.23 (m, 1H), 7.31 (m, 3H), 7.44 (m, 1H).

Example 47

2'-amino-6-(4-(methoxymethyl)phenyl)-1'-methyl-2-phenylspiro[chroman-4,4'-imidazol]-5'(1'H)-one (Compound 54)

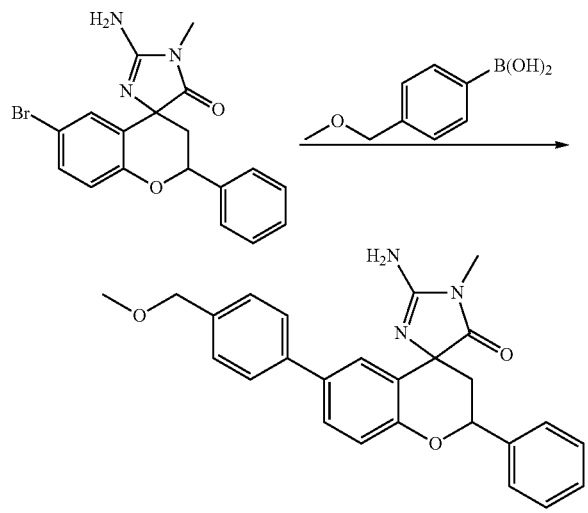

Pd(PPh₃)₂Cl₂ (10 mg) in a 10 mL tube under Ar was treated sequentially with 2'-amino-6-bromo-1'-methyl-2-phenyl-spiro[chroman-4,4'-imidazol]-5'(1'H)-one (20 mg, 0.052 mmol) in 1,4-dioxane (1 mL), Cs₂CO₃ (2 N, 0.3 mL) and 4-(methoxymethyl)phenylboronic acid (16.6 mg, 0.1 mmol). The mixture was heated at 120° C. in a microwave reactor for 30 minutes. The reaction mixture was concentrated in vacuo to give the residue, which was purified by preparative TLC to give pure 2'-amino-6-(4-(methoxymethyl)phenyl)-1'-methyl-2-phenylsp-iro[chroman-4,4'-imidazol]-5'(1'H)-one (3.8 mg, 15%). ¹H-NMR (MeOD): 2.10 (t, 1H), 2.24 (t, 1H), 3.01 (s, 3H), 3.27 (s, 3H), 4.17 (m, 2H), 5.81 (d, 1H), 6.90 (m, 2H), 7.12 (d, 2H), 7.27 (m, 3H), 7.49 (m, 5H).

Example 48

3-((2R,4S)-2'-amino-1'-methyl-5'-oxo-2-phenyl-1',5'-dihydrospiro[chroman-4,4'-imidazole]-6-yl)-N-butylbenzamide (Compound 55a) and 3-((2S,4S)-2'-amino-1'-methyl-5'-oxo-2-phenyl-1',5'-dihydrospiro[chroman-4,4'-imidazole]-6-yl)-N-butylbenzamide (Compound 55b)

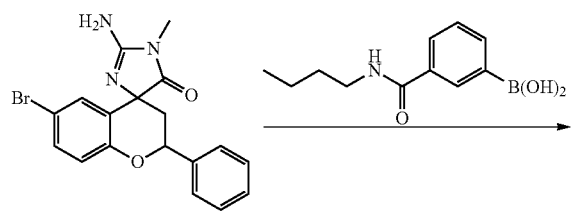

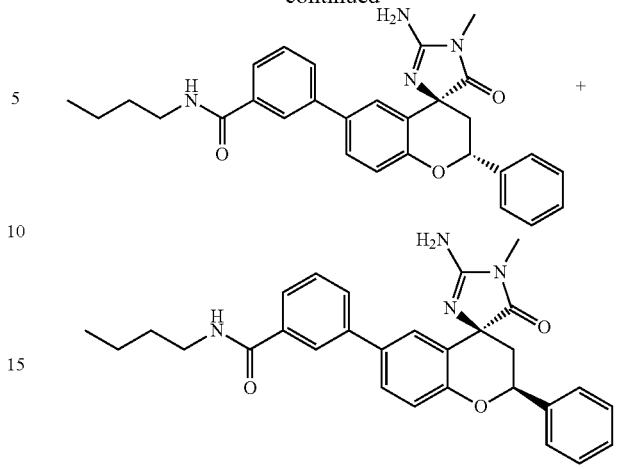

Pd(PPh₃)₂Cl₂ (10 mg) in a 10 mL CEM test tube under Ar was treated sequentially with 2'-amino-6-bromo-1'-methyl-2-phenylspiro[chroman-4,4'-imidazol]-5'(1'H)-one (20 mg, 0.05 mmol) in 1,4-dioxane (1 mL), Cs₂CO₃ (2 N, 0.3 mL) and 3-(butylcarbamoyl)phenylboronic acid (23 mg, 0.1 mmol). The mixture was heated in a microwave reactor at 120° C. for 30 mins. The reaction mixture was concentrated in vacuo to give the residue, which was purified by preparative TLC to give pure 3-(2'-amino-1'-methyl-5'-oxo-2-phenyl-1',5'-dihydrospiro-[chroman-4,4'-imidazole]-6-yl)-N-butylbenzamide (12.4 mg, 50%). cis (2.50 mg, 10%). ¹H-NMR (MeOD): 0.95 (m, 3H), 1.42 (m, 2H), 1.60 (m, 2H), 2.14 (d, 1H), 2.31 (t, 1H), 3.33 (s, 3H), 3.36 (d, 2H), 5.88 (d, 1H), 7.04 (d, 1H), 7.24 (s, 1H), 7.37 (m, 1H), 7.41 (t, 2H), 7.48 (d, 3H), 7.53 (d, 1H), 7.66 (d, 1H), 7.69 (d, 1H), 7.94 (s, 1H). trans (9.91 mg, 40%). ¹H-NMR (MeOD): 0.96 (t, 3H), 1.43 (m, 2H), 1.61 (m, 2H), 2.03 (d, 1H), 2.52 (t, 1H), 3.33 (s, 3H), 3.39 (d, 2H), 5.30 (d, 1H), 7.05 (d, 1H), 7.25 (s, 1H), 7.39 (m, 1H), 7.42 (t, 2H), 7.47 (d, 3H), 7.53 (d, 1H), 7.67 (d, 1H), 7.70 (d, 1H), 7.93 (s, 1H).

Example 49

2'-amino-1'-methyl-2-phenyl-6-(4-(trifluoro methyl)phenyl)spiro[chroman-4,4'-imidazol]-5'(1'H)-one (Compound 56)

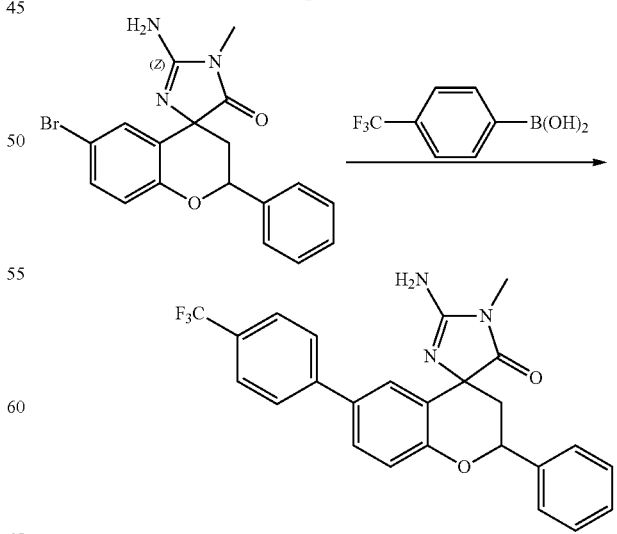

Pd(PPh₃)₂Cl₂ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 4-(trifluoromethyl)phenylboronic acid (20 mg, 0.104 mmol). The mixture was heated at 120° C. under Ar in a microwave reactor for 30 minutes. The reaction mixture was concentrated in vacuo to give the residue, which was purified by preparative HPLC twice to give pure 2'-amino-1'-methyl-2-phenyl-6-(4-(trifluoro methyl)phenyl)spiro[chroman-4,4'-imidazol]-5'(1'H)-one (2.87 mg, 12%). $^1$H-NMR (MeOD): 2.46 (m, 1H), 2.60 (m, 1H), 3.32 (s, 3H), 5.25 & 5.85 (m, 1H), 7.14 (m, 1H), 7.37-7.54 (m, 6H), 7.66-7.78 (m, 5H).

Example 50

2'-amino-6-bromo-2-phenyl-1'-propylspiro[chroman-4,4'-imidazol]-5'(1'H)-one (Compound 57)

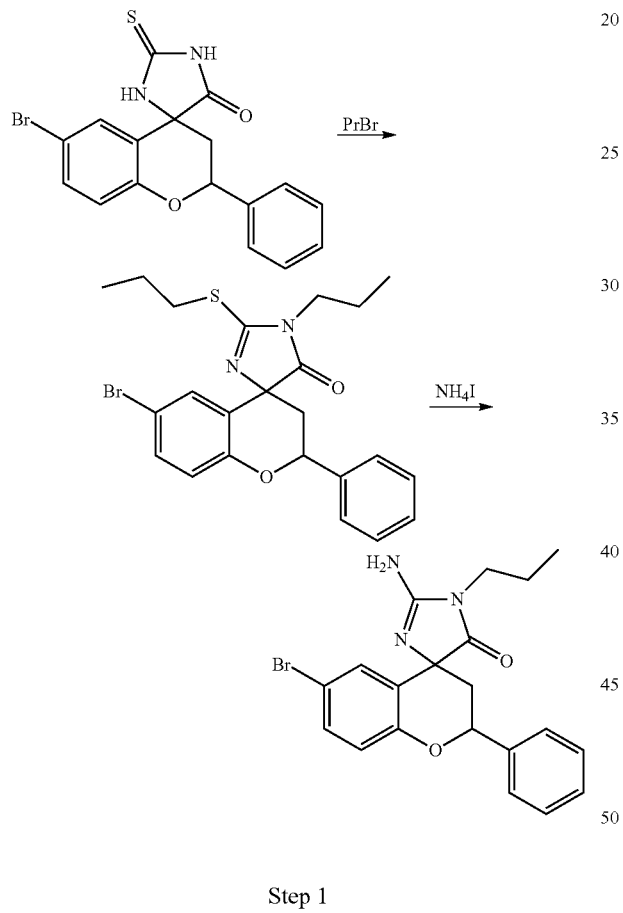

Step 1

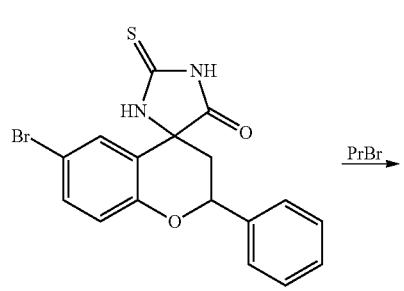

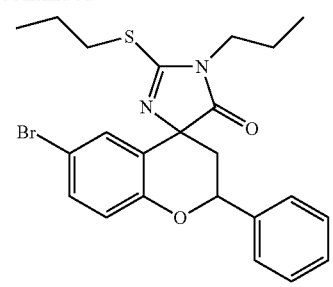

To a mixture of 6-bromo-2-phenyl-2'-thioxospiro[chroman-4,4'-imidazolidin]-5'-one (300 mg, 0.77 mmol) and K$_2$CO$_3$ (427 mg, 3.1 mmol) in CH$_3$CN (6 mL) was added PrBr (380 mg, 3.1 mmol). The reaction mixture was refluxed for 2 h. The mixture was filtered, and the filtrate was concentrated to give a residue, which was purified by preparative TLC to give 6-bromo-2-phenyl-1'-propyl-2'-(propylthio)spiro[chroman-4,4'-imidazol]-5'(1'H)-one (285 mg, 90%). $^1$H-NMR (CDCl$_3$): 0.87 (m, 3H), 1.00 (m, 3H), 1.64 (m, 2H), 1.73 (m, 2H), 1.89 (m, 1H), 2.48 (m, 1H), 3.16 (m, 2H), 3.44 (m, 2H), 5.82 (m, 1H), 6.81 (m, 2H), 7.22 (m, 1H), 7.30 (m, 3H), 7.48 (m, 2H).

Step 2

A solution of 6-bromo-2-phenyl-1'-propyl-2'-(propylthio)spiro[chroman-4,4'-imidazol]-5'(1'H)-one (280 mg, 0.6 mmol) and NH$_4$I (172 mg, 1.2 mmol) in NH$_3$/EtOH (4 mL, 1.5 N) was heated at 110° C. in a tube in a microwave reactor for 2-2.5 h. After cooling, the mixture was concentrated in vacuo to give a residue, which was purified by preparative TLC to afford 2'-amino-6-bromo-2-phenyl-1'-propylspiro[chroman-4,4'-imidazol]-5'(1'H)-one (45 mg, 18%). $^1$H-NMR (MeOD): 0.93 (m, 3H), 1.66 (m, 2H), 2.04 (m, 1H), 2.25 (m, 1H), 3.56 (m, 2H), 5.83 (m, 1H), 6.87 (m, 1H), 7.06 (m, 1H), 7.31 (m, 2H), 7.40 (m, 4H).

Example 50a (2R,4S)-2'-amino-6-bromo-2-phenyl-1'-propylspiro[chroman-4,4'-imidazol]-5'(1'H)-one (Compound 57a)

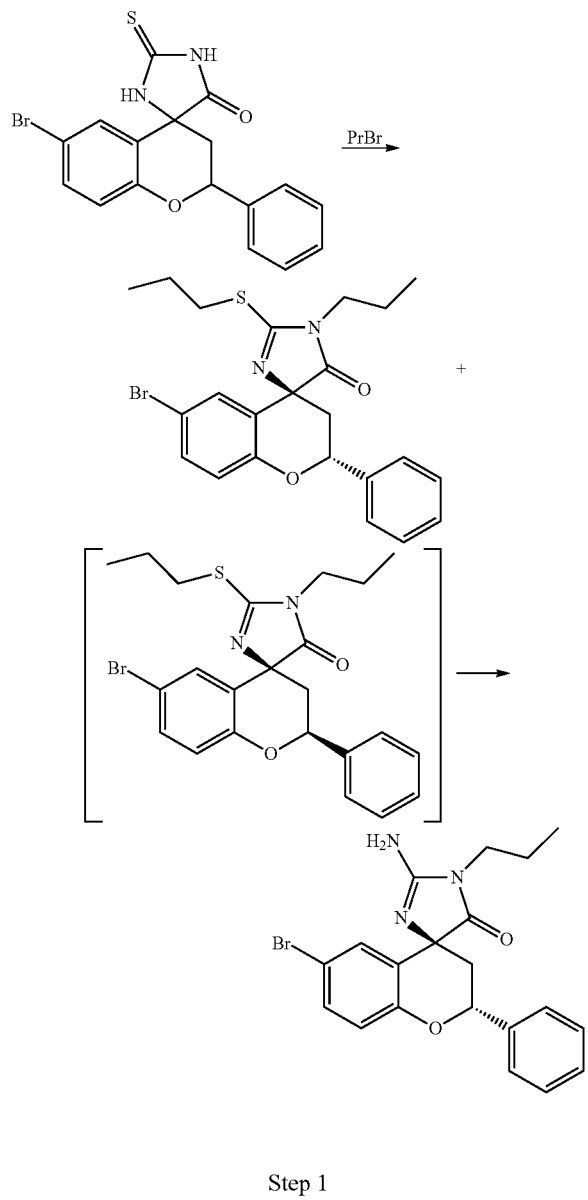

Step 1

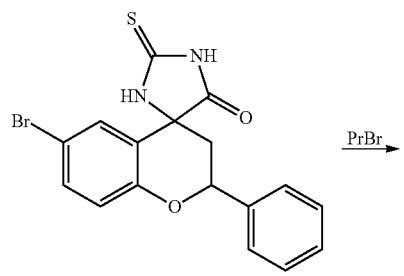

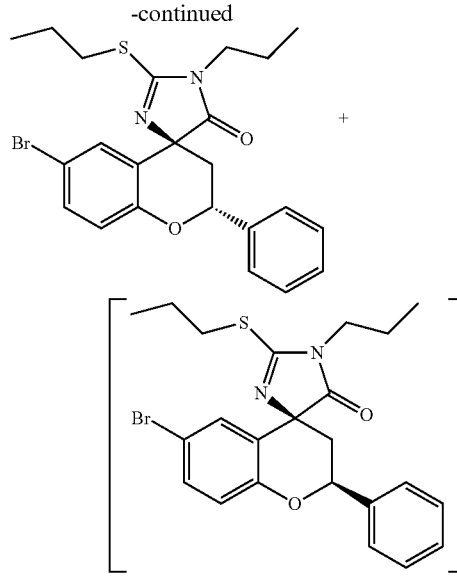

To a mixture of 6-bromo-2-phenyl-2'-thioxospiro[chroman-4,4'-imidazolidin]-5'-one (131 mg, 0.34 mmol) and K$_2$CO$_3$ (186 mg, 1.35 mmol) in CH$_3$CN (5 mL) was added PrBr (166 mg, 1.35 mmol). The reaction mixture was refluxed for 2 h. The mixture was filtered, and the filtrate was concentrated to give a residue, which was purified by preparative TLC to give (2R,4S)-6-bromo-2-phenyl-1'-propyl-2'-(propylthio)spiro[chroman-4,4'-imidazol]-5'(1'H)-one (75 mg, 47%).

Step 2

A solution of (2R,4S)-6-bromo-2-phenyl-1'-propyl-2'-(propylthio)spiro[chroman-4,4'-imidazol]-5'(1'H)-one (75 mg, 0.16 mmol), and NH$_4$I (46 mg, 0.32 mmol) in NH$_3$/EtOH (4 mL, 1.5 N) was heated at 110° C. in a tube in a microwave reactor for 2-2.5 h. After cooling, the mixture was concentrated in vacuo to give a residue, which was purified by preparative TLC to afford (2R,4S)-2'-amino-6-bromo-2-phenyl-1'-propylspiro-[chroman-4,4'-imidazol]-5'(1'H)-one (15 mg, 23%). $^1$H-NMR (MeOD): 1.00 (m, 3H), 1.45 (m, 2H), 2.23 (m, 1H), 2.48 (m, 1H), 3.75 (m, 2H), 5.85 (m, 1H), 6.90 (m, 1H), 7.14 (m, 1H), 7.40 (m, 6H).

Example 51

2'-amino-1'-methyl-2-phenyl-6-(pyridin-4-yl)spiro[chroman-4,4'-imidazol]-5'(1'H)-one (Compound 58)

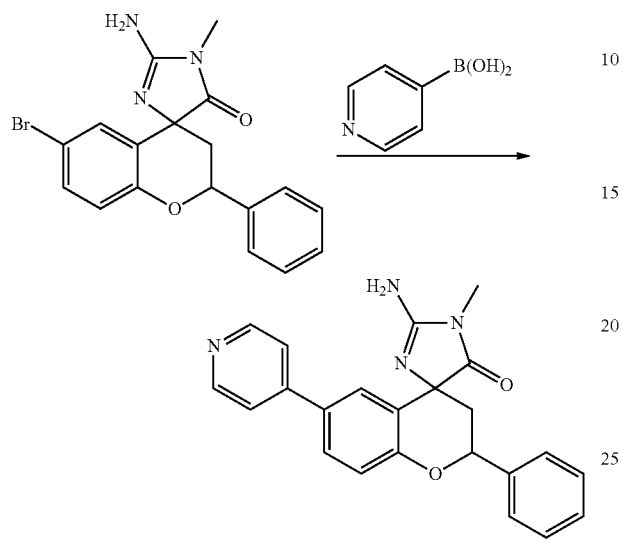

Pd(PPh$_3$)$_2$Cl$_2$ (10 mg) in a 10 mL tube under Ar was treated sequentially with 2'-amino-6-bromo-1'-methyl-2-phenyl-spiro[chroman-4,4'-imidazol]-5'(1'H)-one (20 mg, 0.052 mmol) in 1,4-dioxane (1 mL), Cs$_2$CO$_3$ (2 N, 0.3 mL) and pyridin-4-ylboronic acid (13 mg, 0.1 mmol). The mixture was heated in a microwave reactor at 120° C. for 30 min. The reaction mixture was concentrated in vacuo to give the residue, which was purified by preparative TLC and then by preparative HPLC to give pure 2'-amino-1'-methyl-2-phenyl-6-(pyridin-4-yl)spiro[chroman-4,4'-imidazol]-5'(1'H)-one (2.51 mg, 10%). $^1$H-NMR (MeOD): 2.50 (t, 1H), 2.64 (dd, 1H), 3.37 (s, 3H), 5.91 (d, 1H), 7.26 (d, 1H), 7.45 (m, 5H), 7.82 (d, 1H), 7.94 (t, 1H), 8.16 (s, 2H), 8.71 (s, 2H).

Example 52

2'-amino-6-bromo-1'-(2-cyclopropylethyl)-2-phenyl-spiro[chroman-4,4'-imidazol]-5'(1'H)-one (Compound 59)

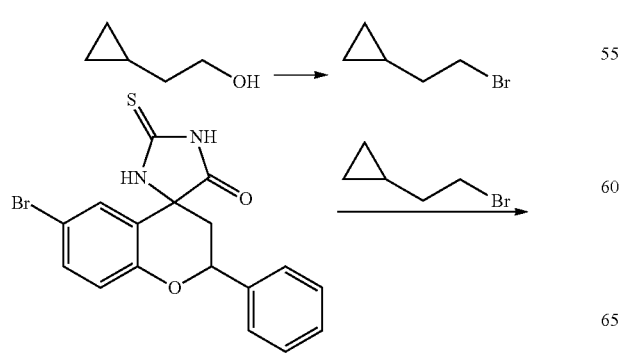

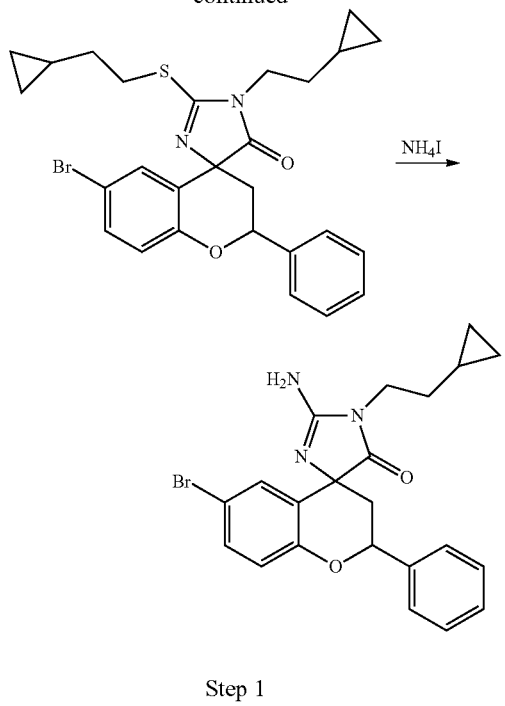

Step 1

A mixture of 2-cyclopropylethanol (2 g, 0.023 mol) and pyridine (0.51 g, 0.006 mol) was added dropwise with magnetic stirring over 2 hours to PBr$_3$ (2.5 g, 0.009 mol) at 0° C. Then ether was added and the mixture was washed with an aqueous NaHCO$_3$ solution and brine. The organic layer was dried over Na$_2$SO$_4$ and concentrated in vacuo to give (2-bromoethyl)cyclopropane (1.3 g, 38%). $^1$H-NMR (CDCl$_3$): 0.01 (m, 2H), 0.40 (m, 2H), 0.69 (m, 1H), 1.51 (m, 2H), 4.08 (m, 2H).

Step 2

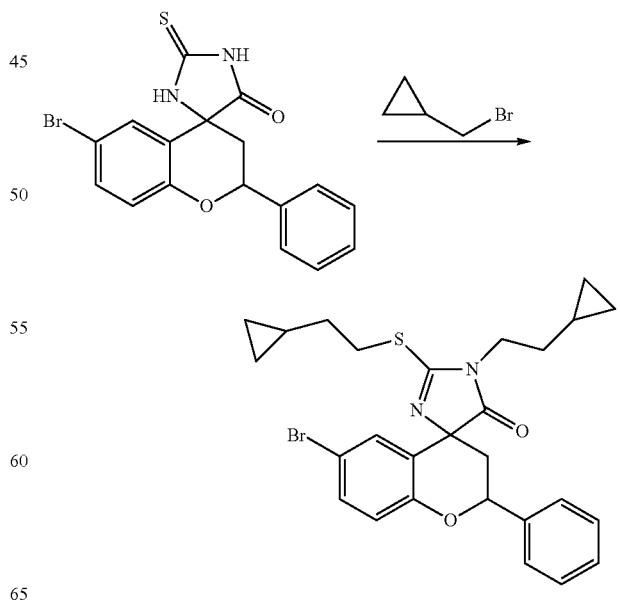

A mixture of 6-bromo-2-phenyl-2'-thioxospiro[chroman-4,4'-imidazolidin]-5'-one (250 mg, 0.644 mmol), excess (2-bromoethyl)cyclopropane (381 mg, 2.58 mmol), and solid K₂CO₃ (356 mg, 2.58 mmol) in CH₃CN (10 mL) was stirred for 4 hours at 60° C. The mixture was filtered and the filtrate was concentrated. The crude product was purified by preparative TLC to give 6-bromo-1'-(2-cyclopropylethyl)-2'-(2-cyclopropylethylthio)-2-phenylspiro[chroman-4,4'-imidazol]-5'(1'H)-one (40 mg, 11%).

Step 3

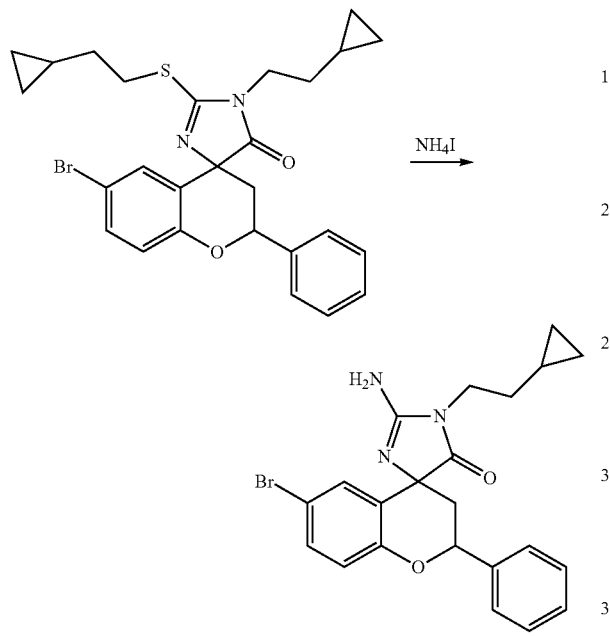

A solution of 6-bromo-1'-(2-cyclopropylethyl)-2'-(2-cyclopropylethylthio)-2-phenylspiro[chroman-4,4'-imidazol]-5'(1'H)-one (40 mg, 0.076 mmol), and NH₄I (22 mg, 0.153 mmol) in a solution of NH₃/EtOH (4 mL, 1.5 N) was heated at 110° C. in a tube in a microwave reactor for 2-2.5 h. After cooling, the mixture was concentrated in vacuo to give a residue, which was purified by preparative TLC to afford 2'-amino-6-bromo-1'-(2-cyclopropylethyl)-2-phenylspiro[chroman-4,4'-imidazol]-5'(1'H)-one (8 mg, 24%). ¹H-NMR (MeOD): 0.01 (m, 2H), 0.34 (m, 2H), 0.61 (m, 1H), 1.48 (m, 2H), 2.10 (m, 1H), 2.37 (m, 1H), 3.67 (m, 2H), 5.12 (d, 0.3H), 5.74 (d, 0.7H), 6.70 (m, 1H), 7.00 (m, 1H), 7.31 (m, 6H).

Example 53

4-(2'-amino-1'-methyl-5'-oxo-2-phenyl-1',5'-dihydrospiro[chroman-4,4'-imidazole]-6-yl)-N-isobutylbenzamide (Compound 60)

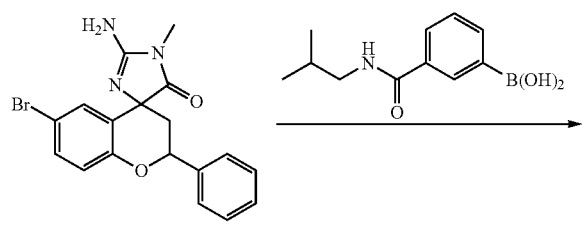

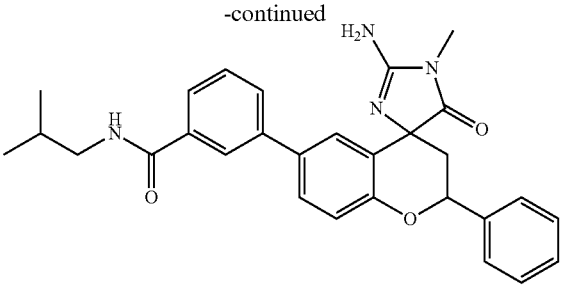

Pd(PPh₃)₂Cl₂ (10 mg) in a 10 mL CEM test tube under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs₂CO₃ (2 N, 0.3 mL) and 4-(isobutylcarbamoyl)-phenyl-boronic acid (23 mg, 0.1 mmol). The mixture was heated at 120° C. in a microwave reactor for 30 mins. The reaction mixture was concentrated in vacuo to give the residue, which was purified by preparative TLC to give pure 4-(2'-amino-1'-methyl-5'-oxo-2-phenyl-1',5'-dihydrospiro[chroman-4,4'-imidazole]-6-yl)-N-isobutylbenzamide (1.28 mg, 5%). ¹H-NMR (MeOD): 0.96 (d, 6H), 1.94 (m, 1H), 2.15 (d, 1H), 2.47 (t, 1H), 3.29 (s, 3H), 3.31 (s, 1H), 3.32 (s, 1H), 5.30 (d, 1H), 7.06 (t, 2H), 7.33 (m, 1H), 7.42 (t, 2H), 7.48 (d, 3H), 7.53 (d, 1H), 7.66 (d, 1H), 7.72 (d, 1H), 7.91 (s, 1H).

Example 54

2'-amino-1'-methyl-2-phenyl-6-(3-(pyrrolidine-1-carbonyl)phenyl)spiro[chroman-4,4'-imidazol]-5'(1'H)-one (Compound 61)

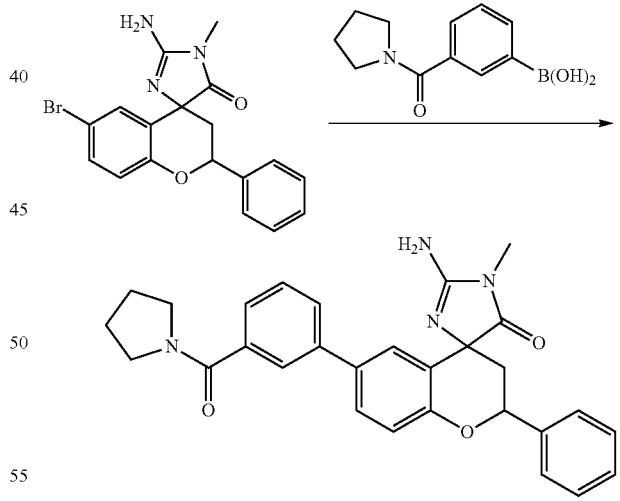

Pd(PPh₃)₂Cl₂ (10 mg) in a 10 mL of tube under Ar₂ was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs₂CO₃ (2 N, 0.3 mL) and 3-(pyrrolidine-1-carbonyl)phenylboronic acid (10 mg, 0.045 mmol). The mixture was heated at 120° C. in a microwave reactor for 0.5 h. The reaction mixture was concentrated in vacuo to give the residue, which was purified by preparative TLC to give pure 2'-amino-1'-methyl-2-phenyl-6-(3-(pyrrolidine-1-carbonyl)phenyl)spiro[chroman-4,4'-imidazol]-5'(1'H)-one (2.10 mg, 8%). $^1$H-NMR (MeOD): 1.82 (m, 2H), 1.91 (m, 2H), 2.04 (m, 1H), 2.21 (m, 1H), 3.02 (s, 3H), 3.39 (t, 2H), 3.52 (t, 2H), 5.82 (d, 1H), 6.95 (d, 1H), 7.15 (m, 1H), 7.27 (m, 1H), 7.34 (m, 3H), 7.46 (m, 4H), 7.54 (m, 2H).

Example 55

N-(4-(2'-amino-1'-methyl-5'-oxo-2-phenyl-1',5'-dihydrospiro[chroman-4,4'-imidazole]-6-yl)benzyl)methanesulfonamide (Compound 62)

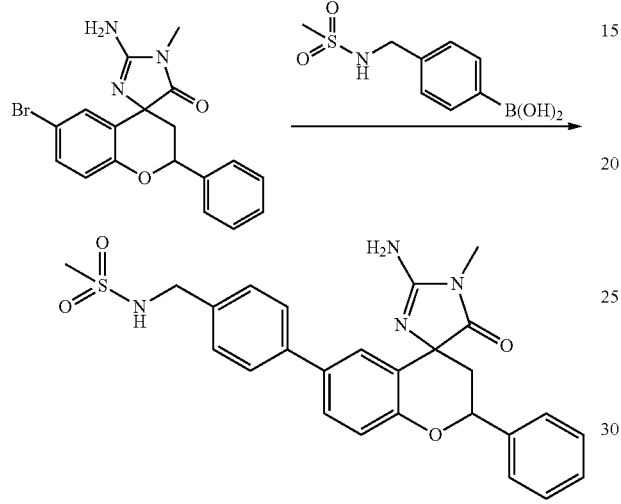

Pd(PPh$_3$)$_2$Cl$_2$ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 4-(methylsulfonamidomethyl)phenylboronic acid (24 mg, 0.104 mmol). The mixture was heated at 120° C. under Ar in a microwave reactor for 30 minutes. The reaction mixture was concentrated in vacuo to give the residue, which was purified by preparative TLC to give N-(4-(2'-amino-1'-methyl-5'-oxo-2-phenyl-1',5'-dihydrospiro[chroman-4,4'-imidazole]-6-yl)benzyl)methanesulfonamide (4.26 mg, 17%). $^1$H-NMR (MeOD): 2.06 (m, 1H), 2.22 (m, 1H), 2.76 (s, 3H), 3.04 (s, 3H), 4.17 (s, 2H), 5.80 (m, 1H), 6.92 (m, 1H), 7.10 (m, 1H), 7.24 (m, 1H), 7.32 (m, 4H), 7.37 (m, 2H), 7.39 (m, 2H), 7.41 (m, 1H).

Example 56

2'-amino-6-bromo-2-(2-fluorophenyl)-1'-methyl-spiro-[chroman-4,4'-imidazol]-5'(1'H)-one (Compound 63)

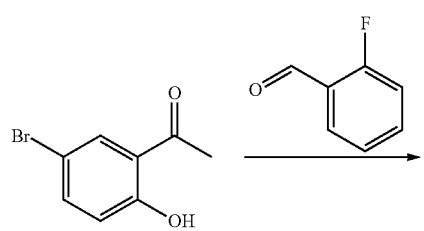

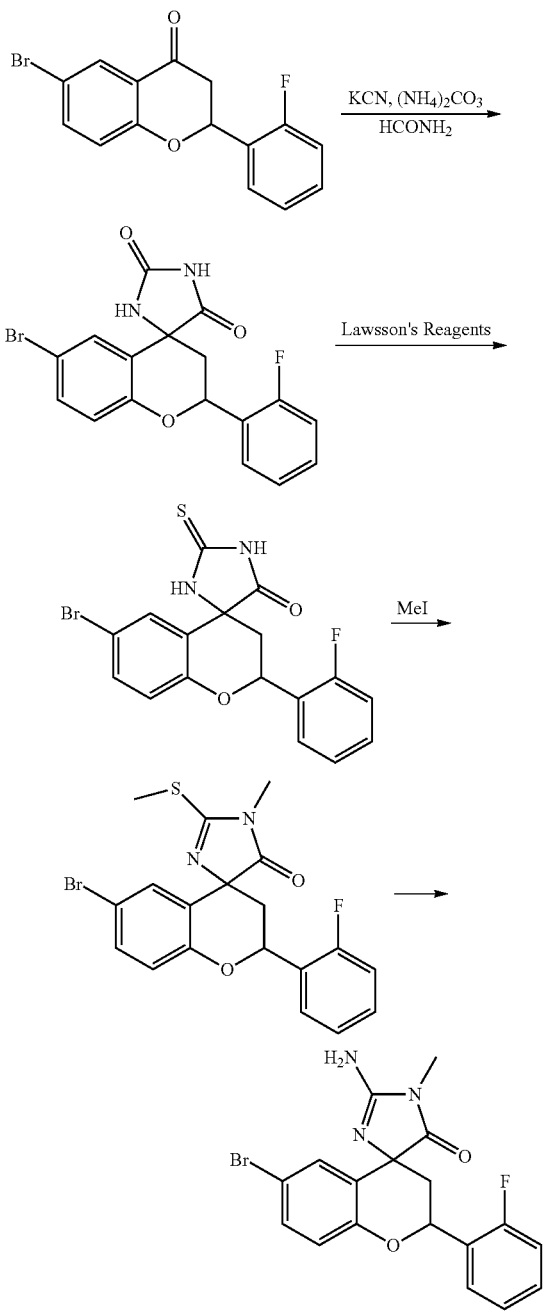

Step 1

-continued

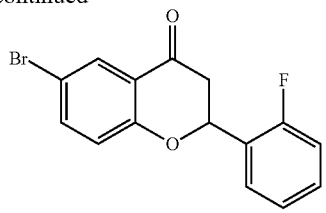

A mixture of 1-(5-bromo-2-hydroxy-phenyl)-ethanone (15 g, 70.1 mmol), 2-fluorobenzaldehyde (8.7 g, 70.1 mmol), and borax (26.7 g, 70.1 mmol) in ethanol (90 mL) and H$_2$O (150 mL) was refluxed for one day. The reaction mixture was cooled, diluted with an equal volume of H$_2$O, and extracted with ether. The ether was dried over anhydrous Na$_2$SO$_4$, filtered, and evaporated to give 6-bromo-2-(2-fluorophenyl) chroman-4-one (15 g, 50%).

Step 2

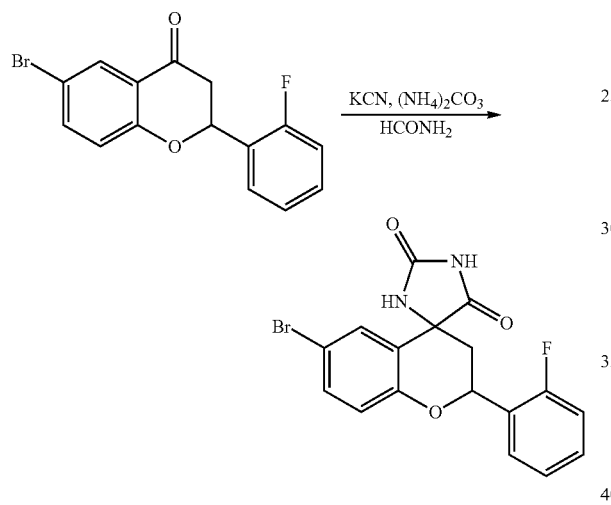

A steel bomb was charged with a mixture of 6-bromo-2-(2-fluorophenyl)chroman-4-one (2 g, 6.25 mmol), KCN (0.82 g, 12.5 mmol), and (NH$_4$)$_2$CO$_3$ (4.5 g, 46.87 mmol). Formamide (25 mL) was added to fill the steel bomb nearly completely. The mixture was heated at 70° C. for 48 h then at 110° C. for another 12 h. The reaction mixture was then cooled and poured over ice. Acidification with concentrated HCl yielded a precipitate which was filtered, washed twice with water, and then dissolved in ethyl acetate, dried over Na$_2$SO$_4$, and filtered. The filtrate was concentrated in vacuo to give a residue, which was purified by column to give 6-bromo-2-(2-fluorophenyl)spiro[chroman-4,4'-imidazolidine]-2',5'-dione (250 mg, 10%).

Step 3

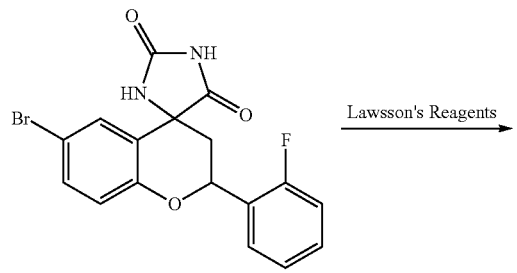

-continued

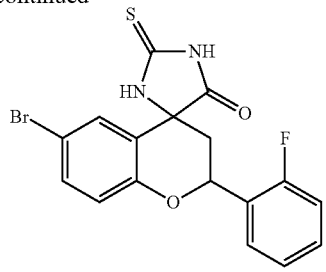

A suspension of 6-bromo-2-(2-fluorophenyl)spiro[chroman-4,4'-imidazolidine]-2',5'-dione (250 mg, 0.64 mmol) and Lawesson's Reagent (259 mg, 0.64 mmol) in anhydrous 1,4-dioxane (20 mL) was heated under reflux for 24 h. The mixture was concentrated in vacuo and the residue was purified by preparative TLC to give 6-bromo-2-(2-fluorophenyl)-2'-thioxospiro-[chroman-4,4'-imidazolidin]-5'-one (180 mg, 67%).

Step 4

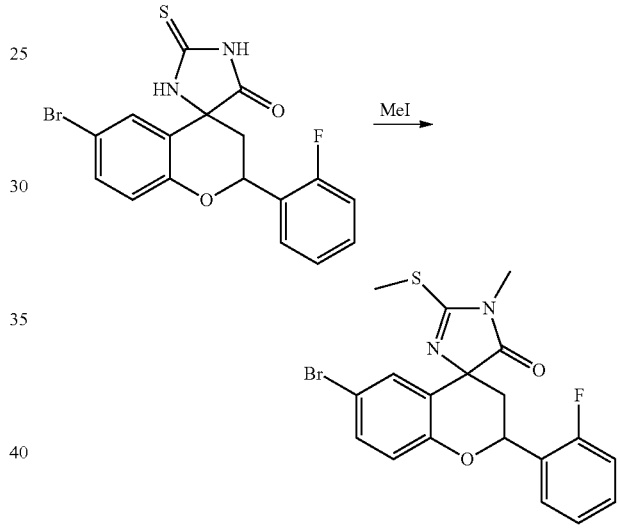

To a solution of 6-bromo-2-(2-fluorophenyl)-2'-thioxospiro[chroman-4,4'-imidazolidin]-5'-one (180 mg, 0.443 mmol) in MeOH (10 mL) was added a solution of NaOH (35.46 mg, 0.887 mmol) in H$_2$O (2 mL). After stirring for 10 minutes, MeI (951 mg, 6.65 mmol) was added. The reaction mixture was refluxed for 2 h. The mixture was concentrated in vacuo to give a residue, which was purified by preparative TLC to give 6-bromo-2-(2-fluorophenyl)-1'-methyl-2'-(methylthio)spiro[chroman-4,4'-imidazol]-5'(1'H)-one (80 mg, 41%).

Step 5

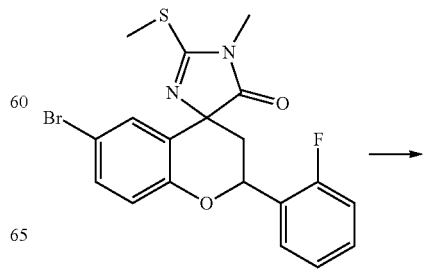

-continued

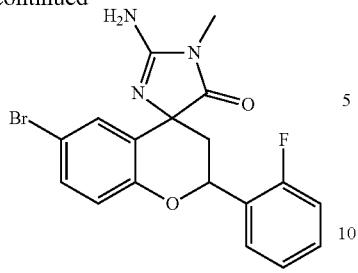

A solution of 6-bromo-2-(2-fluorophenyl)-1'-methyl-2'-(methylthio)spiro-[chroman-4,4'-imidazol]-5'(1'H)-one (80 mg, 0.183 mmol) and NH$_4$I (53.21 mg, 0.367 mmol) in NH$_3$/EtOH (2 mL, 1.5 N) was heated at 110° C. in a tube in a microwave reactor for 3 h. After cooling, the mixture was concentrated in vacuo to give a residue, which was purified by preparative TLC to afford 2'-amino-6-bromo-2-(2-fluorophenyl)-1'-methylspiro-[chroman-4,4'-imidazol]-5'(1'H)-one (52 mg, 70%).

$^1$H-NMR (MeOD): 2.15 (d, 1H), 2.25 (d, 1H), 3.20 (s, 3H), 6.15 (d, 1H), 6.78 (d, 1H), 6.99 (t, 1H), 7.05 (s, 1H), 7.15 (t, 1H), 7.25 (d, 2H), 7.50 (t, 1H).

Example 57

2'-amino-1',6-dimethyl-2-phenylspiro[chroman-4,4'-imidizol]-5'(1'H)-one (Compound 64)

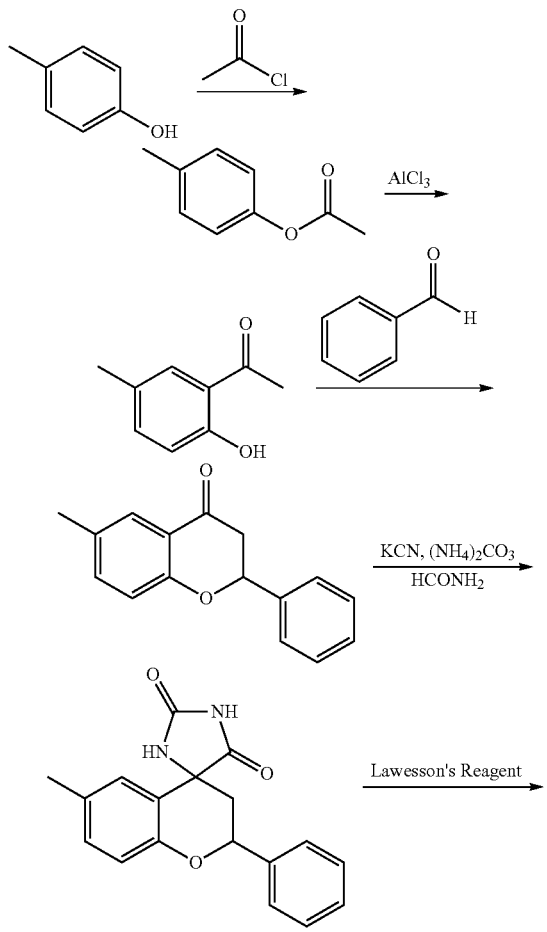

-continued

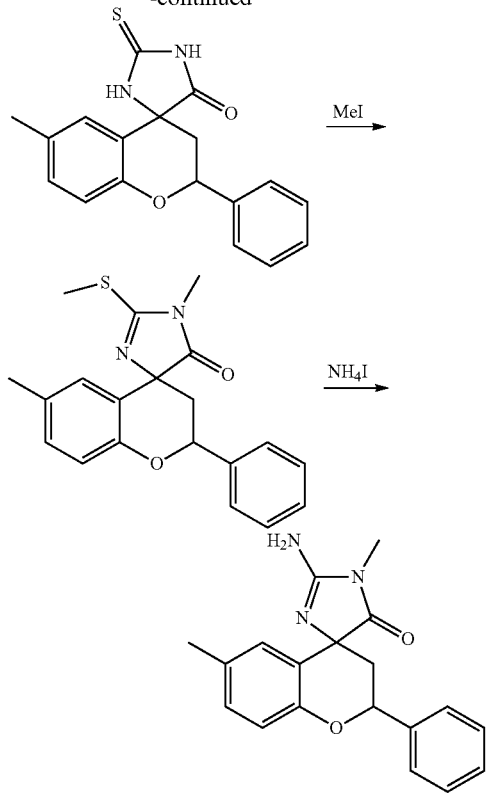

Step 1

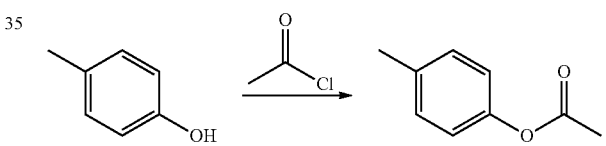

Anhydrous aluminum chloride (88 g, 0.66 mol) was suspended in methylene chloride (1500 mL), and then acetyl chloride (51.5 g, 0.66 mol) was added while stirring and cooling on ice. The mixture was stirred for 20 minutes while cooling on ice and 4-methylphenol (50 g, 0.46 mol) was added. The reaction mixture was stirred at room temperature for 1 h, and then poured into ice water slowly to quench the reaction. After extraction with ethyl acetate, the organic layer was washed with brine and then dried over anhydrous sodium sulfate. After distilling off the solvent under reduced pressure, the residue was purified by silica gel column chromatography to yield acetic acid 4-methyl-phenyl ester (52.6 g, 76%).
$^1$H-NMR (CDCl$_3$): 2.25 (s, 3H), 2.36 (s, 3H), 6.96 (d, 2H), 7.18 (d, 2H).

Step 2

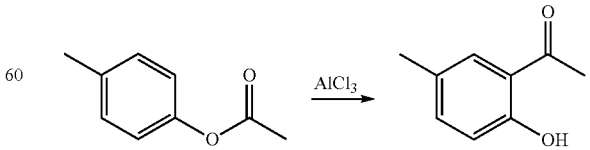

A mixture of 4-methylphenyl acetate (52.6 g, 0.35 mol) and anhydrous aluminum chloride (94 g, 0.70 mol) was stirred at 120-140° C. for 20 minutes. The reaction mixture was cooled to 60-80° C. and ice water was slowly added. The reaction mixture was then extracted with ethyl acetate. The organic layer was washed with brine and dried over anhydrous sodium sulfate. After distilling off the solvent under reduced pressure, the residue was purified by silica gel column chromatography to yield 2'-hydroxy-5'-methyl-acetophenone (32 g, 61%). $^1$H-NMR (CDCl$_3$): 2.28 (s, 3H), 2.57 (s, 3H), 6.83 (d, 1H), 7.25 (d, 1H), 7.46 (s, 1H), 12.01 (s, 1H).

Step 3

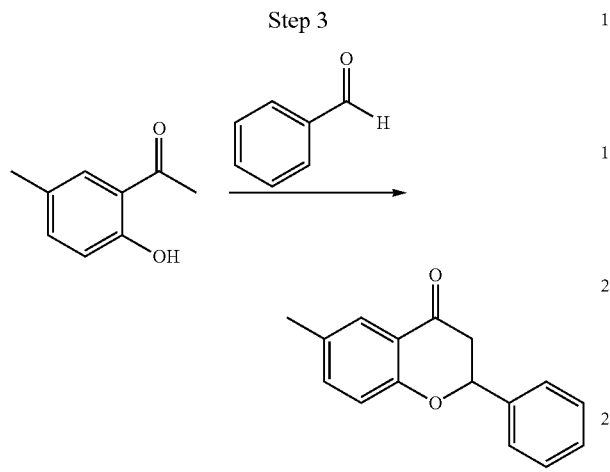

A mixture of 1-(2-hydroxy-5-methyl-phenyl)-ethanone (15 g, 0.10 mol), benzaldehyde (10.6 g, 0.10 mol) and borax (38 g, 0.10 mol) in ethanol (90 mL) and H$_2$O (150 mL) was refluxed for one day. The reaction mixture was cooled, diluted with an equal volume of H$_2$O and extracted with ether. The ether was dried over anhydrous Na$_2$SO$_4$, filtered, and evaporated to give 6-methyl-2-phenyl-chroman-4-one (8.1 g, 34%). $^1$H-NMR (CDCl$_3$): 2.32 (s, 3H), 2.86 (d, 1H), 3.06 (t, 1H), 5.44 (d, 1H), 6.96 (d, 1H), 7.38 (d, 1H), 7.44 (m, 5H), 7.71 (s, 1H).

Step 4

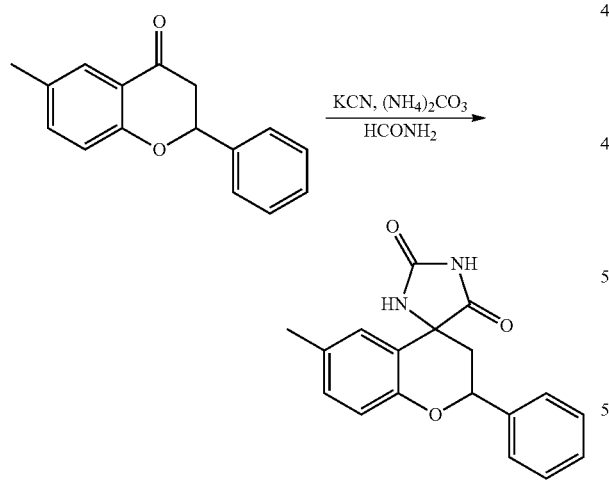

A steel bomb was charged with a mixture of 6-methyl-2-phenyl-chroman-4-one (1 g, 4.2 mmol), potassium cyanide (0.82 g, 12.6 mmol), and (NH$_4$)$_2$CO$_3$ (3.03 g, 31.5 mmol). Formamide (20 mL) was added to fill the steel bomb nearly completely. The mixture was heated at 70° C. for 24 h and then at 110° C. for another 48 h. The reaction mixture was then cooled and poured over ice. Acidification with concentrated HCl was performed to give a precipitate which was filtered, washed twice with water. The precipitate was dissolved in ethyl acetate, dried over Na$_2$SO$_4$, and filtered. The filtrate was concentrated in vacuo to give a residue, which was purified by preparative TLC to give 6-methyl-2-phenylspiro[chroman-4,4'-imidazolidine]-2',5'-dione (0.42 g, 32%).

Step 5

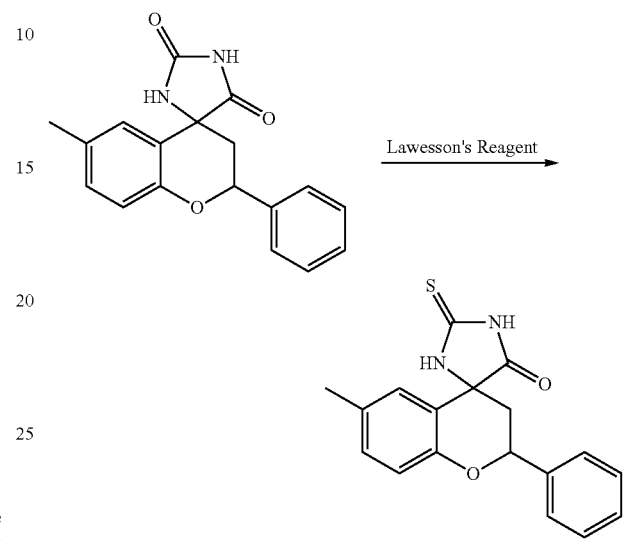

A suspension of 6-methyl-2-phenylspiro[chroman-4,4'-imidazolidine]-2',5'-dione (200 mg, 0.65 mmol) and Lawesson's Reagent (263 mg, 0.65 mmol) in anhydrous 1,4-dioxane (8 mL) was refluxed for 24 h. The mixture was concentrated in vacuo and the residue was purified by preparative TLC to give 6-methyl-2-phenyl-2'-thioxospiro[chroman-4,4'-imidazolidin]-5'-one (35 mg, 17%). $^1$H-NMR (CDCl$_3$): 2.28 (s, 3H), 2.47 (d, 1H), 2.51 (d, 1H), 5.30 (s, 1H), 6.92 (s, 1H), 6.70 (d, 2H), 7.10 (m, 1H), 7.41 (m, 1H), 8.18 (s, 1H).

Step 6

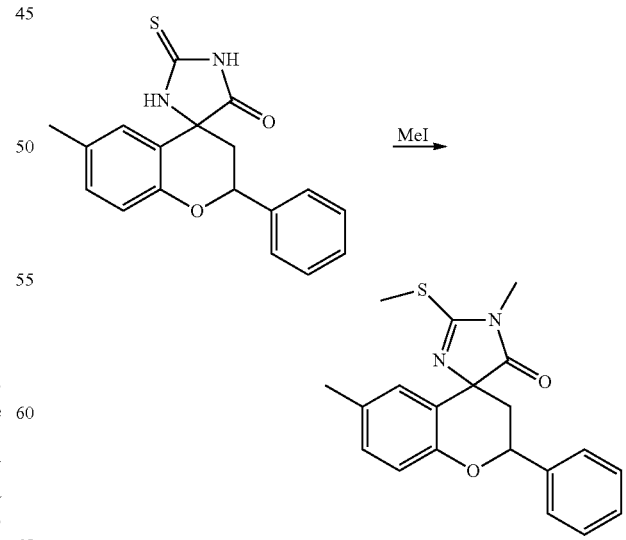

To a solution of 6-methyl-2-phenyl-2'-thioxospiro[chroman-4,4'-imidazolidin]-5'-one (55 mg, 0.17 mmol) in MeOH (5 mL) was added a solution of NaOH (13 mg, 0.34 mmol) in H$_2$O (1 mL). After stirring for 10 min, MeI (363 mg, 2.55 mmol) was added. The reaction mixture was refluxed for 2 h. The mixture was concentrated in vacuo to give a residue, which was purified by preparative TLC to give 1',6-dimethyl-2'-(methylthio)-2-phenylspiro[chroman-4,4'-imidazol]-5'-(1'H)-one (40 mg, 67%).

Step 7

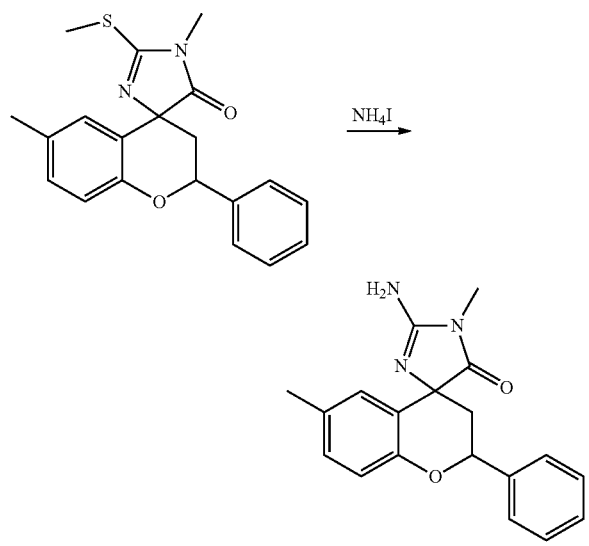

A solution of 1',6-dimethyl-2'-(methylthio)-2-phenylspiro[chroman-4,4'-imidazol]-5'-(1'H)-one (40 mg, 0.12 mmol), and NH$_4$I (35 mg, 0.24 mmol) in NH$_3$/EtOH (4 mL, 1.5N) was heated at 110° C. in a tube in a microwave reactor for 2-2.5 h. After cooling, the mixture was concentrated in vacuo to give a residue, which was purified by preparative TLC and preparative HPLC to afford 2'-amino-1',6-dimethyl-2-phenylspiro[chroman-4,4'-imidizol]-5'(1'H)-one (2.03 mg, 6%). $^1$H-NMR (MeOD): 2.28 (s, 3H), 2.40 (d, 1H), 2.55 (d, 1H), 3.28 (s, 3H), 5.74 (d, 1H), 6.92 (d, 1H), 7.13 (s, 1H), 7.35 (d, 1H), 7.40-7.50 (m, 6H).

Example 58

4-(2'-amino-1'-methyl-5'-oxo-2-phenyl-1',5'-dihydrospiro[chroman-4,4'-imidazole]-6-yl)-N,N-dimethylbenzenesulfonamide (Compound 65)

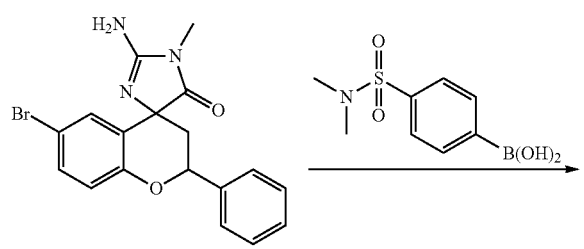

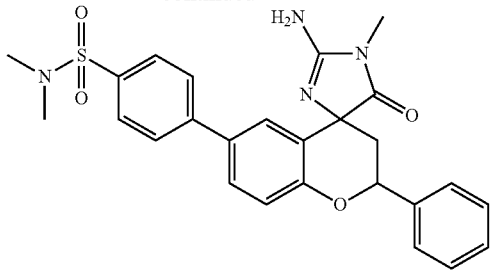

Pd(PPh$_3$)$_2$Cl$_2$ (10 mg) in a 10 mL CEM test tube under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 4-(N,N-dimethyl-sulfamoyl)phenylboronic acid (23.8 mg, 0.104 mmol). The mixture was heated in a microwave reactor at 120° C. for 30 minutes. The reaction mixture was concentrated in vacuo to give the residue, which was purified by preparative TLC and preparative HPLC to give pure 4-(2'-amino-1'-methyl-5'-oxo-2-phenyl-1',5'-dihydrospiro[chroman-4,4'-imidazole]-6-yl)-N,N-dimethylbenzenesulfonamide (2.4 mg, 9%). $^1$H-NMR (CDCl$_3$): 2.31 (t, 1H), 2.57 (t, 1H), 2.78 (s, 6H), 3.33 (d, 3H), 3.56 (s, 2H), 5.88 (d, 1H), 7.20 (d, 1H), 7.26 (s, 1H), 7.48 (m, 5H), 7.57 (m, 1H), 7.62 (d, 2H), 7.80 (d, 2H).

Example 59

2-(2'-amino-1'-methyl-5'-oxo-2-phenyl-1',5'-dihydrospiro[chroman-4,4'-imidazole]-6-yl)-N,N-dimethylbenzamide (Compound 66)

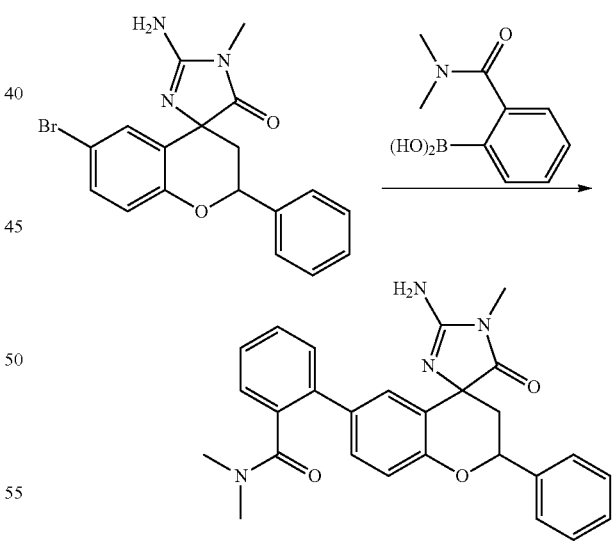

Pd(PPh$_3$)$_2$Cl$_2$ (10 mg, 0.01 mmol) in a 10 mL flask under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 2-(dimethylcarbamoyl)phenylboronic acid (20 mg, 0.104 mmol). The mixture was heated at 120° C. under Ar in a microwave reactor for 30 minutes. The reaction mixture was concentrated in vacuo to give the residue, which was purified by preparative TLC to give 2-(2'-amino-1'-methyl-5'-oxo-2- phenyl-1',5'-dihydrospiro[chroman-4,4'-imidazole]-6-yl)-N,N-dimethylbenzamide (1.60 mg, 6%). ¹H-NMR (MeOD): 2.45 (m, 3H), 2.56 (m, 1H), 2.64 (m, 1H), 2.86 (m, 3H), 3.36 (s, 3H), 5.81 (m, 1H), 7.14 (m, 1H), 7.21 (m, 1H), 7.33 (m, 1H), 7.44 (m, 9H).

Example 60

2'-amino-6-bromo-1',2,2-trimethylspiro[chroman-4,4'-imidazol]-5'(1'H)-one (Compound 67) and 6-bromo-1',2,2-trimethyl-2'-(methylamino)spiro[chroman-4,4'-imidazol]-5'(1'H)-one

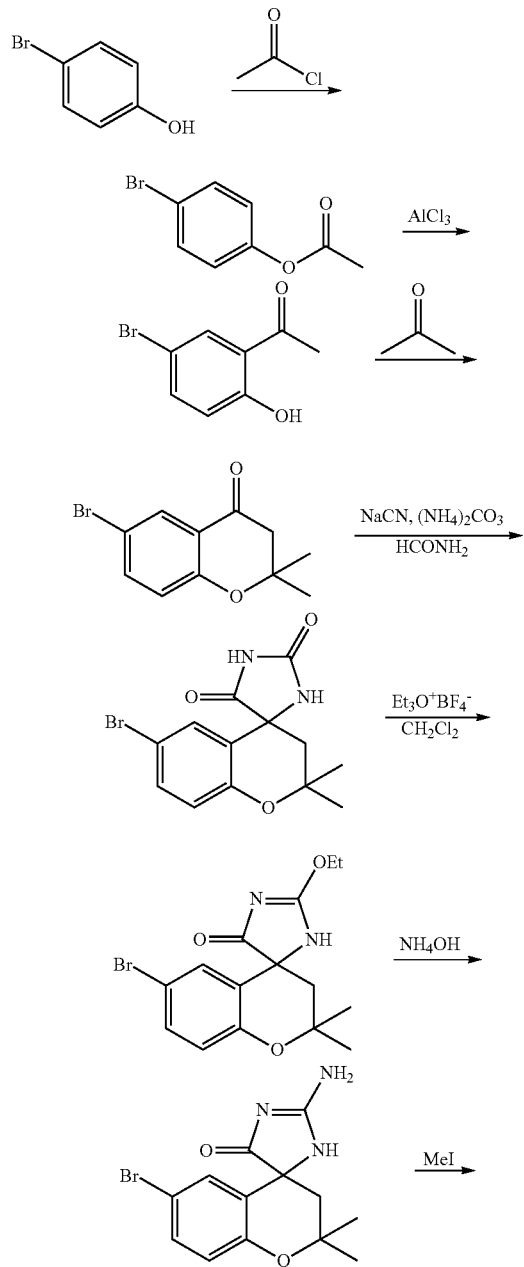

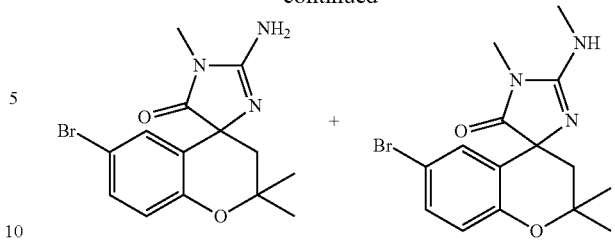

Step 1

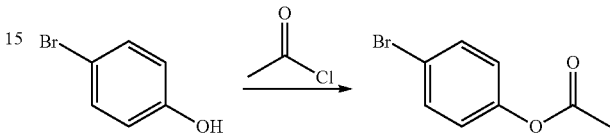

To the suspension of anhydrous aluminum chloride (84.0 g, 0.49 mol) in methylene chloride (1200 mL) was add acetyl chloride (49.2 g, 0.63 mol) while stirring and cooling on ice. The mixture was stirred for 20 minutes while cooling on ice followed by addition of 4-bromophenol (98 g, 0.57 mol). The reaction mixture was stirred at room temperature for 1 h and then ice water was added. The reaction mixture was extracted with ethyl acetate. The combined organic layers were washed with brine, dried over anhydrous sodium sulfate. After distilling off the solvent under reduced pressure, the residue was purified by silica gel column chromatography to yield 4-bromophenyl acetate (104.0 g, 85%). ¹H-NMR (CDCl₃): 2.28 (s, 3H), 6.98 (d, 2H), 7.48 (d, 2H).

Step 2

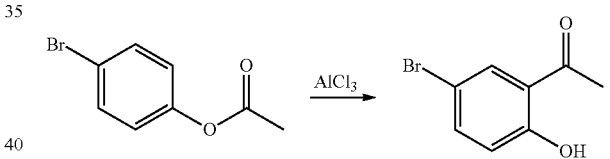

A mixture of 4-bromophenyl acetate (104.0 g, 0.48 mol) and anhydrous aluminum chloride (130.5 g, 0.968 mol) was stirred at 120-140° C. for 20 minutes. The reaction mixture was cooled to 60-80° C. and ice water was added. The reaction mixture was extracted with ethyl acetate. The organic layer was washed with brine and dried over anhydrous sodium sulfate. After distilling off the solvent under reduced pressure, the residue was purified by silica gel column chromatography to yield 1-(5-bromo-2-hydroxyphenyl)-ethanone (101.0 g, 98%). ¹H-NMR (CDCl₃): 2.60 (s, 3H), 6.87 (d, 1H), 7.53 (dd, 1H), 7.81 (s, 1H), 12.12 (s, 1H).

Step 3

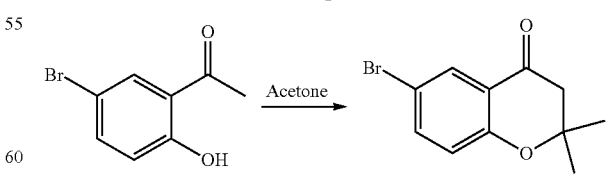

A solution of 1-(5-bromo-2-hydroxyphenyl)-ethanone (21.4 g, 0.1 mol), acetone (365 mL) and pyrrolidine (8.4 mL) in toluene (220 mL) was refluxed for 4 h. To the reaction mixture was added acetone (36.5 mL). The mixture was refluxed for 15 h. Then 1 N HCl (220 mL) was added, and the resulting mixture was extracted with ethyl acetate (200 mL, 3×). The combined organic layers were washed with water (150 mL), brine (150 mL), dried over anhydrous Na$_2$SO$_4$, filtered, and evaporated to give 6-bromo-2,2-dimethyl-chroman-4-one (18.0 g, 71%). $^1$H-NMR (CDCl$_3$): 1.45 (s, 6H), 2.71 (s, 2H), 6.82 (d, 1H), 7.52 (dd, 1H), 7.96 (d, 1H).

Step 4

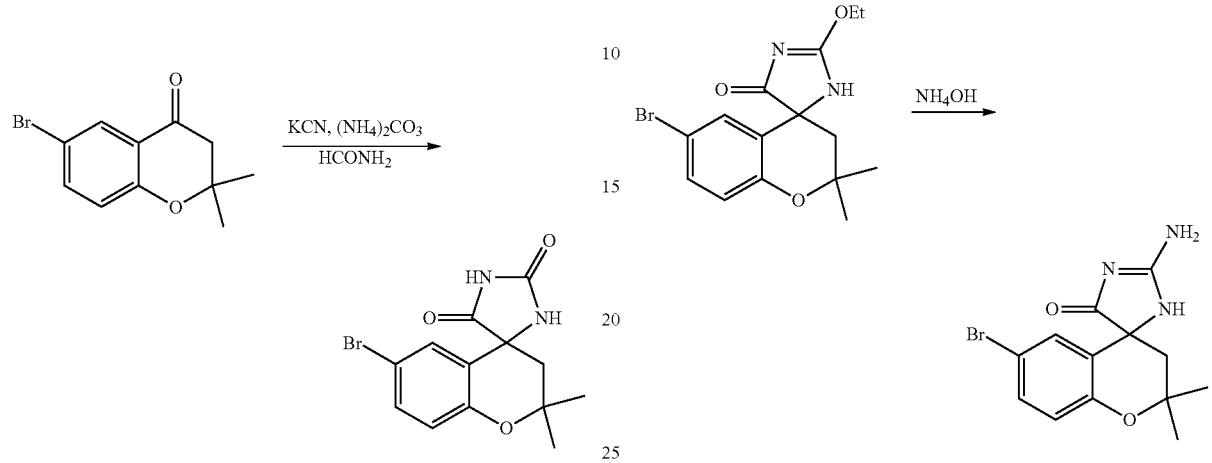

A glass pressure tube was charged with a mixture of 6-bromo-2,2-dimethyl-chroman-4-one (6.4 g, 25 mmol), KCN (3.25 g, 50 mmol), and (NH$_4$)$_2$CO$_3$ (18 g, 187.5 mmol). Formamide (80 mL) was added to fill the pressure tube nearly completely. The resulting mixture was heated at 70° C. for 24 h then at 110° C. for another 48 h. The reaction mixture was then cooled and poured over ice. Acidification with concentrated HCl yielded a precipitate which was filtered, washed twice with water, and then redissolved in ethyl acetate, dried over Na$_2$SO$_4$, and filtered. The filtrate was concentrated in vacuo to give a residue, which was purified by column to give 6-bromo-2,2-dimethylspiro[chroman-4,4'-imidazolidine]-2',5'-dione (8.2 g, 100%). $^1$H-NMR (DMSO): 1.24 (s, 3H), 1.40 (s, 3H), 2.16 (d, 1H), 2.30 (d, 1H), 6.80 (d, 1H), 7.10 (m, 1H), 7.39 (d, 1H), 8.69 (s, 1H), 11.08 (brs, 1H).

Step 5

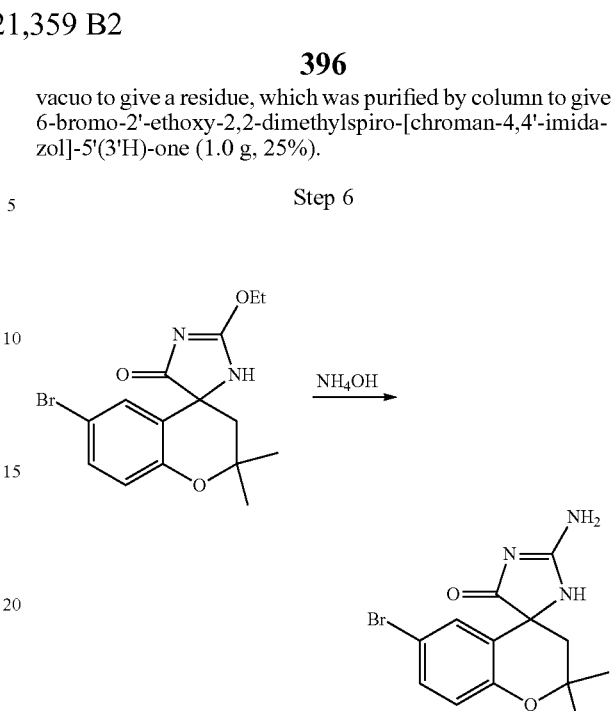

6-Bromo-2,2-dimethylspiro[chroman-4,4'-imidazolidine]-2',5'-dione (4.0 g, 12.3 mmol) and 1 M Et$_3$O.BF$_4$ (4.7 g, 24.7 mmol) were dissolved in dry CH$_2$Cl$_2$ (100 mL). Then the mixture was refluxed for 24 h. The solvent was removed in vacuo to give a residue, which was purified by column to give 6-bromo-2'-ethoxy-2,2-dimethylspiro-[chroman-4,4'-imidazol]-5'(3'H)-one (1.0 g, 25%).

Step 6

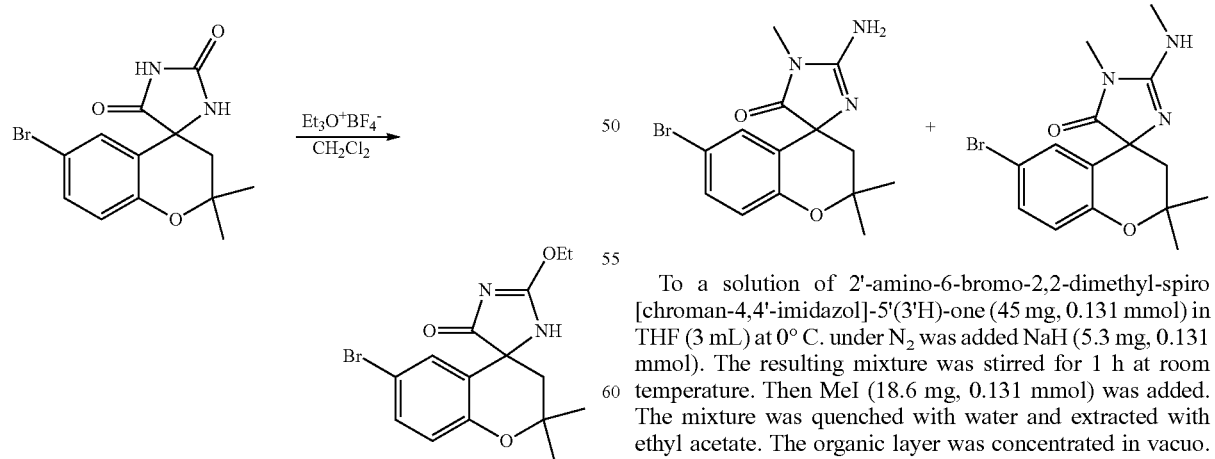

To a solution of 6-bromo-2'-ethoxy-2,2-dimethylspiro [chroman-4,4'-imidazol]-5'(3'H)-one (500 mg, 1.42 mmol) in EtOH (30 mL) was added NH$_3$.H$_2$O (30 mL). The mixture was refluxed for 18 h. The solvent was removed in vacuo to give a residue, which was purified by preparative TLC to give 2'-amino-6-bromo-2,2-dimethylspiro[chroman-4,4'-imidazol]-5'(3'H)-one (120 mg, 30%).

Step 7

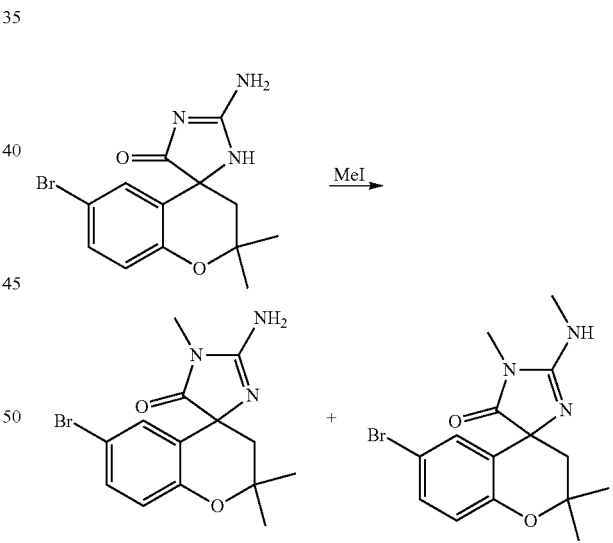

To a solution of 2'-amino-6-bromo-2,2-dimethyl-spiro [chroman-4,4'-imidazol]-5'(3'H)-one (45 mg, 0.131 mmol) in THF (3 mL) at 0° C. under N$_2$ was added NaH (5.3 mg, 0.131 mmol). The resulting mixture was stirred for 1 h at room temperature. Then MeI (18.6 mg, 0.131 mmol) was added. The mixture was quenched with water and extracted with ethyl acetate. The organic layer was concentrated in vacuo. The residue was purified by preparative TLC to give 2'-amino-6-bromo-1',2,2-trimethylspiro[chroman-4,4'-imidazol]-5'(1'H)-one (40 mg, 80%) and 6-bromo-1',2,2-trimethyl-2'-(methylamino)spiro[chroman-4,4'-imidazol]-5'(1'H)-one (5 mg, 10%).

¹H-NMR (MeOD): 1.3 (s, 3H), 1.40 (s, 3H), 1.85 (d, 1H), 2.25 (d, 1H), 3.1 (s, 3H), 6.65 (d, 1H), 6.8 (s, 1H), 7.20 (s, 1H) (67).
¹H-NMR (MeOD): 1.3 (s, 3H), 1.40 (s, 3H), 1.85 (d, 1H), 2.25 (d, 1H), 2.8 (s, 3H), 3.0 (s, 3H), 6.65 (d, 1H), 6.8 (s, 1H), 7.20 (s, 1H).

Example 61

4-(2'-amino-1'-methyl-5'-oxo-2-phenyl-1',5'-dihydrospiro[chroman-4,4'-imidazole]-6-yl)-N,N-dimethylbenzamide (Compound 68)

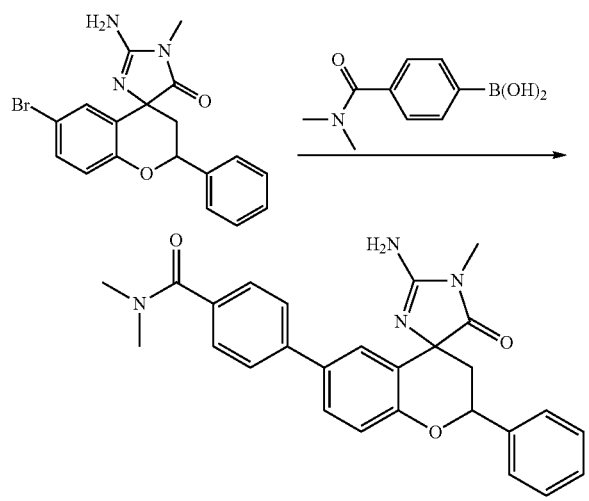

Pd(PPh₃)₂Cl₂ (10 mg) in a 10 mL tube under Ar was treated sequentially with 2'-amino-6-bromo-1'-(cyclohexylmethyl)-2-phenylspiro[chroman-4,4'-imidazol]-5'(1'H)-one (20 mg, 0.052 mmol) in 1,4-dioxane (1 mL), Cs₂CO₃ (2 N, 0.3 mL) and 4-(dimethylcarbamoyl)phenylboronic acid (20.1 mg, 0.104 mmol). The mixture was heated at 120° C. in a microwave reactor for 0.5 h. The reaction mixture was concentrated in vacuo to give the residue, which was purified by preparative TLC to give pure 4-(2'-amino-1'-methyl-5'-oxo-2-phenyl-1',5'-dihydrospiro[chroman-4,4'-imidazole]-6-yl)-N,N-dimethylbenzamide (7.97 mg, 34%). ¹H-NMR (MeOD): 2.07 (m, 1H), 2.24 (m, 1H), 3.00 (m, 6H), 3.11 (m, 3H), 5.22 (d, 0.3H), 5.86 (d, 0.7H), 6.97 (m, 1H), 7.18 (m, 1H), 7.28 (m, 1H), 7.34 (m, 2H), 7.39 (m, 4H), 7.46 (m, 1H), 7.54 (m, 2H).

Example 62

2'-amino-6-bromo-1'-ethyl-2-phenylspiro[chroman-4,4'-imidazol]-5'(1'H)-one (Compound 69)

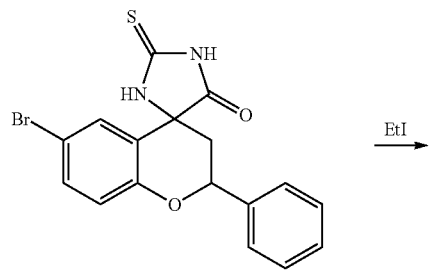

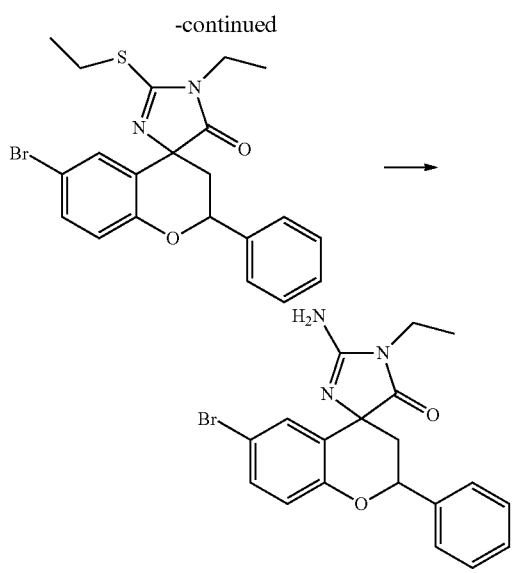

Step 1

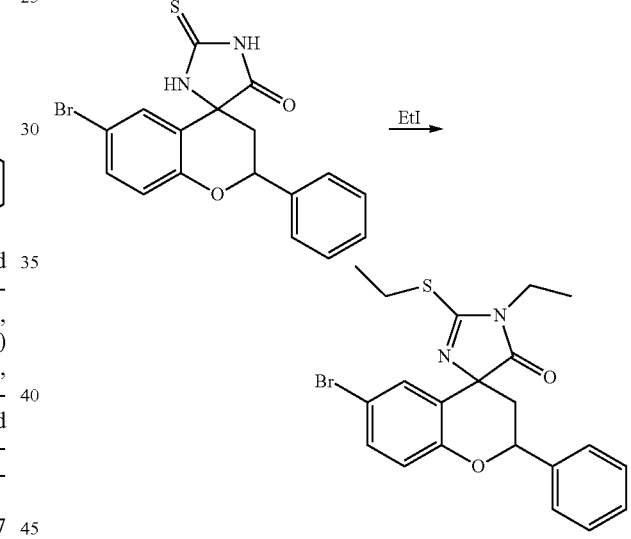

To a mixture of 6-bromo-2-phenyl-2'-thioxospiro[chroman-4,4'-imidazolidin]-5'-one (250 mg, 0.64 mmol) and K₂CO₃ (356 mg, 2.6 mmol) in CH₃CN (8 mL) was added EtI (402 mg, 2.6 mmol). The reaction mixture was refluxed for 2 h. The mixture was filtered, and the filtrate was concentrated to give a residue, which was purified by preparative TLC to give 6-bromo-1'-ethyl-2'-(ethylthio)-2-phenylspiro[chroman-4,4'-imidazol]-5'(1'H)-one (195 mg, 69%).

Step 2

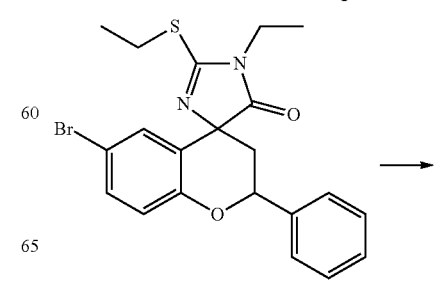

-continued

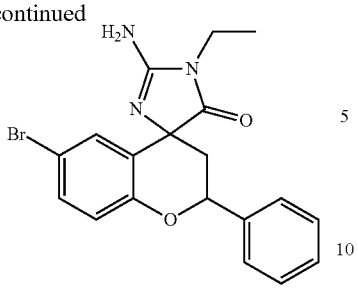

A solution of 6-bromo-1'-ethyl-2'-(ethylthio)-2-phenyl-spiro[chroman-4,4'-imidazol]-5'(1'H)-one (195 mg, 0.44 mmol), NH₄I (128 mg, 0.88 mmol) in NH₃/EtOH (5 mL, 1.5 N) was heated at 110° C. in a tube in a microwave reactor for 2-2.5 h. After cooling, the mixture was concentrated in vacuo to give a residue, which was purified by preparative TLC to afford 2'-amino-6-bromo-1'-ethyl-2-phenylspiro[chroman-4,4'-imidazol]-5'(1'H)-one (42 mg, 24%). ¹H-NMR (MeOD): 1.12 (m, 3H), 1.98 (m, 1H), 3.16 (m, 1H), 3.54 (m, 2H), 5.75 (m, 1H), 6.77 (m, 1H), 6.95 (m, 1H), 7.23 (m, 2H), 7.33 (m, 4H).

Example 63 tert-butyl 2-(2'-amino-1'-methyl-5'-oxo-2-phenyl-1',5'-dihydrospiro[chroman-4,4'-imidazole]-6-yl)-1H-pyrrole-1-carboxylate (Compound 70)

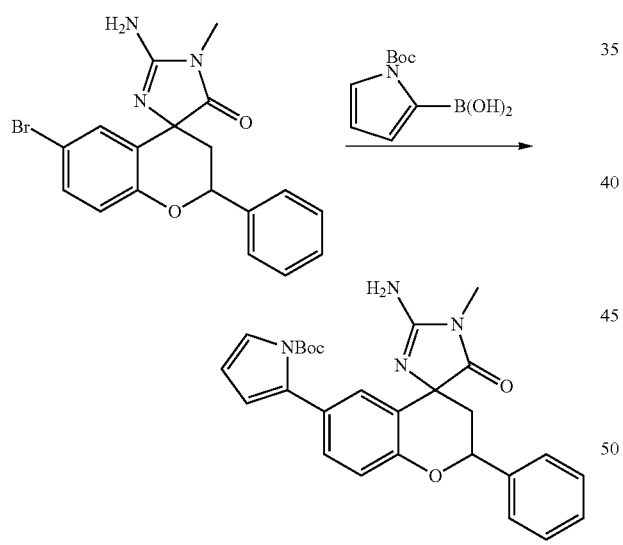

Pd(PPh₃)₂Cl₂ (10 mg) in a 10 mL tube under Ar was treated sequentially with 2'-amino-6-bromo-1'-methyl-2-phenyl-spiro[chroman-4,4'-imidazol]-5'(1'H)-one (30 mg, 0.099 mmol) in 1,4-dioxane (1.2 mL), Cs₂CO₃ (2 N, 0.3 mL) and 1-(tert-butoxycarbonyl)-1H-pyrrol-2-ylboronic acid (30 mg, 0.142 mmol). The mixture was heated at 120° C. in a microwave reactor for 0.5 h. The reaction mixture was concentrated in vacuo to give the residue, which was purified by preparative TLC to give pure tert-butyl 2-(2'-amino-1'-methyl-5'-oxo-2-phenyl-1',5'-dihydrospiro[chroman-4,4'-imidazole]-6-yl)-1H-pyrrole-1-carboxylate (0.8 mg, 2%). ¹H-NMR (MeOD): 1.40 (s, 9H), 2.44 (m, 1H), 2.61 (m, 1H), 3.25 (s, 3H), 5.85 (d, 1H), 6.14 (m, 1H), 6.23 (m, 1H), 7.05 (m, 1H), 7.16 (m, 1H), 7.32 (m, 2H), 7.49 (m, 5H).

Example 64

4-(2'-amino-1'-methyl-5'-oxo-2-phenyl-1',5'-dihydro-spiro[chroman-4,4'-imidazole]-6-yl)-N,N-diethyl-benzamide (Compound 71)

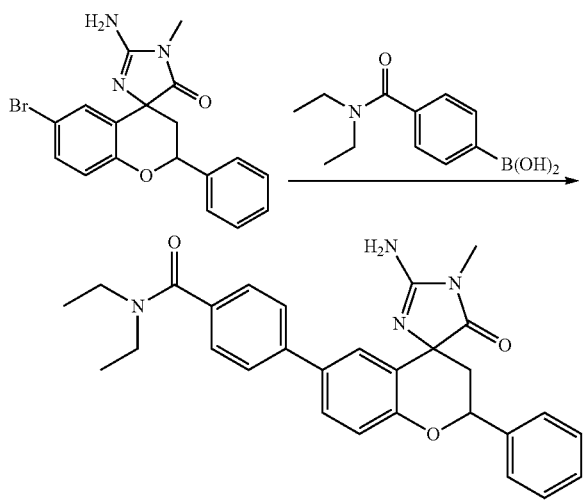

Pd(PPh₃)₂Cl₂ (10 mg) in a 10 mL CEM test tube under Ar was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs₂CO₃ (2 N, 0.3 mL) and 4-(diethylcarbamoyl)phenylboronic acid (23 mg, 0.1 mmol). The mixture was heated in a microwave reactor at 120° C. for 30 mins. The reaction mixture was concentrated in vacuo to give the residue, which was purified by preparative TLC to give pure 4-(2'-amino-1'-methyl-5'-oxo-2-phenyl-1',5'-dihydro-spiro[chroman-4,4'-imidazole]-6-yl)-N,N-diethylbenzamide (6.95 mg, 28%). ¹H-NMR (MeOD): 1.13 (s, 3H), 1.24 (d, 3H), 2.13 (d, 1H), 2.30 (s, 1H), 3.17 (s, 3H), 3.32 (d, 4H), 5.91 (d, 1H), 7.03 (d, 1H), 7.22 (s, 1H), 7.33 (m, 1H), 7.40 (m, 4H), 7.49 (m, 2H), 7.51 (m, 1H), 7.57 (m, 2H).

Example 65

Compound 72

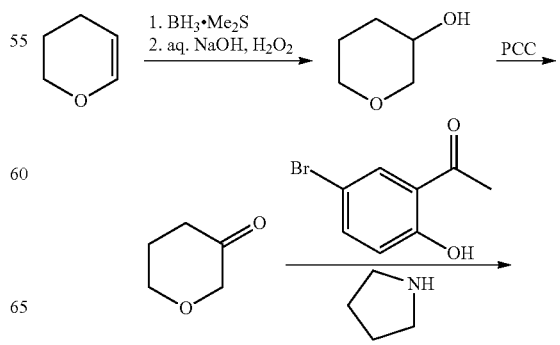

401
-continued

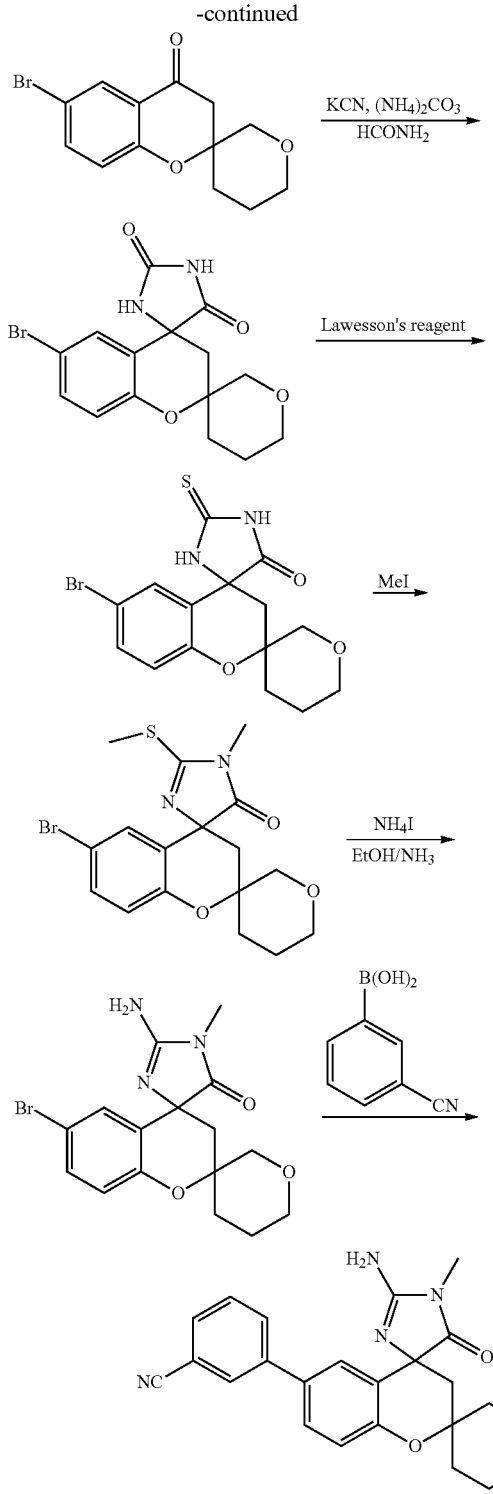

Experimental Data:

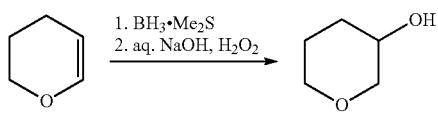

402

Step 1. tetrahydro-pyran-3-ol

To the solution of 3,4-dihydro-2H-pyran (126 g, 1.5 mol) in dry THF (1100 mL) was added a solution of $B_2H_6$ in $Me_2S$ (10 M, 75 mL, 0.75 mol) under nitrogen atmosphere at 0° C. The mixture was stirred at this temperature for 3 h, and then 25° C. for another 2 h. The mixture was warmed to 40° C.~45° C., and aq. NaOH (3 N, 300 mL) and $H_2O_2$ (30%, 170 mL) were added. After stirring for 2 h, the reaction was quenched by saturated brine. The reaction mixture was filtered, and the filtrate was extracted with EtOAc (3×300 mL). The organic phase was washed with aq. $Na_2S_2O_3$ (3×100 mL), dried over $Na_2SO_4$, and concentrated in vacuum to give the crude product, which was purified by distillation to give the product (43 g, 33%). $^1$H-NMR (CDCl$_3$): 1.1.51-1.61 (m, 2H), 1.78-1.91 (m, 4H), 3.40 (m, 1H), 3.54-3.65 (m, 2H), 3.69-3.76 (m, 2H).

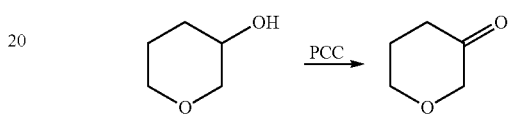

Step 2. dihydro-pyran-3-one

To a solution of tetrahydro-pyran-3-ol (30 g, 0.29 mol) in dry $CH_2Cl_2$ (900 mL) was added 3 Å molecule sieves (30 g) and PCC (94.9 g, 0.44 mol). The mixture was stirred at room temperature overnight. When the reaction was completed, the mixture was filtered through celite, dried over $Na_2SO_4$, and concentrated in vacuum to give the crude product, which was distilled in vacuo to give dihydro-pyran-3-one (10.5 g, 36%). $^1$H-NMR (CDCl$_3$): 2.06-2.13 (m, 2H), 2.53 (m, 2H), 3.85 (m, 2H), 4.02 (s, 2H).

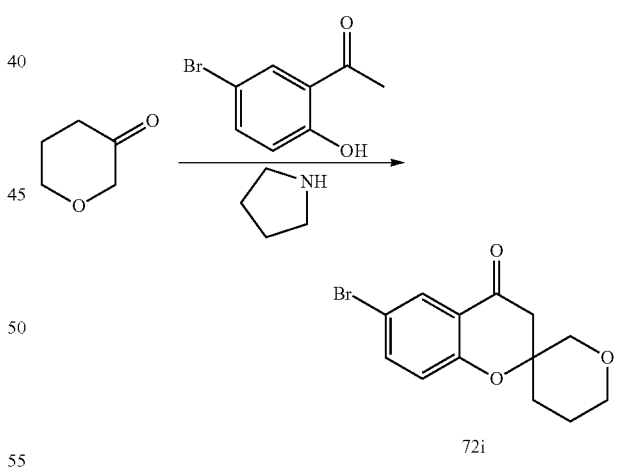

72i

Step 3. Compound 72i

A solution of 1-(5-bromo-2-hydroxy-phenyl)-ethanone (17.3 g, 0.081 mol), dihydro-pyran-3-one (10.5 g, 0.105 mol) and pyrrolidine (7.5 g, 0.105 mol) in toluene (200 mL) was stirred vigorously at room temperature overnight. Then the mixture was refluxed overnight. After cooling, the mixture was treated with water (100 mL) and extracted with ethyl acetate (200 mL*3). The combined organic layers were concentrated and the residue was purified by column to give the product 72i (12 g, 50%). ¹H-NMR (CDCl₃): 1.49 (m, 1H), 1.65 (m, 1H), 1.86 (m, 1H), 2.04 (m, 1H), 2.63 (t, 2H), 3.48 (m, 2H), 3.79 (m, 2H), 6.88 (d, 1H), 7.50 (dd, 1H), 7.89 (m, 1H).

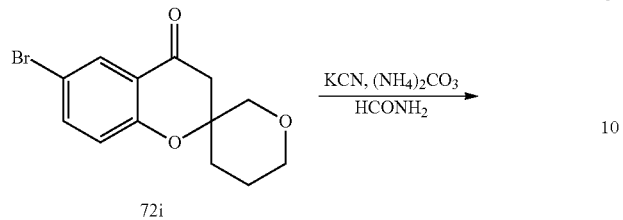

Step 4. Compound 72ii

A pressure tube was charged with a mixture of the compound 72i (12 g, 0.04 mol), KCN (5.27 g, 0.08 mol), and (NH₄)₂CO₃ (28.8 g, 0.3 mol). Formamide (65 mL) was added to fill the pressure tube nearly completely. The mixture was heated at 70° C. for 72 h then at 110° C. for another 3 h. The reaction mixture was then cooled and poured over ice. After acidification with concentrated HCl, the mixture was extracted with ethyl acetate (150 mL*3). The combined organic layers were dried over Na₂SO₄ and filtered. The filtrate was concentrated in vacuo to give the residue, which was purified by column to give the compound 72ii (7.8 g, 53%). ¹H-NMR (CDCl₃): 1.74-2.12 (m, 4H), 2.36 (m, 1H), 2.47 (m, 1H), 3.51-3.55 (m, 4H), 6.85 (m, 1H), 7.18 (m, 1H), 7.32 (m, 1H), 8.18 (d, 1H), 8.93 (s, 1H).

Step 5. Compound 72iii

A suspension of 72ii (600 mg, 1.638 mmol) and Lawesson's Reagent (662 mg, 1.638 mmol) in dry 1,4-dioxane (6 mL) was heated at 110° C. for 0.5 h in a CEM microwave reactor. The mixture was concentrated in vacuo and the residue was purified by column to give the compound 72iii (385 mg, 61%). ¹H-NMR (CDCl₃): 1.52-1.74 (m, 2H), 1.95 (m, 2H), 2.15 (m, 1H), 2.49 (m, 1H), 3.56 (m, 2H), 3.84 (m, 2H), 7.12 (m, 1H), 7.35 (m, 1H), 7.14 (s, 1H), 9.14 (s, 1H).

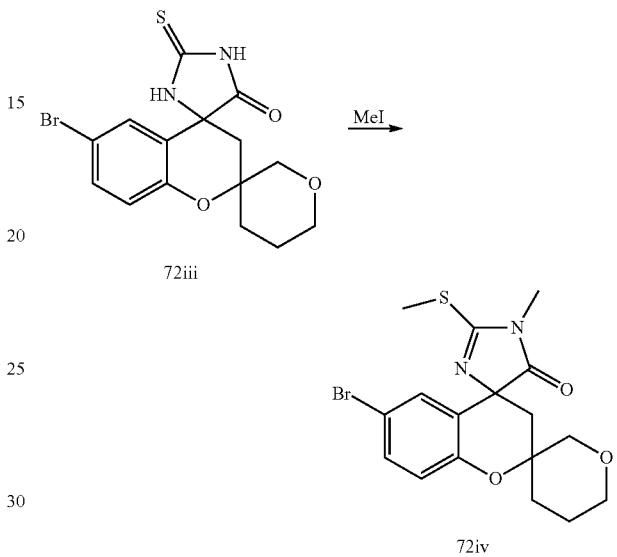

Step 6. Compound 72iv

To a solution of 72iii (192 mg, 0.5 mmol) in MeOH (20 mL) was added a solution of NaOH (1.9 mL, 0.6 N). After stirring for 5 min, MeI (0.4 mL) was added. The reaction mixture was heated at 60° C. for 10 minutes in a microwave reactor. The mixture was concentrated in vacuo to give the residue, which was purified by preparative TLC to give the compound 72iv (93 mg, yield 45%).

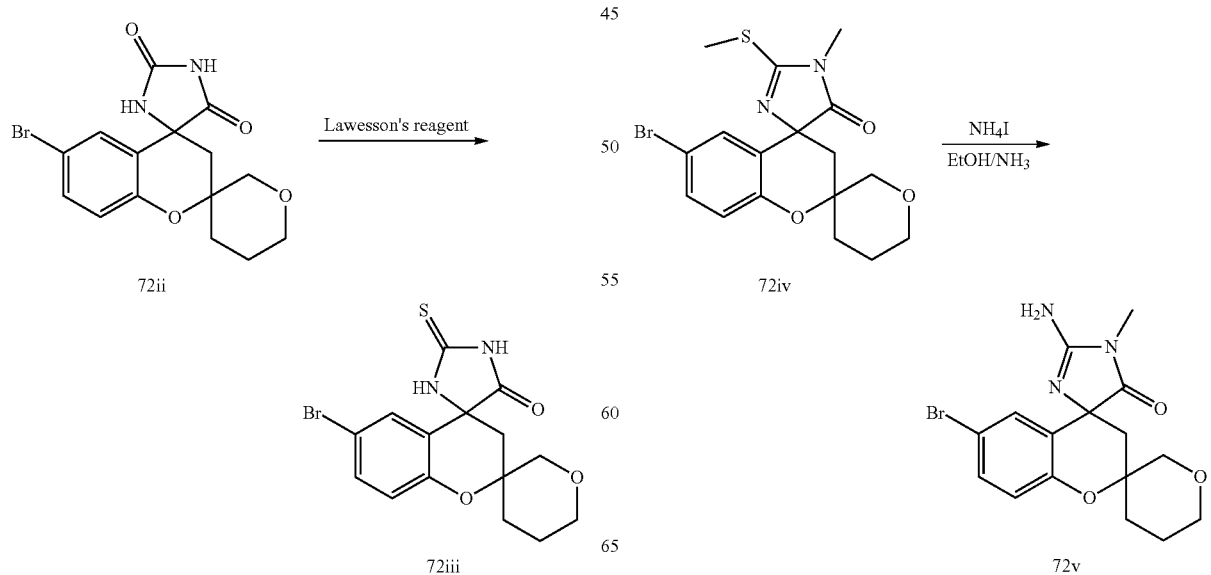

Step 7. Compound 72v

A solution of 72iv (93 mg, 0.227 mmol), NH$_4$I (82 mg, 0.567 mmol) in NH$_3$/EtOH (7 mL, 5 N) was heated at 110° C. in a CEM tube in a microwave reactor for 2 h. After cooling, the mixture was concentrated in vacuum to give the residue, which was purified by preparative TLC to afford the amine 72v (45 mg, 53%).

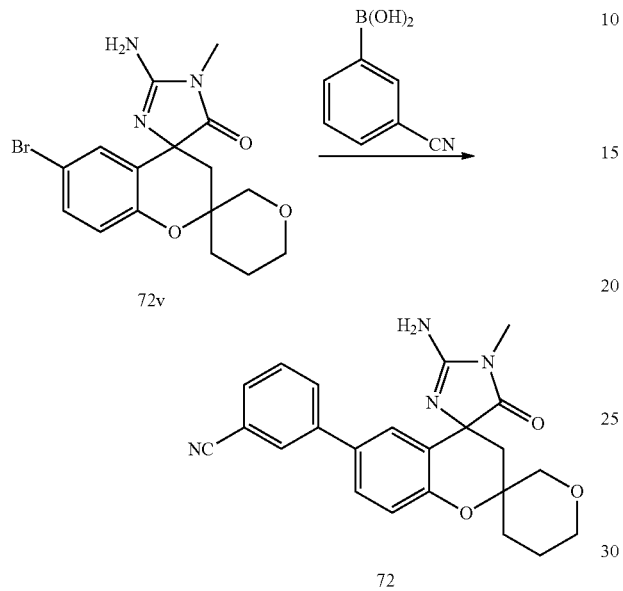

Step 8. Compound 72

Pd(PPh$_3$)$_2$Cl$_2$ (20 mg, 0.029 mmol) in a 10 mL flask under Ar was treated sequentially with the amine 72v (45 mg, 0.12 mmol) in 1,4-dioxane (2 mL), Cs$_2$CO$_3$ (2 N, 0.6 mL) and 3-cyanophenylboronic acid (35.3 mg, 0.24 mmol). The mixture was heated at 120° C. under Ar in a microwave reactor for 30 minutes. The reaction mixture was concentrated in vacuo to give the residue, which was purified by preparative TLC to give pure final product 72 (22.6 mg, 46%). $^1$H-NMR (MeOD): 1.68 (m, 1H), 1.89 (m, 2H), 2.03 (m, 1H), 2.12 (m, 1H), 2.25 (t, 1H), 3.16 (s, 3H), 3.58 (m, 2H), 3.84 & 4.05 (m, 2H), 7.04 (m, 2H), 7.49-7.58 (m, 2H), 7.62 (m, 1H), 7.86 (m, 1H), 7.84 (m, 1H).

Example 65a

Compound 72a and compound 72b

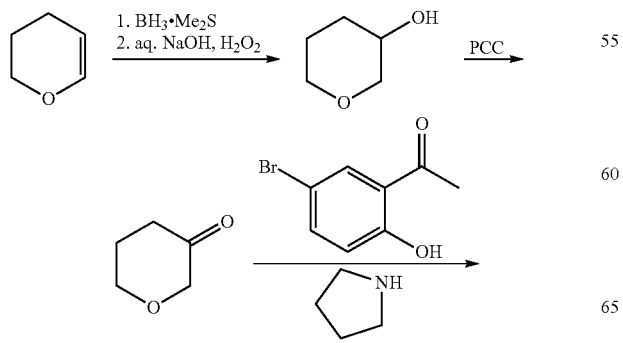

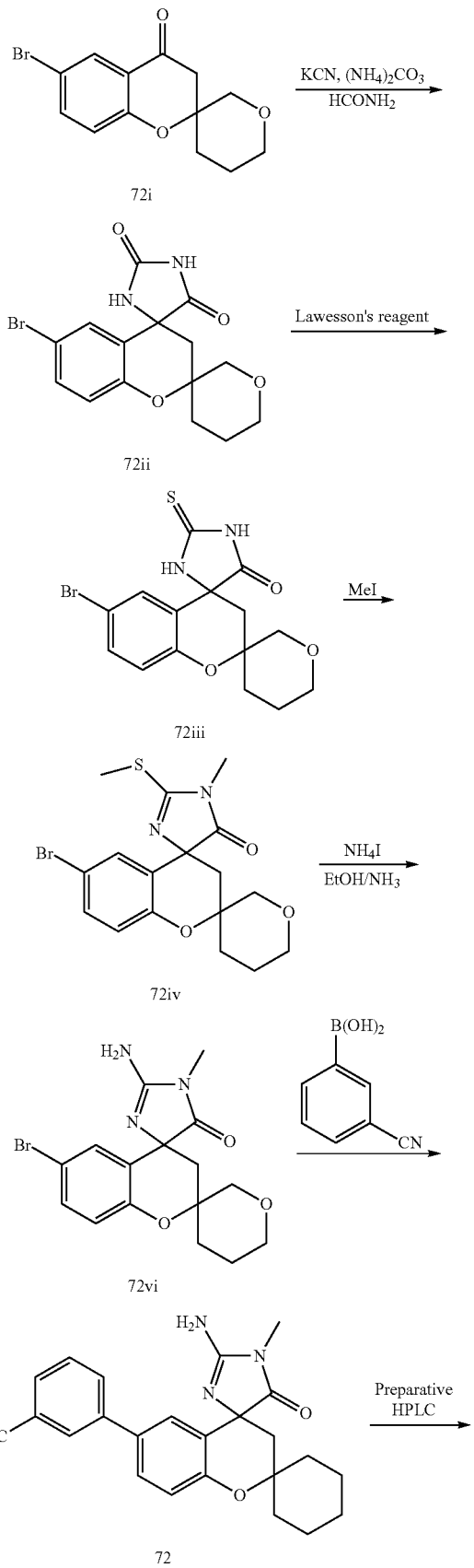

-continued

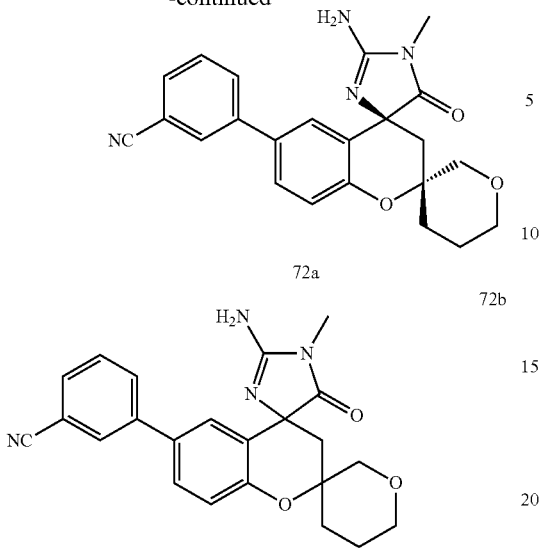

72a

72b

Experimental Data:

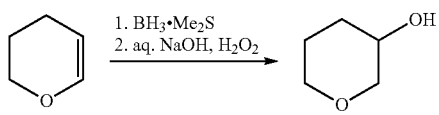

Step 1: tetrahydro-pyran-3-ol

To a solution of 3,4-dihydro-2H-pyran (126 g, 1.5 mol) in dry THF (1100 mL) was added a solution of $B_2H_6$ in $Me_2S$ (10 M, 75 mL, 0.75 mol) under nitrogen atmosphere at 0° C. The mixture was stirred at this temperature for 3 h, and then 25° C. for another 2 h. The mixture was warmed to 40-45° C., and aqueous NaOH (3 N, 300 mL) and $H_2O_2$ (30%, 170 mL) were added. After stirring for 2 h, the reaction was quenched by saturated brine. The reaction mixture was filtered, and the filtrate was extracted with EtOAc (3×300 mL). The organic phase was washed with aq. $Na_2S_2O_3$ (3×100 mL), dried over $Na_2SO_4$, and concentrated in vacuum to give the crude product, which was purified by distillation to give tetrahydro-pyran-3-ol (86 g, 33%). $^1$H-NMR (CDCl$_3$): 1.51-1.61 (m, 2H), 1.78-1.91 (m, 4H), 3.40 (m, 1H), 3.54-3.65 (m, 2H), 3.69-3.76 (m, 2H).

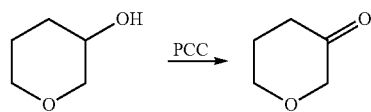

Step 2: dihydro-pyran-3-one

To a solution of tetrahydro-pyran-3-ol (30 g, 0.29 mol) in dry $CH_2Cl_2$ (900 mL) was added 3 Å molecule sieves (30 g) and PCC (94.9 g, 0.44 mol). The mixture was stirred at room temperature overnight. When the reaction was completed, the mixture was filtered through celite, dried over $Na_2SO_4$, and concentrated in vacuum to give the crude product, which was distilled in vacuo to give dihydro-pyran-3-one (10.5 g, 36%). $^1$H-NMR (CDCl$_3$): 2.06-2.13 (m, 2H), 2.53 (m, 2H), 3.85 (m, 2H), 4.02 (s, 2H).

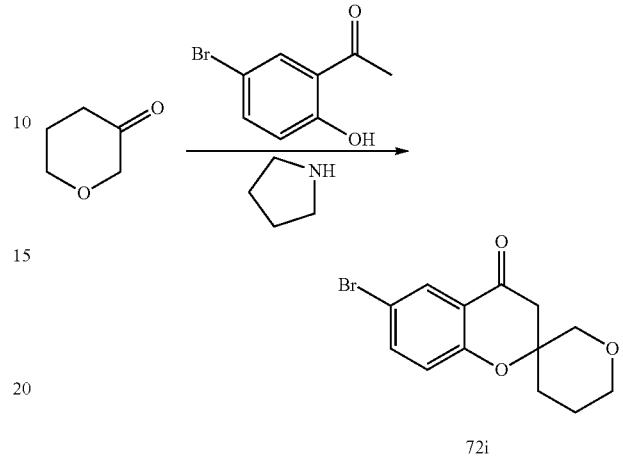

Step 3: Compound 72i

A solution of 1-(5-bromo-2-hydroxy-phenyl)-ethanone (17.3 g, 0.081 mol), dihydro-pyran-3-one (10.5 g, 0.105 mol) and pyrrolidine (7.5 g, 0.105 mol) in toluene (200 mL) was stirred vigorously at room temperature overnight. Then the mixture was refluxed overnight. After cooling, the mixture was treated with water (100 mL), extracted with ethyl acetate (200 mL*3). The combined organic layers were concentrated and the residue was purified by column to give the product 72i (12 g, 50%). $^1$H-NMR (CDCl$_3$): 1.49 (m, 1H), 1.65 (m, 1H), 1.86 (m, 1H), 2.04 (m, 1H), 2.63 (t, 2H), 3.48 (m, 2H), 3.79 (m, 2H), 6.88 (d, 1H), 7.50 (dd, 1H), 7.89 (m, 1H).

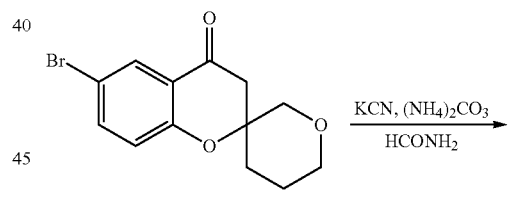

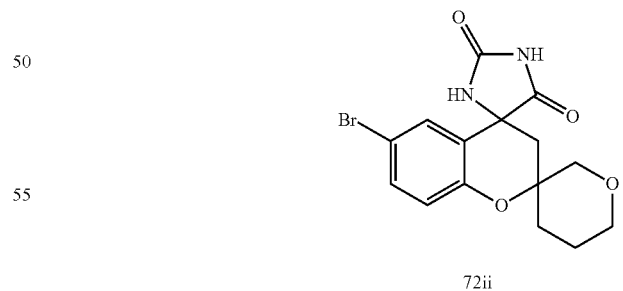

Step 4: Compound 72ii

A pressure tube was charged with a mixture of the compound 72i (12 g, 0.04 mol), KCN (5.27 g, 0.08 mol), and $(NH_4)_2CO_3$ (28.8 g, 0.3 mol). Formamide (65 mL) was added to fill the pressure tube nearly completely. The mixture was heated at 65° C. for 72 h. The reaction mixture was then cooled and poured over ice. After acidification with concentrated HCl, the mixture was extracted with ethyl acetate (200 mL*3). The combined organic layers were dried over Na$_2$SO$_4$ and filtered. The filtrate was concentrated in vacuo to give the residue, which was purified by column to give the compound 2 (7.8 g, 53%). $^1$H-NMR (CDCl$_3$): 1.74-2.12 (m, 4H), 2.36 (m, 1H), 2.47 (m, 1H), 3.51-3.55 (m, 4H), 6.85 (m, 1H), 7.18 (m, 1H), 7.32 (m, 1H), 8.18 (d, 1H), 8.93 (s, 1H).

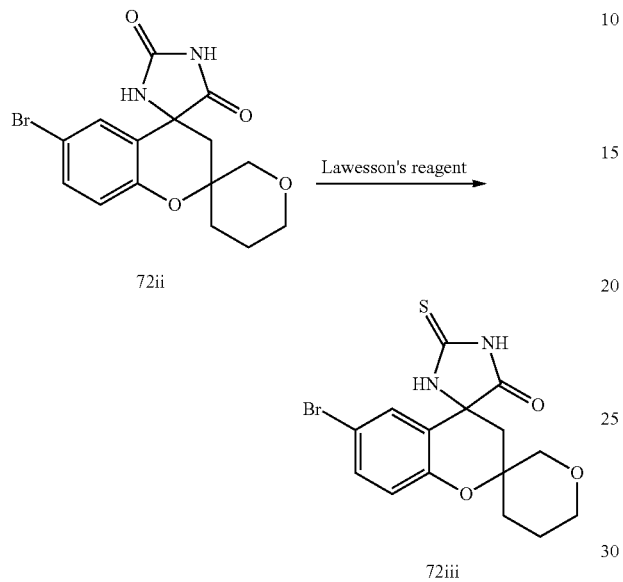

Step 5: Compound 72iii

A suspension of 72ii (600 mg, 1.638 mmol) and Lawesson's Reagent (662 mg, 1.638 mmol) in dry 1,4-dioxane (6 mL) was heated under 110° C. for 0.5 h in a CEM microwave reactor. The mixture was concentrated in vacuo and the residue was purified by column to give the compound 3 (385 mg, 61%). $^1$H-NMR (CDCl$_3$): 1.52-1.74 (m, 2H), 1.95 (m, 2H), 2.15 (m, 1H), 2.49 (m, 1H), 3.56 (m, 2H), 3.84 (m, 2H), 7.12 (m, 1H), 7.35 (m, 1H), 7.14 (s, 1H), 9.14 (s, 1H).

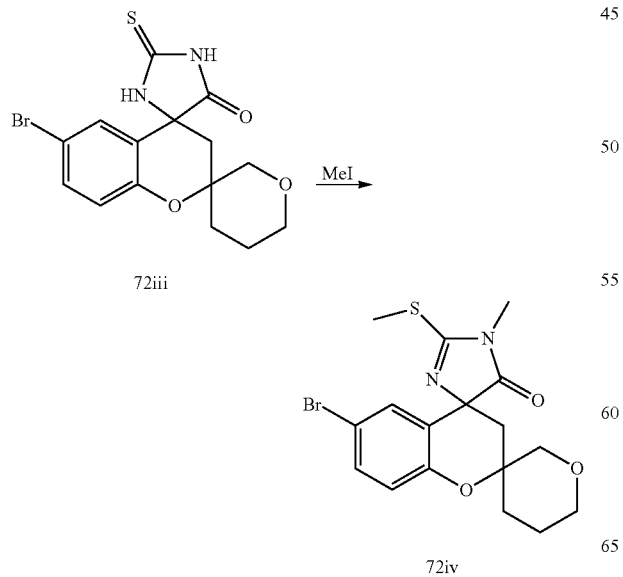

Step 6: Compound 72iv

To a solution of 72iii (385 mg, 1.007 mmol) in MeOH (20 mL) was added a solution of NaOH (3.85 mL, 0.6 N). After stirring for 5 min, MeI (0.8 mL) was added. The reaction mixture was heated at 60° C. for 10 minutes in microwave. The mixture was concentrated in vacuo to give the residue, which was purified by preparative TLC to give the compound 72iv (123 mg, yield 30%).

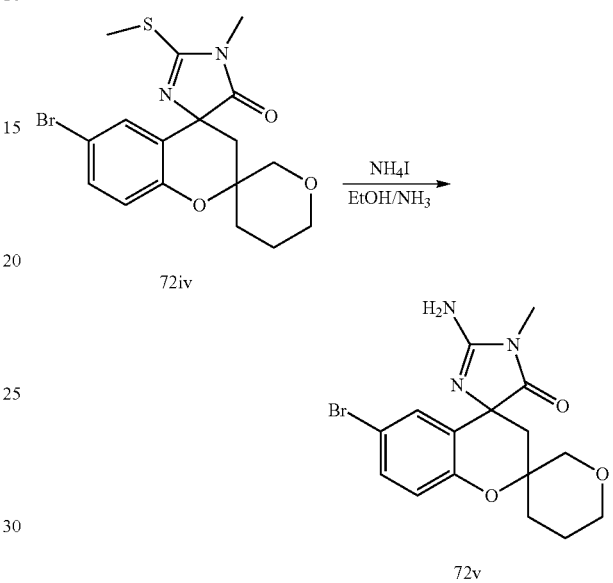

Step 7: Compound 72v

A solution of 72iv (123 mg, 0.3 mmol), NH$_4$I (109 mg, 0.75 mmol) in NH$_3$/EtOH (12 mL, 5 N) was heated at 110° C. in a CEM tube in a microwave reactor for 2 h. After cooling, the mixture was concentrated in vacuo to give the residue, which was purified by preparative TLC to afford the amine 72v (48 mg, 42%).

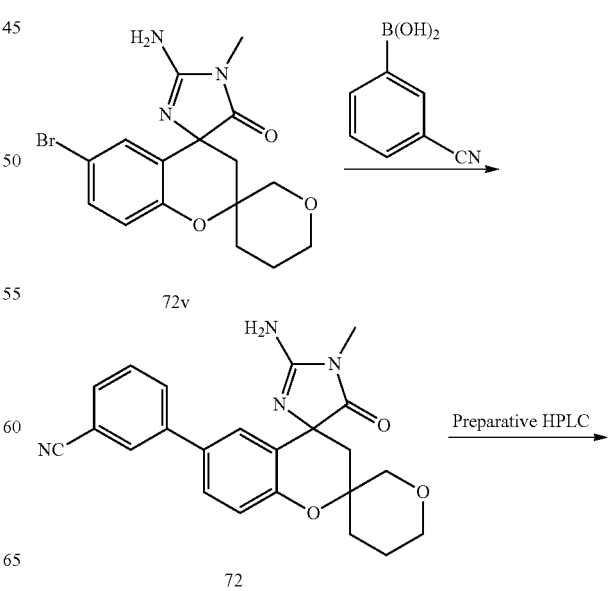

-continued

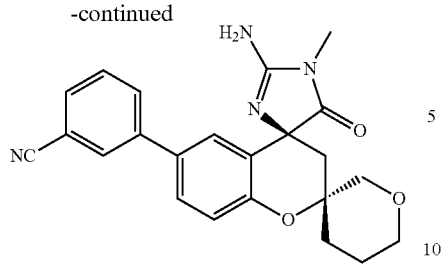

72a

+

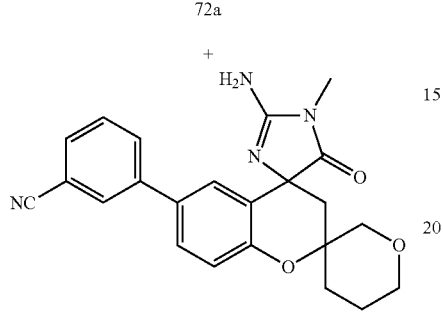

Step 8: Compound 72a

Pd(PPh$_3$)$_2$Cl$_2$ (20 mg) in a 10 mL of microwave tube under Ar$_2$ was treated sequentially with the amine 72v (45 mg, 0.12 mmol) in 1,4-dioxane (1 mL), Cs$_2$CO$_3$ (2 N, 0.3 mL) and 3-cyanophenylboronic acid (35.3 mg, 0.24 mmol). The mixture was heated at 120° C. under Ar in a microwave reactor for 30 min. The reaction mixture was concentrated in vacuo to give the residue, which was purified by preparative TLC followed by preparative HPLC to give pure final products 72 (3.71 mg), compound 72a (6.83 mg) and compound 72b (3.7 mg, total yield 30%).

Compound 72: $^1$H-NMR (MeOD): 1.53-1.69 (m, 1H), 1.88 (m, 1H), 2.06 (m, 2H), 2.32-2.46 (s, 2H), 3.30 (s, 3H), 3.59 (m, 2H), 3.76-3.94 (m, 2H), 7.10 (m, 1H), 7.41 (m, 1H), 7.54 (t, 1H), 7.63 (m, 2H), 7.84 (m, 1H), 7.92 (m, 1H).

Compound 72a: $^1$H-NMR (MeOD): 1.48 (m, 1H), 1.81 (m, 1H), 1.92 (m, 1H), 2.04 (m, 1H), 2.38 (m, 2H), 3.30 (s, 3H), 3.58 (m, 2H), 3.85 (m, 2H), 7.09 (d, 1H), 7.31 (m, 1H), 7.58 (m, 3H), 7.79 (m, 1H), 7.85 (m, 1H).

Compound 72b: $^1$H-NMR (MeOD): 1.65 (m, 1H), 1.92 (m, 1H), 2.02 (m, 1H), 2.10 (m, 1H), 2.45 (s, 2H), 3.31 (s, 3H), 3.63 (m, 2H), 3.77 (m, 2H), 7.09 (m, 1H), 7.40 (m, 1H), 7.55 (t, 1H), 7.64 (m, 2H), 7.83 (m, 1H), 7.92 (m, 1H).

Example 66

Compound 73

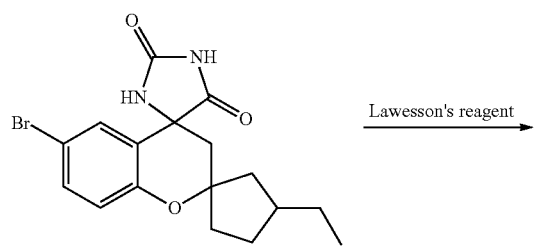

-continued

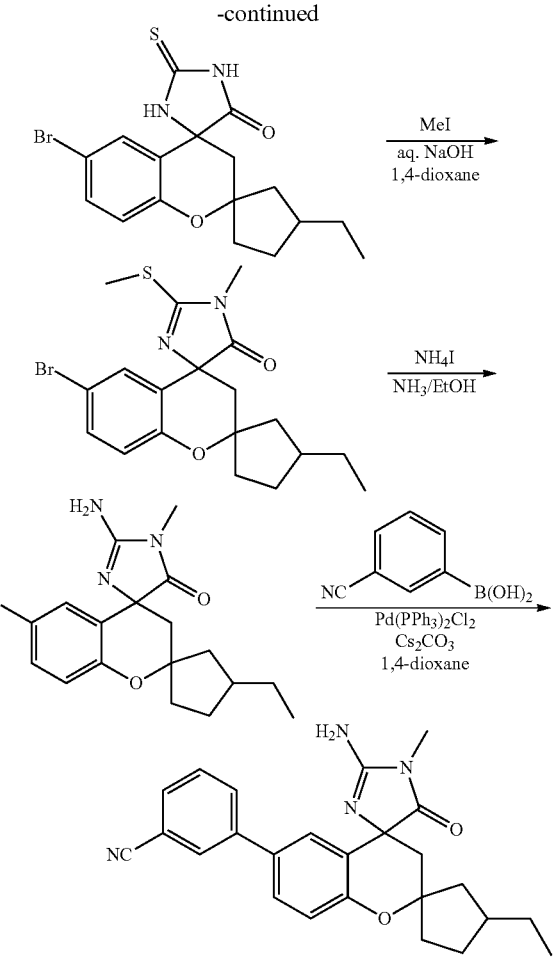

Experimental Data:

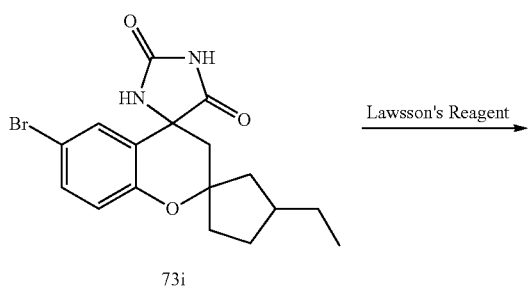

73i

73ii

Step 1. Compound 73ii

A suspension of the compound 73i (300 mg, 0.79 mmol) and Lawesson's Reagent (320 mg, 0.79 mmol) in dry 1,4- dioxane (4 mL) was heated at 110° C. for 45 minutes in a microwave reactor. The mixture was concentrated in vacuo and the residue was purified by preparative TLC (PE: EtOAc=3:1) to give the compound 73ii (229 mg, 73%).

heated at 120° C. in a tube in a microwave reactor for 3 hours. After cooling, the mixture was concentrated in vacuo to give the residue, which was diluted in CH₂Cl₂ and filtered to separate off NH₄I. The solution was concentrated in vacuo and purified by preparative TLC (CH₂Cl₂: CH₃OH 11:1) to afford the compound 73iv (85 mg, 72%).

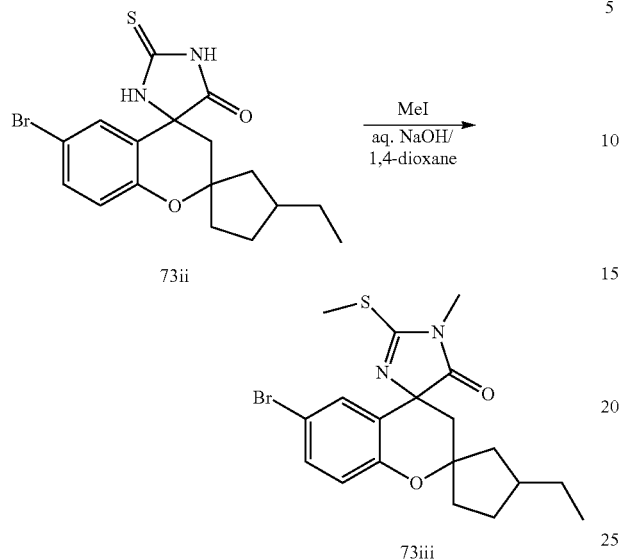

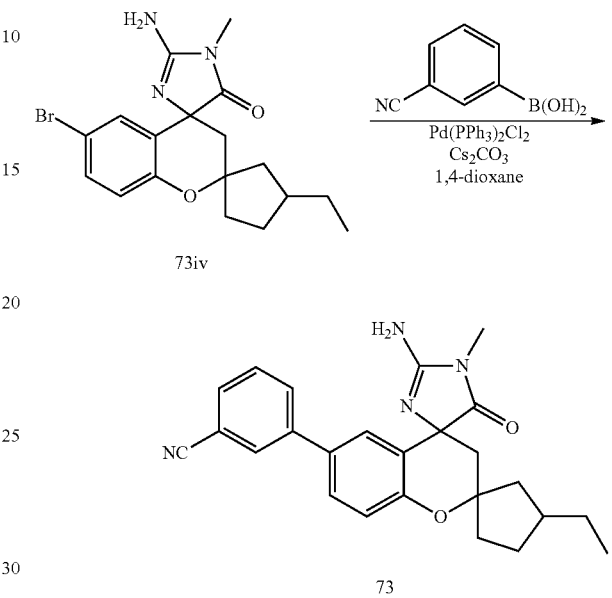

Step 2. Compound 73iii

To a solution of the compound 73ii (187 mg, 0.47 mmol) in 1,4-dioxane (19 mL) was added a solution of NaOH (0.6 N, 1.87 mL) and MeI (0.152 mL). The reaction mixture was heated at 60° C. for 20 minutes in a microwave reactor. The mixture was concentrated in vacuo to give the residue, which was purified by preparative TLC (PE: EtOAc 6:1) to give the compound 73iii (150 mg, 75%). $^1$H NMR (CDCl$_3$/400M): δ 7.25-7.19 (m, 1H), 6.74-6.69 (m, 2H), 3.13 (s, 3H), 2.58-2.50 (m, 4H), 2.31-2.19 (m, 1H), 2.18-2.05 (m, 1H), 2.03-1.95 (m, 1H), 1.90-1.60 (m, 3H), 1.51-1.40 (m, 1H), 1.39-1.15 (m, 3H), 0.95-0.80 (m, 3H).

Step 4. Compound 73

Pd(PPh$_3$)$_2$Cl$_2$ (18 mg) in a 10 mL tube under Ar was treated sequentially with the compound 73iv (55 mg, 0.14 mmol) in 1,4-dioxane (5.2 mL), Cs$_2$CO$_3$ (2 N, 0.78 mL) and 3-cyanophenylboronic acid (41.25 mg, 0.28 mmol). The mixture was heated in a microwave reactor at 120° C. for 35 minutes. The reaction mixture was concentrated in vacuo to give the residue, which was purified by preparative TLC (CH$_2$Cl$_2$: CH$_3$OH 13:1) and then by preparative HPLC to give the Compound 73 (32 mg, 43%). $^1$H NMR (MeOD/400M): δ 7.91 (s, 1H), 7.84 (d, 1H, 9.2 Hz), 7.66-7.40 (m, 3H), 7.39 (s, 1H), 7.02-6.98 (m, 1H), 3.30 (s, 3H), 2.64-2.59 (m, 1H), 2.37-2.32 (m, 1H), 2.30-2.09 (m, 2H), 2.08-1.92 (m, 2H), 1.91-1.66 (m, 1H), 1.65-1.51 (m, 1H), 1.50-1.21 (m, 3H), 0.98-0.88 (m, 3H).

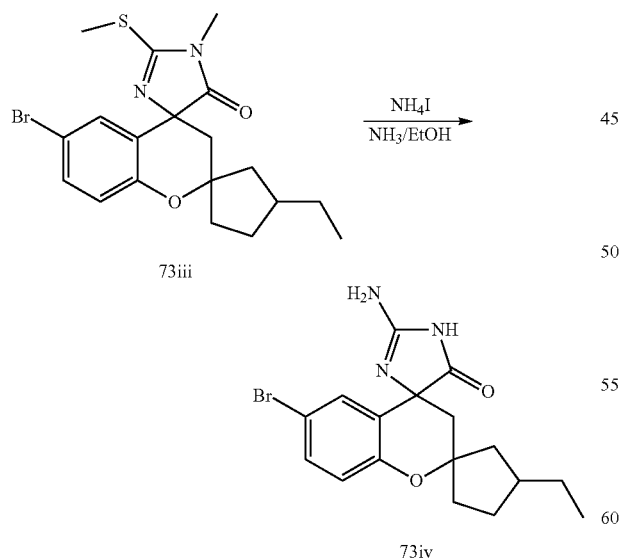

Step 3. Compound 73iv

A solution of the compound 73iii (127 mg, 0.3 mmol), NH₄I (87 mg, 0.6 mmol) in NH₃/EtOH (12.7 mL, 1.5 N) was

Example 67

Compound 75

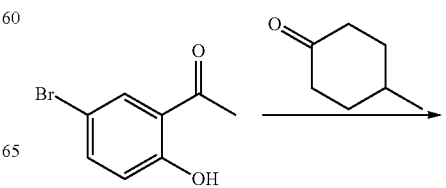

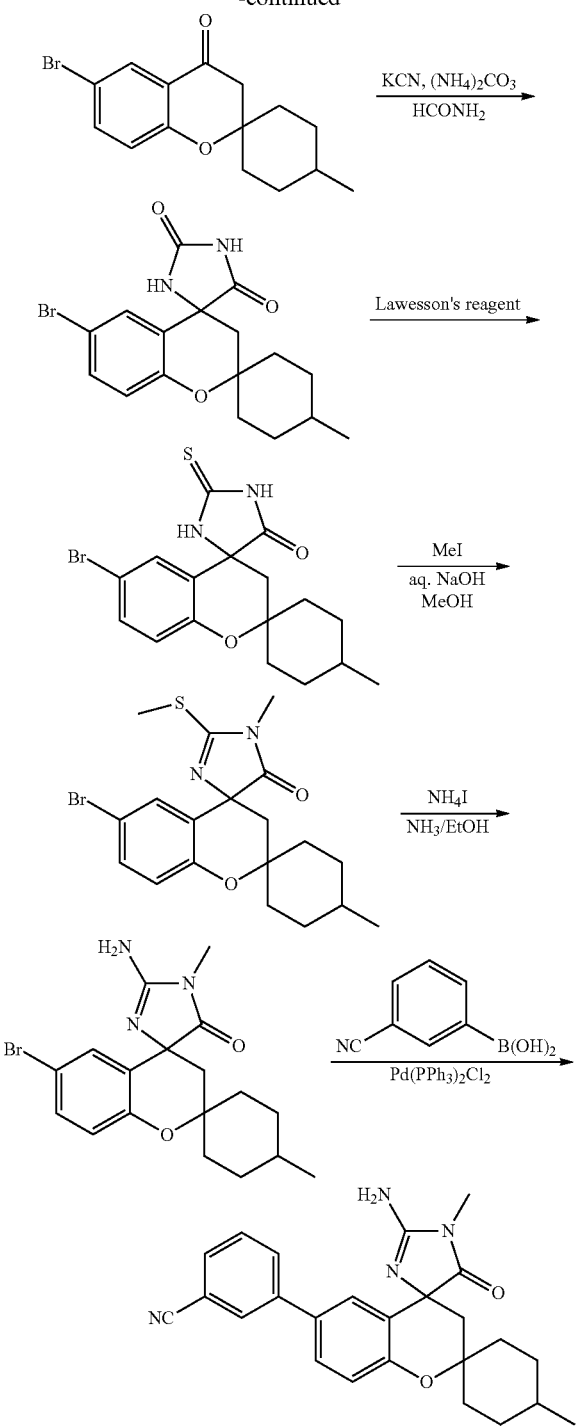

Experimental Data:

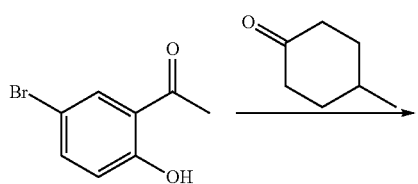

Step 1 6-bromo-4'-methylspiro(chroman-2,1'-cyclohexan)-4-one

A mixture of 1-(5-bromo-2-hydroxy-phenyl)-ethanone (20 g, 0.093 mol), 4-methylcyclohexanone (21.31 g, 0.187 mol) and pyrrolidine (12.63 g, 0.178 mol) in methanol (400 mL) was refluxed for overnight. The reaction mixture was concentrated in vacuo, diluted with an equal volume of $H_2O$ and then added HCl until pH=1. The resulting mixture was extracted with EtOAc. The organic layer was dried over anhydrous $Na_2SO_4$, filtered, and evaporated to give 6-bromo-4'-methylspiro(chroman-2,1'-cyclohexan)-4-one (45 g, 100%).

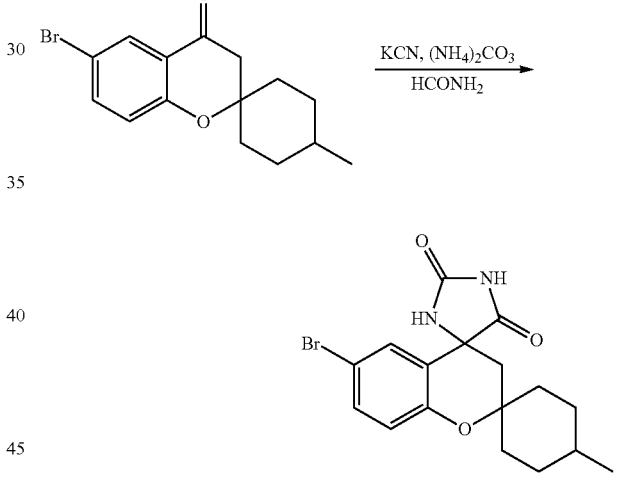

Step 2 6-bromo-4'-methylspiro(chroman-4,4'-imidazolidine)-2',5'-dione

A glass pressure tube was charged with a mixture of 6-bromo-4'-methylspiro(chroman-2,1'-cyclohexan)-4-one (2 g, 6.47 mmol), KCN (0.84 g, 12.94 mmol), and $(NH_4)_2CO_3$ (4.66 g, 48.525 mmol). Formamide (10.352 mL) was added to fill the tube nearly completely. The mixture was heated at 110° C. for 1.5 h with microwave. The reaction mixture was then cooled and poured over ice. Acidification with concentrated HCl gave a precipitate which was filtered, washed twice with water, and then dissolved in ethyl acetate, dried over $Na_2SO_4$ and filtered. The filtrate was concentrated in vacuo to give the residue, which was purified by column to give 6-bromo-4'-methylspiro(chroman-4,4'-imidazolidine)-2',5'-dione (270 mg, 11%).

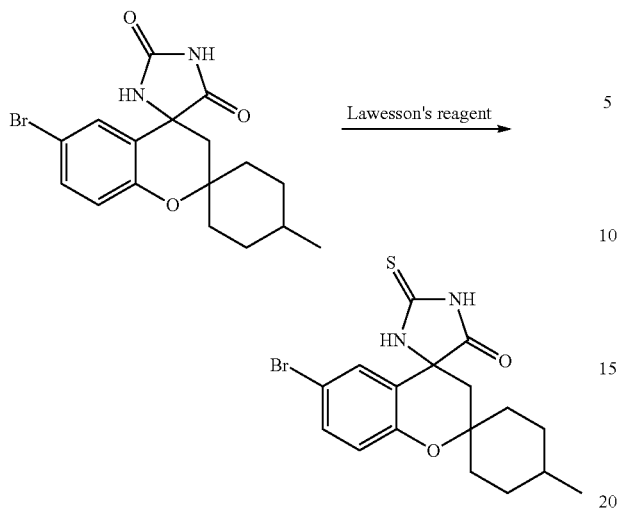

Step 3 6-bromo-4'-methylspiro-2'-thioxospiro[chroman-4,4'-imidazolidin]-5'-one A suspension of 6-bromo-4'-methylspiro(chroman-4,4'-imidazolidine)-2',5'-dione (270 mg, 0.712 mmol) and Lawesson's Reagent (287.81 mg, 0.712 mmol) in dry 1,4-dioxane (10.8 mL) was heated at 120° C. for 30 minutes in a microwave reactor. The mixture was concentrated in vacuo and the residue was purified by preparative TLC to give 6-bromo-4'-methylspiro-2'-thioxospiro[chroman-4,4'-imidazolidin]-5'-one (160 mg, 57%).

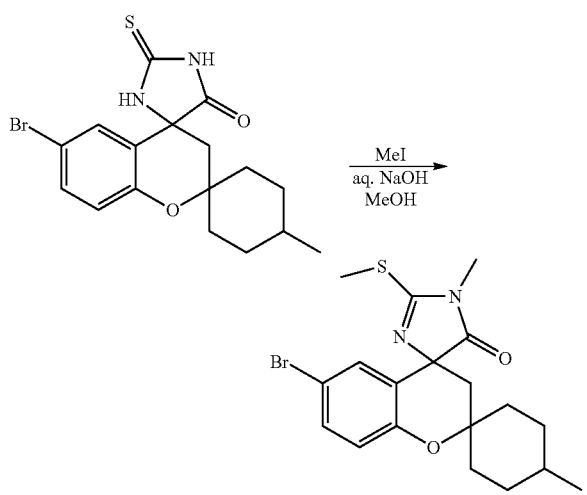

Step 4 6-bromo-4'-methylspiro-1'-methyl-2'-(methylthio)spiro-[chroman-4,4'-imidazol]-5'(1'H)-one To a solution of 6-bromo-4'-methylspiro-2'-thioxospiro[chroman-4,4'-imidazolidin]-5'-one (40 mg, 0.1 mmol) in MeOH (4 mL) was added a solution of NaOH (8 mg, 0.2 mmol) and MeI (57.2 mg, 0.4 mol). The reaction mixture was heated at 60° C. for 10 minutes in a microwave reactor. The mixture was concentrated in vacuo to give the residue, which was purified by preparative TLC to give 6-bromo-4'-methylspiro-1'-methyl-2'-(methylthio)spiro-[chroman-4,4'-imidazol]-5'(1'H)-one (22.5 mg, 53%).

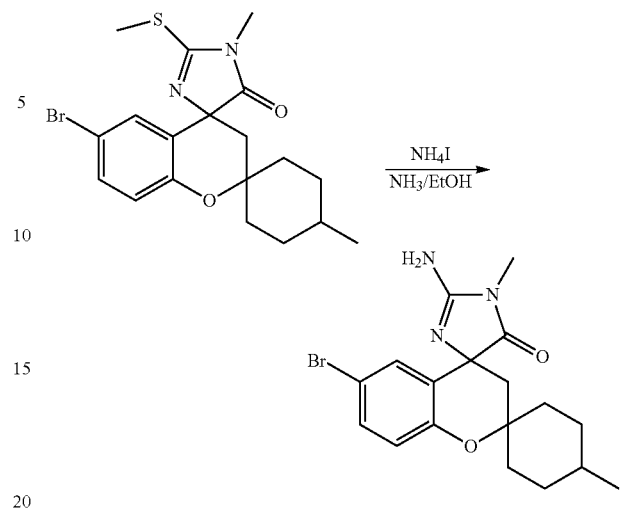

Step 5 2'-amino-6-bromo-4'-methylspiro-1'-methylspiro[chroman-4,4'-imidazol]-5'(1'H)-one A solution of 6-bromo-4'-methylspiro-1'-methyl-2'-(methylthio)spiro-[chroman-4,4'-imidazol]-5'(1'H)-one (90 mg, 0.212 mmol), NH$_4$I (246 mg, 1.696 mmol) in NH$_3$/EtOH (2.5 mL, 8 N) was heated at 120° C. in a tube in a microwave reactor for 2 h. After cooling, the mixture was concentrated in vacuo to give 2'-amino-6-bromo-4'-methylspiro-1'-methylspiro[chroman-4,4'-imidazol]-5'(1'H)-one (80 mg, 100%).

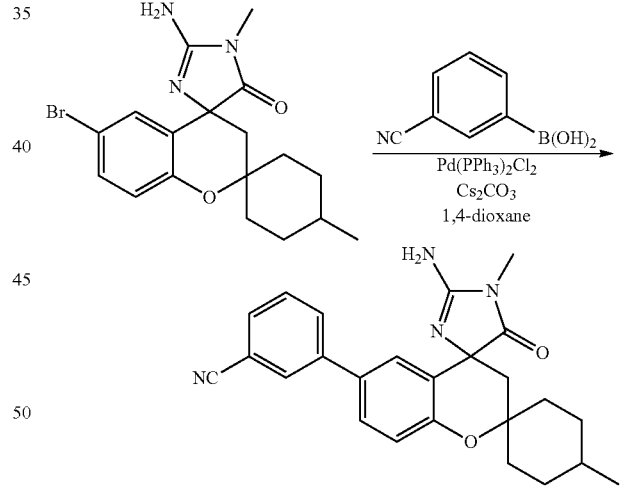

Step 6: Compound 75

Pd(PPh$_3$)$_2$Cl$_2$ (8 mg) in a 10 mL tube under Ar was treated sequentially with 2'-amino-6-bromo-4'-methylspiro-1'-methylspiro[chroman-4,4'-imidazol]-5'(1'H)-one (30 mg, 0.0775 mmol) in 1,4-dioxane (3 mL), Cs$_2$CO$_3$ (2 N, 0.4 mL) and 3-cyanophenylboronic acid (24.03 mg, 0.13175 mmol). The mixture was heated in a microwave reactor at 60° C. for 10 minutes. The reaction mixture was concentrated in vacuo give the residue, which was purified by preparative TLC and then by preparative HPLC to give Compound 75 (6.5 mg, 8%). $^1$H-NMR (MeOD): 0.98 (d, 3H), 1.21 (m, 2H), 1.58 (t, 2H), 1.65 (m, 2H), 2.0 (d, 2H), 2.4 (s, 2H), 2.68 (s, 3H), 3.31 (s, 3H), 7.0 (d, 1H), 7.40 (s, 1H), 7.59 (m, 3H), 7.86 (d, 2H), 7.11 (s, 1H).

Example 68

Compound 76

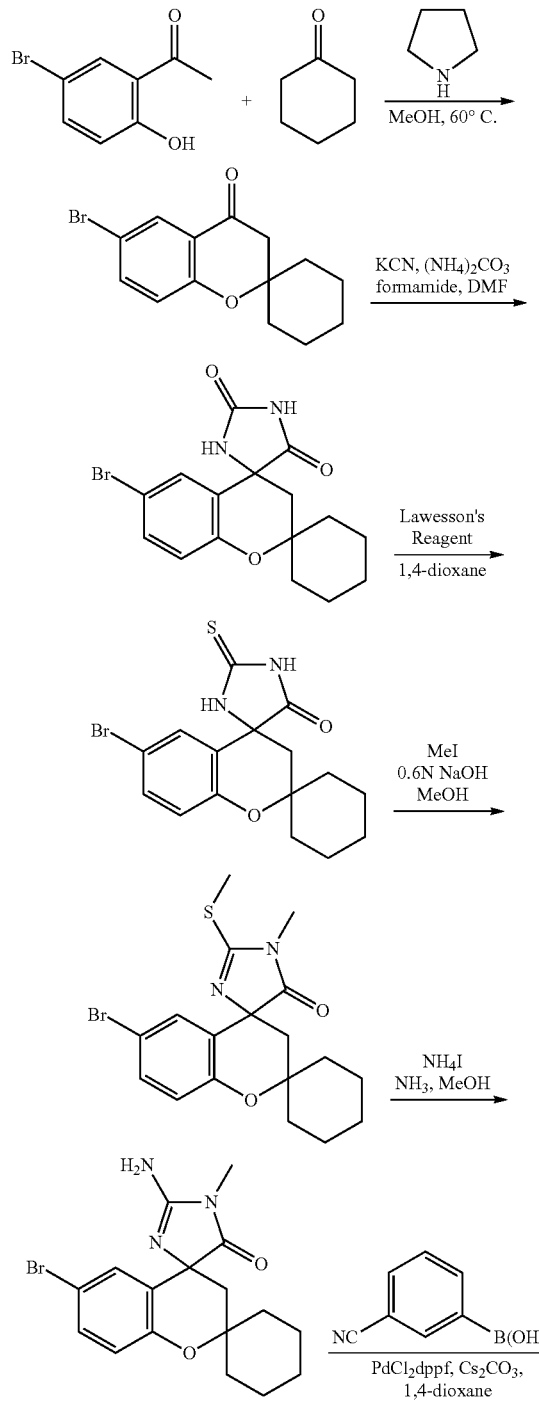

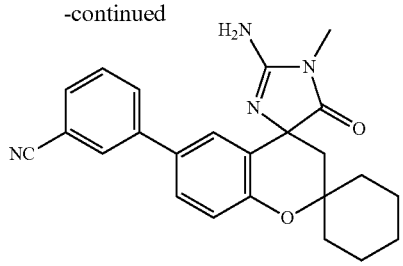

Step 1

In a 50 mL round bottom flask was added 1-(5-bromo-2-hydroxyphenyl)ethanone (2.0 g, 9.3 mmol), followed by cyclohexanone (0.96 mL, 9.3 mmol). MeOH (20 mL) was added to give a clear solution followed by pyrrolidine (1 mL). A condenser was attached to the flask, and the resulting solution was heated at 60° C. overnight. MeOH was removed and the residue was redissolved in EtOAc (30 mL), washed with 1 N NaOH (10 mL) and 1 N HCl (10 mL), and then dried over $Na_2SO_4$. Solvent was removed in vacuo to give 6-bromospiro[chroman-2,1'-cyclohexan]-4-one (2.25 g, 82%), which is used for the next step without purification.

Step 2

A 10 mL CEM microwave test tube was filled with a mixture of 6-bromospiro[chroman-2,1'-cyclohexan]-4-one (0.32 g, 1.08 mmol), KCN (0.15 g, 2.2 mmol), and $(NH_4)_2CO_3$ (0.8 g, 7.7 mmol). A 2:1 mixture of formamide and DMF (6.5 to 7 mL) was added to fill the test tube nearly completely. The resulting mixture as heated in a CEM microwave reactor at 65° C. for 5 hrs. Another 3 tubes (total 1.28 g) were irradiated under the same conditions, and the resulting mixtures were combined, acidified with concentrated HCl, diluted with EtOAc (20 mL), and washed with $H_2O$ (10 mL×3). The organic layer was dried over $Na_2SO_4$, and solvent was removed in vacuo to give a crude product, which was purified by flash chromatography (0 to 60% EtOAc/hexane) to give cyclohexyl-spiro-hydanton (0.61 g, 55% corrected for recovered starting material 0.38 g). MS m/z 365 (M+H$^+$).

Step 3

To a solution of the above hydantoin (0.61 g, 1.66 mmol) in 1,4-dioxane (5 mL) in a 10 mL CEM microwave test tube was added Lawesson's reagent (0.67 g, 1.66 mmol). The resulting mixture was heated in a CEM microwave reactor at 110° C. for 30 min and cooled to room temperature. The solvent was removed in vacuo, and the residue was purified by flash chromatography to give the thiol-cyclohexyl-spiro-hydantoin (0.39 g, 62%). MS m/z 381 (M+H$^+$).

Step 4

To a solution of the above thiol-cyclohexyl-spiro-hydantoin (105.2 mg, 0.27 mmol) in MeOH (5 mL) in a 10 mL CEM microwave test tube was added a 0.6 N NaOH aqueous solution (1.0 mL). After stirring at room temperature for 10 min, MeI (158 mg, 1.08 mmol) was added, and the reaction mixture was heated in a CEM microwave reactor at 60° C. for 10 min. Another 3 tubes (95 mg, 0.25 mmol) were irradiated under the same conditions, and the resulting mixture were combined and concentrated in vacuo to give the crude product, which was purified by flash chromatography to give the dimethylated thiol-cyclohexyl-spiro-hydantoin (318.8 mg, 77%). MS m/z 409 (M+H⁺).

Step 5

To a solution of the above dimethylated thiol-cyclohexyl-spiro-hydantoin (150 mg, 0.37 mmol) in MeOH (1 mL) in a 10 mL CEM microwave test tube was added NH₄I (100 mg, 0.69 mmol) and NH₃/MeOH (7 N, 2 mL). The resulting mixture was heated in a CEM microwave reactor at 120° C. for 30 min. Another tube (100 mg, 0.24 mmol) was also irradiated under the same conditions. The combined mixtures were concentrated in vacuo and the residue was redissolved in EtOAc (10 mL), washed with water (5 mL×3), and dried over Na₂SO₄. The solvent was then removed in vacuo to give the cyclohexyl-acyl-guanidine (181 mg, 78%) as a white solid, which is used for the next step without purification. MS m/z 378 (M+H⁺).

Step 6

To a solution of the above cyclohexyl-acyl-guanidine (50 mg, 0.13 mmol) in 1,4-dioxane (2 mL) was added Cs₂CO₃ (142 mg, 0.43 mmol), 3-cyanophenylboronic acid (29.1 mg, 0.20 mmol), and a catalytical amount of PdCl₂dppf. After degassing, the resulting mixture was heated in a CEM microwave reactor at 120° C. for 40 min Solvent was removed in vacuo and the residue was purified by reversed phase HPLC to give the final product 76 (21.3 mg, 40%) as a TFA salt. ¹H NMR (400 MHz, CD₃COCD₃): 8.44 (br, 1H), 7.98 (s, 1H), 7.94 (d, 1H), 7.76 (m, 2H), 7.68 (m, 2H), 7.18 (d, 1H), 3.42 (s, 3H), 2.62, 2.46 (two d, 2H), 2.06-1.84 (m, 3H), 1.80-1.42 (m, 7H); MS m/z 401 (M+H⁺).

Example 69

Compound 77

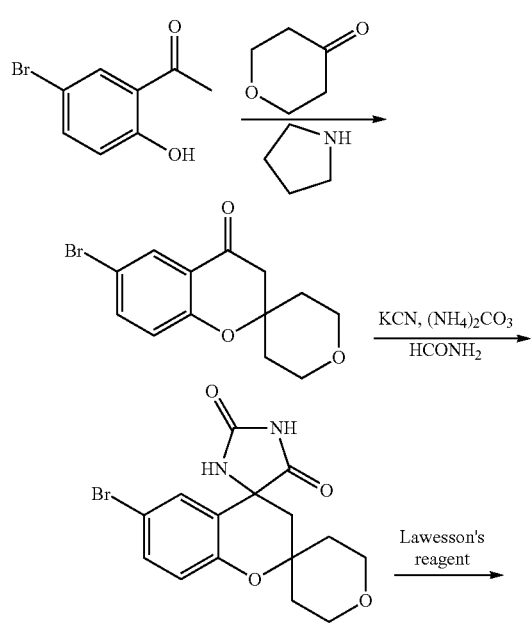

Experimental Data:

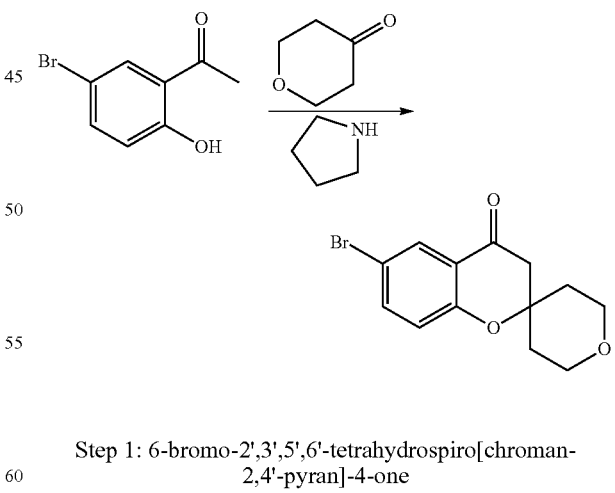

Step 1: 6-bromo-2',3',5',6'-tetrahydrospiro[chroman-2,4'-pyran]-4-one

A mixture of 1-(5-bromo-2-hydroxy-phenyl)-ethanone (10 g, 46.7 mmol), dihydro-2H-pyran-4(3H)-one (9.35 g, 93.45 mmol) and pyrrolidine (6.3 g, 88.8 mmol) in methanol (200 mL) was stirred overnight. The reaction mixture was removed in vacuo, and H₂O was added. The resulting solution was extracted with ethyl acetate. The organic layer was dried over anhydrous Na$_2$SO$_4$, filtered, and evaporated to give 6-bromo-2',3',5',6'-tetrahydrospiro[chroman-2,4'-pyran]-4-one (15 g, 100%). $^1$HNMR (CDCl$_3$): 1.74 (m, 2H), (m, 2H), 1.94 (t, 2H), 2.71 (s, 2H), 3.76 (m, 4H), 6.91 (d, 1H), 7.54 (d, 1H), 7.96 (s, 1H).

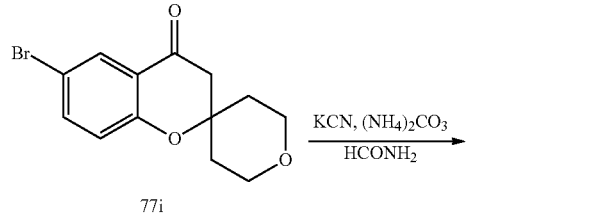

Step 2: Compound 77ii

A mixture of 6-bromo-2',3',5',6'-tetrahydrospiro[chroman-2,4'-pyran]-4-one (10 g, 33.78 mmol), KCN (4.4 g, 67.57 mmol), (NH$_4$)$_2$CO$_3$ (22.7 g, 236.46 mmol) and formamide (60 mL) in a 100 mL steel bomb was heated at 70° C. for 72 hrs. The reaction mixture was cooled and poured into ice water. Acidification with concentrated HCl was performed to give a precipitate which was filtered, washed twice with water, and then dissolved in ethyl acetate, dried over Na$_2$SO$_4$ and filtered. The filtrate was concentrated in vacuo to give the residue, which was purified by column chromatography to give the compound 77ii (9 g, 73%). $^1$H-NMR (MeOD): 1.83 (m, 4H), 2.22 (d, 1H), 2.46 (d, 1H), 3.68 (m, 2H), 3.82 (m, 1H), 3.93 (t, 1H), 6.89 (d, 1H), 7.18 (s, 1H), 7.38 (d, 1H), 8.04 (s, 1H).

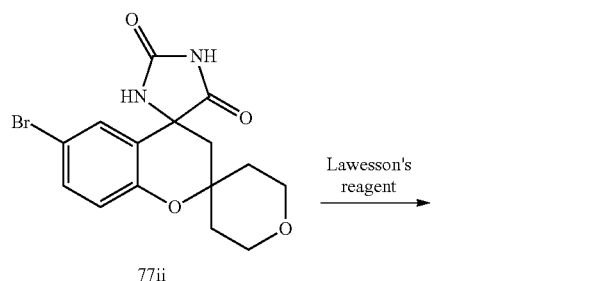

Step 3: Compound 77iii

A mixture of compound 77ii (300 mg, 0.82 mmol) and Lawesson's Reagent (331 mg, 0.82 mmol) in 1,4-dioxane (4.5 mL) was heated at 150° C. in a 10 mL CEM microwave test tube for 50 minutes. The reaction mixture was concentrated to give the residue, which was purified by preparative TLC to give the compound 77iii (40 mg, 13%).

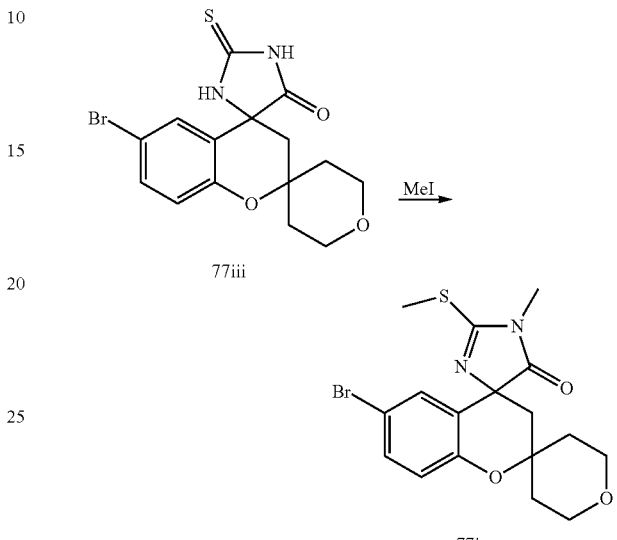

Step 4: Compound 77iv

A mixture of compound 77iii (60 mg, 0.16 mmol), NaOH solution (0.6 N, 06 mL) and CH$_3$I (0.2 mL) in methanol (2 mL) was heated at 60° C. for 5 minutes in a CEM microwave reactor. The reaction mixture was concentrated and the residue was purified by preparative TLC to give the compound 77iv (28 mg, 44%).

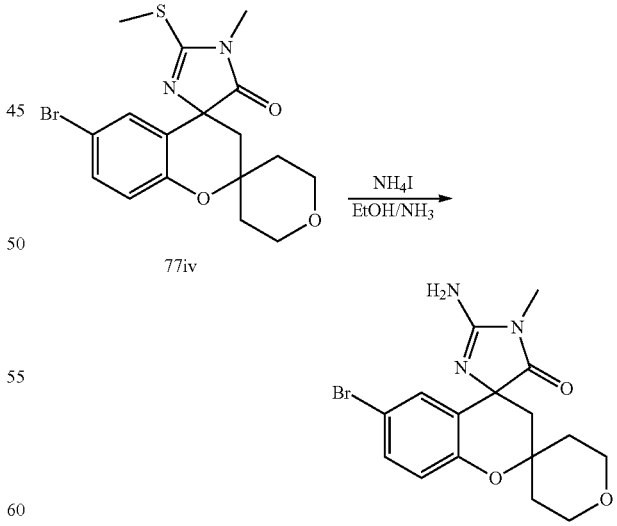

Step 5: Compound 77v

A solution of compound 77iv (28 mg, 0.07 mmol), NH$_4$I (20 mg, 0.14 mmol) in NH$_3$/EtOH (3 mL, 1.5 N) was heated at 120° C. in a 10 mL CEM test tube in a microwave reactor for 3 hrs. After cooling, the mixture was concentrated in vacuo to give the residue, which was used for the next step without further purification (24 mg, 93%).

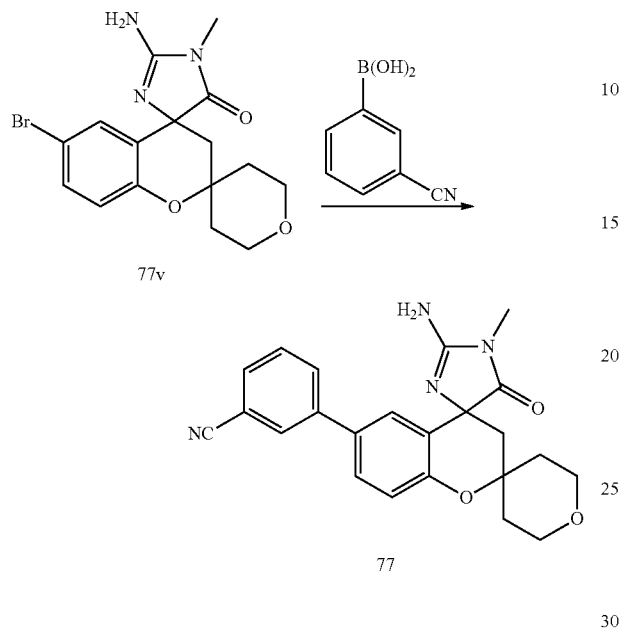

77v

77

Step 6: Compound 77

A mixture of compound 77v (24 mg, 0.06 mmol), 3-cyanophenylboronic acid (18.6 mg, 0.13 mmol), Pd(PPh$_3$)$_2$Cl$_2$ (15 mg, 50%), and aqueous cesium carbonate solution (2 N, 0.3 mL) in dry 1,4-dioxane (1 mL) was heated at 120° C. in a microwave reactor for 35 minutes. The mixture was concentrated to give the residue, which was purified by preparative TLC to give pure final product Compound 77 (1.97 mg, 8%). $^1$H-NMR (MeOD): 1.84 (m, 3H), 2.05 (s, 1H), 2.34 (d, 1H), 2.51 (d, 1H), 3.29 (s, 3H), 3.73 (m, 3H), 3.93 (m, 1H), 7.13 (d, 1H), 7.42 (s, 1H), 7.63 (m, 3H), 7.84 (m, 1H), 7.92 (s, 1H).

Example 70

Compound 78

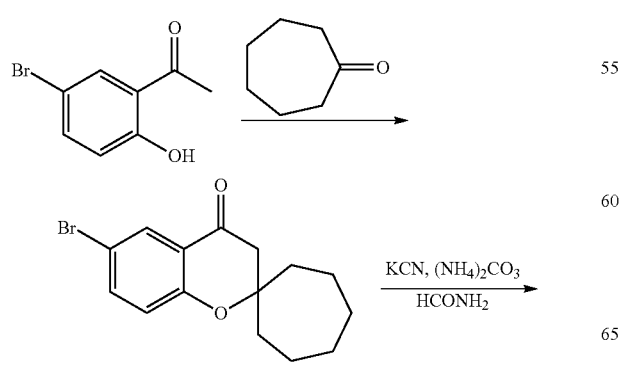

-continued

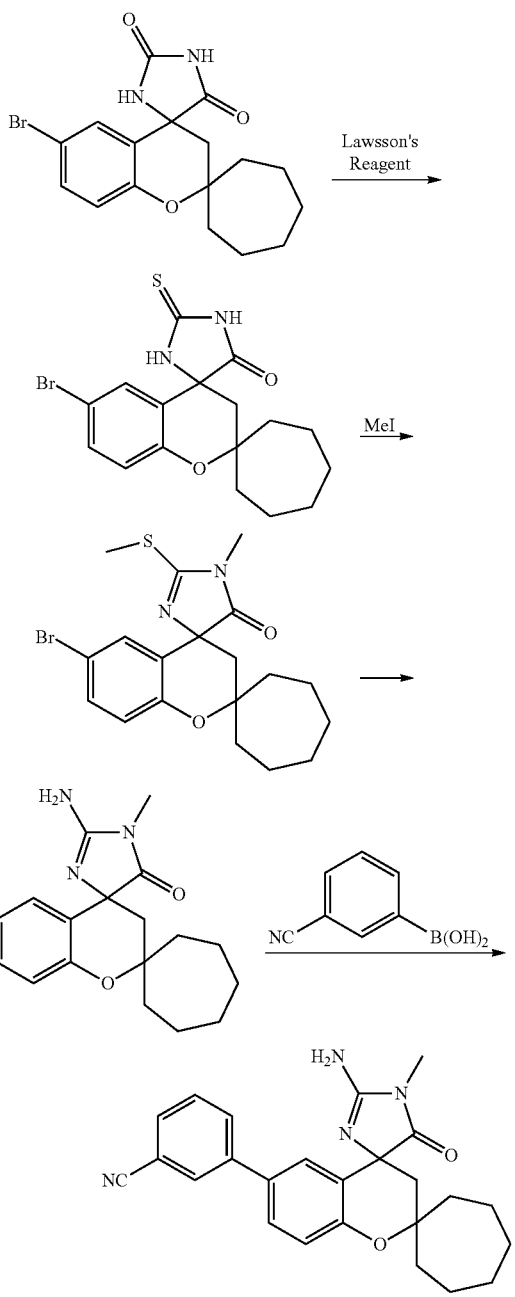

Experimental Data:

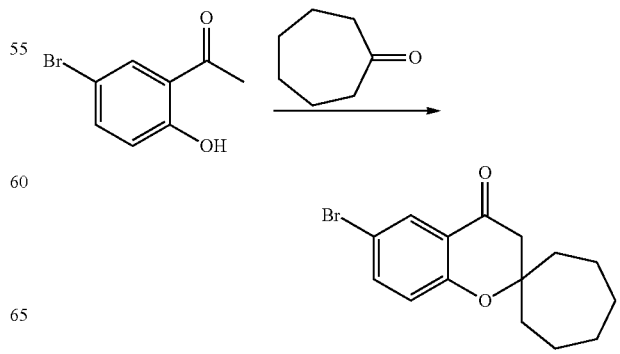

Step 1: 6-bromospiro[chroman-2,1'-cycloheptan]-4-one

A mixture of 1-(5-bromo-2-hydroxy-phenyl)-ethanone (10 g, 46.7 mmol), cycloheptanone (11 mL, 93.5 mmol) and pyrrolidine (7.7 mL, 93.5 mmol) in MeOH (190 mL) was stirred at room temperature overnight. The mixture was concentrated in vacuo to give the residue, which was added water and HCl (36%) until pH=1. The mixture was extracted with EtOAc and then the organic layer was concentrated to give 6-bromospiro[chroman-2,1'-cycloheptan]-4-one (18.3 g, 100%). $^1$H-NMR (CDCl$_3$): 1.34 (m, 1H), 1.49 (m, 1H), 1.62 (m, 10H), 1.71 (m, 1H), 2.02 (m, 1H), 6.78 (m, 1H), 7.47 (m, 1H), 7.86 (m, 1H).

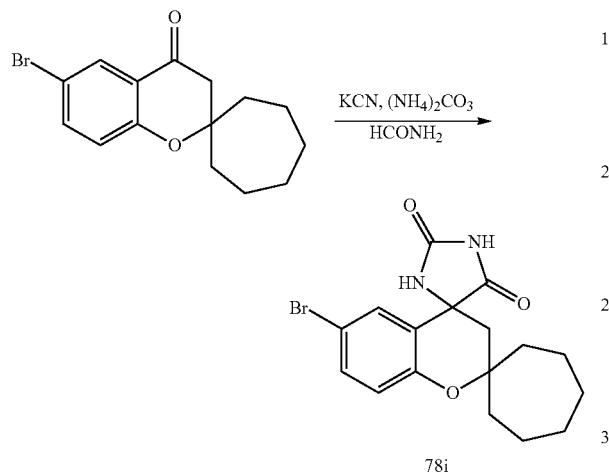

Step 2: Compound 78i

In a steel bomb, a mixture of 6-bromospiro[chroman-2,1'-cycloheptan]-4-one (1.5 g, 4.87 mmol), KCN (0.633 g, 9.74 mmol) and (NH$_4$)$_2$CO$_3$ (3.5 g, 36.52 mmol) in formamide (30 mL) was heated to 70-75° C. for 3 days. The mixture was poured into ice/water. Concentrated HCl was added until pH=1. The mixture was filtered, and the filtrate was extracted with CH$_2$Cl$_2$. The organic layer was concentrated to give compound 78i (370 mg, 20%). $^1$H-NMR (DMSO): 1.79 (m, 4H), 1.96 (m, 6H), 2.13 (m, 1H), 2.22 (m, 2H), 2.36 (m, 1H), 7.19 (m, 1H), 7.50 (m, 1H), 7.72 (m, 1H).

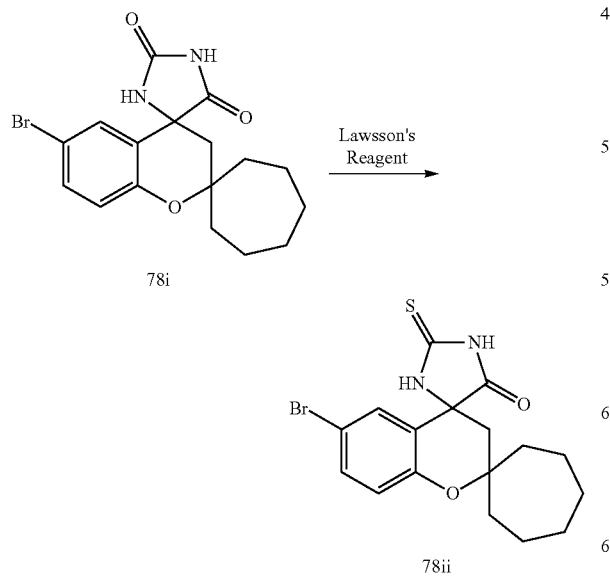

Step 3: Compound 78ii

A mixture of compound 78i (75 mg, 0.20 mmol) and Lawesson's Reagent (80 mg, 0.20 mmol) in 1,4-dioxane (1.2 mL) was stirred at 110° C. overnight. The solvent was removed in vacuo and the residue was purified by preparative TLC to give compound 78ii (10 mg, 13%).

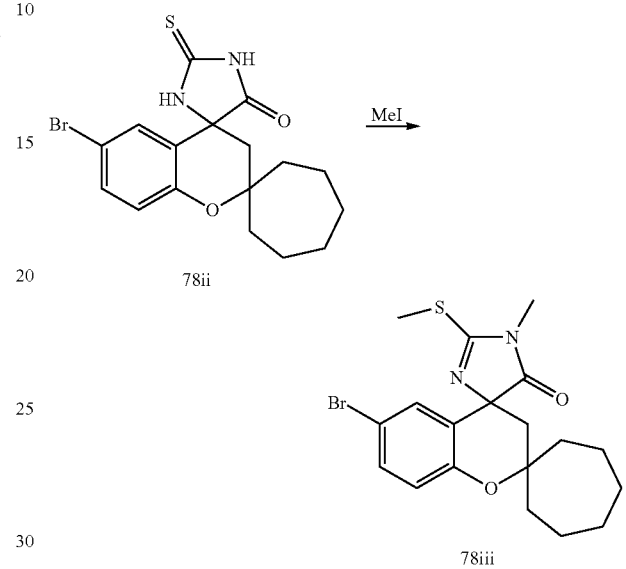

Step 4: Compound 78iii

To a mixture of compound 78ii (35 mg, 0.089 mmol) and NaOH (0.2 mL, 0.6 N) in MeOH (3 mL) was added MeI (52 mg, 0.356 mmol). The reaction mixture was stirred in a microwave reactor at 60° C. for 15 minutes. The mixture was concentrated to give the residue, which was purified by preparative TLC to give compound 78iii (20 mg, 53%).

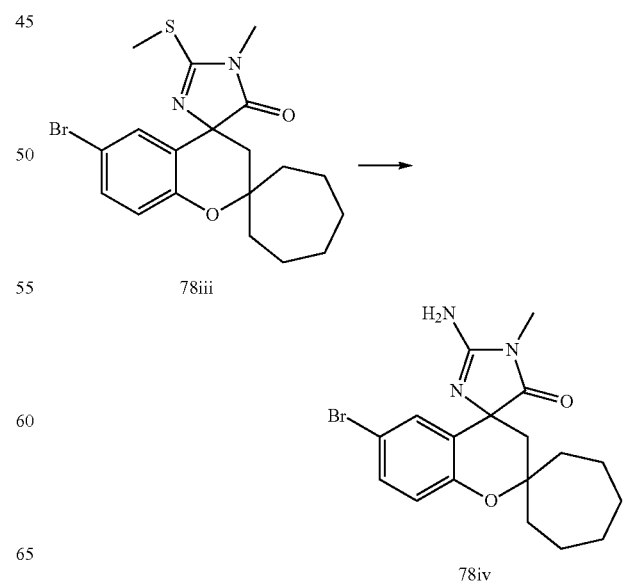

Step 5: Compound 78iv

A solution of compound 78iii (20 mg, 0.047 mmol) and NH₄I (14 mg, 0.094 mmol) in NH₃/EtOH (2 mL, 1.5 N) was heated at 110° C. in a tube in a microwave reactor for 3 h. After cooling, the mixture was concentrated in vacuo to give the residue, which was purified by preparative TLC to afford compound 78iv (10 mg, 50%).

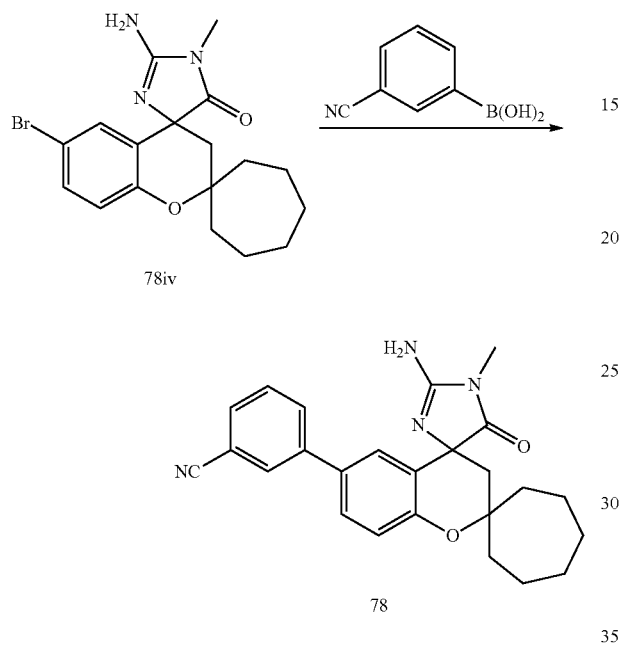

Step 5: Compound 78

Pd(PPh₃)₂Cl₂ (5 mg, 0.005 mmol) in a 10 mL flask under Ar was treated sequentially with compound 78iv (10 mg, 0.025 mmol) in 1,4-dioxane (1 mL), Cs₂CO₃ (2 N, 0.15 mL) and 3-cyanophenylboronic acid (8 mg, 0.05 mmol). The mixture was heated at 120° C. under Ar in a microwave reactor for 30 minutes. The reaction mixture was concentrated in vacuo to give the residue, which was purified by preparative TLC twice to give pure Compound 78 (2.25 mg, 20%). ¹H-NMR (MeOD): 1.41 (m, 2H), 1.60 (m, 4H), 1.80 (m, 3H), 2.01 (m, 3H), 2.16 (m, 1H), 2.22 (m, 1H), 2.82-3.05 (m, 3H), 6.85 (m, 1H), 6.91 (m, 1H), 7.37 (m, 1H), 7.48 (m, 1H), 7.54 (m, 1H), 7.68 (m, 1H), 7.71 (m, 1H).

Example 71

Compound 79

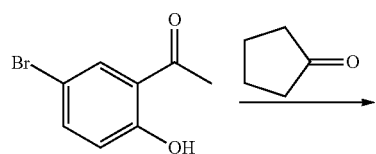

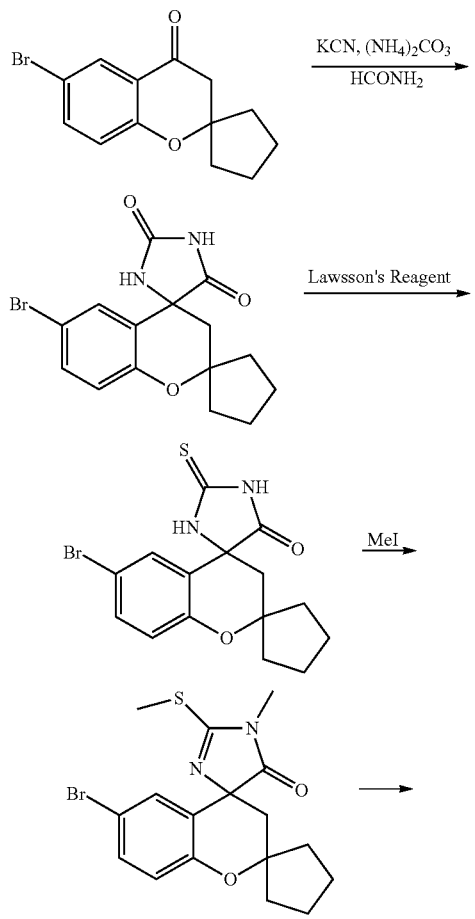

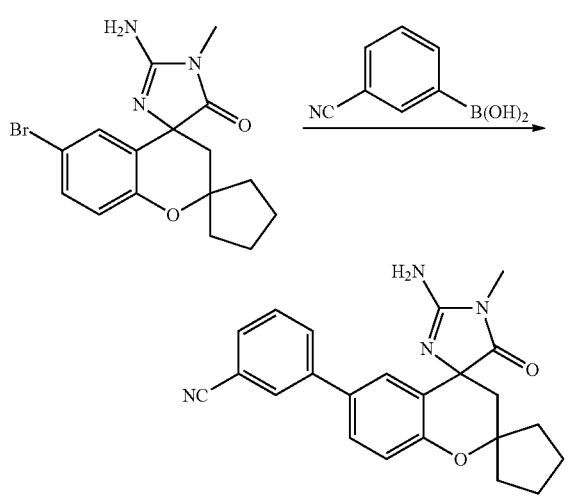

Experimental Data:

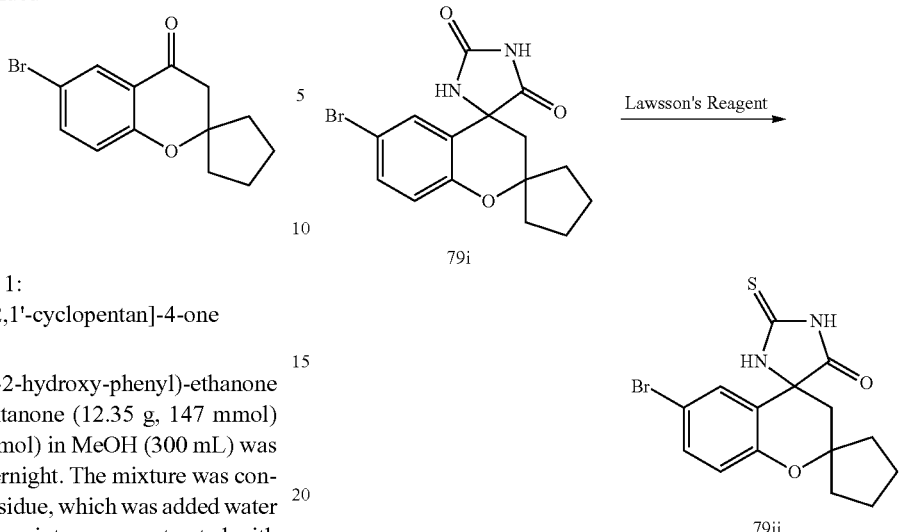

Step 1:
6-bromospiro[chroman-2,1'-cyclopentan]-4-one

A mixture of 1-(5-bromo-2-hydroxy-phenyl)-ethanone (15.8 g, 73.8 mmol), cyclopentanone (12.35 g, 147 mmol) and pyrrolidine (12 mL, 140 mmol) in MeOH (300 mL) was stirred at room temperature overnight. The mixture was concentrated in vacuo to give the residue, which was added water and HCl (36%) until pH=1. The mixture was extracted with EtOAc and then the organic layer was concentrated to give 6-bromospiro[chroman-2,1'-cyclopentan]-4-one (23 g, 100%). $^1$H-NMR (CDCl$_3$): 1.64 (m, 4H), 1.72 (m, 2H), 2.03 (m, 2H), 2.78 (s, 2H), 6.78 (m, 1H), 7.48 (m, 1H), 7.91 (m, 1H).

Step 3: Compound 79ii

A mixture of compound 79i (375 mg, 1.07 mmol) and Lawesson's Reagent (430 mg, 1.07 mmol) in 1,4-dioxane (3.2 mL) was stirred at 110° C. overnight. The solvent was removed in vacuo and the residue was purified by preparative TLC to give compound 79ii (60 mg, 15%). $^1$H-NMR (CDCl$_3$): 1.51 (m, 1H), 1.69 (m, 3H), 1.79 (m, 2H), 1.98 (m, 2H), 2.17 (m, 1H), 2.64 (m, 1H), 6.68 (m, 1H), 7.02 (m, 1H), 7.25 (m, 1H).

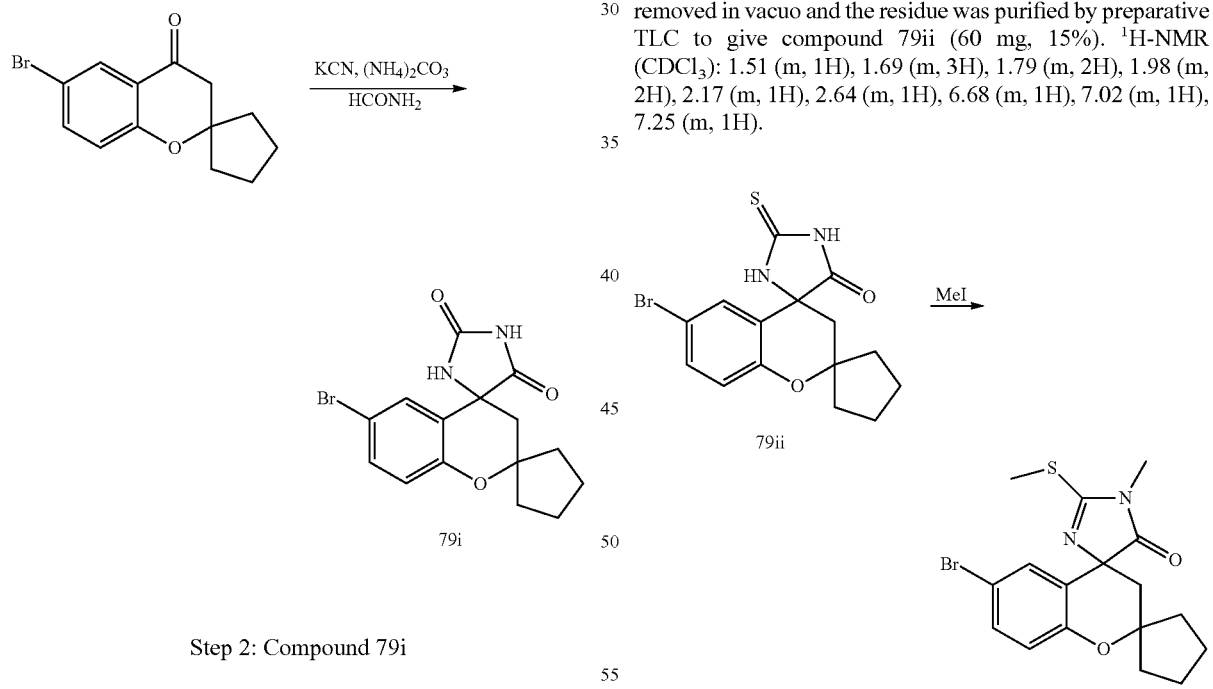

Step 2: Compound 79i

In a steel bomb, a mixture of 6-bromospiro[chroman-2,1'-cyclopentan]-4-one (1.5 g, 5.36 mmol), KCN (0.7 g, 10.72 mmol) and (NH$_4$)$_2$CO$_3$ (3.86 g, 40.22 mmol) in formamide (30 mL) was heated to 80° C. for 3 days. The mixture was poured into ice/water. Concentrated HCl was added until pH=1. The mixture was filtered, and the filtrate was extracted with CH$_2$Cl$_2$. The organic layer was concentrated to give compound 79i (1.75 g, 93%). $^1$H-NMR (CDCl$_3$): 1.42 (m, 1H), 1.61 (m, 5H), 1.76 (m, 1H), 1.92 (m, 2H), 2.57 (m, 1H), 6.57 (m, 1H), 7.00 (s, 1H), 7.13 (m, 1H), 7.91 (m, 1H).

Step 4: Compound 79iii

A mixture of compound 79ii (20 mg, 0.055 mmol) and NaOH (0.2 mL, 0.6 N) in 1,4-dioxan (2 mL) was added MeI (40 mg, 0.275 mmol). The reaction mixture was stirred in a microwave reactor at 60° C. for 10 minutes. The mixture was concentrated to give the residue, which was purified by preparative TLC to give compound 79iii (20 mg, 85%).

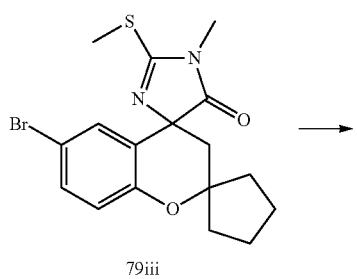

79iii

↓

Br-[structure]-79iv (H₂N, N-Me, spiro cyclopentane chromanone imidazolinone)

Step 5: Compound 79iv

A solution of compound 79iii (20 mg, 0.051 mmol), NH₄I (15 mg, 0.102 mmol) in NH₃/EtOH (2 mL, 1.5 N) was heated at 110° C. in a tube in a microwave reactor for 3 h. After cooling, the mixture was concentrated in vacuo to give the residue, which was purified by preparative TLC to afford compound 79iv (10 mg, 54%).

79iv + NC-C₆H₄-B(OH)₂ →

79 (NC-phenyl substituted product)

Step 6: Compound 79

Pd(PPh₃)₂Cl₂ (5 mg, 0.005 mmol) in a 10 mL flask under Ar was treated sequentially with compound 79iv (10 mg, 0.027 mmol) in 1,4-dioxane (1 mL), Cs₂CO₃ (2 N, 0.15 mL) and 3-cyanophenylboronic acid (8 mg, 0.055 mmol). The mixture was heated at 120° C. under Ar in a microwave reactor for 30 minutes. The reaction mixture was concentrated in vacuo to give the residue, which was purified by preparative TLC twice to give pure Compound 79 (2.25 mg, 21%). $^1$H-NMR (MeOD): 1.69 (m, 4H), 1.86 (m, 3H), 2.04 (m, 1H), 2.22 (m, 1H), 2.49 (m, 1H), 3.07 (s, 3H), 6.82 (m, 1H), 6.96 (m, 1H), 7.11 (m, 2H), 7.39 (m, 1H), 7.52 (m, 1H), 7.70 (m, 1H).

Example 72

Compound 84

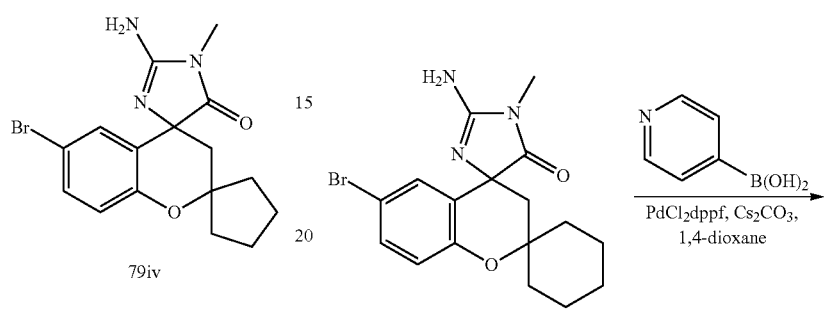

To a solution of the cyclohexyl-acyl-guanidine (57 mg, 0.15 mmol) in 1,4-dioxane (1.5 mL) was added Cs₂CO₃ (161 mg, 0.45 mmol), pyridin-4-ylboronic acid (28 mg, 0.22 mmol), and PdCl₂dppf (6 mg, 5 mol %). After degassing, the resulting mixture was heated in a CEM microwave reactor at 120° C. for 30 min Solvent was removed in vacuo and the residue was purified by reverse phase HPLC to give the final product (9.5 mg, 16.8%) as a TFA salt. $^1$H NMR (400 MHz, CD₃OD): 8.76 (d, 2H), 8.24 (d, 2H), 7.96 (dd, 1H), 7.78 (d, 1H), 7.18 (d, 1H), 3.30 (s, 3H), 2.44 (s, 2H), 2.00-1.80 (m, 3H), 1.76-1.48 (m, 6H), 1.42 (m, 1H); MS m/z 377 (M+H⁺).

Example 73

Compound 81

[structure: Br-chroman-spirocyclohexane-CF₃-hydantoin] → Lawsson's Reagent

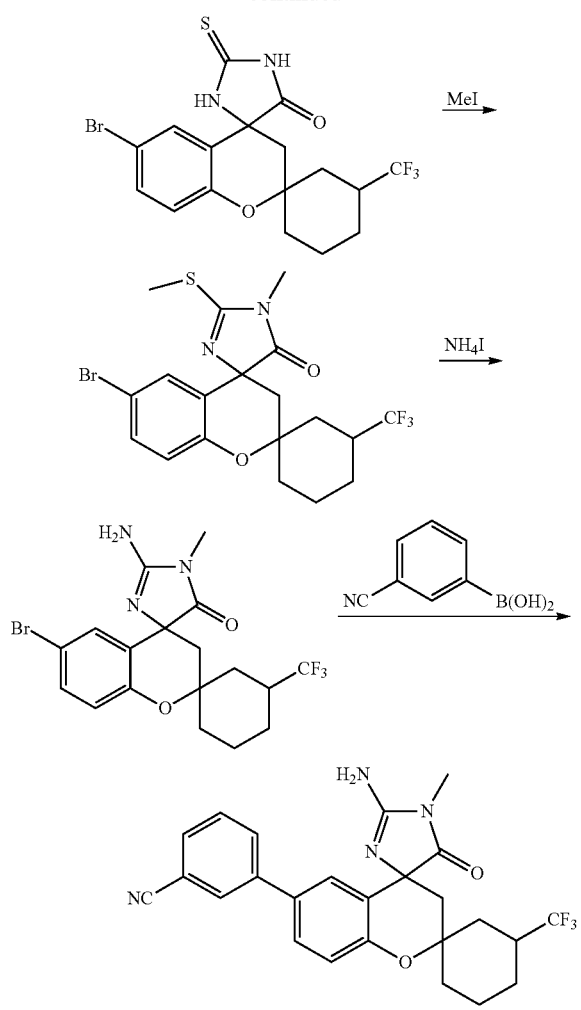

Experimental Data:

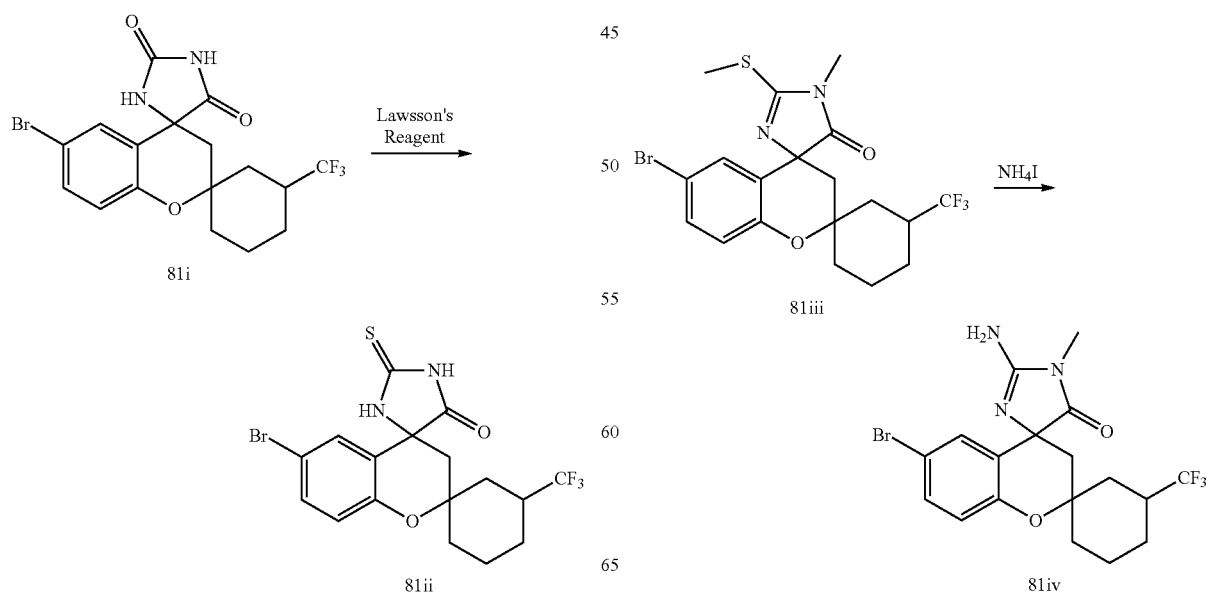

Step 1

A suspension of the compound 81i (300 mg, 0.69 mmol) and Lawesson's Reagent (280 mg, 0.69 mmol) in dry 1,4-dioxane (4 mL) was heated at 120° C. for 30 minutes under microwave. The mixture was concentrated in vacuo and the residue was purified by preparative TLC to give the compound 81ii (160 mg, 50%).

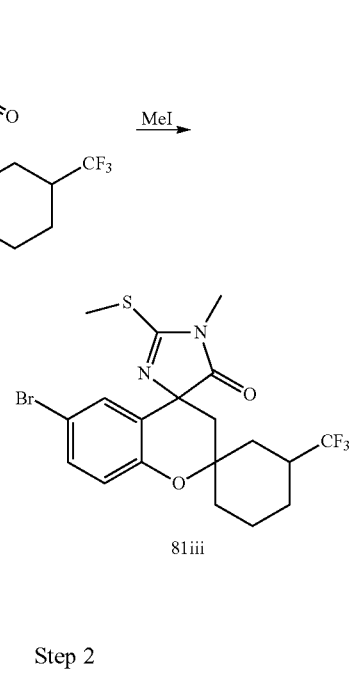

Step 2

To a solution of the compound 81ii (160 mg, 0.36 mmol) in MeOH (12 mL) was added a solution of NaOH (0.6 N, 1.2 mL) and MeI (0.8 mL). The reaction mixture was heated at 60° C. for 10 min in a microwave reactor. The mixture was concentrated in vacuo to give the residue, which was purified by preparative TLC to give the compound 81iii (80 mg, 50%).

Step 3

A solution of the compound 81iii (80 mg, 0.168 mmol) and NH₄I (195 mg, 1.34 mmol) in NH₃/EtOH (2.5 mL, 8 N) was heated at 120° C. in a tube in a microwave reactor for 3 h. After cooling, the mixture was concentrated in vacuo to give compound 81Iv (100 mg, 90%).

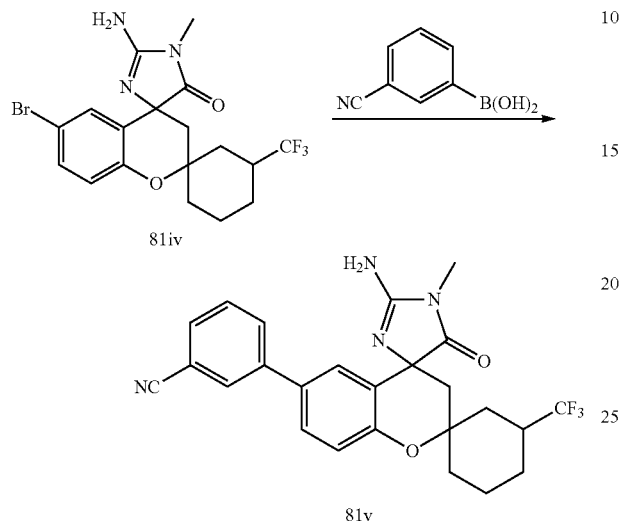

Step 4

Pd(PPh₃)₂Cl₂ (10 mg) in a 10 mL tube under Ar was treated sequentially with the compound 81 (30 mg, 0.067 mmol) in 1,4-dioxane (1.5 mL), Cs₂CO₃ (2 N, 0.4 mL) and 3-cyanophenylboronic acid (19.8 mg, 0.135 mmol). The mixture was heated in a microwave reactor at 120° C. for 35 min. The reaction mixture was concentrated in vacuo to give the residue, which was purified by preparative TLC and then by preparative HPLC to give the compound 81v (4.0 mg, 10%). ¹H-NMR (MeOD): 1.36 (t, 1H), 1.52 (t, 2H), 1.70 (d, 1H), 1.87 (m, 1H), 2.00 (d, 1H), 2.15 (dd, 1H), 2.24 (t, 1H), 2.34 (d, 1H), 2.51 (m, 2H), 3.28 (s, 3H), 7.11 (d, 1H), 7.41 (t, 1H), 7.56 (t, 1H), 7.63 (m, 2H), 7.84 (d, 1H), 7.93 (s, 1H).

Example 74

Compound 82

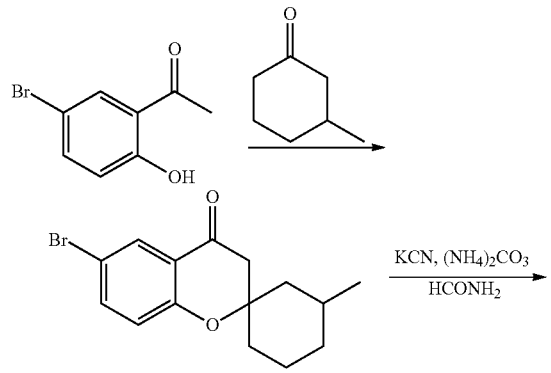

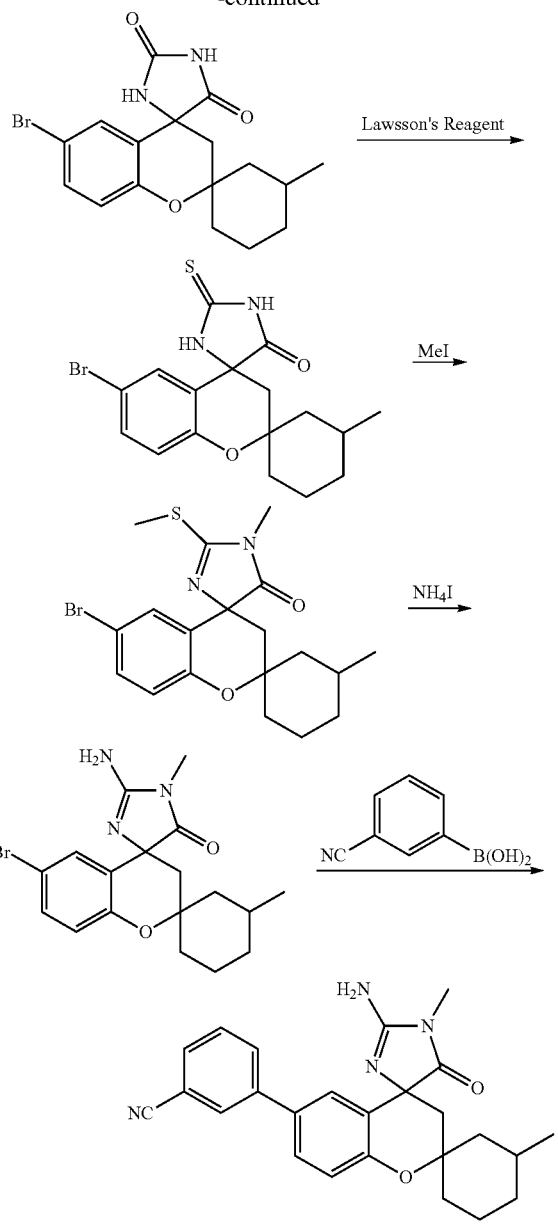

Experimental Data:

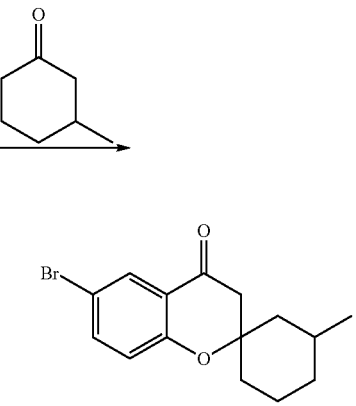

Step 1. 6-bromo-3'-methylspiro[chroman-2,1'-cyclohexan]-4-one

A mixture of 1-(5-bromo-2-hydroxy-phenyl)-ethanone (10 g, 46.7 mmol), 3-methylcyclohexanone (10.5 g, 93.4 mmol) and pyrrolidine (6.3 g, 88.8 mmol) in methanol (200 mL) was stirred overnight. The reaction mixture was concentrated in vacuo, and then $H_2O$ was added. The resulting solution was extracted with ethyl acetate. The organic layer was dried over anhydrous $Na_2SO_4$, filtered, and concentrated in vacuo to give 6-bromo-3'-methylspiro[chroman-2,1'-cyclohexan]-4-one (18 g, 100%). $^1$HNMR (CDCl$_3$): 0.86 (m, 3H), 0.91 (m, 2H), 1.02 (m, 2H), 1.30 (m, 2H), 1.52 (m, 2H), 1.65 (m, 4H), 1.80 (m, 7H), 2.01 (m, 4H), 2.22 (m, 1H), 2.48 (m, 1H), 2.60 (s, 2H), 2.72 (t, 3H), 6.81 (m, 1H), 7.50 (m, 1H), 7.91 (m, 1H).

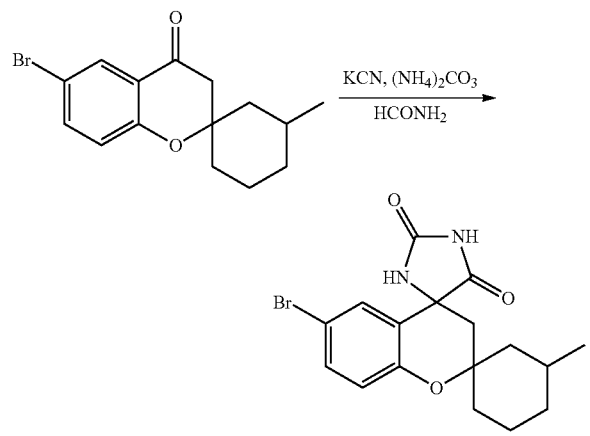

Step 2

A pressure tube was charged with a mixture of 6-bromo-3'-methylspiro[chroman-2,1'-cyclohexan]-4-one (8 g, 19.48 mmol), KCN (3.37 g, 39 mmol), and $(NH_4)_2CO_3$ (17.5 g, 136.36 mmol). Formamide (80 mL) was added to fill the tube nearly completely. The mixture was heated at 80° C. for 78 h. The reaction mixture was then cooled and poured over ice. Acidification with concentrated HCl gave a precipitate which was filtered, washed twice with water, and then dissolved in ethyl acetate. The ethyl acetate solution was dried over $Na_2SO_4$ and filtered. The filtrate was concentrated in vacuo to give the residue, which was purified by column to give the product 82i (8 g, 90%). $^1$HNMR (MeOD): 0.81 (d, 1H), 0.92 (m, 3H), 1.49 (m, 2H), 1.71 (d, 2H), 2.03 (d, 1H), 2.13 (s, 2H), 2.41 (dd, 1H), 6.78 (dd, 1H), 7.12 (d, 1H), 7.30 (m, 1H).

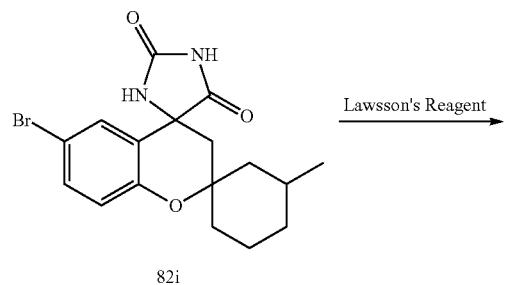

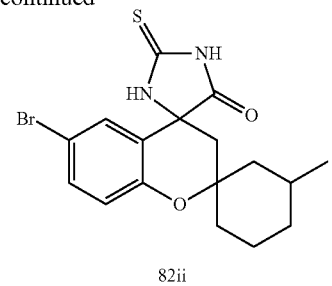

Step 3

A suspension of the compound 82i (375 mg, 1 mmol) and Lawesson's Reagent (400 mg, 1 mmol) in dry 1,4-dioxane (3.5 mL) was heated at 110° C. for 30 min in a microwave reactor. The mixture was concentrated in vacuo and the residue was purified by preparative TLC to give the compound 82ii (100 mg, 30%).

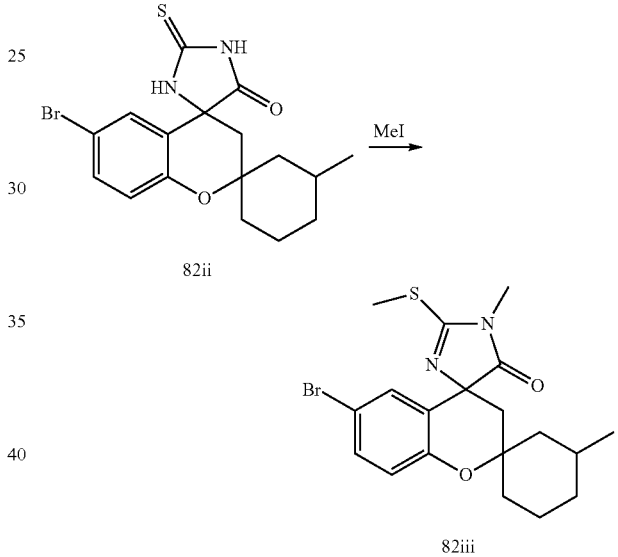

Step 4

To a solution of the compound 82ii (200 mg, 0.51 mmol) in MeOH (10 mL) was added a solution of NaOH (0.6 N, 2 mL) and MeI (0.6 mL). The reaction mixture was heated at 60° C. for 14 min in a microwave reactor. The mixture was concentrated in vacuo to give the residue, which was purified by preparative TLC to give the compound 82iii (90 mg, 45%).

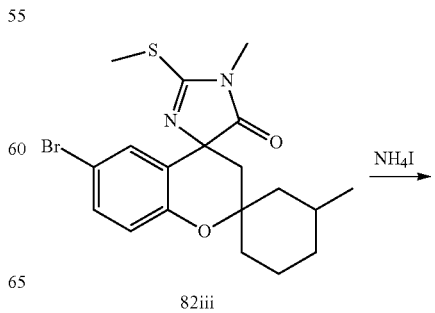

441

-continued

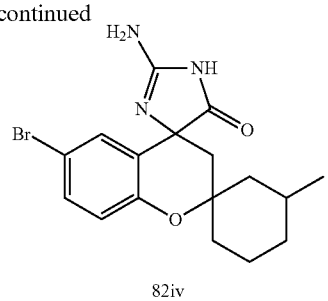

82iv

Step 5

A solution of the compound 82iii (90 mg, 0.21 mmol) and NH₄I (246 mg, 1.7 mmol) in NH₃/EtOH (2.5 mL, 8 N) was heated at 120° C. in a tube in a microwave reactor for 2 h. After cooling, the mixture was concentrated in vacuo to give the compound 82iv (90 mg, 90%).

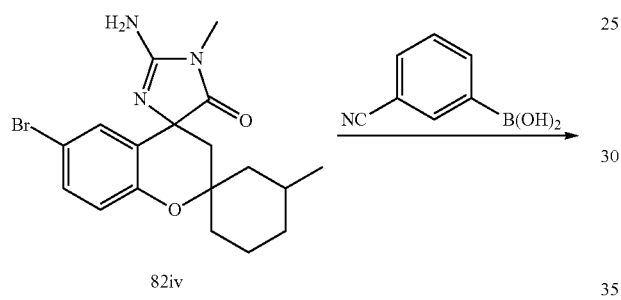

82iv

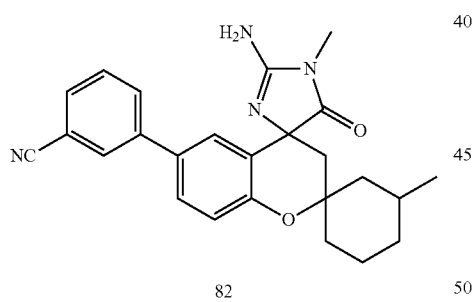

82

Step 6

Pd(PPh₃)₂Cl₂ (10 mg) in a 10 mL tube under Ar was treated sequentially with the compound 82iv (30 mg, 0.076 mmol) in 1,4-dioxane (1 mL), Cs₂CO₃ (2 N, 0.3 mL) and 3-cyanophenylboronic acid (22.56 mg, 0.15 mmol). The mixture was heated in a microwave reactor at 120° C. for 35 min. The reaction mixture was concentrated in vacuo to give the residue, which was purified by preparative TLC and then by preparative HPLC to give Compound 82 (2.58 mg, 10%).
¹H-NMR (MeOD): 0.90 (dd, 3H), 0.95 (d, 1H), 1.25 (m, 2H), 1.60 (m, 2H), 1.90 (m, 4H), 2.30 (dd, 1H), 3.34 (s, 3H), 7.05 (dd, 1H), 7.38 (s, 1H), 7.61 (m, 3H), 7.84 (d, 1H), 7.92 (s, 1H).

442

Example 75

Compound 83

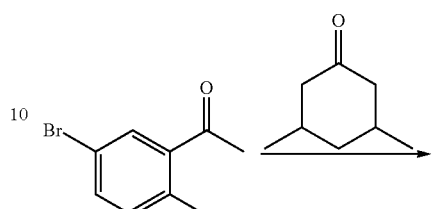

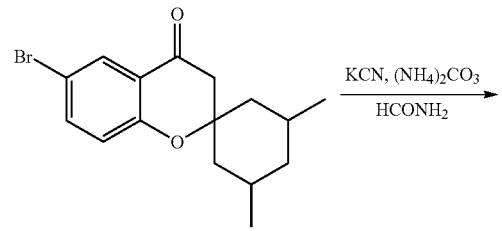

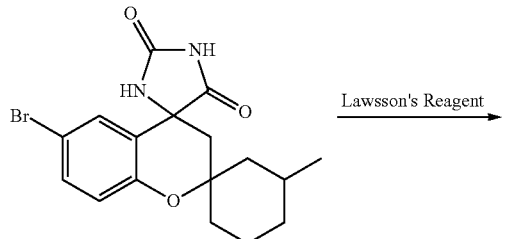

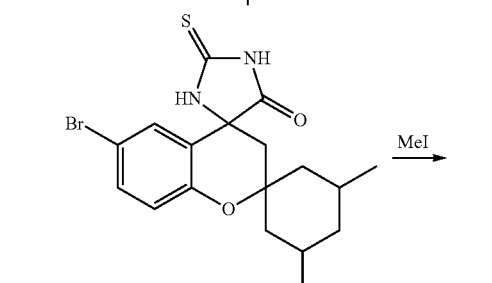

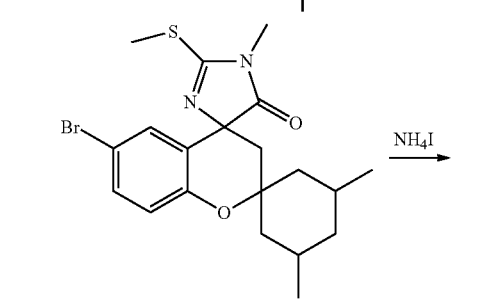

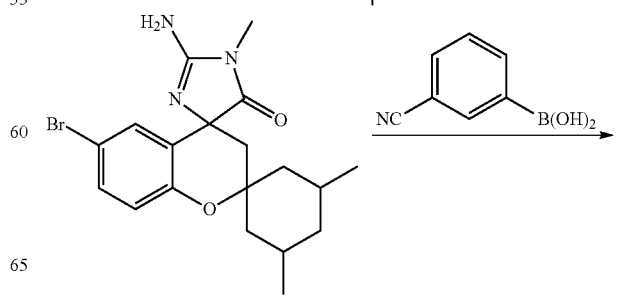

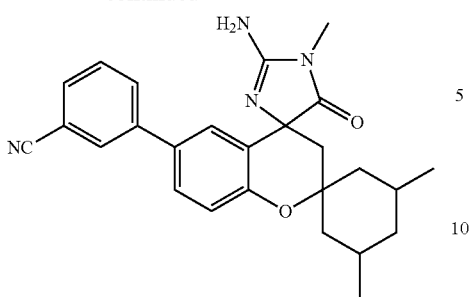

Experimental Data:

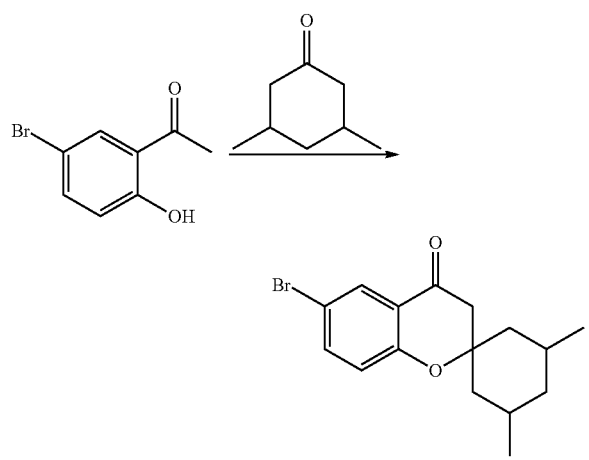

Step 1. 6-bromo-3',5'-dimethylspiro[chroman-2,1'-cyclohexan]-4-one

A mixture of 1-(5-bromo-2-hydroxy-phenyl)-ethanone (6 g, 28 mmol), 3,5-dimethylcyclohexanone (7.12 g, 56 mmol) and pyrrolidine (3.8 g, 53.3 mmol) in methanol (120 mL) was stirred overnight. The reaction mixture was concentrated in vacuo, and H$_2$O was added. The resulting solution was extracted with ethyl acetate. The ethyl acetate solution was dried over anhydrous Na$_2$SO$_4$, filtered, and concentrated in vacuo to give 6-bromo-3',5'-dimethylspiro[chroman-2,1'-cyclohexan]-4-one (10 g, 100%). $^1$HNMR (CDCl$_3$): 0.51 (m, 1H), 0.71 (m, 4H), 0.72 (m, 3H), 0.91 (m, 3H), 1.11 (d, 1H), 1.19 (t, 1H), 1.50 (s, 1H), 1.64 (t, 1H), 1.79 (m, 3H), 1.90 (m, 2H), 2.0 (m, 3H), 2.24 (t, 1H), 2.53 (s, 1H), 2.79 (s, 1H), 6.75 (t, 1H), 7.49 (t, 1H), 7.89 (d, 1H).

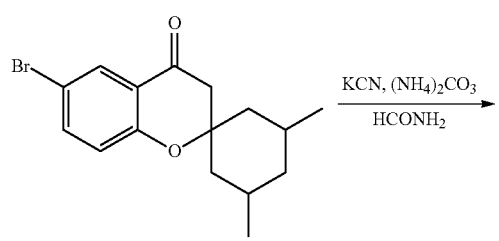

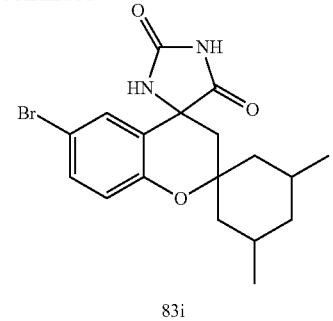

Step 2

A tube was charged with a mixture of 6-bromo-3',5'-dimethylspiro[chroman-2,1'-cyclohexan]-4-one (1.5 g, 4.64 mmol), KCN (0.6 g, 39.3 mmol), and (NH$_4$)$_2$CO$_3$ (3.12 g, 32.48 mmol). Formamide (350 mL) was added to fill the tube nearly completely. The mixture was heated at 110° C. for 4 h in a microwave reactor. The reaction mixture was then cooled and poured over ice. Acidification with concentrated HCl gave a precipitate which was filtered, washed twice with water, and then dissolved in ethyl acetate, dried over Na$_2$SO$_4$ and filtered. The filtrate was concentrated in vacuo to give the residue, which was purified by column to give the compound 83i (700 mg, 40%).

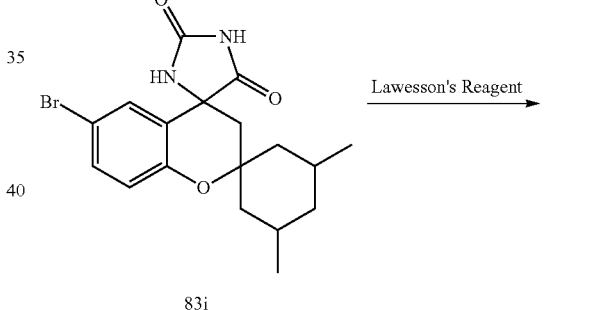

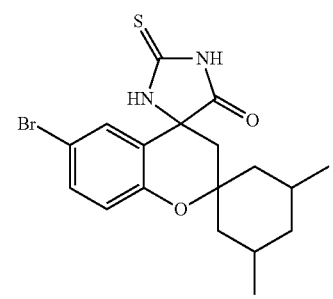

Step 3

A suspension of the compound 83i (375 mg, 0.96 mmol) and Lawesson's Reagent (386 mg, 0.957 mmol) in dry 1,4-dioxane (3.5 mL) was heated at 110° C. for 30 min in a microwave reactor. The mixture was concentrated in vacuo and the residue was purified by preparative TLC to give the compound 83ii (200 mg, 60%).

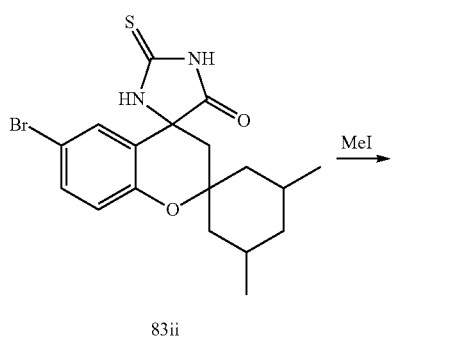

83ii

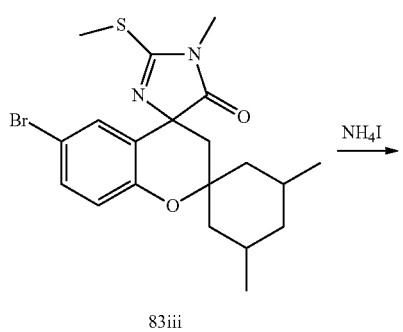

83iii

Step 4

To a solution of the compound 83ii (200 mg, 0.50 mmol) in MeOH (10 mL) was added a solution of NaOH (0.6 N, 2 mL) and MeI (0.6 mL). The reaction mixture was heated at 60° C. for 14 min in a microwave reactor. The mixture was concentrated in vacuo to give the residue, which was purified by preparative TLC to give the compound 83iii (15 mg, 10%).

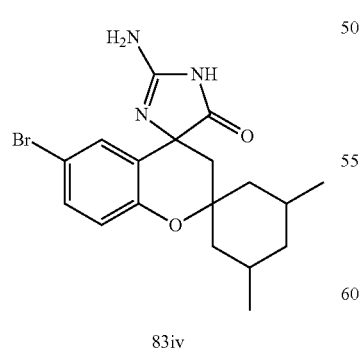

Step 5

A solution of the compound 83iii (15 mg, 0.034 mmol) and NH₄I (39.7 mg, 0.27 mmol) in NH₃/EtOH (2.5 mL, 8 N) was heated at 120° C. in a tube in a microwave reactor for 2 h. After cooling, the mixture was concentrated in vacuo to give the compound 83iv (20 mg, 100%).

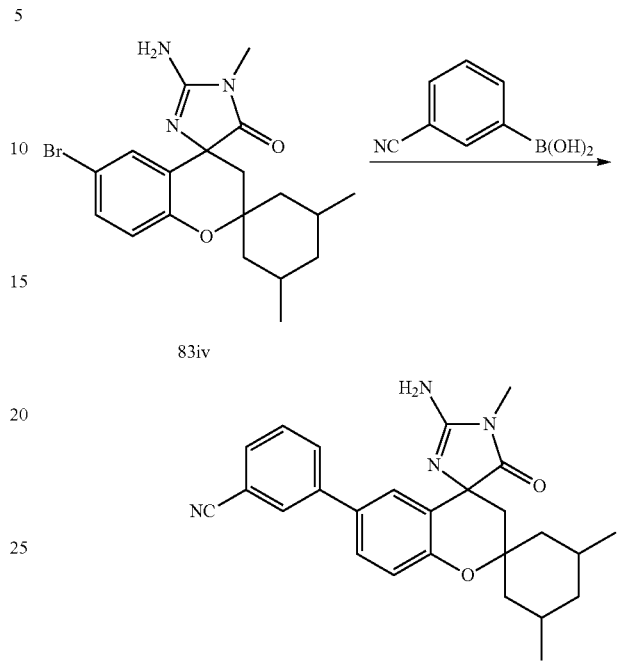

Step 6

Pd(PPh₃)₂Cl₂ (10 mg) in a 10 mL of tube under Ar₂ was treated sequentially with the compound 83iv (20 mg, 0.05 mmol) in 1,4-dioxane (1 mL), Cs₂CO₃ (2 N, 0.3 mL) and 3-cyanophenylboronic acid (14.7 mg, 0.1 mmol). The mixture was heated in a microwave reactor at 120° C. for 35 min. The reaction mixture was concentrated in vacuo to give the residue, which was purified by preparative TLC and then by preparative HPLC to give Compound 83 (2.7 mg, 10%).
¹H-NMR (MeOD): 0.55 (dd, 1H), 0.87 (m, 6H), 1.20 (m, 2H), 1.70 (m, 5H), 2.35 (m, 1H), 2.51 (m, 1H), 6.99 (t, 1H), 7.34 (s, 1H), 7.54 (m, 3H), 7.81 (d, 1H), 7.89 (s, 1H).

Example 76

3-(3'-amino-2'-methyl-2-(tetrahydro-2H-pyran-3-yl)-2'H-spiro[chroman-4,5'-[1,2,4]oxadiazole]-6-yl)benzonitrile (Compound 85)

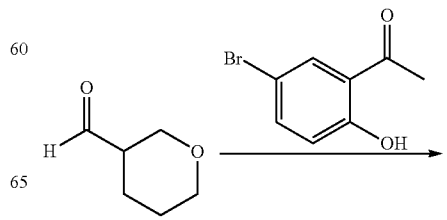

-continued

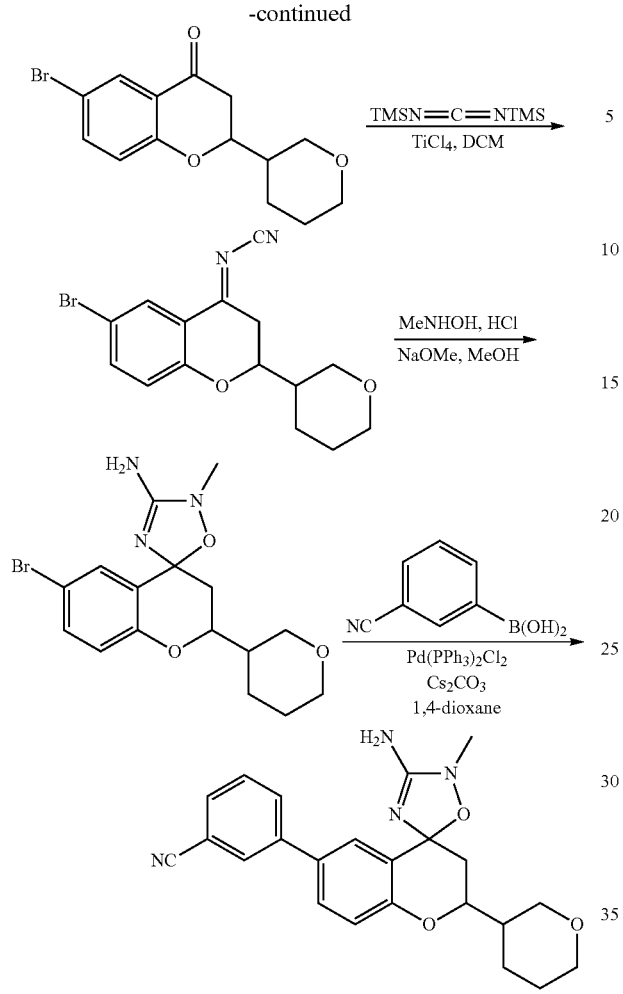

Experimental Data:

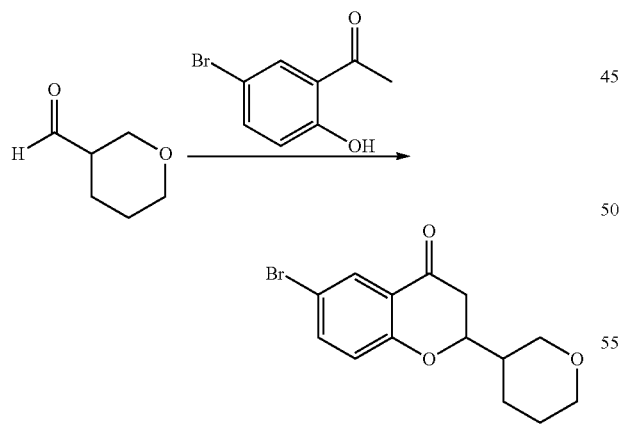

Step 1: 6-bromo-2-(tetrahydro-2H-pyran-3-yl)chroman-4-one

A mixture of 1-(5-bromo-2-hydroxyphenyl)ethanone (39 g, 181.8 mmol), tetrahydro-2H-pyran-3-carbaldehyde (20 g, 181.8 mmol) and borax (69.3 g, 181.8 mmol) in ethanol (240 mL) and $H_2O$ (400 mL) was refluxed for one day. The reaction mixture was cooled, diluted with an equal volume of $H_2O$ and extracted with ethyl acetate. The organic layer was dried over anhydrous $Na_2SO_4$, filtered, and concentrated in vacuo to give 6-bromo-2-(tetrahydro-2H-pyran-3-yl)chroman-4-one (10 g, 20%).

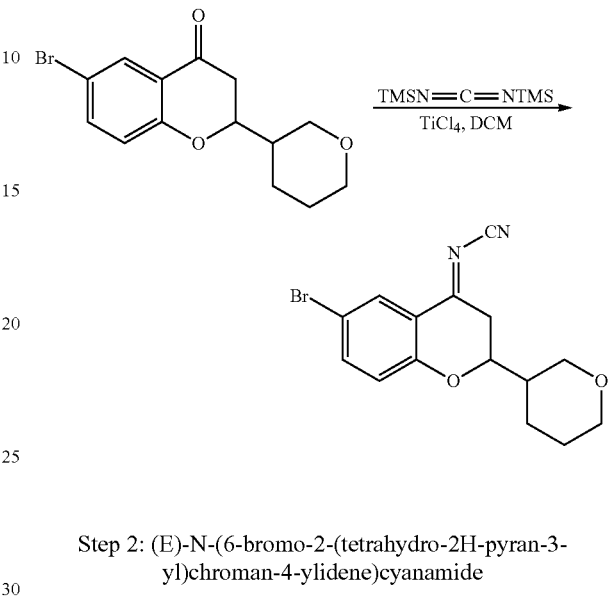

Step 2: (E)-N-(6-bromo-2-(tetrahydro-2H-pyran-3-yl)chroman-4-ylidene)cyanamide

To a solution of 6-bromo-2-(tetrahydro-2H-pyran-3-yl)chroman-4-one (300 mg, 0.98 mmol) in anhydrous DCM (8 mL) was added $TiCl_4$ (1 M solution in DCM, 1.96 mL, 1.96 mmol) dropwise within 15 min at room temperature. It was stirred for 1 h after the addition. To this mixture was added bis-trimethylsilylcarbodiimide (400.7 mg, 2.15 mmol) dropwise. The resulting mixture was stirred for 18 h after the addition. The reaction mixture was poured into ice-water (100 g) and extracted with DCM (3×50 mL). The combined organic phases were dried over anhydrous $Na_2SO_4$, filtered, and concentrated to give (E)-N-(6-bromo-2-(tetrahydro-2H-pyran-3-yl)chroman-4-ylidene)cyanamide (300 mg, 100%), which was used in next step without further purification.

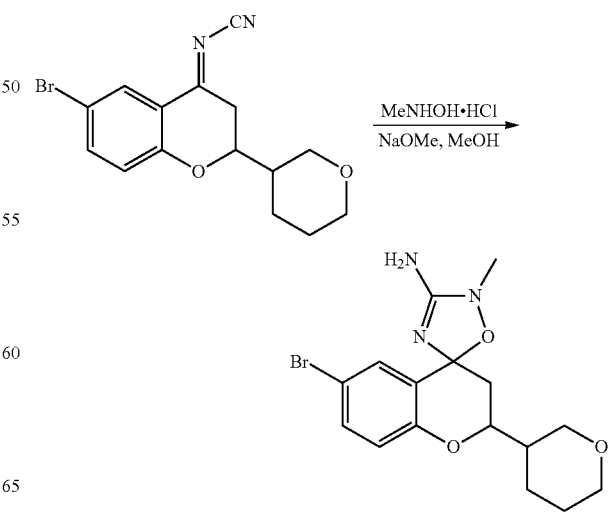

Step 3: 6-bromo-2'-methyl-2-(tetrahydro-2H-pyran-3-yl)-2'H-spiro[chroman-4,5'-[1,2,4]oxa diazol]-3'-amine To a solution of methylhydroxylamine HCl salt (75 mg, 0.9 mmol) in anhydrous MeOH (10 mL) was added NaOMe (25 w % in MeOH, 0.13 mL), followed by (E)-N-(6-bromo-2-(tetrahydro-2H-pyran-3-yl)chroman-4-ylidene)cyanamide (300 mg, 0.9 mmol). After stirring for 10 min, the solvent was removed in vacuo. The residue was redissolved in DCM (20 mL). The mixture was filter, and the solvent was removed in vacuo. The resulting residue was purified by preparative TLC to give 20 mg of 6-bromo-2'-methyl-2-(tetrahydro-2H-pyran-3-yl)-2'H-spiro[chroman-4,5'-[1,2,4]oxadiazol]-3'-amine (50 mg, 10%).

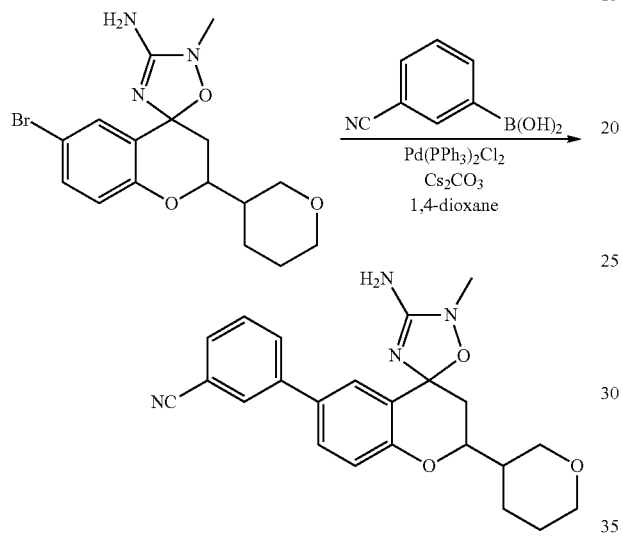

Step 4: 3-(3'-amino-2'-methyl-2-(tetrahydro-2H-pyran-3-yl)-2'H-spiro[chroman-4,5'-[1,2,4]oxadiazole]-6-yl)benzonitrile Pd(PPh$_3$)$_2$Cl$_2$ (10 mg) in a 10 mL tube under Ar was treated sequentially with 6-bromo-2'-methyl-2-(tetrahydro-2H-pyran-3-yl)-2'H-spiro[chroman-4,5'-[1,2,4]oxadiazol]-3'-amine (40 mg, 0.1 mmol) in 1,4-dioxane (2 mL), Cs$_2$CO$_3$ (2 N, 0.4 mL) and 3-cyanophenylboronic acid (31 mg, 0.2 mmol). The mixture was heated in a microwave reactor at 120° C. for 30 min. The reaction mixture was concentrated in vacuo to give the residue, which was purified by preparative TLC and then by preparative HPLC to give pure 3-(3'-amino-2'-methyl-2-(tetrahydro-2H-pyran-3-yl)-2'H-spiro[chroman-4,5'-[1,2,4]oxadiazole]-6-yl)benzonitrile (5 mg, 10%). $^1$H-NMR (MeOD): 1.69 (m, 2.5H), 2.01 (m, 3H), 2.51 (m, 1H), 2.72 (m, 1H), 3.42 (d, 2H), 3.52 (m, 3H), 3.90 (m, 2H), 4.15 (m, 1.5H), 7.02 (d, 1H), 7.59 (t, 1H), 7.68 (m, 2H), 7.94 (m, 3H).

Example 77

3-(3'-amino-2'-methyl-2-(tetrahydro-2H-pyran-4-yl)-2'H-spiro[chroman-4,5'-[1,2,4]-oxadiazole]-6-yl)benzonitrile (Compound 88)

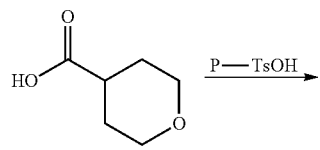

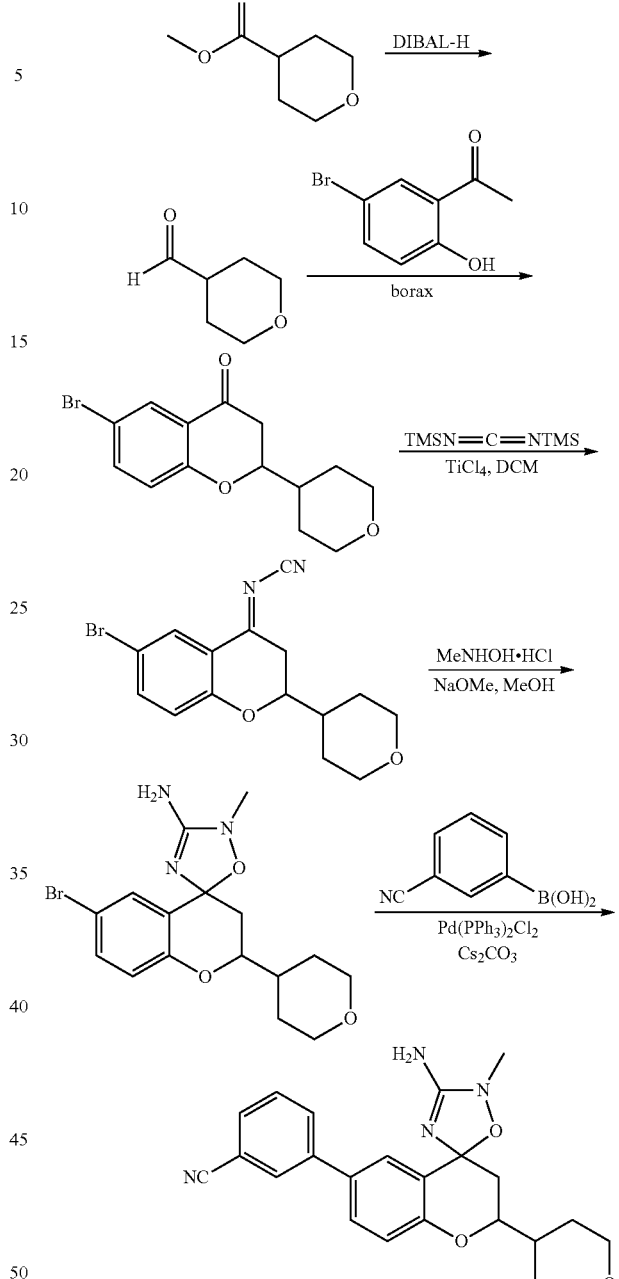

Experimental Data:

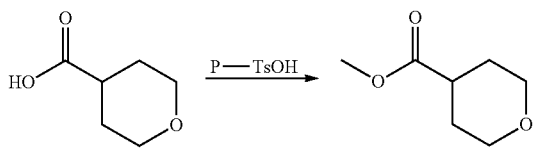

Step 1. methyl tetrahydro-2H-pyran-4-carboxylate

To a solution of tetrahydro-2H-pyran-4-carboxylic acid (50 g, 385 mmol) in anhydrous methanol (500 mL) was added 4-methylbenzenesulfonic acid hydrate (72.5 g, 385 mmol). The mixture was refluxed for 2 hr. The solvent was removed in vacuo. Ethyl ether and water was added. The organic phase was washed with water and brine, then dried over Na₂SO₄, filtered and concentrated to give methyl tetrahydro-2H-pyran-4-carboxylate (8.3 g, 75%), which was used in next step without purification.

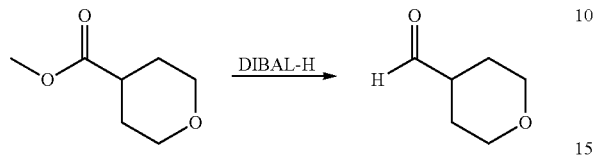

Step 2. tetrahydro-2H-pyran-4-carbaldehyde

To a stirred solution of methyl tetrahydro-2H-pyran-4-carboxylate (1 g, 6.95 mmol) in dried THF was added DIBAL-H (7.6 mL, 7 mmol) at −78° C. The mixture was stirred at the same temperature until the reaction was complete. The mixture was quenched with saturated NH₄Cl. The mixture was filtrated and the filtrate was extracted with ethyl ether for 3 times. The combined organic layers were dried over Na₂SO₄. Filtration followed by concentration in vacuo gave tetrahydro-2H-pyran-4-carbaldehyde (450 mg, 50%), which was used in next step without purification.

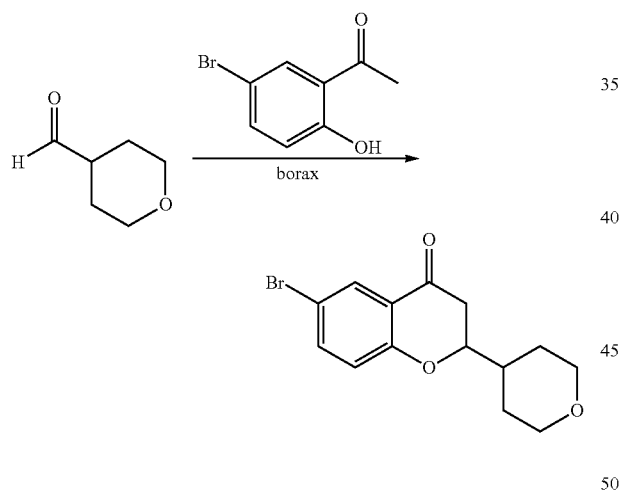

Step 3. 6-bromo-2-(tetrahydro-2H-pyran-4-yl)chroman-4-one

To a stirred solution of 1-(5-bromo-2-hydroxyphenyl)ethanone (943.9 mg, 4.39 mmol) in EtOH (5.6 mL) and H₂O (9.4 mL) was added tetrahydro-2H-pyran-4-carbaldehyde (500 mg, 4.39 mmol) and borax (1.67 g, 4.39 mmol). The mixture was refluxed overnight. Then the mixture was filtered and the filtrate was concentrated in vacuo. The resulting residue was dissolved in CH₂Cl₂ and filtrated. The filtrate was concentrated in vacuo to give the crude product, which was purified by column chromatography to give 6-bromo-2-(tetrahydro-2H-pyran-4-yl)chroman-4-one (270 mg, 20%). ¹H-NMR (CDCl₃, 400 MHz): 1.54 (m, 2H), 1.78 (m, 1H), 1.95 (m, 1H), 2.75 (m, 2H), 3.44 (m, 3H), 4.09 (m, 2H), 4.15 (m, 1H), 6.89 (m, 1H), 7.56 (m, 1H), 8.01 (m, 1H).

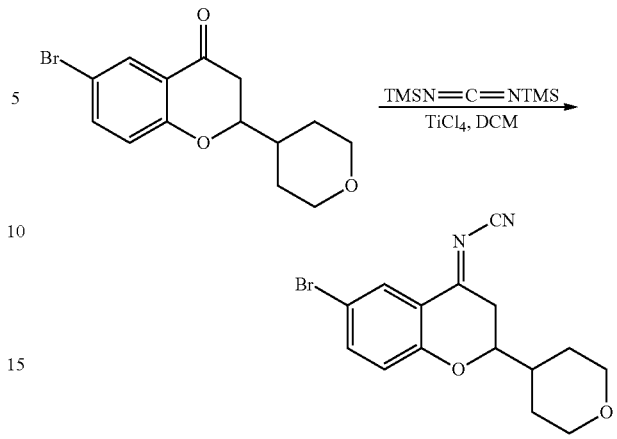

Step 4. (E)-N-(6-bromo-2-(tetrahydro-2H-pyran-4-yl)chroman-4-ylidene)cyanamide

To a solution of 6-bromo-2-(tetrahydro-2H-pyran-4-yl)chroman-4-one (310 mg, 1. mmol) in anhydrous DCM (7.8 mL) was added TiCl₄ (1 M solution in DCM, 2 mL, 2 mmol) dropwise within 15 minutes at room temperature. The reaction mixture was stirred for 1 h after the addition. To this mixture was added bis-trimethylsilylcarbodiimide (0.41 g, 0.49 mL, 2.2 mmol) dropwise. The resulting mixture was stirred for 18 h after the addition. The reaction mixture was poured into ice-water (50 g) and extracted with DCM (3×30 mL). The combined organic phases were dried over anhydrous Na₂SO₄, and filtered. The filtrate was concentrated to give (E)-N-(6-bromo-2-(tetrahydro-2H-pyran-4-yl)chroman-4-ylidene)cyanamide (240 mg, 78%), which was used in next step without further purification.

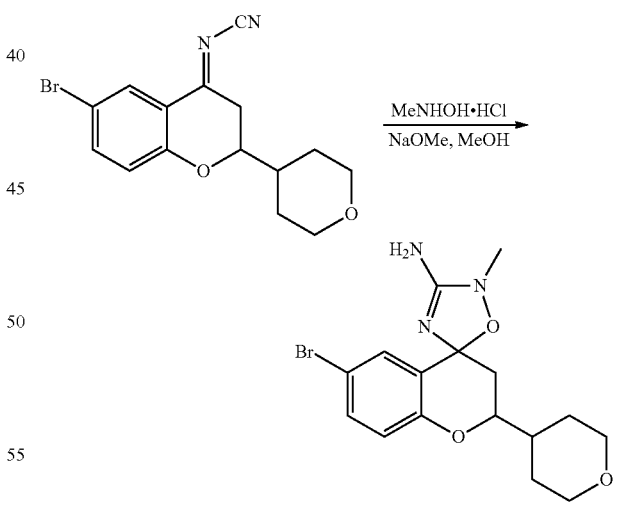

Step 5 6-bromo-2'-methyl-2-(tetrahydro-2H-pyran-4-yl)-2'H-spiro[chroman-4,5'-[1,2,4]oxa-diazol]-3'-amine To a solution of methylhydroxylamine HCl salt (25.08 mg, 0.3 mmol) in anhydrous MeOH (5 mL) was added NaOMe (25% in MeOH (Wt. %), 0.06 mL, 0.27 mmol), followed by (E)-N-(6-bromo-2-(tetrahydro-2H-pyran-4-yl)chroman-4-ylidene)cyanamide (100 mg, 0.3 mmol). After stirring 10 min, the solvent was removed in vacuo. The resulting residue was redissolved in DCM (10 mL), The mixture was filtered and the solvent was removed to give the residue, which was purified by column chromatography to give compound 6-bromo-2'-methyl-2-(tetrahydro-2H-pyran-4-yl)-2'H-spiro[chroman-4,5'-[1,2,4]oxadiazol]-3'-amine (50 mg, 40%).

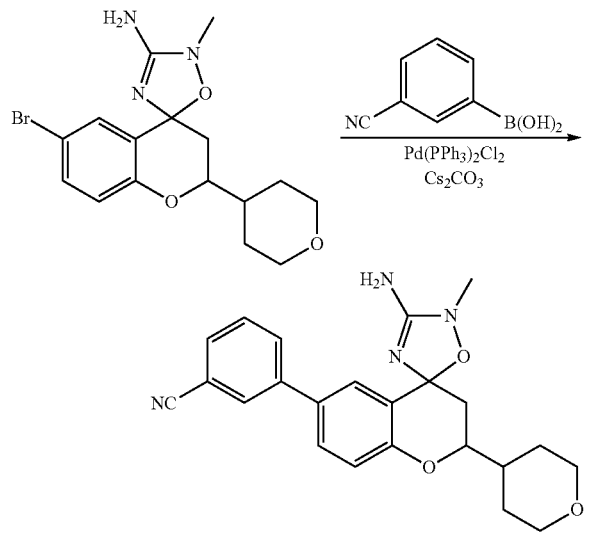

Step 6 3-(3'-amino-2'-methyl-2-(tetrahydro-2H-pyran-4-yl)-2'H-spiro[chroman-4,5'-[1,2,4]-oxadiazole]-6-yl)benzonitrile A mixture of 6-bromo-2'-methyl-2-(tetrahydro-2H-pyran-4-yl)-2'H-spiro[chroman-4,5'-[1,2,4]oxadiazol]-3'-amine (50 mg, 0.131 mmol), 3-cyanophenylboronic acid (40 mg, 0.222 mmol), Cs$_2$CO$_3$ (2 M, 0.5 mL) and Pd(PPh$_3$)$_2$Cl$_2$ (15 mg) in 1,4-dioxane (3 mL) under Ar was stirred in a microwave reactor at 120° C. for 35 minutes. The reaction mixture was concentrated in vacuo to give the residue, which was purified preparative TLC and HPLC to give 3-(3'-amino-2'-methyl-2-(tetrahydro-2H-pyran-4-yl)-2'H-spiro[chroman-4,5'-[1,2,4]oxadiazole]-6-yl)benzonitrile (2.54 mg, 5%). $^1$H-NMR (CDCl$_3$): 1.54 (m, 2H), 1.62 (m, 1H), 1.88 (m, 1H), 2.10 (m, 1H), 2.48 (m, 1H), 3.39 (m, 3H), 3.42 (m, 3H), 4.03 (m, 3H), 6.90 (m, 1H), 7.45 (m, 2H), 7.58 (m, 2H), 7.62 (m, 2H).

Example 78

6-(3,5-difluorophenyl)-2'-methyl-2-(tetrahydro-2H-pyran-3-yl)-2'H-spiro[chroman-4,5'-[1,2,4]oxadiazol]-3'-amine (Compound 90)

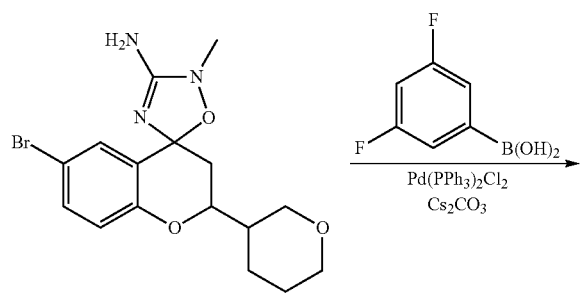

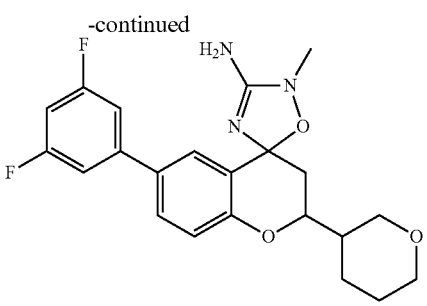

In a 10 mL flask, 6-bromo-2'-methyl-2-(tetrahydro-2H-pyran-3-yl)-2'H-spiro[chroman-4,5'-[1,2,4]oxadiazol]-3'-amine (30 mg, 0.08 mmol), Pd(PPh$_3$)$_2$Cl$_2$ (15 mg), 3,5-difluorophenylboronic acid (25 mg, 0.16 mg) were dissolved in 1,4-dioxane (4.0 mL), followed by addition of Cs$_2$CO$_3$ (2 N, 1 mL). The mixture was heated at 120° C. under Ar in a microwave reactor for 30 minutes. The reaction mixture was concentrated in vacuo to give the residue, which was purified by preparative TLC and HPLC to give 6-(3,5-difluorophenyl)-2'-methyl-2-(tetrahydro-2H-pyran-3-yl)-2'H-spiro[chroman-4,5'-[1,2,4]oxadiazol]-3'-amine (10 mg, 30%). $^1$H-NMR (MeOD): 1.62 (m, 2H), 1.96 (m, 3H), 2.70 (m, 1H), 3.30 (s, 3H), 3.38 (m, 4H), 3.83 (m, 2H), 4.12 (m, 2H), 6.84 (m, 1H), 6.96 (m, 1H), 7.18 (m, 2H), 7.64 (m, 1H), 7.86 (d, 1H).

Example 79

6-(3-fluorophenyl)-2'-methyl-2-(tetrahydro-2H-pyran-3-yl)-2'H-spiro[chroman-4,5'-[1,2,4]oxadiazol]-3'-amine (Compound 93)

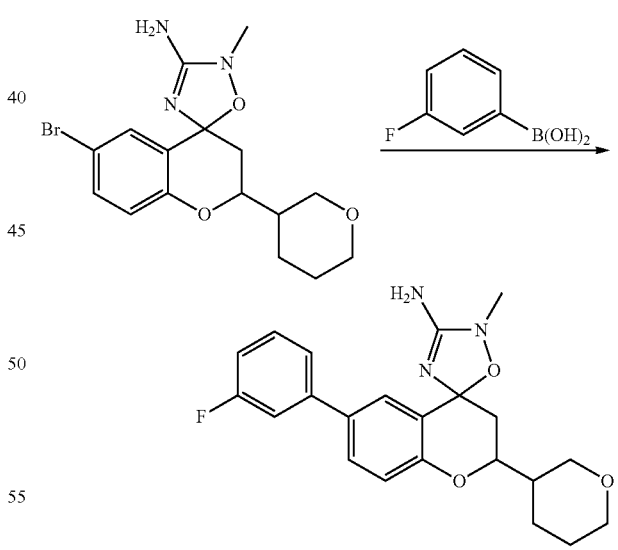

Pd(PPh$_3$)$_2$Cl$_2$ (10 mg) in a 10 mL tube under Ar was treated sequentially with 6-bromo-2'-methyl-2-(tetrahydro-2H-pyran-3-yl)-2'H-spiro[chroman-4,5'-[1,2,4]oxadiazol]-3'-amine (40 mg, 0.1 mmol) in 1,4-dioxane (2 mL), Cs$_2$CO$_3$ (2 N, 0.4 mL) and 3-fluorophenylboronic acid (29.3 mg, 0.2 mmol). The mixture was heated in a microwave reactor at 120° C. for 30 min. The reaction mixture was concentrated in vacuo to give the residue, which was purified by preparative TLC and then by preparative HPLC to give pure product 6-(3-fluorophenyl)-2'-methyl-2-(tetrahydro-2H-pyran-3-yl)-2'H-spiro[chroman-4,5'-[1,2,4]oxadiazol]-3'-amine (5 mg, 10%). ¹H-NMR (MeOD): 1.70 (m, 3H), 2.01 (m, 3H), 2.49 (m, 0.5H), 2.71 (m, 1H), 3.32 (d, 3H), 3.43 (m, 1H), 3.53 (m, 1H), 3.91 (dd, 2H), 4.19 (m, 2H), 7.03 (m, 2H), 7.32 (d, 1H), 7.43 (m, 2H), 7.66 (t, 1H), 7.89 (s, 1H).

Example 80

3-(3'-amino-2'-methyl-2-(pyridine-3-yl)-2'H-spiro[chroman-4,5'-[1,2,4]oxadiazole]-6-yl)benzonitrile (Compound 95)

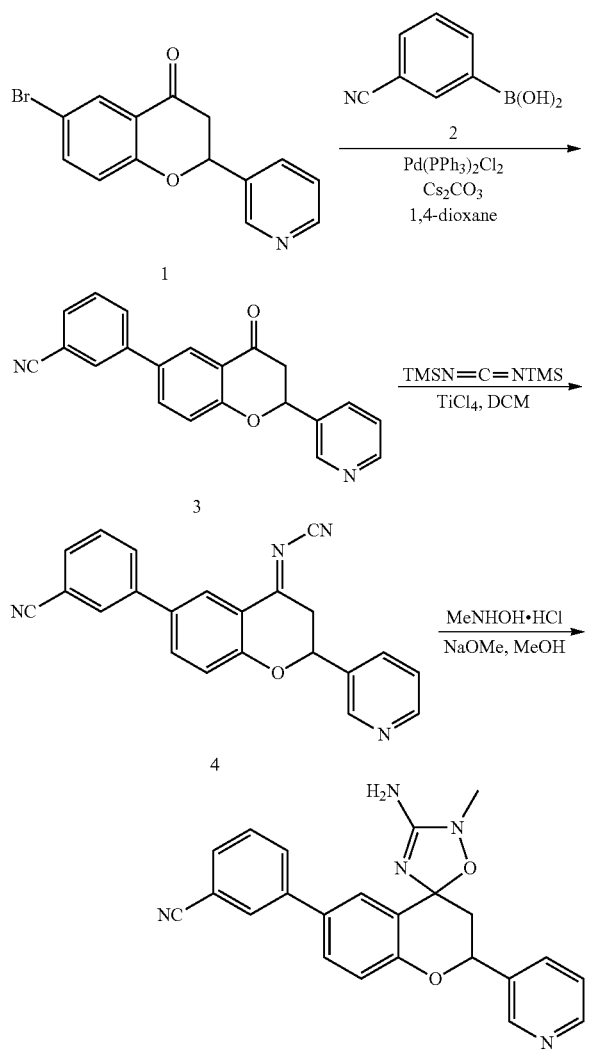

Experimental Data:

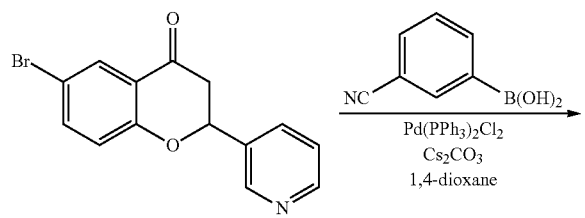

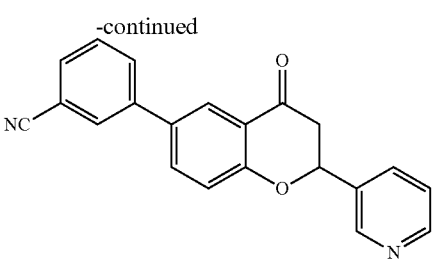

Step 1. 3-(4-oxo-2-(pyridine-3-yl)chroman-6-yl)benzonitrile

A mixture of 6-bromo-2-(pyridine-3-yl)chroman-4-one (300 mg, 1 mmol), 3-cyanophenylboronic acid (294 mg, 2 mmol), Cs₂CO₃ (2 M, 5 mL) and Pd(PPh₃)₂Cl₂ (80 mg) in 1,4-dioxane (10 mL) under Ar was stirred in a microwave reactor at 120° C. for 35 minutes. The reaction mixture was concentrated in vacuo to give the residue, which was purified preparative TLC to give 3-(4-oxo-2-(pyridine-3-yl)chroman-6-yl)benzonitrile (110 mg, 34%). ¹H-NMR (MeOD): 2.97-3.02 (d, 1H), 3.25-3.33 (m, 1H), 5.74-5.78 (d, 1H), 7.23 (d, 1H), 7.52 (m, 1H), 7.60-7.64 (m, 2H), 7.70 (d, 1H), 7.90-7.95 (m, 2H), 7.99 (s, 1H), 8.07 (d, 1H), 8.15 (s, 1H), 8.57 (d, 1H), 8.75 (s, 1H).

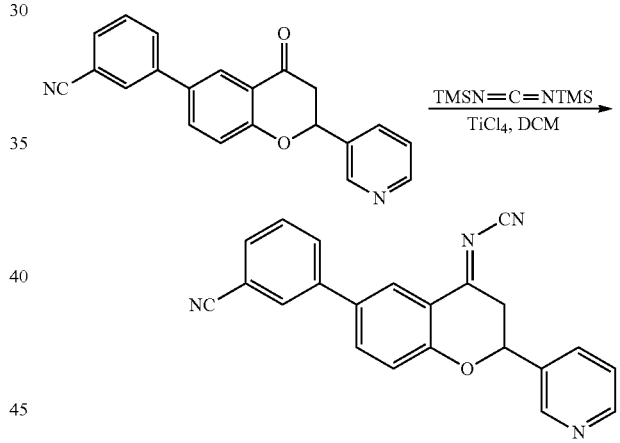

Step 2. (E)-N-(6-(3-cyanophenyl)-2-(pyridine-3-yl)chroman-4-ylidene)cyanamide

To a solution of 3-(4-oxo-2-(pyridine-3-yl)chroman-6-yl)benzonitrile (70 mg, 0.22 mmol) in anhydrous DCM (3 mL) was added TiCl₄ (1 M solution in DCM, 293 mg, 1.54 mmol) dropwise within 15 minutes at room temperature in the absence of light. The resulting mixture was stirred for 1 h after the addition. To this mixture was added bis-trimethylsilylcarbodiimide (164 mg, 0.88 mmol) dropwise. The resulting mixture was stirred overnight. The reaction mixture was poured into ice-water and extracted with DCM. The combined organic phases were dried over anhydrous Na₂SO₄, and filtered.

The filtrate was concentrated to give (E)-N-(6-(3-cyanophenyl)-2-(pyridine-3-yl)chroman-4-ylidene)cyanamide (70 mg, 93%), which was used in next step without further purification.

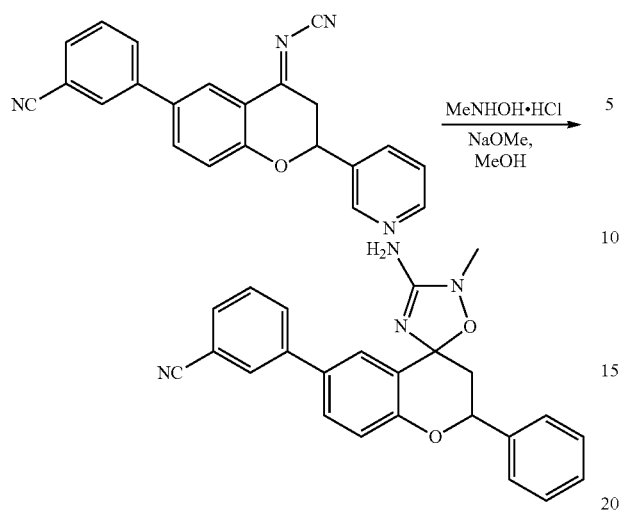

Step 3. 3-(3'-amino-2'-methyl-2-(pyridine-3-yl)-2'H-spiro[chroman-4,5'-[1,2,4]oxadiazole]-6-yl)benzonitrile To a solution of methylhydroxylamine HCl salt (17 mg, 0.2 mmol) in anhydrous MeOH (2 mL) was added NaOMe (25% in MeOH (Wt. %), 0.10 mL, 0.2 mmol), followed by (E)-N-(6-(3-cyanophenyl)-2-(pyridine-3-yl)chroman-4-ylidene) cyanamide (70 mg, 0.2 mmol). After stirring for 10 mins, the solvent was removed in vacuo. The resulting residue was redissolved in DCM (5 mL). The mixture was filtered, and the solvent was removed to give the residue, which was purified by preparative TLC and preparative HPLC to give 3-(3'-amino-2'-methyl-2-(pyridine-3-yl)-2'H-spiro[chroman-4,5'-[1,2,4]oxadiazole]-6-yl)benzonitrile (2.5 mg, 3%). $^1$H-NMR (MeOD): 2.40-2.47 (t, 1H), 2.92-3.16 (m, 1H), 3.46 (s, 3H), 5.61-5.69 (m, 1H), 7.21 (m, 1H), 7.64-7.67 (m, 1H), 7.75 (d, 1H), 7.81-7.88 (m, 2H), 7.96-8.00 (t, 1H), 8.04-8.10 (t, 2H), 8.40 (m, 1H), 8.43 (m, 1H), 8.75 (s, 1H).

Example 81

Compound 97

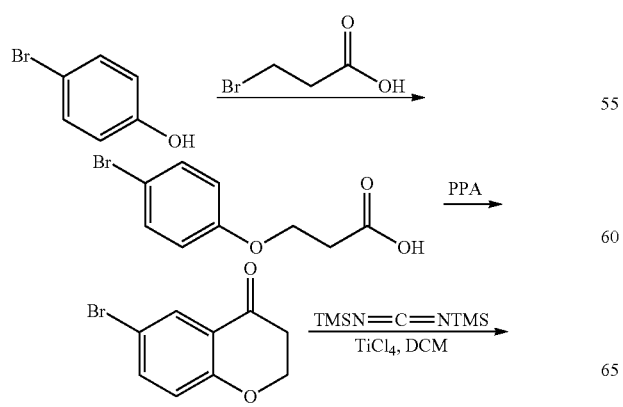

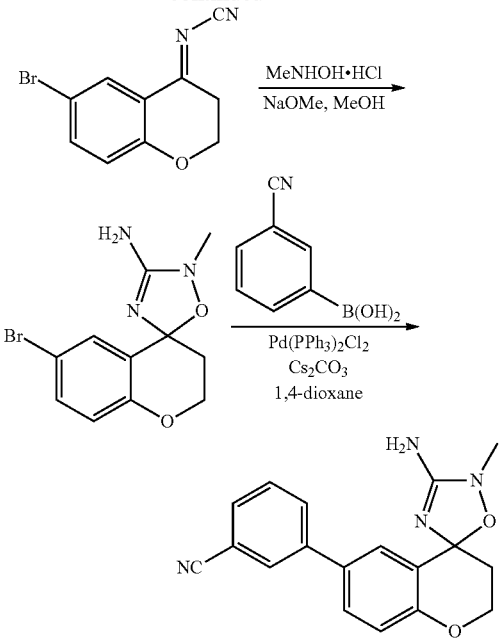

Experimental Data:

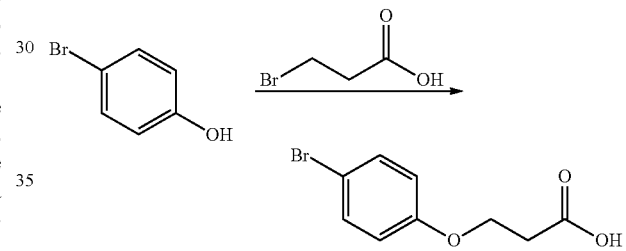

Step 1: 3-(4-Bromophenoxy)propanoic acid

To a solution of aqueous NaOH (0.5 M, 0.2 mol) was slowly added 4-bromophenol (34.4 g, 0.2 mol) at room temperature. After heating to boiling, 3-bromopropanoic acid (30.60 g 0.2 mol) in aqueous NaOH (0.5M, 0.2 mol) was added dropwise to the mixture above. The resulting mixture was then refluxed for 2 h. The mixture was cooled to 0° C. and the pH of the mixture was adjusted to 6-7 with 0.5 N HCl. The resulting mixture was filtered to give a solid cake, which was washed with water and n-pentane and dried to give 3-(4-bromophenoxy)propanoic acid (30 g, 60%). $^1$H-NMR (CDCl$_3$): 2.72 (m, 2H), 4.90 (s, 1H), 5.01 (d, 1H), 5.50 (s, 1H), 6.73 (m, 1H), 7.21-7.43 (m, 6H), 7.61 (m, 1H).

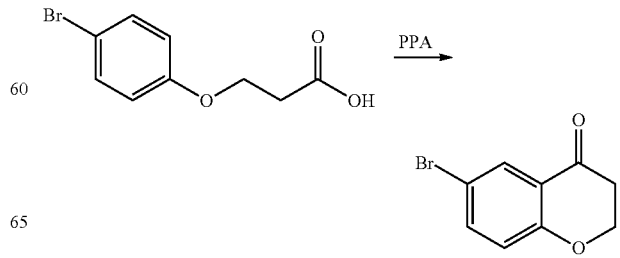

Step 2: 6-Bromochroman-4-one 3-(4-Bromophenoxy)propanoic acid (4.98 g, 20 mmol) was dissolved in PPA (51.1 g, 360 mmol) and the resulting mixture was heated at 110° C. for 4 hour. The mixture was poured into ice-water and extracted with $CH_2Cl_2$ (3×15 mL). The combined organic layers were washed with brine (20 mL), dried over $Na_2SO_4$, and concentrated in vacuo to give the crude product (4 g, 88%).

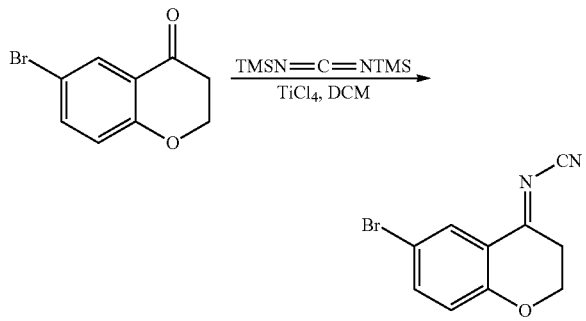

Step 3: N-(6-Bromochroman-4-ylidene)cyanamide

To a solution of 6-bromo-7-fluoro-2-phenylchroman-4-one (289.3 mg, 1.28 mmol) in DCM (10 mL) was added $TiCl_4$ (2.6 mL, 1 M in $CH_2Cl_2$) dropwise within 15 minutes at room temperature. After stirring for 1 h, N,N'-methanediylidenebis(1,1,1-trimethylsilanamine) (0.63 mL, 2.82 mmol) was added dropwise. The mixture was stirred at room temperature overnight and poured into ice-water (50 g). The organic layer was separated and the aqueous layer was extracted with $CH_2Cl_2$. The combined organic layer was dried and concentrated to give crude N-(6-bromochroman-4-ylidene)cyanamide (300 mg, 94%).

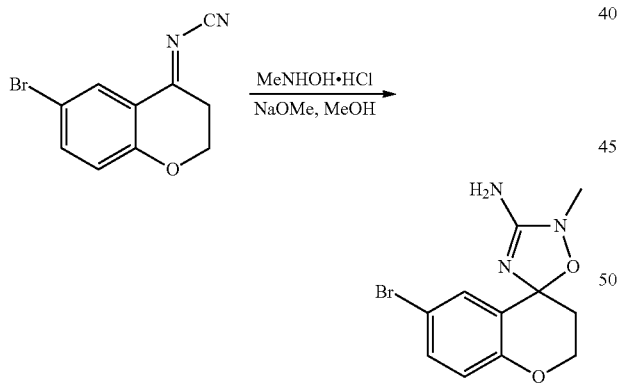

Step 4: 6-bromo-2'-methyl-2'H-spiro[chroman-4,5'-[1,2,4]oxadiazol]-3'-amine

To a solution of N-methyl-hydroxylamine hydrochloride (101 mg, 1.2 mmol) in MeOH (4 mL) was added MeONa (0.24 mL, 25% (Wt.) in MeOH), followed by N-(6-bromochroman-4-ylidene)cyanamide (300 mg, 1.2 mmol). After stirring for 10 minutes, the solvent was removed in vacuo. The resulting residue was purified by preparative TLC to give 6-bromo-2'-methyl-2'H-spiro[chroman-4,5'-[1,2,4]oxadiazol]-3'-amine (315 mg, 88%).

Step 5: 3-(3'-Amino-2'-methyl-2'H-spiro[chroman-4,5'-[1,2,4]oxadiazole]-6-yl)benzonitrile

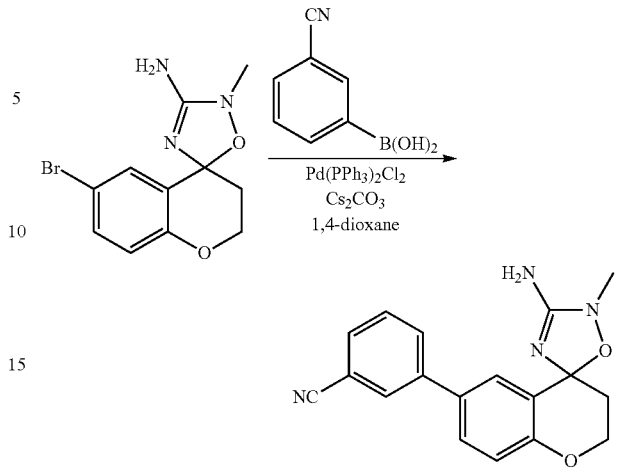

$Pd(PPh_3)_2Cl_2$ (7 mg, 0.01 mmol) in a 10 mL flask under Ar was treated sequentially with 6-bromo-2'-methyl-2'H-spiro[chroman-4,5'-[1,2,4]oxadiazol]-3'-amine (59.4 mg, 0.2 mmol) in 1,4-dioxane (2.0 mL), $Cs_2CO_3$ (2 N, 1 mL) and 3-cyanophenylboronic acid (58.8 mg, 0.4 mmol). The mixture was heated at 120° C. under Ar in a microwave reactor for 30 minutes. The reaction mixture was concentrated in vacuo to give the residue, which was purified by preparative TLC and HPLC to give 3-(3'-amino-2'-methyl-2'H-spiro[chroman-4,5'-[1,2,4]oxadiazole]-6-yl)benzonitrile (6.7 mg, 10%). $^1$H-NMR (MeOD): 2.31 (m, 1H), 2.62 (m, 1H), 3.39 (m, 3H), 4.32 (m, 1H), 4.46 (m, 1H), 7.00 (d, 1H), 7.58-7.71 (m, 3H), 7.95 (m, 3H).

Example 82

6-(3-isopropylphenyl)-2'-methyl-2-(tetrahydro-2H-pyran-3-yl)-2'H-spiro[chroman-4,5'-[1,2,4]oxadiazol]-3'-amine (Compound 101)

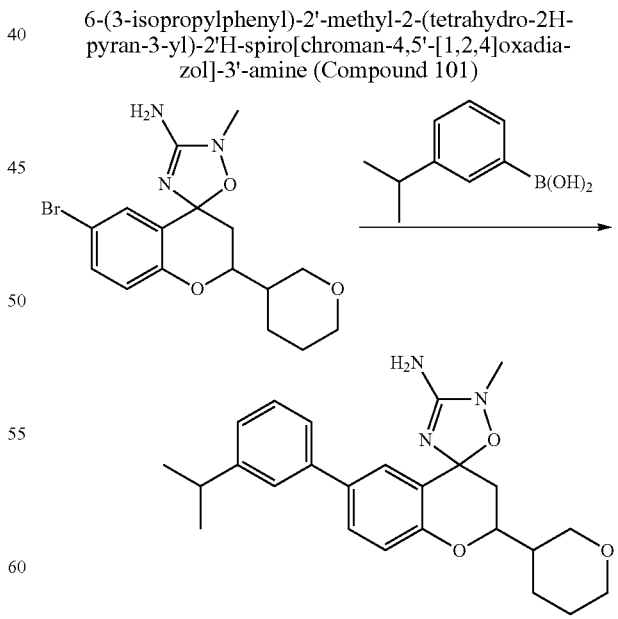

$Pd(PPh_3)_2Cl_2$ (5 mg) in a 10 mL flask under Ar was treated sequentially with the 6-bromo-2'-methyl-2-(tetrahydro-2H-pyran-3-yl)-2'H-spiro[chroman-4,5'-[1,2,4]oxadiazol]-3'-amine (40 mg, 0.105 mmol) in 1,4-dioxane (1 mL), $Cs_2CO_3$ (2 N, 0.2 mL) and 3-isopropylphenylboronic acid (25.8 mg, 144 mmol). The mixture was heated at 120° C. under Ar in a microwave reactor for 30 minutes. The reaction mixture was concentrated in vacuo to give the residue, which was purified by preparative TLC and preparative HPLC to give 6-(3-isopropylphenyl)-2'-methyl-2-(tetrahydro-2H-pyran-3-yl)-2'H-spiro[chroman-4,5'-[1,2,4]oxadiazol]-3'-amine (7.5 mg, 18%). $^1$H NMR (MeOD): 1.31 (d, 6H), 1.68 (m, 2H), 1.92-2.07 (m, 3H), 2.43-2.72 (m, 1H), 2.96 (m, 1H), 3.34 (s, 3H), 3.45-3.58 (m, 2H), 3.83-4.01 (m, 2H), 4.12-4.23 (m, 2H), 6.98 (m, 1H), 7.21 (m, 1H), 7.38 (m, 3H), 7.63 (m, 1H), 7.79 (m, 1H).

Example 83

5-(3'-amino-2'-methyl-2-phenyl-2'H-spiro(chroman-4,5'-(1,2,4)oxadiazole)-6-yl)-2-fluorobenzonitrile (Compound 103)

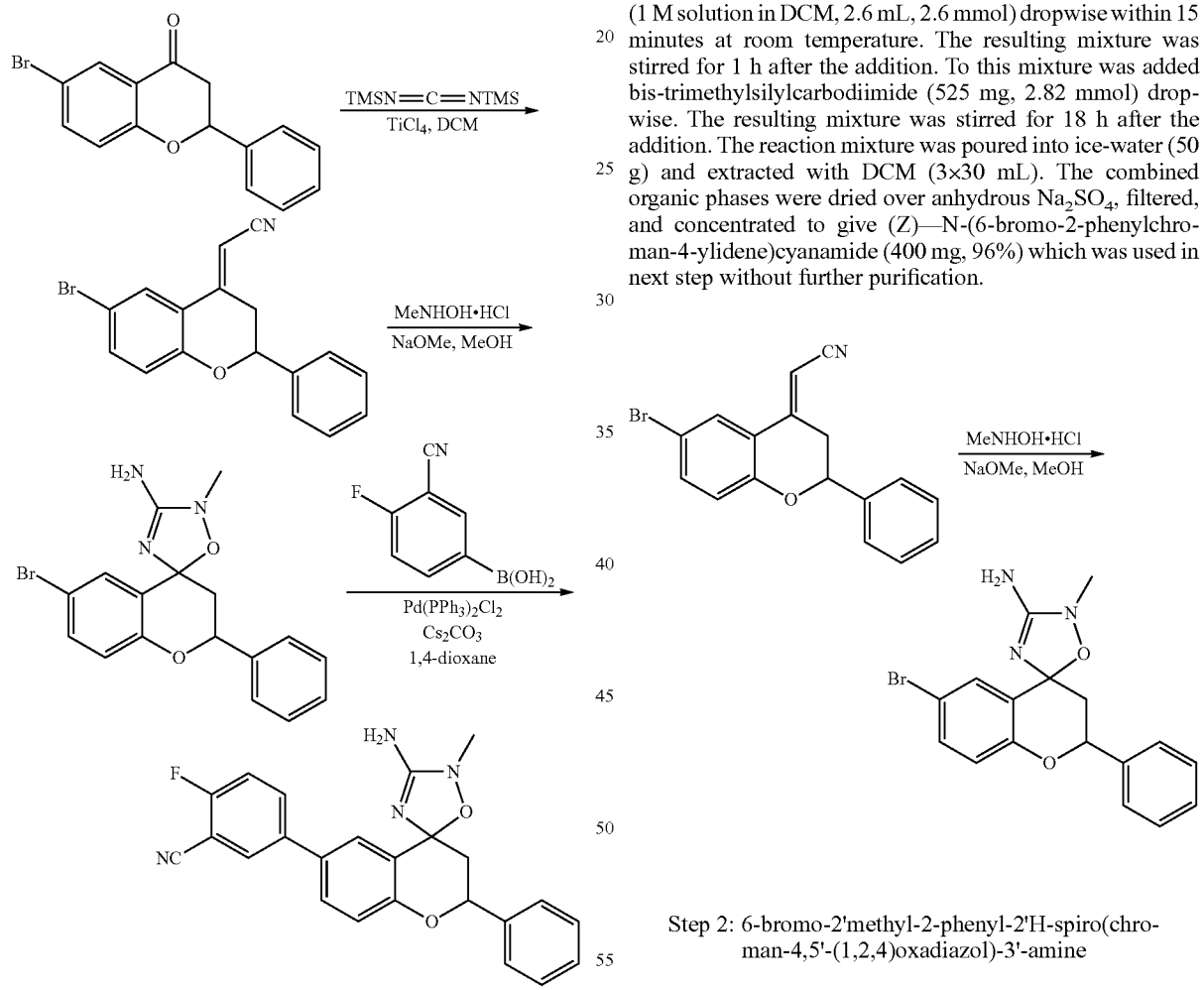

Experimental Data:

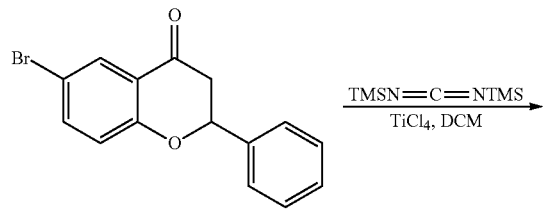

Step 1: (Z)—N-(6-bromo-2-phenylchroman-4-ylidene)cyanamide

To a solution of 6-bromo-2-phenylchroman-4-one (387 mg, 1.28 mmol) in anhydrous DCM (10 mL) was added TiCl$_4$ (1 M solution in DCM, 2.6 mL, 2.6 mmol) dropwise within 15 minutes at room temperature. The resulting mixture was stirred for 1 h after the addition. To this mixture was added bis-trimethylsilylcarbodiimide (525 mg, 2.82 mmol) dropwise. The resulting mixture was stirred for 18 h after the addition. The reaction mixture was poured into ice-water (50 g) and extracted with DCM (3×30 mL). The combined organic phases were dried over anhydrous Na$_2$SO$_4$, filtered, and concentrated to give (Z)—N-(6-bromo-2-phenylchroman-4-ylidene)cyanamide (400 mg, 96%) which was used in next step without further purification.

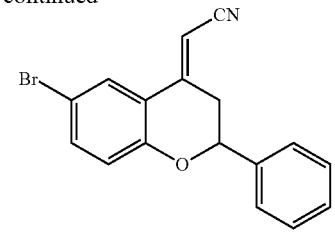

Step 2: 6-bromo-2'methyl-2-phenyl-2'H-spiro(chroman-4,5'-(1,2,4)oxadiazol)-3'-amine To a solution of methylhydroxylamine HCl salt (26 mg, 0.307 mmol) in anhydrous MeOH (10 mL) was added NaOMe (25 wt. % in MeOH, 0.07 mL, 0.276 mmol), followed by (Z)—N-(6-bromo-2-phenylchroman-4-ylidene)cyanamide (100 mg, 0.307 mmol). After stirring for 10 minutes, the solvent was removed in vacuo. The residue was dissolved in DCM (20 mL). The mixture was filtered, and the solvent was removed in vacuo to give 6-bromo-2'methyl-2-phenyl-2'H-spiro(chroman-4,5'-(1,2,4)oxadiazol)-3'-amine (100 mg, 87%), which was used in the next step without further purification.

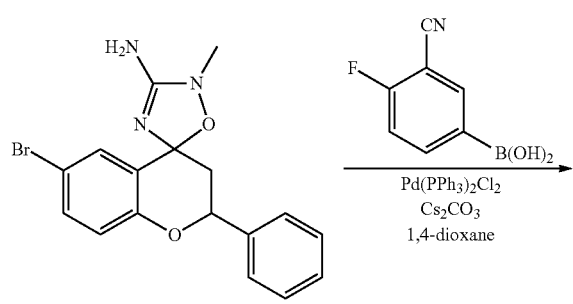

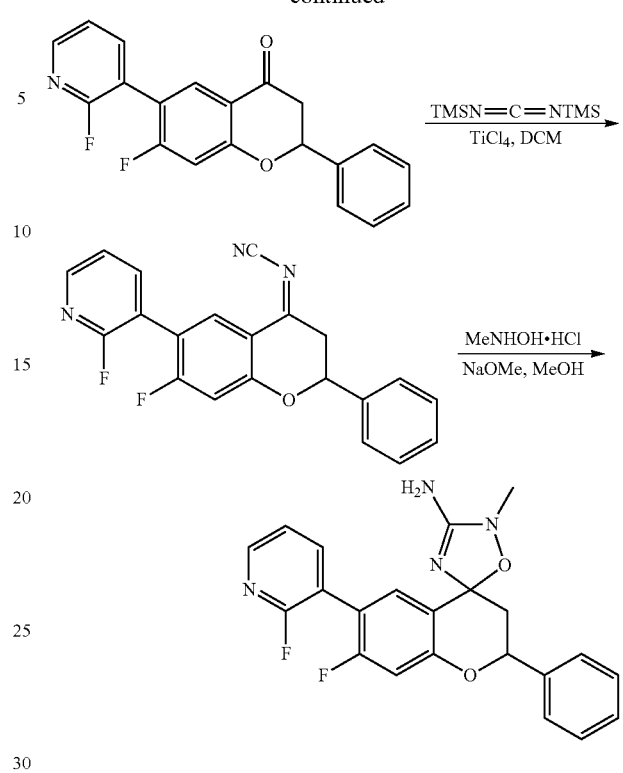

Step 3: 5-(3'-amino-2'-methyl-2-phenyl-2'H-spiro(chroman-4,5'-(1,2,4)oxadiazole)-6-yl)-2-fluorobenzonitrile To a solution of 6-bromo-2'methyl-2-phenyl-2'H-spiro(chroman-4,5'-(1,2,4) oxadiazol)-3'-amine (50 mg, 0.134 mmol), 3-cyano-5-fluorinphenylboronic acid (38 mg, 0.228 mmol) and $Cs_2CO_3$ (109 mg, 0.338 mmol) in 1,4-dioxane (6.7 mL) and $H_2O$ (0.5 mL) was added $PdCl_2(PPh_3)_2$ (13.4 mg). After degassing, the mixture was refluxed for 3 h (black precipitate came out at this point of time). The solvent was removed under reduced pressure and the residue was purified by preparative HPLC to give 5-(3'-amino-2'-methyl-2-phenyl-2'H-spiro(chroman-4,5'-(1,2,4)oxadiazole)-6-yl)-2-fluorobenzonitrile (0.65 mg, 1.2%) as a TFA salt. $^1$H-NMR (MeOD): 2.26 (m, 0.3H), 2.57 (m, 0.7H), 2.72 (m, 1H), 3.31 (m, 3H), 5.26 (m, 1H), 7.00 (m, 1H), 7.34 (m, 4H), 7.45 (m, 2H), 7.61 (s, 1H), 7.94 (d, 3H).

Example 84

7-fluoro-6-(2-fluoropyridin-3-yl)-2'-methyl-2-phenyl-2'H-spiro[chroman-4,5'-[1,2,4]oxadiazol]-3'-amine (Compound 104)

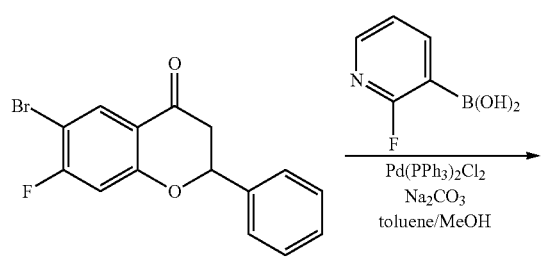

Experimental Data:

Step 1. 7-fluoro-6-(2-fluoropyridin-3-yl)-2-phenyl-chroman-4-one

A mixture of 6-bromo-7-fluoro-2-phenylchroman-4-one (318 mg, 0.994 mmol), 2-fluoropyridin-3-ylboronic acid (210 mg, 1.5 mmol), $Na_2CO_3$ (318 mg, 2.98 mmol), $PPh_3$ (34 mg) and $Pd(PPh_3)_2Cl_2$ (59 mg, 0.1 mmol) in toluene/EtOH (v/v=1/1, 10.5 mL) was degassed and stirred at 110° C. for 20 minutes. The reaction mixture was concentrated in vacuo to give the residue, which was purified by preparative TLC to give 7-fluoro-6-(2-fluoropyridin-3-yl)-2-phenylchroman-4-one (78 mg, 23%).

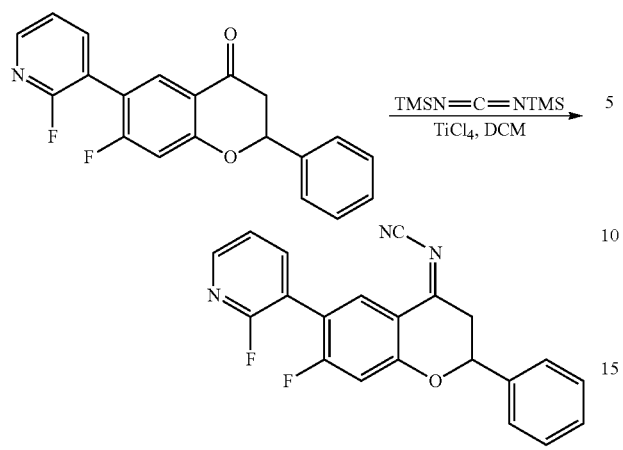

Step 2. 7-fluoro-6-(2-fluoro-pyridin-3-yl)-2-phenyl-chroman-4-ylidene-cyanamide To a solution of 7-fluoro-6-(2-fluoropyridin-3-yl)-2-phenylchroman-4-one (78 mg, 0.23 mmol) in CH$_2$Cl$_2$ (5 mL) under N$_2$ was added TiCl$_4$ (1 M solution in DCM, 1.15 mL, 1.15 mmol) dropwise within 15 minutes at room temperature under dark. After addition, the reaction mixture was stirred for 1 h. To this mixture was added bis-trimethylsilylcarbodiimide (94.3 mg, 0.506 mmol) dropwise. The resulting mixture was stirred overnight. The reaction mixture was poured into ice-water and extracted with DCM. The combined organic phases were dried over anhydrous Na$_2$SO$_4$, and filtered. The filtrate was concentrated to give 7-fluoro-6-(2-fluoro-pyridin-3-yl)-2-phenyl-chroman-4-ylidene-cyanamide (100 mg, 100%).

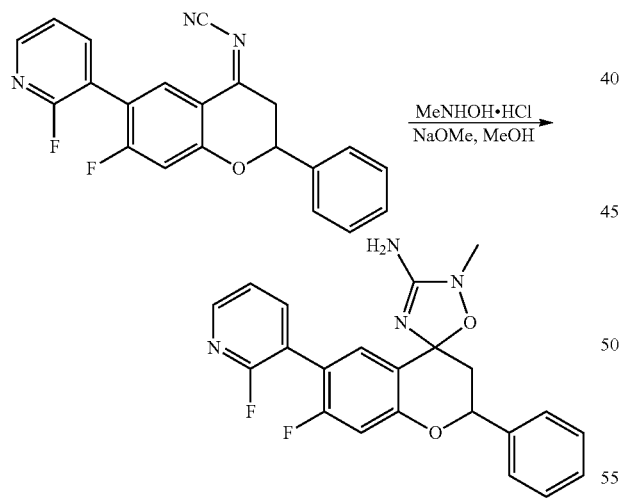

Step 3. 7-fluoro-6-(2-fluoropyridin-3-yl)-2'-methyl-2-phenyl-2'H-spiro[chroman-4,5'-[1,2,4]oxadiazol]-3'-amine To a solution of methylhydroxylamine HCl salt (27 mg, 0.277 mmol) in anhydrous MeOH (3 mL) was added NaOMe (25% in MeOH (Wt. %), 0.10 mL), followed by 7-fluoro-6-(2-fluoro-pyridin-3-yl)-2-phenyl-chroman-4-ylidene-cyanamide (100 mg, 0.277 mmol). After stirring for 10 minutes, the solvent was removed in vacuo. The residue was redissolved in DCM (5 mL). The mixture was filtered, and the solvent was removed to give the residue, which was purified by preparative TLC to give 7-fluoro-6-(2-fluoropyridin-3-yl)-2'-methyl-2-phenyl-2'H-spiro[chroman-4,5'-[1,2,4]oxadiazol]-3'-amine (4.65 mg, 4%). $^1$H-NMR (MeOD): 2.21 (m, 1H), 2.34 (m, 1H), 3.03 (s, 3H), 5.46 (m, 1H), 6.73 (m, 1H), 7.32 (m, 4H), 7.49 (m, 3H), 7.91 (m, 1H), 8.28 (m, 1H).

Example 85

3-(3'-amino-2'-methyl-2-(pyridin-4-yl)-2'H-spiro[chroman-4,5'-[1,2,4]oxadiazole]-6-yl)benzonitrile (Compound 105)

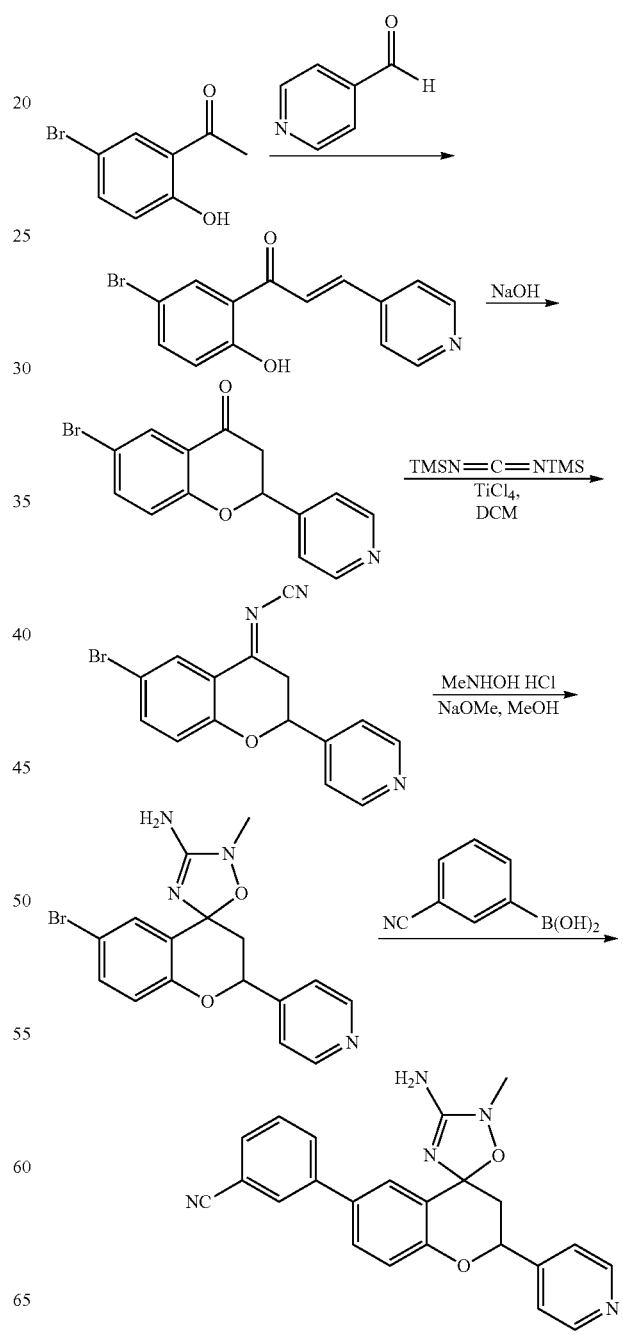

Experimental Data:

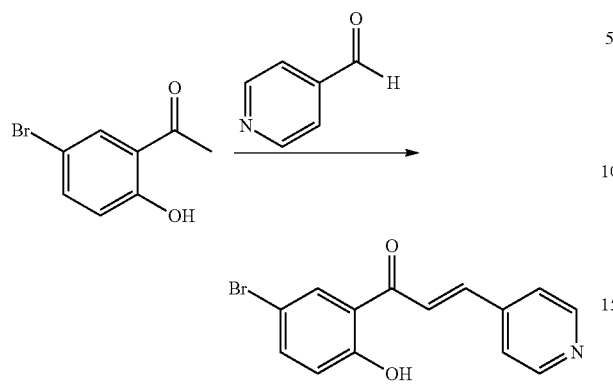

Step 1: (E)-1-(5-bromo-2-hydroxyphenyl)-3-(pyridin-4-yl)prop-2-en-1-one

To a solution of 1-(5-bromo-2-hydroxyphenyl)ethanone (50 g, 0.23 mol) in EtOH (285 mL) and H$_2$O (15 mL) was added isonicotinaldehyde (25 g, 0.23 mol) and NaOH (84 g, 0.23 mol). The reaction mixture was stirred overnight. EtOH was added to the mixture and filtered to give a solid residue. The residue was dissolved in water and acidified by 1 M HCl to give a solid. The solid was collected by filtration to give (E)-1-(5-bromo-2-hydroxyphenyl)-3-(pyridin-4-yl)prop-2-en-1-one (30 g, 40%).

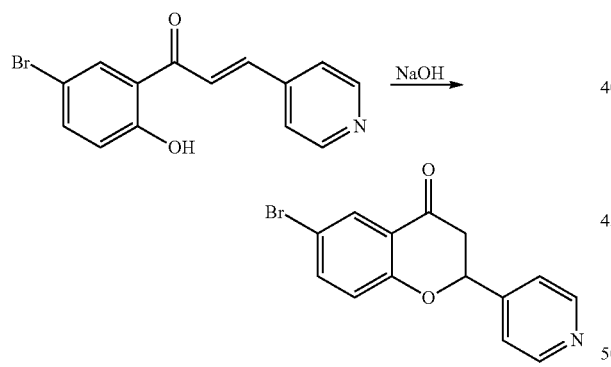

Step 2: 6-bromo-2-(pyridin-4-yl)chroman-4-one

To a solution of (E)-1-(5-bromo-2-hydroxyphenyl)-3-(pyridin-4-yl)prop-2-en-1-one (20 g, 63.3 mmol) in EtOH (160 mL) and H$_2$O (480 mL) was added NaOH (2.53 g, 63.3 mmol). The reaction mixture was stirred overnight. The mixture was filtered to give a solid residue. The solid residue was dissolved in EtOAc. The resulting solution was dried over Na$_2$SO$_4$ and concentrated in vacuo to give 6-bromo-2-(pyridin-4-yl)chroman-4-one (10 g, 50%). $^1$H-NMR (CDCl$_3$): 3.00 (t, 2H), 5.51 (dd, 1H), 7.02 (d, 1H), 7.39 (d, 2H), 7.63 (t, 1H), 8.04 (s, 1H), 8.72 (d, 2H).

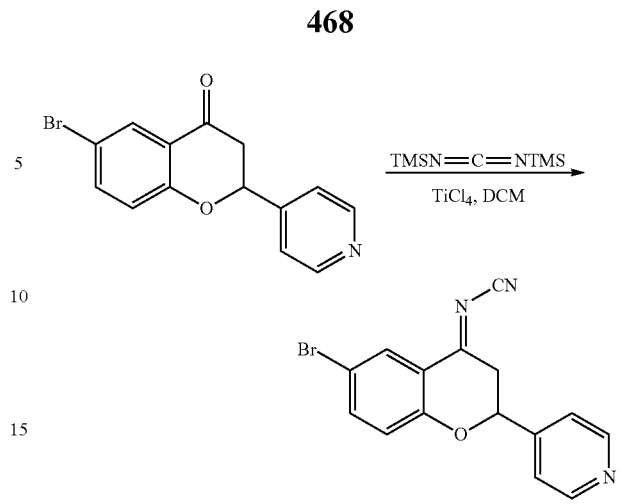

Step 3: (E)-N-(6-bromo-2-(pyridin-4-yl)chroman-4-ylidene)cyanamide

To a solution of 6-bromo-2-(pyridin-4-yl)chroman-4-one (1 g, 3.3 mmol) in anhydrous DCM (25 mL) was added TiCl$_4$ (1 M solution in DCM, 6.6 mL, 6.6 mmol) dropwise within 15 min at room temperature. After the addition, the reaction mixture was stirred for 1 h. To this mixture was added bis-trimethylsilylcarbodiimide (1.35 g, 7.26 mmol) dropwise. The resulting mixture was stirred for another 18 h after the addition. The reaction mixture was poured into ice-water (100 g) and extracted with DCM (3×50 mL). The combined organic phases were dried over anhydrous Na$_2$SO$_4$, filtered, and concentrated to give (E)-N-(6-bromo-2-(pyridin-4-yl)chroman-4-ylidene)cyanamide (1 g, 100%), which was used in the next step without further purification.

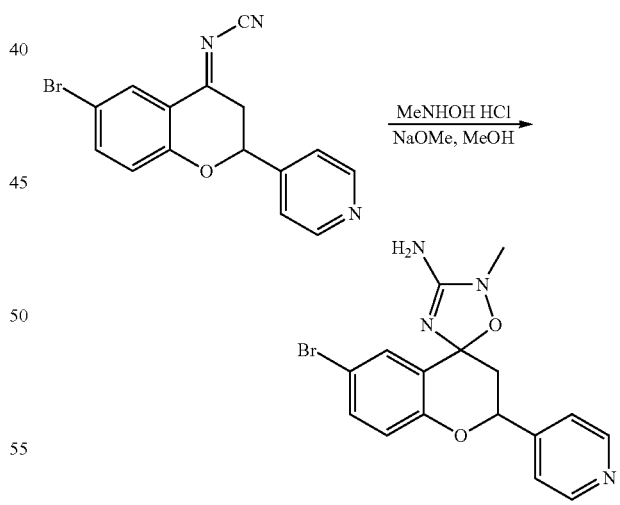

Step 4: 6-bromo-2'-methyl-2-(pyridin-4-yl)-2'H-spiro[chroman-4,5'-[1,2,4]oxadiazol]-3'-amine To a solution of methylhydroxylamine HCl salt (76.9 mg, 0.92 mmol) in anhydrous MeOH (11 mL) was added NaOMe (25 w % in MeOH, 0.19 mL, 0.828 mmol), followed by (E)-N-(6-bromo-2-(pyridin-4-yl)chroman-4-ylidene)cyanamide (300 mg, 0.92 mmol), After stirring for 10 min, the solvent was removed in vacuo. The residue was dissolved in DCM (20 mL). The mixture was filtered, and the solvent was removed in vacuo to give a reside, which was purified by preparative TLC to give 6-bromo-2'-methyl-2-(pyridin-4-yl)-2'H-spiro[chroman-4,5'-[1,2,4]oxadiazol]-3'-amine (80 mg, 30%).

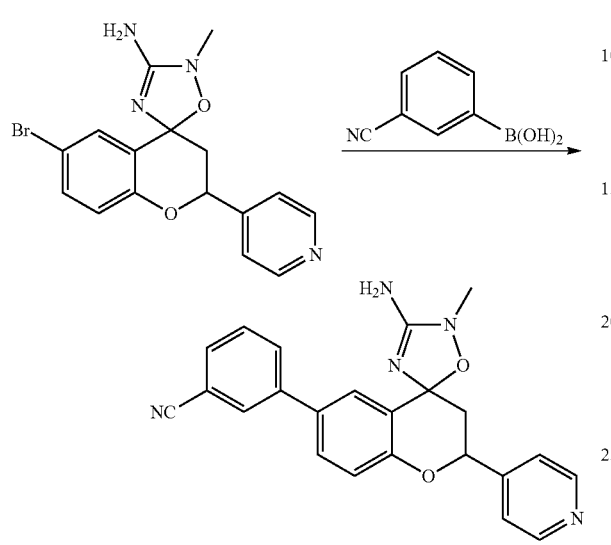

Step 5: 3-(3'-amino-2'-methyl-2-(pyridin-4-yl)-2'H-spiro[chroman-4,5'-[1,2,4]oxadiazole]-6-yl)benzonitrile Pd(PPh$_3$)$_2$Cl$_2$ (10 mg) in a 10 mL tube under Ar was treated sequentially with 6-bromo-2'-methyl-2-(pyridin-4-yl)-2'H-spiro[chroman-4,5'-[1,2,4]oxadiazol]-3'-amine (20 mg, 0.053 mmol) in 1,4-dioxane (1 mL), Cs$_2$CO$_3$ (2 N, 0.3 mL) and 3-cyanophenylboronic acid (14.8 mg, 0.1 mmol). The mixture was heated in a microwave reactor at 120° C. for 30 min. The reaction mixture was concentrated in vacuo to give the residue, which was purified by preparative TLC and then by preparative HPLC to give pure 3-(3'-amino-2'-methyl-2-(pyridin-4-yl)-2'H-spiro[chroman-4,5'-[1,2,4]oxadiazole]-6-yl)benzonitrile (3 mg, 10%). $^1$H-NMR (MeOD): 2.24 (m, 1H), 3.01 (m, 1H), 3.39 (t, 3H), 5.54 (d, 1H), 7.19 (m, 1H), 7.60 (m, 1H), 7.62 (t, 1H), 7.69 (m, 1H), 7.89 (m, 3H), 8.02 (, 2H), 8.70 (s, 2H).

Example 86

3-(3'-amino-2'-methyl-2-(pyridin-2-yl)-2'H-spiro[chroman-4,5'-[1,2,4]oxadiazole]-6-yl)benzonitrile (Compound 106)

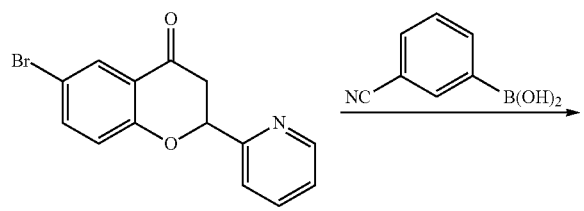

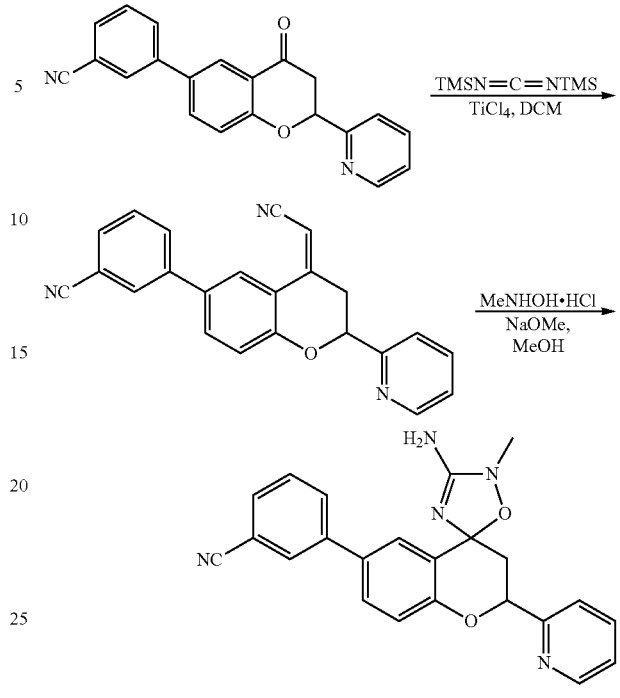

Experimental Data:

Step 1. 3-(4-oxo-2-(pyridin-2-yl)chroman-6-yl)benzonitrile

Pd(PPh$_3$)$_2$Cl$_2$ (20 mg) in a 10 mL flask under Ar was treated sequentially with 6-bromo-2-(pyridin-2-yl)chroman-4-one (300 mg, 1 mmol) in [1,4]dioxane (40 mL), Cs$_2$CO$_3$ (2 N, 5 mL) and 3-cyanophenylboronic acid (250 mg, 1 mmol). The mixture was heated at 120° C. under Ar in a microwave reactor for 30 minutes. The reaction mixture was concentrated in vacuo to give the residue, which was purified by preparative TLC to give 3-(4-oxo-2-(pyridin-2-yl)chroman-6-yl)benzonitrile (110 mg, 60%). $^1$H-NMR (CDCl$_3$): 3.13 (m, 2H), 5.61 (m, 1H), 7.13 (m, 1H), 7.27 (m, 1H), 7.49 (m, 1H), 7.58 (m, 2H), 7.68 (m, 1H), 7.79 (m, 3H), 8.09 (d, 1H), 8.58 (d, 1H).

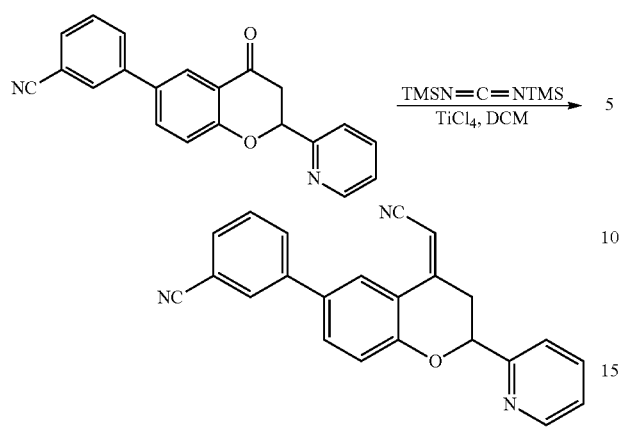

Step 2. (Z)—N-(6-(3-cyanophenyl)-2-(pyridin-2-yl)chroman-4-ylidene)cyanamide

To a solution of 3-(4-oxo-2-(pyridin-2-yl)chroman-6-yl)benzonitrile (50 mg, 0.15 mmol) in DCM (2 mL) was added TiCl$_4$ (1 mL, 1 M in CH$_2$Cl$_2$) dropwise within 15 minutes at room temperature. After stirring for 1 h, N,N'-methanediylidenebis(1,1,1-trimethylsilanamine) (0.07 mL, 0.31 mmol) was added dropwise. The mixture was stirred at room temperature overnight and poured into ice-water (25 g). The organic layer was separated and the aqueous layer was extracted with CH$_2$Cl$_2$. The combined organic layer was dried and concentrated to give crude (Z)—N-(6-(3-cyanophenyl)-2-(pyridin-2-yl)chroman-4-ylidene)cyanamide (100 mg, crude).

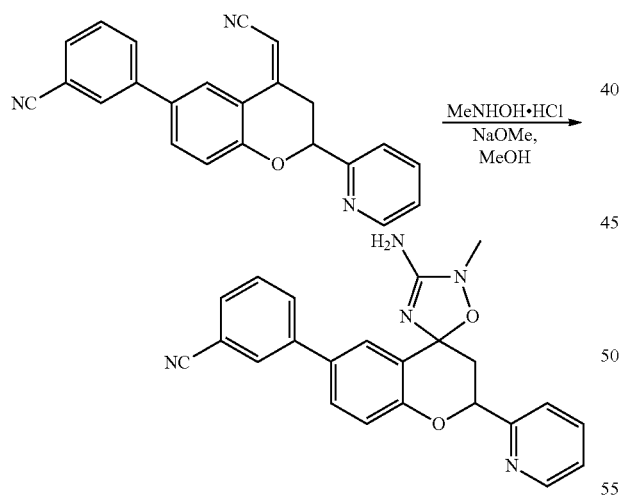

Step 3. 3-(3'-amino-2'-methyl-2-(pyridin-2-yl)-2'H-spiro[chroman-4,5'-[1,2,4]oxadiazole]-6-yl)benzonitrile To a solution of N-methyl-hydroxylamine hydrochloride (14 mg, 0.14 mmol) in MeOH (4 mL) was added MeONa (0.03 mL, 25% (Wt.) in MeOH), followed (Z)—N-(6-(3-cyanophenyl)-2-(pyridin-2-yl)chroman-4-ylidene)cyanamide (50 mg, crude). After stirring for 10 minutes, the solvent was removed in vacuo to give a residue. The residue was purified by preparative TLC to give 3-(3'-amino-2'-methyl-2-(pyridin-2-yl)-2'H-spiro[chroman-4,5'-[1,2,4]oxadiazole]-6-yl)benzonitrile (4.3 mg, 8%). $^1$H-NMR (MeOD): 2.11 (m, 1H), 2.51 (m, 1H), 3.02 (s, 2H), 3.28 (s, 1H), 4.12 (m, 1H), 5.32 (m, 1H), 6.97 (m, 1H), 7.32 (m, 1H), 7.55 (m, 5H), 7.82 (m, 3H), 8.46 (m, 1H).

Example 87

3-(3'-amino-2'-methyl-2-(4-(trifluoromethoxy)phenyl)-2'H-spiro[chroman-4,5'-[1,2,4]oxadiazole]-6-yl)benzonitrile (Compound 107)

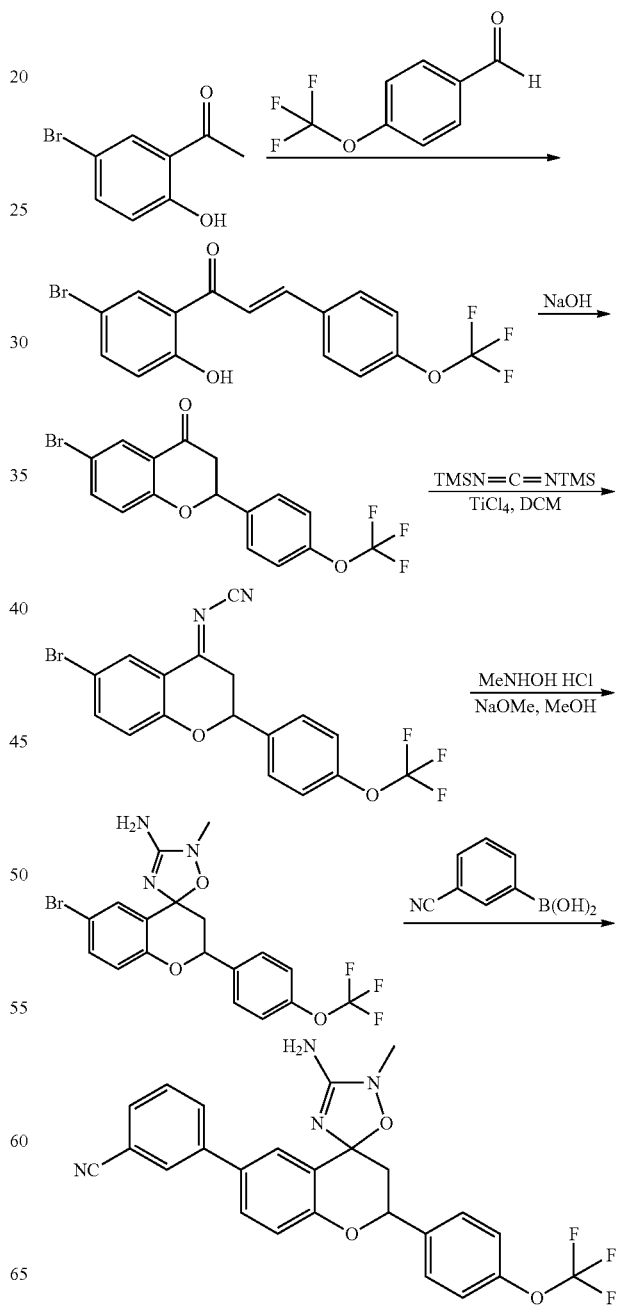

Experimental Data:

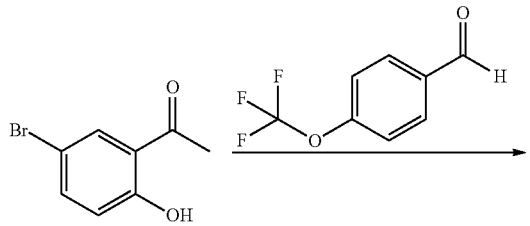

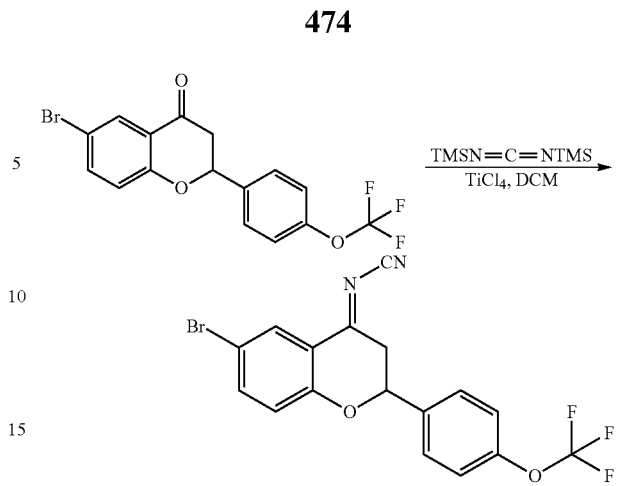

Step 1: (E)-1-(5-bromo-2-hydroxyphenyl)-3-(4-(trifluoromethoxy)phenyl)prop-2-en-1-one To a solution of 1-(5-bromo-2-hydroxyphenyl)ethanone (20 g, 93.4 mmol) in EtOH (114 mL) and H$_2$O (6 mL) was added 4-(trifluoromethoxy)benzaldehyde (17.75 g, 93.4 mmol) and NaOH (33.6 g, 840.6 mmol). The reaction mixture was stirred overnight. Ethoxyethane was added to the mixture and filtered to give a residue. The residue was dissolved in water and acidified by 1 M HCl to give a solid. The solid was collected by filtration to give (E)-1-(5-bromo-2-hydroxyphenyl)-3-(4-(trifluoromethoxy)phenyl)prop-2-en-1-one (30 g, 80%). $^1$H-NMR (CDCl$_3$): 6.87 (d, 1H), 7.21 (d, 2H), 7.49 (m, 1H), 7.52 (m, 1H), 7.59 (d, 2H), 7.84 (t, 1H), 7.92 (s, 1H).

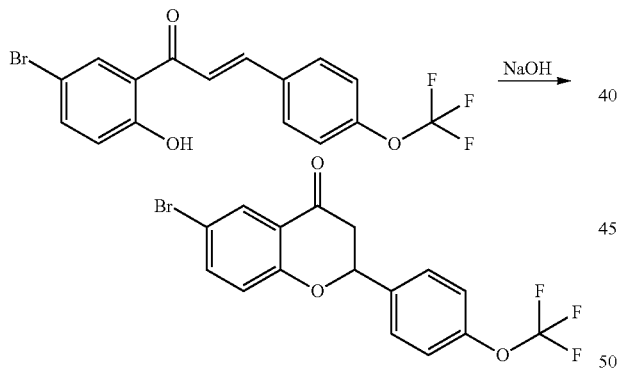

Step 2: 6-bromo-2-(4-(trifluoromethoxy)phenyl)chroman-4-one

To a solution of (E)-1-(5-bromo-2-hydroxyphenyl)-3-(4-(trifluoromethoxy)phenyl)prop-2-en-1-one (8 g, 20 mmol) in EtOH (144 mL) and H$_2$O (432 mL) was added NaOH (800 mg, 20 mmol). The reaction mixture was stirred overnight. The mixture was filtered to give a solid residue. The solid residue was dissolved in EtOAc. The resulting solution was dried over Na$_2$SO$_4$ and then concentrated in vacuo to give 6-bromo-2-(4-(trifluoromethoxy)phenyl)chroman-4-one (6 g, 80%). $^1$H-NMR (CDCl$_3$): 2.91 (d, 1H), 3.04 (m, 1H), 5.49 (dd, 1H), 6.94 (m, 1H), 7.31 (d, 2H), 7.50 (d, 2H), 7.59 (m, 1H), 8.03 (s, 1H).

Step 3: (E)-N-(6-bromo-2-(4-(trifluoromethoxy)phenyl)chroman-4-ylidene)cyanamide To a solution of 6-bromo-2-(4-(trifluoromethoxy)phenyl)chroman-4-one (530 mg, 1.37 mmol) in anhydrous DCM (15 mL) was added TiCl$_4$ (1 M solution in DCM, 2.74 mL, 2.74 mmol) dropwise within 15 min at room temperature. After the addition, the reaction mixture was stirred for 1 h. To this mixture was added Bis-trimethylsilylcarbodiimide (561.6 mg, 3 mmol) dropwise. The resulting mixture was stirred for another 18 h after the addition. The reaction mixture was poured into ice-water (80 g) and extracted with DCM (3×50 mL). The combined organic phases were dried over anhydrous Na$_2$SO$_4$, filtered, and concentrated to give (E)-N-(6-bromo-2-(4-(trifluoromethoxy)phenyl)chroman-4-ylidene) cyanamide (540 mg, 90%), which was used in the next step without further purification.

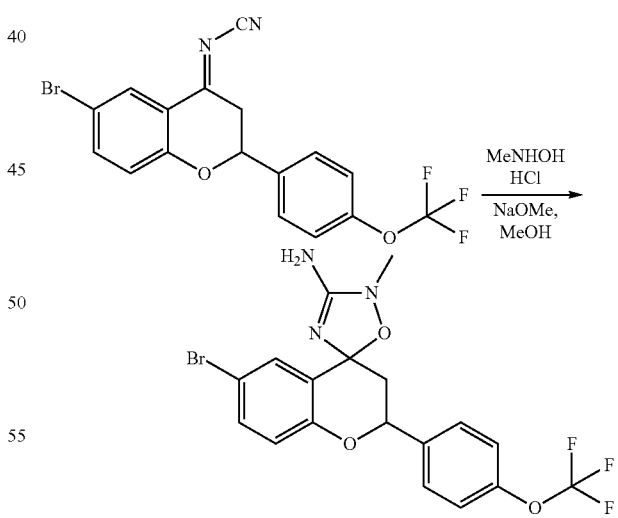

Step 4: 6-bromo-2'-methyl-2-(4-(trifluoromethoxy)phenyl)-2'H-spiro[chroman-4,5'-[1,2,4]-oxadiazol]-3'-amine To a solution of methylhydroxylamine HCl salt (110 mg, 1.317 mmol) in anhydrous MeOH (15 mL) was added NaOMe (25 w % in MeOH, 0.23 mL, 1.02 mmol), followed by (E)-N-(6-bromo-2-(4-(trifluoromethoxy)phenyl)chroman-4-ylidene)cyanamide (540 mg, 1.32 mmol). After stirring for 10 min, the solvent was removed in vacuo. The residue was redissolved in DCM (20 mL). The mixture was filtered and the solvent was removed in vacuo, which was purified by preparative TLC to give 50 mg crude product of 6-bromo-2'-methyl-2-(4-(trifluoromethoxy)phenyl)-2'H-spiro[chroman-4,5'-[1,2,4]oxadiazol]-3'-amine (100 mg, 20%).

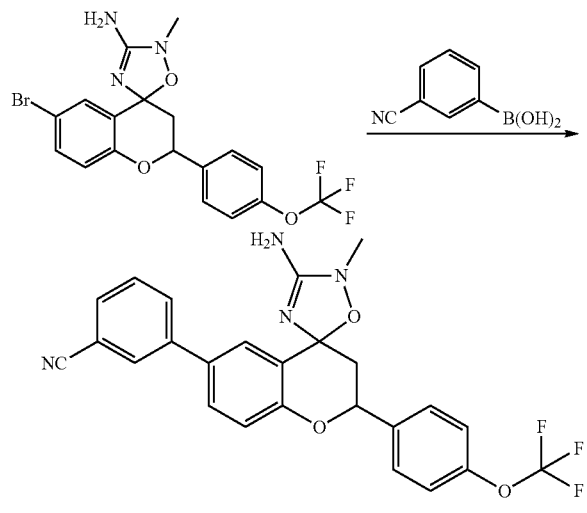

Step 5: 3-(3'-amino-2'-methyl-2-(4-(trifluoromethoxy)phenyl)-2'H-spiro[chroman-4,5'-[1,2,4]oxadiazole]-6-yl)benzonitrile Pd(PPh$_3$)$_2$Cl$_2$ (10 mg) in a 10 mL tube under Ar was treated sequentially with 6-bromo-2'-methyl-2-(4-(trifluoromethoxy)phenyl)-2'H-spiro[chroman-4,5'-[1,2,4]oxadiazol]-3'-amine (50 mg, 0.11 mmol) in 1,4-dioxane (2 mL), Cs$_2$CO$_3$ (2 N, 0.4 mL) and 3-cyanophenylboronic acid (32.4 mg, 0.22 mmol). The mixture was heated in a microwave reactor at 120° C. for 30 min. The reaction mixture was concentrated in vacuo to give the residue, which was purified by preparative TLC and then by preparative HPLC to give pure 3-(3'-amino-2'-methyl-2-(4-(trifluoromethoxy)phenyl)-2'H-spiro[chroman-4,5'-[1,2,4]oxadiazole]-6-yl)benzonitrile (1.39 mg, 5%). $^1$H-NMR (MeOD): 2.34 (t, 1H), 2.89 (d, 1H), 5.41 (t, 1H), 7.13 (d, 1H), 7.37 (t, 2H), 7.64 (m, 3H), 7.70 (d, 1H), 7.78 (t, 1H), 7.94 (t, 1H), 8.04 (m, 2H).

Example 88

2'-methyl-6-phenoxy-2-phenyl-2'H-spiro[chroman-4,5'-[1,2,4]oxadiazol]-3'-amine (Compound 108)

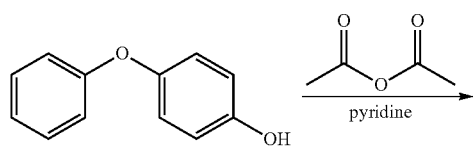

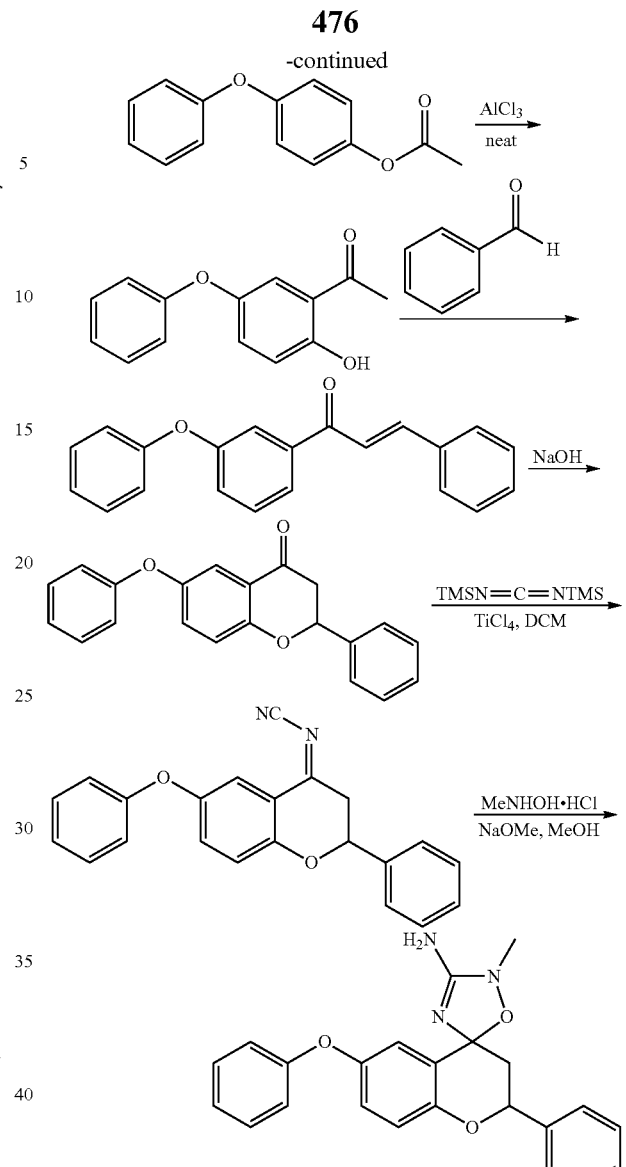

Experimental Data:

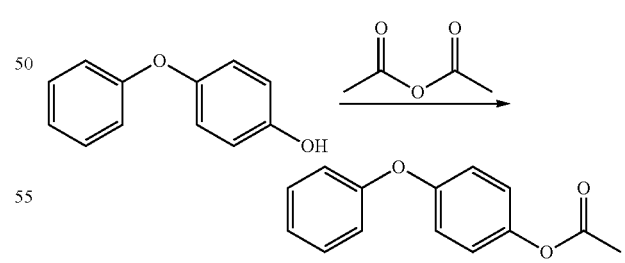

Step 1: 4-phenoxyphenyl acetate

A solution of 4-phenoxy-phenol (169 g, 0.9 mol) in pyridine (500 mL) was treated with acetic anhydride (90 mL). The reaction mixture was stirred at room temperature overnight. The mixture was partitioned between DCM and 10% HCl solution, and the resulting mixture was stirred for 1 h. The organic phase was washed with 10% HCl and water until pH=7. The organic layer was dried and the solvent was evaporated to afford acetic acid 4-phenoxy-phenyl ester (200 g, 97%). $^1$H-NMR (CDCl$_3$): 2.21 (s, 3H), 6.94 (m, 6H), 7.04 (m, 1H), 7.28 (m, 2H).

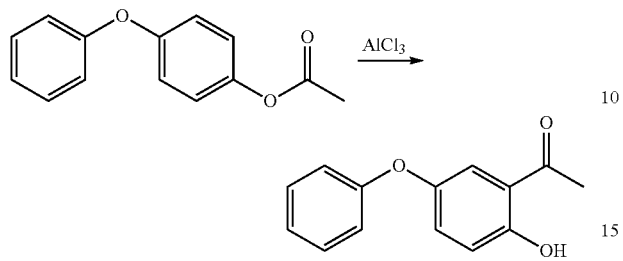

Step 2: 1-(2-hydroxy-5-phenoxyphenyl)ethanone

A mixture of acetic acid 4-phenoxy-phenyl ester (114 g, 0.5 mol) and AlCl$_3$ (133.5 g, 1 mol) was stirred at 120-140° C. for 20-30 minutes. The mixture was cooled to 60-80° C. and ice water was added. The resulting mixture was extracted with EtOAc. The organic layers were washed with brine and dried over Na$_2$SO$_4$. After concentration, the residue was purified by column (25.8 g, 23%). $^1$H-NMR (CDCl$_3$): 2.57 (s, 3H), 6.96 (m, 3H), 7.07 (m, 1H), 7.21 (m, 1H), 7.31 (m, 2H), 7.40 (m, 1H), 12.05 (s, 1H).

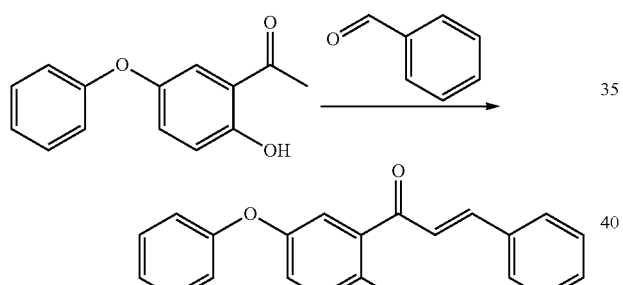

Step 3: (E)-1-(3-phenoxyphenyl)-3-phenylprop-2-en-1-one

In a bottle 1-(2-hydroxy-5-phenoxy-phenyl)-ethanone (5 g, 21.93 mmol), benzaldehyde (2.33 g, 21.93 mmol), EtOH (96%, 26.3 mL) and NaOH (7.02 g, 175.44 mmol) were combined. The mixture was stirred vigorously for 0.5 h and then filtered. The filtrate was poured into HCl (1 N, 200 mL) and filtered to give a solid. The solid was dried to give 3-(3-chloro-phenyl)-1-(2-hydroxy-5-phenoxy-phenyl)-propenone (5.87 g, 85%). $^1$H-NMR (CDCl$_3$): 6.95 (m, 2H), 7.07 (m, 2H), 7.23 (m, 1H), 7.34 (m, 2H), 7.42 (m, 3H), 7.53 (m, 1H), 7.64 (m, 3H), 7.95 (m, 1H), 12.62 (s, 1H).

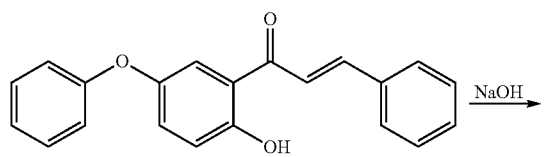

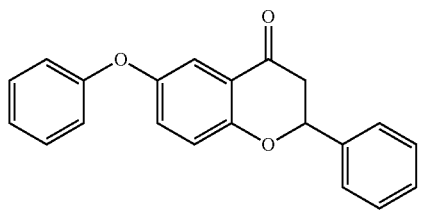

Step 4: 6-phenoxy-2-phenylchroman-4-one 3-(3-Chloro-phenyl)-1-(2-hydroxy-5-phenoxy-phenyl)-propenone (5.85 g, 0.018 mol) was dissolved in H$_2$O (140 mL) and EtOH (46.2 mL) and NaOH (2.74 g, 68 mmol) was added. The mixture was stirred overnight and filtered to give a solid cake. The cake was dissolved in EtOAc and washed with H$_2$O twice. The organic layer was dried and filtered. The filtrate was concentrated to give 6-phenoxy-2-phenyl-chroman-4-one (5.86 g, 100%). $^1$H-NMR (CDCl$_3$): 2.87 (m, 1H), 3.06 (m, 1H), 5.46 (m, 1H), 6.96 (m, 2H), 7.08 (m, 2H), 7.25 (m, 1H), 7.33 (m, 2H), 7.39 (m, 1H), 7.42 (m, 2H), 7.48 (m, 2H), 7.51 (m, 1H).

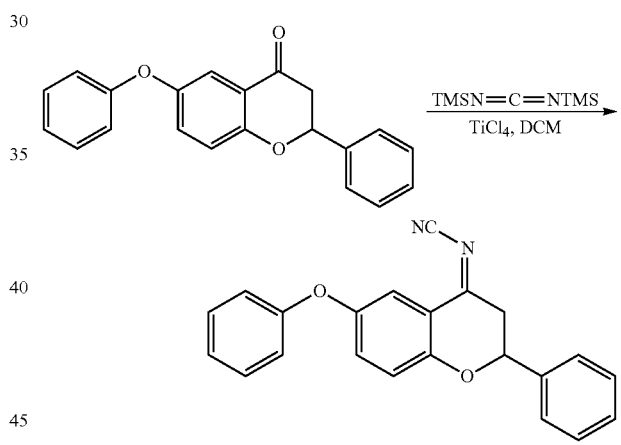

Step 5: (Z)—N-(6-phenoxy-2-phenylchroman-4-ylidene)cyanamide

To a solution of 6-phenoxy-2-phenylchroman-4-one (316 mg, 1 mmol) in anhydrous DCM (7.8 mL) was added TiCl$_4$ (1 M solution in DCM, 2 mL, 2 mmol) dropwise within 15 minutes at room temperature. After addition, the mixture was stirred for 1 h. To this mixture was added bis-trimethylsilyl-carbodiimide (0.41 g, 0.49 mL, 2.2 mmol) dropwise. The resulting mixture was stirred for another 18 h after the addition. The reaction mixture was poured into ice-water (50 g) and extracted with DCM (3×30 mL). The combined organic phases were dried over anhydrous Na$_2$SO$_4$, and filtered. The filtrate was concentrated to give (Z)—N-(6-phenoxy-2-phenylchroman-4-ylidene)cyanamide (340 mg, 90%), which was used in the next step without further purification.

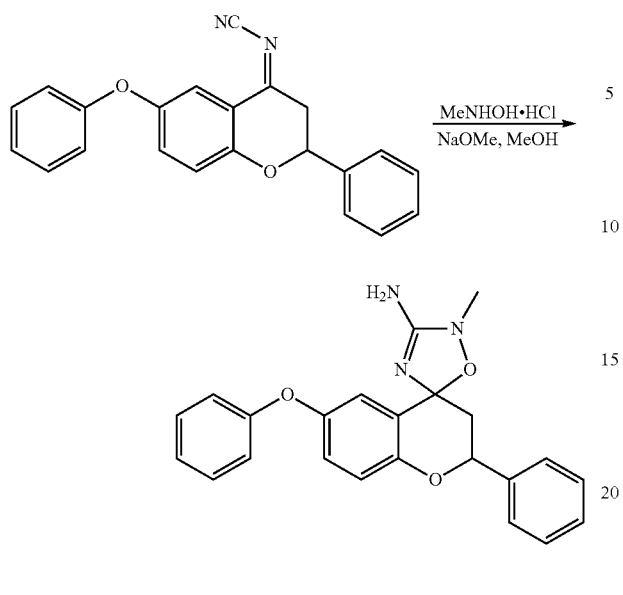

Step 6: 2'-methyl-6-phenoxy-2-phenyl-2'H-spiro[chroman-4,5'-[1,2,4]oxadiazol]-3'-amine To a solution of methylhydroxylamine HCl salt (83.6 mg, 1 mmol) in anhydrous MeOH (11 mL) was added NaOMe (25% in MeOH (Wt. %), 0.2 mL, 0.9 mmol), followed by (Z)—N-(6-phenoxy-2-phenylchroman-4-ylidene)cyanamide (340 mg, 1 mmol). After stirring for 10 min, the solvent was removed in vacuo. The residue was redissolved in DCM (30 mL). The mixture was filter, and the solvent was removed to give the residue, which was purified by column chromatography to give 2'-methyl-6-phenoxy-2-phenyl-2'H-spiro[chroman-4,5'-[1,2,4]oxadiazol]-3'-amine (200 mg, 52%). $^1$H-NMR (CDCl$_3$): 2.41-2.66 (m, 1H), 2.65 (m, 1H), 2.75 (m, 1H), 3.32 (m, 3H), 5.35 (m, 1H), 6.95 (m, 2H), 7.06 (m, 1H), 7.20 (m, 2H), 7.42 (m, 3H), 7.48 (m, 3H), 7.51 (m, 2H).

Example 89

Compound 109

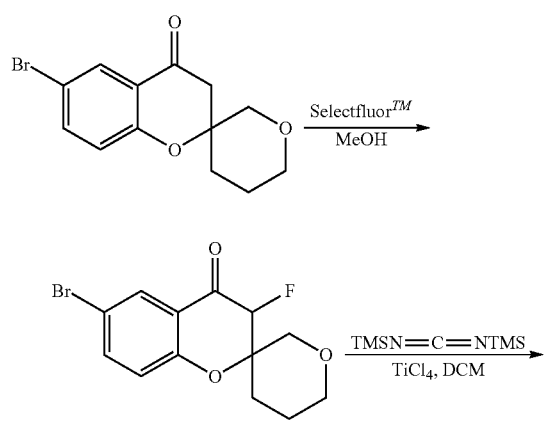

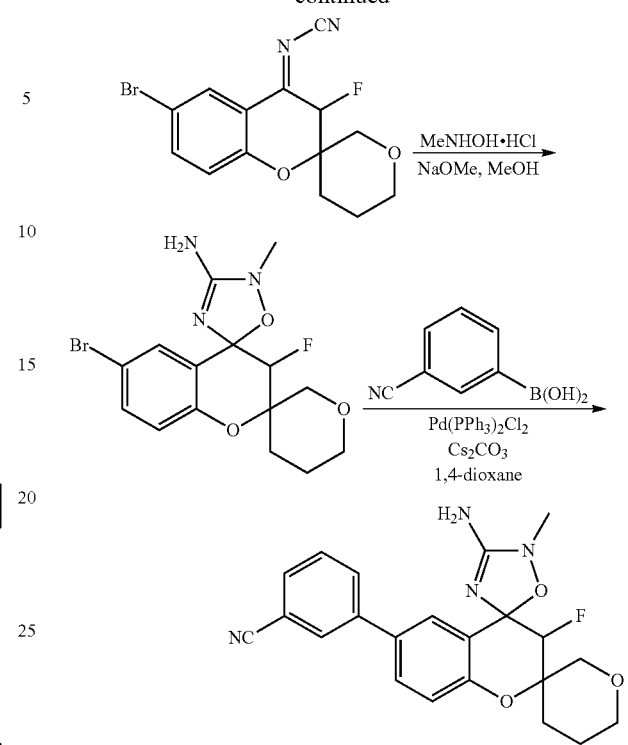

Experimental Data:

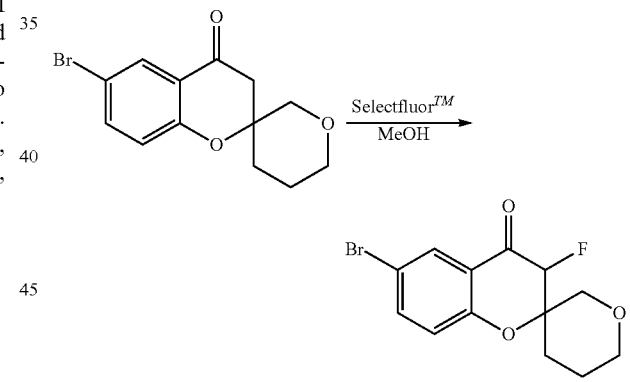

Step 1. 6-bromo-3-fluoro-2',4',5',6'-tetrahydrospiro[chroman-2,3'-pyran]-4-one

To a solution of 6-bromo-2',4',5',6'-tetrahydrospiro[chroman-2,3'-pyran]-4-one (2 g, 6.8 mmol) in MeOH Selectfluor™ (2.5 g, 7.1 mmol) was added. The suspension was refluxed overnight. Then the solvent was removed in vacuo. CH$_2$Cl$_2$ was added to the resulting residue and insoluble material filtered off. The filtrate was washed with H$_2$O, dried and concentrate in vacuo. The crude product was purified by column chromatography to give 6-bromo-3-fluoro-2',4',5',6'-tetrahydrospiro[chroman-2,3'-pyran]-4-one (220 mg, 10%). $^1$H-NMR (CDCl$_3$): 1.72-2.21 (m, 4H), 3.44 (m, 1H), 3.63 (m, 1H), 3.73 (m, 1H), 3.92 (m, 1H), 4.91 (m, 1H), 6.94 (m, 1H), 7.56 (m, 1H), 7.90 (m, 1H).

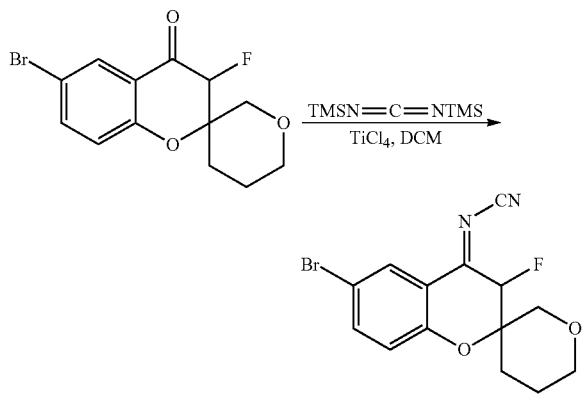

Step 2. (Z)—N-(6-bromo-3-fluoro-2',4',5',6'-tetrahydrospiro[chroman-2,3'-pyran]-4-ylidene)cyanamide To a solution of 6-bromo-3-fluoro-2',4',5',6'-tetrahydrospiro[chroman-2,3'-pyran]-4-one (220 mg, 0.65 mmol) in anhydrous DCM was added TiCl$_4$ (1 M in DCM, 1.4 mL) dropwise within 15 minutes at room temperature. After addition, the mixture was stirred for 1 h. To this mixture was added N,N'-methanediylidenebis(1,1,1-trimethylsilanamine) (264 mg, 1.42 mmol) dropwise. The resulting mixture was stirred for another 18 h after the addition. The reaction mixture was poured into ice-water and extracted with DCM. The combined organic phases were dried over anhydrous Na$_2$SO$_4$, filtered, and the filtrate was concentrated to give crude product, which was used in the next step without further purification.

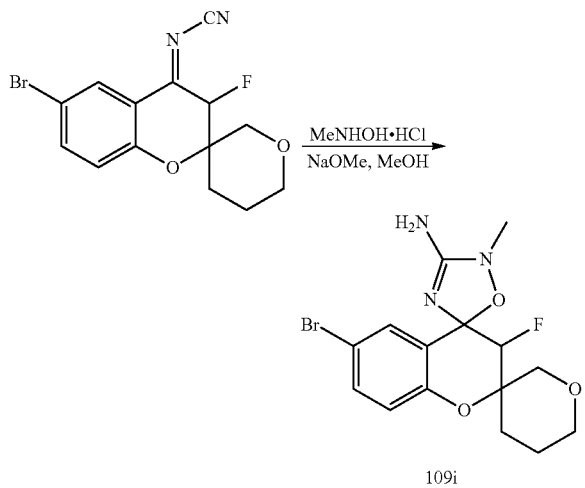

Step 3. Compound 109i

To a solution MeNHOH·HCl (25 mg, 0.3 mmol) in anhydrous MeOH was added NaOMe (14 mg, 25 w % in MeOH), followed by (Z)—N-(6-bromo-3-fluoro-2',4',5',6'-tetrahydrospiro[chroman-2,3'-pyran]-4-ylidene)cyanamide (100 mg, 0.3 mmol). After stirring for 10 minutes, the solvent was removed in vacuo. The residue was dissolved in DCM and the resulting solution was filtered. The filtrate was collected and the solvent was removed to give the crude product, which was purified by column chromatography to give product 109i (50 mg, 44%).

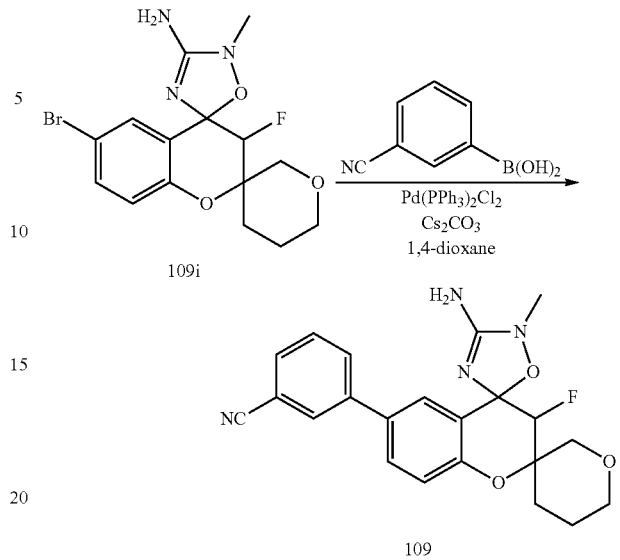

Step 4. Compound 109

Pd(PPh$_3$)$_2$Cl$_2$ (14 mg) in a 10 mL flask under Ar was treated sequentially with compound 109i (50 mg, 0.13 mmol) in 1,4-dioxane (3 mL), Cs$_2$CO$_3$ (2 N, 0.162 mL) and 3-cyanophenylboronic acid (32.6 mg, 0.22 mmol). The mixture was heated at 120° C. for 0.5 h. The reaction mixture was concentrated in vacuo to give the residue, which was purified by preparative TLC followed by preparative HPLC to give pure Compound 109 (10.2 mg, 19%). $^1$H-NMR (MeOD): 1.51-2.10 (m, 2H), 2.16 (m, 2H), 3.41 (d, 3H), 3.48-3.90 (m, 3H), 3.96 (m, 1H), 5.24 (m, 1H), 7.13 (m, 1H), 7.64 (m, 1H), 7.71 (m, 1H), 7.82 (m, 1H), 7.97 (m, 1H), 8.09 (m, 2H).

Example 90

Compound 110

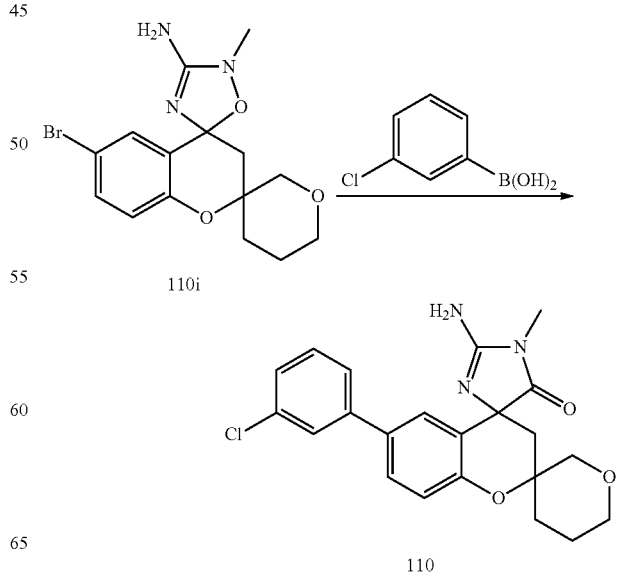

Step 1. Compound 110

Pd(PPh₃)₂Cl₂ (6 mg) under Ar was treated sequentially with the amine 110i (20 mg, 0.062 mmol) in 1,4-dioxane (1.5 mL), Cs₂CO₃ (2 N, 0.25 mL) and 3-chlorophenylboronic acid (16 mg, 0.11 mmol). The mixture was heated at 120° C. under Ar in a microwave reactor for 30 minutes. The reaction mixture was concentrated in vacuo to give the residue, which was purified by preparative TLC and HPLC to give Compound 110 (2.05 mg, 8%). ¹H-NMR (MeOD): 1.45-1.94 (m, 3H), 2.04 (m, 2H), 2.89 (m, 1H), 3.37 (m, 3H), 3.61 (m, 2H), 3.82 (m, 2H), 7.02 (m, 1H), 7.34 (m, 2H), 7.51 (m, 1H), 7.18 (m, 2H), 7.88 (m, 1H).

Example 91

Compound 111

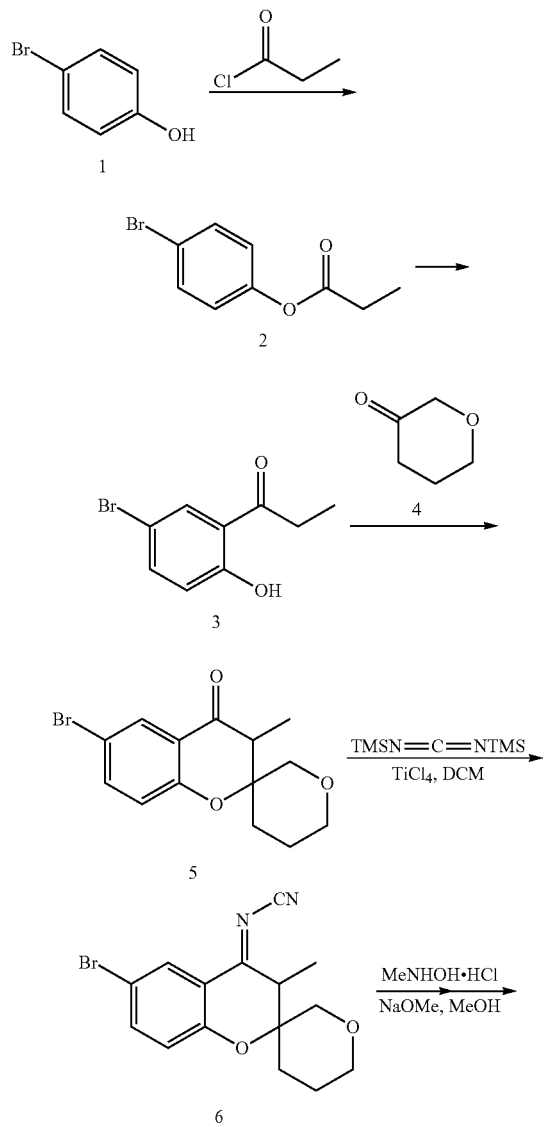

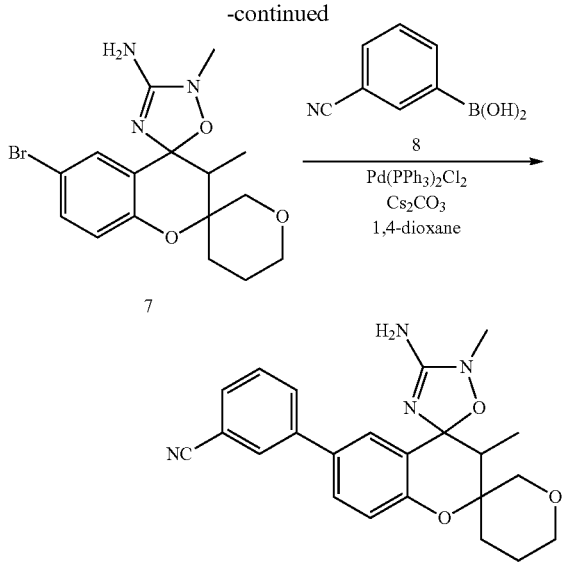

Experimental Data:

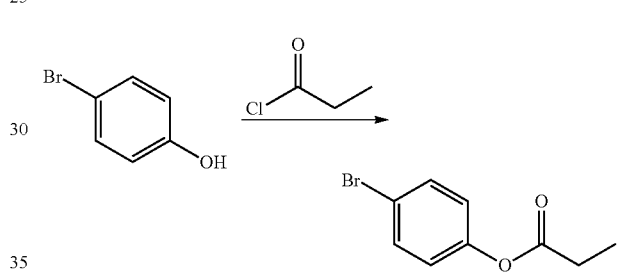

Step 1. 4-bromophenyl propionate

4-Bromophenol (28.4 g, 0.165 mol) and DMAP (0.17 g, 1.4 mmol) were dissolved in dichloromethane (110 mL). The solution was cooled in an ice-bath and triethylamine (24 mL) was added portionwise. Propionyl chloride (16 g, 0.17 mmol) was then added dropwise and the resulting mixture was stirred at room temperature for 2 hrs. The mixture was washed with water, followed by brine, dried and concentrated to give 4-bromophenyl propionate, which was used in the next step without further purification (34 g, 92%). ¹H NMR (MeOD, 400 MHz): 1.12-1.24 (m, 3H), 2.57-2.63 (m, 2H), 7.02-7.06 (m, 2H), 7.51-7.55 (m, 2H).

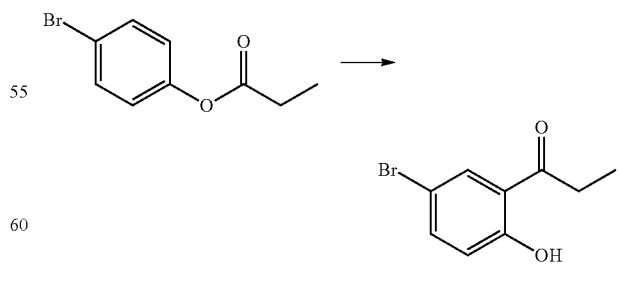

Step 2. 1-(5-bromo-2-hydroxyphenyl)propan-1-one

4-Bromophenyl propionate (34 g, 0.15 mmol) and aluminum chloride (44 g, 0.3 mmol) were heated together at 100°

C. for 30 mins. The solution became dark and hydrogen chloride gas was evolved. After cooling, the reaction mixture was carefully poured into ice water, and the resulting mixture was extracted with dichloromethane. The organic layer was washed with brine, dried and concentrated to give the residue, which was purified by column chromatography to give 1-(5-bromo-2-hydroxyphenyl)propan-1-one. (20 g, 59%) $^1$H NMR (CDCl$_3$, 400 MHz): 1.24 (t, 3H), 2.98-3.04 (m, 2H), 6.88 (d, 1H), 7.52 (t, 1H), 7.76 (s, 1H).

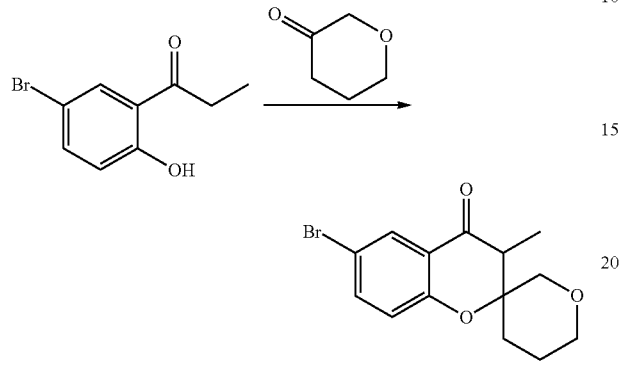

Step 3. 6-bromo-3-methyl-2',4',5',6'-tetrahydrospiro[chroman-2,3'-pyran]-4-one

A mixture of 1-(5-bromo-2-hydroxyphenyl)propan-1-one (5.7 g, 25 mol), dihydro-2H-pyran-3(4H)-one (5 g, 50 mmol) and pyrrolidine (3.4 g, 48 mmol) in methanol (80 mL) was stirred overnight. The reaction mixture was removed in vacuo, and H$_2$O was added. The resulting solution was extracted with ethyl acetate. The ethyl acetate solution was dried over anhydrous Na$_2$SO$_4$, filtered, and evaporated to give 6-bromo-3-methyl-2',4',5',6'-tetrahydrospiro[chroman-2,3'-pyran]-4-one (1.2 g, 16%). $^1$HNMR (CDCl$_3$): 1.16-1.27 (m, 3H), 1.51-1.57 (m, 1H), 1.66-1.73 (m, 1H), 1.91-2.08 (m, 2H), 2.59-2.69 (m, 1H), 3.46-3.56 (m, 2H), 3.88-3.98 (m, 2H), 6.97 (m, 1H), 7.58 (m, 1H), 7.95 (s, 1H).

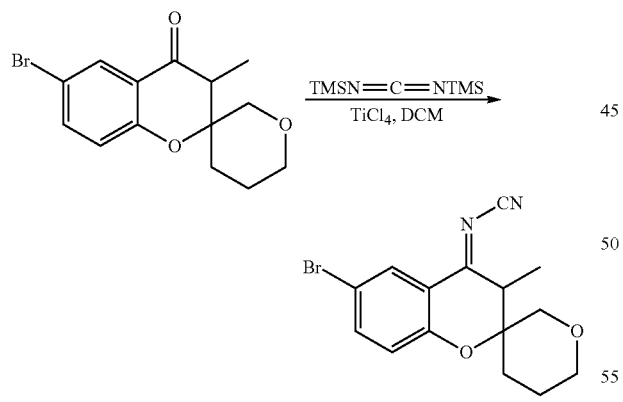

Step 4. (E)-N-(6-bromo-3-methyl-2',4',5',6'-tetrahydrospiro[chroman-2,3'-pyran]-4-ylidene)cyanamide A solution of 6-bromo-3-methyl-2',4',5',6'-tetrahydrospiro[chroman-2,3'-pyran]-4-one (200 mg, 0.65 mmol) and TiCl$_4$ (864 mg, 4.55 mmol) in anhydrous DCM (8 mL) was heated at 50 under microwave for 5 mins. Then bis-trimethylsilyl-carbodiimide (360 mg, 1.95 mmol) was added and the mixture was heated at 65° C. for another 1 hr. The reaction mixture was poured into ice-water and extracted with DCM. The combined organic phases were dried over anhydrous Na$_2$SO$_4$, filtered and concentrated to give (E)-N-(6-bromo-3-methyl-2',4',5',6'-tetrahydrospiro[chroman-2,3'-pyran]-4-ylidene)cyanamide (300 mg, crude), which was used in the next step without further purification.

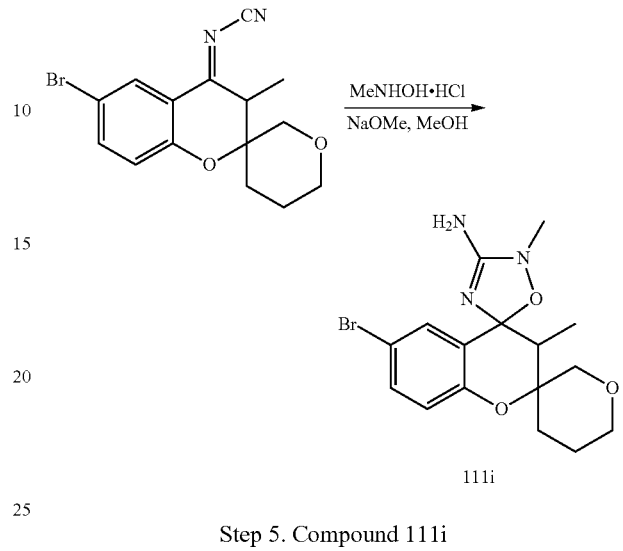

Step 5. Compound 111i

To a solution of methylhydroxylamine HCl salt (84 mg, 1 mmol) in anhydrous MeOH (10 mL) was added NaOMe (25% in MeOH (Wt. %), 0.3 mL, 1 mmol), followed by (E)-N-(6-bromo-3-methyl-2',4',5',6'-tetrahydrospiro[chroman-2,3'-pyran]-4-ylidene)cyanamide (346 mg, 1 mmol). After stirring for 10 mins, the solvent was removed in vacuo. The residue was redissolved in DCM (10 mL). The mixture was filtered and concentrated to give the residue, which was purified by preparative TLC to give Compound 111i (100 mg, 25%). $^1$H-NMR (CDCl$_3$): 1.02-1.11 (m, 3H), 1.89-2.17 (m, 2H), 1.17-2.24 (m, 2H), 3.05 (s, 3H), 3.63-3.68 (m, 1H), 3.95-4.33 (m, 2H), 4.25-4.40 (s, 2H), 6.79-6.87 (m, 1H), 7.30-7.39 (m, 1H), 7.47 (s, 1H).

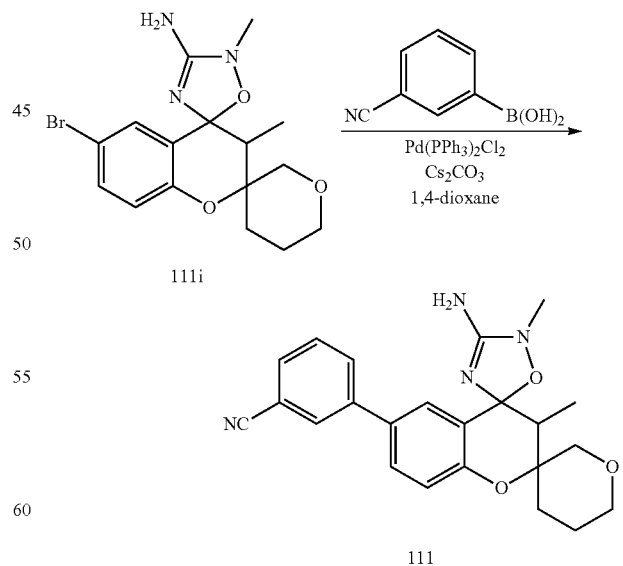

Step 6. Compound 111

A mixture of Compound 111i (69 mg, 0.18 mmol), 3-cyanophenylboronic acid (53 mg, 0.36 mmol), Cs$_2$CO$_3$ (2 M, 1 mL) and Pd(PPh₃)₂Cl₂ (30 mg) in 1,4-dioxane (5 mL) under Ar was stirred under microwave at 120° C. for 35 minutes. The reaction mixture was concentrated in vacuo to give the residue, which was purified by preparative TLC and preparative HPLC to give Compound 111 (10 mg, 14%). ¹H-NMR (MeOD): 0.99-1.30 (m, 3H), 1.45-2.00 (m, 2H), 2.00-2.70 (m, 2H), 3.38 (m, 3H), 3.40-3.60 (m, 1H), 3.61-3.65 (m, 2H), 3.80-4.10 (m, 2H), 7.07-7.17 (m, 1H), 7.59-7.79 (m, 3H), 7.90-8.01 (m, 3H).

Example 92

Compound 113a and 113b

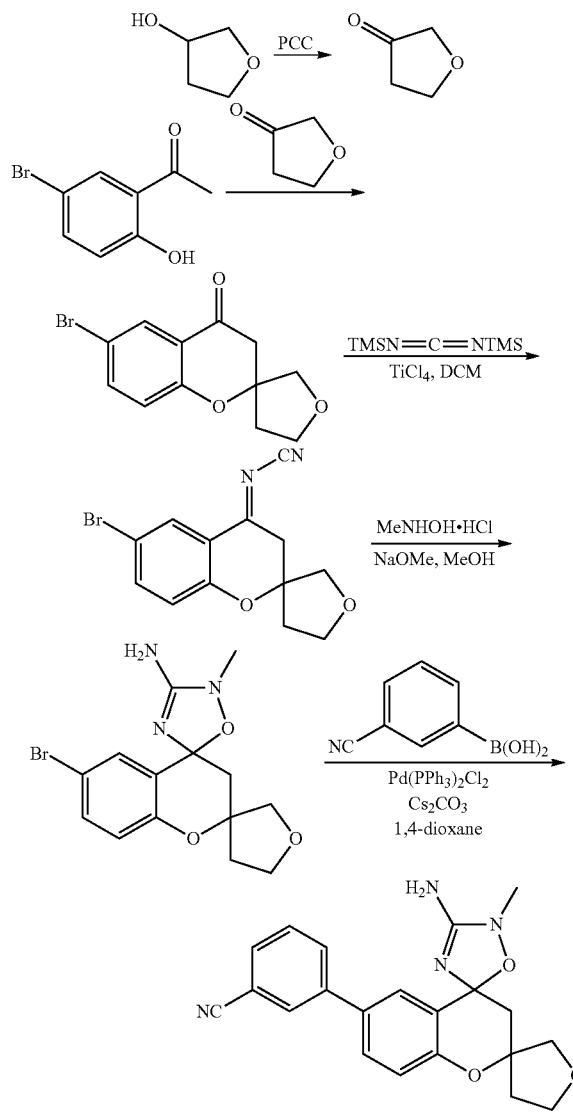

PCC (110.2 g, 0.515 mol). The mixture was stirred at room temperature overnight. When the reaction was completed, the mixture was filtered through celite and the filtrate was dried over Na₂SO₄ and concentrated in vacuo to give the crude product, which was distilled in vacuo to give product (7.07 g, 29%). ¹H-NMR (MeOD): 2.45 (m, 2H), 3.8 (m, 2H), 4.2 (m, 2H).

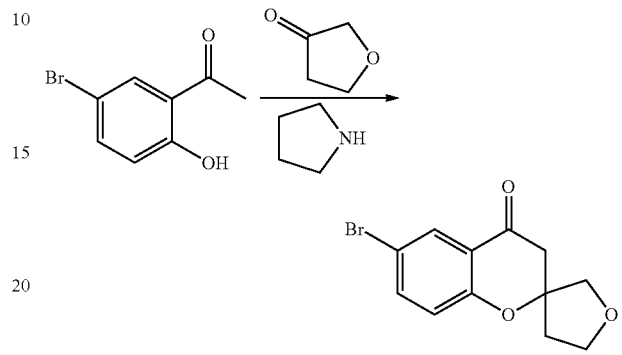

Step 2: 6-bromo-4',5'-dihydro-2'H-spiro[chroman-2,3'-furan]-4-one

A solution of 1-(5-bromo-2-hydroxy-phenyl)-ethanone (4.97 g, 23.23 mmol), dihydrofuran-3(2H)-one (3 g, 34.87 mmol) and pyrrolidine (2.48 g, 34.87 mmol) in toluene (60 mL) was refluxed overnight. After cooling, the mixture was treated with water and acidified with concentrated HCl to pH around 1. The resulting solution was extracted with ethyl acetate and washed with brine. The combined organic layers were concentrated and the residue was purified by column to give 6-bromo-4',5'-dihydro-2'H-spiro[chroman-2,3'-furan]-4-one (1.7 g, 30%). ¹H-NMR (CDCl₃): 1.9 (m, 1H), 2.3 (m, 1H), 2.8 (m, 2H), 3.65 (m, 1H), 3.9 (m, 1H), 4.0 (m, 2H), 6.8 (m, 1H), 7.5 (m, 1H), 7.9 (m, 1H).

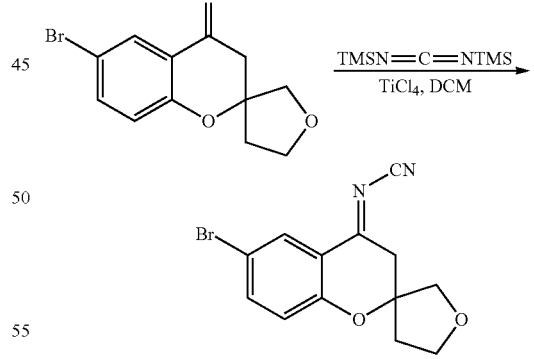

Step 3: (E)-N-(6-bromo-4',5'-dihydro-2'H-spiro[chroman-2,3'-furan]-4-ylidene)cyanamide To a solution of 6-bromo-4',5'-dihydro-2'H-spiro[chroman-2,3'-furan]-4-one (206 mg, 0.731 mmol) in anhydrous DCM (6 mL) was added TiCl₄ (281 mg, 1.48 mmol) dropwise within 15 minutes at room temperature and resulting mixture was stirred for 1 h. To this mixture was added N,N'-methanediylidenebis(1,1,1-trimethylsilanamine) (300 mg, 1.61

Experimental Data:

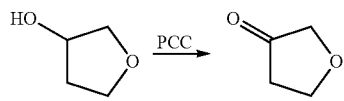

Step 1: dihydrofuran-3(2H)-one

To a solution of tetrahydrofuran-3-ol (29.7 g, 0.337 mol) in dry DCM (1 L) was added 3 Å molecule sieves (35 g) and mmol). The resulting mixture was stirred for another 18 hours after addition. The reaction mixture was poured into water-ice and extracted with DCM. The combined organic phases were dried over anhydrous Na$_2$SO$_4$, filtered and concentrated to give crude product (225 mg, 100%), which was used in the next step without further purification.

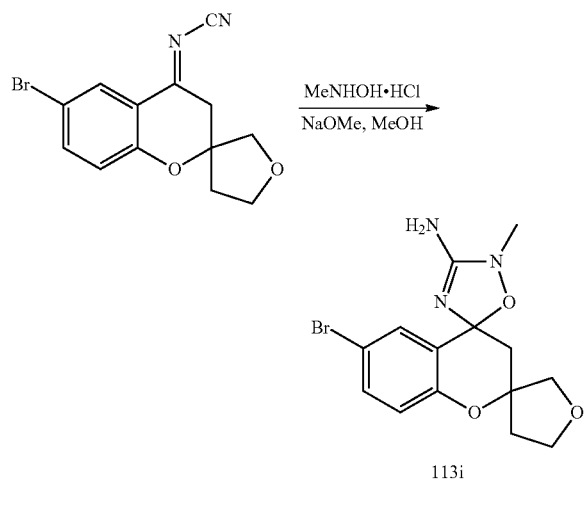

Step 4: Compound 113i

To a solution of N-methylhydroxylamine hydrochloride (62 mg, 0.735 mmol) in anhydrous MeOH (8.6 mL) was added NaOMe (25%, 0.143 mL), followed by (E)-N-(6-bromo-4',5'-dihydro-2'H-spiro[chroman-2,3'-furan]-4-ylidene)cyanamide (225 mg, 0.735 mmol). After stirring for 10 min, the solvent was removed in vacuo and the residue was dissolved in DCM. The resulting solution was filtered, and solvent was removed in vacuo to give compound 113i (52 mg, 20%). $^1$H-NMR (CDCl$_3$): 2.0 (m, 2H), 2.25 (m, 2H), 3.0 (d, 3H), 3.65 (m, 1H), 3.8 (m, 1H), 3.9 (m, 2H), 6.65 (d, 1H), 7.25 (d, 2H), 7.45 (d, 1H).

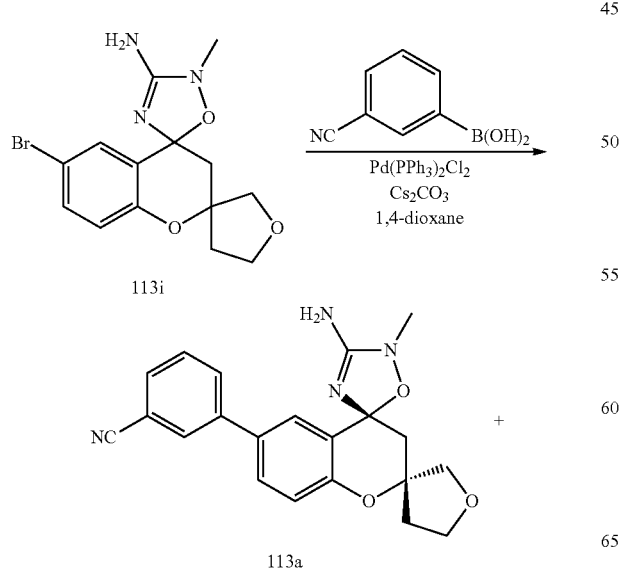

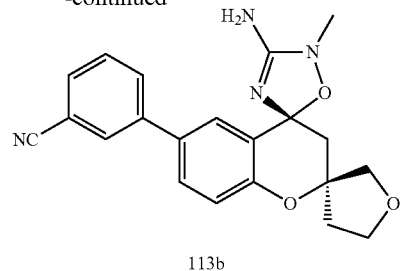

Step 5: Compound 113

Pd(PPh$_3$)$_2$Cl$_2$ (5 mg, 0.005 mmol) in a 10 mL flask under Ar was treated sequentially with compound 113i (30 mg, 0.085 mmol) in 1,4-dioxane (1 mL), Cs$_2$CO$_3$ (2 N, 0.3 mL) and 3-cyanophenylboronic acid (30.94 mg, 0.17 mmol). The mixture was heated at 120° C. under microwave for 30 minutes. The reaction mixture was concentrated in vacuo to give the residue, which was purified by preparative TLC to give pure isomer 113a (5.52 mg, 17%) and 113b (2.81 mg, 9%). $^1$H-NMR (MeOD): 2.15 (m, 1H), 2.35 (m, 1H), 2.55 (m, 1H), 2.8 (m, 1H), 3.35 (m, 3H), 3.8 (m 1H), 3.95 (m, 2H), 4.1 (m, 1H), 7.0 (m, 1H), 7.55 (m, 1H), 7.7 (m, 2H), 7.9 (m, 1H), 8.0 (m, 2H) (113a). $^1$H-NMR (MeOD): 2.15 (m, 2H), 2.4 (m, 1H), 2.8 (m, 1H), 3.35 (m, 3H), 3.8 (m, 1H), 3.95 (m, 2H), 4.05 (m, 1H), 7.0 (m, 1H), 7.6 (m, 1H), 7.7 (m, 2H), 7.9 (m, 1H), 8.0 (m, 2H) (113b).

Example 93

Compound 114

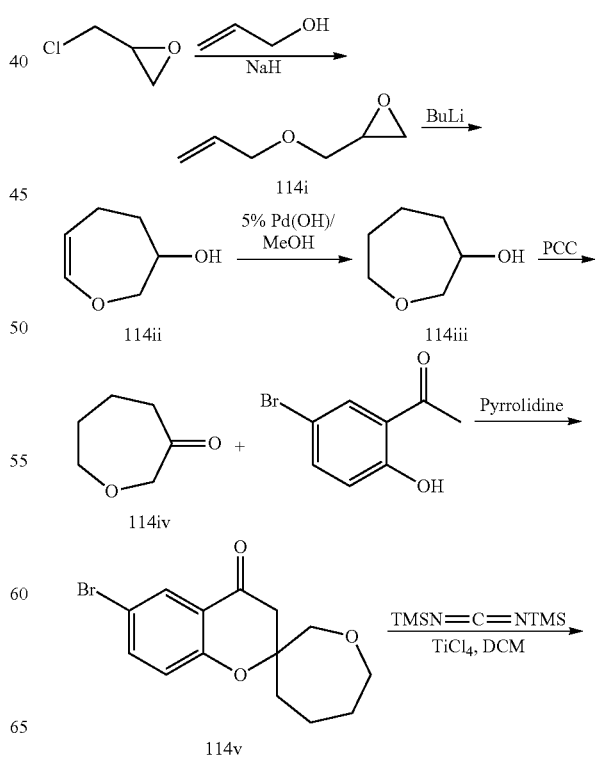

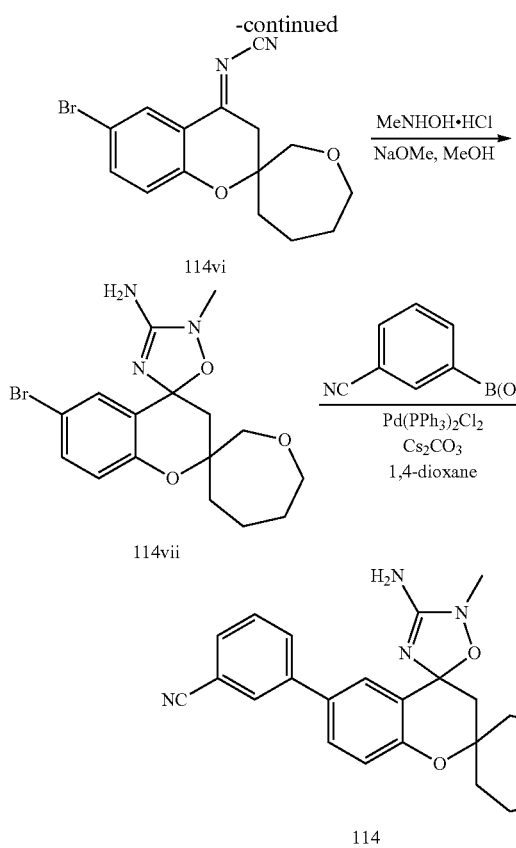

Experimental Data:

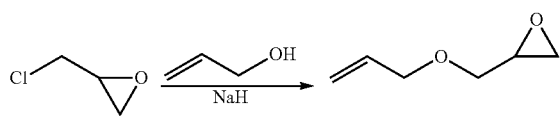

Step 1. 2-(allyloxymethyl)oxirane

An oil slurry of NaH (68 g of a 60% suspension) was rinsed with petroleum ether and added to THF (1600 mL). The prop-2-en-1-ol (1.6 mol, 108.92 mL) was then added and the resulting solution was stirred for 2 hours. Chloromethyl-oxirane (639.12 mL) was added and the solution was stirred for 16 hours at room temperature followed by refluxation for 4 h. After the excess base was neutralized with 30% methanolic H₂SO₄, the solution was filtered, concentrated under reduced pressure and distilled under vacuo to give (Z)-2,3,4,5-tetrahydrooxepin-3-ol as colorless oil.

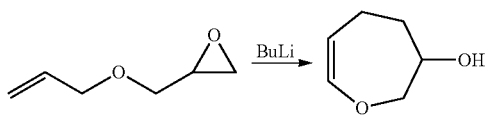

Step 2. (Z)-2,3,4,5-tetrahydrooxepin-3-ol 1.3 M sBuLi in hexane (1.3 M, 38.5 mL) was added dropwise to a solution of allyl glycidyl ether 114i (0.05 mol, 5.93 mL) and HMPT (26 mL) in anhydrous THF (260 mL) at −78° C. under argon. After stirring for 30 minutes at the same temperature, the reaction was quenched with phosphate buffer (pH=7.0, 30 mL). The reaction mixture was saturated with solid NaCl and extracted with ethyl acetate (6×30 mL). The combined organic layers were dried over anhydrous Na₂SO₄ and concentrated under reduced pressure below 25. The resulting mixture was separated by flash chromatography on silica gel (PE:EA=7:1-5:1) to give (Z)-2,3,4,5-tetrahydrooxepin-3-ol (925 mg, yield 16%). ¹H-NMR (CDCl₃/400M): δ 6.32-6.30 (m, 1H), 4.82-4.78 (m, 1H), 4.04-3.94 (m, 2H), 3.93-3.88 (m, 1H), 2.28-2.15 (m, 1H), 2.14-2.05 (m, 1H), 2.04-1.95 (m, 1H), 1.89 (br, 1H, OH), 1.76-1.68 (m, 1H).

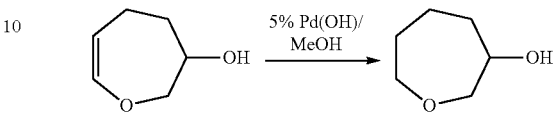

Step 3. oxepan-3-ol

To a solution of (Z-2,3,4,5-tetrahydrooxepin-3-ol (114ii) (6.9 mmol, 786 mg) in MeOH (7.86 mL), was added Pd(OH)₂ (78.6 mg) at room temperature under protection of H₂. The reaction mixture was stirred at room temperature for 4 hours. TLC showed that the reaction was completed. The reaction mixture was filtered through celite and the filtrate was concentrated to give oxepan-3-ol (730 mg, yield 91%). ¹H-NMR (CDCl₃/400M): δ 3.89-3.85 (m, 1H), 3.81-3.73 (m, 1H), 3.72-3.62 (m, 3H), 1.85-1.75 (m, 3H), 1.74-1.62 (m, 2H), 1.60-1.52 (m, 1H).

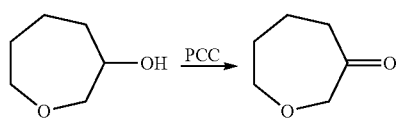

Step 4. oxepan-3-one

PCC (9.4 mmol, 2.02 g) was added to a solution of oxepan-3-ol (114iii) (6.27 mmol, 727 mg) in 18.8 mL CH₂Cl₂. The resulting mixture was stirred at room temperature overnight. Upon completion, the reaction mixture was filtered through silica and the filtrate was concentrated to give oxepan-3-one (290 mg, yield 41%). ¹H-NMR (CDCl₃/400M): δ 4.07 (s, 2H), 3.80-3.78 (m, 2H), 3.70-3.67 (m, 2H), 1.90-1.85 (m, 2H), 1.77-1.72 (m, 2H).

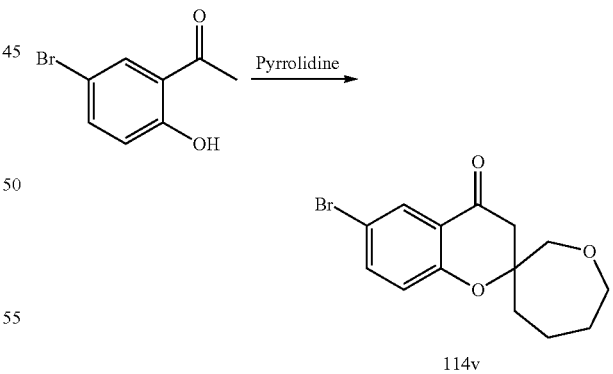

Step 5. Compound 114v

A mixture of 1-(5-bromo-2-hydroxyphenyl)ethanone (0.698 mmol, 150 mg) and oxepan-3-one (1.395 mmol, 159.1 mg) was added pyrrolidine (1.33 mmol, 0.1143 mL) in MeOH (2.85 mL). The reaction mixture was refluxed overnight. The mixture was concentrated in vacuo to give the residue, which was added water and HCl (36%) until pH=1. The resulting mixture was extracted with EtOAc and the organic layer was concentrated to give the crude product, which was purified by preparative TLC (PE:EA=3:1) to give compound 114v (63 mg, yield 29%). ¹H-NMR (CDCl₃/400M): δ 7.94 (d, 1H, J=2.8 Hz), 7.56-7.53 (m, 1H), 6.90 (d, 1H, J=8.8 Hz), 4.00 (d, 1H, J=16 Hz), 3.91-3.82 (m, 1H), 3.75-3.67 (m, 1H), 3.64 (d, 1H, J=14 Hz), 2.79-2.65 (m, 2H), 2.09-2.00 (m, 1H), 1.92-1.68 (m, 4H), 1.55-1.42 (m, 1H).

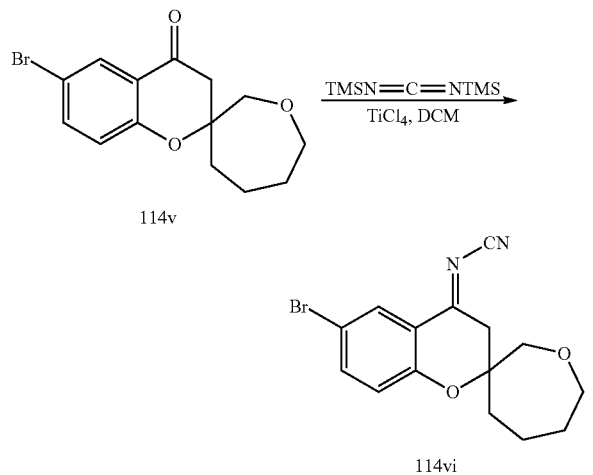

Step 6. Compound 114vi

To a solution of compound 114v (223 mg, 0.72 mmol) in anhydrous DCM (5.6 mL) was added TiCl₄ (1 M solution in DCM, 2.87 mL, 2.87 mmol) dropwise within 15 minutes at room temperature and the resulting mixture was stirred for 1 h after the addition. To this mixture was added bis-trimethylsilylcarbodiimide (400 mg, 0.48 mL, 2.15 mmol) dropwise. The resulting mixture was stirred for another 18 h after the addition. The reaction mixture was poured into ice-water (20 g) and extracted with DCM (3×20 mL). The combined organic phases were dried over anhydrous Na₂SO₄, filtered, and concentrated to give compound 114vi as light brown solid (168 mg), which was used for next step without further purification.

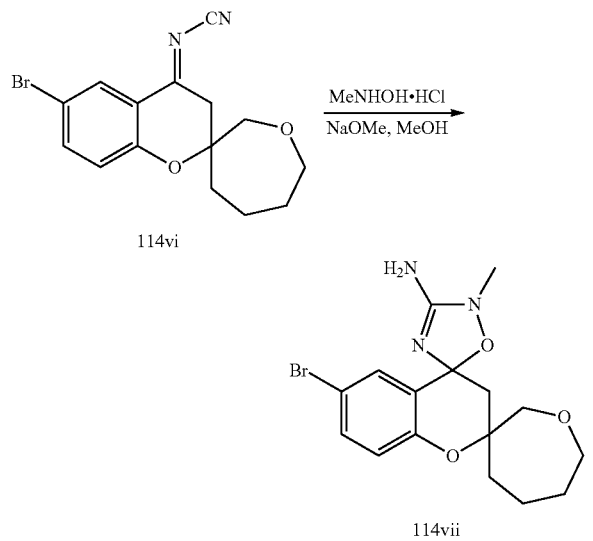

Step 7. Compound 114vii

To a solution of methylhydroxylamine HCl salt (42 mg, 0.50 mmol) in anhydrous MeOH (5.9 mL) was added NaOMe (25 w % in MeOH, 98.5 uL, 0.45 mmol), followed by cyanamide 114vi (168 mg, 0.50 mmol), After stirring for 1 hour, the solvent was removed in vacuo. The resulting residue was redissolved in DCM (15 mL). The mixture was filtered, and the solvent was removed in vacuo to give the crude product, which was purified by preparative TLC (CH₂Cl₂: MeOH 12:1) to give the pure product 114vii (114 mg, 59%).

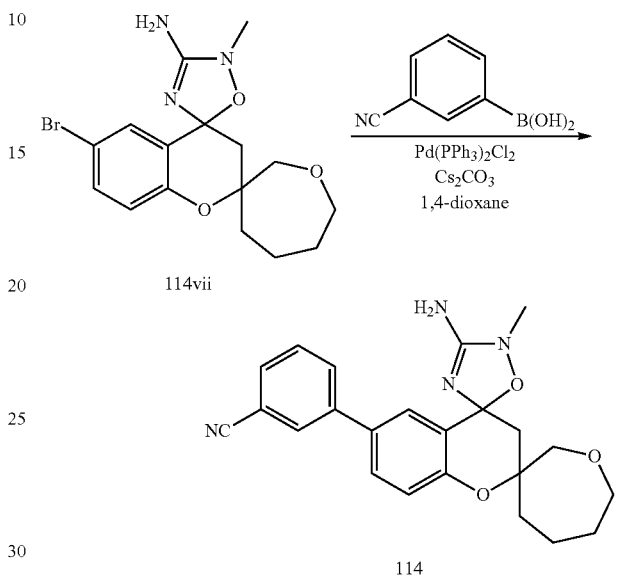

Step 8. Compound 114

Pd(PPh₃)₂Cl₂ (18.4 mg) in a 10 mL tube under Ar was treated sequentially with the compound 114vii (50 mg, 0.131 mmol) in 1,4-dioxane (5.0 mL), Cs₂CO₃ (2 N, 0.73 mL) and 3-cyanophenylboronic acid (38.5 mg, 0.262 mmol). The mixture was heated under microwave at 120° C. for 30 minutes. The reaction mixture was concentrated in vacuo to give the residue, which was purified by preparative TLC (CH₂Cl₂: MeOH 10:1) and preparative HPLC to give the target compound Compound 114. ¹H-NMR (MeOD/400M): δ 7.99-7.97 (m, 1H), 7.95-7.87 (m, 2H), 7.72-7.68 (m, 1H), 7.67-7.62 (m, 1H), 7.61-7.55 (m, 1H), 7.15-6.98 (m, 1H), 3.92-3.85 (m, 2H), 3.82-3.65 (m, 2H), 3.41-3.35 (m, 3H), 3.05-2.88 (m, 1H), 2.15-2.05 (m, 1H), 2.04-2.01 (m, 1H), 2.00-1.95 (m, 1H), 1.92-1.71 (m, 3H), 1.68-1.48 (m, 1H).

Example 94

Compound 115

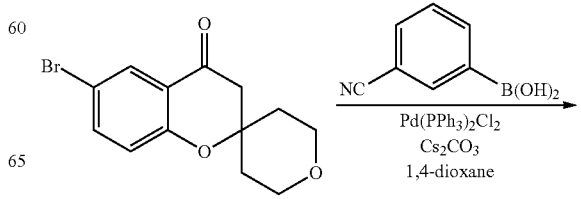

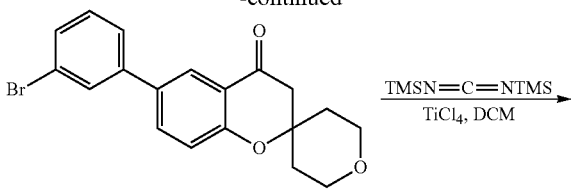

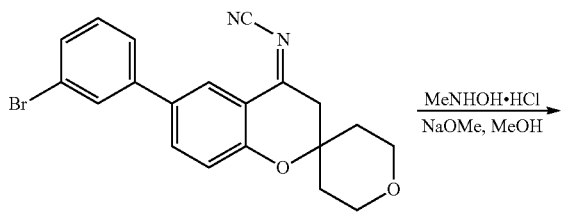

Experimental Data:

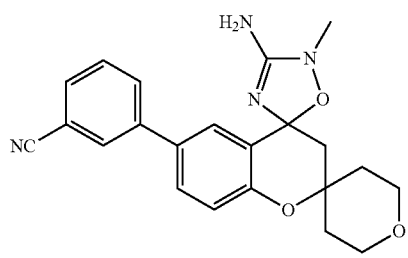

Step 1. 3-(4-oxo-2',3',5',6'-tetrahydrospiro[chroman-2,4'-pyran]-6-yl)benzonitrile A mixture of 6-bromo-2',3',5',6'-tetrahydrospiro[chroman-2,4'-pyran]-4-one (300 mg, 1 mmol), 3-cyanophenylboronic acid (298 mg, 2 mmol), Cs₂CO₃ (2 M, 4 mL) and Pd(PPh₃)₂Cl₂ (80 mg) in 1,4-dioxane (10 mL) under Ar was stirred under microwave at 120° C. for 35 minutes. The reaction mixture was concentrated in vacuo to give the residue, which was purified by preparative TLC to give 3-(4-oxo-2',3',5',6'-tetrahydrospiro[chroman-2,4'-pyran]-6-yl)benzonitrile (140 mg, 43%). ¹H-NMR (CDCl₃): 1.81-1.85 (m, 2H), 2.00-2.04 (d, 2H), 2.80 (s, 2H), 3.78-3.87 (m, 4H), 7.14 (d, 1H), 7.52-7.56 (t, 1H), 7.61-7.64 (d, 1H), 7.71-7.74 (d, 1H), 7.78 (d, 1H), 7.80 (s, 1H), 8.07 (s, 1H).

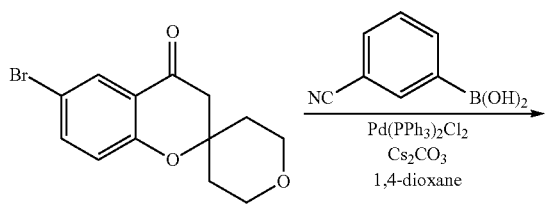

Step 2. (Z)—N-(6-(3-cyanophenyl)-2',3',5',6'-tetrahydrospiro[chroman-2,4'-pyran]-4-ylidene)cyanamide A solution of 3-(4-oxo-2',3',5',6'-tetrahydrospiro[chroman-2,4'-pyran]-6-yl)benzonitrile (170 mg, 0.53 mmol) and TiCl₄ (403 mg, 2.12 mmol) in anhydrous DCM (5 mL) was heated at 50 under microwave for 5 mins. Then bis-trimethylsilylcarbodiimide (198 mg, 1.06 mmol) was added and the mixture was heated at 60 for another 30 mins. The reaction mixture was poured into ice-water and extracted with DCM. The combined organic phases were dried over anhydrous Na₂SO₄, filtered and concentrated to give (Z)—N-(6-(3-cyanophenyl)-2',3',5',6'-tetrahydrospiro[chroman-2,4'-pyran]-4-ylidene)cyanamide (147 mg, crude), which was used in the next step without further purification.

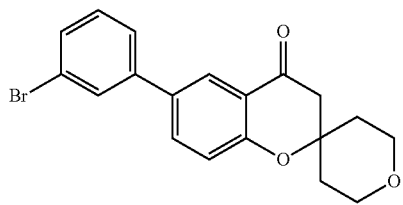

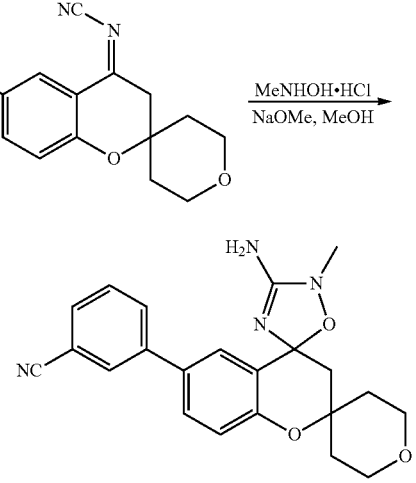

Step 3. Compound 115

To a solution of methylhydroxylamine HCl salt (36 mg, 0.43 mmol) in anhydrous MeOH (5 mL) was added NaOMe (25% in MeOH (Wt. %), 0.10 mL, 0.39 mmol), followed by (Z)—N-(6-(3-cyanophenyl)-2',3',5',6'-tetrahydrospiro[chroman-2,4'-pyran]-4-ylidene)cyanamide (147 mg, 0.43 mmol). After stirred for 10 mins, the solvent was removed in vacuo. The residue was redissolved in DCM (5 mL). The mixture was filtered and concentrated to give the residue, which was purified by preparative TLC to give Compound 115 (39.7 mg, 24%). ¹H-NMR (CDCl₃): 1.79-1.90 (m, 3H), 2.03-2.07 (d, 1H), 2.24 (d, 1H), 2.33 (d, 1H), 3.09 (s, 3H) 3.73-3.82 (m, 3H), 3.91-3.97 (m, 1H), 6.97 (d, 1H), 7.41-7.43 (d, 1H), 7.47-7.51 (t, 1H), 7.56-7.58 (m, 2H), 7.74-7.81 (m, 2H).

Example 95

Compound 116

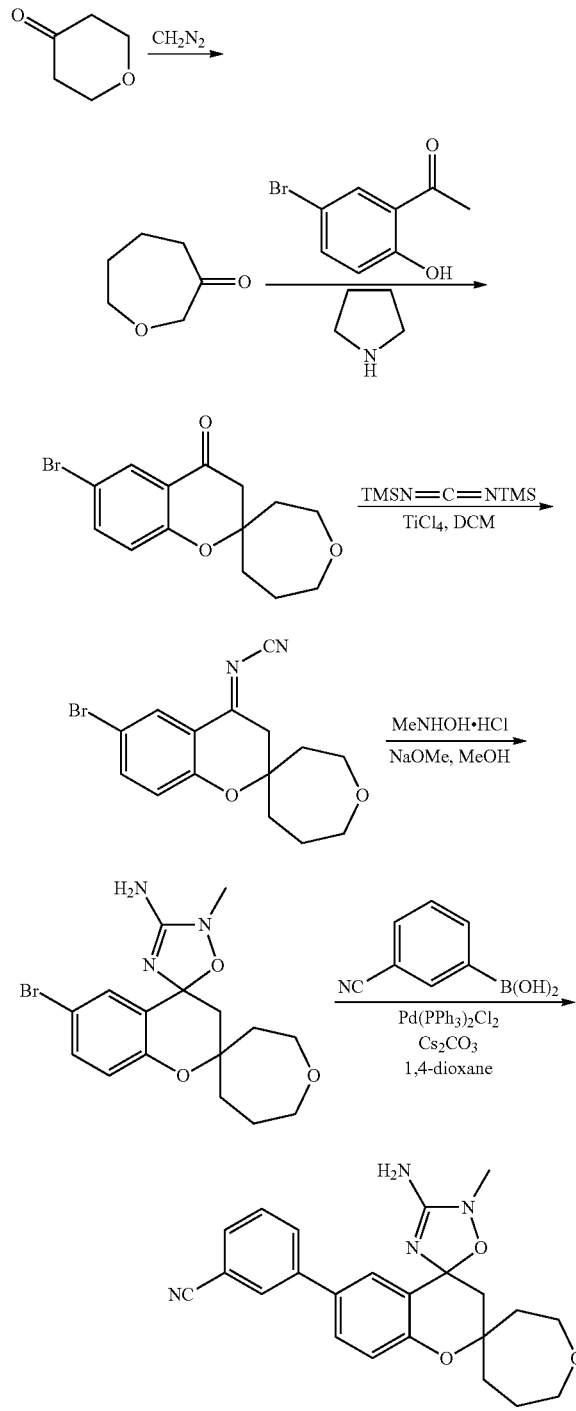

Experimental Data:

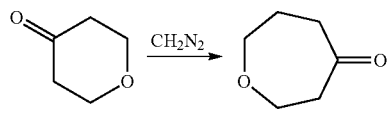

Step 1: oxepan-4-one

To a solution of tetrahydro-pyran-4-one (15 g, 0.15 mol) in Et₂O (90 mL) was added dropwise a solution of CH₂N₂ (1 M in Et₂O, 300 mL) at 0° C. After addition, MeOH (75 mL) was added dropwise. The reaction mixture was allowed to warm to room temperature and stir for 2 hours. The remaining diazomethane was destroyed with a few drops of acetic acid. The solvent was removed under reduced pressure to give oxepan-4-one, which was used in the next step directly without purification. ¹H-NMR (CDCl₃): 1.79 (m, 2H), 2.61 (m, 4H), 3.81 (m, 4H).

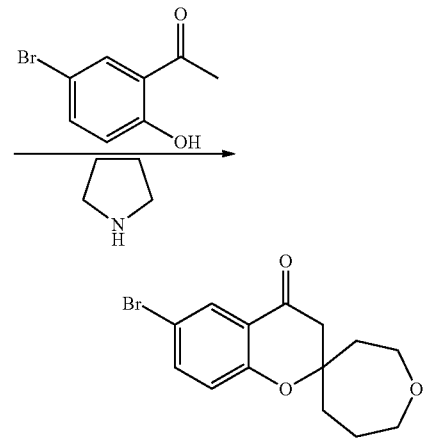

Step 2: Compound 116i

A mixture of oxepan-4-one (10 g, 87.7 mmol), 1-(5-bromo-2-hydroxy-phenyl)-ethanone (13 g, 58.5 mmol) and pyrrolidine (6.2 g, 87.7 mmol) in MeOH (150 mL) was refluxed overnight. The solvent was removed in vacuo. The residue was diluted with water, acidified with con. HCl to pH=1. The solution was extracted with EtOAc, washed with brine, and concentrated. The residue was purified by preparative HPLC to give compound 116i (220 mg, 1%). ¹H-NMR (CDCl₃): 1.52 (m, 1H), 1.84 (m, 2H), 1.98 (m, 1H), 2.13 (m, 2H), 2.70 (m, 2H), 3.65 (m, 1H), 3.74 (m, 3H), 6.81 (d, 1H), 7.49 (m, 1H), 7.90 (m, 1H).

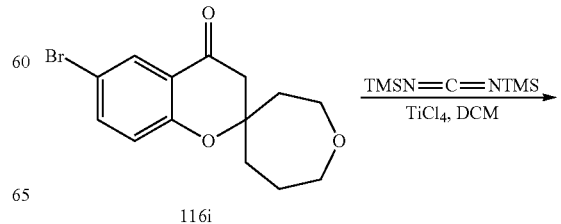

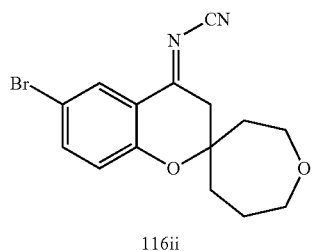

116ii

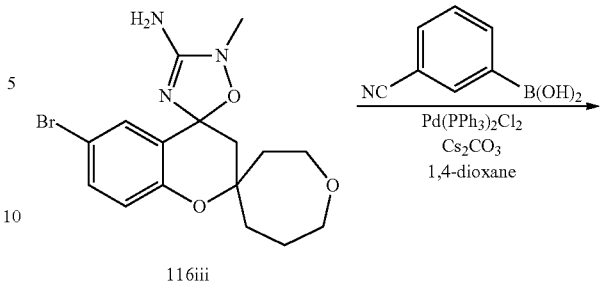

116iii

Step 3: Compound 116ii

To a solution of compound 116i (200 mg, 0.645 mmol) in anhydrous DCM (7 mL) was added TiCl$_4$ (1 M solution in DCM, 1.29 mL, 1.29 mmol) dropwise within 15 min at room temperature. The mixture was stirred another 1 h after the addition. To this mixture was added bis-trimethylsilylcarbodiimide (264 mg, 1.42 mmol) dropwise. The resulting mixture was stirred for another 18 h after the addition. The reaction mixture was poured into ice-water and extracted with DCM. The combined organic phases were dried over anhydrous Na$_2$SO$_4$, filtered, and concentrated to give compound 116ii, which was used in the next step without further purification.

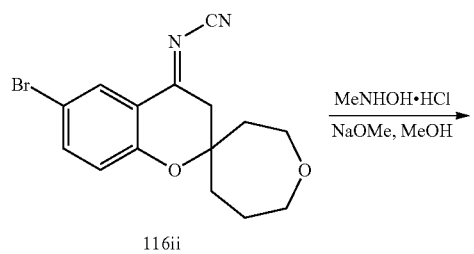

116ii

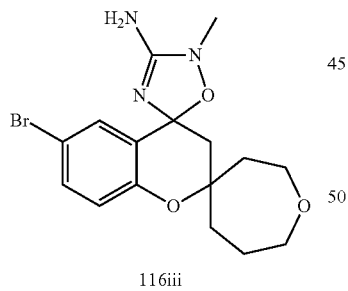

116iii

Step 4: Compound 116iii

To a solution of methylhydroxylamine HCl salt (38 mg, 0.45 mmol) in anhydrous MeOH (6 mL) was added NaOMe (25 w % in MeOH, 0.09 mL, 0.42 mmol), followed by compound 116ii (155 mg, 0.45 mmol). After stirring 10 min, the solvent was removed in vacuo. The residue was redissolved in DCM. The mixture was filtered, and the solvent was removed in vacuo to give crude product of compound 116iii, which was purified by preparative TLC (60 mg, 34%).

116

Step 5: Compound 116

Pd(PPh$_3$)$_2$Cl$_2$ (8 mg) in a 10 mL of tube under Ar$_2$ was treated sequentially with compound 116iii (30 mg, 0.0787 mmol) in 1,4-dioxane (1 mL), Cs$_2$CO$_3$ (2 N, 0.3 mL) and 3-cyanophenylboronic acid (23 mg, 0.157 mmol). The mixture was heated at 120° C. in a microwave reactor for 0.5 h. The reaction mixture was concentrated in vacuo to give the residue, which was purified by preparative TLC to give pure Compound 116 (3 mg, 10%). $^1$H-NMR (MeOD): 1.71 (m, 1H), 2.05 (m, 4H), 2.20 (m, 3H), 3.01 (m, 1H), 3.38 (m, 3H), 3.71 (m, 2H), 3.81 (m, 2H), 7.06 (m, 0.7H), 7.20 (m, 0.3H), 7.64 (m, 1H), 7.72 (m, 1H), 7.97 (m, 3H), 8.30 (m, 0.3H).

Example 96

Compound 117

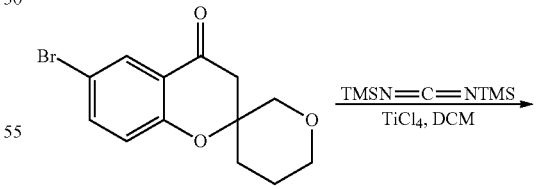

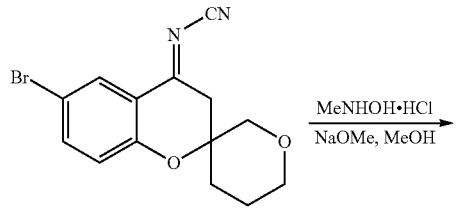

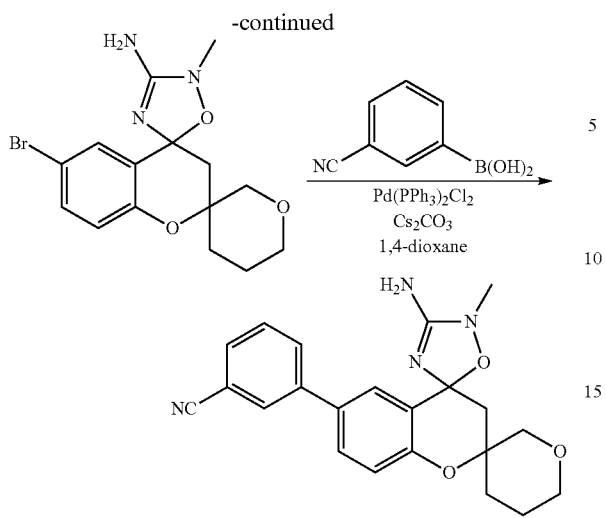

Experimental Data:

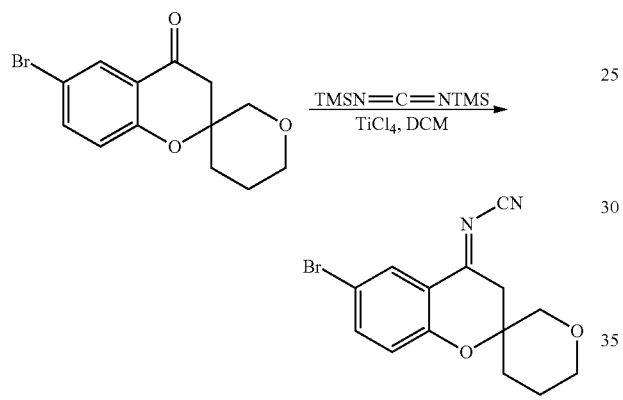

Step 1: (E)-N-(6-bromo-2',4',5',6'-tetrahydrospiro [chroman-2,3'-pyran]-4-ylidene)cyanamide To a solution of 6-bromo-2',4',5',6'-tetrahydrospiro[chroman-2,3'-pyran]-4-one (379 mg, 1.28 mmol) in anhydrous DCM (10 mL) was added TiCl₄ (1 M solution in DCM, 2.6 mL, 2.6 mmol) dropwise within 15 minutes at room temperature. The mixture was stirred another 1 h after the addition. To this mixture was added bis-trimethylsilylcarbodiimide (0.525 g, 0.63 mL, 2.82 mmol) dropwise. The resulting mixture was stirred for another 18 h after the addition. The reaction mixture was poured into ice-water (50 g) and extracted with DCM (3×30 mL). The combined organic phases were dried over anhydrous $Na_2SO_4$, and filtered. The filtrate was concentrated to give (E)-N-(6-bromo-2',4',5',6'-tetrahydrospiro [chroman-2,3'-pyran]-4-ylide-ne)cyanamide (350 mg, 90%), which was used for next step without further purification.

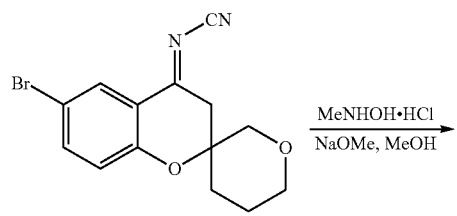

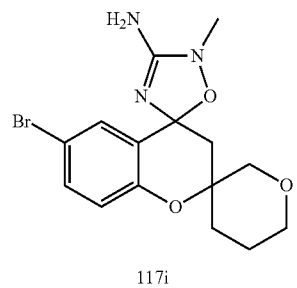

Step 2: Compound 117i

To a solution of methylhydroxylamine HCl salt (62.7 mg, 0.75 mmol) in anhydrous MeOH (8 mL) was added NaOMe (25% in MeOH (Wt. %), 0.15 mL, 0.675 mmol), followed by (E)-N-(6-bromo-2',4',5',6'-tetrahydrospiro[chroman-2,3'-pyran]-4-ylidene)cyanamide (240 mg, 0.75 mmol). After stirring for 10 min, the solvent was removed in vacuo. The residue was redissolved in DCM (10 mL). The mixture was filtered, and the solvent was removed to give the residue, which was purified by column chromatography to give compound 117i (140 mg, 50%).

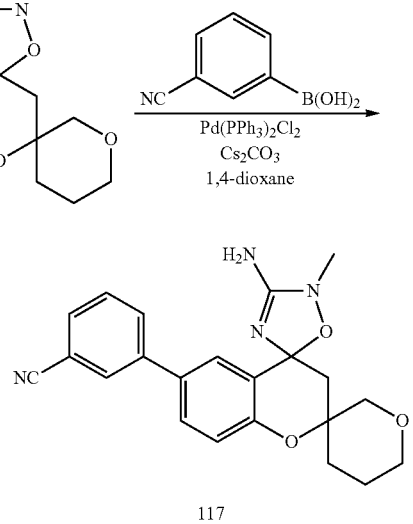

Step 3: Compound 117

A mixture of compound 117i (50 mg, 0.157 mmol), 3-cyanophenylboronic acid (40 mg, 0.266 mmol), $Cs_2CO_3$ (2 M, 0.5 mL) and $Pd(PPh_3)_2Cl_2$ (15 mg) in 1,4-dioxane (3 mL) under Ar was stirred in microwave at 120° C. for 35 minutes. The reaction mixture was concentrated in vacuo to give the residue, which was purified by preparative TLC and HPLC to give compound 2 (15 mg, 20%). ¹H-NMR (MeOD): 1.61 (m, 1H), 1.78 (m, 2H), 2.11 (m, 2H), 2.93 (m, 1H), 3.37 (m, 3H), 3.64 (m, 2H), 3.75 (m, 2H), 7.09 (m, 1H), 7.67 (m, 1H), 7.75 (m, 2H), 7.97 (m, 3H).

Example 97

3-(3''-Imino-2''-methylspiro[spiro(chroman-2,1''-cyclohexane)-4,5'-[1,2,4]oxadiazolidine]-6-yl)benzonitrile (Compound 118)

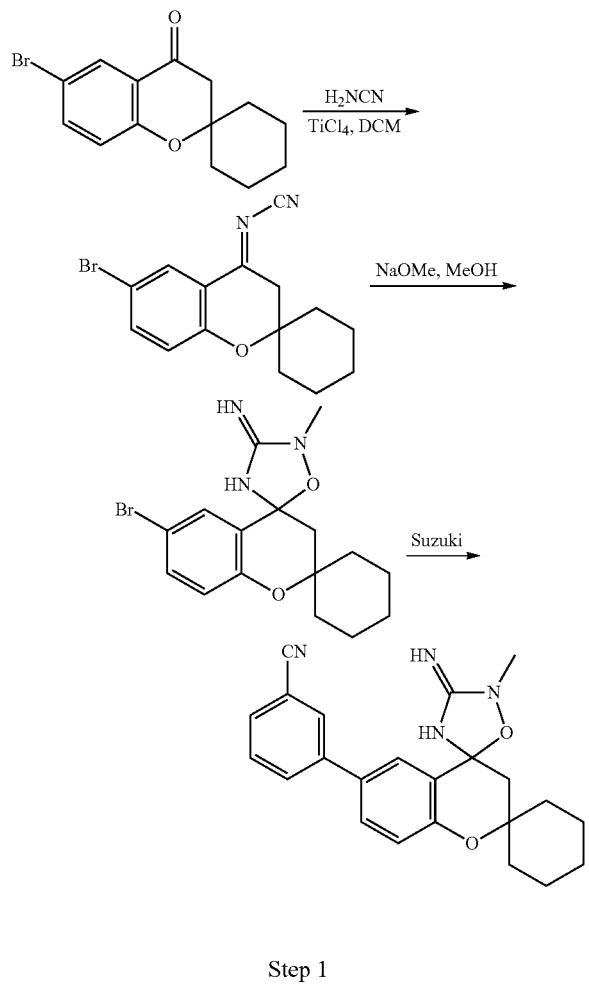

Step 1

To a solution of 6-bromospiro[chroman-2,1'-cyclohexan]-4-one (379 mg, 1.28 mmol) in anhydrous DCM (10 mL) was added TiCl$_4$ (1 M solution in DCM, 2.6 mL, 2.6 mmol) dropwise within 15 min at rt. The mixture was stirred for another 1 h after the addition. To this mixture was added bis-trimethylsilylcarbodiimide (0.525 g, 0.63 mL, 2.82 mmol) dropwise. The resulting mixture was stirred for another 18 h after the addition. The reaction mixture was poured into ice-water (50 g) and extracted with DCM (3×30 mL). The combined organic phases were dried over anhydrous Na$_2$SO$_4$, filtered, and concentrated to give N-(6-bromospiro[chroman-2,1'-cyclohexane]-4-ylidene)cyanamide as a light brown solid (410 mg), which was used in the next step without further purification. MS ESI+ve m/z 319 (M+H)$^+$.

Step 2

To a solution of methylhydroxylamine HCl salt (107 mg, 1.28 mmol) in anhydrous MeOH (15 mL) was added NaOMe (25 w % in MeOH, 0.25 mL, 1.15 mmol), followed by N-(6-bromospiro[chroman-2,1'-cyclohexane]-4-ylidene)cyanamide (410 mg, 1.28 mmol). After stirring for 10 min, the solvent was removed in vacuo. The resulting residue was redissolved in DCM (20 mL). The mixture was filter, and the solvent was removed in vacuo to give 515 mg crude product of 6-bromo-2''-methylspiro[spiro(chroman-2,1'-cyclohexane)-4,5''-[1,2,4]oxadiazolidin]-3''-imine, which is used for next step without further purification. MS ESI+ve m/z 366 (M+H)$^+$.

Step 3

To a solution of 6-bromo-2''-methylspiro[spiro(chroman-2,1'-cyclohexane)-4,5''-[1,2,4]oxadiazolidin]-3''-imine (77 mg, 0.2 mmol), 3-cyanophenylboronic acid (62 mg, 0.34 mmol), and Cs$_2$CO$_3$ (163 mg, 0.5 mmol) in 1,4-dioxane (10 mL) and H$_2$O (0.5 mL) in a 25 mL round-bottom flask equipped with a condenser was added PdCl$_2$(PPh$_3$)$_2$ (20 mg). After degassing by vacuum and purge with N$_2$, the mixture was refluxed for 3 h (a black precipitate comes out at this time). The solvent was removed under reduced pressure and the residue was purified by preparative HPLC to give 3-(3''-imino-2''-methylspiro[spiro(chroman-2,1'-cyclohexane)-4,5''-[1,2,4]oxadiazolidine]-6-yl)benzonitrile (18 mg) as a TFA salt. MS ESI+ve m/z 389 (M+H)$^+$. $^1$H NMR (400 MHz, CD$_3$OD): 8.29-7.02 (m, 12H), 3.38 and 3.34 (s and s, 3H), 2.86 (m, 1H), 2.12-1.40 (m, 11H).

Example 98

Compound 119

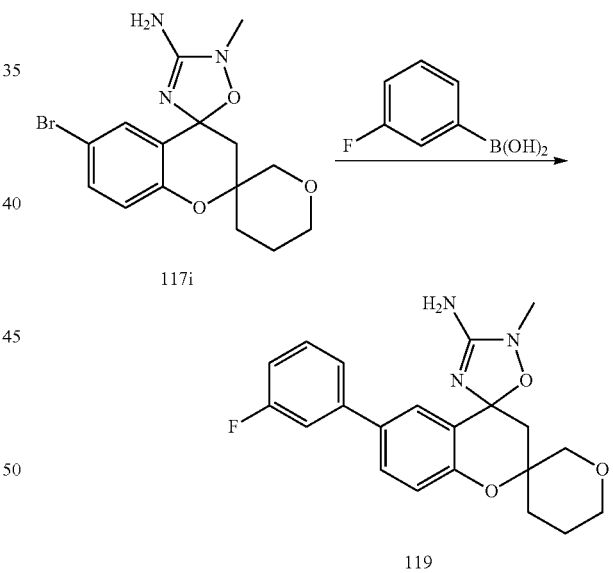

Step 1. Compound 119

Pd(PPh$_3$)$_2$Cl$_2$ (10 mg) in a 10 mL tube under Ar was treated sequentially with compound 117i (50 mg, 0.136 mmol) in 1,4-dioxane (2 mL), Cs$_2$CO$_3$ (2 N, 0.4 mL) and 3-fluorophenylboronic acid (38.4 mg, 0.272 mmol). The mixture was heated under microwave at 120° C. for 30 min. The reaction mixture was concentrated in vacuo to give the residue, which was purified by preparative TLC and then by preparative HPLC to give pure Compound 119 (13 mg, 25%). $^1$H-NMR (MeOD): 1.61 (m, 1H), 1.92 (m, 2H), 2.13 (m, 2H), 2.69 (t, 1H), 3.32 (d, 3H), 3.61 (m, 2H), 3.84 (m, 2H), 7.02 (m, 2H), 7.33 (d, 1H), 7.42 (m, 2H), 7.62 (d, 1H), 7.79 (d, 1H).

Example 99

Compound 120

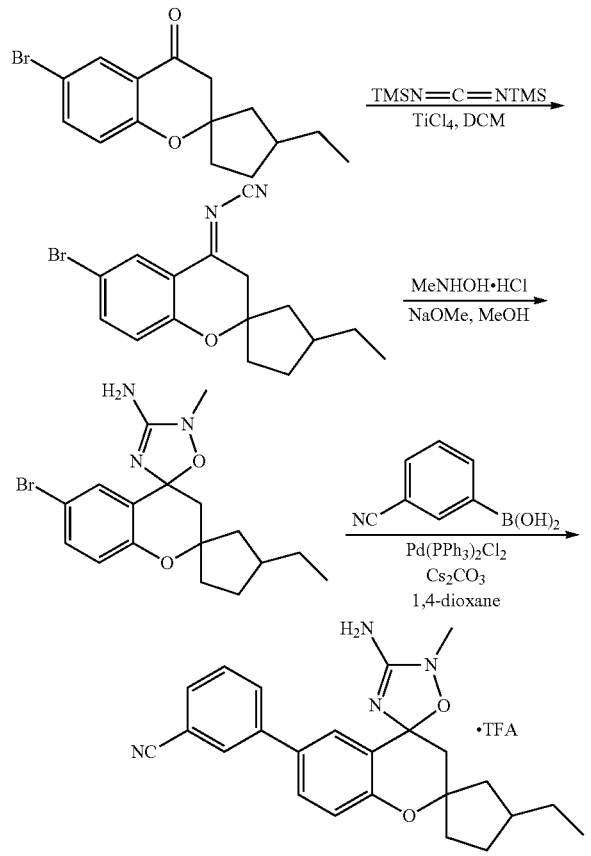

Experimental Data:

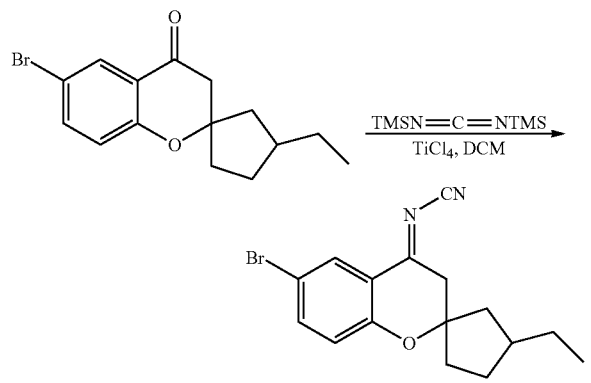

Step 1: (E)-N-(6-bromo-3'-ethylspiro[chroman-2,1'-cyclopentane]-4-ylidene)cyanamide To a solution of 6-bromo-3'-ethylspiro[chroman-2,1'-cyclopentan]-4-one (226 mg, 0.73 mmol) in anhydrous DCM (5.7 mL) was added TiCl₄ (1 M solution in DCM, 1.5 mL, 1.49 mmol) dropwise within 15 min at room temperature. The mixture was stirred another 1 h after the addition. To this mixture was added Bis-trimethylsilylcarbodiimide (300 mg, 0.36 mL, 1.61 mmol) dropwise. The resulting mixture was stirred for another 18 h after the addition. The reaction mixture was poured into ice-water (20 g) and extracted with DCM (3×20 mL). The combined organic phases were dried over anhydrous Na₂SO₄, filtered, and concentrated to give (E)-N-(6-bromo-3'-ethylspiro[chroman-2,1'-cyclopentane]-4-ylidene)cyanamide as light brown solid (225 mg), which was used in the next step without further purification.

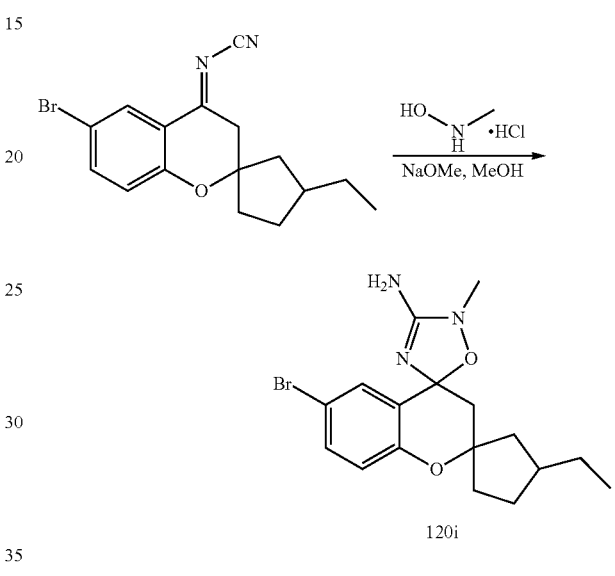

120i

Step 2: Compound 120i

To a solution of methylhydroxylamine HCl salt (60 mg, 0.72 mmol) in anhydrous MeOH (8.5 mL) was added NaOMe (25 w % in MeOH, 0.14 mL, 0.65 mmol), followed by (E)-N-(6-bromo-3'-ethylspiro[chroman-2,1'-cyclopentane]-4-ylidene)cyanamide (225 mg, 0.72 mmol). After stirring for 10 min, the solvent was removed in vacuo. The residue was redissolved in DCM (15 mL). The mixture was filter, and the solvent was removed in vacuo to give the crude product, which was purified by preparative TLC (CH₂Cl₂: MeOH 12:1) to give the pure product 120i (174 mg, 63%). ¹H NMR (CDCl₃): 7.50 (s, 1H), 7.27 (d, 1H), 6.67 (d, 1H), 3.10 (s, s, 3H), 2.42-2.23 (m, 2H), 2.22-2.05 (m, 2H), 2.04-1.92 (m, 2H), 1.90-1.65 (m, 2H), 1.49-1.39 (m, 1H), 1.35-1.22 (m, 2H), 0.92-0.79 (m, 3H).

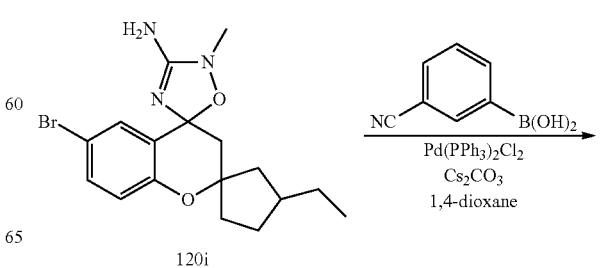

120i

-continued

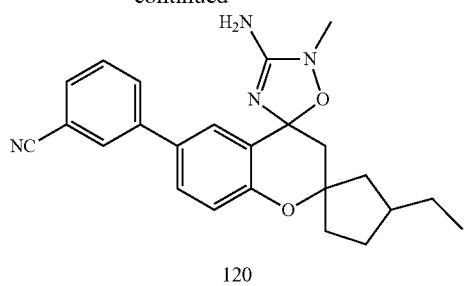

120

Step 3: Compound 120

Pd(PPh$_3$)$_2$Cl$_2$ (18.5 mg) in a 10 mL tube under Ar was treated sequentially with the compound 120i (50 mg, 0.13 mmol) in 1,4-dioxane (4.9 mL), Cs$_2$CO$_3$ (2 N, 0.74 mL) and 3-cyanophenylboronic acid (39 mg, 0.26 mmol). The mixture was heated under microwave at 120° C. for 45 min. The reaction mixture was concentrated in vacuo to give the residue, which was purified by preparative TLC (PE:EA 1:1.5) and then by preparative HPLC to give Compound 120 (2.44 mg, 5%). $^1$H NMR (MeOD/400M): δ 7.99 (s, 1H), 7.95-7.92 (m, 2H), 7.71-7.64 (m, 2H), 7.62-7.60 (m, 1H), 7.00-6.96 (m, 1H), 3.39 (s, s, 3H), 2.78-2.67 (m, 1H), 2.45-2.33 (m, 1H), 2.31-2.19 (m, 1H), 2.18-2.02 (m, 3H), 2.01-1.87 (m, 2H), 1.48-1.31 (m, 3H), 1.01-0.89 (m, 3H).

Example 100

Compound 121

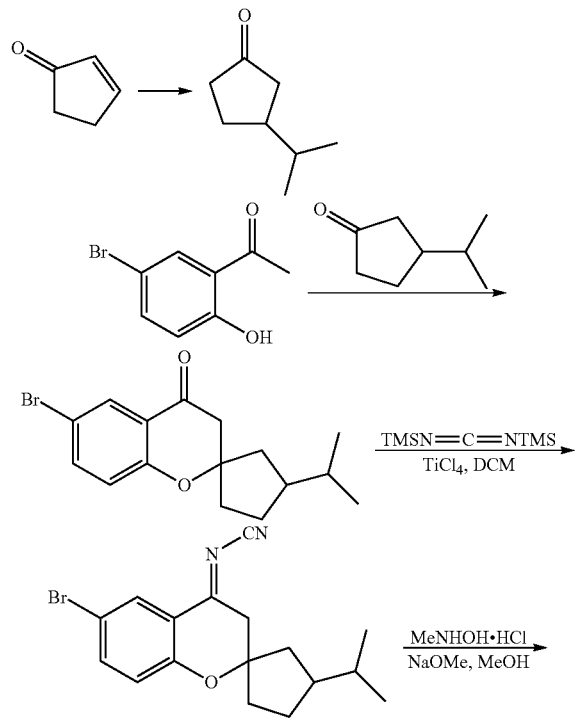

-continued

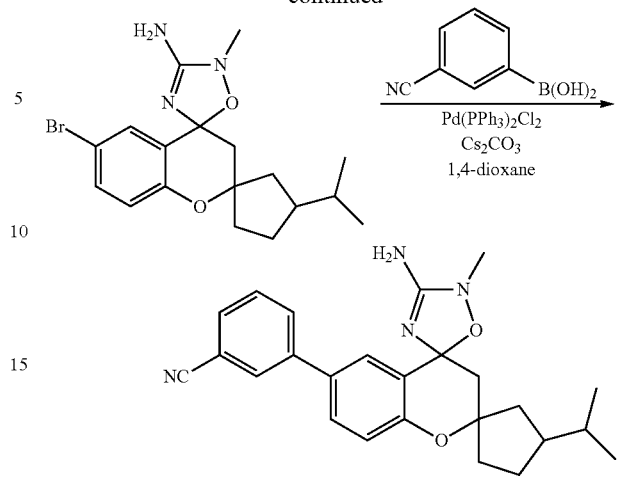

Experimental Data:

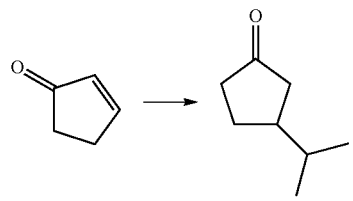

Step 1. 3-isopropylcyclopentanone

To a solution of cyclopent-2-enone (1.5 mL, 18.27 mmol), CuBr—SMe$_2$ (188 mg, 0.91 mmol), chlorotrimethylsilane (4.59 mL, 36.54 mmol) and HMPA (6.55 g, 36.54 mmol) in THF (30 mL) was added isopropylmagnesium bromide (36.54 mL, 1 M in THF) at −70° C. After stirring for 1 h at −70° C., the reaction mixture was quenched with HCl (10%). The mixture was extracted with Et$_2$O. The organic layer was washed with aqueous NaHCO$_3$ and brine. After dried over Na$_2$SO$_4$, the organic layer was concentrated to give 3-isopropylcyclopentanone (4 g, 100%).

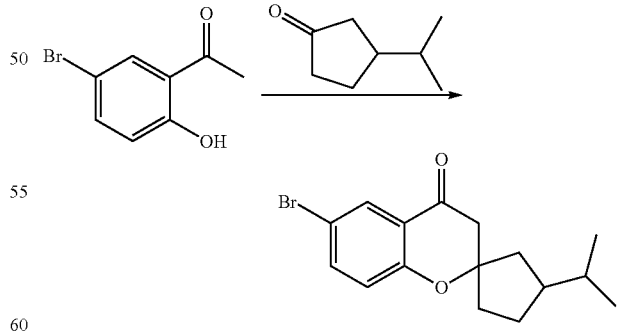

Step 2. 6-bromo-3'-isopropylspiro[chroman-2,1'-cyclopentan]-4-one

A mixture of 3-isopropylcyclopentanone (0.5 g, 3.962 mmol), 1-(5-bromo-2-hydroxyphenyl)ethanone (0.424 g, 1.98 mmol) and pyrrolidine (0.143 g, 1.98 mmol) in MeOH (25 mL) was refluxed overnight. The solvent was removed in vacuo to give crude 6-bromo-3'-isopropylspiro[chroman-2, 1'-cyclopentan]-4-one (500 mg, 79%). ¹H-NMR (CDCl₃): 0.78 (m, 3H), 0.82 (m, 3H), 1.34 (m, 1H), 1.58 (m, 3H), 1.75 (m, 1H), 1.91 (m, 2H), 2.08 (m, 1H0, 2.73 (s, 2H), 6.74 (m, 1H), 7.44 (m, 1H), 7.89 (d, 1H).

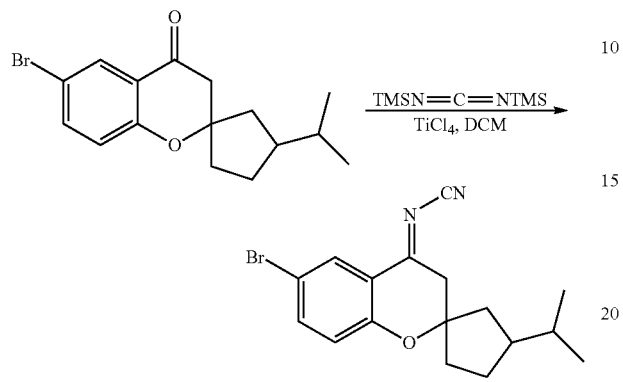

Step 3. N-(6-bromo-3'-isopropylspiro[chroman-2,1'-cyclopentane]-4-ylidene)cyanamide To a solution of 6-bromo-3'-isopropylspiro[chroman-2,1'-cyclopentan]-4-one (250 mg, 0.776 mmol) in DCM (10 mL) was added TiCl₄ (1.55 mL, 1 M in CH₂Cl₂) dropwise within 15 minutes at room temperature. After stirring for 1 h, N,N'-methanediylidenebis(1,1,1-trimethylsilanamine) (0.38 mL, 1.707 mmol) was added dropwise. The mixture was stirred at room temperature overnight and poured into ice-water (25 g). The aqueous layer was extracted with CH₂Cl₂, which was combined with the organic layer. The organic layer was dried and concentrated to give crude N-(6-bromo-3'-isopropylspiro [chroman-2,1'-cyclopentane]-4-ylidene)cyanamide (250 mg, 93%). ¹H-NMR (CDCl₃): 0.82 (m, 6H), 1.36 (m, 2H), 1.69 (m, 3H), 1.96 (m, 3H), 3.10 (d, 2H), 6.75 (m, 1H), 7.52 (m, 1H), 8.04 (d, 1H).

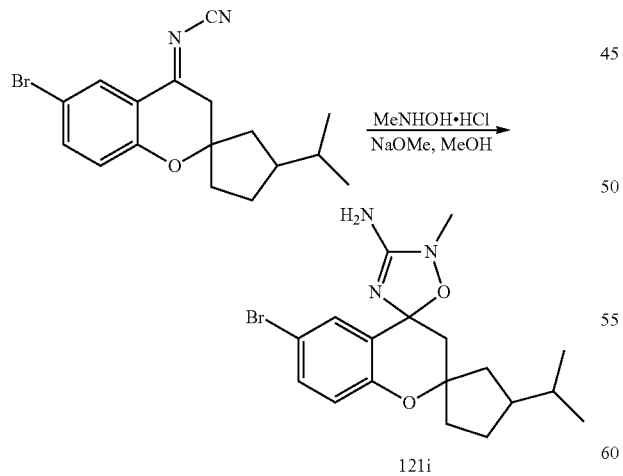

Step 4. Compound 121i

To a solution of N-methyl-hydroxylamine hydrochloride (72 mg, 0.723 mmol) in MeOH (15 mL) was added MeONa (0.154 mL, 25% (Wt.) in MeOH), followed by N-(6-bromo-3'-isopropylspiro[chroman-2,1'-cyclopentane]-4-ylidene) cyanamide (250 mg, 0.723 mmol). After stirred for 10 minutes, the solvent was removed in vacuo. The residue was purified by preparative TLC to give compound 121i (148 mg, 52%). ¹H-NMR (CDCl₃): 0.82 (m, 6H), 1.26 (m, 3H), 1.93 (m, 5H), 2.27 (m, 2H), 3.04 (m, 3H), 6.62 (m, 1H), 7.22 (m, 1H), 7.42 (m, 1H).

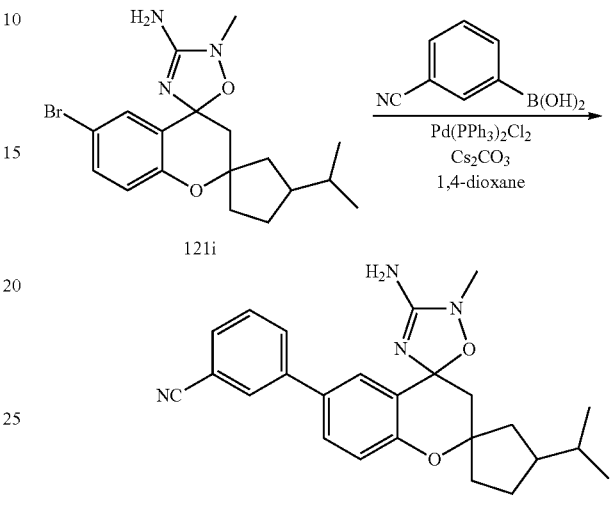

Step 5. Compound 121

Pd(PPh₃)₂Cl₂ (10 mg) in a 10 mL flask under Ar was treated sequentially with compound 121i (50 mg, 0.127 mmol) in 1,4-dioxane (3 mL), Cs₂CO₃ (2 N, 0.16 mL) and 3-cyanophenylboronic acid (33 mg, 0.216 mmol). The mixture was heated at 120° C. under Ar in a microwave reactor for 30 minutes. The reaction mixture was concentrated in vacuo to give the residue, which was purified by preparative TLC and HPLC to give Compound 121 (25.43 mg, 48%). ¹H-NMR (MeOD): 0.91 (m, 6H), 1.42 (m, 2H), 1.53-1.98 (m, 3H), 1.99-2.27 (m, 3H), 2.38 (m, 1H), 2.71 (m, 0.8H), 3.01 (m, 0.3H) 3.38 (m, 3H), 7.02 (m, 1H), 7.67 (m, 3H), 7.96 (m, 2.8H), 8.30 (m, 0.2H).

Example 101

Compound 122

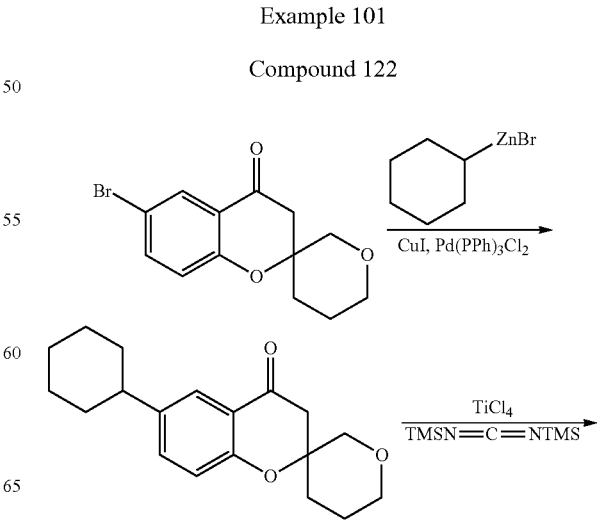

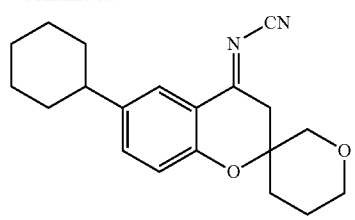

Step 2. (E)-N-(6-cyclohexyl-2',4',5',6'-tetrahydrospiro[chroman-2,3'-pyran]-4-ylidene)cyan-amide To a solution of 6-cyclohexyl-2',4',5',6'-tetrahydrospiro[chroman-2,3'-pyran]-4-one (240 mg, 0.804 mmol) in anhydrous DCM (10 mL) was added TiCl₄ (1 M solution in DCM, 608.6 mg, 3.2 mmol) dropwise within 15 min at room temperature. The mixture was stirred for 1 h after the addition. To this mixture was added Bis-trimethylsilylcarbodiimide (380.6 mg, 3.12 mmol) dropwise. The resulting mixture was stirred for another 18 h after the addition. The reaction mixture was poured into ice-water (100 g) and extracted with DCM (3×50 mL). The combined organic phases were dried over anhydrous Na₂SO₄, filtered, and concentrated to give (E)-N-(6-cyclohexyl-2',4',5',6'-tetrahydrospiro[chroman-2,3'-pyran]-4-ylidene)cyanamide (20 mg, 10%), which was used for next step without further purification.

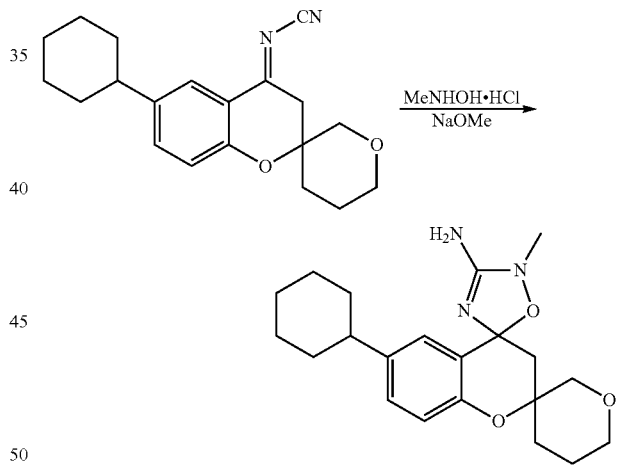

Step 3. Compound 122

To a solution of methylhydroxylamine HCl salt (5.16 mg, 0.06 mmol) in anhydrous MeOH (10 mL) was added NaOMe (25 w % in MeOH, 0.08 mL), followed by (E)-N-(6-cyclohexyl-2',4',5',6'-tetrahydrospiro[chroman-2,3'-pyran]-4-ylidene)cyanamide (20 mg, 0.06 mmol), After stirring for 10 min, the solvent was removed in vacuo. The residue was redissolved in DCM (20 mL), the mixture was filtered and the solvent was removed in vacuo, which was purified by preparative TLC to give Compound 122 (5.24 mg, 30%). ¹H-NMR (MeOD): 1.24 (m, 2H), 1.37 (m, 4H), 1.52 (m, 1H), 1.72 (d, 1.5H), 1.79 (d, 5H), 1.88 (t, 1H), 2.04 (m, 1H), 2.42

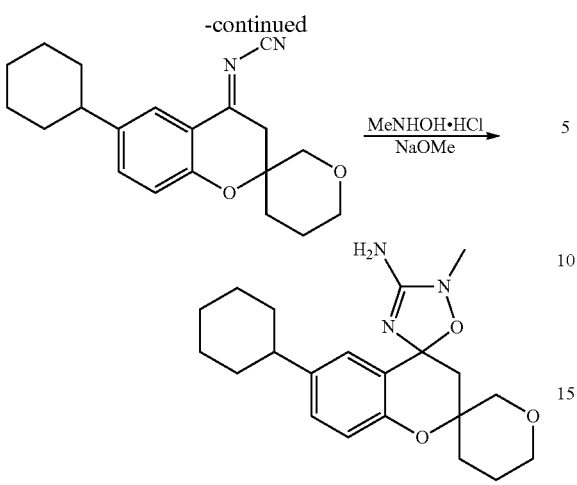

Experimental Data:

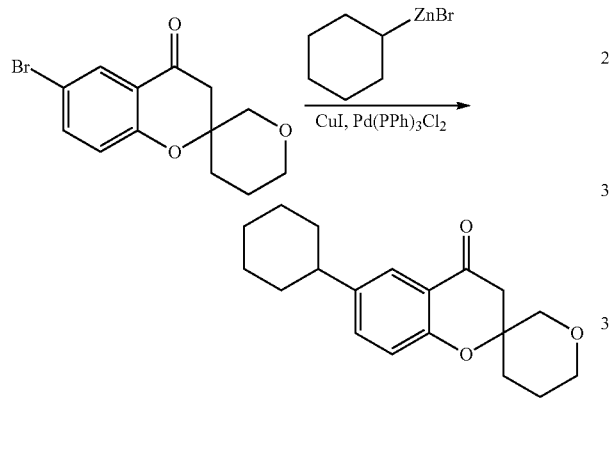

Step 1. 6-cyclohexyl-2',4',5',6'-tetrahydrospiro[chroman-2,3'-pyran]-4-one

Pd(PPh₃)₂Cl₂ (60 mg) in a 40 mL tube under Ar was treated sequentially with 6-bromo-2',4',5',6'-tetrahydrospiro[chroman-2,3'-pyran]-4-one (600 mg, 2.01 mmol) in THF (20 mL*3), CuI (600 mg) and cyclohexylzinc(II) bromide (8.1 mL, 4.02 mmol). The mixture was heated under microwave at 160° C. for 10 min. The reaction mixture was concentrated in vacuo to give the residue, which was purified by column chromatography to give 6-cyclohexyl-2',4',5',6'-tetrahydrospiro[chroman-2,3'-pyran]-4-one (200 mg, 30%). ¹H-NMR (CDCl₃): 1.31 (t, 4H), 1.48 (m, 1H), 1.62 (m, 5H), 1.76 (d, 4H), 1.89 (m, 1H), 2.06 (d, 1H), 2.49 (s, 1H), 2.61 (m, 2H), 3.49 (m, 2H), 3.79 (m, 2H), 6.88 (d, 1H), 7.29 (d, 2H), 7.61 (s, 1H).

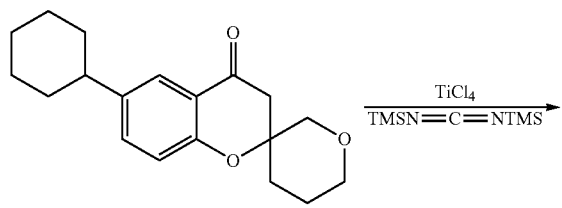

(m, 1H), 3.01 (d, 3H), 3.50 (m, 2H), 3.69 (d, 0.5H), 3.74 (m, 1H), 3.90 (d, 0.5H), 6.71 (d, 1H), 7.04 (d, 1H), 7.19 (d, 1H).

Example 102

Compound 124

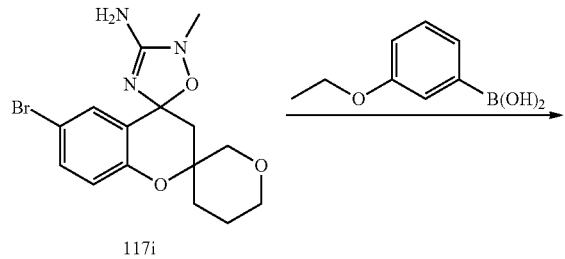

Step 1: Compound 124

Pd(PPh$_3$)$_2$Cl$_2$ (15 mg) in a 10 mL of flask under Ar$_2$ was treated sequentially with the amine 117i (40 mg, 0.13 mmol) in 1,4-dioxane (2.3 mL), Cs$_2$CO$_3$ (2 N, 0.5 mL) and 3-ethoxybenzonitrile (31 mg, 0.19 mmol). The mixture was heated at 120° C. under Ar under microwave for 30 minutes. The reaction mixture was concentrated in vacuo to give the residue, which was purified by preparative TLC and HPLC to give Compound 124 (2.2 mg, 4%). $^1$H-NMR (MeOD): 1.26 (m, 3H), 1.51 (m, 1H), 1.75-2.06 (m, 3H), 2.66-2.92 (m, 1H), 3.22 (m, 3H), 3.32 (m, 1H), 3.52 (m, 2H), 3.69 (m, 2H), 3.98 (m, 2H), 6.77 (m, 1H), 6.91 (m, 1H), 7.02 (m, 2H), 7.22 (m, 1H), 7.38-7.54 (m, 1H), 7.69-8.11 (m, 1H).

Example 103

Compound 125

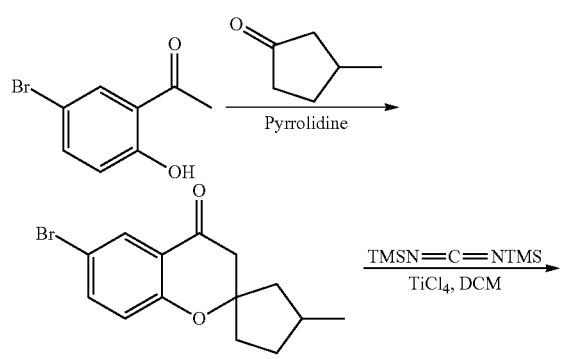

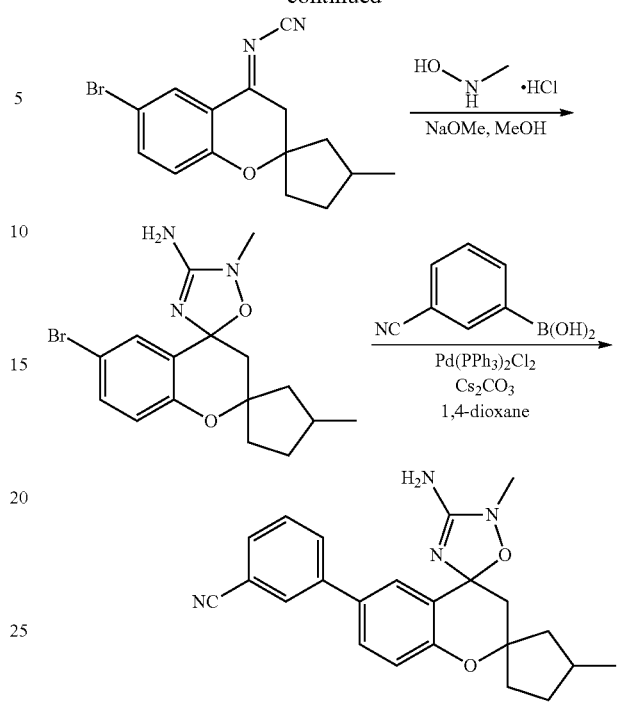

Experimental Data:

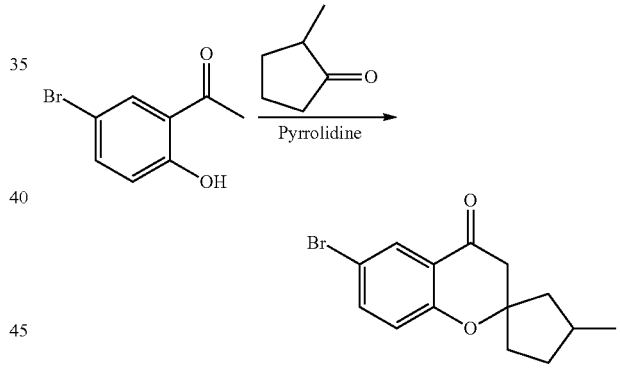

Step 1: 6-bromo-3'-methylspiro[chroman-2,1'-cyclopentan]-4-one

A mixture of 1-(5-bromo-2-hydroxy-phenyl)-ethanone (2.193 g, 10.2 mmol), 3-methylcyclopentanone (2 g, 20.4 mmol) and pyrrolidine (1.67 mL, 19.43 mmol) in MeOH (42 mL) was stirred at room temperature overnight, followed by reflux for 2 days. The mixture was concentrated in vacuo to give the residue, which was added water and HCl (36%) until pH=1. The mixture was extracted with EtOAc and then the organic layer was concentrated to give 6-bromo-3'-methylspiro[chroman-2,1'-cyclopentan]-4-one, which was purified by chromatography (PE:EA 300:1-200:1) (2.3 g, 76%). $^1$H NMR (CDCl$_3$): 7.94 (d, 1H), 7.52-7.49 (m, 1H), 6.83-6.79 (m, 1H), 2.79 (m, 2H), 2.39-2.22 (m, 0.5H), 2.21-1.95 (m, 3H), 1.91-1.75 (m, 1H), 1.67-1.57 (m, 1H), 1.51-1.41 (m, 0.5H), 1.31-1.15 (m, 1H), 1.08-0.98 (m, 3H).

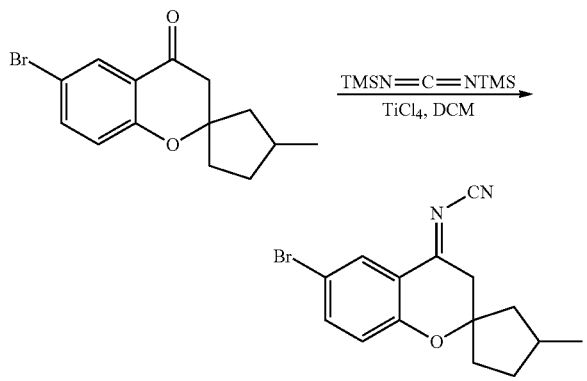

Step 2: (E)-N-(6-bromo-3'-methylspiro[chroman-2,1'-cyclopentane]-4-ylidene)cyanamide To a solution of 6-bromo-3'-methylspiro[chroman-2,1'-cyclopentan]-4-one (216 mg, 0.73 mmol) in anhydrous DCM (5.7 mL) was added TiCl$_4$ (1 M solution in DCM, 1.5 mL, 1.49 mmol) dropwise within 15 min at room temperature. The mixture was stirred for 1 h after the addition. To this mixture was added bis-trimethylsilylcarbodiimide (300 mg, 0.36 mL, 1.61 mmol) dropwise. The resulting mixture was stirred for another 18 h after the addition. The reaction mixture was poured into ice-water (20 g) and extracted with DCM (3×20 mL). The combined organic phases were dried over anhydrous Na$_2$SO$_4$, filtered, and concentrated to give (E)-N-(6-bromo-3'-methylspiro[chroman-2,1'-cyclopentane]-4-ylidene)cyanamide as light brown solid (225 mg), which was used in the next step without further purification.

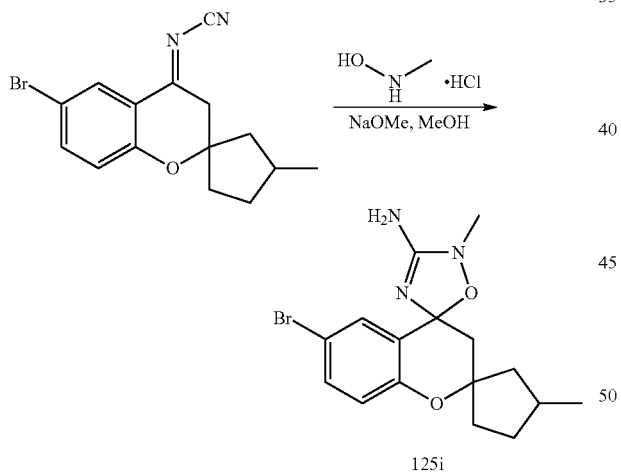

Step 3: Compound 125i

To a solution of methylhydroxylamine HCl salt (59 mg, 0.71 mmol) in anhydrous MeOH (8.3 mL) was added NaOMe (25 w % in MeOH, 0.14 mL, 0.63 mmol), followed by (E)-N-(6-bromo-3'-methylspiro[chroman-2,1'-cyclopentane]-4-ylidene)cyanamide (225 mg, 0.71 mmol). After stirring for 10 min, the solvent was removed in vacuo. The residue was redissolved in DCM (15 mL). The mixture was filtered, and the solvent was removed in vacuo to give the crude product, which was purified by preparative TLC (CH$_2$Cl$_2$: MeOH 12:1) to give the pure product 125I (197 mg, 76%).

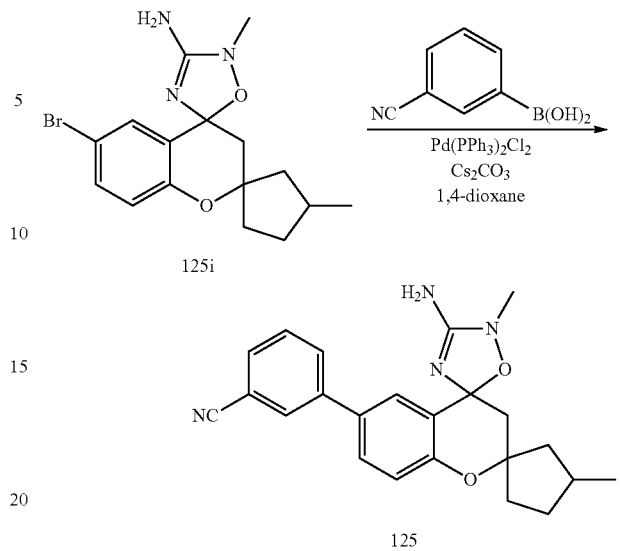

Step 4: Compound 125

Pd(PPh$_3$)$_2$Cl$_2$ (19.2 mg) in a 10 mL tube under Ar was treated sequentially with the compound 125i (50 mg, 0.14 mmol) in 1,4-dioxane (5.1 mL), Cs$_2$CO$_3$ (2 N, 0.76 mL) and 3-cyanophenylboronic acid (40 mg, 0.27 mmol). The mixture was heated under microwave at 120° C. for 45 min. The reaction mixture was concentrated in vacuo to give the residue, which was purified by preparative TLC (PE:EA 1:1.5) to give Compound 125 (2.26 mg, 4%). $^1$H-NMR (MeOD): 7.92 (s, 1H), 7.89-7.87 (m, 1H), 7.75 (s, 1H), 7.66-7.64 (m, 1H), 7.61-7.55 (m, 2H), 7.32-7.24 (m, 1.5H), 6.97-6.88 (m, 1.5H), 3.20 (s, 3H), 2.41-2.31 (m, 2H), 2.12-2.08 (m, 2H), 1.90-1.65 (m, 2H), 1.60-1.40 (m, 2H), 1.14-1.11 (m, 1H), 1.09-1.01 (m, 3H).

Example 104

Compound 126

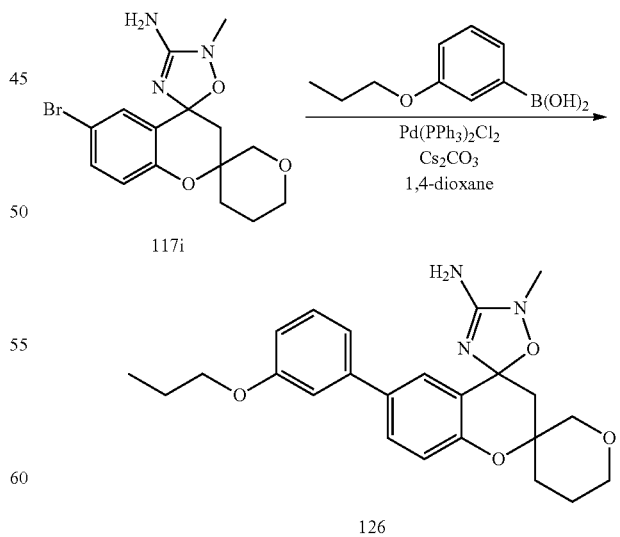

Step 1: Compound 126

Pd(PPh$_3$)$_2$Cl$_2$ (10 mg, 0.01 mmol) in a 10 mL flask under Ar was treated sequentially with the compound 117i (40 mg, 0.088 mmol) in 1,4-dioxane (1 mL), Cs₂CO₃ (2 N, 0.2 mL) and 3-propoxyphenylboronic acid (32 mg, 0.176 mmol). The mixture was heated at 120° C. under Ar under microwave for 30 minutes. The reaction mixture was concentrated in vacuo to give the residue, which was purified by preparative TLC to give Compound 126 (5 mg, 15%). ¹H-NMR (MeOD): 1.06 (m, 3H), 1.53-1.68 (m, 1H), 1.74-1.91 (m, 3H), 1.93-2.13 (m, 2H), 2.79-2.98 (m, 1H), 3.56-3.68 (m, 2H), 3.72-3.89 (m, 2H), 3.97 (t, 2H), 6.88 (d, 1H), 7.01-7.17 (m, 3H), 7.33 (t, 1H), 7.63 (d, 1H), 7.81 (m, 1H).

Example 105

Compound 127a and 127b

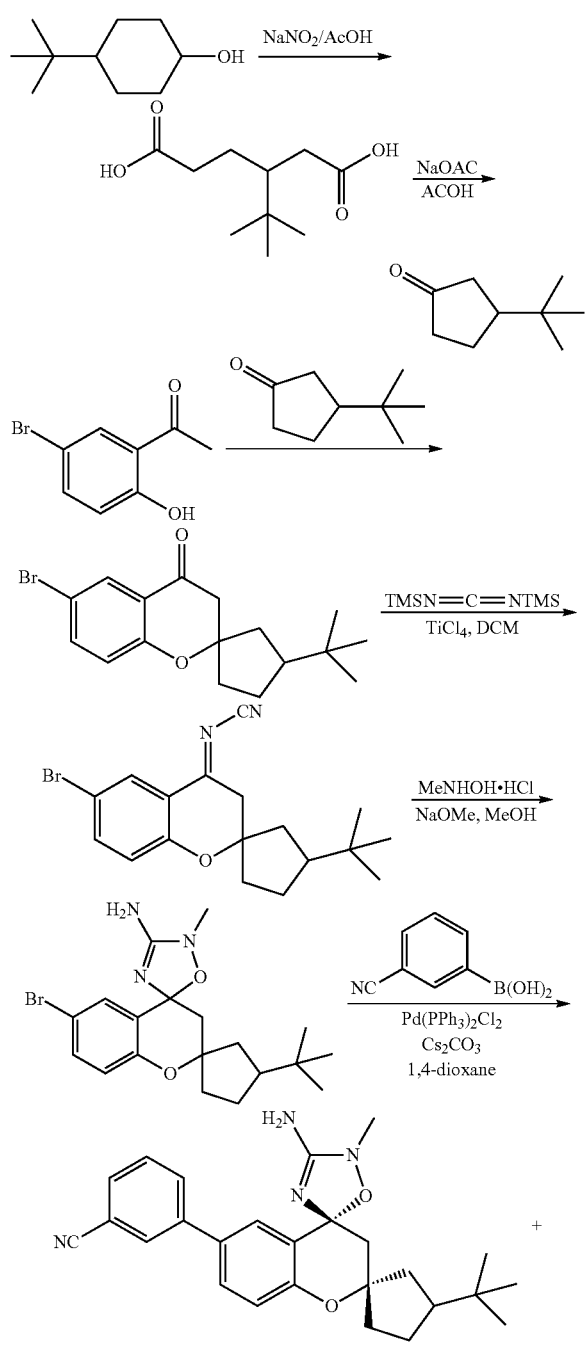

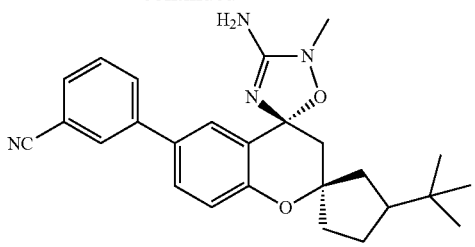

Experimental Data:

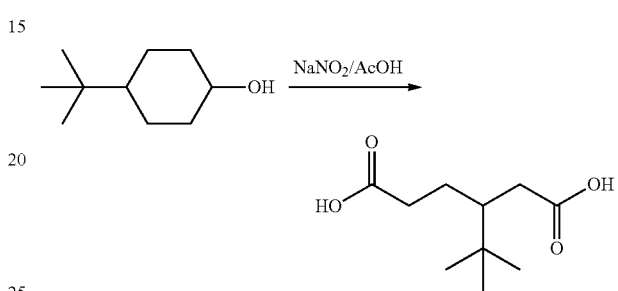

Step 1. 3-tert-butylhexanedioic acid 4-tert-butylcyclohexanol (10 g, 64.1 mmol) was dissolved in trifluoroacetic acid and then NaNO₂ (17.09 g, 256.4 mmol) was added to the solution at 0° C. under an air. After the resulting solution was stirred at room temperature for 5 hours, the solvent was removed in vacuo at room temperature and the residue was added into an aqueous 5% NaHCO₃. After the solution was treated with methylene chloride, the aqueous solution was acidified with 10% HCl solution followed by extraction with ethyl acetate to give 3-tert-butyl-6-hydroxyhexanoic acid (5.26 g, 41%).

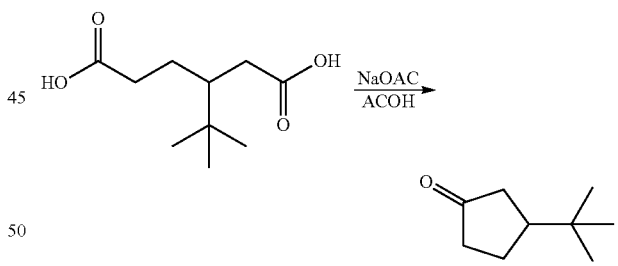

Step 2. 3-tert-butylcyclopentanone

A suspension of the 3-tert-butyl-6-hydroxyhexanoic acid (1 g, 4.95 mmol), anhydrous NaOAc (0.321 g, 3.91 mmol) and acetic anhydride was refluxed for 5 hours during which time the solution mixture turned black. After the reaction mixture was cooled to room temperature, the formed acetic acid and remaining acetic anhydride were removed on a rotary evaporator and then under high vacuum. The residue was then dissolved in ethyl acetate, filtered through a plug of celite to remove the precipitate NaOAc, and concentrated in vacuo to give the crude product of 3-tert-butylcyclopentanone (0.557 g, 58%).

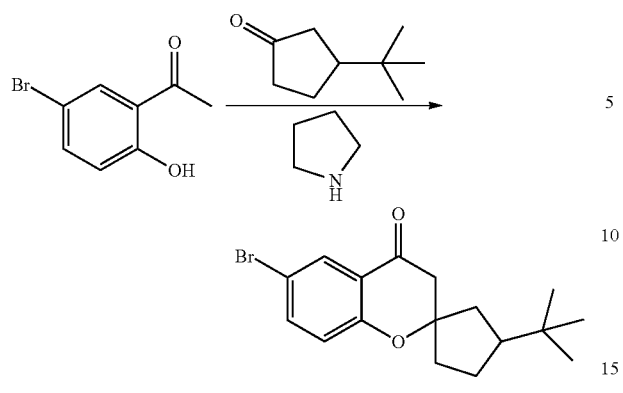

Step 3. 6-bromo-3'-tert-butylspiro[chroman-2,1'-cyclopentan]-4-one

A mixture of 1-(5-bromo-2-hydroxy-phenyl)-ethanone (573 mg, 2.68 mmol), 3-tert-butylcyclopentanone (750 g, 5.36 mol) and pyrrolidine (362 mg, 5.092 mol) in methanol was refluxed overnight. The reaction mixture was removed in vacuo. The residue was diluted with an equal volume of H₂O and then added HCl until pH=1. The mixture was extracted with EtOAc. The organic layer was dried over anhydrous Na₂SO₄, filtered, and evaporated to give 6-bromo-3'-tert-butylspiro[chroman-2,1'-cyclopentan]-4-one (0.8 g, 89%). ¹H NMR (CDCl₃): 0.77 (s, 9H), 1.34 (m, 1H), 1.48 (m, 2H), 1.63 (m, 2H), 1.81 (m, 2H), 2.09 (m, 2H), 2.72 (m, 2H), 6.73 (t, 1H), 7.47 (d, 1H), 7.89 (s, 1H).

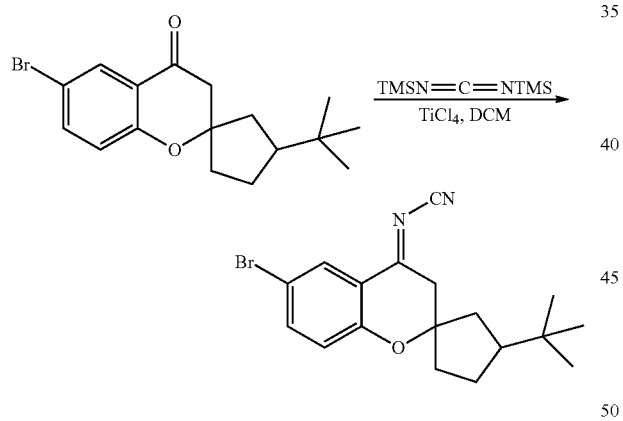

Step 4. (E)-N-(6-bromo-3'-tert-butylspiro[chroman-2,1'-cyclopentane]-4-ylidene)cyanamide To a solution of 6-bromo-3'-tert-butylspiro[chroman-2,1'-cyclopentan]-4-one (200 mg, 0.60 mmol) in dried CH₂Cl₂ (10 mL) was added TiCl₄ (1 M solution in DCM, 1.20 mmol) dropwise within 15 minutes. The mixture was stirred for 1 h after addition. To this mixture was added bis-trimethylsilyl-carbodiimide (244 mg, 1.31 mmol) dropwise. The resulting mixture was stirred for 18 h after addition. The reaction mixture was poured into ice-water (30 g) and extracted with CH₂Cl₂. The combined organic layer was washed with brine, dried over Na₂SO₄, filtered and concentrated to give (E)-N-(6-bromo-3'-tert-butylspiro[chroman-2,1'-cyclopentane]-4-ylidene)cyanamide (200 mg, crude), which was used for the next step without further purification.

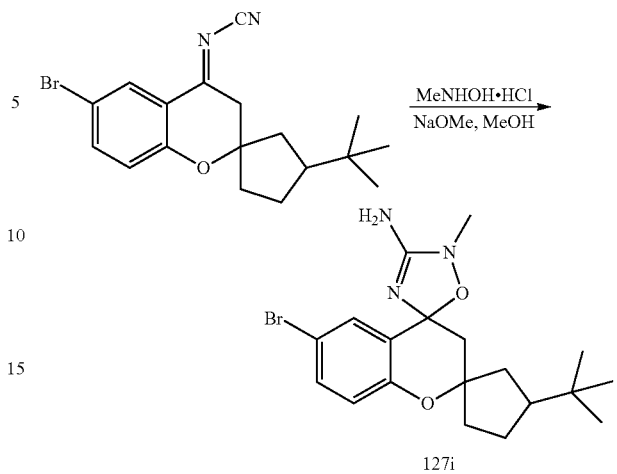

Step 5. Compound 127i

To a solution of MeNHOH.HCl (46.3 mg, 0.55 mmol) in anhydrous MeOH (5 mL) was added NaOMe (25 wt % in MeOH, 0.11 mL, 0.50 mmol), followed by (E)-N-(6-bromo-3'-tert-butylspiro[chroman-2,1'-cyclopentane]-4-ylidene)cyanamide (200 mg, 0.55 mmol). After stirring for 30 minutes, the solvent was removed in vacuo. The residue was redissolved in CH₂Cl₂ and filtered. The filtrate was concentrated to give the residue, which was purified by preparative TLC to afford compound 127i (86 mg, 38%). ¹H NMR (CDCl₃): 1.48-1.61 (m, 1H), 1.73-2.28 (m, 4H), 2.98 (d, 3H), 3.47-3.63 (m, 2H), 3.27 (m, 2H), 3.98 (m, 1H), 6.81-6.93 (m, 4H), 7.02 (m, 2H), 7.24 (m, 2H).

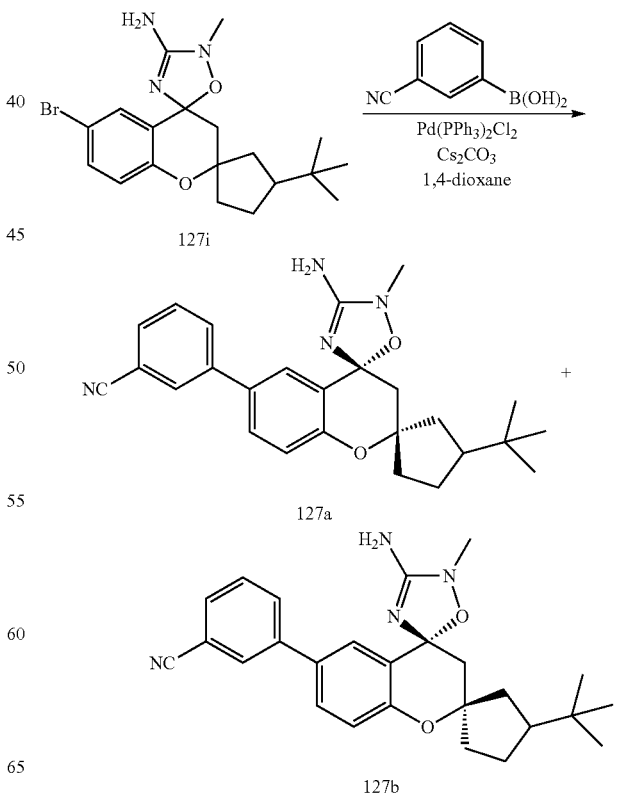

Step 6. Compound 127a and 127b

Pd(PPh$_3$)$_2$Cl$_2$ (5 mg) in a 10 mL flask under Ar was treated sequentially with the compound 127i (42 mg, 0.103 mmol) in 1,4-dioxane (1 mL), Cs$_2$CO$_3$ (2 N, 0.2 mL) and 3-cyanophenylboronic acid (28.1 mg, 0.154 mmol). The mixture was heated at 120° C. under Ar under microwave for 30 minutes. The reaction mixture was concentrated in vacuo to give the residue, which was purified by preparative TLC and preparative HPLC to give Compound 127a (7 mg, 16%) and Compound 127b (11 mg, 25%). $^1$H NMR (MeOD): 0.84-0.96 (m, 9H), 1.52-1.64 (m, 1H), 1.77 (m, 1H), 1.96 (m, 2H), 2.03-2.14 (m, 2H), 2.38 (t, 1H), 2.76 (d, 1H), 3.39 (s, 3H), 6.98 (m, 1H), 7.58-7.73 (m, 3H), 7.99 (m, 3H) (127a). $^1$H NMR (MeOD): 0.88-0.97 (m, 9H), 1.36 (m, 1H), 1.56-2.07 (m, 6H), 2.43 (m, 1H), 2.73 (m, 1H), 3.41 (s, 3H), 7.01 (m, 1H), 7.59-7.74 (m, 3H), 7.93-8.31 (m, 3H) (127b).

Example 106

Compound 128

Step 1: 1-chloro-3-methoxypropane

3-Methoxypropan-1-ol (23.85 g, 0.294 mmol) was dissolved in pyridine (20.6 mL) and cooled to 5° C. SOCl$_2$ (28.4 mL) was added dropwise under stirring. After the addition was completed, the reaction mixture was refluxed for 3 h and poured onto crashed ice in concentrated HCl (20 mL). The organic layer was separated and dried over K$_2$CO$_3$ and filtered. The filtrate was concentrated to give the residue, which was purified by fractional distillation to give 1-chloro-3-methoxypropane (13 g, 41%). $^1$H-NMR (CDCl$_3$): 1.99 (m, 2H), 3.33 (s, 3H), 3.49 (t, 2H), 3.62 (t, 2H).

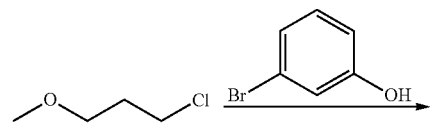

Experimental Data:

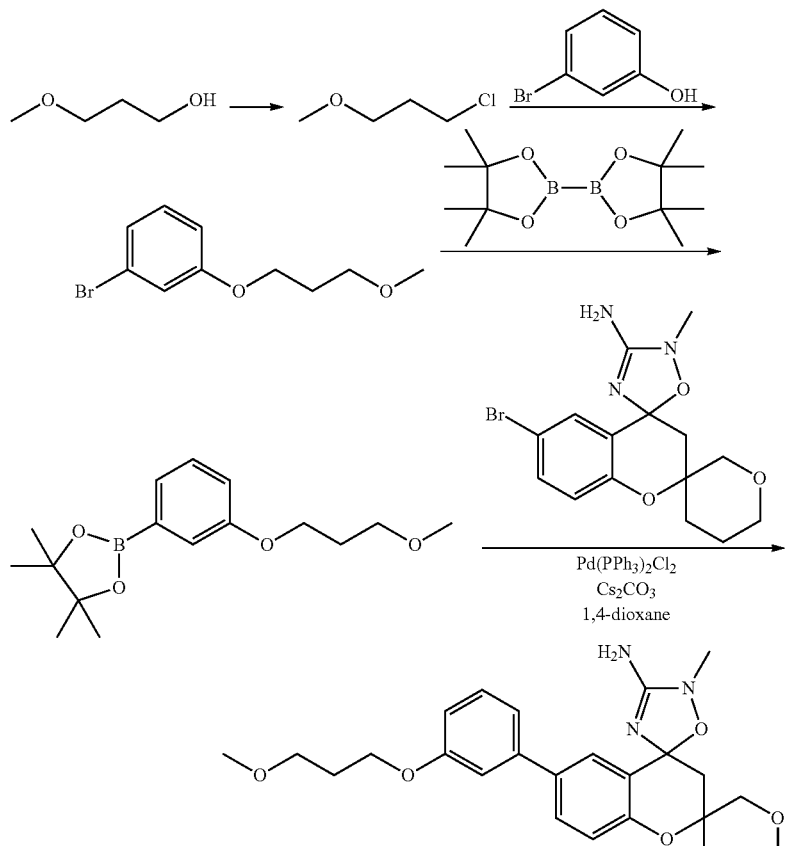

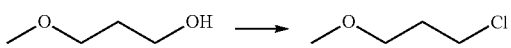

-continued

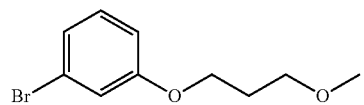

Step 2: 1-bromo-3-(3-methoxypropoxy)benzene

A mixture of 3-bromophenol (5 g, 29 mmol), 1-chloro-3-methoxypropane (4.33 g, 40 mmol) and K₂CO₃ (8 g, 57.8 mmol) in DMF (90 mL) was stirred at 100° C. for 2 h. the reaction mixture was filtered and the filtrate was evaporated in vacuo. The residue was taken up in t-BuME, and the organic layer was washed with aqueous NaOH (1N), water (50 mL) and brine. The organic layer was dried and concentrated to give 1-bromo-3-(3-methoxypropoxy)benzene (7 g, 99%). ¹H-NMR (CDCl₃): 2.02 (m, 2H), 3.33 (s, 3H), 3.54 (m, 2H), 4.02 (m, 2H), 6.82 (m, 1H), 7.11 (m, 3H).

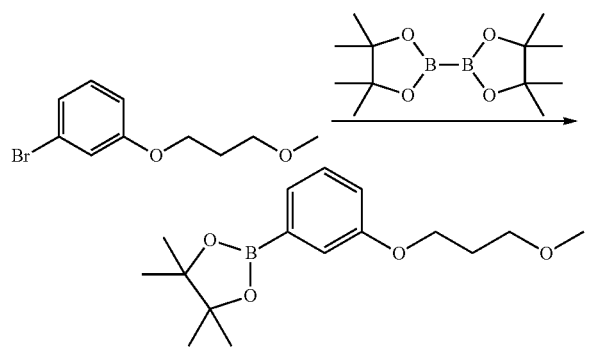

Step 3: 2-(3-(3-methoxypropoxy)phenyl)-4,4,5,5-tetramethyl-1,3,2-dioxaborolane 1-Bromo-3-(3-methoxypropoxy)benzene (1 g, 4.61 mmol), 4,4,4',4',5,5,5',5'-octamethyl-2,2'-bi(1,3,2-dioxaborolane) (2.27 g, 5.07 mmol), K₂CO₃ (2.55 g, 18.44 mmol) and Pd(PPh₃)₂Cl₂ (250 mg, 0.277 mmol) in 1,4-dioxane (40 mL) was refluxed under Ar for 12 h. The reaction mixture was cooled to room temperature, diluted with EtOAc, washed with brine, dried and concentrated to give the residue, which was purified by preparative TLC to give 2-(3-(3-methoxypropoxy)phenyl)-4,4,5,5-tetramethyl-1,3,2-dioxaborolane (65 mg, 6%).

Step 4: Compound 128

Pd(PPh₃)₂Cl₂ (12 mg) in a 10 mL of flask under Ar was treated sequentially with the amine 117i (40 mg, 0.13 mmol) in 1,4-dioxane (1.5 mL), Cs₂CO₃ (2 M, 0.5 mL) and 2-(3-(3-methoxypropoxy)phenyl)-4,4,5,5-tetramethyl-1,3,2-dioxaborolane (50 mg, 0.19 mmol). The mixture was heated under Ar at 120° C. under microwave for 30 minutes. The reaction mixture was concentrated in vacuo to give the residue, which was purified by preparative TLC and HPLC to give Compound 128 (1.47 mg, 3%). ¹H-NMR (MeOD): 1.52 (m, 1H), 1.75 (m, 2H), 1.98 (m, 5H), 2.71-2.98 (m, 2H), 3.37 (m, 6H), 3.55 (m, 4H), 3.76 (m, 2H), 4.01 (m, 2H), 6.81 (m, 1H), 6.92 (m, 1H), 7.02 (m, 2H), 7.24 (m, 1H), 7.58 (m, 1H), 7.76 (m, 1H).

Example 107

Compound 129

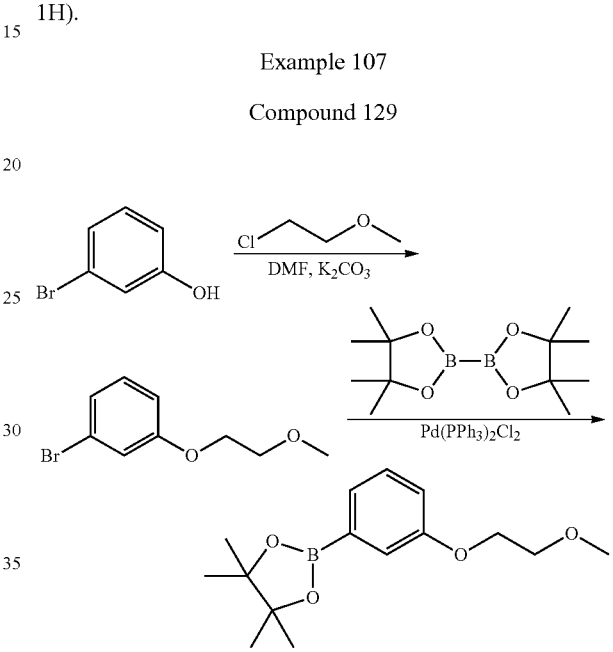

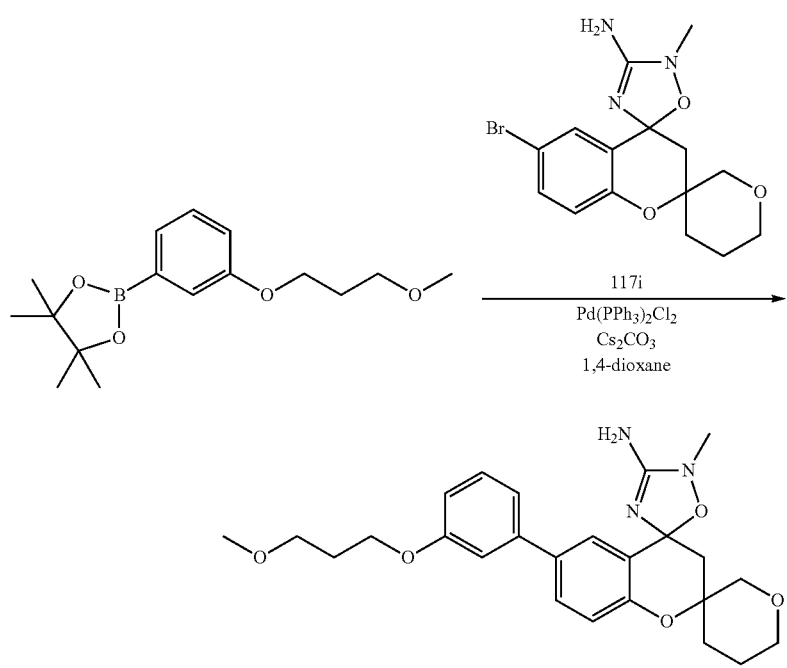

128

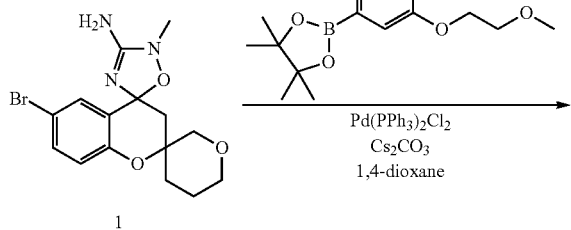

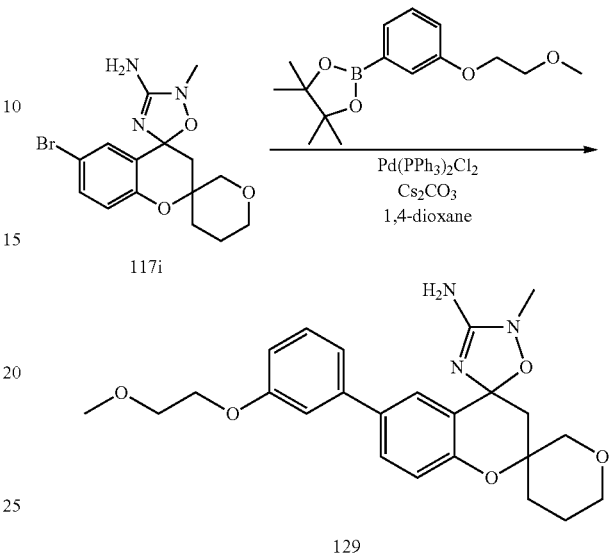

Experimental Data:

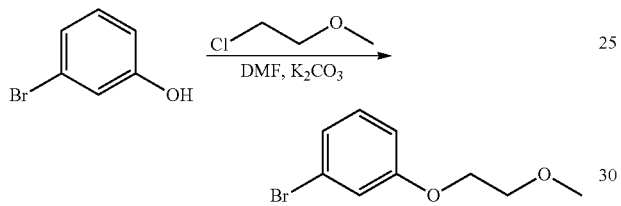

Step 1: 1-bromo-3-(2-methoxyethoxy)benzene

A mixture of 3-bromophenol (5 g, 28.9 mmol), 1-chloro-2-methoxyethane (3.77 g, 40 mmol) and $K_2CO_3$ (12.63 g, 0.178 mol) in DMF (90 mL) was stirred at 100° C. for 4.5 hours. The reaction mixture was filtered and the filtrate was concentrated in vacuo. The residue is taken up in 100 ml of tert-butyl methyl ether, and the organic phase was washed once each with 50 ml of 1 N NaOH, 50 ml of water and 50 ml of brine. The organic layer was dried with sodium sulphate, filtered and concentrated to give 1-bromo-3-(2-methoxyethoxy)benzene (5.28 g, 79%).

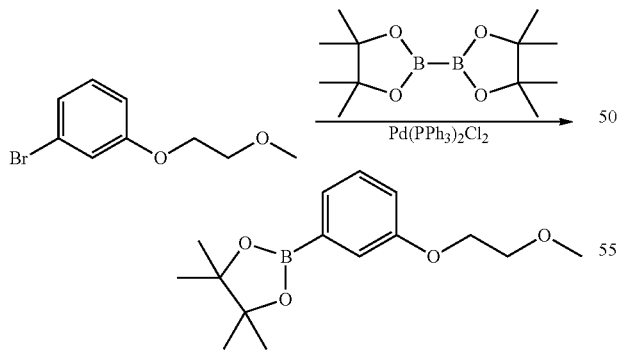

Step 2: 2-(3-(2-methoxyethoxy)phenyl)-4,4,5,5-tetramethyl-1,3,2-dioxaborolane 1-Bromo-3-(2-methoxyethoxy)benzene (2 g, 12.6 mmol), $K_2CO_3$ (6.96 g, 50 mmol) and $Pd(PPh_3)_2Cl_2$ (0.687 g, 0.756 mmol) were dissolved in 1,4-dioxane (90 ml). The mixture was refluxed for 12 hours. The reaction mixture was cooled to room temperature, diluted with ethyl acetate, washed with brine, dried over $Na_2SO_4$ and concentrated in vacuo. The residue was purified by preparative TLC to give 24342-methoxyethoxy)phenyl)-4,4,5,5-tetramethyl-1,3,2-dioxaborolane (900 mg, 26%).

Step 3: Compound 129

$Pd(PPh_3)_2Cl_2$ (8 mg) in a 10 mL tube under Ar was treated sequentially with compound 117i (50 mg, 0.139 mmol) in 1,4-dioxane (2.5 mL), $Cs_2CO_3$ (2 N, 0.4 mL) and 2-(3-(2-methoxyethoxy)phenyl)-4,4,5,5-tetramethyl-1,3,2-dioxaborolane (66 mg, 0.236 mmol). The mixture was heated under microwave at 120° C. for 30 minutes. The reaction mixture was concentrated in vacuo to give the residue, which was purified by preparative TLC and then by preparative HPLC to give pure product of Compound 129 (4.43 mg, 7%). $^1$H-NMR (MeOD): 1.60 (s, 1H), 1.91 (m, 2H), 2.12 (m, 2H), 2.85 (m, 1H), 3.0 (m, 0.5H), 3.07 (m, 3H), 3.35 (s, 3H), 3.45 (s, 3H), 3.65 (m, 2H), 3.8 (m, 4H), 4.2 (s, 2H), 6.95 (s, 1H), 7.05 (t, 1H), 7.2 (m, 2H), 7.35 (m, 1H), 7.65 (d, 1H), 7.8-7.9 (m, 1H), 8.25 (s, 0.2H)

Example 108

Compound 130

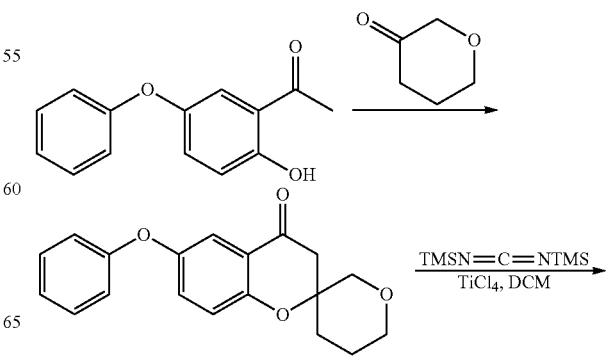

527

-continued

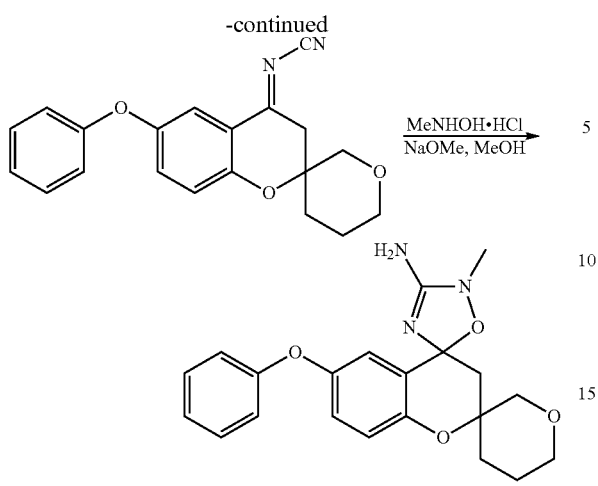

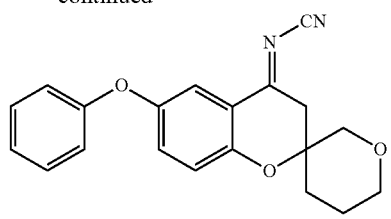

Experimental Data:

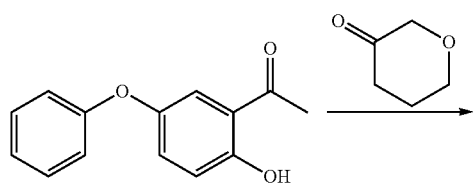

Step 1: 6-phenoxy-2',4',5',6'-tetrahydrospiro[chroman-2,3'-pyran]-4-one

To a solution of 1-(2-hydroxy-5-phenoxyphenyl)ethanone (2.0 g, 8.77 mmol) in toluene (30 mL) was added dihydro-2H-pyran-3(4H)-one (1.14 g, 11.40 mmol) and pyrrolidine (0.81 g, 11.40 mmol), and the reaction mixture was refluxed overnight. After cooling, the mixture was concentrated. The residue was washed with 1 N HCl, brine, dried and concentrated to give the crude product, which was purified by chromatography to afford 6-phenoxy-2',4',5',6'-tetrahydrospiro[chroman-2,3'-pyran]-4-one (1.40 g, 52%). $^1$H-NMR (CDCl$_3$): 0.79 (m, 1H), 1.52 (m, 2H), 1.67 (m, 1H), 1.92 (m, 1H), 2.08 (m, 1H), 2.57-2.61 (q, 2H), 3.51 (m, 2H), 3.88 (m, 2H), 6.89 (d, 2H), 7.03 (m, 2H), 7.18 (m, 1H), 7.26 (t, 2H), 7.39 (m, 1H).

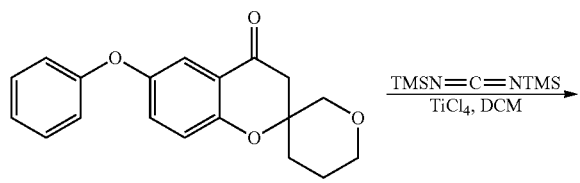

528

-continued

Step 2: (E)-N-(6-phenoxy-2',4',5',6'-tetrahydrospiro[chroman-2,3'-pyran]-4-ylidene)cyan amide To a solution of 6-phenoxy-2',4',5',6'-tetrahydrospiro[chroman-2,3'-pyran]-4-one (500 mg, 1.27 mmol) and triethylamine (227 mg, 0.73 mmol) in dried CH$_2$Cl$_2$ (10 mL) was added TiCl$_4$ (1 M solution in DCM, 1.47 mmol) dropwise within 15 minutes. The mixture was stirred for 1 h after addition. To this mixture was added bis-trimethylsilylcarbodiimide (300 mg, 1.16 mmol) dropwise. The resulting mixture was stirred for 18 h after addition. The reaction mixture was poured into ice-water (50 g) and extracted with CH$_2$Cl$_2$. The combined organic layer was washed with brine, dried over Na$_2$SO$_4$, filtered and concentrated to give (E)-N-(6-phenoxy-2',4',5',6'-tetrahydrospiro[chroman-2,3'-pyran]-4-ylidene)cyan amide (100 mg, crude), which was used for the next step without further purification.

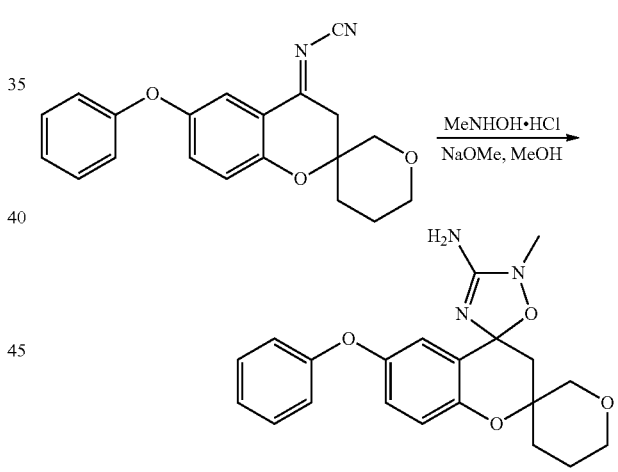

Step 3: Compound 130

To a solution of MeNHOH.HCl (25 mg, 0.30 mmol) in anhydrous MeOH (5 mL) was added NaOMe (25 w % in MeOH, 0.06 mL, 0.27 mmol), followed by (E)-N-(6-phenoxy-2',4',5',6'-tetrahydrospiro[chroman-2,3'-pyran]-4-ylidene)cyanamide (100 mg, 0.30 mmol). After stirring for 30 minutes, the solvent was removed in vacuo. The residue was redissolved in CH$_2$Cl$_2$ and filtered. The filtrate was concentrated to give the residue, which was purified by preparative TLC to afford Compound 130 (29 mg, 25%). $^1$H-NMR (CDCl$_3$): 1.48-1.61 (m, 1H), 1.73-2.28 (m, 4H), 2.98 (d, 3H), 3.47-3.63 (m, 2H), 3.27 (m, 2H), 3.98 (m, 1H), 6.81-6.93 (m, 4H), 7.02 (m, 2H), 7.24 (m, 2H).

Example 109

3-(3'-amino-2'-methyl-2-phenyl-2'H-spiro[chroman-4,5'-[1,2,4]oxadiazole]-6-yl)benzonitrile (Compound 96)

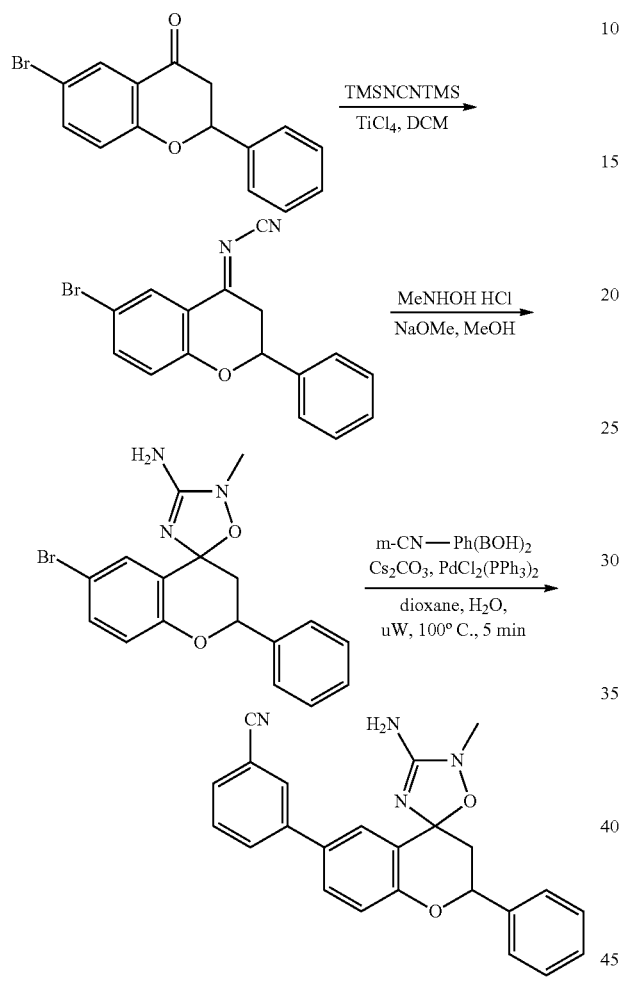

Step 1: Preparation of (E)-N-(6-bromo-2-phenyl-chroman-4-ylidene)cyanamide

To a solution of 6-bromo-2-phenylchroman-4-one (1.016 g, 3.35 mmol) in anhydrous DCM under $N_2$ atmosphere was added 1 M $TiCl_4$ (in DCM, 6.7 mL, 6.7 mmol) dropwise within 15 min at room temperature. The mixture was stirred for 1 h after the addition. To this mixture was added bis-trimethylsilylcarbodiimide (1.374 g, 7.37 mmol) dropwise. The resulting mixture was stirred for another 24 h after the addition. The reaction mixture was poured into ice-water (100 g), stirred for a while and filtered through a pad of Celite. The filtrate was extracted with DCM (3×30 mL). The combined organic phases were dried over anhydrous $Na_2SO_4$, filtered, and concentrated to give (E)-N-(6-bromo-2-phenyl-chroman-4-ylidene)cyanamide as light brown solid (899 mg), which was used in the next step without further purification. MS ESI+ve m/z 327 (M+H)$^+$.

Step 2: Preparation of 6-bromo-2'-methyl-2-phenyl-2'H-spiro[chroman-4,5'-[1,2,4]oxadiazol]-3'-amine To a solution of methylhydroxylamine HCl salt (280 mg, 3.35 mmol) in anhydrous MeOH (15 mL) was added NaOMe (25 w % in MeOH, 0.67 mL, 3.02 mmol), followed by (E)-N-(6-bromo-2-phenylchroman-4-ylidene)cyanamide (899 mg, 2.75 mmol) solution in MeOH (20 mL), After stirring for 10 min, the solvent was removed in vacuo. The residue was redissolved in DCM (20 mL), filtered, and the solvent was removed in vacuo to give 825 mg crude product of 6-bromo-2'-methyl-2-phenyl-2'H-spiro[chroman-4,5'-[1,2,4]oxadiazol]-3'-amine as a yellow solid. 270 mg of the crude product was purified on preparative HPLC to give pure title compound as a TFA salt. MS ESI+ve m/z 374 (M+H)$^+$.

Step 3: Preparation of 3-(3'-amino-2'-methyl-2-phenyl-2'H-spiro[chroman-4,5'-[1,2,4]oxadiazole]-6-yl)benzonitrile To a solution of 6-bromo-2'-methyl-2-phenylspiro[chroman-4,5'-[1,2,4]oxadiazolidin]-3'-imine TFA salt (45 mg, 0.092 mmol), 3-cyanophenylboronic acid (20 mg, 0.14 mmol) and $Cs_2CO_3$ (60 mg, 0.18 mmol) in 1,4-dioxane (3 mL) and $H_2O$ (0.5 mL) in a 10 mL CEM microwave test tube was added $PdCl_2(PPh_3)_2$ (10 mg). After degassing by purging with $N_2$, the mixture was heated to 100° C. for 5 min in a CEM microwave reactor. The solvent was removed under reduced pressure and the residue was purified by preparative HPLC to give 3-(3'-amino-2'-methyl-2-phenyl-2'H-spiro[chroman-4,5'-[1,2,4]oxadiazole]-6-yl)benzonitrile (10 mg) as a TFA salt. MS ESI+ve m/z 397 (M+H)$^+$. $^1$H-NMR (400 MHz, DMSO-$d_6$): 8.14-8.12 (m, 2H), 8.03 (d, J=8.4 Hz, 1H), 7.84-7.79 (m, 2H), 7.66 (t, J=8.0 Hz, 1H), 7.54-7.40 (m, 5H), 7.09 (d, J=8.8 Hz, 1H), 5.29 (d, 11.6 Hz, 1H), 3.34 (s, 3H), 2.75 (d, 14.0 Hz, 1H), 2.37 (dd, J=14.4, 13.2 Hz, 1H).

Example 110

2'-methyl-2-phenyl-6-(pyridin-3-yl)-2'H-spiro[chroman-4,5'-[1,2,4]oxadiazol]-3'-amine (Compound 102)

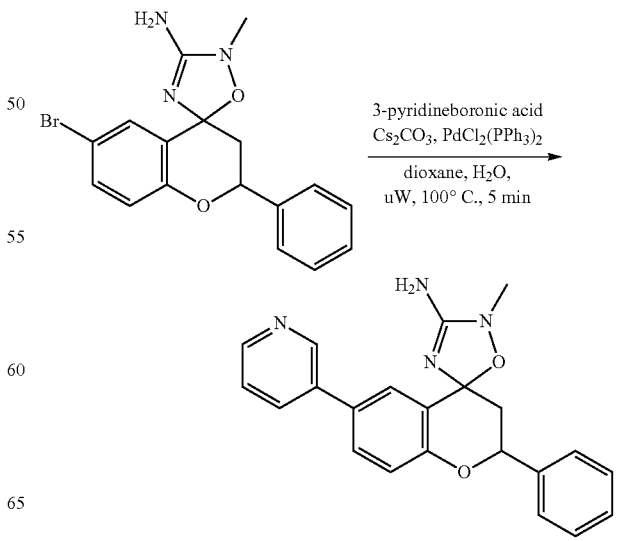

To a solution of 6-bromo-2'-methyl-2-phenyl-2'H-spiro[chroman-4,5'-[1,2,4]oxadiazol]-3'-amine TFA salt (65 mg, 0.13 mmol), 3-pyridineboronic acid (64 mg, 0.52 mmol) and $Cs_2CO_3$ (127 mg, 0.39 mmol) in 1,4-dioxane (3 mL) and $H_2O$ (0.5 mL) in a 10 mL CEM microwave test tube was added $PdCl_2(PPh_3)_2$ (10 mg). After degassing by purging with $N_2$, the mixture was heated to 100° C. for 5 min in a CEM microwave reactor.

The solvent was removed under reduced pressure and the residue was purified by preparative HPLC to give 2'-methyl-2-phenyl-6-(pyridin-3-yl)-2'H-spiro[chroman-4,5'-[1,2,4]oxadiazol]-3'-amine (17 mg) as a TFA salt. MS ESI+ve m/z 393 (M+H)$^+$. $^1$H-NMR (400 MHz, CD$_3$OD): 9.19 (br s, 1H), 8.87 (d, J=7.6 Hz, 1H), 8.78 (br s, 1H), 8.23 (d, J=2.4 Hz, 1H), 8.11 (t, J=6.4 Hz, 1H), 7.91 (dd, J=8.8, 2.4 Hz, 1H), 7.54-7.38 (m, 5H), 7.21 (d, J=8.8 Hz, 1H), 5.37 (d, 12.8 Hz, 1H), 3.43 (s, 3H), 2.88 (dd, J=14.4, 2.0 Hz, 1H), 2.42 (dd, J=14.4, 12.8 Hz, 1H).

Example 111

3-(2,2-bis(hydroxymethyl)-3'-imino-2'-methylspiro[chroman-4,5'-[1,2,4]oxadiazolidine]-6-yl)benzonitrile (Compound 100) and 3-(3''-imino-2''-methylspiro[spiro(chroman-2,1'-(4,4-dimethyl-3,5-dioxane))-4,5''-[1,2,4]oxadiazolidine]-6-yl)benzonitrile (Compound 123)

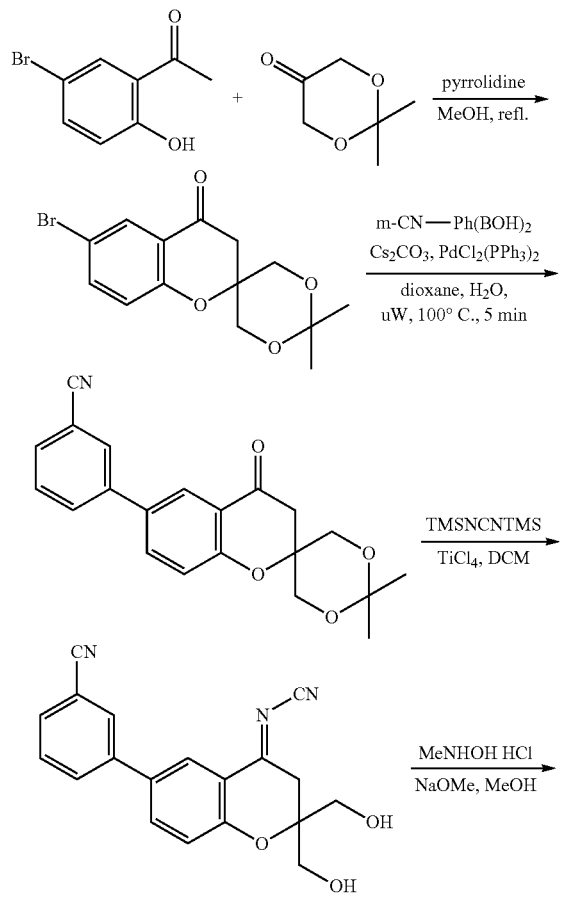

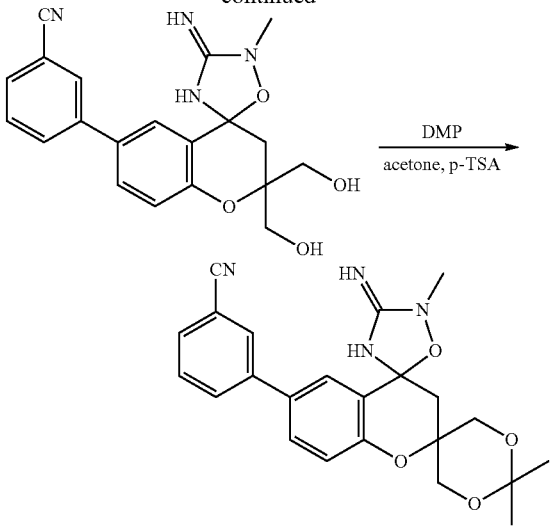

Step 1: Preparation of 6-bromo-2',2'-dimethylspiro[chroman-2,5'-[1,3]dioxan]-4-one A solution of 2,2-dimethyl-1,3-dioxan-5-one (2.290 g, 17.62 mmol), 5'-bromo-2-hydroxy-acetophone (3.576 g, 17.62 mmol) in MeOH containing pyrrolidine (1 mL) was refluxed for 2 h. The solvent was removed under reduced pressure, and the residue was dissolved in ethyl acetate, and washed with 1 M NaOH, 1 M HCl, $H_2O$ and brine successively, dried, and filtered. The filtrate was concentrated to dryness. The crude product was further purified by flash chromatography on silica gel (40 g, eluted with ethyl acetate in hexane 0-25%) give 6-bromo-2',2'-dimethylspiro[chroman-2,5'-[1,3]dioxan]-4-one as a brownish solid (2.06 g).

Step 2: Preparation of 3-(2',2'-dimethyl-4-oxospiro[chroman-2,5'-[1,3]dioxane]-6-yl)benzonitrile To a solution of 6-bromo-2',2'-dimethylspiro[chroman-2,5'-[1,3]dioxan]-4-one (498 mg, 1.5 mmol), 3-cyanophenylboronic acid (440 mg, 3.0 mmol) and $Cs_2CO_3$ (1.460 mg, 4.5 mmol) in 1,4-dioxane (4 mL) and $H_2O$ (0.5 mL) in a 10 mL CEM microwave test tube was added $PdCl_2(PPh_3)_2$ (75 mg). After degassed by purging with $N_2$, the mixture was heated to 100° C. for 5 min in a CEM microwave reactor. The solvent was removed under reduced pressure and the residue was purified by flash chromatography on silica gel (12 g, eluted with ethyl acetate in hexane 0-30%) give 3-(2',2'-dimethyl-4-oxospiro[chroman-2,5'-[1,3]dioxane]-6-yl)benzonitrile as a yellowish solid (298 mg). MS ESI+ve m/z 350 (M+H)$^+$.

Step 3: Preparation of (E)-N-(6-(3-cyanophenyl)-2,2-bis(hydroxymethyl)chroman-4-ylidene)cyanamide To a solution of 3-(2',2'-dimethyl-4-oxospiro[chroman-2,5'-[1,3]dioxane]-6-yl)benzonitrile (155 mg, 0.44 mmol) in anhydrous DCM (10 mL) under $N_2$ atmosphere was added 1 M $TiCl_4$ (in DCM, 0.88 mL, 0.88 mmol) dropwise within 15 min at room temperature. The mixture was stirred for 1 h after the addition. To this mixture was added bis-trimethylsilylcarbodiimide (181 mg, 217 μL 0.97 mmol) dropwise. The resulting mixture was stirred for another 20 h after the addition. The reaction mixture was poured into ice-water (25 g), stirred for 30 min and filtered through a pad of Celite. The separated aqueous phase of the filtrate was extracted with DCM once. The combined organic phases were dried over anhydrous Na₂SO₄, filtered, and concentrated to give yellowish gel like solid (E)-N-(6-(3-cyanophenyl)-2,2-bis(hydroxymethyl) chroman-4-ylidene)cyanamide (160 mg), which was used in the next step without further purification. MS ESI+ve m/z 374 (M+H)⁺.

Step 4: Preparation of 3-(2,2-bis(hydroxymethyl)-3'-imino-2'-methylspiro[chroman-4,5'-[1,2,4]oxadiazolidine]-6-yl)benzonitrile (Compound 100)

To a solution of methylhydroxylamine HCl salt (36.7 mg, 0.44 mmol) in anhydrous MeOH (5 mL) was added NaOMe (25 w % in MeOH, 90 µL, 0.39 mmol), followed by a solution of (E)-N-(6-(3-cyanophenyl)-2,2-bis(hydroxymethyl)chroman-4-ylidene)cyanamide (147 mg, 0.44 mmol) solution in MeOH (2 mL) after 5 min. After stirring for 10 min, the solvent was removed in vacuo. The residue was redissolved in DCM (20 mL), filtered, and the solvent was removed in vacuo to give crude product, which was purified by preparative HPLC to afford 43 mg of 3-(2,2-bis(hydroxymethyl)-3'-imino-2'-methylspiro[chroman-4,5'-[1,2,4]oxadiazolidine]-6-yl)benzonitrile TFA salt as a white solid. MS ESI+ve m/z 381 (M+H)⁺. ¹H NMR (400 MHz, CD₃OD): 7.98-7.90 (m, 3H), 7.72-7.58 (m, 3H), 7.07 (d, J=8.4 Hz, 1H), 3.86-3.70 (m, 4H), 3.67 (s, 3H), 2.84 (d, J=14.8 Hz, 1H), 2.43 (d, J=14.8 Hz, 1H).

Step 5: Preparation of 3-(3"-imino-2"-methylspiro [spiro(chroman-2,1'-(4,4-dimethyl-3,5-dioxane))-4, 5"-[1,2,4]oxadiazolidine]-6-yl)benzonitrile (Compound 123)

To a solution of 3-(2,2-bis(hydroxymethyl)-3'-imino-2'-methylspiro[chroman-4,5'-[1,2,4]oxadiazolidine]-6-yl)benzonitrile TFA salt (16 mg, 0.03 mmol) in 2,2-dimethoxypropane (2.5 mL) and acetone (0.5 mL) was added catalytic amount of anhydrous p-TSA. The reaction was monitored by HPLC, very low conversion was found at 2 h. Excess of p-TSA (>1 eq.) was added and stirred for another 20 min. The reaction mixture turned cloudy. HPLC showed only a little starting material left. TEA (0.5 mL) was added and the reaction mixture was stirred for another 5 min and concentrated to dryness. The residue was purified by preparative HPLC to afford 3-(3"-imino-2"-methylspiro[spiro(chroman-2,1'-(4,4-dimethyl-3,5-dioxane))-4,5"-[1,2,4]oxadiazolidine]-6-yl) benzonitrile TFA salt (8 mg). MS ESI+ve m/z 421 (M+H)⁺. ¹H NMR (400 MHz, CD₃OD): 7.90 (d, J=1.2 Hz, 1H), 7.87 (m, 1H), 7.66 (m, 2H), 7.61-7.56 (m, 2H), 7.03 (d, J=8.4 Hz, 1H), 4.12-3.85 (m, 4H), 3.09 (s, 3H), 2.42 (d, J=14.4 Hz, 1H), 2.01-1.43 (m, 1H), 1.47 (s, 3H), 1.43 (s, 3H).

Example 112

3-(2'-amino-1',2,2-trimethyl-5'-oxo-1',5'-dihydrospiro[chroman-4,4'-imidazole]-6-yl)benzonitrile (Compound 132)

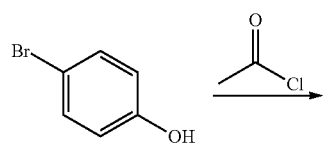

Step 1

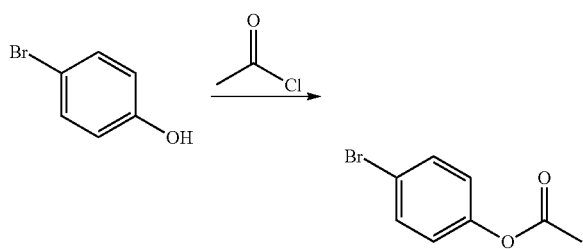

Anhydrous aluminum chloride (84 g, 0.486 mol) is suspended in methylene chloride (1200 mL), and then acetyl chloride (49.2 g, 0.629 mol) is added while stirring and cooling on ice. The mixture is stirred for 20 minutes while cooling on ice and 4-bromophenol (98 g, 0.57 mol) is added. The reaction mixture is stirred at room temperature for 1 h, and then ice water is added and extraction is performed with ethyl acetate. The organic layer is washed with brine and then dried over anhydrous sodium sulfate. After distilling off the solvent under reduced pressure, the residue is purified by silica gel column chromatography to yield acetic acid 4-bromo-phenyl ester (104 g, 85%). $^1$H-NMR (CDCl$_3$): 2.28 (s, 3H), 6.98 (d, 2H), 7.48 (d, 2H).

Step 2

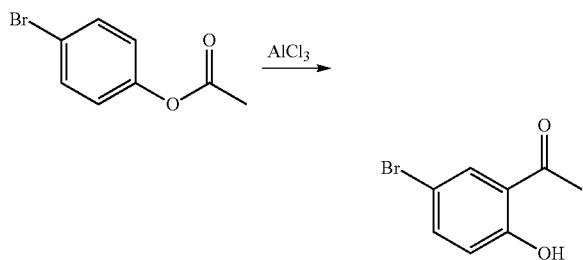

A mixture of 4-bromophenyl acetate (104 g, 0.484 mol) and anhydrous aluminum chloride (130.5 g, 0.968 mol) is stirred at 120-140° C. for 20 minutes. The reaction mixture is cooled to 60-80° C., ice water is added and extraction is performed with ethyl acetate. The organic layer is washed with brine and dried over anhydrous sodium sulfate. After distilling off the solvent under reduced pressure, the residue is purified by silica gel column chromatography to yield the 1-(5-bromo-2-hydroxy-phenyl)-ethanone (101 g, 98%).
$^1$H-NMR (CDCl$_3$): 2.60 (s, 3H), 6.87 (d, 1H), 7.53 (dd, 1H), 7.81 (s, 1H), 12.12 (s, 1H).

Step 3

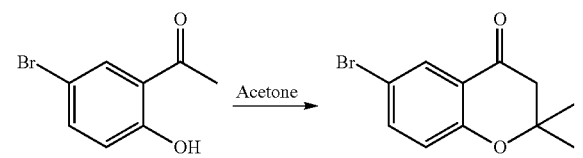

A solution of 1-(5-bromo-2-hydroxy-phenyl)-ethanone (21.4 g, 0.1 mol), acetone (365 mL) and pyrrolidine (8.4 mL) in toluene (220 mL) is refluxed for 4 h. To the reaction mixture is added acetone (36.5 mL), the mixture is refluxed for 15 h. Then 1 N HCl (220 mL) is added, extracted with ethyl acetate (200 mL 3×). The combined organic layers were washed with water (150 mL), brine (150 mL), dried over anhydrous Na$_2$SO$_4$, filtered, and evaporated to give 6-bromo-2,2-dimethyl-chroman-4-one (18 g, 71%).
$^1$H-NMR (CDCl$_3$): 1.45 (s, 6H), 2.71 (s, 2H), 6.82 (d, 1H), 7.52 (dd, 1H), 7.96 (d, 1H).

Step 4

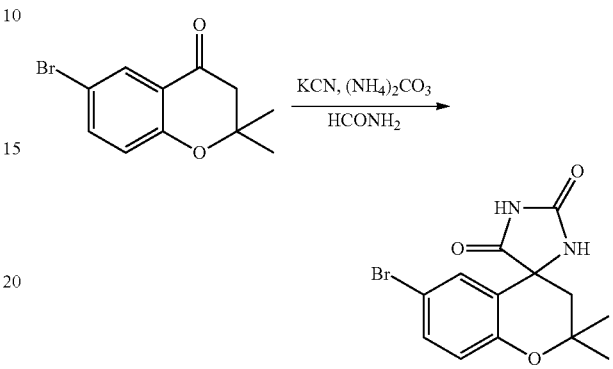

A glass pressure tube is charged with a mixture of 6-bromo-2,2-dimethyl-chroman-4-one (6.4 g, 25 mmol), KCN (3.25 g, 50 mmol), and (NH$_4$)$_2$CO$_3$ (18 g, 187.5 mmol). Formamide (80 mL) is added to fill the pressure tube nearly completely. The mixture is heated at 70° C. for 24 h then at 110° C. for another 48 h. The reaction mixture is then cooled and poured over ice. Acidification with concentrated HCl yields a precipitate which is filtered, washed twice with water, and then resolved in ethyl acetate, dried over Na$_2$SO$_4$, and filtered. The filtrate is concentrated in vacuo to give a residue, which is purified by column to give 6-bromo-2,2-dimethyl-spiro[chroman-4,4'-imidazolidine]-2',5'-dione (8.2 g, 100%).
$^1$H-NMR (DMSO): 1.24 (s, 3H), 1.40 (s, 3H), 2.16 (d, 1H), 2.30 (d, 1H), 6.80 (d, 1H), 7.10 (m, 1H), 7.39 (d, 1H), 8.69 (s, 1H), 11.08 (brs, 1H).

Step 5

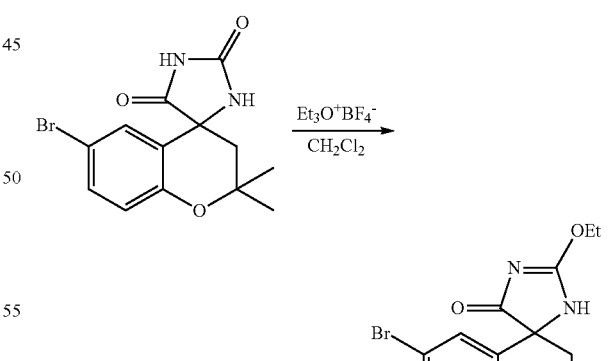

6-Bromo-2,2-dimethylspiro[chroman-4,4'-imidazolidine]-2',5'-dione (4 g, 12.3 mmol) and 1 M Et$_3$O.BF$_4$ (4.7 g, 24.7 mmol) is dissolved in dry CH$_2$Cl$_2$ (100 mL). Then the mixture is heated to reflux for 24 h. The solvent is removed in vacuo to give a residue, which is purified by column to give 6-bromo-2'-ethoxy-2,2-dimethylspiro[chroman-4,4'-imidazol]-5'(37-1)-one (1 g, 25%).

Step 6

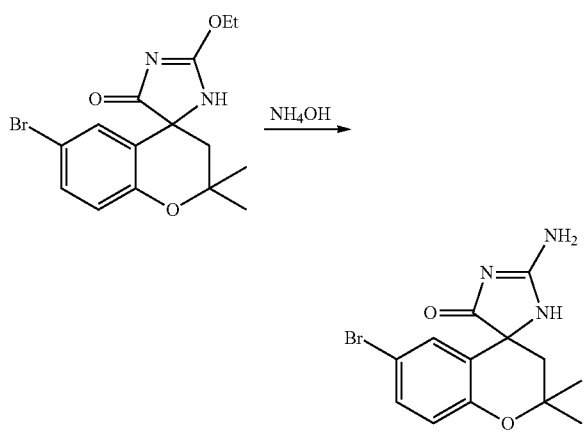

6-Bromo-2'-ethoxy-2,2-dimethylspiro[chroman-4,4'-imidazol]-5'(3'H)-one (500 mg, 1.42 mmol) is dissolved in 30 mL of EtOH, and NH$_3$·H$_2$O (30 mL) is added. The mixture is heated to reflux for 18 h. The mixture is removed in vacuo to give a residue, which is purified by preparative TLC to give 2'-amino-6-bromo-2,2-dimethylspiro-[chroman-4,4'-imidazol]-5'(3'H)-one (120 mg, 30%).

Step 7


NaH (5.3 mg, 0.131 mmol) is added to a solution of 2'-amino-6-bromo-2,2-dimethyl-spiro[chroman-4,4'-imidazol]-5'(3'H)-one (45 mg, 0.131 mmol) in THF (3 mL) at 0° C. under N$_2$. The mixture is stirred for 1 h at room temperature. Then MeI (18.6 mg, 0.131 mmol) is added. The mixture is quenched with water and extracted with ethyl acetate. The organic layer is concentrated in vacuo. The residue is purified by preparative TLC to give 2'-amino-6-bromo-1',2,2-trimethylspiro[chroman-4,4'-imidazol]-5'(1'H)-one (40 mg, 80%).

$^1$H-NMR (MeOD): 1.3 (s, 3H), 1.40 (s, 3H), 1.85 (d, 1H), 2.25 (d, 1H), 3.1 (s, 3H), 6.65 (d, 1H), 6.8 (s, 1H), 7.20 (s, 1H).

Step 8

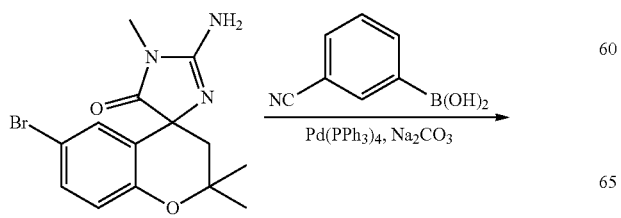

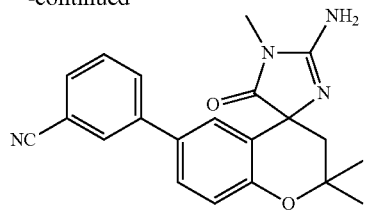

Pd(PPh$_3$)$_4$ (15.13 mg, 0.013 mmol) is added to the solution of 2'-amino-6-bromo-1',2,2-trimethylspiro[chroman-4,4'-imidazol]-5'(1'H)-one (44.15 mg, 0.13 mmol) and 3-cyanophenylboronic acid (19.25 mg, 0.13 mmol) in dimethylbenzene (5 mL) and an aqueous solution of Na$_2$CO$_3$ (2 M, 0.24 mL). The mixture is heated at 90° C. in an oil bath overnight. The mixture is concentrated to give the crude product, which is purified by preparative TLC to give the desired product 3-(2'-amino-1',2,2-trimethyl-5'-oxo-1',5'-dihydrospiro[chroman-4,4'-imidazole]-6-yl)benzonitrile (10 mg, 15%).

$^1$H-NMR (MeOD): 2.1 (s, 6H), 3.30 (s, 3H), 4.0 (s, 2H), 7.7 (t, 2H), 7.9 (d, 2H), 8.1 (d, 2H), 8.3 (s, 1H).

Example 113

2'-amino-1'-methyl-2-phenylspiro[chroman-4,4'-imidazol]-5'(1'H)-one (Comp. 133)

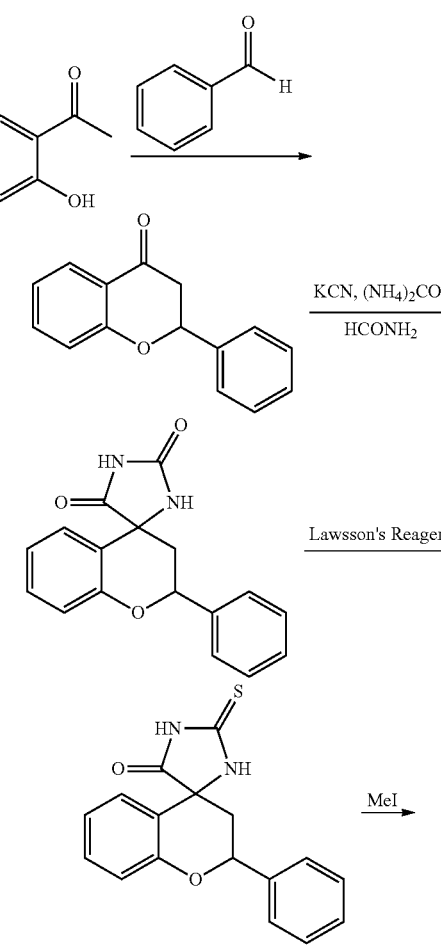

-continued

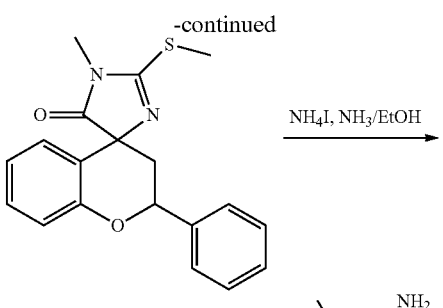

NH₄I, NH₃/EtOH →

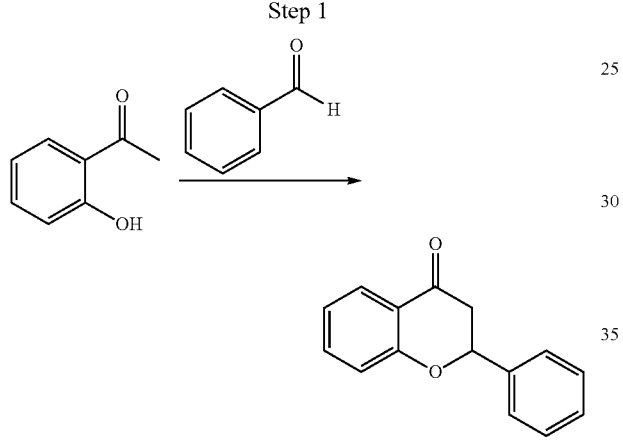

Step 1

A mixture of 1-(2-hydroxyphenyl)ethanone (30 g, 220 mmol), benzaldehyde (23.3 g, 220 mmol) and borax (84 g, 220 mmol) in ethanol (180 mL) and H₂O (300 mL) was refluxed for one day. The reaction mixture was cooled, diluted with an equal volume of H₂O, and extracted with ether. The combined organic layers were dried over anhydrous Na₂SO₄, filtered, and evaporated. The residue was purified by column to give 2-phenylchroman-4-one (20 g, 40%).

Step 2

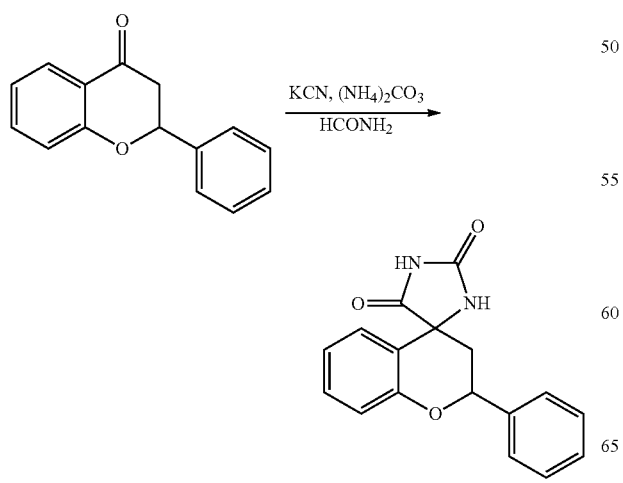

A glass pressure tube is charged with a mixture of 2-phenylchroman-4-one (8 g, 35.7 mmol), KCN (4.64 g, 71.4 mmol), and (NH₄)₂CO₃ (25.7 g, 267.7 mmol). Formamide (100 mL) is added to fill the pressure tube nearly completely. The mixture is heated at 70° C. for 24 h then at 110° C. for another 48 h. The reaction mixture is then cooled and poured over ice. Acidification with concentrated HCl gives a precipitate which is filtered, washed twice with water, and then resolved in ethyl acetate, dried over Na₂SO₄, and filtered. The filtrate is concentrated in vacuo to give a residue, which is purified by column to give 2-phenylspiro[chroman-4,4'-imidazolidine]-2',5'-dione (2 g, 20%).

Step 3

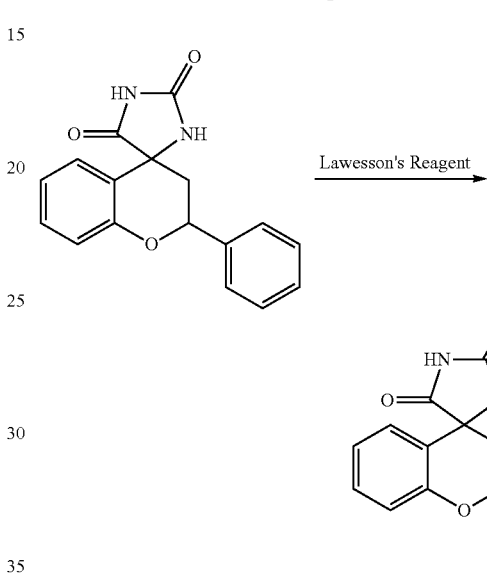

A suspension of 2-phenylspiro[chroman-4,4'-imidazolidine]-2',5'-dione (600 mg, 2.04 mmol) and Lawesson's Reagent (825 mg, 2.04 mmol) in dry 1,4-dioxane (28 mL) is heated under reflux for 24 h. The mixture is concentrated in vacuo and the residue is purified by column to give 2-phenyl-2'-thioxospiro[chroman-4,4'-imidazolidin]-5'-one (300 mg, 50%).

Step 4

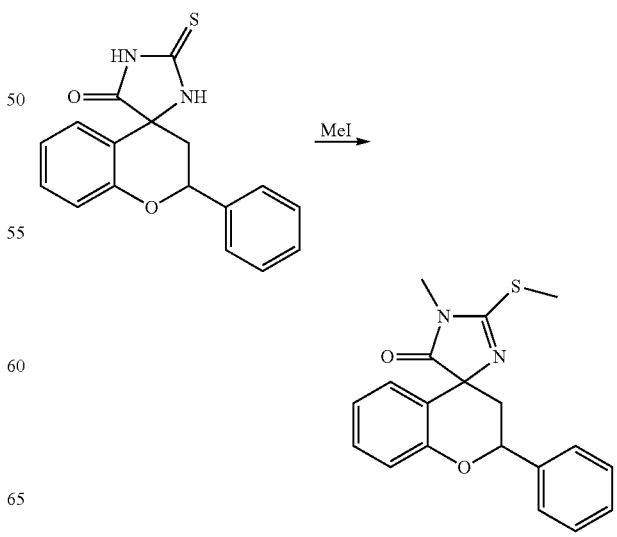

To a solution of 2-phenyl-2'-thioxospiro[chroman-4,4'-imidazolidin]-5'-one (200 mg, 0.645 mmol) in MeOH (10 mL) is added a solution of NaOH (51.6 mg, 1.29 mmol) in H₂O (2 mL). After stirring for 10 minutes, MeI (922 mg, 6.45 mmol) is added. The reaction mixture is heated under reflux for 2 h. The mixture is concentrated in vacuo to give a residue, which is purified by preparative TLC to give 1'-methyl-2'-(methylthio)-2-phenylspiro[chroman-4,4'-imidazol]-5'(1'H)-one (50 mg, 30%).

Step 5

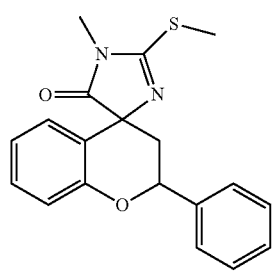

NH₄I, NH₃/EtOH →

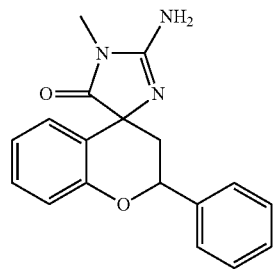

A solution of 1'-methyl-2'-(methylthio)-2-phenylspiro[chroman-4,4'-imidazol]-5'(1'H)-one (50 mg, 0.148 mmol) and NH₄I (42.9 mg, 0.296 mmol) in NH₃/EtOH (4 mL, 1.5 N) is heated at 110° C. in a tube under microwave reactor for 2-2.5 h. After cooling, the mixture is concentrated in vacuo to give a residue, which is purified by preparative TLC to afford 2'-amino-1'-methyl-2-phenylspiro[chroman-4,4'-imidazol]-5'(1'H)-one (5 mg, 10%).

¹H-NMR (MeOD): 2.0 (d, 1H), 2.35 (t, 1H), 3.0 (s, 3H), 5.2 (d, 0.376H), 5.75 (d, 1H), 6.78 (m, 2H), 6.99 (d, 1H), 7.16 (t, 1H), 7.2 (m, 3H), 7.4 (m, 2H).

Example 114

Compound 134

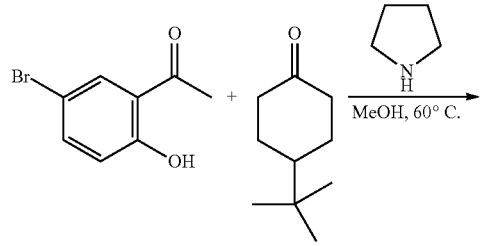

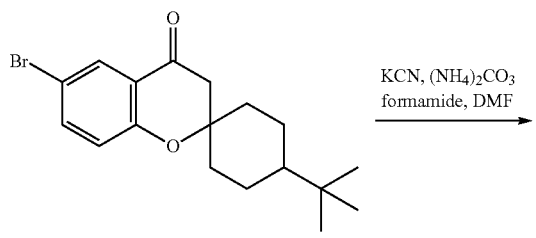

134i

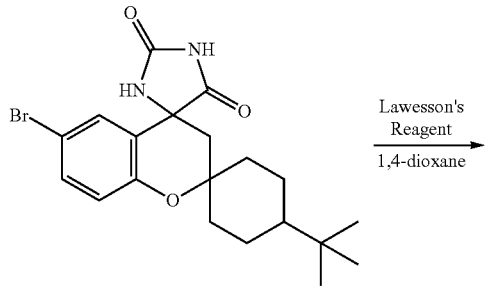

134ii

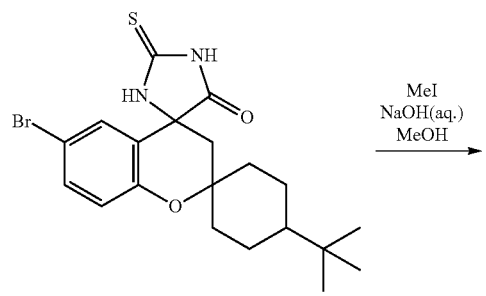

134iii

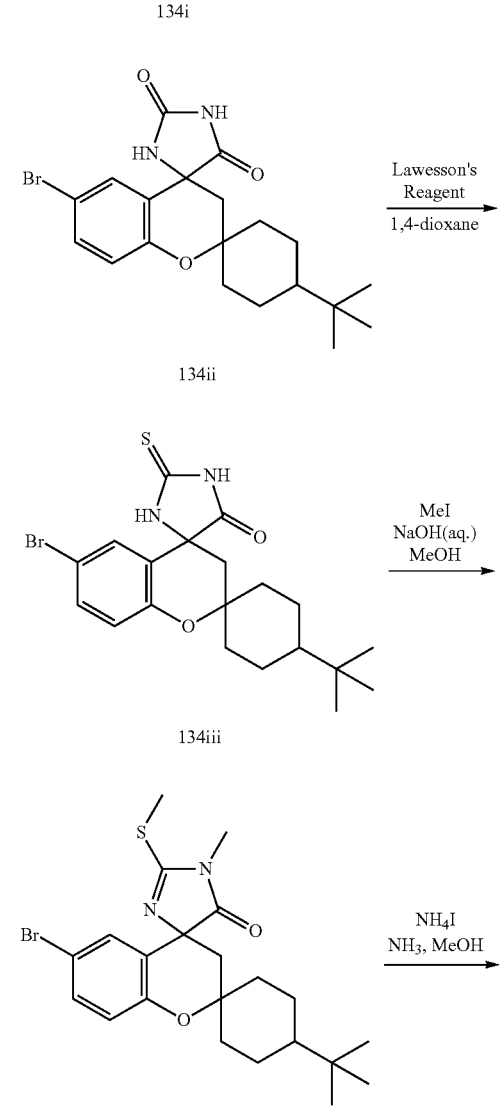

134iv

134v

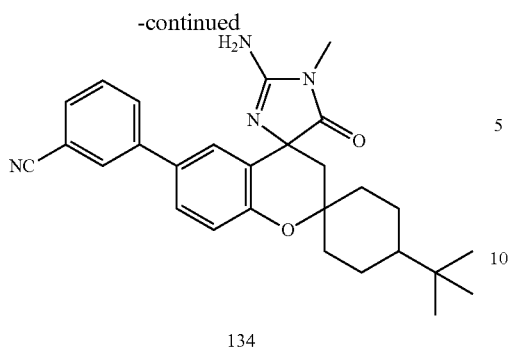

134

Step 1

To a 50 mL round bottom flask is added 1-(5-bromo-2-hydroxyphenyl)ethanone (2.0 g, 9.3 mmol), followed by 4-tert-butylcyclohexanone (1.43 g, 9.3 mmol). MeOH (20 mL) is added to give a clear solution, followed by pyrrolidine (1 mL). A condenser is attached to the RB flask, and the resulting solution is heated at 60° C. for two hours. MeOH is removed and the residue is redissolved in EtOAc (30 mL), washed with 1 N NaOH (10 mL), and 1 N HCl (10 mL), and dried over $Na_2SO_4$. Solvent is removed in vacuo to give 6-bromo-4'-t-butylspiro[chroman-2,1'-cyclohexan]-4-one (2.41 g, 74%), which is used for the next step without purification.

Step 2

A 10 mL CEM microwave test tube is filled with a mixture of 6-bromo-4'-t-butylspiro[chroman-2,1'-cyclohexan]-4-one (0.4 g, 1.1 mmol), KCN (0.15 g, 2.2 mmol), and $(NH_4)_2CO_3$ (0.8 g, 7.7 mmol). A 2:1 mixture of formamide and DMF (6.5 to 7 mL) is added to fill the test tube nearly completely. The resulting mixture is heated in a CEM microwave reactor at 65° C. for 5 hrs. Another 4 tubes (total 1.87 g) are irradiated under the same conditions, and the resulting mixture is combined, acidified with concentrated HCl, diluted with EtOAc (20 mL), and washed with $H_2O$ (10 mL×3). The organic layer is dried over $Na_2SO_4$, and solvent is removed in vacuo to give a crude product, which is purified by flash chromatography column (0 to 60% EtOAc/hexane) to give the hydantoin 134ii (42 g, 26% corrected for recovered starting material 0.52 g). MS m/z 421 (M+H$^+$).

Step 3

To a solution of the above hydantoin (0.42 g, 1.0 mmol) in 1,4-dioxane (5 mL) in a 10 mL CEM microwave test tube, there is added Lawesson's reagent (0.40 g, 1.0 mmol). The resulting mixture is heated in a CEM microwave reactor at 110° C. for 30 min and cooled to rt. The solvent is removed in vacuo, and the residue is purified by flash chromatography column to give the thiol-hydantoin 134iii (0.35 g, 81%). MS m/z 437 (M+H$^+$).

Step 4

To a solution of the above thio-hydantoin (100 mg, 0.23 mmol) in MeOH (2 mL) in a 10 mL CEM microwave test tube, there is added a 0.6 N NaOH aqueous solution (0.5 mL). After stirring at rt for 10 min, MeI (0.5 mL, excess) is added and the reaction mixture is heated in a CEM microwave reactor at 60° C. for 10 min. The resulting mixture is concentrated in vacuo to give the crude product, which is purified by flash chromatography column to give the dimethy thiol-hydrantoin 134iv (25.5 mg, 24%). MS m/z 465 (M+H$^+$).

Step 5

To a solution of the above dimethylated thiol-hydantoin (25.5 mg, 0.05 mmol) in $NH_3$/MeOH (7 N, 1 mL) in a CEM microwave test tube, there is added $NH_4I$ (24 mg, 0.15 mmol). The resulting mixture is heated in a CEM microwave reactor at 110° C. for 3 hrs. After the reaction is done, the mixture is concentrated in vacuo to give the crude product, which is purified by reversed phase HPLC to give the acyl-guanidine 134v (23 mg, 84%) as a TFA salt. MS m/z 434 (M+H$^+$).

Step 6

To a solution of the above acyl-guanidine (23 mg, 0.04 mmol) in 1,4-dioxane (1 mL) there is added excess amount of $Cs_2CO_3$, 3-cyanophenylboronic acid, and catalytical amount of 1,1'-Bis(diphenylphosphino)ferrocene palladium dichloride. After degassing, the resulting mixture is heated in a CEM microwave reactor at 120° C. for 30 min Solvent is removed in vacuo and the residue is purified by reversed phase HPLC to give the final product compound 134 (2.5 mg, 11%) as a TFA salt.

$^1$H NMR (400 MHz, $CD_3OD$): 8.16-7.84 (m, 2H), 7.78-7.64 (m, 3H), 7.52 (s, 1H), 7.14 (m, 1H), 3.38 (s, 3H), 3.20, 3.14 (two s, 2H), 2.80-2.10 (m, 3H), 1.98-1.10 (m, 6H), 0.98 (s, 9H); MS m/z 457 (M+H$^+$).

Example 115

3-(2'-Amino-1'-benzyl-5'-oxo-2-phenyl-1',5'-dihydrospiro[chroman-4,4'-imidazole]-6-yl)benzonitrile (Cmpds. 135a and 135b)

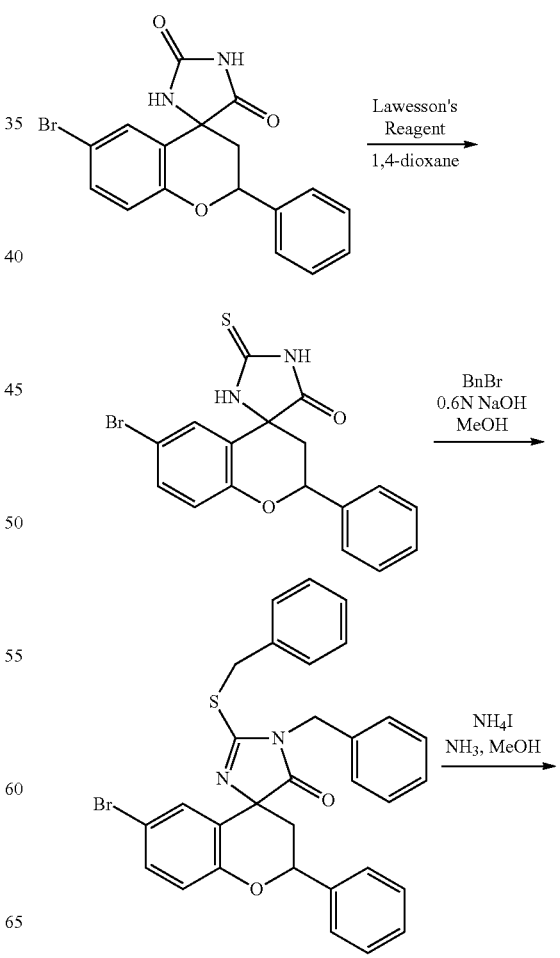

-continued

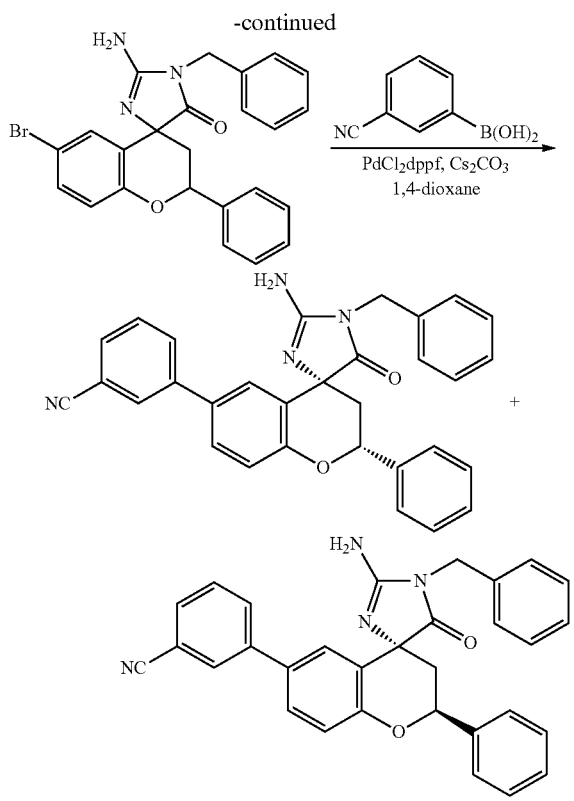

Step 1

To a solution of 6-bromo-2-phenylspiro[chroman-4,4'-imidazolidine]-2',5'-dione (440 mg, 1.18 mmol) in 1,4-dioxane (3.6 mL) in a 10 mL CEM microwave test tube, there is added Lawesson's reagent (477 mg, 1.18 mmol). The resulting mixture is heated in a CEM microwave reactor at 110° C. for 40 min and cooled to rt. The solvent is removed in vacuo, and the residue is purified by flash chromatography column to give 6-bromo-2-phenyl-2'-thioxospiro[chroman-4,4'-imidazolidin]-5'-one (238 mg, 52%). MS m/z 389 (M+H$^+$).

Step 2

To a solution of 6-bromo-2-phenyl-2'-thioxospiro[chroman-4,4'-imidazolidin]-5'-one (110 mg, 0.28 mmol) in MeOH (5 mL) in a 10 mL CEM microwave test tube is added a 0.6 N NaOH aqueous solution (1.0 mL). After stirring at rt for 10 min, MeI (158 mg, 1.08 mmol) is added, and the reaction is continued with stirring at rt for 2 hrs. Upon removing the solvent in vacuo, the residue is purified by flash chromatography column to give 1'-benzyl-2'-(benzylthio)-6-bromo-2-phenylspiro[chroman-4,4'-imidazol]-5'(1'H)-one (63.3 mg, 39%). MS m/z 569 (M+H$^+$).

Step 3

To a solution of 1'-benzyl-2'-(benzylthio)-6-bromo-2-phenylspiro[chroman-4,4'-imidazol]-5'(1'H)-one (60 mg, 0.10 mmol) in MeOH/EtOH (1:1, 2 mL) in a 10 mL CEM microwave test tube is added NH$_4$I (50 mg, 0.34 mmol) and NH$_3$/MeOH (7 N, 2 mL). The resulting mixture is heated in a CEM microwave reactor at 120° C. for 60 min. The cooled mixture is concentrated in vacuo and the residue is purified by a reversed HPLC to give 2'-amino-1'-benzyl-6-bromo-2-phenylspiro[chroman-4,4'-imidazol]-5'(1'H)-one (17.3 mg, 34%) as a TFA salt. MS m/z 462 (M+H$^+$).

Step 4

To a solution of 2'-amino-1'-benzyl-6-bromo-2-phenylspiro[chroman-4,4'-imidazol]-5'(1'H)-one (17.3 mg, 0.04 mmol) in 1,4-dioxane (1.5 mL) there is added Cs$_2$CO$_3$ (excess), 3-cyanophenylboronic acid (excess), and catalytical amount of PdCl$_2$dppf. After degassing, the resulting mixture is heated in a CEM microwave reactor at 130° C. for 30 min Solvent is removed in vacuo and the residue is purified by reversed phase HPLC to give 3-((2R,4R)-2'-amino-1'-benzyl-5'-oxo-2-phenyl-1',5'-dihydrospiro[chroman-4,4'-imidazole]-6-yl)benzonitrile (6.0 mg, 33%) as a TFA salt (135a) and 3-((2S,4R)-2'-amino-1'-benzyl-5'-oxo-2-phenyl-1',5'-dihydrospiro[chroman-4,4'-imidazole]-6-yl)benzonitrile (0.86 mg, 4.8%) as a TFA salt. (135b).

$^1$H NMR (400 MHz, CD$_3$OD): 7.84-7.60 (m, 4H), 7.74-7.24 (m, 12H), 7.12 (d, 1H), 5.92 (d, 1H), 4.62 (s, 2H), 2.60 (d, 1H), 2.42 (d, 1H); MS m/z 485 (M+H$^+$) (135a).

$^1$H NMR (400 MHz, CD$_3$OD): 7.74-7.36 (m, 16H), 7.16 (d, 1H), 5.24 (d, 1H), 5.08, 5.00 (two d, 2H), 2.64 (d, 1H), 2.56 (d, 1H); MS m/z 485 (M+H$^+$) (135b).

Example 116

Compound 136

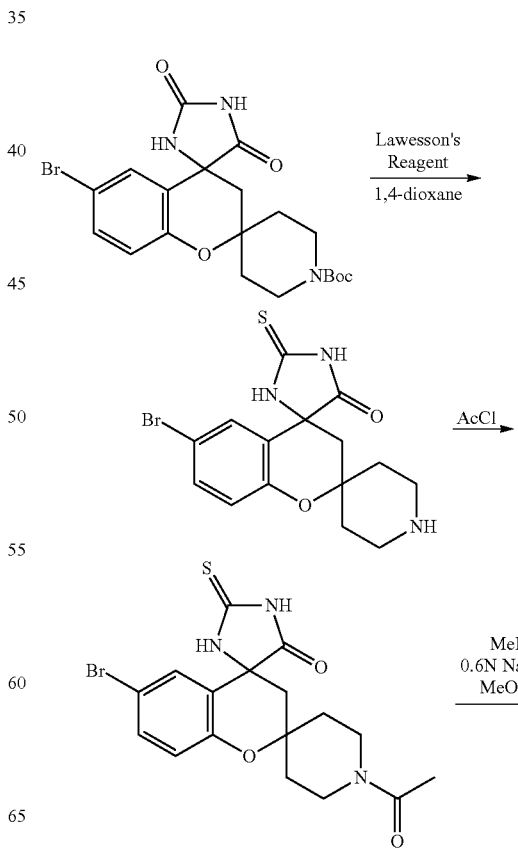

-continued

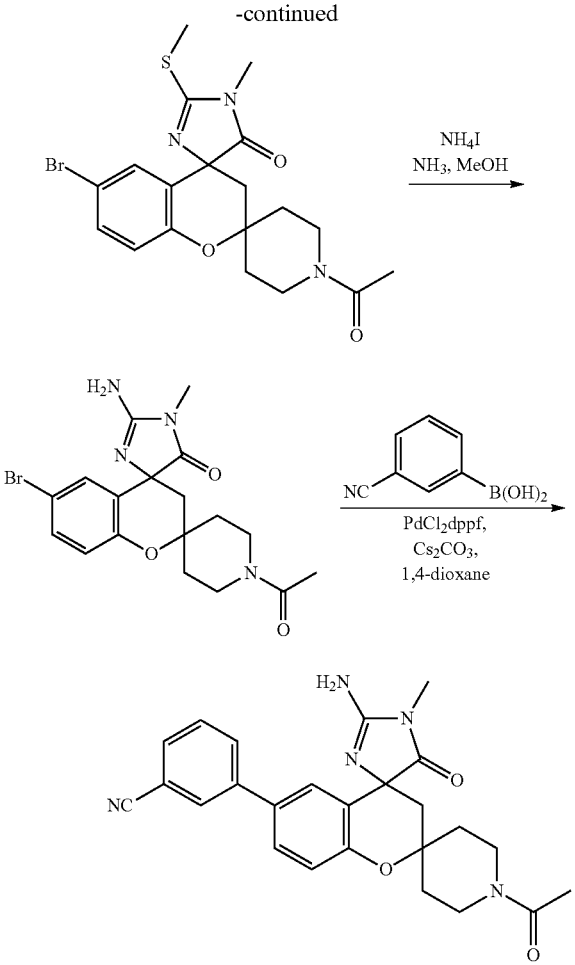

Step 1

To a solution of the 4-N-Boc-piperidinyl-spiro-hydantoin (167.3 mg, 0.36 mmol) in 1,4-dioxane (4.5 mL) in a 10 mL CEM microwave test tube, there is added Lawesson's reagent (144.0 mg, 0.36 mmol). The resulting mixture is heated in a CEM microwave reactor at 150° C. for 40 min and cooled to rt. The solvent is removed in vacuo to give a crude thiol-4-piperidinyl-spiro-hydantoin, which is used for the next step without purification. MS m/z 382 (M+H⁺).

Step 2

To a solution of the above crude product in MeCN/H₂O (3:1, 1 mL) there is added K₂CO₃ (excess) followed by acetyl chloride (excess). The resulting solution is stirred at rt for 10 min, and solvent is removed in vacuo. The residue is purified by reversed phase HPLC to give the thio-4-N-acyl-piperidinyl-spiro-hydantoin (80 mg, 52% two steps). MS m/z 424 (M+H⁺).

Step 3

To a solution of the thio-4-N-acyl-piperidinyl-spiro-hydantoin (80 mg, 0.19 mmol) in MeOH (6 mL) in a 10 mL CEM microwave test tube, there is added a 0.6 N NaOH aqueous solution (1.0 mL). After stirring at rt for 10 min, MeI (100 μL, excess) is added, the reaction mixture is stirred at rt for 30 min, and then heated in a CEM microwave reactor at 60° C. for 20 min. The resulting mixture is concentrated in vacuo to give crude dimethylated thiol-4-N-acyl-piperidinyl-spiro-hydantoin, which is used for the next step without purification. MS m/z 452 (M+H⁺).

Step 4

To a solution of the dimethylated thiol-4-N-acyl-piperidinyl-spiro-hydantoin (0.19 mmol) in MeOH (1 mL) in a 10 mL CEM microwave test tube, there is added NH₄I (excess) and NH₃/MeOH (7 N, 1.5 mL). The resulting mixture is heated in a CEM microwave reactor at 120° C. for 30 min. Upon cooling, solvent is removed in vacuo and the residue is purified by a reversed phase HPLC to give 4-N-acyl-piperidinyl-spiro-acyl-guanidine (20 mg, 25%) as a TFA salt. MS m/z 421 (M+H⁺).

Step 5

To a solution of 4-N-acyl-piperidinyl-spiro-acyl-guanidine (20 mg, 0.05 mmol) in 1,4-dioxane (1.5 mL) there is added Cs₂CO₃ (excess), 3-cyanophenylboronic acid (excess), and catalytical amount of PdCl₂dppf. After degassing, the resulting mixture is heated in a CEM microwave reactor at 120° C. for 30 min Solvent is removed in vacuo and the residue is purified by a reversed phase HPLC to give the 4-N-acyl-piperidinyl-spiro-acyl-guanidine final product compound 136 (7.0 mg, 32%) as a TFA salt.

¹H NMR (400 MHz, CD₃OD): 7.94 (m, 1H), 7.86 (m, 1H), 7.66 (m, 2H), 7.60 (m, 1H), 7.48 and 7.40 (two d, 1H), 7.16 (m, 1H), 3.34 (m, 1H), 3.86-3.40 (m, 3H), 3.22 (m, 1H), 3.10, 3.06 (two s, 3H), 2.56, 2.40 (two m, 2H), 2.20-1.96 (m, 5H), 1.90-1.62 (m, 2H); MS m/z 444 (M+H⁺).

Example 117

4-(2'-amino-1'-methyl-5'-oxo-2-phenyl-1',5'-dihydrospiro[chroman-4,4'-imidazole]-6-yl)-N-(2-(dimethylamino)ethyl)benzamide (Compound 137)

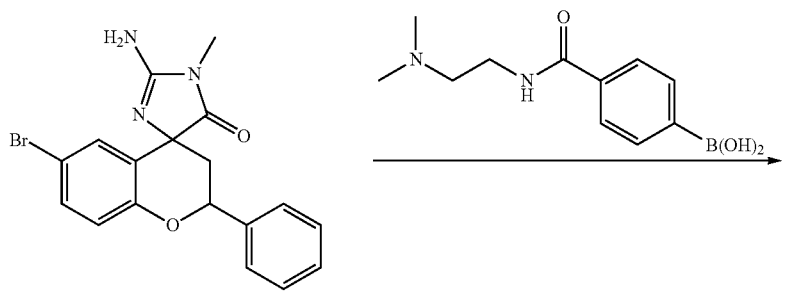

-continued

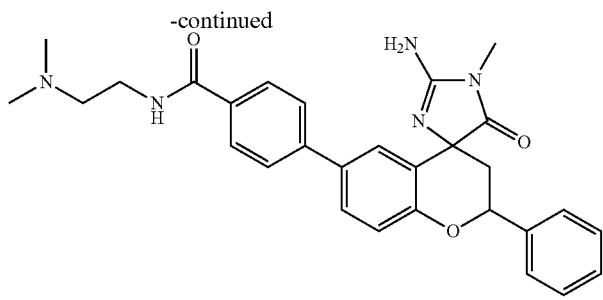

Pd(PPh$_3$)$_2$Cl$_2$ (10 mg, 0.01 mmol) in a 10 mL of flask under Ar$_2$ was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 4-(2-(dimethylamino)ethylcarbamoyl)phenylboronic acid (25 mg, 0.104 mmol). The mixture was heated under 120 at Ar$_2$ under microwave for 30 minutes. The reaction mixture was concentrated in vacuo to give the residue, which was purified preparative TLC and HPLC to give 4-(2'-amino-1'-methyl-5'-oxo-2-phenyl-1',5'-dihydrospiro[chroman-4,4'-imidazole]-6-yl)-N-(2-(dimethylamino)ethyl)benzamide (4.68 mg, 18%). $^1$H-NMR (MeOD): 2.47 (m, 1H), 2.63 (m, 1H), 3.01 (s, 6H), 3.30 (s, 3H), 3.42 (m, 2H), 3.79 (m, 2H), 5.88 (m, 1H), 7.17 (m, 1H), 7.39 (m, 1H), 7.46 (m, 2H), 7.52 (m, 2H), 7.58 (m, 1H), 7.71 (m, 1H), 7.76 (m, 2H), 7.96 (m, 2H).

Example 118

3-(2'-amino-5'-oxo-2-phenyl-1'-(2,2,2-trifluoroethyl)-1',5'-dihydrospiro[chroman-4,4'-imidazole]-6-yl)benzonitrile (Compound 138)

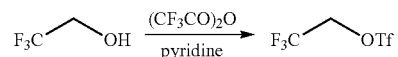

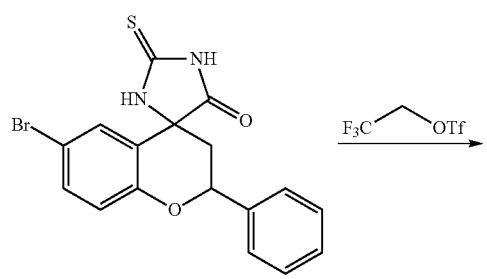

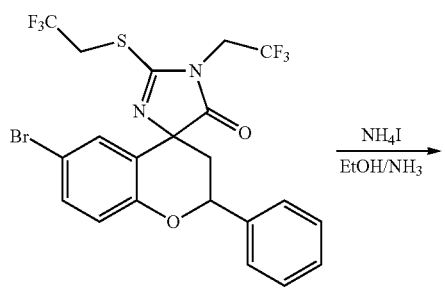

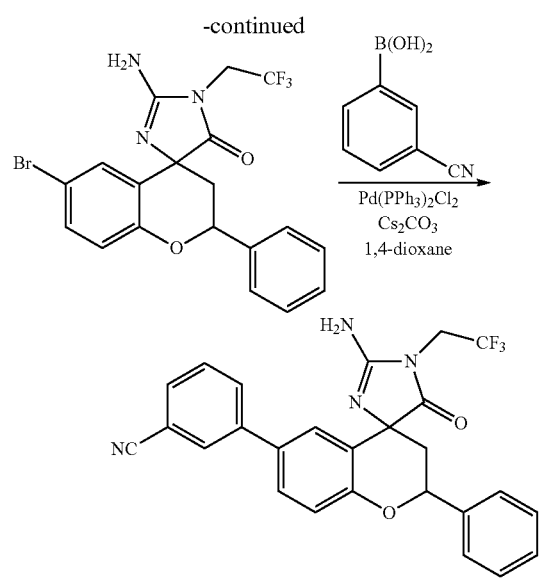

Experimental Data:

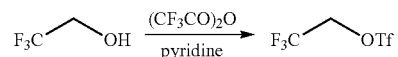

Step 1: trifluoro-methanesulfonic acid 2,2,2-trifluoro-ethyl ester

Combine 2,2,2-trifluoro-ethanol (6.2 mL), pyridine (6.8 mL) and CH$_2$Cl$_2$ (20 mL) cooled in an ice bath. Add Tf$_2$O (25 g) over about 45 minutes. After 15 minutes, add water, separate the layers and extract with water. The organic layer was dried over Na$_2$SO$_4$ and concentrated through a short path distillation apparatus (8 g, 54%).

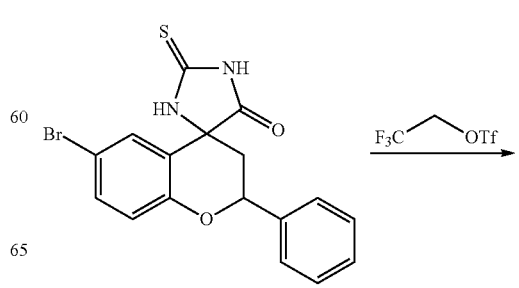

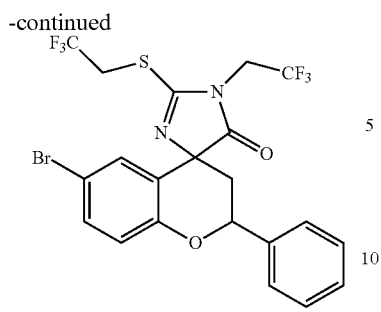

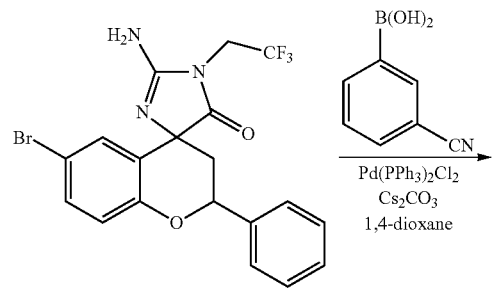

Step 2: 6-bromo-2-phenyl-1'-(2,2,2-trifluoroethyl)-2'-(2,2,2-trifluoroethylthio)spiro[chroman-4,4'-imidazol]-5'(1'H)-one To a solution of 6-bromo-2-phenyl-2'-thioxospiro[chroman-4,4'-imidazolidin]-5'-one (113 mg, 0.29 mmol) in DMF (7 mL) was added Cs$_2$CO$_3$ (190 mg, 0.58 mmol) and 2,2,2-trifluoroethyl trifluoromethanesulfonate (204 mg, 0.87 mmol). After stirring for 2 days, the mixture was extracted from water with EtOAc. The combined organic layers were washed with water and brine, dried and then concentrated to give the residue, which was purified by preparative TLC to give 6-bromo-2-phenyl-1'-(2,2,2-trifluoroethyl)-2'-(2,2,2-trifluoroethylthio)spiro[chroman-4,4'-imidazol]-5'(1'H)-one (60 mg, 36%).

Step 4: 3-(2'-amino-5'-oxo-2-phenyl-1'-(2,2,2-trifluoroethyl)-1',5'-dihydrospiro[chroman-4,4'-imidazole]-6-yl)benzonitrile Pd(PPh$_3$)$_2$Cl$_2$ (10 mg) in a 10 mL of tube under Ar$_2$ was treated sequentially with 2'-amino-6-bromo-2-phenyl-1'-(2,2,2-trifluoroethyl)spiro[chroman-4,4'-imidazol]-5'(1'H)-one (20 mg, 0.044 mmol) in 1,4-dioxane (1 mL), Cs$_2$CO$_3$ (2 M, 0.3 mL) and 3-cyanophenylboronic acid (13 mg, 0.088 mmol). The mixture was heated at 120 under microwave reactor for 0.5 h. The reaction mixture was concentrated in vacuo to give the residue, which was purified by preparative TLC to give pure 3-(2'-amino-5'-oxo-2-phenyl-1'-(2,2,2-trifluoroethyl)-1',5'-dihydrospiro[chroman-4,4'-imidazole]-6-yl)benzonitrile (3.7 mg, 12%). $^1$H-NMR (MeOD): 2.27 (m, 1H), 2.35 (m, 1H), 3.87 (m, 2H), 5.83 (m, 1H), 7.01 (d, 1H), 7.26 (m, 1H), 7.32 (m, 5H), 7.59 (m, 3H), 7.76 (m, 1H), 7.81 (m, 1H).

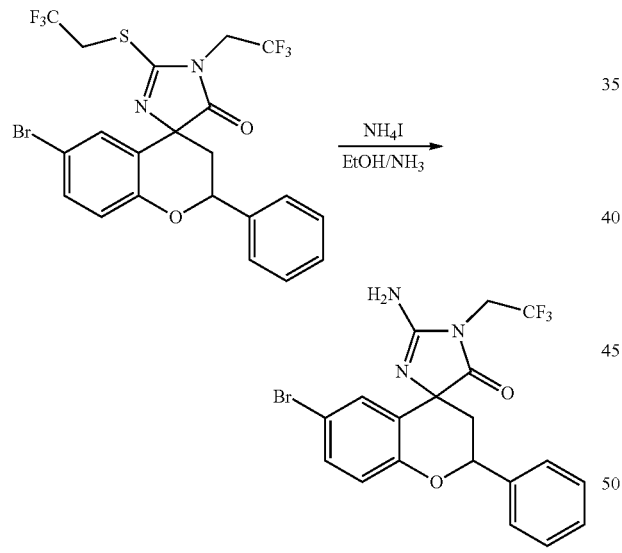

Step 3: 2'-amino-6-bromo-2-phenyl-1'-(2,2,2-trifluoroethyl)spiro[chroman-4,4'-imidazol]-5'(1'H)-one A solution of 6-bromo-2-phenyl-1'-(2,2,2-trifluoroethyl)-2'-(2,2,2-trifluoroethylthio)spiro[chroman-4,4'-imidazol]-5'(1'H)-one (60 mg), NH$_4$I (10 mg) in a solution of NH$_3$/EtOH (2 mL, 1.5 N) was heated at 110 in a tube under microwave reactor for 2-2.5 h. After cooling, the mixture was concentrated in vacuum to give the residue, which was purified by preparative TLC to afford 2'-amino-6-bromo-2-phenyl-1'-(2,2,2-trifluoroethyl)spiro[chroman-4,4'-imidazol]-5'(1'H)-one (30 mg, 61%).

Example 119

2'-amino-6-(4-(benzyloxy)phenyl)-1'-methyl-2-phenylspiro[chroman-4,4'-imidazol]-5'(1'H)-one (Compound 139)

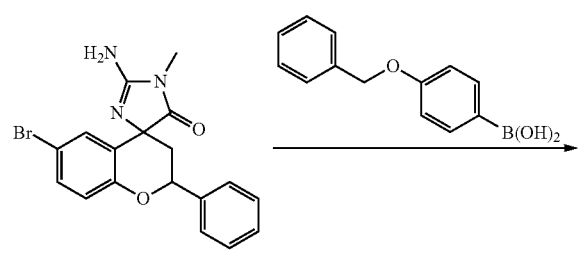

553
-continued

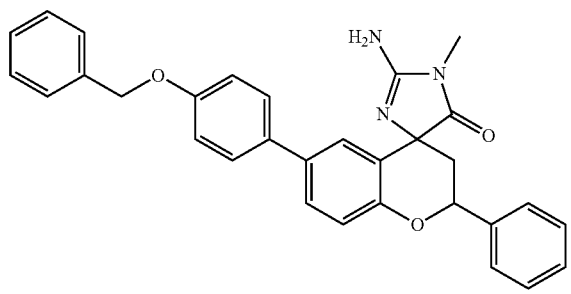

Pd(PPh$_3$)$_2$Cl$_2$ (10 mg, 0.01 mmol) in a 10 mL of flask under Ar$_2$ was treated sequentially with 2'-amino-6-bromo-1'-methyl-2-phenylspiro[chroman-4,4'-imidazol]-5'(1'H)-one (20 mg, 0.052 mmol) in 1,4-dioxane (1 mL), Cs$_2$CO$_3$ (2 N, 0.3 mL) and 4-(benzyloxy)phenylboronic acid (24 mg, 0.104 mmol). The mixture was heated under 120 at Ar$_2$ under microwave for 30 minutes. The reaction mixture was concentrated in vacuo to give the residue, which was purified preparative TLC and HPLC to give 2'-amino-6-(4-(benzyloxy)phenyl)-1'-methyl-2-phenylspiro[chroman-4,4'-imidazol]-5'(1'H)-one (1.75 mg, 7%). $^1$H-NMR (MeOD): 2.46 (m, 1H), 2.59 (m, 1H), 3.29 (s, 3H), 5.12 (s, 2H), 5.83 (m, 1H), 7.04 (m, 2H), 7.09 (m, 1H), 7.31 (m, 1H), 7.38 (m, 4H), 7.45 (m, 4H), 7.50 (m, 4H), 7.56 (m, 1H).

Example 120

2'-methyl-3'-(phenoxyamino)-2-phenyl-2'H-spiro[chroman-4,5'-[1,2,4]oxadiazol]-6-ol (Compound 140)

554
-continued

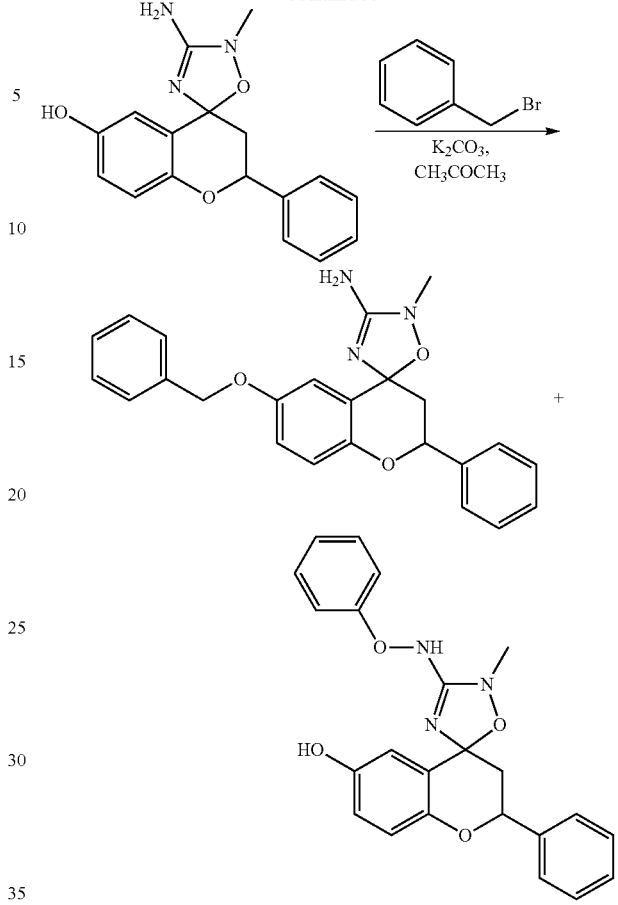

Experimental Data:

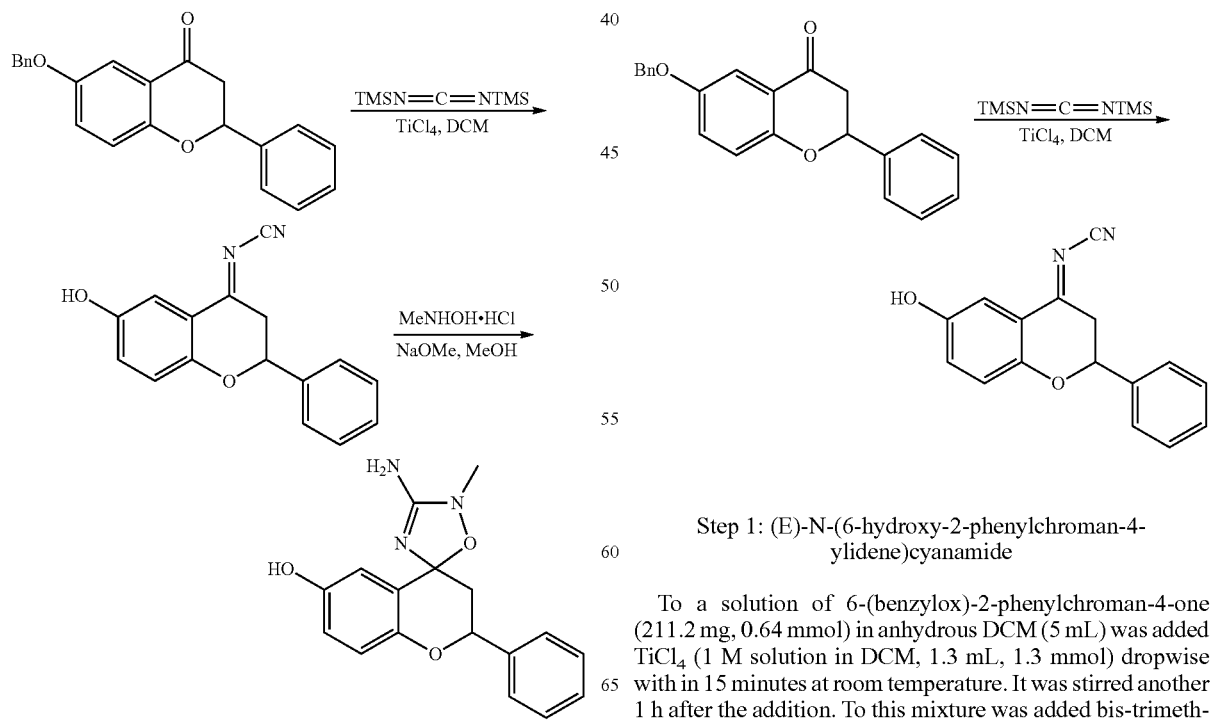

Step 1: (E)-N-(6-hydroxy-2-phenylchroman-4-ylidene)cyanamide

To a solution of 6-(benzylox)-2-phenylchroman-4-one (211.2 mg, 0.64 mmol) in anhydrous DCM (5 mL) was added TiCl$_4$ (1 M solution in DCM, 1.3 mL, 1.3 mmol) dropwise with in 15 minutes at room temperature. It was stirred another 1 h after the addition. To this mixture was added bis-trimethylsilylcarbodiimide (262 mg, 0.32 mL, 1.408 mmol) dropwise. The resulting mixture was stirred for another 18 h after the addition. The reaction mixture was poured into ice-water (25 g), extracted with DCM (3×15 mL). The combined organic phases were dried over anhydrous $Na_2SO_4$, filtered, and then concentrated to give (E)-N-(6-hydroxy-2-phenyl-chroman-4-ylidene)cyanamide (140 mg, 83%), which was used for next step without further purification.

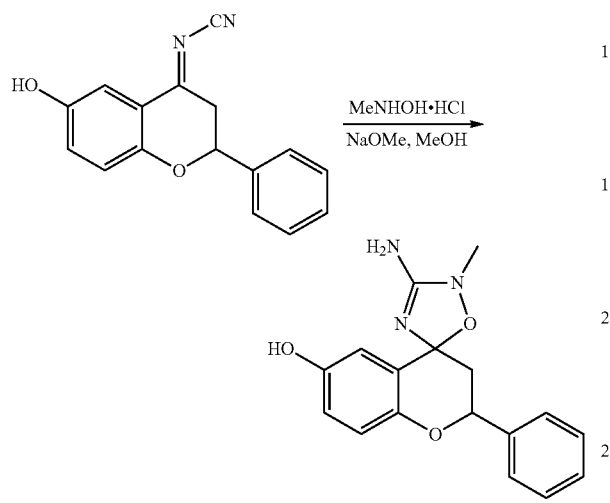

Step 2: 3'-amino-2'-methyl-2-phenyl-2'H-spiro[chroman-4,5'-[1,2,4]oxadiazol]-6-ol To a solution of methylhydroxylamine HCl salt (28 mg, 0.326 mmol) in anhydrous MeOH (8 mL) was added NaOMe (25 wt. % in MeOH, 15.83 mg, 0.294 mmol), followed by (E)-N-(6-hydroxy-2-phenylchroman-4-ylidene)cyanamide (86 mg, 0.326 mmol). After stirred 10 minutes, the solvent was removed in vacuum. The residue was dissolved in DCM (15 mL) and filtered, and the solvent was removed in vacuum to give the crude product, which was purified by preparative TLC to give 3'-amino-2'-methyl-2-phenyl-2'H-spiro[chroman-4,5'-[1,2,4]oxadiazol]-6-ol (20 mg, 20%). $^1$HNMR ($CDCl_3$): 7.30-7.51 (m, 5H), 6.95 (s, 1H), 6.69 (m, 2H), 5.15 (t, 3H), 2.98 (s, 3H), 2.28 (d, 2H), 1.17 (s, 1H).

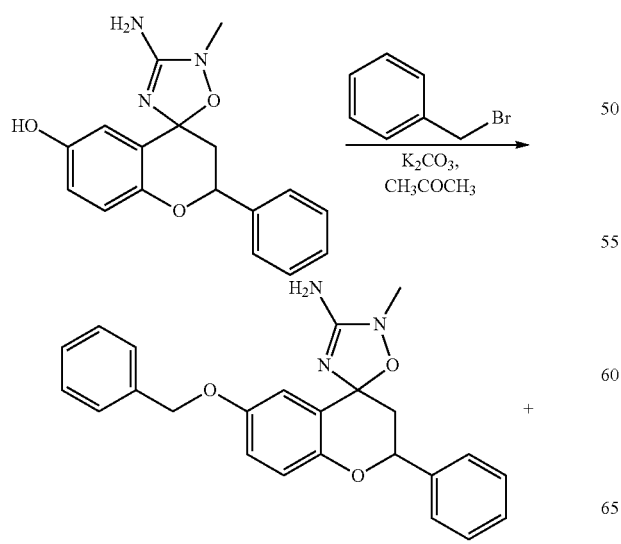

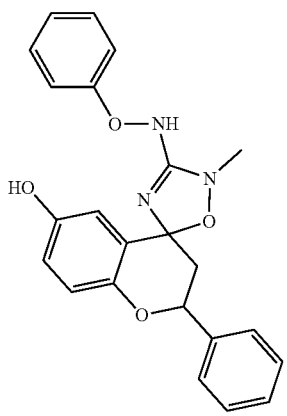

Step 3: 6-(benzyloxy)-2'-methyl-2-phenyl-2'H-spiro[chroman-4,5'-[1,2,4]oxadiazol]-3'-amine and 2'-Methyl-3'-(phenoxyamino)-2-phenyl-2'H-spiro[chroman-4,5'-[1,2,4]oxadiazol]-6-ol A mixture of 3'amino-2'-methyl-2-phenyl-2'H-spiro(chroman-4,5'-(1,2,4)oxadiazol)-6-ol (30 mg, 0.096 mmol), (bromomethyl)benzene (21.45 mg, 0.125 mmol) and $K_2CO_3$ (16 mg, 0.115 mmol) was dissolved in acetone, then the mixture was stirred at room temperature for 24 hours. The mixture was filtrated and concentrated. The residue was purified by preparative HPLC to give 6-(benzyloxy)-2'-methyl-2-phenyl-2'H-spiro[chroman-4,5'-[1,2,4]oxadiazol]-3'-amine (140) (0.95 mg, 3%). $^1$H-NMR (MeOD): 7.32-7.56 (m, 10H), 6.91-7.23 (m, 3H), 5.12 (d, 2H), 5.23 (t, 2H), 3.31 (s, 3H) 2.73 (m, 1H), 2.32 (m, 1H);

2'-methyl-3'-(phenoxyamino)-2-phenyl-2'H-spiro[chroman-4,5'-[1,2,4]oxadiazol]-6-ol (1.05 mg, 3%). $^1$H-NMR (MeOD): 7.32 (s, 6H), 7.20 (s, 2H), 7.06 (s, 2H), 6.83 (d, 1H), 6.74 (t, 2H), 4.91 (d, 1H), 4.25 (d, 1H), 3.36 (s, 3H), 2.37 (d, 2H), 1.86 (t, 3H)

Example 121

6-bromo-2'-methyl-2-(pyridin-2-yl)-2'H-spiro[chroman-4,5'-[1,2,4]oxadiazol]-3'-amine (Compound 142)

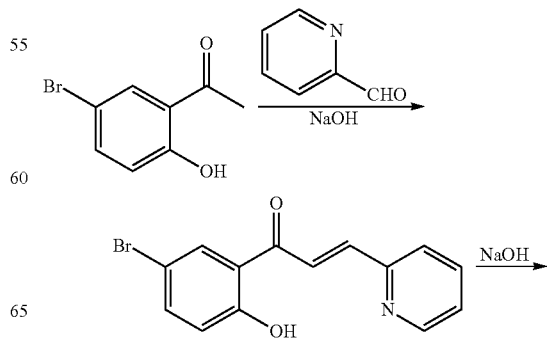

-continued

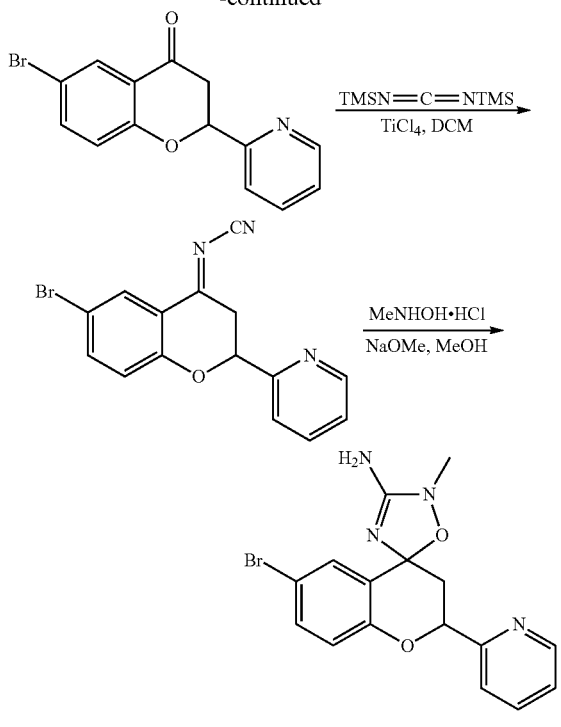

Experimental Data:

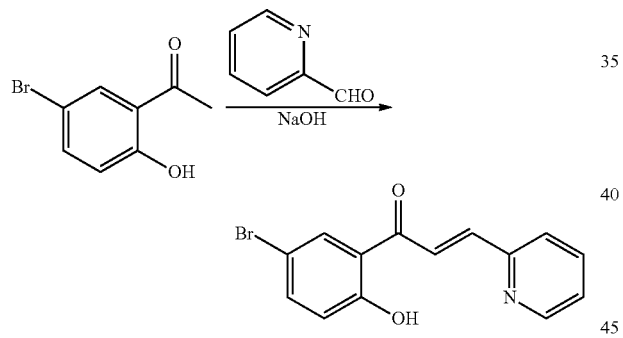

Step 1: 1-(5-bromo-2-hydroxy-phenyl)-3-pyridin-2-yl-propenone

In a bottle were combined 1-(5-bromo-2-hydroxy-phenyl)-ethanone (12 g, 56 mmol), pyridine-2-carbaldehyde (5.4 mL, 56 mmol), EtOH (96%, 67 mL) and NaOH (19.75 g, 494 mmol). The mixture was stirred vigorously for 0.5 h and then filtered. The mixture was poured into HCl (1 N, 500 mL) and filtered. The solid was dried to give 1-(5-bromo-2-hydroxyphenyl)-3-pyridin-2-yl-propenone (10 g, 59%).

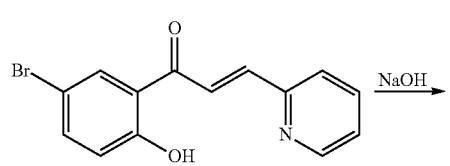

-continued

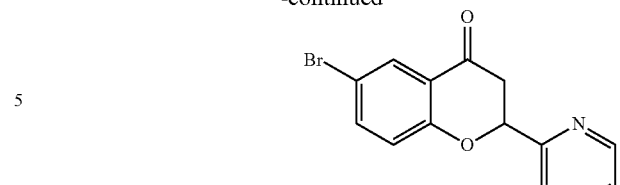

Step 2: 6-bromo-2-pyridin-2-yl-chroman-4-one 1-(5-Bromo-2-hydroxy-phenyl)-3-pyridin-2-yl-propenone (13 g, 43 mmol) was dissolved in $H_2O$ (321 mL) and EtOH (107 mL). Then NaOH (1.72 g, 43 mmol) was added. The mixture was stirred overnight and filtered. The cake was dissolved in EtOAc and washed with $H_2O$ twice. The organic layer was dried and filtered. The filtrate was concentrated to give 6-bromo-2-pyridin-2-yl-chroman-4-one (2.22 g, 17%). $^1$H-NMR (CDCl$_3$): 3.14 (m, 2H), 5.57 (m, 1H), 6.98 (m, 1H), 7.29 (m, 1H), 7.57 (m, 1H), 7.76 (m, 1H), 8.00 (m, 1H), 8.61 (m, 1H).

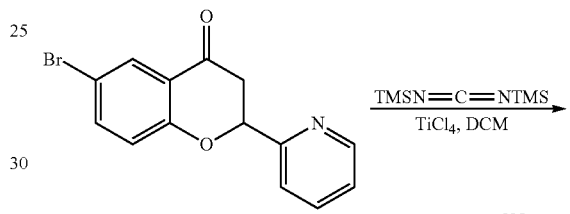

Step 3:
6-bromo-2-pyridin-2-yl-chroman-4-ylidene-cyanamide

To a solution of 6-bromo-2-pyridin-2-yl-chroman-4-one (303 mg, 1 mmol) in DCM (10 mL) was added TiCl$_4$ (4 mL, 1 M in CH$_2$Cl$_2$) dropwise within 15 minutes at room temperature. After stirring for 1 h, N,N'-methanediylidenebis(1,1,1-trimethylsilanamine) (0.5 mL, 2.2 mmol) was added dropwise. The mixture was stirred at room temperature overnight and poured into ice-water (50 g). The aqueous layer was extracted with CH$_2$Cl$_2$, which was combined with the organic layer. The organic layer was dried and concentrated to give crude 6-bromo-2-pyridin-2-yl-chroman-4-ylidene-cyanamide (300 mg, 92%).

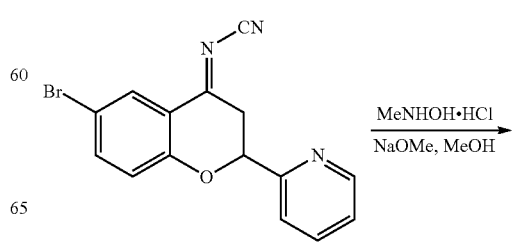

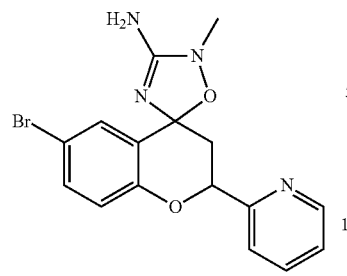

Step 4: 6-bromo-2'-methyl-2-(pyridin-2-yl)-2'H-spiro[chroman-4,5'-[1,2,4]oxadiazol]-3'-amine To a solution of N-methyl-hydroxylamine hydrochloride (31 mg, 0.31 mmol) in MeOH (4 mL) was added MeONa (0.06 mL, 25% (Wt.) in MeOH), followed by 6-bromo-2-pyridin-2-yl-chroman-4-ylidene-cyanamide (100 mg, 0.31 mmol). After stirred for 10 minutes, the solvent was removed in vacuo. The residue was purified by preparative TLC to give 6-bromo-2'-methyl-2-(pyridin-2-yl)-2'H-spiro[chroman-4,5'-[1,2,4]oxadiazol]-3'-amine (45 mg, 40%). $^1$H-NMR (MeOD): 2.13 (m, 1H), 2.48 (m, 1H), 3.08 (m, 3H), 5.32 (m, 1H), 6.86 (m, 1H), 7.36 (m, 2H), 7.51 (m, 1H), 7.68 (m, 1H), 7.90 (m, 1H), 8.52 (m, 1H).

Example 122

6-bromo-2'-methyl-2-(pyridine-3-yl)-2'H-spiro-[chroman-4,5'-[1,2,4]oxadiazol]-3'-amine (Compound 143)

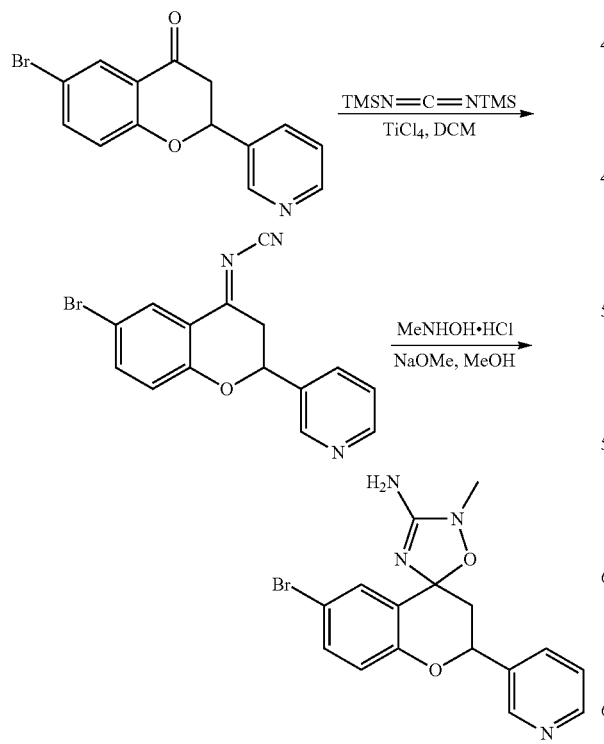

Experimental Data:

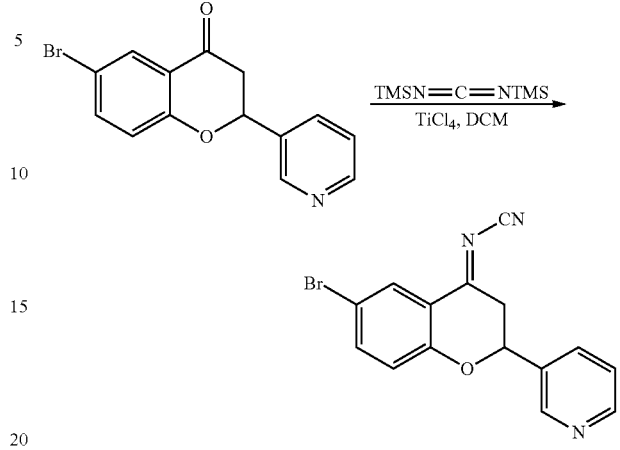

Step 1: (E)-N-(6-bromo-2-(pyridine-3-yl)chroman-4-ylidene)cyanamide

To a solution of 6-bromo-2-(pyridine-3-yl)chroman-4-one (1.0 g, 3.3 mmol) in anhydrous DCM (20 mL) was added TiCl$_4$ (1 M solution in DCM, 2.5 g, 13.2 mmol) dropwise within 15 minutes at room temperature in absence of light. It was stirred for another 1 h after the addition. To this mixture was added bis-trimethylsilylcarbodiimide (1.35 g, 7.26 mmol) dropwise. The resulting mixture was stirred overnight. The reaction mixture was poured into ice-water, extracted with DCM. The combined organic phases were dried over anhydrous Na$_2$SO$_4$, and filtered. The filtrate was concentrated to give (E)-N-(6-bromo-2-(pyridine-3-yl)chroman-4-ylidene)cyanamide (687 mg, 64%), which was used for next step without further purification.

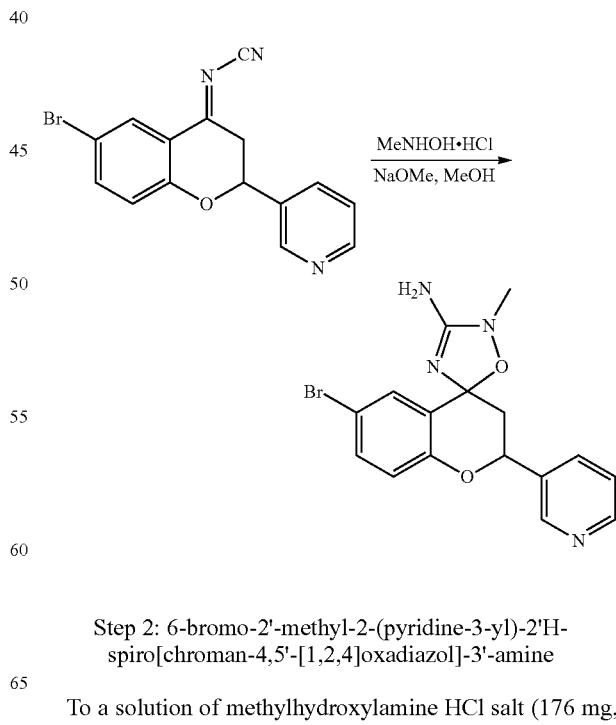

Step 2: 6-bromo-2'-methyl-2-(pyridine-3-yl)-2'H-spiro[chroman-4,5'-[1,2,4]oxadiazol]-3'-amine To a solution of methylhydroxylamine HCl salt (176 mg, 2.1 mmol) in anhydrous MeOH (15 mL) was added NaOMe (25% in MeOH (Wt. %), 0.47 mL, 1.89 mmol), followed by (E)-N-(6-bromo-2-(pyridine-3-yl)chroman-4-ylidene)cyanamide (687 mg, 2.1 mmol). After stirred for 10 mins, the solvent was removed in vacuo. The residue was redissolved in DCM (15 mL). The mixture was filtered, and the solvent was removed to give the residue, which was purified by preparative TLC to give 6-bromo-2'-methyl-2-(pyridine-3-yl)-2'H-spiro-[chroman-4,5'-[1,2,4]oxadiazol]-3'-amine (190 mg, 24%). $^1$H-NMR (MeOD): 2.18-2.25 (m, 1H), 2.39 (m, 1H), 3.09 (s, 3H), 5.34-5.38 (m, 1H), 6.81-6.86 (t, 1H), 7.37-7.40 (m, 1H), 7.45-7.55 (m, 1H), 7.62 (s, 1H), 7.97-7.99 (m, 1H), 8.52-8.54 (m, 1H), 8.66 (d, 1H).

Example 123

8-chloro-2'-methyl-2'H,11H-spiro[dibenzo[b,f]oxepine-10,5'-[1,2,4]oxadiazol]-3'-amine (Compound 144)

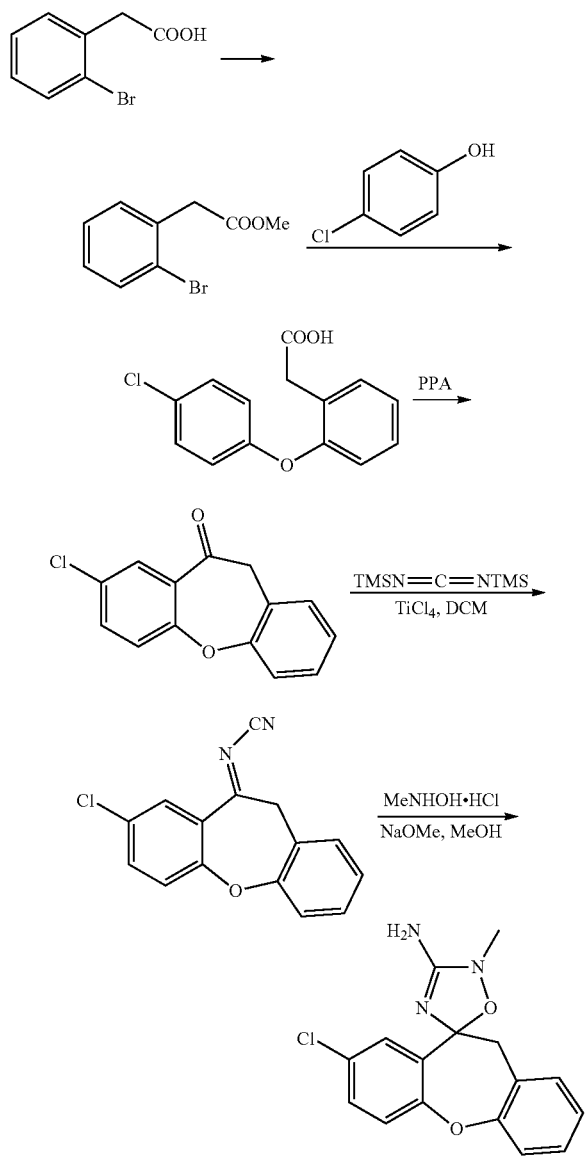

Experimental Data:

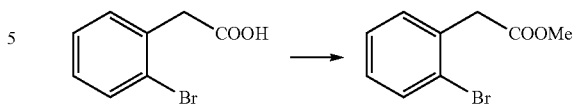

Step 1: methyl 2-(2-bromophenyl)acetate

To a solution of 2-(2-bromophenyl)acetic acid (2 g, 9.3 mmol) in anhydrous methanol (20 mL) was added 4-methylbenzenesulfonic acid hydrate (1.767 g, 9.3 mmol). The mixture was heated to reflux for 3 hr. The solvent was removed in vacuum. Ethyl ether and water was added. The organic phase was washed with water and brine, then dried over $Na_2SO_4$, filtered and concentrated to give methyl 2-(2-bromophenyl)acetate (2 g, 80%), which was used for next step without purification.

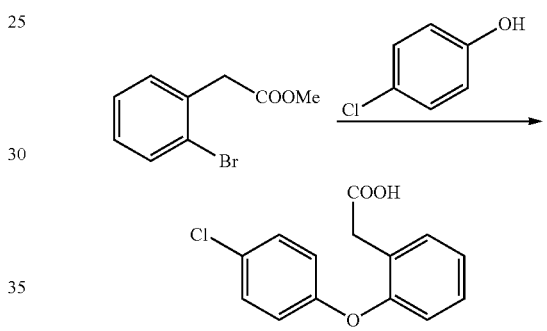

Step 2: 2-(2-(4-chlorophenoxy)phenyl)acetic acid 2-(2-Bromophenyl)acetate (10 g, 43.7 mmol) and 4-chlorophenol (5.61 g, 43.7 mmol) were dissolved in dioxane (150 mL) whiling warming to 50. To the resulting solution were added, under stirring in an inert nitrogen atmosphere, cesium carbonate (28.35 g, 87.4 mmol) and copper (I) chloride (1.73 g, 17.48 mmol). Finally N,N-dimethylglycine (0.9 g, 8.74 mmol) was added to the green suspension. The mixture was heated at 110 for 2 days while stirring. The mixture was filtrated over dicalite, which was washed with dioxane (20 mL). The dioxane was removed in vacuum to leave brownish oil. EtOAc was added to the oil and the pH of the resulting mixture was adjusted to 1 by addition of 1 M HCl. The organic phase was washed with saturated brine, dried over $Na_2SO_4$ and concentrated under vacuum to yield the crude product, which was purified by column chromatography to give 2-(2-(4-chlorophenoxy)phenyl)acetic acid (8 g, 70%).

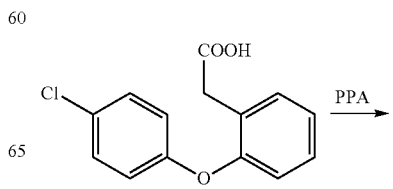

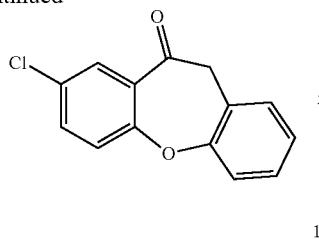

Step 3: 8-chlorodibenzo[b,f]oxepin-10(11H)-one

The solution of 2-(2-(4-chlorophenoxy)phenyl)acetic acid (2.1 g, 8 mmol) and PPA (21 g, 148 mmol) was heated to reflux overnight. Then the mixture was and the filtrate was removed in vacuo, dissolved in CH₂Cl₂, filtrated. The solvents were evaporated to give the crude product, which was purified by column chromatography to give 6-bromo-2-(tetrahydro-2H-pyran-4-yl)chroman-4-one (1.7 g, 80%).

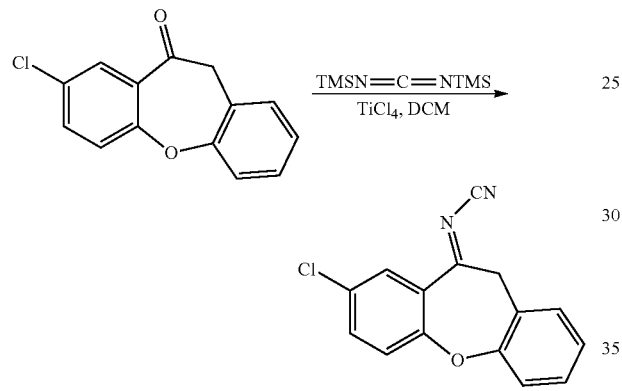

Step 4: (E)-N-(8-chlorodibenzo[b,f]oxepin-10(11H)-ylidene)cyanamide

To a solution of 8-chlorodibenzo[b,f]oxepin-10(11H)-one (732 mg, 3.84 mmol) in anhydrous DCM (30 mL) was added TiCl₄ (1 M solution in DCM, 7.8 mL, 7.8 mmol) dropwise within 15 minutes at room temperature. It was stirred another 1 h after the addition. To this mixture was added bis-trimethylsilylcarbodiimide (1.48 g, 1.89 mL, 8.46 mmol) dropwise. The resulting mixture was stirred for another 18 h after the addition. The reaction mixture was poured into ice-water (100 g), extracted with DCM (3×50 mL). The combined organic phases were dried over anhydrous Na₂SO₄, and filtered. The filtrate was concentrated to give (E)-N-(8-chlorodibenzo[b,f]oxepin-10(11H)-ylidene)cyanamide (500 mg, 68%), which was used for next step without further purification.

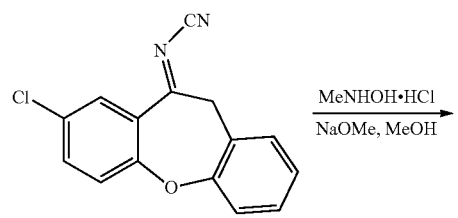

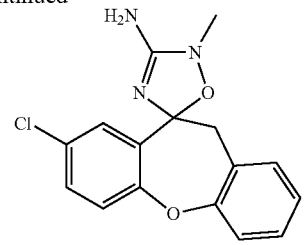

Step 5: 8-chloro-2'-methyl-2'H,11H-spiro[dibenzo[b,f]oxepine-10,5'-[1,2,4]oxadiazol]-3'-amine To a solution of methylhydroxylamine HCl salt (50.16 mg, 0.6 mmol) in anhydrous MeOH (6 mL) was added NaOMe (25% in MeOH (Wt. %), 0.12 mL, 0.54 mmol), followed by (E)-N-(8-chlorodibenzo[b,f]oxepin-10(11H)-ylidene)cyanamide (160 mg, 0.6 mmol). After stirred 10 min, the solvent was removed in vacuum. The residue was redissolved in DCM (10 mL). The mixture was filter, and the solvent was removed to give the residue, which was purified by column chromatography to give compound 144 (100 mg, 80%).
¹H-NMR (CDCl₃): 3.20 (m, 2H), 3.48 (m, 2H), 1.95 (m, 1H), 3.51 (m, 1H), 7.12 (m, 1H), 7.18 (m, 3H), 7.22 (m, 2H), 7.32 (m, 1H), 7.48 (m, 1H).

Example 124

6-bromo-7-fluoro-2'-methyl-2-phenyl-2'H-spiro[chroman-4,5'-[1,2,4]oxadiazol]-3'-amine (Compound 146)

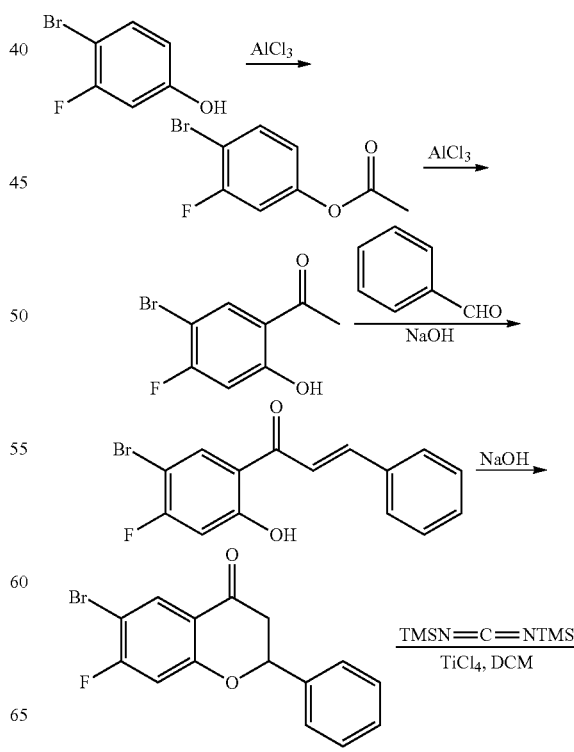

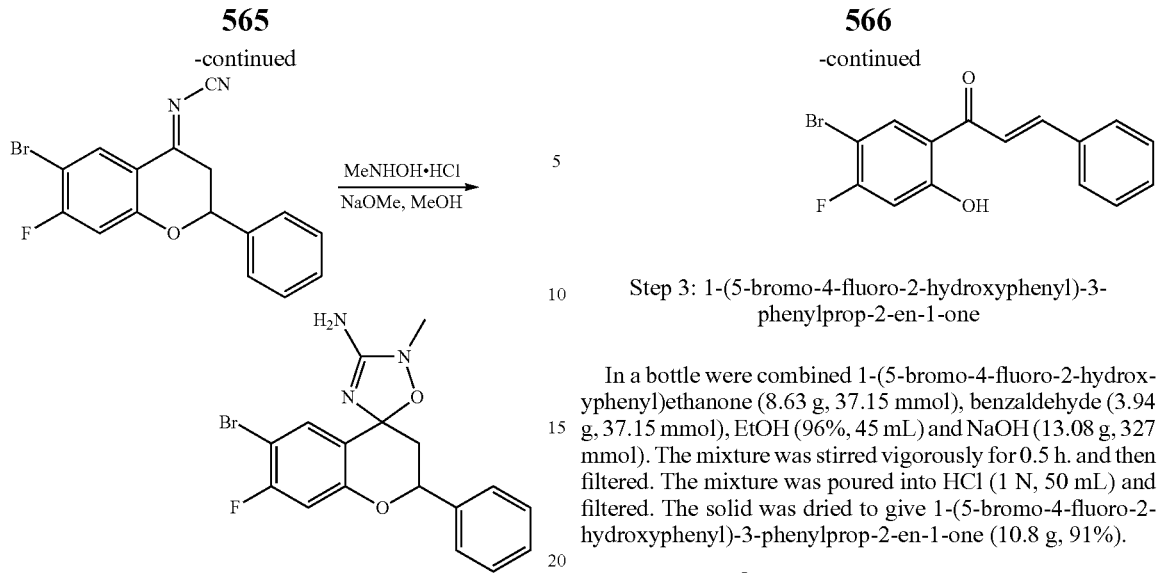

Experimental Data:

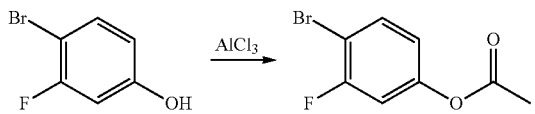

Step 1: 4-bromo-3-fluorophenyl acetate

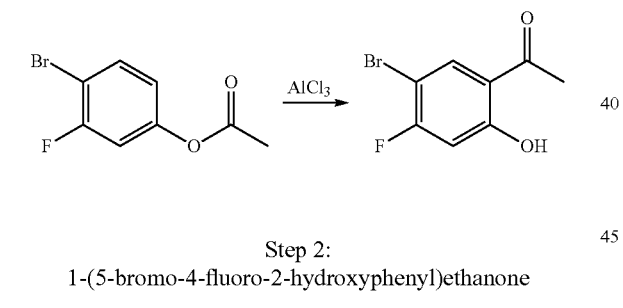

Step 2:
1-(5-bromo-4-fluoro-2-hydroxyphenyl)ethanone

A mixture of 4-bromo-3-fluorophenyl acetate (30 g, 0.13 mol) and AlCl$_3$ (34.32 g, 0.26 mol) was stirred at 120-140 for 2 h. The reaction mixture was cooled to 60-80 and ice-water was added and extraction was performed with EtOAc. The organic layer was washed with brine, dried and concentrated to give the residue, which was purified by column chromatography to give 1-(5-bromo-4-fluoro-2-hydroxyphenyl) ethanone (20 g, 67%). $^1$H-NMR (CDCl$_3$): 2.61 (s, 3H), 6.76 (d, 1H), 7.92 (d, 1H), 12.41 (s, 1H).

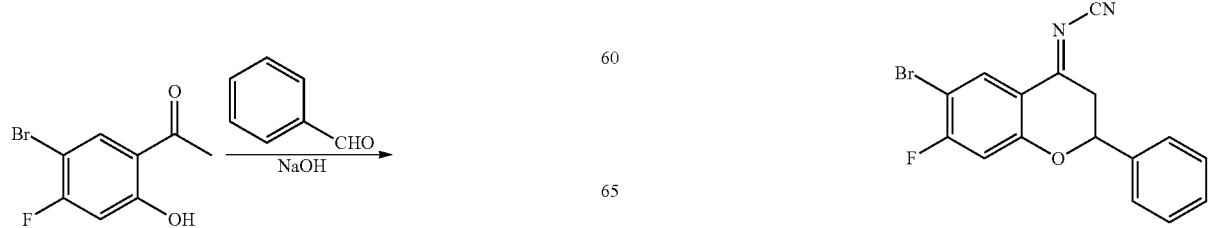

Step 3: 1-(5-bromo-4-fluoro-2-hydroxyphenyl)-3-phenylprop-2-en-1-one

In a bottle were combined 1-(5-bromo-4-fluoro-2-hydroxyphenyl)ethanone (8.63 g, 37.15 mmol), benzaldehyde (3.94 g, 37.15 mmol), EtOH (96%, 45 mL) and NaOH (13.08 g, 327 mmol). The mixture was stirred vigorously for 0.5 h. and then filtered. The mixture was poured into HCl (1 N, 50 mL) and filtered. The solid was dried to give 1-(5-bromo-4-fluoro-2-hydroxyphenyl)-3-phenylprop-2-en-1-one (10.8 g, 91%).

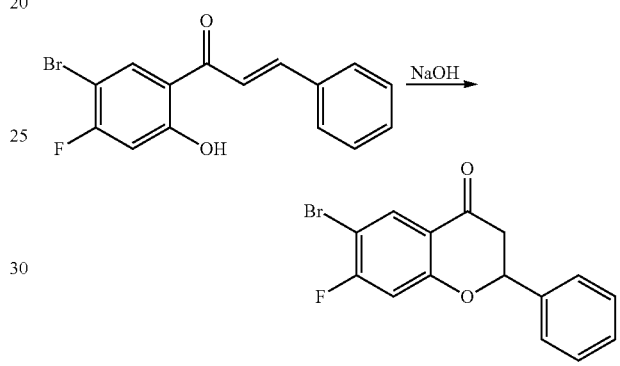

Step 4: 6-bromo-7-fluoro-2-phenylchroman-4-one 1-(5-Bromo-4-fluoro-2-hydroxyphenyl)-3-phenylprop-2-en-1-one (10.8 g, 33.75 mmol) was dissolved in H$_2$O (252 mL) and EtOH (84 mL). Then NaOH (1.35 g, 33.75 mmol) was added. The mixture was stirred overnight and filtered. The cake was dissolved in EtOAc and washed with H$_2$O twice. The organic layer was dried and filtered. The filtrate was concentrated to give 6-bromo-7-fluoro-2-phenylchroman-4-one (5.8 g, 54%). $^1$H-NMR (CDCl$_3$): 2.85 (m, 1H), 3.04 (m, 1H), 5.43 (m, 1H), 6.78 (m, 1H), 7.37 (m, 5H), 8.07 (m, 1H).

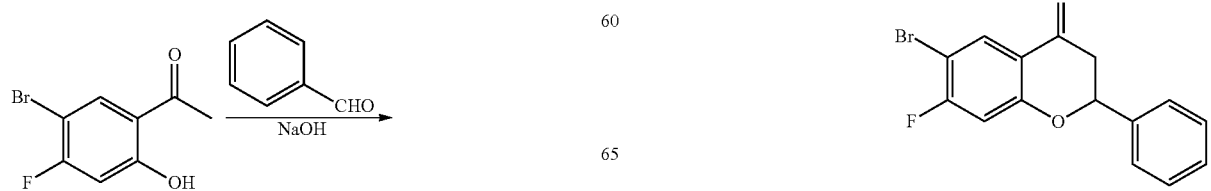

Step 5: N-(6-bromo-7-fluoro-2-phenylchroman-4-ylidene)cyanamide

To a solution of 6-bromo-7-fluoro-2-phenylchroman-4-one (400 mg, 1.25 mmol) in DCM (10 mL) was added TiCl₄ (2.5 mL, 1 M in CH₂Cl₂) dropwise within 15 minutes at room temperature. After stirring for 1 h, N,N'-methanediylidenebis(1,1,1-trimethylsilanamine) (0.62 mL, 2.75 mmol) was added dropwise. The mixture was stirred at room temperature overnight and poured into ice-water (50 g). The aqueous layer was extracted with CH₂Cl₂, which was combined with the organic layer. The organic layer was dried and concentrated to give crude N-(6-bromo-7-fluoro-2-phenylchroman-4-ylidene)cyanamide (327 mg, 78%). $^1$H-NMR (CDCl₃): 3.19 (m, 1H), 3.49 (m, 1H), 5.34 (m, 1H), 6.81 (d, 1H), 7.41 (m, 5H), 8.27 (d, 1H).

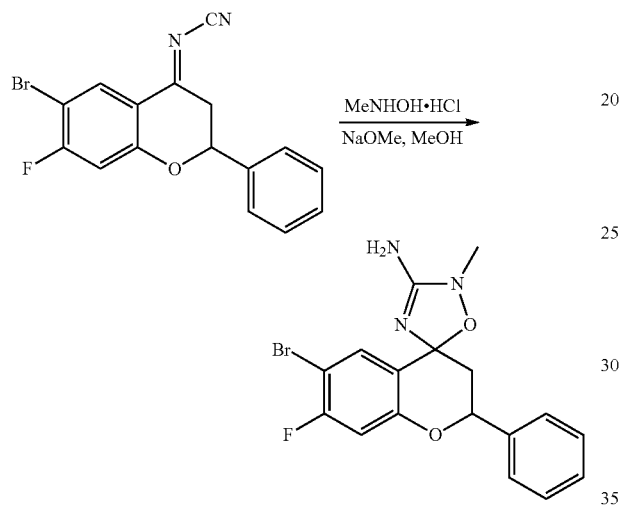

Step 6: 6-bromo-7-fluoro-2'-methyl-2-phenyl-2'H-spiro[chroman-4,5'-[1,2,4]oxadiazol]-3'-amine To a solution of N-methyl-hydroxylamine hydrochloride (35 mg, 0.355 mmol) in MeOH (5 mL) was added MeONa (0.07 mL, 25% (Wt.) in MeOH), followed by N-(6-bromo-7-fluoro-2-phenylchroman-4-ylidene)cyanamide (122 mg, 0.355 mmol). After stirred for 10 minutes, the solvent was removed in vacuo. The residue was purified by preparative TLC to give 6-bromo-7-fluoro-2'-methyl-2-phenyl-2'H-spiro[chroman-4,5'-[1,2,4]oxadiazol]-3'-amine (30 mg, 30%). $^1$H-NMR (MeOD): 2.18 (m, 1H), 2.33 (m, 1H), 3.08 (d, 3H), 5.28 (m, 1H), 6.75 (m, 1H), 7.38 (m, 5H), 7.61 (m, 1H).

Example 125

Compound 148

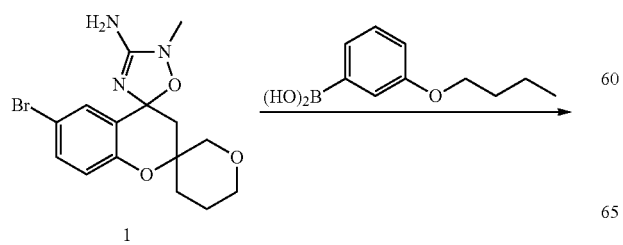

Step 1: Compound 148

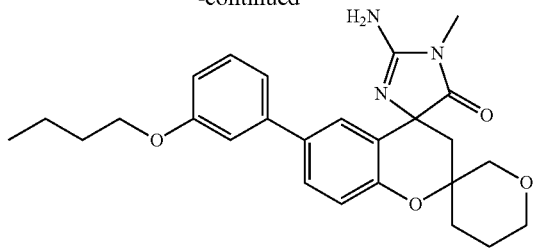

Pd(PPh₃)₂Cl₂ (10 mg, 0.01 mmol) in a 10 mL of flask under Ar₂ was treated sequentially with the amine 117i (52 mg, 0.14 mmol) in [1,4]dioxane (2 mL), Cs₂CO₃ (2 N, 0.5 mL) and 3-butoxyphenylboronic acid (51 mg, 0.28 mmol). The mixture was heated under 120 at Ar₂ under microwave for 30 minutes. The reaction mixture was concentrated in vacuo to give the residue, which was purified preparative TLC to give pure final product (6.50 mg, 10%). $^1$H-NMR (MeOD): 1.01 (m, 3H), 1.32 (m, 1H), 1.53 (m, 2H), 1.79 (m, 2H), 1.87-2.05 (m, 4H), 2.95 (m, 1H), 3.35 (m, 3H), 3.63 (m, 2H), 3.76-3.87 (m, 2H), 4.04 (m, 2H), 6.87 (m, 1H), 7.12 (m, 3H), 7.35 (m, 1H) 7.50 (m, 0.5H), 7.68 (m, 0.5H), 7.82 (m, 1H).

Example 126

3-(3'-amino-2'-methyl-3-phenyl-3,4-dihydro-2H,2'H-spiro[benzo[b]oxepine-5,5'-[1,2,4]oxadiazole]-7-yl)benzonitrile (Compound 153)

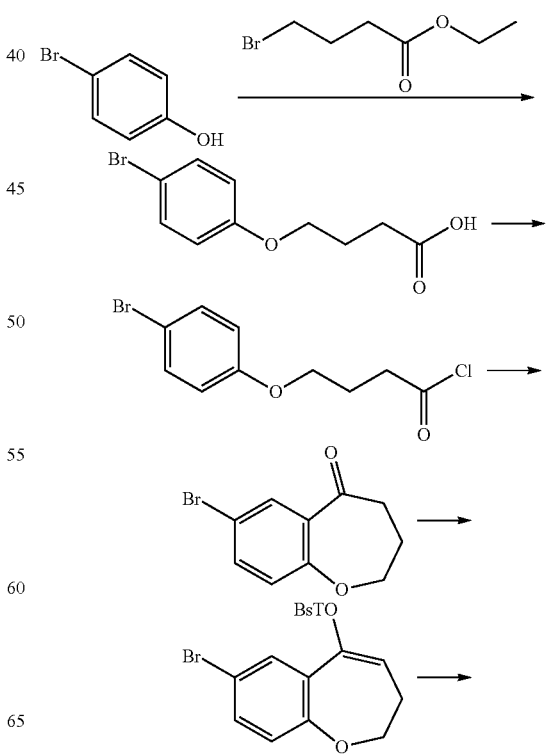

-continued

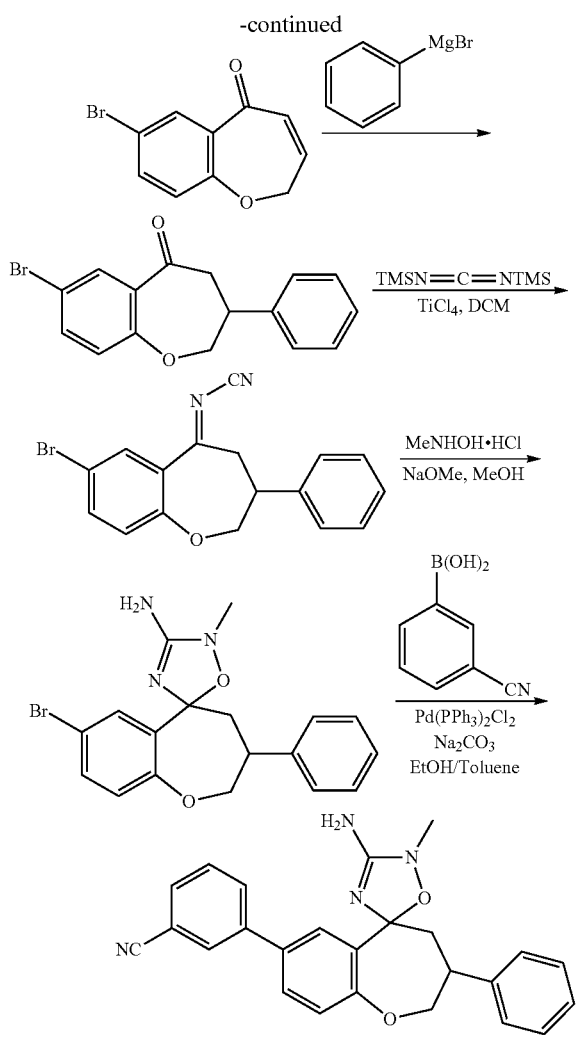

Experimental Data:

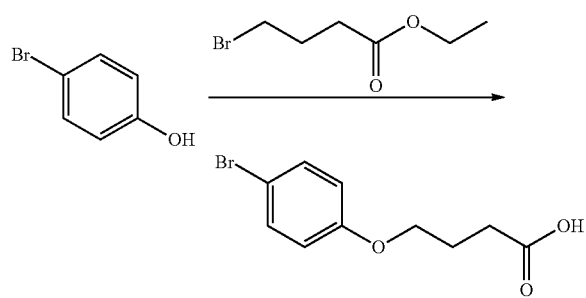

Step 1. 4-(4-Bromophenoxy)butanoic acid

4-Bromo-phenol (172 g, 1 mol), 4-bromo-butyric acid ethyl ester (212 g, 1.1 mol) and K$_2$CO$_3$ (250 g, 1.8 mol) was dissolved in DMF (1000 mL), the mixture was stirred at room temperature overnight. the solvent was removed and water was added to the residue, the mixture was extracted with ethyl acetate, the organic layer was washed with brine, and dried over Na$_2$SO$_4$ the solvent was removed, to the residue was added NaOH (3M, 1000 mol) and CH$_3$OH (600 mL), the mixture was stirred at 70 for 30 minutes and concentrated, the residue was dissolved in H$_2$O and the mixture was washed with diethylether, the aqueous layer was acidified with HCl, and the mixture was extracted with ethyl acetate, the organic layer was washed with brine, dried over Na$_2$SO$_4$, concentrated to give crude 4-(4-bromophenoxy)butanoic acid (239 g, 98%).

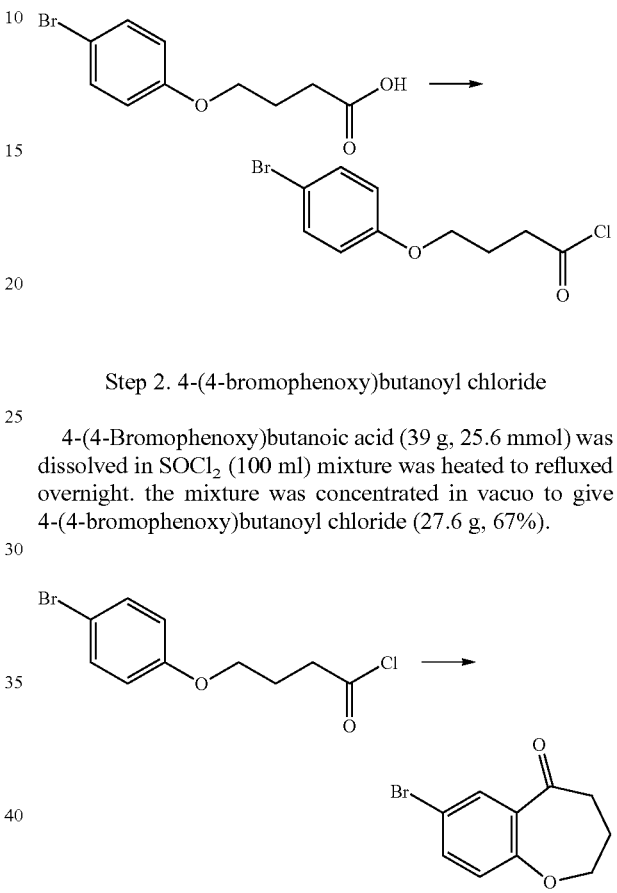

Step 2. 4-(4-bromophenoxy)butanoyl chloride 4-(4-Bromophenoxy)butanoic acid (39 g, 25.6 mmol) was dissolved in SOCl$_2$ (100 ml) mixture was heated to refluxed overnight. the mixture was concentrated in vacuo to give 4-(4-bromophenoxy)butanoyl chloride (27.6 g, 67%).

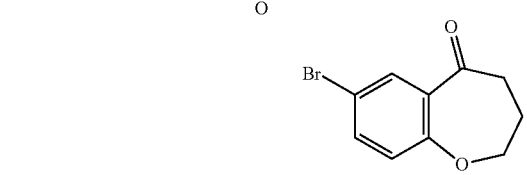

Step 3.
7-bromo-3,4-dihydrobenzo[b]oxepin-5(2H)-one

A solution of 4-(4-bromophenoxy)butanoyl chloride (27.6 g, 100 mmol) in DCM (200 mL) was added dropwise to a solution of AlCl$_3$ (50 g, 0.38 mol) in DCM (100 mL) at within 40 minutes, the mixture was stirred at 0 for 1.5 hours, and then stirred at room temperature overnight. the mixture was added to a stirred mixture of concentrated hydrochloric (500 mL) and ice, and then stirred for 1.5 hours. The mixture was extracted with DCM, washed with NaHCO$_3$, dried over Na$_2$SO$_4$ and concentrated to give crude 7-bromo-3,4-dihydrobenz o[b]oxepin-5(2H)-one (25 g, 96%).

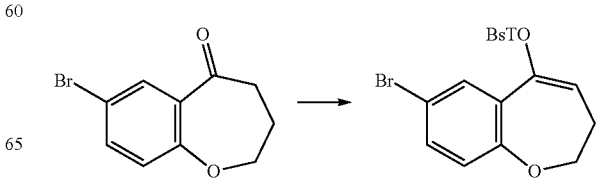

Step 4. (7-bromo-2,3-dihydrobenzo[b]oxepin-5-yloxy)(tert-butyl)dimethylsilane

To a 7-bromo-3,4-dihydrobenz o[b]oxepin-5(2H)-one (3 g, 12.6 mmol) and triethylamine (10 mL, 18.9 mmol) in DCM (100 mL) was added tert-butyldimethyl(trifluoromethylsulfonyl)silane (3.06 g, 12.4 mmol) dropwise under argon at room temperature, the mixture was stirred for 1 hour at room temperature. The mixture was washed with NaHCO₃, dried over Na₂SO₄, concentrated to give crude (7-bromo-2,3-dihydrobenzo[b]oxepin-5-yloxy)(tert-butyl)dimethylsilane (3.40 g, 81%).

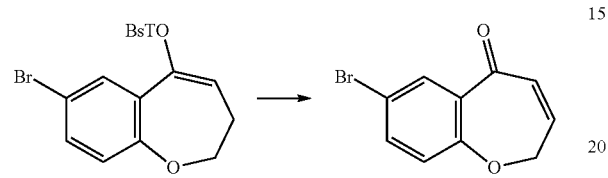

Step 5. 7-bromobenzo[b]oxepin-5(2H)-one 2,4,6-Collidine (5.6 ml), DDQ (9.0 g, 40 mmol) and (7-bromo-2,3-dihydrobenzo[b]oxepin-5-yloxy)(tert-butyl)dimethylsilane was dissolved in toluene, the mixture was stirred for 5.5 hours at room temperature. the mixture was concentrated in vacuo and then purified by column chromatography to give 7-bromobenzo[b]oxepin-5(2H)-one (4.5 g, 94%). ¹H-NMR (MeOD): 4.71 (m, 2H), 6.38 (m, 1H), 6.76 (m, 1H), 6.99 (m, 1H), 7.54 (m, 1H), 8.06 (m, 1H).

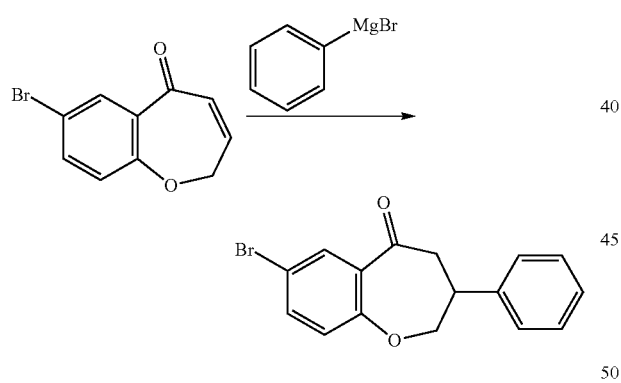

Step 6. 7-bromo-3-phenyl-3,4-dihydrobenzo[b]oxepin-5(2H)-one

To a solution of 7-bromobenzo[b]oxepin-5(2H)-one (1.33 g, 5.6 mmol), CuBr—SMe₂ (60 mg, 0.3 mmol) and HMPA (2.058 g, 11.5 mmol) in THF (30 mL) was added phenylmagnesium bromide (3.0 M, 3.7 mL) at −78, the mixture was stirred at −78 for 1 hour. The mixture was quenched by HCl (10%, 5 mL), extracted with ethoxyethane, and then washed with NaHCO₃, brine, dried over Na₂SO₄, concentrated and purified by column chromatography to give 7-bromo-3-phenyl-3,4-dihydrobenzo[b]oxepin-5(2H)-one (300 mg, 17%). ¹H-NMR(CH₂D₂): 3.11 (m, 2H), 3.49 (m, 1H), 4.28 (m, 2H), 6.93 (m, 1H), 7.17 (m, 1H), 7.23 (m, 4H), 7.45 (m, 1H), 7.83 (m, 1H)

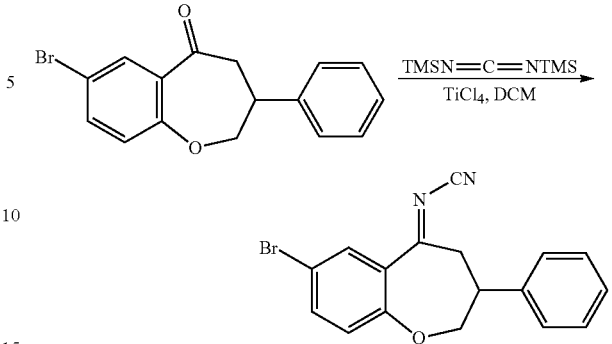

Step 7. N-(7-bromo-3-phenyl-3,4-dihydrobenzo[b]oxepin-5(2H)-ylidene)cyanamide

To a solution of 7-bromo-3-phenyl-3,4-dihydrobenzo[b]oxepin-5(2H)-one (158 mg, 0.5 mmol) in DCM (5 mL) was added TiCl₄ (1 mL, 1 M in CH₂Cl₂) dropwise within 15 minutes at room temperature. After stirring for 1 h, N,N'-methanediylidenebis(1,1,1-trimethylsilanamine) (0.25 mL, 1.11 mmol) was added dropwise. The mixture was stirred at room temperature overnight and poured into ice-water (25 g). The aqueous layer was extracted with CH₂Cl₂, which was combined with the organic layer. The organic layer was dried and concentrated to give crude N-(7-bromo-3-phenyl-3,4-dihydrobenzo[b]oxepin-5(2H)-ylidene)cyanamide (160 mg, 94%).

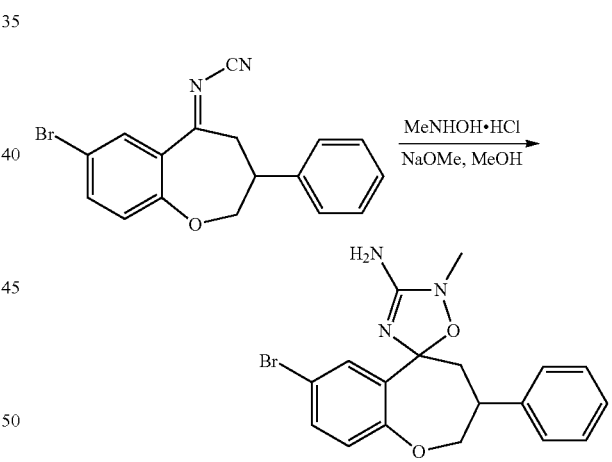

Step 8. 7-bromo-2'-methyl-3-phenyl-3,4-dihydro-2H,2'H-spiro[benzo[b]oxepine-5,5'-[1,2,4]oxadiazol]-3'-amine To a solution of N-methyl-hydroxylamine hydrochloride (42 mg, 0.5 mmol) in MeOH (10 mL) was added MeONa (0.1 mL, 25% (Wt.) in MeOH), followed by N-(7-bromo-3-phenyl-3,4-dihydrobenzo[b]oxepin-5(2H)-ylidene)cyanamide (170 mg, 0.5 mmol). After stirred for 10 minutes, the solvent was removed in vacuo. The residue was purified by preparative TLC to give 6-bromo-2'-methyl-2'H-spiro[chroman-4,5'-[1,2,4]oxadiazol]-3'-amine (140 mg, 72%).

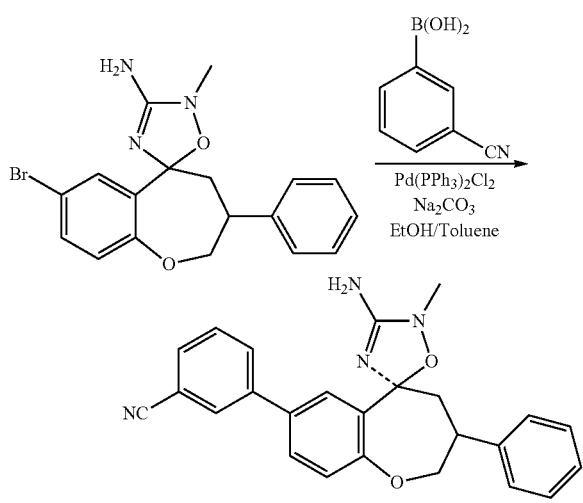

Step 9. 3-(3'-amino-2'-methyl-3-phenyl-3,4-dihydro-2H,2'H-spiro[benzo[b]oxepine-5,5'-[1,2,4]oxadiazole]-7-yl)benzonitrile Pd(PPh₃)₂Cl₂ (3 mg, 0.003 mmol) in a 10 mL of flask under Ar₂ was treated sequentially with 7-bromo-2'-methyl-3-phenyl-3,4-dihydro-2H,2'H-spiro[benzo[b]oxepine-5,5'-[1,2,4]oxadiazol]-3'-amine (77.4 mg, 0.2 mmol) in [1,4]dioxane (2.0 mL), Cs₂CO₃ (2 N, 1 mL) and 3-cyanophenylboronic acid (58.8 mg, 0.4 mmol) The mixture was heated under 120 at Ar₂ under microwave for 30 minutes. The reaction mixture was concentrated in vacuo to give the residue, which was purified preparative TLC and HPLC to give 3-(3'-amino-2'-methyl-3-phenyl-3,4-dihydro-2H,2'H-spiro[benzo[b]oxepine-5,5'-[1,2,4]oxadiazole]-7-yl)benzonitrile (20 mg, 24%). ¹H-NMR (MeOD): 2.67 (m, 2H), 3.48 (m, 3H), 3.65 (m, 1H), 3.88 (m, 0.3H), 4.19 (m, 0.7H), 4.50 (d, 1H), 7.23 (m, 6H), 7.66 (m, 3H), 7.81 (m, 1H), 8.02 (m, 3H).

Example 127

Compound 154

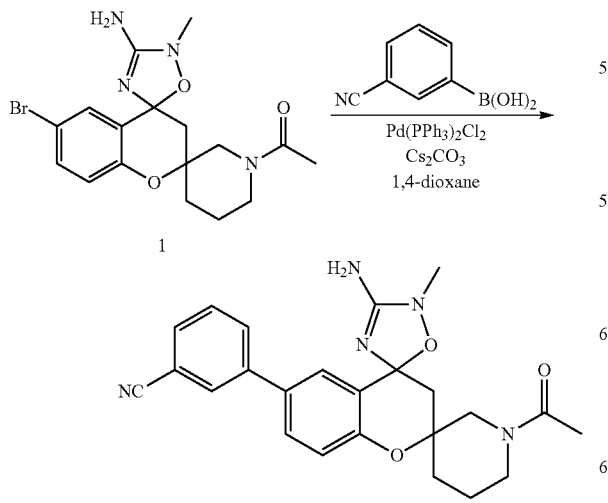

Step 1: Compound 154

Pd(PPh₃)₂Cl₂ (10 mg) in a 10 mL of tube under Ar₂ was treated sequentially with 1 (40 mg, 0.1 mmol) in 1,4-dioxane (2 mL), Cs₂CO₃ (2 N, 0.4 mL) and 3-cyanophenylboronic acid (29 mg, 0.2 mmol). The mixture was heated under microwave at 120 for 30 min. The reaction mixture was concentrated in vacuo to give the residue, which was purified by preparative TLC and then by preparative HPLC to give the target molecule compound 154 (11 mg, 10%). ¹H-NMR (MeOD): 1.80 (m, 1H), 2.01 (s, 3H), 2.23 (m, 2H), 2.74 (m, 1H), 3.05 (m, 1H), 3.39 (m, 3H), 3.61 (s, 2H), 3.92 (m, 1H), 4.34 (m, 1H), 7.02 (m, 1H), 7.64 (m, 2H), 7.92 (m, 2H).

Example 128

3-(2-(2,2-dimethyltetrahydro-2H-pyran-4-yl)-3'-imino-2'-methylspiro[chroman-4,5'-[1,2,4]oxadiazolidine]-6-yl)benzonitrile (Compound 155)

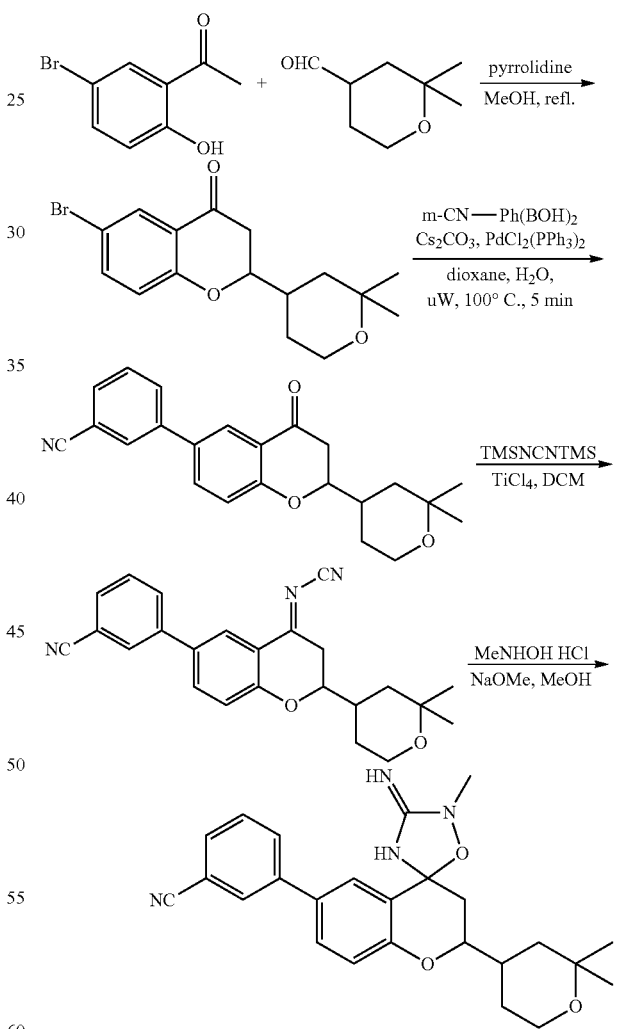

Step 1: Preparation of 6-bromo-2-(2,2-dimethyltetrahydro-2H-pyran-4-yl)chroman-4-one A solution of 2,2-dimethyltetrahydro-2H-pyran-4-carbaldehyde (1.858 g, 13.08 mmol), 5'-bromo-2-hydroxy-acetophone (2.813 g, 13.08 mmol) in MeOH (30 mL) containing pyrrolidine (1 mL) was heated to reflux for 2 h. The solvent was removed under reduced pressure, and the residue was dissolved in ethyl acetate, and washed with 1 M NaOH, 1 M HCl, H$_2$O and brine successively, and dried, and filtered. The filtrate was concentrated to dryness. The crude product was further purified by flash chromatography on silica gel (40 g, eluted with ethyl acetate in hexane 0-30%) give 6-bromo-2-(2,2-dimethyltetrahydro-2H-pyran-4-yl)chroman-4-one as a brownish solid (2.32 g). MS ESI+ve m/z 339 (M+H)$^+$.

Step 2: Preparation of 3-(2-(2,2-dimethyltetrahydro-2H-pyran-4-yl)-4-oxochroman-6-yl)benzonitrile To a solution of crude 6-bromo-2-(2,2-dimethyltetrahydro-2H-pyran-4-yl)chroman-4-one (460 mg, 1.36 mmol), 3-cyanophenylboronic acid (299 mg, 2.0 mmol) and Cs$_2$CO$_3$ (866 mg, 2.72 mmol) in 1,4-dioxane (5 mL) and H$_2$O (1 mL) charged in a 10 mL CEM microwave test tube was added PdCl$_2$(PPh$_3$)$_2$ (50 mg), then the system was degassed by sweeping N$_2$ and capped. Then the mixture was heated to 100° C. for 10 min in a CEM microwave reactor. The solvent was removed under reduced pressure and the residue was purified by flash chromatography on silica gel give (3-(2-(2,2-dimethyltetrahydro-2H-pyran-4-yl)-4-oxochroman-6-yl)benzonitrile (251 mg). MS ESI+ve m/z 362 (M+H)$^+$.

Step 3: Preparation of (E)-N-(6-(3-cyanophenyl)-2-(2,2-dimethyltetrahydro-2H-pyran-4-yl)chroman-4-ylidene)cyanamide To a solution of 3-(2-(2,2-dimethyltetrahydro-2H-pyran-4-yl)-4-oxochroman-6-yl)benzonitrile (251 mg, 0.69 mmol) in anhydrous DCM (15 mL) under N$_2$ atmosphere was added 1 M TiCl$_4$ (in DCM, 1.4 mL, 1.4 mmol) dropwise within 5 min at room temperature. It was stirred another 1 h after the addition. To this mixture was added Bis-trimethylsilylcarbodiimide (283 mg, 340 µL 1.52 mmol) dropwise. The resulting mixture was stirred for another 20 h after the addition. The reaction mixture was poured into ice-water (20 g), It was transferred to a separating funnel after stirred for 30. The separated aqueous phase was extracted with DCM (2×20 mL). The combined organic phases were dried over anhydrous Na$_2$SO$_4$, and filtered, and concentrated to give yellowish gel like solid (E)-N-(6-(3-cyanophenyl)-2-(2,2-dimethyltetrahydro-2H-pyran-4-yl)chroman-4-ylidene)cyanamide (276 mg), which was used for next step without further purification. MS ESI+ve m/z 386 (M+H)$^+$.

Step 4: Preparation of 3-(2-(2,2-dimethyltetrahydro-2H-pyran-4-yl)-3'-imino-2'-methylspiro[chroman-4,5'-[1,2,4]oxadiazolidine]-6-yl)benzonitrile To a solution of methylhydroxylamine HCl salt (58 mg, 0.69 mmol) in anhydrous MeOH (3 mL) was added NaOMe (25 w % in MeOH, 140 µL, 0.62 mmol), 10 min later, followed by a solution of crude (E)-N-(6-(3-cyanophenyl)-2-(2,2-dimethyltetrahydro-2H-pyran-4-yl)chroman-4-ylidene)cyanamide obtained in step 3 (276 mg, 0.69 mmol) solution in MeOH (5 mL), After stirred 10 min, the solvent was removed in vacuum. The residue was redissolved in DCM (20 mL) and filtered, and the solvent was removed in vacuum to give crude product, which was purified by preparative HPLC to afford 130 mg of 3-(2-(2,2-dimethyltetrahydro-2H-pyran-4-yl)-3'-imino-2'-methylspiro[chroman-4,5'-[1,2,4]oxadiazolidine]-6-yl)benzonitrile TFA salt as a white solid. MS ESI+ve m/z 433 (M+H)$^+$. $^1$H NMR (400 MHz, CD$_3$OD): 8.00-7.92 (m, 3H), 7.74-7.68 (m, 2H), 7.62 (t, J=7.6 Hz, 1H), 7.05 (d, J=8.4 Hz, 1H), 4.07 (dd, J=12.4, 5.6 Hz, 1H), 3.78 (m, 2H), 3.38, 3.44, 3.43 (s, 3H, several isomers), 2.20 (m, 1H), 2.01 (m, 1H), 1.88 (m, 1H), 1.66 (m, 1H), 1.49-1.32 (m, 2H), 1.29 (s, 3H), 1.26 (m, 3H).

Example 129

3-(2-Amino-1-methyl-5-oxo-2'-phenyl-1,5-dihydrospiro[imidazole-4,4'-thiochroman]-6'-yl)benzonitrile (Cmpd. 156)

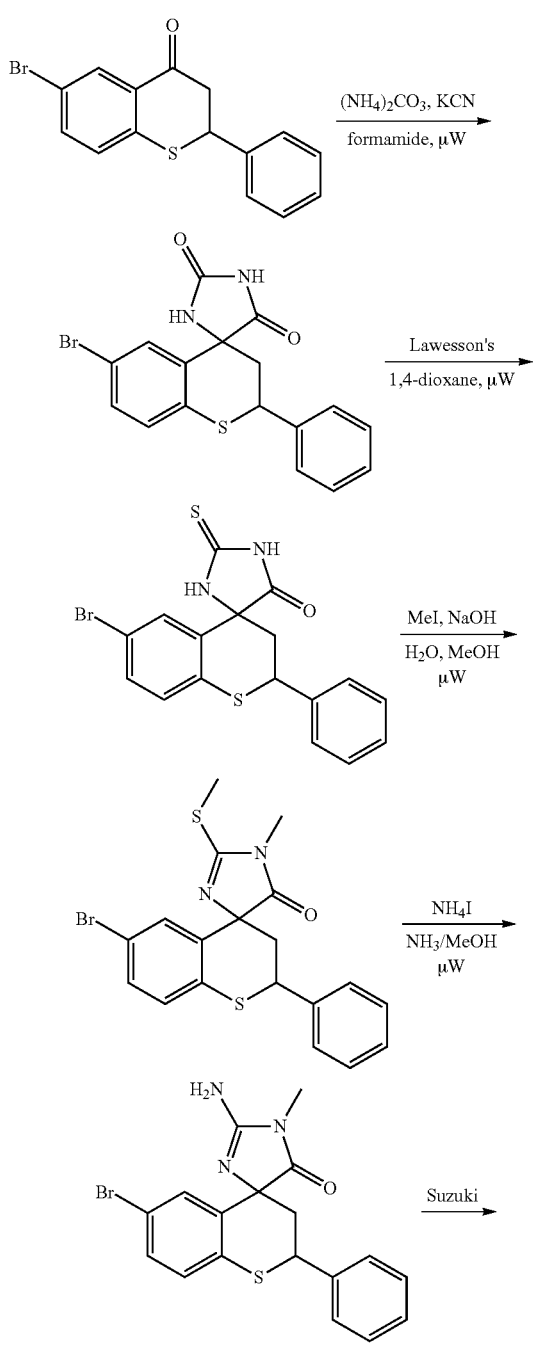

-continued

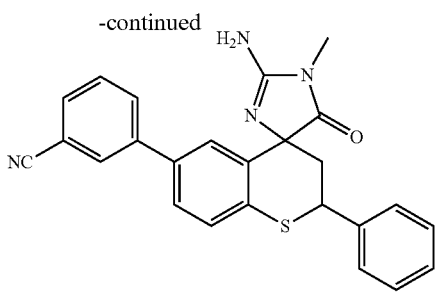

Step 1

To a 10 mL CEM microwave test tube charged with 6-bromo-2-phenylthiochroman-4-one (344 mg, 1.08 mmol), KCN (150 mg, 2.2 mmol), and $(NH_4)_2CO_3$ (800 mg, 7.7 mmol) is added formamide (6.5 mL). The resulting mixture is heated in a CEM microwave reactor at 60° C. for 1.5 hrs, 65° C. for 1.5 hrs, then 70° C. for 2 hrs. The resulting mixture is diluted with EtOAc (20 mL) and washed with $H_2O$ (3×10 mL). The organic layer is dried over $Na_2SO_4$, and solvent is removed in vacuo to give a crude product, which is purified by flash chromatography column (0 to 60% EtOAc/hexane) to give the 6'-bromo-2'-phenylspiro[imidazolidine-4,4'-thiochroman]-2,5-dione (237 mg). MS ESI+ve m/z 389 (M+H)$^+$.

Step 2

A solution of 6'-bromo-2'-phenylspiro[imidazolidine-4,4'-thiochroman]-2,5-dione (237 mg, 0.61 mmol) and Lawesson's reagent (246 mg, 0.61 mmol) in 1,4-dioxane (3 mL) in a 10 mL CEM microwave test tube is heated in a CEM microwave reactor at 110° C. for 30 min. After cooled to rt, the solvent is removed in vacuo, and the residue is purified by flash chromatography column to give 6'-bromo-2'-phenyl-2-thioxospiro[imidazolidine-4,4'-thiochroman]-5-one (200 mg, 81%). MS ESI+ve m/z 405 (M+H)$^+$.

Step 3

To a solution of 6'-bromo-2'-phenyl-2-thioxospiro[imidazolidine-4,4'-thiochroman]-5-one (100 mg, 0.25 mmol) in MeOH (2 mL) charged in a 10 mL CEM microwave test tube is added a 0.6 N NaOH aqueous solution (0.5 mL). After stirring at rt for 10 min, MeI (0.5 mL, excess) is added, and the reaction mixture is heated in a CEM microwave reactor at 60° C. for 10 min. In another 10 mL CEM microwave test tube, the same reaction is repeated with the same amounts of starting material, reagents, and solvent. The resulting mixtures are combined, and diluted with ethyl acetate, and washed with $H_2O$ and brine successively, dried over anhydrous $Na_2SO_4$, filtered, and concentrated in vacuo to give the crude product, which is purified by preparative HPLC to give 6'-bromo-1-methyl-2-(methylthio)-2'-phenylspiro[imidazole-4,4'-thiochroman]-5(1H)-one (56 mg) MS ESI+ve m/z 433 (M+H)$^+$.

Step 4

A suspension of 6'-bromo-1-methyl-2-(methylthio)-2'-phenylspiro[imidazole-4,4'-thiochroman]-5(1H)-one (56 mg, 0.13 mmol) and $NH_4I$ (100 mg, excess) in 7 M $NH_3$/MeOH (4 mL) and 1,4-dioxane (1 mL) charged in a 10 mL CEM microwave test tube is heated to 110° C. for 1 h. The solvent is removed in vacuo and the residue is purified by preparative HPLC to give 2-amino-6'-bromo-1-methyl-2'-phenylspiro[imidazole-4,4'-thiochroman]-5(1H)-one as TFA salt. MS ESI+ve m/z 402 (M+H)$^+$.

Step 5

To a solution of 2-amino-6'-bromo-1-methyl-2'-phenylspiro[imidazole-4,4'-thiochroman]-5(1H)-one TFA salt (70 mg, 0.14 mmol), 3-cyanophenylboronic acid (51 mg, 0.34 mmol), and $Cs_2CO_3$ (250 mg) in 1,4-dioxane (4 mL) and $H_2O$ (0.5 mL) charged in a 10 mL CEM microwave test tube is added $PdCl_2(PPh_3)_2$ (20 mg). Then the system is degassed by sweeping with $N_2$. The tube is capped and heated to 110° C. for 30 min in a CEM microwave reactor. Solvent is removed in vacuo and the residue is purified by preparative HPLC to give 3-(2-amino-1-methyl-5-oxo-2'-phenyl-1,5-dihydrospiro-[imidazole-4,4'-thiochroman]-6'-yl)benzonitrile (30 mg) as a TFA salt. MS ESI+ve m/z 425 (M+H)$^+$.

$^1$H NMR (400 MHz, $CD_3OD$): less polar isomer: 8.00-7.87 (m, 2H), 7.72-7.59 (m, 3H), 7.52-7.33 (m, 7H), 5.26 and 4.65 (dd and dd, 1H), 3.34 and 3.25 (s and s, 3H), 2.84-2.60 (m, 2H); more polar isomer: 7.99-7.87 (m, 2H), 7.72-7.57 (m, 3H), 7.51-7.33 (m, 7H), 5.30 (dd, 1H), 3.34 and 3.08 (s and s, 3H), 2.82-2.63 (m, 2H).

Example 130

3-(2-Amino-1-methyl-1',5-dioxo-2'-phenyl-1,5-dihydrospiro[imidazole-4,4'-thiochroman]-6'-yl)benzonitrile (Cmpd 157)

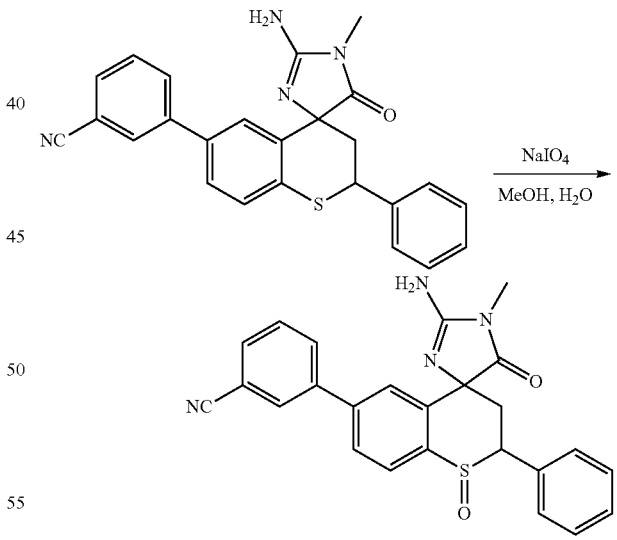

To a solution of 3-(2-amino-1-methyl-5-oxo-2'-phenyl-1, 5-dihydrospiro[imidazole-4,4'-thiochroman]-6'-yl)benzonitrile TFA salt (27 mg, 0.05 mmol) in MeOH (5 mL) and $H_2O$ (0.1 mL) is added $NaIO_4$ (21.4 mg, 0.10 mmol). The resulting mixture is stirred overnight at rt, then purified by preparative HPLC to give 3-(2-amino-1-methyl-1',5-dioxo-2'-phenyl-1,5-dihydrospiro[imidazole-4,4'-thiochroman]-6'-yl)benzonitrile TFA salt (16 mg) with 5 mg of recovered starting material. MS ESI+ve m/z 441 (M+H)$^+$.

$^1$H NMR (400 MHz, CD$_3$OD): 8.10-7.41 (m, 12H), 5.20 (dd, 1H), 3.61 (m, 1H), 3.26, 3.25 and 3.11 (s, s and s, 3H), 2.70 (m, 1H).

Example 131

3-(2-Amino-1-methyl-1',1',5-trioxo-2'-phenyl-1,5-dihydrospiro[imidazole-4,4'-thiochroman]-6'-yl)benzonitrile (Cmpd. 158)

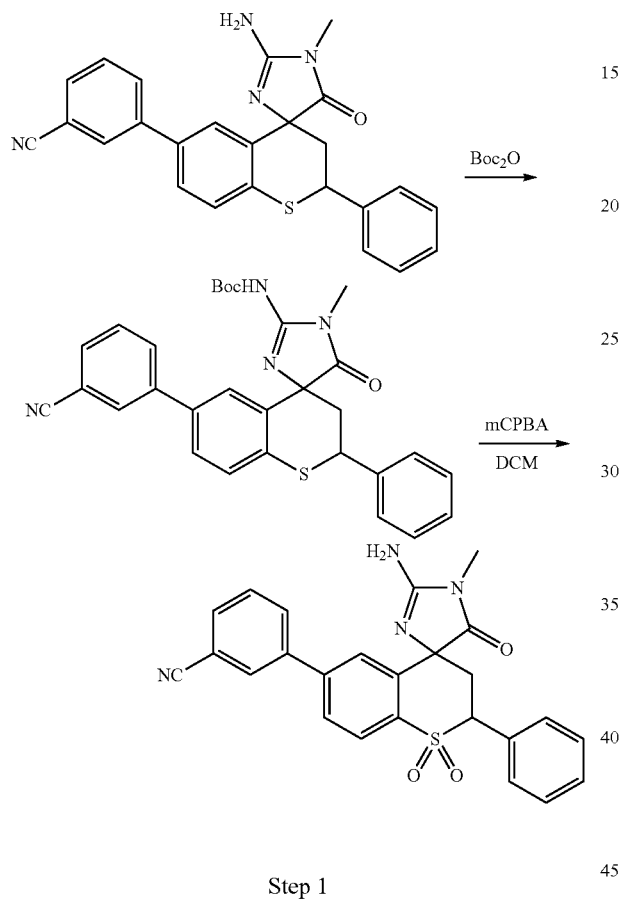

Step 1

A crude product of 3-(2-amino-1-methyl-5-oxo-2'-phenyl-1,5-dihydrospiro[imidazole-4,4'-thiochroman]-6'-yl)benzonitrile (60 mg, 0.14 mmol) from Suzuki coupling is dissolved in THF (10 mL). To this solution is added TEA (1 mL, excess) and Boc$_2$O (250 mg). The resulting mixture is stirred for 12 h at rt and concentrated. The residue is dissolved in ethyl acetate (15 mL), washed with 1 M HCl and brine successively, and dried over Na$_2$SO$_4$. The solvent is removed in vacuo to give a crude product, which is purified by preparative HPLC to give 3-(N-Boc-2-amino-1-methyl-1',5-dioxo-2'-phenyl-1,5-dihydrospiro[imidazole-4,4'-thiochroman]-6'-yl)benzonitrile. MS ESI+ve m/z 525 (M+H)$^+$.

Step 2

To a solution of 3-(N-Boc-2-amino-1-methyl-1',5-dioxo-2'-phenyl-1,5-dihydrospiro[imidazole-4,4'-thiochroman]-6'-yl)benzonitrile (5 mg) in DCM (3 mL) at 0° C. is added mCPBA (40 mg, excess). The mixture is stirred for 10 min at 0° C., then it is allowed to warm to rt for 1.5 h. NaHCO$_3$ (40 mg) is added and evaporated to dryness. The residue is dissolved in MeOH, filtered, and purified by preparative HPLC to give 3-(2-amino-1-methyl-1',1',5-trioxo-2'-phenyl-1,5-dihydrospiro[imidazole-4,4'-thiochroman]-6'-yl)benzonitrile TFA salt (6 mg). MS ESI+ve m/z 457 (M+H)$^+$.

$^1$H NMR (400 MHz, CD$_3$OD): 8.12-7.42 (m, 12H), 5.20 (dd, 1H), 3.59 (m, 1H), 3.32 and 3.21 (s and s, 3H), 2.83 (m, 1H).

Example 132

Compound 163

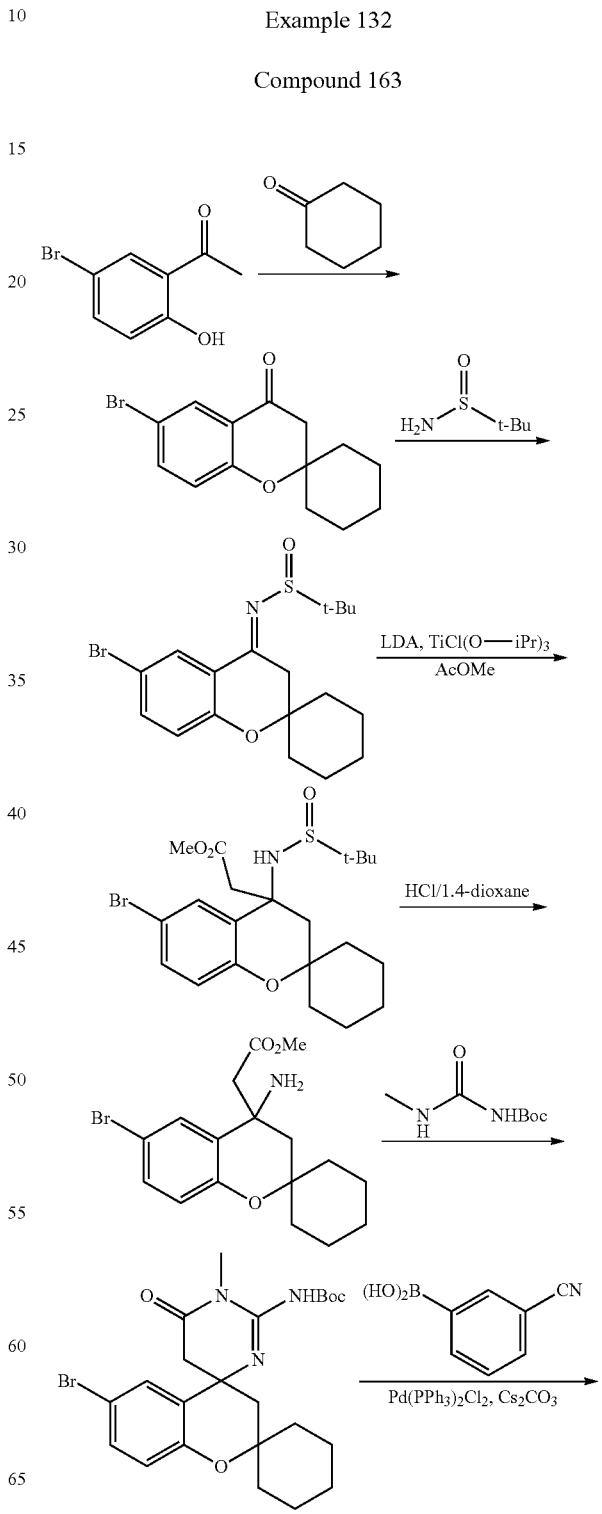

-continued

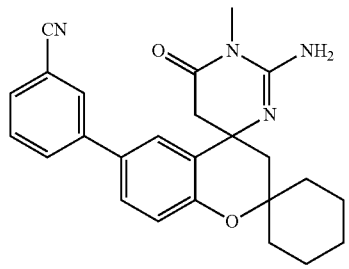

Experimental Data:

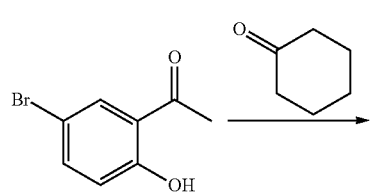

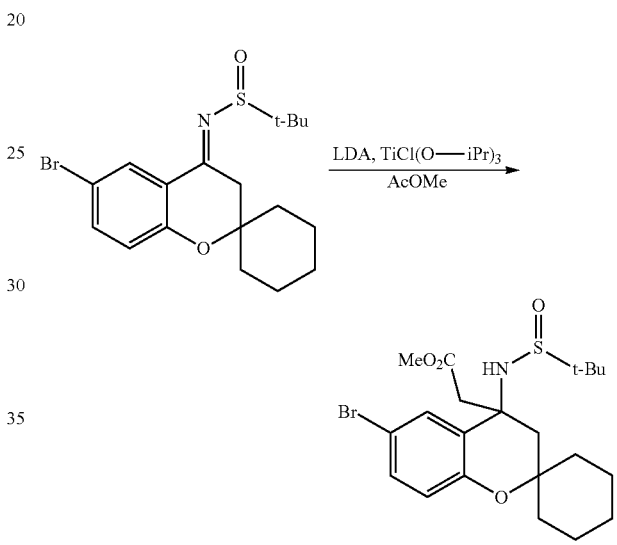

Step 1.
6-bromospiro[chroman-2,1'-cyclohexan]-4-one

To a solution of 1-(5-bromo-2-hydroxy-phenyl)-ethanone (60 g, 280 mmol) and pyrrolidine (37.8 g, 532 mmol) in methanol (1200 mL) was added cyclohexanone (55 g, 560 mmol), and the mixture was reflux overnight. The solvent was removed in vacuo, and then added H$_2$O and HCl to make the mixture to PH=1, extracted with ethyl acetate. The organic layer was dried over anhydrous Na$_2$SO$_4$, filtered, and evaporated to give 6-bromospiro[chroman-2,1'-cyclohexan]-4-one (90 g, 100%). $^1$H NMR (CDCl$_3$): 1.49 (d, 4H), 1.64 (d, 4H), 1.83 (s, 1H), 1.98 (d, 2H), 2.11 (t, 1H), 2.31 (s, 1H), 2.68 (s, 1H), 6.87 (d, 1H), 7.50 (d, 1H), 7.92 (s, 1H).

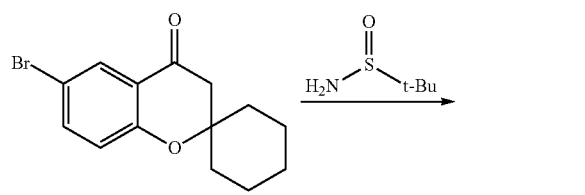

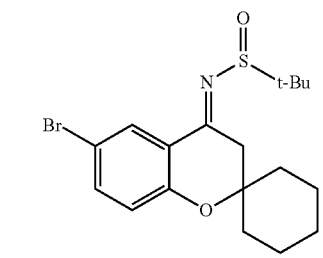

Step 2. (E)-N-(6-bromospiro[chroman-2,1'-cyclohexane]-4-ylidene)-2-methylprop-ane-2-sulfinamide The compound of 2-methylpropane-2-sulfinamide (29.54 g, 244.2 mmol) was added the solution of 6-bromospiro[chroman-2,1'-cyclohexan]-4-one (78.97 g, 268.6 mmol) in dry THF (900 mL), and then tetraisopropoxytitanium (193.1 g, 488.3 mmol) was added, The reaction mixture was reflux overnight. The mixture was removed in vacuo, and then quenched by brine, extracted with ethyl acetate. The ethyl acetate was dried over anhydrous Na$_2$SO$_4$, filtered, and evaporated to give (E)-N-(6-bromospiro[chroman-2,1'-cyclohexane]-4-ylidene)-2-methylpropane-2-sulfinamide (50 g, 40%). $^1$H NMR (CDCl$_3$): 1.30 (s, 10H), 1.51 (m, 5H), 1.62 (m, 4H), 1.83 (d, 2H), 3.07 (d, 1H), 3.43 (d, 1H), 5.29 (s, 2H), 6.79 (d, 1H), 7.41 (dd, 1H), 7.96 (d, 1H).

Step 3. methyl 2-(6-bromo-4-(1,1-dimethylethylsulfinamido)spiro[chroman-2,1'-cyclohexane]-4-yl)acetate To a solution of methyl acetate (1.86 g, 0.025 mol) in THF (18 mL) was added LDA (2 M in THF) was added dropwise via a syring at −78. After stirring at −78 for 30 minutes, a solution of (E)-N-(6-bromospiro[chroman-2,1'-cyclohexane]-4-ylidene)-2-methylpropane-2-sulfonamide (5.0 g, 0.0126 mol) in THF (7.4 mL) was added dropwise via a syring. The mixture was stirring at −78 for 3 h. The reaction was quenched with aqueous NH$_4$Cl solution and allowed to warming to room temperature. The mixture was diluted with water and extracted with EtOAc. The organic layer was dried over Na$_2$SO$_4$, filtered and concentrated to give the product, which was purified by chromatography to afford methyl 2-(6-bromo-4-(1,1-dimethylethylsulfinamido)spiro[chroman-2,1'-cyclohexane]-4-yl)acetate (1.4 g, 33%). $^1$H NMR (CDCl$_3$): 1.23 (s, 9H), 1.36-1.52 (m, 4H), 1.57 (m, 1H), 1.66 (m, 3H), 1.86 (d, 2H), 2.24 (d, 1H), 2.67 (d, 1H), 2.93 (s, 3H), 3.71 (s, 3H), 5.34 (s, 1H), 6.79 (d, 1H), 7.26 (s, 1H), 7.39 (s, 1H).

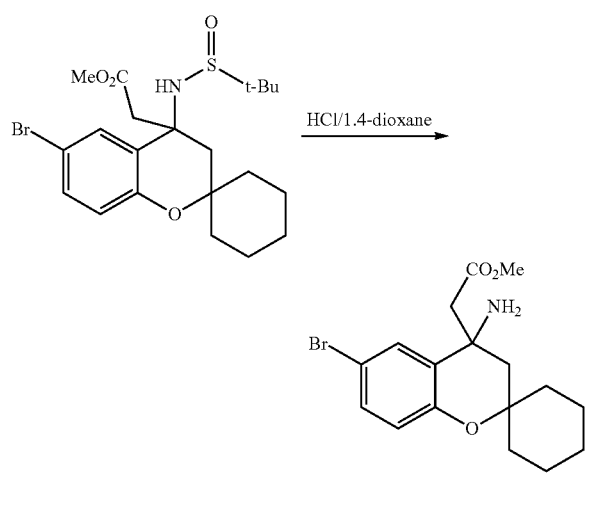

Step 4. methyl 2-(4-amino-6-bromospiro[chroman-2,1'-cyclohexane]-4-yl)acetate To a solution of methyl 2-(6-bromo-4-(1,1-dimethylethylsulfinamido)spiro[chroman-2,1'-cyclohexane]-4-yl)acetate (200 mg, 0.42 mmol) in MeOH (2 mL) was added 4 N HCl/1,4-dioxane (2 mL). After stirring for 30 minutes, the mixture was concentrated. The residue was dissolved in MeOH (1 mL) stirring for 5 minutes and evaporated again to afford methyl 2-(4-amino-6-bromospiro[chroman-2,1'-cyclohexane]-4-yl)acetate (140 mg, 90%). $^1$H NMR (CDCl$_3$): 1.22-1.38 (m, 1H), 1.39-1.52 (m, 6H), 1.72-1.88 (m, 3H), 1.93-2.02 (d, 2H), 2.13-2.24 (t, 1H), 2.59 (d, 1H), 2.86 (d, 1H), 3.65 (s, 3H), 6.74 (d, 1H), 7.24 (s, 1H), 7.52 (s. 1H).

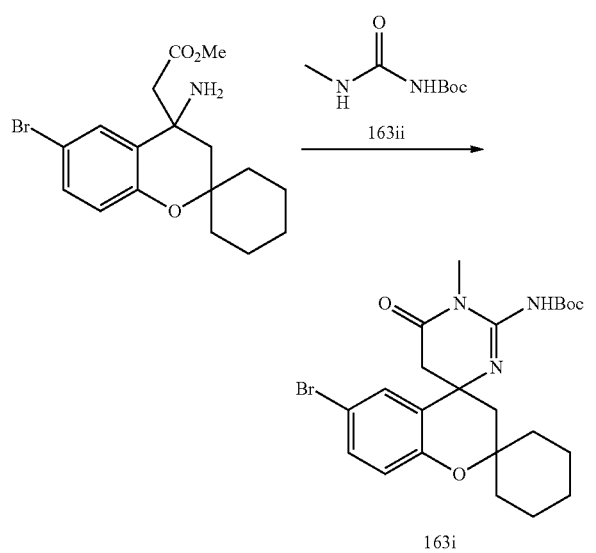 [SMILES: COC(=O)CC1(N)CC2(CCCCC2)Oc2ccc(Br)cc21 ; CNC(=O)NC(=O)OC(C)(C)C ; CN1C(=O)CC2(CC3(CCCCC3)Oc3ccc(Br)cc32)N=C1NC(=O)OC(C)(C)C]

Step 5. Compound 163i

To a solution of methyl 2-(4-amino-6-bromospiro[chroman-2,1'-cyclohexane]-4-yl)acetate (400 mg, 1.09 mmol), EDCI (226 mg, 1.14 mmol) and DIEA (703 mg, 5.45 mmol) in DMF (4 mL) was added the compound 163ii (207 mg, 1.09 mmol), and the resulting mixture was stirred at room temperature overnight. Water was added and the mixture was extracted with EtOAc. The organic layer was washed with water, brine, dried over Na$_2$SO$_4$, and concentrated to give the crude product, which was purified by preparative TLC to afford the compound 163i (80 mg, 165%). $^1$H NMR (CDCl$_3$): 1.38 (s, 2H), 1.42 (s, 9H), 1.53 (m, 5H), 1.76 (m, 3H), 1.91 (d, 1H), 2.13 (d, 1H), 2.68 (d, 1H), 3.03 (d, 1H), 3.31 (s, 3H), 6.73 (d, 1H), 7.29 (d, 1H), 7.43 (s, 1H).

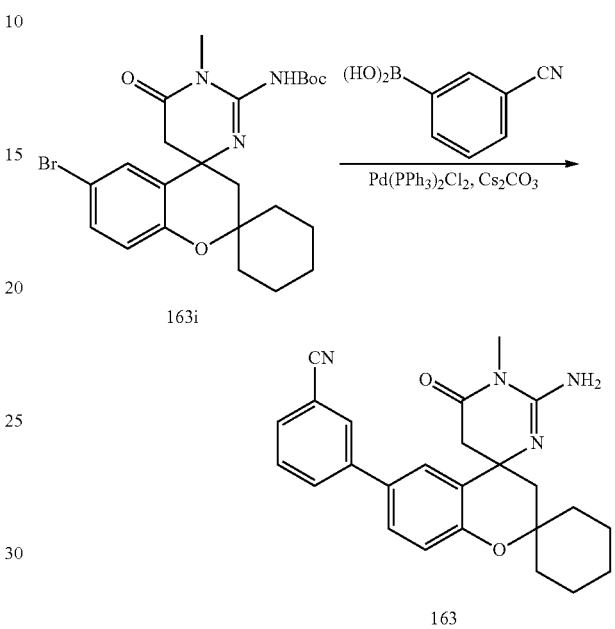

Step 6. Compound 163

Pd(PPh$_3$)$_2$Cl$_2$ (8 mg) in a 10 mL of flask under Ar$_2$ was treated sequentially with the compound 1 (80 mg, 0.16 mmol) in 1,4-dioxane (1 mL), Cs$_2$CO$_3$ (2 N, 0.3 mL) and 3-cyanophenylboronic acid (44 mg, 0.24 mmol). The mixture was heated under 120 at Ar$_2$ under microwave for 30 minutes. The reaction mixture was concentrated in vacuo to give the residue, which was purified preparative TLC and preparative HPLC to give compound 163 (20 mg, 30%). $^1$H NMR (MeOD): 1.32-1.71 (m, 7H), 1.78-1.91 (m, 2H), 1.98 (m, 1H), 2.12 (d, 1H), 2.44 (d, 1H), 2.93 (d, 1H), 3.38 (s, 3H), 3.68 (d, 1H), 7.09 (d, 1H), 7.62-7.72 (m, 3H), 7.89-8.03 (m, 3H).

Example 133

Compound 164

Experimental Data:

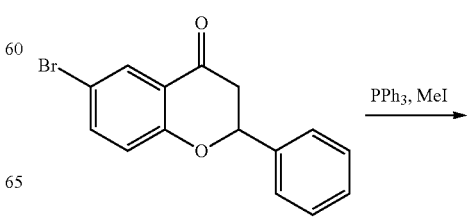

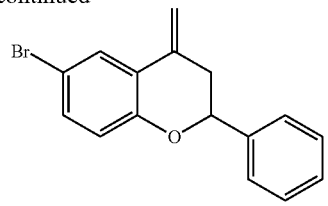

Step 1. 6-bromo-4-methylene-2-phenylchroman

A solution of n-BuLi (2.5 M, 3.80 mL) was added to a mixture of PPh$_3$.MeI. (4.092 g, 10.13 mmol) in THF at −10. The mixture was stirred for 1 h at the same temperature, and then 6-bromo-2-phenylchroman-4-one (2 g, 6.62 mmol) was added. The mixture was allowed to warm to room temperature and stirred for 3 h. The resulting mixture was concentrated and purified by column chromatography to give 6-bromo-4-methylene-2-phenylchroman (400 mg, 20%). $^1$H-NMR (CDCl$_3$): 2.76 (m, 2H), 4.90 (d, 1H), 5.01 (m, 1H), 5.48 (d, 1H), 6.76 (d, 1H), 7.31 (m, 6H), 7.62 (d, 1H).

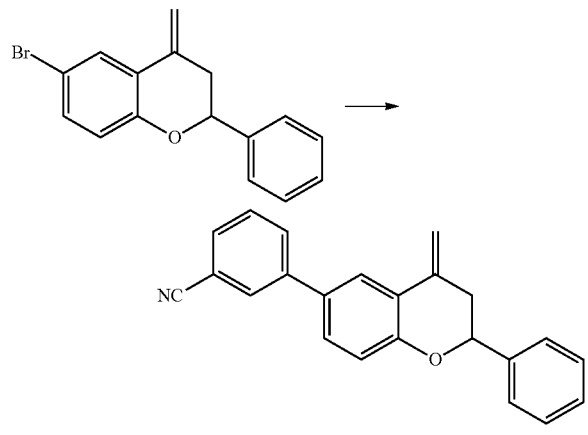

Step 2.
3-(4-methylene-2-phenyl-chroman-6-yl)-benzonitrile

Pd(PPh$_3$)$_2$Cl$_2$ (40 mg) in a 100 mL of flask under Ar$_2$ was treated sequentially with 6-bromo-4-methylene-2-phenyl-chroman (200 mg, 0.67 mmol) in [1,4]dioxane (20 mL), Cs$_2$CO$_3$ (2 N, 3.33 mL) and 3-cyanophenylboronic acid (167 mg, 1.13 mmol). The mixture was heated under 120 at Ar$_2$ under microwave for 30 minutes. The reaction mixture was concentrated in vacuo to give the residue, which was purified preparative TLC to give 3-(4-methylene-2-phenyl-chroman-6-yl)-benzonitrile (110 mg, 51%). $^1$H-NMR (CDCl$_3$): 2.81 (m, 2H), 4.96 (d, 1H), 5.10 (m, 1H), 5.61 (d, 1H), 7.98 (d, 1H), 7.29 (m, 1H), 7.35 (m, 3H), 7.41 (m, 2H), 7.46 (m, 1H), 7.52 (m, 1H), 7.72 (m, 2H), 7.79 (d, 1H).

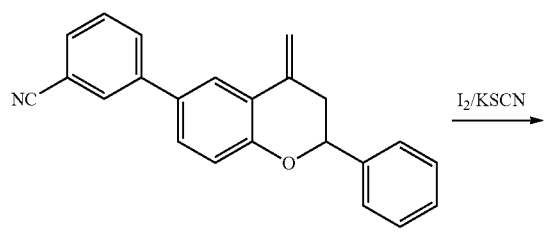

Step 3. 3-(4-iodomethyl-4-isothiocyanato-2-phenyl-chroman-6-yl)-benzonitrile

To a solution of 3-(4-methylene-2-phenyl-chroman-6-yl)-benzonitrile (50 mg, 0.156 mmol) in CHCl$_3$ (5 mL) was added I$_2$ (93 mg, 0.367 mmol), KSCN (76 mg, 0.78 mmol) and catalyst amount t-BtNBr. The mixture was stirred overnight and used directly.

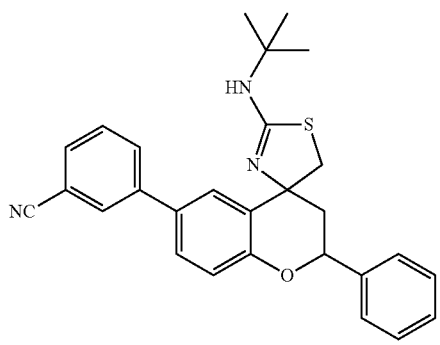

Step 4. 3-(2'-(tert-butylamino)-2-phenyl-5'H-spiro[chroman-4,4'-thiazole]-6-yl)benzonitrile t-BuNH$_2$ (55 mg, 0.75 mmol) was added to 3-(4-iodomethyl-4-isothiocyanato-2-phenyl-chroman-6-yl)-benzonitrile (190.5 mg, 0.375 mmol) in CHCl$_3$ above and the mixture was stirred for 20 minutes. The solvent was removed in vacuo to give the residue, which was purified by preparative TLC to give 3-(2'-(tert-butylamino)-2-phenyl-5'H-spiro[chroman-4,4'-thiazole]-6-yl)benzonitrile (35 mg, 21%).

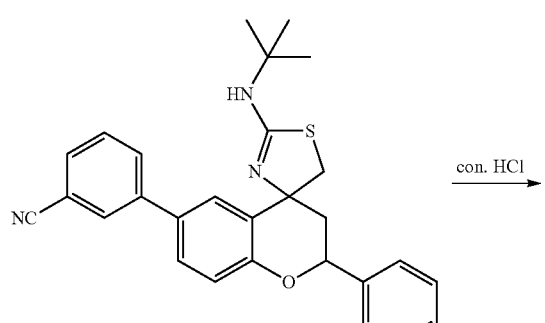

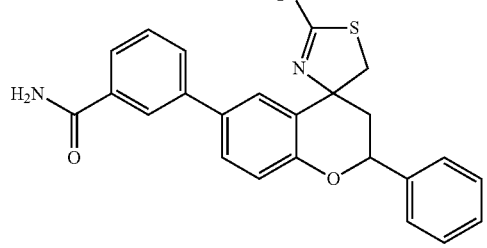

Step 4. 3-(2'-amino-2-phenyl-5'H-spiro[chroman-4,4'-thiazole]-6-yl)benzamide

A mixture of 3-(2'-(tert-butylamino)-2-phenyl-5'H-spiro[chroman-4,4'-thiazole]-6-yl)benzonitrile (30 mg, 0.066 mmol) in concentrated HCl (5 mL) was stirred at 100 for 2 h. Aqueous NaOH (6 N) was added until pH=8. The mixture was extracted with EtOAc and the organic layer was dried and concentrated to give the residue, which was purified by preparative TLC to give 3-(2'-amino-2-phenyl-5'H-spiro[chroman-4,4'-thiazole]-6-yl)benzamide (20 mg, 73%).

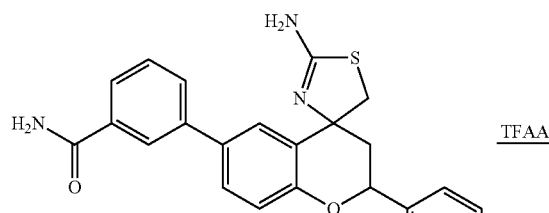

Step 5. 3-(2'-amino-2-phenyl-5'H-spiro[chroman-4,4'-thiazole]-6-yl)benzonitrile

To a solution of 3-(2'-amino-2-phenyl-5'H-spiro[chroman-4,4'-thiazole]-6-yl)benzamide (20 mg, 0.048 mmol) and DIEA (21 mg, 0.096 mmol) in CH$_2$Cl$_2$ was added TFAA (0.2 mL) at 0. The mixture was stirred at room temperature for 1 h and concentrated to give the residue, which was purified by preparative TLC to give 3-(2'-amino-2-phenyl-5'H-spiro[chroman-4,4'-thiazole]-6-yl)benzonitrile (1.53 mg, 8%). $^1$H-NMR (MeOD): 2.27 (m, 2H), 3.36 (m, 1H), 3.84 (m, 1H), 5.24 (m, 1H), 6.92 (m, 1H), 7.31 (m, 4H), 7.48 (m, 4H), 7.81 (m, 3H).

Example 134

3-(2'-Amino-2-phenyl-5',6'-dihydrospiro[chroman-4,4'-[1,3]thiazine]-6-yl)benzonitrile (Cmpd. 165)

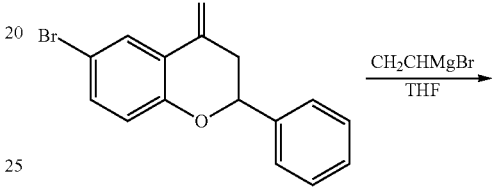

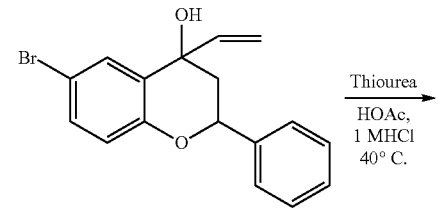

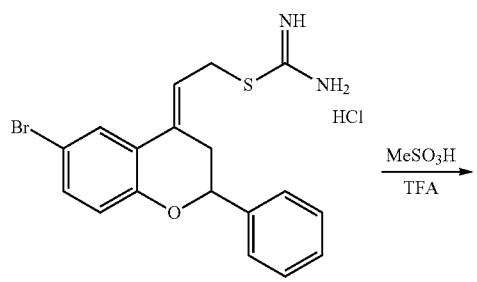

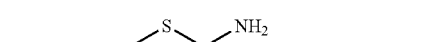

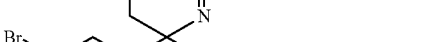

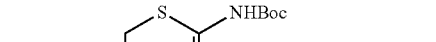

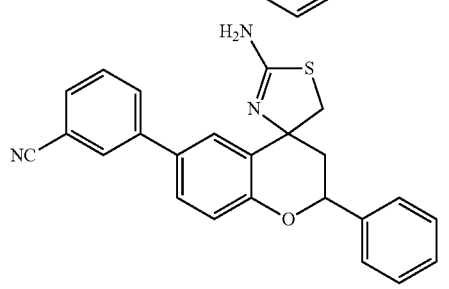

Step 1

To a solution of 6-bromo-2-phenylchroman-4-one (2.021 g, 6.67 mmol) in anhydrous THF (35 mL) at −78° C. is added a solution of vinylmagnesiun bromide in THF (1 M, 10 mL, 10 mmol) dropwise within 30 min. The reaction temperature is allowed to warm to rt and stirred for another 2 h. The reaction is chilled to 0° C. and quenched with sat. aq. $NH_4Cl$ and extracted with ethyl acetate (2×40 mL). The combined organic phases are washed with $H_2O$, brine, and dried over $Na_2SO_4$, and filtered. The filtrate is concentrated and the residue is purified through flash chromatography on silica gel to afford 6-bromo-2-phenyl-4-vinylchroman-4-ol as an oil (1.961 g. 89%). MS ESI+ve m/z 313 (M+H—$H_2O$)⁺.

Step 2

The mixture of 6-bromo-2-phenyl-4-vinylchroman-4-ol (345 mg, 1.04 mmol) and thiourea (97 mg, 1.56 mmol) in HOAc (3 mL) and 1 M HCl (1.2 mL) is heated to 40° C. for 12 h. The solvent is removed under reduced pressure to give a white solid as a mixture of 2-(6-bromo-2-phenylchroman-4-ylidene)ethyl carbamimidothioate HCl salt and thiourea.

It is used for next step without purification. MS ESI+ve m/z 313 (M+H-thiourea)⁺ 389 (weak) (M+H)⁺.

Step 3

The above mixture of 2-(6-bromo-2-phenylchroman-4-ylidene)ethyl carbamimidothioate HCl salt and thiourea is dissolved in TFA (4 mL) containing $MeSO_3H$ (0.4 mL) and stirred at rt for 1 h. The solvent is removed under reduced pressure. The residue is dissolved in ethyl acetate and washed with sat $NaHCO_3$. The separated aqueous phase is extracted with ethyl acetate once and the combined organic phases are washed with brine, and dried over $Na_2SO_4$, and filtered. The filtrate is concentrated to give crude 6-bromo-2-phenyl-5',6'-dihydrospiro[chroman-4,4'-[1,3]thiazin]-2'-amine, which is used for next step without further purification.

MS ESI+ve m/z 389 (M+H)⁺.

¹H NMR (400 MHz, $CD_3OD$): less polar isomer: 7.17 (s, 1H), 7.50-6.65 (m 7H), 5.36 and 5.13 (d, 1H), 3.53-1.28 (m, 6H); more polar isomer: 7.41-6.71 (m, 8H), 4.66 and 4.39 (m, 1H), 3.35-2.00 (m, 6H).

Step 4

The above crude product of 6-bromo-2-phenyl-5',6'-dihydrospiro[chroman-4,4'-[1,3]thiazin]-2'-amine is dissolved in THF (5 mL). To this solution is added TEA (1 mL) and $Boc_2O$ (227 mg, 1.04 mmol). The solution is concentrated after being stirred 2 h at rt. The crude product is purified through flash chromatography on silica gel to afford t-butyl 6-bromo-2-phenyl-5',6'-dihydrospiro[chroman-4,4'-[1,3]thiazine]-2'-ylcarbamate 415 mg (81% for 3 steps). MS ESI+ve m/z 489 (M+H)⁺.

Step 5

A solution of t-butyl 6-bromo-2-phenyl-5',6'-dihydrospiro[chroman-4,4'-[1,3]thiazine]-2'-ylcarbamate (41 mg, 0.084 mmol), 3-cyanophenylboronic acid (23.5 mg, 0.16 mmol), $Cs_2CO_3$ (78 mg, 0.24 mmol), and a catalytic amount of Pd(dppf)Cl₂ in 1,4-dioxane (4 mL) and $H_2O$ (0.4 mL) is heated at 110° C. in microwave oven for 10 min. Then, 4 mL of 4 M HCl in 1,4-dioxane is added and stirred another 2 h at rt. Water (10 mL) is added and extracted with EA. The separated organic phase is washed with brine, and dried over $Na_2SO_4$, and filtered. The filtrate is concentrated to give a crude product which is purified through preparative HPLC to give 3-(2'-amino-2-phenyl-5',6'-dihydrospiro[chroman-4,4'-[1,3]thiazine]-6-yl)benzonitrile. MS ESI+ve m/z 412 (M+H)⁺.

¹H NMR (400 MHz, $CD_3OD$): less polar isomer: 8.03 (s, 1H), 7.96 (m 1H), 7.88 (s, 1H), 7.70-7.60 (m, 3H), 7.53-7.52 (m, 2H), 7.46-7.38 (m, 3H), 7.16 (d, 1H), 5.19 (d, 1H), 3.54 (td, 1H), 3.32 (m, 1H), 2.81 (td, 1H), 2.58 (d, 1H), 2.36-2.27 (m, 2H); more polar isomer: 7.41-6.78 (m, 12H), 4.69 (m, 1H), 3.37-3.24, 3.04-2.88, 3.63, 3.42, 2.29-2.15, 1.28 (m, 6H).

Example 135

2-Phenyl-6-(pyridin-3-yl)-5',6'-dihydrospiro[chroman-4,4'-[1,3]thiazin]-2'-amine (Cmpd. 166)

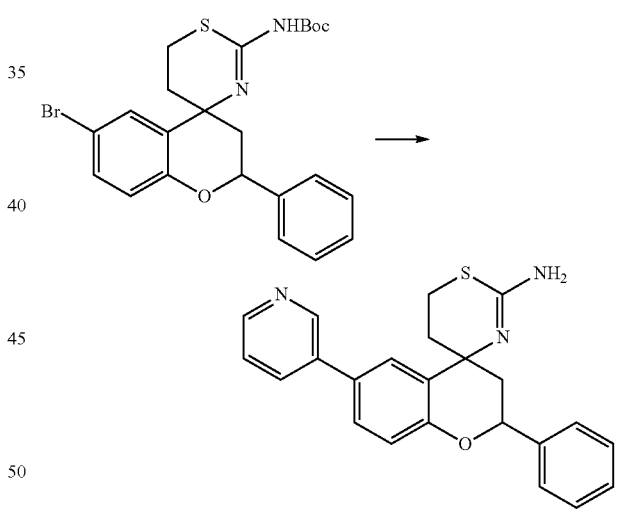

To a solution of t-butyl 6-bromo-2-phenyl-5',6'-dihydrospiro[chroman-4,4'-[1,3]thiazine]-2'-ylcarbamate (39 mg, 0.08 mmol), 3-cyanophenylboronic acid (19.7 mg, 0.16 mmol), and $Cs_2CO_3$ (120 mg) in 1,4-dioxane (4 mL) and $H_2O$ (0.5 mL) charged in a 10 mL CEM microwave test tube is added $PdCl_2(PPh_3)_2$ (20 mg). The system is degassed by sweeping with $N_2$. The tube is capped and heated to 110° C. for 30 min in a CEM microwave reactor. Solvent is removed in vacuo and the residue is purified by preparative HPLC to give 2-phenyl-6-(pyridin-3-yl)-5',6'-dihydrospiro[chroman-4,4'-[1,3]thiazin]-2'-amine (1.7 mg) as a TFA salt. MS ESI+ve m/z 389 (M+H)⁺.

¹H NMR (400 MHz, $CD_3OD$): 8.59 (D, 1H), 8.00-7.15 (m, 11H), 5.22 (d, 1H), 3.56 (m, 1H), 3.26 (m, 1H), 2.82 (td, 1H), 2.60 (dd, 1H), 2.38 (m, 1H), 2.32 (m, 1H).

Example 136

3-(2''-Amino-5'',6''-dihydrospiro[spiro(chroman-2,1'-(4-t-butylcyclohexan))-4,4''-[1,3]thiazine]-6-yl)benzonitrile (Cmpd. 167)

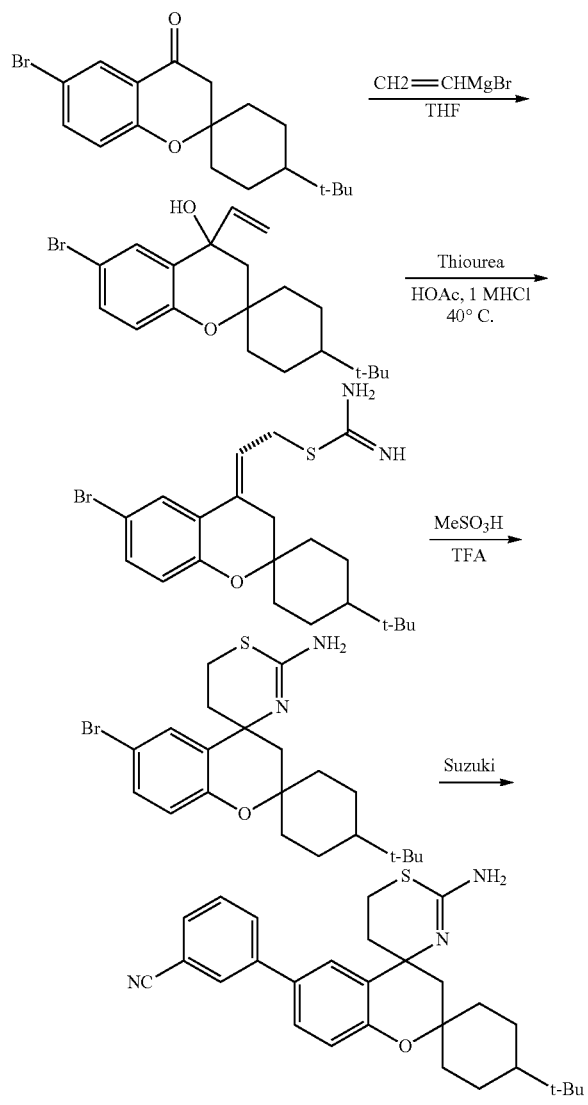

Step 1

To a solution of 6-bromo-4'-t-butylspiro[chroman-2,1'-cyclohexan]-4-one (2.155 g, 6.13 mmol) in anhydrous THF (20 mL) at −78° C. is added a solution of vinylmagnesium bromide in THF (1 M, 9.2 mL, 9.2 mmol) dropwise within 30 min. The reaction temperature is allowed to warm to rt and stirred for another 2 h. The reaction is chilled to 0° C. and quenched with sat. aq. NH$_4$Cl, and extracted with ethyl acetate (2×40 mL). The combined organic phases are washed with H$_2$O and brine, then dried over Na$_2$SO$_4$, and filtered. The filtrate is concentrated and the residue is purified through flash chromatography on silica gel to afford 6-bromo-4'-tert-butyl-4-vinylspiro[chroman-2,1'-cyclohexan]-4-ol as an oil (1.907 g, 82%). MS ESI+ve m/z 361 (M+H—H$_2$O)$^+$.

Step 2

The mixture of 6-bromo-2-phenyl-4-vinylchroman-4-ol (1.114 g, 2.94 mmol) and thiourea (345 mg, 4.41 mmol) in HOAc (9 mL) and 1 M HCl (3.6 mL) is heated to 40° C. for 12 h. The solvent is removed under reduced pressure to give a white solid as a mixture of 2-(6-bromo-4'-t-butylspiro-[chroman-2,1'-cyclohexane]-4-ylidene)ethyl carbamimidothioate HCl salt and excess thiourea. It is used in the next step without purification. MS ESI+ve m/z 361 (M+H-thiourea)$^+$ 437 (weak) (M+H)$^+$.

Step 3

The above crude product is dissolved in TFA (8 mL) containing MeSO$_3$H (0.8 mL) and stirred at rt for 1 h. The solvent is removed under reduced pressure. The residue is dissolved in ethyl acetate and washed with sat NaHCO$_3$. The separated aqueous phase is extracted with ethyl acetate once, and the combined organic phases are washed with brine, and dried over Na$_2$SO$_4$, and filtered. The filtrate is concentrated to give crude product. Pure 6-bromo-5'',6''-dihydrospiro[spiro(chroman-2,1'-(4-t-butylcyclohexan))-4,4''-[1,3]thiazin]-2''-amine is obtained by preparative HPLC. MS ESI+ve m/z 437 (M+H)$^+$.

Step 4

To a solution of 6-bromo-5'',6''-dihydrospiro[spiro(chroman-2,1''-(4-t-butylcyclohexane))-4,4'-[1,3]thiazin]-2''-amine TFA salt (47 mg, 0.07 mmol) and 3-cyanophenylboronic acid (21 mg, 0.14 mmol) in 1,4-dioxane (3 mL) charged in a 10-mL microwave test tube is added Cs$_2$CO$_3$ (146 mg, 0.45 mmol) and H$_2$O (0.5 mL), followed by a catalytic amount of PdCl$_2$dppf. The system is degassed by sweeping with N$_2$. Then it is capped and heated 10 min at 130° C. in microwave. The separated organic phase is concentrated and then purified through preparative HPLC to afford cis- and trans-3-(2''-amino-5'',6''-dihydrospiro[spiro(chroman-2,1''-(4-t-butylcyclohexane))-4,4'-[1,3]thiazine]-6-yl)benzonitrile respectively. MS ESI+ve m/z 460 (M+H)$^+$.

$^1$H NMR (400 MHz, CD$_3$OD): less polar isomer: 8.00 (s, 1H), 7.93 (d, 1H), 7.72 (s, 1H), 7.68-7.58 (m, 3H), 7.06 (d, 1H), 3.53 (td, 1H), 3.28 (m, 1H), 0.91 (s, 9H); more polar isomer: 8.00 (s, 1H), 7.93 (d, 1H), 7.71-7.59 (m, 4H), 7.02 (d, 1H), 3.58 (td, 1H), 3.34 (m, 1H), 0.91 (s, 9H).

Example 137

3-(2''-Amino-5'',6''-dihydrospiro[spiro(chroman-2,1'-cyclohexane)-4,4''-[1,3]thiazine]-6-yl)benzonitrile (Cmpd 168)

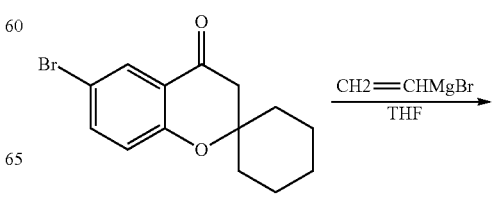

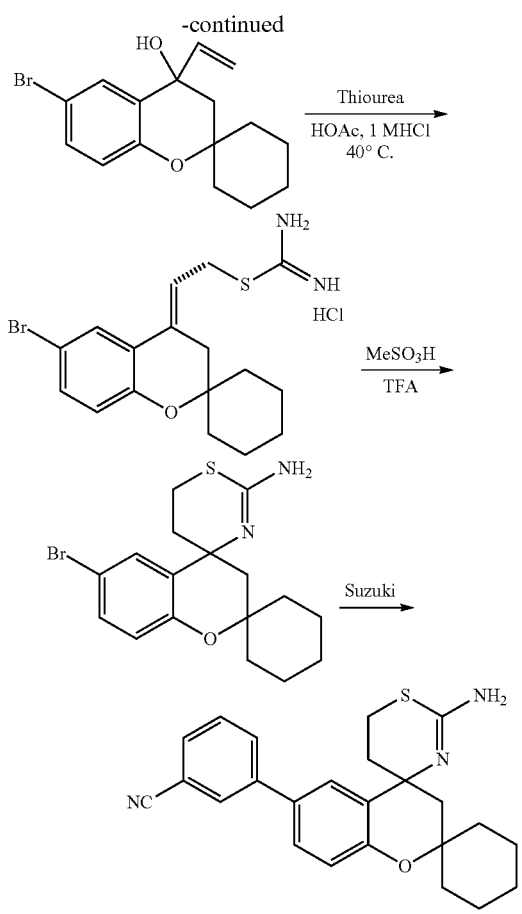

is removed under reduced pressure. The residue is dissolved in ethyl acetate and washed with sat NaHCO₃. The separated aqueous phase is extracted with ethyl acetate once, and the combined organic phases are washed with brine, and dried over Na₂SO₄, and filtered. The filtrate is concentrated to give crude 6-bromo-5",6"-dihydrospiro[spiro(chroman-2,1'-cyclohexan)-4,4'-[1,3]thiazin]-2"-amine. Pure product is obtained by preparative HPLC. MS ESI+ve m/z 437 (M+H)⁺.

Step 4

To a solution of 6-bromo-5",6"-dihydrospiro[spiro(chroman-2,1"-(4-t-butylcyclohexane))-4,4'-[1,3]thiazin]-2"-amine TFA salt (70 mg, 0.14 mmol) and 3-cyanophenylboronic acid (41 mg, 0.28 mmol) in 1,4-dioxane (3 mL) charged in a 10-mL microwave test tube is added Cs₂CO₃ (200 mg, 0.61 mmol) and H₂O (0.5 mL), followed by a catalytic amount of PdCl₂(PPh₃)₂. The system is degassed by sweeping with N₂. Then it is capped and heated for 30 min at 110° C. in microwave. The separated organic phase is concentrated and the purified through preparative HPLC to afford 3-(2"-amino-5",6"-dihydrospiro[spiro(chroman-2,1'-cyclohexane)-4,4'-[1,3]thiazine]-6-yl)benzonitrile representatively. MS ESI+ve m/z 460 (M+H)⁺.

¹H NMR (400 MHz, CD₃OD): 8.00 (s, 1H), 7.92 (d, 1H), 7.71 (s, 1H), 7.68-7.59 (m, 3H), 7.07 (d, 1H), 3.53 (td, 1H), 3.28 (m, 1H), 2.56 (td, 1H), 2.37-2.29 (m, 2H), 2.18 (d, 1H), 1.90-1.82 (m, 3H), 1.67-1.61 (m, 4H), 1.55-1.37 (m, 3H).

Example 138

3-(2'-Imino-1'-methyl-6'-oxo-2-phenyl-2',3',5',6'-tetrahydro-1'H-spiro[chroman-4,4'-pyrimidine]-6-yl) benzonitrile (Cmpd. 169)

Step 1

To a solution of 6-bromospiro[chroman-2,1'-cyclohexan]-4-one (383 mg, 1.30 mmol) in anhydrous THF (10 mL) at −78° C. is added a solution of vinylmagnesiun bromide in THF (1 M, 1.95 mL, 1.95 mmol) dropwise within 10 min. The reaction temperature is allowed to warm to rt and stirred for another 2 h. The reaction is chilled to 0° C. and quenched with sat. aq. NH₄Cl, and extracted with ethyl acetate (2×30 mL). The combined organic phases are washed with H₂O, brine, dried over Na₂SO₄, and filtered. The filtrate is concentrated to give crude 6-bromo-4-vinylspiro[chroman-2,1'-cyclohexan]-4-ol as an oil, which is used for the next step without further purification. MS ESI+ve m/z 305 (M+H—H₂O)⁺.

Step 2

The mixture of above crude product and thiourea (242 mg, 3.9 mmol) in HOAc (20 mL) and 1 M HCl (4 mL) is heated to 40° C. for 24 h. The solvent is removed under reduced pressure to give a white solid as a mixture of 2-(6-bromo-4'-t-butylspiro[chroman-2,1'-cyclohexane]-4-ylidene)ethyl carbamimidothioate HCl salt and excess thiourea. It is used for the next step without purification. MS ESI+ve m/z 381 (M+H)⁺.

Step 3

The above crude product is dissolved in TFA (5 mL) contain MeSO₃H (0.5 mL) and stirred at rt overnight. The solvent

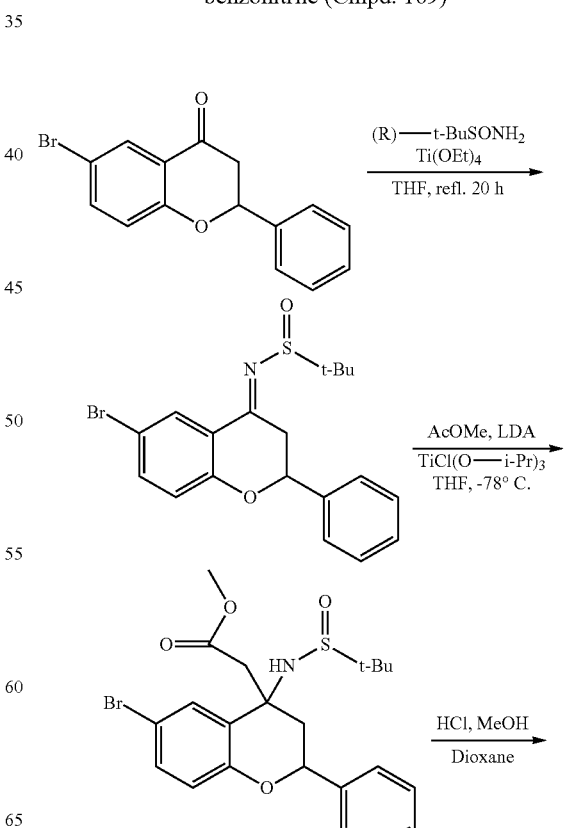

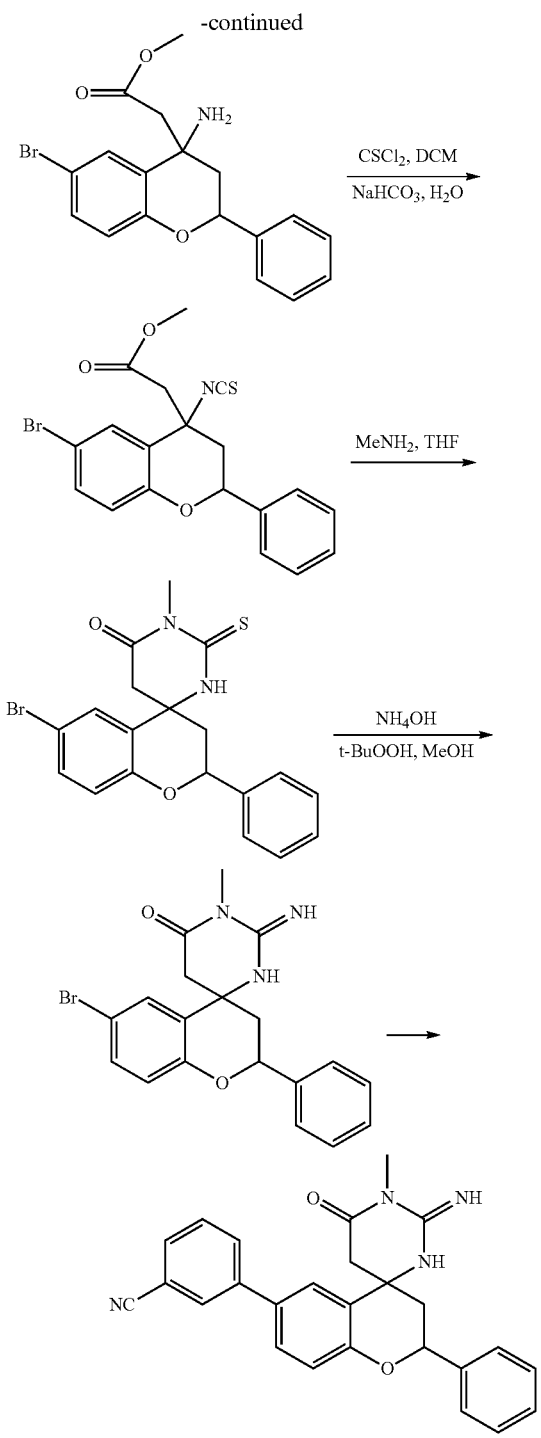

Step 1

To a solution of 6-bromo-2-phenylchroman-4-one (2.010 g, 6.63 mmol) and 2-methyl-2-propane sulfonamide (804 mg, 6.63 mmol) in anhydrous THF (22 mL) is added Ti(OEt)$_4$ (3.025 g, 2.80 mL, 13.22 mmol). The resulting mixture is heated to reflux for 20 h. Brine (10 mL) is added after the mixture is cooled to rt, and stirred vigorously for 10 min. The mixture is filtered through a pad of Celite, and washed with ethyl acetate (50 mL). The filtrate is washed with brine, dried over anhydrous Na$_2$SO$_4$, filtered, and concentrated. The residue is purified through chromatography on silica gel to afford N-(6-bromo-2-phenylchroman-4-ylidene)-2-methylpropane-2-sulfinamide 1.05 g, 39%) as a light yellow solid. MS ESI+ve m/z 406 (M+H)$^+$.

Step 2

To a solution of methyl acetate (383 mg, 0.41 mL, 5.17 mmol) in anhydrous THF (10 mL) at −78° C. under N$_2$ atmosphere is added 2 M LDA solution in THF (3.4 mL, 6.8 mmol) dropwise, and the solution is stirred another 30 min at the same temperature after the addition. To this mixture is added TiCl(OiPr)$_3$ (1.681 g, 6.45 mmol) dropwise. The mixture is then stirred another 30 min at −78° C. To this mixture is added a solution of N-(6-bromo-2-phenylchroman-4-ylidene)-2-methylpropane-2-sulfinamide (1.050 g, 2.58 mmol) in anhydrous THF (10 mL) dropwise within 30 min. The reaction mixture is stirred another 3 h at −78° C. then quenched with sat. aq. NH$_4$Cl. The mixture is stirred 10 min after being warmed to rt and filtered through a pad of Celite, and washed with EA (80 mL). The filtrate is transferred to separating funnel and the separated organic phase is washed with brine, and dried over anhydrous Na$_2$SO$_4$, filtered and concentrated, and the residue is purified through chromatography on silica gel to afford methyl 2-(6-bromo-4-(1,1-dimethylethylsulfinamido)-2-phenylchroman-4-yl)acetate 427 mg as an oil. MS ESI+ve m/z 480 (M+H)$^+$.

Step 3

A solution of methyl 2-(6-bromo-4-(1,1-dimethylethylsulfinamido)-2-phenylchroman-4-yl)acetate (427 mg, 0.89 mmol) in MeOH (7 mL) and 4 M HCl solution in 1,4-dioxane (14 mL) is stirred at rt for 30 min. The solvent is removed under reduced pressure to give 418 mg methyl 2-(4-amino-6-bromo-2-phenylchroman-4-yl)acetate HCl salt as a white foam, which is used for next step without further purification. MS ESI+ve m/z 376 (M+H)$^+$.

Step 4

The above crude product is added to a solution of NaHCO$_3$ (714 mg, 8.5 mmol) in H$_2$O (10 mL), which is chilled at 0° C. To this stirred mixture was added thiophosgene (71 μL, 107 mg, 0.93 mmol) and the mixture stirred for 1 h at 0° C. The reaction is diluted with DCM and the separated organic phase is washed with semi-saturated brine, dried over anhydrous Na$_2$SO$_4$, filtered, and concentrated to produce methyl 2-(6-bromo-4-isothiocyanato-2-phenylchroman-4-yl)acetate as an oil (384 mg). MS ESI+ve m/z 359 (M-NCS)$^+$.

Step 5

To a solution of 2-(6-bromo-4-isothiocyanato-2-phenylchroman-4-yl)acetate (192 mg, 0.46 mmol) in DCM (5 mL) is added a solution of 2 M MeNH$_2$ in THF (1.3 mL), and stirred for 1 h. The solvent is removed under reduced pressure and the residue is dissolved in DCM (2 mL) and hexane (2 mL) and evaporated to afford 6-bromo-1'-methyl-2-phenyl-2'-thioxo-2',3'-dihydro-1'H-spiro[chroman-4,4'-pyrimidin]-6' (5'H)-one as a white foam (209 mg), which is used for the next step without further purification. MS ESI+ve m/z 417 (M+H)$^+$.

Step 6

To a solution of the above crude product in MeOH (9 mL) is added concentrated aqueous NH$_4$OH (4.5 mL), followed by t-butyl hydroperoxide solution (ca. 5.5 M in nonane, 1 mL). The resulting suspension is stirred overnight. The resulting clear solution is concentrated in vacuo and the residue is purified through preparative HPLC to give 6-bromo-2'-imino-1'-methyl-2-phenyl-2',3'-dihydro-1'H-spiro[chroman-4,4'-pyrimidin]-6'(5'H)-one TFA salt. MS ESI+ve m/z 400 (M+H)$^+$.

Step 7

To a solution of 6-bromo-2'-imino-1'-methyl-2-phenyl-2',3'-dihydro-1'H-spiro[chroman-4,4'-pyrimidin]-6'(5'H)-one TFA salt (20 mg, 0.039 mmol) and 3-cyanophenylboronic acid (12 mg, 0.078 mmol) in 1,4-dioxane (3 mL) charged in a 10-mL microwave test tube is added $Cs_2CO_3$ (63 mg, 0.195 mmol) and $H_2O$ (0.5 mL), followed by $Pd(PPh_3)_2Cl_2$ (8 mg). The resulting mixture is heated 30 min at 130° C. in microwave. The separated organic phase is concentrated and then purified through preparative HPLC to afford cis- and trans-3-(2'-imino-1'-methyl-6'-oxo-2-phenyl-2',3',5',6'-tetrahydro-1'-spiro[chroman-4,4'-pyrimidine]-6-yl)benzonitrile. MS ESI+ve m/z 423 (M+H)$^+$.

$^1$H NMR (400 MHz, $CD_3OD$): less polar isomer: 8.02 (s, 1H), 7.97-7.88 (m, 2H), 7.71-7.60 (m, 3H), 7.52-7.49 (m, 2H), 7.44-7.37 (m, 3H), 7.15 and 7.10 (d and d, 1H), 5.34 and 5.17 (d and d, 1H), 3.90 and 2.90 (d and d, 1H), 3.57 (m, 1H), 3.35 (s, 3H), 2.54 (t, 1H), 2.34 (m, 1H); more polar isomer: 8.02 (s, 1H), 7.99-7.91 (m, 2H), 7.70-7.60 (m, 3H), 7.53-7.49 (m, 2H), 7.44-7.35 (m, 3H), 7.15 and 7.09 (d and d, 1H), 5.36 and 5.23 (dd and d, 1H), 3.84 and 2.73 (d and d, 1H), 3.44 (m, 1H), 3.00 and 2.94 (s and s, 3H).

Example 139

2'-Imino-1'-methyl-2-phenyl-6-(pyridin-3-yl)-2',3'-dihydro-1'H-spiro[chroman-4,4'-pyrimidin]-6'(5'H)-one (Cmpd. 170)

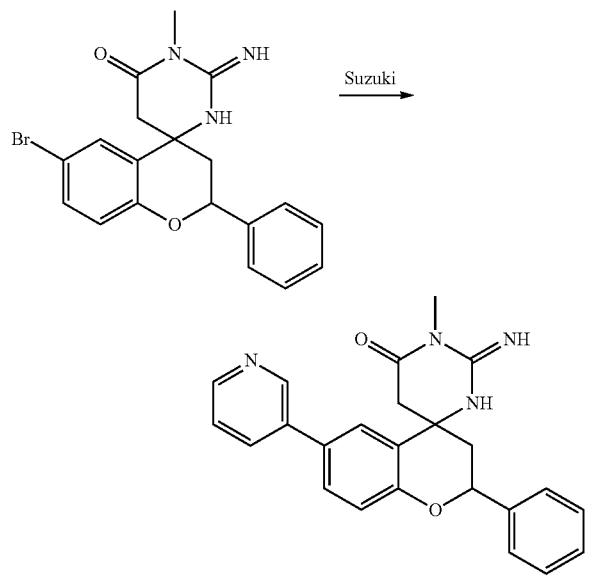

To a solution of 6-bromo-2'-imino-1'-methyl-2-phenyl-2',3'-dihydro-1'H-spiro[chroman-4,4'-pyrimidin]-6'(5'H)-one TFA salt (12 mg, 0.023 mmol) and pyridin-3-ylboronic acid (9 mg, 0.070 mmol) in 1,4-dioxane (3 mL) charged in a 10-mL microwave test tube is added $Cs_2CO_3$ (63 mg, 0.195 mmol) and $H_2O$ (0.5 mL), followed by $Pd(PPh_3)_2Cl_2$ (8 mg). The resulting mixture is heated for 30 min at 130° C. in CEM microwave reactor. The separated organic phase is concentrated and the purified through preparative HPLC to afford cis- and trans-2'-imino-1'-methyl-2-phenyl-6-(pyridin-3-yl)-2',3'-dihydro-1'H-spiro[chroman-4,4'-pyrimidin]-6'(5'H)-one. MS ESI+ve m/z 423 (M+H)$^+$.

$^1$H NMR (400 MHz, $CD_3OD$): less polar isomer: 8.70 (m, 2H), 8.08 (s, 1H), 8.00 (s, 1H), 7.78 (m, 2H), 7.52-7.37 (m, 5H), 7.18 (m, 1H), 5.37 and 5.20 (d and d, 1H), 3.90 and 2.91 (d and d, 1H), 3.35 (s, 3H), 2.60-2.29 (m, 2H); more polar isomer: 9.16 (s, 1H), 8.82-8.73 (m, 2H), 8.15-8.04 (m, 2H), 7.80 (m, 1H), 7.51-7.35 (m, 5H), 7.22 and 7.17 (d and d, 1H), 5.39 and 5.27 (d and d, 1H), 3.86 and 2.76 (d and d, 1H), 3.46 (s, 1H), 2.99 and 2.94 (s and s, 3H), 2.57-2.31 (m, 2H).

Example 140

2'-Iimino-1'-methyl-2-phenyl-6-(pyridin-4-yl)-2',3'-dihydro-1'H-spiro[chroman-4,4'-pyrimidin]-6'(5'H)-one (Cmpd. 171)

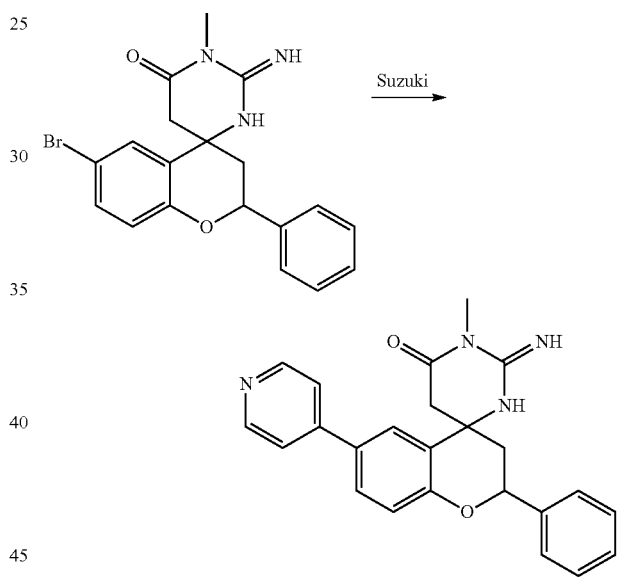

To a solution of 6-bromo-2'-imino-1'-methyl-2-phenyl-2',3'-dihydro-1'H-spiro[chroman-4,4'-pyrimidin]-6'(5'H)-one TFA salt (12 mg, 0.023 mmol) and pyridin-4-ylboronic acid (9 mg, 0.070 mmol) in 1,4-dioxane (3 mL) charged in a 10-mL microwave test tube is added $Cs_2CO_3$ (63 mg, 0.195 mmol) and $H_2O$ (0.5 mL), followed by $Pd(PPh_3)_2Cl_2$ (8 mg). The resulting mixture is heated for 30 min at 130° C. in CEM microwave reactor. The separated organic phase is concentrated and then purified through preparative HPLC to afford cis- and trans-2'-imino-1'-methyl-2-phenyl-6-(pyridin-4-yl)-2',3'-dihydro-1'H-spiro[chroman-4,4'-pyrimidin]-6'(5'H)-one. MS ESI+ve m/z 423 (M+H)$^+$.

$^1$H NMR (400 MHz, $CD_3OD$): less polar isomer: 8.80 (m, 2H), 8.35-8.24 (m, 3H), 7.51-7.40 (m, 5H), 7.23 (m, 1H), 5.43 and 5.24 (d and d, 1H), 3.95 and 2.94 (d and d, 1H), 3.56 (m, 1H), 3.36 (s, 3H), 2.60-2.35 (m, 2H); more polar isomer: 8.81 (d, 2H), 8.41-8.31 (m, 3H), 8.02 (m, 1H), 7.54-7.51 (m, 2H), 7.46-7.37 (m, 3H), 7.27 and 7.22 (d and d, 1H), 5.45 and 5.32 (d and d, 1H), 3.92 and 2.79 (d and d, 1H), 3.47 (s, 1H), 3.00 and 2.96 (s and s, 3H), 2.56-2.34 (m, 2H).

Example 141

3-(3″-imino-2″-methylspiro[spiro(chroman-2,1′-cyclohexane)-4,5″-[1,2,4]triazolidine]-6-yl)benzonitrile (Compound 175)

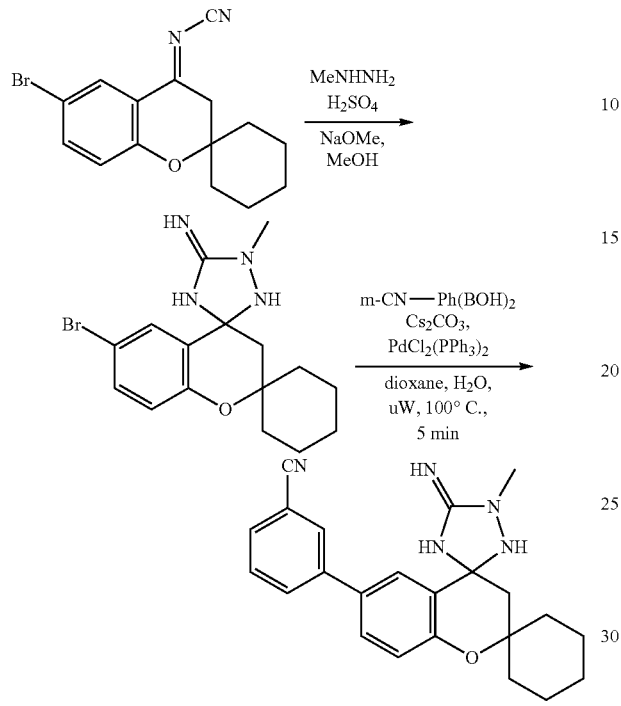

Step 1: Preparation of 6-bromo-2″-methylspiro[spiro(chroman-2,1′-cyclohexane)-4,5″-[1,2,4]triazolidine]-3″-imine To a solution of methylhydrazine $H_2SO_4$ salt (144 mg, 1.0 mmol) in anhydrous MeOH (8 mL) was added NaOMe (25 w % in MeOH, 0.46 mL, 2.0 mmol), 1 h later, followed by (E)-N-(6-bromospiro[chroman-2,1′-cyclohexane]-4-ylidene)cyanamide (319 mg, 1.0 mmol), After stirred 20 min, the solvent was removed in vacuum. The residue was redissolved in DCM (20 mL) and filtered, and the solvent was removed in vacuum to give crude product.

It was purified on preparative HPLC to 6-bromo-2″-methylspiro[spiro(chroman-2,1′-cyclohexane)-4,5″-[1,2,4]-triazolidine]-3″-imine TFA salt as a white solid. MS ESI+ve m/z 365 (M+H)$^+$.

Example 142

Preparation of (2S,4S/2R,4R)-6-(3,5-difluorophenyl)-2′-methyl-2-((S/R)-tetrahydro-2H-pyran-3-yl)-2′H-spiro[chroman-4,5′-[1,2,4]oxadiazol]-3′-amine (326) and (2S,4R/2R,4S)-6-(3,5-difluorophenyl)-2′-methyl-2-((S/R)-tetrahydro-2H-pyran-3-yl)-2′H-spiro[chroman-4,5′-[1,2,4]oxadiazol]-3′-amine (322)

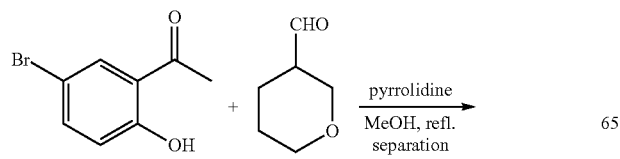

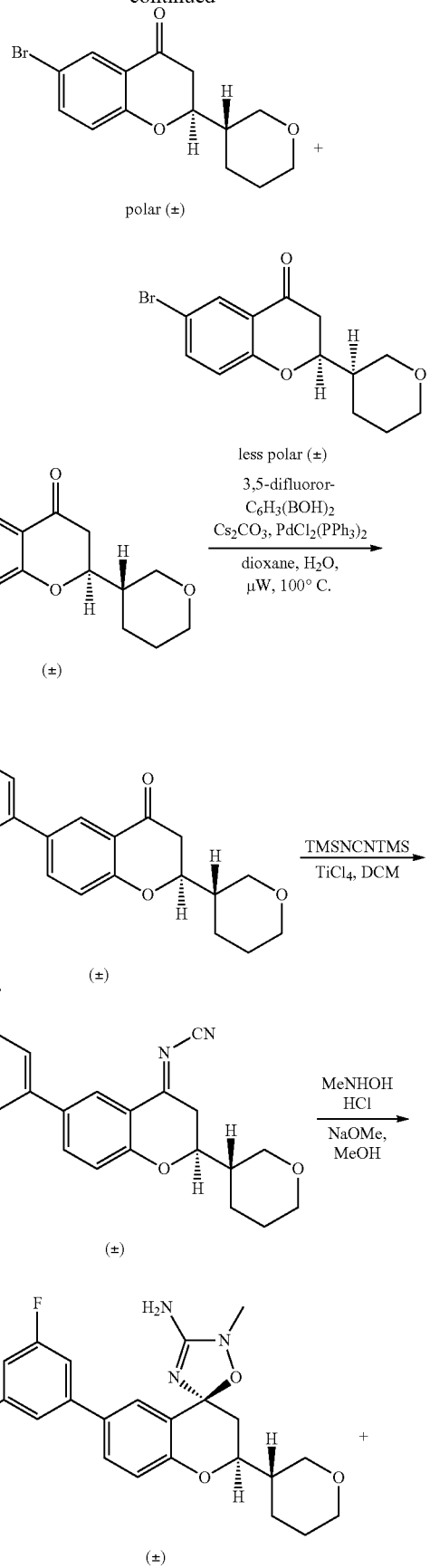

-continued

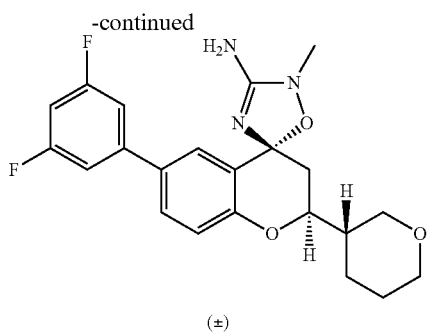

(±)

Step 1: Preparation of (S/R)-6-bromo-2-((S/R)-tetrahydro-2H-pyran-3-yl)chroman-4-one and (S/R)-6-bromo-2-((R/S)-tetrahydro-2H-pyran-3-yl)chroman-4-one To a solution of 1-(5-bromo-2-hydroxyphenyl)ethanone (6.069 g, 28.23 mmol) and tetrahydro-2H-pyran-3-carbaldehyde (3.218 g, 28.23 mmol) in MeOH (50 mL) was added pyrrolidine (1.5 mL). The resulting solution was heated to reflux and monitored with LC-MS. 50% conversion was achieved after 2 h. After 12 h, there was no improvement in conversion. The reaction mixture was cooled down to room temperature and the solvent was removed under reduced pressure. The residue was purified by flash chromatography on silica gel and eluted with EA in hexane (0-30%) to produce 1.981 g of 6-bromo-2-(tetrahydro-2H-pyran-3-yl)chroman-4-one. 1.321 g of 6-bromo-2-(tetrahydro-2H-pyran-3-yl)chroman-4-one was further purified by preparative HPLC to give (S/R)-6-bromo-2-((S/R)-tetrahydro-2H-pyran-3-yl)chroman-4-one (A) (669 mg, polar isomer on preparative HPLC) and (S/R)-6-bromo-2-((R/S)-tetrahydro-2H-pyran-3-yl)chroman-4-one (B)(512 mg, less polar isomer on preparative HPLC). MS ESI+ve m/z 311 (M+H)+.

Step 2: Preparation of (S/R)-6-(3,5-difluorophenyl)-2-((S/R)-tetrahydro-2H-pyran-3-yl)chroman-4-one To a 10 mL CEM microwave test tube was charged with Cs$_2$CO$_3$ (600 mg, 1.84 mmol), PdCl$_2$(PPh$_3$)$_2$ (42 mg, 0.06 mmol), (S/R)-6-bromo-2-((S/R)-tetrahydro-2H-pyran-3-yl)chroman-4-one (285.5 mg, 0.92 mmol), 3,5-difluorophenylboronic acid (232 mg, 1.47 mmol), dioxane (5 mL) and H$_2$O (0.5 mL), the system was swept with N$_2$ and capped, and heated in a CEM microwave reactor at 100 C for 8 min. In another tube charged with the same amount of reagents and starting material, repeated the same reaction at the same temperature and reaction time. The combined reaction mixtures were evaporated. The residue was dissolved in MeOH and filtered. The filtrate was evaporated and purified by flash chromatography on silica gel and eluted with EA in hexane (0-40%) to give (S/R)-6-bromo-2-((S/R)-tetrahydro-2H-pyran-3-yl)chroman-4-one (520 mg). $^1$H NMR (400 MHz, CDCl$_3$) δ: 8.06 (d, J=2.4 Hz, 1H), 7.67 (dd, J=8.8, 2.4, 1H), 7.11-7.06 (m, 3H), 6.77 (m, 1H), 4.34 (m, 1H), 4.22 (m, 1H), 3.91 (m, 1H), 3.47-3.41 (m, 2H), 2.82-2.69 (m, 2H), 2.10 (m, 1H), 1.88 (m, 1H), 1.71-1.65 (m, 2H), 1.41 (m, 1H); $^{19}$F NMR (375 Hz, CDCl$_3$) δ: −109.82; MS ESI+ve m/z 345 (M+H)+.

Step 3: Preparation of N—((S/R)-6-(3,5-difluorophenyl)-2-((S/R)-tetrahydro-2H-pyran-3-yl)chroman-4-ylidene)cyanamide To a solution of (S/R)-6-bromo-2-((S/R)-tetrahydro-2H-pyran-3-yl)chroman-4-one (509 mg, 1.52 mmol) in anhydrous DCM (15 mL) under N$_2$ atmosphere was added 1 M TiCl$_4$ (in DCM, 4 mL, 4 mmol) dropwise within 15 min at room temperature. It was stirred another 1 h after the addition. To this mixture was added Bis-trimethylsilylcarbodiimide (0.623 g, 0.75 mL, 3.34 mmol) dropwise. The resulting mixture was stirred overnight after the addition. The reaction mixture was poured into ice-water (35 g), and stirred for 10 min, then it was transferred to a separating funnel, the separated aqueous phase was extracted 2 times with DCM. The combined organic phases were dried over anhydrous Na$_2$SO$_4$, and filtered, and concentrated to give N—((S/R)-6-(3,5-difluorophenyl)-2-((S/R)-tetrahydro-2H-pyran-3-yl)chroman-4-ylidene)cyanamide as light brown solid (580 mg), which was used for next step without further purification. MS ESI+ve m/z 369 (M+H)+.

Step 4: Preparation of (2S,4S/2R,4R)-6-(3,5-difluorophenyl)-2'-methyl-2-((S/R)-tetrahydro-2H-pyran-3-yl)-2'H-spiro[chroman-4,5'-[1,2,4]oxadiazol]-3'-amine and (2S,4R/2R,4S)-6-(3,5-difluorophenyl)-2'-methyl-2-((S/R)-tetrahydro-2H-pyran-3-yl)-2'H-spiro[chroman-4,5'-[1,2,4]oxadiazol]-3'-amine To a solution of N-methylhydroxylamine hydrochloride (129 mg, 1.54 mmol) in MeOH (10 mL) was added 25 wt % NaOMe in MeOH (0.32 mL, 1.39 mmol). The resulting mixture was stirred 5 min and transferred through a syringe to a suspension of N—((S/R)-6-(3,5-difluorophenyl)-2-((S/R)-tetrahydro-2H-pyran-3-yl)chroman-4-ylidene)cyanamide (crude from previous step, 1.52 mmol) in MeOH (8 mL). The mixture was stirred at room temperature for 20 min Solvent was removed under reduced pressure. The residue was taken in hexane and filtered, the cake was collected and purified by preparative PHLC to gave (2S,4S/2R,4R)-6-(3,5-difluorophenyl)-2'-methyl-2-((S/R)-tetrahydro-2H-pyran-3-yl)-2'H-spiro[chroman-4,5'-[1,2,4]oxadiazol]-3'-amine as TFA salt and (2S,4R/2R,4S)-6-(3,5-difluorophenyl)-2'-methyl-2-((S/R)-tetrahydro-2H-pyran-3-yl)-2'H-spiro[chroman-4,5'-[1,2,4]oxadiazol]-3'-amine as TFA salt.

Compound 326: $^1$H NMR (400 MHz, CD$_3$OD) δ: 7.93 (d, J=2.0 Hz, 1H), 7.69 (td, J=8.4, 2.4 Hz, 1H), 7.26-7.22 (m, 2H), 7.01 (m, 1H), 6.91 (m, 1H), 4.22-4.14 (m, 2H), 3.88 (m, 1H), 3.45 (m, 2H), 3.43 (s, 3H), 2.60 (dd, J=10.0, 2.8 Hz, 1H), 2.45 (dd, J=14.0, 10.0 Hz, 1H), 2.07-1.93 (m, 2H), 1.70-1.50 (m, 3H); $^{19}$F NMR (375 Hz, CD$_3$OD) δ: −111.95; MS ESI+ve m/z 416 (M+H)+.

Compound 322: $^1$H NMR (400 MHz, CD$_3$OD) δ: 7.93 (d, J=2.0 Hz, 1H), 7.70 (dd, J=8.8, 2.4 Hz, 1H), 7.28-7.23 (m, 2H), 7.02 (d, J=8.8 Hz, 1H), 6.93 (m, 1H), 4.22-4.17 (m, 2H), 3.89 (brd, J=11.2 Hz, 1H), 3.50-3.43 (m, 2H), 3.37 (s, 3H), 2.75 (dd, J=14.0, 2.4 Hz, 1H), 2.03-1.72 (m, 3H), 1.72-1.66 (m, 2H), 1.55 (m, 1H); $^{19}$F NMR (375 Hz, CD$_3$OD) δ: −111.95; MS ESI+ve m/z 416 (M+H)+.

Example 143

Preparation of Compound 210

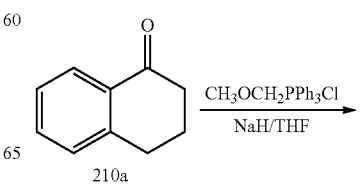

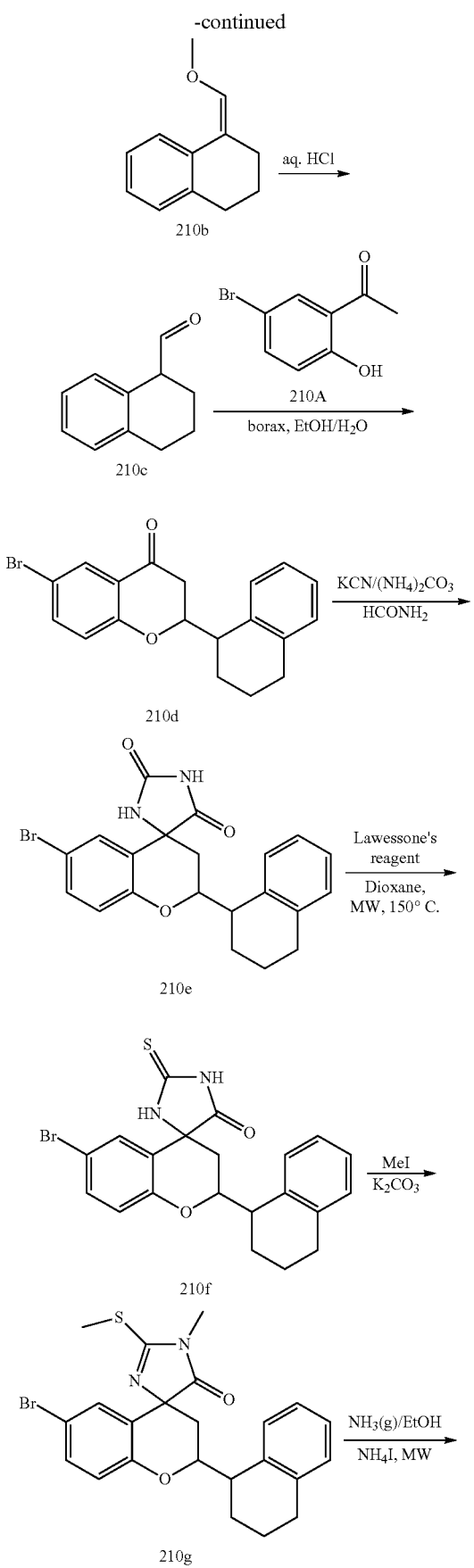

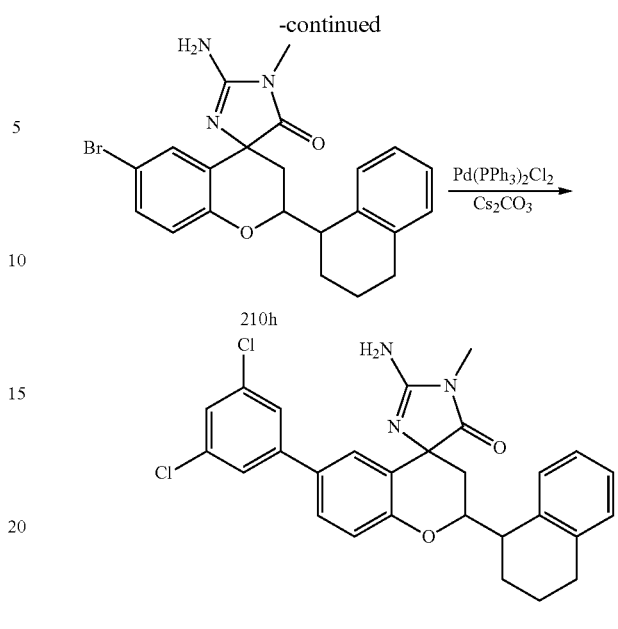

Experimental Data

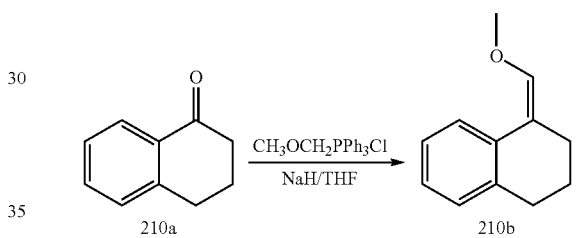

To a solution of CH₃OCH₂PPh₃Cl (171.4 g, 0.5 mol) in THF (1000 mL), was added NaH (20.4 g, 0.51 mol, 60%) at room temperature, and the solution was stirred at room temperature for 15 minutes. A solution of compound 210a (65.73 g, 0.45 mol) in THF was added at room temperature, after being stirred for 30 minutes, the reaction mixture was refluxed for 6 hours. Ethanol was added, the mixture was extracted with EtOAc. The organic phase was dried over Na₂SO₄, filtered, and evaporated under reduced pressure, and purified by column chromatography to give the compound 210b (49.85 g, 64%). ¹H-NMR (CDCl₃ 400 MHz): δ7.27-7.29 (m, 1H), 7.23-7.25 (m, 1H), 7.02 (m, 1H), 6.98-7.00 (m, 2H), 6.54 (s, 1H), 3.65 (s, 3H), 3.64 (s, 1H), 2.63-2.67 (m, 2H), 2.42-2.45 (m, 2H), 1.67-1.73 (m, 2H).

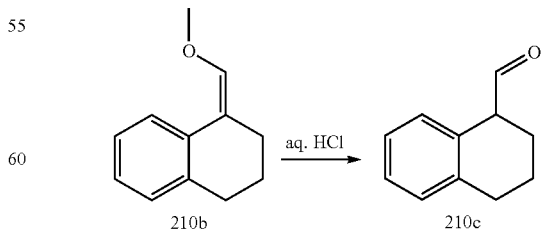

To a solution of compound 210b (30 g, 0.172 mol) in CH₃OH (300 mL) was added aqueous HCl solution (1500 mL, 2 mol/L). The reaction mixture was refluxed overnight, evaporate in vacuo, extracted with diethyl ether, dried over Na₂SO₄, and evaporated to give the crude compound 210c (21 g, 76%), which was used for the next step without purification. ¹H-NMR (CDCl₃ 400 MHz): δ9.60 (m, 1H), 7.14-7.19 (m, 2H), 7.08-7.13 (m, 2H), 3.52 (s, 1H), 2.11-2.19 (m, 1H), 1.85-1.87 (m, 1H), 1.68-1.75 (m, 2H).

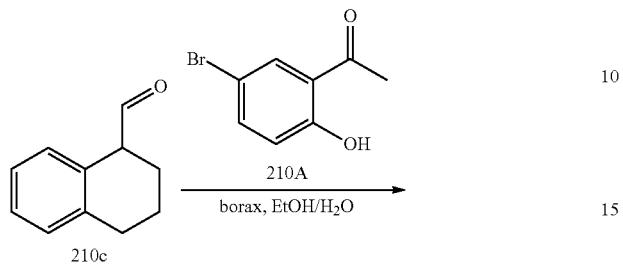

To a stirred solution of compound 210A (28.1 g, 0.131 mol) in a mixture of EtOH (128 mL) and water (211 mL) was added compound 210c (21 g, 0.131 mol) and borax (49.9 g, 0.131 mol). The mixture was refluxed for 2 days, filtrates, and dissolved in CH₂Cl₂. After filtration and evaporation, the crude product was purified by HPLC preparation to give the compound 210d (11.5 g, 25%). ¹H-NMR (CDCl₃ 300 MHz): δ7.90-7.91 (m, 1H), 7.46-7.51 (m, 1H), 7.11-7.19 (m, 1H), 7.04-7.09 (m, 3H), 6.81-6.86 (m, 1H), 4.58-4.79 (m, 1H), 3.32-3.48 (m, 1H), 2.66-2.79 (m, 3H), 2.47-2.62 (m, 1H), 1.96-2.06 (m, 1H), 1.75-1.95 (m, 2H), 1.68-1.74 (m, 1H).

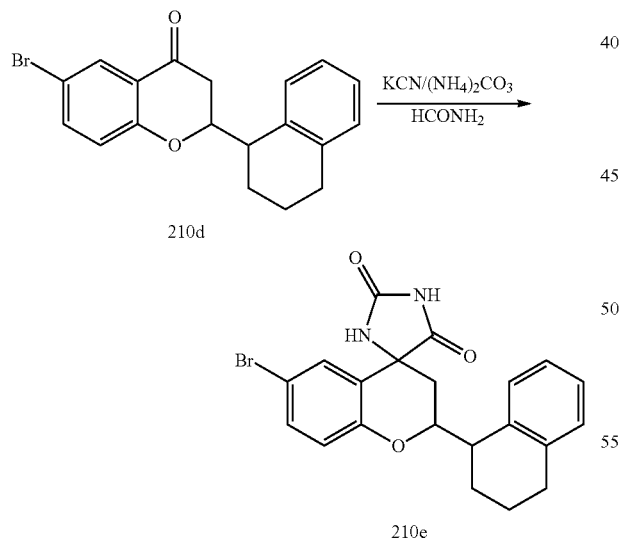

A steel slave was charged with a mixture of compound 210d (6 g, 16.85 mmol), KCN (2.19 g, 33.7 mmol) and (NH₄)₂CO₃ (11.81 g, 123 mmol). Formamide (200 mL) was added. The mixture was heated at 70° C. for 72 hours, cooled, and poured into ice. After acidification with concentrated HCl solution to pH=1, the mixture was filtered, and the solid was dissovled in CH₂Cl₂ (500 mL). The organic layer was washed with water (2×500 mL), dried over Na₂SO₄, filtered, and concentrated in vacuo. The residue was purified by column chromatography (DCM/MeOH=50:1) to give the compound 210e (7 g, 97%) as orange solid. ¹H-NMR (CDCl₃ 400 MHz): δ7.40 (m, 2H), 7.13 (m, 4H), 6.83 (m, 1H), 5.1 (d, J=12.0 Hz, 1H), 3.2 (m, 1H), 2.70 (m, 1H), 2.65 (m, 4H), 1.70 (m, 2H), 1.65 (m, 1H).

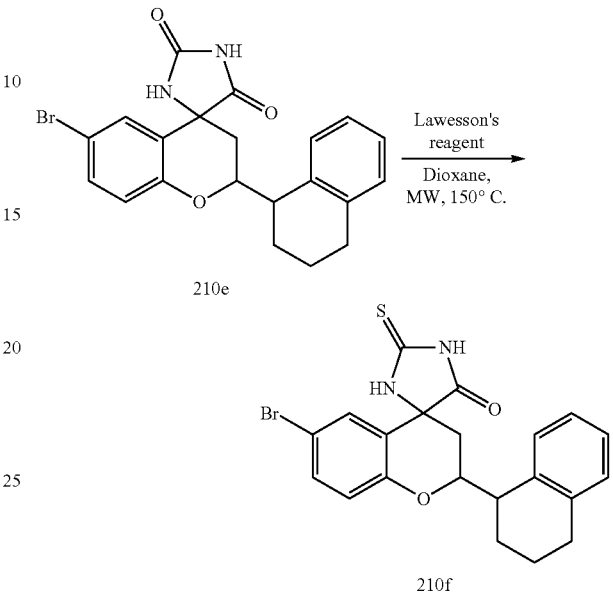

To solution of compound 210e (0.4 g, 0.94 mmol) and Lawesson' reagent (0.38 g, 0.94 mmol) in dioxane (20 mL) was heated under 150° C. for 25 minutes in a microwave reactor. The mixture was cooled, and concentrated in vacuo. The residue was purified by column chromatography (PE/EtOAc=20:1) to give the compound 210f (0.15 g, 36%) as a light orange solid. ¹H-NMR (CDCl₃ 400 MHz): δ7.31 (d, J=4.0 Hz, 1H), 7.12 (s, 1H), 7.05 (m, 3H), 6.95 (d, J=20.0 Hz, 1H), 6.76 (m, 1H), 4.95 (m, 1H), 3.22 (m, 1H), 2.65 (s, 2H), 2.05 (m, 2H), 1.90 (m, 2H), 1.70 (m, 1H), 1.55 (s, 1H).

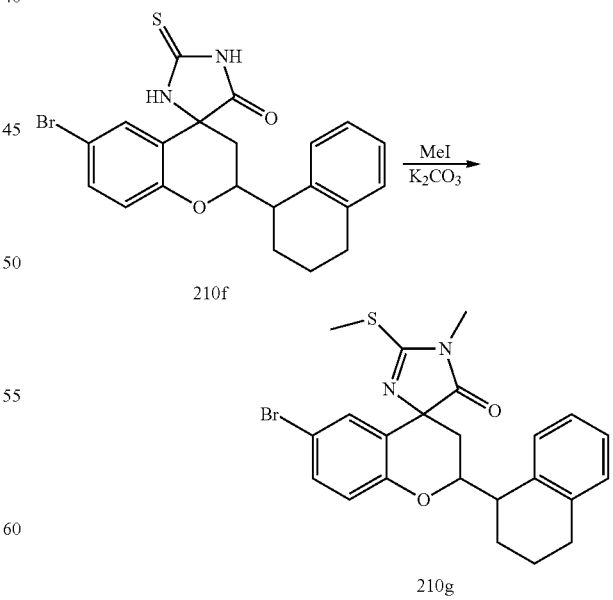

To a solution of compound 210f (100 mg, 0.226 mmol) in CH₃CN (2 mL) was added K₂CO₃ (125 mg, 0.904 mmol) and MeI (128 mg, 0.904 mmol). The mixture was stirred at room temperature for 3 hours. The solution was filtered, and the filtrate was concentrated in vacuo. The residue was purified by preparative TLC (PE:EtOAc=3:1) to give the compound 210g (74 mg, 70%) as a white solid. $^1$H-NMR (CDCl$_3$ 400 MHz): δ7.25 (d, J=8.0 Hz, 1H), 7.15 (d, J=8.0 Hz, 1H), 7.04 (m, 3H), 6.72 (m, 1H), 5.05 (m, 1H), 3.17 (m, 1H), 2.97 (s, 1H), 2.75 (m, 2H), 2.56 (s, 3H), 2.46 (d, J=12.0 Hz, 2H), 2.22 (m, 1H), 1.95 (m, 2H), 1.82 (m, 1H), 1.65 (m, 2H).

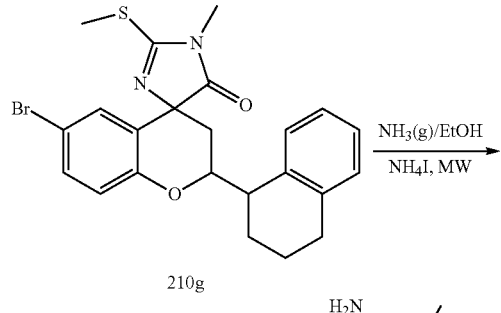

A solution of compound 210g (50 mg, 0.106 mmol) and NH$_4$I (123 mg, 0.851 mmol) in a solution of NH$_3$/EtOH (5 mL, 0.5 N) was heated at 120° C. in a CEM tube under microwave reactor for 3 hours. The mixture was concentrated in vacuo, and the residue was added CH$_2$Cl$_2$ (20 mL) and filtered. The filtrate was concentrated in vacuo, and the residue was purified by preparative TLC (CH$_2$Cl$_2$: MeOH=10:1) to give the compound 210h (36 mg, 77%) as yellow oil. $^1$H-NMR (CDCl$_3$ 400 MHz): δ7.19 (d, J=4.0 Hz, 2H), 7.02 (m, 4H), 6.78 (m, 1H), 5.23 (m, 1H), 3.09 (m, 1H), 3.02 (s, 3H), 2.67 (m, 3H), 2.20 (m, 1H), 1.90 (m, 3H), 1.76 (m, 2H).

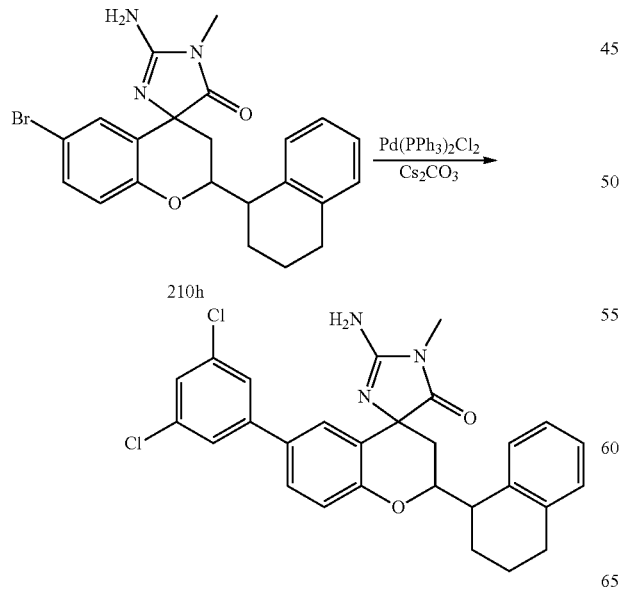

To a solution of compound 210g (30 mg, 0.068 mmol), 3,5-dichlorophenylboronic acid (16 mg, 0.082 mmol), and Cs$_2$CO$_3$ (0.5 mL, 6 mmol, 2 M, aqueous) in dioxane (1.5 mL) was added Pd(PPh$_3$)$_2$Cl$_2$ (5 mg). The mixture was heated at 120° C. in a microwave reactor for 15 minutes under nitrogen atmosphere. The reaction mixture was filtered, and the filtrate was concentrated in vacuo. The residue was purified by preparative TLC (CH$_2$Cl$_2$: MeOH=10:1) and HPLC to give the compound 210 (4 mg, 12%) as a solid. $^1$HNMR (CD$_3$OD 400 MHz): δ7.49 (m, 3H), 7.45 (d, J=12.0 Hz, 1H), 7.38 (m, 2H), 7.05 (m, 3H), 6.92 (d, J=8.0 Hz, 1H), 5.05 (m, 1H), 3.22 (s, 3H), 2.70 (m, 2H), 2.56 (s, 1H), 2.35 (d, J=12.0 Hz, 1H), 2.24 (m, 1H), 1.96 (m, 2H), 1.68 (m, 1H), 1.19 (s, 1H); ESI MS: 506 [M+H]$^+$.

Example 144

Preparation of (±)-(2S,4S)-6-(3,5-difluorophenyl)-2'-methyl-2-((R)-tetrahydro-2H-pyran-3-yl)-2'H-spiro[chroman-4,5'-[1,2,4]oxadiazol]-3'-amine (323) and (±)-(2S,4R)-6-(3,5-difluorophenyl)-2'-methyl-2-((R)-tetrahydro-2H-pyran-3-yl)-2'H-spiro[chroman-4,5'-[1,2,4]oxadiazol]-3'-amine (316)

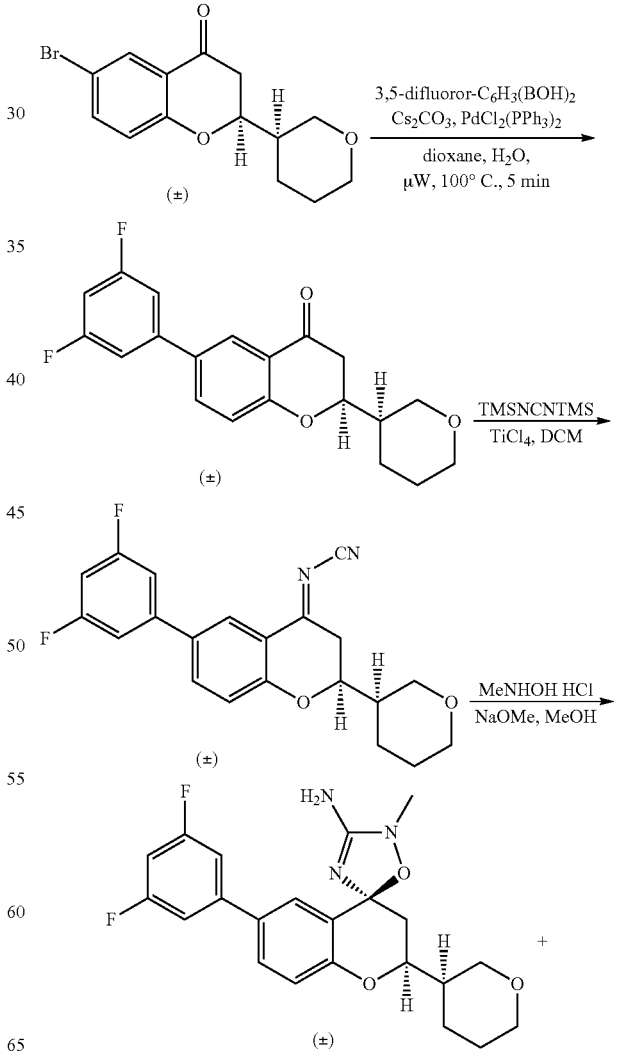

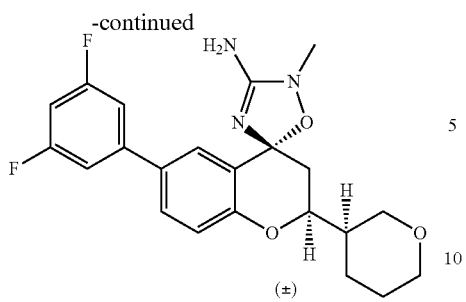

(±)

Step 1: Preparation of (S/R)-6-(3,5-difluorophenyl)-2-((R/S)-tetrahydro-2H-pyran-3-yl)chroman-4-one To a 10 mL CEM microwave test tube was charged with $Cs_2CO_3$ (391 mg, 1.20 mmol), $PdCl_2(PPh_3)_2$ (30 mg, 0.04 mmol), (S/R)-6-bromo-2-((R/S)-tetrahydro-2H-pyran-3-yl)chroman-4-one (185.7 mg, 0.60 mmol), 3,5-difluorophenylboronic acid (142 mg, 0.90 mmol), dioxane (3 mL) and $H_2O$ (0.3 mL), the system was swept with $N_2$ and capped, and heated in a CEM microwave reactor at 100 C for 8 min. Another tube charged with the same amount of reagents and starting material was repeated the same reaction at the same temperature and reaction time. Combined the reaction mixture and evaporated. The residue was dissolved in MeOH and filtered. The filtrate was evaporated and purified by flash chromatography on silica gel and eluted with EA in hexane (0-40%) to give (S/R)-6-(3,5-difluorophenyl)-2-(R/S)-tetrahydro-2H-pyran-3-yl)chroman-4-one (281 mg). $^1$H NMR (400 MHz, $CDCl_3$) δ: 8.07 (s, 1H), 7.68 (dd, J=8.4, 2.0, 1H), 7.09-7.06 (m, 3H), 6.77 (m, 1H), 4.38 (m, 1H), 3.97-3.90 (m, 2H), 3.52-3.43 (m, 2H), 2.84-2.65 (m, 2H), 2.05 (m, 2H), 1.73-1.61 (m, 4H); $^{19}$F NMR (375 Hz, $CDCl_3$) δ: -109.82; MS ESI+ve m/z 345 (M+H)$^+$.

Step 2: Preparation of N—((S/R)-6-(3,5-difluorophenyl)-2-((R/S)-tetrahydro-2H-pyran-3-yl)chroman-4-ylidene)cyanamide To a solution of (S/R)-6-(3,5-difluorophenyl)-2-(R/S)-tetrahydro-2H-pyran-3-yl)chroman-4-one (273 mg, 0.82 mmol) in anhydrous DCM (10 mL) under $N_2$ atmosphere was added 1 M $TiCl_4$ (in DCM, 2.1 mL, 2.1 mmol) dropwise within 15 min at room temperature. It was stirred another 1 h after the addition. To this mixture was added Bis-trimethylsilylcarbodiimide (0.336 g, 0.40 mL, 3.34 mmol) dropwise. The resulting mixture was stirred overnight after the addition. The reaction mixture was poured into ice-water (35 g), and stirred for 10 min, then it was transferred to a separating funnel, the separated aqueous phase was extracted twice with DCM. The combined organic phases were dried over anhydrous $Na_2SO_4$, and filtered, and concentrated to give N—((S/R)-6-(3,5-difluorophenyl)-2-((R/S)-tetrahydro-2H-pyran-3-yl)chroman-4-ylidene)cyanamide as light brown solid (100% yield), which was used for next step without further purification. MS ESI+ve m/z 369 (M+H)$^+$.

Step 3: Preparation of (2S/2R)-6-(3,5-difluorophenyl)-2'-methyl-2-((R/S)-tetrahydro-2H-pyran-3-yl)-2'H-spiro[chroman-4,5'-[1,2,4]oxadiazol]-3'-amine To a solution of N-methylhydroxylamine hydrochloride (71 mg, 0.85 mmol) in MeOH (4 mL) was added 25 wt % NaOMe in MeOH (0.17 mL, 0.75 mmol). The resulting mixture was stirred 5 min and then transferred through a syringe to a suspension of above crude product in MeOH (8 mL). The mixture was stirred at room temperature for 20 min Solvent was removed under reduced pressure. The residue was purified by preparative PHLC to gave compound 323 (2S,4S/2R,4R)-6-(3,5-difluorophenyl)-2'-methyl-2-4R/S)-tetrahydro-2H-pyran-3-yl)-2'H-spiro[chroman-4,5'-[1,2,4]oxadiazol]-3'-amine and compound 316 (2S,4R/2R,4S)-6-(3,5-difluorophenyl)-2'-methyl-2-((R/S)-tetrahydro-2H-pyran-3-yl)-2'H-spiro[chroman-4,5'-[1,2,4]oxadiazol]-3'-amine.

Compound 323: $^1$H NMR (400 MHz, $CD_3OD$) δ: 7.93 (d, J=2.4 Hz, 1H), 7.67 (td, J=8.8, 2.4 Hz, 1H), 7.26-7.22 (m, 2H), 7.01 (d, J=8.8 Hz, 1H), 6.90 (m, 1H), 4.24 (m, 1H), 3.958 (m, 1H), 3.86 (m, 1H), 3.53-3.46 (m, 2H), 3.44 (s, 3H), 2.57 (dd, J=14.0, 2.4 Hz, 1H), 2.41 (dd, J=14.0, 10.8 Hz, 1H), 2.04-2.02 (m, 2H), 1.74-1.63 (m, 3H); $^{19}$F NMR (375 Hz, $CD_3OD$) δ: -111.92; MS ESI+ve m/z 416 (M+H)$^+$.

Compound 316: $^1$H NMR (400 MHz, $CD_3OD$) δ: 7.93 (d, J=2.4 Hz, 1H), 7.70 (dd, J=8.4, 2.0 Hz, 1H), 7.26-7.24 (m, 2H), 7.01 (d, J=8.4 Hz, 1H), 6.91 (m, 1H), 4.24 (m, 1H), 3.97 (m, 1H), 3.89 (m, 1H), 3.57-3.43 (m, 2H), 3.37 (s, 3H), 2.65 (dd, J=14.4, 2.4 Hz, 1H), 2.08-1.95 (m, 3H), 1.73-1.64 (m, 3H); $^{19}$F NMR (375 Hz, $CD_3OD$) δ: -111.95; MS ESI+ve m/z 416 (M+H)$^+$.

Example 145

Preparation of 3-(3'-amino-2'-methyl-2-((tetrahydrofuran-2-yl)methyl)-2'H-spiro[chroman-4,5'-[1,2,4]oxadiazole]-6-yl)benzonitrile (Compounds 360, 366 and 367)

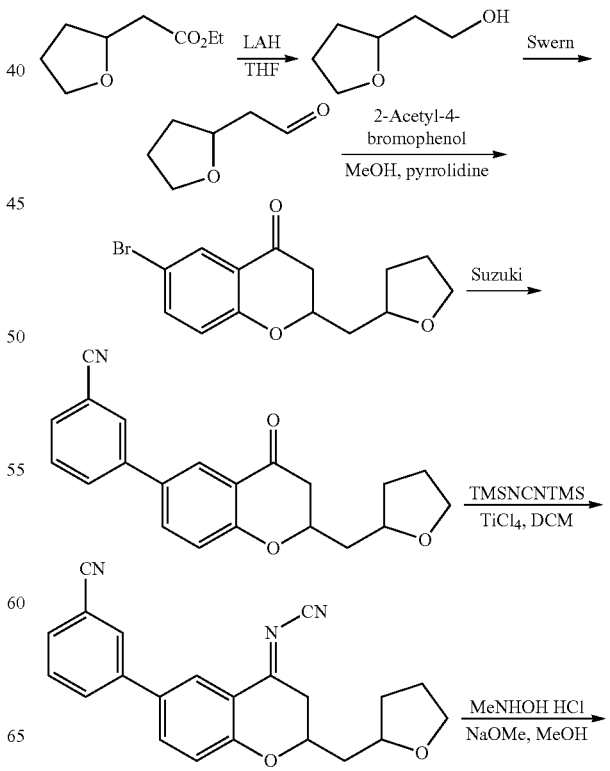

-continued

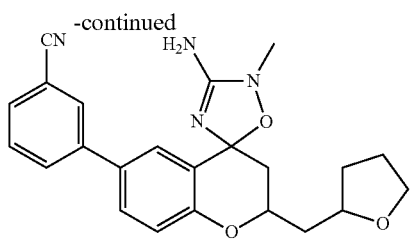

Step 1: Preparation of 2-(tetrahydrofuran-2-yl)ethanol

To a solution of ethyl 2-(tetrahydrofuran-2-yl)acetate (3.051 g, 19.29 mmol) in anhydrous THF (50 mL) chilled to 0° C. was added 1 M LAH/THF solution (14.5 mL, 14.5 mmol) dropwise. The resulting mixture was stirred for another 30 min after the addition. $Na_2SO_4 \cdot 10 H_2O$ (18 g) was added slowly to quench the reaction at 0° C. The reaction mixture was stirred for another 1 h at room temperature and filtered through a short pad of Celite and washed with THF. The filtrate was dried over anhydrous $Na_2SO_4$, and filtered, and concentrated to give 1.85 g of 2-(tetrahydrofuran-2-yl) ethanol, which was used for next step without further purification.

Step 2: Preparation of 2-(tetrahydrofuran-2-yl)acetaldehyde

To a solution of oxalyl chloride (3.666 g, 2.52 mL, 28.88 mmol) in anhydrous DCM (60 mL) at −78° C. was added a solution of DMSO (3.761 g, 3.42 mL, 48.14 mmol) in anhydrous DCM (10 mL) through a pressure equalizing addition funnel in such a rate maintaining reaction temperature below −72° C. The reaction was stirred another 30 min after the addition. Then, a solution of 2-(tetrahydrofuran-2-yl)ethanol (2.792 g, 24.07 mmol) in DCM (30 mL) was added in such a rate maintaining the reaction temperature below −70° C. The reaction was stirred another 30 min after the addition, then TEA (12.167 g, 16.76 mL, 120.35 mmol) is added at −78° C. The reaction temperature was allowed to warm to room temperature slowly without removing dry ice-acetone bath and stirred overnight. The reaction mixture was washed with $H_2O$ (100 mL), 1 M HCl (2×150 mL), $H_2O$ (100 mL), brine (100 mL) successively, then, dried over anhydrous $Na_2SO_4$, and filtered, and concentrated to give 2.1 g of 2-(tetrahydrofuran-2-yl)acetaldehyde. It was used for next step without further purification.

Step 3: Preparation of 6-bromo-2-((tetrahydrofuran-2-yl)methyl)chroman-4-one The solution of 2-Acetyl-4-bromophenol (1.754 g, 8.16 mmol), 2-(tetrahydrofuran-2-yl)acetaldehyde (2.1 g) and purrolidine (0.4 mL) in MeOH was heated to reflux for 2 h. The reaction mixture was cool down to room temperature and evaporated. The residue was dissolved in EA, washed with 1 M HCl, 1 M NaOH (2×50 mL), brine (100 mL) successively, then, dried over anhydrous $Na_2SO_4$, and filtered, and concentrated. The residue was purified by flash chromatography on silica gel eluting with EA in hexane (0-20%) to give 6-bromo-2-((tetrahydrofuran-2-yl)methyl)chroman-4-one (464 mg); MS ESI+ve m/z 311 (M+H)$^+$.

Step 4: Preparation of 3-(4-oxo-2-((tetrahydrofuran-2-yl)methyl)chroman-6-yl)benzonitrile To a 10 mL CEM microwave test tube was charged with $Cs_2CO_3$ (971 mg, 2.98 mmol), $PdCl_2(PPh_3)_2$ (52.2 mg, 0.075 mmol), (S/R)-6-bromo-2-((R/S)-tetrahydro-2H-pyran-3-yl) chroman-4-one (464 mg, 1.49 mmol), 3-cyanophenylboronic acid (329 mg, 2.24 mmol), dioxane (4 mL) and $H_2O$ (0.4 mL), the system was swept with $N_2$ and capped, and heated in a CEM microwave reactor at 100° C. for 10 min. Due to incompletion of the reaction, $PdCl_2(PPh_3)_2$ (10 mg) and 3-cyanophenylboronic acid (100 mg) was added and heated for another 10 min at 100° C. The reaction mixture was diluted with EA, washed with brine, dried over anhydrous $Na_2SO_4$, and filtered, and concentrated. The residue was purified by flash chromatography on silica gel eluting with EA in hexane (0-20%) to give 3-(4-oxo-2-((tetrahydrofuran-2-yl)methyl) chroman-6-yl)benzonitrile (233 mg). MS ESI+ve m/z 334 (M+H)$^+$.

Step 5: Preparation of N-(6-(3-cyanophenyl)-2-((tetrahydrofuran-2-yl)methyl)chroman-4-ylidene)cyanamide To a solution of 3-(4-oxo-2-((tetrahydrofuran-2-yl)methyl)chroman-6-yl)benzonitrile (233 mg, 0.70 mmol) in anhydrous DCM (18 mL) under $N_2$ atmosphere was added 1 M $TiCl_4$ (in DCM, 1.4 mL, 1.4 mmol) dropwise within 15 min at room temperature. It was stirred another 1 h after the addition. To this mixture was added Bis-trimethylsilylcarbodiimide (0.287 g, 0.35 mL, 1.54 mmol) dropwise. The resulting mixture was stirred overnight after the addition. The reaction mixture was poured into ice-water (25 g), and stirred for 30 min, then it was transferred to a separating funnel, the separated aqueous phase was extracted twice with DCM (2×30 mL). The combined organic phases were dried over anhydrous $Na_2SO_4$, and filtered, and concentrated to give N-(6-(3-cyanophenyl)-2-((tetrahydrofuran-2-yl)methyl) chroman-4-ylidene)cyanamide as light brown solid, which was used for next step without further purification. MS ESI+ve m/z 358 (M+H)$^+$.

Step 6: Preparation of 3-(3'-amino-2'-methyl-2-((tetrahydrofuran-2-yl)methyl)-2'H-spiro[chroman-4,5'-[1,2,4]oxadiazole]-6-yl)benzonitrile To a solution of N-methylhydroxylamine hydrochloride (58.5 mg, 0.70 mmol) in MeOH (4 mL) was added 25 wt % NaOMe in MeOH (0.14 mL, 0.63 mmol). The resulting mixture was stirred 5 min and then transferred through a syringe to a suspension of above crude product MeOH (4 mL). The mixture was stirred at room temperature for 10 min Solvent was removed under reduced pressure. The residue was purified by preparative PHLC to gave 3 isomers of 3-(3'-amino-2'-methyl-2-((tetrahydrofuran-2-yl)methyl)-2'H-spiro[chroman-4,5'-[1,2,4]oxadiazole]-6-yl)benzonitrile as TFA salt.

Compound 360: $^1$H NMR (400 MHz, CD$_3$OD) δ: 7.99-7.96 (m, 2H), 7.92 (d, J=8.0 Hz, 1H), 7.71-7.68 (m, 2H), 7.61 (t, J=8.0 Hz, 1H), 7.03 (d, J=8.0 Hz, 1H), 4.51 (m, 1H), 4.21 (m, 1H), 3.87 (m, 1H), 3.77 (m, 1H), 3.43 (s, 3H), 2.66 (dd, J=14.0, 2.4 Hz, 1H), 2.36 (dd, J=14.0, 2.8 Hz, 1H), 2.15-1.81 (m, 5H), 1.58 (m, 1H); MS ESI+ve m/z 405 (M+H)$^+$.

Compound 367: $^1$H NMR (400 MHz, CD$_3$OD) δ: 8.00-7.91 (m, 3H), 7.79-7.68 (m, 2H), 7.62 (t, J=8.0 Hz, 1H), 7.03 (t, J=8.0 Hz, 1H), 4.49 (m, 1H), 4.23/4.11 (m, 1H), 3.88 (m, 1H), 3.76 (m, 1H), 3.43/3.38 (s, 3H), 2.78-2.39 (m, 2H), 2.16-1.62 (m, 5H), 1.61 (m, 1H); MS ESI+ve m/z 405 (M+H)$^+$.

Compound 366: (most polar, major): $^1$H NMR (400 MHz, CD$_3$OD) δ: 7.99-7.91 (m, 3H), 7.72-7.67 (m, 2H), 7.61 (t, J=8.0 Hz, 1H), 7.03 (d, J=8.0 Hz, 1H), 4.45 (m, 1H), 4.23/

4.15 (m, 1H), 3.89 (m, 1H), 3.77 (m, 1H), 3.38 (s, 3H), 2.76 (d, J=10.4 Hz, 1H), 2.17-1.83 (m, 6H), 1.528 (m, 1H); MS ESI+ve m/z 405 (M+H)+.

Example 146

Preparation of 3-(2"H-3"-amino-2"-methyl-spiro(spiro(chroman-2,3'-[2,4,5,6-tetrahydro-6-methyl-pyran])-4,5"-[1,2,4]oxadiazole)-6-yl)benzonitrile (compound 387)

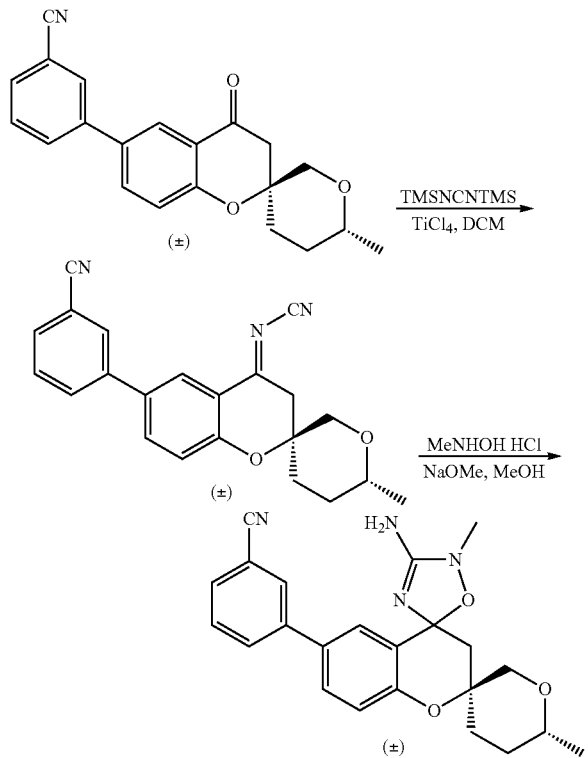

Step 1: Preparation of N-((2S,6'R/2R,6'S)-6-(3-cyanophenyl)-6'-methyl-2',4',5',6'-tetrahydrospiro[chroman-2,3'-pyran]-4-ylidene)cyanamide To a solution of 3-((2S,6'R//2R,6'S)-6'-methyl-4-oxo-2',4', 5',6'-tetrahydrospiro[chroman-2,3'-pyran]-6-yl)benzonitrile (37.4 mg, 0.11 mmol) in anhydrous DCM (5 mL) under $N_2$ atmosphere was added 1 M $TiCl_4$ (in DCM, 0.22 mL, 0.22 mmol) dropwise within 5 min at room temperature. The mixture was stirred another 1 h after the addition. To this mixture was added Bis-trimethylsilylcarbodiimide (0.45 mg, 0.054 mL, 0.24 mmol) dropwise. The resulting mixture was stirred overnight after the addition. The reaction mixture was poured into ice-water (5 g), and stirred for 30 min, then it was transferred to a separating funnel, the separated aqueous phase was extracted twice with DCM (2×10 mL). The combined organic phases were dried over anhydrous $Na_2SO_4$, and filtered, and concentrated to give N-((2S,6'R/2R,6'S)-6-(3-cyanophenyl)-6'-methyl-2',4',5',6'-tetrahydrospiro[chroman-2,3'-pyran]-4-ylidene)cyanamide as light brown solid, which was used for next step without further purification. MS ESI+ve m/z 358 (M+H)+.

Step 2: Preparation of 3-(3"-amino-2"-methyl-4",5"-dihydro-2"H-spiro(spiro(chroman-2,3'-[(2S,6R/2R, 6S)-2,4,5,6-tetrahydro-6-methyl-pyran])-4,5"-[1,2,4] oxadiazole)-6-yl)benzonitrile To a solution of N-methylhydroxylamine hydrochloride (623 mg, 7.46 mmol) in MeOH (10 mL) was added 25 wt % NaOMe in MeOH (1.54 mL, 6.71 mmol). The resulting mixture was stirred 5 min and then diluted with MeOH to total volume 20 mL. 0.295 mL of this solution was added to a suspension of above crude product MeOH (3 mL). The mixture was stirred at room temperature for 20 min Solvent was removed under reduced pressure. The residue was purified by preparative PHLC to gave 3-(3"-amino-2"-methyl-4",5"-dihydro-2"H-spiro(spiro(chroman-2,3'-[(2S,6R/2R,6S)-2,4,5, 6-tetrahydro-6-methyl-pyran])-4,5"-[1,2,4]oxadiazole)-6-yl)benzonitrile as TFA salt. $^1$H NMR (400 MHz, $CD_3OD$) δ: $^1$H NMR (400 MHz, $CD_3OD$) δ: 7.88 (s, 1H), 7.84 (d, J=8.0 Hz, 1H), 7.79 (dd, J=7.6, 2.4 Hz, 1H), 7.68-7.56 (m, 3H), 7.10 (m, 1H), 4.20 (dd, J=12.8, 2.0 Hz, 0.5H), 3.91 (dd, J=12.4, 2.4 Hz, 0.5H), 3.59-3.41 (m, 2H), 3.53 (s, 1.5H), 3.34 (s, 1.5H), 2.80-1.48 (m, 6H), 1.23 (d, J=6.4 Hz, 1.5H), 1.21 (d, J=6.4 Hz, 1.5H); MS ESI+ve m/z 405 (M+H)+.

Example 147

Preparation of 3-(3"-amino-2"-methyl-4",5"-dihydro-2"H-spiro(spiro(chroman-2,3'-[(2R,6R/2S,6S)-2, 4,5,6-tetrahydro-6-methyl-pyran])-(4R/4S)-4,5"-[1,2, 4]oxadiazole)-6-yl)benzonitrile (compound 272) and 3-(3"-amino-2"-methyl-4",5"-dihydro-2"H-spiro (spiro(chroman-2,3'-[(2R,6R/2S,6S)-2,4,5,6-tetrahydro-6-methyl-pyran])-(4S/4S)-4,5"-[1,2,4]oxadiazole)-6-yl)benzonitrile (Compound 275)

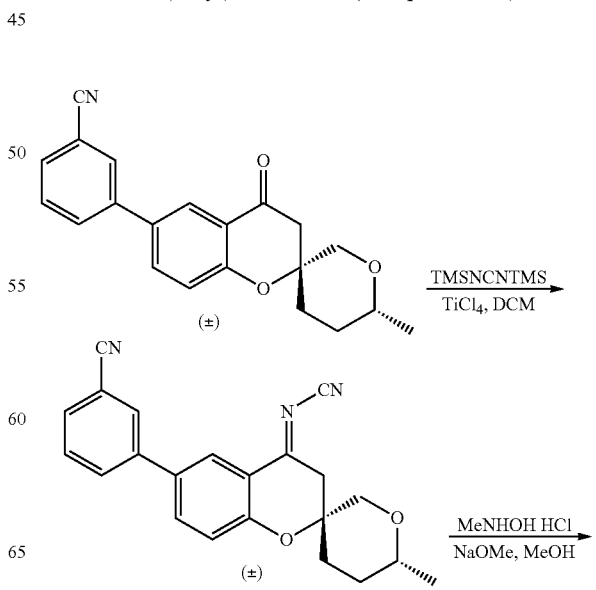

-continued

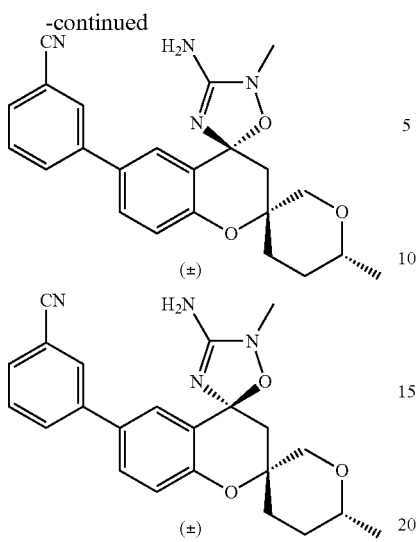

Step 1: Preparation of N-((2R,6'R/2S,6'S)-6-(3-cyanophenyl)-6'-methyl-2',4',5',6'-tetrahydrospiro[chroman-2,3'-pyran]-4-ylidene)cyanamide To a solution of 3-((2R,6'R//2S,6'S)-6'-methyl-4-oxo-2',4',5',6'-tetrahydrospiro[chroman-2,3'-pyran]-6-yl)benzonitrile (37.4 mg, 0.11 mmol) in anhydrous DCM (5 mL) under $N_2$ atmosphere was added 1 M $TiCl_4$ (in DCM, 0.22 mL, 0.22 mmol) dropwise within 5 min at room temperature. The mixture was stirred another 1 h after the addition. To this mixture was added Bis-trimethylsilylcarbodiimide (0.45 mg, 0.054 mL, 0.24 mmol) dropwise. The resulting mixture was stirred overnight after the addition. The reaction mixture was poured into ice-water (5 g), and stirred for 30 min, then it was transferred to a separating funnel, the separated aqueous phase was extracted twice with DCM (2×10 mL). The combined organic phases were dried over anhydrous $Na_2SO_4$, and filtered, and concentrated to give N-((2R,6'R/2S,6'S)-6-(3-cyanophenyl)-6'-methyl-2',4',5',6'-tetrahydrospiro[chroman-2,3'-pyran]-4-ylidene)cyanamide as light brown solid, which was used for next step without further purification. MS ESI+ve m/z 358 $(M+H)^+$.

Step 2: Preparation of 3-(3"-amino-2"-methyl-4",5"-dihydro-2"H-spiro(spiro(chroman-2,3'-[(2R,6R/2S,6S)-2,4,5,6-tetrahydro-6-methyl-pyran])-(4R/4S)-4,5"-[1,2,4]oxadiazole)-6-yl)benzonitrile and 3-(3"-amino-2"-methyl-4",5"-dihydro-2"H-spiro(spiro(chroman-2,3'-[(2R,6R/2S,6S)-2,4,5,6-tetrahydro-6-methyl-pyran])-(4S/4S)-4,5"-[1,2,4]oxadiazole)-6-yl)benzonitrile To a solution of N-methylhydroxylamine hydrochloride (623 mg, 7.46 mmol) in MeOH (10 mL) was added 25 wt % NaOMe in MeOH (1.54 mL, 6.71 mmol). The resulting mixture was stirred 5 min and then diluted with MeOH to total volume 20 mL. 0.295 mL of this solution was added to a suspension of above crude product MeOH (3 mL). The mixture was stirred at room temperature for 20 min Solvent was removed under reduced pressure. The residue was purified by preparative PHLC to gave 3-(3"-amino-2"-methyl-4",5"-dihydro-2"H-spiro(spiro(chroman-2,3'-[(2R,6R/2S,6S)-2,4,5,6-tetrahydro-6-methyl-pyran])-(4R/4S)-4,5"-[1,2,4]oxadiazole)-6-yl)benzonitrile and 3-(3"-amino-2"-methyl-4",5"-dihydro-2"H-spiro(spiro(chroman-2,3'-[(2R,6R/2S,6S)-2,4,5,6-tetrahydro-6-methyl-pyran])-(4S/4S)-4,5"-[1,2,4]oxadiazole)-6-yl)benzonitrile as TFA salt.

Compound 272: $^1$H NMR (400 MHz, $CD_3OD$) δ: 8.01-7.91 (m, 3H), 7.74-7.68 (m, 2H), 7.62 (t, J=8.0 Hz, 1H), 7.02 (d, J=8.4 Hz, 1H), 3.81 (dd, J=10.8, 2.8 Hz, 1H), 3.62-3.58 (m, 2H), 3.40 (s, 3H), 2.50 (m, 1H), 2.10 (dd, J=14.4, 1.6 Hz, 1H), 1.76 (m, 1H), 1.65 (m, 1H), 1.46 (m, 1H), 1.22 (d, J=6.0 Hz, 3H); MS ESI+ve m/z 405 $(M+H)^+$.

Compound 275: $^1$H NMR (400 MHz, $CD_3OD$) δ: 7.99 (d, J=1.2 Hz, 1H), 7.96-7.91 (m, 2H), 7.74-7.68 (m, 2H), 7.61 (m, 1H), 7.01 (d, J=8.8 Hz, 1H), 4.20 (d, J=11.2 Hz, 1H), 3.59 (m, 1H), 3.39 (s, 3H), 3.5 (m, 1H), 2.06-2.00 (m, 3H), 1.83 (m, 1H), 1.60-1.41 (m, 2H), 1.23 (d, J=6.4 Hz, 3H); MS ESI+ve m/z 405 $(M+H)^+$.

Example 148

Preparation of 3-(spiro[spiro(chroman-2,4'-(1-acetylpiperidine))-4,5'-(3-amino-2-methyl-2H-[1,2,4]oxadiazole)]-6-yl)benzonitrile (Compound 409)

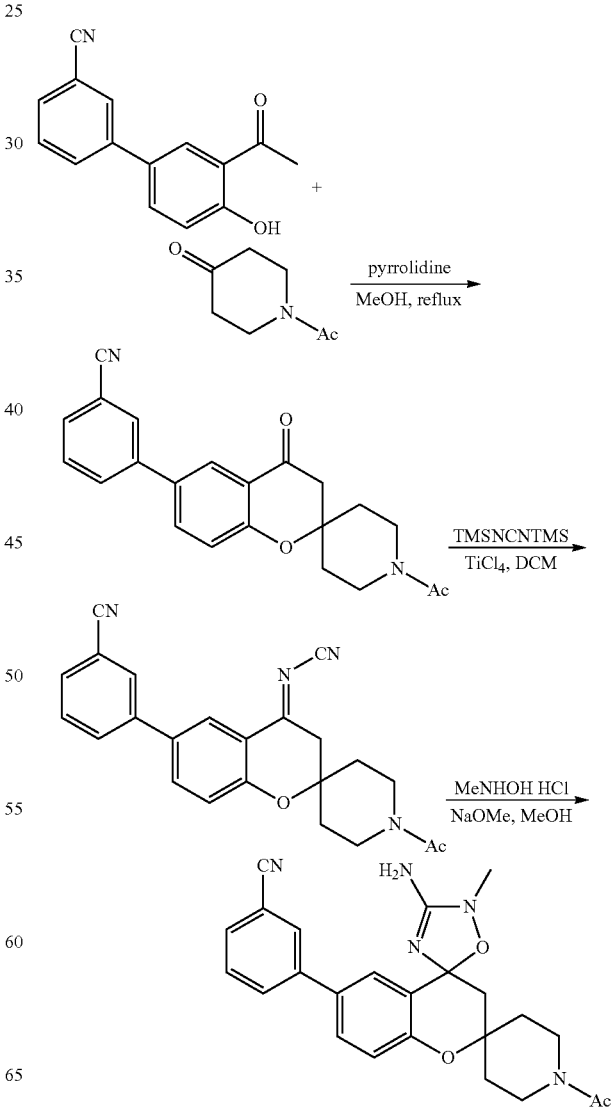

Step 1: Preparation of 3-(1'-acetyl-4-oxospiro[chroman-2,4'-piperidine]-6-yl)benzonitrile To a solution of 3'-acetyl-4'-hydroxybiphenyl-3-carbonitrile (0.802 g, 3.38 mmol) and 1-acetylpiperidin-4-one (0.477 g, 3.38 mmol) in MeOH (50 mL) was added pyrrolidine (0.4 mL). The resulting solution was heated to reflux for 1.5 h. The reaction mixture was cool down to room temperature and the solvent was removed under reduced pressure. The residue was dissolved in DCM and washed with aqueous 1 M HCl, aqueous 1 M NaOH, and brine successively. Solvent was removed under reduced pressure after dried over anhydrous $Na_2SO_4$, to yield 0.768 g of 3-(1'-acetyl-4-oxospiro[chroman-2,4'-piperidine]-6-yl)benzonitrile as a light brown solid. It was used for next step without further purification. MS ESI+ve m/z 361 $(M+H)^+$.

Step 2: Preparation of N-(1'-acetyl-6-(3-cyanophenyl)spiro[chroman-2,4'-piperidine]-4-ylidene)cyanamide To a solution of 3-(1'-acetyl-4-oxospiro[chroman-2,4'-piperidine]-6-yl)benzonitrile (60 mg, 0.167 mmol) in anhydrous DCM (5 mL) under $N_2$ atmosphere was added 1 M $TiCl_4$ (in DCM, 0.35 mL, 0.35 mmol) dropwise within 15 min at room temperature. It was stirred another 1 h after the addition. To this mixture was added Bis-trimethylsilylcarbodiimide (0.086 mL, 0.367 mmol) dropwise. The resulting mixture was stirred overnight. The reaction mixture was quenched with ice-water (5 g), and stirred for 20 min, then it was transferred to a separating funnel, the separated aqueous phase was extracted 2 times with DCM. The combined organic phases were dried over anhydrous $Na_2SO_4$, and filtered, and concentrated to give N-(1'-acetyl-6-(3-cyanophenyl)spiro[chroman-2,4'-piperidine]-4-ylidene)cyanamide as light brown solid which was used for next step without further purification. MS ESI+ve m/z 385 $(M+H)^+$.

Step 3: Preparation of 3-(spiro[spiro(chroman-2,4'-(1-acetylpiperidine))-4,5'-(3-amino-2-methyl-2H-[1,2,4]oxadiazole)]-6-yl)benzonitrile To a suspension of above crude product was added a solution of N-methylhydroxylamine in MeOH (0.373 M, 0.45 mL, prepared from N-methylhydroxylamine HCl salt and 0.9 eq 25 wt % NaOMe/MeOH in MeOH). The mixture was stirred at room temperature for 20 min Solvent was removed under reduced pressure. The residue was purified by preparative PHLC to yield the desired product. $^1$H NMR (400 MHz, $CD_3OD$) δ: 8.00 (s, 2H), 7.94 (m, 1H), 7.77-7.60 (m, 3H), 7.11 (dd, J=8.8, 2.4 Hz, 1H), 4.29 (m, 1H), 3.86-3.40 (m, 2H), 3.38 (s, 3H), 2.98 (m, 1H), 2.82 (d, J=14.8, 1H), 2.22 (d, J=14.8, 1H), 2.14 (s, 3H), 2.17-1.64 (m, 4H); MS ESI+ve m/z 432 $(M+H)^+$.

Example 149

Preparation of Compounds 302 and 311

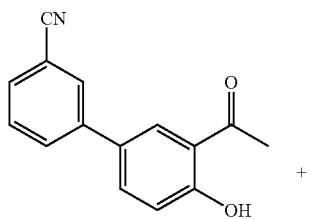

+

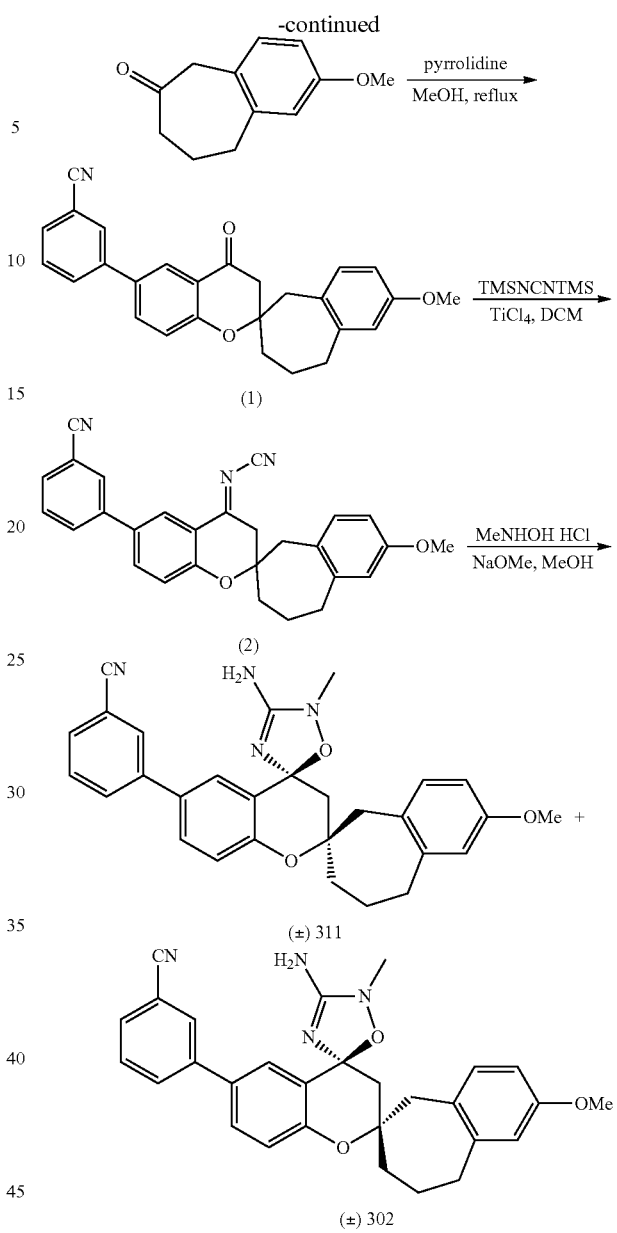

Step 1: Preparation of Compound (1)

To a 3'-acetyl-4'-hydroxybiphenyl-3-carbonitrile (0.273 g, 1.15 mmol) and 2-methoxy-8,9-dihydro-5H-benzo[7]annulen-6(7H)-one (0.219 g, 1.15 mmol) in MeOH (5 mL) was added pyrrolidine (0.12 mL). The resulting solution was heated to reflux for 4 h. The reaction mixture was cool down to room temperature and the solvent was removed under reduced pressure. The residue was purified by flash chromatography on silica gel to yield 310 mg of compound (1). MS ESI+ve m/z 410 $(M+H)^+$.

Step 2: Preparation of Compound (2)

To a solution of compound (1) (55 mg, 0.13 mmol) in anhydrous DCM (5 mL) under $N_2$ atmosphere was added 1 M $TiCl_4$ (in DCM, 0.26 mL, 0.26 mmol) dropwise within 15 min at room temperature. It was stirred another 1 h after the addition. To this mixture was added Bis-trimethylsilylcarbodiimide (0.080 mL, 0.34 mmol) dropwise. The resulting mixture was stirred overnight. The reaction mixture was quenched with ice-water (5 g), and stirred for 20 min, then it was transferred to a separating funnel, the separated aqueous phase was extracted 2 times with DCM. The combined organic phases were dried over anhydrous $Na_2SO_4$, and filtered, and concentrated to give 65 mg desired crude compound (2) as light brown solid which was used for next step without further purification. MS ESI+ve m/z 434 (M+H)+.

Step 3: Preparation of Compounds 302 and 311

To s suspension of the crude product obtained from previous step in MeOH (3 mL) was added a solution of N-methylhydroxylamine in MeOH (0.373 M, 0.35 mL, prepared from N-methylhydroxylamine HCl salt and 0.9 eq 25 wt % NaOMe/MeOH in MeOH). The mixture was stirred at room temperature for 20 min, followed by adding another portion of N-methylhydroxylamine in MeOH (0.373 M, 2 mL). Solvent was removed under reduced pressure after stirred another 20 min. The residue was purified by preparative PHLC to yield two isomers of the desired product as TFA salt.

Compound 302: $^1$H NMR (400 MHz, $CD_3OD$) δ: 8.00-7.85 (m, 3H), 7.73-7.59 (m, 3H), 7.07 (d, J=8.4 Hz, 1H), 7.01 (d, J=8.8 Hz, 1H), 7.74-7.69 (m, 2H), 3.78 (m, 3H), 3.34 (m, 3H), 2.99-1.55 (m, 10H); MS ESI+ve m/z 481 (M+H)+.

Compound 311: $^1$H NMR (400 MHz, $CD_3OD$) δ: 8.02-7.94 (m, 3H), 7.73-7.60 (m, 3H), 6.90 (d, J=8.8 Hz, 1H), 6.86 (d, J=8.0 Hz, 1H), 6.70 (d, J=2.8 Hz, 1H), 6.62 (dd, J=8.4, 2.4 Hz, 1H), 3.75 (m, 3H), 3.37 (m, 3H), 3.08-1.63 (m, 10H); MS ESI+ve m/z 481 (M+H)+.

Example 150

Preparation of 2''-methyl-6-(phenylethynyl)-2''H-spiro[spiro[chroman-2,1'-(3-oxacyclohexane)]-4,5'-[1,2,4]oxadiazol]-3''-amine (Compound 454)

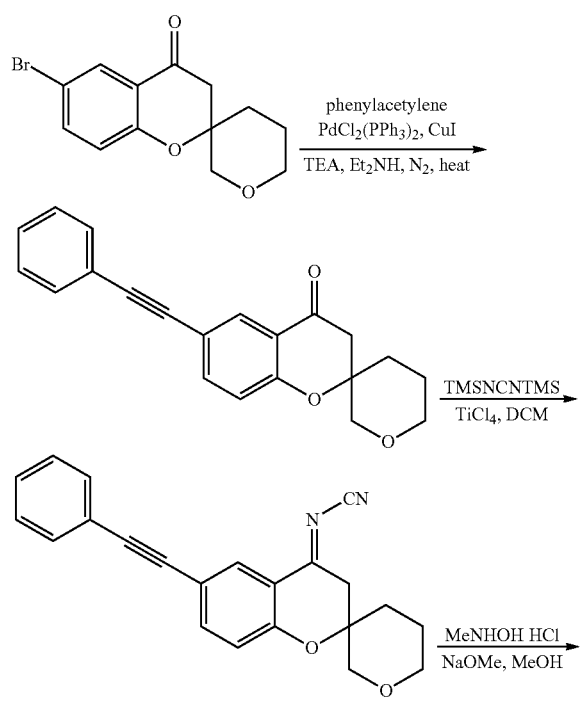

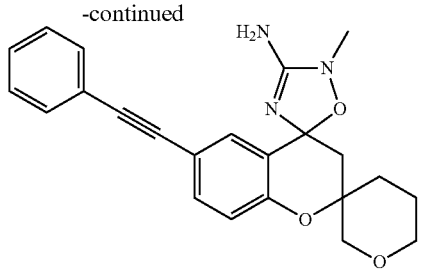

Step 1: Preparation of 6-(phenylethynyl)-2',4',5',6'-tetrahydrospiro[chroman-2,3'-pyran]-4-one An oven dried 3-necked round bottom flask equipped with condenser was charged with 6-bromo-2',4',5',6'-tetrahydrospiro[chroman-2,3'-pyran]-4-one (223 mg, 0.75 mmol), TEA (3 mL) and DEA (0.8 mL) under $N_2$ atmosphere. To this solution was added CuI (5.7 mg, 0.03 mmol), $PdCl_2(PPh_3)_2$ (21 mg, 0.03 mmol) and $PPh_3$ (16 mg, 0.06 mmol). The system was degas once again, then phenylacetylene (0.41 mL, 3.75 mmol) was added and the mixture was heated to 80° C. (oil bath) with stirring. The reaction was evaporated after 12 h and the residue was purified by flash chromatography (12 g silica gel, eluted with EA in hexane in a gradient of 0-25%, v/v) to afford 6-(phenylethynyl)-2',4',5',6'-tetrahydrospiro[chroman-2,3'-pyran]-4-one (216 mg, yield: 90%). MS ESI+ve m/z 319 (M+H)+.

Step 2: Preparation of N-(6-(phenylethynyl)-2',4',5',6'-tetrahydrospiro[chroman-2,3'-pyran]-4-ylidene) cyanamide To a solution of 6-(phenylethynyl)-2',4',5',6'-tetrahydrospiro[chroman-2,3'-pyran]-4-one (86 mg, 0.27 mmol) in anhydrous DCM (10 mL) under $N_2$ atmosphere was added 1 M $TiCl_4$ (in DCM, 0.54 mL, 0.54 mmol) dropwise within 15 min at room temperature. It was stirred another 1 h after the addition. To this mixture was added Bis-trimethylsilylcarbodiimide (0.16 mL, 0.427 mmol) dropwise. The resulting mixture was stirred 80 h. The reaction mixture was quenched with ice-water (15 g), and stirred for 30 min, then it was transferred to a separating funnel, the separated aqueous phase was extracted 2 times with DCM. The combined organic phases were dried over anhydrous $Na_2SO_4$, and filtered, and concentrated to give 112 mg the crude desired product as light yellow solid, which was used for next step without further purification. MS ESI+ve m/z 343 (M+H)+.

Step 3: Preparation of 2''-methyl-6-(phenylethynyl)-2''H-spiro[spiro[chroman-2,1'-(3-oxacyclohexane)]-4,5'-[1,2,4]oxadiazol]-3''-amine To s suspension of the crude product (34 mg, 0.10 mmol) obtained from previous step in MeOH (2 mL) was added a solution of N-methylhydroxylamine in MeOH (prepared from N-methylhydroxylamine HCl salt (8.4 mg, 0.10 mmol) inanhydrous MeOH (4 mL) and 25 wt % NaOMe/MeOH (21 μL, 0.09 mmol), stirred 5 min). The mixture was stirred at room temperature for 20 min. Due to low conversion, another portion of N-methylhydroxylamine (prepared in the same way, 3 fold scale) was added and stirred over night. Solvent was removed under reduced pressure. The residue was purified by preparative PHLC to yield 8.2 mg of the title compound as TFA salt. $^1$H NMR (400 MHz, $CD_3OD$) δ: 7.81 (d, J=6.8 Hz, 1H), 7.55-7.47 (m, 4H), 7.40-7.33 (m, 4H), 6.98 (d, J=8.8 Hz, 1H), 3.88-3.73 (m, 2H), 3.65-3.55 (m, 2H), 3.37 (s, 3H), 2.84 (d, J=14.8 Hz, 1H), 2.12-1.55 (m, 5H); MS ESI+ve m/z 390 (M+H)$^+$.

Example 151

Preparation of 2"-methyl-6-(cyclopropylethynyl)-2"H-spiro[spiro[chroman-2,1'-(3-oxacyclohexane)]-4,5'-[1,2,4]oxadiazol]-3"-amine (Compound 407)

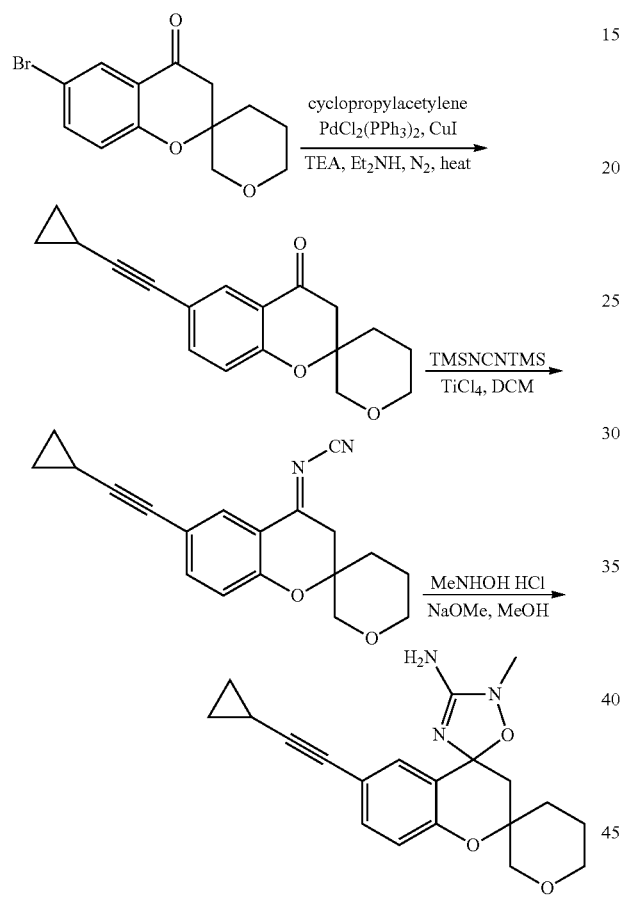

Step 1: Preparation of 6-(cyclopropylethynyl)-2',4',5',6'-tetrahydrospiro[chroman-2,3'-pyran]-4-one An oven dried 3-necked round bottom flask equipped with condenser was charged with 6-bromo-2',4',5',6'-tetrahydrospiro[chroman-2,3'-pyran]-4-one (223 mg, 0.75 mmol), TEA (3 mL) and DEA (0.8 mL) under N$_2$ atmosphere. To this solution was added CuI (5.7 mg, 0.03 mmol), PdCl$_2$(PPh$_3$)$_2$ (21 mg, 0.03 mmol) and PPh$_3$ (16 mg, 0.06 mmol). The system was degas once again, then cyclopropyl acetylene (0.6 mL, excess) was added and the mixture was heated to 52° C. (oil bath) with stirring. The reaction was evaporated after 12 h and the residue was purified by flash chromatography (12 g silica gel, eluted with EA in hexane in a gradient of 0-20%, v/v) to afford 6-(cyclopropylethynyl)-2',4',5',6'-tetrahydrospiro[chroman-2,3'-pyran]-4-one (202 mg, yield: 93%). MS ESI+ve m/z 283 (M+H)$^+$.

Step 2: Preparation of (6-(cyclopropylethynyl)-2',4',5',6'-tetrahydrospiro[chroman-2,3'-pyran]-4-ylidene)cyanamide To a solution of 6-(cyclopropylethynyl)-2',4',5',6'-tetrahydrospiro[chroman-2,3'-pyran]-4-one (76 mg, 0.27 mmol) in anhydrous DCM (15 mL) under N$_2$ atmosphere was added 1 M TiCl$_4$ (in DCM, 0.54 mL, 0.54 mmol) dropwise within 15 min at room temperature. It was stirred another 1 h after the addition. To this mixture was added Bis-trimethylsilylcarbodiimide (0.16 mL, 0.427 mmol) dropwise. The resulting mixture was stirred 80 h. The reaction mixture was quenched with ice-water (15 g), and stirred for 30 min, then it was transferred to a separating funnel, the separated aqueous phase was extracted 2 times with DCM. The combined organic phases were dried over anhydrous Na$_2$SO$_4$, and filtered, and concentrated to give 106 mg the crude desired product as light yellow solid, which was used for next step without further purification. MS ESI+ve m/z 307 (M+H)$^+$.

Step 3: 2"-methyl-6-(cyclopropylethynyl)-2"H-spiro[spiro[chroman-2,1'-(3-oxacyclohexane)]-4,5'-[1,2,4]oxadiazol]-3"-amine To s suspension of the crude product obtained from previous step in MeOH (5 mL) was added a solution of N-methylhydroxylamine in MeOH (prepared from N-methylhydroxylamine HCl salt (36 mg, 0.43 mmol) inanhydrous MeOH (4 mL) and 25 wt % NaOMe/MeOH (88 µL, 0.39 mmol), stirred 5 min). The mixture was stirred at room temperature for 12 h. Solvent was removed under reduced pressure. The residue was purified by preparative PHLC to yield 16 mg of the title compound as TFA salt. $^1$H NMR (400 MHz, CD$_3$OD) δ: 7.58 (s, 1H), 7.34 (d, J=8.4 Hz, 1H), 6.87 (d, J=8.4 Hz, 1H), 3.84-3.70 (m, 2H), 3.63-3.54 (m, 2H), 3.35 (s, 3H), 2.79 (d, J=14.8 Hz, 1H), 2.09-1.78 (m, 4H), 1.64 (m, 1H), 1.52 (m, 1H), 1.42 (m, 1H), 0.85 (m, 2H), 0.71 (m, 2H); MS ESI+ve m/z 354 (M+H)$^+$.

Example 152

Preparation of 3-(3"-amino-2",7-dimethyl-2"H-spiro[spiro[chroman-2,1'-(3-oxacyclohexane)]-4,5'-[1,2,4]oxadiazole]-6-yl)benzonitrile (Compound 432)

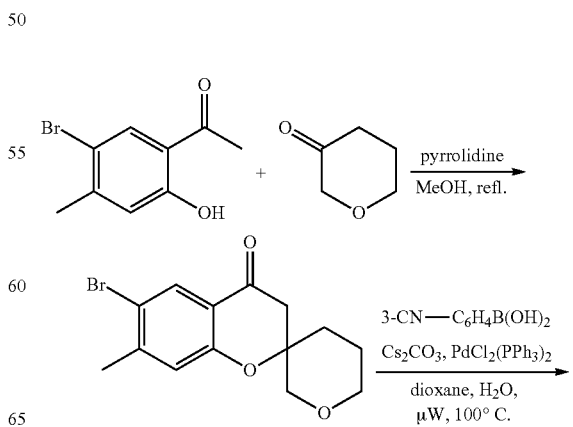

-continued

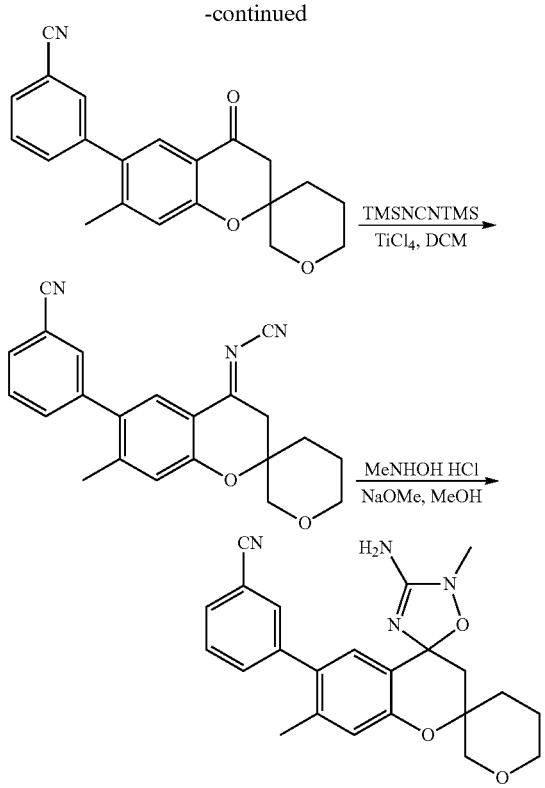

Step 1: Preparation of 6-bromo-7-methyl-2',4',5',6'-tetrahydrospiro[chroman-2,3'-pyran]-4-one A solution of 2-Acetyl-4-bromophenol (920 mg, 4.02 mmol), dihydro-2H-pyran-3(4H)-one (402 mg, 4.02 mmol) and pyrrolidine (0.5 mL) in MeOH (10 mL) was heated to reflux for 2 h. The reaction mixture was cooled down to room temperature and evaporated. The residue was purified by flash chromatography on silica gel eluting with EA in hexane (0-20%) to give 6-bromo-7-methyl-2',4',5',6'-tetrahydrospiro[chroman-2,3'-pyran]-4-one (593 mg); MS ESI+ve m/z 311 (M+H)$^+$.

Step 2: Preparation of 3-(7-methyl-4-oxo-2',4',5',6'-tetrahydrospiro[chroman-2,3'-pyran]

To a 10 mL CEM microwave test tube was charged with $Cs_2CO_3$ (147 mg, 0.45 mmol), $PdCl_2(PPh_3)_2$ (8 mg, 0.011 mmol), 6-bromo-7-methyl-2',4',5',6'-tetrahydrospiro[chroman-2,3'-pyran]-4-one (70 mg, 0.225 mmol), 3-cyanophenylboronic acid (43 mg, 0.293 mmol), dioxane (4 mL) and $H_2O$ (0.2 mL), the system was swept with $N_2$ and sealed, and heated in a CEM microwave reactor at 100° C. for 10 min. The reaction mixture was filtered, and concentrated. The residue was purified by flash chromatography on silica gel eluting with EA in hexane (0-20%) to give 3-(7-methyl-4-oxo-2',4', 5',6'-tetrahydrospiro[chroman-2,3'-pyran]-6-yl)benzonitrile (72 mg). MS ESI+ve m/z 334 (M+H)$^+$.

Step 3: Preparation of (6-(3-cyanophenyl)-7-methyl-2',4',5',6'-tetrahydrospiro[chroman-2,3'-pyran]-4-ylidene)cyanamide To a solution of 3-(7-methyl-4-oxo-2',4',5',6'-tetrahydrospiro[chroman-2,3'-pyran]-6-yl)benzonitrile (72 mg, 0.22 mmol) in anhydrous DCM (15 mL) under $N_2$ atmosphere was added 1 M $TiCl_4$ (in DCM, 0.44 mL, 0.44 mmol) dropwise within 15 min at room temperature. It was stirred another 1 h after the addition. To this mixture was added Bis-trimethylsilylcarbodiimide (0.114 mL, 0.506 mmol) dropwise. The resulting mixture was stirred overnight. The reaction mixture was quenched with ice-water (10 g), and stirred for 30 min, then it was transferred to a separating funnel, the separated aqueous phase was extracted 3 times with DCM. The combined organic phases were dried over anhydrous $Na_2SO_4$, and filtered, and concentrated to give 104 mg the crude desired product as light yellow solid, which was used for next step without further purification. MS ESI+ve m/z 358 (M+H)$^+$.

Step 4: Preparation of 3-(3"-amino-2",7-dimethyl-2"H-spiro[spiro[chroman-2,1'-(3-oxacyclohexane)]-4,5'-[1,2,4]oxadiazol]-6-yl)benzonitrile To s suspension of the crude product obtained from previous step in EtOH (3 mL) was added a solution of N-methylhydroxylamine in EtOH (0.6 mL, 0.22 mmol); prepared from N-methylhydroxylamine HCl salt (184 mg, 2.20 mmol) in anhydrous EtOH (5 mL) and 21 wt % NaOEt/EtOH (0.74 mL, 1.98 mmol), stirred 5 min and dilute with EtOH to total volume 6 mL). The mixture was stirred at room temperature for 20 min Solvent was removed under reduced pressure. The residue was purified by preparative PHLC to yield 39 mg of desired compound as TFA salt. $^1$H NMR (400 MHz, $CD_3OD$) δ: 7.74-7.58 (m, 4H), 7.45 (d, J=6.4 Hz, 1H), 6.92 (s, 1H), 3.90-3.56 (m, 4H), 3.33 (s, 3H), 2.88 (m, 2H), 2.22 (s, 3H), 2.15-1.54 (m, 4H); MS ESI+ve m/z 405 (M+H)$^+$.

Example 153

Preparation of 3-(spiro[spiro[chroman-2,4'-(1-acetylpiperidine)]-4,4'-(2-amino-1-methyl-5-oxo-1H-imidazole)]-6-yl)benzonitrile (Compound 460)

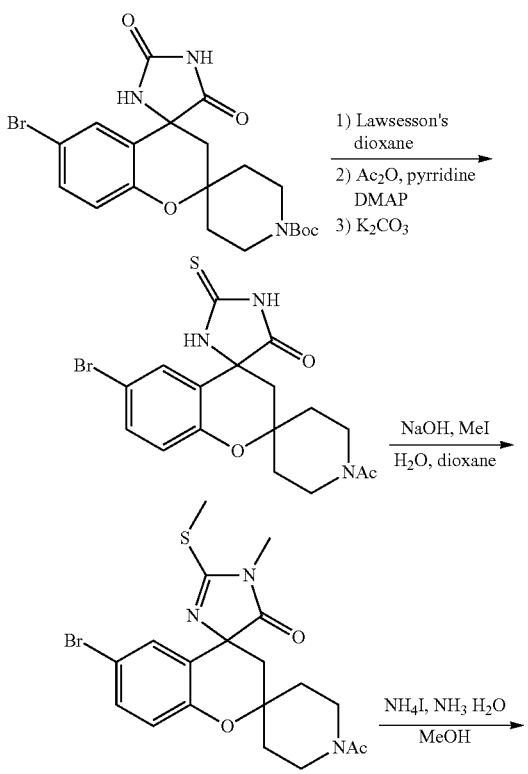

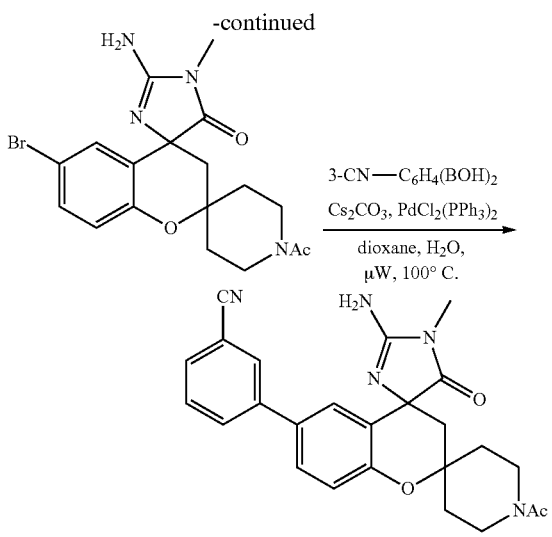

Step 1: Preparation of 6-bromo-spiro[spiro[chroman-2,4'-(1-acetylpiperidine)]-4,4'42-thioxoimidazolidin)]-5"-one The solution of 6-bromospiro[spiro[chroman-2,4'-(1-(tert-butoxycarbonyl)piperidine)]-4,4'-imidazolidine]-2",5"-dione (127.7 mg, 0.274 mmol) and Lawesson's reagent (110.7 mg, 0.274 mmol) in 1,4-dioxane (5 mL) in a 10 mL CEM microwave test tube was heated in a CEM microwave reactor at 150° C. for 40 min. To this reaction mixture was added acitic acid anhydride (0.05 mL) and pyridine (0.07 mL), followed by one piece of DMAP, then the reaction mixture was stirred at room temperature for 20 min MeOH (2 mL) was added to quench the reaction and stirred another 30 min K$_2$CO$_3$ (150 mg) was added and stirred another 30. The solvent was removed under reduced pressure, and the residue was dissolved in MeOH again and filtered. The filtrate was purified by preparative HPLC to yield 33 mg of the desired product. MS ESI+ve m/z 424 (M+H)$^+$.

Step 2: Preparation of 6-bromo-spiro[spiro[chroman-2,4'-(1-acetylpiperidine)]-4,4'41-methyl-2-(methylthio)-imidazol)]-5"(1"H)-one To a solution of 6-bromo-spiro[spiro[chroman-2,4'-(1-acetylpiperidine)]-4,4'-(2-thioxoimidazolidin)]-5"-one (34 mg, 0.08 mmol) in MeOH (5 mL) charged in a 10 mL CEM microwave test tube was added a 0.6 N NaOH aqueous solution (0.5 mL). After stirring at room temperature for 10 min, MeI (0.07 mL) was added, and the reaction mixture was heated in a CEM microwave reactor at 60° C. for 10 min. The resulting mixture was diluted with EA, and washed with H$_2$O, and brine successively, and dried over anhydrous Na$_2$SO$_4$, and filtered, and concentrated to produce the crude product. It was used for next step without further purification. MS ESI+ve m/z 452 (M+H)$^+$.

Step 3: Preparation of 6-bromo-spiro[spiro[chroman-2,4'-(1-acetylpiperidine)]-4,4'41-methyl-2-amino-imidazol)]-5"(1"H)-one A suspension of above crude product and NH$_4$I (150 mg, excess) in dioxane (1 mL) and 7 M NH$_3$/MeOH (3 mL) charged in a 10 mL CEM microwave test tube was heated to 110° C. for 1 h. Due to incompletion of the reaction, the reaction was heated at 120° C. for another 30 min. The solvent was removed in vacuum and the residue was purified by preparative HPLC to give 8 mg of the desired product as a TFA salt. MS ESI+ve m/z 421 (M+H)$^+$.

Step 4: Preparation of 3-(spiro[spiro[chroman-2,4'-(1-acetylpiperidine)]-4,4'42-amino-1-methyl-5-oxo-1H-imidazole)]-6-yl)benzonitrile To a solution of above product TFA salt (8 mg, 0.14 mmol), 3-cyanophenylboronic acid (51 mg, 0.07 mmol) and Cs$_2$CO$_3$ (30 mg, 0.09 mmol) in 1,4-dioxane (3 mL) and H$_2$O (0.5 mL) charged in a 10 mL CEM microwave test tube was added PdCl$_2$(PPh$_3$)$_2$ (2 mg), then the system was degassed by sweeping N$_2$. The tube was capped and heated to 100° C. for 10 min in a CEM microwave reactor. Solvent was removed in vacuum and the residue was purified by preparative HPLC to give 5 mg of the desired product as a TFA salt. $^1$H NMR (400 MHz, CD$_3$OD): 7.95 (s, 1H), 7.94 (s, 1H), 7.87 (m, 1H), 7.75-7.46 (m, 3H), 7.15 (d, J=8.4 Hz, 1H), 4.32 (m, 1H), 3.82-3.48 (m, 2H), 3.32 (s, 3H), 3.26-3.05 (m, 1H), 2.53 (d, J=14.8 Hz, 1H), 2.37 (d, J=14.8 Hz, 1H), 2.14 and 2.11 (s and s, 3H), 2.10-2.00 (m, 2H), 1.87-1.62 (m, 2H); MS ESI+ve m/z 444 (M+H)$^+$.

Example 154

Preparation of Compounds 188, 282 and 335

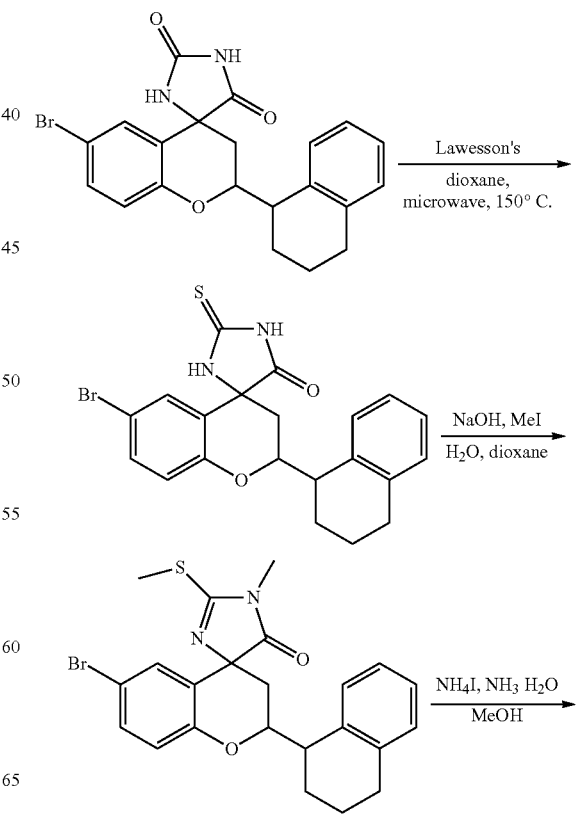

-continued

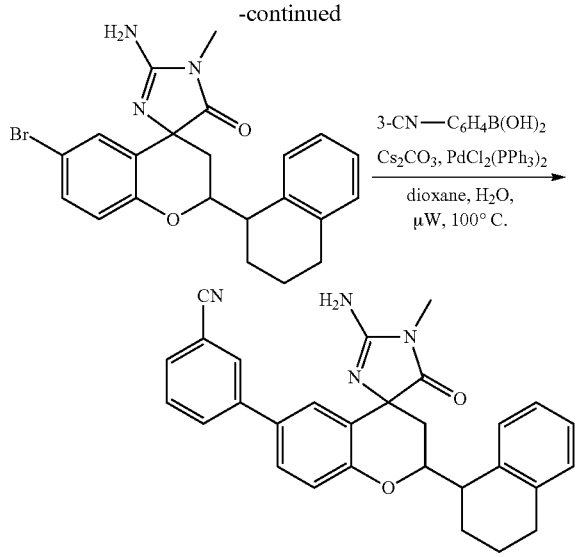

Step 1: Preparation of 6-bromo-2-(1,2,3,4-tetrahydronaphthalen-1-yl)-2'-thioxospiro[chroman-4,4'-imidazolidin]-5'-one A solution of 6-bromo-2-(1,2,3,4-tetrahydronaphthalen-1-yl)-2'-thioxospiro[chroman-4,4'-imidazolidin]-5'-one (67.4 mg, 0.158 mmol) and Lawesson's reagent (63.8 mg, 0.158 mmol) in dioxane (3 mL) charged in a 10 mL CEM microwave test tube was heated to 140° C. in a CEM microwave reactor for 30 min Solvent was removed under reduced pressure, and purified by flash chromatography on silica gel to yield 46 mg of the desired product as white solid. MS ESI+ve m/z 443 (M+H)$^+$.

Step 2: Preparation of 6-bromo-1'-methyl-2'-(methylthio)-2-(1,2,3,4-tetrahydronaphthalen-1-yl)spiro[chroman-4,4'-imidazol]-5'(1'H)-one To a solution of 6-bromo-2-(1,2,3,4-tetrahydronaphthalen-1-yl)-2'-thioxospiro[chroman-4,4'-imidazolidin]-5'-one (46 mg, 0.10 mmol) in MeOH (3 mL) charged in a 10 mL CEM microwave test tube was added a 0.6 N NaOH aqueous solution (0.35 mL). After stirring at room temperature for 10 min, MeI (0.5 mL, excess) was added, and the reaction mixture was heated in a CEM microwave reactor at 60° C. for 10 min. The reaction mixtures was diluted with ethyl acetate, and washed with H$_2$O, brine successively, and dried over anhydrous Na$_2$SO$_4$, and filtered, and concentrated to produce the desired crude product, which was used for next step without further purification. MS ESI+ve m/z 471 (M+H)$^+$.

Step 3: Preparation of 2'-amino-6-bromo-1'-methyl-2-(1,2,3,4-tetrahydronaphthalen-1-yl)spiro[chroman-4,4'-imidazol]-5'(1'H)-one A suspension of above product and NH$_4$I (100 mg, excess) in 7 M NH$_3$/MeOH (4 mL) and 1,4-dioxane (1.5 mL) charged in a 10 mL CEM microwave test tube was heated to 110° C. for 1 h. Another portion of NH$_4$I (100 mg, excess) was added and heated to 110° C. for another 1 h due to incompletion. The solvent was removed in vacuum and the residue was purified by preparative HPLC to yield the desired product as TFA salt. MS ESI+ve m/z 440 (M+H)$^+$.

Step 4: Preparation of 3-(2'-amino-1'-methyl-5'-oxo-2-(1,2,3,4-tetrahydronaphthalen-1-yl)-1',5'-dihydrospiro[chroman-4,4'-imidazole]-6-yl)benzonitrile To a solution of 2-amino-6'-bromo-1-methyl-2'-phenyl-spiro[imidazole-4,4'-thiochroman]-5(1H)-one TFA salt (20 mg, 0.036 mmol), 3-cyanophenylboronic acid (7 mg, 0.047 mmol) and Cs$_2$CO$_3$ (30 mg, 0.092 mmol) in 1,4-dioxane (4 mL) and H$_2$O (0.5 mL) charged in a 10 mL CEM microwave test tube was added PdCl$_2$(PPh$_3$)$_2$ (3 mg, 0.004 mmol), then the system was degassed by sweeping N$_2$. The tube was capped and heated to 110° C. for 10 min in a CEM microwave reactor. Solvent was removed in vacuum and the residue was purified by preparative HPLC to yield 4 isomers of the desired product as a TFA salt.

Compound 188: $^1$H NMR (400 MHz, CD$_3$OD) δ: 7.96 (m, 1H), 7.88 (m, 1H), 7.68-7.52 (m, 4H), 7.28 (m, 1H), 7.11 (m, 4H), 5.38 (m, 1H), 3.31 (s, 3H), 3.03 (m, 2H), 2.78 (m, 2H), 2.24-1.68 (m, 5H); MS ESI+ve m/z 463 (M+H)$^+$.

Compound 282: $^1$H NMR (400 MHz, CD$_3$OD) δ: 7.95 (d, J=1.6 Hz, 1H), 7.87 (dd, J=7.6, 1.2 Hz, 1H), 7.67-7.56 (m, 3H), 7.48 (d, J=2.4 Hz, 1H), 7.30 (m, 1H), 7.13-7.11 (m, 4H), 5.34, 5.20 (two m, 1H), 3.41 (m, 1H), 3.31 (s, 3H), 2.78 (m, 2H), 2.24 (m, 1H), 2.14-1.84 (m, 4H), 1.76 (m, 1H); MS ESI+ve m/z 463 (M+H)$^+$.

Compound 335: $^1$H NMR (400 MHz, CD$_3$OD) δ: 7.92 (d, J=1.6 Hz, 1H), 7.85 (dd, J=6.0, 1.6 Hz, 1H), 7.67-7.64 (m, 2H), 7.58 (m, 1H), 7.38 (d, J=2.4 Hz, 1H), 7.34 (m, 1H), 7.12-7.11 (m, 4H), 3.31 (s, 3H), 2.79 (m, 2H), 2.35 (m, 1H), 2.11 (m, 2H), 1.93 (m, 4H), 1.78 (m, 1H); MS ESI+ve m/z 463 (M+H)$^+$.

Example 155

Preparation of 3-(spiro[spiro[chroman-2,1'-(3-oxacyclohexane)]-4,5'-(3-amino-2-methyl-2,6-dihydro-[1,2,4]oxadiazine)]-6-yl)benzonitrile (compound 455)

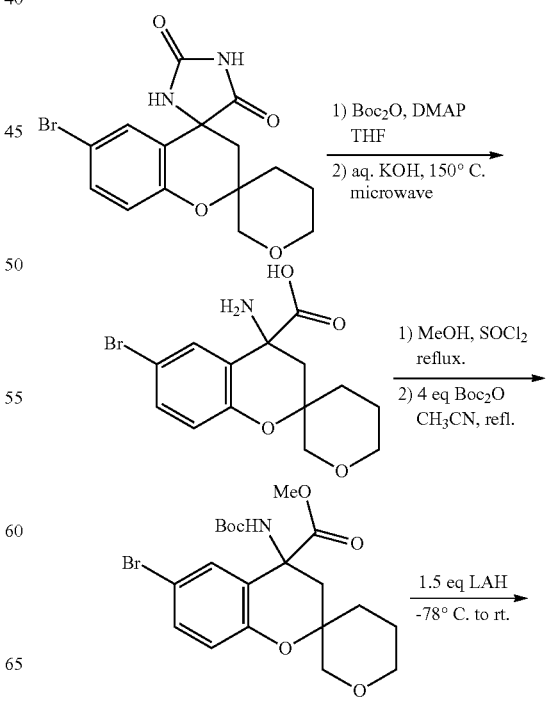

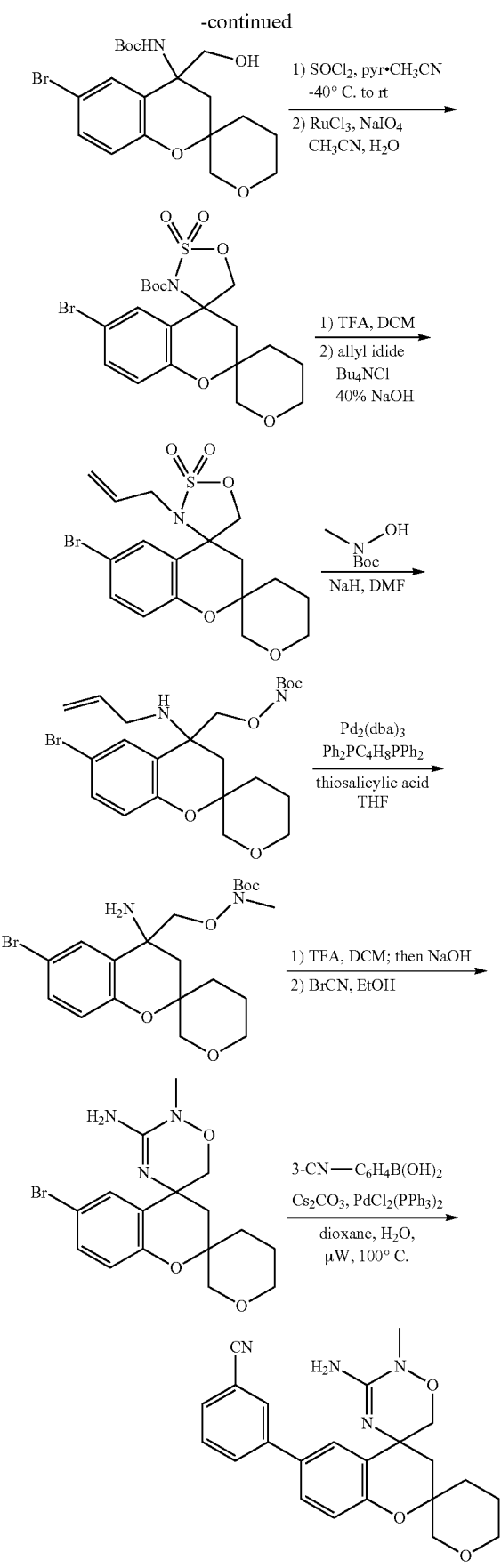

Step 1: Preparation of 4-amino-6-bromo-2',4',5',6'-tetrahydrospiro[chroman-2,3'-pyran]-4-carboxylic acid To a solution of 6-bromo-spiro[spiro[chroman-2,1'-(3-oxacyclohexane)]-4,4'-imidazolidine]-2",5"-dione (1.004 g, 2.74 mmol) in THF (30 mL) was added Boc$_2$O (1.791 g, 8.21 mmol), followed by DMAP (100 mg). The mixture was stirred at room temperature for 30 min. The solvent was removed under reduced pressure and the residue was purified by flash chromatography on silica gel to yield 410 mg of 6-bromo-spiro[spiro[chroman-2,1'-(3-oxacyclohexane)]-4,4'-(1,3-di-Boc-imidazolidine)]-2",5"-dione. The product was dissolved in 2 M KOH (4.4 mL). The solution was charged in a 10 mL CEM microwave test tube and heated to 150° C. for 2 h. The reaction mixture was acidified with 6 M HCl to pH 2 and evaporated to dryness. The residue was filtered through a funnel and washed with MeOH. The filtrate was concentrated to yield 232 mg of the desired product.

Step 2: Preparation of methyl 6-bromo-4-(tert-butoxycarbonylamino)-2',4',5',6'-tetrahydrospiro[chroman-2,3'-pyran]-4-carboxylate To a solution of 4-amino-6-bromo-2',4',5',6'-tetrahydrospiro[chroman-2,3'-pyran]-4-carboxylic acid (232 mg, 0.68 mmol) in MeOH (10 mL) chilled to 0° C. was added SOCl$_2$ (0.5 mL), the mixture was heated to reflux for 12 h. Every other 8-16 h, the reaction was cooled to 0° C. again and SOCl$_2$ (1 mL) was added carefully, and then the mixture was heated to reflux. The reaction was monitored by LC-MS, 90% conversion was achieved after repeat 6-8 times. In a separated reaction repeat the same reaction with starting material (300 mg, 0.88 mmol) till greater than 90% conversion. The two reactions was combined and evaporated. The residue was dissolved in EA, washed with saturated aqueous NaHCO$_3$, followed by brine. The organic layer was dried over anhydrous Na$_2$SO$_4$, and filtered, and concentrated to dryness. The residue was dissolved in CH$_3$CN (20 mL) containing Boc$_2$O (1.203 g, 5.51 mmol) and NaHCO$_3$ (1.159 g, 13.8 mmol). The mixture was heated to reflux overnight. The reaction mixture was cooled to room temperature and diluted with EA, washed with H$_2$O, the separated aqueous phase was extracted with EA once. The combined organic phases were washed with brine, dried over anhydrous Na$_2$SO$_4$, and filtered, and concentrated to dryness. The residue was purified by flash chromatography on silica gel to yield 314 mg of the desired product. MS ESI+ve m/z 478 (M+Na)$^+$.

Step 3: Preparation of tert-butyl 6-bromo-4-(hydroxymethyl)-2',4',5',6'-tetrahydrospiro[chroman-2,3'-pyran]-4-ylcarbamate To a solution of 6-bromo-4-(tert-butoxycarbonylamino)-2',4',5',6'-tetrahydrospiro[chroman-2,3'-pyran]-4-carboxylate (314 mg, 0.69 mmol) in anhydrous THF (10 mL) at −78° C. under N$_2$ atmosphere was added 1 M LAH (in THF, 1.4 mL, 1.4 mmol) dropwise. The mixture was stirred for 30 min at this temperature and then warmed to room temperature and stirred overnight. The reaction mixture was cooled to 0° C. and quenched with Na$_2$SO$_4$.H$_2$O carefully, then stirred several hours. The reaction was filtered through a short pad of Celite and washed with THF. The filtrate was evaporated to give 165 mg of the desired product as colorless oil. MS ESI+ve m/z 428 (M+H)$^+$.

Step 4: Preparation of tert-butyl 6-bromo-spiro[spiro[chroman-2,1'-(3-oxacyclohexane)]-4,4'-(2,2-dioxo[1,2,3]oxathiazolidine)]-3"-carboxylate To a solution of SOCl$_2$ (0.07 mL, 114.7 mg, 0.964 mmol) in anhydrous in CH$_3$CN (2 mL) at –40° C. under N$_2$ atmosphere was added a solution of tert-butyl 6-bromo-4-(hydroxymethyl)-2',4',5',6'-tetrahydrospiro[chroman-2,3'-pyran]-4-ylcarbamate (165 mg, 0.386 mmol) in anhydrous in CH$_3$CN (15 mL, low solubility) dropwise, followed by pyridine (0.156 mL, 153 mg, 1.93 mmol). The reaction was allowed to warm to room temperature within 1 h, and stirred another 2 h at room temperature. The solvent was removed under reduced pressure. The residue was dissolved in EA, and filtered. The filtrate was concentrated to dryness, the residue was dissolved in CH$_3$CN (6 mL) and H$_2$O (3 mL) and chilled to 0° C. To the solution was added RuO$_2$ (8 mg, 0.06 mmol) and NaIO$_4$ (124 mg, 0.579 mmol). The mixture was stirred 30 min at this temperature and warm to room temperature and stirred another 2 h. RuCl$_3$ (8 mg, 0.039 mmol) and NaIO$_4$ (624 mg, 2.92 mmol) was added. The mixture was stirred another 1 h and diluted with EA, washed with brine. The organic layer was dried over anhydrous Na$_2$SO$_4$, and filtered, and concentrated to dryness to yield 146 mg of the desired product. MS ESI+ve m/z 512 (M+Na)$^+$.

Step 5: Preparation of 3"-allyl-6-bromo-spiro[spiro[chroman-2,1'-(3-oxacyclohexane)]-4,4'-(2,2-dioxo[1,2,3]oxathiazolidine)]

A solution of tert-butyl 6-bromo-spiro[spiro[chroman-2,1'-(3-oxacyclohexane)]-4,4'-(2,2-dioxo[1,2,3]oxathiazolidine)]-3"-carboxylate (146 mg, 0.37 mmol) in DCM (4 mL) and TFA (1 mL) was stirred 3 h at room temperature. Solvents were removed under reduced pressure and the residue was dissolved in DCM (8 mL) at room temperature. To this solution was added allyl iodide (0.4 mL, large excess), Bu$_4$NCl (16 mg, 0.058 mmol) and 40% NaOH (3 mL). The resulting mixture was stirred at room temperature for 16 h. The separated organic phase was washed with H$_2$O, brine successively, and dried over anhydrous Na$_2$SO$_4$, and filtered, and concentrated to dryness. The residue was purified by flash chromatography on silica gel (4 g) to yield 73 mg of the desired product. MS ESI+ve m/z 294 (M+H-allyl-NSO$_3$)$^+$.

Step 6: Preparation of tert-butyl (4-(allylamino)-6-bromo-2',4',5',6'-tetrahydrospiro[chroman-2,3'-pyran]-4-yl)methoxy(methyl)carbamate To a solution of tert-butyl hydroxy(methyl)carbamate (112 mg, 0.76 mmol, prepared according the procedure described in *Org. Lett* 2007, 9, 4009) in anhydrous DMF (2 mL) at room temperature under N$_2$ atmosphere was added NaH (60%, 30 mg, 0.76 mmol). The mixture was stirred for 15 min, then a solution of 3"-allyl-6-bromo-spiro[spiro[chroman-2,1'-(3-oxacyclohexane)]-4,4'-(2,2-dioxo[1,2,3]oxathiazolidine)] (73 mg, 0.17 mmol) in anhydrous DMF (1 mL) was added. The resulting mixture was stirred 16 h (color changed from light yellow to green, then to light orange in the end). The reaction was quenched with saturated aqueous NH$_4$Cl and extracted with EA, the separated organic phase was washed with H$_2$O, brine successively, and dried over anhydrous Na$_2$SO$_4$, and filtered, and concentrated to dryness. The residue was used for next step without further purification. MS ESI+ve m/z 497 (M+H)$^+$.

Step 7: Preparation of tert-butyl (4-amino-6-bromo-2',4',5',6'-tetrahydrospiro[chroman-2,3'-pyran]-4-yl)methoxy(methyl)carbamate A solution of Pd$_2$(dba)$_3$ (7.6 mg, 0.038 mmol) and 1,4-bis(diphenylphosphino)butane (3.6 mg, 0.038 mmol) in THF (3 mL) under N$_2$ atmosphere was stirred for 15 min. Then the solution was added to a solution of tert-butyl (4-(allylamino)-6-bromo-2',4',5',6'-tetrahydrospiro[chroman-2,3'-pyran]-4-yl)methoxy(methyl)carbamate produced in previous step in THF (3 mL), followed by thiosalicylic acid (14 mg, 0.91 mmol). The mixture was stirred for 16 h. The solvent was removed under reduced pressure. The residue was purified by preparative HPLC to recover 28 mg of starting material as TFA salt and 10 mg of the desired product as TFA salt. MS ESI+ve m/z 457 (M+H)$^+$.

Step 8: Preparation of 6-bromo-spiro[spiro[chroman-2,1'-(3-oxacyclohexane)]-4,5'-(2-methyl-2,6-dihydro-[1,2,4]oxadiazin)]-3"-amine The solution of tert-butyl (4-amino-6-bromo-2',4',5',6'-tetrahydrospiro[chroman-2,3'-pyran]-4-yl)methoxy(methyl)carbamate in 4 M HCl/dioxane (2 mL) was stirred 1 h. Due to incompletion of the reaction 4 M HCl/dioxane (3 mL) was added and stirred overnight. The solvent was removed under reduced pressure. The residue was dissolved in DCM (10 mL), washed with 1 M NaOH (10 mL). The separated aqueous phase was extracted with DCM twice. The combined organic phases were combined and dried over anhydrous Na$_2$SO$_4$, and filtered, and concentrated to dryness. The residue was dissolved in EtOH (3 mL). To this solution was added a solution of cyanogen bromide (0.5 M in THF, 0.052 mL, 0.026 mmol). The resulting mixture was stirred overnight. The solvent was removed under reduced pressure. The residue was dissolved in DCM and washed with 1 M NaOH. The separated aqueous phase was extracted with DCM twice. The combined organic phases were combined and dried over anhydrous Na$_2$SO$_4$, and filtered, and concentrated to dryness to yield the desired product. It was used for next step without further purification. MS ESI+ve m/z 382 (M+H)$^+$.

Step 9: Preparation of 3-(spiro[spiro[chroman-2,1'-(3-oxacyclohexane)]-4,5'-(3-amino-2-methyl-2,6-dihydro-[1,2,4]oxadiazine)]-6-yl)benzonitrile To a solution of above crude product, 3-cyanophenylboronic acid (12 mg, 0.08 mmol) and Cs$_2$CO$_3$ (48 mg, 0.147 mmol) in 1,4-dioxane (4 mL) and H$_2$O (0.5 mL) charged in a 10 mL CEM microwave test tube was added PdCl$_2$(PPh$_3$)$_2$ (6 mg, 0.008 mmol), then the system was degassed by sweeping N$_2$. The tube was capped and heated to 110° C. for 10 min in a CEM microwave reactor. Solvent was removed in vacuum and the residue was purified by preparative HPLC to yield 3.82 mg of the desired product as a TFA salt. $^1$H NMR (400 MHz, CD$_3$OD) δ: 7.99 (s, 1H), 7.91 (d, J=7.6 Hz, 1H), 7.74 (m, 1H), 7.69-7.59 (m, 3H), 7.09 (dd, J=8.4, 2.8 Hz, 1H), 4.48-4.26 (m, 2H), 3.87-3.70 (m, 2H), 3.65-3.53 (m, 2H), 3.48 (s, 3H), 2.49, 2.43 (two d, J=14.4 Hz, 1H), 2.19, 2.14 (two d, J=14.4 Hz, 1H), 1.97 (m, 2H), 1.81 (m, 1H), 1.57 (m, 1H); MS ESI+ve m/z 405 (M+H)$^+$.

Example 156

Preparation of Compound 313

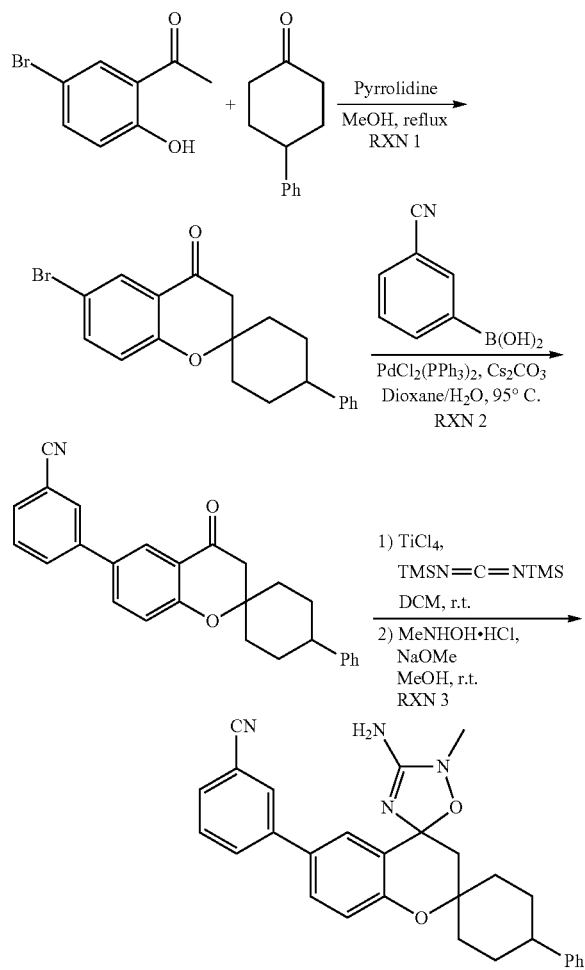

Step 1. 6-bromo-4'-phenylspiro[chroman-2,1'-cyclohexan]-4-one (RXN 1):

In a 50 mL round bottom flask was placed 5-bromo-2-hydroxyacetophenone (1 g, 4.65 mmol) and 4-phenylcyclohexanone (810 mg, 4.65 mmol). They were dissolved in MeOH (9.3 mL). To this solution was added pyrrolidine (764 μL, 9.30 mmol) dropwise. To the flask was attached a condenser and the reaction mixture was heated at reflux overnight (~14 hours). The next morning the volatiles were remove under reduced pressure and the crude material was purified by flash chromatography (ISCO, 40 g SiO₂ cartridge, Ethyl Acetate/Hexanes as the eluents). The corresponding fractions were combined and concentrated yielding 6-bromo-4'-phenylspiro[chroman-2,1'-cyclohexan]-4-one (1.12 g, 3.03 mmol, 65%).

M+H=370.9, 372.9

$^1$H NMR=(CDCl$_3$, 400 MHz) δ 7.98 (d, J=2.4 Hz, 1H), 7.57 (dd, J=8.8, 2.8 Hz, 1H), 7.34-7.31 (m, 2H), 7.26-7.20 (m, 3H), 6.96 (d, J=8.8 Hz, 1H), 2.72 (s, 2H), 2.58 (m, 1H), 2.25 (dd, J=15.2, 2.4 Hz, 2H), 1.92 (m, 2H), 1.76 (m, 2H), 1.56 (dt, J=14.0, 4.0 Hz) ppm.

Step 2. 3-(4-oxo-4'-phenylspiro[chroman-2,1'-cyclohexane]-6-yl)benzonitrile (RXN 2):

In a 50 mL round bottom flask was placed 6-bromo-4'-phenylspiro[chroman-2,1'-cyclohexan]-4-one (300 mg, 0.811 mmol), 3-cyanobenzeneboronic acid (155 mg, 1.06 mmol), PdCl$_2$(PPh$_3$)$_2$ (57 mg, 0.08 mmol) and cesium carbonate (661 mg, 2.03 mmol). This solid mixture was dissolved in a Dioxane/water mixture (8 mL, 6:1 ratio, respectively). The solution was purged with a N$_2$ stream for 30 seconds. A condenser was attached to the flask and the reaction was allowed to stir at 95° C. for 1 hour. At this time, the mixture was filtered through a Celite plug. The plug was rinsed with dichloromethane (20 mL) and water (20 mL). The phases in the filtrate were separated. The aqueous phase was back-extracted with dichloromethane twice (5 mL/each). The combined organic phases were dried over MgSO$_4$, filtered and concentrated under reduce pressure. The crude material was purified by flash chromatography (ISCO, 12 g SiO$_2$ cartridge, ethyl acetate/hexanes as the eluents). The corresponding fractions were combined and concentrated under reduce pressure yielding 3-(4-oxo-4'-phenylspiro[chroman-2,1'-cyclohexane]-6-yl)benzonitrile (173 mg, 0.440 mmol, 58% yield) as a light yellow oil.

M+H=394.0

$^1$H NMR=(CDCl$_3$, 400 MHz) δ 8.09 (d, J=2.0 Hz, 1H), 7.86 (s, 1H), 7.81 (d, J=7.6 Hz, 1H), 7.73 (dd, J=8.8, 2.4 Hz, 1H), 7.62 (d, J=8.0 Hz, 1H), 7.54 (t, J=7.6 Hz, 1H), 7.36-7.32 (m, 2H), 7.29-7.21 (m, 3H) 7.18 (d, J=8.8 Hz, 1H), 2.79 (s, 2H), 2.61 (m, 1H), 2.31 (d, J=12.8 Hz, 2H), 1.98 (m, 2H), 1.79 (d, J=12.4 Hz, 2H), 1.60 (dt, J=14.0, 3.6 Hz, 2H) ppm.

Step 3. Preparation of Compound 313 (RXN 3)

In a 20 mL vial was placed the cyanoketone (98 mg, 0.249 mmol), and it was azeotroped twice with toluene (2 mL/each). Dichloromethane (6 mL) was added followed by TiCl$_4$ (500 μL, 0.500 mmol, 1M in DCM). The reaction mixture was allowed to stir at room temperature for 1 hour. At that time bis-trimethylsilylcarbodiimide (179 μL, 0.797 mmol) was added and the solution was allowed to stir overnight (14 hours) at room temperature. The reaction was quenched with ice cold water (5 mL). The two phases were separated and the aqueous phase was back-extracted twice with dichloromethane (2 mL/each). The combined organic phases were dried over MgSO$_4$, filtered, concentrated under reduce pressure and azeotroped with toluene (2 mL). In a separate flame dried 4 mL vial was placed MeNH(OH).HCl (23 mg, 0.275 mmol) and it was dissolved in MeOH (4 mL). To this solution was added NaOMe (50 μL, 25% in MeOH) and the solution was stirred for 5 minutes at room temperature. This solution was transferred, via syringe, to the cyanoimine prepared above and stirred at room temperature for 1 hour. After the hour, the reaction mixture was concentrated under reduce pressure and the crude material was purified on a HPLC (Gilson, 10-90% CH$_3$CN/H$_2$O with 0.1% TFA as the eluent). The corresponding fractions were combined and concentrated yielding the final product (12.7 mg, 0.027 mmol, 11% yield) as a white solid.

M+H=465.1

$^1$H NMR=(CD$_3$OD, 400 MHz) δ 8.00 (bs, 1H), 7.98 (d, J=2.4 Hz, 1H), 7.95-7.93 (m, 1H) 7.75 (dd, J=8.8, 2.4 Hz, 1H), 7.70-7.68 (m, 1H), 7.62 (t, J=8.0 Hz, 1H), 7.31-7.25 (m, 4H), 7.18-7.16 (m, 1H), 7.15 (d, J=8.4 Hz, 1H), 3.40 (s, 3H), 2.76 (d, J=15.2 Hz, 1H), 2.66-2.58 (m, 1H), 2.41-2.37 (m, 1H), 2.25-1.99 (m, 4H), 1.88-1.59 (m 4H) ppm.

Example 157

Preparation of Compound 388

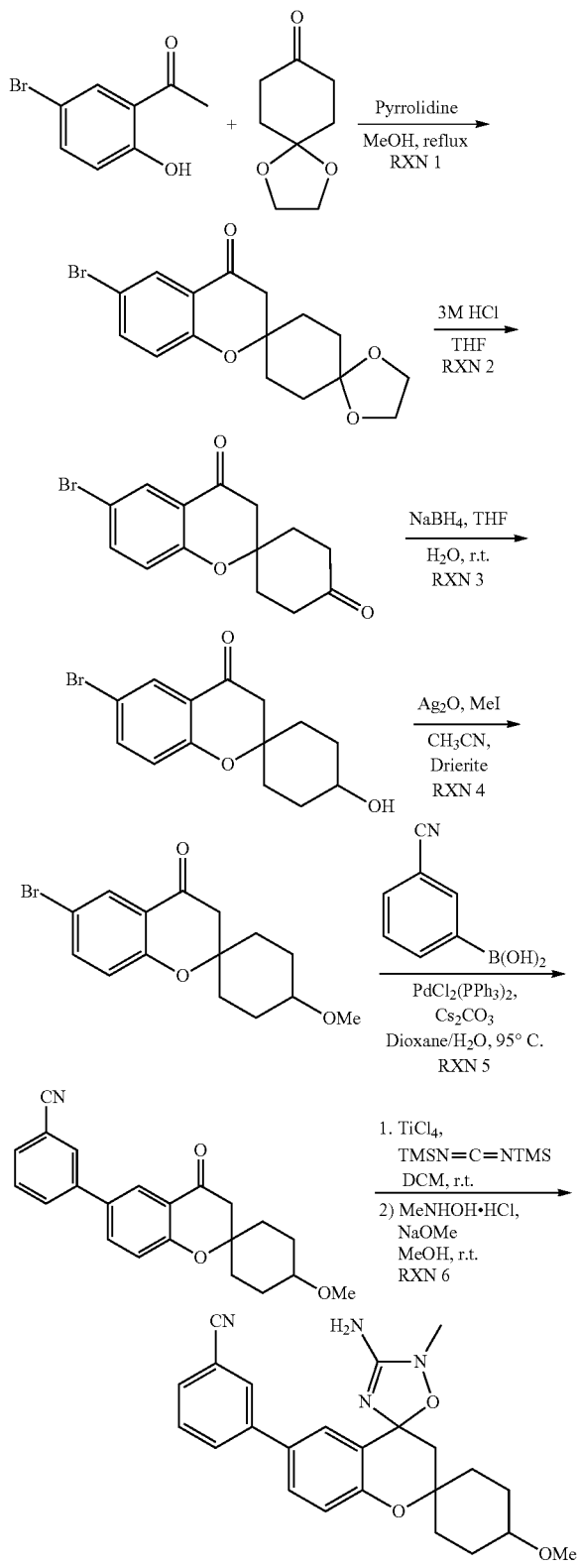

Step 1: Benzopyran Formation (RXN 1)

In a 50 mL round bottom flask was placed 5-bromo-2-hydroxyacetophenone (1 g, 4.65 mmol) and 1,4-cyclohexanedione mono-ethylelene ketal (726 mg, 4.65 mmol). They were dissolved in MeOH (9.3 mL). To this solution was added pyrrolidine (764 µL, 9.30 mmol) dropwise. To the flask was attached a condenser and the reaction mixture was heated at reflux overnight (~14 hours). The next morning a precipitate was observed in the reaction media. The reaction was allowed to cool down to room temperature and then placed on an ice bath. The solid was collected by filtration and it was rinsed with cold MeOH. The light yellow solid collected corresponded to the benzopyran (1.43 g, adduct. 4.06 mmol, 87% yield).

M+H=352.9, 354.9

$^1$H NMR=(CDCl$_3$, 400 MHz) δ 7.96 (d, J=2.8 Hz, 1H), 7.55 (dd, J=8.8, 2.8 Hz, 1H), 6.88 (d, J=8.8 Hz, 1H), 3.96 (m, 4H), 2.70 (s, 2H), 2.09 (m, 2H), 1.95 (ddd, J=13.2, 13.2, 3.6 Hz, 2H), 1.75 (ddd, J=13.6, 13.6, 4.0 Hz, 2H), 1.60 (m, 2H) ppm.

Step 2: 6-bromospiro[chroman-2,1'-cyclohexane]-4,4'-dione (RXN 2)

In a 20 mL vial was placed the previous spiro compound (400 mg, 1.136 mmol) and it was dissolve in THF (5 mL). To this solution was added 3M HCl (5 mL) at room temperature. The reaction was allowed to stir at room temperature until total consumption of the starting ketal (judge by TLC). After completion the reaction was slowly quenched with saturated aqueous NaHCO$_3$ until pH 7 was reached. The solution was diluted with ethyl acetate (20 mL). The phases were separated and the aqueous phase was back-extracted with ethyl acetate twice (10 mL/each). The combined organic phases were washed with brine, dried over Na$_2$SO$_4$, filtered and concentrated under reduce pressure. The crude material was purified by flash chromatography (ISCO, 40 g SiO$_2$ cartridge, ethyl acetate/hexanes as the eluents). The corresponding fractions were combined and concentrated under reduce pressure yielding 6-bromospiro[chroman-2,1'-cyclohexane]-4,4'-dione (254 mg, 0.825 mmol, 73% yield).

M+H=308.8, 311.0

$^1$H NMR=(CDCl$_3$, 400 MHz) δ 8.01 (d, J=2.8 Hz, 1H), 7.62 (dd, J=8.8, 2.8 Hz, 1H), 6.96 (d, J=8.8 Hz, 1H), 2.80 (s, 2H), 2.71 (ddd, J=14.8, 14.8, 6.0 Hz, 2H), 2.44 (m, 2H), 2.32 (m, 2H), 1.90 (ddd, J=14.0, 14.0, 5.2 Hz, 2H) ppm.

Step 3: 6-bromo-4'-hydroxyspiro[chroman-2,1'-cyclohexan]-4-one (RXN 3)

In a 25 mL round bottom flask was placed 6-bromospiro[chroman-2,1'-cyclohexane]-4,4'-dione (240 mg, 0.779 mmol) and it was dissolved in THF (7.8 mL). To this solution was added NaBH$_4$ (30 mg, 0.789 mmol) and the reaction was allowed to stir at room temperature for 5 minutes. At that time, TLC indicated total consumption of the diketone. The reaction was diluted with water (10 mL) and ethyl acetate (10 mL) and it was allowed to stir for 15 minutes. The phases were separated and the aqueous phase was back-extracted with ethyl acetate twice (5 mL/each). The combined organic phases were washed with brine, dried over Na$_2$SO$_4$, filtered and concentrated under reduce pressure. The crude material was purified by flash chromatography (ISCO, 40 g SiO$_2$ cartridge, ethyl acetate/hexanes as the eluents). A 3:1 mixture of separable isomers formed. The less-polar product (judge by TLC) was cleanly separated by flash chromatography (ISCO, 40 g SiO$_2$ cartridge, ethyl acetate/hexanes as the eluents) and use for further development. The corresponding fractions for less-polar product were combined and concentrated under reduce pressure yielding one of the isomers of 6-bromo-4'-hydroxyspiro[chroman-2,1'-cyclohexan]-4-one (58 mg, 0.187 mmol, 24% yield).

M+H=310.9, 312.9

$^1$H NMR═(CDCl$_3$, 400 MHz) δ 7.96 (d, J=2.4 Hz, 1H), 7.56 (dd, J=8.8, 2.4 Hz, 1H), 6.90 (d, J=8.8 Hz, 1H), 3.70 (m, 1H), 2.67 (s, 2H), 2.14 (m, 2H), 1.83-1.67 (m, 4H), 1.46 (ddd, J=14.0, 14.0, 4.4 Hz, 2H) ppm.

Step 4. 6-bromo-4'-methoxyspiro[chroman-2,1'-cyclohexar]-4-one (RXN 4)

In a 20 mL vial was placed 6-bromo-4'-hydroxyspiro[chroman-2,1'-cyclohexan]-4-one (46 mg, 0.148 mmol) and it was azeotroped with acetonitrile (3 mL). The solid was dissolved in acetonitrile (1 mL). To this heterogenous solution was added Ag$_2$O (103 mg, 0.444 mmol) followed by freshly grounded Drierite (160 mg). Then MeI (185 μL, 2.97 mmol) was added, the vial was capped and the reaction was allowed to stir at room temperature. After 2 days stirring the alcohol was totally consumed. The reaction mixture was filtered through a plug of Celite and the cake was rinsed with ethyl acetate three times (2 mL/each). The filtrate was concentrated yielding crude 6-bromo-4'-methoxyspiro[chroman-2,1'-cyclohexan]-4-one (48 mg, 0.148 mmol, 100% yield) which by $^1$H NMR looked>90% pure.

M+H=324.9, 326.9

$^1$H NMR═(CDCl$_3$, 400 MHz) δ 7.95 (d, J=2.4 Hz, 1H), 7.54 (dd, J=8.8, 2.4 Hz, 1H), 6.88 (d, J=8.8 Hz, 1H), 3.36 (s, 3H), 3.21 (m, 1H), 2.67 (s, 2H), 2.14 (m, 2H), 1.85 (m, 2H), 1.67 (m, 2H), 1.44 (ddd, J=13.6, 13.6, 4.0 Hz) ppm.

Step 5: 3-(4'-methoxy-4-oxospiro[chroman-2,1'-cyclohexane]-6-yl)benzonitrile (RXN 5)

In a μwave vial was placed 6-bromo-4'-methoxyspiro[chroman-2,1'-cyclohexan]-4-one (48 mg, 0.148 mmol), 3-cyanobenzeneboronic acid (28 mg, 0.191 mmol), PdCl$_2$(PPh$_3$)$_2$ (10 mg, 0.014 mmol) and cesium carbonate (121 mg, 0.371 mmol). This solid mixture was dissolved in a Dioxane/water mixture (2.0 mL, 6:1 ratio, respectively). The solution was purged with a N$_2$ stream for 20 seconds. The vessel was placed in the μwave and heated to 100° C. for 5 minutes. After that time, the mixture was filtered through a Celite plug. The plug was rinsed with dichloromethane (10 mL) and water (10 mL). The phases in the filtrate were separated. The aqueous phase was back-extracted with dichloromethane (5 mL). The combined organic phases were washed with water, brine, dried over MgSO$_4$, filtered and concentrated under reduce pressure. The crude material was purified by flash chromatography (ISCO, 12 g SiO$_2$ cartridge, ethyl acetate/hexanes as the eluents). The corresponding fractions were combined and concentrated under reduce pressure yielding 3-(4'-methoxy-4-oxospiro[chroman-2,1'-cyclohexane]-6-yl)benzonitrile (32 mg, 0.092 mmol, 62% yield).

M+H=348.1

$^1$H NMR═(CDCl$_3$, 400 MHz) δ 8.05 (d, J=2.4 Hz, 1H), 7.83 (dd, J=1.6, 1.6 Hz, 1H), 7.78 (ddd, J=8.0, 1.6, 1.6 Hz, 1H), 7.69 (dd, J=8.4, 2.4 Hz, 1H), 7.60 (ddd, J=7.6, 1.6, 1.6 Hz, 1H), 7.52 (t, J=7.6 Hz, 1H), 7.09 (d, J=8.4 Hz, 1H), 3.37 (s, 3H), 3.24 (m, 1H), 2.73 (s, 2H), 2.19 (m, 2H), 1.88 (m, 2H), 1.72 (m, 2H), 1.48 (ddd, J=14.0, 14.0, 4.0 Hz, 2H) ppm.

Step 6: Preparation of Compound 389 (RXN 6)

In a 20 mL vial was placed 3-(4'-methoxy-4-oxospiro[chroman-2,1'-cyclohexane]-6-yl)benzonitrile (32 mg, 0.092 mmol), and it was azeotroped with toluene (2 mL). Dichloromethane (3 mL) was added followed by TiCl$_4$ (184 μL, 0.184 mmol, 1M in DCM). The reaction mixture was allowed to stir at room temperature for 1 hour. At that time bis-trimethylsilylcarbodiimide (66 μL, 0.294 mmol) was added and the solution was allowed to stir overnight (14 hours) at room temperature. The reaction was quenched with ice cold water (5 mL). The two phases were separated and the aqueous phase was back-extracted twice with dichloromethane (2 mL/each). The combined organic phases were dried over MgSO$_4$, filtered, concentrated under reduce pressure and azeotroped with toluene (2 mL). In a separate flame dried 4 mL vial was placed MeNH(OH).HCl (9 mg, 0.108 mmol) and it was dissolved in MeOH (2 mL). To this solution was added NaOMe (19 μL, 25% in MeOH) and the solution was stirred for 5 minutes at room temperature. This solution was transferred, via syringe, to the cyanoimine prepared above and stirred at room temperature for 1 hour. After that time, the reaction mixture was concentrated under reduce pressure and the crude material was purified on a HPLC (Gilson, 10-90% CH$_3$CN/H$_2$O with 0.1% TFA as the eluent). The corresponding fractions were combined and concentrated yielding the final product (7.1 mg, 0.017 mmol, 18% yield) as a colorless oil.

M+H=419.1

$^1$H NMR═(CD$_3$OD, 400 MHz) δ 7.99 (bs, 1H), 7.96 (d, J=2.4 Hz, 1H), 7.94-7.91 (m, 1H), 7.74-7.71 (dd, J=8.8, 2.4 Hz, 1H), 7.71-7.67 (m, 1H), 7.66-7.59 (m, 1H), 7.05 (d, J=8.8 Hz, 1H), 3.38 (s, 3H), 3.37 (s, 3H), 3.34 (m, 1H), 2.76 (d, J=14.8 Hz, 1H), 2.17 (d, J=14.8 Hz, 1H), 2.22-213 (m, 1H), 2.01-1.78 (m, 4H), 1.73-1.47 (m, 3H) ppm.

Example 158

Preparation of Compounds 379, 403 and 408

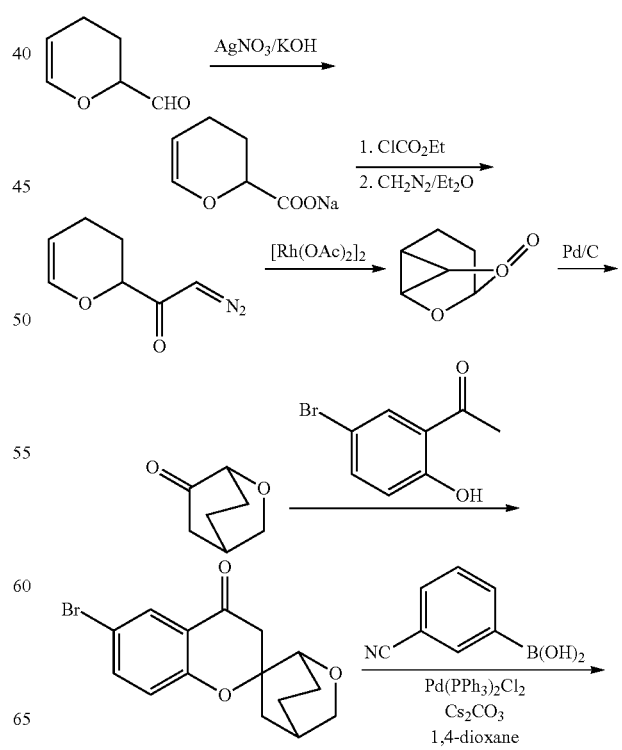

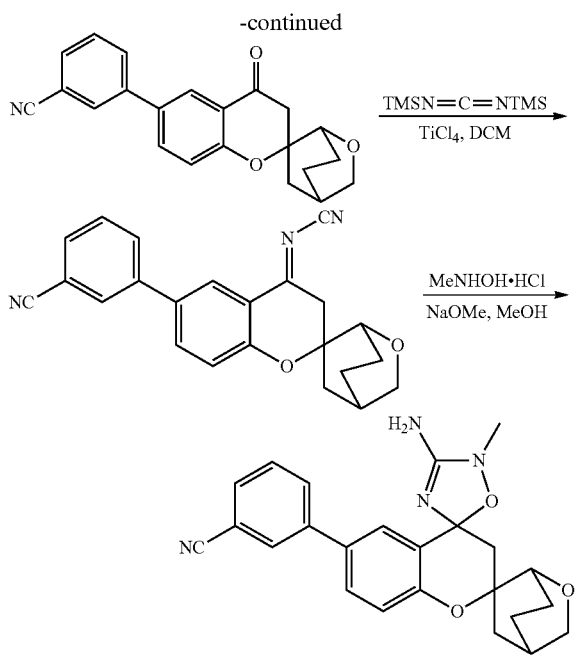

Experimental Data:

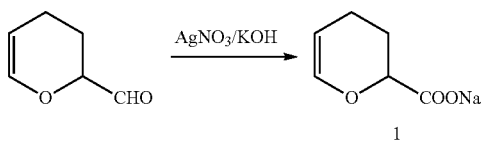

Preparation of Compound 1

A solution of AgNO$_3$ (155 g, 913 mmol) in water (200 mL) was added to a stirred solution of 3,4-dihydro-2H-pyran-2-carbaldehyde (31 g, 277 mmol) in ethanol (900 mL), followed by addition of a solution of KOH (102 g, 1.83 mol) in water (900 mL) in 1 hour. The mixture was filtered and evaporated. The residue was extracted with ether. The aqueous layer was adjusted to pH=3 with 6 N HCl and extracted with ether. The organic layer was evaporated and the residue was treated with 1 N NaOH (332 mL, 332 mmol).

The mixture was co-evaporated with methanol to dryness to give compound 1 (39 g, 94%). $^1$H-NMR (400 MHz D$_2$O): δ6.24 (d, 1H), 4.16 (dd, 1H), 1.93 (d, 2H), 1.65-1.85 (m, 2H).

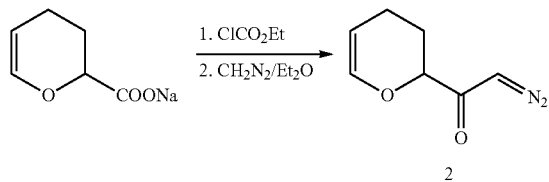

Preparation of Compound 2

To a suspension of sodium 3,4-dihydro-2H-pyran-2-carboxylate (13.6 g, 90.9 mmol) in THF (150 mL) was added triethylamine (919 mg, 9.1 mmol), DMF (336 mg, 4.6 mmol), followed by addition of isobutyl chloroformate (13.6 g, 100 mmol) at −10° C. After being stirred at room temperature for 2 hours, the mixture was added a solution of diazomethane in ether (1 N, 500 mL, 500 mmol) at −78° C. The reaction mixture was stirred at room temperature overnight. The diazomethane was bumped off by N$_2$ for 2 h hours and filtered. The filtrate was concentrated, and the residue was purified by silica gel column by using dichloromethane as eluant to give the compound 2 (11.8 g, 86%).

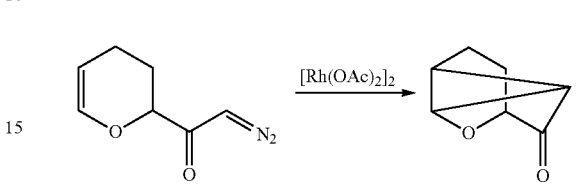

Preparation of Compound 3

To a suspension of rhodium acetate dimer (120 mg) in dichloromethane (60 mL) was added a solution of 2-diazo-1-(3,4-dihydro-2H-pyran-2-yl)-ethanone (6 g, 39.5 mmol) in dichloromethane (60 mL). When the addition was completed, the reaction was stirred for another 1 hour. The mixture was washed with 5% aqueous NaHCO$_3$ and concentrated. The residue was purified by flash chromatograph to give the compound 3 (2 g, 41%).

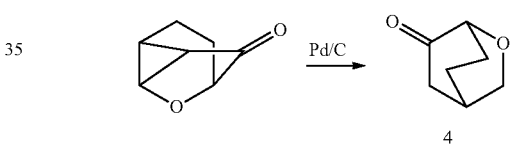

Preparation of Compound 4

To a solution of 6-oxa-tricyclo[3.2.1.0$^{2,7}$]octan-8-one (0.5 g, 4 mmol) in ethyl acetate (10 mL) was added Pd/C (100 mg). The mixture was stirred at room temperature under H$_2$ (50 psi) for 6 hours. The mixture was filtered, the filtrate was concentrated to give the compound 4 (440 mg, 87%).

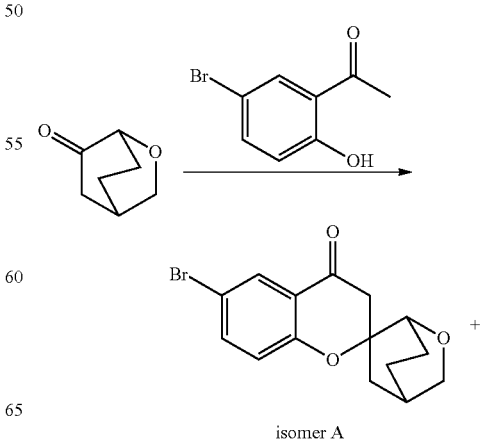

isomer A

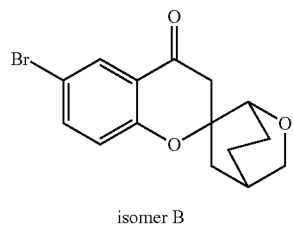

isomer B

Preparation of Isomer A and Isomer B

A solution of 2-oxa-bicyclo[2.2.2]octan-6-one (252 mg, 2 mmol), 1-(5-bromo-2-hydroxy-phenyl)-ethanone (215 mg, 1 mmol) and pyrrolidine (142 mg, 2 mmol) in toluene (5 mL) was refluxed overnight. The mixture was treated with 1 N HCl, and the aqueous layer was adjusted to pH=10 and extracted with ethyl acetate. The combined organic layer was washed with brine, dried, and concentrated. The residue was purified by preparative TLC to give the Isomer A (160 mg, 50%) and Isomer B (90 mg, 28%).

Isomer A: $^1$H-NMR (400 MHz CDCl$_3$): δ7.89 (d, 1H), 7.46 (m, 1H), 6.78 (d, 1H), 3.79 (d, 1H), 3.66 (t, 1H), 3.61 (m, 1H), 2.90 (m, 2H), 2.00 (m, 3H), 1.81 (m, 2H), 1.64 (m, 2H).

Isomer B: $^1$H-NMR (400 MHz CDCl$_3$): δ7.86 (d, 1H), 7.48 (dd, 1H), 6.91 (d, 1H), 3.88 (m, 1H), 3.80 (m, 2H), 2.69 (d, 2H), 2.01 (m, 2H), 1.60-1.85 (m, 4H), 1.46 (m, 1H).

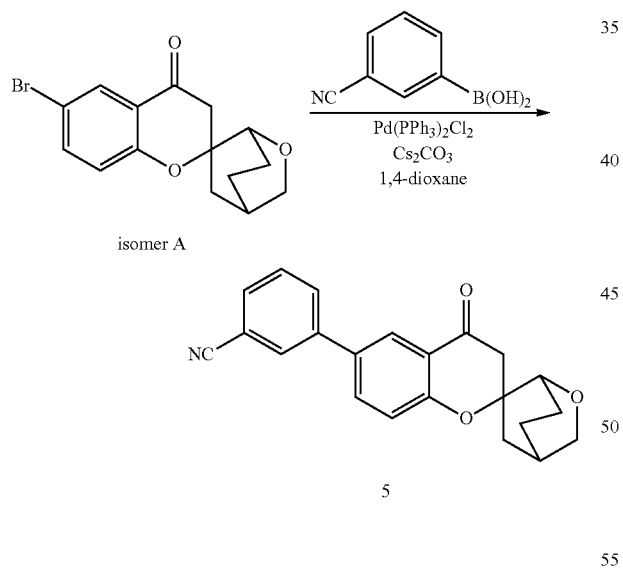

Preparation of Compound 5

A mixture of Pd(PPh$_3$)$_2$Cl$_2$ (35 mg, 0.05 mmol), Isomer A (160 mg, 0.5 mmol), Cs$_2$CO$_3$ (2 N, 0.5 mL, 1 mmol) and 3-cyanophenylboronic acid (147 mg, 1 mmol) in 1,4-dioxane (1 mL) was stirred at 100° C. in microwave for 30 minutes. The reaction mixture was treated with ethyl acetate and water. The organic layer was concentrated in vacuo to give the crude product, which was purified by preparative TLC to give the compound 5 (50 mg, 29%).

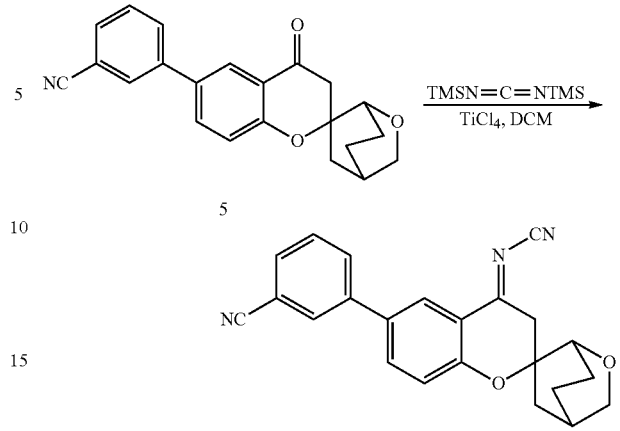

Preparation of Compound 6

To a solution of compound 5 (50 mg, 0.145 mmol) in anhydrous DCM (2 mL) was added TiCl$_4$ (0.72 mL, 0.72 mmol, 1 M in DCM) at room temperature. It was stirred at 50° C. in microwave for 10 minutes. To this mixture was added N,N'-methanediylidenebis(1,1,1-trimethylsilanamine) (135 mg, 0.72 mmol). The resulting mixture was stirred at 60° C. in microwave for another 15 minutes. The reaction mixture was poured into ice-water, extracted with DCM. The combined organic phases were dried and concentrated to give the crude compound 6 (60 mg, crude), which was used in the next step without further purification.

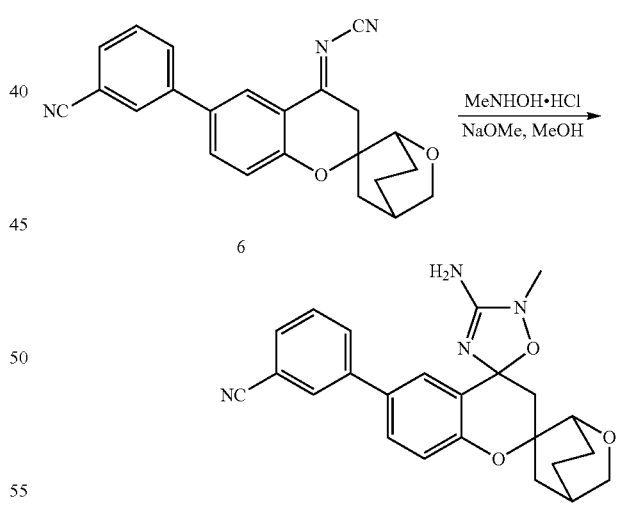

Preparation of Compound 408 and Compound 403

To a solution of MeNHOH.HCl (60.56 mg, 0.73 mmol) in anhydrous MeOH (3 mL) was added NaOMe (35 mg, 0.65 mmol, 25 w % in MeOH), followed by compound 6 (60 mg, 0.145 mmol, crude). After being stirred for 1 h, the solvent was removed in vacuum. The residue was dissolved in DCM, and the mixture was filtered, and the solvent was removed in vacuum to give the crude product, which was purified by preparative TLC followed by preparative HPLC to give compound 408 (4.47 mg, 7%) and compound 403 (2 mg, 3%).

compound 408: ¹H-NMR (400 MHz CD₃OD): δ7.95 (m, 3H), 7.72 (m, 2H), 7.63 (m, 1H), 7.00-7.20 (m, 1H), 4.03 (s, 1H), 3.91 (m, 1H), 3.88 (m, 1H), 3.37 (m, 3H), 3.17 (m, 1H), 2.21 (d, 1H), 2.17 (m, 1H), 1.90 (m, 4H), 1.78 (m, 2H); ESI MS: m/z 417 [M+H]⁺.

compound 403: ¹H-NMR (400 MHz CD₃OD): δ7.99 (m, 2H), 7.95 (m, 1H), 7.73 (m, 2H), 7.64 (m, 1H), 7.00-7.20 (m, 1H), 3.92-4.05 (m, 1H), 3.62-3.74 (m, 2H), 3.31 (t, 3H), 3.13 (m, 1H), 2.35 (m, 1H), 2.19 (d, 1H), 1.85-2.15 (m, 4H), 1.78 (m, 2H); ESI MS m/z 417 [M+H]⁺.

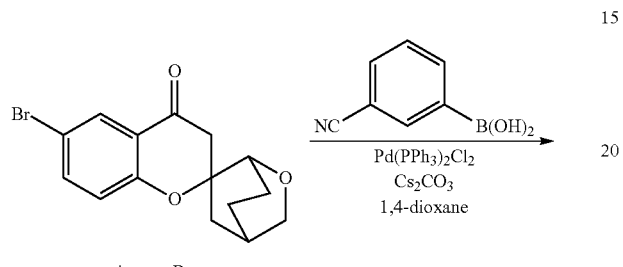

isomer B

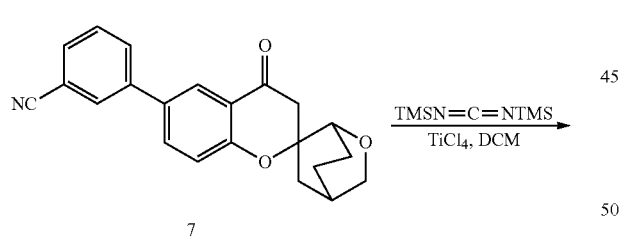

7

Preparation of Compound 7

By using the same strategy as compound 5, compound 7 was made (60 mg, 62%) from Isomer B.

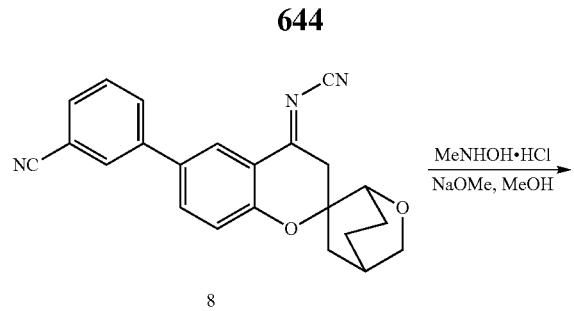

8

Preparation of Compound 8

By using the same synthetic strategy as compound 6, compound 8 was obtained (80 mg, crude).

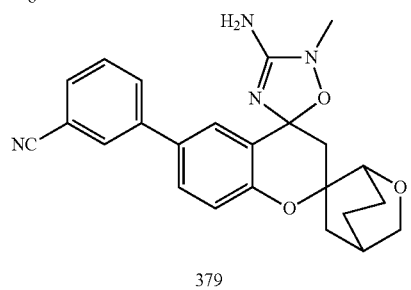

379

Preparation of Compound 379

By using the synthetic strategy for compound 408, compound 379 (9.44 mg, 13%) was obtained. ¹H-NMR (400 MHz, CD₃OD): δ7.98 (m, 1H), 7.91 (m, 2H), 7.73 (m, 1H), 7.65 (m, 1H), 7.60 (m, 1H), 7.07 (t, 1H), 3.93 (m, 2H), 3.85 (m, 1H), 3.34 (m, 3H), 2.97 (m, 1H), 2.24 (d, 1H), 2.10-2.18 (m, 2H), 1.72-1.87 (m, 4H), 1.60 (m, 1H); ESI MS: m/z 417 [M+11]⁺.

Example 159

Preparation of Compound 350

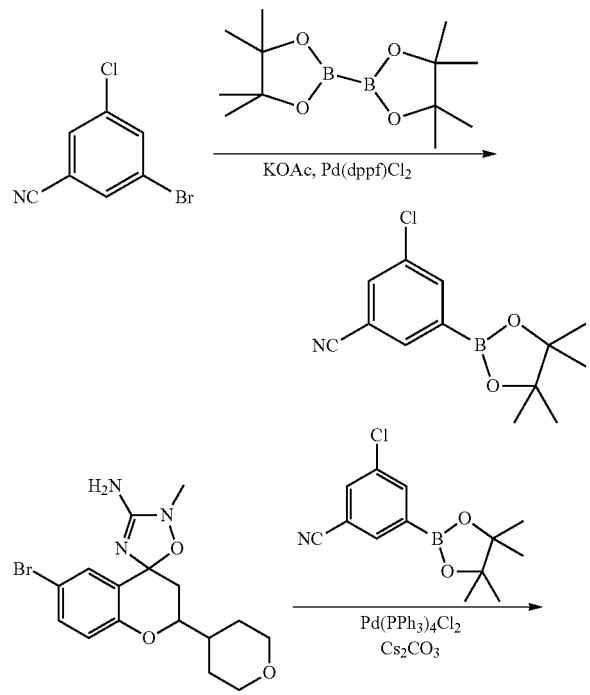

Preparation of Compound 1

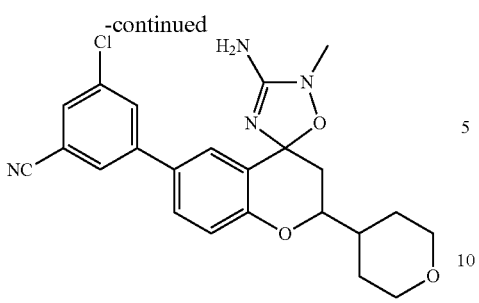

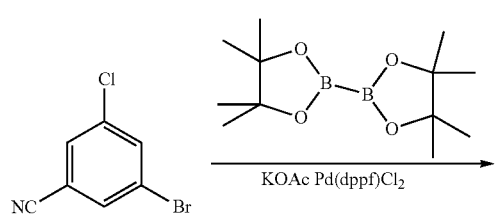

A mixture of 3-bromo-5-chlorobenzonitrile (1 g, 4.74 mmol), 4,4,4',4',5,5,5',5'-octamethyl-2,2'-bi(1,3,2-dioxaborolane) (1.3 g, 5.12 mmol), KOAc (1.366 g, 13.8 mmol) and Pd(dppf)Cl$_2$ (236 mg) in 1,4-dioxane (30 mL) under Ar$_2$ was stirred in microwave at 100° C. for 1.2 hours. The reaction mixture was concentrated in vacuo to give the residue, which was purified by chromatography to give compound 1 (70 mg, 7%).

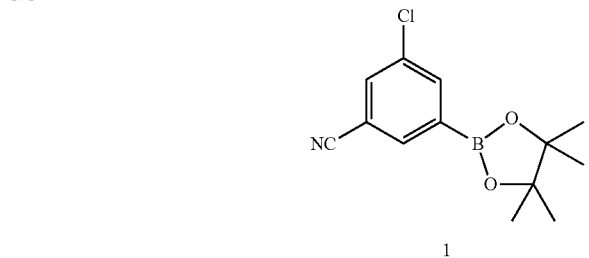

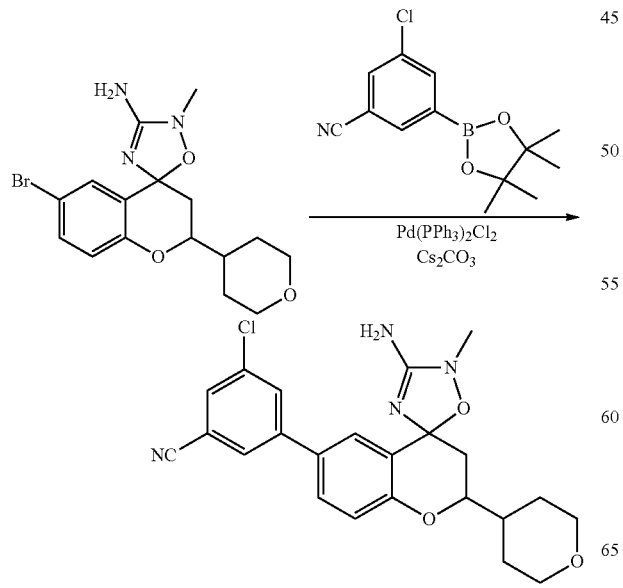

Preparation of Compound 350

A mixture of 6-bromo-2'-methyl-2-(tetrahydro-2H-pyran-4-yl)-2'H-spiro[chroman-4,5'-[1,2,4]oxadiazol]-3'-amine (50 mg, 0.13 mmol), 3-chloro-5-(4,4,5,5-tetramethyl-1,3,2-dioxaborolan-2-yl)benzonitrile (51.285 mg, 0.195 mmol), Cs$_2$CO$_3$ (2 M, 0.35 mL) and Pd(PPh$_3$)$_2$Cl$_2$ (9.25 mg) in 1,4-dioxane (1.25 mL) under Ar$_2$ was stirred in microwave at 120° C. for 35 minutes. The reaction mixture was concentrated in vacuo to give the residue, which was purified preparative TLC and HPLC to give compound 350 (1.34 mg, 2%). $^1$H-NMR (400 MHz CD$_3$OD): δ7.91 (m, 1H), 7.89 (m, 2H), 7.65 (m, 2H), 6.94 (m, 1H), 3.88-4.01 (m, 3H), 3.38 (m, 2H), 3.27 (m, 3H), 2.36-2.60 (m, 1H), 1.72-1.94 (m, 3H), 1.54 (m, 3H); ESI MS: m/z 439 [M+H]$^+$.

Example 160

Preparation of Compounds 394, 416 and 443

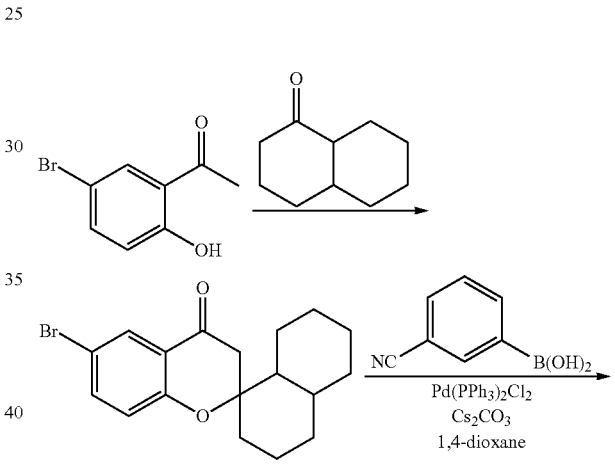

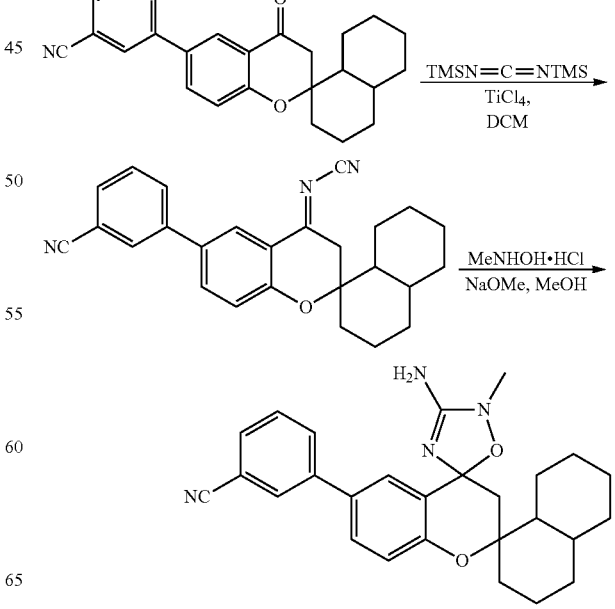

Preparation of Compound 1

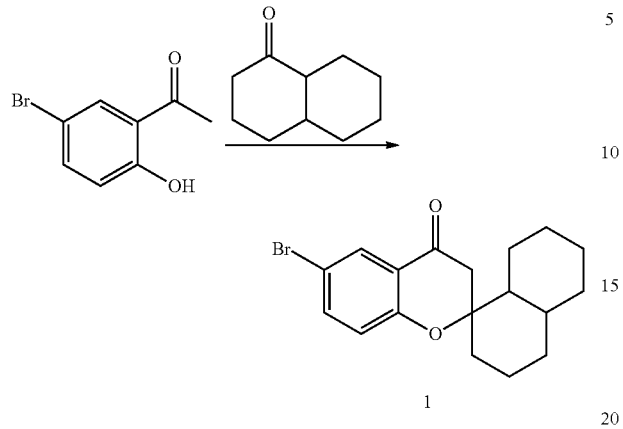

A mixture of 1-(5-bromo-2-hydroxy-phenyl)-ethanone (1.9 g, 8.88 mmol), octahydronaphthalen-1(2H)-one (900 mg, 5.92 mol) and pyrrolidine (546 mg, 7.69 mol) in toluene (30 mL) was refluxed overnight. The reaction mixture was removed in vacuum. The residue was diluted with $H_2O$, and added HCl (PH=1). The mixture was extracted with EtOAc. The organic layer was dried over anhydrous $Na_2SO_4$, filtered, and evaporated to give the compound 1 (474 mg, 15%). $^1H$ NMR (400 MHz $CDCl_3$): δ7.96 (m, 1H), 7.53 (m, 1H), 6.88 (m, 1H), 2.61-3.22 (m, 2H), 2.22 (m, 1H), 1.56-1.97 (m, 7H), 0.95-1.43 (m, 8H).

Preparation of Compound 2

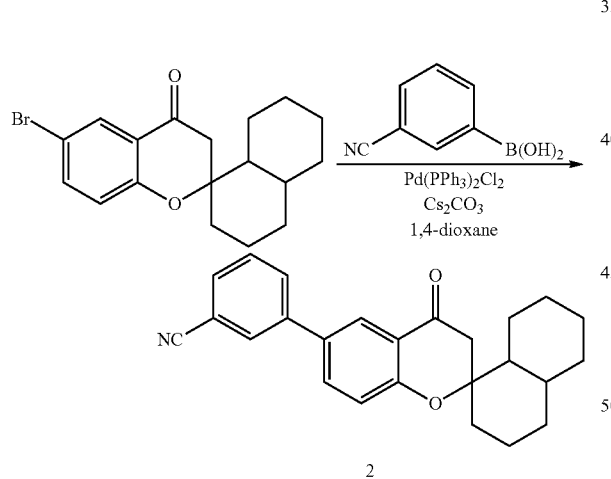

$Pd(PPh_3)_2Cl_2$ (30 mg) in a 50 mL of flask under $Ar_2$ was treated sequentially with the 6-bromo-3',4',4a',5',6',7',8',8a'-octahydro-2'H-spiro[chroman-2,1'-naphthalen]-4-one (300 mg, 0.86 mmol) in 1,4-dioxane (6 mL), $Cs_2CO_3$ (2 N, 1.3 mL) and 3-cyanophenylboronic acid (235 mg, 1.29 mmol). The mixture was heated under 100° C. under $Ar_2$ in a microwave for 6 minutes. The reaction mixture was concentrated in vacuo to give the residue, which was purified by preparative TLC to give the compound 2 (286 mg, 90%). $^1H$ NMR (400 MHz $CDCl_3$): δ8.01 (m, 1H), 7.76 (m, 2H), 7.63 (m, 1H), 7.54 (m, 1H), 7.46 (m, 1H), 7.01 (m, 1H), 2.52-3.21 (m, 2H), 2.23 (m, 1H), 1.89 (m, 2H), 1.69 (m, 4H), 1.53 (m, 2H), 1.38 (m, 4H), 1.26 (m, 2H), 1.13 (m, 1H), 0.98 (m, 2H).

Preparation of Compound 3

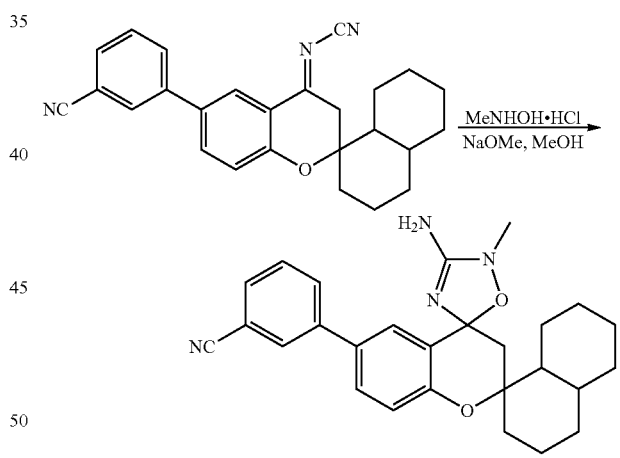

A solution of 3-(4-oxo-3',4',4a',5',6',7',8',8a'-octahydro-2'H-spiro[chroman-2,1'-naphthalene]-6-yl)benzonitrile (110 mg, 0.296 mmol) and $TiCl_4$ (225 mg, 1.184 mmol) in anhydrous dichloromethane (5 mL) was heated at 50° C. under microwave for 5 minutes. The bis-trimethylsilylcarbodiimide (110 mg, 0.592 mmol) was added and the mixture was heated at 60° C. for 20 min. The reaction mixture was poured into water, and extracted with dichloromethane. The combined organic phases were dried over anhydrous $Na_2SO_4$, filtered, and concentrated to give the compound 3 (145 mg, crude), which was used in the next step directly.

Preparation of Compounds 443, 416 and 394

To a solution of methylhydroxylamine HCl salt (31 mg, 0.367 mmol) in anhydrous MeOH (5 mL) was added NaOMe (25% in MeOH (Wt. %), 0.1 mL), followed by (E)-N-(6-(3-cyanophenyl)-3',4',4a',5',6',7',8',8a'-octahydro-2'H-spiro[chroman-2,1'-naphthalne]-4-ylidene)cyanamide (145 mg, 0.367 mmol). After being stirred for 10 min., the solvent was removed in vacuo. The residue was redissolved in DCM (10 mL). The mixture was filtered and concentrated to give compound 443 $^1H$-NMR (400 MHz $CD_3OD$): δ8.02 (m, 1H), 7.95 (m, 1H), 7.70-7.74 (m, 1H), 7.62-7.69 (m, 2H), 6.99-7.15 (m, 1H), 3.36-3.43 (m, 3H), 2.95-3.25 (m, 1H), 2.35-2.49 (m, 1H), 1.97-2.04 (m, 3H), 1.74-1.81 (m, 3H), 1.74 (m, 2H), 1.58 (m, 2H), 1.48-1.57 (m, 3H), 1.05-1.47 (m, 3H); ESI MS: m/z 443 [M+H]⁺.

compound 416: δ8.02 (m, 1H), 7.96 (m, 2H), 7.70-7.74 (m, 1H), 7.62-7.68 (m, 2H), 7.03-7.18 (m, 1H), 3.32-3.39 (m, 3H), 2.75-2.94 (m, 1H), 2.20-2.50 (m, 1H), 1.97-2.15 (m, 3H), 1.75-1.93 (m, 3H), 1.68 (m, 2H), 1.59 (m, 2H), 1.44-1.50 (m, 3H), 1.29-1.33 (m, 3H); ESI MS: m/z 443 [M+H]⁺.

compound 394: δ8.01 (m, 1H), 7.94 (m, 2H), 7.63-7.74 (m, 3H), 7.01-7.17 (m, 1H), 3.35-3.42 (m, 3H), 2.75-3.03 (m, 1H), 2.42-2.58 (m, 1H), 1.96-2.24 (m, 2H), 1.73-1.95 (m, 6H), 1.48-1.68 (m, 3H), 1.15-1.37 (m, 5H); ESI MS: m/z 443 [M+H]⁺.

Example 161

Preparation of Compound 334

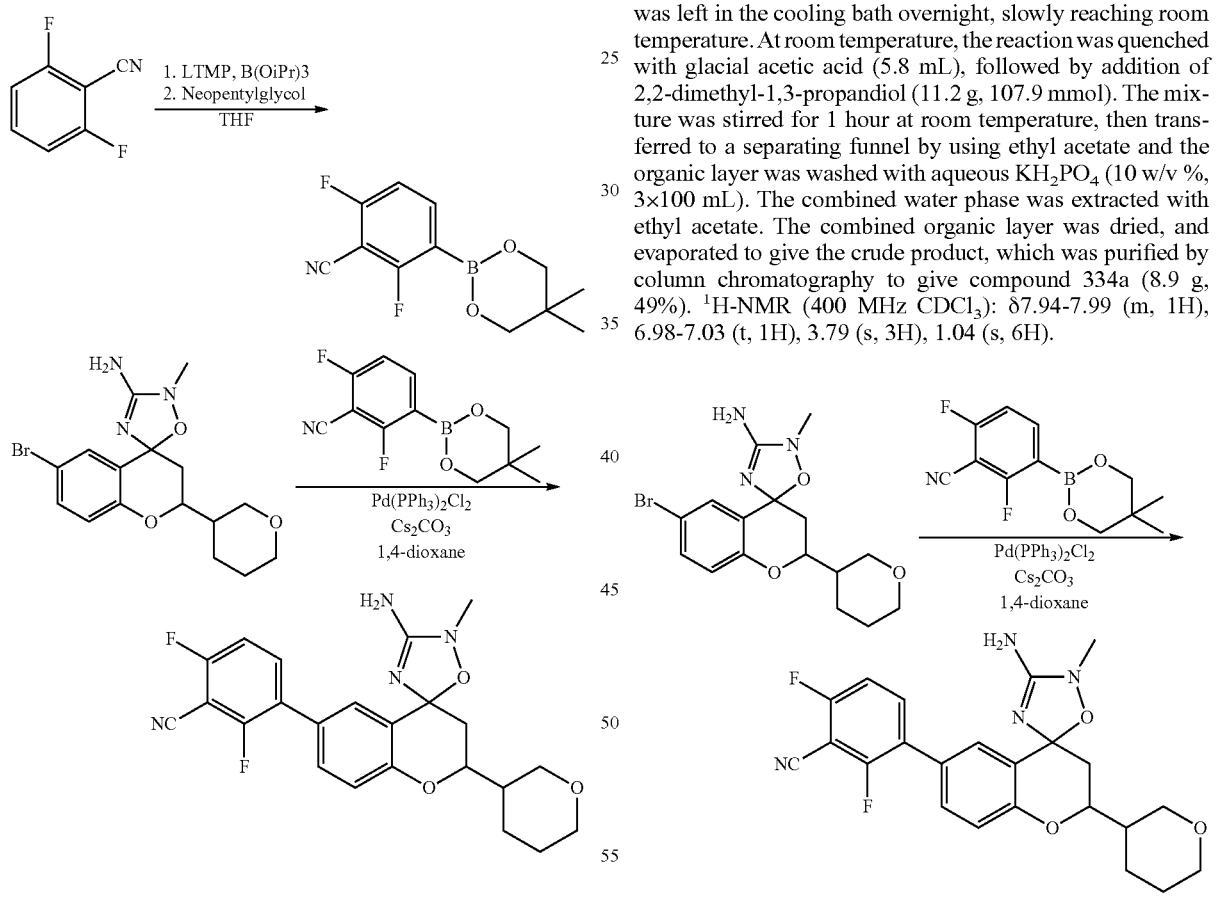

Experimental Data:

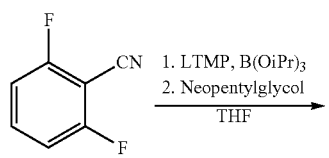

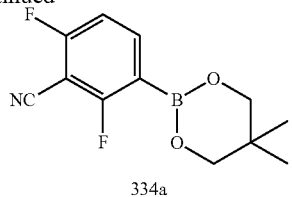

334a

Preparation of Compound 334a

In a 500 mL dry three-neck flask under N₂, 2,2,6,6-tetramethylpiperidine (14.6 mL, 86.4 mmol) was dissolved in dry THF (140 mL) and cooled to −10° C. before n-BuLi (2.5 M in hexane, 35 mL, 86.4 mmol) was added over 2 min. The mixture was stirred for 10 minutes before cooling to −78° C. At −78° C., B(O¹Pr)₃ (23.3 mL, 100.7 mmol) was added over 2 minutes, and stirred for 5 minutes at −78° C. before 2,6-difluorobenzonitrile (10 g, 71.9 mmol) dissolved in dry THF (75 mL) was added dropwise over 5 minutes. The reaction was left in the cooling bath overnight, slowly reaching room temperature. At room temperature, the reaction was quenched with glacial acetic acid (5.8 mL), followed by addition of 2,2-dimethyl-1,3-propandiol (11.2 g, 107.9 mmol). The mixture was stirred for 1 hour at room temperature, then transferred to a separating funnel by using ethyl acetate and the organic layer was washed with aqueous KH₂PO₄ (10 w/v %, 3×100 mL). The combined water phase was extracted with ethyl acetate. The combined organic layer was dried, and evaporated to give the crude product, which was purified by column chromatography to give compound 334a (8.9 g, 49%). ¹H-NMR (400 MHz CDCl₃): δ7.94-7.99 (m, 1H), 6.98-7.03 (t, 1H), 3.79 (s, 3H), 1.04 (s, 6H).

Preparation of Compound 334

A mixture of 6-bromo-2'-methyl-2-(tetrahydro-2H-pyran-3-yl)-2'H-spiro[chroman-4,5'-[1,2,4]oxadiazol]-3'-amine (50 mg, 0.13 mmol), 3-(5,5-dimethyl-1,3,2-dioxaborinan-2-yl)-2,6-difluorobenzonitrile (65 mg, 0.26 mmol), Cs₂CO₃ (2 M, 0.7 mL) and Pd(PPh₃)₂Cl₂ (30 mg) in 1,4-dioxane (3 mL) under Ar₂ was heated at 120° C. under microwave for 30 minutes. The reaction mixture was concentrated in vacuo to give the residue, which was purified preparative TLC and preparative HPLC to give compound 334 (2.67 mg, 5%). $^1$H-NMR (400 MHz CD$_3$OD): δ7.84-7.90 (m, 2H), 7.59-7.61 (t, 1H), 7.32-7.37 (t, 1H), 7.08 (t, 1H), 3.93-4.24 (m, 2H), 3.50-3.90 (m, 2H), 3.37-3.43 (m, 1H), 3.36 (s, 3H), 2.76-2.80 (m, 1H), 2.48-2.69 (m, 1H), 1.98-2.13 (m, 3H), 1.69-1.75 (m, 2H); ESI MS: m/z 441 [M+H]$^+$.

Example 162

Preparation of Compound 320

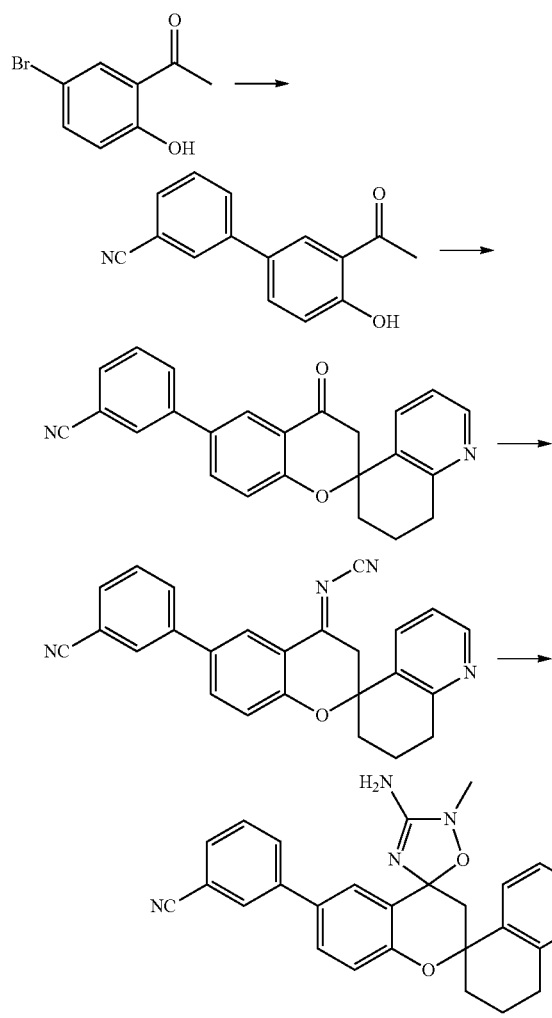

Experimental Data:

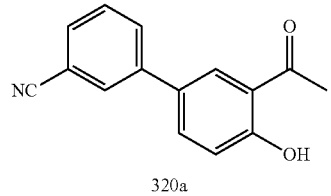

320a

Preparation of Compound 320a

A mixture of 1-(5-bromo-2-hydroxy-phenyl)-ethanone (600 mg, 2.8 mmol), 3-cyanophenylboronic acid (700 mg, 4.76 mmol), Cs$_2$CO$_3$ (2.8 mL, 2 M) and Pd(PPh$_3$)$_2$Cl$_2$ (50 mg) in 1,4-dioxane (24 mL) was degassed, and stirred in microwave at 100° C. for 5 minutes. The organic layer was concentrated in vacuo to give the residue, which was purified preparative TLC to give the compound 320a (560 mg, 84%).

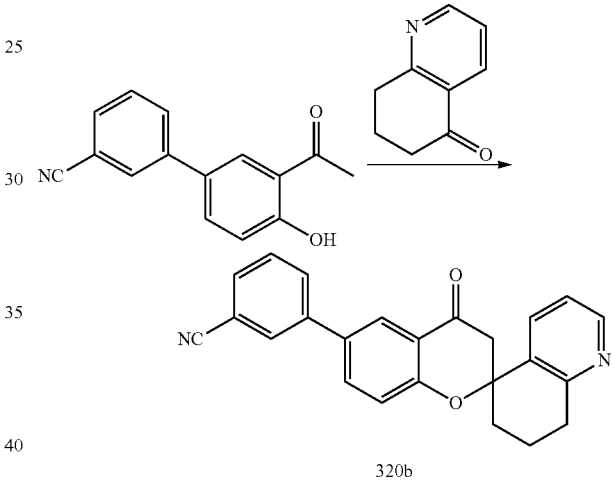

320b

Preparation of Compound 320b

A mixture of 3'-acetyl-4'-hydroxy-biphenyl-3-carbonitrile (215 mg, 0.91 mmol), 7,8-dihydroquinolin-5(6H)-one (200 mg, 1.36 mmol) and pyrrolidine (97 mg, 1.36 mmol) in MeOH (5 mL) was refluxed overnight. The solvent was removed in vacuo to give the residue, which was purified by preparative TLC to give the compound 320b (55 mg, 16%). $^1$H-NMR (400 MHz CDCl$_3$): δ8.81 (m, 1H), 8.58 (m, 1H), 8.09 (s, 1H), 7.76 (m, 4H), 7.56 (m, 2H), 7.04 (d, 1H), 3.32 (m, 2H), 3.28 (m, 1H), 2.94 (m, 1H), 2.21 (m, 3H), 1.96 (m, 1H).

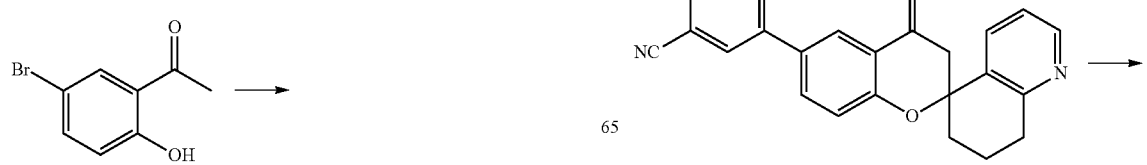

653

-continued

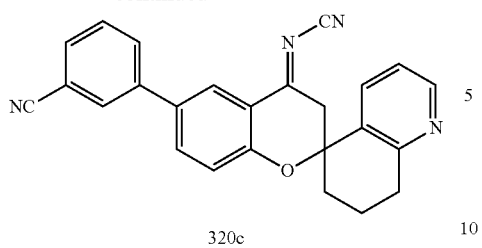

320c

Preparation of Compound 320c

To a solution of 3-(4-oxo-7',8'-dihydro-6'H-spiro[chroman-2,5'-quinoline]-6-yl)benzonitrile (100 mg, 0.273 mmol) in CH$_2$Cl$_2$ (2 mL) under N$_2$ was added TiCl$_4$ (1 M solution in DCM, 1.1 mL, 1.1 mmol). It was stirred in microwave at 50° C. for 5 minutes. Bis-trimethylsilylcarbodiimide (112 mg, 0.6 mmol) was added. The resulting mixture was stirred in microwave at 60° C. for 10 minutes. The reaction mixture was poured into ice-water, and extracted with DCM. The combined organic phases were dried over anhydrous Na$_2$SO$_4$, and filtered. The filtrate was concentrated to give the compound 320c (100 mg, crude).

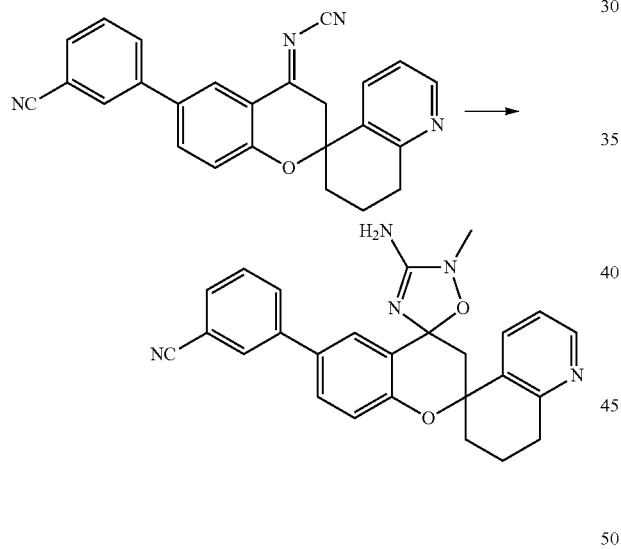

Preparation of Compound 320

To a solution of methylhydroxylamine HCl salt (25 mg, 0.256 mmol) in anhydrous MeOH (5 mL) was added NaOMe (25% wt. in MeOH, 5 drops), and N-(6-(3-cyanophenyl)-7',8'-dihydro-6'H-spiro[chroman-2,5'-quinoline]-4-ylidene)cyanamide (100 mg, 0.256 mmol). After being stirred for 10 minutes, the solvent was removed in vacuo. The residue was redissolved in DCM (5 mL). The mixture was filtered, and the solvent was removed to give the residue, which was purified by preparative HPLC to give compound 320 (4.99 mg, 2%). $^1$H-NMR (400 MHz CD$_3$OD): δ8.55-8.92 (m, 2H), 7.92-8.47 (m, 3H), 7.42-7.91 (m, 4H), 7.15 (m, 1H), 3.56 (m, 1H), 3.38 (m, 3H), 2.95-3.24 (m, 3H), 2.56 (m, 1H), 2.02-2.42 (m, 3H); ESI MS m/z 438 [M+H]$^+$.

654

Example 163

Preparation of Compounds 305 and 345

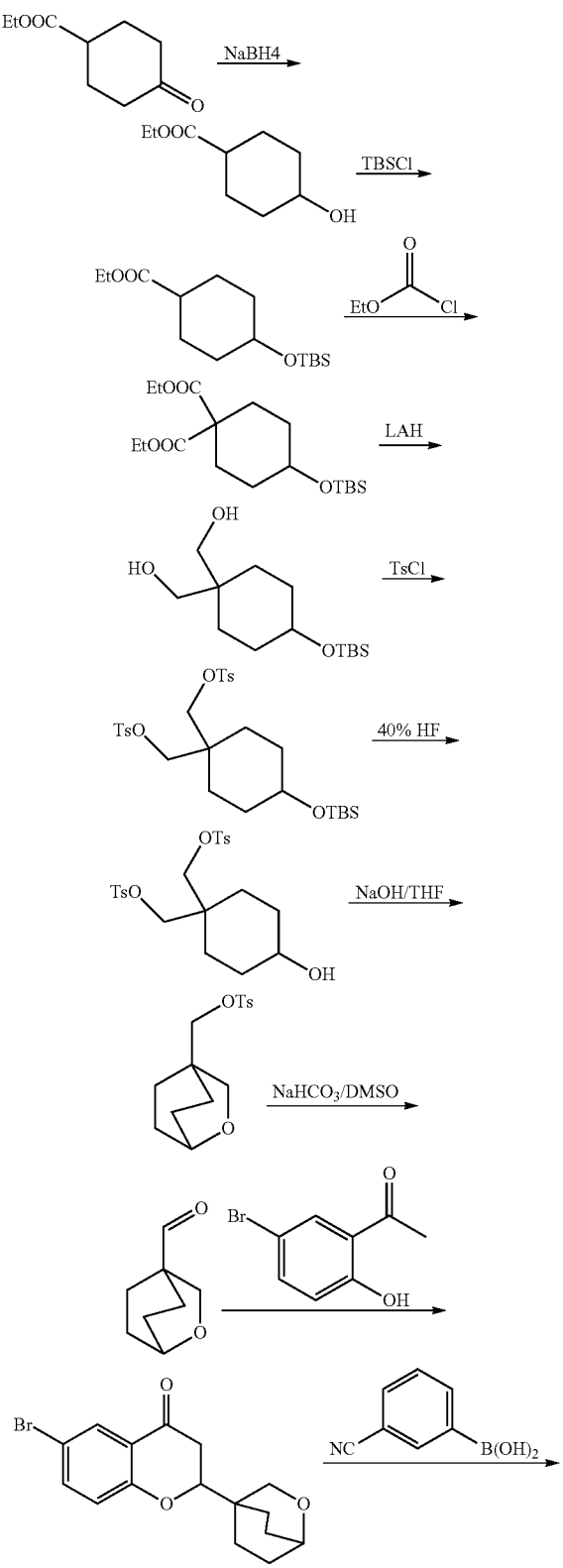

-continued

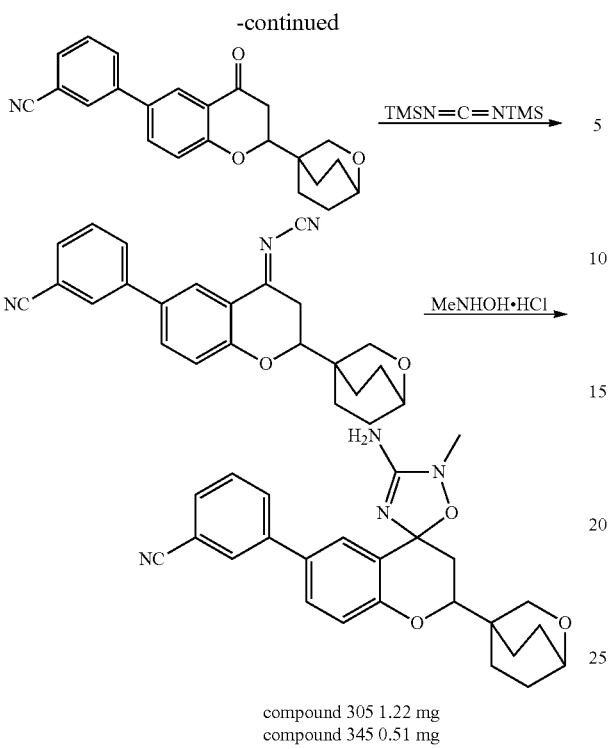

compound 305 1.22 mg
compound 345 0.51 mg

Experimental Data:

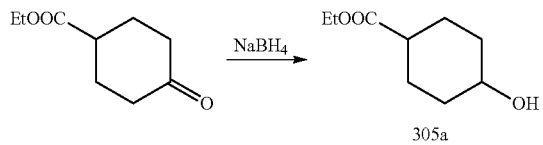 [SMILES: CCOC(=O)C1CCC(=O)CC1 ; "NaBH4" ; CCOC(=O)C1CCC(O)CC1]

305a

Preparation of Compound 305a

To a solution of ethyl 4-oxocyclohexanecarboxylate (118 g, 0.69 mol) in MeOH (1 L) was added NaBH$_4$ (44 g, 1.17 mol), and the mixture was stirred at room temperature for 3 hours. The reaction was quenched with water and extracted with EtOAc. The organic layer was washed with brine, dried over Na$_2$SO$_4$, and concentrated to give the compound 305a (105 g, 89%). $^1$H NMR (400 MHz CDCl$_3$): δ4.10 (m, 2H), 3.52 (m, 1H), 2.32 (m, 1H), 1.89 (m, 4H), 1.48 (m, 4H), 1.21 (t, 3H).

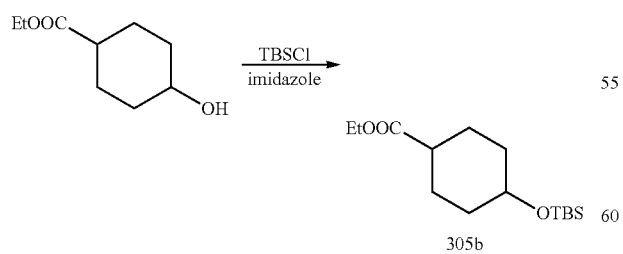

305b

Preparation of Compound 305b

To a solution of ethyl 4-hydroxycyclohexanecarboxylate (105 g, 0.61 mol) in DMF (700 mL) was added imidazole (83 g, 12.2 mol) and TBSCl (101 g, 0.67 mol). The resulting mixture was stirred overnight. Ether was added, and the aqueous layer was washed with 1 N HCl, and extracted ether. The combined organic layer was washed 1 N HCl and brine, dried over NaSO$_4$, and concentrated to give the compound 305b (215 g, 100%).

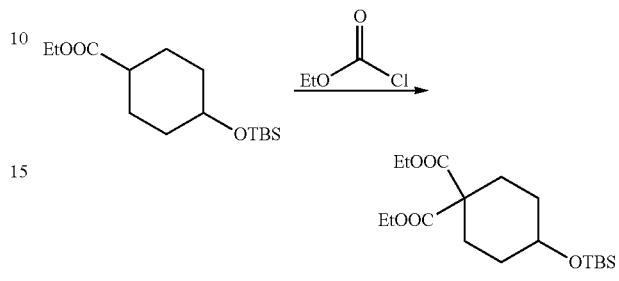

305c

Preparation of Compound 305c

A three necked flask was charged with THF (300 mL) and diisopropylamine (68.9 g, 0.68 mol). The mixture was cooled to −70° C., n-BuLi (2.5 M, 286 mL, 0.714 mol) was added via syringe, and the mixture was stirred 30 minutes. Ethyl 4-(tert-butyldimethylsilyloxy)cyclohexanecarboxylate (195 g, 0.68 mol) was added dissolved in THF (20 mL) at −70° C. After 1 hour stirring, ethyl carbonochloridate (76.8 g, 0.7 mol) was added dropwise, and the reaction was stirred for 2 hours. The mixture was warmed to 0° C., and quenched with water, and extracted with EtOAc. The organic layer was washed with brine, 1 N HCl, water, dried, and concentrated to give the residue, which was purified by chromatography to afford the compound 305c (146 g, 60%). $^1$H NMR (400 MHz CDCl$_3$): δ4.14 (m, 4H), 2.25 (m, 2H), 1.83 (m, 2H), 1.68 (m, 2H), 1.47 (m, 2H), 1.21 (m, 6H), 0.85 (s, 10H), 0.00 (s, 6H).

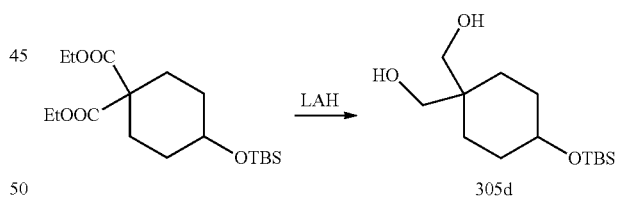

305d

Preparation of Compound 305d

LiAlH$_4$ (8 g, 0.21 mol) was suspended in 400 mL of dry THF in a ice-cooled bath, the solution of diethyl 4-(tert-butyldimethylsilyloxy)cyclohexane-1,1-dicarboxylate (50 g, 0.14 mol) dissolved in 150 mL of THF was added dropwise. After being stirred for 1 hour, 8 mL of H$_2$O and 8 mL of 10% NaOH solution were added at 0° C. The mixture was stirred at room temperature and filtered. The filtrate was concentrated, and the residue was re-crystalized from petrol ether to afford the compound 305d (25 g, 68%). $^1$H NMR (400 MHz CDCl$_3$): δ3.62 (m, 3H), 3.48 (s, 2H), 2.62 (s, 2H), 1.68 (m, 4H), 1.42 (m, 2H), 1.16 (m, 2H), 0.85 (s, 9H), 0.00 (s, 6H).

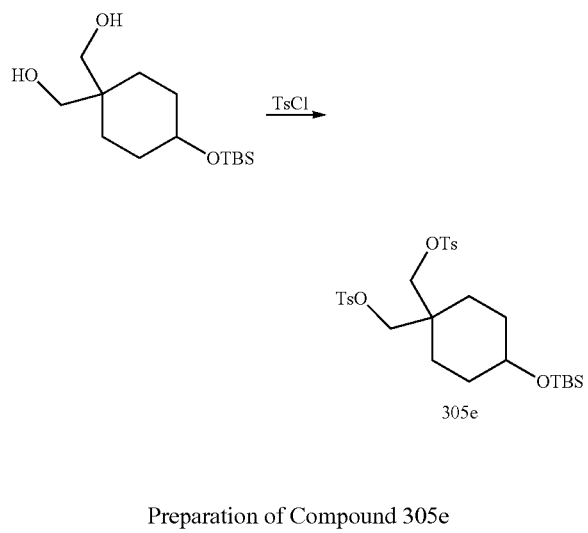

Preparation of Compound 305e

To a solution of (4-(tert-butyldimethylsilyloxy)cyclohexane-1,1-diyl)dimethanol (10 g, 37 mmol) and pyridine (5.85 g, 74 mmol) in CHCl₃ (120 mL) in an ice-water bath was added TsCl (21 g, 111 mmol) in one portion. After being stirred for 20 minutes, the ice-water bath was removed, and the mixture was stirred at room temperature overnight.

The solution was diluted with CH₂Cl₂, washed with 1 N HCl, water and brine, dried, and concentrated. The residue was purified by chromatography to afford the compound 305e (18.5 g, 86%). ¹H NMR (400 MHz CDCl₃): δ7.70 (d, 4H), 7.33 (d, 4H), 3.82 (s, 2H), 3.79 (s, 2H), 3.58 (s, 1H), 2.47 (d, 6H), 1.53 (m, 2H), 1.27 (m, 6H), 0.85 (s, 9H), 0.00 (s, 6H).

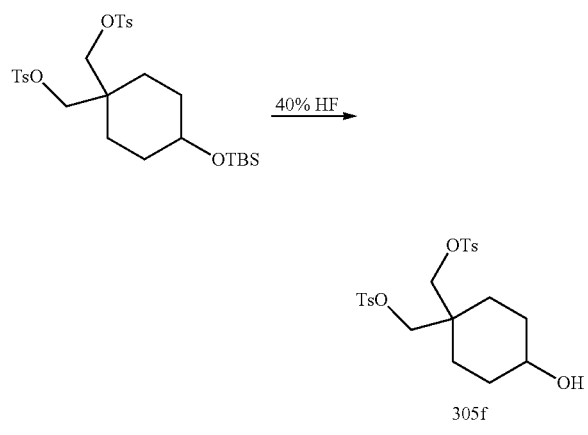

Preparation of Compound 305f

To a solution of (4,4-bis(tosylmethyl)cyclohexyloxy)(tert-butyl)dimethylsilane (18.5 g, 31.8 mmol) in CH₃CN (200 mL) was added 40% HF (45 mL), and the mixture was stirred at room temperature for 30 minutes. The reaction mixture was poured into the saturated aqueous NaHCO₃ solution and extracted with EtOAc. The organic layer was dried and concentrated to give the compound 305f (14 g, 100%). ¹H NMR (400 MHz CDCl₃): δ7.66 (d, 4H), 7.23 (d, 4H), 3.81 (s, 2H), 3.68 (s, 2H), 3.59 (s, 1H), 2.41 (s, 6H), 1.92 (s, 1H), 1.56 (m, 4H), 1.22 (m, 4H).

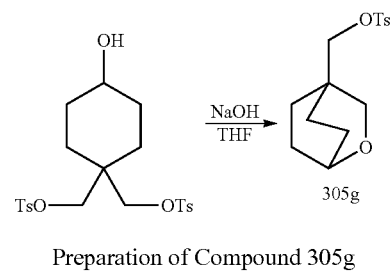

Preparation of Compound 305g

To a solution of 4,4-bis(tosylmethyl)cyclohexanol (15 g, 34.5 mmol) in dry THF (500 ml) was added powdered NaOH (25 g, 625 mmol). The reaction mixture was stirred under reflux for 48 hours, cooled to room temperature, diluted with water, and extracted with EA. The organic layer was dried and concentrated to give the crude product, which was purified by chromatography to afford the compound 305g (6 g, 70%). ¹H-NMR (400 MHz CDCl₃): δ7.77 (d, 2H), 7.36 (d, 2H), 3.78 (m, 1H), 3.66 (s, 2H), 3.65 (s, 2H), 2.46 (s, 3H), 1.98 (m, 2H), 1.62 (m, 1H), 1.60 (m, 2H), 1.57 (m, 1H), 1.47 (m, 2H).

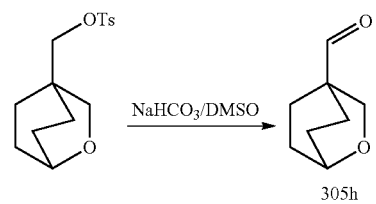

Preparation of Compound 305h

DMSO (30 mL) was heated to 150° C. for 10 min, and cooled to room temperature under N₂. Toluene-4-sulfonic acid 2-oxa-bicyclo[2.2.2]oct-4-ylmethyl ester (1 g, 3.38 mmol) and NaHCO₃ (2.83 g, 33.8 mmol) were added. The mixture was heated to 150° C. for 4 hours. After being cooled to room temperature, the mixture was treated with water and ethyl acetate. The organic layer was washed with water and brine, dried, and concentrated to give the crude product, which was purified by preparative TLC to give the compound 305h (200 mg, 42%). ¹H-NMR (400 MHz CDCl₃): δ9.41 (s, 1H), 3.89 (m, 2H), 3.85 (m, 1H), 2.10 (m, 2H), 1.85 (m, 2H), 1.75 (m, 2H), 1.62 (m, 4H).

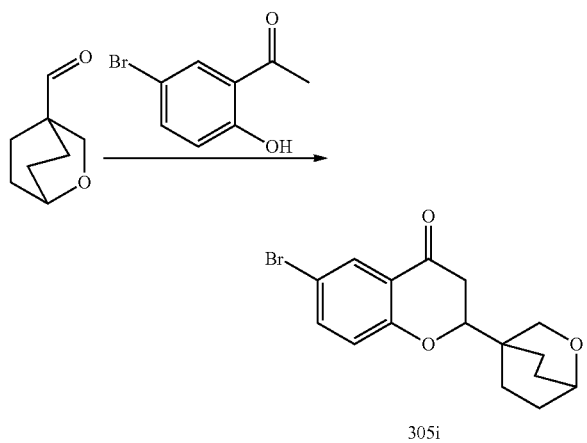

Preparation of Compound 305i

A solution of 2-oxa-bicyclo[2.2.2]octane-4-carbaldehyde (200 mg, 1.43 mmol), 1-(5-bromo-2-hydroxy-phenyl)-ethanone (307 mg, 1.43 mmol) and Na$_2$B$_4$O$_7$.10H$_2$O (545 mg, 1.43 mmol) in a mixture of ethanol (6 mL) and water (10 mL) was reflux for overnight. The mixture was concentrated. The residue was added water and ethyl acetate.

The organic layer was dried, and concentrated to give the crude product, which was purified by preparative TLC to give the compound 305i (320 mg, 67%).

50° C. in microwave for 10 minutes. To this mixture was added N,N'-methanediylidenebis(1,1,1-trimethylsilanamine) (182 mg, 0.98 mmol). The resulting mixture was stirred at 60° C. in microwave for another 15 minutes. The reaction mixture was poured into ice-water, and extracted with DCM. The combined organic phases were dried and concentrated to give the crude compound 305k (70 mg, 94%), which was used in the next step without further purification.

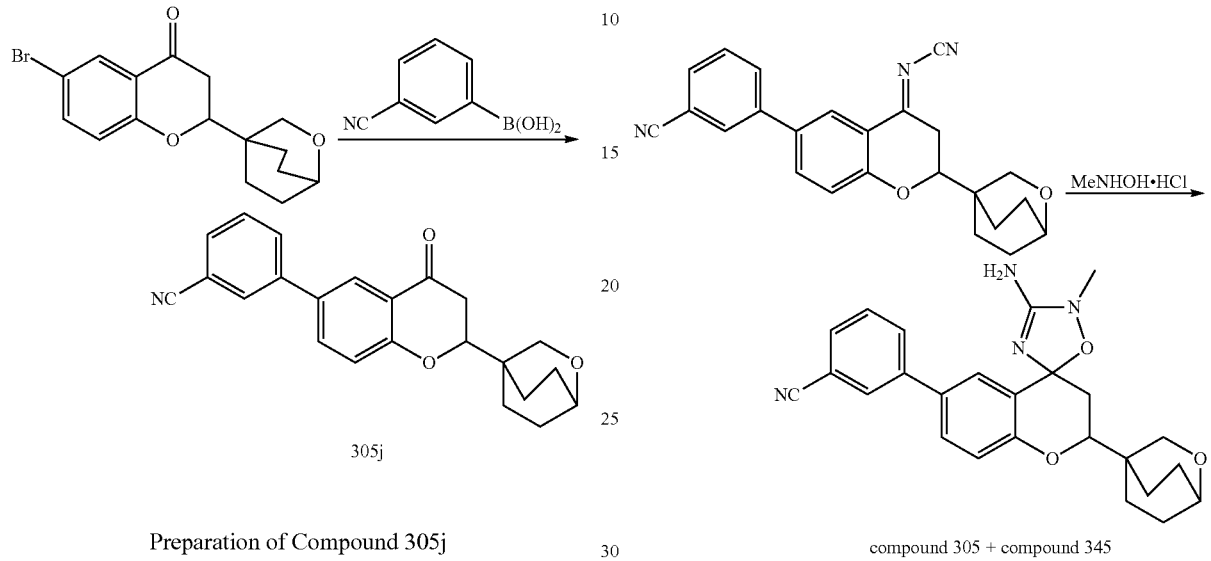

compound 305 + compound 345

Preparation of Compound 305j

A mixture of Pd(PPh$_3$)$_2$Cl$_2$ (66 mg, 0.095 mmol), 6-bromo-2-(2-oxa-bicyclo[2.2.2]oct-4-yl)-chroman-4-one (320 mg, 0.95 mmol), Cs$_2$CO$_3$ (2 N, 4.75 mL, 9.5 mmol) and 3-cyanophenylboronic acid (281 mg, 1.9 mmol) in 1,4-dioxane (3 mL) was stirred at 100° C. in microwave for 20 minutes. The reaction mixture was treated with ethyl acetate and water. The organic layer was concentrated in vacuo to give the crude product, which was purified by preparative TLC to give the compound 10 (70 mg, 20%).

Preparation of Compound 305 and compound 345

To a solution MeNHOH.HCl (76.32 mg, 0.91 mmol) in anhydrous MeOH (2 mL) was added NaOMe (44.4 mg, 0.82 mmol, 25 w % in MeOH) and 6-(3-cyano-phenyl)-2-(2-oxabicyclo[2.2.2]oct-4-yl)-chroman-4-ylidene-cyanamide (70 mg, 0.18 mmol, crude). After being stirred for 2 hours, the solvent was removed in vacuum, and the residue was dissolved in DCM. The mixture was filtered, and the solvent was removed in vacuum to give the crude product, which was purified by preparative TLC and preparative HPLC to give compound 305 (1.22 mg, 2%) $^1$H-NMR (400 MHz CD$_3$OD): δ7.98 (s, 1H), 7.92 (d, 2H), 7.70 (t, 2H), 7.61 (t, 1H), 7.03 (d, 1H), 4.03 (d, 1H), 3.96 (d, 1H), 3.81 (m, 2H), 3.35 (s, 3H), 2.60 (d, 1H), 2.07 (m, 2H), 1.90 (m, 3H), 1.75 (m, 4H); ESI MS: m/z 431 [M+H]$^+$ and compound 345 (0.51 mg, 1%). $^1$H-NMR (400 MHz CD$_3$OD): δ7.86 (s, 1H), 7.80 (d, 1H), 7.74 (s, 1H), 7.57 (t, 2H), 7.51 (t, 3H), 6.90 (d, 1H), 3.93 (m, 1H), 3.85 (s, 1H), 3.71 (m, 2H), 3.38 (s, 3H), 3.03 (m, 2H), 1.97 (m, 2H), 1.75 (m, 2H), 1.65 (m, 4H); ESI MS: m/z 431 [M+H]$^+$.

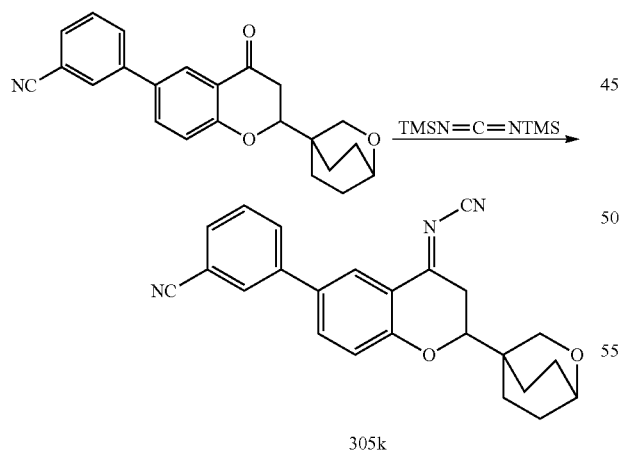

305k

Example 164

Preparation of Compound 319

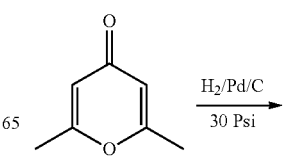

Preparation of Compound 305k

To a solution of 3-[2-(2-oxa-bicyclo[2.2.2]oct-4-yl)-4-oxo-chroman-6-yl]-benzonitrile (70 mg, 0.19 mmol) in anhydrous DCM (5 mL) was added TiCl$_4$ (0.98 mL, 0.98 mmol, 1 M in DCM) at room temperature. The mixture was stirred at

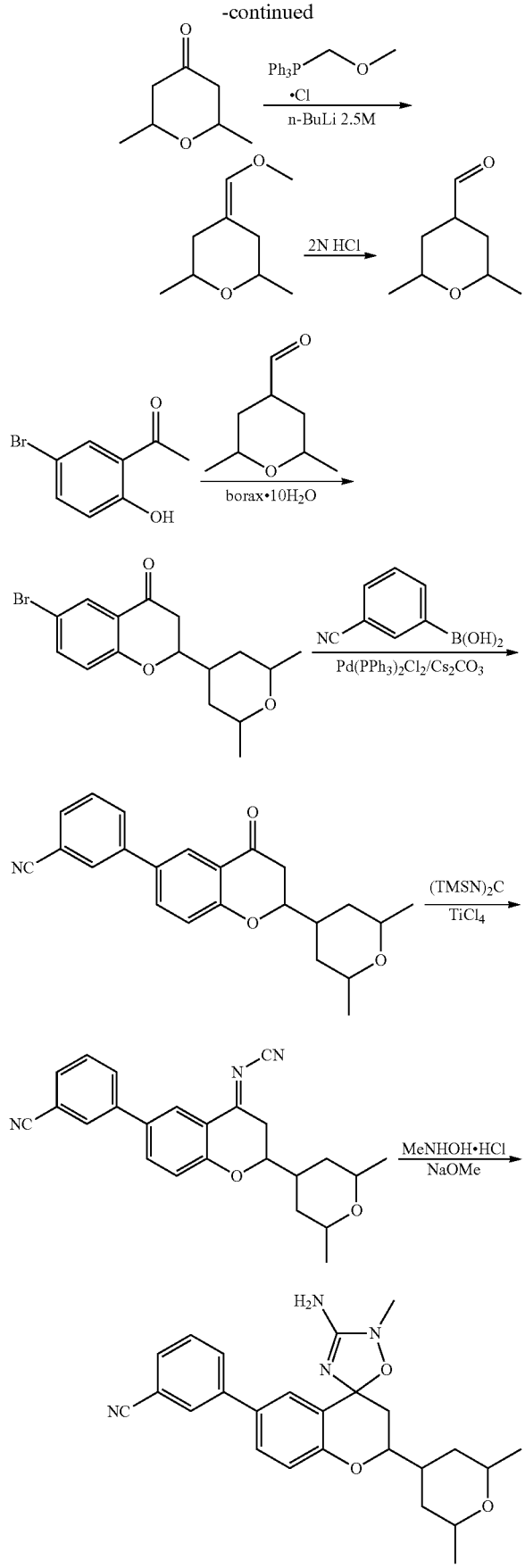

Experimental Data:

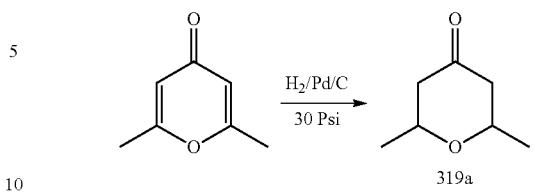

Preparation of Compound 319a 2,6-Dimethyl-4H-pyran-4-one (12 g, 96.8 mmol) was dissolved in ethanol (60 mL), and 10% Pd/C (1.2 g) was added. The mixture was hydronated under $H_2$ (30 Psi) at room temperature for 24 hours, passed through celite, and concentrated under reduced pressure at 30° C. to give the compound 319a (12 g, crude).

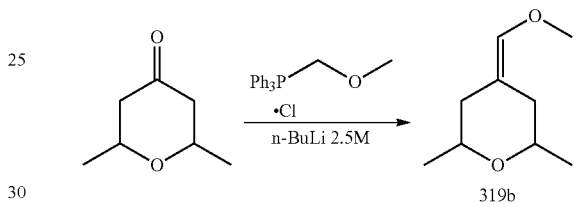

Preparation of Compound 319b

To a solution of witting reagent (46.3 g, 135 mmol) in THF (375 mL) at 0° C. was added dropwise a solution of 2.5 M n-BuLi (in hexane, 25.3 mL). The reaction mixture was warmed to room temperature, stirred for 1 hour, recooled to 0° C., and added a solution of 2,6-dimethyldihydro-2H-pyran-4(3H)-one (12 g, 93.8 mmol) in THF (60 mL) dropwise. The reaction mixture was stirred at 0° C. for 3 hours. The reaction mixture was concentrated under reduced pressure at about 25-30° C. The crude product was purified by silica gel column to give the compound 319b (2.3 g, 16%). $^1$H-NMR (400 MHz CDCl$_3$): δ 5.79-5.80 (t, 1H), 3.53 (s, 3H), 2.59-2.68 (m, 1H), 1.88-1.95 (m, 1H), 1.70-1.82 (m, 1H), 1.50-1.59 (m, 1H), 1.20 (d, 3H, J=6.4 Hz), 1.18 (d, 3H, J=6.0 Hz).

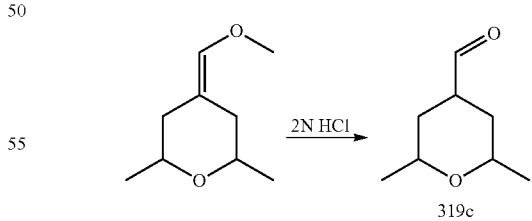

Preparation of Compound 319c

A solution of 4-(methoxymethylene)-2,6-dimethyltetrahydro-2H-pyran (2.1 g, 13.7 mmol) in a mixture of HCl (2 M, 64 mL) and $H_2O$ (21 mL) was refluxed for 2 hours. The mixture was extracted by $CH_2Cl_2$, after drying and concentration, the crude compound 319c (1.9 g) was obtained.

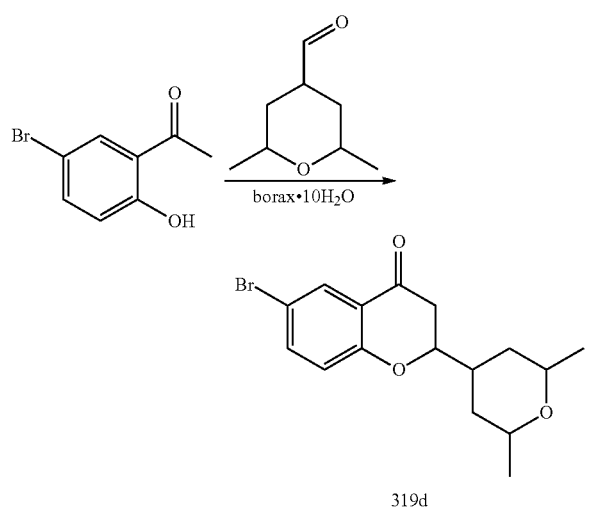

319d

Preparation of Compound 319d

The mixture of 1-(5-bromo-2-hydroxyphenyl)ethanone (2.9 g, 13.5 mmol), 2,6-dimethyltetrahydro-2H-pyran-4-carbaldehyde (1.9 g, 13.5 mmol) and borax (5.1 g, 13.5 mmol) in a mixture of ethanol (17 mL) and water (29 mL) was refluxed overnight. The reaction mixture was cooled by ice-water bath and dissolved in EtOAc. The organic layer was separated and concentrated to give the residue, which was purified by silica gel column to give the pure compound 319d (2.9 g, 64%).

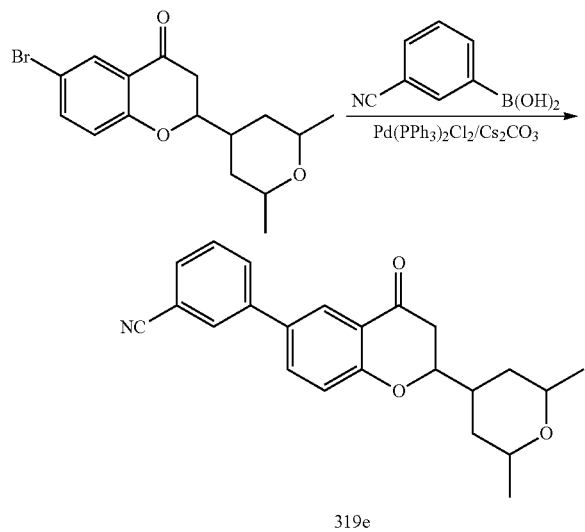

319e

Preparation of Compound 319e $Pd(PPh_3)_2Cl_2$ (20.7 mg, 0.03 mmol) in a tube under $Ar_2$ was treated sequentially with 6-bromo-2-(2,6-dimethyltetrahydro-2H-pyran-4-yl)chroman-4-one (200 mg, 0.59 mmol), 3-cyanophenylboronic acid (173.5 mg, 1.18 mmol) in [1,4]-dioxane (23.6 mL) and $Cs_2CO_3$ (2 M, 3.54 mL). The mixture was heated at 100° C. under $Ar_2$ for 5 minutes in a microwave reactor. The reaction mixture was extracted with EtOAc, concentrated, and purified by preparative TLC to give compound 319e (140 mg, 66%). $^1$H-NMR (400 MHz CDCl$_3$): δ8.09 (s, 1H), 7.81-7.85 (m, 1H), 7.75-7.80 (m, 1H), 7.66-7.72 (m, 1H), 7.56-7.62 (m, 1H), 7.48-7.55 (m, 1H), 7.05-7.10 (m, 1H), 4.20-4.30 (m, 1H), 3.71-3.76 (m, 1H), 3.42-3.58 (m, 2H), 2.71-2.78 (m, 1H), 2.01-2.11 (m, 1H), 1.89-1.95 (m, 1H), 1.61-1.69 (m, 1H), 1.20-1.28 (m, 6H), 1.05-1.19 (m, 2H).

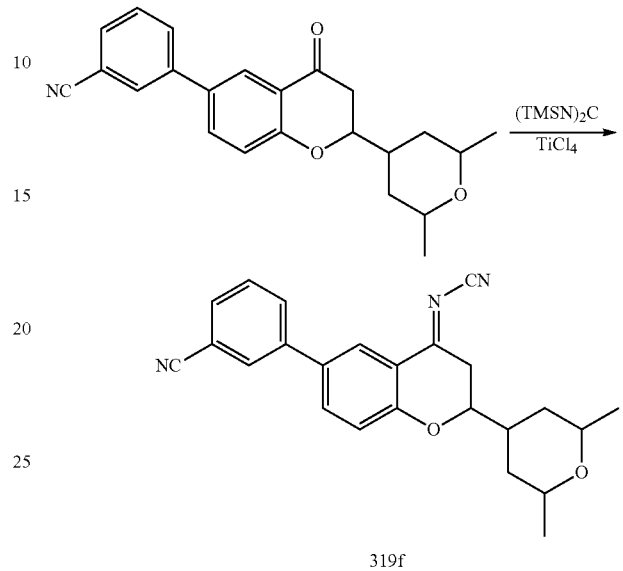

319f

Preparation of Compound 319f

A solution of 3-(2-(2,6-dimethyltetrahydro-2H-pyran-4-yl)-4-oxochroman-6-yl)benzonitrile (70 mg, 0.19 mmol) and TiCl$_4$ (258 mg, 1.36 mmol) in CH$_2$Cl$_2$ (7 mL) was heated at 50° C. for 5 minutes in a microwave. Then N,N'-methanediylidenebis(1,1,1-trimethylsilanamine) (0.17 mL, 0.78 mmol) was added and heated at 60° C. for 10 minutes in a microwave. CH$_2$Cl$_2$ was added, and the solution was extracted with dichloromethane. The CH$_2$Cl$_2$ was removed under reduced pressure to give the crude compound 319f (80 mg).

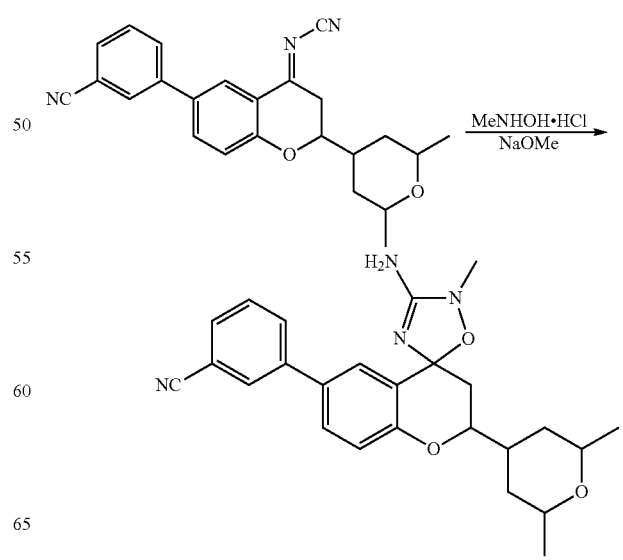

Preparation of Compound 319

To a solution of N-methylhydroxylamine hydrochloride (18.9 mg, 0.23 mmol) in anhydrous MeOH (2.65 mL) was added NaOMe (25% w % in MeOH, 44.2 uL) and (E)-N-(6-(3-cyanophenyl)-2-(2,6-dimethyltetrahydro-2H-pyran-4-yl)chroman-4-ylidene)cyanamide (80 mg, 0.23 mmol). After being stirred for 1 hour, the solvent was removed in vacuo. The residue was redissolved in $CH_2Cl_2$ (10 mL), and filtered, and the solvent was removed in vacuo to give the crude product, which was purified by preparative TLC to give compound 319 (6.53 mg, 7.3%). $^1$H-NMR (400 MHz $CD_3OD$): δ7.80-7.91 (m, 3H), 7.56-7.65 (m, 2H), 7.48-7.55 (m, 1H), 6.91-6.98 (m, 1H), 3.91-4.05 (m, 1H), 3.40-3.51 (m, 2H), 3.28-3.34 (m, 3H), 2.55-2.65 (m, 1H), 1.86-2.05 (m, 2H), 1.80-1.85 (m, 1H), 1.60-1.65 (m, 1H), 1.13 (d, 6H, J=6.0 Hz), 0.95-1.10 (m, 2H); ESI MS: m/z 433 [M+H]$^+$.

Example 165

Preparation of Compound 327

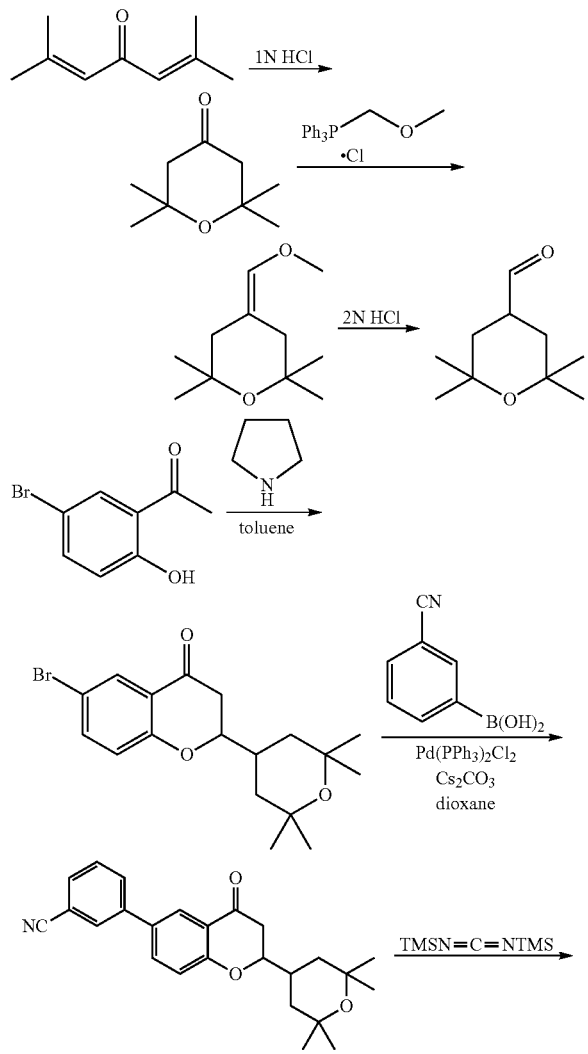

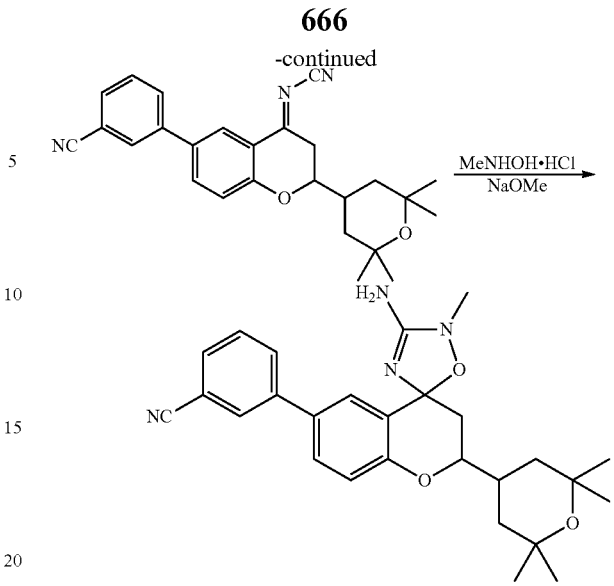

Experimental Data:

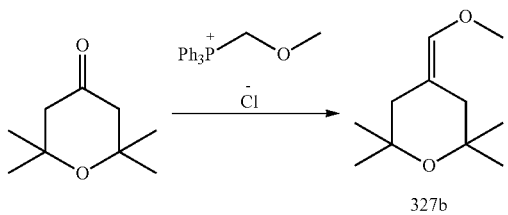

Preparation of Compound 327a 2,6-Dimethylhepta-2,5-dien-4-one (90 g) was dissolved in 1 N HCl (700 mL), and the mixture was stirred for seven days at 40° C. The mixture was extracted with ether, and the organic phase was concentrated. The residue was purified by distillation to afford the compound 327a (26 g, 20%). $^1$H-NMR (400 MHz $CDCl_3$): δ2.38 (s, 4H), 1.29 (s, 12H).

Preparation of Compound 327b

To a solution of (methoxymethyl)-triphenylphosphonium chloride (40 g, 115 mmol) in anhydrous THF (50 mL) was added n-BuLi (41 ml, 103 mmol) dropwise at −78° C. The mixture was warmed to room temperature and stirred for 1 hour at room temperature. 2,2,6,6-Tetramethyldihydro-2H-pyran-4(3H)-one (10 g, 64 mmol) was added, and the mixture was stirred for another 2 h. The reaction was quenched by sat. $NH_4Cl$ solution, and extracted with EtOAc. The combined organic phase was dried over anhydrous $Na_2SO_4$ and concentrated. The residue was purified by column chromatography to afford the compound 327b (5.3 g, 45%). ¹H-NMR (400 MHz CDCl₃): δ5.85 (s, 1H), 3.50 (s, 3H), 2.10 (s, 2H), 1.82 (s, 2H), 1.12 (s, 12H).

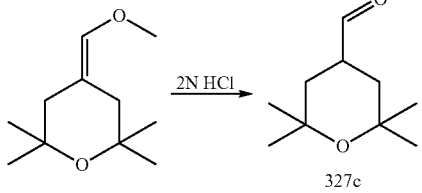

327c

Preparation of Compound 327c

To a solution of 4-(methoxymethylene)-2,2,6,6-tetramethyltetrahydro-2H-pyran (5.3 g) was added 2 N HCl (30 mL). The mixture was refluxed for 3 h, TLC showed that the reaction was completed. The mixture was extracted with ethyl acetate. The organic layer was washed with saturated sodium bicarbonate, dried over anhydrous sodium sulfate, and concentrated to get the product. ¹H-NMR (400 MHz CDCl₃): δ9.62 (s, 1H), 2.73 (m, 1H), 2.01 (m, 1H), 1.86 (m, 1H), 1.78 (m, 2H), 1.69 (m, 2H), 1.31 (m, 2H), 1.22 (m, 12H).

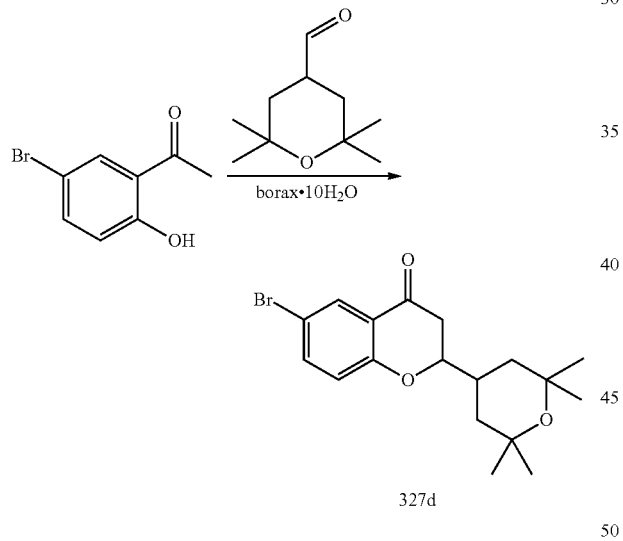

327d

Preparation of Compound 327d

A mixture of 1-(5-bromo-2-hydroxyphenyl)-ethanone (8.2 g, 37.9 mmol), 2,2,6,6-tetramethyltetrahydro-2H-pyran-4-carbaldehyde (3.2 g, 18.9 mmol) and borax (7.2 g) was dissolved in ethanol:water=3:5 (80 mL), and the mixture was refluxed overnight. The solvent was removed in vacuum, water and EtOAc were added. The combined organic phase was dried over Na₂SO₄ and concentrated. The residue was purified by silica gel column to afford the compound 327d (3.5 g, 51%). ¹H-NMR (400 MHz CDCl₃: δ7.93 (m, 1H), 7.50 (m, 1H), 6.83 (m, 1H), 4.11 (m, 1H), 2.62 (d, 2H), 2.19 (m, 1H), 1.78 (d, 1H), 1.52 (m, 1H), 1.20 (m, 14H), 1.12 (m, 1H).

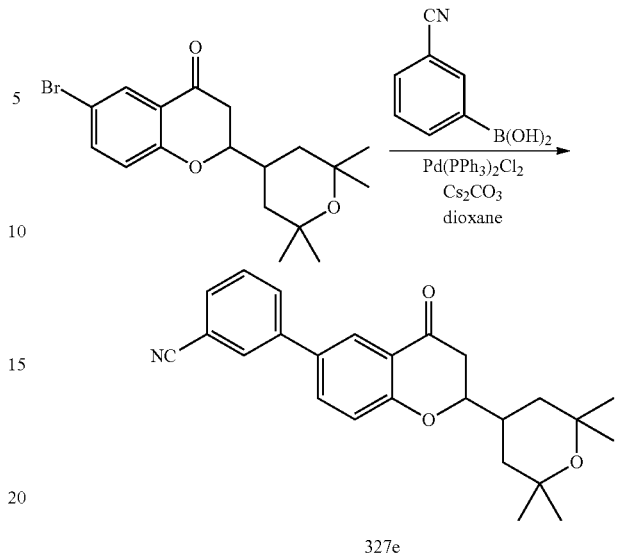

327e

Preparation of Compound 327e

A mixture of 6-bromo-2-(2,2,6,6-tetramethyltetrahydro-2H-pyran-4-yl)chroman-4-one (150 mg), 3-cyanophenylboronic acid (90 mg), Cs₂CO₃ (2 M, 1 mL) and Pd(PPh₃)₂Cl₂ (30 mg) in 1,4-dioxane (5 mL) under N₂ was stirred in microwave at 100° C. for 5 minutes. The reaction mixture was concentrated in vacuo to give the residue, which was purified by preparative TLC and HPLC to give the compound 327e (80 mg, 51%).

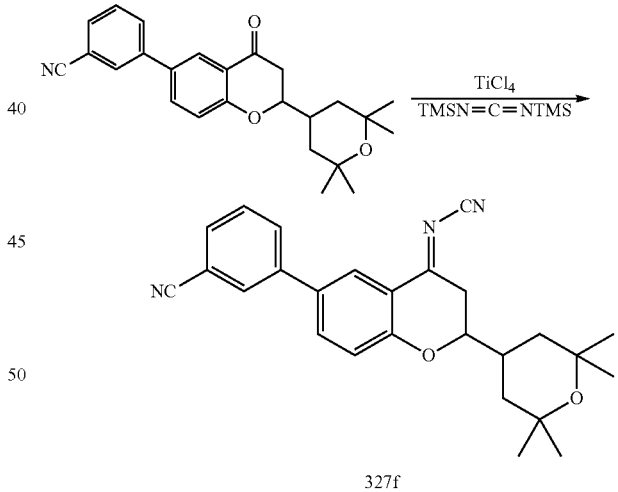

327f

Preparation of Compound 327f

To a solution of 3-(4-oxo-2-(2,2,6,6-tetramethyltetrahydro-2H-pyran-4-yl) chroman-6-yl)benzonitrile (80 mg, 0.207 mmol) in dichloromethane (5 mL) was added titanium (IV) chloride (0.2 mL, 1 M solution in dichloromethane) dropwise, and the mixture was stirred in microwave for 5 minutes at 50° C. This mixture was added compound N,N'-methanediylidenebis(1,1,1-trimethylsilanamine) (77 mg, 0.415 mmol) dropwise. The resulting mixture was stirred in microwave for 10 minutes at 60° C. The reaction mixture was poured into ice-water, and extracted with dichloromethane. The organic phase was dried over anhydrous sodium sulfate, and concentrated to give the product.

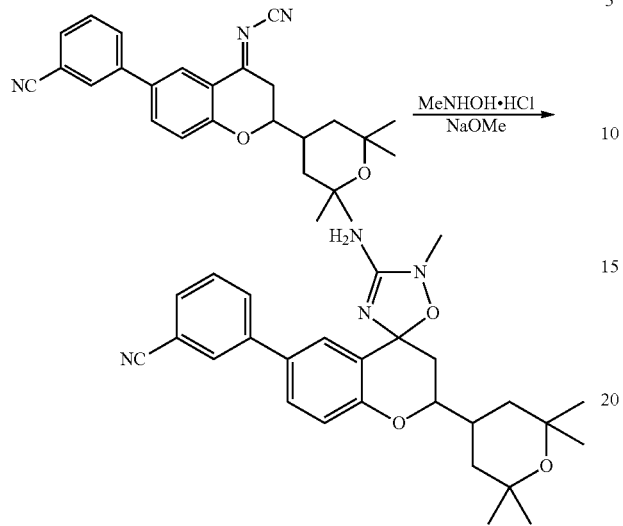

Preparation of Compound 327

To a solution of N-methylhydroxylamine hydrochloride (16 mg, 0.194 mmol) in anhydrous methanol (1 mL) was added sodium methanolate (25% in methanol, 94 mg, 0.174 mmol), and ((E)-N-(6'-(3-cyanophenyl)-5,7,8,9-tetrahydrospiro[benzo[7]-annulene-6,2'-chroman]-4'-ylidene)-cyanamide (80 mg, 0.194 mmol). After being stirred for 10 minutes, the solvent was removed in vacuum. The residue was redissolved in dichloromethanae. The mixture was filtrated, concentrated, and purified by preparative TLC and HPLC to give compound 327 (3.94 mg, 4%). $^1$H-NMR (400 MHz CD$_3$OD): δ8.01 (m, 3H), 7.75 (m, 2H), 7.66 (m, 1H), 7.09 (m, 1H), 4.13 (m, 1H), 3.42 (m, 3H), 2.56 (m, 1H), 2.37 (m, 1H), 2.07 (m, 1H), 1.94 (m, 1H), 1.70 (m, 1H), 1.40 (m, 1H), 1.23 (m, 12H); ESI MS: m/z 461 [M+H]$^+$.

Example 166

Preparation of Compound 402

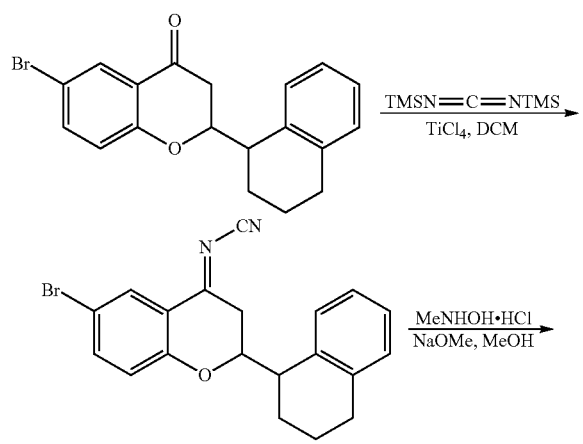

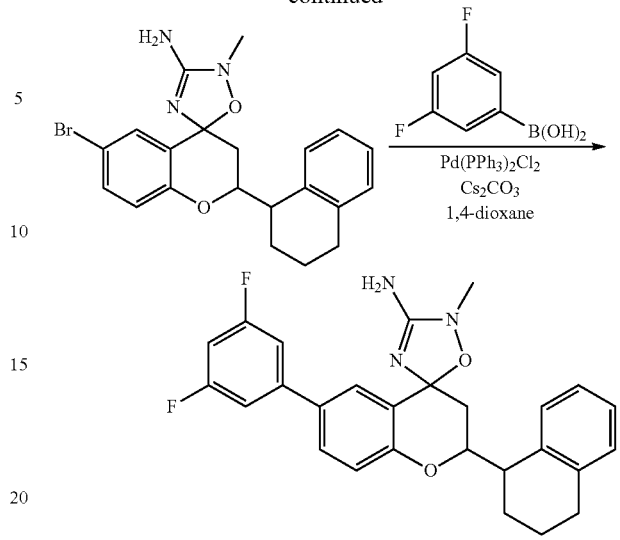

Experimental Data:

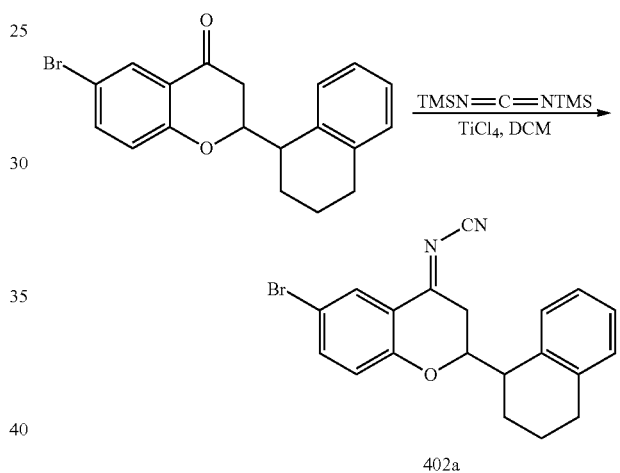

Preparation of Compound 402a

To a solution of 6-bromo-3',4'-dihydro-2'H-spiro[chroman-2,1'-naphthalen]-4-one (50 mg, 0.15 mmol) in DCM (10 mL) was added TiCl$_4$ (111 mg, 0.58 mmol) dropwise. After the mixture was stirred at 50° C. under Ar$_2$ in microwave for 5 minutes, N,N'-methanediylidenebis(1,1,1-trimethylsilanamine) (108 mg, 0.58 mmol) was added dropwise. The mixture was stirred at 60° C. under Ar$_2$ in microwave for 10 minutes, and poured into ice-water (50 mL). The aqueous layer was extracted with CH$_2$Cl$_2$. The organic layer was dried and concentrated to give the crude compound 402a (50 mg, crude).

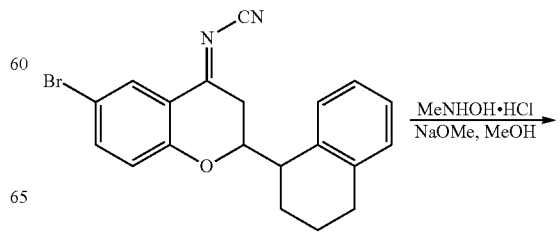

3H), 3.02 (m, 1H), 2.87 (m, 2H), 2.53 (m, 1H), 2.45 (m, 1H), 2.03 (m, 1H), 1.86 (m, 2H); ESI MS: m/z 448 [M+H]$^+$.

Example 167

Preparation of Compound 324

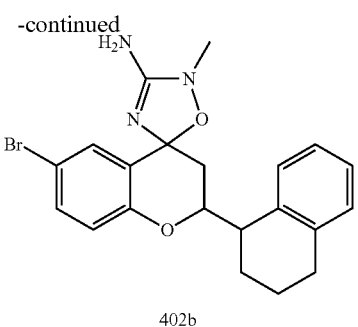

402b

Preparation of Compound 402b

To a solution of N-methyl-hydroxylamine hydrochloride (11.3 mg, 0.14 mmol) in MeOH (3 mL) was added MeONa (0.029 mL, 25% in MeOH) and (E)-N-(6-bromo-3',4'-dihydro-2'H-spiro[chroman-2,1'-naphthalene]-4-ylidene)cyanamide (50 mg, 0.14 mmol). After being stirred for 10 minutes, the solvent was removed in vacuo, and the residue was purified by preparative TLC to give the compound 402b (20 mg, 35%).

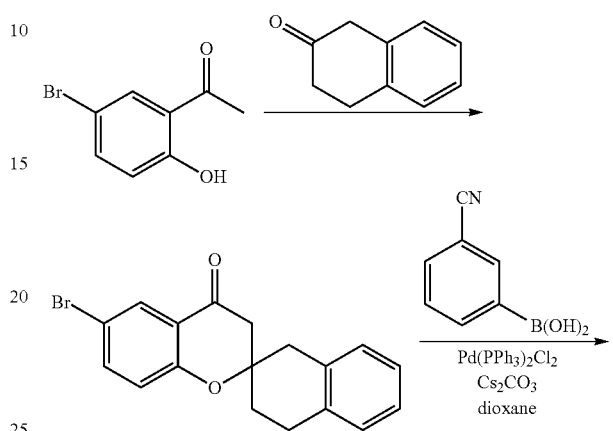

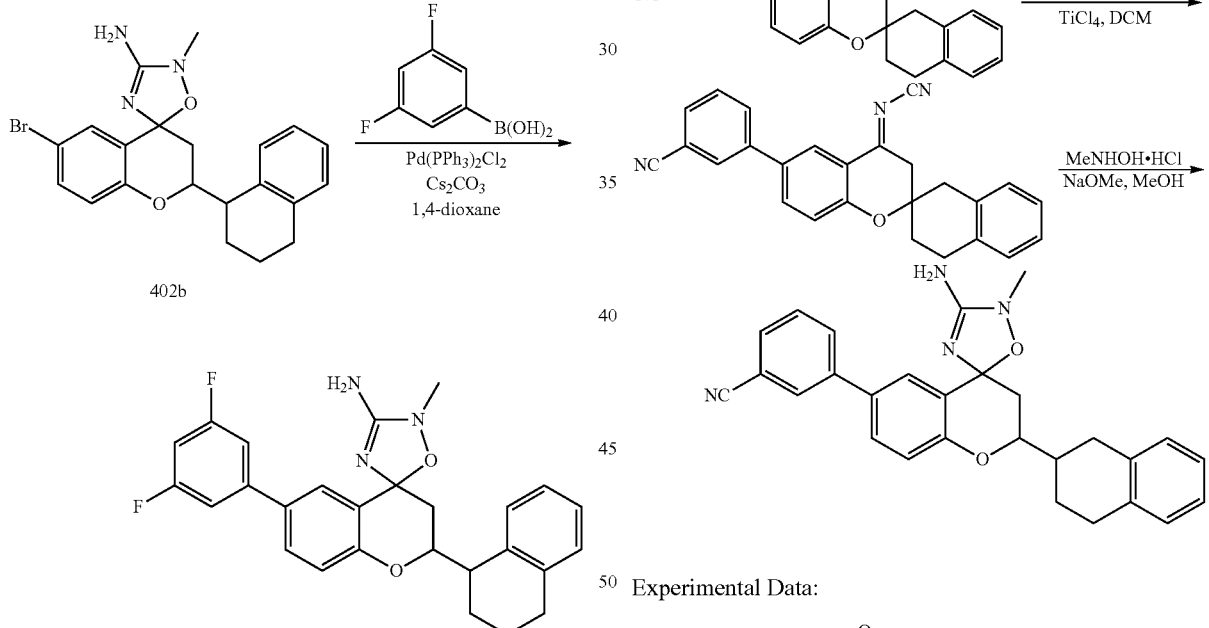

Preparation of Compound 402

Pd(PPh$_3$)$_2$Cl$_2$ (5 mg, 0.01 mmol) in a 10 mL of flask under Ar$_2$ was treated sequentially with compound 402b (20 mg, 0.058 mmol) in [1,4]dioxane (2.0 mL), Cs$_2$CO$_3$ (2 N, 1 mL) and 3,5-difluorophenylboronic acid (15.8 mg, 0.1 mmol). The mixture was heated under 100° C. under Ar$_2$ in microwave for 5 minutes. The reaction mixture was concentrated in vacuo to give the residue, which was purified by preparative TLC and HPLC to give compound 402 (1.44 mg, 7%). $^1$H-NMR (400 MHz CD$_3$OD): δ7.98 (s, 1H), 7.72 (d, 1H), 7.54 (m, 1H), 7.28 (m, 4H), 7.17 (m, 1H), 7.01 (d, 1H), 6.90 (m, 1H), 3.38 (s, Experimental Data:

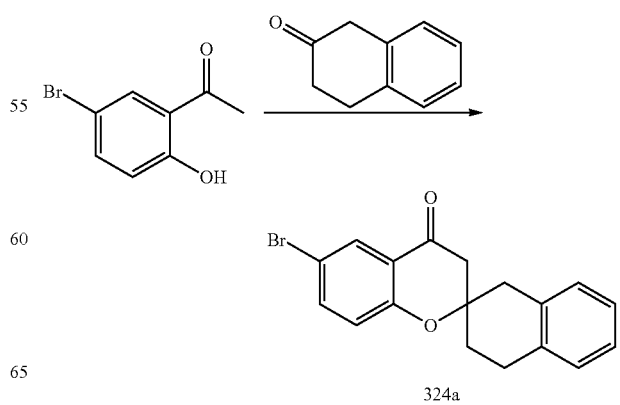

324a

Preparation of Compound 324a 1-(5-Bromo-2-hydroxyphenyl)-ethanone (7 g, 34 mmol) and 3,4-dihydronaphthalen-2(1H)-one (5 g, 34 mmol) were dissolved in toluene (150 mL), and pymolidine (4.9 g, 69 mmol) was added. The reaction mixture was refluxed overnight, concentrated, washed with water, and extracted with EtOAc. The organic phase was dried and concentrated to give the crude product, which was purified by a silica gel column to afford the compound 324a (500 mg, 5%). $^1$H-NMR (400 MHz CDCl$_3$): δ7.92 (s, 1H), 7.46 (d, 1H), 7.10 (m, 3H), 6.97 (d, 1H), 6.75 (d, 1H), 3.12 (d, 1H), 2.92 (d, 2H), 2.81 (d, 1H), 2.72 (d, 2H), 2.20 (m, 1H), 1.85 (m, 1H).

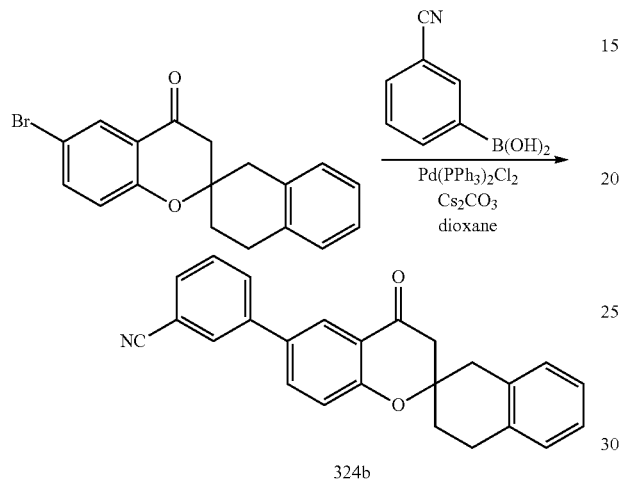

324b

Preparation of Compound 324b

Pd(PPh$_3$)$_2$Cl$_2$ (10 mg) under Ar$_2$ was treated sequentially with the 6-bromo-3',4'-dihydro-1'H-spiro[chroman-2,2'-naphthalen]-1'-one (150 mg, 0.44 mmol) in [1,4]dioxane (4 mL), Cs$_2$CO$_3$ (2 N, 1 mL) and 3-cyanophenylboronic acid (119 mg, 0.66 mmol). The mixture was heated at 120° C. in microwave for 20 minutes. The reaction mixture was concentrated in vacuo to give the residue, which was purified preparative TLC to give the compound 324b (60 mg, 38%). $^1$H-NMR (400 MHz CDCl$_3$): δ8.15 (s, 1H), 7.45-7.80 (m, 6H), 6.95-7.19 (m, 4H), 3.19 (d, 2H), 2.92 (m, 3H), 2.75 (m, 2H), 2.28 (m, 1H), 1.89 (m, 1H).

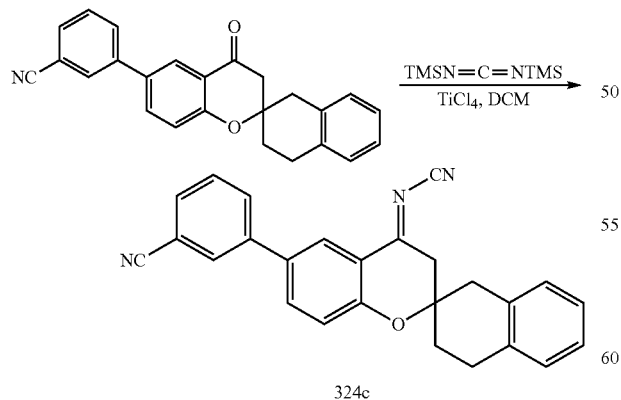

324c

Preparation of Compound 324c

To a solution of 3-(4-oxo-3',4'-dihydro-1'H-spiro[chroman-2,2'-naphthalene]-6-yl)benzonitrile (80 mg, 0.22 mmol) in dried CH$_2$Cl$_2$ (5 mL) was added TiCl$_4$ (1 M solution in DCM, 0.88 mmol) dropwise within 15 minutes, and the mixture was stirred for 1 h. bis-Trimehtlysilylcarbodiimide (164 mg, 0.88 mmol) was added dropwise, and the resulting mixture was stirred overnight. The reaction mixture was poured into ice-water, extracted with CH$_2$Cl$_2$, washed with brine, dried over Na$_2$SO$_4$, filtered, and concentrated to give compound 324c (70 mg, crude), which was used for the next step without further purification.

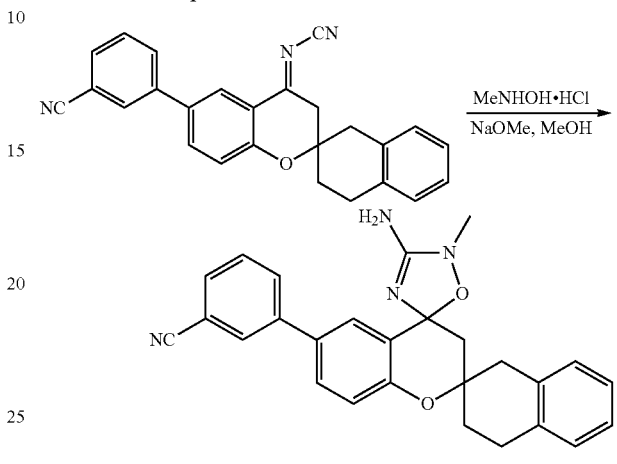

Preparation of Compound 324

To a solution of MeNHOH.HCl (15 mg, 0.18 mmol) in anhydrous MeOH (3 mL) was added NaOMe (25 wt % in MeOH, 35 mg, 0.0.16 mmol), followed by (E)-N-(6-(3-cyanophenyl)-3',4'-dihydro-1'H-spiro[chroman-2,2'-naphthalene]-4-ylidene)cyanamide (70 mg, 0.18 mmol). After being stirred for 5 minutes, the solvent was removed in vacuum. The residue was re-dissolved in CH$_2$Cl$_2$ and filtered. The filtrate was concentrated to give the residue, which was purified by preparative TLC and preparative HPLC to afford compound 324 (10.15 mg, 13%). $^1$H NMR (400 MHz CD$_3$OD): δ7.89 (m, 3H), 7.58 (m, 3H), 7.04 (m, 4H), 6.88 (m, 1H), 3.29 (d, 3H), 3.13 (m, 3H), 2.73 (m, 2H), 2.22 (m, 2H), 1.96 (m, 1H); ESI MS: m/z 437 [M+H]$^+$.

Example 168

Preparation of Compound 315

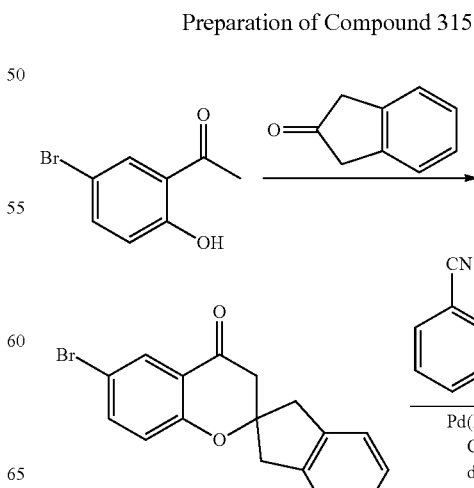

-continued

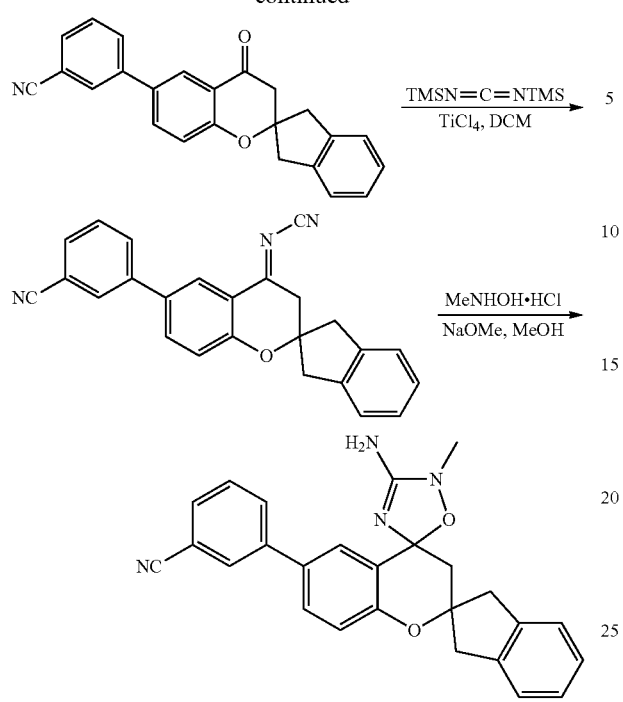

Experimental Data:

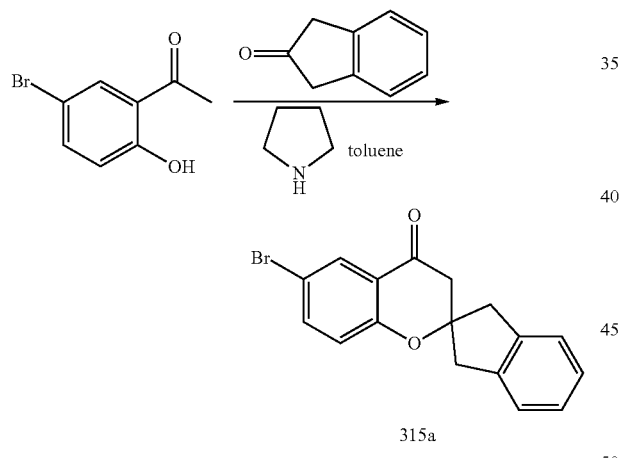

Preparation of Compound 315a

A mixture of compound 1-(5-bromo-2-hydroxyphenyl)-ethanone (2 g, 9.3 mmol), 1H-inden-2(3H)-one (2.46 g, 18.6 mmol) and pyrrolidine (0.99 g, 1.2 mL) in toluene (20 mL) was refluxed overnight, concentrated, washed with 1 M HCl, extracted with dichloromethane, dried over anhydrous sodium sulfate, and concentrated to afford 2.3 g of the crude product. 500 mg the crude product was purified by preparative TLC to afford the compound 315a (100 mg). $^1$H-NMR (400 MHz CD$_3$OD): δ7.90 (s, 1H), 7.57 (d, 1H), 7.16 (m, 4H), 6.83 (d, 1H), 3.31 (s, 1H), 3.29 (m, 2H), 3.17 (d, 2H), 3.03 (s, 2H).

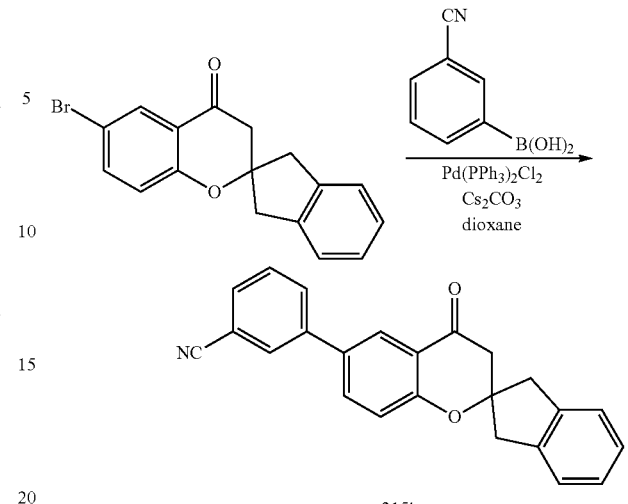

Preparation of Compound 315b

A mixture of 6-bromo-1',3'-dihydrospiro[chroman-2,2'-inden]-4-one (100 mg, 0.30 mmol), 3-cyanophenylboronic acid (83 mg, 0.46 mmol), Cs$_2$CO$_3$ (2 M, 0.5 mL) and Pd(PPh$_3$)$_2$Cl$_2$ (5 mg) in 1,4-dioxane (3 mL) under N$_2$ was stirred in microwave at 100° C. for 20 minutes. The reaction mixture was concentrated in vacuo to give the residue, which was purified preparative TLC to give compound 315b (40 mg, 37%). $^1$H-NMR (400 MHz CDCl$_3$): δ8.04 (s, 1H), 7.77 (s, 1H), 7.74 (d, 1H), 7.42-7.63 (m, 4H), 7.19 (m, 3H), 6.81 (d, 1H), 3.37 (d, 2H), 3.12 (d, 2H), 2.97 (s, 2H).

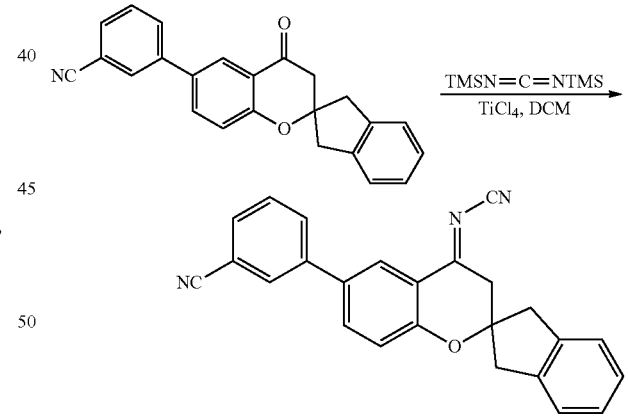

Preparation of Compound 315c

To a solution of 3-(4-oxo-1',3'-dihydrospiro[chroman-2,2'-indene]-6-yl)benzonitrile (40 mg, 0.11 mmol) in dichloromethane (2 mL) was added titanium (IV) chloride (1 M solution in dichloromethane, 43 mg, 0.23 mmol) dropwise, and the mixture was stirred in microwave for 20 minutes at 50° C. To this mixture was added N,N-methanediylidenebis (1,1,1-trimethylsilanamine) (64 mg, 0.34 mmol) dropwise. The resulting mixture was stirred in microwave for 10 minutes at 60° C. The reaction mixture was poured into ice-water, extracted with dichloromethane. The organic phase was dried over anhydrous sodium sulfate, and concentrated to give the compound 315c, which was used directly for the next step.

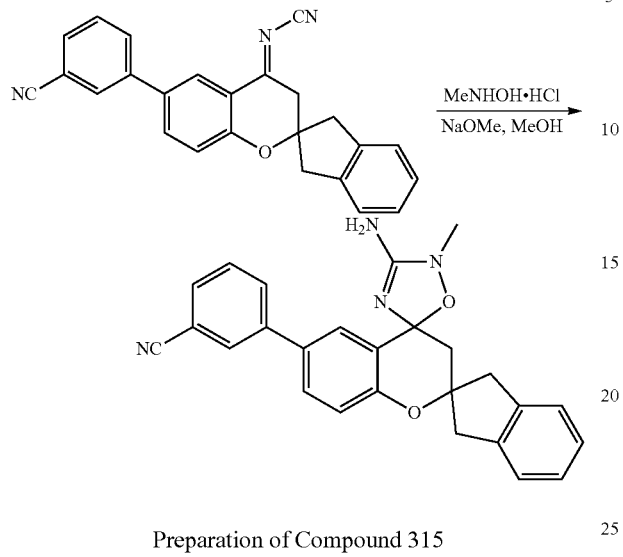

Preparation of Compound 315

To a solution of N-methylhydroxylamine hydrochloride (14 mg, 0.16 mmol) in anhydrous methanol (2 ml) was added sodium methanolate (25% in methanol, 0.026 mL, 0.12 mmol), and (E)-N-(6-(3-cyanophenyl)-1',3'-dihydrospiro[chroman-2,2'-indene]-4-ylidene)cyanamide (50 mg, 0.13 mmol). After being stirred 10 min, the solvent was removed in vacuum, and the residue was redissolved in dichloromethanae (10 mL), after filtration and concentration, the residue was purified by preparative TLC to give compound 315. $^1$H-NMR (400 MHz CDCl$_3$): δ7.76 (s, 1H), 7.72 (s, 1H), 7.60 (s, 1H), 7.42 (s, 4H), 7.38 (m, 3H), 7.18 (m, 4H), 6.76 (d, 1H), 3.15-3.36 (m, 6H), 3.12 (s, 3H); ESI MS: m/z 423 [M+H]$^+$.

Example 169

Preparation of Compound 273

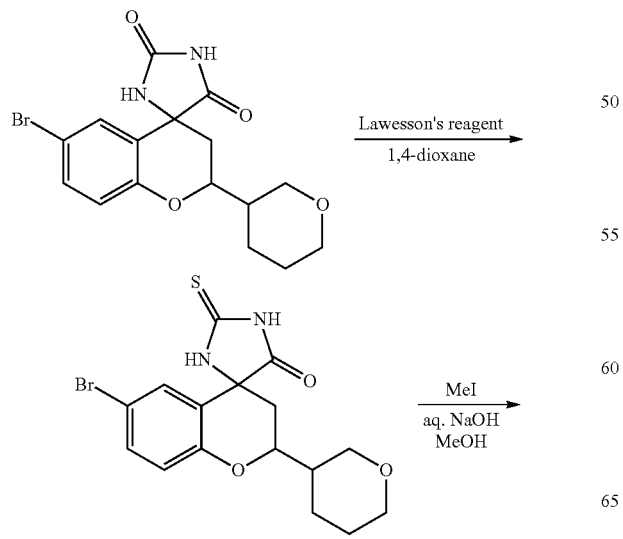

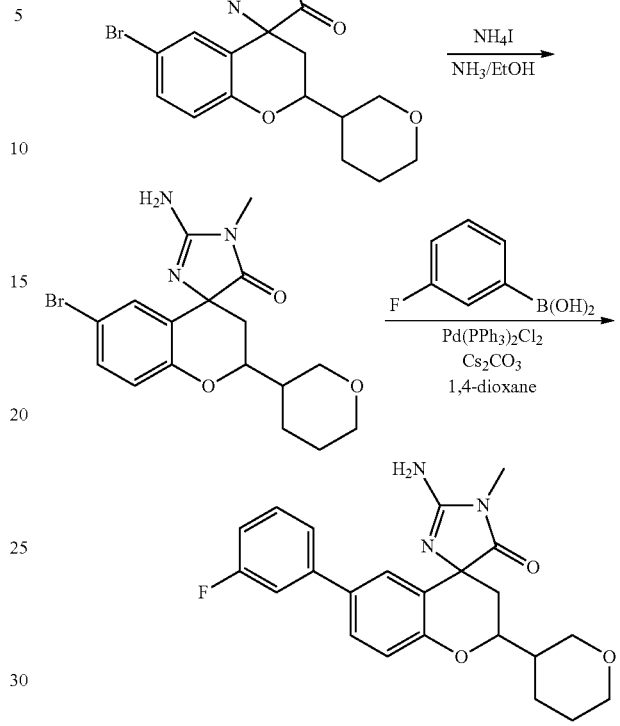

Experimental Data:

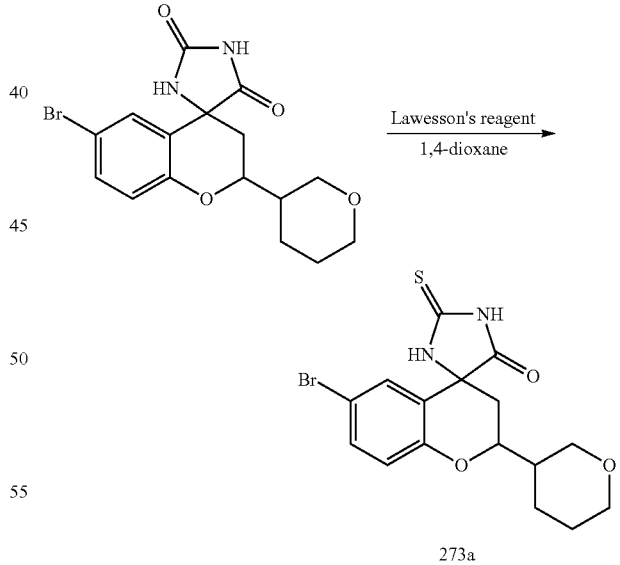

Preparation of Compound 273a

A suspension of 6-bromo-2-(tetrahydro-2H-pyran-3-yl) spiro[chroman-4,4'-imidazolidine]-2',5'-dione (320 mg, 0.84 mmol) and Lawesson's Reagent (340.2 mg, 0.84 mmol) in dry 1,4-dioxane (4 mL) was heated at 120° C. for 30 minutes in microwave. The mixture was concentrated in vacuo and the residue was purified by preparative TLC to give the compound 273a (300 mg, 90%).

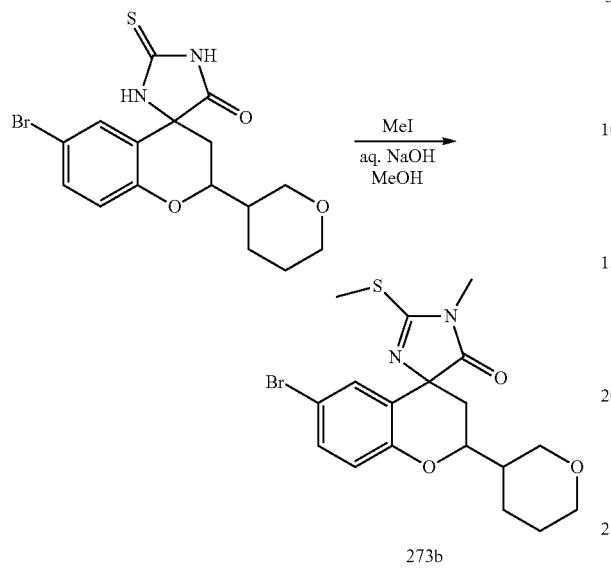

273b

Preparation of Compound 273b

To a solution of 6-bromo-2-(tetrahydro-2H-pyran-3-yl)-2'-thioxospiro[chroman-4,4'-imidazolidin]-5'-one (120 mg, 0.3 mmol) in MeOH (16 mL) was added NaOH (0.6 N, 1.2 mL) and MeI (0.3 mL). The reaction mixture was heated at 60° C. for 8 minutes in microwave. The mixture was concentrated in vacuo to give the residue, which was purified by preparative TLC to give the compound 273b (80 mg, 60%).

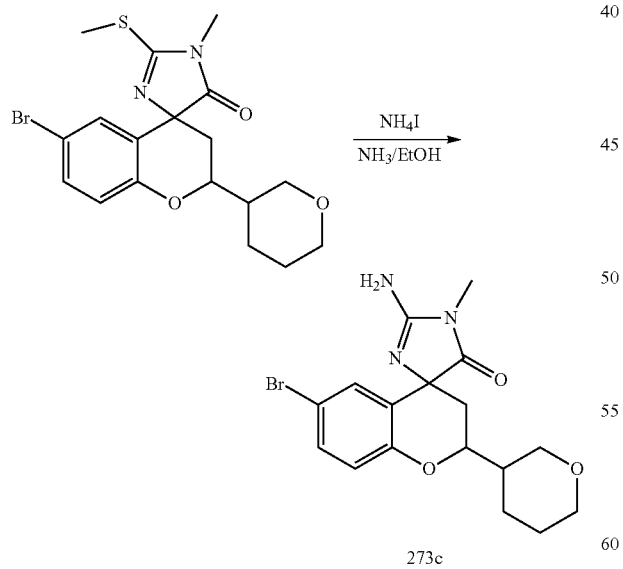

273c

Preparation of Compound 273c

A solution of 6-bromo-1'-methyl-2'-(methylthio)-2-(tetrahydro-2H-pyran-3-yl)-spiro[chroman-4,4'-imidazol]-5'(1'H)-one (75 mg, 0.177 mmol), NH$_4$I (200 mg) in NH$_3$/EtOH (2 mL, 8 N) was heated at 120° C. in a tube in a microwave reactor for 2 hours. After cooling, the mixture was concentrated in vacuum to afford the compound 273c (70 mg, 100%).

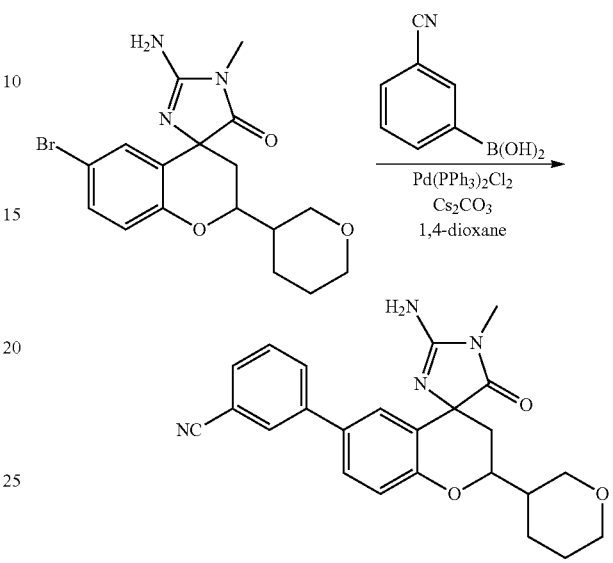

Preparation of Compound 273

Pd(PPh$_3$)$_2$Cl$_2$ (10 mg) in a 10 mL of tube under Ar$_2$ was treated sequentially with a solution of 2'-amino-6-bromo-1'-methyl-2-(tetrahydro-2H-pyran-3-yl)spiro[chroman-4,4'-imidazol]-5'(1'H)-one (35 mg, 0.089 mmol) in 1,4-dioxane (2 mL), Cs$_2$CO$_3$ solution (2 N, 0.4 mL), and 3-cyanophenylboronic acid (25 mg, 0.18 mmol). This mixture was heated in microwave at 12° C. for 30 min, and concentrated in vacuo to give the residue, which was purified by preparative TLC and preparative HPLC to give compound 273 (4.9 mg, 10%). $^1$H-NMR (400 MHz CD$_3$OD): δ7.58 (m, 1H), 7.41 (m, 2H), 7.29 (m, 2H), 7.01 (m, 2H), 4.68 (dd, 0.7H), 4.21 (m, 0.6H), 3.88 (dd, 1.6H), 3.49 (m, 2H), 3.31 (m, 3H), 3.10 (m, 2H), 2.41 (m, 1H), 2.24 (m, 1H), 1.97 (m, 2H), 1.68 (m, 2H); ESI MS: m/z 410 [M+H]$^+$.

Example 170

Preparation of Compound 267

Experimental Data:

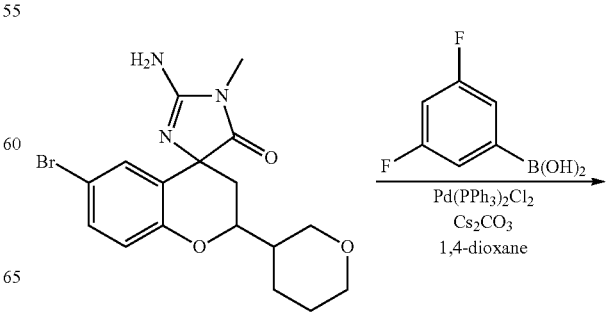

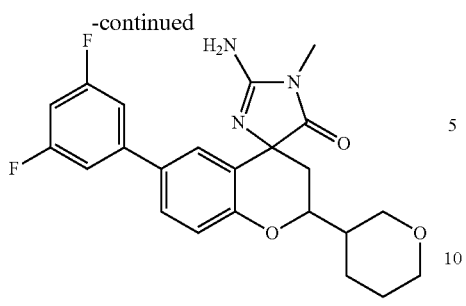

Preparation of Compound 267

By using the same synthetic strategy for compound 273 described in Example 169, compound 267 (2.74 mg, 5%) was obtained. $^1$H-NMR (400 MHz CD$_3$OD): δ7.94 (d, 1H), 7.86 (m, 1H), 7.61 (m, 1H), 7.50 (m, 1H), 7.21 (m, 2H), 7.05 (m, H), 6.89 (m, 1H), 4.70&4.40 (m, 1H), 3.88 (dd, 2H), 3.49 (m, 2H), 3.24 (s, 3H), 3.08 (t, 2H), 2.48 (m, 1H), 2.18 (t, 1H), 1.97 (m, 2H), 1.68 (m, 2H); ESI MS: m/z 428 [M+H]$^+$.

Example 171

Preparation of Compounds 230 and 453

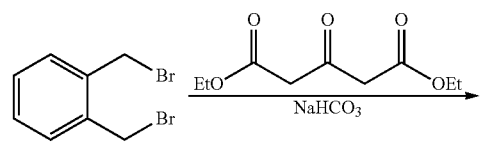

By using the same strategy for compound 273 described in Example 169, compound 230 (2.00 mg, 10%) and compound 453 (1.81 mg, 9%) were obtained.

compound 230: $^1$H-NMR (400 MHz CD$_3$OD): δ7.89 (m, 2H), 7.53-7.68 (m, 3H), 7.38-7.50 (m, 1H), 7.06 (d, 1H), 4.51 (m, 1H), 3.77 (m, 2H), 3.25-3.22 (m, 3H), 2.44 (m, 1H), 2.18 (m, 2H), 1.90 (m, 1H), 1.63 (m, 1H), 1.33 (m, 2H), 1.24-1.28 (m, 6H); ESI MS: m/z 445 [M+H]$^+$ compound 453: $^1$H-NMR (400 MHz CD$_3$OD): δ7.86-7.94 (m, 2H), 7.48-7.67 (m, 6H), 7.08 (d, 1H), 4.58 (m, 1H), 3.76 (m, 2H), 3.06 (m, 3H), 2.46 (m, 1H), 2.13 (m, 2H), 1.89 (m, 1H), 1.61 (m, 1H), 1.45 (m, 2H), 1.27-1.39 (m, 6H); ESI MS: m/z 889 [2M+H]$^+$.

Example 172

Preparation of Compound 451

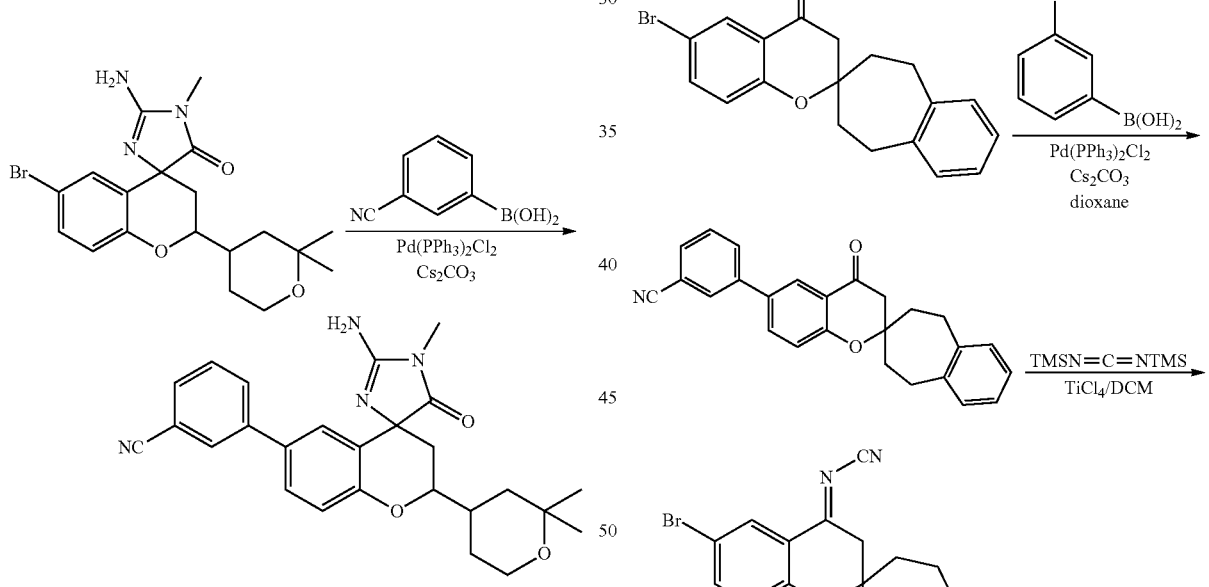

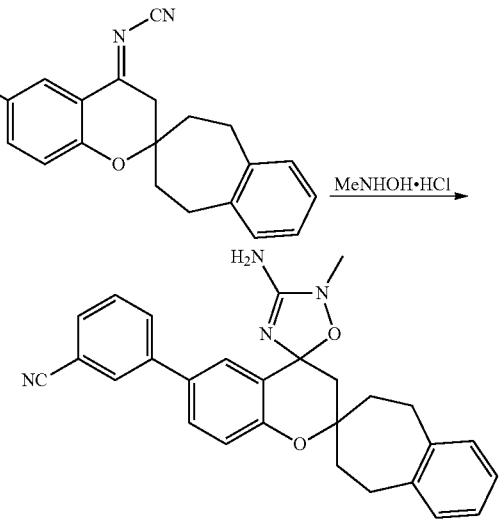

Experimental Data:

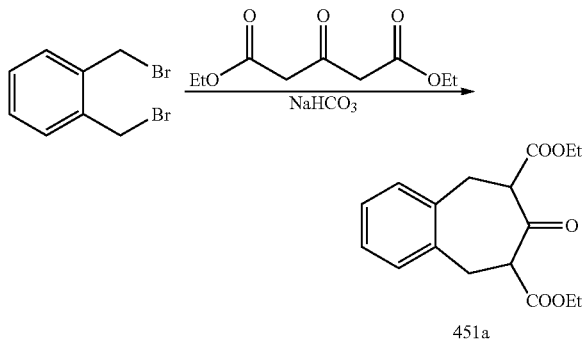

Preparation of Compound 451a

To a vigorously stirred mixture of Bu$_4$NI (33.2 g, 90 mmol) in a mixture of 5% aqueous NaHCO$_3$ solution (1200 mL) and CH$_2$Cl$_2$ (280 mL) was added dropwise at room temperature a solution of 1,2-bis(bromomethyl)benzene (39.3 g, 15 mmol) and diethyl 3-oxopentanedioate (39.4 g, 1.3 mmol) in CH$_2$Cl$_2$ (280 mL). After 21 h, the reaction mixture was quenched with aqueous NH$_4$Cl solution, and the organic layer was separated, dried, and evaporated in vacuo, purified by silica gel column to give compound 451a (40 g, crude).

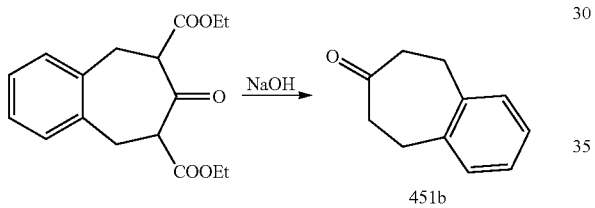

Preparation of Compound 451b

A mixture of 7-oxo-6,7,8,9-tetrahydro-5H-benzo[7]annulene-6,8-dicarboxylate (27.8 g, 91.0 mmol), NaOH (8%, 480 mL) in ethanol (730 mL) was refluxed for 2.5 h, the mixture was concentrated to removed to remove most ethanol, and then extracted with CH$_2$Cl$_2$. The combined organic layer was washed with H$_2$O and brine, dried over Na$_2$SO$_4$, filtered, and concentrated to give the compound 451b (10 g, 69%).

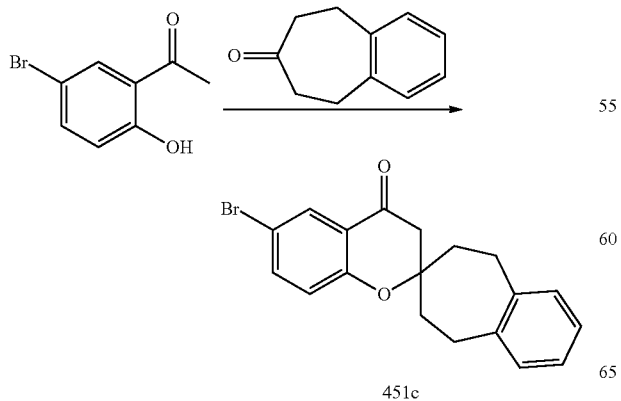

Preparation of Compound 451c 1-(5-Bromo-2-hydroxyphenyl)-ethanone (2.14 g, 10 mmol), pyrroidine (1.065 g, 15 mmol) and 3-(4-oxo-3',4'-dihydro-2'H-spiro[chroman-2,1'-naphthalene]-6-yl)benzonitrile (2.4 g, 15 mmol) was dissolved in CH$_3$OH (20 mL), the mixture was refluxed for 24 hour. The mixture was poured into ice-water (20 mL), extracted with EA for (3×15 mL), washed with brine (20 mL), dried over Na$_2$SO$_4$, and concentrated in vacuo to give the crude product, which was purified by silica gel column to give the compound 451c (1.21 g, 34%). $^1$H-NMR (400 MHz CDCl$_3$): δ7.93 (s, 1H), 7.51 (d, 1H), 7.15 (m, 1H), 7.05 (m, 4H), 6.89 (d, 1H), 3.20 (m, 2H), 2.63 (m, 2H), 2.43 (m, 2H), 2.26 (m, 2H), 1.55 (m, 2H).

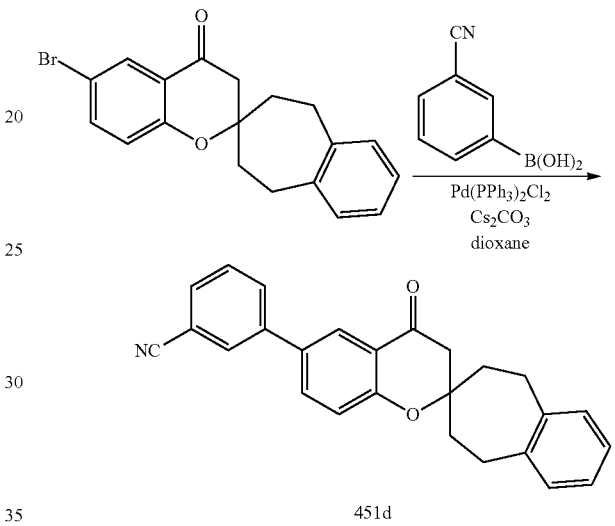

Preparation of Compound 451d

Pd(PPh$_3$)$_2$Cl$_2$ (5 mg, 0.01 mmol) in a 10 mL of flask under Ar$_2$ was treated sequentially with 6'-bromo-5,6,8,9-tetrahydrospiro[benzo[7]annulene-7,2'-chroman]-4'-one (150 mg, 0.42 mmol) in [1,4]dioxane (2.0 mL), Cs$_2$CO$_3$ solution (2 N, 1 mL), and 3-cyanophenylboronic acid (124 mg, 0.84 mmol). The mixture was heated at 100° C. under Ar$_2$ in microwave for 5 minutes. The reaction mixture was concentrated, and purified by preparative TLC to give the compound 451d (40 mg, 25%).

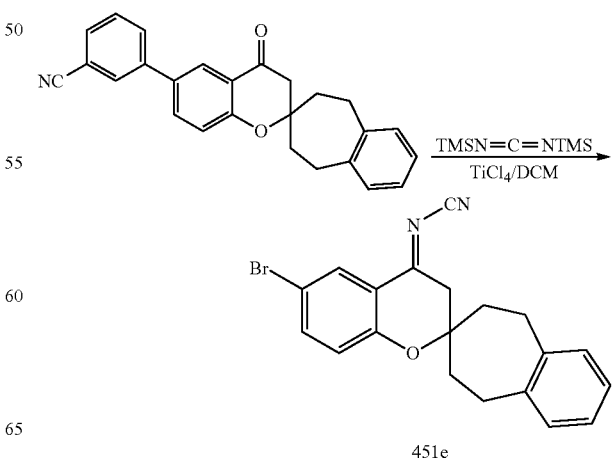

Preparation of Compound 451e

To a solution of 3-(4'-oxo-5,6,8,9-tetrahydrospiro[benzo[7]annulene-7,2'-chroman]-6'-yl)benzonitrile (40 mg, 0.1 mmol) in DCM (6 mL) was added TiCl$_4$ (37.6 mg, 0.2 mmol) dropwise, and the mixture was stirred at 50° C. under Ar$_2$ in microwave for 5 minutes. N,N'-Methanediylidenebis(1,1,1-trimethylsilanamine) (37 mg, 0.2 mmol) was added dropwise, the mixture was stirred at 60° C. under Ar$_2$ in microwave for 10 minutes and poured into ice-water (50 mL). The aqueous layer was extracted with CH$_2$Cl$_2$, the organic layer was dried and concentrated to give the crude compound 451e (30 mg, 71%).

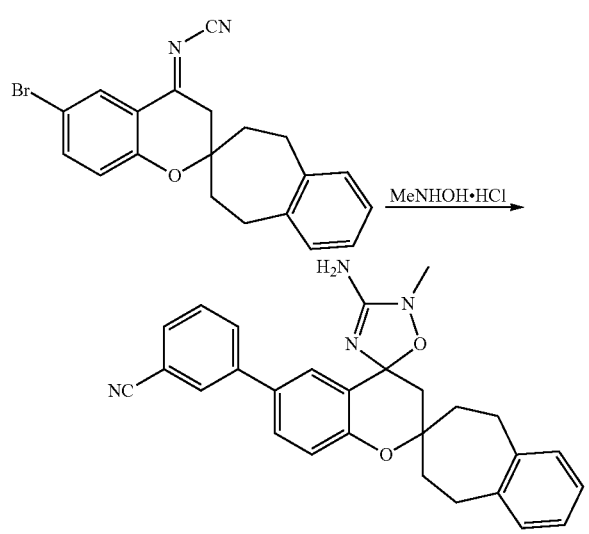

Preparation of Compound 451

To a solution of N-methyl-hydroxylamine hydrochloride (6.2 mg, 0.07 mmol) in MeOH (2 mL) was added MeONa (0.014 mL, 25% in MeOH), and (E)-N-(6-(3-cyanophenyl)-3',4'-dihydro-2'H-spiro[chroman-2,1'-naphthalene]-4-ylidene)cyanamide (30 mg, 0.07 mmol). After being stirred for 20 minutes, the solvent was removed in vacuo, and the residue was purified by preparative TLC to give compound 451 (6.5 mg, 13%). $^1$H-NMR (400 MHz CDCl$_3$): δ7.88 (m, 3H), 7.53-7.69 (m, 3H), 7.00 (m, 5H), 3.28 (s, 3H), 2.80-3.07 (m, 2H), 2.24-2.63 (m, 4H), 2.02 (m, 2H), 1.53-1.84 (m, 2H); ESI MS: m/z 451 [M+H]$^+$.

Example 173

Preparation of Compound 217

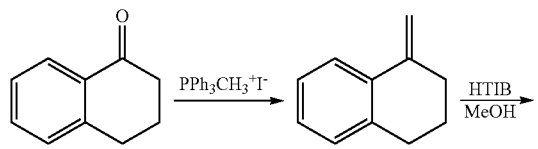

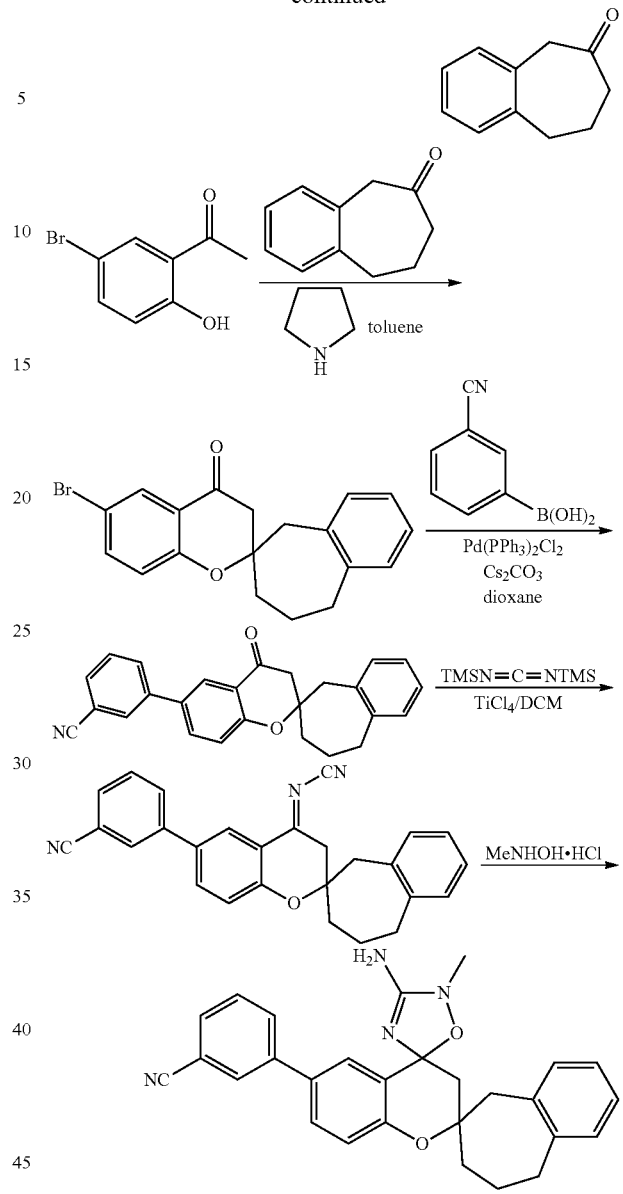

Experimental Data:

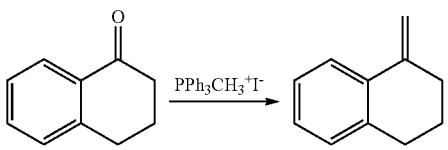

Preparation of Compound 217a

A solution of n-BuLi (88 mL, 2.5 M) was added to a mixture of PPh$_3$CH$_3$$^+$Me$^-$ (100 g, 246 mmol) in THF (600 mL) at −10° C. After the mixture was stirred for 1 h at the this temperature, 3,4-dihydronaphthalen-1(2H)-one (20 g, 137 mmol) was added. The mixture was warmed to room temperature and stirred for 3 hours, concentrated, and purified by column chromatography to afford the compound 217a (9.6 g, 49%). ¹H-NMR (400 MHz CDCl₃): δ7.64 (d, 1H), 7.17 (m, 2H), 7.15 (m, 1H), 5.48 (s, 1H), 4.95 (s, 1H), 2.83 (t, 2H), 2.53 (t, 2H), 1.91 (m, 2H).

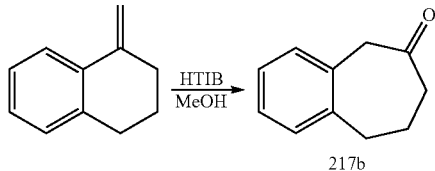

Preparation of Compound 217b

Crystalline HTIB (18.9 g, 48.1 mmol) was added to a stirred solution of 1-methylene-1,2,3,4-tetrahydronaphthalene (6.6 g, 45.8 mmol) in 95% methanol (200 mL). The mixture was stirred for 20 minutes at room temperature, and the solvent was removed in vacuo. The mixture was partitioned between dichloromethane and water, and the organic phase was concentrated in vacuo, the residue was purified by a silica gel column to afford the compound 217b (3.9 g, 53%). ¹H-NMR (400 MHz CDCl₃): δ7.19 (m, 4H), 3.72 (s, 2H), 2.94 (t, 2H), 2.53 (t, 2H), 1.99 (m, 2H).

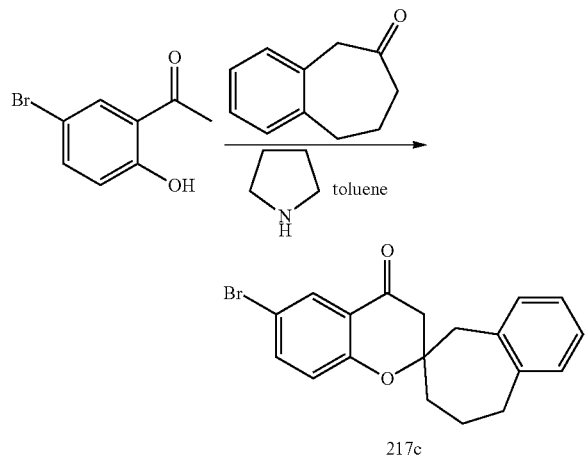

Preparation of Compound 217c

A mixture of 8,9-dihydro-5H-benzo[7]annulen-6(7H)-one (2 g, 12.5 mmol), 1-(5-bromo-2-hydroxyphenyl)ethanone (5.4 g, 25.0 mmol) and pyrrolidine (1.3 g, 1.5 ml) in toluene (50 mL) was refluxed overnight. The resulting mixture was concentrated, and the residue was washed with 1 M HCl, extracted with dichloromethane, dried over anhydrous sodium sulfate and concentrated to afford 2.3 g crude product. The crude product was purified by flash column chromatography on silica gel to afford the compound 217c (1 g, 22%). ¹H-NMR (400 MHz CDCl₃): δ7.91 (s, 1H), 7.76 (d, 1H), 7.08 (m, 3H), 6.75 (d, 1H), 6.68 (d, 1H), 3.21 (d, 1H), 3.00 (d, 1H), 2.75 (m, 2H), 2.52 (m, 2H), 2.10 (t, 2H), 1.87 (m, 1H), 1.52 (m, 1H).

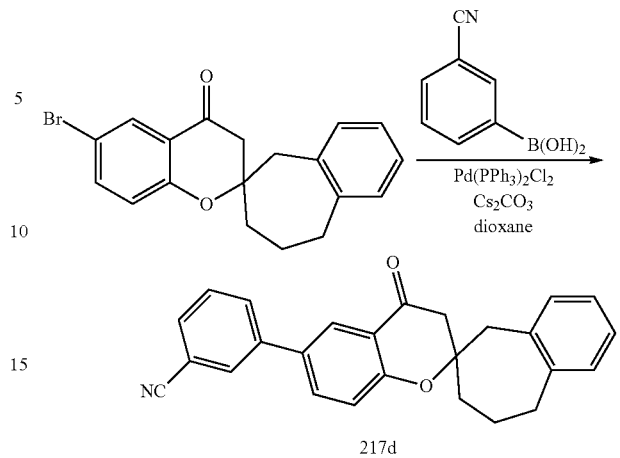

Preparation of Compound 217d

A mixture of 6'-bromo-5,7,8,9-tetrahydrospiro[benzo[7]annulene-6,2'-chroman]-4'-one (100 mg, 0.28 mmol), 3-cyanophenylboronic acid (102 mg, 0.56 mmol), Cs₂CO₃ (2 M, 0.5 mL) and Pd(PPh₃)₂Cl₂ (5 mg) in 1,4-dioxane (3 mL) under N₂ was stirred in microwave at 100° C. for 20 minutes. The reaction mixture was concentrated in vacuo, the residue was purified by preparative HPLC to afford the compound 217d (80 mg, 75%). ¹H-NMR (400 MHz CDCl₃): δ8.04 (s, 1H), 7.77 (s, 1H), 7.74 (d, 1H), 7.55 (m, 4H), 7.19 (m, 3H), 6.81 (d, 1H), 3.37 (d, 2H), 3.12 (d, 2H), 2.97 (s, 2H), 2.54 (m, 1H).

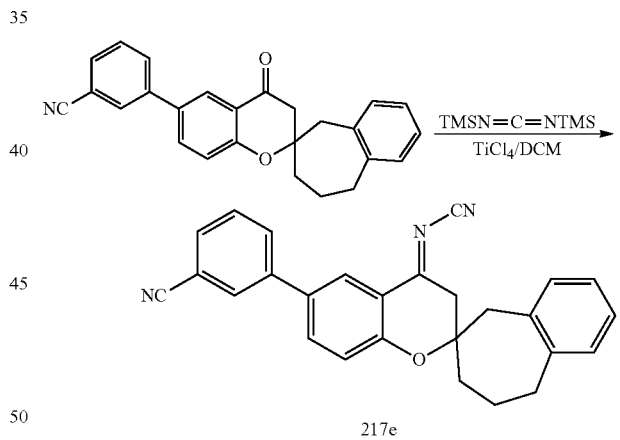

Preparation of Compound 217e

To a solution of 6'-(3-bromophenyl)-5,7,8,9-tetrahydrospiro[benzo[7]annulene-6,2'-chroman]-4'-one (80 mg, 0.21 mmol) in dichloromethane (2 mL) was added titanium (IV) chloride (1 M solution in dichloromethane, 161 mg, 0.85 mmol) dropwise, and the mixture was stirred in microwave for 20 minutes at 50° C. The mixture was added N,N'-methanediylidenebis(1,1,1-trimethylsilanamine) (118 mg, 0.85 mmol) dropwise, and stirred in microwave for 10 minutes at 60° C. The reaction mixture was poured into ice-water, and extracted with dichloromethane. The organic phase was dried over anhydrous sodium sulfate and concentrated to give the product 217e.

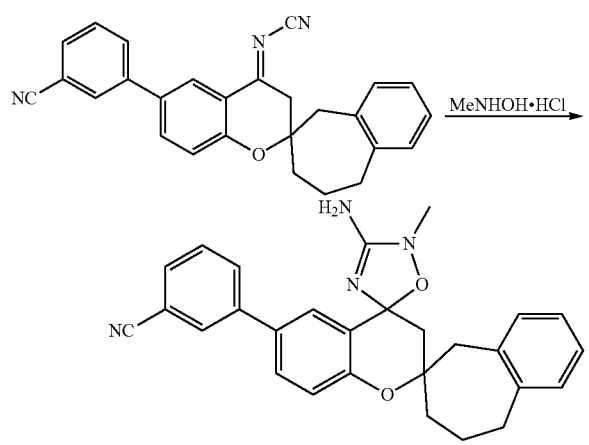

Preparation of Compound 217

To a solution of N-methylhydroxylamine hydrochloride (18 mg, 0.21 mmol) in anhydrous methanol (2 mL) was added sodium methanolate (25% in methanol, 0.041 mL, 0.19 mmol), and ((E)-N-(6'-(3-cyanophenyl)-5,7,8,9-tetrahydrospiro[benzo[7]annulene-6,2'-chroman]-4'-ylidene)-cyanamide (85 mg, 0.21 mmol). After being stirred for 10 minutes, the solvent was removed in vacuum, and the residue was redissolved in dichloromethanae (10 mL). After filtration, the solvent was removed, the residue was purified by preparative TLC and preparative HPLC to give compound 217 (2.80 mg, 2.9%). $^1$H-NMR (400 MHz CD$_3$OD): δ7.78 (m, 1H), 7.53 (m, 4H), 7.07 (m, 4H), 6.62-6.70 (m, 1H), 3.35 (m, 1H), 3.02 (m, 1H), 2.97 (d, 3H), 2.74 (m, 3H), 2.42 (m, 1H), 1.95 (m, 3H), 1.52 (m, 1H); ESI MS: m/z 451 [M+H]$^+$.

Example 174

Preparation of Compound 434

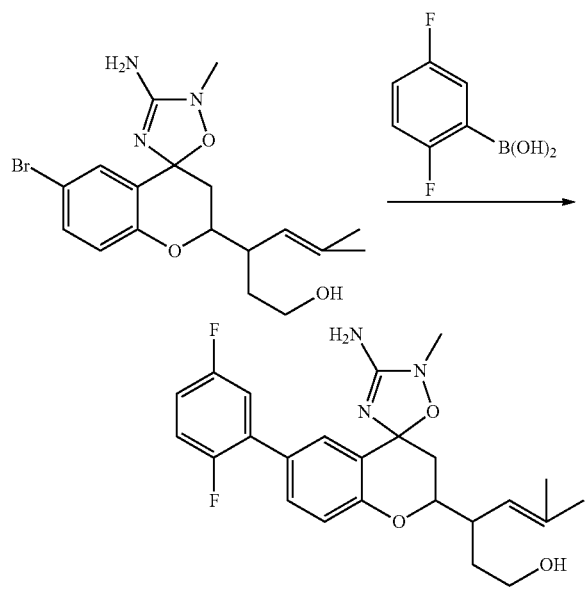

Preparation of Compound 434

Pd(PPh$_3$)$_2$Cl$_2$ (10 mg) in a 10 mL of tube under Ar$_2$ was treated sequentially with the solution of 3-(3'-amino-6-bromo-2'-methyl-2'H-spiro[chroman-4,5'-[1,2,4]oxadiazole]-2-yl)-5-methylhex-4-en-1-ol (35 mg, 0.085 mmol) in 1,4-dioxane (2 mL), Cs$_2$CO$_3$ (2 N, 0.3 mL), and 2,5-difluorophenylboronic acid (26.8 mg, 0.17 mmol). The mixture was heated in microwave at 12° C. for 20 minutes. The reaction mixture was concentrated in vacuo, the residue was purified by preparative TLC and preparative HPLC to give compound 434 (5 mg, 10%). $^1$H-NMR (400 MHz CDCl$_3$): δ8.70 (bs, 2H), 7.49-7.61 (m, 2H), 6.84-7.05 (m, 4H), 4.88-5.12 (m, 1H), 4.02-4.23 (m, 1H), 3.55-3.72 (d, 2H), 3.24 (d, 3H), 2.74 (s, 1H), 2.34-2.51 (m, 1H), 2.05 (m, 1H), 1.84 (m, 1H), 1.68 (m, 6H), 1.42 (s, 1H), 1.21 (d, 1H); ESI MS: m/z 444 [M+H]$^+$.

Example 175

Preparation of Compounds 341 and 384

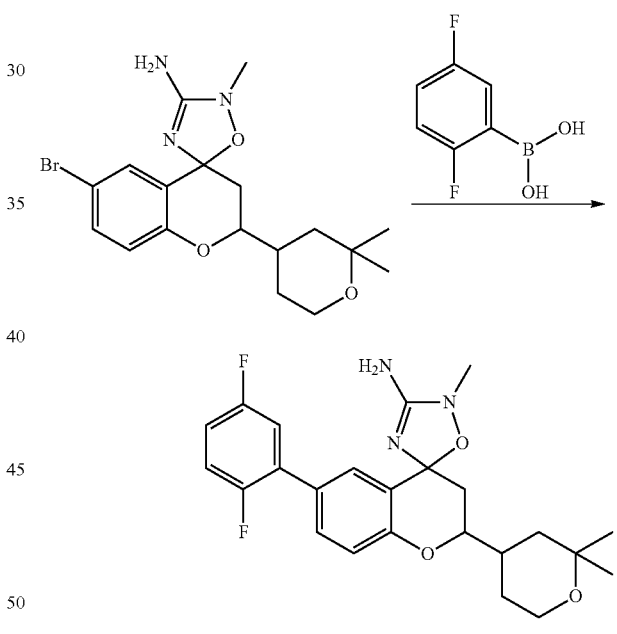

By using the same strategy as compound 434 described in Example 174, compound 341 (8.13 mg, 36%) & compound 384 (0.99 mg, 12%) were obtained.

compound 341: $^1$H-NMR (400 MHz CD$_3$OD): δ7.82 (d, 1H), 7.60 (m, 1H), 7.23 (m, 2H), 7.12 (m, 2H), 4.09 (m, 1H), 3.78 (m, 2H), 3.38 (m, 3H), 2.68 (d, 1H), 2.22 (m, 1H), 1.85-1.95 (m, 2H), 1.68 (m, 1H), 1.32-1.50 (m, 2H), 1.28 (d, 6H); ESI MS: m/z 444 [M+H]$^+$, compound 384: $^1$H-NMR (400 MHz CD$_3$OD): δ7.82 (d, 1H), 7.60 (m, 1H), 7.23 (m, 2H), 7.12 (m, 2H), 4.09 (m, 1H), 3.78 (m, 2H), 3.38 (m, 3H), 2.68 (d, 1H), 2.22 (m, 1H), 1.85-1.95 (m, 2H), 1.68 (m, 1H), 1.32-1.50 (m, 2H), 1.28 (d, 6H); ESI MS: m/z 444 [M+H]$^+$.

Example 176

Preparation of Compound 456

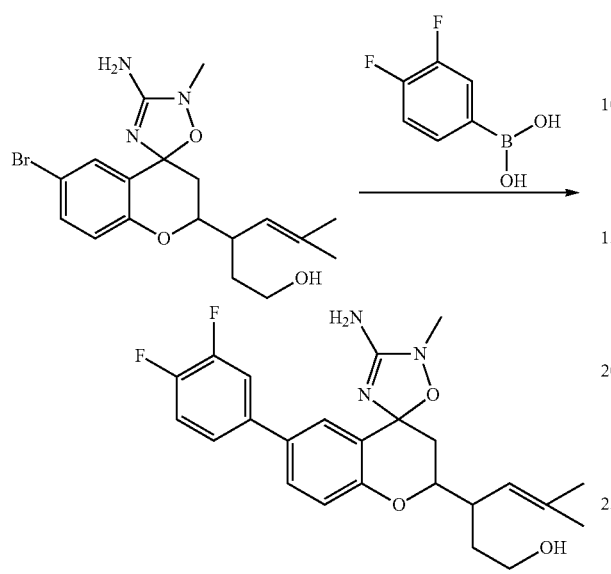

By using the same strategy as compound 434 described in Example 174, compound 456 was obtained (5.31 mg, 14%). ¹H-NMR (400 MHz CDCl₃): δ7.19-7.71 (m, 3H), 6.80-7.15 (m, 3H), 4.91-5.07 (m, 1H), 3.98-4.33 (m, 1H), 3.65-3.75 (m, 1H), 3.50-3.60 (m, 1H), 3.20-3.30 (s, 3H), 2.70-2.80 (t, 1H), 2.20-2.60 (m, 6H), 1.70-1.80 (d, 3H), 1.55-1.65 (d, 3H); ESI MS: m/z 444 [M+H]⁺.

Example 177

Preparation of Compounds 362 and 365

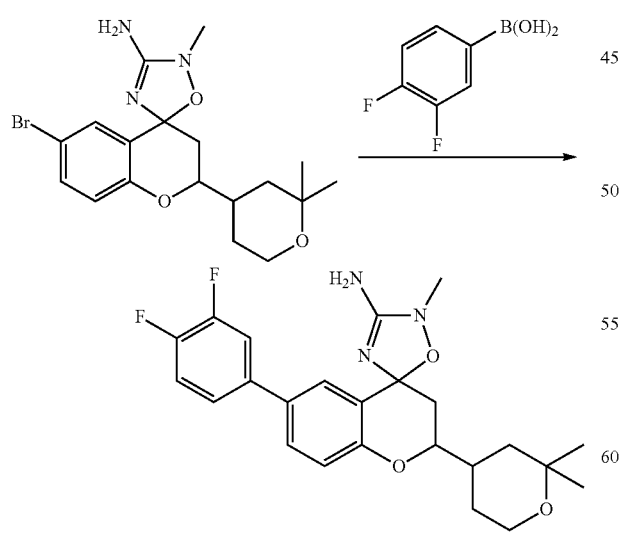

By using the same strategy as compound 434 described in Example 174, compound 365 (2.40 mg, 8%) and compound 362 (0.79 mg, 3%) were obtained.

compound 365: ¹H-NMR (400 MHz CD₃OD): δ7.83 (s, 1H), 7.63 (d, 1H), 7.49 (m, 1H), 7.38 (m, 1H), 7.27 (m, 1H), 6.99 (d, 1H), 4.04 (m, 1H), 3.74 (m, 2H), 3.34 (m, 3H), 2.65 (d, 1H), 2.16 (m, 1H), 1.98 (m, 1H), 1.84 (m, 1H), 1.62 (m, 1H), 1.41 (m, 2H), 1.22 (d, 6H); ESI MS: m/z 444 [M+H]⁺.

compound 362: ¹H-NMR (400 MHz CD₃OD): δ7.86 (s, 1H), 7.64 (d, 1H), 7.52 (m, 1H), 7.32 (m, 2H), 7.03 (d, 1H), 4.06 (m, 1H), 3.78 (m, 2H), 3.43 (m, 3H), 2.68 (d, 1H), 2.18 (m, 1H), 1.94 (m, 2H), 1.63 (m, 1H), 1.47 (m, 1H), 1.37 (m, 1H), 1.23 (m, 6H); ESI MS: m/z 444 [M+H]⁺.

Example 178

Preparation of Compound 404

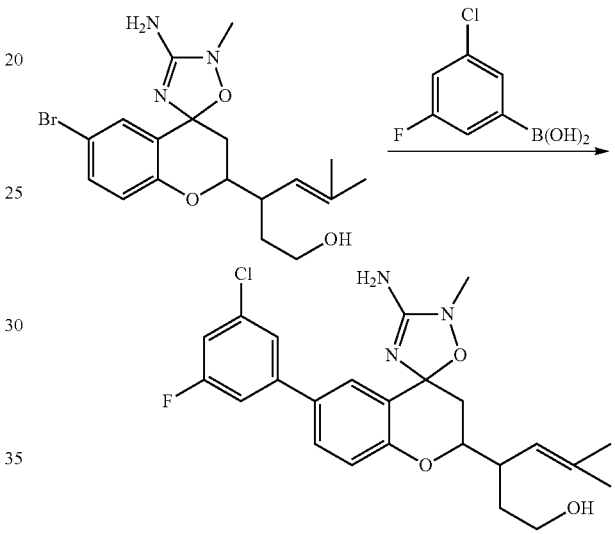

Preparation of Compound 404

By using the same strategy as compound 434 described in Example 174, compound 404 (1.92 mg, 5%) was obtained. ¹H-NMR (400 MHz CD₃OD): δ7.88 (s, 1H), 7.62 (m, 1H), 7.48 (m, 1H), 7.32 (m, 1H), 7.13 (m, 1H), 6.99 (m, 1H), 5.06 (m, 1H), 4.29 & 4.07 (m, 1H), 3.63 (m, 1H), 3.51 (m, 1H), 3.37 (m, 3H), 2.88 (m, 1H), 2.57 (m, 1H), 2.15 (m, 1H), 1.88 (m, 1H), 1.72 (m, 6H); ESI MS: m/z 460 [M+H]⁺.

Example 179

Preparation of Compounds 295 and 299

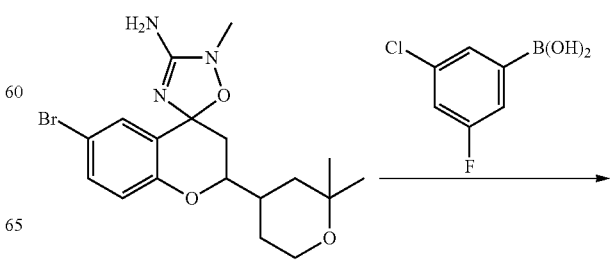

-continued

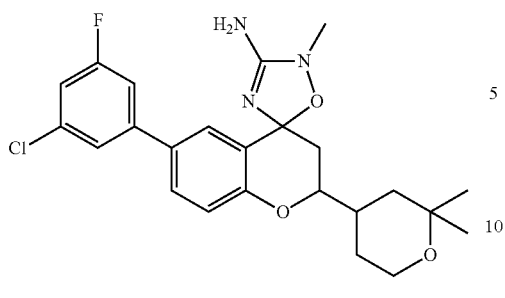

By using the same synthetic strategy for compound 434 described in Example 174, compound 295 (3.07 mg, 9%) and compound 299 (1.18 mg, 3%) were obtained.

compound 295: ¹H-NMR (400 MHz CD$_3$OD): δ7.92 (s, 1H), 7.68 (d, 1H), 7.48 (m, 1H), 7.36 (d, 1H), 7.14 (d, 1H), 7.02 (m, 1H), 4.05 (m, 1H), 3.74 (m, 2H), 3.39 (m, 3H), 2.64 (d, 1H), 2.16 (m, 1H), 1.96 (m, 1H), 1.84 (m, 1H), 1.62 (m, 1H), 1.42 (m, 2H), 1.23 (m, 6H); ESI MS: m/z 460 [M+H]⁺.

compound 299: ¹H-NMR (400 MHz CD$_3$OD): δ7.89 (s, 1H), 7.67 (m, 1H), 7.44 (m, 1H), 7.31 (m, 1H), 7.14 (m, 1H), 6.99 (m, 1H), 4.04 (m, 1H), 3.72 (m, 2H), 3.46 (m, 3H), 2.18 (m, 1H), 1.98 (m, 1H), 1.84 (m, 1H), 1.62 (m, 1H), 1.41 (m, 2H), 1.22 (m, 6H); ESI MS: m/z 460 [M+H]⁺.

Example 180

Preparation of Compound 377

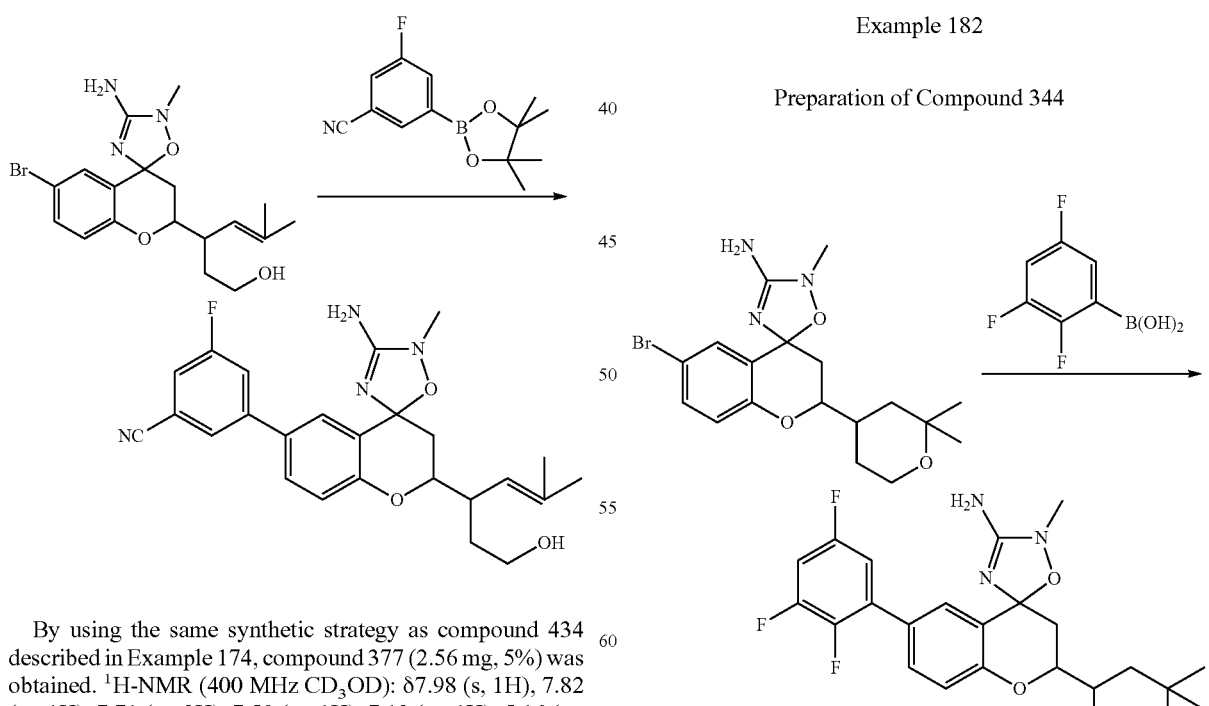

By using the same synthetic strategy as compound 434 described in Example 174, compound 377 (2.56 mg, 5%) was obtained. ¹H-NMR (400 MHz CD$_3$OD): δ7.98 (s, 1H), 7.82 (m, 1H), 7.71 (m, 2H), 7.50 (m, 1H), 7.12 (m, 1H), 5.16 (m, 1H), 5.01 (m, 1H), 4.32 (m, 0.5H), 4.12 (m, 0.5H), 3.66 (m, 1H), 3.52 (m, 1H), 3.48 (s, 3H), 2.79 (m, 1H), 2.61 (m, 1H), 1.86-2.20 (m, 2H), 1.76 (m, 6H), 1.45 (m, 1H); ESI MS: m/z 451 [M+H]⁺.

Example 181

Preparation of Compound 260

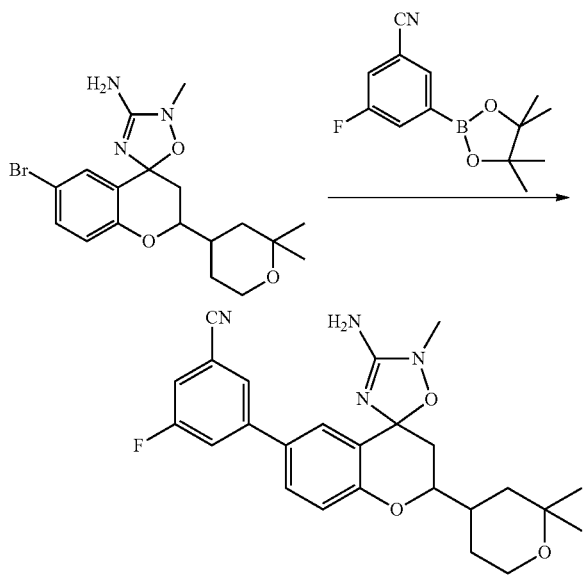

By using the same strategy as compound 434 described in Example 174, compound 260 was obtained (2.31 mg, 10%). ¹H-NMR (400 MHz CD$_3$OD): δ8.03 (m, 1H), 7.88 (m, 1H), 7.74 (m, 2H), 7.52 (m, 1H), 7.03 (m, 1H), 4.09 (m, 1H), 3.78 (m, 2H), 3.44 (m, 3H), 2.51-2.67 (m, 1H), 1.82-2.32 (m, 3H), 1.38-1.72 (m, 3H), 1.28 (m, 6H); ESI MS: m/z 451 [M+H]⁺.

Example 182

Preparation of Compound 344

By using the same strategy as compound 434 described in Example 174, compound 344 (2.7 mg, 12%) was obtained.

$^1$H-NMR (400 MHz CD$_3$OD): δ7.86 (m, 1H), 7.62 (m, 1H), 7.12 (m, 3H), 4.12 (m, 1H), 3.82 (m, 2H), 3.41 (m, 3H), 2.61 (m, 1H), 2.23 (m, 1H), 1.98 (m, 2H), 1.64 (m, 1H), 1.42 (m, 2H), 1.29 (m, 6H); ESI MS: m/z 462 [M+H]$^+$.

Example 183

Preparation of Compounds 420, 392 and 441

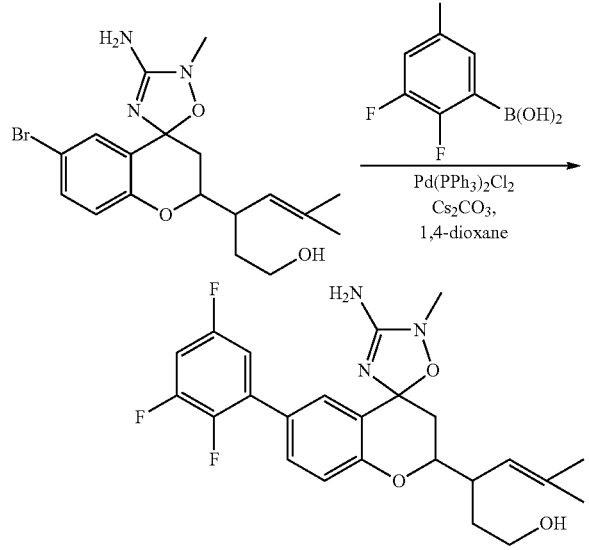

By using the same synthetic strategy as compound 434 described in Example 174, compound 420 (3.19 mg, 8%), compound 392 (0.49 mg, 1%), and compound 441 (1.18 mg, 3%) were obtained.

compound 420: $^1$H NMR (400 MHz CD$_3$OD): δ7.82 (s, 1H), 7.62 (d, 1H), 7.03-7.18 (m, 3H), 5.15 (m, 1H), 4.11-4.31 (m, 1H), 3.63 (m, 1H), 3.54 (m, 1H), 3.32 (s, 3H), 2.91 (m, 1H), 2.61 (m, 1H), 1.87-2.18 (m, 2H), 1.76 (d, 6H), 1.51 (m, 1H); ESI MS: m/z 462 [M+H]$^+$.

compound 392: $^1$H NMR (400 MHz CD$_3$OD): δ7.82 (d, 1H), 7.57 (t, 1H), 6.98-7.21 (m, 3H), 4.93-5.14 (m, 1H), 4.10-4.35 (m, 1H), 3.63 (m, 1H), 3.54 (m, 1H), 3.37 (d, 3H), 2.89 (m, 1H), 2.62 (m, 1H), 2.33 (m, 0.5H), 1.88-2.19 (m, 2H), 1.76 (d, 6H), 1.51 (m, 1H).

compound 441: $^1$H NMR (400 MHz CD$_3$OD): δ7.82 (d, 1H), 7.56 (m, 1H), 6.98-7.19 (m, 3H), 5.12 (m, 1H), 4.38 (m, 1H), 3.64 (m, 1H), 3.56 (m, 1H), 3.45 (s, 0.5H), 3.37 (d, 3H), 3.13 (m, 0.5H), 2.88 (m, 1H), 2.49 (m, 1H), 2.32 (m, 1H), 2.08 (m, 1H), 1.92 (m, 1H), 1.72 (t, 6H), 1.48 (m, 1H); ESI MS: m/z 462 [M+H]$^+$.

Example 184

Preparation of Compound 436a and 436b

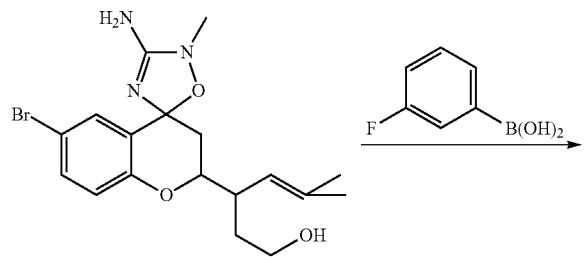

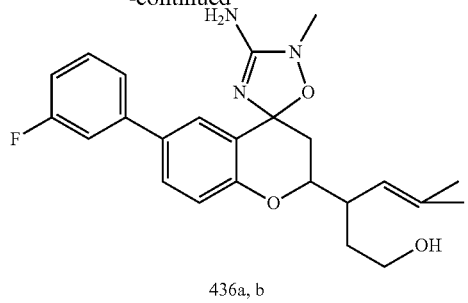

436a, b

By using the same synthetic strategy as compound 434 described in Example 174, compound 436a (6.61 mg, 16%) and compound 436b (1.30 mg, 3%) were obtained.

compound 436a: $^1$H-NMR (400 MHz CD$_3$OD): δ7.86 (d, 1H), 7.66 (dd, 1H), 7.41 (m, 2H), 7.32 (d, 1H), 7.01 (m, 2H), 4.97-5.13 (m, 1H), 4.01-4.35 (m, 1H), 3.63 (m, 1H), 3.52 (m, 1H), 3.34 (d, 3H), 2.87 (m, 1H), 2.45-2.66 (m, 1H), 2.12 (m, 1H), 2.05 (t, 1H), 1.90 (m, 1H), 1.76 (d, 3H), 1.71 (d, 3H), 1.40-1.65 (m, 1H); ESI MS: 426 [M+H]$^+$.

compound 436b: $^1$H-NMR (400 MHz CD$_3$OD): δ7.86 (m, 1H), 7.67 (m, 1H), 7.41 (m, 2H), 7.34 (t, 1H), 7.01 (m, 2H), 4.95-5.15 (m, 1H), 4.01-4.35 (m, 1H), 3.65 (m, 1H), 3.52 (m, 1H), 3.34-3.45 (d, 3H), 2.90 (m, 1H), 2.50-2.70 (m, 1H), 2.30 (t, 1H), 2.15 (m, 1H), 1.92 (m, 1H), 1.78 (d, 3H), 1.72 (d, 3H), 1.48 (m, 1H); ESI MS: 426 [M+H]$^+$.

Example 185

Preparation of Compound 339

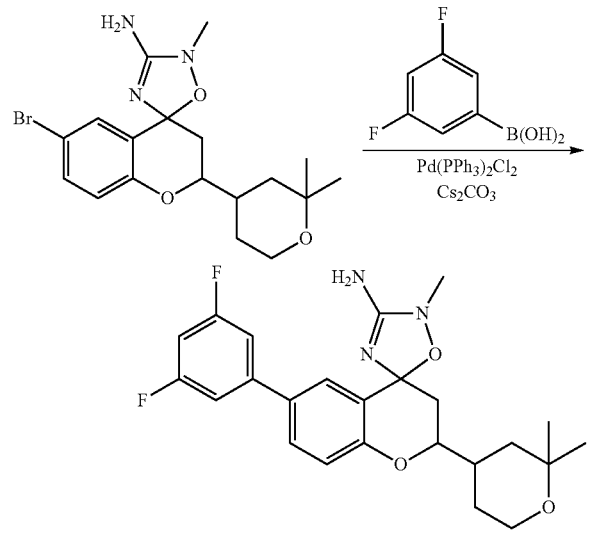

By using the same synthetic strategy as compound 434 described in Example 174, compound 339 (4.73 mg, 22%) was obtained. $^1$H-NMR (400 MHz CD$_3$OD): δ7.92 (m, 1H), 7.69 (m, 1H), 7.25 (m, 2H), 6.92 (m, 1H), 6.67 (m, 1H), 4.29 (m, 1H), 3.67 (m, 3H), 3.40 (m, 3H), 2.84 (m, 1H), 2.46 (m, 2H), 2.04 (m, 1H), 1.88 (m, 3H), 1.69 (m, 3H), 1.42-1.24 (m, 2H); ESI MS: m/z 444 [M+H]$^+$.

Example 186

Preparation of Compounds 421, 444 and 419

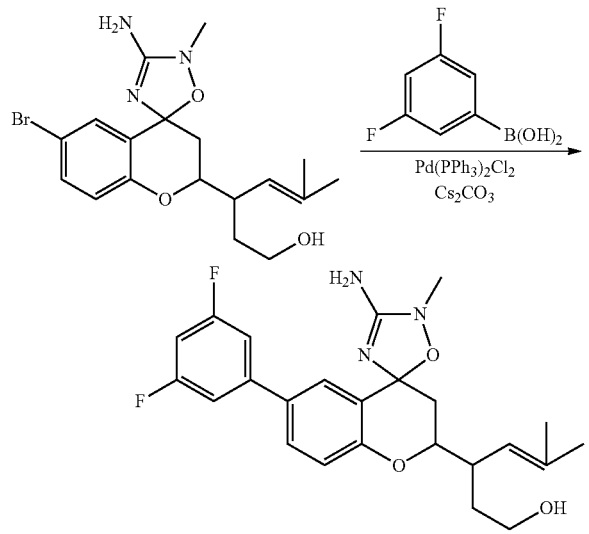

By using the same synthetic strategy as compound 434 described in Example 174, compound 421 (2.38 mg, 7%), compound 444 (1.05 mg, 3%), and compound 419 (0.51 mg, 1.5%) were obtained; ESI MS: m/z 444 [M+H]+.

compound 421: $^1$H-NMR (400 MHz CD$_3$OD): δ7.93 (m, 1H), 7.72 (m, 1H), 7.25 (m, 2H), 7.05 (m, 1H), 6.90 (m, 1H), 5.0-5.2 (m, 2H), 4.1-4.4 (m, 1H), 3.62 (m, 1H), 3.62 (m, 1H), 3.51 (m, 1H), 3.43 (m, 3H), 2.9 (m, 1H), 2.51-2.74 (m, 1H), 2.0-2.2 (m, 2H), 1.75-1.80 (m, 6H), 1.45-1.50 (m, 1H); ESI MS: m/z 444 [M+H]+.

compound 444: $^1$H-NMR (400 MHz CD$_3$OD): δ7.85 (m, 1H), 7.55-7.65 (m, 1H), 7.19 (m, 2H), 6.97 (m, 1H), 6.82 (m, 1H), 4.0-4.25 (m, 1H), 3.62 (m, 1H), 3.61 (m, 1H), 3.51 (m, 2H), 3.35 (m, 1H), 3.23 (m, 3H), 2.84 (m, 1H), 2.25-2.50 (m, 1H), 2.23 (m, 1H), 1.65-1.70 (m, 6H), 1.30-1.45 (m, 2H); ESI MS: m/z 444 [M+H]+.

compound 419: $^1$H-NMR (400 MHz CD$_3$OD): δ7.93 (m, 1H), 7.67 (m, 1H), 7.25 (m, 2H), 6.80-7.01 (m, 2H), 4.44 (m, 1H), 3.56-3.65 (m, 3H), 3.45 (m, 3H), 2.90 (m, 1H), 2.3-2.50 (m, 2H), 2.22 (m, 1H), 1.65-1.70 (m, 6H), 1.45 (m, 2H); ESI MS: m/z 444 [M+H]+.

Example 187

Preparation of Compound 248

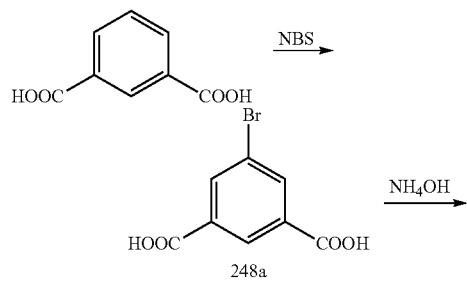

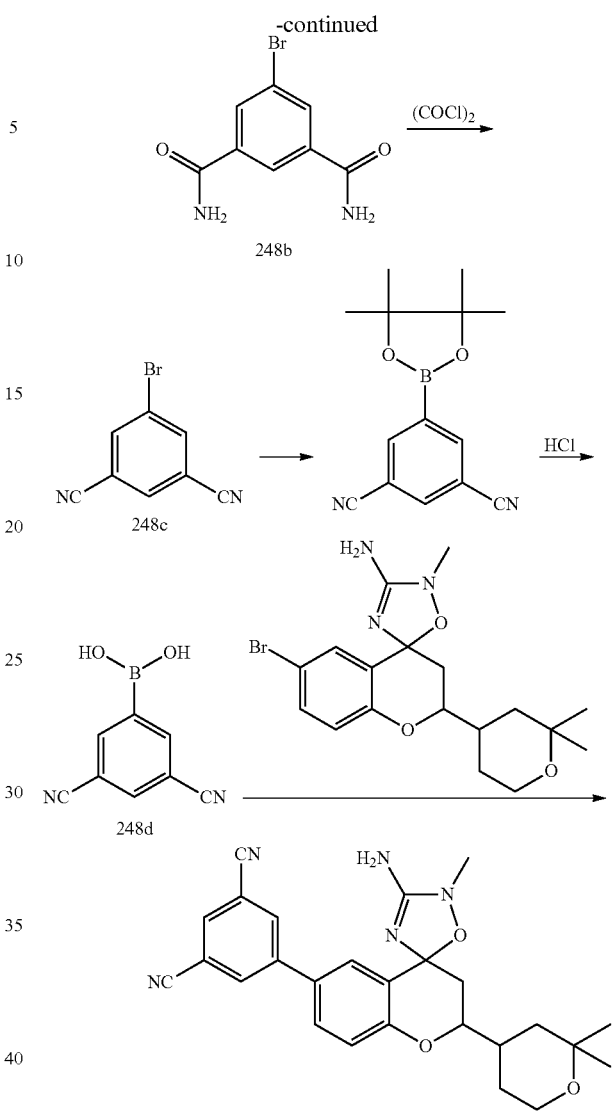

Experimental Data:

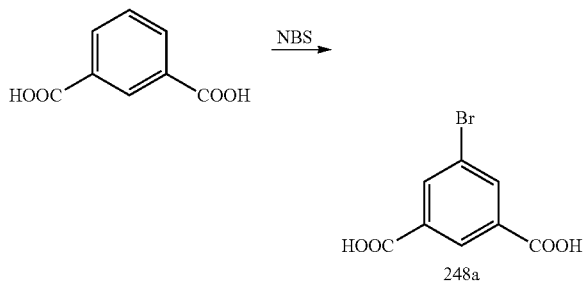

Preparation of Compound 248a

The isophthalic acid (19.8 g, 300 mmol) was taken up in concentrated H$_2$SO$_4$ (136 mL) and heated at 60° C. To this solution was added NBS (64.4 g, 360 mmol) in three portions every 20 minutes. When the reaction was completed based on TLC analysis, the mixture was poured into crushed ice (300 g) to get the solid. After filtration, the mixture was washed with water and hexane, and dried to give compound 248a (51 g, 70%). $^1$H-NMR (400 MHz DMSO-d$_6$): δ8.35-8.40 (s, 1H), 8.20-8.30 (s, 2H).

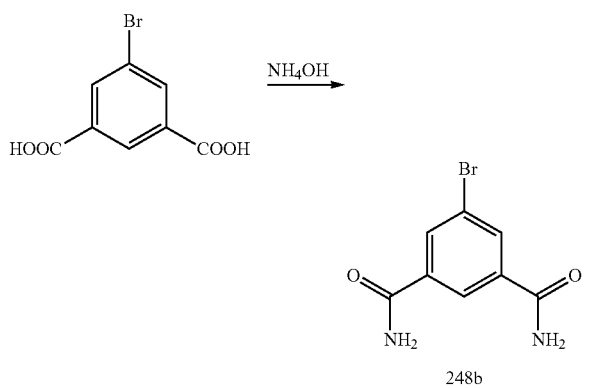

Preparation of Compound 248b

A solution of 5-bromo-isophthalic acid (48 g, 197 mmol) in tulene was added SOCl$_2$ (48 mL) and DMF (4 mL) at room temperature over 10 minute. The reaction mixture was refluxed for 3.5 hr and cooled to °C. The reaction mixture was added dropwise to NH$_4$OH (400 mL) for 1 hr. The mixture was filtered to give the compound 248b (42 g, 87.5%). $^1$H-NMR (400 MHz DMSO-d$_6$): δ8.30-8.40 (s, 1H), 8.10-8.20 (m, 4H), 7.50-7.60 (s, 2H).

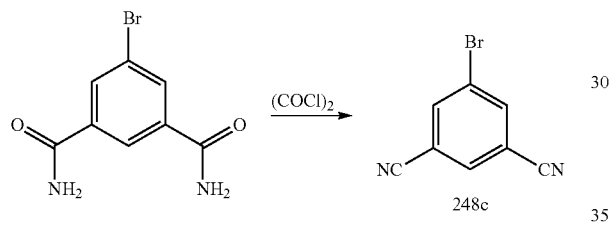

Preparation of Compound 248c

To a solution of dry DMF in dry CH$_3$CN at −5° C. to 0° C. under a nitrogen atmosphere was added (ClCO)$_2$ over 10 minutes. After being stirred for 15 minutes, 5-bromo-isophthalamide (42 g, 174 mmol) was added in one portion, and the mixture was stirred at ° C. for 1.5 hrs. Pyridine was added dropwise over 5 minutes, and the mixture was stirred at 0° C. for 2 hrs. 1 M HCl (80 mL) was added, and the mixture was extracted with ether (200 mL) for 2 times. The organic layer was concentrated in vacuo to give the compound 248c (28 g, 78.2%). $^1$H-NMR (400 MHz CDCl$_3$): δ8.00-8.10 (s, 2H), 7.70-7.80 (s, 1H).

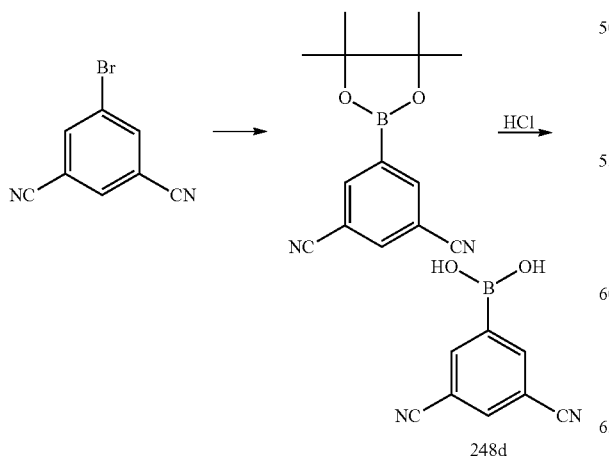

Preparation of Compound 248d

A solution of 4,4,4',4',5,5,5',5'-octamethyl-2,2'-bi(1,3,2-dioxaborolane) (5.96 g, 24 mmol), 5-bromo-isophthalonitrile (4.52 g, 22 mmol), KOAc (6.28 g, 64 mmol) and PdCl$_2$(dppf)$_2$ in DMSO (30 mL). The mixture was degassed, heated at 8° C. for 4 hr. Water (20 mL) was added, and the mixture was extracted with ether (40 mL) for 3 times. The organic layer was added 1N HCl (20 mL), dried over Na$_2$SO$_4$ and concentrated in vacuo to give the compound 248d (0.6 g, 10%). $^1$H-NMR (400 MHz DMSO-d$_6$): δ8.60-8.70 (s, 2H), 8.45-8.50 (s, 1H), 8.30-8.40 (s, 2H).

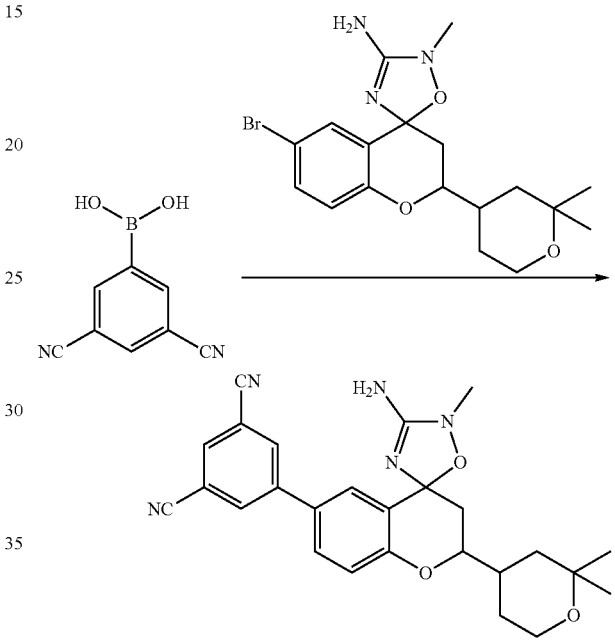

Preparation of Compound 248

By using the same strategy as compound 434 as described in Example 174, compound 248 (2.22 mg, 6%) was obtained. $^1$H-NMR (400 MHz CD$_3$OD): δ8.32-8.34 (m, 2H), 8.10-8.20 (m, 2H), 7.70-7.80 (m, 1H), 7.00-7.10 (m, 1H), 3.77 (m, 1H), 3.43-3.45 (m, 2H), 3.31-3.32 (m, 3H), 2.68-2.71 (m, 1H), 1.41-1.23 (m, 5H), 1.20-1.35 (m, 7H); ESI MS: m/z 458 [M+H]$^+$.

Example 188

Preparation of Compound 297

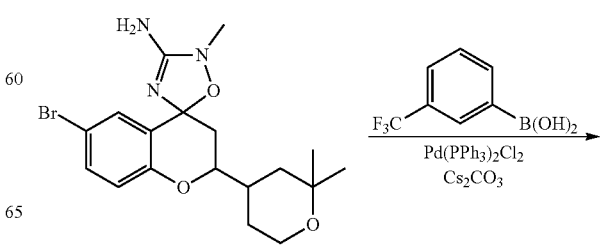

-continued

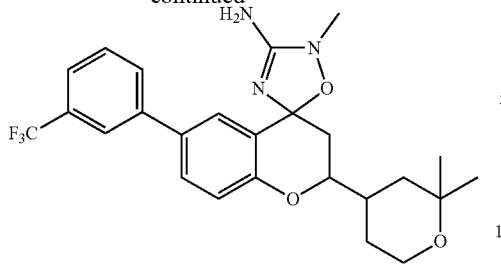

By using the same strategy as compound 434 as described in Example 174, compound 297 (7.44 mg, 32%) was obtained. ¹H-NMR (400 MHz CD₃OD): δ7.85 (m, 3H), 7.71 (m, 1H), 7.66 (m, 2H), 7.00 (m, 1H), 4.0 (m, 1H), 3.77 (m, 2H), 3.30 (m, 3H), 2.69 (m, 1H), 2.20 (m, 1H), 1.88-2.10 (m, 2H), 1.63 (m, 1H), 1.47 (m, 2H), 1.26 (m, 6H); ESI MS: m/z 476 [M+H]⁺.

Example 189

Preparation of Compounds 442, 450 and 423

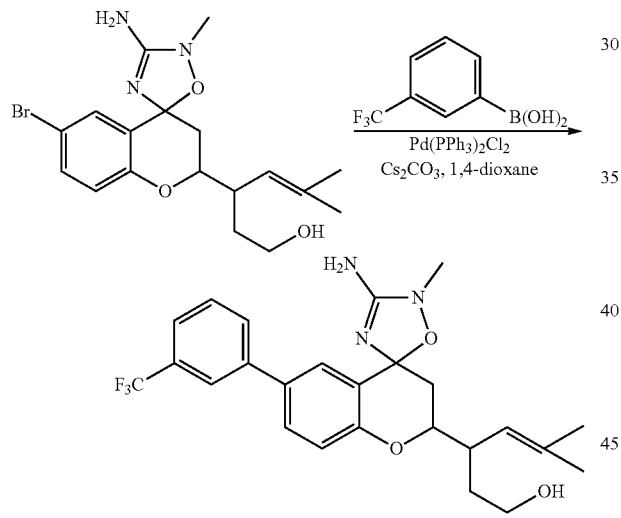

By using the same strategy as compound 434 as described in Example 174, compound 442 (4.31 mg, 10%), compound 450 (1.23 mg, 3%), and compound 423 (0.65 mg, 2%) were obtained.

compound 442: ¹H NMR (400 MHz CD₃OD): δ7.88 (m, 3H), 7.70 (d, 1H), 7.59 (d, 2H), 7.04 (d, 1H), 5.13 (d, 1H), 5.02 (d, 1H), 4.19-4.33 (m, 1H), 3.61 (d, 2H), 3.37 (s, 3H), 2.86 (m, 1H), 2.61 (m, 1H), 1.82-2.18 (m, 2H), 1.75 (d, 6H), 1.51 (m, 1H); ESI MS: m/z 476 [M+H]⁺.

compound 450: ¹H NMR (400 MHz CD₃OD): δ7.82 (m, 3H), 7.58 (m, 3H), 6.96 (m, 1H), 5.03 (m, 0.6H), 4.21 (m, 0.5H), 4.01 (m, 1H), 3.52 (m, 2H), 3.31 (d, 3H), 2.81 (m, 1H), 2.48 (m, 1H), 2.23 (m, 1H), 1.82-2.10 (m, 2H), 1.67 (d, 6H), 1.38 (m, 1H); ESI MS: m/z 476 [M+H]⁺.

compound 423: ¹H NMR (400 MHz CD₃OD): δ7.79 (m, 3H), 7.63 (m, 3H), 6.95 (t, 1H), 5.06 (m, 1H), 4.22 (m, 1H), 3.45-3.52 (m, 2H), 3.30 (d, 3H), 2.72 (m, 2H), 2.48 (m, 1H), 2.23 (m, 0.5H), 1.97 (m, 0.5H), 1.83 (m, 1H), 1.66 (t, 6H), 1.23 (m, 1H); ESI MS: m/z 476 [M+H]⁺.

Example 190

Preparation of Compound 412

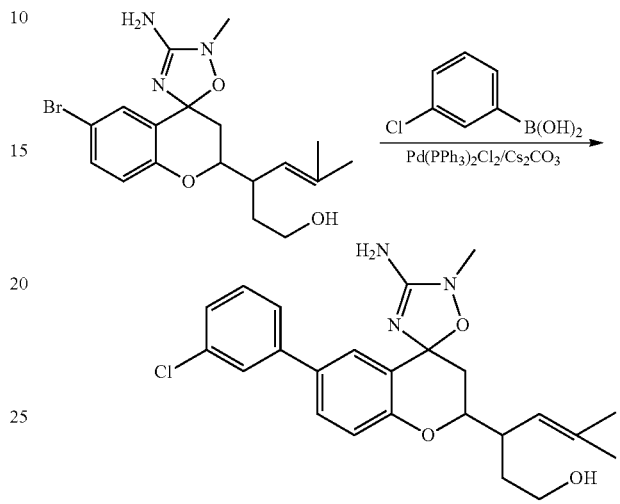

By using the same strategy as compound 434 as described in Example 174, compound 412 (5.16 mg, 12%) was obtained. ¹H-NMR (400 MHz CD₃OD): δ7.85-7.95 (m, 1H), 7.66-7.72 (m, 1H), 7.61-7.65 (m, 1H), 7.52-7.60 (m, 1H), 7.40-7.48 (m, 1H), 7.31-7.38 (m, 1H), 7.04-7.05 (m, 1H), 4.98-5.20 (m, 2H), 4.09-4.39 (m, 1H), 3.62-3.75 (m, 1H), 3.56-3.61 (m, 1H), 3.38 (s, 3H), 2.90-2.94 (m, 1H), 2.57-2.70 (m, 1H), 2.07-2.21 (m, 1H), 1.90-2.06 (m, 1H), 1.81-1.83 (m, 3H), 1.75-1.77 (m, 3H), 1.48-1.70 (m, 1H); ESI MS: m/z 442 [M+H]⁺.

Example 191

Preparation of Compound 264

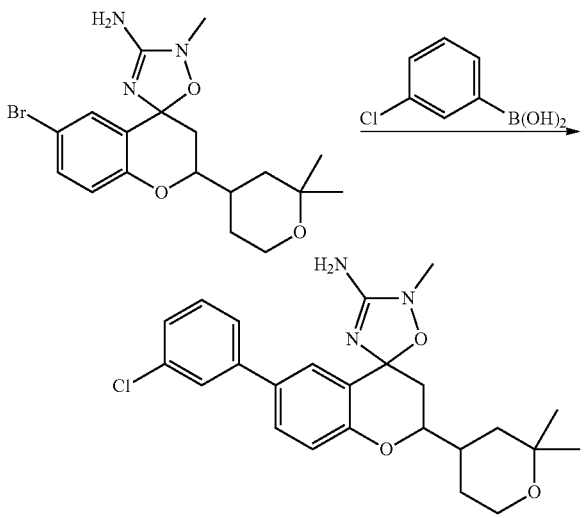

Compound 1

By using the same strategy as compound 434 as described in Example 174, compound 264 (2.20 mg, 10%) was obtained. $^1$H-NMR (400 MHz CD$_3$OD): δ7.85 (m, 1H), 7.64 (m, 1H), 7.59 (m, 1H), 7.50 (m, 1H), 7.39 (t, 1H), 7.32 (m, 1H), 7.01 (d, 1H), 4.03 (m, 1H), 3.76 (d, 2H), 3.32-3.42 (m, 3H), 2.67 (d, 1H), 2.18 (m, 1H), 1.98 (m, 1H), 1.86 (m, 1H), 1.63 (m, 1H), 1.25-1.50 (m, 2H), 1.23 (d, 6H); ESI MS: m/z 442 [M+H]$^+$.

Example 192

Preparation of Compound 294

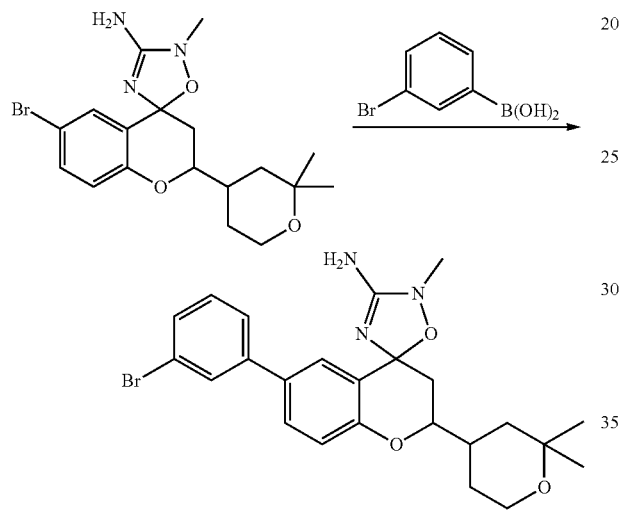

Pd(PPh$_3$)$_4$ (10 mg) in a 10 mL of tube under Ar$_2$ was treated sequentially with a solution of 6-bromo-2-(2,2-dimethyltetrahydro-2H-pyran-4-yl)-2'-methyl-2'H-spiro[chroman-4,5'-[1,2,4]oxadiazol]-3'-amine (50 mg, 0.12 mmol) in THF (5 mL), K$_2$CO$_3$ (2 N, 0.1 mL) and 3-bromophenylboronic acid (24.6 mg, 0.12 mmol). The mixture was refluxed overnight, and concentrated in vacuo, the residue was purified by preparative TLC and preparative HPLC to give compound 294 (1.62 mg, 3%). $^1$H-NMR (400 MHz CD$_3$OD): δ7.84 (m, 1H), 7.75 (s, 1H), 7.66 (m, 1H), 7.56 (t, 1H), 7.48 (m, 1H), 7.34 (t, 1H), 7.02 (m, 1H), 4.01-4.12 (m, 1H), 3.73 (m, 2H), 3.38 (d, 3H), 2.67 (d, 1H), 2.10-2.26 (m, 1H), 1.98 (t, 1H), 1.72-1.90 (m, 1H), 1.61-1.69 (m, 1H), 1.36-1.49 (m, 2H), 1.22-1.31 (m, 6H); ESI MS: m/z 488 [M+3H]$^+$.

Example 193

Preparation of Compound 391

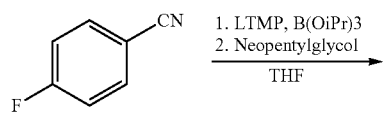

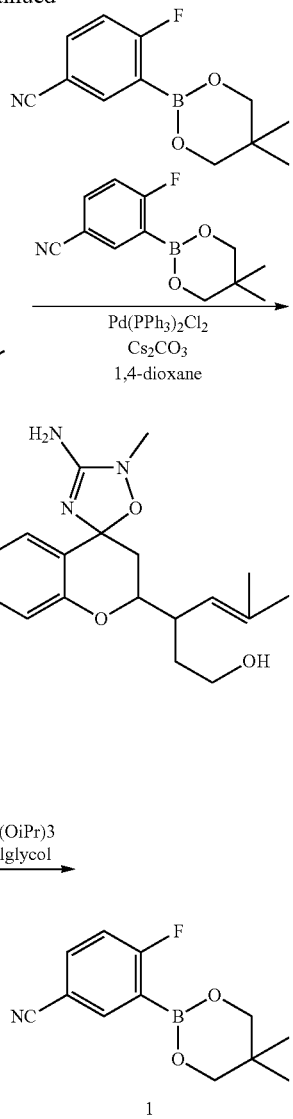

Experimental Data:

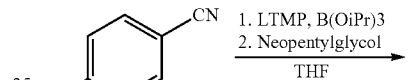

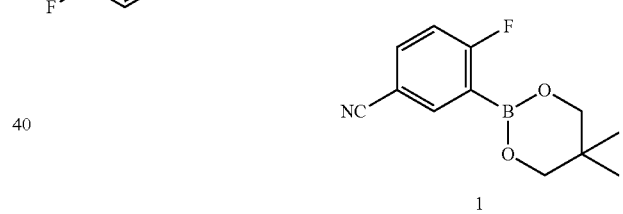

Preparation of Compound 1

Under nitrogen, 2,2,6,6-tetramethylpiperidine (7.1 g, 49.6 mmol) was dissolved in dry THF (100 mL) and cooled to −10° C. before n-BuLi (2.5 M in hexane, 19.8, 49.6 mmol) was added in 2 minutes. The mixture was stirred for 10 minutes, cooled down to −78° C., added B(Oi-Pr)$_3$ (10.8 g, 57.4 mmol) in 2 minutes, stirred for 5 minutes, added the solution of 4-fluorobenzonitrile (5 g, 41 mmol) in dry THF (140 mL) dropwise in 5 minutes. The reaction mixture was left in the cooling bath overnight, slowly warmed to room temperature, quenched with glacial acetic acid (3.3 mL), added of 2,2-dimethyl-1,3-propandiol (6.4 g, 61.5 mmol), stirred for 1 hr at room temperature, added ethyl acetate, and washed with aqueous KH$_2$PO$_4$ solution (10 w/v %, 3×100 mL). The water phase was extracted with ethyl acetate, and the combined organic layer was dried and evaporated to give the crude product, which was recrystallize to give the compound 1 (1 g, 10%). $^1$H-NMR (CDCl$_3$): δ8.00 (m, 1H), 7.62 (m, 1H), 7.03 (m, 1H), 3.75 (d, 4H), 1.01 (s, 6H).

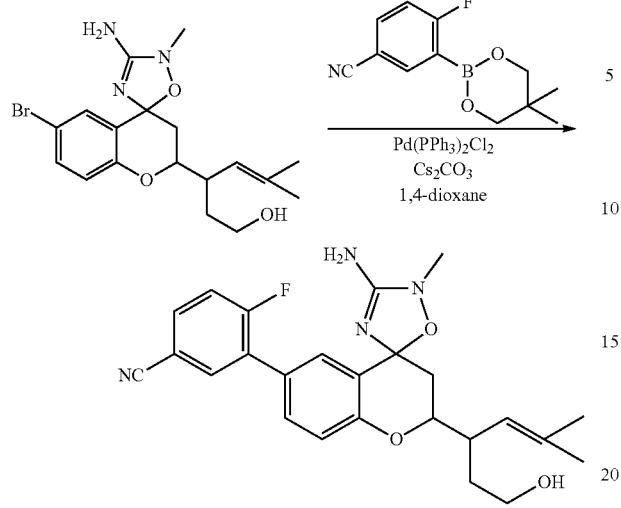

By using the procedure for compound 434 as described in Example 174, compound 391 (5.38 mg, 2.6%) was obtained. $^1$H-NMR (400 MHz CD$_3$OD): δ7.91 (m, 1H), 7.71-7.88 (m, 2H), 7.63 (m, 1H), 7.38-7.43 (m, 1H), 7.04 (d, 1H), 4.48-5.12 (m, 1H), 4.08-4.35 (m, 1H), 3.44-3.69 (m, 2H), 3.34 (m, 3H), 2.89 (m, 1H), 2.49-2.65 (m, 1H), 1.84-2.19 (m, 2H), 1.68-1.73 (m, 6H), 1.51 (m, 1H), 1.26 (m, 1H); ESI MS: m/z 451 [M+H]$^+$.

Example 194

Preparation of Compound 261

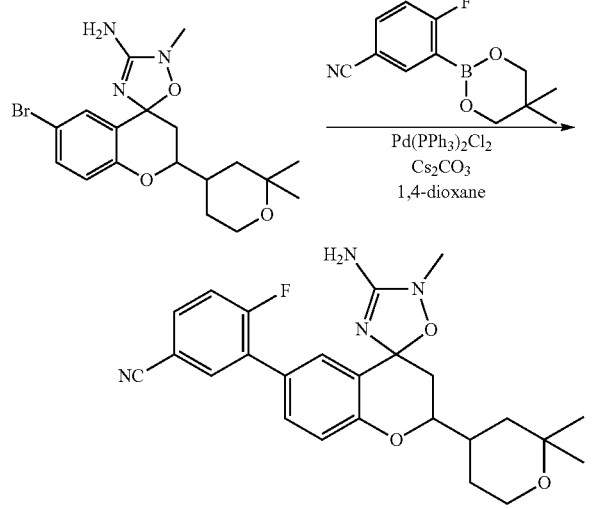

By using the same procedure for compound compound 434 as described in Example 174, compound 261 (1.52 mg, 4%) was obtained. $^1$H-NMR (400 MHz CD$_3$OD): δ7.68 (d, 1H), 7.56 (m, 2H), 7.47 (m, 1H), 7.18 (m, 1H), 6.91 (d, 1H), 4.03 (m, 1H), 3.71 (m, 1H), 3.66 (m, 1H), 3.31 (m, 1H), 3.27 (s, 3H), 2.34-2.56 (m, 1H), 1.92-2.23 (m, 2H), 1.65-1.87 (m, 1H), 1.56 (m, 1H), 1.48 (m, 1H), 1.33 (m, 1H), 1.23 (m, 3H), 1.18 (m, 3H); ESI MS: m/z 451 [M+H]$^+$.

Example 195

Preparation of Compound 425

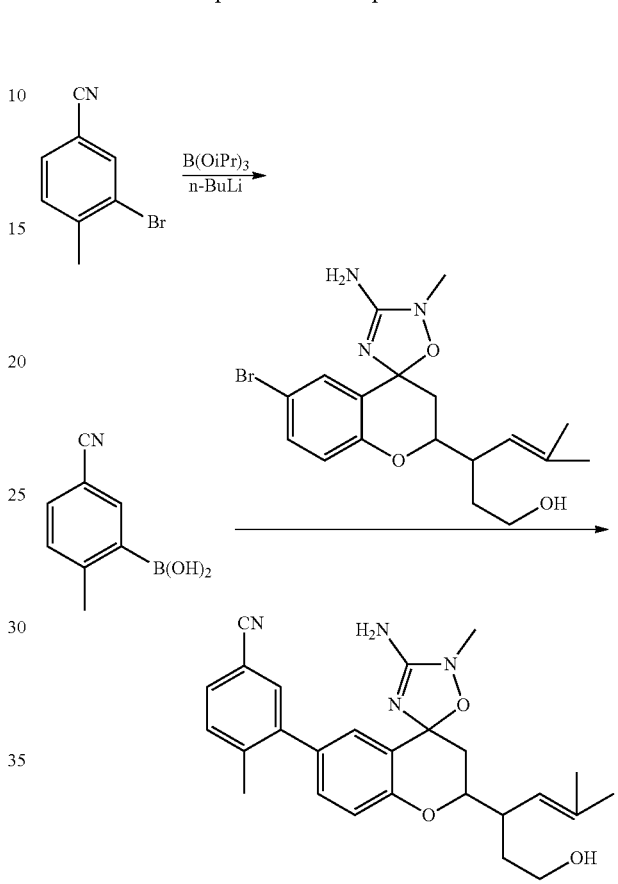

Experimental Data:

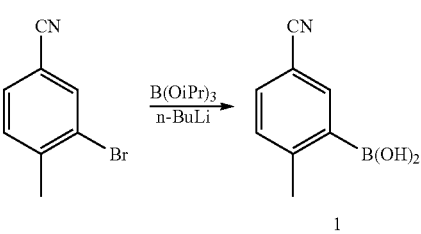

Preparation of Compound 1

A stirred solution of 3-bromo-4-methylbenzonitrile (3.5 g, 17.86 mmol) in dry THF was added n-BuLi (10.71 m L) solution dropwise at −78° C., and the mixture was stirred for 15 minutes, followed by the addition of triisopropyl borate (6.71 g, 35.71 mmol) in one portion. The reaction flask was kept in a cooling bath for 30 min, and room temperature for 3 hours. The solvent was removed, and the residue was dissolved in ether. The solution was washed with 1N HCl solution and water, dried over Na$_2$SO$_4$, filtered, and concentrated in vacuo. The residue was purified by recrystallyzation from the mixture of CH$_2$Cl$_2$ and hexane to give 5-cyano-2-methylphenylboronic acid (800 mg, 20%). $^1$H-NMR (CDCl$_3$ 400 MHz): δ7.50-7.78 (m, 2H), 7.30 (d, 1H), 2.42 (d, 3H).

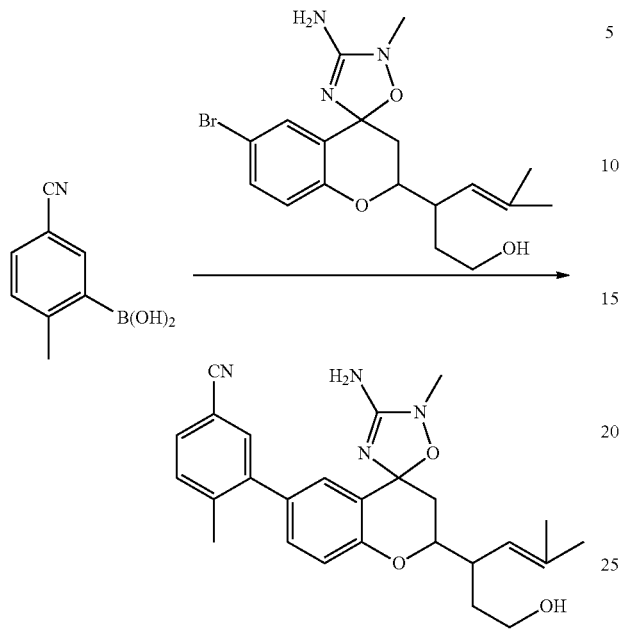

By using the same procedure for compound 434 as described in Example 174, compound 425 (5 mg, 10%) was obtained. $^1$H-NMR (400 MHz CD$_3$OD): δ7.48 (t, 2H), 7.38 (m, 2H), 7.16 m, 1H), 6.88 (d, 1H), 5.06 (d, 1H), 4.89 (d, 1H), 4.03-4.28 (m, 1H), 3.54-3.72 (m, 2H), 3.18-3.32 (m, 3H), 2.72 (m, 1H), 2.15-2.32 (m, 8H), 1.61-1.73 (m, 6H); ESI MS: m/z 447 [M+H]$^+$.

Example 196

Preparation of Compound 292

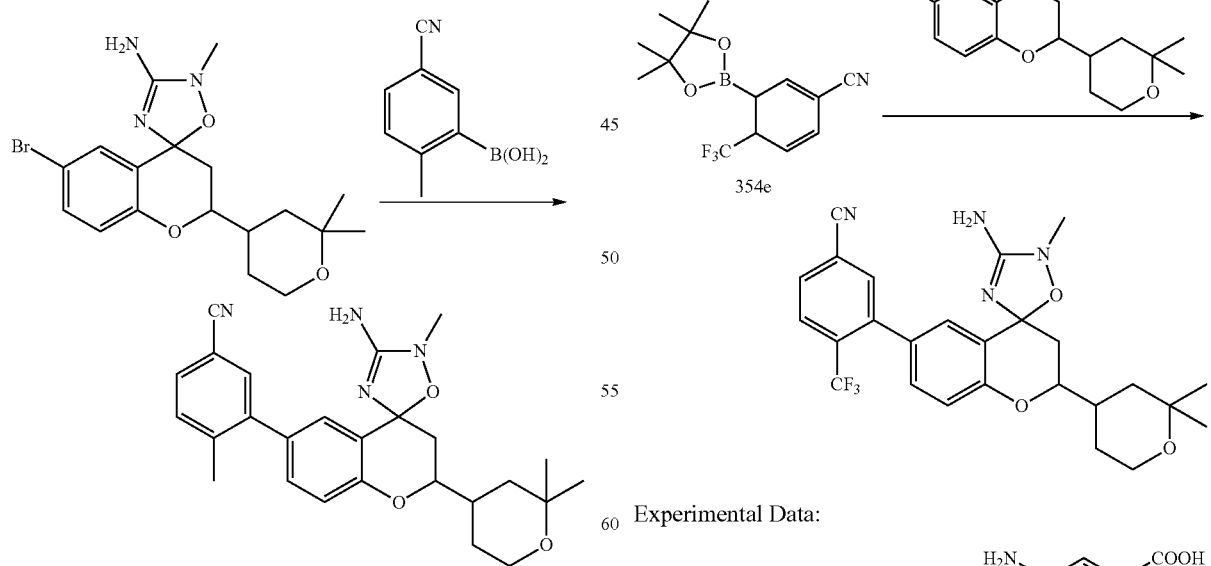

By using the same procedure as compound 434 as described in Example 174, compound 292 (5 mg, 10%) was obtained. $^1$H-NMR (400 MHz CD$_3$OD): δ7.54-7.62 (m, 1H), 7.52 (d, 1H), 7.45 (d, 1H), 7.32-7.38 (m, 1H), 7.00 (t, 1H), 4.05 (d, 1H), 3.76 (m, 2H), 3.36 (s, 3H), 2.63 (d, 1H), 2.41- 2.58 (m, 0.4H), 2.31 (s, 3H), 2.11-2.27 (m, 1H), 2.04 (t, 1H), 1.82-1.92 (m, 1H), 1.61-1.69 (m, 1H), 1.40-1.52 (m, 1H), 1.34 (t, 1H), 1.22-1.31 (m, 6H); ESI MS: m/z 447 [M+H]$^+$.

Example 197

Preparation of Compound 354

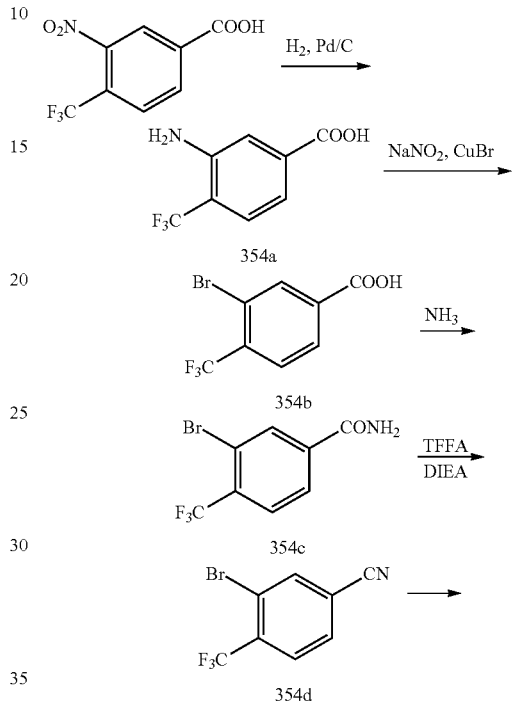

Experimental Data:

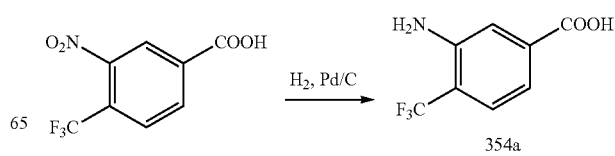

Preparation of Compound 354a

A solution of 3-nitro-4-(trifluoromethyl)benzoic acid (10 g, 43 mmol) in EtOH (100 mL) was added Pd/C (1 g, 10%). The reaction was carried under H$_2$ at room temperature overnight. The solution was filtered, and the filtrate was concentrated to give the compound 354a (10.2 g, crude). $^1$H NMR (400 MHz DMSO-d$_6$): δ7.42 (s, 2H), 7.08 (s, 1H), 5.82 (s, 2H).

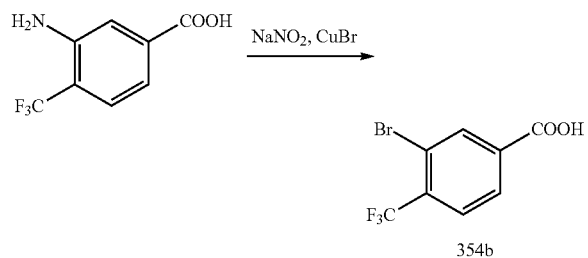

Preparation of Compound 354b

3-Amino-4-(trifluoromethyl)benzoic acid (10.2 g, 0.05 mol) was dissolved in a solution of 47% HBr (40 mL) in H$_2$O (80 mL). A solution of NaNO$_2$ (4.12 g, 0.06 mol) in H$_2$O (40 mL) was added dropwise at 0° C. After being stirred for 30 minutes, the mixture was added the solution of CuBr (12.16 g, 0.085 mol) in a mixture of HBr (40 mL) and H$_2$O (60 mL) at 0° C. and heated at 75° C. for 2 h, treated with 20% NaOH until PH>10. The resulting copper salts were removed by filtration. The mixture was acidified to PH=1 with HCl solution, extracted with DCM, dried over Na$_2$SO$_4$, filtered, and concentrated to give the crude compound 354b (9.4 g, 70%). $^1$H NMR (400 MHz DMSO-d$_6$): δ8.27 (m, 1H), 8.09 (m, 1H), 7.98 (d, 1H).

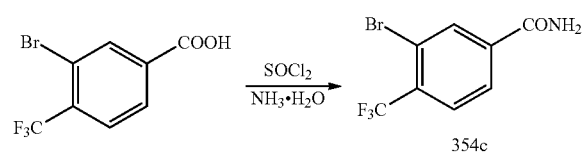

Preparation of Compound 354c

A solution of 3-bromo-4-(trifluoromethyl)benzoic acid (9.4 g, 35 mmol) in SOCl$_2$ (60 mL) was refluxed for 2 hours. After removal of the extra SOCl$_2$, NH$_3$·H$_2$O (40 mL) was added dropwise at −50° C., and the mixture was stirred at room temperature overnight. The mixture was concentrated, added H$_2$O, extracted with DCM. The organic layer was dried and concentrated to give the compound 354c (10.2 g, crude).

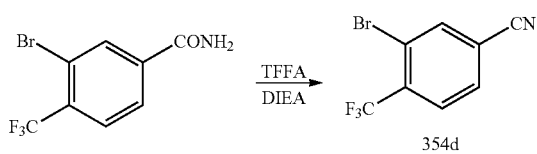 [SMILES: NC(=O)c1ccc(C(F)(F)F)c(Br)c1 ; "TFFA" ; N#Cc1ccc(C(F)(F)F)c(Br)c1]

Preparation of Compound 354d

To a solution of 3-bromo-4-(trifluoromethyl)benzamide (5 g. 18.7 mmol) in DCM (50 mL) was added TFAA (11.75 g, 56 mmol) and DIEA (12 g, 94 mmol) at 0° C., and the mixture was stirred at ° C. for 2 hour. The solution was washed by 1 N HCl, water and brine, dried, and concentrated, the residue was purified by chromatography to afford the compound 354d (2.3 g, 49%). $^1$H NMR (400 MHz CDCl$_3$): δ7.94 (s, 1H), 7.73 (t, 1H), 7.66 (t, 1H).

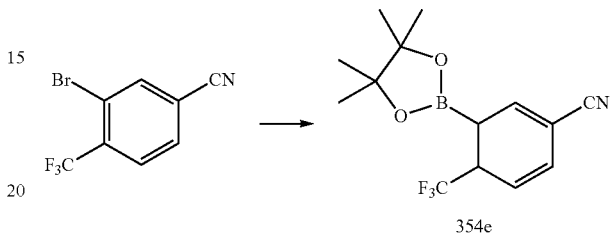

Preparation of Compound 354e

To a solution of 3-bromo-4-(trifluoromethyl)benzonitrile (288 mg, 0.91 mmol) in 1,4-dioxane (8 mL) was added 4,4,4',4',5,5,5',5'-octamethyl-2,2'-bi(1,3,2-dioxaborolane) (254 mg, 1 mmol), KOAc (268 mmol, 2.74 mmol) and Pd(dppf)Cl$_2$ under N$_2$. The reaction mixture was heated at 100° C. in microwave for 1 hour, and filtered. The filtration was concentrated, and the residue was purified by preparative TLC to afford the compound 354e (83 mg, 31%). $^1$H NMR (400 MHz CDCl$_3$): δ7.97 (s, 1H), 7.72 (m, 2H), 1.30 (s, 12H).

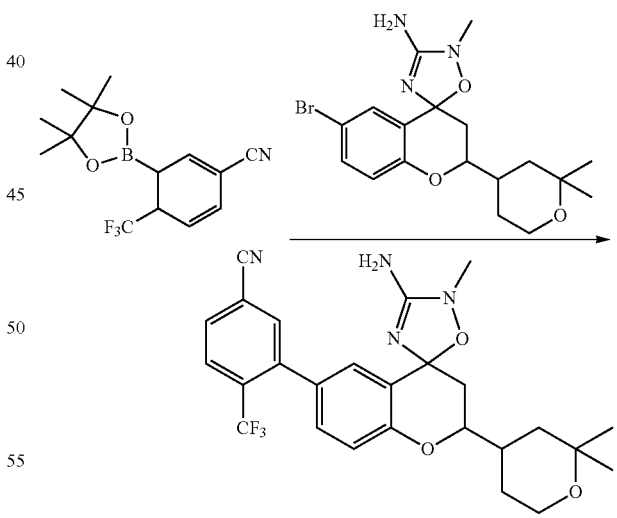

Preparation of Compound 354

By using the same procedure for compound 434 as described in Example 174, compound 354 (5.12 mg, 21%) was obtained. $^1$H NMR (400 MHz CD$_3$OD): δ7.98 (m, 2H), 7.77 (s, 1H), 7.63 (m, 1H), 7.42 (m, 1H), 7.02 (m, 1H), 4.12 (m, 1H), 3.79 (m, 2H), 3.48 (s, 3H), 2.71 (d, 1H), 2.51 (m, 1H), 2.24 (m, 1H), 2.07 (t, 1H), 1.95 (m, 1H), 1.68 (m, 1H), 1.49 (m, 2H), 1.38 (d, 6H); ESI MS: m/z 501 [M+H]⁺.

Example 198

Preparation of Compound 430

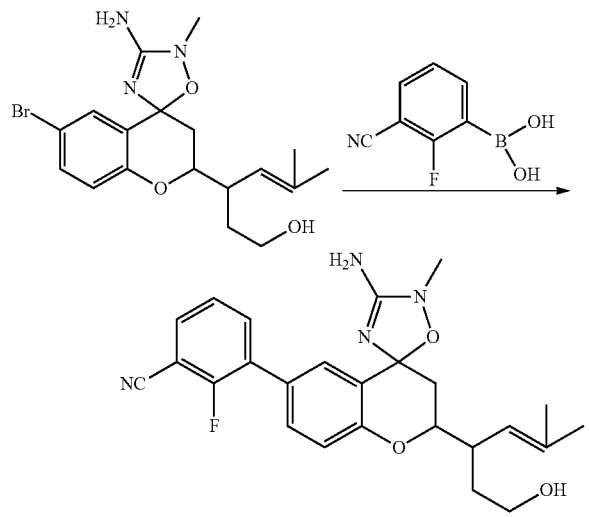

Preparation of Compound 430

By using the same strategy for compound 434 as described in Example 174, compound 430 (6.1 mg, 12%) was obtained. ¹H-NMR (400 MHz CD₃OD): δ7.68 (m, 3H), 7.46 (m, 1H), 7.32 (m, 1H), 6.92 (m, 1H), 5.02 (m, 1H), 4.38 (m, 1H), 4.21 (m, 0.5H), 3.98 (m, 0.5H), 3.52 (m, 1H), 3.41 (m, 1H), 3.24 (m, 3H), 2.78 (m, 1H), 2.48 (m, 1H), 1.75-2.09 (m, 2H), 1.65 (m, 6H), 1.45 (m, 1H); ESI MS: m/z 451 [M+H]⁺.

Example 199

Preparation of Compounds 312 and 306

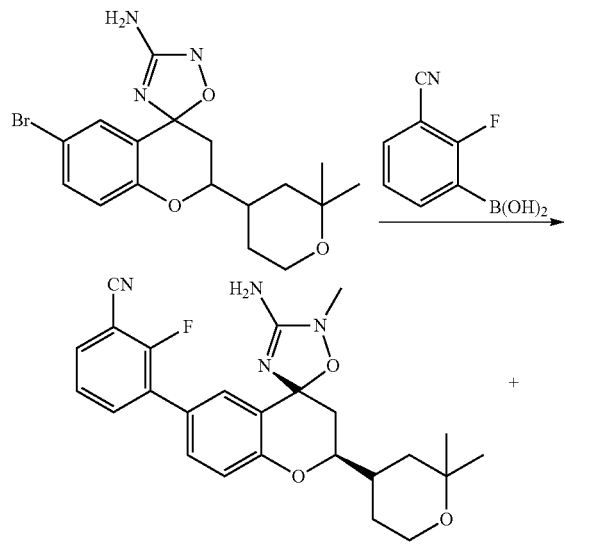

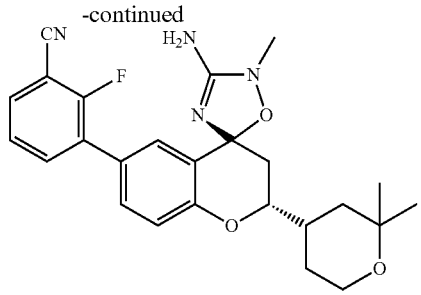

By using the same synthetic strategy for compound 434 as described in Example 174, compound 312 and compound 306 (5.50 mg, 25%) were obtained.

compound 312: ¹H-NMR (400 MHz CD₃OD): δ7.82-7.84 (d, 2H), 7.77-7.80 (d, 1H), 7.70-7.73 (t, 1H), 7.56-7.60 (d, 1H), 7.40-7.42 (t, 1H), 7.02-7.06 (t, 1H), 4.05-4.08 (t, 1H), 3.72-3.77 (m, 2H), 3.28-3.39 (m, 3H), 2.65-2.69 (m, 1H), 2.17-2.18 (m, 1H), 2.01-2.02 (m, 1H), 1.83-1.86 (m, 1H), 1.62-1.65 (m, 1H), 1.44-1.48 (m, 1H), 1.33-1.36 (m, 1H), 1.24-1.30 (m, 6H); ESI MS: m/z 451 [M+H]⁺.

compound 306: ¹H-NMR (400 MHz CD₃OD): δ7.82-7.84 (d, 2H), 7.77-7.80 (d, 1H), 7.70-7.73 (t, 1H), 7.56-7.60 (d, 1H), 7.40-7.42 (t, 1H), 7.02-7.06 (t, 1H), 4.05-4.08 (t, 1H), 3.73-3.78 (m, 2H), 3.33-3.46 (m, 3H), 2.65-2.69 (m, 1H), 2.17-2.18 (m, 1H), 2.01-2.02 (m, 1H), 1.83-1.86 (m, 1H), 1.62-1.65 (m, 1H), 1.44-1.48 (m, 1H), 1.33-1.36 (m, 1H), 1.24-1.30 (m, 6H); ESI MS: m/z 451 [M+H]⁺.

Example 200

Preparation of Compound 257

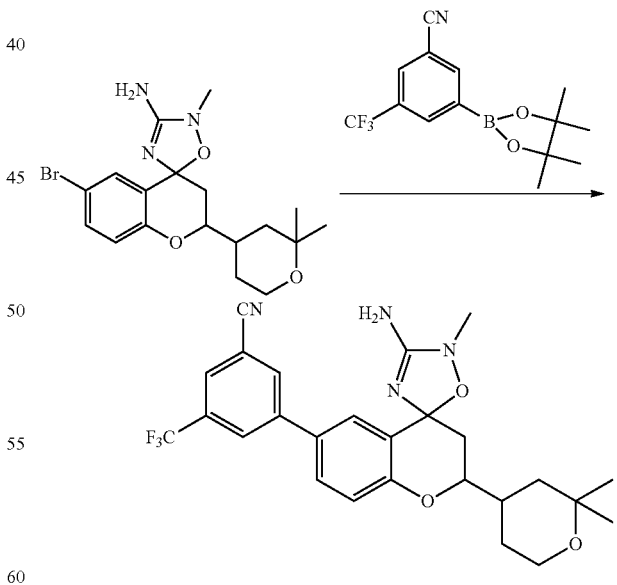

By using the same synthetic strategy for compound 434 as described in Example 174, compound 257 (0.5 mg, 3%) was obtained. ¹H-NMR (400 MHz CD₃OD): δ8.31 (s, 1H), 8.22 (s, 1H), 8.05 (s, 1H), 7.73-7.81 (d, 1H), 7.08-7.11 (d, 1H), 4.08-4.12 (m, 2H), 3.74-3.82 (m, 2H), 3.44-3.49 (m, 3H), 2.66-2.74 (m, 1H), 2.13-2.31 (m, 2H), 1.96-2.08 (t, 1H), 1.80-1.92 (m, 1H), 1.62-1.69 (m, 1H), 1.38-1.51 (m, 1H), 1.22-1.30 (m, 6H); ESI MS: m/z 501 [M+H]+.

Example 201

Preparation of Compound 300

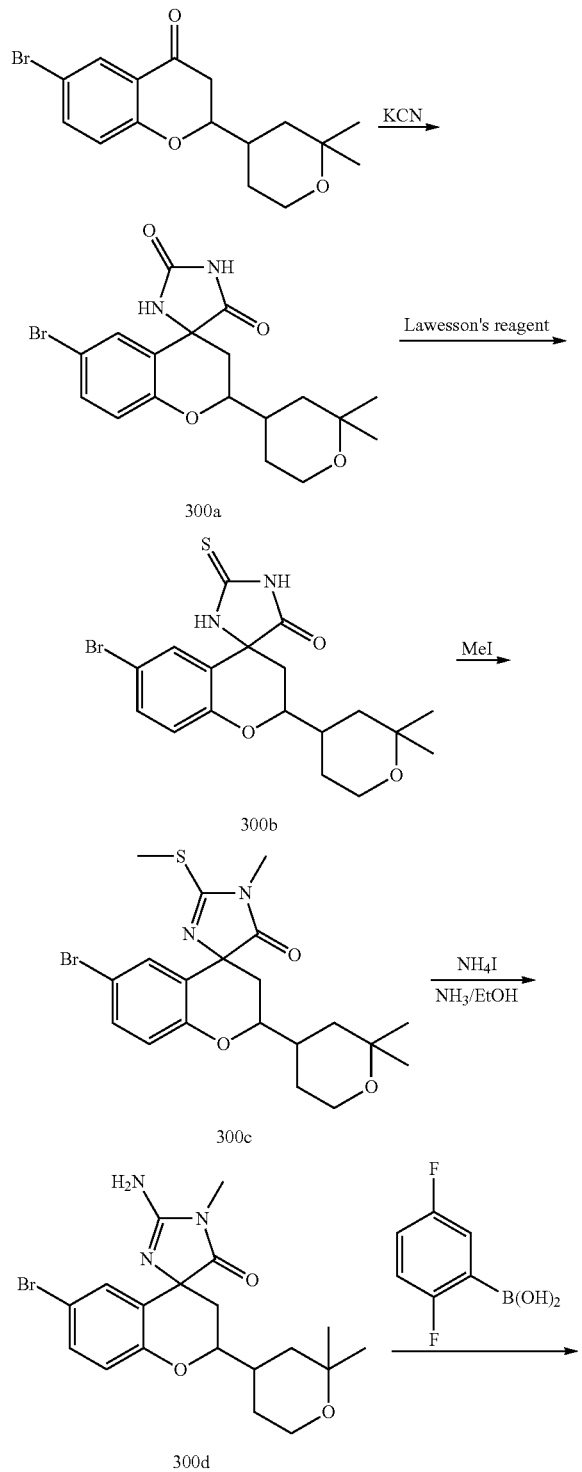

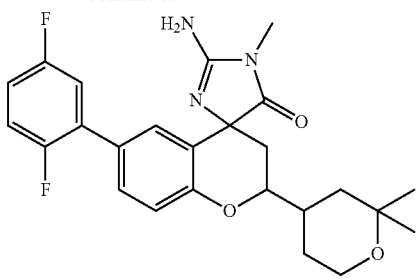

Experimental Data:

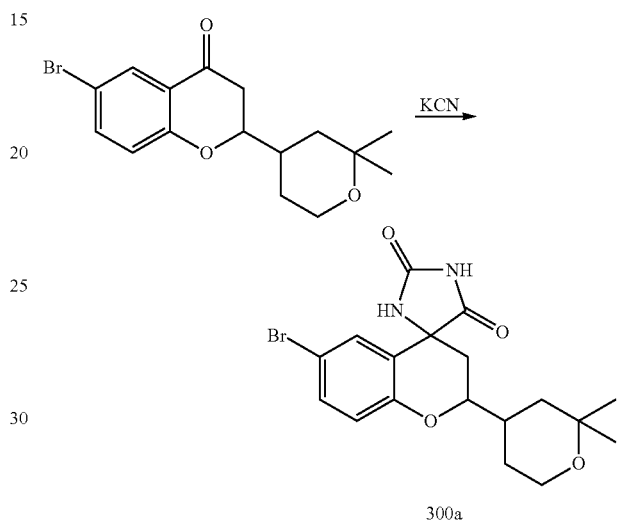

Preparation of Compound 300a

A glass tube was charged with a mixture of 6-bromo-2-(2,2-dimethyltetrahydro-2H-pyran-4-yl)chroman-4-one (3 g, 8.88 mmol), KCN (1.14 g, 17.76 mmol), and (NH$_4$)$_2$CO$_3$ (5.96 g, 62.12 mmol). After formamide (20 mL) was added to fill the tube completely, the mixture was heated at 70° C. for 2 days and at 110° C. for 1 day, cooled, and poured into ice. After acidification with concentrated HCl solution, the precipitate was filtered, washed with water, solved in ethyl acetate, dried over Na$_2$SO$_4$, and filtered. The filtrate was concentrated in vacuo to give the compound 300a (2.6 g, 70%). $^1$H-NMR (400 MHz CDCl$_3$): δ8.61 (br, 1H, CONH), 7.20-7.29 (m, 2H), 6.71-6.74 (m, 1H), 6.03-6.05 (m, 1H), 4.47-4.52 (m, 1H), 3.66-3.77 (m, 1H), 3.58-3.64 (m, 1H), 2.15-2.18 (m, 1H), 1.89-1.98 (m, 1H), 1.64-1.76 (m, 2H), 1.30-1.50 (m, 2H), 1.14-1.21 (m, 6H).

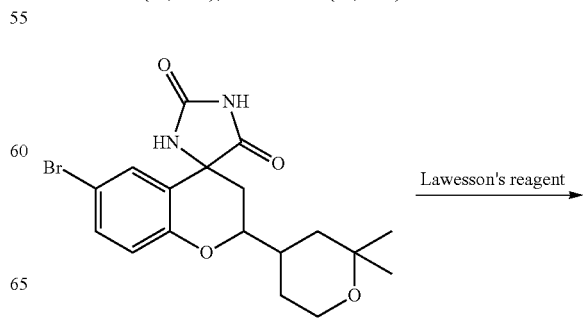

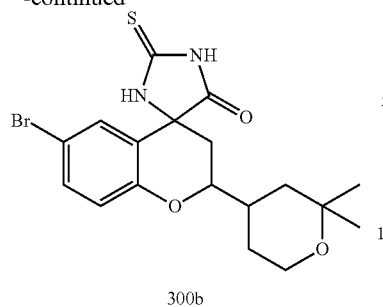

300b

Preparation of Compound 300b

A suspension of 6-bromo-2-(2,2-dimethyltetrahydro-2H-pyran-4-yl)spiro[chroman-4,4'-imidazolidine]-2',5'-dione (2.6 g, 6.37 mmol) and Lawesson's Reagent (2.574 g, 6.36 mmol) in dry 1,4-dioxane (36 mL) was heated at 120° C. for 30 minutes in microwave. The mixture was concentrated in vacuo and the residue was purified by column chromatography to give the compound 300b (1.4 g, 50%).

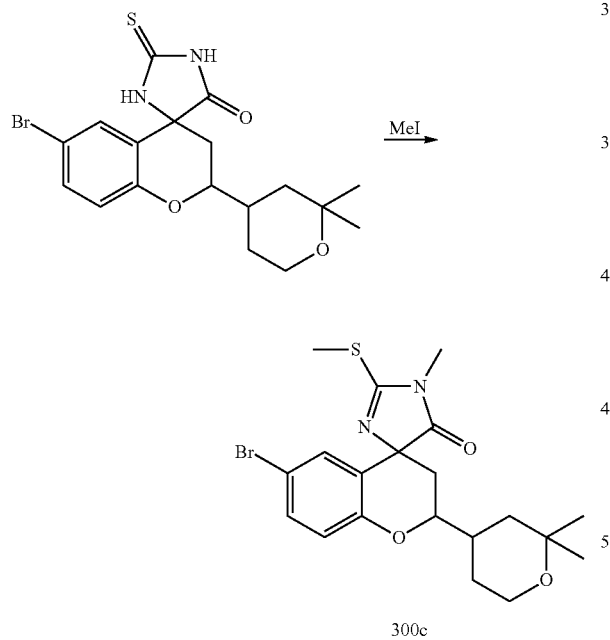

300c

Preparation of Compound 300c

To a solution of 6-bromo-2-(2,2-dimethyltetrahydro-2H-pyran-4-yl)-2'-thioxospiro-[chroman-4,4'-imidazolidin]-5'-one (1.4 g, 3.3 mmol) in MeOH (70 mL) was added NaOH (0.6 N, 12 mL) and MeI (12 mL). The reaction mixture was refluxed for 60 min, and concentrated in vacuo, the residue was purified by column chromatography to give the compound 300c (200 mg, 13%).

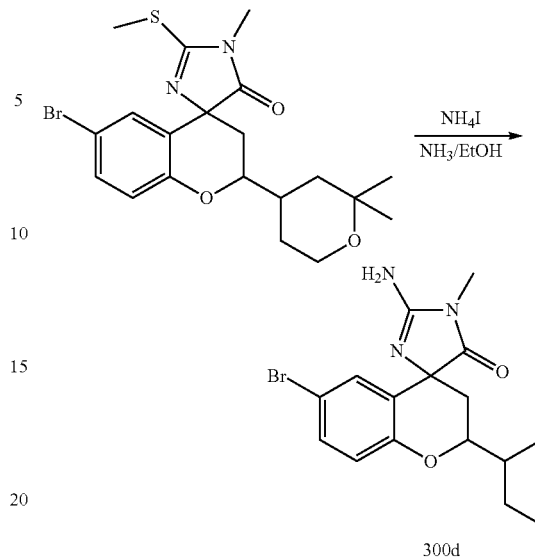

300d

Preparation of Compound 300d

A solution of 6-bromo-2-(2,2-dimethyltetrahydro-2H-pyran-4-yl)-1'-methyl-2'-(methylthio)spiro[chroman-4,4'-imidazol]-5'(1'H)-one (200 mg, 0.44 mmol), NH$_4$I (200 mg) in NH$_3$/EtOH (15 mL, 1 N) was heated at 120° C. in a tube in a microwave reactor for 2.5 h. After cooling, the mixture was concentrated in vacuum to afford the compound 300d (100 mg, 50%).

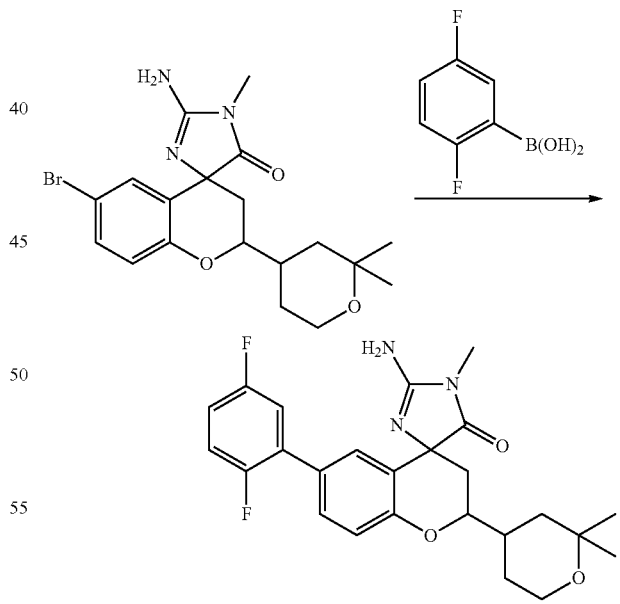

Preparation of Compound 300

By using the same synthetic strategy for compound 434 as described in Example 174, compound 300 (1.96 mg, 10%) was obtained. $^1$H-NMR (400 MHz CDCl$_3$): δ7.49 (d, 1H), 7.35 (d, 1H), 7.17 (m, 2H), 7.06 (m, 2H), 4.58 (m, 1H), 3.79

(d, 2H), 3.28 (s, 1.3H), 3.08 (d, 1.5H), 2.47 (m, 1H), 2.16 (m, 2H), 1.92 (t, 1H), 1.63 (m, 1H), 1.42 (m, 2H), 1.26 (m, 6H); ESI MS: m/z 444 [M+H]$^+$.

Example 202

Preparation of Compounds 431 and 254

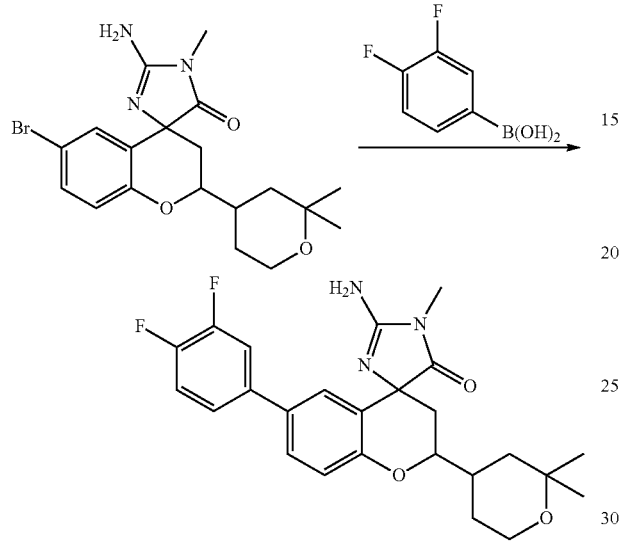

By using the same synthetic strategy for compound 434 as described in Example 174, compounds 431 and 254 were obtained.

compound 431: (2.19 mg, 10%), $^1$H-NMR (400 MHz CD$_3$OD): δ7.52 (d, 1H), 7.48 (t, 1H), 7.52 (d, 1H), 7.48 (t, 1H), 7.40 (s, 1H), 7.32 (t, 1H), 7.28 (t, 1H), 7.00 (t, 1H), 4.55-4.57 (m, 1H), 3.76 (d, 2H), 3.07 (d, 3H), 2.43 (d, 1H), 2.06-2.17 (m, 2H), 1.85-1.91 (m, 1H), 1.57-1.66 (m, 1H), 1.32-1.45 (m, 2H), 1.22-1.31 (m, 6H); ESI MS: m/z 456 [M+H]$^+$.

compound 254 (7.53 mg, 35%), $^1$H-NMR (400 MHz MeOD): 7.56 (d, 1H), 7.48 (t, 1H), 7.40 (s, 1H), 7.32 (t, 1H), 7.28 (t, 1H), 7.00 (t, 1H), 4.53-4.56 (m, 1H), 3.76 (d, 2H), 3.24 (s, 3H), 2.43 (d, 1H), 2.10-2.16 (m, 2H), 1.88-1.91 (m, 1H), 1.58-1.60 (m, 1H), 1.38-1.44 (m, 2H), 1.22-1.31 (m, 6H); ESI MS: m/z 456 [M+H]$^+$.

Example 203

Preparation of Compounds 417 and 190

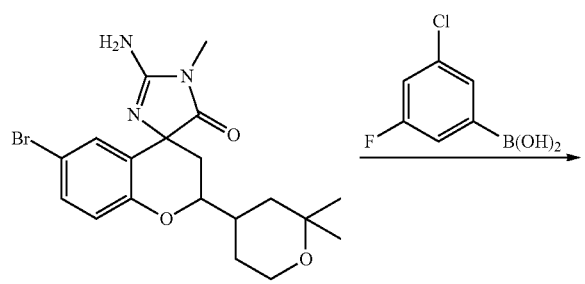

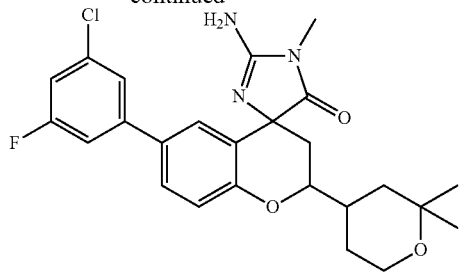

By using the same synthetic strategy for compound 434 as described in Example 174, two compounds were obtained.

compound 417 (1.59 mg, 15%), $^1$H-NMR (400 MHz CD$_3$OD): δ7.59 (d, 1H), 7.43 (d, 2H), 7.32 (d, 1H), 7.12 (d, 1H), 7.03 (d, 1H), 4.56-4.67 (m, 1H), 3.76 (d, 2H), 3.09 (d, 3H), 2.43 (d, 1H), 2.08-2.15 (m, 2H), 1.87-1.91 (m, 1H), 1.59-1.62 (m, 1H), 1.32-1.43 (m, 2H), 1.21-1.26 (m, 6H); ESI MS: m/z 472 [M+H]$^+$.

compound 190 (3.97 mg, 20%), $^1$H-NMR (400 MHz CD$_3$OD): δ7.59 (d, 1H), 7.43 (d, 2H), 7.32 (d, 1H), 7.12 (d, 1H), 7.03 (d, 1H), 4.54-4.57 (m, 1H), 3.76 (d, 2H), 3.22 (s, 3H), 2.43 (d, 1H), 2.06-2.17 (m, 2H), 1.84-1.93 (m, 1H), 1.61-1.69 (m, 1H), 1.36-1.49 (m, 2H), 1.22-1.31 (m, 6H); ESI MS: m/z 472 [M+H]$^+$.

Example 204

Preparation of Compound 194

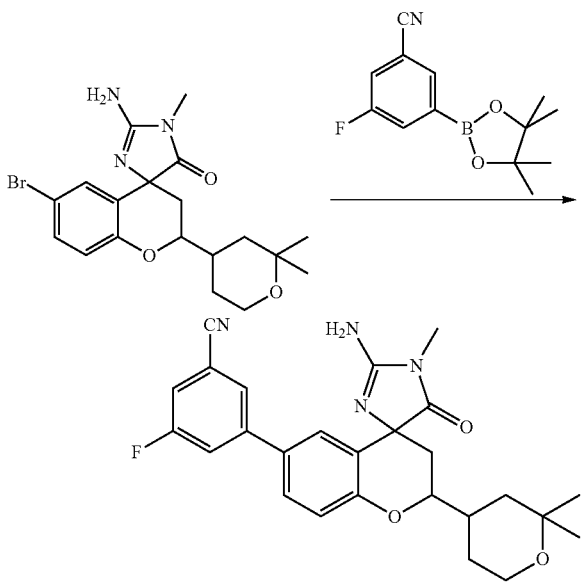

By using the same synthetic strategy for compound 434 as described in Example 174, compound 194 (4.61 mg, 21%) was obtained. $^1$H-NMR (400 MHz CD$_3$OD): δ7.71-7.74 (m, 1H), 7.54-7.64 (m, 2H), 7.38-7.46 (m, 2H), 6.97-7.00 (m, 1H), 4.35-4.51 (m, 0.6H), 3.66 (m, 0.4H), 3.16 (m, 2H), 2.93 (m, 1H), 2.32 (m, 1H), 2.06-2.20 (m, 2H), 1.70-1.90 (m, 2H), 1.31-1.60 (m, 2H), 1.15-1.18 (m, 2H); ESI MS: m/z 463 [M+H]$^+$.

Example 205

Preparation of Compound 229

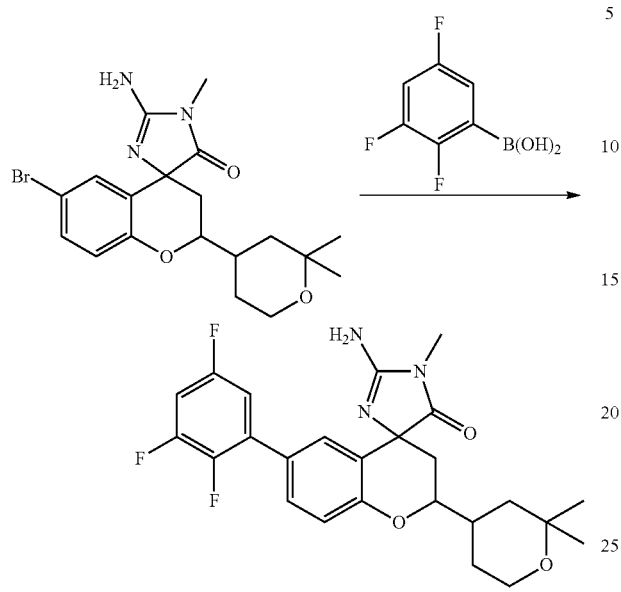

By using the same synthetic strategy for compound 434 as described in Example 174, compound 229 (3.11 mg, 15%) was obtained. $^1$H-NMR (400 MHz CD$_3$OD): δ7.51 (d, 1H), 7.40 (s, 1H), 7.03-7.11 (m, 3H), 4.56-4.59 (m, 1H), 3.75 (d, 2H), 3.24 (s, 3H), 2.43 (d, 1H), 2.08-2.27 (m, 2H), 1.84-1.93 (m, 1H), 1.52-1.62 (m, 1H), 1.32-1.45 (m, 2H), 1.22-1.27 (m, 6H); ESI MS: m/z 474 [M+H]$^+$.

Example 206

Preparation of Compounds 452 and 241

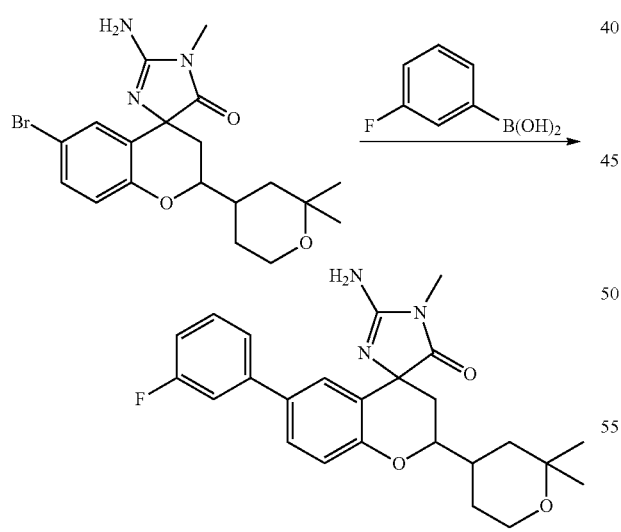

By using the same synthetic strategy for compound 434 as described in Example 174, compound 452 and compound 241 (3.57 mg, 18%) were obtained.

compound 452: $^1$H-NMR (400 MHz CD$_3$OD): δ7.54 (d, 1H), 7.25-7.40 (m, 4H), 7.01-7.04 (m, 3H), 4.55-4.56 (m, 1H), 3.74 (d, 2H), 3.06 (d, 3H), 2.43 (d, 1H), 2.11 (m, 2H), 1.84-1.93 (m, 1H), 1.61-1.64 (m, 1H), 1.34-1.42 (m, 2H), 1.22-1.31 (m, 6H); ESI MS: m/z 438 [M+H]$^+$.

compound 241: $^1$H-NMR (400 MHz CD$_3$OD): δ7.54 (d, 1H), 7.29-7.40 (m, 4H), 7.00-7.04 (m, 2H), 4.52-4.60 (m, 1H), 3.79 (d, 2H), 3.26 (s, 3H), 2.43 (d, 1H), 2.09-2.20 (m, 2H), 1.86-1.93 (m, 1H), 1.60-1.65 (m, 1H), 1.36-1.49 (m, 2H), 1.22-1.31 (m, 6H); ESI MS: m/z 438 [M+H]$^+$.

Example 207

Preparation of Compounds 372 and 231

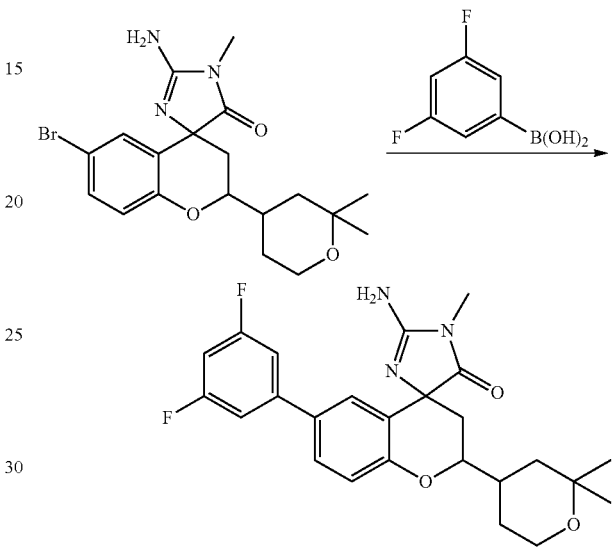

By using the same synthetic strategy for compound 434 as described in Example 174, compound 372 (0.86 mg, 4%) and compound 231 (1.25 mg, 5%) were obtained.

compound 372: $^1$H NMR (400 MHz CD$_3$OD): δ7.46-7.77 (m, 2H), 6.89-7.21 (m, 4H), 4.56 (m, 1H), 3.78 (m, 2H), 3.06 (d, 3H), 2.44 (m, 1H), 2.14 (m, 2H), 1.91 (m, 1H), 1.60-1.70 (m, 1H), 1.43 (m, 2H), 1.28 (m, 6H); ESI MS: m/z 456 [M+H]$^+$.

compound 231: $^1$H NMR (400 MHz CD$_3$OD): δ7.53 (m, 1H), 7.38 (m, 1H), 7.18 (m, 2H), 6.96 (m, 1H), 6.75 (m, 1H), 4.47 (m, 0.7H), 3.84 (m, 0.3H), 3.66 (m, 2H), 3.23 (s, 3H), 2.01-2.42 (m, 3H), 1.89 (m, 1H), 1.53 (m, 1H), 1.30-1.36 (m, 2H), 1.17 (m, 6H); ESI MS: m/z 456 [M+H]$^+$.

Example 208

Preparation of Compound 185

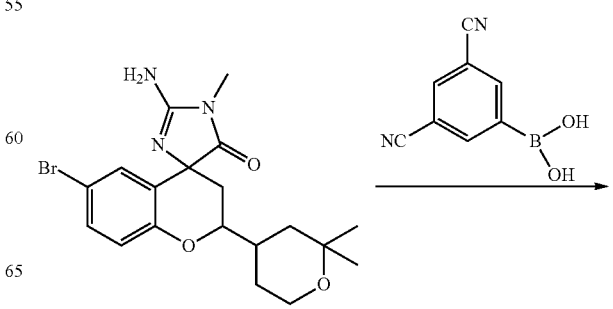

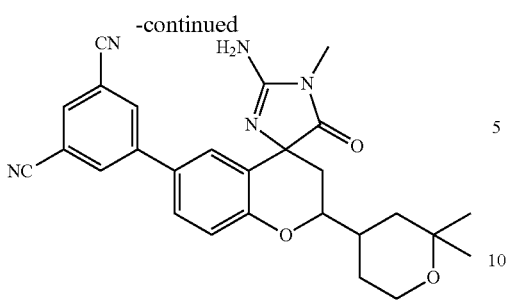

By using the same synthetic strategy for compound 434 as described in Example 174, compound 185 (2.26 mg, 4%) was obtained. $^1$H-NMR (400 MHz CD$_3$OD): δ8.28 (m, 2H), 8.10 (m, 1H), 7.68 (m, 1H), 7.60 (m, 1H), 7.12 (m, 1H), 4.61 (m, 1H), 3.78 (m, 2H), 3.34 (s, 1H), 3.26 (s, 2H), 2.48 (m, 1H), 2.12-2.19 (m, 2H), 1.91 (m, 1H), 1.63 (m, 1H), 1.46 (m, 2H), 1.25 (m, 6H); ESI MS: m/z 470 [M+H]$^+$.

Example 209

Preparation of Compound 200

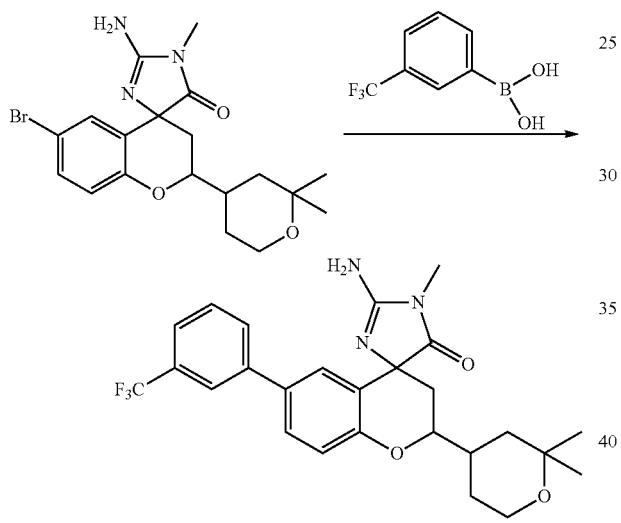

By using the same synthetic strategy for compound 434 as described in Example 174, compound 200 (4.49 mg, 19%) was obtained. $^1$H-NMR (400 MHz CD$_3$OD): δ7.77-7.82 (m, 2H), 7.51-7.63 (m, 3H), 7.35-7.46 (m, 1H), 7.06-7.09 (m, 1H), 4.56-4.60 (m, 0.8H), 3.96 (m, 0.2H), 3.75-3.78 (m, 2H), 3.32 (s, 1H), 3.24 (s, 2H), 2.42-2.48 (m, 1H), 2.12-2.19 (m, 2H), 1.90-1.93 (m, 1H), 1.61-1.65 (m, 1H), 1.37-1.46 (m, 2H), 1.25-1.30 (m, 6H); ESI MS: m/z 488 [M+H]$^+$.

Example 210

Preparation of Compound 197

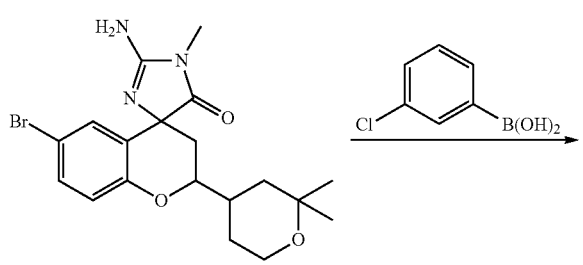

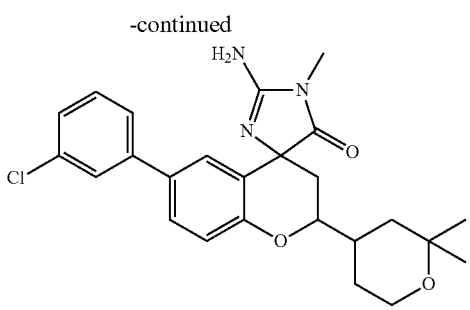

By using the same synthetic strategy for compound 434 as described in Example 174, compound 197 (1.61 mg, 7%) was obtained. $^1$H NMR (400 MHz CD$_3$OD): δ7.54 (m, 2H), 7.46 (m, 1H), 7.38 (m, 2H), 7.30 (m, 1H), 7.02 (m, 1H), 4.56 (m, 1H), 3.76 (m, 2H), 3.24 (s, 3H), 2.46 (m, 1H), 2.12 (m, 2H), 1.90 (m, 1H), 1.62 (m, 1H), 1.44 (m, 1H), 1.38 (m, 1H), 1.27 (s, 3H), 1.23 (s, 3H); ESI MS: m/z 454 [M+H]$^+$.

Example 211

Preparation of Compound 246

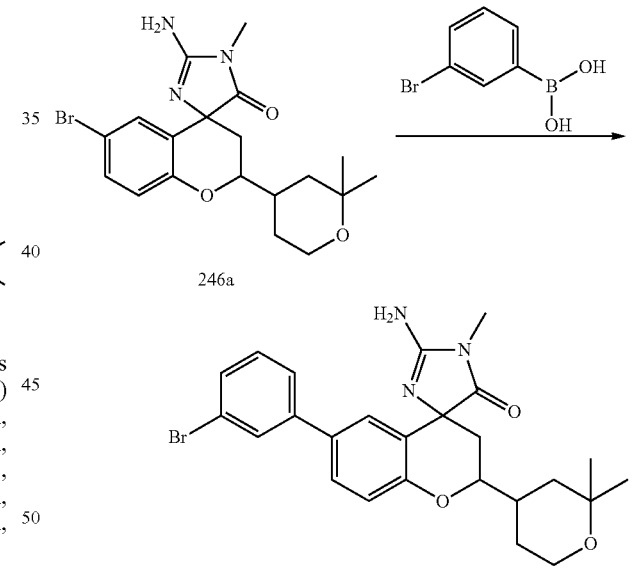

Pd(PPh$_3$)$_4$ (3 mg) under Ar$_2$ was treated sequentially with the compound 246a (20 mg, 0.05 mmol), K$_2$CO$_3$ (2 N, 40 uL) in THF (1 mL), and 3-bromophenylboronic acid (11 mg, 0.1 mmol). The mixture was refluxed overnight, concentrated in vacuo, the residue was purified by preparative TLC and preparative HPLC to give compound 246 (2.0 mg, 7%). $^1$H-NMR (400 MHz CD$_3$OD): δ7.66 (d, 1H), 7.51 (m, 1H), 7.47 (m, 1H), 7.38-7.41 (t, 1H), 7.35-7.39 (d, 1H), 7.24-7.28 (t, 1H), 6.97-7.00 (t, 1H), 4.53-4.56 (m, 1H), 3.70-3.72 (m, 2H), 3.25 (s, 3H), 2.36-2.40 (m, 1H), 2.05-2.12 (m, 2H), 1.84-1.85 (m, 1H), 1.54-1.58 (m, 1H), 1.31-1.38 (m, 2H), 1.19-1.28 (m, 6H); ESI MS: m/z 500 [M+H]$^+$.

Example 212

Preparation of Compound 218

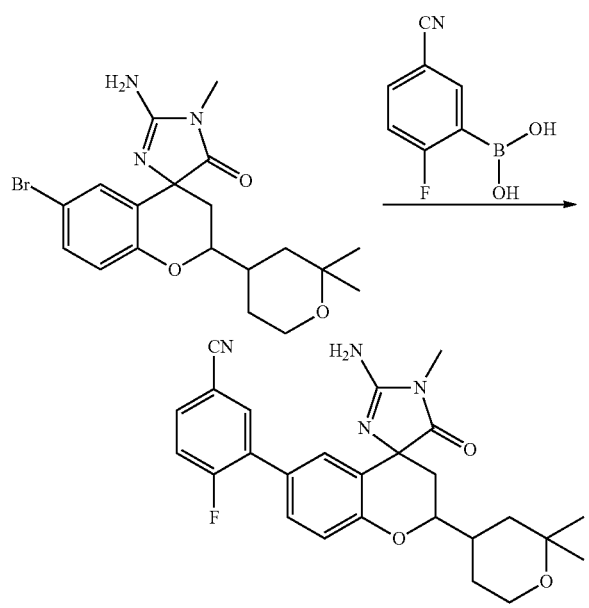

By using the same synthetic strategy for compound 434 as described in Example 174, compound 218 (1.08 mg, 3%) was obtained. $^1$H NMR (400 MHz CD$_3$OD): δ7.86-7.88 (d, 1H), 7.72-7.76 (d, 1H), 7.51-7.53 (m, 1H), 7.35-7.40 (m, 2H), 7.06-7.08 (d, 1H), 3.76-3.79 (m, 2H), 3.23 (s, 2H), 2.40-2.48 (m, 1H), 2.12-2.16 (m, 2H), 1.87-1.96 (m, 1H), 1.60-1.65 (m, 1H), 1.30-1.38 (m, 2H), 1.22-1.28 (m, 6H); ESI MS: m/z 463 [M+H]$^+$.

Example 213

Preparation of Compounds 222 and 437

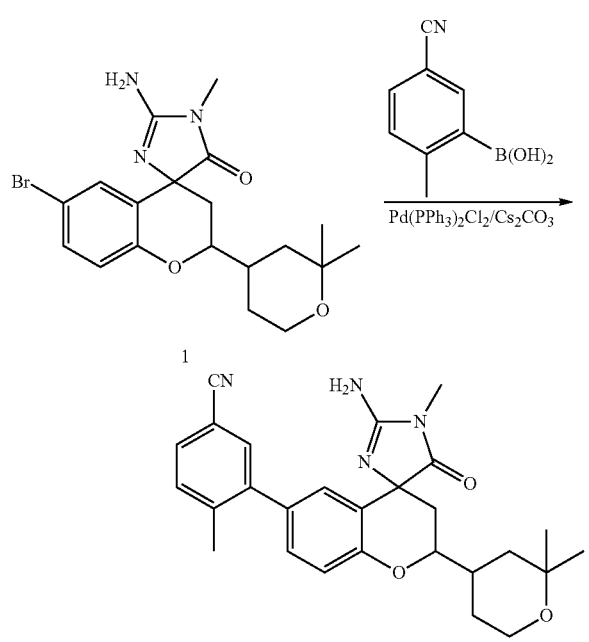

By using the same synthetic strategy for compound 434 as described in Example 174, compound 222 (2.45 mg, 7%) and compound 437 (1.08 mg, 6%) were obtained.

compound 222: $^1$H-NMR (400 MHz CD$_3$OD): δ7.51-7.53 (d, 1H), 7.37-7.43 (m, 2H), 7.20-7.22 (m, 1H), 7.10 (d, 1H), 6.95-7.00 (m, 1H), 4.51-4.54 (m, 1H), 3.70-3.72 (m, 2H), 2.92-3.02 (s, 3H), 2.37-2.47 (m, 1H), 2.21 (m, 3H), 2.04-2.10 (m, 2H), 1.80-1.87 (m, 1H), 1.55-1.58 (m, 1H), 1.38-1.43 (m, 2H), 1.18 (m, 6H); ESI MS: m/z 459 [M+H]$^+$.

compound 437: $^1$H-NMR (400 MHz CD$_3$OD): δ7.51-7.52 (d, 1H), 7.34-7.40 (m, 2H), 7.18-7.22 (m, 1H), 7.07 (s, 1H), 6.94-7.00 (m, 1H), 4.50 (m, 0.7H), 3.85 (m, 0.3H), 3.64-3.70 (m, 2H), 3.12 (s, 3H), 2.39 (m, 0.8H), 2.23 (m, 0.4H), 2.16-2.20 (m, 3H), 2.03-2.07 (m, 2H), 1.79-1.85 (m, 1H), 1.52-1.57 (m, 1H), 1.25-1.35 (m, 2H), 1.17 (m, 6H); ESI MS: m/z 459 [M+H]$^+$.

Example 214

Preparation of Compound 284

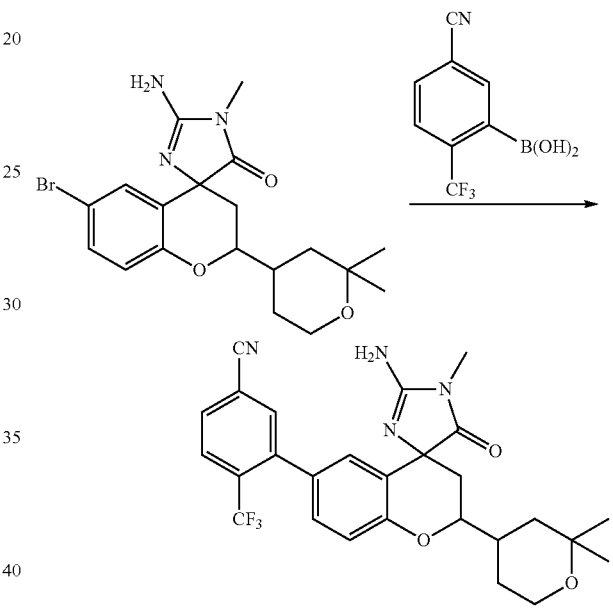

By using the same synthetic strategy for compound 434 as described in Example 174, compound 284 (3.89 mg, 16%) was obtained. $^1$H NMR (400 MHz CD$_3$OD): δ7.88-7.95 (m, 2H), 7.68-7.71 (m, 1H), 7.27-7.30 (m, 1H), 7.00-7.08 (m, 2H), 4.55-4.60 (m, 1H), 3.70-3.79 (m, 2H), 3.19 (s, 3H), 2.42-2.47 (m, 1H), 2.10-2.29 (m, 2H), 1.82-1.91 (m, 1H), 1.60-1.65 (m, 1H), 1.37-1.43 (m, 2H), 1.27-1.30 (m, 6H); ESI MS: m/z 513 [M+H]$^+$.

Example 215

Preparation of Compound 212

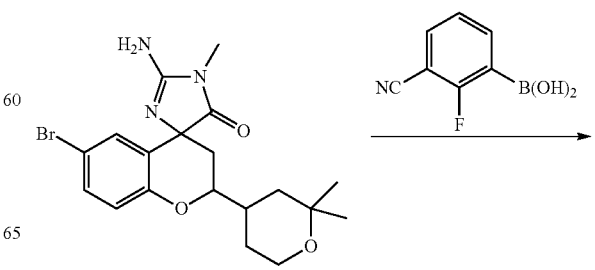

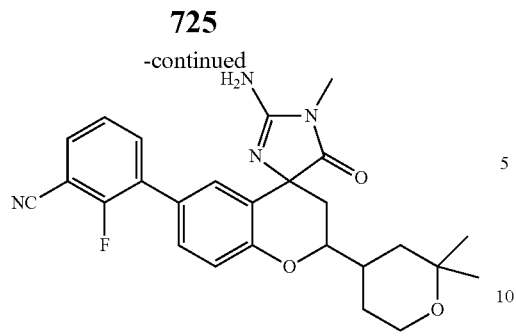

By using the same synthetic strategy for compound 434 as described in Example 174, compound 212 (2.02 mg, 9%) was obtained. $^1$H NMR (400 MHz CD$_3$OD): δ7.70-7.80 (m, 2H), 7.50-7.52 (m, 1H), 7.31-7.44 (m, 2H), 7.09-7.11 (m, 1H), 4.59-4.62 (m, 1H), 3.78-3.80 (m, 2H), 3.26 (s, 3H), 2.46-2.50 (m, 1H), 2.14-2.21 (m, 2H), 1.92-1.95 (m, 1H), 1.62-1.64 (m, 1H), 1.35-1.48 (m, 2H), 1.26-1.32 (m, 6H); ESI MS: m/z 463 [M+H]$^+$.

Example 216

Preparation of Compound 213

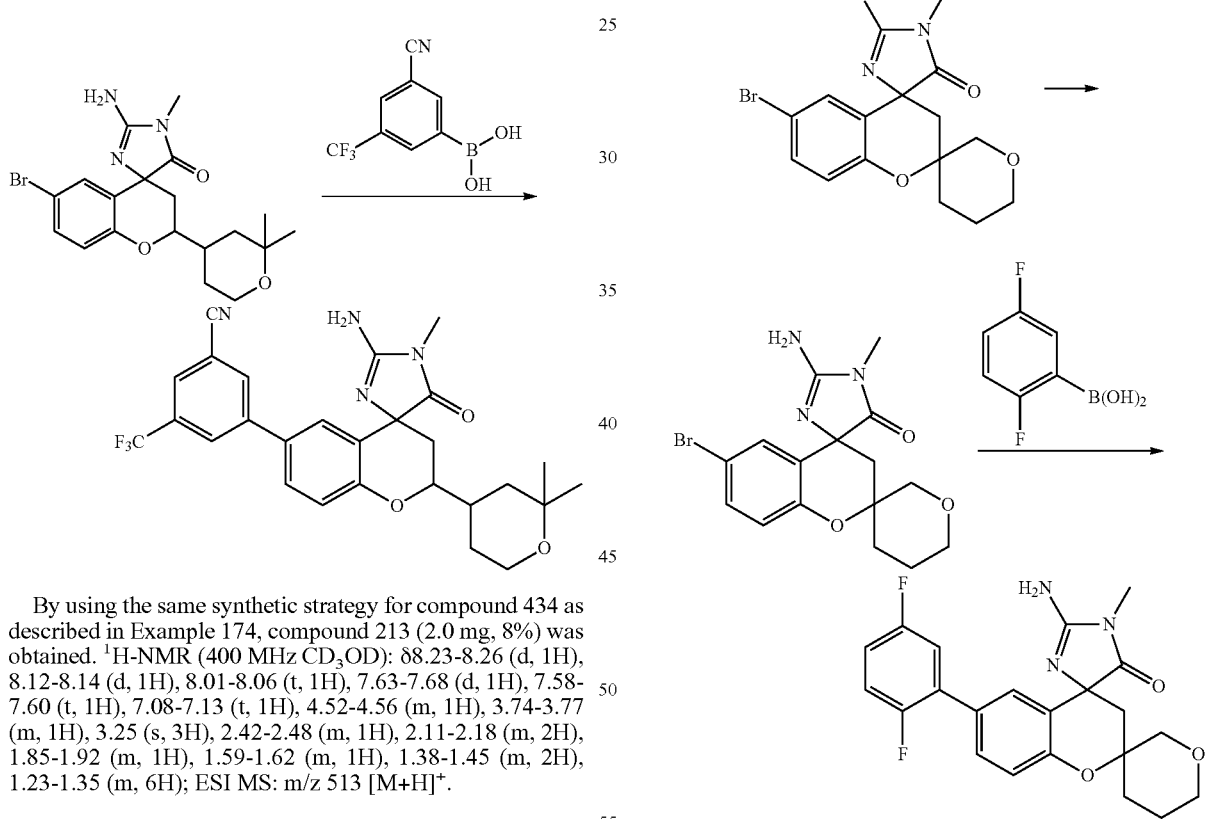

By using the same synthetic strategy for compound 434 as described in Example 174, compound 213 (2.0 mg, 8%) was obtained. $^1$H-NMR (400 MHz CD$_3$OD): δ8.23-8.26 (d, 1H), 8.12-8.14 (d, 1H), 8.01-8.06 (t, 1H), 7.63-7.68 (d, 1H), 7.58-7.60 (t, 1H), 7.08-7.13 (t, 1H), 4.52-4.56 (m, 1H), 3.74-3.77 (m, 1H), 3.25 (s, 3H), 2.42-2.48 (m, 1H), 2.11-2.18 (m, 2H), 1.85-1.92 (m, 1H), 1.59-1.62 (m, 1H), 1.38-1.45 (m, 2H), 1.23-1.35 (m, 6H); ESI MS: m/z 513 [M+H]$^+$.

Example 217

Preparation of Compound 332

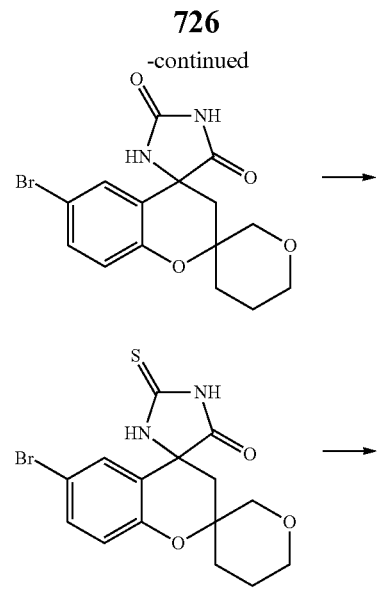

Experimental Data:

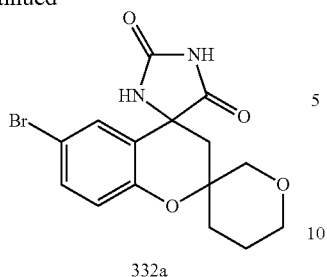

332a

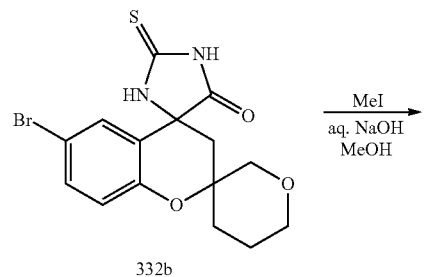

332b

Preparation of Compound 332a

A steel autoclave was charged with a mixture of 6-bromo-2',4',5',6'-tetrahydrospiro[chroman-2,3'-pyran]-4-one (8.6 g, 28.86 mmol), KCN (3.75 g, 57.72 mmol) and $(NH_4)_2CO_3$ (19.4 g, 202.02 mmol) in formamide (80 mL). The mixture was stirred at 70° C. for 2 days and at 110° C. for 1 day. The reaction mixture was then cooled to room temperature and poured into ice (80 g). The solution was acidified with concentrated HCl solution to pH=1, and filtered. The filter cake was washed with water (15 mL×2), and dissolved in ethyl acetate (200 mL). After drying over $Na_2SO_4$ and concentrated in vacuo, the pure compound 332a (8 g, 80%) was obtained. $^1$H-NMR (CDCl$_3$ 400 MHz): δ7.30-7.26 (m, 1H), 7.16 (d, 1H), 6.83-6.69 (m, 1H), 3.79 (m, 1H), 3.61 (m, 1H), 3.49 (m, 2H), 2.42 (m, 1H), 2.06 (d, 1H), 1.88-1.73 (m, 2H), 1.67-1.51 (m, 2H).

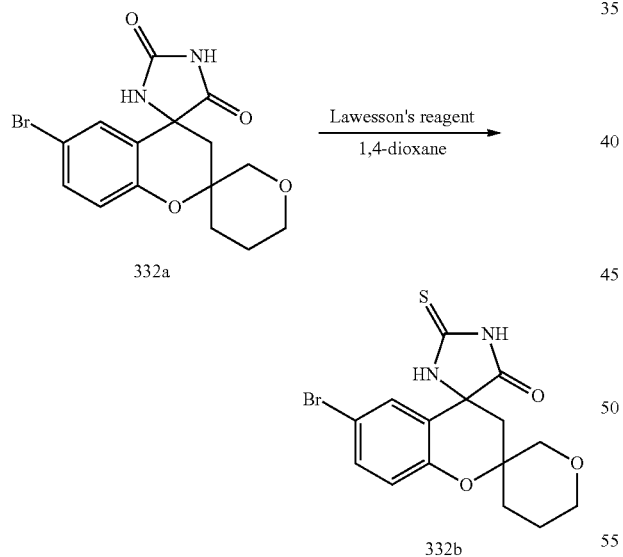

Preparation of Compound 332b

A suspension of the compound 332a (9 g, 24.57 mmol) and Lawesson's Reagent (9.9 g, 24.57 mmol) in dry 1,4-dioxane (135 mL) was heated at 120° C. in microwave for 30 min. The mixture was concentrated in vacuo, and the residue was purified by column chromatography to give the compound 332b (8 g, 85%).

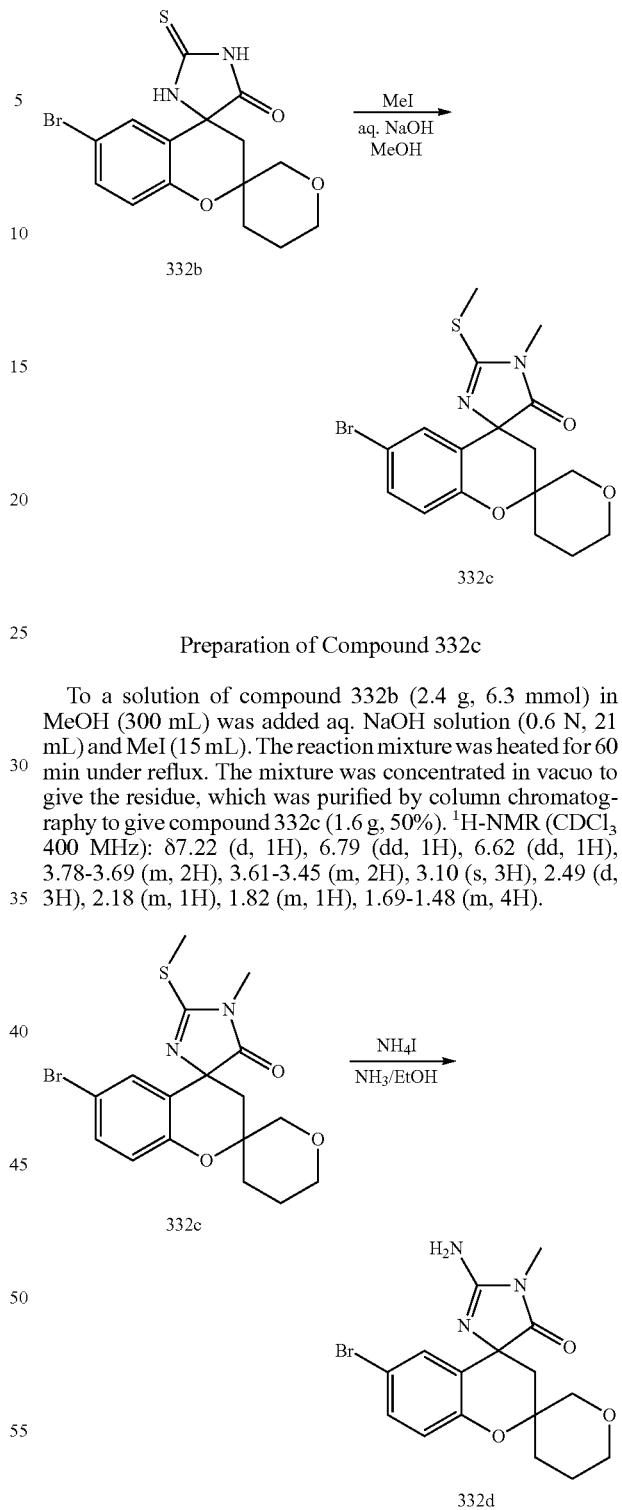

Preparation of Compound 332c

To a solution of compound 332b (2.4 g, 6.3 mmol) in MeOH (300 mL) was added aq. NaOH solution (0.6 N, 21 mL) and MeI (15 mL). The reaction mixture was heated for 60 min under reflux. The mixture was concentrated in vacuo to give the residue, which was purified by column chromatography to give compound 332c (1.6 g, 50%). $^1$H-NMR (CDCl$_3$ 400 MHz): δ7.22 (d, 1H), 6.79 (dd, 1H), 6.62 (dd, 1H), 3.78-3.69 (m, 2H), 3.61-3.45 (m, 2H), 3.10 (s, 3H), 2.49 (d, 3H), 2.18 (m, 1H), 1.82 (m, 1H), 1.69-1.48 (m, 4H).

Preparation of Compound 332d

A solution of the compound 332c (1.54 g, 37.56 mmol), $NH_4I$ (1.4 g) in a solution of $NH_3$/EtOH (140 mL, 8 N) was heated at 120° C. in microwave for 2.5 hrs. After being cooled, the mixture was concentrated in vacuum to give the compound 332d (1.5 g, crude), which was used for the next step directly.

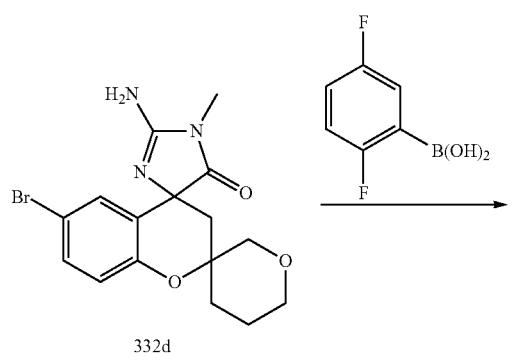

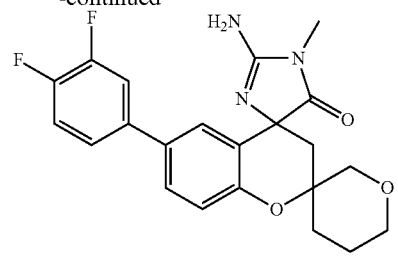

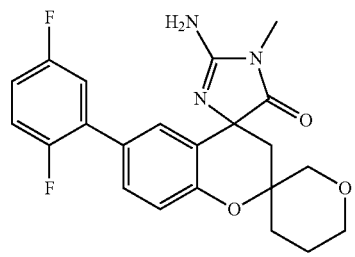

Preparation of Compound 332

Pd(PPh$_3$)$_2$Cl$_2$ (10 mg) in a 10 mL of tube under Ar$_2$ was treated sequentially with the compound 332d (20 mg, 0.05 mmol) in 1,4-dioxane (2 mL), aq. Cs$_2$CO$_3$ solution (2 N, 0.3 mL) and 2,5-difluorophenylboronic acid (16.67 mg, 0.1 mmol). The mixture was heated at 120° C. under microwave for 20 min. The reaction mixture was concentrated in vacuo, the residue was purified by preparative TLC and preparative HPLC to give the pure compound 332 (4.11 mg, 10%) as a TFA salt. $^1$H-NMR (CD$_3$OD 400 MHz): δ7.46-7.50 (m, 1H), 7.25-7.30 (m, 1H), 7.12-7.20 (m, 2H), 7.01-7.11 (m, 2H), 3.75-3.96 (m, 2H), 3.55-3.68 (m, 2H), 3.26 (s, 3H), 2.30-2.48 (m, 2H), 1.79-2.10 (m, 3H), 1.51-1.61 (m, 1H); ESI MS: m/z 414.0 [M+H]$^+$.

Example 218

Preparation of Compound 351

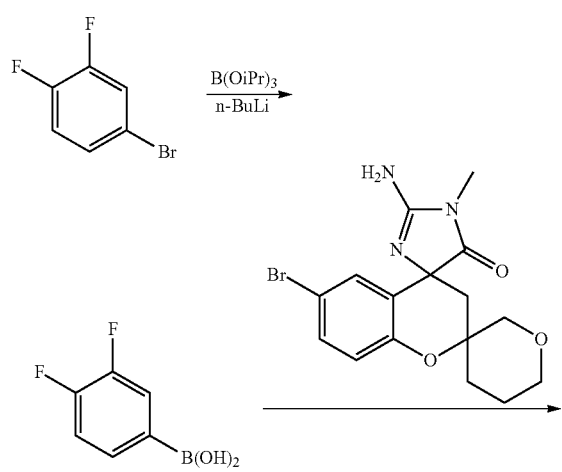

Experimental Data:

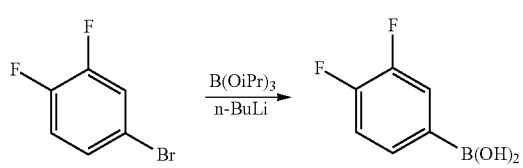

Preparation of 3,4-difluorophenylboronic acid

To a stirred solution of 4-bromo-1,2-difluorobenzene (3.5 g, 17.86 mmol) in dry THF was cooled to –78° C., was added a n-BuLi (10.71 mL) solution dropwise. After completion of the addition, the mixture was stirred for 15 min, and triisopropyl borate (6.71 g, 35.71 mmol) was added in one portion. The reaction flask was kept in a cooling bath for 30 min, and warmed to room temperature for 3 hours. The solvent was removed, the residue was dissolved in ether, washed with 1N HCl and water, dried over Na$_2$SO$_4$, filtered, and concentrated in vacuo, the residue was purified by recrystallization with CH$_2$Cl$_2$ and hexane to give the pure 3,4-difluorophenylboronic acid (800 mg, 20%).

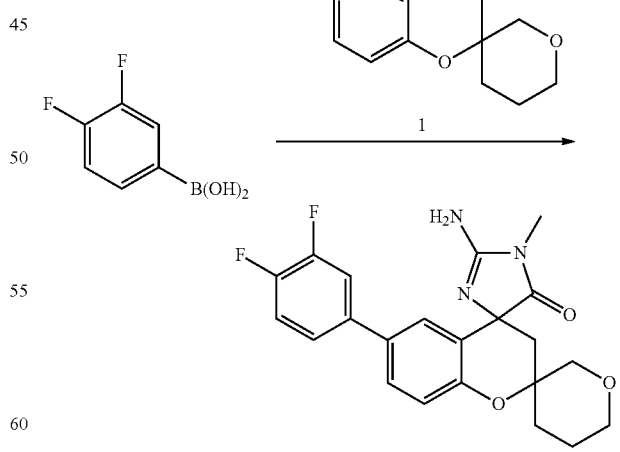

Preparation of Compound 351

By using the same synthetic strategy for compound 332 described in Example 217, compound 351 (5 mg, 12%) was obtained. ¹H-NMR (CD₃OD 400 MHz): δ7.51-7.54 (m, 1H), 7.39-7.45 (m, 1H), 7.19-7.28 (m, 3H), 7.00-7.03 (m, 1H), 3.70-3.87 (m, 2H), 3.50-3.59 (m, 2H), 3.24 (s, 3H), 2.26-2.39 (m, 2H), 1.74-2.04 (m, 3H), 1.50-1.54 (m, 1H); ESI MS: m/z 414.0 [M+H]⁺.

Example 219

Preparation of Compound 286

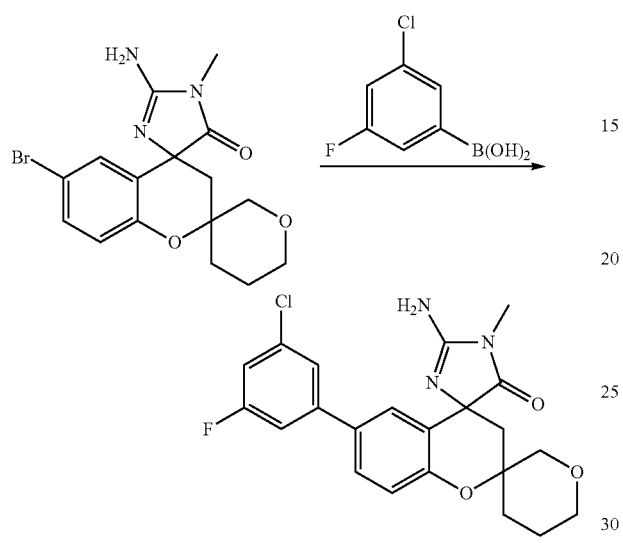

By using the same synthetic strategy for compound 332 described in Example 217, compound 286 (2.58 mg, 6%) was obtained. ¹H-NMR (CD₃OD 400 MHz): δ7.61-7.63 (m, 1H), 7.38-7.41 (m, 2H), 7.28 (m, 1H), 7.10-7.16 (m, 2H), 3.76-3.97 (m, 2H), 3.57-3.69 (m, 2H), 3.31 (s, 3H), 3.04-3.10 (m, 2H), 2.31-2.52 (m, 2H), 1.79-2.16 (m, 3H), 1.55-1.71 (m, 1H); ESI MS: m/z 430.0 [M+H]⁺.

Example 220

Preparation of Compounds 215 and 270

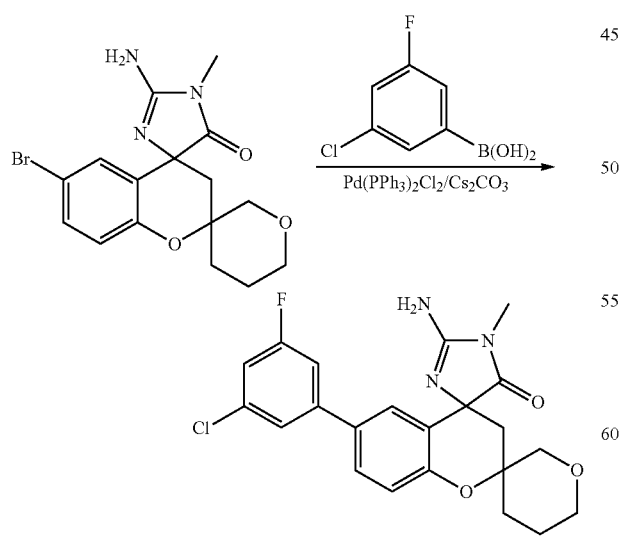

By using the same synthetic strategy for compound 332 described in Example 217, compound 215 (6.22 mg, 18%) and compound 270 (1.07 mg, 3%) were obtained.

compound 215: ¹H-NMR (CD₃OD 400M): δ7.62-7.64 (m, 1H), 7.42-7.44 (m, 2H), 7.29-7.32 (m, 1H), 7.10-7.16 (m, 2H), 3.83-3.94 (m, 2H), 3.61-3.66 (m, 2H), 3.31 (s, 3H), 2.33-2.46 (m, 2H), 1.78-2.10 (m, 3H), 1.53-1.64 (m, 1H). ESI MS: m/z 430.0 [M+H]⁺.

compound 270: ¹H-NMR (CD₃OD 400M): δ7.61-7.64 (m, 1H), 7.40-7.43 (m, 2H), 7.28-7.31 (m, 1H), 7.09-7.18 (m, 2H), 3.75-3.80 (m, 2H), 3.61-3.64 (m, 2H), 3.31 (s, 3H), 2.45 (s, 2H), 1.90-2.15 (m, 3H), 1.60-1.68 (m, 1H); ESI MS: m/z 430.0 [M+H]⁺.

Example 221

Preparation of Compounds 250 and 356

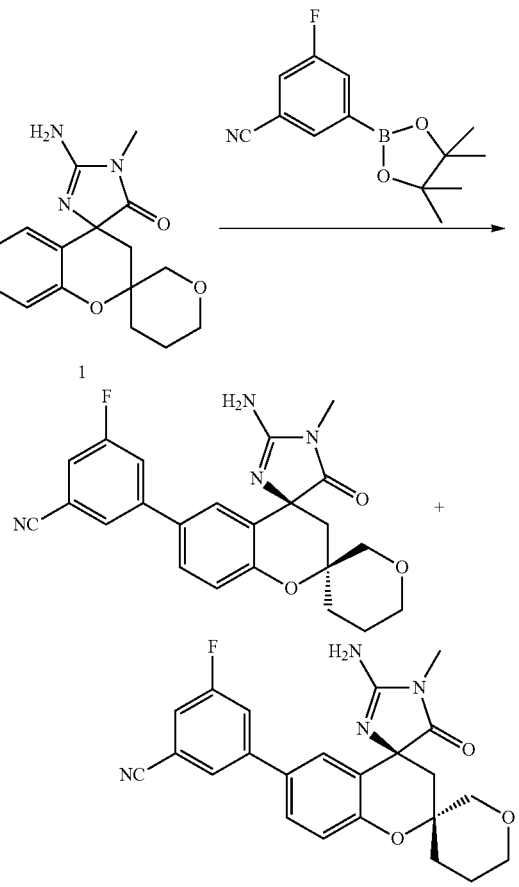

By using the same synthetic strategy for compound 332 described in Example 217, compound 250 (2.48 mg, 11%) and compound 356 (1.75 mg, 8%) were obtained.

compound 250: ¹H-NMR (CD₃OD 400 MHz): δ7.76 (s, 1H), 7.61-7.66 (m, 2H), 7.42-7.44 (m, 2H), 7.06-7.08 (m, 1H), 3.76-3.88 (m, 2H), 3.51-3.57 (m, 2H), 3.24 (s, 3H), 2.27-2.40 (m, 2H), 1.72-2.05 (m, 3H), 1.48-1.58 (m, 1H); ESI MS: m/z 420.9 [M+H]⁺.

compound 356: ¹H-NMR (CD₃OD 400 MHz): 7.83 (m, 1H), 7.69-7.73 (m, 2H), 7.49-7.52 (m, 2H), 7.12-7.15 (m, 1H), 3.77-3.80 (m, 2H), 3.63-3.66 (m, 2H), 3.33 (s, 3H), 2.47 (s, 2H), 1.94-2.14 (m, 3H), 1.69 (m, 1H); ESI MS: m/z 420.9 [M+H]⁺.

Example 222

Preparation of Compound 346

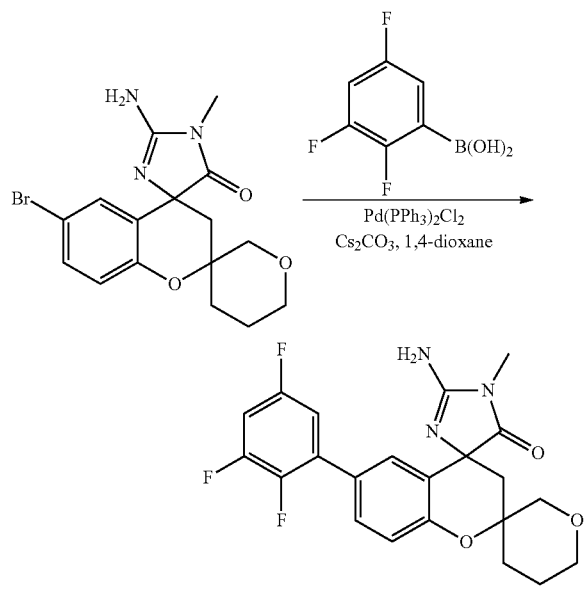

By using the same synthetic strategy for compound compound 332 described in Example 217, compound 346 (8.2 mg, 19%) was obtained. $^1$H NMR (CDCl$_3$ 400 MHz) δ7.53-7.55 (m, 1H), 7.32 (m, 1H), 6.98-7.18 (m, 3H), 3.77-3.95 (m, 2H), 3.55-3.72 (m, 2H), 3.28 (s, 3H), 3.02-3.12 (m, 1H), 2.41-2.54 (m, 1H), 1.80-2.18 (m, 3H), 1.55-1.71 (m, 1H); ESI MS: m/z 432.0 [M+H]$^+$.

Example 223

Preparation of Compounds 280 and 359

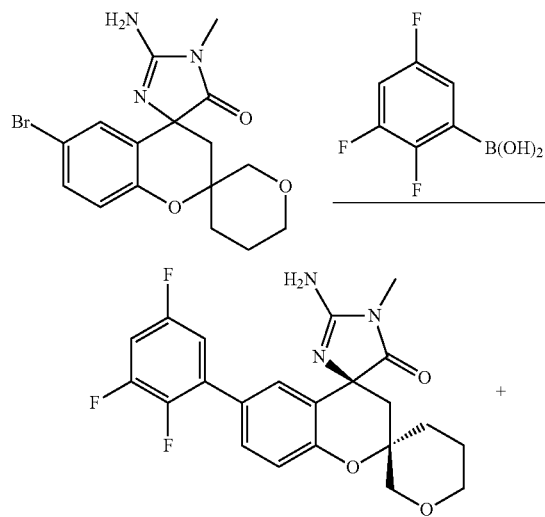

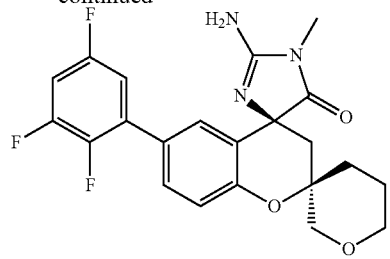

By using the same synthetic strategy for compound 332 described in Example 217, compound 280 (1.76 mg, 9%) and compound 359 (0.61 mg, 3%) were obtained.

compound 280: $^1$H-NMR (CD$_3$OD 400 MHz): δ7.51-7.53 (m, 1H), 7.31 (m, 1H), 7.07-7.14 (m, 2H), 7.00-7.04 (m, 1H), 3.90-3.93 (m, 1H), 3.80-3.86 (m, 1H), 3.56-3.64 (m, 2H), 3.26 (s, 3H), 2.32-2.46 (m, 2H), 1.97-2.09 (m, 1H), 1.88-1.96 (m, 1H), 1.77-1.80 (m, 1H), 1.55-1.62 (m, 1H); ESI MS: m/z 432.0 [M+H]$^+$.

compound 359: $^1$H-NMR (CD$_3$OD 400 MHz): δ7.45-7.51 (m, 1H), 7.29 (m, 1H), 7.07-7.14 (m, 2H), 7.00-7.04 (m, 1H), 3.75-3.78 (m, 2H), 3.57-3.62 (m, 2H), 3.26 (s, 3H), 2.45 (m, 2H), 2.09-2.13 (m, 1H), 1.90-1.97 (m, 1H), 1.73-1.88 (m, 1H), 1.62-1.71 (m, 1H); ESI MS: m/z 432.1 [M+H]$^+$.

Example 224

Preparation of Compound 347

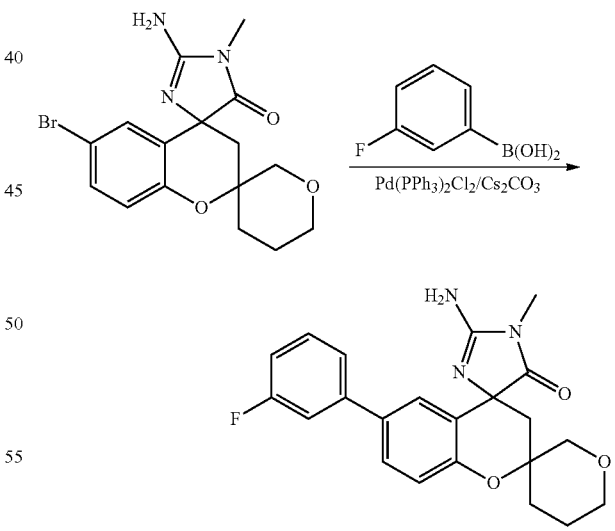

By using the same synthetic strategy for compound 332 described in Example 217, compound 347 (5.16 mg, 25%) was obtained. $^1$H-NMR (CD$_3$OD 400 MHz): δ7.61-7.77 (m, 1H), 7.29-7.47 (m, 4H), 7.02-7.11 (m, 2H), 3.77-3.95 (m, 2H), 3.58-3.64 (m, 2H), 3.26 (s, 3H), 2.28-2.46 (m, 2H), 1.79-2.17 (m, 3H), 1.56-1.71 (m, 1H); ESI MS: m/z 395.1 [M+H]$^+$.

Example 225

Preparation of Compound 314

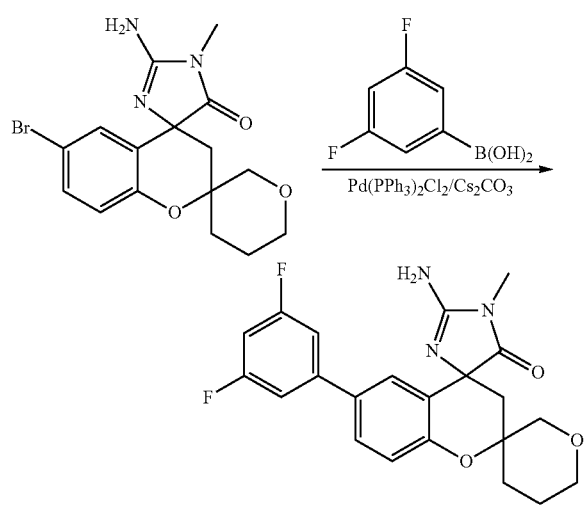

By using the same synthetic strategy for compound 332 described in Example 217, compound 314 (4.2 mg, 10%) was obtained. $^1$H-NMR (CDCl$_3$ 400 MHz): δ7.62-7.67 (m, 1H), 7.39-7.44 (m, 1H), 7.18-7.27 (m, 2H), 7.7.09-7.14 (m, 1H), 6.89-6.94 (m, 1H), 3.79-4.00 (m, 2H), 3.59-3.79 (m, 2H), 3.32 (s, 3H), 2.29-2.52 (m, 2H), 1.80-2.18 (m, 3H), 1.56-1.74 (m, 1H); ESI MS: m/z 414.0 [M+H]$^+$.

Example 226

Preparation of Compounds 255 and 309

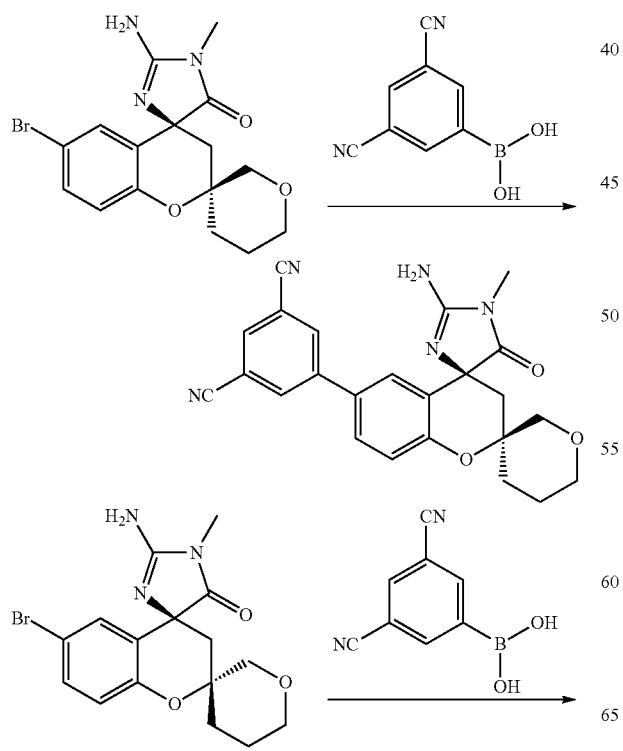

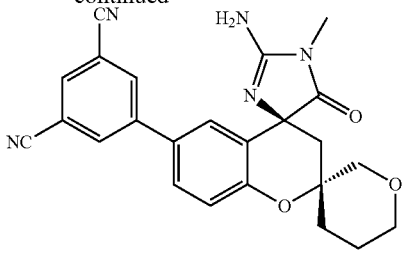

By using the same synthetic strategy for compound 332 described in Example 217, compound 255 (1.08 mg, 3%) and compound 309 (1.08 mg, 3%) were obtained.

compound 255: $^1$H NMR (CD$_3$OD 400 MHz): δ8.17-8.18 (d, 2H), 8.01 (s, 1H), 7.62-7.65 (m, 1H), 7.43-7.45 (m, 1H), 7.04-7.07 (m, 1H), 3.67-3.85 (m, 2H), 3.47-3.55 (m, 2H), 3.21 (s, 3H), 2.25-2.38 (m, 2H), 1.72-1.97 (m, 3H), 1.49-1.52 (m, 1H); ESI MS: m/z 428.1 [M+H]$^+$.

compound 309: $^1$H NMR (CD$_3$OD 400 MHz): δ8.17-8.18 (d, 2H), 8.01 (s, 1H), 7.62-7.64 (m, 1H), 7.42-7.43 (m, 1H), 7.04-7.06 (m, 1H), 3.67-3.72 (m, 2H), 3.52-3.55 (m, 2H), 3.21 (s, 3H), 2.37 (s, 2H), 1.78-2.06 (m, 3H), 1.55-1.62 (m, 1H); ESI MS: m/z 427.9 [M+H]$^+$.

Example 227

Preparation of Compounds 259 and 325

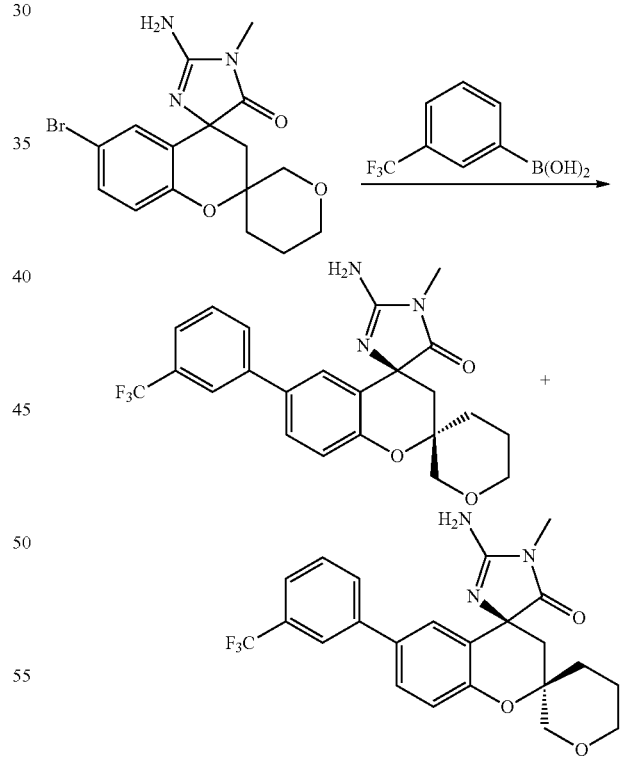

By using the same synthetic strategy for compound 332 described in Example 217, compound 259 (2.60 mg, 12%) and compound 325 (0.73 mg, 4%) were obtained.

compound 259: $^1$H-NMR (CD$_3$OD 400 MHz): δ7.78-7.80 (m, 2H), 7.60-7.65 (m, 3H), 7.40 (s, 1H), 7.12-7.14 (m, 1H), 3.83-3.95 (m, 2H), 3.60-3.64 (m, 2H), 3.26 (s, 3H), 2.33-2.47 (m, 2H), 1.81-2.09 (m, 3H), 1.58-1.63 (m, 1H); ESI MS: m/z 446.0 [M+H]$^+$.

compound 325: ¹H-NMR (CD₃OD 400 MHz): δ7.78-7.80 (m, 2H), 7.60-7.65 (m, 3H), 7.38-7.39 (m, 1H), 7.11-7.13 (m, 1H), 3.74-3.85 (m, 2H), 3.56-3.67 (m, 2H), 3.26 (s, 3H), 2.47 (s, 2H), 1.87-2.15 (m, 3H), 1.59-1.68 (m, 1H); ESI MS: m/z 446.0 [M+H]⁺.

Example 228

Preparation of Compound 290

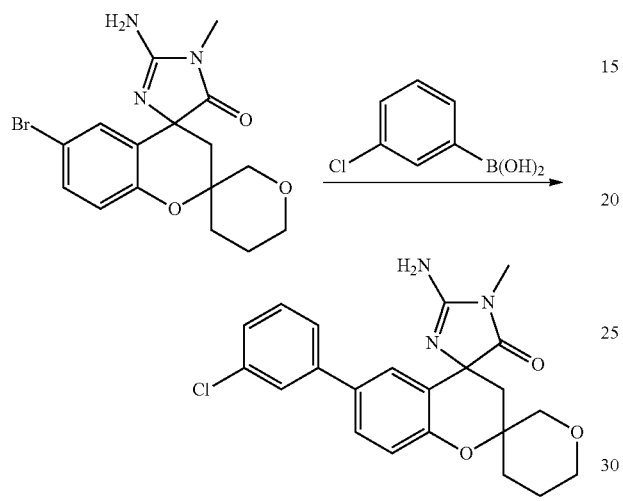

By using the same synthetic strategy as compound 332 described in Example 217, compound 290 (2.42 mg, 11%) was obtained, ¹H NMR (CD₃OD 400 MHz): δ7.61 (m, 2H), 7.45 (m, 1H), 7.33 (m, 3H), 7.10 (m, 0.1H), 3.84 (m, 2H), 3.63 (m, 2H), 2.65-3.10 (m, 3H), 2.48 (m, 2H), 2.10 (m, 2H), 1.93 (m, 1H), 1.64 (m, 1H); ESI MS: 412 [M+H]⁺.

Example 229

Preparation of Compounds 224 and 289

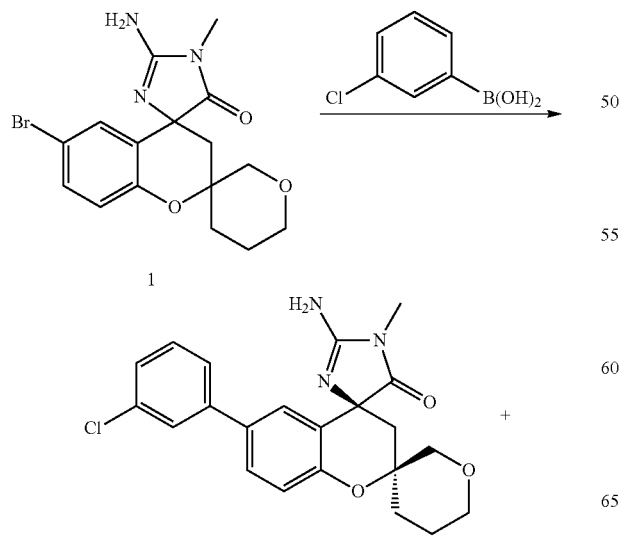

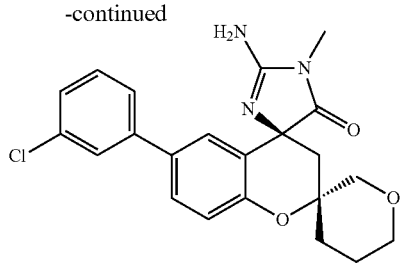

By using the same synthetic strategy as compound 332 described in Example 217, compound 224 (2.78 mg, 13%) and compound 289 (2.10 mg, 9%) were obtained.

compound 224: ¹H NMR (CD₃OD 400 MHz): δ7.53-7.59 (m, 2H), 7.44-7.45 (m, 1H), 7.29-7.38 (m, 3H), 7.07-7.09 (d, 1H), 3.81-3.92 (m, 2H), 3.58-3.62 (m, 2H), 3.26 (s, 3H), 2.31-2.44 (m, 2H), 1.77-2.06 (m, 3H), 1.52-1.62 (m, 1H); ESI MS: m/z 412.0 [M+H]⁺.

compound 289: ¹H NMR (CD₃OD 400 MHz): δ7.57-7.67 (m, 2H), 7.46-7.51 (m, 1H), 7.35-7.44 (m, 3H), 7.10-7.12 (m, 1H), 3.75-3.85 (m, 2H), 3.61-3.69 (m, 2H), 3.26 (s, 3H), 2.48 (m, 2H), 1.90-2.18 (m, 3H), 1.64-1.72 (m, 1H); ESI MS: m/z 412.0 [M+H]⁺.

Example 230

Preparation of Compounds 318 and 336

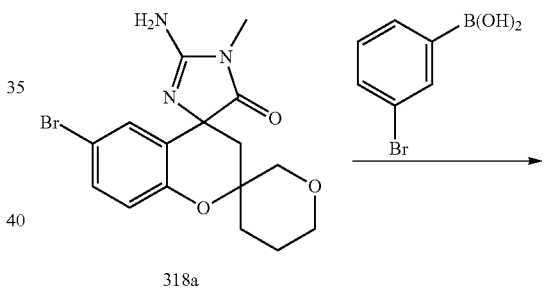

318a

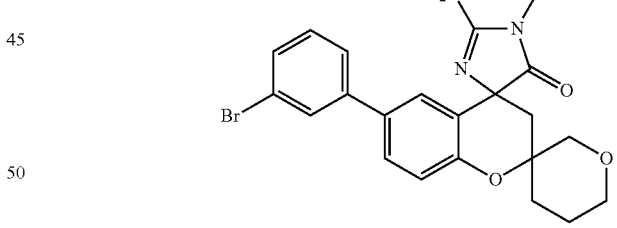

The solution of compound 318a (20 mg), 3-bromophenyl-boronic acid (11 mg), and
K₂CO₃ (2 N, 0.06 mL) in THF (5 mL) was added Pd(PPh₃)₄ (3 mg) under N₂. The mixture was refluxed overnight, the solvent was removed in vacuum, and the crude product was purified by preparative TLC and HPLC to give compound 318 (2.72 mg, 11%) and compound 336 (0.78 mg, 3%).

compound 318: ¹H-NMR (CD₃OD 400 MHz): δ7.70-7.69 (m, 1H), 7.58-7.60 (m, 1H), 7.45-7.52 (m, 2H), 7.32-7.34 (m, 2H), 7.09-7.11 (m, 1H), 3.89-3.97 (m, 1H), 3.79-3.88 (m, 1H), 3.58-3.64 (m, 2H), 3.41 (s, 3H), 2.31-2.46 (m, 2H), 1.78-2.08 (m, 3H), 1.56-1.62 (m, 1H); ESI MS: m/z 457.8 [M+H]⁺.

compound 336: ¹H-NMR (CD₃OD 400 MHz): δ7.60 (m, 1H), 7.48-7.52 (m, 1H), 7.36-7.42 (m, 2H), 7.20-7.24 (m, 2H), 6.98-7.00 (m, 1H), 3.72-3.63 (m, 2H), 3.48-3.56 (m, 2H), 3.41 (s, 3H), 2.36 (s, 2H), 1.83-2.06 (m, 3H), 1.52-1.62 (m, 1H); ESI MS: m/z 457.8 [M+H]⁺.

Example 231

Preparation of Compound 288

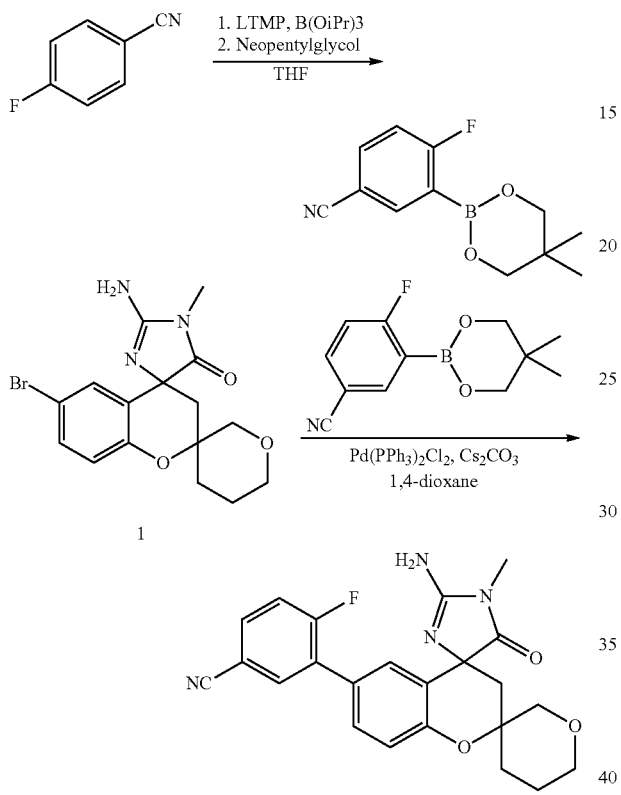

Experimental Data:

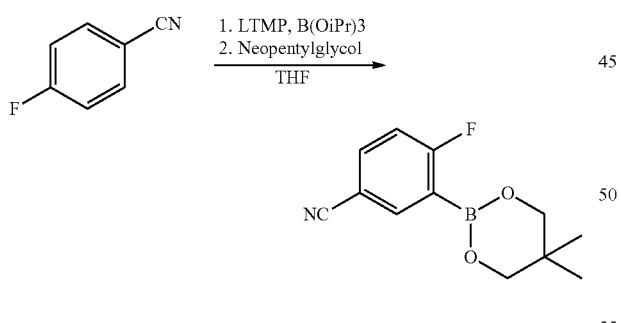

Preparation of 3-(5,5-Dimethyl-1,3,2-dioxaborinan-2-yl)-4-fluorobenzonitrile

The solution of 2,2,6,6-tetramethylpiperidine (7.1 g, 49.6 mmol) in dry THF (100 mL) at −10° C. in a 500 mL dry three-neck flask was added n-BuLi (2.5 M in hexane, 19.8, 49.6 mmol) over 2 min under N₂, and the mixture was stirred for 10 min. At −78° C., B(OⁱPr)₃ (10.8 g, 57.4 mmol) was added over 2 min, and the mixture was stirred for 5 min, followed by addition of a solution of 4-fluorobenzonitrile (5 g, 41 mmol) in dry THF (140 mL) over 5 mins. The reaction mixture was left in the cooling bath overnight, and warmed to room temperature. At room temperature, the reaction mixture was quenched with glacial acetic acid (3.3 mL), and 2,2-dimethyl-1,3-propandiol (6.4 g, 61.5 mmol) was added. The mixture was stirred for 1 h at room temperature, and was added ethyl acetate. The organic layer was washed with aqueous KH₂PO₄ (10 w/v %, 3×100 mL). The water phase was extracted with ethyl acetate, and the combined organic layer was dried and evaporated to give 3-(5,5-dimethyl-1,3,2-dioxaborinan-2-yl)-4-fluorobenzonitrile (1 g, 10%). ¹H-NMR (CDCl₃ 400 MHz): δ8.00 (m, 1H), 7.62 (m, 1H), 7.03 (m, 1H), 3.75 (d, 4H), 1.01 (s, 6H).

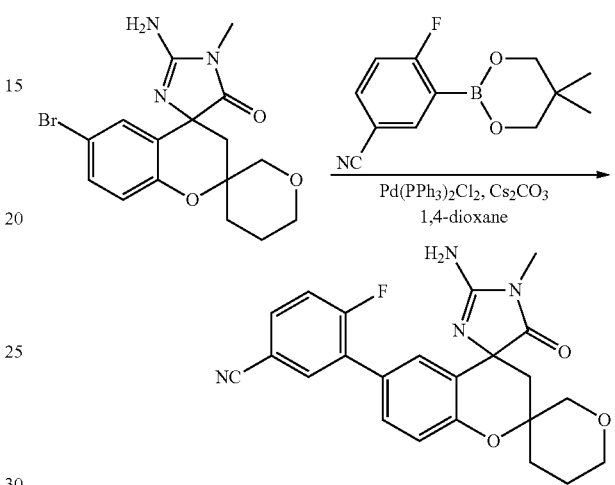

Preparation of Compound 288

By using the same synthetic strategy as compound 332 described in Example 217, compound 288 (2.15 mg, 10%) was obtained. ¹H-NMR (CD₃OD 400 MHz): δ7.86-7.84 (m, 1H), 7.74-7.77 (m, 1H), 7.55-7.57 (m, 1H), 7.35-7.40 (m, 2H), 7.11-7.14 (m, 1H), 3.78-3.98 (m, 2H), 3.56-3.68 (m, 2H), 3.29 (s, 3H), 2.34-2.49 (m, 2H), 1.78-2.18 (m, 3H), 1.58-1.75 (m, 1H); ESI MS: m/z 421.2 [M+H]⁺.

Example 232

Preparation of Compound 368

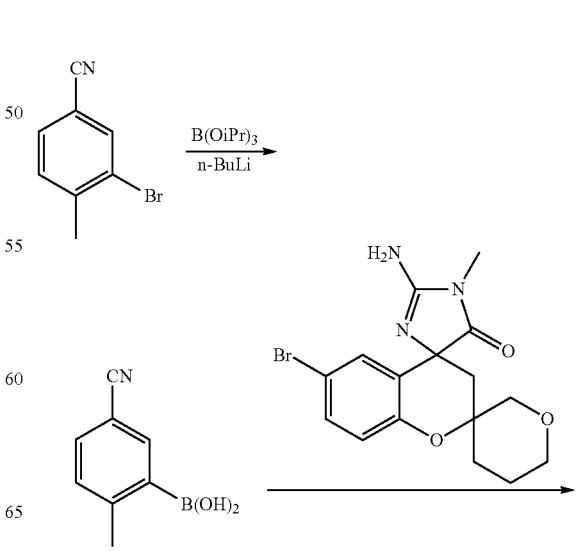

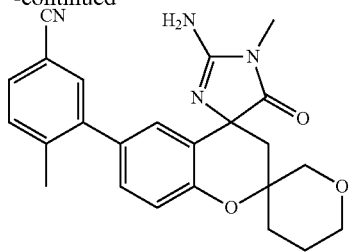

Experimental Data:

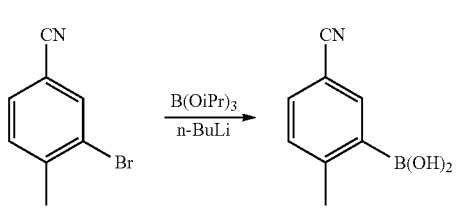

Preparation of 5-cyano-2-methylphenylboronic acid

To a stirred solution of 3-bromo-4-methylbenzonitrile (3.5 g, 17.86 mmol) in dry THF at −78° C. was added n-BuLi (2N, 10.71 mL) dropwise. The mixture was stirred for 15 min., and added triisopropyl borate (6.71 g, 35.71 mmol). The reaction flask was kept in the cooling bath for 30 min., and at room temperature for 3 hours. The solvent was removed, and the residue was dissolved in ether. The organic phase was washed with 1N HCl solution and water, dried over $Na_2SO_4$, and filtered. The filtrate was concentrated in vacuo, and the residue was crystallized from a mixture of $CH_2Cl_2$ and hexane to give 5-cyano-2-methylphenylboronic acid (800 mg, 20%). $^1$H-NMR (CDCl$_3$ 400 MHz): δ7.50-7.78 (m, 2H), 7.30 (d, 1H), 2.42 (s, 3H).

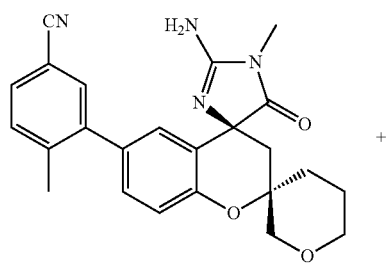

Preparation of Compound 368

By using the same synthetic strategy as compound 332 described in Example 217, compound 368 (15 mg, 15%) was obtained. $^1$H-NMR (CD$_3$OD 400 MHz): δ7.56-7.58 (d, 1H), 7.41-7.48 (m, 2H), 7.27-7.31 (m, 1H), 7.06-7.11 (m, 2H), 3.77-3.98 (m, 2H), 3.56-3.68 (m, 2H), 3.24 (s, 3H), 2.99-3.02 (m, 2H), 2.30-2.51 (m, 1H), 2.26 (m, 3H), 1.80-2.15 (m, 3H), 1.52-1.68 (m, 1H); ESI MS: m/z 417.1 [M+H]$^+$.

Example 233

Preparation of Compounds 277 and 413

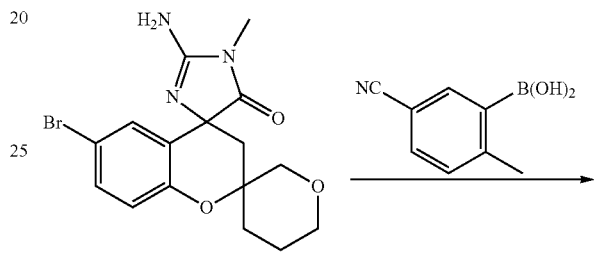

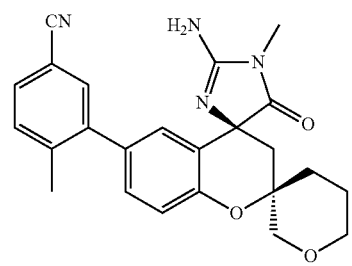

By using the same synthetic strategy as compound 332 described in Example 217, compound 277 (2.71 mg, 13%) and compound 413 (1.25 mg, 6%) were obtained.

compound 277: $^1$H-NMR (CD$_3$OD 400 MHz): δ7.81-7.84 (m, 1H), 7.67-7.72 (m, 2H), 7.55-7.57 (m, 1H), 7.32-7.37 (m, 2H), 4.16-4.19 (m, 1H), 4.06-4.13 (m, 1H), 3.84-3.88 (m, 2H), 3.49 (s, 3H), 2.72-2.57 (m, 2H), 2.51 (s, 3H), 2.06-2.37 (m, 3H), 1.80-1.91 (m, 1H); ESI MS: m/z 417.1 [M+H]$^+$.

compound 413: $^1$H-NMR (CD$_3$OD 400 MHz): δ7.81-7.83 (m, 1H), 7.66-7.71 (m, 2H), 7.54-7.56 (m, 1H), 7.31-7.35 (m, 2H), 4.02-4.05 (m, 2H), 3.86-3.89 (m, 2H), 3.49 (s, 3H), 2.70 (s, 2H), 2.50 (s, 3H), 2.11-2.39 (m, 3H), 1.86-1.96 (m, 1H); ESI MS: m/z 417.1 [M+H]$^+$.

Example 234

Preparation of Compounds 380 and 449

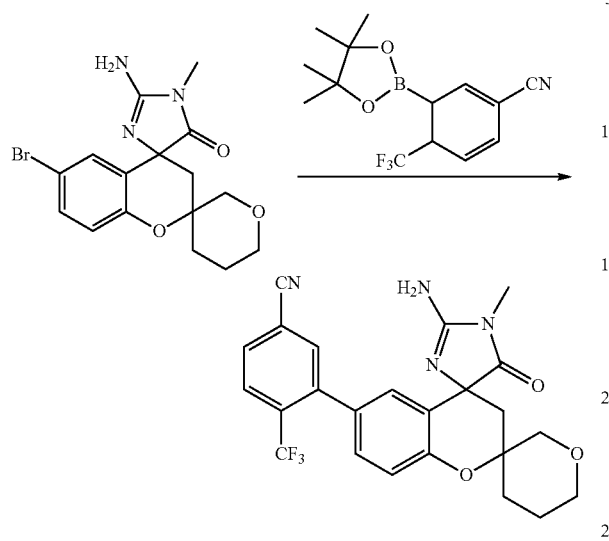

By using the same synthetic strategy as compound 332 described in Example 217, compound 380 (1.12 mg, 4%), and compound 449 (1.73 mg, 7%) were obtained.

compound 380: $^1$H NMR (CD$_3$OD 400 MHz): δ7.90-7.96 (m, 2H), 7.72 (s, 1H), 7.32-7.34 (d, 1H), 7.14 (s, 1H), 7.08-7.10 (d, 1H), 3.84-3.98 (m, 2H), 3.58-3.65 (m, 2H), 3.24 (s, 3H), 2.33-2.50 (m, 2H), 1.81-2.12 (m, 3H), 1.59-1.63 (m, 1H); ESI MS: m/z 471.0 [M+H]$^+$.

compound 449: $^1$H NMR CD$_3$OD 400 MHz): δ7.89-7.95 (m, 2H), 7.70 (s, 1H), 7.30-7.33 (d, 1H), 7.12 (s, 1H), 7.05-7.07 (d, 1H), 3.76-3.79 (m, 2H), 3.61-3.64 (m, 2H), 3.22 (s, 3H), 2.41-2.50 (m, 2H), 1.90-2.14 (m, 3H), 1.63-1.65 (m, 1H); ESI MS: m/z 471.0 [M+H]$^+$.

Example 235

Preparation of Compound 291

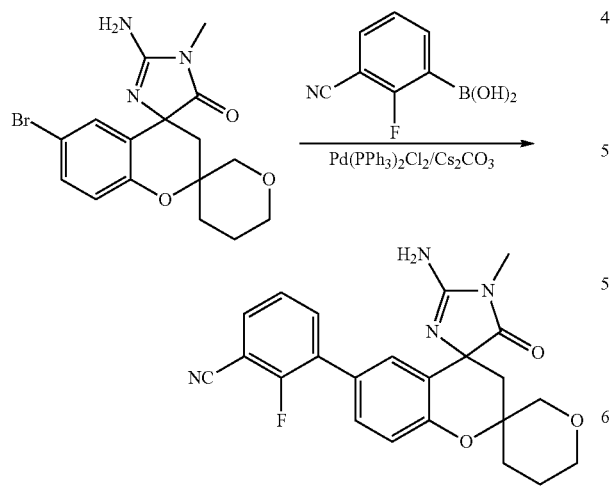

By using the same synthetic strategy as compound 332 described in Example 217, compound 291 (1.63 mg, 7%) was obtained. $^1$H-NMR (CD$_3$OD 400M): δ7.70-7.77 (m, 2H), 7.53-7.55 (m, 1H), 7.35-7.43 (m, 2H), 7.12-7.15 (m, 1H), 3.83-3.96 (m, 2H), 3.58-3.65 (m, 2H), 3.28 (s, 3H), 2.35-2.49 (m, 2H), 1.85-2.08 (m, 3H), 1.55-1.68 (m, 1H); ESI MS: m/z 421.0 [M+H]$^+$.

Example 236

Preparation of Compounds 216 and 304

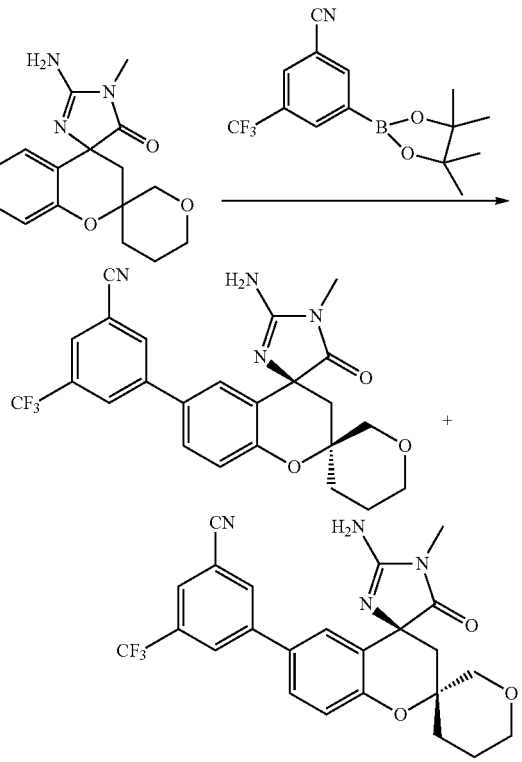

By using the same synthetic strategy as compound 332 described in Example 217, compound 216 (0.8 mg, 4%) and compound 304 (0.8 mg, 4%) were obtained.

compound 216: $^1$H-NMR (CD$_3$OD 400 MHz): δ8.14 (s, 1H), 8.05 (s, 1H), 7.95 (s, 1H), 7.61-7.64 (dd, 1H), 7.44-7.45 (d, 1H), 7.06-7.08 (dd, 1H), 3.74-3.86 (m, 2H), 3.48-3.56 (m, 2H), 3.21 (s, 3H), 2.25-2.38 (m, 2H), 1.72-1.98 (m, 3H), 1.49-1.52 (m, 1H); ESI MS: m/z 471.1 [M+H]$^+$.

compound 304: $^1$H-NMR (CD$_3$OD 400 MHz): δ8.18 (s, 1H), 8.08 (s, 1H), 7.98 (s, 1H), 7.65-7.67 (dd, 1H), 7.47-7.48 (d, 1H), 7.09-7.11 (d, 1H), 3.71-3.80 (m, 2H), 3.54-3.60 (m, 2H), 3.24 (s, 3H), 2.41 (s, 2H), 1.80-2.11 (m, 3H), 1.59-1.62 (m, 1H); ESI MS: m/z 471.1 [M+H]$^+$.

Example 237

Preparation of Compound 414

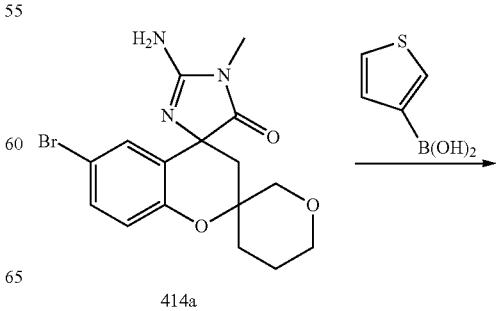

414a

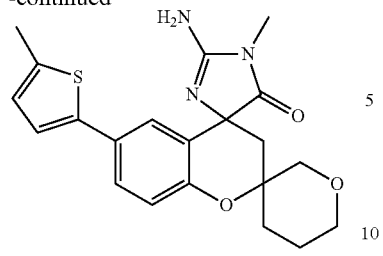

The mixture of compound 1 (30 mg, 0.08 mmol), 5-methylthiophen-3-ylboronic acid (17 mg, 0.12 mmol), Pd(PPh₃)₄ (1 mg, 0.001) and Na₂CO₃ (2 M, 0.30 mL), in the mixture of EtOH (0.2 mL) and toluene (1 mL) was heated at 120° C. under Ar₂ overnight.

The reaction mixture was extracted with EtOAc, concentrated, and purified by preparative TLC and HPLC to give compound 414 (4.50 mg, 14%), ¹H-NMR (CD₃OD 400 MHz): δ7.41-7.44 (m, 1H), 7.09-7.11 (m, 1H), 6.96-6.97 (m, 1H), 6.89-6.92 (m, 1H), 6.61 (m, 1H), 3.61-3.83 (m, 2H), 3.46-3.58 (m, 2H), 3.25 (s, 3H), 2.26-2.42 (m, 5H), 1.67-2.03 (m, 3H), 1.44-1.62 (m, 1H); ESI MS: m/z 398.0 [M+H]⁺.

Example 238

Preparation of Compound 301

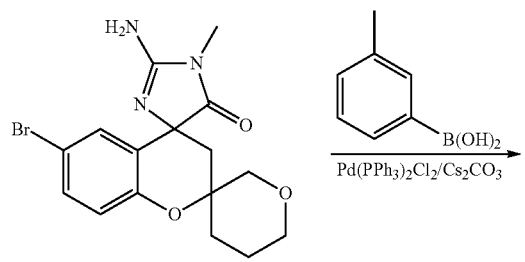

By using the same synthetic strategy as compound 332 described in Example 217, compound 301 (3.45 mg, 16%) was obtained. ¹H-NMR (CD₃OD 400 MHz): δ7.60 (m, 1H), 7.26-7.34 (m, 4H), 7.13-7.15 (m, 1H), 7.06-7.09 (m, 1H), 3.75-3.95 (m, 2H), 3.62-3.67 (m, 2H), 3.30 (s, 3H), 2.34-2.49 (m, 5H), 1.81-2.12 (m, 3H), 1.56-1.72 (m, 1H); ESI MS: m/z 392.1 [M+H]⁺.

Example 239

Preparation of Compounds 296 and 405

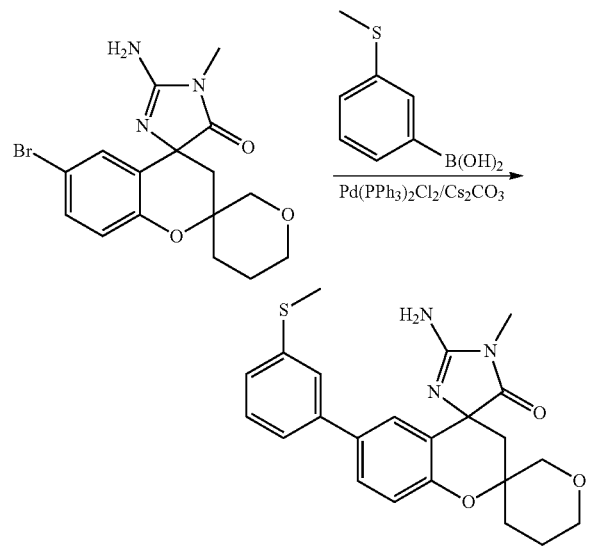

By using the same synthetic strategy as compound 332 described in Example 217, compound 296 (4.32 mg, 20%) and compound 405 (1.40 mg, 6%) were obtained.

compound 296: ¹H-NMR (CD₃OD 400 MHz): δ7.55-7.61 (m, 1H), 7.36-7.40 (m, 1H), 7.23-7.35 (m, 3H), 7.18-7.22 (m, 1H), 7.05-7.10 (m, 1H), 3.80-3.95 (m, 2H), 3.55-3.65 (m, 2H), 3.38 (s, 3H), 2.50 (s, 3H), 2.31-2.48 (m, 2H), 1.77-2.07 (m, 3H), 1.55-1.65 (m, 1H); EI MS: /z 424.1 [M+H]⁺.

compound 405: ¹H-NMR (CD₃OD 400M): δ7.55-7.61 (m, 1H), 7.31-7.40 (m, 2H), 7.23-7.30 (m, 2H), 7.18-7.22 (m, 1H), 7.05-7.10 (m, 1H), 3.75-3.85 (m, 2H), 3.62-3.65 (m, 2H), 3.31 (s, 3H), 2.50 (s, 3H), 2.46 (s, 2H), 1.88-2.16 (m, 3H), 1.61-1.71 (m, 1H): ESI MS: m/z 424.1 [M+H]⁺.

Example 240

Preparation of Compounds 262 and 357

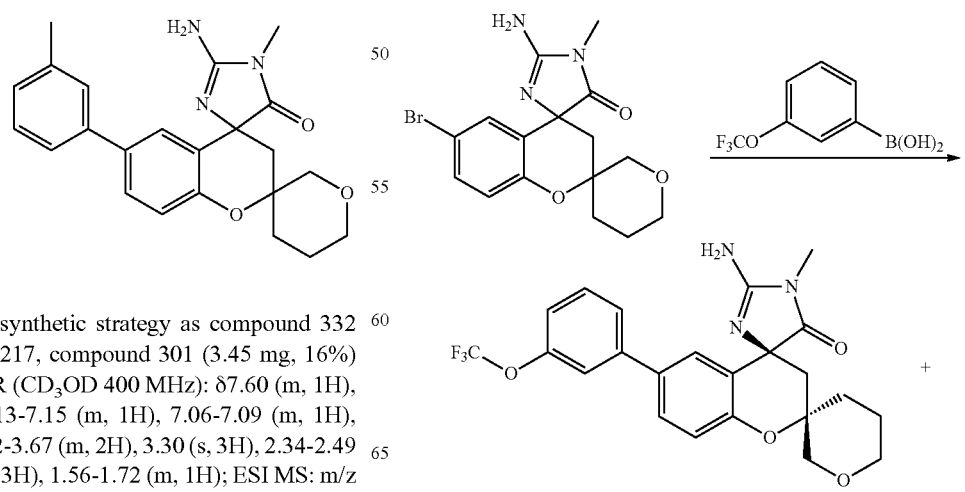

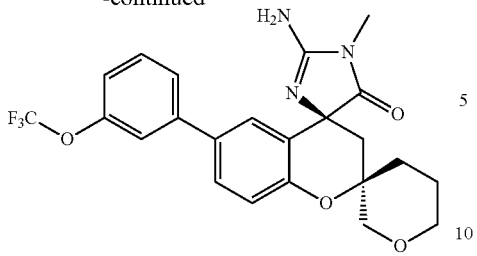

By using the same synthetic strategy as compound 332 as described in Example 217, compound 262 (8.46 mg, 40%), $^1$H-NMR (CD$_3$OD 400M): δ7.58 (dd, 1H), 7.42-7.51 (m, 2H), 7.37 (s, 1H), 7.31 (s, 1H), 7.18 (d, 1H), 7.06 (d, 1H), 3.89-3.92 (m, 1H), 3.80-3.84 (m, 1H), 3.50-3.60 (m, 2H), 3.26 (s, 3H), 2.42 (d, 1H), 2.34 (d, 1H), 1.97-2.05 (m, 1H), 1.89-1.98 (m, 1H), 1.79-1.84 (m, 1H), 1.52-1.62 (m, 1H); ESI MS: m/z 462.1 [M+H]$^+$, and compound 357 (2.47 mg, 10%), $^1$H-NMR (CD$_3$OD 400M): δ7.58 (dd, 1H), 7.42-7.51 (m, 2H), 7.37 (s, 1H), 7.31 (s, 1H), 7.18 (d, 1H), 7.06 (d, 1H), 3.74-3.80 (m, 2H), 3.52-3.63 (m, 2H), 3.26 (s, 3H), 2.63 (s, 1H), 2.42 (s, 2H), 1.85-2.13 (m, 3H), 1.52-1.62 (m, 1H); ESI MS: m/z 462.1 [M+H]$^+$ were obtained.

Example 241

Preparation of Compounds 243 and 337

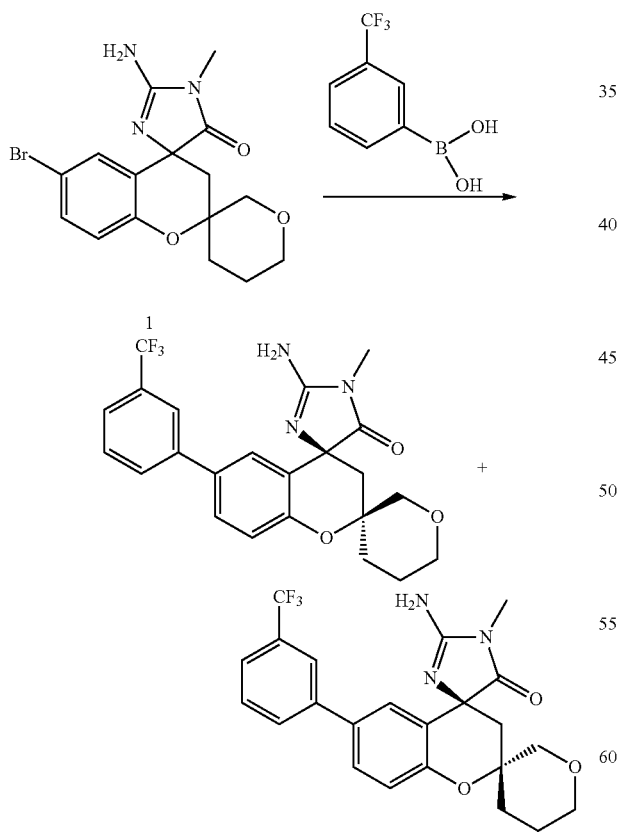

By using the same synthetic strategy as compound 332 described in Example 217, compound 243 (3.23 mg, 14%) and compound 337 (1.95 mg, 8%) were obtained.

compound 243: $^1$H-NMR (CD$_3$OD 400 MHz): δ7.70-7.71 (m, 2H), 7.48-7.56 (m, 3H), 7.31 (s, 1H), 7.02-7.04 (d, 1H), 3.72-3.85 (m, 2H), 3.47-3.56 (m, 2H), 3.27 (s, 3H), 2.24-2.37 (m, 2H), 1.72-2.03 (m, 3H), 1.48-1.52 (m, 1H); ESI MS: m/z 446.1 [M+H]$^+$.

compound 337: $^1$H-NMR (CD$_3$OD 400 MHz): δ7.68-7.72 (m, 2H), 7.48-7.56 (m, 3H), 7.30 (s, 1H), 7.01-7.03 (d, 1H), 3.67-3.76 (m, 2H), 3.49-3.59 (m, 2H), 3.20 (s, 3H), 2.37 (s, 2H), 1.79-2.08 (m, 3H), 1.52-1.64 (m, 1H); ESI MS: m/z 446.1 [M+H]$^+$.

Example 242

Preparation of Compounds 411 and 448

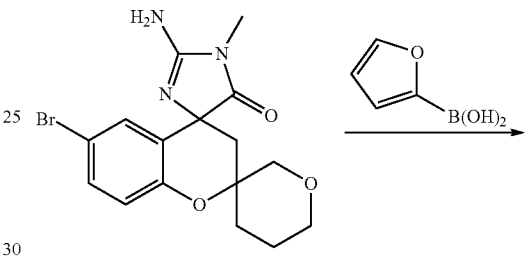

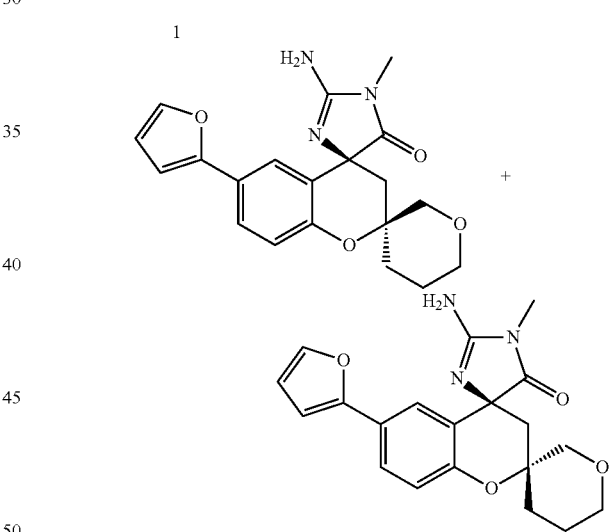

By using the same synthetic strategy as compound 332 described in Example 217, compound 411 (2.61 mg, 14%) and compound 448 (1.24 mg, 6%) were obtained.

compound 411: $^1$H-NMR (CD$_3$OD 400 MHz): δ7.61 (m, 1H), 7.43 (d, 1H), 7.28 (d, 1H), 6.97 (d, 1H), 6.63 (m, 1H), 6.40 (m, 1H), 3.74-3.86 (m, 2H), 3.49-3.56 (m, 2H), 3.26 (s, 3H), 2.25-3.39 (m, 2H), 1.71-2.05 (m, 3H), 1.50-1.54 (m, 1H); ESI MS: m/z 368.0 [M+H]$^+$.

compound 448: $^1$H-NMR (CD$_3$OD 400 MHz): δ7.61 (m, 1H), 7.43 (d, 1H), 7.28 (d, 1H), 6.97 (d, 1H), 6.61 (m, 1H), 6.40 (m, 1H), 3.72 (m, 2H), 3.56 (m, 2H), 3.26 (s, 3H), 2.38 (s, 2H), 1.79-2.06 (m, 3H), 1.61 (m, 1H); ESI MS: m/z 368.0 [M+H]$^+$.

Example 243

Preparation of Compounds 428 and 458

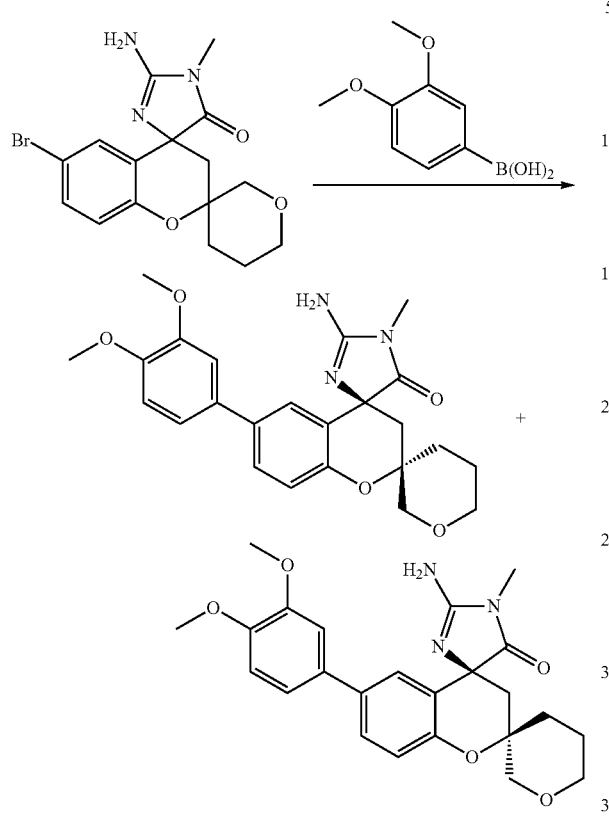

By using the same synthetic strategy as compound 332 described in Example 217, compound 428 (5.50 mg, 25%) and compound 458 (1.49 mg, 15%) were obtained.

compound 428: $^1$H-NMR (CD$_3$OD 400 MHz): δ7.52-7.55 (m, 1H), 7.19 (d, 1H), 7.03-7.05 (m, 3H), 6.95-6.97 (d, 1H), 3.91 (d, 1H), 3.78-3.91 (m, 7H), 3.55-3.67 (m, 2H), 3.26 (s, 3H), 2.33-2.46 (m, 1H), 1.97-2.05 (m, 1H), 1.89-1.98 (m, 1H), 1.78-1.84 (m, 1H), 1.52-1.62 (m, 1H); ESI MS: m/z 438.2 [M+H]$^+$.

compound 458: $^1$H-NMR (CD$_3$OD 400 MHz): δ7.52 (d, 1H), 7.18 (s, 1H), 7.01 (m, 3H), 6.92 (d, 1H), 3.83 (d, 6H), 3.69-3.79 (m, 2H), 3.52-3.64 (m, 2H), 3.26 (s, 3H), 2.41 (s, 2H), 2.03-2.12 (m, 1H), 1.98-2.03 (m, 1H), 1.84-1.93 (m, 1H), 1.52-1.62 (m, 1H); ESI MS: m/z 438.2 [M+H]$^+$.

Example 244

Preparation of Compounds 276 and 340

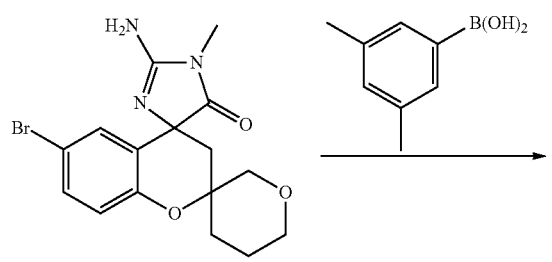

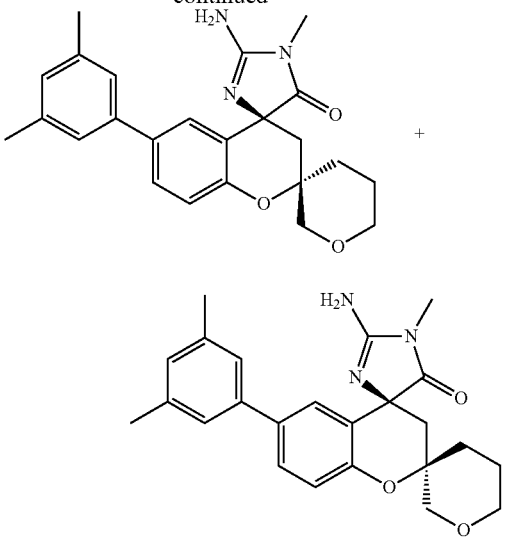

By using the same synthetic strategy as compound 332 described in Example 217, compounds 276 and 340 were obtained.

compound 276 (3.55 mg, 17%), $^1$H-NMR (CD$_3$OD 400 MHz): δ7.57-7.58 (m, 1H), 7.27-7.28 (d, 1H), 7.13 (s, 2H), 7.07-7.10 (d, 1H), 6.99 (s, 1H), 3.83-3.98 (m, 2H), 3.59-3.68 (m, 2H), 3.33 (s, 3H), 2.32-2.52 (m, 8H), 1.82-2.13 (m, 3H), 1.58-1.67 (m, 1H); ESI MS: m/z 406.0 [M+H]$^+$.

compound 340 (0.93 mg, 4%), $^1$H-NMR (CD$_3$OD 400 MHz): δ7.55-7.58 (m, 1H), 7.23-7.24 (d, 1H), 7.11 (s, 2H), 7.05-7.07 (d, 1H), 6.97 (s, 1H), 3.75-3.85 (m, 2H), 3.58-3.67 (m, 2H), 3.31 (s, 3H), 2.46 (s, 2H), 2.34 (m, 6H), 1.88-2.16 (m, 3H), 1.66-1.72 (m, 1H); ESI MS: m/z 406.1 [M+H]$^+$.

Example 245

Preparation of Compound 364

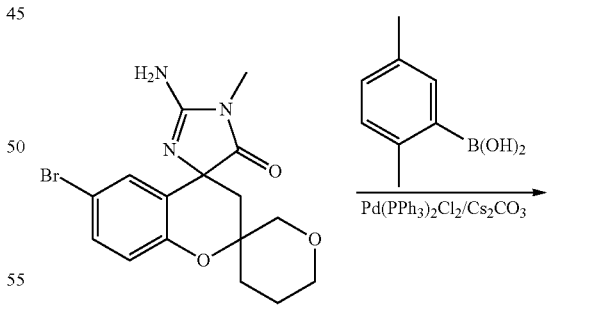

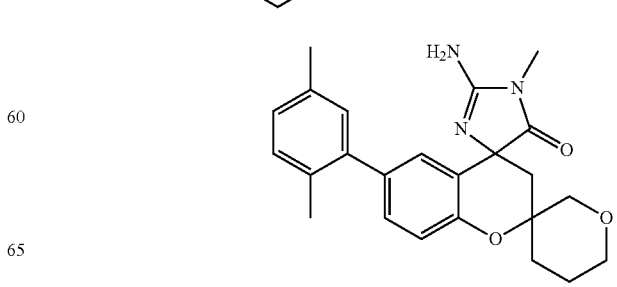

By using the same synthetic strategy as compound 332 described in Example 217, compound 364 (5.67 mg, 27%) was obtained. ¹H-NMR (CD₃OD 400M): δ7.25-7.30 (m, 1H), 7.10-7.14 (m, 1H), 7.01-7.09 (m, 2H), 6.98-7.00 (m, 1H), 6.90-6.96 (m, 1H), 3.75-3.98 (m, 2H), 3.58-3.68 (m, 2H), 3.26 (s, 3H), 2.31-2.48 (m, 2H), 2.29 (s, 3H), 2.12 (s, 3H), 2.01-2.10 (m, 1H), 1.90-2.00 (m, 1H), 1.78-1.88 (m, 1H), 1.55-1.68 (m, 1H); ESI MS: m/z 406.1 [M+H]⁺.

Example 246

Preparation of Compounds 307 and 321

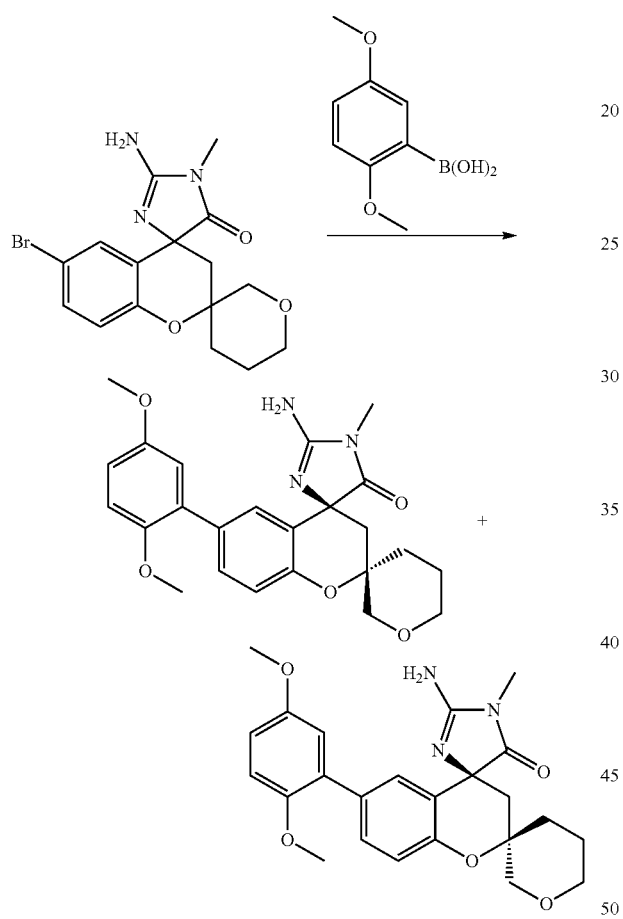

By using the same synthetic strategy as compound 332 described in Example 217, compound 307 (7.91 mg, 35%) and compound 321 (2.23 mg, 10%) were obtained.

compound 307: ¹H-NMR (CD₃OD 400 MHz): δ7.39-7.42 (d, 1H), 7.11 (s, 1H), 6.92 (d, 1H), 6.89 (d, 1H), 6.81 (d, 1H), 6.72 (s, 1H), 3.78-3.90 (m, 2H), 3.72 (s, 3H), 3.66 (s, 3H), 3.52-3.61 (m, 2H), 3.26 (s, 3H), 2.42 (d, 1H), 2.31 (d, 1H), 1.97-2.05 (m, 1H), 1.89-1.98 (m, 1H), 1.78-1.84 (m, 1H), 1.52-1.62 (m, 1H); ESI MS: m/z 438.1 [M+H]⁺.

compound 321: ¹H-NMR (CD₃OD 400 MHz): δ7.39-7.42 (d, 1H), 7.10 (s, 1H), 6.92 (d, 1H), 6.89 (d, 1H), 6.79 (d, 1H), 6.72 (s, 1H), 3.74 (s, 2H), 3.72 (s, 3H), 3.66 (s, 3H), 3.52-3.61 (m, 2H), 3.24 (s, 3H), 2.41 (d, 2H), 1.97-2.09 (m, 1H), 1.89-1.98 (m, 1H), 1.78-1.84 (m, 1H), 1.52-1.62 (m, 1H); ESI MS: m/z 438.1 [M+H]⁺.

Example 247

Preparation of Compounds 233 and 310

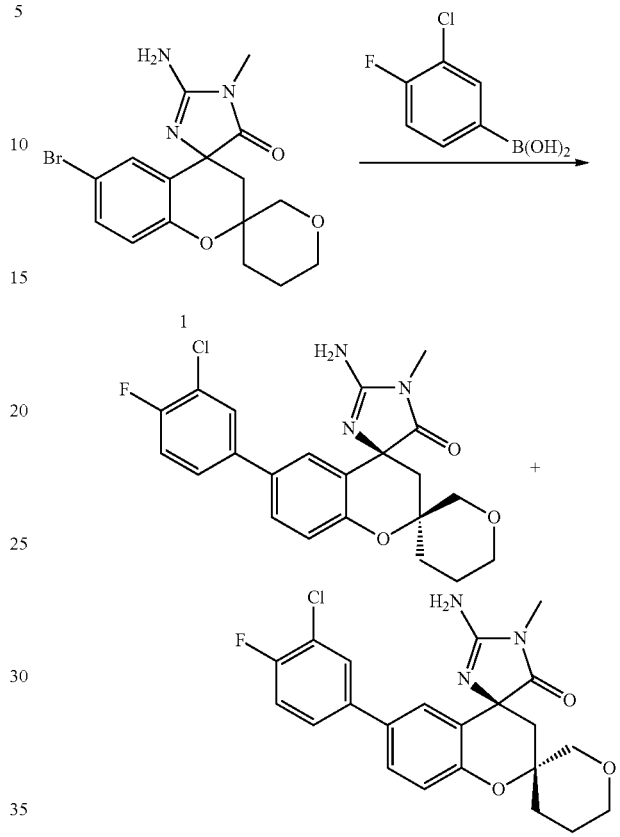

By using the same synthetic strategy as compound 332 described in Example 217, compound 233 (6.55 mg, 23%) and compound 310 (2.18 mg, 8%) were obtained.

compound 233: ¹H NMR (CD₃OD 400 MHz): δ7.67-7.69 (d, 1H), 7.59-7.61 (d, 1H), 7.49-7.51 (m, 1H), 7.37 (s, 1H), 7.26-7.31 (t, 1H), 7.10-7.12 (d, 1H), 3.92-3.96 (m, 2H), 3.58-3.69 (m, 2H), 3.33 (s, 3H), 3.34-2.48 (m, 2H), 1.82-2.08 (m, 3H), 1.56-1.67 (m, 1H); ESI MS: m/z 430.0 [M+H]⁺.

compound 310: ¹H NMR (CD₃OD 400 MHz): δ7.68-7.71 (d, 1H), 7.60-7.62 (d, 1H), 7.49-7.51 (m, 1H), 7.37 (s, 1H), 7.28-7.32 (t, 1H), 7.10-7.13 (d, 1H), 3.79-3.82 (m, 2H), 3.64-3.68 (m, 2H), 3.34 (s, 3H), 2.48 (s, 2H), 1.92-1.98 (m, 3H), 1.65-1.75 (m, 1H). ESI MS m/z 430.0 [M+H]⁺.

Example 248

Preparation of Compounds 287 and 385

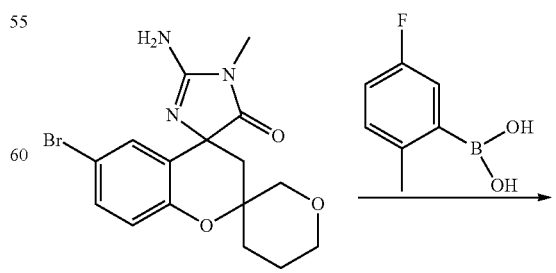

-continued

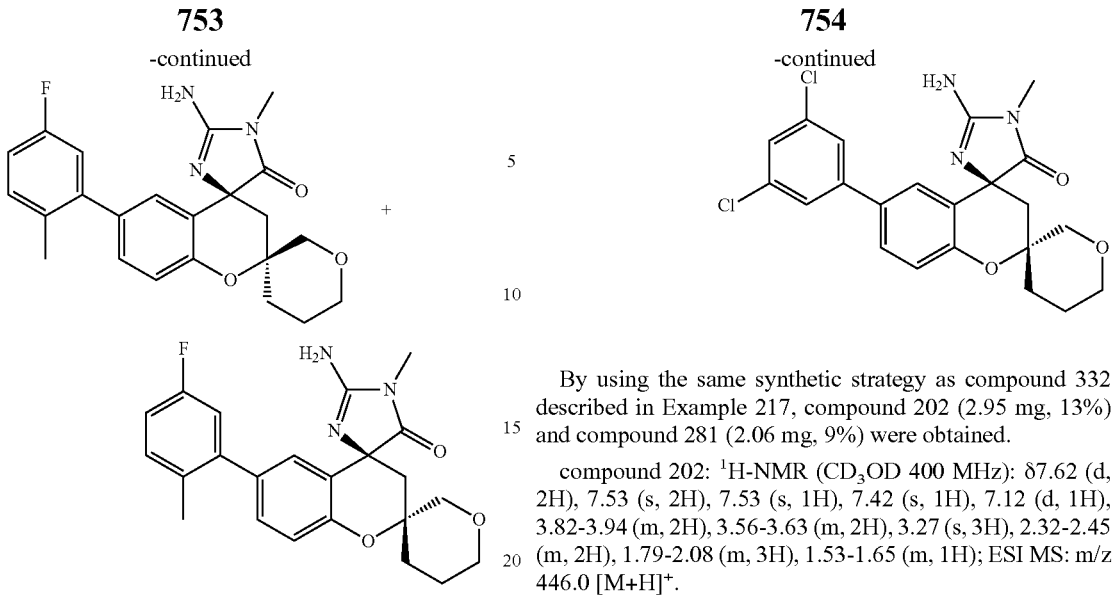

By using the same synthetic strategy as compound 332 described in Example 217, compound 287 (3.25 mg, 15%) and compound 385 (2.49 mg, 12%) were obtained.

compound 287: ¹H-NMR (CD₃OD 400 MHz): δ7.12-7.21 (m, 2H), 6.96-6.98 (m, 2H), 6.83-6.88 (m, 1H), 6.75-6.78 (m, 1H), 3.73-3.85 (m, 2H), 3.47-3.54 (m, 2H), 3.16 (s, 3H), 2.23-2.36 (m, 2H), 2.05 (s, 3H), 1.62-2.03 (m, 3H), 1.52 (m, 1H); ESI MS: m/z 410.1 [M+H]⁺.

compound 385: ¹H-NMR (CD₃OD 400 MHz): δ7.18-7.21 (m, 2H), 6.94-6.97 (m, 2H), 6.83-6.88 (m, 1H), 6.75-6.78 (m, 1H), 3.69-3.74 (m, 2H), 3.51-3.56 (m, 2H), 3.16 (s, 3H), 2.36 (s, 2H), 2.05 (s, 3H), 1.62-2.03 (m, 3H), 1.52 (m, 1H); ESI MS: m/z 410.1 [M+H]⁺.

Example 249

Preparation of Compounds 202 and 281

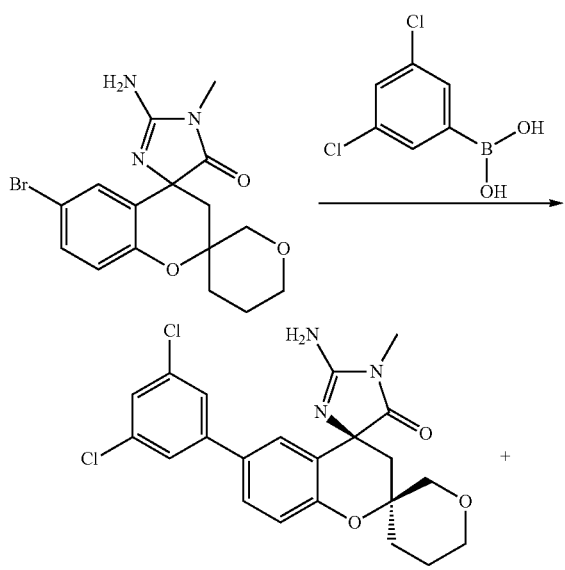

-continued

By using the same synthetic strategy as compound 332 described in Example 217, compound 202 (2.95 mg, 13%) and compound 281 (2.06 mg, 9%) were obtained.

compound 202: ¹H-NMR (CD₃OD 400 MHz): δ7.62 (d, 2H), 7.53 (s, 2H), 7.53 (s, 1H), 7.42 (s, 1H), 7.12 (d, 1H), 3.82-3.94 (m, 2H), 3.56-3.63 (m, 2H), 3.27 (s, 3H), 2.32-2.45 (m, 2H), 1.79-2.08 (m, 3H), 1.53-1.65 (m, 1H); ESI MS: m/z 446.0 [M+H]⁺.

compound 281: ¹H-NMR (CD₃OD 400 MHz): δ7.62 (d, 2H), 7.53 (s, 2H), 7.52 (d, 2H), 7.12 (d, 1H), 3.78-3.87 (m, 2H), 3.56-3.63 (m, 2H), 3.38 (s, 3H), 2.49 (s, 2H), 1.88-2.18 (m, 3H), 1.52 (m, 1H); ESI MS: m/z 446.0 [M+H]⁺.

Example 250

Preparation of Compound 397

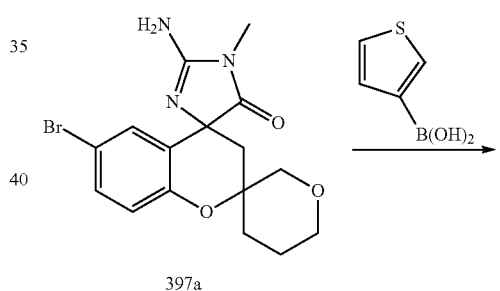

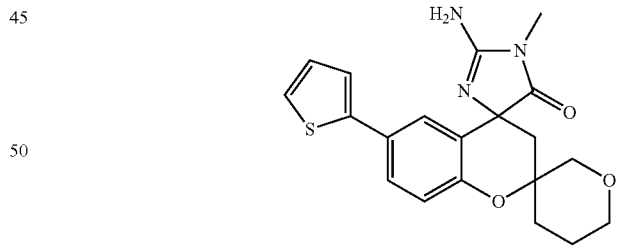

The solution of compound 397a (30 mg, 0.08 mmol), thiophen-3-ylboronic acid (15.2 mg, 0.12 mmol), Pd(PPh₃)₄ (1 mg, 0.001) and Na₂CO₃ (2 M, 0.30 mL) in a mixture of EtOH (0.2 mL) and toluene (1 mL) was heated at 120° C. under Ar₂ overnight. The reaction mixture was extracted with EtOAc, concentrated, and purified by preparative TLC and preparative HPLC to give compound 397 (7.37 mg, 24%). ¹H-NMR (CD₃OD 400 MHz): δ7.58-7.63 (m, 1H), 7.52 (m, 1H), 7.41 (m, 1H), 7.35 (m, 1H), 7.29 (m, 1H), 6.98-7.01 (m, 1H), 3.72-3.94 (m, 2H), 3.56-3.62 (m, 2H), 3.25 (s, 3H), 2.26-2.42 (m, 2H), 1.78-2.08 (m, 3H), 1.53-1.63 (m, 1H); ESI MS: m/z 384.1 [M+H]⁺.

Example 251

Preparation of Compounds 358 and 427

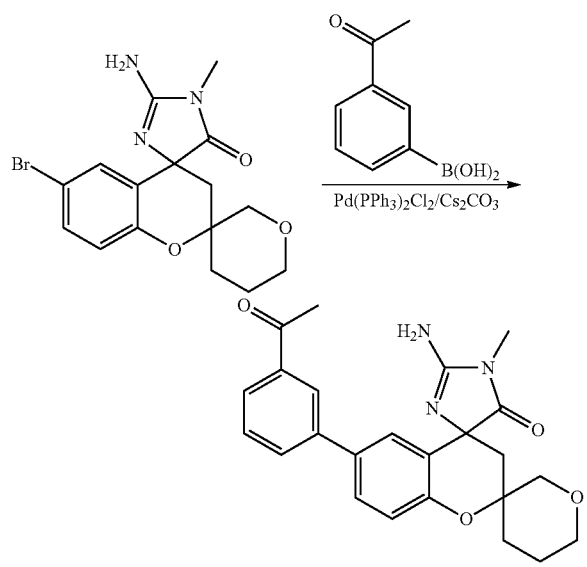

By using the same synthetic strategy as compound 332 described in Example 217, compound 358 (6.53 mg, 30%) and compound 427 (3.67 mg, 16%) were obtained.

compound 358: $^1$H-NMR (CD$_3$OD 400 MHz): δ8.06 (s, 1H), 7.92-7.95 (m, 1H), 7.76-7.78 (m, 1H), 7.62-7.64 (m, 1H), 7.51-7.55 (m, 1H), 7.35 (m, 1H), 7.09-7.11 (m, 1H), 3.94 (m, 1H), 3.83 (m, 1H), 3.55-3.62 (m, 2H), 3.28 (s, 3H), 2.62 (s, 3H), 2.32-2.47 (m, 2H), 1.80-2.08 (m, 3H), 1.59 (m, 1H); ESI MS: m/z 420.0 [M+H]$^+$.

compound 427: $^1$H-NMR (CD$_3$OD 400 MHz): δ8.07 (m, 1H), 7.93-7.95 (m, 1H), 7.76-7.78 (m, 1H), 7.62-7.65 (m, 1H), 7.52-7.56 (t, 1H), 7.34 (s, 1H), 7.08-7.11 (d, 1H), 3.75-3.79 (m, 2H), 3.60-3.64 (m, 2H), 3.28 (s, 3H), 2.62 (s, 3H), 2.45 (m, 2H), 1.89-2.13 (m, 3H), 1.65 (m, 1H); ESI MS: m/z 420.0 [M+H]$^+$.

Example 252

Preparation of Compounds 386 and 429

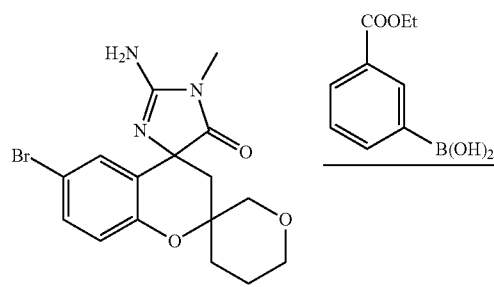

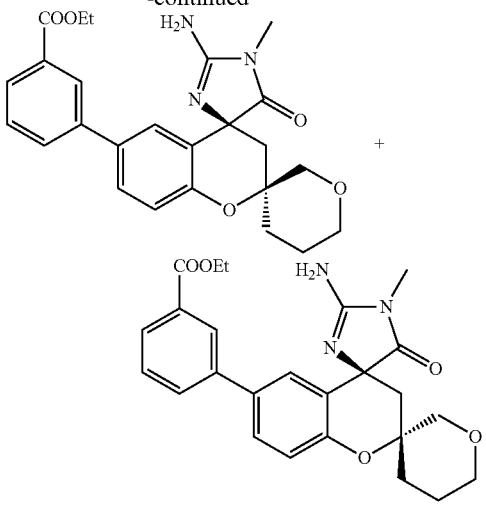

By using the same synthetic strategy as compound 332 described in Example 217, compound 386 (3.77 mg, 16%) and compound 429 (1.98 mg, 8%) were obtained.

compound 386: $^1$H-NMR (CD$_3$OD 400 MHz): δ8.14 (s, 1H), 7.98 (m, 1H), 7.80 (m, 1H), 7.62 (m, 1H), 7.53 (t, 1H), 7.38 (d, 1H), 7.13 (m, 1H), 4.42 (m, 2H), 3.92 (m, 2H), 3.63 (m, 2H), 3.33 (s, 3H), 2.35-2.49 (m, 2H), 1.82-2.13 (m, 3H), 1.62 (m, 1H), 1.42 (m, 3H); ESI MS: m/z 449.9 [M+H]$^+$.

compound 429: $^1$H-NMR (CD$_3$OD 400 MHz): δ8.14 (s, 1H), 7.98 (m, 1H), 7.78 (m, 1H), 7.64 (m, 1H), 7.55 (m, 1H), 7.36 (s, 1H), 7.13 (m, 1H), 4.38-4.43 (m, 2H), 3.78-3.82 (m, 2H), 3.62-3.67 (m, 2H), 3.31 (s, 3H), 2.48 (s, 2H), 1.91-2.18 (m, 3H), 1.68 (m, 1H), 1.40-1.43 (m, 3H); ESI MS: m/z 449.9 [M+H]$^+$.

Example 253

Preparation of Compounds 342 and 378

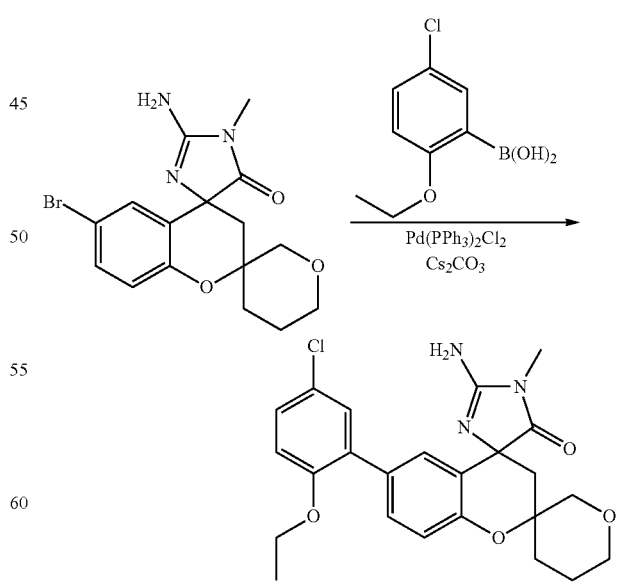

By using the same synthetic strategy as compound 332 described in Example 217, compound 342 (5.08 mg, 21%) and compound 378 (1.84 mg, 8%) were obtained.

compound 342: ¹H-NMR (CD₃OD 400 MHz): δ7.44-7.47 (m, 1H), 7.21-7.25 (m, 3H), 6.98-7.05 (m, 2H), 3.96-4.01 (m, 2H), 3.83-3.94 (m, 2H), 3.60-3.63 (m, 2H), 3.26 (s, 3H), 2.32-2.46 (m, 2H), 179-2.10 (m, 3H), 1.55-1.64 (m, 1H), 1.27-1.31 (t, 3H); ESI MS: m/z 456.0 [M+H]⁺.

compound 378: ¹H-NMR (CD₃OD 400 MHz): δ7.35-7.38 (m, 1H), 7.11-7.16 (m, 3H), 6.89-6.96 (m, 2H), 3.87-3.93 (m, 2H), 3.68-3.71 (m, 2H), 3.52-3.56 (m, 2H), 3.20 (m, 3H), 2.38 (s, 2H), 1.80-2.06 (m, 3H), 1.53-1.62 (m, 1H), 1.17-1.23 (t, 3H); ESI MS: m/z 456.0 [M+H]⁺.

Example 254

Preparation of Compounds 389 and 440

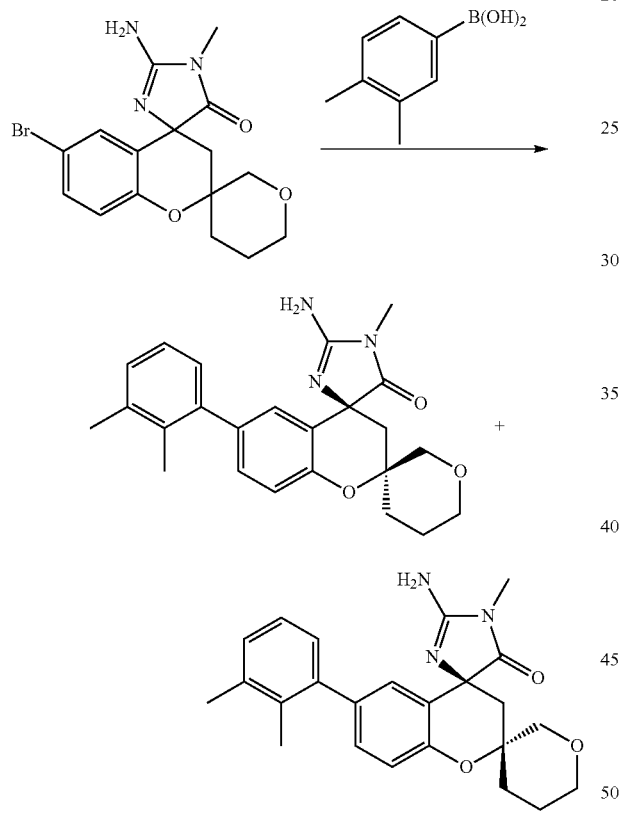

By using the same synthetic strategy as compound 332 described in Example 217, compound 389 (3.55 mg, 17%) and compound 440 (0.93 mg, 4%) were obtained.

compound 389: ¹H-NMR (CD₃OD 400 MHz): δ7.25 (m, 1H), 7.03-7.12 (m, 3H), 6.92-6.95 (m, 2H), 3.95 (m, 1H), 3.86 (m, 1H), 3.60-3.64 (m, 2H), 3.25 (s, 3H), 2.32-2.47 (m, 2H), 2.29 (s, 3H), 2.05-2.10 (m, 4H), 1.82-2.03 (m, 2H), 1.57-1.64 (m, 1H); ESI MS: m/z 406.0 [M+H]⁺.

compound 440: ¹H-NMR (CD₃OD 400 MHz): δ7.26 (m, 1H), 7.03-7.14 (m, 3H), 6.93-6.96 (m, 2H), 3.79-3.82 (m, 2H), 3.64-3.67 (m, 2H), 3.26 (s, 3H), 2.47 (s, 2H), 2.30 (s, 3H), 1.90-2.18 (m, 6H), 1.67 (m, 1H); ESI MS: m/z 406.1 [M+H]⁺.

Example 255

Preparation of Compounds 214 and 256

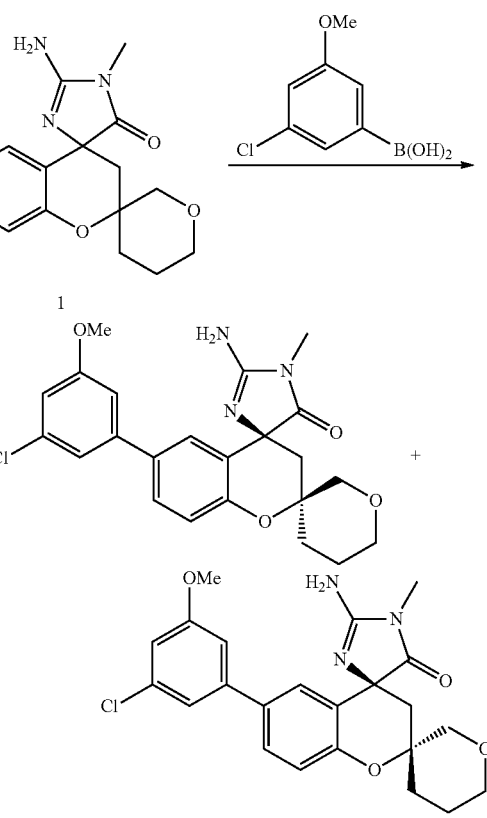

By using the same synthetic strategy as compound 332 described in Example 217, compound 214 (5.35 mg, 18%) and compound 256 (1.17 mg, 4%) were obtained.

compound 214: ¹H NMR (CD₃OD 400 MHz): δ7.53 (d, 1H), 7.25 (s, 1H), 7.02-7.07 (m, 2H), 6.92 (s, 1H), 6.86 (s, 1H), 3.88 (d, 1H), 3.82 (m, 4H), 3.51-3.59 (m, 2H), 3.24 (s, 3H), 2.27-2.40 (m, 2H), 1.75-2.01 (m, 3H), 1.57 (m, 1H); ESI MS: m/z 442.0 [M+H]⁺.

compound 256: ¹H NMR (CD₃OD 400 MHz): δ7.55 (d, 1H), 7.29 (s, 1H), 7.05-7.10 (m, 2H), 6.96 (s, 1H), 6.89 (s, 1H), 3.81 (s, 3H), 3.74-3.78 (m, 2H), 3.59-3.62 (m, 2H), 3.28 (s, 3H), 2.43 (s, 2H), 1.88-2.13 (m, 3H), 1.65 (m, 1H); ESI MS: m/z 442.0 [M+H]⁺.

Example 256

Preparation of Compounds 376, 395 and 435

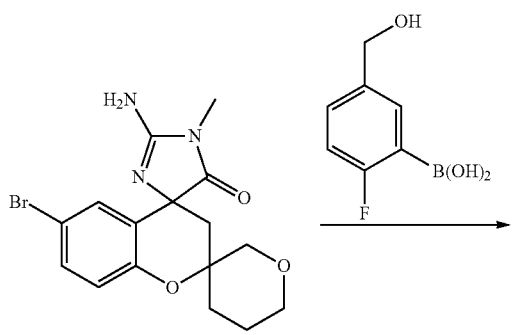

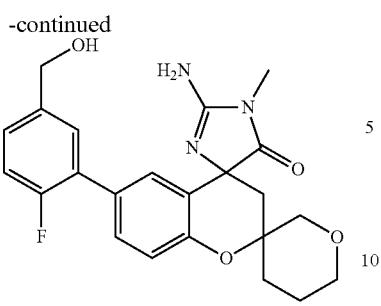

By using the same synthetic strategy as compound 332 described in Example 217, compound 376 (2.60 mg, 12%), compound 395 (1.03 mg, 5%) and compound 435 (1.58 mg, 7%) were obtained.

compound 376: $^1$H-NMR (CD$_3$OD 400 MHz): δ7.50 (m, 1H), 7.36 (m, 1H), 7.28 (m, 1H), 7.22 (s, 1H), 7.06-7.13 (m, 2H), 4.58 (s, 2H), 3.80-3.96 (m, 2H), 3.55-3.65 (m, 2H), 3.26 (s, 3H), 2.31-2.46 (m, 2H), 1.78-2.06 (m, 3H), 1.58 (m, 1H); ESI MS: m/z 426.0 [M+H]$^+$.

compound 395: $^1$H-NMR (CD$_3$OD 400 MHz): δ7.49 (m, 1H), 7.35 (m, 1H), 7.29 (m, 1H), 7.22 (m, 1H), 7.05-7.12 (m, 2H), 4.59 (s, 2H), 3.75-3.96 (m, 2H), 3.53-3.62 (m, 2H), 3.26 (s, 3H), 2.31-2.46 (m, 2H), 1.77-2.14 (m, 3H), 1.55-1.72 (m, 1H); ESI MS: m/z 426.0 [M+H]$^+$.

compound 435: $^1$H-NMR (CD$_3$OD 400 MHz): δ7.50 (m, 1H), 7.35 (m, 1H), 7.28 (m, 1H), 7.21 (s, 1H), 7.05-7.13 (m, 2H), 4.58 (s, 2H), 3.69-3.78 (m, 2H), 3.60-3.63 (m, 2H), 3.22 (s, 3H), 2.45 (s, 2H), 1.83-2.09 (m, 3H), 1.62-1.72 (m, 1H); ESI MS: m/z 426.0 [M+H]$^+$.

Example 257

Preparation of Compound 253

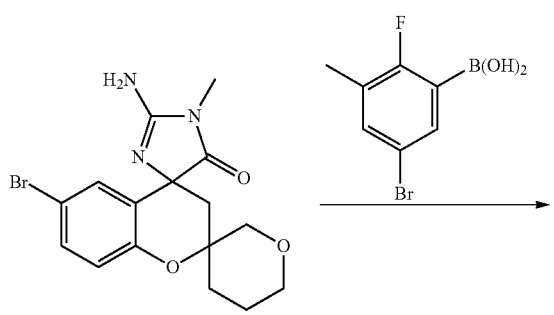

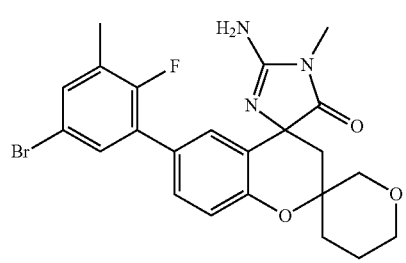

The solution of compound 253a (30 mg), and 5-bromo-2-fluoro-3-methylphenylboronic acid (18 mg), and K$_2$CO$_3$ (2 N, 0.1 mL) in THF (1 mL) was added Pd(PPh$_3$)$_4$ (4.5 mg) under N$_2$, and the mixture was refluxed overnight. The solvent was removed in vacuum, and the crude material was purified by preparative TLC and HPLC to give compound 253 (0.85 mg, 2%). $^1$H-NMR (CD$_3$OD 400 MHz): δ7.48 (m, 1H), 7.34-7.39 (m, 2H), 7.26 (m, 1H), 7.09 (m, 1H), 3.76-3.97 (m, 2H), 3.57-3.68 (m, 2H), 3.29 (m, 3H), 2.33-2.48 (m, 2H), 2.29 (s, 3H), 1.80-2.18 (m, 3H), 1.56-1.72 (m, 1H); ESI MS: m/z 488.0 [M+H]$^+$.

Example 258

Preparation of Compound 207

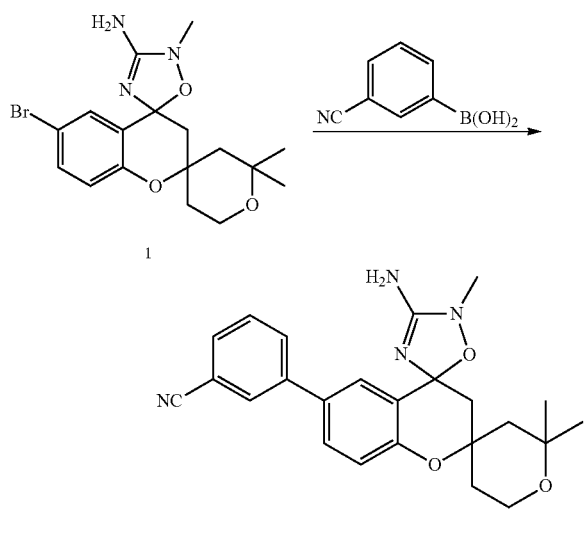

Pd(PPh$_3$)$_2$Cl$_2$ (2 mg) was added to the mixture of 6-bromo-2-(2,2-dimethyltetrahydro-2H-pyran-4-yl)-2'-methyl-2'H-spiro[chroman-4,5'-[1,2,4]oxadiazol]-3'-amine (20 mg, 0.05 mmol), Cs$_2$CO$_3$ (32 mg, 0.10 mmol) and 3-cyanophenylboronic acid (18 mg, 0.10 mmol) in dioxane (3 mL) under Ar$_2$. The mixture was heated at 120° C. in microwave for 15 minutes, and concentrated in vacuo. The residue was purified by preparative TLC and HPLC to give compound 207 (6.49 mg, 31%). $^1$H-NMR (CD$_3$OD): δ7.90-8.05 (m, 3H), 7.60-7.80 (m, 3H), 7.02-7.10 (m, 1H), 4.05-4.15 (m, 1H), 3.78-3.85 (m, 2H), 3.37-3.45 (m, 3H), 2.68-2.75 (d, 1H), 2.10-2.30 (m, 1H), 1.85-2.05 (m, 2H), 1.60-1.68 (m, 1H), 1.32-1.50 (m, 2H), 1.27-1.30 (d, 6H); ESI MS: m/z=433 [M+H]$^+$.

Example 259

Preparation of Compounds 203 and 263

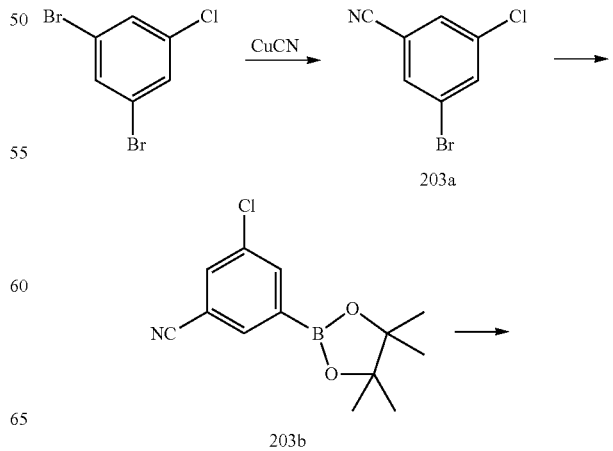

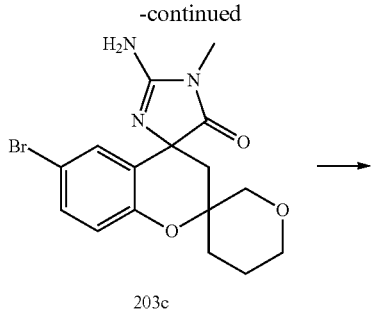

203c

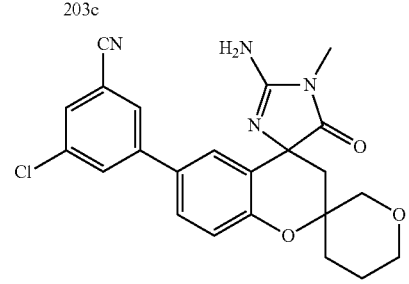

Experimental Data:

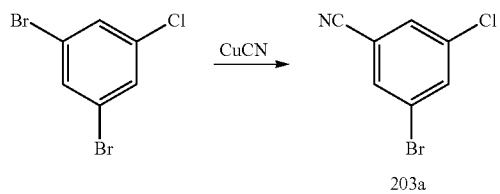

203a

Preparation of Compound 203a

A solution of 1,3-dibromo-5-chlorobenzene (10 g, 37.34 mmol), pyridine (6.03 mL), and copper (I) cyanide (3.34 g, 37.34 mmol) in DMF (57.74 mL) was refluxed under nitrogen for 2 days. The reaction was difficult to be monitored by TLC, when the impurities were observed, the reaction was cooled to room temperature. The reaction mixture was quenched with 40 mL of ether, the precipitate was filtered and washed with ether (20 mL×2). The organic layer was washed with a mixture of water and concentrated ammonium hydroxide (2:1, 40 mL), saturated ammonium chloride solution (40 mL×2), and saturated sodium bicarbonate solution (40 mL). The organic layer was dried over anhydrous sodium sulfate, and concentrated. The residue was purified by column chromatography to give the compound 203a (2 g, 25%).

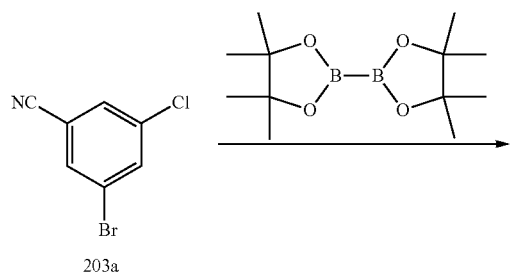

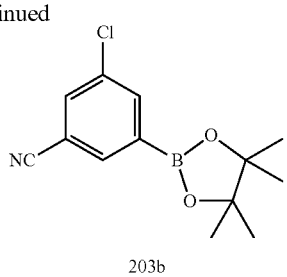

203b

Preparation of Compound 3

A mixture of [1,10-bis(diphenylphosphino)-ferrocenyl] dichloropalladium(II) (0.256 g, 0.279 mmol), potassium acetate (1.365 g, 13.95 mmol), bis(pinacolato)diboron (1.3 g, 5.12 mmol) and 3-bromo-5-fluorobenzonitrile (1 g, 4.65 mmol) in anhydrous DMSO (15 mL) was refluxed under $N_2$ atmosphere overnight. The mixture was extracted with ethyl acetate, dried and concentrated, the residue was purified by preparative TLC to afford the compound 203b (0.08 g, 7%). $^1$H-NMR (CDCl$_3$): δ7.90 (t, 2H), 7.65 (t, 1H), 1.18 (d, 12H, J=5.2 Hz).

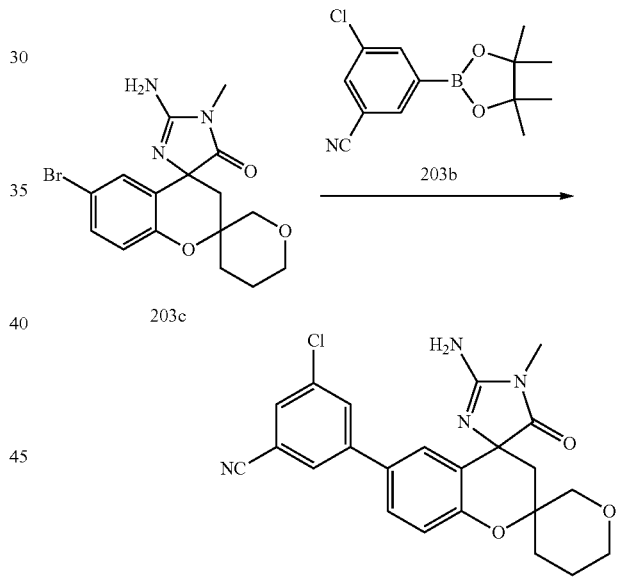

Preparation of Compounds 203 and 263

A mixture of compound 203c (20 mg, 0.0526 mmol), 3-chloro-5-(4,4,5,5-tetramethyl-1,3,2-dioxaborolan-2-yl) benzonitrile (20.8 mg, 0.079 mmol), Cs$_2$CO$_3$ solution (2 M, 0.3 mL), and Pd(PPh$_3$)$_2$Cl$_2$ (5 mg) in 1,4-dioxane (1 mL) under Ar$_2$ was stirred in microwave at 120° C. for 18 minutes. The reaction mixture was concentrated in vacuo, and the residue was purified by preparative TLC to give compound 203 (1.26 mg, 5%), and compound 263 (1.45 mg, 7%).

compound 203: $^1$H-NMR (400 Hz CD$_3$OD): δ7.85-7.95 (m, 2H), 7.50-7.70 (m, 2H), 7.40-7.50 (m, 1H), 7.05-7.12 (m, 1H), 3.80-3.95 (m, 2H), 3.55-3.65 (m, 2H), 3.25-3.35 (m, 3H), 2.3-2.5 (m, 2H), 1.82-2.00 (m, 3H), 1.50-1.55 (m, 1H); ESI MS: m/z=437 [M+H]$^+$.

compound 263: ¹H-NMR (400 Hz CD₃OD): δ7.91 (m, 2H), 7.72 (m, 2H), 7.47 (m, 1H), 7.12 (m, 1H), 3.71 (m, 2H), 3.61 (m, 2H), 3.30 (m, 3H), 2.43 (m, 2H), 1.82-2.20 (m, 3H), 1.65 (m, 1H); ESI MS: m/z=437 [M+H]⁺.

Example 260

Preparation of Compounds 410 and 446

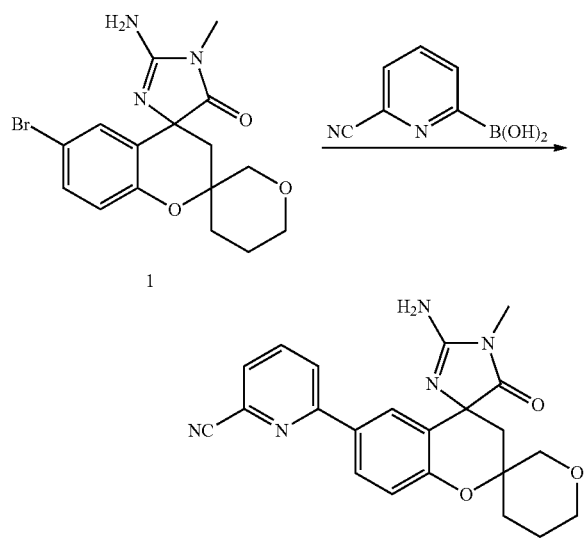

Pd(PPh₃)₂Cl₂ (10 mg) in a 10 mL of tube under Ar₂ was treated sequentially with the solution of compound 1 (20 mg, 0.05 mmol) in 1,4-dioxane (2 mL), Cs₂CO₃ (2 N, 0.3 mL), and 6-cyanopyridin-2-ylboronic acid (14.8 mg, 0.1 mmol). The mixture was heated in microwave at 12° C. for 20 min. The reaction mixture was concentrated in vacuo, the residue was purified by preparative TLC and HPLC to give compound 410 and compound 446 (0.84+0.98 mg, 8%).

compound 410: ¹H NMR (CD₃OD): δ7.94 (t, 2H), 7.64 (m, 1H), 7.31 (m, 1H), 7.04 (d, 1H), 6.86 (t, 1H), 3.82 (t, 1H), 3.57 (t, 2H), 3.47 (s, 1H), 3.38 (s, 3H), 2.19 (t, 2H), 1.82 (t, 2H), 1.51-1.71 (m, 2H); ESI MS: m/z=404 [M+H]⁺.

compound 446: ¹H NMR (CD₃OD): δ8.12 (d, 1H), 8.04 (m, 2H), 7.79 (t, 2H), 7.17 (t, 1H), 3.82 (d, 1H), 3.66 (t, 2H), 3.47 (s, 1H), 2.17 (s, 1H), 2.04 (t, 1H), 1.94 (t, 1H), 1.68 (s, 1H); ESI MS: m/z=404 [M+H]⁺.

Example 261

Preparation of Compounds 424 and 459

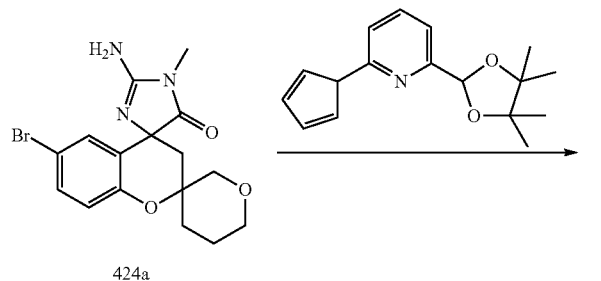

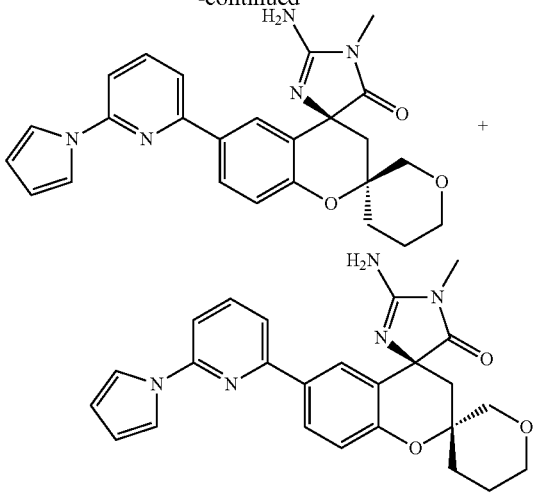

Pd(PPh₃)₂Cl₂ (10 mg) under Ar₂ was added to the mixture of compound 424a (20 mg, 0.05 mmol), Cs₂CO₃ (32 mg, 0.10 mmol) and 2-(cyclopenta-2,4-dienyl)-6-(4,4,5,5-tetramethyl-1,3-dioxolan-2-yl)pyridine (21 mg, 0.08 mmol) in [1,4] dioxane (1 mL). The mixture was heated at 120° C. in microwave for 20 minutes, and concentrated in vacuo, the residue was purified by preparative TLC and HPLC to give compound 424 (1.66 mg, 7%) and compound 459 (1.22 mg, 6%).

compound 424: ¹H NMR (400 MHz CD₃OD): δ8.05-8.15 (m, 1H), 7.80-7.95 (m, 2H), 7.60-7.70 (m, 3H), 7.40-7.50 (m, 1H), 7.10-7.20 (m, 1H), 6.30-6.40 (t, 2H), 3.85-3.95 (m, 2H), 3.55-3.70 (m, 2H), 3.30-3.40 (s, 3H), 2.35-2.53 (m, 2H), 1.80-2.12 (m, 3H), 1.55-1.65 (m, 1H); ESI MS: m/z=443 [M+H]⁺.

compound 425: ¹H NMR (400 MHz CD₃OD): δ8.10-8.15 (m, 1H), 7.80-7.95 (m, 2H), 7.60-7.70 (m, 3H), 7.40-7.50 (m, 1H), 7.10-7.15 (m, 1H), 6.30-6.40 (t, 2H), 3.75-3.85 (m, 2H), 3.60-3.70 (m, 2H), 3.30-3.40 (s, 3H), 2.40-2.60 (m, 2H), 1.90-2.28 (m, 3H), 1.65-1.75 (m, 1H); ESI MS: m/z=444 [M+H]⁺.

Example 262

Preparation of Compound 439

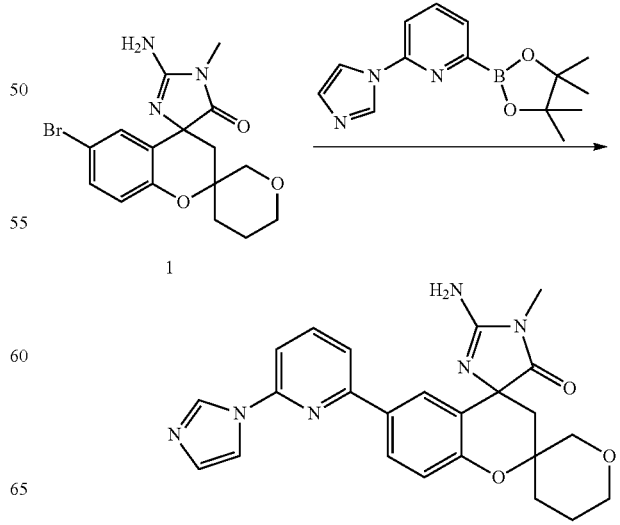

By using the same synthetic strategy as compound 424 described in Example 261, compound 439 (1.46 mg, 7%) was obtained. ¹H NMR (400 MHz CD₃OD): δ9.45-9.55 (s, 1H), 8.20-8.30 (m, 2H), 8.05-8.15 (t, 1H), 7.95-8.05 (d, 1H), 7.75-7.85 (d, 1H), 7.70-7.75 (d, 1H), 7.55-7.65 (s, 1H), 7.14-7.20 (t, 1H), 3.90-4.00 (s, 1H), 3.76-3.82 (m, 1H), 3.52-3.67 (m, 2H), 3.30-3.40 (s, 3H), 2.30-2.50 (m, 2H), 1.81-2.03 (m, 2H), 1.51-1.70 (m, 2H); ESI MS: m/z=445 [M+H]⁺.

Example 263

Preparation of Compounds 433 and 457

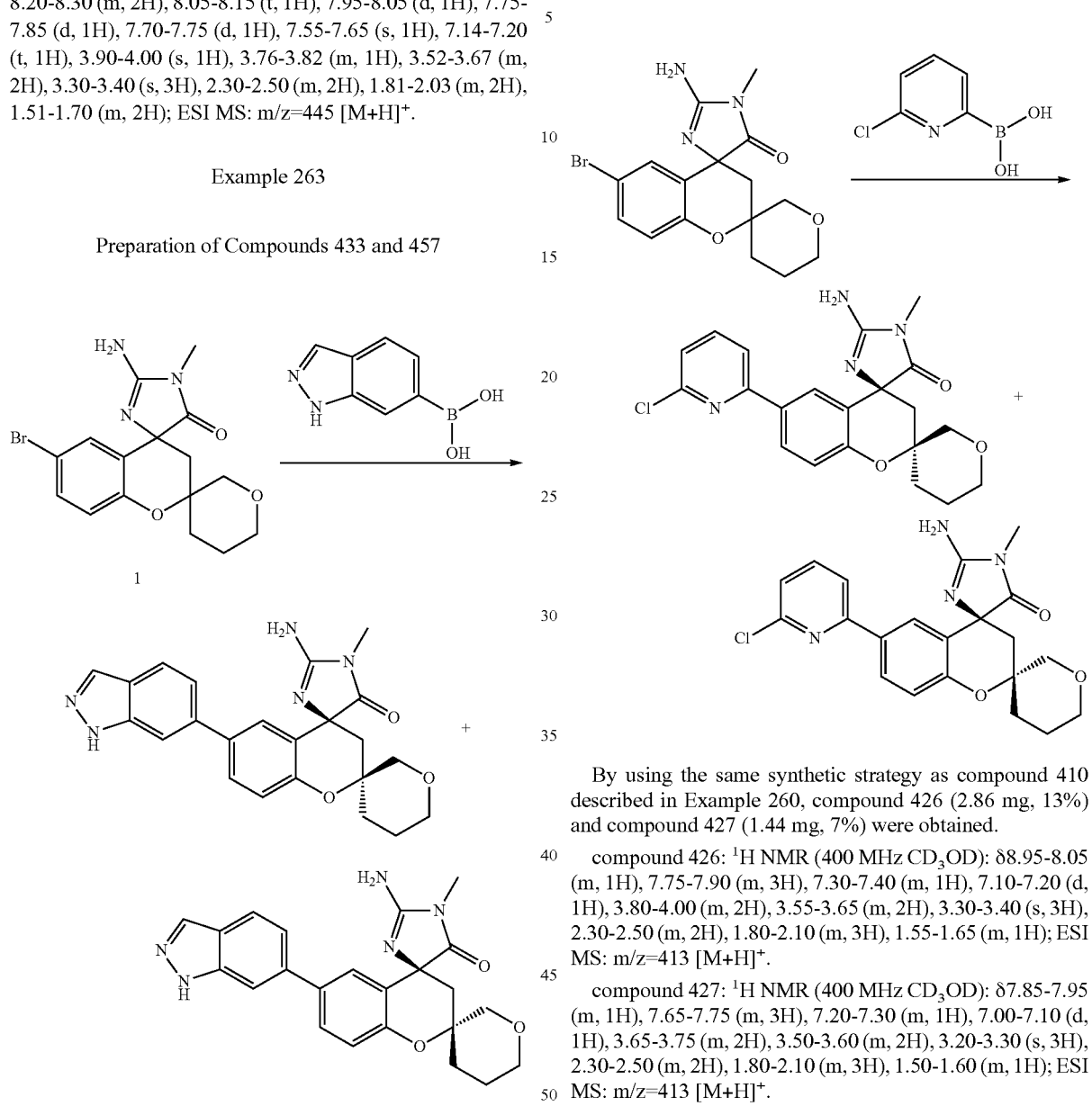

By using the same synthetic strategy as compound 410 described in Example 260, compound 433 (2.26 mg, 10%) and compound 457 (1.69 mg, 8%) were obtained.

compound 433: ¹H NMR (400 MHz CD₃OD): δ8.05-8.10 (s, 1H), 7.80-7.90 (d, 1H), 7.65-7.75 (m, 2H), 7.30-7.45 (m, 2H), 7.09-7.12 (d, 1H), 3.75-3.95 (m, 2H), 3.50-3.70 (m, 2H), 3.20-3.40 (s, 3H), 2.40-2.4540 (m, 1H), 2.30-2.40 (m, 1H), 1.62-2.03 (m, 3H), 1.50-1.55 (m, 1H); ESI MS: m/z=418 [M+H]⁺.

compound 457: ¹H NMR (400 MHz CD₃OD): δ7.90-8.00 (s, 1H), 7.65-7.75 (d, 1H), 7.55-7.65 (m, 2H), 7.20-7.30 (m, 2H), 7.00-7.05 (d, 1H), 3.65-3.75 (m, 2H), 3.50-3.60 (m, 2H), 3.20-3.0 (m, 3H), 2.30-2.40 (s, 2H), 1.75-2.10 (m, 3H), 1.50-1.60 (m, 1H); ESI MS: m/z=418 [M+H]⁺.

Example 264

Preparation of Compounds 426 and 447

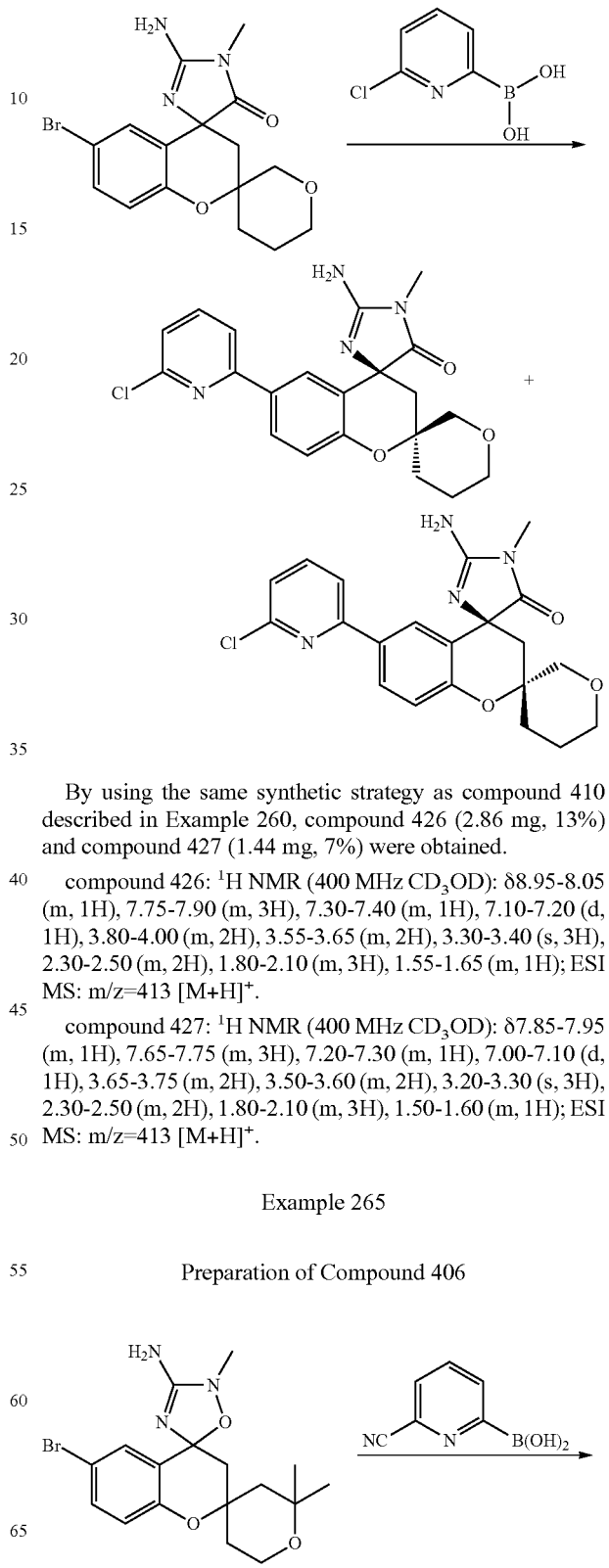

By using the same synthetic strategy as compound 410 described in Example 260, compound 426 (2.86 mg, 13%) and compound 427 (1.44 mg, 7%) were obtained.

compound 426: ¹H NMR (400 MHz CD₃OD): δ8.95-8.05 (m, 1H), 7.75-7.90 (m, 3H), 7.30-7.40 (m, 1H), 7.10-7.20 (d, 1H), 3.80-4.00 (m, 2H), 3.55-3.65 (m, 2H), 3.30-3.40 (s, 3H), 2.30-2.50 (m, 2H), 1.80-2.10 (m, 3H), 1.55-1.65 (m, 1H); ESI MS: m/z=413 [M+H]⁺.

compound 427: ¹H NMR (400 MHz CD₃OD): δ7.85-7.95 (m, 1H), 7.65-7.75 (m, 3H), 7.20-7.30 (m, 1H), 7.00-7.10 (d, 1H), 3.65-3.75 (m, 2H), 3.50-3.60 (m, 2H), 3.20-3.30 (s, 3H), 2.30-2.50 (m, 2H), 1.80-2.10 (m, 3H), 1.50-1.60 (m, 1H); ESI MS: m/z=413 [M+H]⁺.

Example 265

Preparation of Compound 406

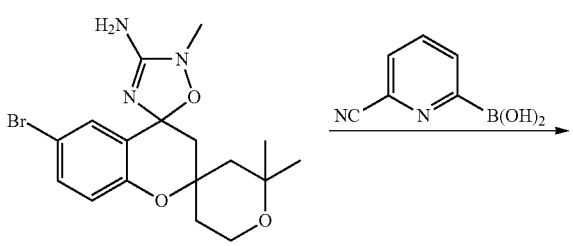

-continued

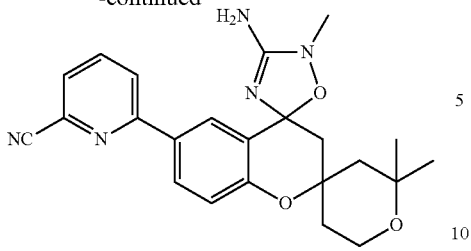

By using the same synthetic strategy as compound 410 described in Example 260, compound 406 (2.37 mg, 11%) was obtained. $^1$H NMR (400 MHz CD$_3$OD): δ8.35-8.45 (m, 2H), 7.95-8.20 (m, 2H), 7.70-7.80 (m, 1H), 7.45-7.55 (m, 1H), 7.30-7.45 (m, 1H), 7.00-7.10 (m, 1H), 4.05-4.15 (m, 1H), 3.70-3.80 (m, 2H), 3.30-3.50 (m, 3H), 2.55-2.65 (m, 1H), 2.10-2.30 (m, 1H), 1.80-2.05 (m, 2H), 1.60-1.70 (m, 1H), 1.30-1.50 (m, 2H), 1.15-1.30 (m, 6H); ESI MS: m/z=434 [M+H]$^+$.

Example 266

Preparation of Compound 445

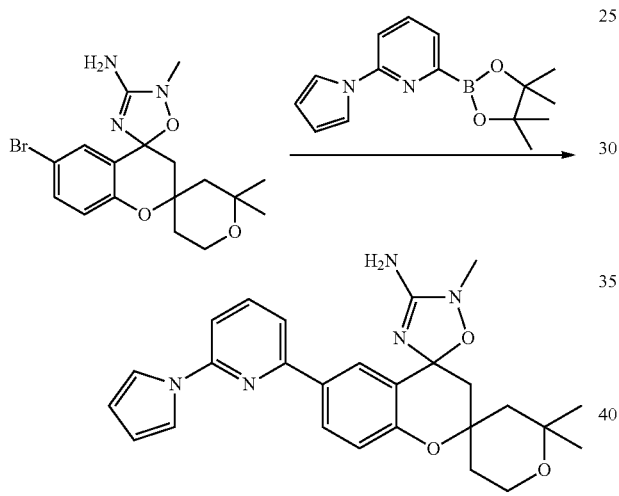

By using the same synthetic strategy as compound 424 described in Example 261, compound 445 (2.15 mg, 9%) was obtained. $^1$H NMR (400 MHz CD$_3$OD): δ8.35-8.45 (m, 1H), 8.15-8.20 (m, 1H), 7.85-7.95 (m, 1H), 7.50-7.65 (m, 3H), 7.40-7.50 (m, 1H), 7.00-7.10 (m, 1H), 6.25-6.35 (m, 2H), 4.05-4.15 (m, 1H), 3.75-3.85 (m, 2H), 3.35-3.50 (m, 3H), 2.65-2.75 (m, 1H), 2.15-2.30 (m, 1H), 2.00-2.10 (m, 1H), 1.85-1.95 (m, 1H), 1.65-1.75 (m, 1H), 1.35-1.55 (m, 2H), 1.25-1.35 (m, 6H); ESI MS: m/z=474 [M+H]$^+$.

Example 267

Preparation of Compound 400

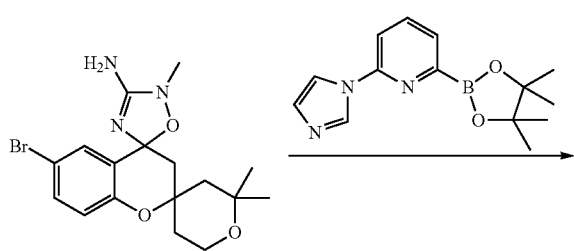

-continued

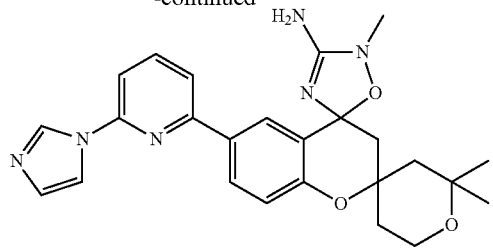

By using the same synthetic strategy as compound 424 described in Example 261, compound 400 (2.23 mg, 10%) was obtained. $^1$H NMR (400 MHz CD$_3$OD): δ9.50-9.60 (s, 1H), 8.35-8.45 (m, 1H), 8.25-8.35 (m, 2H), 8.10-8.20 (m, 1H), 8.00-8.10 (m, 1H), 7.85-7.95 (m, 1H), 7.70-7.80 (m, 1H), 7.55-7.65 (m, 1H), 7.00-7.10 (m, 1H), 4.05-4.15 (m, 1H), 3.60-3.70 (m, 2H), 3.35-3.50 (m, 3H), 2.65-2.75 (m, 1H), 2.15-2.30 (m, 1H), 2.00-2.10 (m, 1H), 1.85-1.95 (m, 1H), 1.60-1.70 (m, 1H), 1.35-1.50 (m, 2H), 1.25-1.35 (m, 6H); ESI MS: m/z=475 [M+H]$^+$.

Example 268

Preparation of Compounds 361 and 369

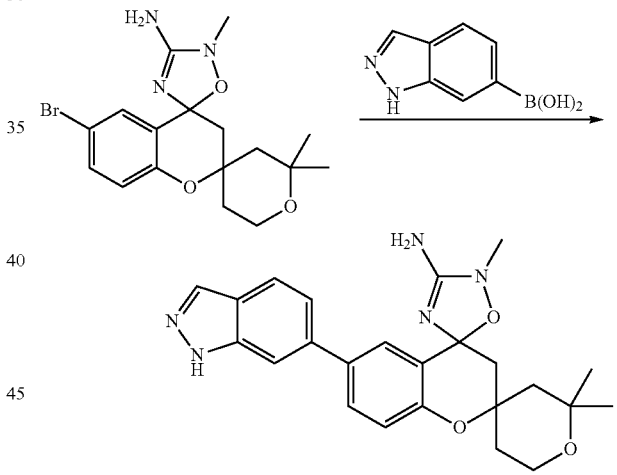

By using the same synthetic strategy as compound 410 described in Example 260, compound 361 (2.13 mg, 10%) and compound 369 (0.60 mg, 3%) were obtained.

compound 361: $^1$H NMR (400 MHz CD$_3$OD): δ8.00-8.10 (s, 1H), 7.90-8.00 (m, 1H), 7.80-7.90 (m, 1H), 7.70-7.80 (m, 2H), 7.65-7.70 (s, 1H), 7.35-7.45 (m, 1H), 7.00-7.10 (m, 1H), 4.05-4.15 (m, 1H), 3.75-3.85 (m, 2H), 3.35-3.50 (m, 3H), 2.65-2.75 (m, 1H), 2.15-2.30 (m, 1H), 2.00-2.10 (m, 1H), 1.85-1.95 (m, 1H), 1.60-1.70 (m, 1H), 1.30-1.55 (m, 2H), 1.20-1.30 (m, 6H); ESI MS: m/z=448 [M+H]$^+$.

compound 369: $^1$H NMR (400 MHz CD$_3$OD): δ7.90-8.00 (s, 1H), 7.80-7.90 (m, 1H), 7.70-7.80 (m, 1H), 7.60-7.70 (m, 1H), 7.55-7.60 (s, 1H), 7.35-7.45 (m, 1H), 6.90-7.00 (m, 2H), 3.90-4.00 (m, 1H), 3.65-3.75 (m, 2H), 3.35-3.50 (m, 3H), 2.65-2.75 (m, 1H), 2.00-2.20 (m, 1H), 1.85-1.95 (m, 1H), 1.75-1.85 (m, 1H), 1.60-1.70 (m, 1H), 1.30-1.55 (m, 2H), 1.20-1.30 (m, 6H); ESI MS: m/z=448 [M+H]$^+$.

Example 269

Preparation of Compound 393

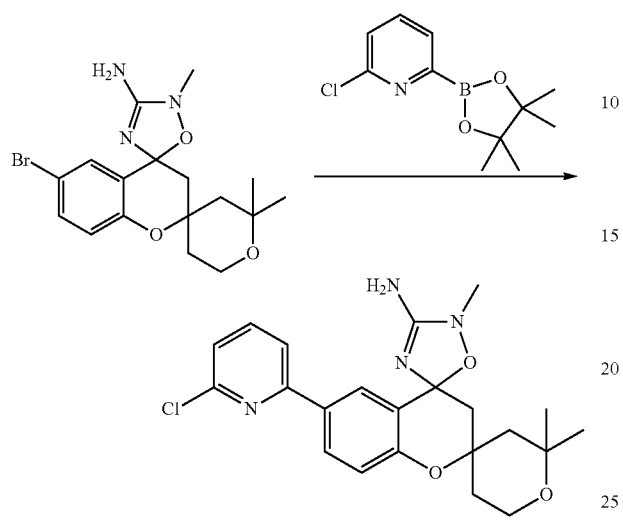

By using the same synthetic strategy as compound 424 described in Example 261, compound 393 (1.31 mg, 6%) was obtained. $^1$H NMR (400 MHz CD$_3$OD): δ8.20-8.30 (s, 1H), 7.90-8.00 (m, 1H), 7.70-7.80 (m, 2H), 7.20-7.30 (m, 1H), 6.95-7.00 (m, 1H), 3.95-4.05 (m, 1H), 3.60-3.70 (m, 2H), 3.25-3.40 (m, 3H), 2.65-2.75 (m, 1H), 2.00-2.20 (m, 1H), 1.85-1.95 (m, 1H), 1.70-1.85 (m, 1H), 1.50-1.60 (m, 1H), 1.35-1.45 (m, 2H), 1.10-1.20 (m, 6H); ESI MS: m/z=443 [M+H]$^+$.

Example 270

Preparation of Compound 196

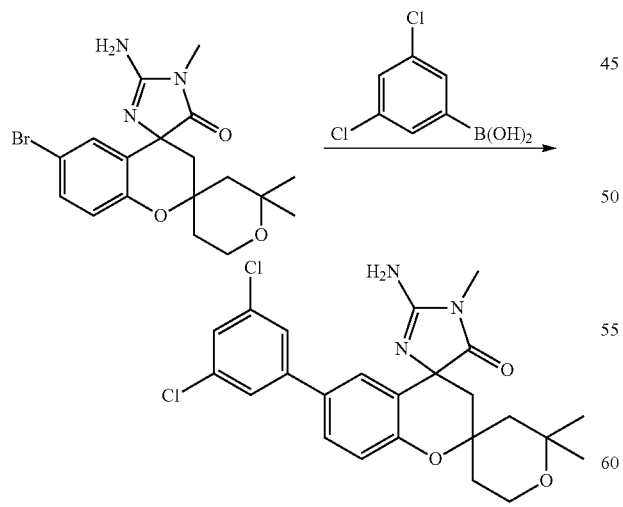

By using the same synthetic strategy as compound 410 described in Example 260, compound 196 (7.58 mg, 32%) was obtained. $^1$H-NMR (400 Hz CD$_3$OD): 7.50-7.60 (m, 3H), 7.40-7.50 (s, 1H), 7.30-7.40 (s, 1H), 7.00-7.10 (m, 1H), 4.50-4.60 (m, 1H), 3.70-3.80 (m, 2H), 3.20-3.30 (s, 3H), 2.35-2.50 (m 1H), 2.05-2.15 (m, 2H), 1.85-1.95 (m, 1H), 1.55-1.65 (m, 1H), 1.30-1.50 (m, 2H), 1.15-1.30 (m, 6H); ESI MS: m/z=488 [M+H]$^+$.

Example 271

Preparation of Compound 182

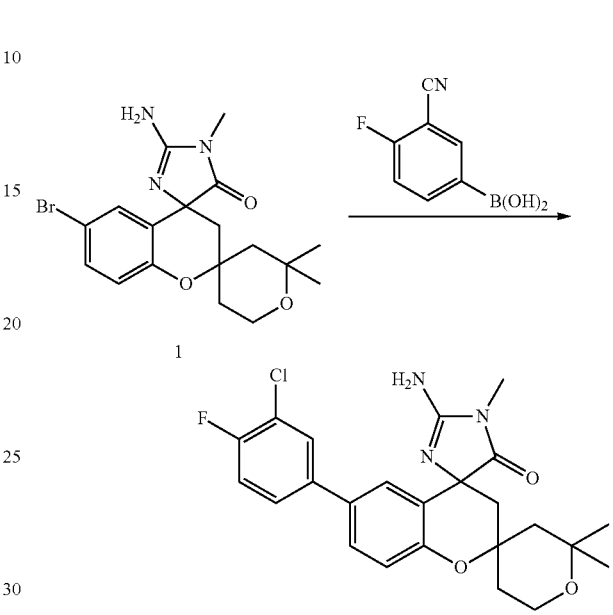

By using the same synthetic strategy as compound 410 described in Example 260, compound 182 (2.11 mg, 12%) was obtained. $^1$H-NMR (400 Hz CD$_3$OD): δ7.80-8.00 (m, 2H), 7.50-7.60 (m, 1H), 7.30-7.50 (m, 2H), 7.00-7.10 (m, 1H), 4.50-4.60 (m, 0.7H), 3.90-4.00 (m, 0.3H), 3.70-3.80 (m, 2H), 3.30-3.35 (s, 1H), 3.20-3.30 (s, 2H), 2.35-2.50 (m 1H), 2.05-2.30 (m, 2H), 1.85-1.95 (m, 1H), 1.55-1.65 (m, 1H), 1.30-1.50 (m, 2H), 1.15-1.30 (m, 6H); ESI MS: m/z=463 [M+H]$^+$.

Example 272

Preparation of Compounds 268 and 187

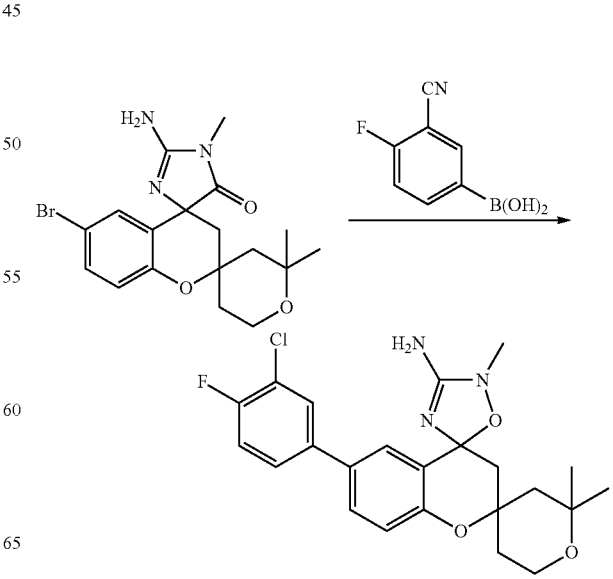

By using the same synthetic strategy as compound 410 described in Example 260, compound 268 and compound 187 (3.52 mg, 16%) were obtained.

compound 268: $^1$H-NMR (400 Hz CD$_3$OD): δ7.55-7.65 (m, 1H), 7.45-7.55 (m, 2H), 7.30-7.40 (m, 1H), 7.20-7.30 (m, 1H), 6.90-7.10 (m, 1H), 4.50-4.60 (m, 1H), 3.00-3.20 (m, 3H), 2.35-2.50 (m 1H), 2.05-2.30 (m, 2H), 1.85-1.95 (m, 1H), 1.55-1.65 (m, 1H), 1.30-1.50 (m, 2H), 1.15-1.30 (m, 6H); ESI MS: m/z=460 [M+H]$^+$.

compound 187: $^1$H-NMR (400 Hz CD$_3$OD): δ7.60-7.70 (m, 1H), 7.45-7.55 (m, 2H), 7.30-7.40 (s, 1H), 7.20-7.30 (m, 1H), 6.90-7.10 (m, 1H), 4.50-4.60 (m, 1H), 3.70-3.80 (m, 2H), 3.20-3.30 (s, 3H), 2.40-2.50 (m 1H), 2.05-2.20 (m, 2H), 1.85-1.95 (m, 1H), 1.55-1.65 (m, 1H), 1.30-1.50 (m, 2H), 1.15-1.30 (m, 6H); ESI MS: m/z=460 [M+H]$^+$.

Example 273

Preparation of Compounds 271 and 328

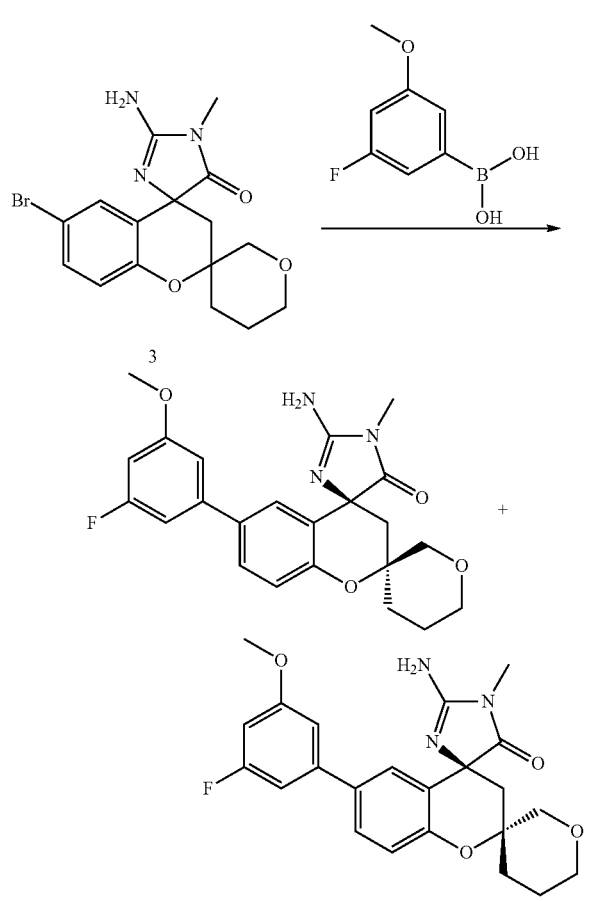

By using the same synthetic strategy as compound 410 described in Example 260, compound 271 (1.69 mg, 8%) and compound 328 (1.54 mg, 7%) were obtained.

compound 271: $^1$H NMR (400 Hz CD$_3$OD): δ7.55-7.65 (m, 1H), 7.30-7.40 (s, 1H), 7.05-7.15 (m, 1H), 6.80-6.90 (m, 2H), 6.60-6.70 (m, 1H), 3.75-4.00 (m, 5H), 3.55-3.65 (m, 2H), 3.30-3.40 (s, 3H), 2.30-2.50 (m, 2H), 1.80-2.10 (m, 3H), 1.50-1.70 (m, 1H); ESI MS: m/z=426 [M+H]$^+$.

compound 328: $^1$H NMR (400 Hz CD$_3$OD): δ7.50-7.60 (m, 1H), 7.30-7.40 (s, 1H), 6.95-7.05 (m, 1H), 6.75-6.85 (m, 2H), 6.55-6.65 (m, 1H), 3.25-3.30 (s, 3H), 3.15-3.25 (m, 2H), 3.50-3.60 (m, 2H), 3.30-3.40 (s, 3H), 2.35-2.45 (s, 2H), 1.80-2.10 (m, 3H), 1.55-1.65 (m, 1H); ESI MS: m/z=426 [M+H]$^+$.

Example 274

Preparation of Compound 223

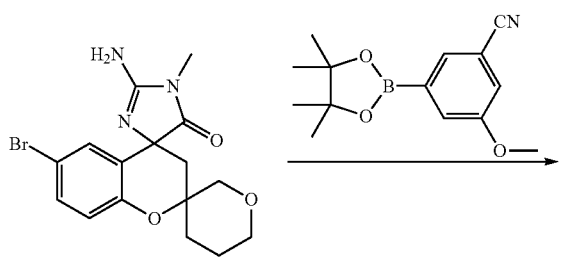

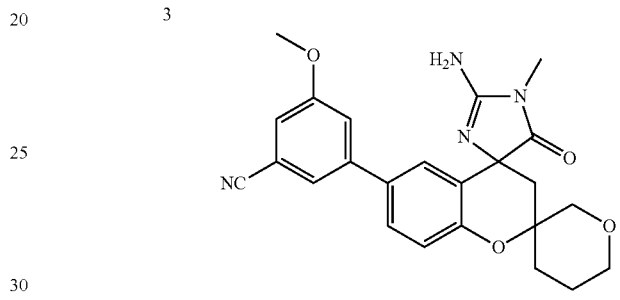

By using the same synthetic strategy as compound 410 described in Example 260, compound 223 (4.50 mg, 20%) was obtained. $^1$H NMR (400 Hz CD$_3$OD): δ7.60-7.70 (m, 1H), 7.45-7.50 (s, 1H), 7.30-7.40 (m, 2H), 7.20-7.25 (m, 1H), 7.05-7.15 (m, 1H), 3.70-4.00 (m, 5H), 3.55-3.65 (m, 2H), 3.30-3.40 (s, 3H), 2.30-2.50 (m, 2H), 1.80-2.10 (m, 3H), 1.50-1.70 (m, 1H); ESI MS: m/z=433 [M+H]$^+$.

Example 275

Preparation of Compounds 283 and 333

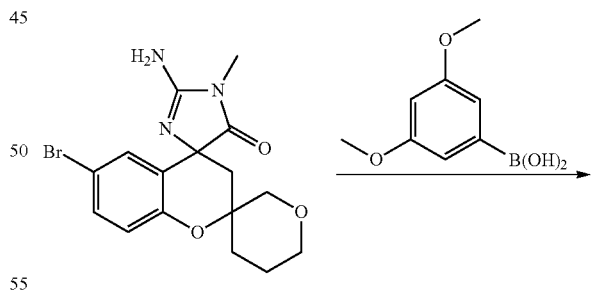

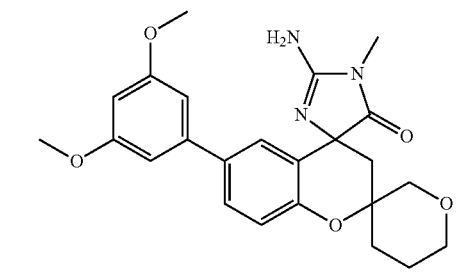

By using the same synthetic strategy as compound 410 described in Example 260, compound 283 (1.97 mg, 7%) and compound 333 (1.78 mg, 6%) were obtained.

compound 283: $^1$H NMR (400 Hz CD$_3$OD): δ7.50-7.60 (m, 1H), 7.10-7.20 (m, 1H), 6.95-7.05 (m, 1H), 6.50-6.60 (s, 2H), 6.35-6.45 (s, 1H), 3.70-4.00 (m, 8H), 3.50-3.65 (m, 2H), 3.30-3.40 (s, 3H), 2.35-2.50 (m, 2H), 1.70-2.10 (m, 3H), 1.50-1.70 (m, 1H); ESI MS: m/z=438 [M+H]$^+$.

compound 333: $^1$H NMR (400 Hz CD$_3$OD): δ7.50-7.60 (m, 1H), 7.20-7.30 (s, 1H), 7.00-7.10 (m, 1H), 6.60-6.70 (s, 2H), 6.40-6.50 (s, 1H), 3.75-3.85 (m, 6H), 3.60-3.70 (m, 2H), 3.30-3.40 (s, 3H), 2.40-2.50 (s, 2H), 1.90-2.20 (m, 3H), 1.60-1.80 (m, 1H); ESI MS: m/z=438 [M+H]$^+$.

Example 276

Preparation of Compound 193

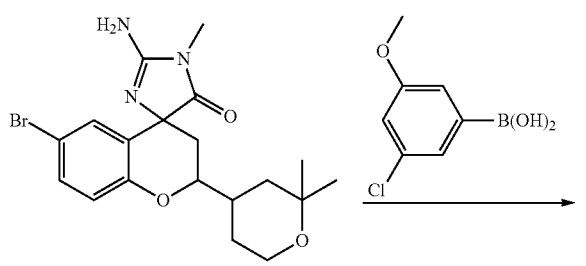

By using the same synthetic strategy as compound 410 described in Example 260, compound 193 (2.76 mg, 12%) was obtained. $^1$H NMR (400 Hz CD$_3$OD): δ7.50-7.60 (m, 1H), 7.20-7.40 (m, 1H), 7.05-7.15 (m, 1H), 6.95-7.05 (m, 2H), 6.85-6.90 (s, 1H), 4.50-4.60 (m, 1H), 3.80-3.85 (s, 3H), 3.70-3.80 (m, 2H), 3.20-3.30 (s, 3H), 2.00-2.50 (m, 3H), 1.85-1.95 (m, 1H), 1.55-1.65 (m, 1H), 1.30-1.50 (m, 2H), 1.20-1.30 (m, 6H); ESI MS: m/z=484 [M+H]$^+$.

Example 277

Preparation of Compound 183

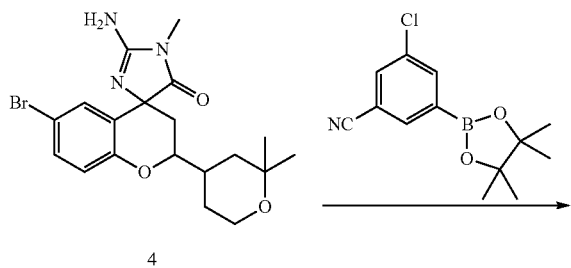

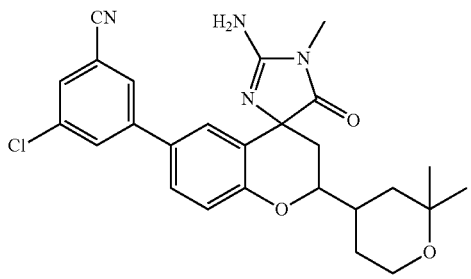

By using the same synthetic strategy as compound 424 described in Example 261, compound 183 (2.38 mg, 10%) was obtained. $^1$H NMR (400 Hz CD$_3$OD): δ7.85-7.95 (m, 2H), 7.60-7.75 (m, 2H), 7.40-7.55 (m, 1H), 7.05-7.15 (m, 1H), 4.50-4.60 (m, 1H), 3.80-3.85 (s, 3H), 3.70-3.80 (m, 2H), 3.35-3.45 (m, 3H), 2.05-2.50 (m, 3H), 1.85-1.95 (m, 1H), 1.55-1.65 (m, 1H), 1.40-1.50 (m, 2H), 1.30-1.40 (m, 6H); ESI MS: m/z=479 [M+H]$^+$.

Example 278

Preparation of Compound 184

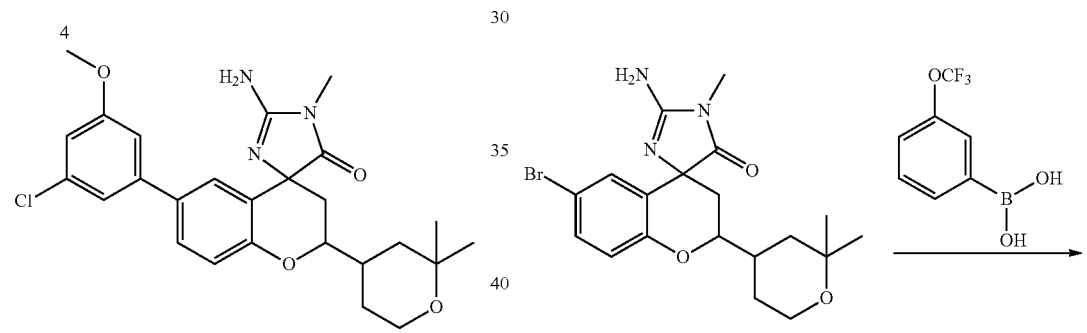

By using the same synthetic strategy as compound 410 described in Example 260, compound 184 (2.0 mg, 15%) was obtained. $^1$H NMR (400 Hz CD$_3$OD): δ7.40-7.65 (m, 5H), 7.15-7.25 (m, 1H), 7.00-7.10 (m, 1H), 4.50-4.60 (m, 1H), 3.70-3.80 (m, 2H), 3.20-3.25 (s, 3H), 2.40-2.50 (m, 2H), 2.00-2.20 (m, 2H), 1.80-1.90 (m, 1H), 1.55-1.65 (m, 1H), 1.30-1.50 (m, 2H), 1.20-1.30 (m, 6H); ESI MS: m/z=504 [M+H]$^+$.

Example 279

Preparation of Compound 195

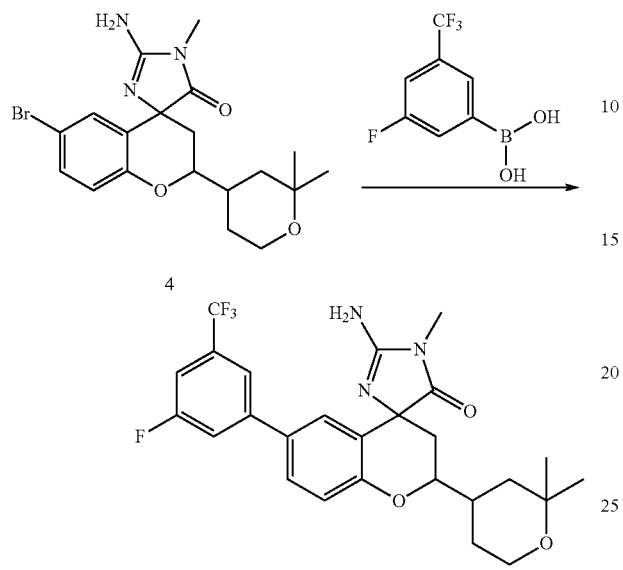

By using the same synthetic strategy as compound 410 described in Example 260, compound 195 (2.0 mg, 8%) was obtained. ¹H NMR (400 Hz CD₃OD): δ7.55-7.70 (m, 3H), 7.50-7.55 (s, 1H), 7.30-7.40 (m, 1H), 7.00-7.10 (m, 1H), 4.50-4.60 (m, 1H), 3.70-3.80 (m, 2H), 3.20-3.25 (s, 3H), 2.40-2.50 (m, 1H), 2.00-2.20 (m, 2H), 1.85-1.95 (m, 1H), 1.55-1.65 (m, 1H), 1.30-1.50 (m, 2H), 1.20-1.30 (m, 6H); ESI MS: m/z=506 [M+H]⁺.

Example 280

Preparation of Compound 418

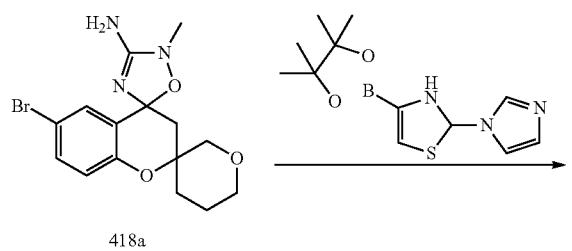

Pd(PPh₃)₂Cl₂ (10 mg) in a 10 mL tube was treated sequentially with the solution of compound 418a (20 mg, 0.05 mmol) in 1,4-dioxane (2 mL), Cs₂CO₃ solution (2 N, 0.3 mL), and 2-(1H-imidazol-1-yl)-4-(4,4,5,5-tetramethyl-1,3,2-dioxaborolan-2-yl)-2,3-dihydrothiazole (27.7 mg, 0.1 mmol) under Ar₂. The mixture was heated in microwave at 120° C. for 20 min., concentrated in vacuo, and the residue was purified by preparative TLC and HPLC to give compound 418 (1.45 mg, 12%). ¹H-NMR (400 MHz CD₃OD): δ8.51 (d, 1H), 7.86 (t, 1H), 7.73 (s, 1H), 7.62 (s, 1H), 7.52 (d, 1H), 7.17 (d, 1H), 7.00 (s, 1H), 3.62-3.86 (m, 2H), 3.52 (d, 2H), 3.24 (s, 3H), 2.28-2.41 (m, 2H), 2.02 (s, 1H), 1.92 (s, 1H), 1.83 (d, 1H), 1.54 (s, 1H); ESI MS: m/z 451.2 [M+Na]⁺.

Example 281

Preparation of Compound 370

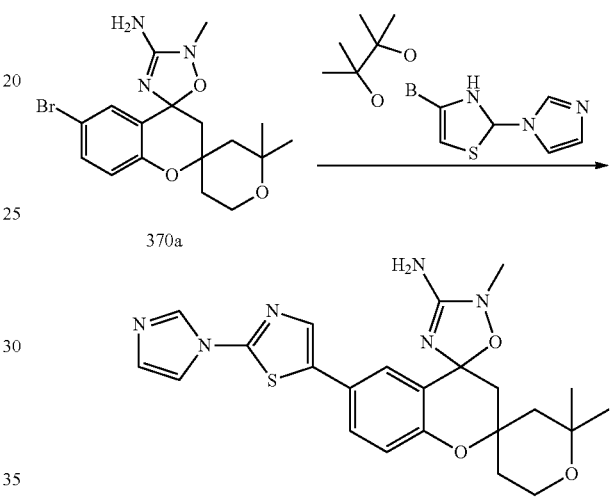

Pd(PPh₃)₂Cl₂ (10 mg) in a 10 mL of tube under Ar₂ was treated sequentially with the compound 370a (20 mg, 0.05 mmol) in 1,4-dioxane (2 mL), Cs₂CO₃ (2 N, 0.3 mL) and 2-(1H-imidazol-1-yl)-4-(4,4,5,5-tetramethyl-1,3,2-dioxaborolan-2-yl)-2,3-dihydrothiazole (27.7 mg, 0.1 mmol). The mixture was heated under microwave at 120° C. for 20 min. The reaction mixture was concentrated in vacuo, and the residue was purified by preparative TLC and HPLC to give compound 370 (1.58 mg, 14%). ¹H-NMR (400 MHz CD₃OD): δ8.52 (s, 1H), 8.21 (s, 1H), 7.94 (d, 1H), 7.82 (s, 1H), 7.68 (s, 1H), 7.21 (s, 1H), 6.96 (t, 1H), 4.03 (d, 1H), 3.73 (t, 2H), 3.41 (d, 3H), 2.64 (d, 1H), 2.19 (s, 1H), 1.98 (t, 1H), 1.84 (t, 1H), 1.63 (t, 1H), 1.32-1.51 (m, 2H), 1.26 (d, 6H); ESI MS: m/z 481.3 [M+H]⁺.

Example 282

Preparation of Compounds 245 and 247

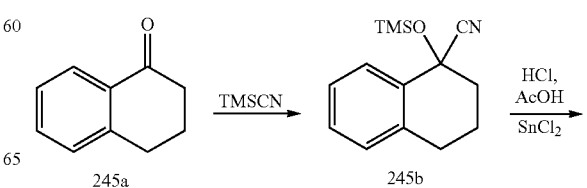

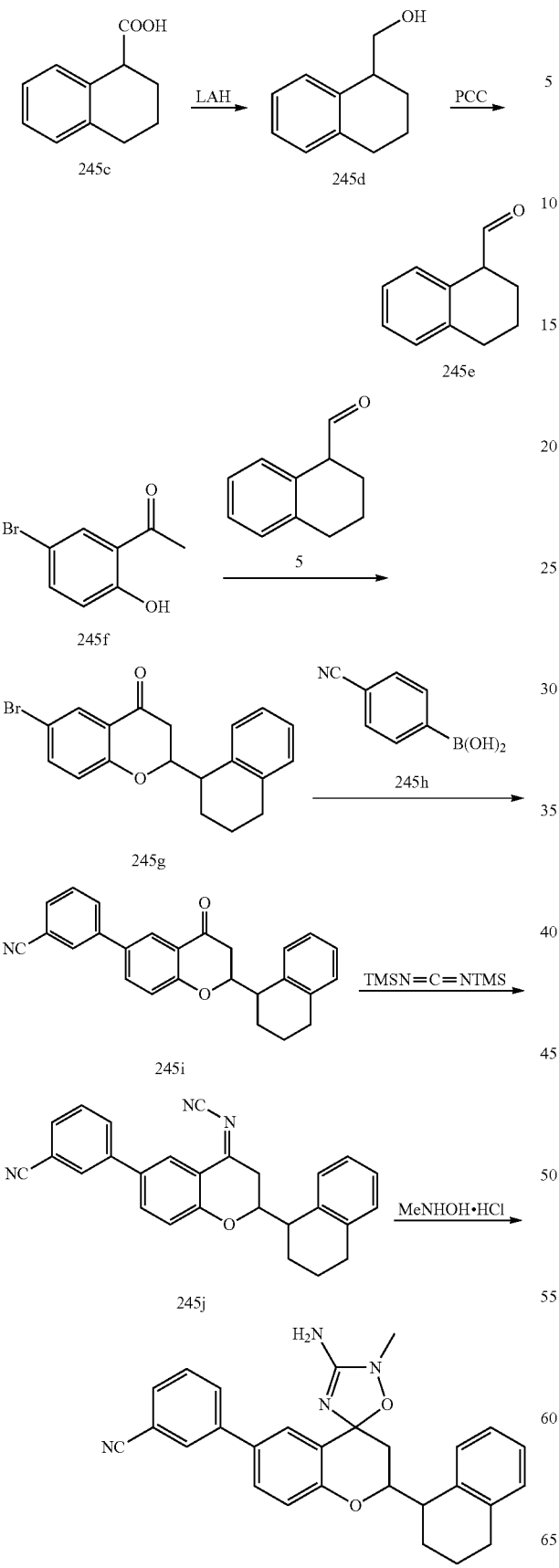

Experimental Data:

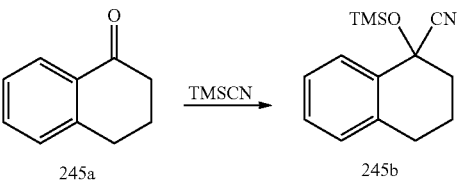

Preparation of Compound 245b

A mixture of compound 245a (20 g, 137 mmol) and zinc (II) iodide (0.874 g, 2.74 mmol) in $CH_2Cl_2$ (300 mL) was slowly added trimethylsilanecarbonitrile (40.9 mL, 205.5 mmol) at 0° C. This mixture was stirred at room temperature overnight, washed with 300 mL of saturated aqueous sodium bicarbonate solution. The organic layer was dried ($MgSO_4$), and concentrated in vacuo to give the compound 245b (32 g, 97%), which was used for the next step without purification.

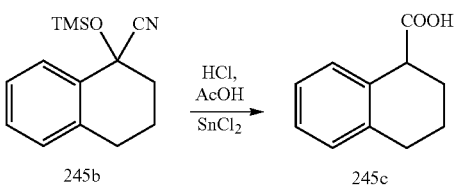

Preparation of Compound 245c

A mixture of compound 245b (16.1 g, 65.5 mmol) and $SnCl_2 \cdot 2H_2O$ (56 g, 248.3 mmol) in a mixture of acetic acid (60 mL) and concentrated HCl solution (60 mL) was refluxed overnight. The mixture was extracted with $CH_2Cl_2$ (150 mL×3). The combined organic phase was washed with 2N sodium hydroxide solution (100 mL×3). The combined basic washes were extracted with ether (100 mL×2), and subsequently acidified to pH=2 with 5N HCl solution. The acidic aqueous mixture was extracted with EA (150 mL×3), and the combined organic layer was dried and concentrated in vacuo to give the compound 245c (10 g, 85%), which was used for the next step without purification. $^1$H-NMR (400 MHz $CDCl_3$): δ10.7 (br s, 1H), 7.05-7.20 (m, 4H), 3.76 (m, 1H), 2.78 (m, 2H), 2.08 (m, 2H), 1.85-2.01 (m, 2H).

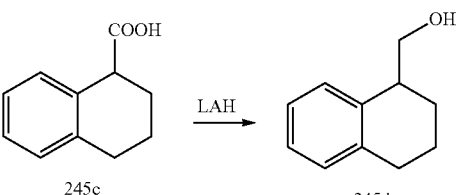

Preparation of Compound 245d

To a stirred solution of LAH (3.5 g, 92 mmol) in THF (50 mL) was cooled to 0° C., and was added compound 245c (8 g, 45.5 mmol). The mixture was stirred overnight, quenched by water (3.5 mL) and aqueous NaOH (10%, 3.5 mL) at 0° C., and filtered. The cake was washed with EtOAc for 3 times, and the filtrate was dried and concentrated in vacuo to give the compound 245d (7.2 g, 98%). $^1$H-NMR (400 MHz CDCl$_3$): δ7.05-7.20 (m, 4H), 3.76 (m, 2H), 2.98 (m, 1H), 2.78 (m, 2H), 1.65-1.94 (m, 5H).

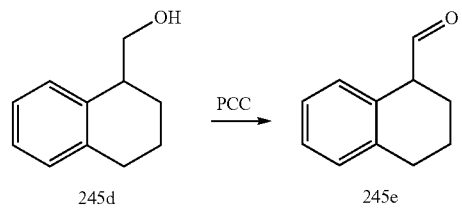

Preparation of Compound 245e

To a solution of compound 245d (3 g, 18.5 mmol) in dry CH$_2$Cl$_2$ (60 mL) was added 3 Å molecule series (1.9 g) and PCC (6 g, 27.8 mmol). The mixture was stirred at room temperature for 2 h, and TLC showed that the reaction was completed. The mixture was filtered through celite, dried over Na$_2$SO$_4$, and concentrated in vacuo to give the compound 245e (1.4 g, 46%).

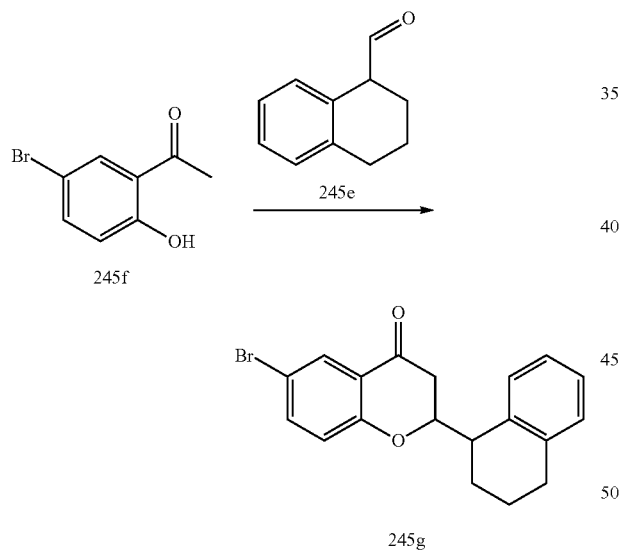

Preparation of Compound 245g

To a stirred solution of compound 245f (1.8 g, 8.7 mmol) in a mixture of EtOH (11.4 mL) and H$_2$O (18.3 mL) was added compound 245e (1.4 g, 8.7 mmol) and borax (3.31 g, 8.7 mmol). The mixture was refluxed for 2 days. The mixture was filtrated, and the filtrate was removed in vacuo. The residue was dissolved in CH$_2$Cl$_2$, and filtrated.

The solvents were evaporated, the crude product was purified by column chromatography to give the compound 245g (600 mg, crude).

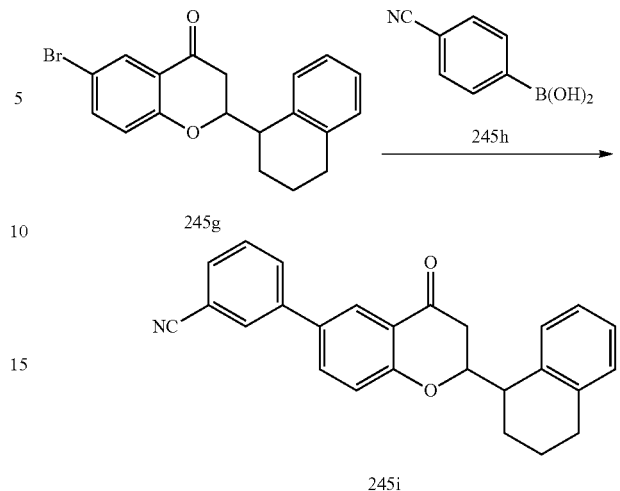

Preparation of Compound 245i

To a solution of compound 245g (300 mg, 0.84 mmol), compound 245h (247 mg, 1.68 mmol), Cs$_2$CO$_3$ solution (2 M, 1.0 mL) in 1,4-dioxane (4.2 mL) was added Pd(PPh$_3$)$_2$Cl$_2$ (15 mg) under N$_2$. The mixture was stirred at 100° C. for 6 minutes, and cooled to room temperature. After extraction, the organic layer was dried and concentrated. The residue was purified by TLC to give the compound 245i (100 mg, 31%). $^1$H-NMR (400 MHz CDCl$_3$): δ8.00 (m, 1H), 7.74 (m, 3H), 7.63 (m, 1H), 7.52 (m, 1H), 7.48 (m, 1H), 7.06 (m, 4H), 4.61-4.32 (m, 1H), 3.21-3.47 (m, 1H), 2.74 (m, 3H), 2.58 (m, 1H), 2.08 (m, 1H), 1.84 (m, 2H), 1.75 (m, 1H).

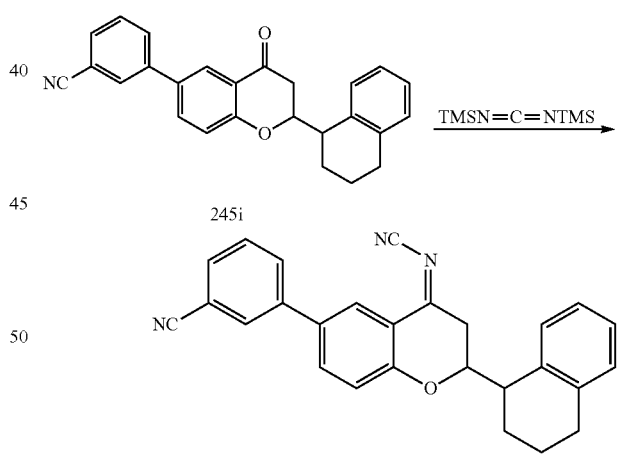

Preparation of Compound 245j

To a solution of compound 245i (75 mg, 0.20 mmol) in CH$_2$Cl$_2$ (2 mL) was added TiCl$_4$ (1 M in DCM, 74 mg, 0.40 mmol). The mixture was stirred in microwave at 50° C. for 10 minutes. Bis-trimethylsilylcarbodiimide (74 mg, 0.40 mmol) was added, and the resulting mixture was stirred in microwave at 60° C. for 10 minutes. The reaction mixture was poured into the ice-water, extracted with DCM, dried over anhydrous Na₂SO₄, and filtered. The filtrate was concentrated in vacuo to give the compound 245j (70 mg, 87.5%).

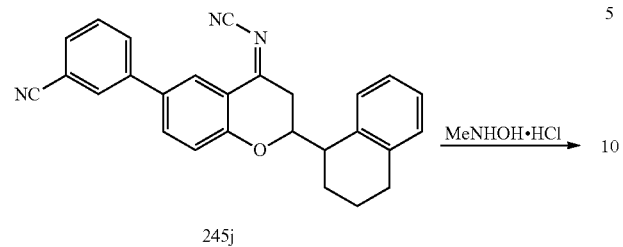

245j

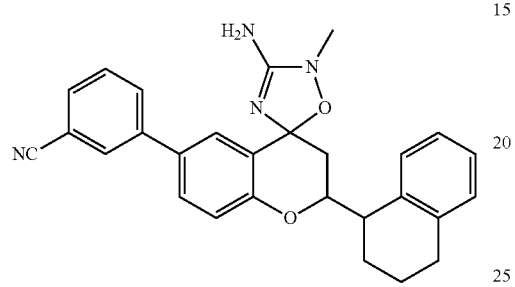

Preparation of Compounds 245 and 247

To a solution of methylhydroxylamine HCl salt (16 mg, 0.17 mmol) in anhydrous MeOH (5 mL) was added NaOMe (10% in MeOH, 24 mg, 0.16 mmol) and compound 245j (70 mg, 0.17 mmol). After being stirred for 20 minutes, the solvent was removed in vacuo, and the residue was dissolved in DCM (5 mL). The mixture was filtered, and the solvent was removed, the residue was purified by preparative HPLC to give the compound 245 (6.48 mg, 8%) and compound 247 (1.5 mg, 2%).

compound 245: ¹H-NMR (400 MHz CD₃OD): δ7.98 (m, 1H), 7.92 (m, 2H), 7.72 (m, 2H), 7.59 (m, 1H), 7.30 (m, 1H), 7.15 (m, 3H), 7.00 (m, 1H), 461-4.74 (m, 1H), 3.47 (m, 1H), 3.33 (m, 3H), 2.78 (m, 2H), 2.45-2.61 (m, 1H), 1.85-2.10 (m, 4H), 1.75 (m, 1H); ESI MS: m/z 451 [M+H]⁺.

compound 247: ¹H-NMR (400 MHz CD₃OD): δ7.92-7.97 (m, 3H), 7.59-7.72 (m, 3H), 7.34 (m, 1H), 7.14 (m, 3H), 7.00 (m, 1H), 461-4.74 (m, 1H), 3.36 (m, 4H), 2.78 (m, 2H), 2.45-2.61 (m, 2H), 1.85-2.10 (m, 3H), 1.75 (m, 1H); ESI MS: m/z 451 [M+H]⁺.

Example 283

Preparation of Compounds 279 and 331

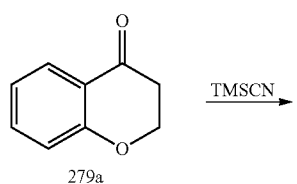

279a

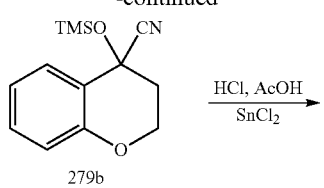

279b

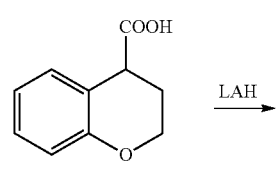

279c

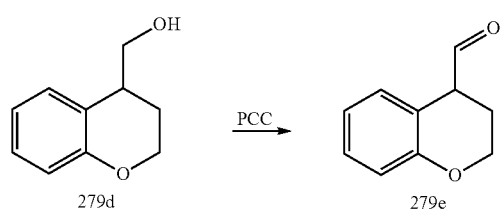

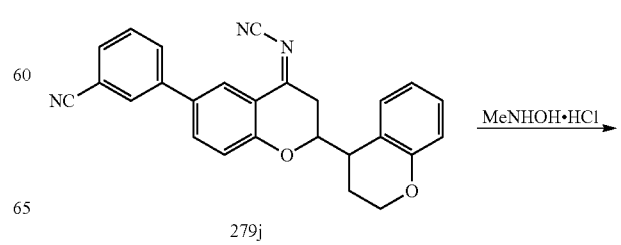

-continued

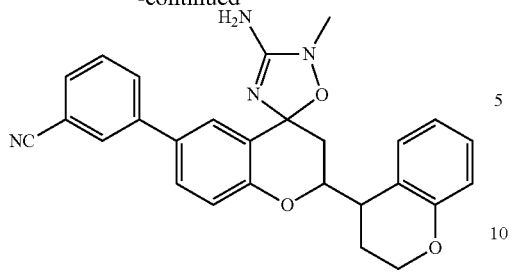

Experimental Data:

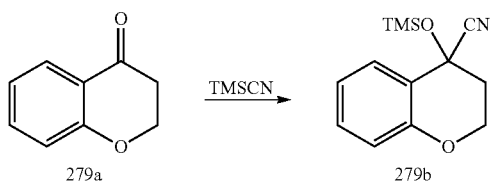

Preparation of Compound 279b

To the mixture of compound 279a (15 g, 67.5 mmol) and zinc (II) iodide (0.6 g, 1.25 mmol) in $CH_2Cl_2$ (300 mL) was cooled to 0° C., and slowly added trimethylsilanecarbonitrile (15 g, 101.8 mmol). The mixture was stirred at room temperature overnight, washed with 300 mL of saturated aqueous sodium bicarbonate solution, and the organic layer was dried ($MgSO_4$), and concentrated in vacuo to give the compound 279b (25 g, 98%), which was used for the next step without purification. $^1$H-NMR (400 MHz CDCl$_3$): δ7.45 (m, 1H), 7.11 (m, 1H), 6.85 (m, 1H), 6.71 (m, 1H), 4.18 (m, 2H), 2.22 (m, 2H), 0.05 (m, 9H).

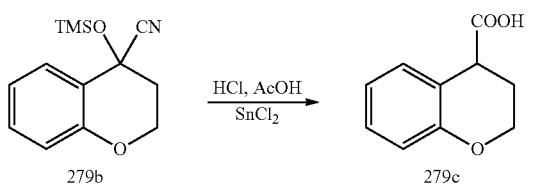

Preparation of Compound 279c

A mixture of compound 279b (16.2 g, 65.5 mmol) and SnCl (56 g, 248.3 mmol) in a mixture of acetic acid (60 mL) and concentrated HCl (60 mL) was heated to reflux for 3 days. The mixture was extracted with $CH_2Cl_2$ (150 mL×3), washed with 2N sodium hydroxide (100 mL×3). The combined basic washes were extracted with ether (100 mL×2), and subsequently acidified to pH=2 with 5N HCl solution. The acidic aqueous mixture was extracted with EA (150 mL×3), and the combined organic layer was dried and concentrated in vacuo to give the compound 279c (10 g, 85%), which was used for the next step without purification. $^1$H-NMR (400 MHz CDCl$_3$): δ8.05-9.05 (m, 1H), 7.20 (m, 1H), 7.05 (m, 1H), 6.85 (m, 2H), 4.21 (m, 2H), 3.51-3.74 (m, 1H), 2.01-2.31 (m, 2H).

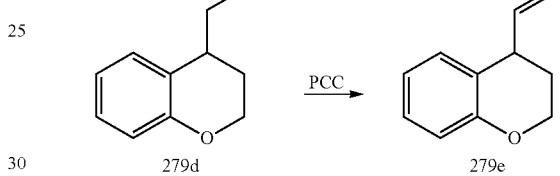

Preparation of Compound 279d

To a stirred solution of LAH (5.34 g, 140.5 mmol) in THF (100 mL) under $N_2$ was added compound 279c (10 g, 56.18 mmol) at 0° C. The mixture was stirred overnight. Aqueous NaOH (1 N, 12 mL) was added at 0°, and the mixture was filtered. The cake was washed with EtOAc for three times, and the filtrate was dried and concentrated to give the compound 279d (7.8 g, 86%).

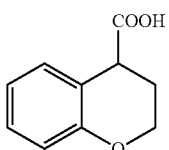

Preparation of Compound 279e

To a solution of compound 279d (3 g, 18.5 mmol) in dry $CH_2Cl_2$ (60 mL) was added 3 Å molecule series (1.9 g) and PCC (6 g, 27.8 mmol). The mixture was stirred at room temperature for 2 h, and TLC showed that the reaction was completed. The mixture was filtered through celite, dried over $Na_2SO_4$, and concentrated in vacuum to give the compound 279e (1.6 g, 53%). $^1$H-NMR (400 MHz CDCl$_3$): δ9.62 (m, 1H), 7.82 (m, 1H), 7.45 (m, 1H), 7.05-7.21 (m, 2H), 4.50 (m, 2H), 4.11 (m, 1H), 2.75 (m, 2H).

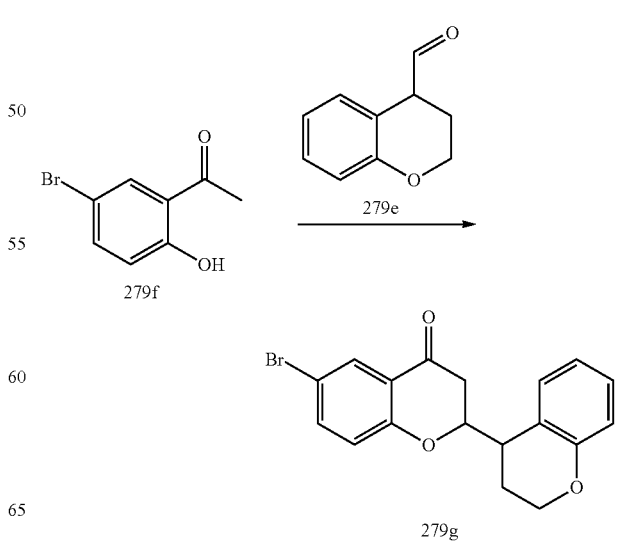

Preparation of Compound 279g

To a stirred solution of compound 279f (2.12 g, 10 mmol) in a mixture of EtOH (13 mL) and H$_2$O (21.3 mL) was added compound 279e (1.6 g, 10 mmol) and borax (3.81 g, 10 mmol). The mixture was refluxed overnight. The mixture was filtrated, and the filtrate was removed in vacuo. The residue was dissolved in CH$_2$Cl$_2$. After filtration, the solvents were evaporated, the crude product was purified by column chromatography to give the compound 279g (600 mg, crude).

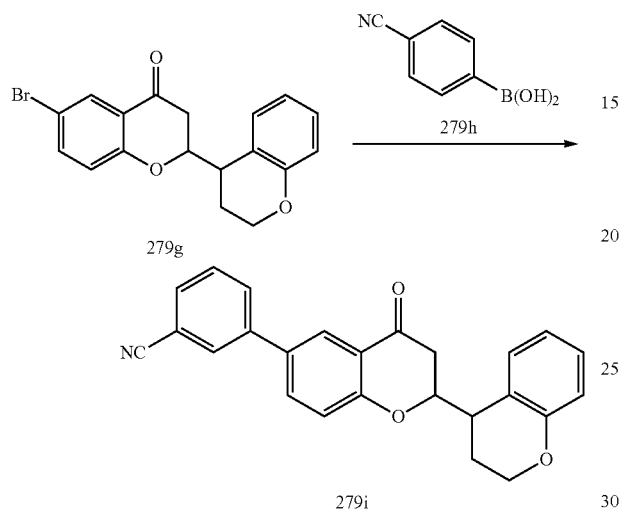

Preparation of Compound 279i

To a solution of compound 279g (100 mg, 280 mmol), compound 279h (61.74 mg, 420 mmol), Cs$_2$CO$_3$ solution (2 M, 1.5 mL) in 1,4-dioxane (4 mL) was added Pd(PPh$_3$)$_2$Cl$_2$ (25 mg) under N$_2$. The mixture was stirred at 100° C. for 20 min, cooled to room temperature, dried, and concentrated. The residue was purified by pre-TLC to give the compound 279i (30 mg, crude).

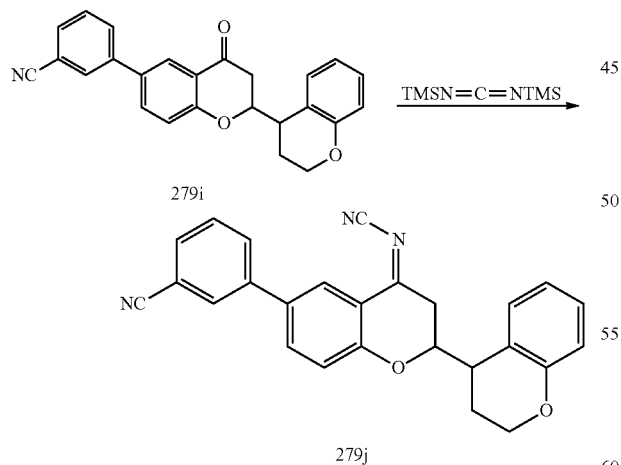

Preparation of Compound 279j

To a solution of compound 279i (30 mg, 0.079 mmol) in CH$_2$Cl$_2$ (1 mL) was added TiCl$_4$ (1 M in DCM, 0.157 mL, 0.157 mmol). This mixture was stirred in microwave at 50° C. for 10 minutes, and bis-trimethylsilylcarbodiimide (0.039 mL, 0.174 mmol) was added. The resulting mixture was stirred in microwave at 60° C. for 10 minutes, poured into ice-water, extracted with DCM. The combined organic phases were dried over anhydrous Na$_2$SO$_4$, and filtered. The filtrate was concentrated to give the compound 279j (30 mg, crude).

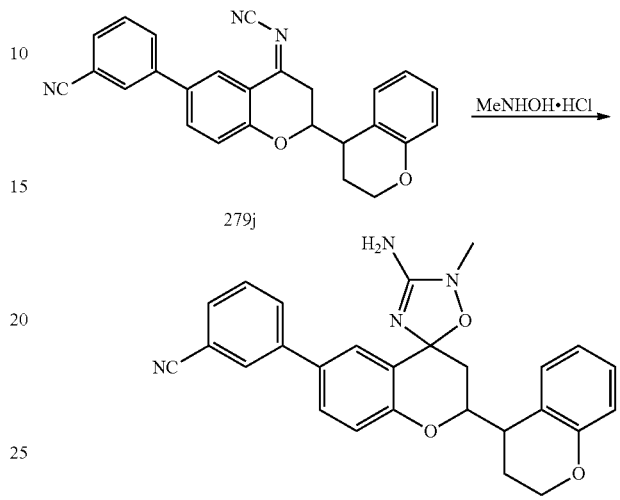

Preparation of Compounds 279 and 331

To a solution of methylhydroxylamine HCl salt (6.2 mg, 0.074 mmol) in anhydrous MeOH (2 mL) was added NaOMe (10% in MeOH (Wt. %), 3.6 mg, 0.067 mmol), followed by compound 279j (30 mg, 0.074 mmol). After being stirred at room temperature for 20 minutes, the solvent was removed in vacuo. The residue was dissolved in DCM (5 mL), and the mixture was filtered. The solvent was removed, and the residue was purified by preparative HPLC to give the compound 279 (2.03 mg, 6%), and compound 331 (1.12 mg, 4%).

compound 279: $^1$H-NMR (400 MHz CD$_3$OD): δ7.91 (m, 3H), 7.55-7.62 (m, 3H), 7.22 (m, 1H), 7.01 (m, 2H), 6.71 (m, 2H), 4.51 (m, 1H), 4.22 (m, 2H), 3.33 (m, 3H), 2.88 (m, 1H), 2.55-2.61 (m, 1H), 2.33 (m, 1H), 2.05 (m, 2H); ESI MS: m/z 453 [M+H]$^+$.

compound 331: $^1$H-NMR (400 MHz CD$_3$OD): δ7.88 (m, 3H), 7.51-7.63 (m, 3H), 7.19 (m, 1H), 7.01-7.32 (m, 2H), 6.70-6.82 (m, 2H), 4.57 (m, 1H), 4.13-4.25 (m, 2H), 3.42 (m, 3H), 2.88-3.05 (m, 1H), 2.33-2.61 (m, 3H), 2.05 (m, 2H); ESI MS: m/z 453 [M+H]$^+$.

Example 284

Preparation of Compound 396

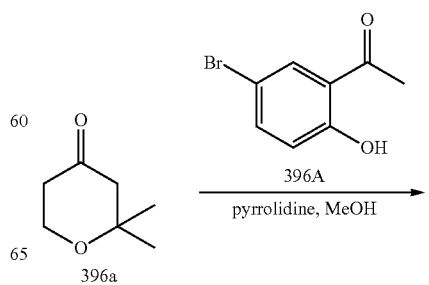

-continued

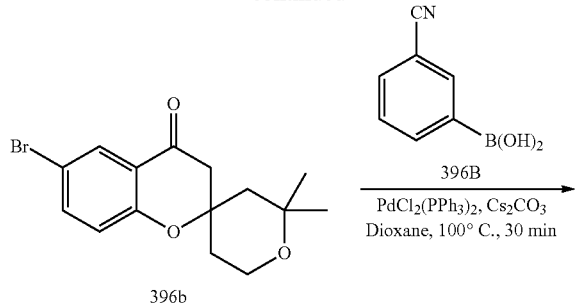

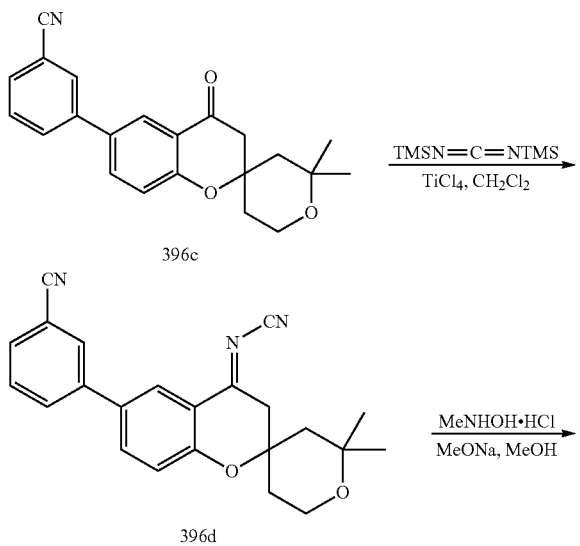

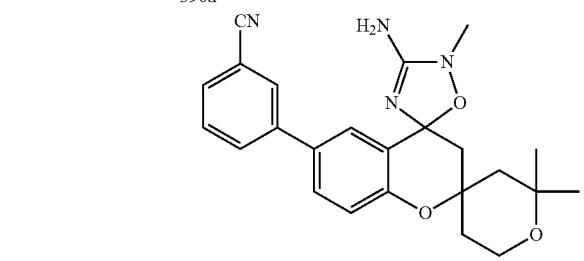

Experimental Data

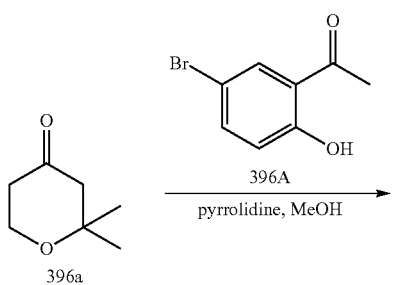

To a stirred solution of compound 396a (0.64 g, 5 mmol) in MeOH (40 mL) was added compound 396A (0.72 g, 3.3 mmol) and pyrrolidine (0.41 mL). The mixture was refluxed overnight. TLC showed that the reaction was completed, and the solvent was removed under reduced pressure. The residue was dissolved in EtOAc (100 mL), washed with brine (60 mL), dried over $Na_2SO_4$ and concentrated. The residue was purified by pre-TLC (petroleum ether:EA=5:1) to give the compound 396b (359 mg, yield 22%) as a yellow solid. $^1$H-NMR (CDCl$_3$ 400 MHz): δ7.91 (s, 1H), 7.49-7.52 (d, 1H), 6.80-6.83 (d, 1H), 3.96-4.04 (t, 1H), 3.62-3.67 (dd, 1H), 2.51-2.69 (dd, 2H), 1.87-1.97 (t, 2H), 1.58-1.68 (m, 1H), 1.33-1.37 (d, 1H), 1.27 (s, 3H), 1.12 (s, 3H).

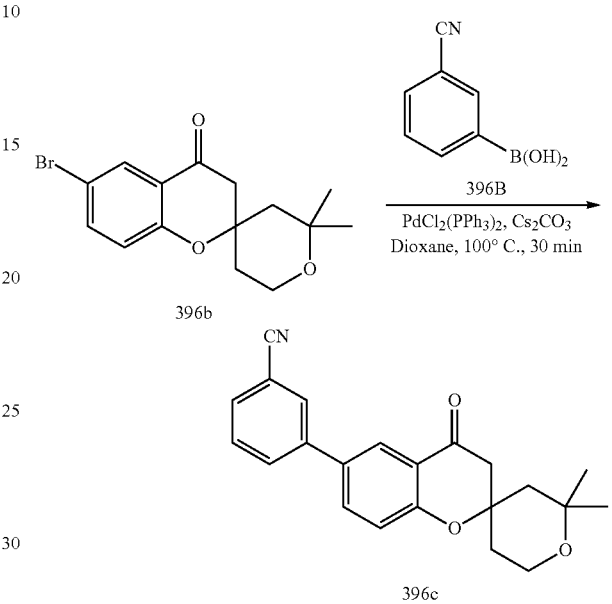

To a solution of compound 396b (124 mg, 0.38 mmol), 3-cyanophenylboronic acid (112 mg, 0.76 mmol), $Cs_2CO_3$ (2 M, 2.25 mL) in 1,4-dioxane (4 mL) under $N_2$ was added Pd(PPh$_3$)$_2$Cl$_2$ (37 mg). The mixture was stirred in microwave at 100° C. for 30 minutes, cooled to room temperature, TLC showed that the reaction was completed. After work up and purification by pre-TLC (petroleum ether:EA=5:1), compound 396c (118 mg, 89%) was obtained as a white solid. $^1$H-NMR (CDCl$_3$ 400 MHz): δ8.01 (s, 1H), 7.72-7.78 (t, 2H), 7.63-7.67 (d, 1H), 7.55-7.57 (d, 1H), 7.45-7.50 (t, 1H), 7.02-7.05 (d, 1H), 4.01-4.10 (t, 1H), 3.65-3.72 (m, 1H), 2.57-2.76 (q, 2H), 1.92-2.03 (t, 1H), 1.37-1.49 (m, 1H), 1.32 (s, 3H), 1.14 (s, 3H).

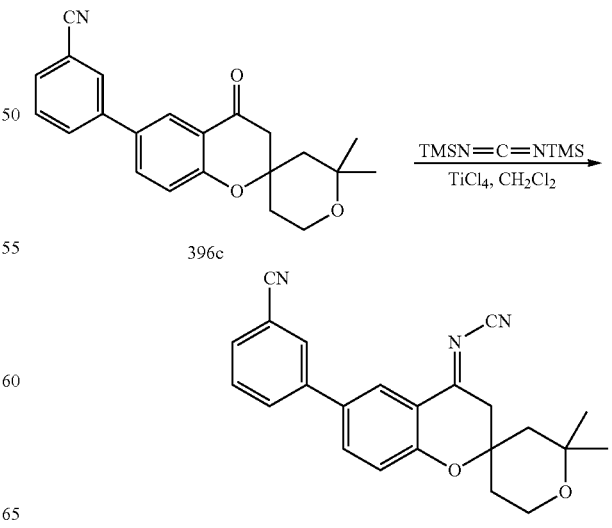

To a solution of compound 396c (60 mg, 0.173 mmol) in CH$_2$Cl$_2$ (4 mL) was added TiCl$_4$ (1 M in CH$_2$Cl$_2$, 0.22 mL, 0.224 mmol). This mixture was stirred at room temperature for 1 h, bis-trimethylsilylcarbodiimide (0.085 mL, 0.38 mmol) was added, and the resulting mixture was stirred at room temperature overnight. TLC showed that the reaction was completed, the reaction mixture was poured into ice-water (12 mL), and extracted with CH$_2$Cl$_2$ (20 mL×2). The combined organic phases were dried over anhydrous Na$_2$SO$_4$, and filtered. The filtrate was concentrated to give the compound 396d (66 mg, crude, 100%) as a white solid, which was used directly for the next step without purification.

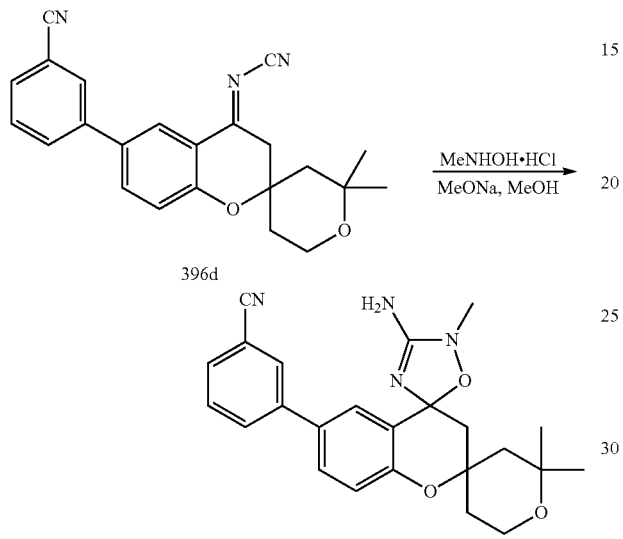

To a solution of MeNHOH.HCl (7.2 mg, 0.086 mmol) in anhydrous MeOH (3 mL) was added MeONa (10% in MeOH, 40 mg, 0.077 mmol) and compound 396d (32 mg, 0.086 mmol). After being stirred for 30 min at room temperature, TLC showed that the reaction was completed. The solvent was removed under reduced pressure. and the residue was dissolved in CH$_2$Cl$_2$ (10 mL). The mixture was filtered, and the filtrate was concentrated. The residue was purified by prep-TLC and pre-HPLC to give compound 396 (3.94 mg, yield 11%) as a white solid. $^1$H-NMR (CD$_3$OD 400 MHz): δ7.87-7.91 (t, 2H), 7.67-7.68 (s, 2H), 7.56-7.63 (m, 2H), 6.95-6.98 (d, 1H), 4.17-4.25 (m, 0.6H), 3.95-4.01 (t, 0.4H), 3.68-3.74 (m, 0.6H), 3.58-3.65 (m, 0.4H), 3.10 (s, 3H), 1.75-2.38 (m, 4H), 1.54-1.74 (m, 2H), 1.52 (s, 1.4H), 1.34 (s, 1.6H), 1.23 (s, 1.4H), 1.65 (s, 1.6H); ESI MS: 419 [M+H]$^+$.

Example 285

Preparation of Compound 206

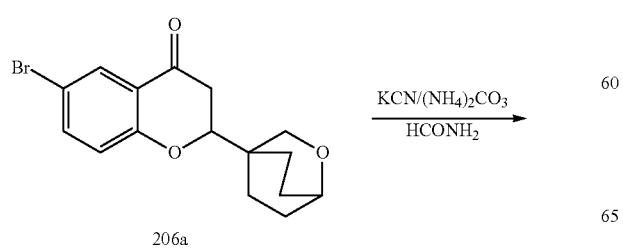

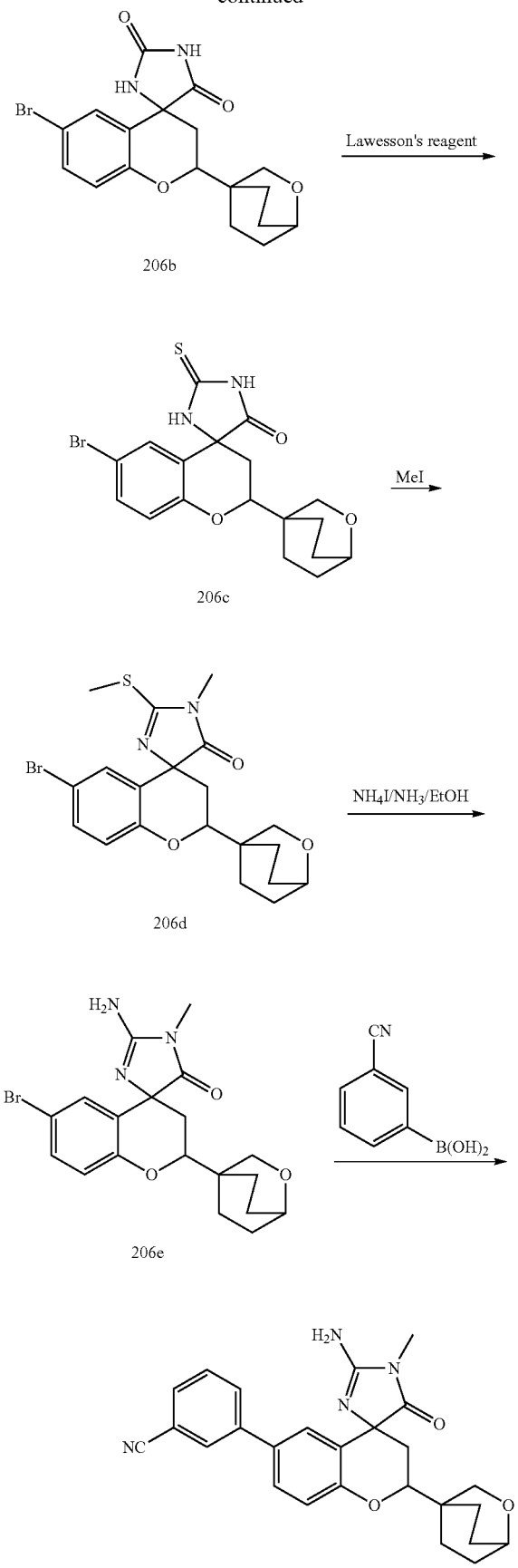

Experimental Data:

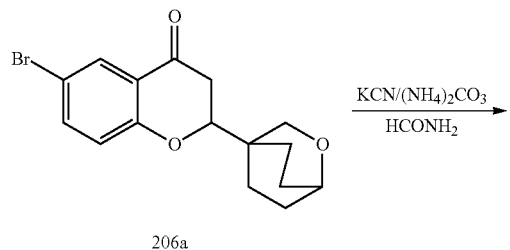

206a

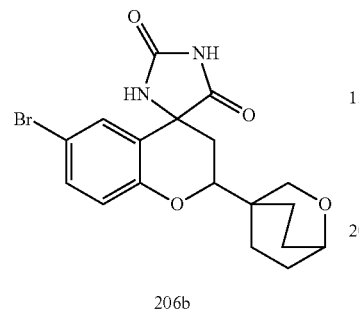

206b

Preparation of Compound 206b

A mixture of compound 206a (0.5 g, 1.48 mmol), KCN (193 g, 3 mmol), and (NH$_4$)$_2$CO$_3$ (1.1 g, 11 mmol) in a mixture of formamide (34 mL) and DMF (3 mL) was heated at 110° C. in a microwave reactor for 2 h. The reaction mixture was cooled and poured into ice water. The mixture was acidified with concentrate HCl solution. The resulting precipitate was filtered, washed twice with water, and dissolved in ethyl acetate. The organic solution was dried over Na$_2$SO$_4$, and filtered. The filtrate was concentrated in vacuo, and the residue was purified by silica gel column to give the compound 206b (480 mg, 60%). $^1$H-NMR (400 Hz CDCl$_3$): δ7.30 (m, 1H), 7.29 (m, 1H), 7.23 (m, 1H), 7.23 (m, 1H), 6.77 (m, 1H), 4.46 (m, 1H), 3.96 (m, 1H), 3.75 (m, 2H), 2.11 (m, 5H), 1.93 (m, 1H), 1.67 (m, 7H).

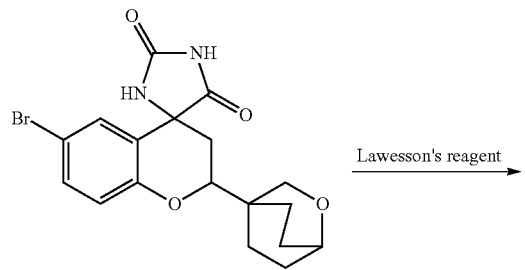

206b

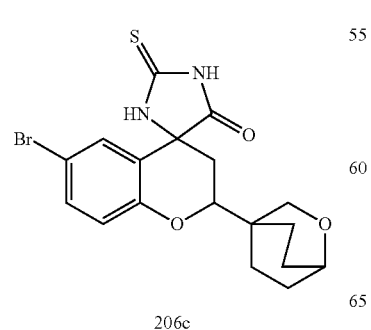

206c

Preparation of Compound 206c

A suspension of compound 206b (360 mg, 0.89 mmol) and Lawesson's Reagent (358 mg, 0.89 mmol) in dry 1,4-dioxane (5 mL) was heated at 120° C. in microwave for 0.5 h. The mixture was concentrated in vacuo, and the residue was purified by TLC to give the compound 206c (114 mg, 40%).

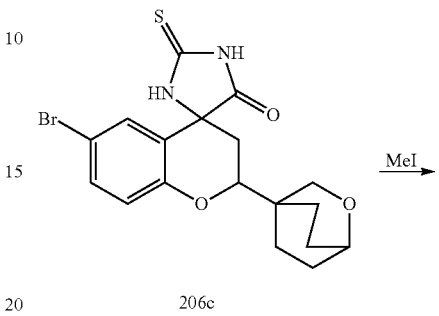

206c

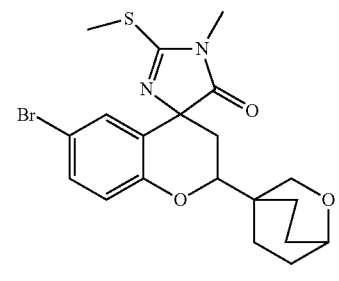

206d

Preparation of Compound 206d

To a solution of compound 206c (100 mg, 0.24 mmol) in MeOH (25 mL) was added NaOH solution (0.5 mL, 0.3 mol, 0.6 N aq.) and MeI (240 mg, 1.7 mmol). The reaction mixture was heated at 60° C. in microwave reactor for 15 min, and concentrated in vacuo. The residue was purified by preparative TLC to give the compound 206d (47 mg, 44%).

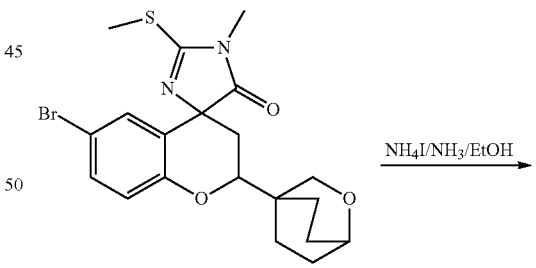

206d

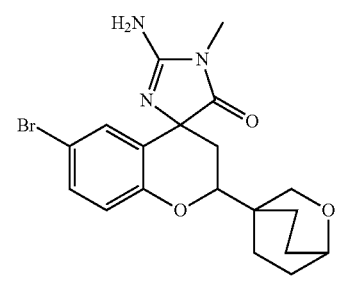

206e

Preparation of Compound 206e

A solution of compound 206d (47 mg, 0.1 mmol), NH₄I (38 mg, 0.26 mmol) in NH₃/EtOH (4 mL, 1.5 N) in a tube was heated at 120° C. in a microwave reactor for 2 h. After being cooled down, the mixture was concentrated in vacuum, the residue was purified by preparative TLC to afford the compound 206e (20 mg, 47%).

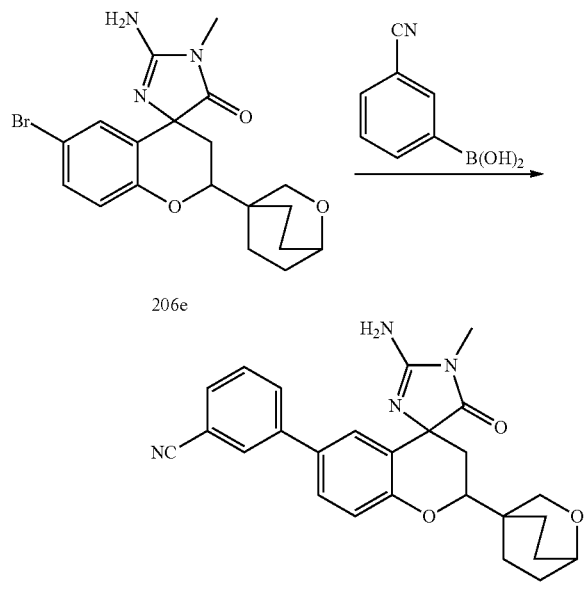

Preparation of Compound 206

Pd(PPh₃)₂Cl₂ (8 mg, 0.011 mmo), Cs₂CO₃ (2 N, 0.3 mL) and 3-cyanophenylboronic acid (10 mg, 0.068 mmol) were added to a solution of compound 5 (20 mg, 0.048 mmol) in 1,4-dioxane (1 mL) in a 10 mL tube. The mixture was heated at 12° C. in a microwave reactor for 20 min, concentrated in vacuo, the residue was purified by preparative TLC and HPLC to give compound 206 (5.26 mg, 25%). ¹H-NMR (400 Hz CD₃OD): δ7.80-8.00 (m, 2H), 7.50-7.65 (m, 3H), 7.30-7.50 (m, 1H), 7.00-7.10 (m, 1H), 4.40-4.50 (m, 1H), 3.95-4.05 (m, 1H), 3.70-3.80 (m, 2H), 3.30-3.35 (m, 1H), 3.20-3.25 (s, 2H), 2.30-2.45 (m, 1H), 2.00-2.20 (m, 3H), 1.65-1.85 (m, 6H); ESI MS: m/z=443 [M+H]⁺.

Example 286

Preparation of Compound 422

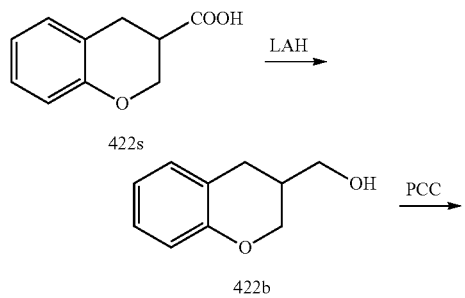

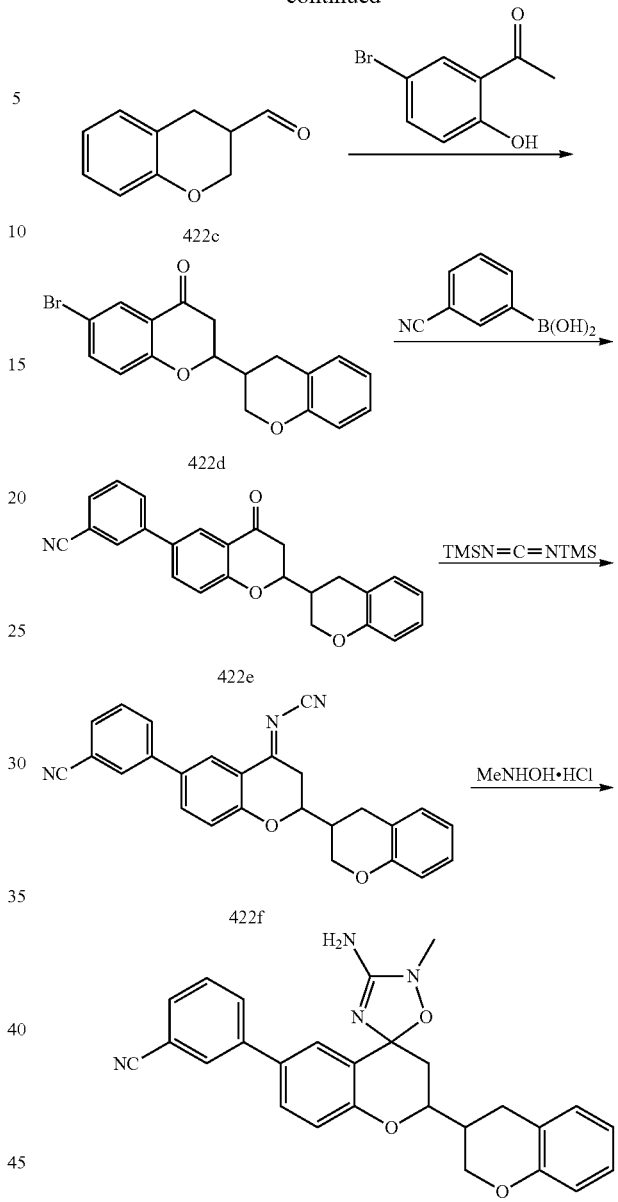

Experimental Data:

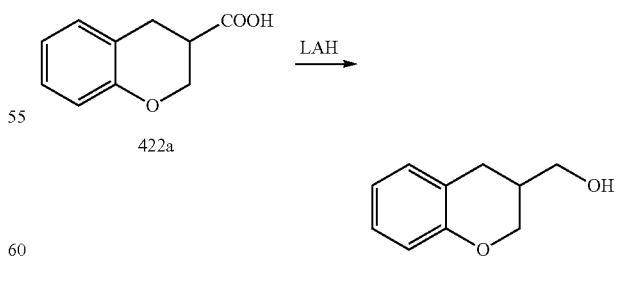

Preparation of Compound 422b

The solution of LAH (640 mg, 16.8 mmol) in 20 mL of dry THF at 0° C. was added the solution of compound 422a (2 g, 11.2 mmol) in THF (10 mL) dropwise, and the reaction mixture was stirred at room temperature for 2 hour. The reaction was quenched with 7 mL of H$_2$O and 7 mL of 10% NaOH solution. The solution was filtered, and the filtrate was concentrated to give the compound 422b (1.8 g, 100%). $^1$H NMR (400 MHz CDCl$_3$): δ7.12 (m, 2H), 6.87 (m, 2H), 4.34 (m, 1H), 4.08 (m, 1H), 3.75 (m, 2H), 2.91 (m, 1H), 2.53 (m, 13H), 2.29 (m, 1H).

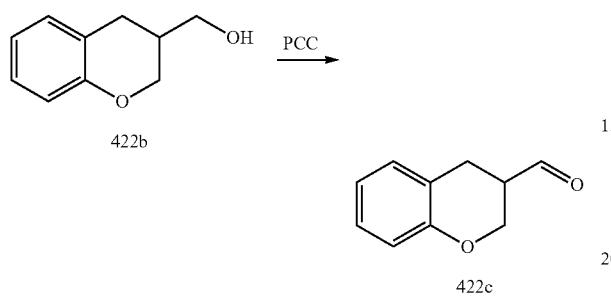

Preparation of Compound 422c

To a solution of compound 422b (970 mg, 5.99 mmol) in DCM (25 mL) was added 3 Å molecular sieves (500 mg) and PCC (1.94 g, 8.98 mmol). The reaction mixture was stirred at room temperature for 2 h, filtered, washed with DCM, dried, and concentrated to give compound 422c (681 mg, 71%). $^1$H NMR (400 MHz CDCl$_3$): δ7.04-7.22 (m, 2H), 6.73-6.88 (m, 2H), 2.91-3.13 (m, 3H), 1.31-4.42 (m, 2H).

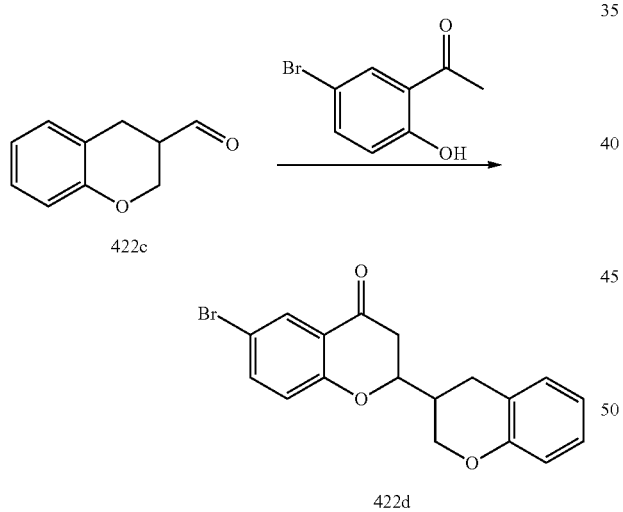

Preparation of Compound 422d

To a solution of compound 422c (681 mg, 4.23 mmol) in a mixture of H$_2$O (6 mL) and EtOH (3.6 mL) was added 1-(5-bromo-2-hydroxyphenyl)ethanone (1.09 mg, 5.08 mmol) and borax (2.42 mg, 6.35 mmol). The reaction mixture was refluxed overnight, cooled, and filtered. EtOH was removed, and the aqueous was extracted with DCM (30 mL×3). The organic layer was dried, concentrated, and purified by preparative TLC to afford the compound 422d (170 mg, 11%). $^1$H NMR (400 MHz CDCl$_3$): δ7.92 (s, 1H), 7.51 (m, 1H), 7.06 (m, 2H), 6.72-6.88 (m, 3H), 4.45 (m, 1H), 4.22-4.38 (m, 1H), 4.08 (m, 1H), 2.95 (m, 1H), 2.52-2.89 (m, 3H), 2.46 (m, 1H).

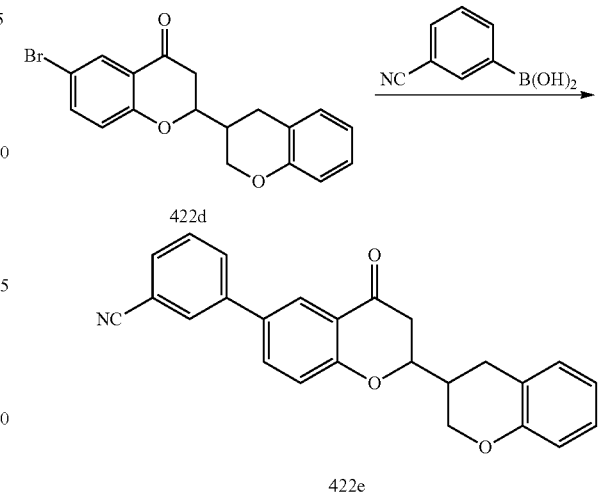

Preparation of Compound 422e

Pd(PPh$_3$)$_2$Cl$_2$ (10 mg) in a 10 mL of flask under N$_2$ was treated sequentially with the solution of compound 422d (90 mg, 0.25 mmol) in 1,4-dioxane (1.5 mL), Cs$_2$CO$_3$ solution (2 N, 0.25 mL), and 3-cyanophenylboronic acid (37 mg, 0.5 mmol). The mixture was heated at 100° C. under N$_2$ in microwave for 10 minutes. The organic layer was concentrated in vacuo, and the residue was purified by preparative TLC to give the compound 422e (75 mg, 78%). $^1$H NMR (400 MHz CDCl$_3$): δ8.03 (s, 1H), 7.77 (m, 2H), 7.66 (m, 1H), 7.54 (m, 1H), 7.48 (m, 1H), 6.99-7.11 (m, 3H), 6.72-6.88 (m, 2H), 4.49 (m, 1H), 4.11-4.30 (m, 2H), 2.62-3.03 (m, 4H), 2.48 (m, 1H).

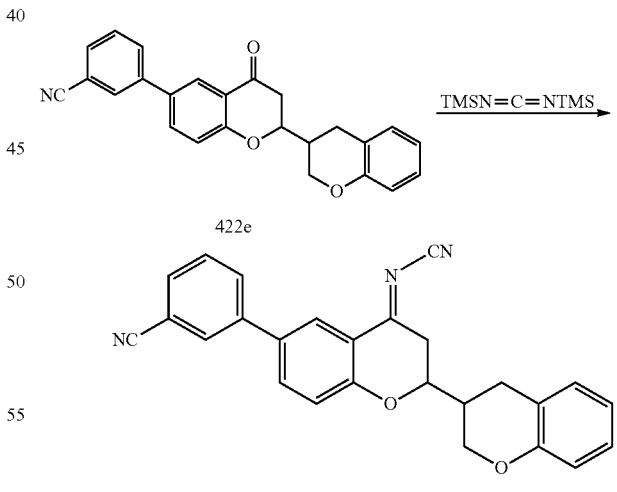

Preparation of Compound 422f

To a solution of compound 422e (85 mg, 0.22 mmol) in dried CH$_2$Cl$_2$ (5 mL) was added TiCl$_4$ (1 M solution in DCM, 0.44 mL) at room temperature dropwise within 15 minutes. The mixture was stirred for 1 h, and added bis-trimethylsilylcarbodiimide (125 mg, 0.66 mmol) dropwise. The resulting mixture was stirred overnight, poured into ice-water, and extracted with CH₂Cl₂. The combined organic layer was washed with brine, dried over Na₂SO₄, filtered, and concentrated to give the compound 422f (100 mg, crude), which was used for the next step without further purification.

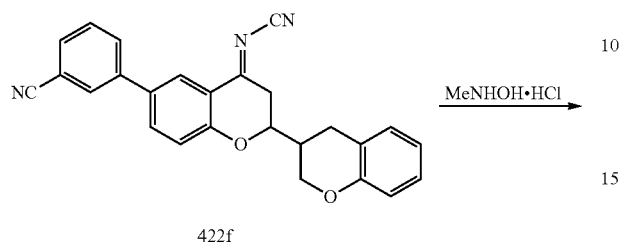

422f

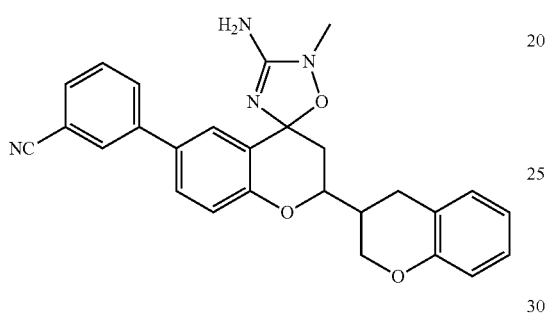

Preparation of Compound 422

To a solution of MeNHOH.HCl (21 mg, 0.25 mmol) in anhydrous MeOH (3 mL) was added NaOMe (10% in MeOH, 122 mg, 0.225 mmol) and compound 422f (100 mg, 0.25 mmol) at room temperature. After being stirred for 10 minutes, the solvent was removed in vacuum. The residue was dissolved in CH₂Cl₂ and filtered. The filtrate was concentrated, the residue was purified by preparative TLC and HPLC to afford the compound 422 (5.5 mg, 5%). ¹H NMR (400 MHz CD₃OD): δ7.98 (m, 3H), 7.66 (m, 3H), 7.09 (m, 3H), 6.81 (d, 2H), 4.46 (m, 2H), 4.17 (m, 1H), 3.43 (m, 3H), 2.70-3.09 (m, 3H), 2.49 (m, 1H), 2.11 (m, 1H); ESI MS: m/z 452 [M+H]⁺.

Example 287

Preparation of Compound 219

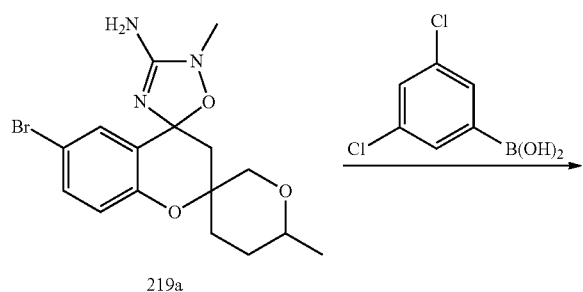

219a

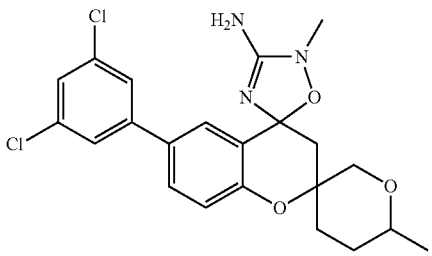

Preparation of Compound 219

A mixture of compound 219a (30 mg, 0.079 mmol), 3,5-dichlorophenylboronic acid (22 mg, 0.12 mmol), Cs₂CO₃ solution (2 M, 0.3 mL), and Pd(PPh₃)₂Cl₂ (5 mg) in 1,4-dioxane (1 mL) under N₂ was stirred at 120° C. for 15 minutes. The reaction mixture was concentrated in vacuum, the residue was purified by preparative TLC and HPLC to give the compound 219 (1.85 mg, 5%). ¹H-NMR (400 MHz CD₃OD): δ7.91 (m, 1H), 7.67 (m, 1H), 7.58 (m, 2H), 7.45 (m, 1H), 7.12 (m, 1H), 4.18 (m, 0.3H), 3.82 (m, 0.7H), 3.58 (m, 2H), 3.37 (m, 3H), 3.16 (m, 0.6H), 2.48 (m, 0.4H), 1.95-2.20 (m, 2H), 1.41-1.96 (m, 3H), 1.21 (m, 3H); ESI MS: m/z 448 [M+H]⁺.

Example 288

Preparation of Compound 371

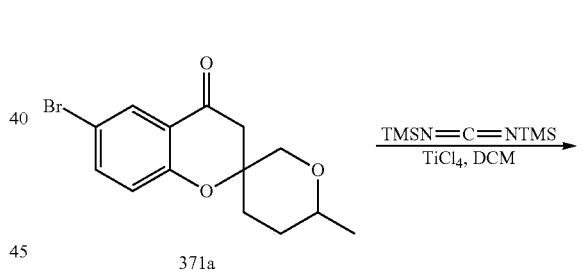

371a

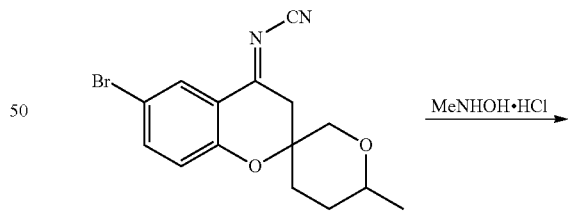

371b

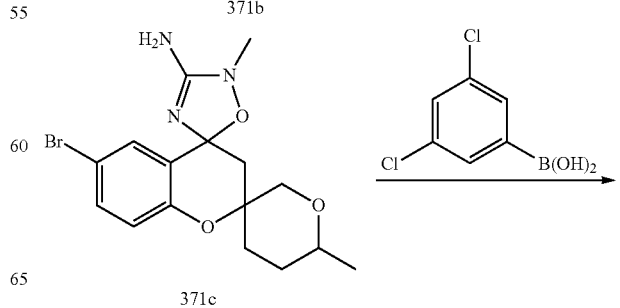

371c

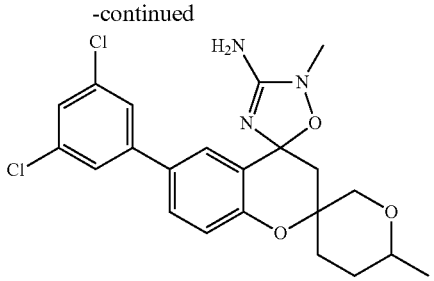

Experimental Data:

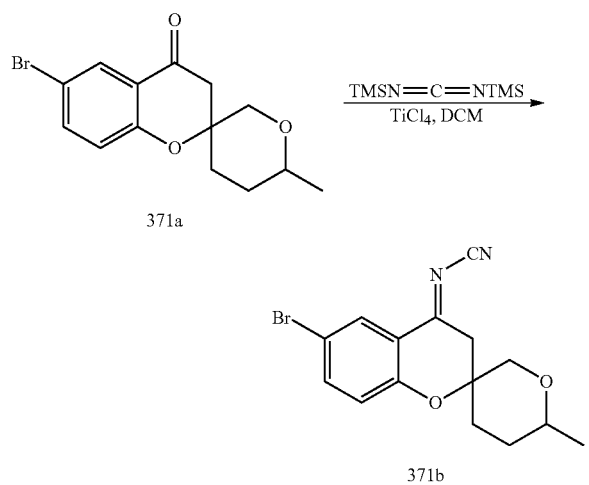

Preparation of Compound 371b

To a solution of compound 371a (100 mg, 0.32 mmol) in CH$_2$Cl$_2$ (15 mL) was added TiCl$_4$ (1 M in DCM, 0.65 mL, 0.65 mmol). This mixture was stirred for 1 h at room temperature. Bis-trimethylsilylcarbodiimide (0.157 mL, 0.704 mmol) was added, and the resulting mixture was stirred overnight. The reaction mixture was poured into ice-water, extracted with DCM, dried over anhydrous Na$_2$SO$_4$, filtered, and concentrated to give the compound 371b (30 mg, 28%).

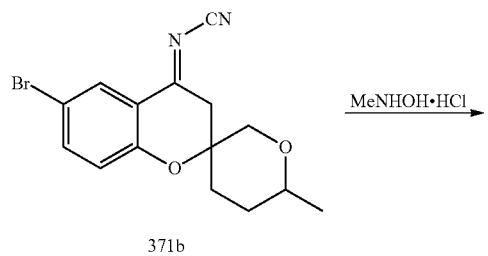

Preparation of Compound 371c

To a solution of methylhydroxylamine HCl salt (7.56 mg, 0.090 mmol) in anhydrous MeOH (2 mL) was added NaOMe (10% in MeOH, 0.045 mL) at room temperature, followed by addition of compound 371b (30 mg, 0.09 mmol). After being stirred for 25 minutes, the solvent was removed in vacuo, and the residue was redissolved in DCM (50 mL). The mixture was filtered, and the solvent was removed. The residue was purified by TLC to give the compound 371c (20 mg, 59%). $^1$H-NMR (400 MHz CDCl$_3$): δ7.45 (m, 1H), 7.21 (m, 1H), 6.60 (m, 1H), 4.08 (m, 1H), 3.80 (m, 1H), 3.32-3.52 (m, 2H), 3.00 (m, 3H), 2.65 (m, 1H), 2.3 (m, 3H), 2.11-2.2 (m, 2H), 1.22 (m, 3H).

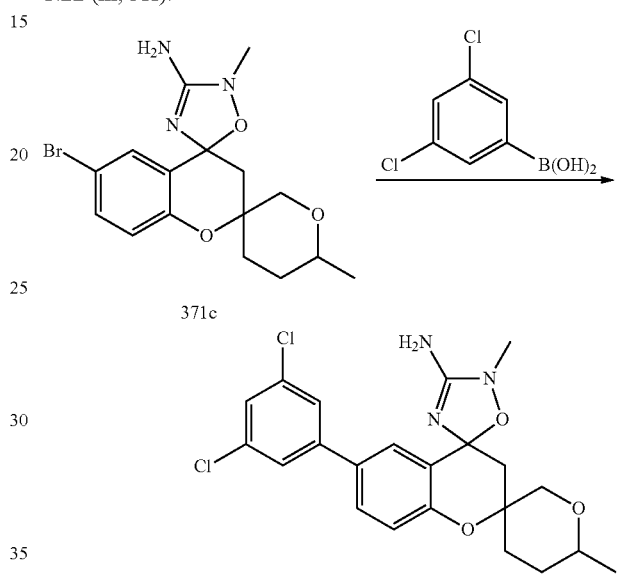

Preparation of Compound 371

A mixture of compound 371c (20 mg, 0.052 mmol), 3,5-dichlorophenylboronic acid (14.7 mg, 0.078 mmol), Cs$_2$CO$_3$ solution (2 M, 0.300 mL), and Pd(PPh$_3$)$_2$Cl$_2$ (5 mg) in 1,4-dioxane (1 mL) under Ar$_2$ was stirred in microwave at 120° C. for 18 minutes. The reaction mixture was concentrated in vacuum, and the residue was purified by preparative TLC and HPLC to give compound 371 (1.50 mg, 7%). $^1$H-NMR (400 MHz CD$_3$OD): δ8.00 (m, 1H), 7.70 (m, 1H), 7.55 (m, 2H), 7.45 (m, 1H), 7.00 (m, 1H), 3.88-4.20 (m, 1H), 3.50 (m, 2H), 3.33 (m, 3H), 2.55-2.72 (m, 2H), 1.80-2.22 (m, 2H), 1.50-1.88 (m, 2H), 1.3 (m, 3H); ESI MS: m/z 448 [M+H]$^+$.

Example 289

Preparation of Compound 274

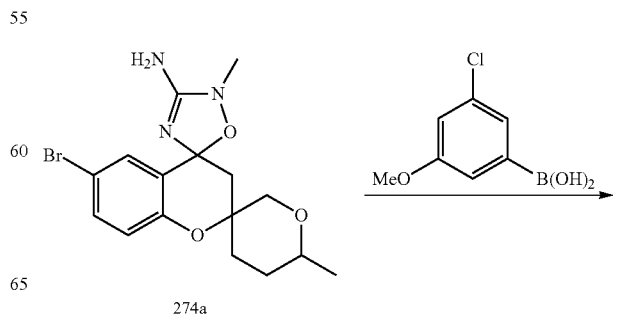

-continued

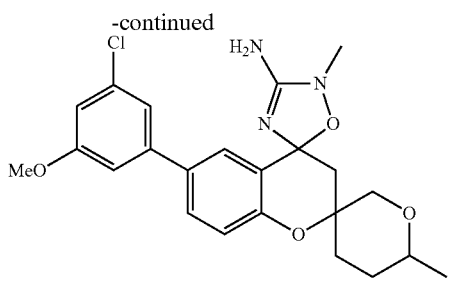

A mixture of compound 274a (25 mg, 0.116 mmol), 3-chloro-5-methoxyphenylboronic acid (43.15 mg, 0.232 mmol), Cs$_2$CO$_3$ solution (2 M, 0.375 mL), and Pd(PPh$_3$)$_2$Cl$_2$ (6.25 mg) in 1,4-dioxane (1 mL) under Ar$_2$ was stirred in microwave at 120° C. for 15 minutes. The reaction mixture was concentrated in vacuum, the residue was purified by preparative TLC and HPLC to give the compound 274 (1.17 mg, 6%). $^1$H-NMR (400 MHz CD$_3$OD): δ7.66-7.91 (m, 3H), 7.55 (m, 1H), 7.35 (m, 1H), 7.00 (m, 1H), 3.88-4.20 (m, 1H), 3.50 (m, 2H), 3.33 (m, 3H), 2.55-2.72 (m, 2H), 1.80-2.22 (m, 2H), 1.50-1.88 (m, 2H), 1.30 (m, 3H); ESI MS: m/z 444 [M+H]$^+$.

Example 290

Preparation of Compound 232

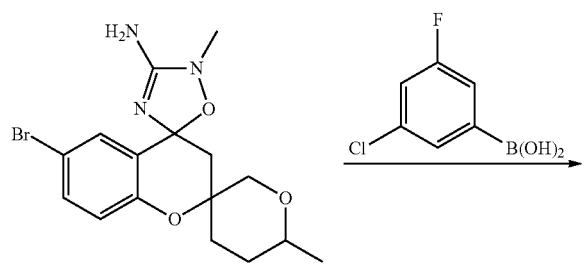

A mixture of compound 232a (25 mg, 0.066 mmol), 3-chloro-5-fluorophenylboronic acid (23 mg, 0.132 mmol), Cs$_2$CO$_3$ solution (2 M, 0.325 mL), and Pd(PPh$_3$)$_2$Cl$_2$ (6.25 mg) in 1,4-dioxane (1.2 mL) under Ar$_2$ was stirred in microwave at 120° C. for 15 minutes. The reaction mixture was concentrated in vacuum, the residue was purified by preparative TLC and HPLC to give compound 232 (2.65 mg, 9%). $^1$H-NMR (400 MHz CD$_3$OD): δ7.00 (m, 1H), 6.75 (m, 1H), 6.55 (m, 1H), 6.45 (m, 1H), 6.00-6.20 (m, 2H), 2.88-3.20 (m, 1H), 2.60 (m, 2H), 2.50 (m, 3H), 1.55-2.21 (m, 1H), 1.00-1.18 (m, 2H), 0.55-1.04 (m, 3H), 0.3 (m, 3H); ESI MS: m/z 432 [M+H]$^+$.

Example 291

Preparation of Compound 298

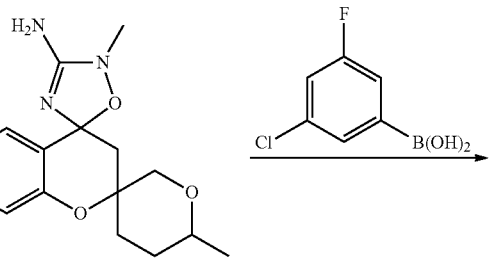

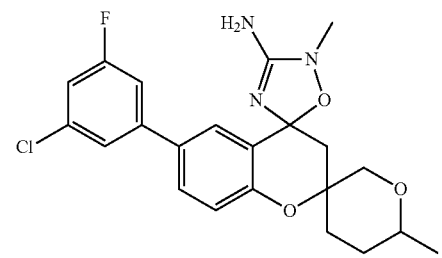

A mixture of compound 298a (35 mg, 0.092 mmol), 3-chloro-5-fluorophenylboronic acid (32 mg, 0.184 mmol), Cs$_2$CO$_3$ solution (2 M, 0.525 mL), and Pd(PPh$_3$)$_2$Cl$_2$ (9 mg) in 1,4-dioxane (1.8 mL) under Ar$_2$ was stirred in microwave at 120° C. for 15 minutes. The reaction mixture was concentrated in vacuum, the residue was purified by preparative TLC and HPLC to give compound 298 (2.73 mg, 7%). $^1$H-NMR (400 MHz CD$_3$OD): δ7.00 (m, 1H), 6.75 (m, 1H), 6.55 (m, 1H), 6.45 (m, 1H), 6.00-6.20 (m, 2H), 2.88-3.20 (m, 1H), 2.60 (m, 2H), 2.50 (m, 3H), 1.55-2.21 (m, 1H), 1.00-1.18 (m, 2H), 0.55-1.04 (m, 3H), 0.3 (m, 3H); ESI MS: m/z 432 [M+H]$^+$.

Example 292

Preparation of Compound 236

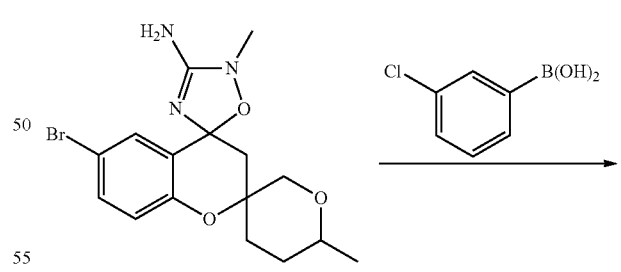

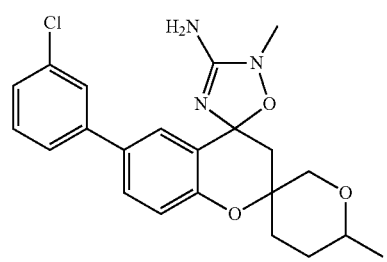

A mixture of compound 236a (30 mg, 0.079 mmol), 3-chlorophenylboronic acid (18 mg, 0.12 mmol), Cs$_2$CO$_3$ solution (2 M, 0.3 mL), and Pd(PPh$_3$)$_2$Cl$_2$ (5 mg) in 1,4-dioxane (1 mL) under N$_2$ was stirred at 100° C. for 15 minutes. The reaction mixture was concentrated in vacuum, the residue was purified by preparative TLC and HPLC to give the compound 236 (2.16 mg, 10%). $^1$H-NMR (400 MHz CD$_3$OD): δ7.85 (m, 1H), 7.67 (m, 1H), 7.62 (m, 1H), 7.52 (m, 1H), 7.41 (m, 1H), 7.32 (m, 1H), 6.98 (m, 1H), 4.19 (m, 0.3H), 3.86 (m, 0.7H), 3.58 (m, 2H), 3.36 (m, 3H), 3.16 (m, 0.6H), 2.48 (m, 0.4H), 2.12 (m, 2H), 1.72 (m, 1H), 1.41-1.74 (m, 2H), 1.18 (m, 3H); ESI MS: m/z 414 [M+H]$^+$.

Example 293

Preparation of Compound 303

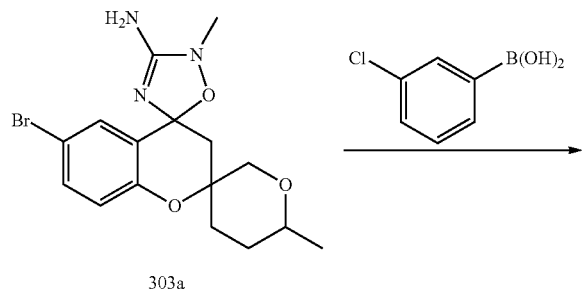

303a

A mixture of compound 303a (30 mg, 0.079 mmol), 3-chlorophenylboronic acid (25 mg, 0.159 mmol), Cs$_2$CO$_3$ (2 M, 0.45 mL) and Pd(PPh$_3$)$_2$Cl$_2$ (7.5 mg) in 1,4-dioxane (1.5 mL) under Ar$_2$ was stirred in microwave at 120° C. for 15 minutes. The reaction mixture was concentrated in vacuum, the residue was purified by preparative TLC and HPLC to give compound 303 (2.78 mg, 8%). $^1$H-NMR (400 MHz CD$_3$OD): δ7.91 (m, 1H), 7.33-7.67 (m, 5H), 7.10 (m, 1H), 4.02 (m, 1H), 3.52 (m, 2H), 3.33 (m, 3H), 266-2.71 (m, 1H), 2.35 (m, 1H), 1.80-2.22 (m, 2H), 1.50-1.77 (m, 2H), 1.3 (m, 3H); ESI MS: m/z 414 [M+H]$^+$.

Example 294

Preparation of Compound 249

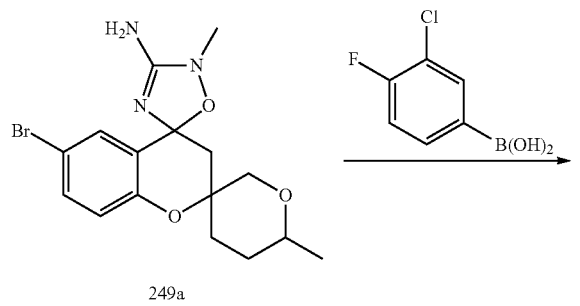

249a

-continued

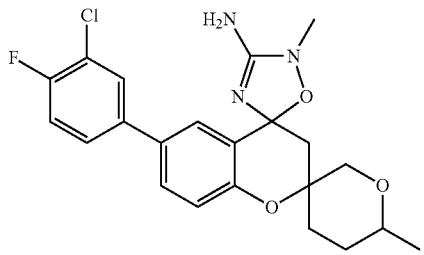

A mixture of compound 249a (20 mg, 0.052 mmol), 3-chloro-4-fluorophenylboronic acid (18.27 mg, 0.105 mmol), Cs$_2$CO$_3$ (2 M, 0.300 mL) and Pd(PPh$_3$)$_2$Cl$_2$ (5 mg) in 1,4-dioxane (1 mL) under Ar$_2$ was stirred in microwave at 120° C. for 15 minutes. The reaction mixture was concentrated in vacuum, the residue was purified by preparative TLC and HPLC to give compound 249 (2.88 mg, 13%). $^1$H-NMR (400 MHz CD$_3$OD): δ7.66-7.91 (m, 3H), 7.55 (m, 1H), 7.35 (m, 1H), 7.00 (m, 1H), 3.88-4.20 (m, 1H), 3.50 (m, 2H), 3.33 (m, 3H), 2.55-2.72 (m, 2H), 1.80-2.22 (m, 2H), 1.50-1.88 (m, 2H), 1.3 (m, 3H); ESI MS: m/z 432 [M+H]$^+$.

Example 295

Preparation of Compound 330

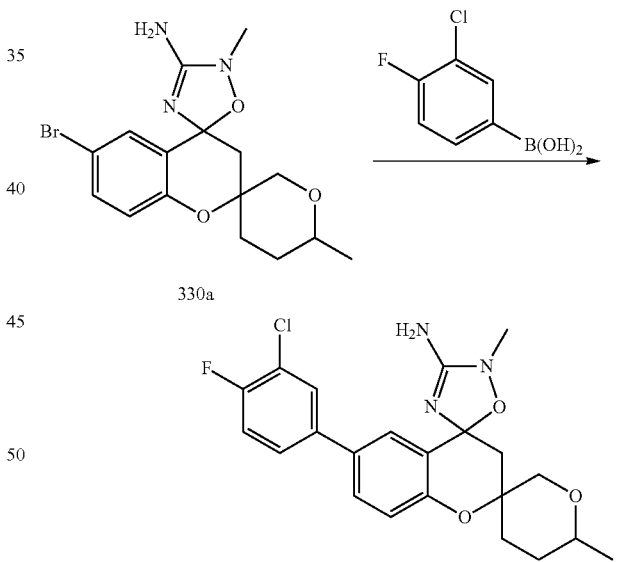

330a

A mixture of compound 330a (30 mg, 0.079 mmol), 3-chloro-4-fluorophenylboronic acid (27 mg, 0.157 mmol), Cs$_2$CO$_3$ solution (2 M, 0.450 mL, and Pd(PPh$_3$)$_2$Cl$_2$ (7.5 mg) in 1,4-dioxane (1.5 mL) under Ar$_2$ was stirred in microwave at 120° C. for 15 minutes. The reaction mixture was concentrated in vacuum, the residue was purified by preparative TLC and HPLC to give compound 330 (2.02 mg, 7%). $^1$H-NMR (400 MHz CD$_3$OD): δ7.66-7.91 (m, 3H), 7.55 (m, 1H), 7.35 (m, 1H), 7.00 (m, 1H), 3.88-4.20 (m, 1H), 3.50 (m, 2H), 3.33 (m, 3H), 2.55-2.72 (m, 2H), 1.80-2.22 (m, 2H), 1.50-1.88 (m, 2H), 1.3 (m, 3H); ESI MS: m/z 432 [M+H]$^+$.

Example 296

Preparation of Compound 208

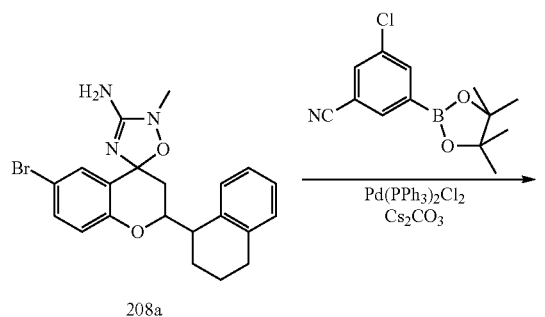

A mixture of compound 296a (20 mg, 0.047 mmol), 3-chloro-5-(4,4,5,5-tetramethyl-1,3,2-dioxaborolan-2-yl)benzonitrile (24.6 mg, 0.094 mmol), $Cs_2CO_3$ solution (2 M, 0.300 mL), and $Pd(PPh_3)_2Cl_2$ (5 mg) in 1,4-dioxane (1 mL) under $Ar_2$ was stirred in microwave at 120° C. for 20 minutes. The reaction mixture was concentrated in vacuum, and the residue was purified by preparative TLC and HPLC to give compound 208 (1.15 mg, 5%). $^1$H-NMR (400 MHz $CD_3OD$): δ8.00 (m, 3H), 7.71 (m, 2H), 7.35 (m, 1H), 7.00 (m, 4H), 4.66 (m, 1H), 3.45 (m, 1H), 3.38 (m, 3H), 2.75 (m, 2H), 2.40-2.61 (m, 2H), 2.01 (m, 3H), 1.75 (m, 1H); ESI MS: m/z 485 [M+H]$^+$.

Example 297

Preparation of Compound 198

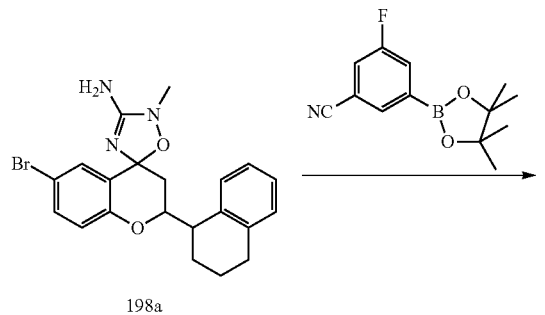

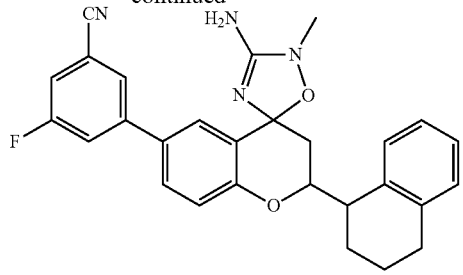

To a solution of compound 198a (20 mg, 0.047 mmol), 3-fluoro-5-(4,4,5,5-tetramethyl-1,3,2-dioxaborolan-2-yl)benzonitrile (17 mg, 0.071 mmol), and $Cs_2CO_3$ solution (2M, 0.3 mL) in [1,4]-dioxane (0.7 mL) was added $Pd(PPh_3)_2Cl_2$ (0.5 mg). The mixture was heated at 120° C. in microwave for 15 minutes. The reaction mixture was concentrated in vacuo to give the residue, which was purified by preparative TLC and HPLC to give compound 198 (3.13 mg, 14%). $^1$H-NMR (400 MHz $CD_3OD$): δ8.01 (s, 1H), 7.85 (m, 1H), 7.75 (m, 2H), 7.50 (m, 1H), 7.32 (s, 1H), 7.17 (m, 3H), 7.02 (m, 1H), 4.64 (m, 1H), 3.40 (m, 1H), 3.30 (m, 3H), 2.81 (s, 2H), 2.61 (m, 1H), 2.43 (m, 1H), 2.06 (m, 3H), 1.75 (s, 1H); ESI MS: m/z 469 [M+H]$^+$.

Example 298

Preparation of Compound 240

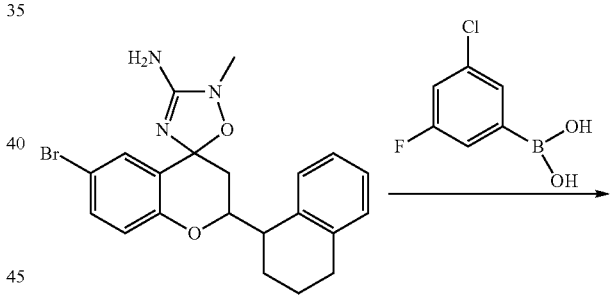

$Pd(PPh_3)_2Cl_2$ (10 mg) under $Ar_2$ was treated sequentially with the solution of compound 298a (20 mg, 0.047 mmol) in [1,4]dioxane (1 mL), $Cs_2CO_3$ solution (2 M, 0.3 mL), and 3-chloro-5-fluorophenylboronic acid (12 mg, 0.07 mmol). The mixture was heated at 120° C. in microwave for 15 minutes, and concentrated in vacuo. The residue was purified by preparative TLC and HPLC to give compound 298 (7.7 mg, 34%). $^1$H-NMR (400 MHz $CD_3OD$): δ6.95-7.91 (m, 10H), 4.65 (m, 1H), 3.45 (m, 1H), 3.35 (m, 3H), 2.82 (m, 2H), 2.45 and 2.65 (d, 1H), 2.00 (m, 4H), 1.75 (m, 1H); ESI MS: m/z 478 [M+H]⁺.

Example 299

Preparation of Compound 239

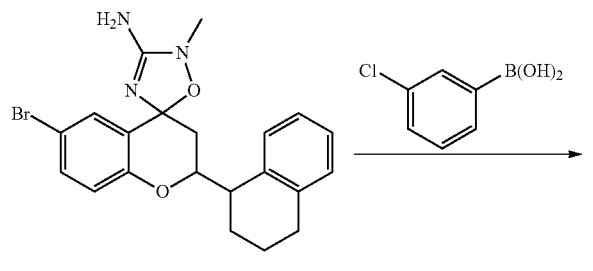

A mixture of compound 299a (20 mg, 0.047 mmol), 3-chlorophenylboronic acid (14 mg, 0.07 mmol), Cs₂CO₃ solution (2 M, 0.3 mL), and Pd(PPh₃)₂Cl₂ (5 mg) in 1,4-dioxane (1 mL) under N₂ was stirred at 120° C. for 15 minutes. The reaction mixture was concentrated in vacuum, and the residue was purified by preparative TLC and HPLC to give compound 299. ¹H-NMR (400 MHz CD₃OD): δ7.86 (m, 1H), 7.62 (m, 2H), 7.47 (m, 2H), 7.30 (m, 2H), 7.12 (m, 3H), 6.96 (m, 1H), 4.76 (m, 0.5H), 4.64 (m, 0.5H), 3.42 (m, 1H), 3.34 (m, 3H), 2.82 (m, 2H), 2.52 (m, 1H), 2.02 (m, 4H), 1.74 (m, 1H); ESI MS: m/z 460 [M+H]⁺.

Example 300

Preparation of Compounds 235 and 252

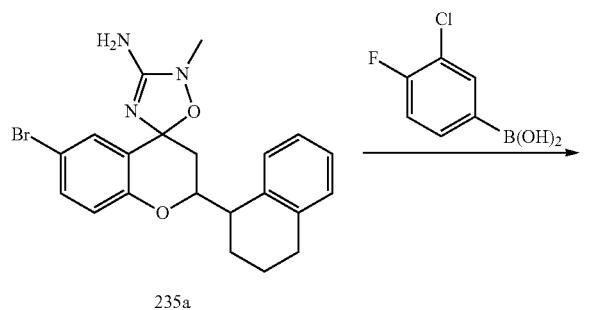

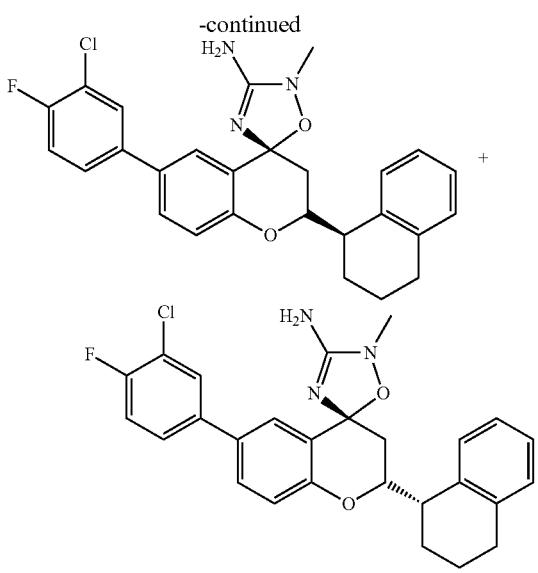

A mixture of compound 235a (20 mg, 0.047 mmol), 3-chloro-4-fluorophenylboronic acid (12 mg, 0.07 mmol), Cs₂CO₃ solution (2 M, 0.3 mL), and Pd(PPh₃)₂Cl₂ (5 mg) in 1,4-dioxane (1 mL) under N₂ was stirred at 120° C. for 15 minutes. The reaction mixture was concentrated in vacuum, and the residue was purified by preparative TLC and HPLC to give compound 235 (2.7 mg, 12%) and compound 252 (1.12 mg, 5%).

compound 235: ¹H-NMR (400 MHz CD₃OD): δ7.87 (m, 1H), 7.72 (m, 2H)ₘ, 7.53 (m, 1H), 7.32 (m, 2H), 7.16 (m, 3H), 7.02 (m, 1H), 4.62-4.82 (m, 1H), 3.48 (m, 1H), 3.35 (s, 3H), 2.83 (m, 2H), 2.42-2.68 (m, 1H), 1.85-2.18 (m, 4H), 1.78 (m, 1H); ESI MS: m/z 478 [M+H]⁺.

compound 252: ¹H-NMR (400 MHz CD₃OD): δ7.78 (m, 1H), 7.38-7.66 (m, 3H), 7.22 (m, 2H), 7.06 (m, 3H), 6.92 (m, 1H), 4.48-4.67 (m, 1H), 3.47 (m, 1H), 3.37 (m, 3H), 2.71 (m, 2H), 2.24-2.51 (m, 1H), 1.80-2.08 (m, 4H), 1.48 (m, 1H); ESI MS: m/z 478 [M+H]⁺.

Example 301

Preparation of Compounds 201 and 221

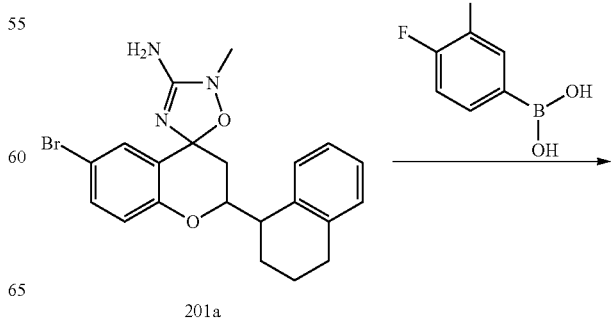

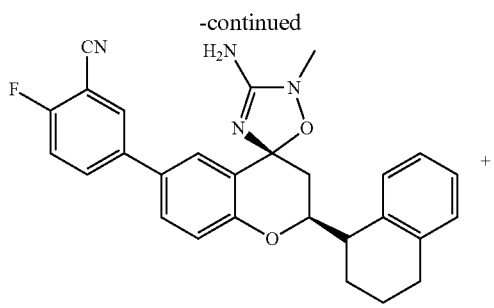

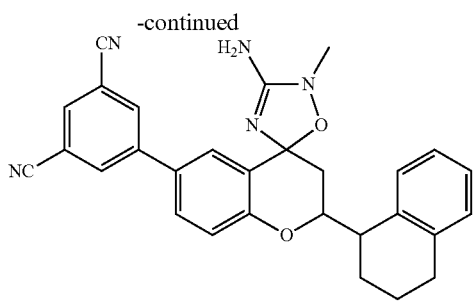

A mixture of compound 1 (20 mg, 0.048 mmol), 3,5-dicyanophenylbronic acid (16 mg, 0.094 mmol), Cs$_2$CO$_3$ solution (2 M, 0.300 mL), and Pd(PPh$_3$)$_2$Cl$_2$ (8 mg) in 1,4-dioxane (1 mL) was stirred in microwave at 120° C. for 18 minutes under Ar$_2$. The reaction mixture was concentrated in vacuum, the residue was purified by preparative TLC and HPLC to give compound 180 (2.78 mg, 13%). $^1$H-NMR (400 MHz CD$_3$OD): δ8.29 (s, 2H), 8.06 (d, 2H), 7.74 (m, 1H), 7.30 (m, 1H), 7.15 (m, 3H), 7.00 (m, 1H), 4.63 (m, 1H), 3.40 (m, 1H), 3.30 (m, 3H), 2.80 (m, 2H), 2.62 (m, 1H), 2.40 (m, 1H), 2.08 (m, 3H), 1.75 (m, 1H); ESI MS: m/z 476 [M+H]$^+$.

Pd(PPh$_3$)$_2$Cl$_2$ (10 mg) in a 10 mL of tube under Ar$_2$ was treated sequentially with the compound 201a (21 mg, 0.05 mmol) in 1,4-dioxane (2 mL), Cs$_2$CO$_3$ solution (2 N, 0.3 mL), and 3-cyano-4-fluorophenylboronic acid (22 mg, 0.13 mmol). The mixture was heated in microwave at 120° C. for 20 minutes, concentrated in vacuo, and purified by preparative TLC and HPLC to give compound 201 (1.90 mg, 3.4%) and compound 221 (1.25 mg, 2.9%).

compound 201: $^1$H-NMR (400 MHz CD$_3$OD): δ7.91-8.04 (m, 3H), 7.65-7.71 (m, 1H), 7.33-7.48 (m, 2H), 7.11-7.20 (m, 3H), 6.95-7.06 (m, 1H), 4.52-4.62 (m, 1H), 3.48-3.52 (m, 1H), 3.33-3.40 (m, 3H), 2.79-2.90 (m, 2H), 2.40-2.65 (m, 1H), 1.85-2.16 (m, 4H), 1.70-1.82 (m, 1H); ESI MS: m/z 470 [M+H]$^+$.

compound 221: $^1$H-NMR (400 MHz CD$_3$OD): δ7.91-8.02 (m, 3H), 7.66-7.69 (m, 1H), 7.33-7.44 (m, 2H), 7.11-7.15 (m, 3H), 6.98-7.07 (m, 1H), 4.58-4.65 (m, 1H), 3.45-3.52 (m, 1H), 3.33-3.43 (m, 3H), 2.75-2.83 (m, 2H), 2.41-2.62 (m, 1H), 1.92-2.16 (m, 4H), 1.71-1.80 (m, 1H); ESI MS: m/z 470 [M+H]$^+$.

Example 302

Preparation of Compound 180

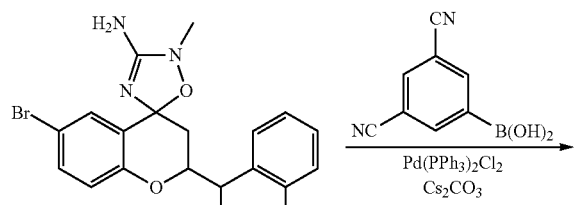

Example 303

Preparation of Compound 278

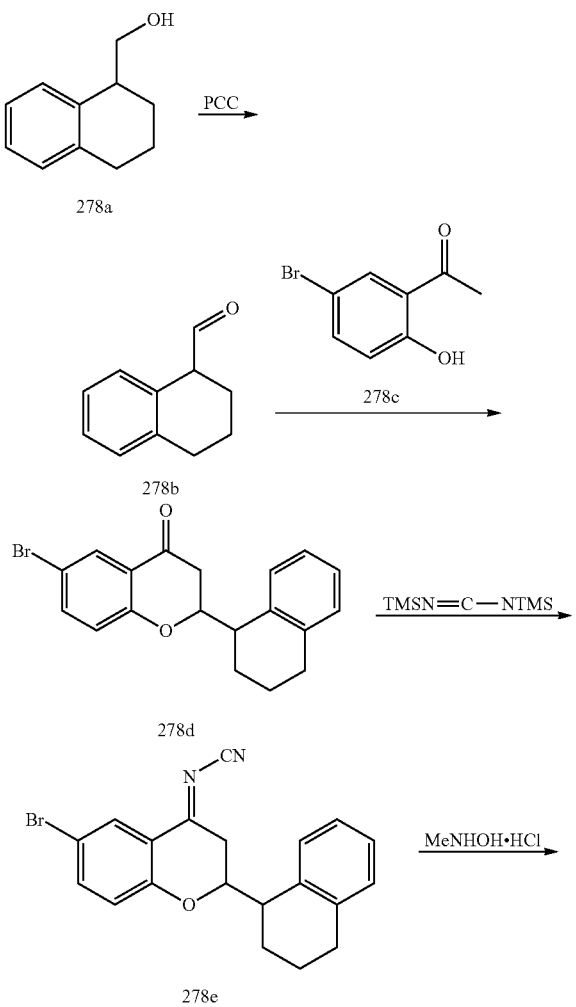

-continued

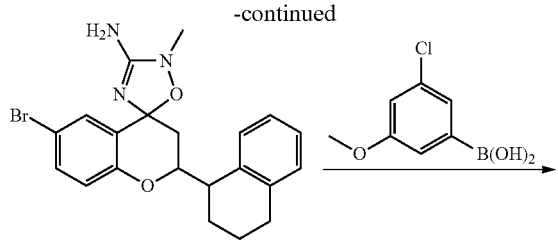

278f

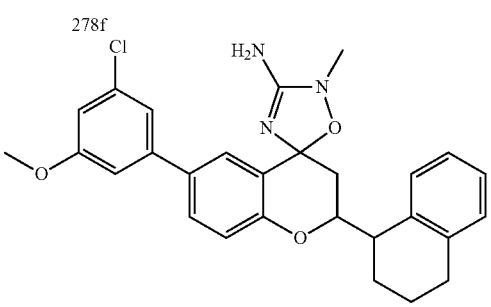

Experimental Data:

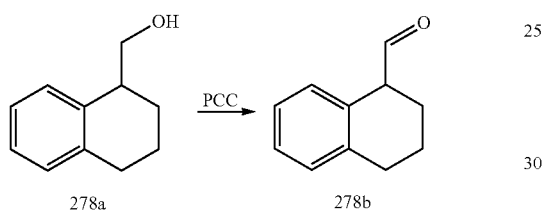

278a     278b

Preparation of Compound 278b

To a solution of compound 278a (2 g, 12.5 mmol) in dry CH$_2$Cl$_2$ (40 mL) was added 3 Å molecule series (1.3 g) and PCC (4.05 g, 18.75 mmol). The mixture was stirred at room temperature for 2 h. When the reaction was completed, the mixture was filtered through celite, dried over Na$_2$SO$_4$, and concentrated in vacuum to give the compound 278b (1.4 g, 68%).

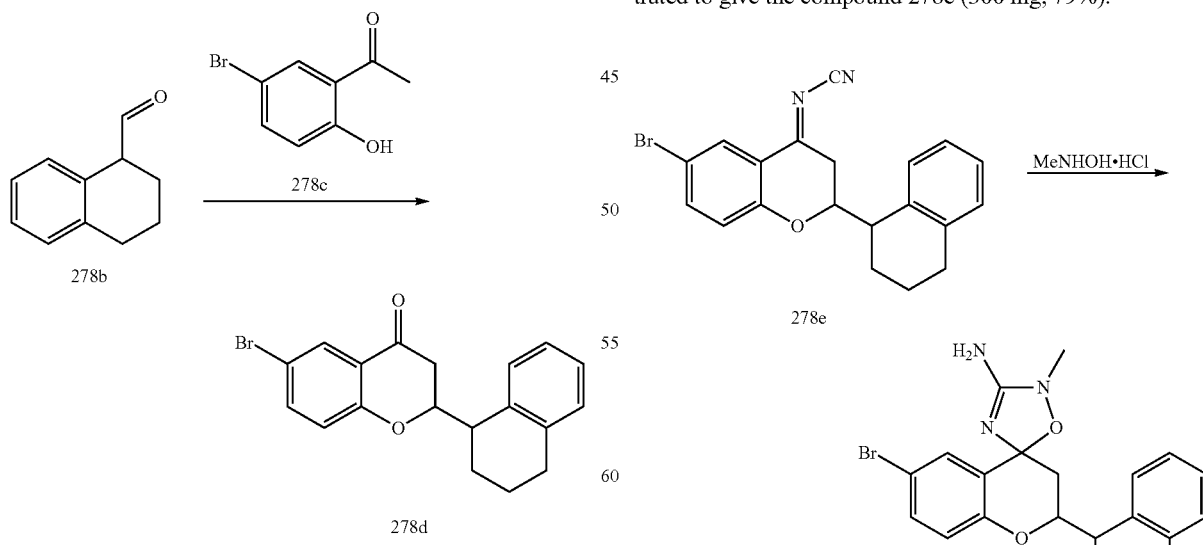

Preparation of Compound 278d

To a stirred solution of compound 278c (1.8 g, 8.7 mmol) in a mixture of EtOH (11.4 mL) and H$_2$O (18.3 mL) was added compound 2 (1.4 g, 8.7 mmol) and borax (3.31 g, 8.7 mmol). The mixture was refluxed for 2 days, filtrated, and concentrated in vacuo. The crude product was purified by column chromatography and pre-HPLC to give the compound 278d (600 mg, 20%).

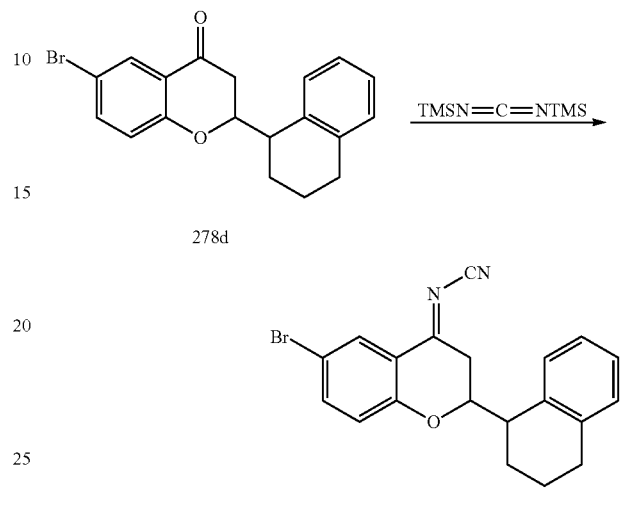

Preparation of Compound 278e

To a solution of compound 278d (356 mg, 1 mmol) in CH$_2$Cl$_2$ (25 mL) was added TiCl$_4$ (1 M in DCM, 2 mg, 2 mmol). This mixture was stirred at room temperature for 60 minutes. Bis-trimethylsilylcarbodiimide (372 mg, 2 mmol) was added, and the resulting mixture was stirred overnight. The reaction mixture was poured into ice-water, extracted with DCM. The combined organic phases were dried over anhydrous Na$_2$SO$_4$, and filtered. The filtrate was concentrated to give the compound 278e (300 mg, 79%).

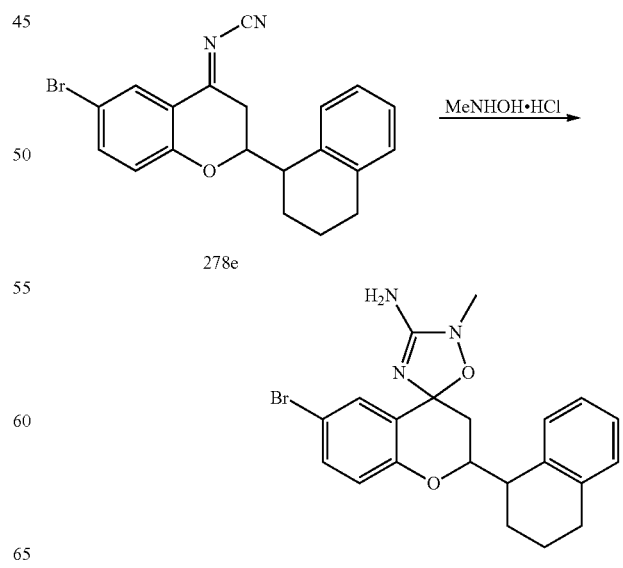

Preparation of Compound 278f

To a solution of methylhydroxylamine HCl salt (66 mg, 0.79 mmol) in anhydrous MeOH (10 mL) was added NaOMe (10% in MeOH, 38.4 mg, 0.71 mmol) and compound 278e (300 mg, 0.79 mmol) at room temperature. After being stirred for 20 minutes, the solvent was removed in vacuo. The residue was dissolved in DCM (5 mL). The mixture was filtered, and the solvent was removed. The residue was purified by pre-TLC to give compound 278f (280 mg, 83%). $^1$H-NMR (400 MHz CDCl$_3$): δ7.53 (m, 1H), 7.27 (m, 2H), 7.08 (m, 3H), 6.65 (m, 1H), 4.53 (m, 1H), 3.31 (m, 1H), 3.15 (m, 1H), 3.05 (m, 3H), 2.74 (m, 3H), 2.18 (m, 1H), 1.94 (m, 2H), 1.75 (m, 1H).

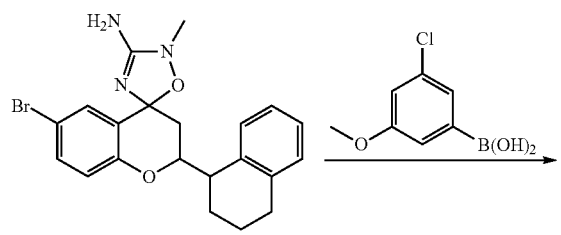

Preparation of Compound 278

To a solution of compound 278f (20 mg, 0.05 mmol), 3-chloro-5-methoxyphenylboronic acid (18.6 mg, 0.1 mmol), Cs$_2$CO$_3$ solution (2 M, 0.5 mL) in 1,4-dioxane (1 mL) under N$_2$ was added Pd(PPh$_3$)$_2$Cl$_2$ (5 mg). The mixture was stirred at 100° C. for 6 minutes. After being cooled to room temperature, the organic layer was dried, and concentrated to give the residue, which was purified by preparative HPLC to give compound 278 (2.20 mg, 10%). $^1$H-NMR (400 MHz CD$_3$OD): δ7.86 (m, 1H), 7.69 (m, 1H), 7.48 (m, 1H), 7.30 (m, 2H), 7.11 (m, 3H), 7.01 (m, 1H), 6.95 (m, 1H), 461-4.74 (m, 1H), 3.81-4.08 (m, 3H), 3.47 (m, 1H), 3.33 (m, 3H), 2.78 (m, 2H), 2.45-2.61 (m, 1.4H), 1.85-2.10 (m, 3.6H), 1.75 (m, 1H); ESI MS: m/z 490 [M+H]$^+$.

Example 304

Preparation of Compound 269

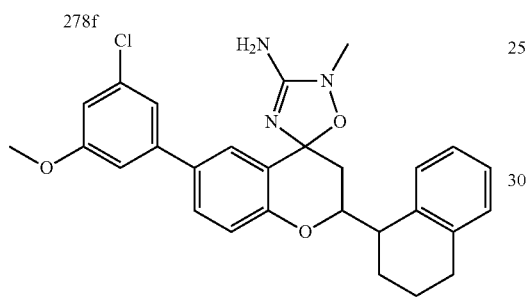

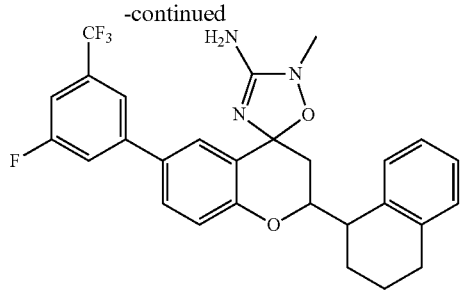

Pd(PPh$_3$)$_2$Cl$_2$ (5 mg) in a 10 mL of flask under N$_2$ was treated sequentially with the compound 269a (20 mg, 0.047 mmol) in 1,4-dioxane (1 mL), Cs$_2$CO$_3$ solution (2 N, 0.1 mL), and 3-fluoro-5-(trifluoromethyl)phenylboronic acid (19.5 mg, 0.094 mmol). The mixture was heated under 120° C. at N$_2$ under microwave for 20 minutes, and the reaction mixture was concentrated in vacuo, the residue was purified by preparative TLC and HPLC to give compound 269 (5.1 mg, 21%). $^1$H NMR (400 MHz CD$_3$OD): δ7.98 (s, 1H), 7.69 (m, 3H), 7.39 (d, 2H), 7.08 (m, 4H), 4.67 (m, 1H), 3.47 (m, 1H), 3.36 (m, 3H), 2.81 (m, 2H), 2.52 (m, 1H), 2.10 (m, 4H), 1.73 (m, 1H), 1.38 (m, 1H); ESI MS: m/z 512 [M+H]$^+$.

Example 305

Preparation of Compound 226

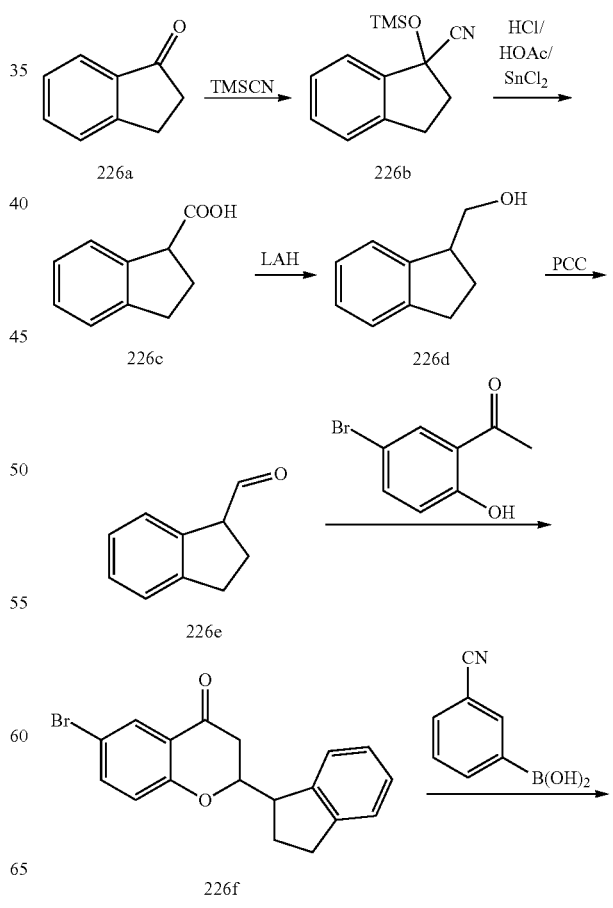

-continued

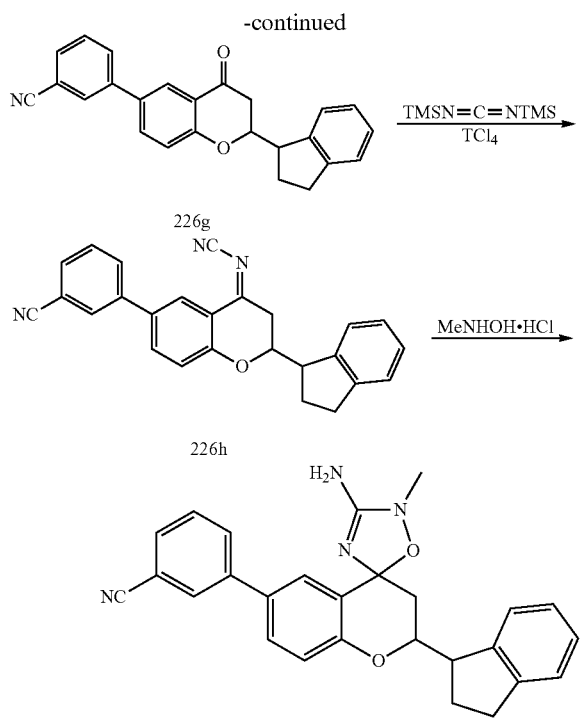

Experimental Data:

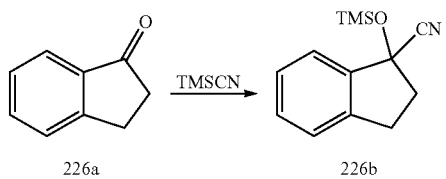

Preparation of Compound 226b

To a solution of compound 226a (20 g, 151 mmol) and 1.9 g of Zinc iodide in 400 mL of dichloromethane was added 15 g (151 mmol) of cyanotrimethylsilane 0° C. After being stirred overnight, the mixture was warmed to room temperature, washed with 300 mL of saturated aqueous sodium bicarbonate solution, dried, filtrated, and concentrated in vacuum to give the compound 226b (26.84 g, 77%). $^1$H NMR (400 MHz CDCl$_3$): δ7.35-7.40 (m, 1H), 7.02-7.21 (m, 3H), 2.79-2.90 (m, 2H), 2.48-2.55 (m, 1H), 2.23-2.28 (m, 1H), 0.01-0.19 (m, 9H).

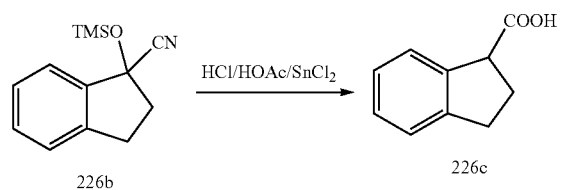

Preparation of Compound 226c

A solution of compound 226b (26.84 g, 116 mmol) and SnCl$_2$.2H$_2$O (104.86 g, 464 mmol) in 100 mL of a mixture of acetic acid and concentrated hydrochloric acid (10:1) was refluxed for 1 day. After being cooled to room temperature, the mixture was extracted with 150 mL of dichloromethane, and the organic layers were washed with 130 mL of 2 N sodium hydroxide solution. The basic washes were extracted with 100 mL of ether, and acidified to PH=2 with 5 N hydrochloric acid solution. The acidic aqueous mixture was extracted with 150 mL of EtOAc. The combined organic layers were dried, filtered, and concentrated in vacuo to give the compound 226c. $^1$H-NMR (400 MHz CDCl$_3$): δ7.35-7.40 (m, 1H), 7.21-7.31 (m, 3H), 4.07-4.19 (m, 1H), 3.11-3.21 (m, 1H), 2.89-2.98 (m, 1H), 2.32-2.54 (m, 2H).

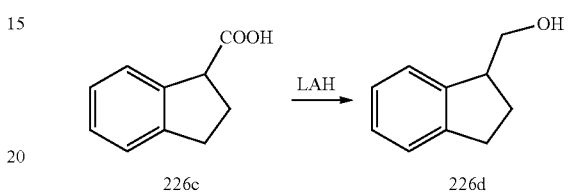

Preparation of Compound 226d

The solution of LiAlH$_4$ (2.1 g, 54 mmol) in 50 mL of dry THF was added a solution of compound 226c in THF (40 mL). The reaction mixture was stirred at room temperature for 2 h, quenched with 2.1 mL of H$_2$O and 2.1 mL of 10% NaOH, filtered, and concentrated to give the compound 226d. $^1$H-NMR (400 MHz CDCl$_3$): δ7.05-7.30 (m, 4H), 3.62-3.87 (m, 2H), 3.27-3.49 (m, 1H), 2.71-3.01 (m, 2H), 2.11-2.38 (m, 1H), 1.83-1.94 (m, 1H).

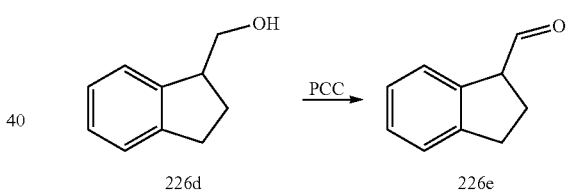

Preparation of Compound 226e

To a solution of compound 226d (2 g, 13.5 mmol) in DCM (50 mL) was added PCC (4.36 g, 20 mmol) and 3 Å molecule serves (2.0 g), and the mixture was stirred at room temperature for 1 h. After work up and purification, compound 226e (1.9 g, 96%) was obtained. $^1$H-NMR (400 MHz CDCl$_3$): δ2.21-2.54 (m, 2H), 2.81-3.18 (m, 2H), 3.91-4.01 (m, 1H), 7.18-7.30 (m, 4H), 9.66-9.67 (m, 1H).

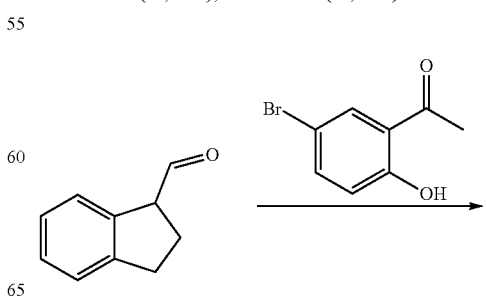

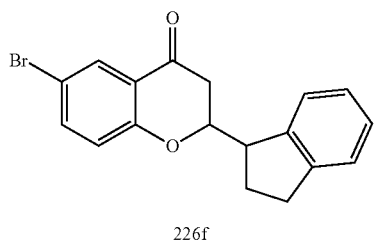

Preparation of Compound 226f

To a solution of 1-(5-bromo-2-hydroxyphenyl)-ethanone (2.79 g, 12.99 mmol) in a mixture of EtOH (18 mL) and H$_2$O (28.8 mL) was added compound 226e (1.9 g, 12.99 mmol) and borax (4.96 g, 12.99 mmol). The mixture was refluxed overnight, filtered, and concentrated. The residue was dissolved in EtOAc, and the organic layer was washed with brine, dried, and concentrated. The residue was purified by chromatography to afford the compound 226f (1.0 g, 22.4%). $^1$H NMR (400 MHz CDCl$_3$): δ7.89-7.91 (m, 1H), 7.34-7.56 (m, 2H), 7.12-7.27 (m, 3H), 6.80-6.89 (m, 1H), 4.52-4.56 (m, 1H), 3.52-3.67 (m, 1H), 2.87-3.09 (m, 2H), 2.51-2.81 (m, 2H), 2.22-2.26 (m, 1H), 1.97-2.21 (m, 1H).

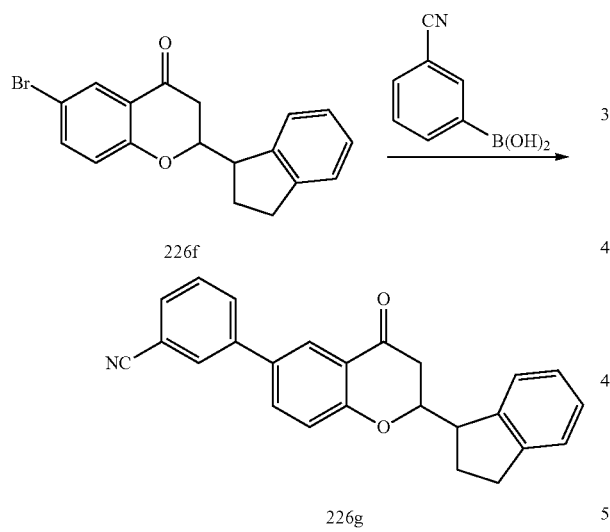

Preparation of Compound 226g

To a solution of compound 226f (320 mg, 0.93 mmol) in 1,4-dixoane (5 mL) was added 3-cyanophenylboronic acid (273 mg, 1.86 mmol), Pd(PPh$_3$)$_2$Cl$_2$ (20 mg) and Cs$_2$CO$_3$ solution (2 M, 1.4 mL). The reaction mixture was stirred in microwave at 100° C. for 10 minutes. The organic layer was concentrated, and the residue was purified by HPLC to give the compound 226g (127 mg, 38%). $^1$H-NMR (400 MHz CDCl$_3$): δ2.21-2.41 (m, 1H), 2.52-2.76 (m, 2H), 2.81-3.01 (m, 2H), 3.57-3.69 (m, 1H), 4.52-4.67 (m, 1H), 7.02-7.26 (m, 6H), 7.42-7.79 (m, 4H), 7.99-8.01 (m, 1H).

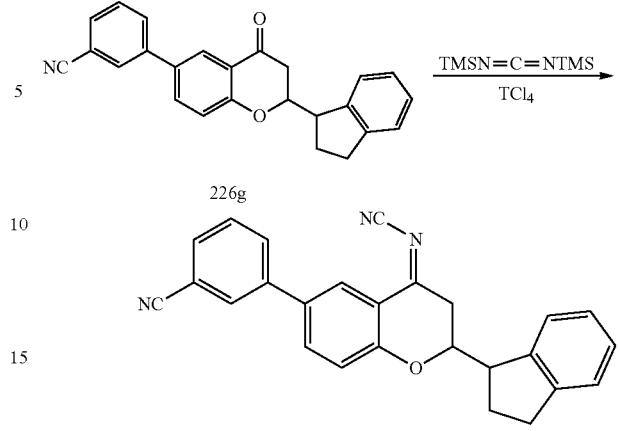

Preparation of Compound 226h

To a solution of compound 226g (127 mg, 0.35 mmol) in DCM (18 mL) was added TiCl$_4$ (194.3 mg, 1.04 mmol) at room temperature. After being stirred for 1 h, bis-trimethyl-silylcarbodiimide (131 mg, 0.70 mmol) was added, and the mixture was stirred at room temperature overnight. The reaction was quenched with ice water and extracted with DCM. The organic layer was washed with water and brine, dried, and concentrated to give the compound 226h (79 mg, 58%).

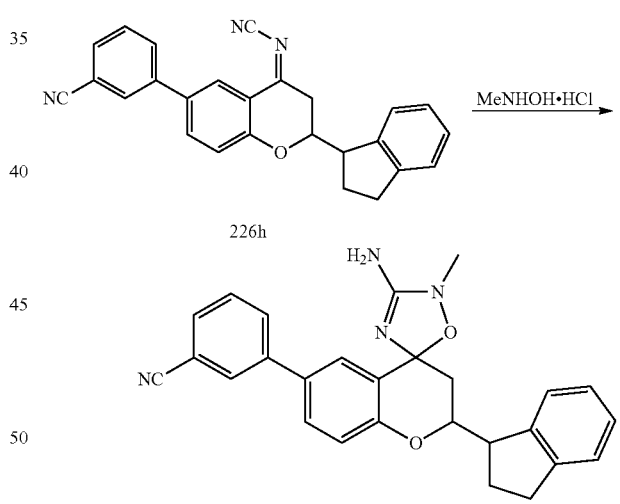

Preparation of Compound 226

To a solution of MeNHOH.HCl (16.9 mg, 0.2 mmol) in anhydrous MeOH (3 mL) was added NaOMe (10% in MeOH, 98 mg, 0.18 mmol) at room temperature and 226h (79 mg, 0.2 mmol). After being stirred for 5 minutes, the mixture was concentrated in vacuum, and the residue was redissolved in CH$_2$Cl$_2$ and filtered. The filtrate was concentrated, and the residue, was purified by preparative TLC and HPLC to give compound 226 (18 mg, 20%). $^1$H-NMR (400 MHz CD$_3$OD): δ7.85-7.90 (m, 3H), 7.50-7.66 (m, 3H), 7.16-7.25 (m, 2H), 6.90-7.11 (m, 3H), 4.39-4.71 (m, 1H), 3.57-3.59 (m, 2H), 3.32-3.55 (s, 3H), 2.61-2.98 (m, 2H), 2.45-2.58 (m, 1H), 2.00-2.25 (m, 1H), 1.57-1.97 (m, 1H); ESI MS: m/z 437 [M+H]$^+$.

Example 306

Preparation of Compound 204

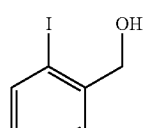
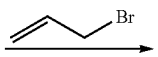

204a

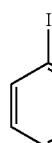

204b

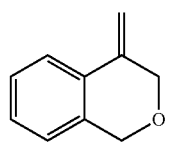

204c  204d

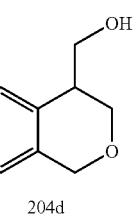

204e

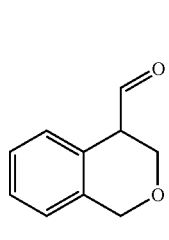

204f

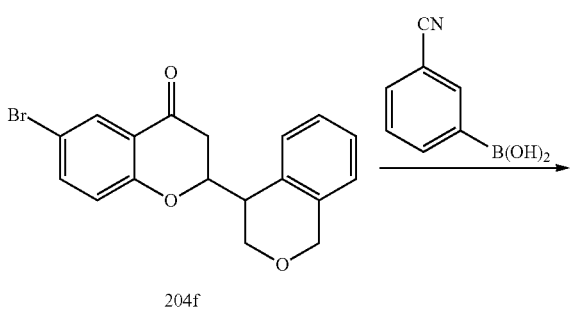

204g

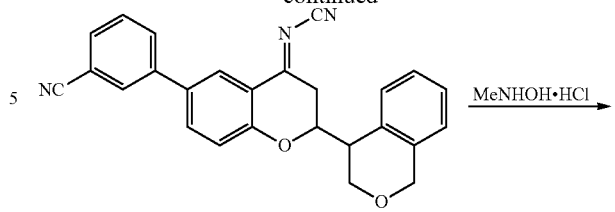

204h

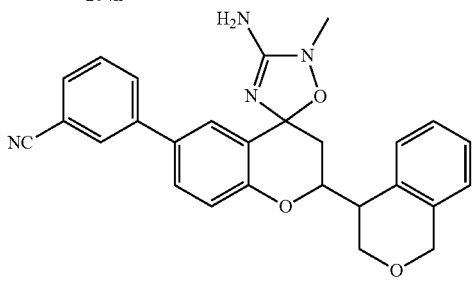

Experimental Data:

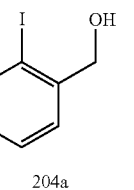

204a

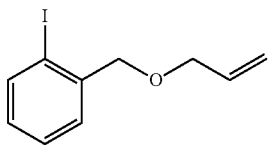

204b

Preparation of Compound 204b

NaH (5.12 g, 128 mmol) was added to a solution of compound 204a (25 g, 107 mmol) in THF (200 mL) at room temperature in small portions. Allyl bromide (11.1 mL, 128 mmol) was added via syringe, and the mixture was stirred overnight at room temperature, quenched by the addition of H$_2$O (100 mL) slowly, and diluted with 300 mL of Et$_2$O. The organic layer was washed with H$_2$O and brine, dried (magnesium sulfate), filtered, and concentrated in vacuo to yield the compound 204b (31 g crude, 100%) as faint yellow oil. $^1$H-NMR (400 MHz CDCl$_3$): δ7.45 (m, 1H), 7.11 (m, 1H), 6.85 (m, 1H), 7.81-7.83 (d, 1H), 7.45-7.47 (t, 1H), 7.33-7.37 (t, 1H), 6.96-7.00 (t, 1H), 5.95-6.05 (m, 1H), 5.33-5.39 (d, 1H), 5.22-5.26 (d, 1H), 4.50 (s, 2H), 4.11-4.13 (d, 2H).

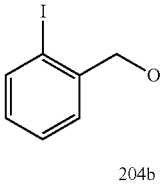 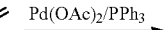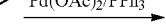

204b

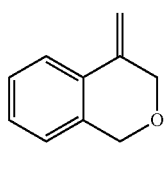

204c

Preparation of Compound 204c

The solution of compound 204b (55 g, 201 mmol) in a mixture 250 mL of CH$_3$CN and 145 mL of Et$_3$N was degassed, and added Pd(OAc)$_2$ (2.23 g, 10 mmol) and PPh$_3$ (5.28 g, 20.1 mmol). The mixture was heated at 80° C. until TLC indicated completion of the reaction. The mixture was cooled to room temperature, diluted with Et$_2$O (500 mL), washed with 1 N HCl, NaHCO$_3$, and brine, dried (sodium sulfate), filtered, and concentrated in vacuo to yield the compound 204c (15 g, 51%) as oil. $^1$H-NMR (400 MHz CDCl$_3$): δ7.59-7.63 (d, 1H), 7.15-7.19 (t, 2H), 6.95-6.98 (d, 1H), 5.54 (s, 1H), 4.94 (s, 1H), 4.74 (s, 2H), 4.38 (s, 2H).

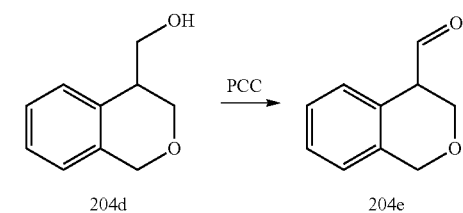

204c → 204d

Preparation of Compound 204d

To a solution of compound 204c (13 g, 89 mmol) in THF (400 mL) was added a solution of B$_2$H$_6$·THF (1.0 M, 45 mL, 45 mmol) under N$_2$ at 0° C. The mixture was stirred at room temperature for 3 hours, added aqueous NaOH solution (3 N, 22 mL, 67 mmol) and H$_2$O$_2$ (30%, 15.2 mL, 134 mmol) at room temperature, stirred for 2 hours, quenched by addition of brine. The reaction mixture was extracted with EtOAc, and the organic layer was washed with aq. Na$_2$S$_2$O$_3$, dried, and concentrated to give the crude compound 204d (10 g, 69%). $^1$H-NMR (400 MHz CDCl$_3$): δ7.59-7.63 (d, 1H), 7.17-7.24 (m, 3H), 6.99-7.01 (t, 1H), 4.73-4.89 (q, 2H), 4.25-4.28 (d, 1H), 3.61-3.95 (m, 3H), 2.83-2.84 (m, 1H).

204d → 204e

Preparation of Compound 204e

To a solution of compound 204d (5 g, 30 mmol) in dry CH$_2$Cl$_2$ (150 mL) was added 3 Å molecule series (6 g) and PCC (9.7 g, 45 mmol). The mixture was stirred at room temperature for 1 h, when the reaction was completed, the mixture was filtered through celite, dried over Na$_2$SO$_4$, and concentrated in vacuum to give the compound 204e (5 g, crude, 100%).

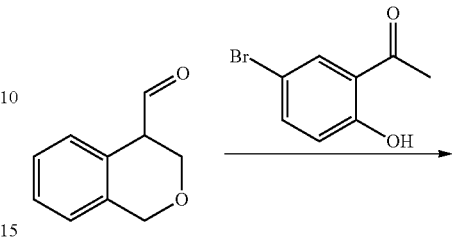

204e

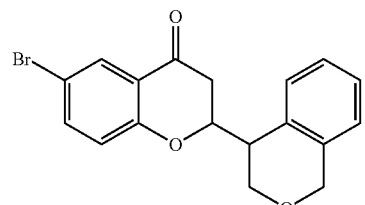

204f

Preparation of Compound 204f

To a stirred solution of compound 204e (6.5 g, 30 mmol) in a mixture of EtOH (50 mL) and H$_2$O (80 mL) was added isochroman-4-carbaldehyde (5.0 g, 30 mmol) and borax (11.4 g, 30 mmol). The mixture was refluxed overnight, filtrated, and concentrated in vacuo. The residue was dissolved in CH$_2$Cl$_2$, after filtration. the solvents were evaporated, and the crude product was purified by column chromatography to give the compound 204f (200 mg, 2%). $^1$H-NMR (400 MHz CDCl$_3$): δ7.89 (s, 1H), 7.48-7.51 (d, 1H), 7.13-7.21 (m, 3H), 6.95-6.97 (d, 1H), 6.88-6.90 (d, 1H), 4.69-4.81 (q, 3H), 4.38-4.41 (dd, 1H), 3.73-3.77 (dd, 1H), 3.02-3.04 (d, 1H), 2.72-2.77 (dd, 1H), 2.54-2.61 (t, 1H).

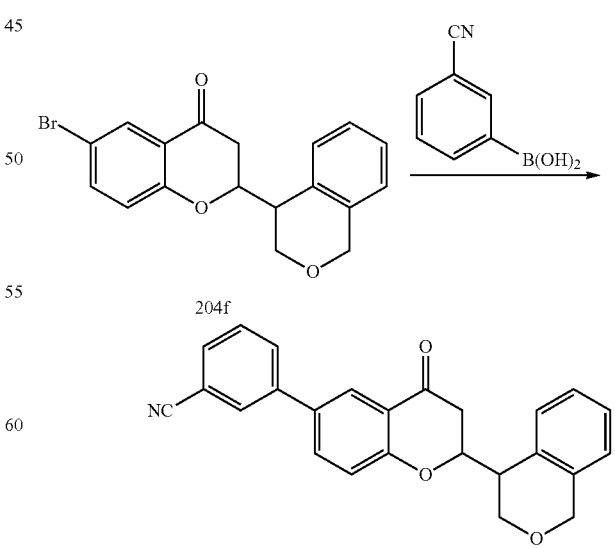

204f

204g

823

Preparation of Compound 204g

To a solution of compound 204f (123 mg, 0.84 mmol) in a mixture of Cs$_2$CO$_3$ solution (2 M, 2.25 mL) and 1,4-dioxane (5 mL) was added Pd(PPh$_3$)$_2$Cl$_2$ (37.5 mg) under N$_2$. The mixture was stirred in microwave at 100° C. for 20 minutes. After being cooled to room temperature, the mixture was concentrated, and the residue was purified by TLC to give the compound 204g (31 mg, 19%). $^1$H-NMR (400 MHz CDCl$_3$): δ2.40-2.45 (d, 0.7H), 2.58-2.83 (m, 0.3H), 3.07-3.19 (m, 1.6H), 3.72-3.86 (m, 1.4H), 4.53-4.57 (d, 1H), 4.71-4.79 (m, 3H), 6.98-7.00 (d, 1H), 7.07-7.09 (d, 1H), 7.18-7.19 (m, 3H), 7.45-7.49 (t, 1H), 7.54-7.56 (d, 1H), 7.64-7.66 (d, 1H), 7.72-7.78 (t, 2H), 8.01 (s, 1H).

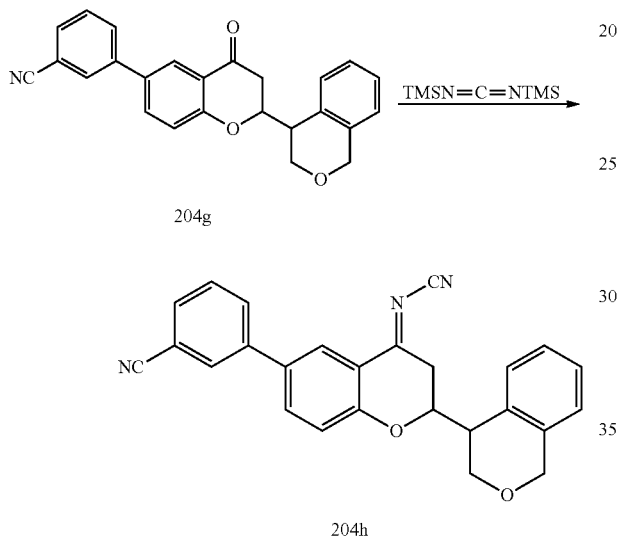

Preparation of Compound 204h

To a solution of compound 204g in CH$_2$Cl$_2$ (2 mL) was added TiCl$_4$ (1 M in DCM, 0.22 mL, 0.22 mmol), and the mixture was stirred in microwave at 50° C. for 10 minutes. The bis-trimethylsilylcarbodiimide (0.053 mL, 0.237 mmol) was added, and the resulting mixture was stirred in microwave at 60° C. for 10 minutes. The reaction mixture was poured into ice-water, extracted with DCM, dried over anhydrous Na$_2$SO$_4$, filtered, and concentrated to give the compound 204h (42 mg, crude, 96%).

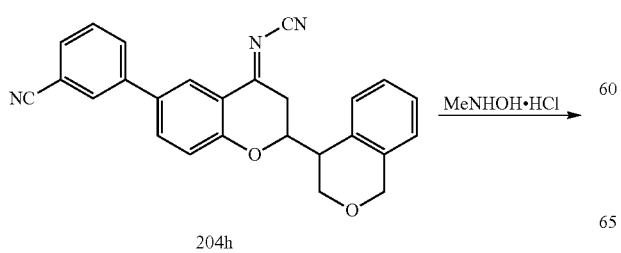

824

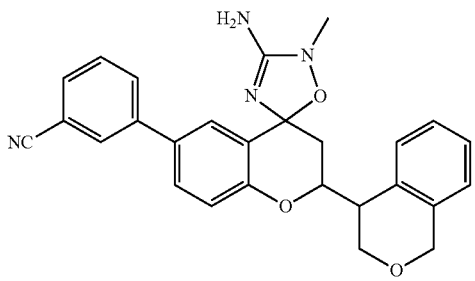

Preparation of Compound 204

To a solution of methylhydroxylamine HCl salt (9.1 mg, 0.108 mmol) in anhydrous MeOH (3 mL) was added NaOMe (10% in MeOH, 52 mg, 0.097 mmol) and compound 204h (42 mg, 0.108 mmol). After being stirred for 20 minutes, the solvent was removed in vacuo, and the residue was dissolved in DCM (5 mL). The mixture was filtered, and the solvent was removed, and the residue was purified by preparative HPLC to give the compound compound 204 (18 mg, 41%). $^1$H-NMR (400 MHz CD$_3$OD): δ7.90-7.98 (m, 3H), 7.60-7.75 (m, 3H), 7.35 (m, 1H), 7.25-7.27 (m, 2H), 7.08-7.10 (m, 2H), 4.73-4.83 (m, 4H), 4.42-4.53 (m, 1H), 3.82-3.94 (m, 1H), 3.21-3.40 (m, 3H), 2.52-2.78 (m, 1H), 2.29-2.31 (m, 1H); ESI MS: m/z 453 [M+H]$^+$.

Example 307

Preparation of Compound 349

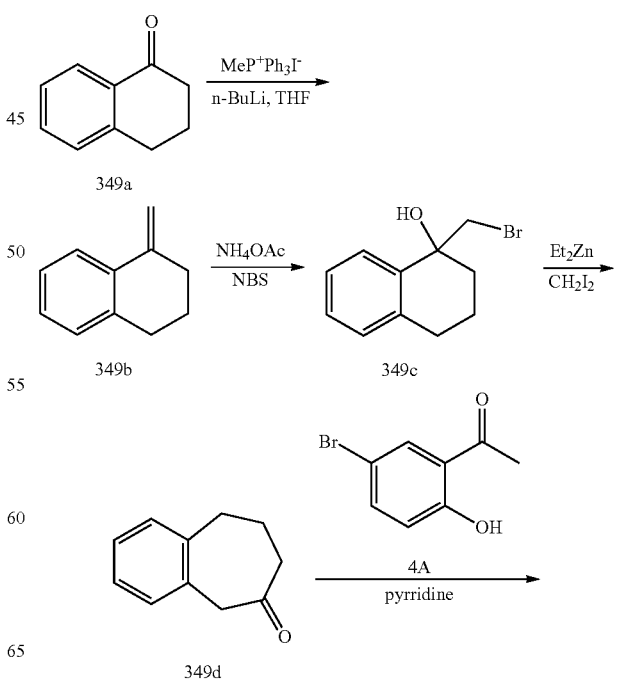

-continued

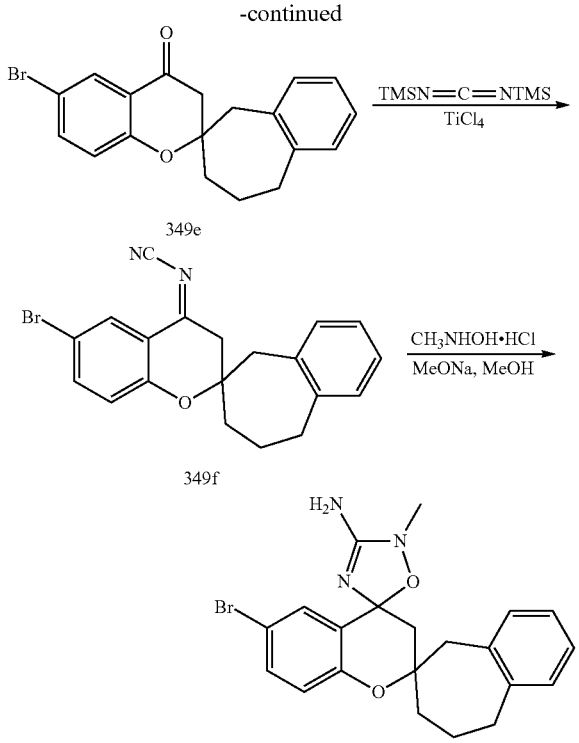

Experimental Data

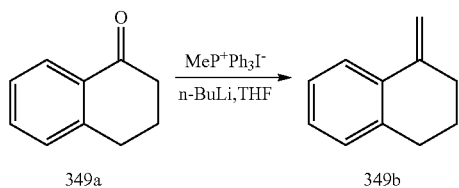

To a solution of methyltriphenylphosphonium iodide (250 g, 0.615 mol) in anhydrous THF (1500 mL) was cooled to −100° C. n-BuLi (220 mL, 0.55 mol, 2.5 M in hexane) was added dropwise at this temperature under nitrogen atmosphere, and the mixture was stirred at −100° C. for 1 hour. Compound 349a (50 g, 0.343 mol) was added dropwise at −100° C., and the mixture was warmed to room temperature, and stirred at this temperature for 3 hours. The reaction was quenched with water, and extracted with EtOAc (×500 mL). The organic layer was dried over $Na_2SO_4$, filtered, and concentrated in vacuo. The residue was purified by column chromatography (petroleum ether/EtOAc=100:1) to give the compound 349b (36.5 g, 74%) as a colorless liquid. $^1H$ MNR (CDCl$_3$, 400 MHz): δ7.55 (d, 1H), 7.05 (m, 3H), 5.37 (s, 1H), 4.85 (s, 1H), 2.48 (t, 2H), 2.44 (t, 2H). 1.78 (t, 2H),

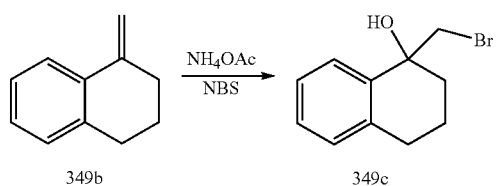

To a solution of 1-methylene-1,2,3,4-tetrahydronaphthalene (10 g, 61.0 mol) in a mixture of acetone (100 mL) and water (25 mL) was added NH$_4$OAc (0.47 g, 0.61 mmol) and NBS (15.1 g, 67.1 mmol). The mixture was stirred at room temperature for 30 minutes, concentrated in vacuo, and extracted with EtOAc (3×100 mL). The combined organic layers were dried over Na$_2$SO$_4$, filtered, and concentrated in vacuo, the residue was purified by column chromatography (petroleum ether/EtOAc=5:1) to give the compound 349c (10 g, 68%) as a colorless liquid. $^1$H-MNR(CDCl$_3$, 400 MHz): δ7.45 (d, 1H), 7.15 (m, 2H), 7.07 (m, 1H), 3.65 (m, 2H), 2.81 (m, 2H), 2.36 (m, 1H), 1.84 (m, 2H), 1.64 (m, 1H)

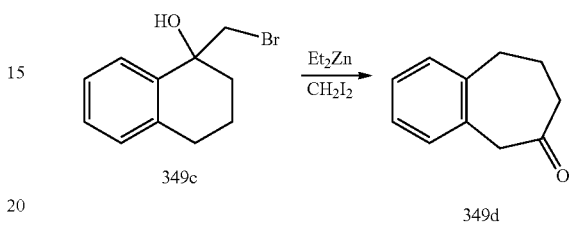

To a solution of diethylzinc (25 mL, 23.1 mmol) in dry CH$_2$CL$_2$ (50 mL) was added diiodomethane (6.19 g, 23.1 mmol) at 0° C. under nitrogen. The mixture was stirred at 0° C. for 20 minutes, and followed by the addition of the solution of compound 349c (10 g, 38.5 mmol) in dried CH$_2$CL$_2$ (33 mL). The mixture was stirred at room temperature for 4 hours, and concentrated NH$_4$Cl aqueous solution (30 mL) was added. The organic layer was washed with water, and dried over Na$_2$SO$_4$, filtered, and concentrated in vacuo, the residue was purified by column chromatography (petroleum ether/EtOAc=30:1~5:1) to give compound 349d (4.4 g, 71%) as a colorless liquid. $^1$H-NNR (CDCl$_3$, 400 MHz): δ7.17 (m, 4H), 3.72 (s, 2H), 2.95 (t, 2H), 2.00 (m, 2H), 2.58 (t, 2H).

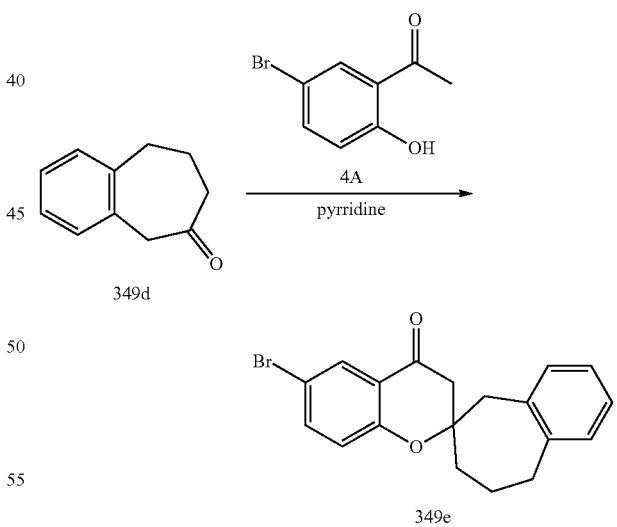

To a solution of 8,9-dihydro-5H-benzo[7]annulen-6(7H)-one (0.898 g, 5.61 mmol) in dried MeOH (5 mL) was added 1-(5-bromo-2-hydroxyphenyl)ethanone (1 g, 4.67 mmol) and pyrrolidine (0.6 mL). The mixture was stirred at room temperature for 1 hour, and refluxed overnight. The mixture was concentrated in vacuo, the residue was purified by column chromatography (petroleum ether/EtOAc=30:1~5:1) to give the compound 349e (341 mg, 20%) as an orange solid. $^1$H MNR (CDCl$_3$, 400 MHz): δ8.01 (d, 1H), 7.51 (m, 1H), 7.17

(m, 3H), 6.81 (m, 1H), 6.72 (m, 1H), 3.32 (m, 1H), 3.10 (m, 1H), 2.65 (m, 2H), 2.63 (m, 2H), 2.12 (m, 2H), 1.95 (m, 1H), 1.55 (m, 1H).

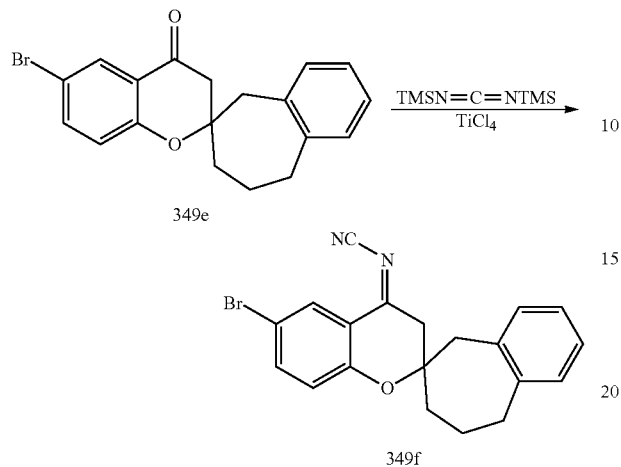

To a solution of compound 349e (2 g, 5.62 mmol) in dry CH$_2$Cl$_2$ (140 mL) was added TiCl$_4$ (16.8 mL, 16.8 mmol, 1 M in CH$_2$Cl$_2$) at 15° C. under N$_2$ atmosphere. The mixture was stirred at 15° C. for 1 hour. and added N,N'-methanediylidenebis(1,1,1-trimethylsilanamine) (2.77 mL, 12.36 mmol). The mixture was stirred at 15° C. overnight, poured into ice, and extracted with CH$_2$Cl$_2$ (3×100 mL). The combined organic layers were dried over Na$_2$SO$_4$, filtered, and concentrated in vacuo, to give the crude compound 349f (1.9 g, 90%) as a yellow solid, which was used for the next step directly without purification.

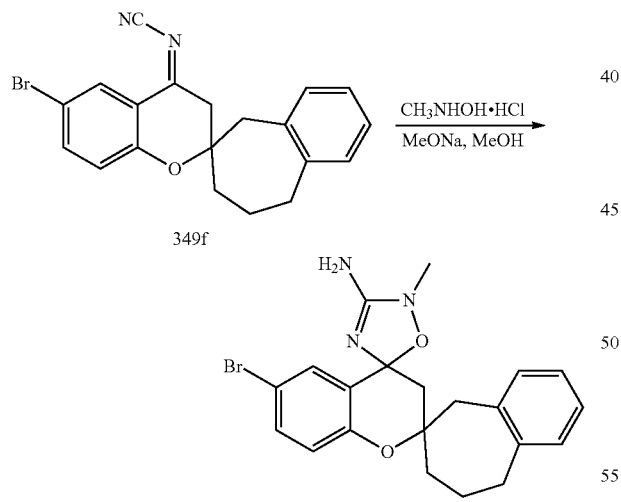

To a solution of N-methylhydroxylamine hydrochloride (415 mg, 5 mmol) in dry MeOH (124 mL) was added MeONa (2.7 mL, 5 mmol, 10% in MeOH) solution and compound 349f (1.9 g, 5 mmol) in portions. The mixture was stirred at 20° C. till the solid was dissolved completely. Water (300 mL) was added, and the mixture was extracted with CH$_2$Cl$_2$ (3×300 mL). The combined organic layers were washed with brine, dried over Na$_2$SO$_4$ and concentrated in vacuo, the residue was purified by column chromatography (CH$_2$Cl$_2$/MeOH=50:1) to give the compound 349 (1.03 g, 48%) as a yellow solid. $^1$H-NMR (CDCl$_3$ 400 MHz): δ7.42 (d, J=3.2 Hz, 1H), 7.04 (m, 4H), 6.53 (m, 1H), 3.35 (m, 1H), 2.95 (m, 4H), 2.76 (m, 2H), 2.36 (m, 1H), 2.13 (m, 1H), 1.95 (m, 2H), 1.87 (m, 2H); MS: m/z 428 [M+H]$^+$.

Example 308

Preparation of Compound 191

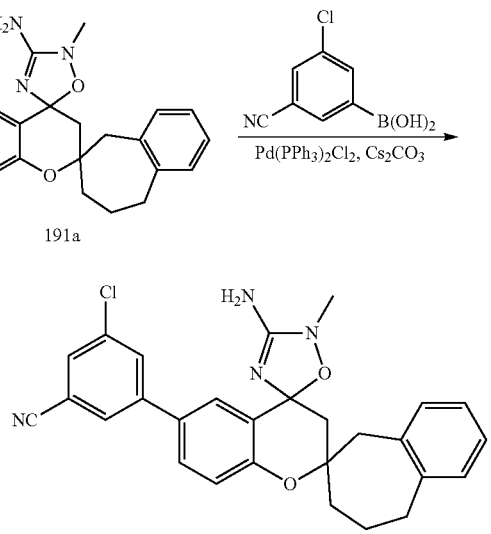

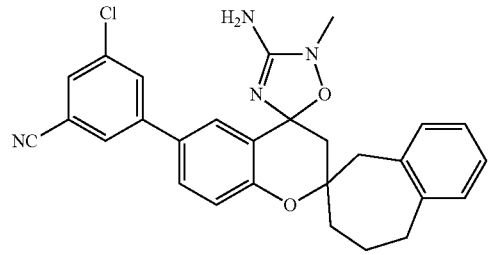

An dried flask was charged with compound 191a (20 mg, 0.046 mmol) in 1,4-dioxane (1 mL), Cs$_2$CO$_3$ solution (2 N, 0.5 mL), and 3-chloro-5-cyanophenyl-boronic acid (12.7 mg, 0.07 mmol) sequentially. Pd(PPh$_3$)$_2$Cl$_2$ (5 mg) was added under nitrogen atmosphere, and the mixture was heated at 120° C. in microwave for 10 minutes. The reaction mixture was concentrated in vacuo, and the residue was purified by preparative TLC and HPLC to give compound 191 (2 mg, 8%) as a white solid. $^1$H NMR (CD$_3$OD 400 MHz): δ7.73-8.35 (m, 5H), 6.89-7.35 (m, 5H), 3.30-3.56 (m, 3H), 2.85-2.96 (m, 4H), 2.81 (s, 1H), 2.40-2.49 (m, 1H), 1.93-2.21 (m, 3H), 1.49-1.70 (m, 1H); ESI MS: m/z 485 [M+H]$^+$.

Example 309

Preparation of Compound 186

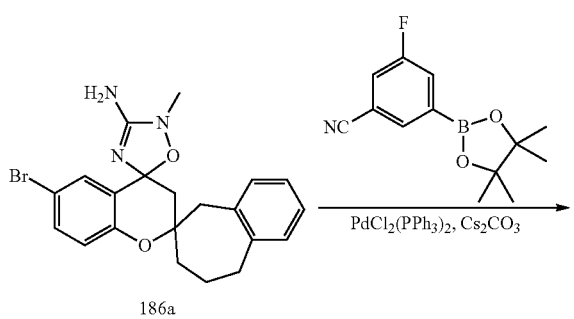

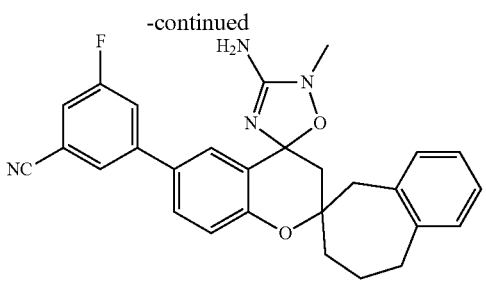

By using the same synthetic procedure as compound 191 described in Example 308, compound 186 (2.41 mg, 11%) was obtained as a white solid. $^1$H-NMR (400 MHz CD$_3$OD): δ7.95 (m, 1H), 7.81 (m, 1H), 7.68 (m, 2H), 7.48 (m, 1H), 7.09 (m, 3H), 6.86 (m, 2H), 3.45 (m, 1H), 3.32 (m, 3H), 3.12 (m, 1H), 2.47-2.93 (m, 3H), 2.36 (m, 1H), 2.12 (m, 1H), 1.87 (m, 2H), 1.35-1.64 (m, 1H); ESI MS: m/z 469 [M+H]$^+$.

Example 310

Preparation of Compound 227

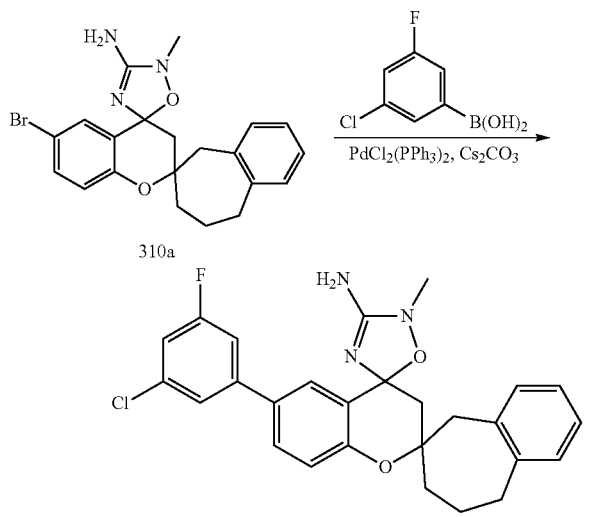

By using the same synthetic procedure as compound 191 described in Example 308, compound 227 (1.90 mg, 8%) was obtained as a white solid. $^1$H-NMR (400 MHz CD$_3$OD): δ8.80-8.30 (m, 1H), 7.68 (m, 1H), 7.48 (m, 1H), 7.33 (m, 1H) 7.14 (m, 4H), 7.03 (m, 1H), 6.86 (m, 1H), 3.51 (m, 1H), 3.48 (m, 3H), 3.15 (m, 1H), 2.72-3.02 (m, 3H), 2.33-2.52 (m, 1H) 2.08-2.25 (m, 1H), 1.41-1.74 (m, 1H); ESI MS: m/z 478 [M+H]$^+$.

Example 311

Preparation of Compound 189

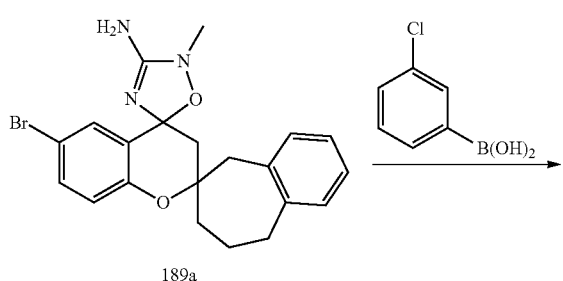

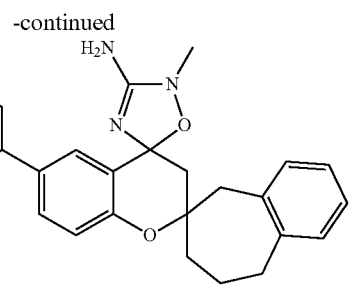

By using the same synthetic procedure as compound 191 described in Example 308, compound 189 (2.3 mg, 11%) was obtained as a white solid. $^1$H NMR (CD$_3$OD 400 MHz): δ7.76 (m, 1H), 7.53 (m, 2H), 7.41 (m, 1H), 7.28 (m, 2H), 7.02 (m, 3H), 6.71-6.95 (m, 2H), 3.41 (m, 1H), 3.28 (s, 3H), 3.02 (m, 1H), 2.51-2.85 (m, 3H), 2.33 (m, 1H), 2.08 (m, 1H), 1.85 (m, 2H), 1.31-1.63 (m, 1H); ESI MS: m/z 460 [M+H]$^+$.

Example 312

Preparation of Compound 192

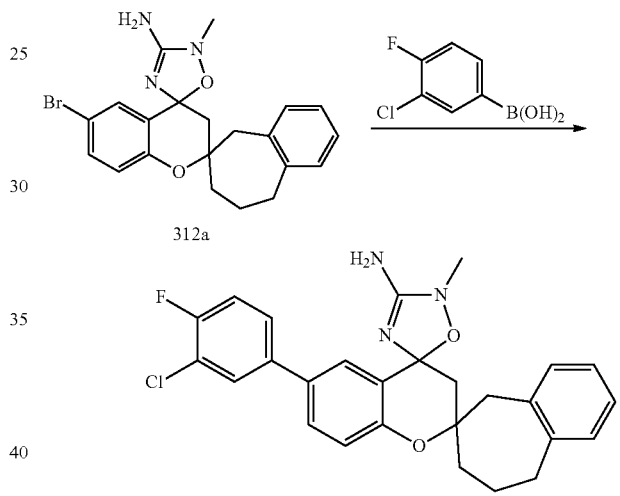

By using the same synthetic procedure as compound 191 described in Example 308, compound 192 (2.64 mg, 12%) was obtained as a white solid. $^1$H-NMR (400 MHz CD$_3$OD): δ7.70-8.20 (m, 1H), 7.66 (m, 1H), 7.58 (m, 1H), 7.48 (m, 1H), 7.22 (m, 1H) 7.09 (m, 3H), 6.86 (m, 2H), 3.46 (m, 1H), 3.37 (m, 3H), 3.08 (m, 1H), 2.71-2.93 (m, 3H), 2.41 (m, 1H), 2.12 (m, 1H), 1.80-2.03 (m, 2H), 1.38-1.70 (m, 1H); ESI MS: m/z 478 [M+H]$^+$.

Example 313

Preparation of Compound 199

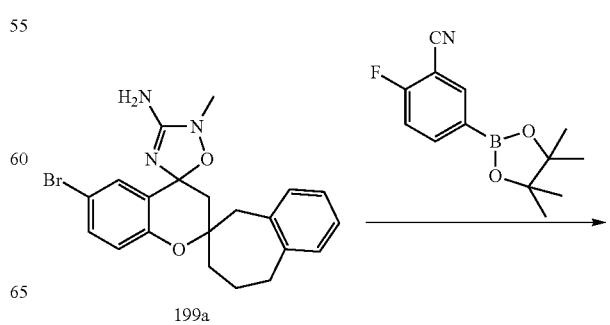

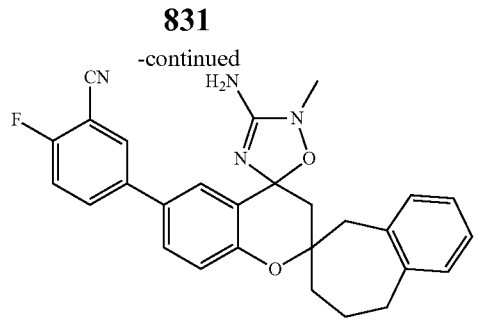

By using the same synthetic procedure as compound 191 described in Example 308, compound 199 (2.45 mg, 12%) was obtained as a white solid. $^1$H-NMR (400 MHz, CD$_3$OD): δ7.95 (m, 3H), 7.61 (s, 1H), 7.36 (m, 1H), 7.2 (s, 3H), 6.95 (m, 1H), 6.85 (m, 1H), 3.44 (d, 1H), 3.30 (m, 3H), 3.08 (m, 1H), 2.65 (m, 3H), 2.41 (m, 1H), 2.13 (s, 1H), 1.91 (s, 2H), 1.55 (m, 1H); ESI MS: m/z 469 [M+H]$^+$.

Example 314

Preparation of Compound 178

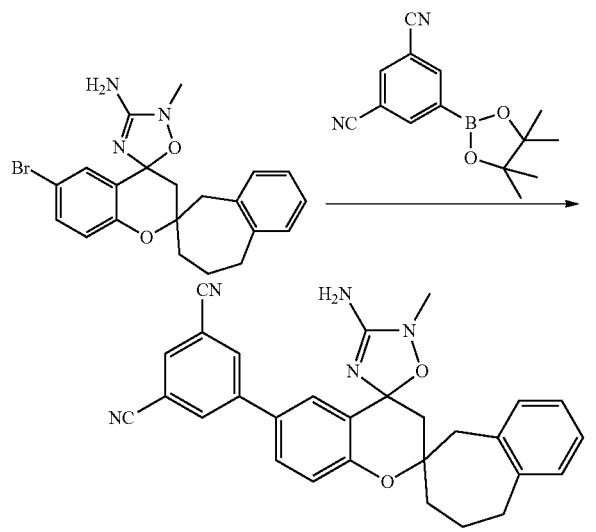

By using the same synthetic procedure as compound 191 described in Example 308, compound 178 (1.84 mg, 10%) was obtained as a white solid. $^1$H-NMR (400 MHz CD$_3$OD): δ8.35 (m, 2H), 8.11 (m, 2H), 7.75 (d, 1H) 7.20 (m, 2H), 7.0 (s, 1H), 6.95 (m, 1H), 6.85 (m, 1H), 3.44 (d, 1H), 3.30 (m, 3H), 3.08 (m, 1H), 2.65 (m, 3H), 2.41 (m, 1H), 2.13 (s, 1H), 1.91 (s, 2H), 1.55 (m, 1H); ESI MS: m/z 476 [M+H]$^+$.

Example 315

Preparation of Compound 234

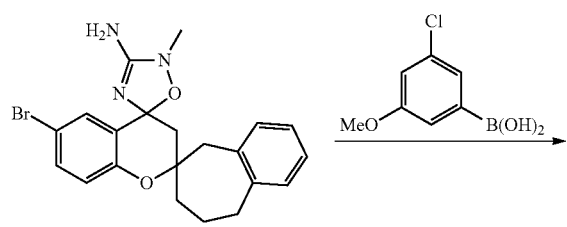

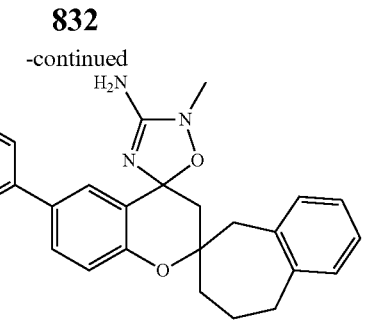

By using the same synthetic procedure as compound 191 described in Example 308, compound 234 (2.71 mg, 12%) was obtained as a white solid. $^1$H-NMR (400 MHz CD$_3$OD): δ7.78-8.31 (m, 1H), 7.64 (m, 1H), 7.18 (m, 4H), 6.88 (m, 4H), 3.88 (m, 3H), 3.52 (m, 1H), 3.37 (m, 3H), 3.15 (m, 1H), 2.91 (m, 3H), 2.44 (m, 1H), 2.22 (m, 1H), 2.01 (m, 2H), 1.48-1.76 (m, 1H); ESI MS: m/z 460 [M+H]$^+$.

Example 316

Preparation of Compound 242

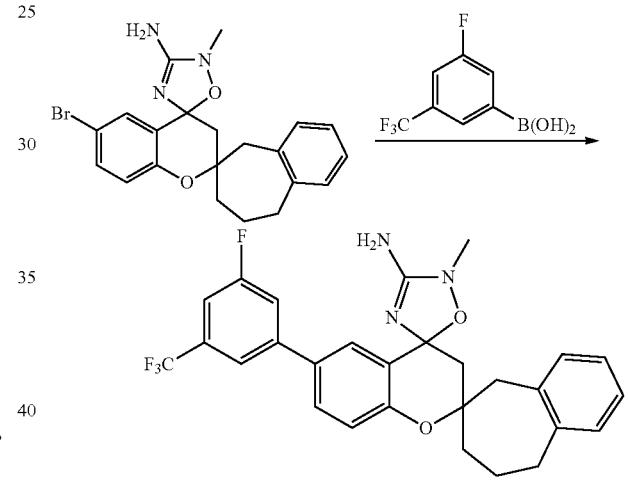

By using the same synthetic procedure as compound 191 described in Example 308, compound 242 (2.63 mg, 11%) was obtained, $^1$H-NMR (400 MHz CD$_3$OD): δ7.86-8.27 (m, 1H), 7.62 (m, 3H), 7.38 (m, 1H), 6.76-7.18 (m, 5H), 3.42 (m, 1H), 3.27 (m, 3H), 3.02 (m, 1H), 2.77 (m, 3H), 2.35 (m, 1H), 2.12 (m, 1H), 1.86 (m, 2H), 1.31-1.62 (m, 1H); ESI MS: m/z 490 [M+H]$^+$.

Example 317

Preparation of Compound 181

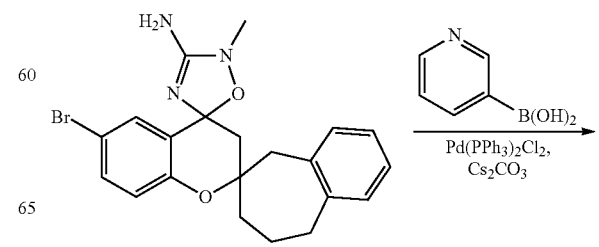

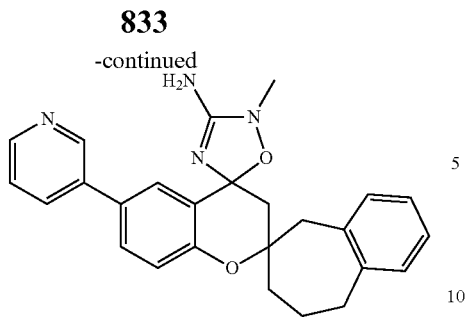

By using the same synthetic procedure as compound 191 described in Example 308, compound 181 (5 mg, 10%) was obtained as a white solid. $^1$H-NMR (400 MHz CD$_3$OD): δ8.64 (m, 1H), 8.40 (m, 1H), 7.98 (m, 1H), 7.62 (m, 1H), 7.48 (m, 2H), 6.83-7.08 (m, 4H), 6.7-6.83 (m, 1H), 3.32 (m, 2H), 3.06 (m, 1H), 2.92 (s, 3H), 2.82 (m, 2H), 2.7 (m, 1H), 1.57-2.1 (m, 3H), 1.53 (m, 1H); MS: m/z 427 [M+H]$^+$.

Example 318

Preparation of Compound 352

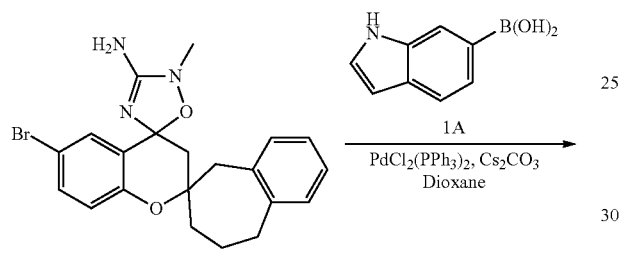

By using the same synthetic procedure as compound 191 described in Example 308, compound 352 (5 mg, 11%) was obtained as a white solid. $^1$H-NMR (400 MHz CD$_3$OD): δ7.9 (m, 1H), 7.82 (m, 1H), 7.71 (m, 1H), 7.61 (m, 1H), 7.3 (m, 2H), 7.28 (m, 4H), 7.0 (m, 1H), 6.48 (m, 1H), 3.56 (m, 2H), 3.39 (s, 3H), 3.27 (m, 1H), 2.95 (m, 3H), 2.5-2.8 (m, 1H), 2.39 (m, 1H), 2.01 (m, 2H); MS: m/z 465 [M+H]$^+$.

Example 319

Preparation of Compound 381

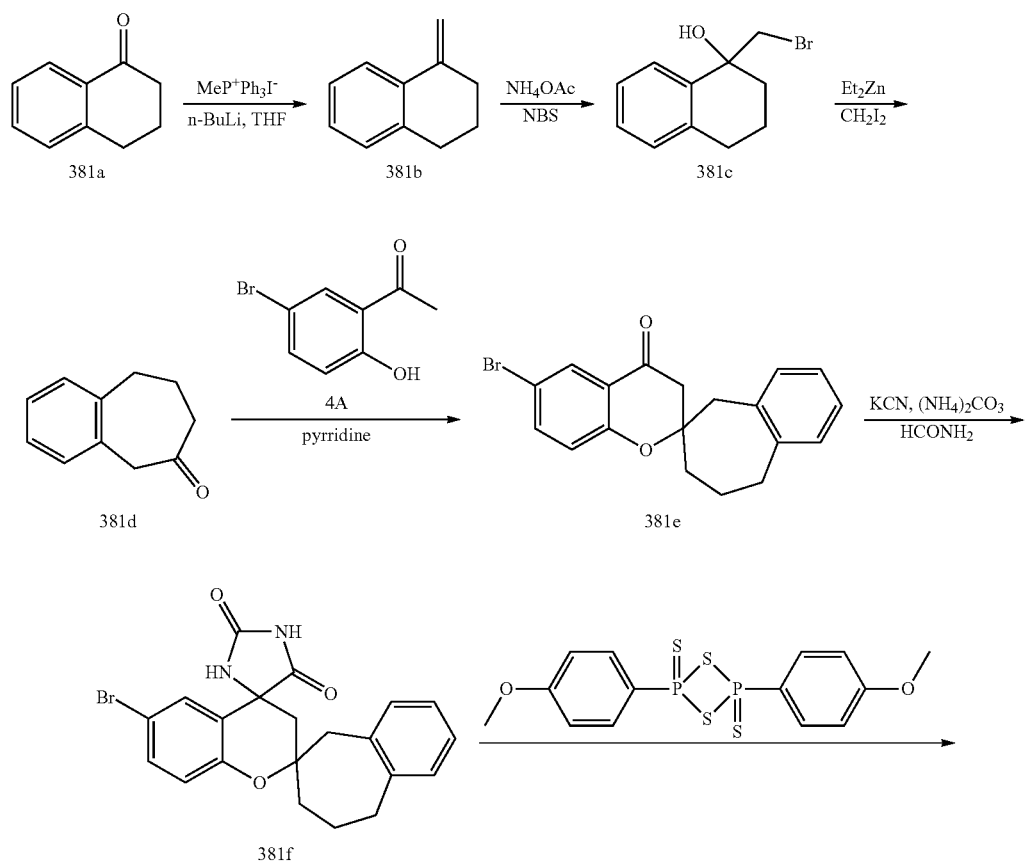

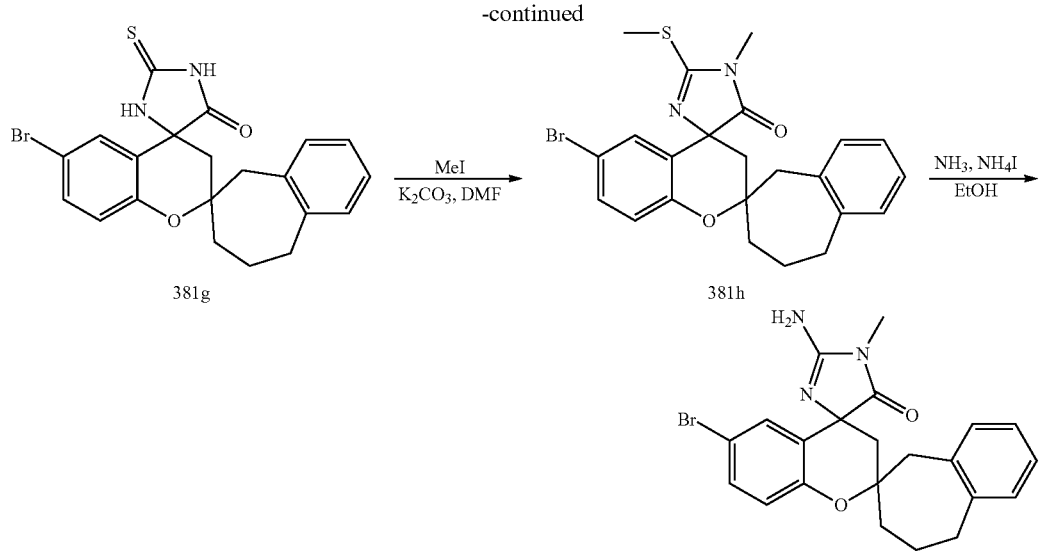

Experimental Data

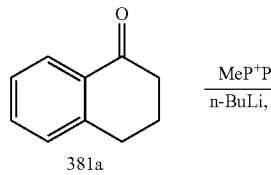

The solution of methyltriphenylphosphonium iodide (250 g, 0.615 mol) in anhydrous THF (1500 mL) was added n-BuLi (220 mL, 0.55 mol, 2.5 M in hexane) dropwise at −10° C. under nitrogen. The mixture was stirred at −10° C. for 1 hour, compound 381a (50 g, 0.343 mol) was added, and the mixture was warmed to room temperature, and stirred for 3 hours. The reaction was quenched with water, and extracted with EtOAc (×500 mL). The organic layer was dried over Na$_2$SO$_4$, filtered, and concentrated in vacuo, the residue was purified by column chromatography (petroleum ether/EtOAc=100:1) to give the compound 381b (36.5 g, 74%) as a colorless liquid. $^1$H-MNR (CDCl$_3$, 400 MHz): δ7.55 (d, 1H), 7.05 (m, 3H), 5.37 (s, 1H), 4.85 (s, 1H), 2.48 (t, 2H), 2.44 (t, 2H). 1.78 (t, 2H).

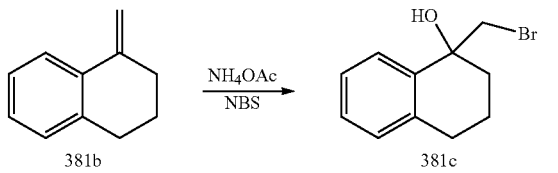

To a solution of 1-methylene-1,2,3,4-tetrahydronaphthalene (10 g, 61.0 mol) in a mixture of acetone (100 mL) and water (25 mL) was added NH$_4$OAc (0.47 g, 0.61 mmol) and NBS (15.1 g, 67.1 mmol). The mixture was stirred at room temperature for 30 minutes, concentrated in vacuo, and extracted with EtOAc (3×100 mL). The combined organic layers were dried over Na$_2$SO$_4$, filtered, and concentrated in vacuo. The residue was purified by column chromatography (petroleum ether/EtOAc=5:1) to give the compound 381c (10 g, 68%) as a colorless liquid. $^1$H-MNR (CDCl$_3$, 400 MHz): δ7.45 (d, 1H), 7.15 (m, 2H), 7.07 (m, 1H), 3.65 (m, 2H), 2.81 (m, 2H), 2.36 (m, 1H), 1.84 (m, 2H), 1.64 (m, 1H).

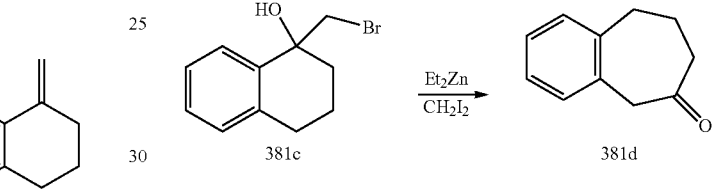

To a solution of diethylzinc (25 mL, 23.1 mmol) in dried CH2CL2 (50 mL) was added diiodomethane (6.19 g, 23.1 mmol) at 0° C. under nitrogen. The mixture was stirred at 0° C. for 20 minutes, and the solution of compound 381c (10 g, 38.5 mmol) in dry CH$_2$CL$_2$ (33 mL) was added. The ice bath was removed, after the mixture was stirred at room temperature for 4 hours, the concentrated NH$_4$Cl solution (30 mL) was added. The organic layer was washed with water, and dried over Na$_2$SO$_4$, filtered, and concentrated in vacuo, the residue was purified by column chromatography (petroleum ether/EtOAc=30:1~5:1) to give compound 381d (4.4 g, 71%) as a colorless liquid. $^1$H-MNR (CDCl$_3$, 400 MHz): δ7.17 (m, 4H), 3.72 (s, 2H), 2.95 (t, 2H), 2.00 (m, 2H), 2.58 (t, 2H).

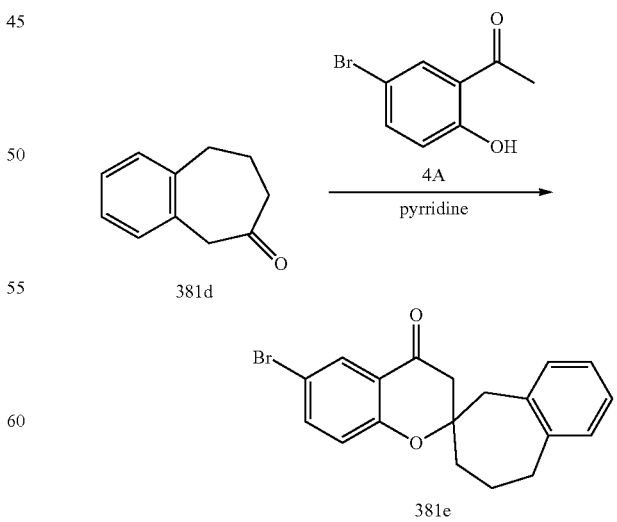

To a solution of 8,9-dihydro-5H-benzo[7]annulen-6(7H)-one (0.898 g, 5.61 mmol) in dry MeOH (5 mL) was added 1-(5-bromo-2-hydroxyphenyl)ethanone (1 g, 4.67 mmol) and pyrrolidine (0.6 mL). The mixture was stirred at room temperature for 1 hour, and refluxed overnight, and concentrated in vacuo. The residue was purified by column chromatography (petroleum ether/EtOAc=30:1~5:1) to give the compound 381e (341 mg, 20%) as an orange solid. ¹H-MNR (CDCl₃, 400 MHz): δ8.01 (d, 1H), 7.51 (m, 1H), 7.17 (m, 3H), 6.81 (m, 1H), 6.72 (m, 1H), 3.32 (m, 1H), 3.10 (m, 1H), 2.65 (m, 2H), 2.63 (m, 2H), 2.12 (m, 2H), 1.95 (m, 1H), 1.55 (m, 1H).

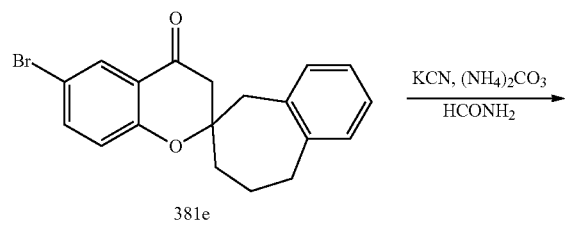

381e

A steel slave was charged with a mixture of compound 381e (3 g, 8.1 mmol), KCN (1.053 g, 16.2 mmol), and (NH₄)₂CO₃ (8.532 g, 60.75 mmol). Formamide (30 mL) was added to fill the tube completely. The mixture was heated at 70° C. for 72 hours, at 110° C. for 3 hours, cooled, and poured into ice water. After acidification with concentrated HCl solution (pH=1), the mixture was extracted with EtOAc (50 mL×3), and the combined organic layers were dried over Na₂SO₄, filtered, and concentrated in vacuo. The residue was purified by column chromatography (CH₂Cl₂/MeOH=50:1) to give the compound 381f (1.5 g, 43%) as an orange solid. ¹H-MNR (CDCl₃, 400 MHz): δ7.17 (m, 1H), 6.96 (m, 5H), 6.65 (m, 1H), 3.32 (m, 1H), 3.25-3.05 (m, 2H), 2.83 (m, 1H), 2.73 (m, 2H), 2.22 (m, 1H), 2.12 (m, 1H), 1.75 (m, 2H).

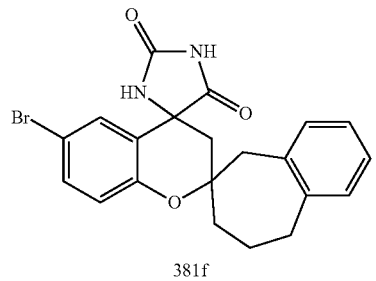

381f

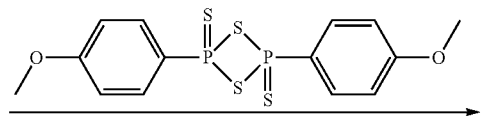

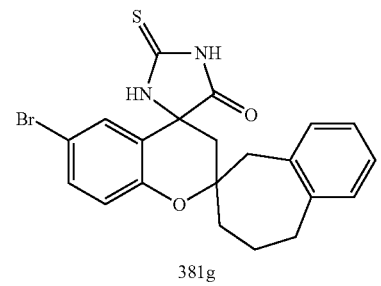

381g

To a solution of compound 381f (1 g, 2.348 mmol) and Lawesson' reagent (948.6 mg, 2.348 mmol) in 1,4-dioxane (22.5 mL) was heated under 120° C. for 35 minutes in a microwave reactor. The mixture was cooled, and concentrated in vacuo. The residue was purified by column chromatography (petroleum ether/EtOAc=20:1) to give the compound 381g (0.5 g, 48%) as an orange solid. ¹H-NMR (CDCl₃, 400 MHz): δ7.35 (m, 1H), 7.21 (m, 5H), 6.75 (m, 1H), 3.91 (m, 3H), 3.41 (m, 1H), 2.38 (m, 1H), 2.15 (m, 1H), 2.02 (m, 3H), 1.45 (m, 2H).

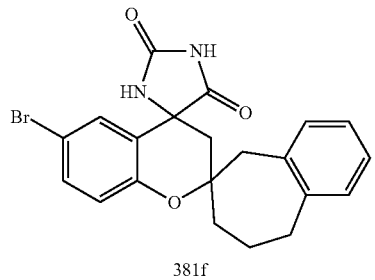

381f

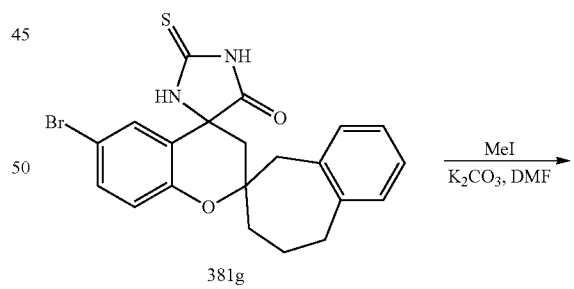

381g

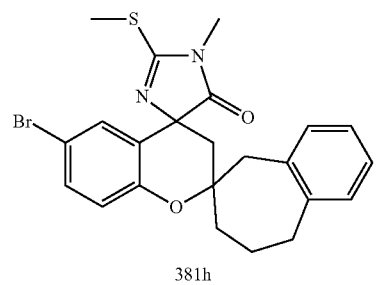

381h

839

To a solution of compound 381g (500 mg, 1.311 mmol) in MeOH (30 mL) was added NaOH solution (4.35 mL, 2.601 mmol, 0.6 N, aqueous). The mixture was stirred at room temperature for 5 minutes, added MeI (0.71 mL, 1.31 mmol), and stirred for another 5 minutes. The mixture was stirred in a microwave reactor at 60° C. for 10 minutes, concentrated in vacuo, added water (30 mL), and extracted with EtOAc (30 mL×3). The combined organic layers were dried over $Na_2SO_4$, filtered, and concentrated in vacuo. The residue was purified by preparative TLC (petroleum ether/EtOAc=3:1) to give the compound 381h (60 mg, 11%) as a yellow oil. $^1$H-MNR ($CDCl_3$, 400 MHz): δ7.35 (m, 1H), 7.15 (m, 2H), 7.05 (m, 2H), 6.65-6.82 (m, 2H), 3.62 (m, 1H), 3.15 (s, 3H), 2.83 (m, 3H), 2.62 (s, 3H), 2.11 (m, 3H), 1.94 (m, 2H), 1.66 (m, 1H), 1.51 (m, 1H).

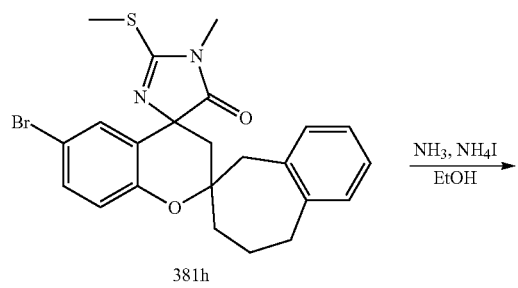

The solution of compound 381h (20 mg, 0.043 mmol) and $NH_4I$ (62.64 mg, 0.432 mmol) in a solution of $NH_3$/EtOH (1.72 mL, 5 N) was heated at 120° C. in a CEM tube in microwave reactor for 3 hours. The mixture was concentrated in vacuo, the residue was added $CH_2Cl_2$, filtered, and concentrated in vacuo. The residue was purified by preparative HPLC to give the compound compound 381 (4.37 mg, 23%) as a white solid. $^1$H-MNR ($CD_3OD$, 400 MHz): δ7.41 (m, 2H), 7.15 (m, 3H), 6.85 (m, 1H), 6.75 (d, 1H), 3.35-3.55 (m, 1H), 3.27 (s, 3H), 3.05 (m, 1H), 2.96 (m, 2H), 2.35 (m, 3H), 1.95 (m, 2H), 1.65 (m, 1H); ESI MS: 440 [M+H]$^+$.

Example 320

Preparation of Compound 179

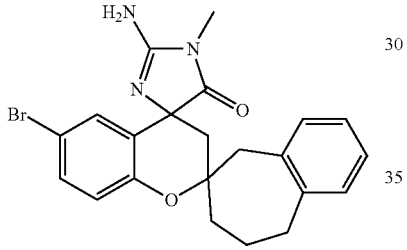

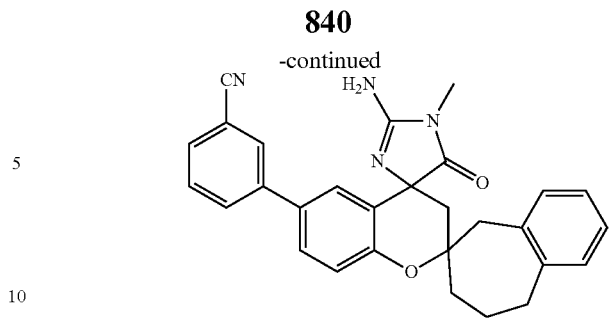

The solution of compound 179a (20 mg, 0.045 mol), 3-cyanophenyl-boronic acid (10 mg, 0.068 mmol), $Cs_2CO_3$ solution (0.3 mL, 2M, aqueous), $Pd(PPh_3)_2Cl_2$ (0.5 mg) in 1,4-dioxane (1 mL) under nitrogen was heated at 120° C. in microwave for 15 minutes. The dark reaction mixture was filtered, and concentrated in vacuo, the residue was purified by preparative TLC ($CH_2Cl_2$:MeOH=10:1) and HPLC to give the compound compound 179 (1.3 mg, 6%) as a yellow solid. $^1$H-NMR ($CD_3OD$, 400 MHz): δ7.88 (s, 1H), 7.78 (d, J=3.0 Hz 1H), 7.60 (d, J=4.0 Hz 1H), 7.53 (m, 2H), 7.37 (s, 1H), 7.05 (m, 2H), 6.97 (m, 1H), 6.83 (m, 2H), 3.33 (m, 1H), 3.17 (s, 3H), 2.99 (m, 1H), 2.25 (m, 2H), 2.46 (m, 1H), 2.38 (s, 2H), 1.98 (m, 1H), 1.86 (m, 1H) 1.55 (m, 1H); ESI MS: 463 [M+H]$^+$.

Example 321

Preparation of Compound 238

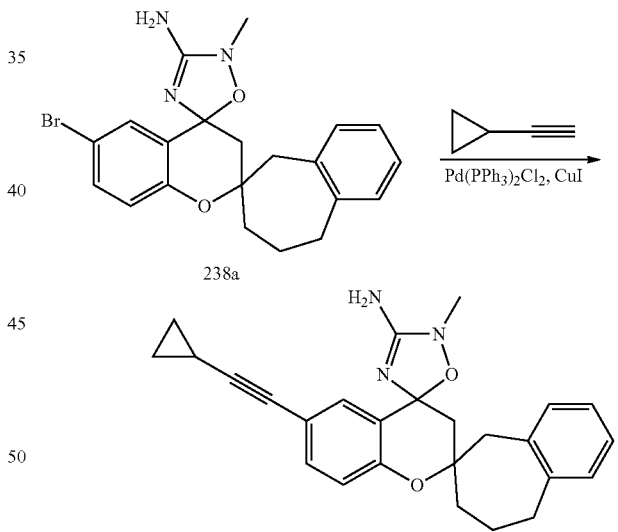

A dry flask was charged with compound 238a (107 mg, 0.25 mmol), TEA (1 mL) and DEA (0.3 mL) under $N_2$ atmosphere. To this solution was added CuI (2.0 mg, 0.01 mmol), and $PdCl_2(PPh_3)_2$ (7 mg, 0.01 mmol). The system was degassed, and cyclopropyl acetylene (0.25 mL, excess) was added, and the mixture was heated to 52° C. with stirring. The reaction was evaporated, and the residue was purified by preparative TLC ($CH_2Cl_2$: MeOH=10:1) and HPLC to afford compound 238 (17 mg, 16.4%). $^1$H-NMR (400 MHz $CDCl_3$): δ7.55 (m, 1H), 7.34 (d, J=17.6 Hz, 1H), 7.16 (m, 4H), 6.73 (m, 1H), 3.49 (d, J=13.6 Hz, 1H), 3.30 (d, J=11.6 Hz, 1H), 3.05 (m, 1H), 2.85 (m, 4H), 2.42 (m, 1H), 2.15 (m, 1H), 1.96 (m, 2H), 1.45 (m, 2H), 0.90 (m, 4H); ESI MS: m/z 414 [M+H]$^+$.

Example 322

Preparation of Compound 265

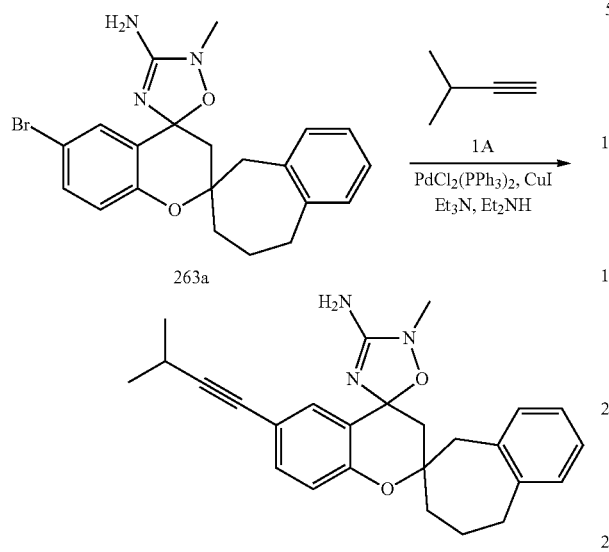

A deoxygenated solution of compound 263a (50 mg, 0.12 mmol) in triethylamine (2 mL) was treated with triphenylphosphine (1.2 mg, 4.7 umol), palladium acetate (0.5 mg, 2.3 umol) and copper (I) iodide (0.4 g, 2.3 umol). After 10 minutes, 3,3-dimethyl-1-butyne (0.2 mL) was added via syringe. The reaction was refluxed for 12 hours, and cooled to room temperature. The solution was filtered, and partitioned between diethyl ether (10 mL) and water (10 mL). The organic layer was dried (MgSO$_4$), evaporated, and the resulting crude product was purified by preparative TLC (CH$_2$Cl$_2$/MeOH=10:1) and HPLC to yield compound 263 (1.5 mg, 3%) as a white solid. $^1$H-NMR (400 MHz CD$_3$OD): δ7.38-7.91 (m, 2H), 7.24 (m, 1H), 7.15 (m, 3H), 6.56-6.81 (m, 1H), 3.41 (m, 1H), 3.15 (s, 3H), 3.02 (m, 1H), 2.91 (m, 1H), 2.62-2.84 (m, 5H), 2.35 (m, 1H), 2.17 (m, 1H), 1.86 (m, 2H), 1.36 (m, 1H), 1.18 (m, 1H), 1.14 (t, J=7.2 Hz, 6H); ESI MS: 416 [M+H]$^+$.

Example 323

Preparation of Compound 308

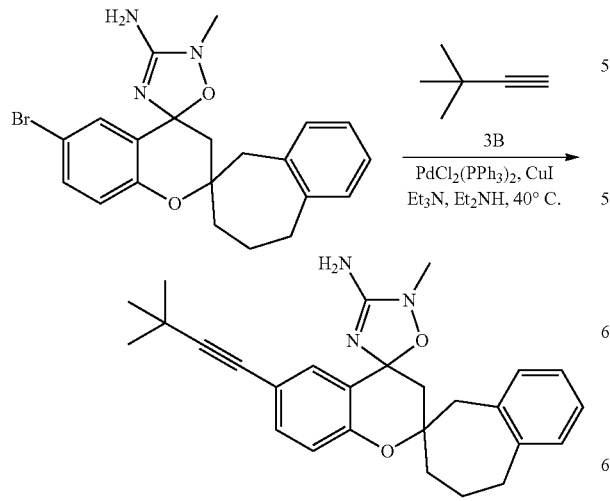

By using the same synthetic procedure as compound 238 described in Example 321, compound 308 (5.3 mg, 9%) was obtained as a white solid. $^1$H-NMR (400 MHz CD$_3$OD): δ7.48-7.92 (m, 1H), 7.21-7.35 (m, 1H), 7.08 (m, 3H), 6.81-6.95 (m, 1H), 6.56-6.70 (m, 1H), 3.21 (d, 3H), 2.73 (m, 3H), 2.32 (m, 1H), 2.06 (m, 1H), 1.87 (m, 2H), 2.35 (m, 1H), 1.31-1.63 (m, 1H), 1.20 (d, J=7.2 Hz, 9H); ESI MS: 430 [M+H]$^+$.

Example 324

Preparation of Compound 317

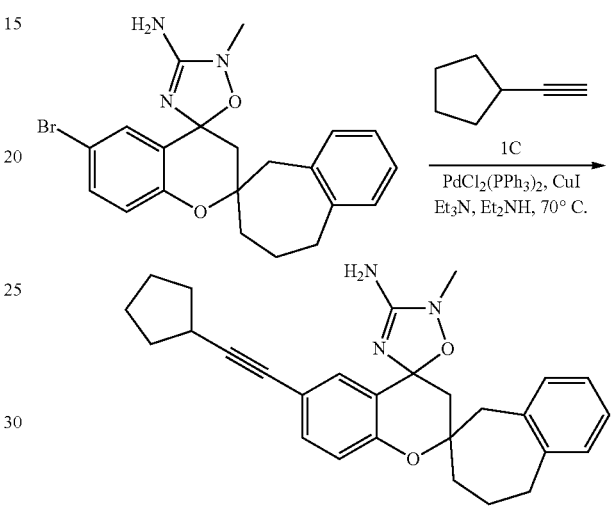

By using the same synthetic procedure as compound 238 described in Example 321, compound 317 (7.4 mg, 14%) was obtained as a white solid. $^1$H-NMR (CD$_3$OD, 400 MHz): δ7.48-7.92 (m, 1H), 7.21-7.35 (m, 1H), 7.08 (m, 3H), 6.81-6.95 (m, 1H), 6.72 (m, 2H), 3.21 (d, 3H), 2.93 (m, 1H), 2.76 (m, 4H), 2.32 (m, 1H), 2.06 (m, 1H), 1.93 (m, 4H), 1.66 (m, 6H), 1.31 (m, 1H); ESI MS: 442 [M+H]$^+$.

Example 325

Preparation of Compound 373

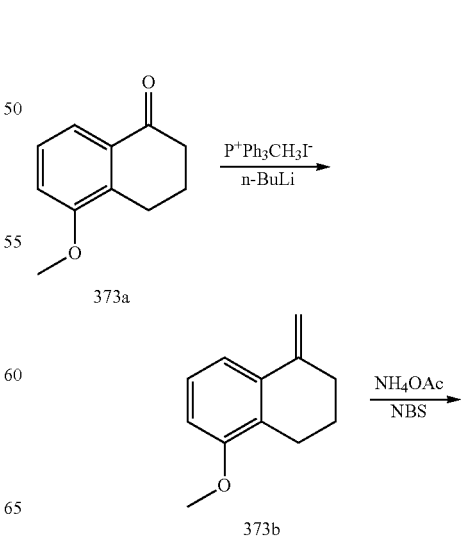

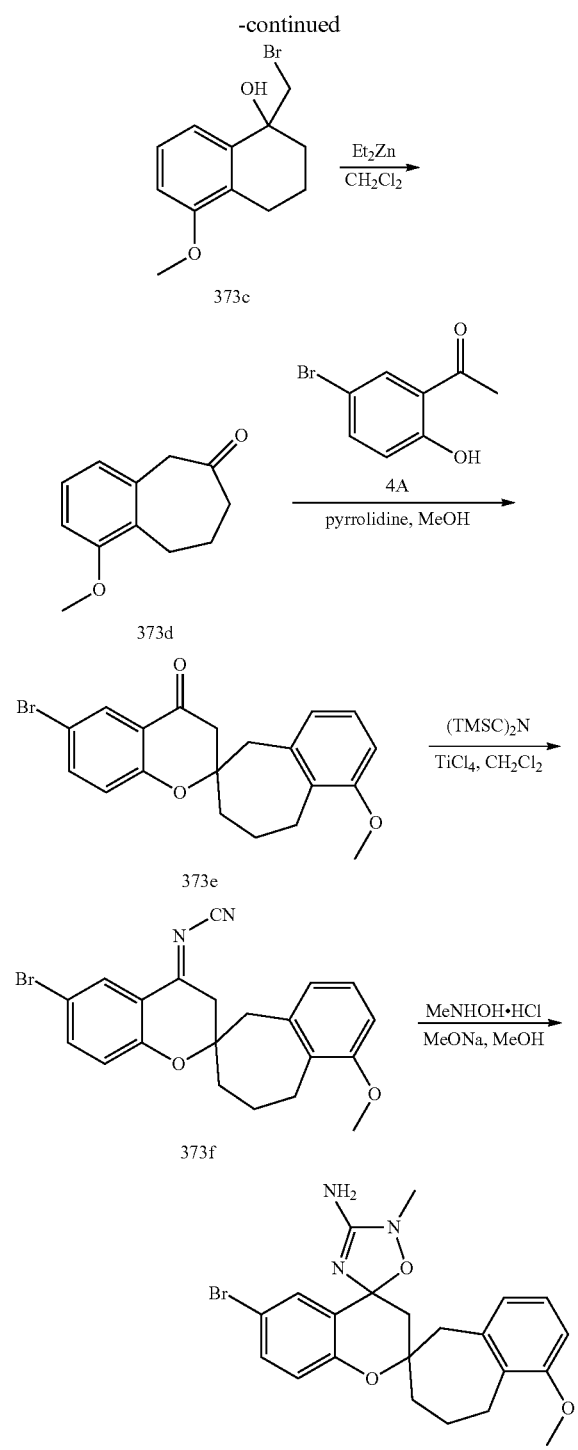

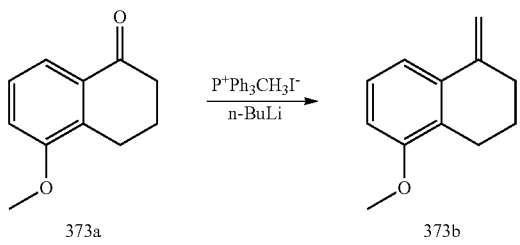

Experimental Data

A solution of n-BuLi (88 mL, 2.5M) was added to a solution of PPh$_3$CH$_3^+$I$^-$ (100 g, 246 mmol) in THF (600 mL) at −10° C. The mixture was cooled to −10° C., and stirred for 1 h. Compound 373a (20 g, 137 mmol) was added, and the mixture was warmed to ambient temperature, and stirred for 3 hours. The resulting mixture was quenched by addition of saturated NH$_4$Cl solution (200 mL), extracted with EtOAc (3×150 mL), washed with brine, dried over Na$_2$SO$_4$, concentrated, and purified by column chromatography (petroleum ether:EA=100:1) to give the compound 373b (13.1 g, 66%) as colorless liquid. $^1$H-NMR (CDCl$_3$ 400 MHz): δ7.25 (m, 1H), 7.12 (m, 1H), 6.72 (m, 1H), 3.8 (s, 3H), 5.45 (s, 1H), 4.95 (s, 1H), 2.48 (m, 2H), 2.25 (m, 2H), 1.89 (m, 2H).

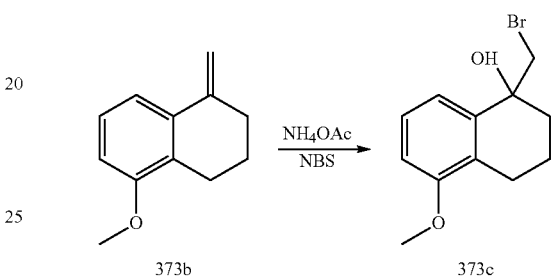

To a suspension of compound 373b (1 g, 5.7 mmol) and NH$_4$OAc (44.3 mg, 0.57 mmol) in acetone (11 mL), was added NBS (1.4 g, 6.27 mmol) and water (3 mL). The mixture was stirred at ambient temperature, concentrated in vacuo, and purified by column chromatography (petroleum ether:EA=50:1) to give the compound 373c (0.5 g, 45%) as yellow liquid. $^1$H-NMR (CDCl$_3$ 400 MHz): δ7.23 (m, 2H), 6.69 (m, 1H), 3.74 (s, 3H), 2.31 (m, 2H), 2.66 (m, 1H), 2.65 (m, 1H), 2.55 (m, 1H), 1.80-1.91 (m, 1H).

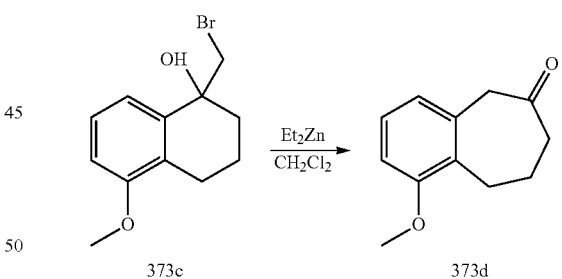

To a solution of Et$_2$Zn (0.44 mL, 0.44 mmol, 1 M) in dichloromethane (3 mL) was added diiodo methane (118 mg, 0.44 mmol) at 0° C. under nitrogen atmosphere. After being stirred for 20 minutes, compound 373c (200 mg, 0.737 mmol) was added, and the mixture was warmed to room temperature. After being stirred for 2 h, the reaction mixture was quenched by addition of saturated NH$_4$Cl solution (10 mL), extracted with CH$_2$Cl$_2$ (3×10 mL), washed with brine, dried over Na$_2$SO$_4$, concentrated, and purified on column chromatography (petroleum ether:EA=50:1) to give the compound 373d (86 mg, 61%). $^1$H-NMR (CDCl$_3$ 400 MHz): δ7.13 (m, 1H), 6.73-6.85 (m, 2H), 3.82 (s, 3H), 3.72 (m, 2H), 3.00 (m, 2H), 2.52 (m, 2H), 1.95 (m, 2H).

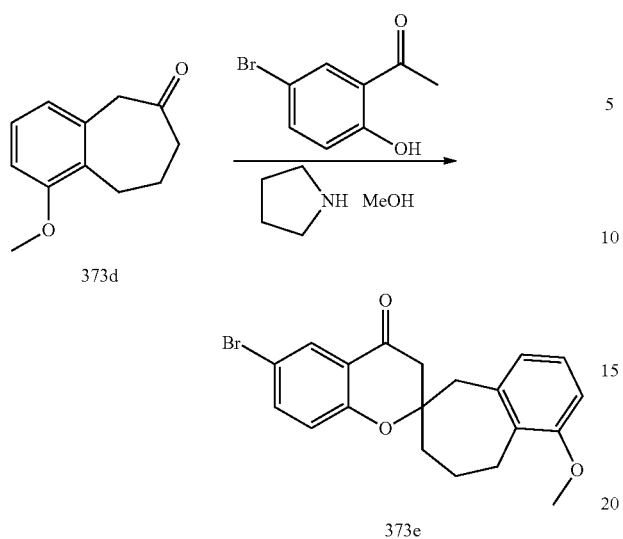

373d

373e

The mixture of compound 373d (3.8 g, 20.0 mmol), 1-(5-Bromo-2-hydroxy-phenyl)-ethanone (3.56 g, 16.7 mmol) and pyrrolidine (5 mL) in MeOH (20 mL) was stirred at ambient temperature for 1 h and at refluxing overnight. The solvent was removed in vacuo, and the crude product was purified by silica column chromatography (petroleum ether: EA=10:1) to give the compound 373e as a yellow solid (3 g, 50%). $^1$H-NMR (CDCl$_3$ 400 MHz): δ7.98 (s, 1H), 7.53 (d, 1H), 7.03 (t, 1H), 6.75 (t, 2H), 6.48 (d, J=7.6 Hz, 1H), 3.82 (s, 3H), 3.02-3.42 (m, 3H), 2.47-2.71 (m, 3H), 2.13 (m, 2H), 1.88 (m, 1H), 1.48 (m, 1H),

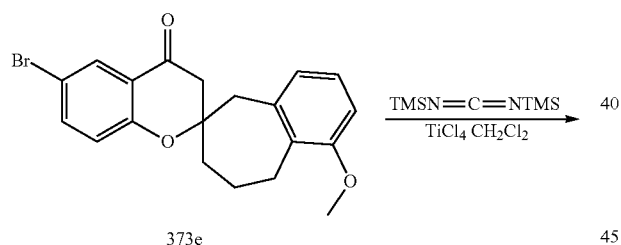

373e

373f

To a solution of compound 373e (200 mg, 0.51 mmol) in CH$_2$Cl$_2$ (15 mL) was added TiCl$_4$ solution (1 M in CH$_2$Cl$_2$, 1.02 mL, 1.02 mmol). The mixture was stirred in microwave at 50° C. for 10 minutes. After being cooled to room temperature, N,N'-methanediylidenebis(1,1,1-trimethyl silanamine) (189.4 mg, 1.02 mmol) was added. The mixture was stirred at 60° C. for 10 minutes, poured into ice-water, extracted with CH$_2$Cl$_2$ (2×50 mL). The combined organic layer was washed with brine (100 mL), dried, and concentrated to give the compound 373f (168 mg, 100%) as a yellow solid, which was used for the next step directly without purification. $^1$H-NMR (CDCl$_3$ 400 MHz): δ8.14 (s, 1H), 7.58 (d, J=2.4 Hz, 1H), 7.03 (t, 1H), 6.78 (m, 2H), 6.40 (d, J=7.2 Hz, 1H), 3.82 (s, 3H), 3.23 (m, 2H), 3.02 (m, 2H), 2.50-2.70 (m, 2H), 2.13 (m, 2H), 1.95 (m, 1H), 1.28 (m, 1H).

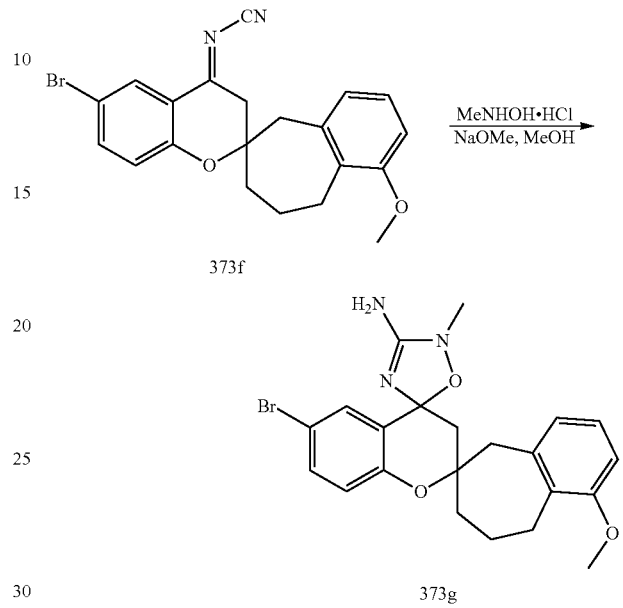

373f

373g

To a solution of methylhydroxylamine HCl salt (32.8 mg, 0.4 mmol) in anhydrous MeOH (12 mL) was added NaOMe (10% in MeOH, 20 drops) and compound 373f (168 mg, 0.4 mmol). After being stirred for 10 minutes, the solvent was removed in vacuum, and the residue was dissolved in CH$_2$Cl$_2$ (25 mL). The mixture was filtered, concentrated, and purified by preparative HPLC to give compound 373 as a yellow solid (27 mg, 14%). $^1$H-NMR (CDCl$_3$ 400 MHz): δ7.58 (d, J=2.4 Hz, 1H), 7.03 (m, 2H), 6.78 (m, 3H), 3.82 (s, 3H), 3.45 (m, 1H), 3.32 (m, 1H), 1.85 (m, 2H), 2.91-3.12 (m, 4H), 2.45-2.55 (m, 2H), 2.35 (m, 1H), 2.27 (m, 1H), 2.13 (m, 1H), 2.05 (m, 1H); ESI MS: 458 [M+H]+

Example 326

Preparation of Compound 225

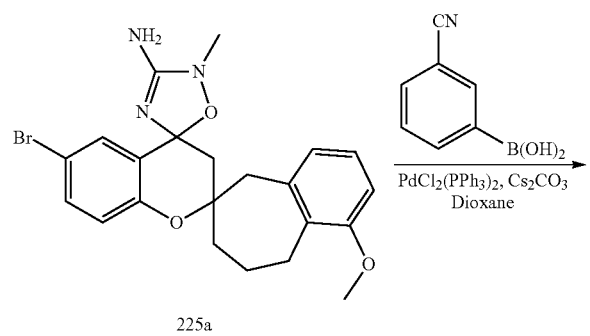

225a

-continued

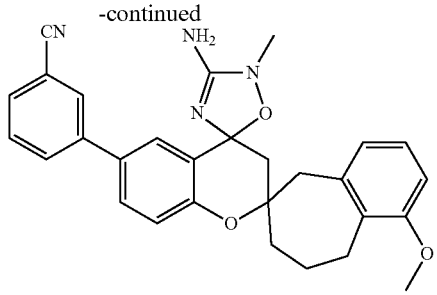

A mixture of compound 225a (27 mg, 0.06 mmol), 3-cyanophenylboronic acid (14 mg, 0.09 mmol), Cs₂CO₃ solution (2 M, 0.3 mL), and Pd(PPh₃)₂Cl₂ (1 mg) in 1,4-dioxane (1 mL) was stirred at 100° C. under N₂ for 45 minutes. The reaction mixture was concentrated in vacuum and purified by preparative TLC (CH₂Cl₂: MeOH=10:1) and HPLC to give compound 225 as a white solid (0.3 mg, 25%). ¹H-NMR (CD₃OD, 400 MHz): δ8.04 (m, 3H), 7.03 (m, 3H), 7.71 (m, 2H), 6.52 (m, 1H), 3.8 (m, 3H), 3.40 (m, 2H), 3.28 (m, 1H), 3.13 (m, 2H), 2.85 (m, 1H), 2.4-2.60 (m, 1H), 2.23 (m, 1H), 1.95 (m, 2H), 1.51 (m, 3H).

Example 327

Preparation of Compound 399

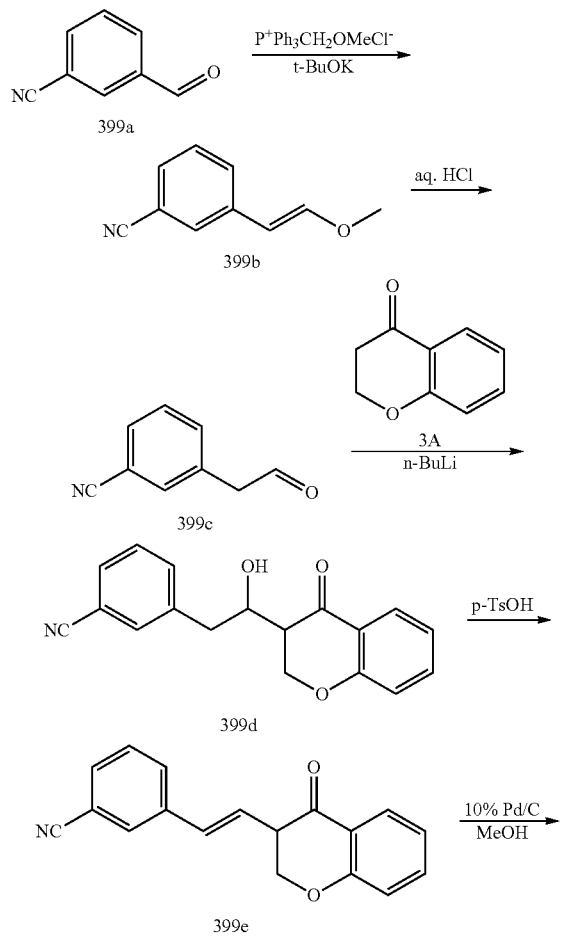

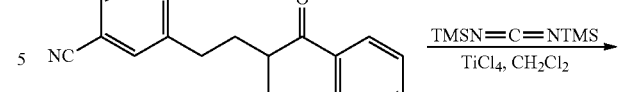

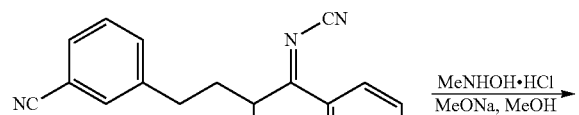

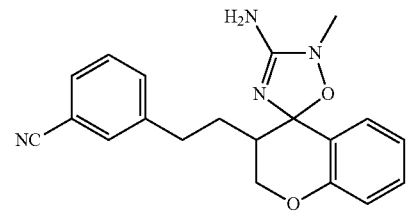

Experimental Data

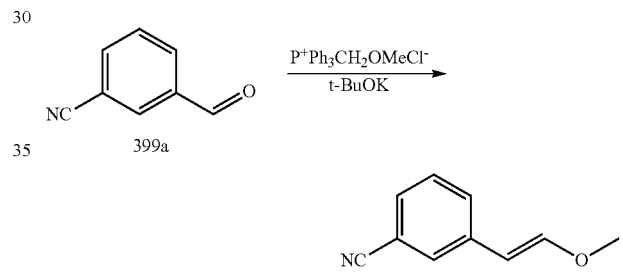

To a solution of P⁺Ph₃CH₂OMeCl⁻ (50 g, 145 mmol) in THF (200 mL) was added t-BuOK (16.2 g, 145 mmol) in THF (200 mL) under N₂ at −20° C., and the reaction mixture was stirred for 80 min. The solution of compound 399a (12.65 g, 96.6 mmol) in THF (100 mL) at −20° C. was added, and the reaction mixture was stirred at −20° C. for 90 min and at room temperature overnight. The reaction mixture was quenched by water (150 mL), and extracted with EtOAc (3×100 mL). The combined organic layers were dried by Na₂SO₄ concentrated, and purified by column chromatography (petroleum ether:EA=20:1) to afford the compound 399b as yellow liquid (3 g, 19.6%). ¹H-NMR (CDCl₃, 400 MHz): δ7.87-7.91 (m, 1H), 7.40-7.58 (m, 1H), 7.23-7.27 (m, 1H), 6.99-7.18 (m, 1H), 6.15-6.17 (d, 1H), 5.66-5.70 (d, 1H), 3.84 (s, 3H).

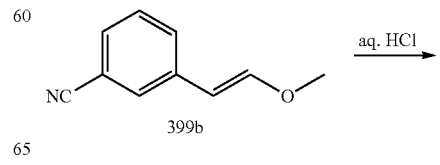

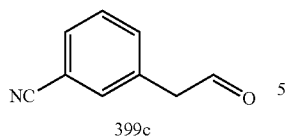

To a solution of compound 399b (2.44 g, 15.32 mmol) in acetone (20 mL) was added HCl (1N, 10 mL) under $N_2$. The mixture was refluxed for 80 min, and concentrated in vacuo. The aqueous layer was extracted with EtOAc (3×25 mL), and the combined organic layers were washed with brine (2×30 mL). The organic layer was dried over $Na_2SO_4$ and concentrated to give the compound 399c as yellow liquid, which was used for the next step directly without further purification (2 g, 88%). $^1$H-NMR (CDCl$_3$, 400 MHz): δ9.80 (s, 1H), 7.62-7.63 (d, 1H), 7.27-7.60 (m, 3H), 3.80 (d, 2H).

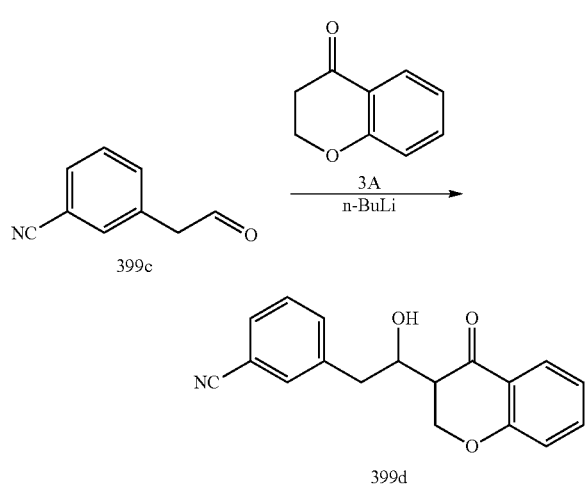

To a solution of chroman-4-one (1.23 g, 8.28 mmol) in THF (20 mL) was added n-BuLi (3.3 mL, 8.28 mmol) at −78° C. under nitrogen atmosphere. The resulting mixture was stirred at this temperature for 1 hour, after addition of the solution of compound 399c (1.2 g, 8.28 mmol) in THF (10 mL), the mixture was stirred for another 1.5 hours at −78° C., quenched by saturate $NH_4Cl$ solution (5 mL), and extracted with EtOAc (3×20 mL). The combine organic layers were washed by brine, dried over $Na_2SO_4$ and concentrated. The crude product was purified by column chromatography (petroleum ether:EA=20:1) to afford the compound 399d as a white solid (2 g, 83%). $^1$H-NMR (CDCl$_3$, 400 MHz): δ7.81-7.84 (m, 1H), 7.32-7.54 (m, 5H), 6.90-6.99 (m, 2H), 4.38-4.60 (m, 3H), 2.78-2.89 (m, 3H).

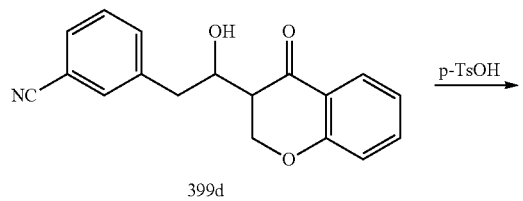

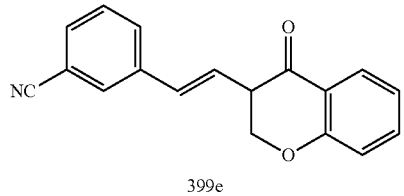

To a solution of compound 399d (50 mg, 0.17 mmol) in toluene (3 mL) was added p-TsOH (3.2 mg, 0.017 mmol) under nitrogen atmosphere. The mixture was heated at 120° C. for 1 hour, and the solvent was evaporated. The residue was purified by preparative TLC (petroleum ether: EtOAc=5:1) to afford the compound 399e as a white solid (10 mg, 21.3%). $^1$H-NMR (CDCl$_3$, 400 MHz): δ7.95-7.97 (m, 1H), 7.42-7.95 (m, 5H), 7.05-7.10 (m, 2H), 6.65 (d, 1H), 6.41-6.44 (m, 2H), 4.65-4.69 (m, 1H), 4.51-4.55 (m, 1H), 3.63-3.66 (m, 1H).

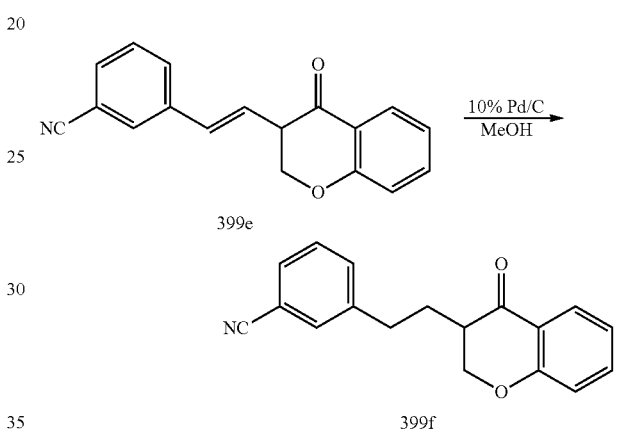

To a stirred solution of compound 399e (220 mg, 0.81 mmol) in MeOH (20 mL) was added 10% palladium on carbon, and the resulting suspension was stirred under $H_2$ balloon at room temperature for 3 hours. The catalyst was filtrated through a pad of celite, and the filtrate was evaporated. The crude product was purified by preparative TLC (petroleum ether: EtOAc=5:1) to give the compound 399f (50 mg, 23%) as a white solid. $^1$H-NMR (CDCl$_3$, 400 MHz): δ7.80-7.83 (m, 1H), 7.31-7.44 (m, 5H), 6.87-7.19 (m, 2H), 4.43-4.47 (m, 1H), 4.19-4.24 (m, 1H), 2.57-2.60 (m, 3H), 2.11-2.18 (m, 1H), 1.59-1.77 (m, 1H).

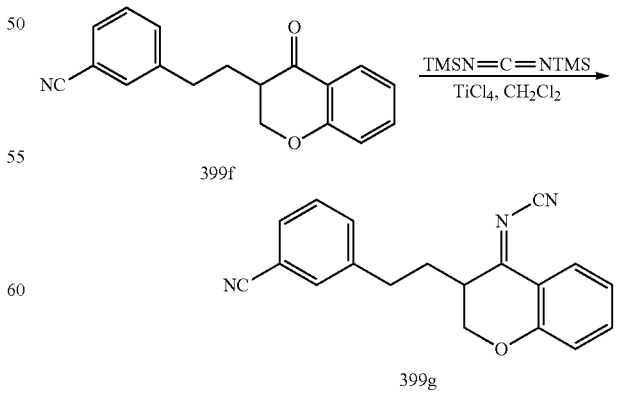

To a solution of compound 399f (100 mg, 0.36 mmol) in dry $CH_2Cl_2$ (5 mL) was added $TiCl_4$ (1 M solution in $CH_2Cl_2$, 0.72 mmol) dropwise within 15 minutes. The mixture was stirred for another 1 h, bis-trimehtlysilylcarbodiimide (202 mg, 1.08 mmol) was added dropwise, and the mixture was stirred for 18 h. The reaction mixture was poured into ice-water (10 g), and extracted with CH$_2$Cl$_2$. The combined organic layers were washed with brine, dried over Na$_2$SO$_4$, filtered, and concentrated to give the compound 399g (60 mg, crude), which was used for the next step directly without further purification.

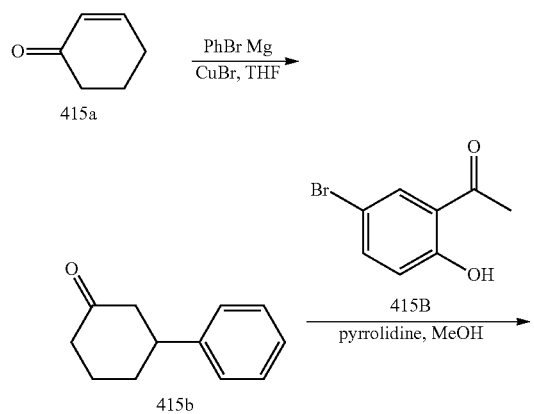

To a solution of MeNHOH.HCl (16 mg, 0.20 mmol) in anhydrous MeOH (3 mL) was added NaOMe (25% in MeOH, 0.20 mmol) and compound 399g (60 mg, 0.20 mmol). After being stirred for 5 minutes, the solvent was removed in vacuum. The residue was dissolved in CH$_2$Cl$_2$ and filtered. The filtrate was concentrated, and the residue was purified by preparative TLC and HPLC to give compound 399 as a white solid. $^1$H-NMR (CD$_3$OD, 400 MHz): δ7.34-7.53 (m, 5H), 7.26-7.30 (m, 1H), 6.95-6.97 (m, 1H), 6.78-6.93 (m, 1H), 4.07-4.33 (m, 2H), 2.88 (s, 3H), 2.83-2.88 (m, 1H), 2.67-2.71 (m, 1H), 2.32-2.36 (m, 1H), 1.53-1.67 (m, 2H); ESI MS: 349 [M+H]$^+$.

Example 328

Preparation of Compound 415

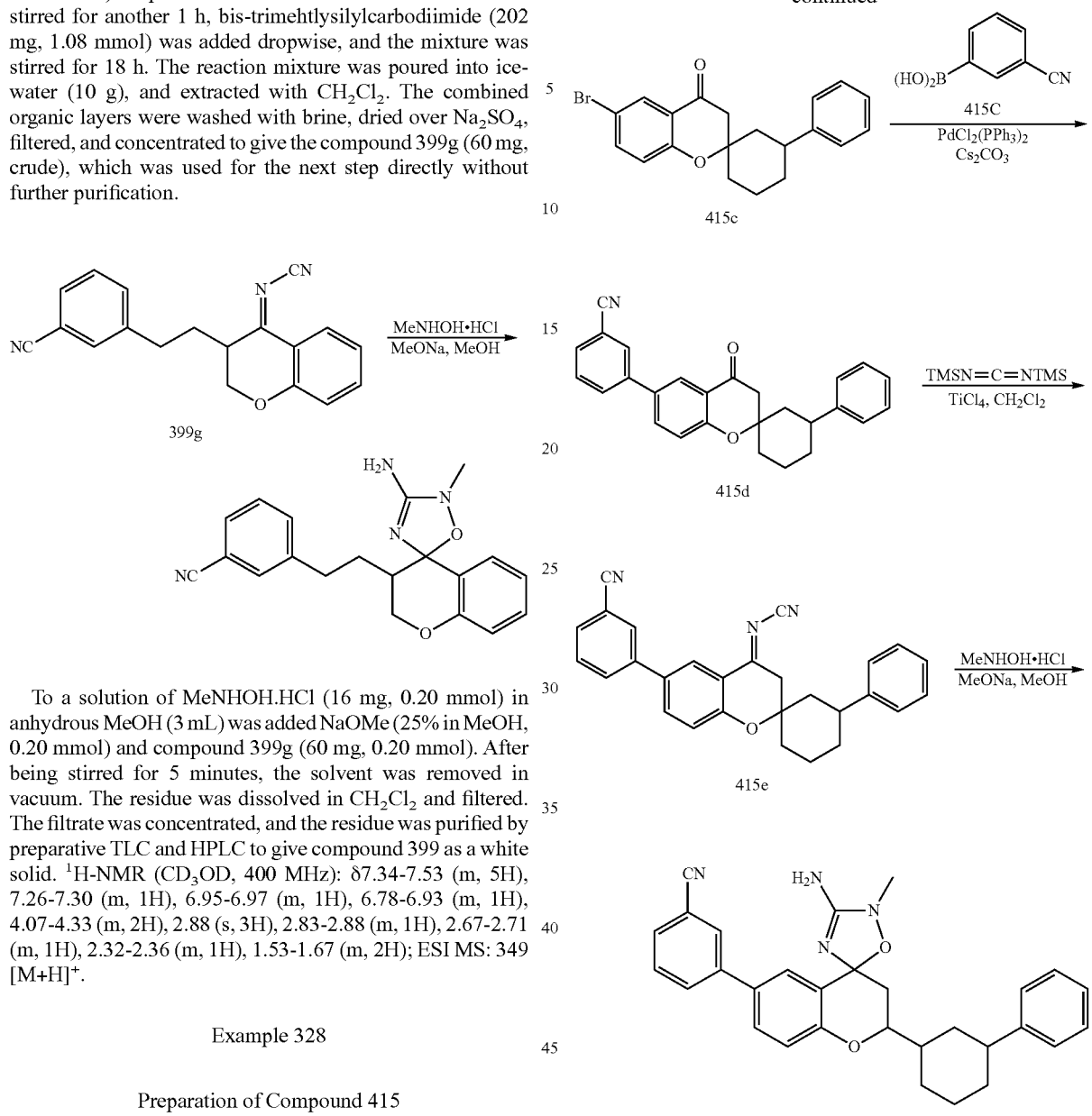

Experimental Data

Grignard reagent was prepared from Mg (0.56 g, 23 mmol) and compound 415a (4 g, 25.6 mmol) in THF (10 mL) in the presence of I$_2$ and a catalytic amount of CuBr (0.16 g, 1.1 mmol). The solution of compound 415a (2 g, 20.8 mmol) in THF (5 mL) was added dropwise at 0° C. After being stirred at room temperature (18° C.) for 3 hours, the aqueous HCl solution (1 N) was added, and the mixture was extracted with EA. After drying with anhydrous MgSO$_4$, the solution was concentrated under reduced pressure, the residue was purified by silica gel column chromatography (petroleum ether: EA=20:1) to give the compound 415b (2 g, yield 55%). $^1$H-NMR (CDCl$_3$, 400 MHz): δ7.36 (m, 2H), 7.27 (m, 3H), 3.04 (m, 1H), 2.65-2.39 (m, 2H), 2.18 (m, 1H), 1.85 (m, 1H), 1.31 (m, 1H), 0.96 (m, 3H).

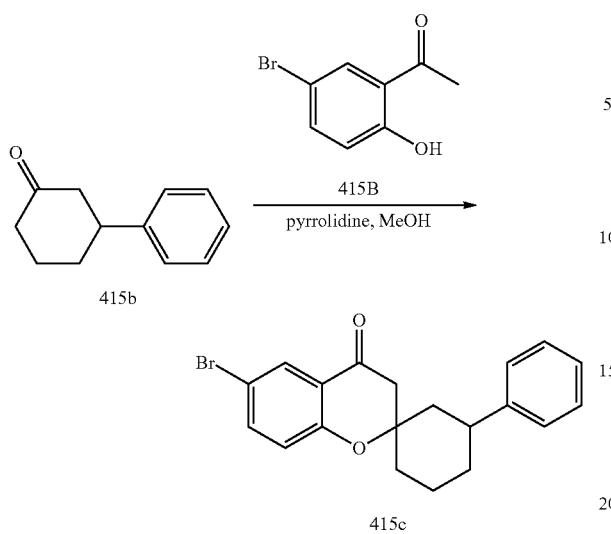

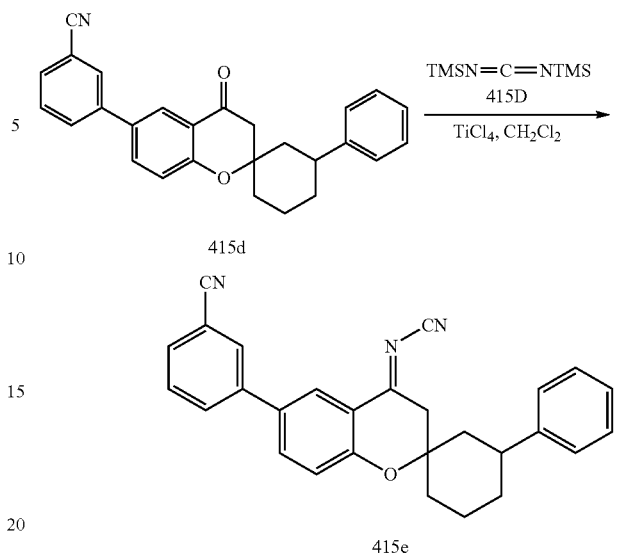

A mixture of compound 415b (2 g, 11.5 mmol), compound 415B (1.2 g, 5.6 mmol), and pyrrolidine (1 mL) in anhydrous MeOH (140 mL) was refluxed overnight. The solvent was removed, the crude product was purified by silica column (petroleum ether:EA=80:1) to give the compound 415c (1.16 g, yield 27%). $^1$H-NMR (CDCl$_3$, 300 MHz): δ7.89-7.85 (m, 1H), 7.52-7.48 (m, 1H), 7.26-7.11 (m, 5H), 6.9-6.73 (m, 1H), 2.97-2.91 (m, 1H), 2.63-2.5 (m, 2H), 2.22-2.08 (m, 2H), 1.87-1.69 (m, 2H), 1.51-1.43 (m, 2H), 0.85-0.72 (m, 1H).

To a solution of compound 415d (50 mg, 0.127 mmol) in CH$_2$Cl$_2$ (3 mL) was added TiCl$_4$ (0.635 mL, 0.635 mmol). After being stirred in microwave at 5° C. for 1 hour, compound 415D (0.064 mL, 0.28 mmol) was added, and the resulting mixture was stirred in microwave at 7° C. for 30 minutes. The reaction mixture was poured into ice-water (10 mL), extracted with CH$_2$Cl$_2$ (15 mL×2), dried over anhydrous Na$_2$SO$_4$, and filtered. The filtrate was concentrated to give the compound 415e (93 mg, yield 95%) as yellow oil, which was used directly for the next step without purification.

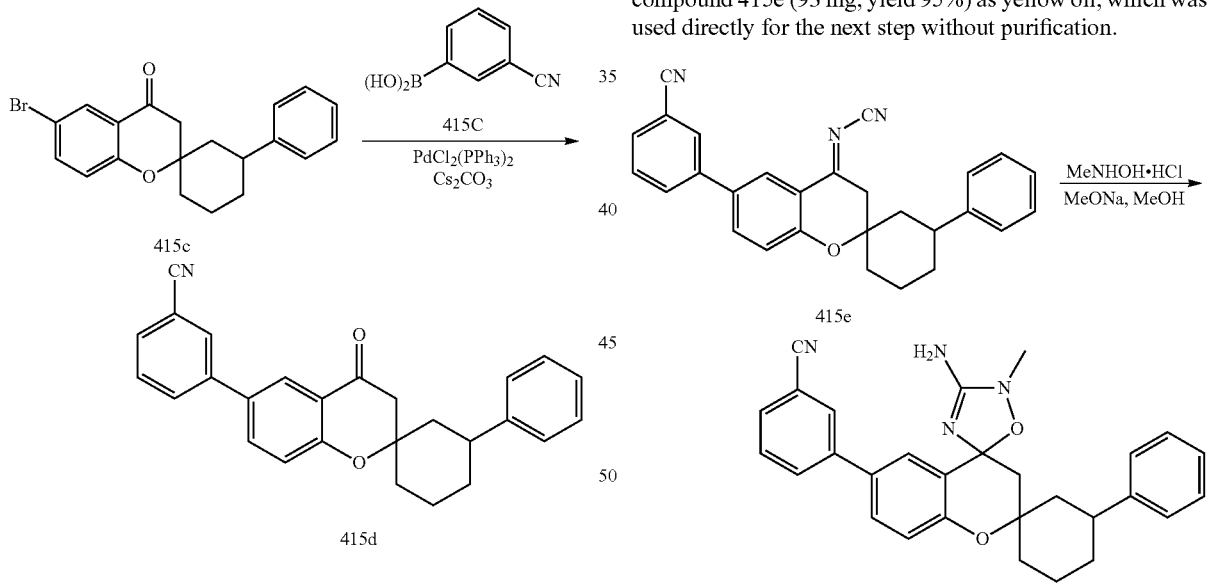

To a solution of compound 415c (200 mg, 0.535 mmol), compound 415C (102 mg, 0.7 mmol), Cs$_2$CO$_3$ (2 mL) in dioxane (10 mL) was added Pd(PPh$_3$)$_2$Cl$_2$ (50 mg, 0.05 mmol), and the mixture was refluxed overnight. Water was added to quench the reaction, and the mixture was extracted with EA. The organic layer was washed by brine, dried over anhydrous Na$_2$SO$_4$ and evaporated to afford the crude product, which was purified by preparative TLC (petroleum ether:EA=5:1) to give the compound 415d (145 mg, yield 69%). $^1$H-NMR (CDCl$_3$, 400 MHz): δ7.99-7.98 (m, 1H), 7.9-7.85 (m, 1H), 7.67-7.65 (m, 1H), 7.61-7.44 (m, 6H), 7.25 (m, 1H), 7.0 (m, 1H), 2.74 (m, 2H), 2.2-2 (m, 2H), 1.98 (m, 1H), 1.53-1.44 (m, 4H), 1.28 (m, 1H).

To a solution of methylhydroxylamine HCl salt (10.08 mg, 0.12 mmol) in anhydrous MeOH (2.5 mL) was added NaOMe (10% in MeOH, 0.061 mL) and compound 415e (50 mg, 0.12 mmol). After being stirred for 20 minutes, the solvent was removed in vacuo, and the residue was dissolved in CH$_2$Cl$_2$ (20 mL). The mixture was filtered, and the solvent was removed, the residue was purified by pre-TLC and HPLC to give the compound 415 (3.20 mg, yield 7%) as a white solid. $^1$H-NMR (CD$_3$OD 400 MHz): δ8.09 (s, 1H), 7.95-8.03 (m, 3H), 7.72-7.77 (m, 2H), 7.66-7.64 (m, 2H), 7.20-7.32 (m, 2H), 7.15-7.21 (m, 2H), 3.42 (s, 3H), 3.23 (m, 1H), 2.68-2.97

(s, 2H), 2.19-2.23 (m, 2H), 1.95-2.04 (m, 2H), 1.71-1.74 (m, 2H), 1.56-1.73 (m, 2H); ESI MS: m/z 465 [M+H]$^+$.

Example 329

Preparation of Compound 329

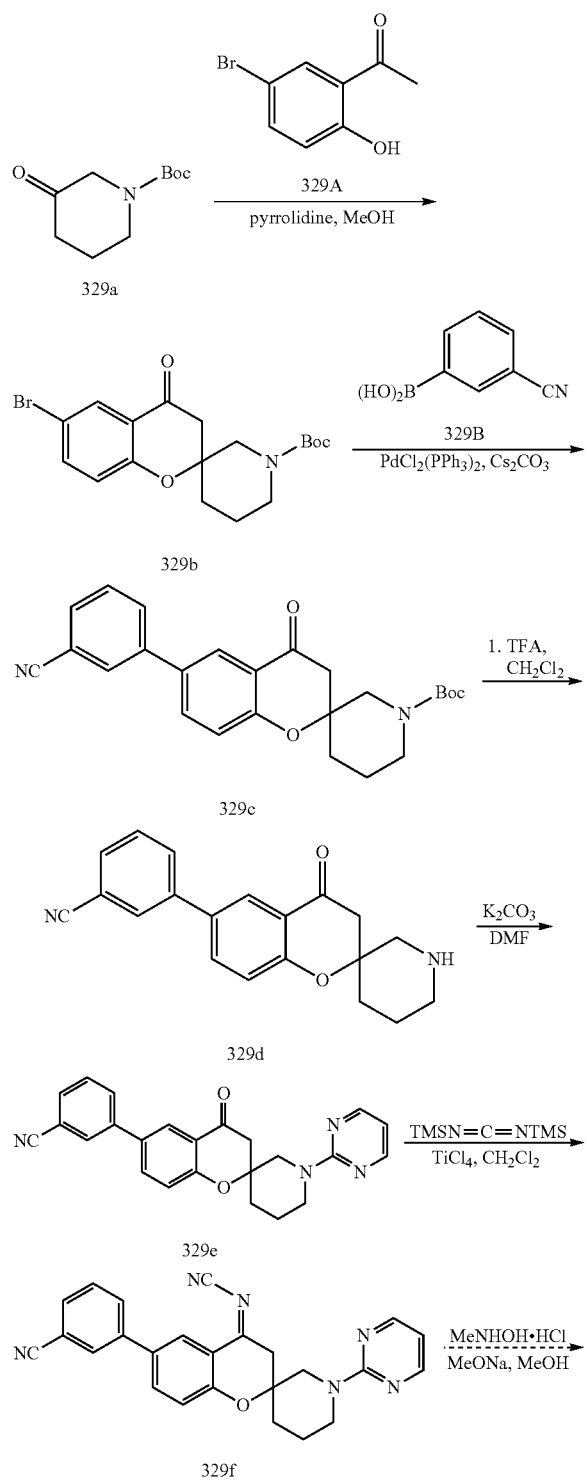

Experimental Data

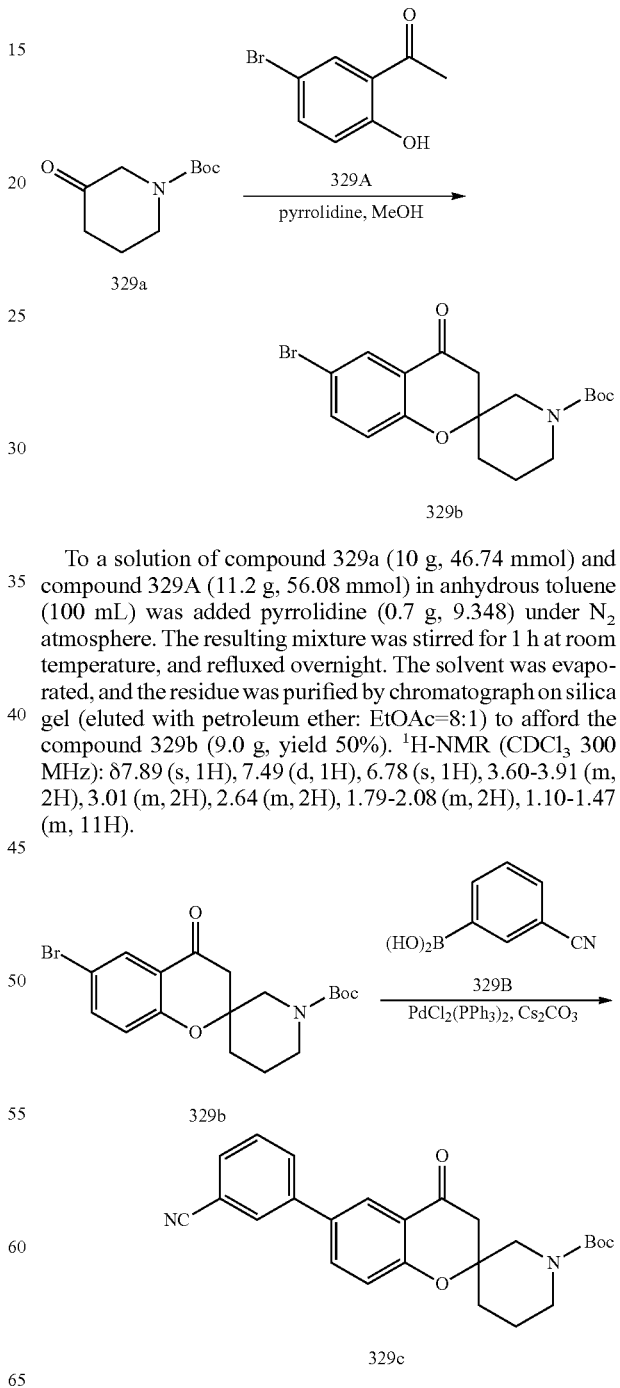

To a solution of compound 329a (10 g, 46.74 mmol) and compound 329A (11.2 g, 56.08 mmol) in anhydrous toluene (100 mL) was added pyrrolidine (0.7 g, 9.348) under N$_2$ atmosphere. The resulting mixture was stirred for 1 h at room temperature, and refluxed overnight. The solvent was evaporated, and the residue was purified by chromatograph on silica gel (eluted with petroleum ether: EtOAc=8:1) to afford the compound 329b (9.0 g, yield 50%). $^1$H-NMR (CDCl$_3$ 300 MHz): δ7.89 (s, 1H), 7.49 (d, 1H), 6.78 (s, 1H), 3.60-3.91 (m, 2H), 3.01 (m, 2H), 2.64 (m, 2H), 1.79-2.08 (m, 2H), 1.10-1.47 (m, 11H).

To a mixture of compound 329b (17 g, 47.04 mmol), compound 329B (8.2 g, 55.95 mmol) and Cs$_2$CO$_3$ aqueous solution (2 M, 150 mL) in dioxane (200 mL) was added Pd (dppf)$_2$Cl$_2$ (4.2 g, 4.704 mmol) under N$_2$ atmosphere. The mixture was refluxed overnight, water was added to quench the reaction, and the mixture was extracted with EtOAc (100 mL×3). The organic layer was washed by sat.NaCl solution, dried over Na$_2$SO$_4$ and evaporated. The residue was purified by chromatograph silica gel (diluted with EtOAc:petroleum ether=1:30 to 1:3) to afford the compound 329c (15 g, yield 76%)

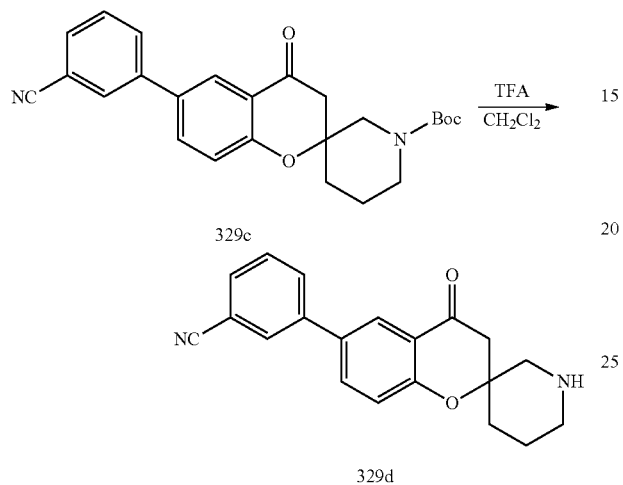

To a solution of compound 329c (7.5 g, 0.01744 mol) in CH$_2$Cl$_2$ (100 mL) was added TFA (20 mL) at 0° C. The reaction mixture was warmed to room temperature, and stirred overnight. The solvent was evaporated at room temperature to afford the compound 329d (5.0 g, yield 88%), which was used for the next step directly without purification.

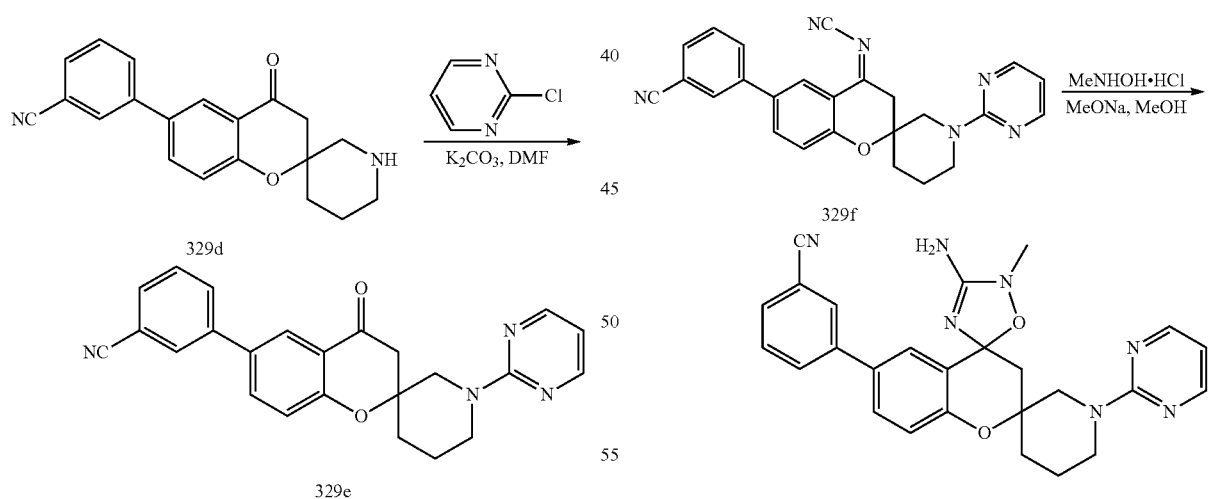

To a solution of compound 329d (2 g, 6.289 mmol), and 2-chloropyrimidine (0.9 g, 8.176 mmol) in DMF (30 mL) was added K$_2$CO$_3$ (1.7 g, 12.58 mmol). The mixture was stirred at 5° C. overnight. Water (30 mL) was added to quench the reaction, and the mixture was extracted with EtOAc (×50 mL). The organic layers were washed with brine (20 mL×3), dried over Na$_2$SO$_4$, and evaporated in vacuum. The residue was purified by chromatograph on silica gel (eluting with petroleum ether:EA=8:1) to afford the compound 329e (0.8 g, yield 40%). $^1$H-NMR (CDCl$_3$ 300 MHz): δ8.5 (d, 2H), 8.02 (s, 1H), 7.74 (m, 2H), 7.40-7.62 (m, 3H), 6.70 (d, 1H), 6.39 (t, 1H), 4.41 (d, 1H), 4.07-4.21 (m, 1H), 3.50-3.67 (m, 2H), 2.62-2.89 (m, 2H), 2.04-2.17 (m, 1H), 1.75-1.95 (m, 2H), 1.58 (m, 1H).

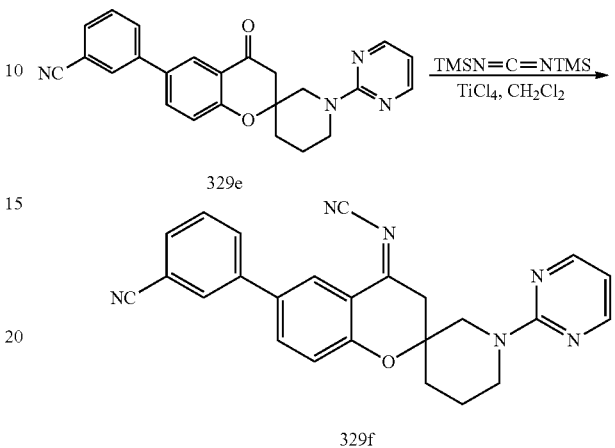

To a solution of compound 329e (200 mg, 0.50 mmol) in CH$_2$Cl$_2$ (2 mL) was added TiCl$_4$ (1 M 4.04 mL, 4.0404 mmol). The mixture was stirred for 15 min at 50° C. in microwave. TMSN=C=NTMS (280 mg, 2.02 mmol) was added, and the mixture was stirred for 30 min at 60° C. in microwave. The reaction mixture was poured into ice-water, and extracted with EtOAc (5 mL). The organic layer was dried over Na$_2$SO$_4$ and evaporated to afford the compound 329f (40 mg, yield 19%), which was used for the next step directly without purification.

A solution of compound 329f (40 mg, 0.095 mmol) in dry MeOH (3 mL) was added MeNHOH.HCl (8 mg, 0.095 mmol) and NaOCH$_3$ (25% in MeOH, 0.02 mL). The resulting mixture was stirred for 10 min at room temperature, and concentrated. The residue was dissolved in CH$_2$Cl$_2$ and the solid was filtered off. The filtrate was evaporated, and purified by prep-TLC and pr-HPLC to afford compound 329 (7.3 mg, yield 21%). $^1$H-NMR (CD$_3$OD 400 MHz): δ8.36 (m, 1H), 8.25 (m, 1H), 8.11 (m, 1H), 8.01 (m, 2H), 7.94 (m, 1H), 7.71 (m, 1H), 7.63 (m, 2H), 7.28-7.42 (m, 1H), 6.47-6.65 (m, 2H), 4.21-4.64 (m, 2H), 3.47-3.60 (m, 1H), 3.40 (s, 3H), 3.10-3.37 (m, 2H), 3.88-3.91 (m, 1H), 1.97-2.27 (m, 5H); ESI MS: m/z 468 [M+H]$^+$.

Example 330

Preparation of Compound 355

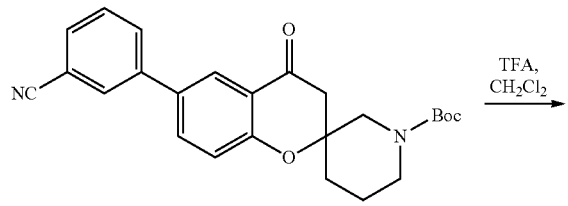

355a

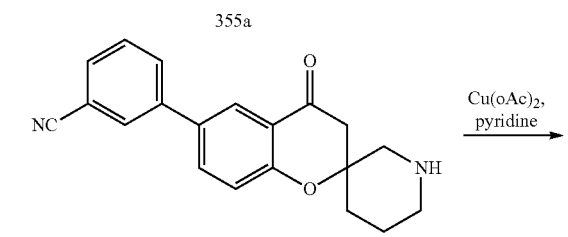

355b

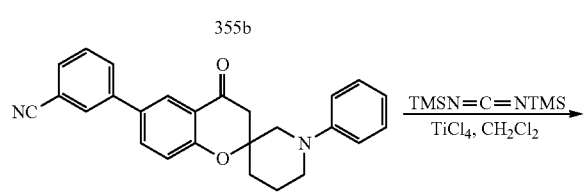

355c

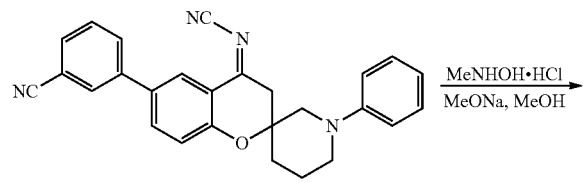

355d

Experimental Data

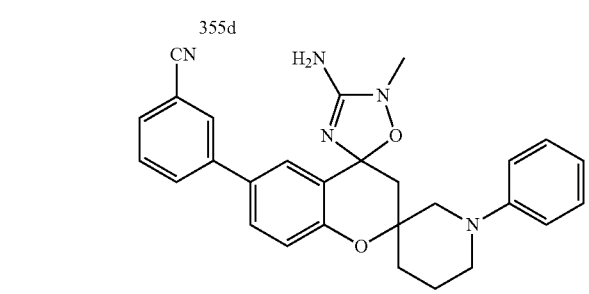

355a

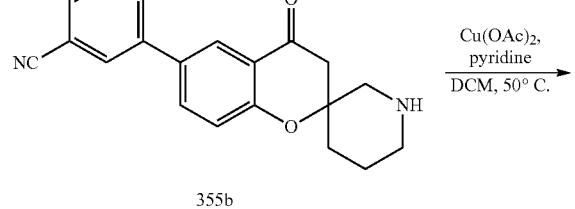

355b

To a solution of compound 355a (7.5 g, 17.44 mmol) in CH$_2$Cl$_2$ (100 mL) was added TFA (20 mL) at 0° C. The reaction mixture was warmed to room temperature, and stirred overnight. The solvent was evaporated to afford the compound 355b (5.0 g, yield 88%), which was used for the next step directly without purification.

355b

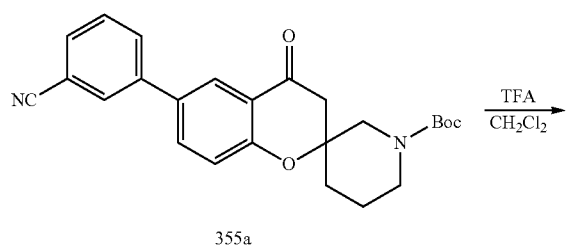

355c

To a solution of compound 355b (1 g, 3.145 mmol), pyridine (14 mL) in CH$_2$Cl$_2$ (30 mL) was added phenylboronic acid (0.96 g, 6.289 mmol), and Cu(OAc)$_2$ (1.16 g, 6.29 mmol). The reaction mixture was stirred at 5° C. overnight. Water (30 mL) was added to quench the reaction, and the mixture was extracted by EtOAc (50 mL). The organic layers were washed with brine (20 mL×3), dried over Na$_2$SO$_4$, and evaporated in vacuum. The residue was purified by chromatograph silica gel (petroleum ether:EA=8:1) to afford the compound 355c (0.5 g, yield 40%). $^1$H-NMR (CDCl$_3$ 400 MHz): δ8.12 (s, 1H), 7.89 (s, 1H), 7.84 (d, 1H), 7.72 (m, 1H), 7.64 (m, 1H), 7.57 (m, 1H), 7.24 (m, 2H), 7.07 (d, 1H), 6.87 (m, 3H), 3.02 (m, 1H), 3.23-3.34 (m, 2H), 3.10-3.20 (m, 1H), 2.02-2.12 (m, 3H), 1.71-1.91 (m, 3H).

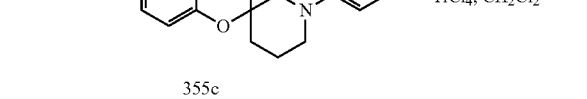

355c

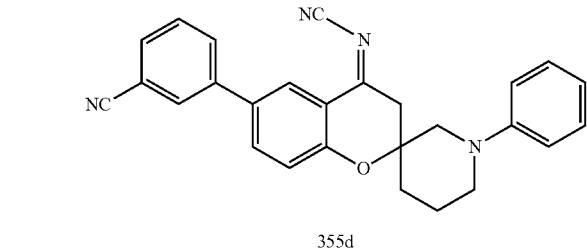

355d

To a solution of compound 355c (100 mg, 0.25 mmol) in CH₂Cl₂ (2 mL) was added TiCl₄ (1 M 0.76 mL, 0.76 mmol). The mixture was stirred for 15 min at 50° C. in microwave. TMSN=C=NTMS (106 mg, 0.76 mmol) was added, and the mixture was stirred for 30 min at 60° C. in microwave. The reaction mixture was poured into ice-water, and extracted with EtOAc (5 mL). The organic layer was dried over Na₂SO₄ and evaporated to afford the compound 355d (20 mg, yield 19%), which was used for the next step directly without purification.

A solution of compound 355d (20 mg, 0.04785 mmol) in dry MeOH was added MeNHOH.HCl (14 mg, 0.04785 mmol), and the solution of NaOCH₃ (25% (wt %) in MeOH, 0.02 mL). The mixture was stirred for 10 min at room temperature, and concentrated. The residue was dissovled in CH₂Cl₂ and the solid was filtered off. The filtrate was evaporated, and purified by TLC and pr-HPLC to afford the compound 355 (7.5 mg, yield: 34%). ¹H-NMR (CD₃OD 400 MHz): δ8.04 (s, 2H), 7.89 (m, 1H), 7.75 (m, 2H), 7.64 (m, 1H), 7.44 (m, 1H), 7.12-7.26 (m, 2H), 6.78-7.03 (m, 3H), 3.44-3.59 (m, 1H), 3.40 (s, 3H), 3.03-3.30 (m, 5H), 1.78-2.23 (m, 6H); ESI MS: m/z 466 [M+H]⁺.

Example 331

Preparation of Compound 390

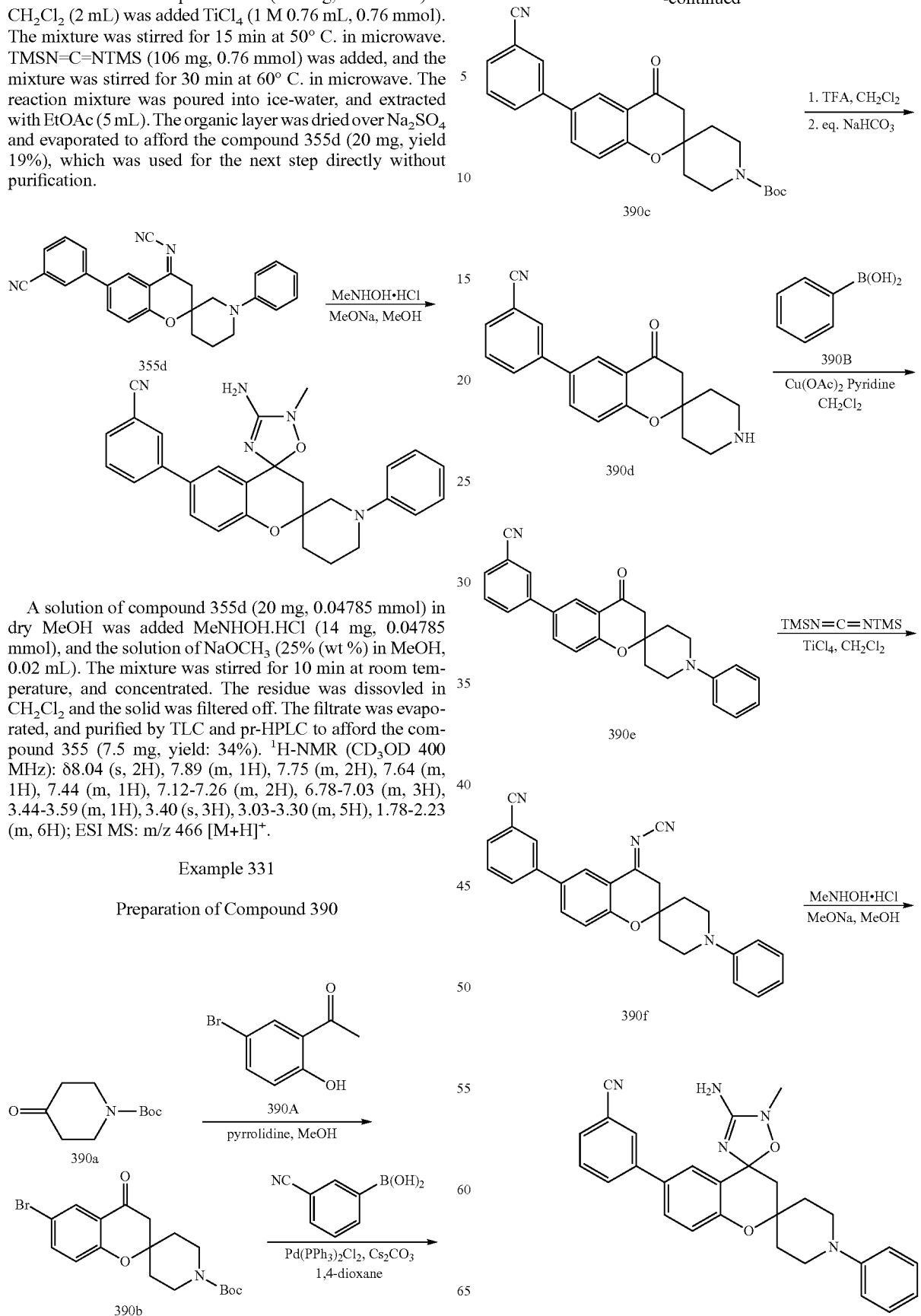

Experimental Data

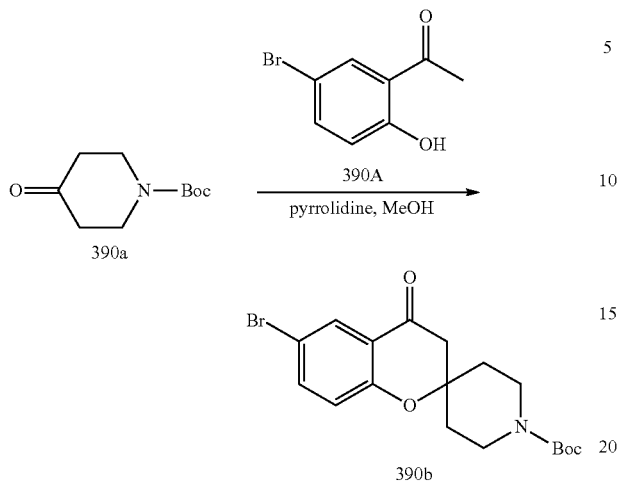

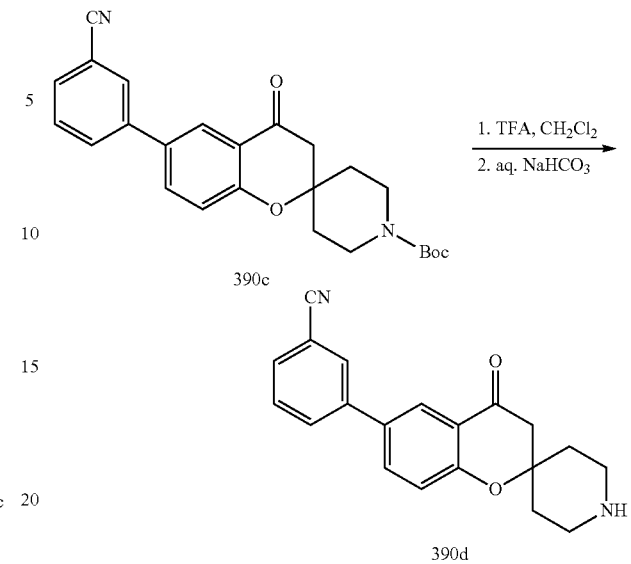

The mixture of compound 390a (27.8 g, 139 m mol), compound 390A and pyrrolidine (9.43 g, 132 mmol) in MeOH (150 mL) was stirred at ambient temperature for 1 h, and refluxed overnight. The solvent was removed in vacuo, the residue was purified by column chromatography on silica gel with petroleum ether: EtOAc=20:1 to give the compound 390b (20 g, 72%) as a yellow solid. $^1$H-NMR (CDCl$_3$ 400 MHz): δ7.82 (s, 1H), 7.47 (d, 1H), 6.82 (d, 1H), 3.61 (m, 4H), 2.61 (s, 2H), 2.32 (m, 4H) 1.5 (s, 9H).

To a solution of compound 390c (2 g, 4.7 mmol) in anhydrous CH$_2$Cl$_2$ (8 mL) was added TFA 2 mL), the mixture was stirred for 2 hours. TLC (petroleum ether:EtOAc=5:1) showed that the reaction was completed, the mixture was neutralized with sat. NaHCO$_3$ solution (50 mL) until no CO$_2$ was evolved. The organic layer was washed with brine (100 mL), and concentrated to give the compound 390d as a yellow solid (1.39 g, 92%), which was used for the next step directly without purification.

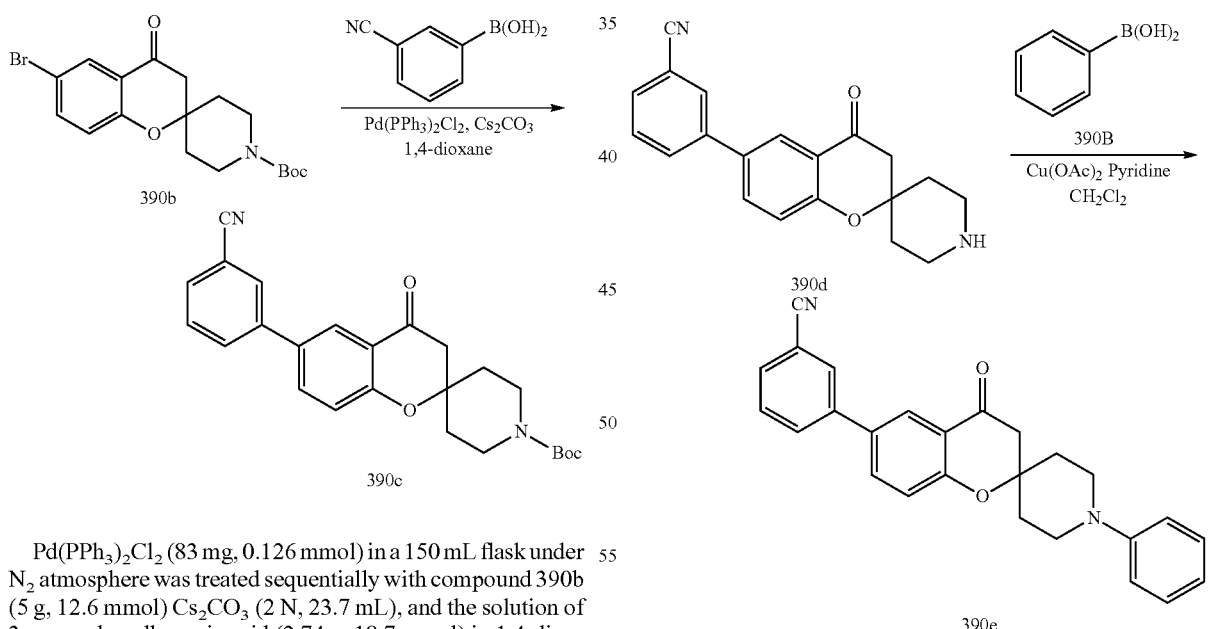

Pd(PPh$_3$)$_2$Cl$_2$ (83 mg, 0.126 mmol) in a 150 mL flask under N$_2$ atmosphere was treated sequentially with compound 390b (5 g, 12.6 mmol) Cs$_2$CO$_3$ (2 N, 23.7 mL), and the solution of 3-cyanophenylboronic acid (2.74 g, 18.7 mmol) in 1,4-dioxane (50 mL), The mixture was refluxed for 1 hour, poured into water, extracted with EtOAc (100 mL×2), washed with brine (200 mL), dried over Na$_2$SO$_4$, and concentrated. The residue was purified by column chromatography on silica gel (petroleum ether:EtOAc=10:1) to give the compound 390c (3 g, 57%) as a yellow solid. $^1$H-NMR (CDCl$_3$ 300 MHz): δ8.0 (m, 1H) 7.73 (m, 2H) 7.63 (m, 1H), 7.56 (m, 1H), 7.47 (m, 1H), 7.0 (d, 1H), 3.82 (m, 2H), 3.21 (s, 2H), 2.70 (s, 2H), 2.01 (m, 2H), 1.63 (m, 2H), 1.39 (s, 9H).

A mixture of compound 390d (1 g, 3 mmol), 390B (0.946 g, 7.7 mmol), and Cu(OAc)$_2$ (1.13 g, 6 mmol) in a mixture of CH$_2$Cl$_2$ (20 mL) and pyridine (10 mL) was refluxed overnight. The reaction mixture was poured into water, extracted with CH$_2$Cl$_2$ (50 mL×2), washed with brine (100 mL), dried over Na$_2$SO$_4$, concentrated, and purified by column chromatography on silica gel (petroleum ether: EtOAc=10:1) to give the compound 390e (440 mg, 35%) as a yellow solid.

¹H-NMR (CDCl₃ 400 MHz): δ8.0 (s, 1H), 7.74 (m, 2H), 7.72 (m, 1H), 7.65 (m, 1H), 7.49 (m, 1H), 7.23 (m, 2H), 7.19 (m, 1H), 6.99 (m, 2H), 6.79 (m, 1H), 3.42 (m, 2H), 3.20 (m, 2H), 2.75 (s, 2H), 2.14 (m, 2H), 1.83 (m, 2H).

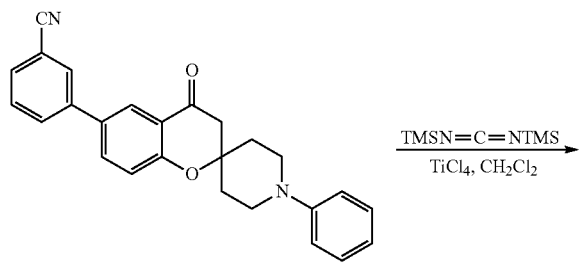

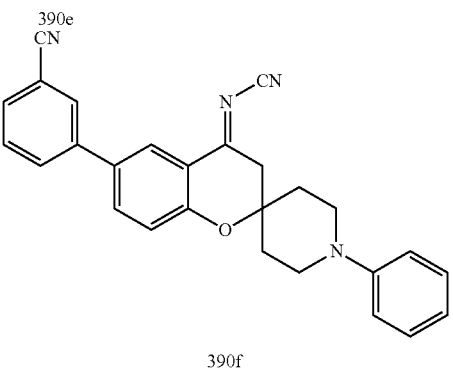

To a solution of compound 390e (100 mg, 0.25 mmol) in anhydrous CH₂Cl₂ (2 mL) was added TiCl₄ (0.5 mL) under N₂ atmosphere, and the mixture was stirred in microwave at 50° C. for 15 min. TMSN=C=TMS (93 mg, 0.5 mmol) was added, and the mixture was stirred in microwave at 60° C. for 15 min. The mixture was poured into ice-water (5 mL), extracted with CH₂Cl₂ (20×2), washed with brine (50 mL), dried over Na₂SO₄ and concentrated to give the compound 390f (74 mg) as a yellow solid, which was used for the next step directly without purification.

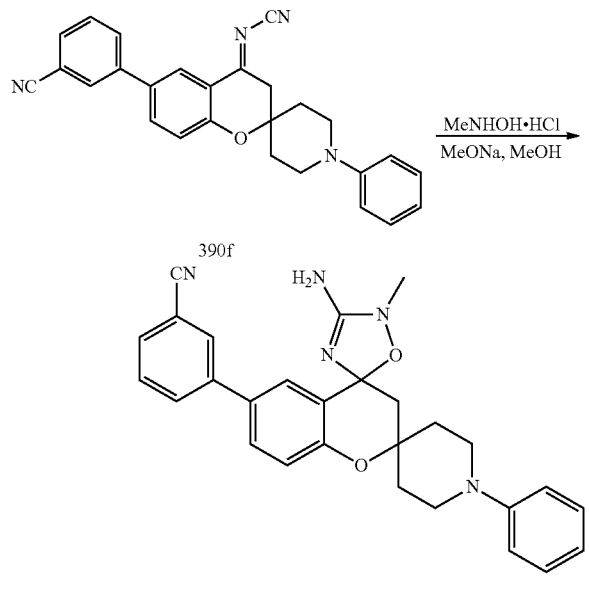

To a solution of MeNHOH·HCl (14.8 mg, 0.17 mmol) in MeOH (4 mL) was added MeONa (95 mg, 0.17 mmol, 10% in MeOH) and compound 390f (74 mg, 0.17 mmol), After being stirred for 10 minutes, the reaction was completed based on LCMS, and the solvent was removed in vacuo. The residue was purified by prep-TLC and HPLC to afford compound 390 (12 mg, 15%) as a white solid. ¹H-NMR (CD₃OD 400 MHz): δ8.05 (m, 2H), 7.95 (m, 1H), 7.82 (m, 1H), 7.76 (m, 1H), 7.69 (m, 1H), 731-7.49 (m, 4H), 7.29 (m, 2H), 3.75 (m, 2H), 3.54 (m, 2H), 3.47 (s, 3H), 2.90 (d, 1H), 2.46 (m, 1H), 2.12-2.42 (m, 4H); ESI MS: m/z 466 [M+H]⁺.

Example 332

Preparation of Compound 353

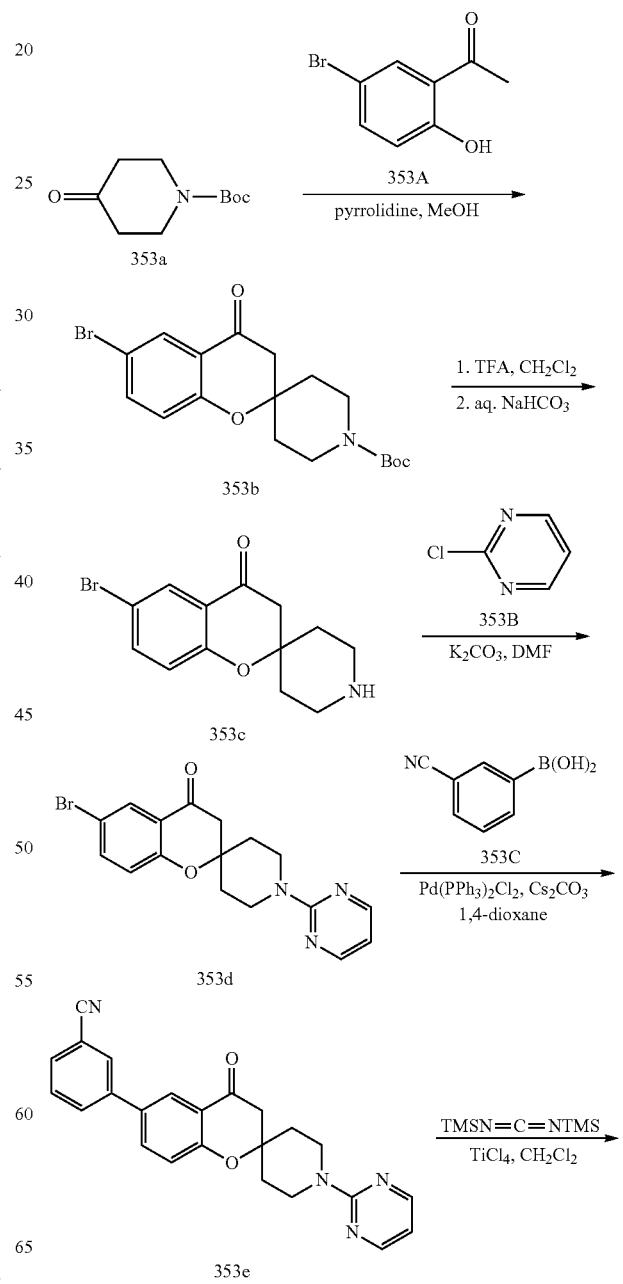

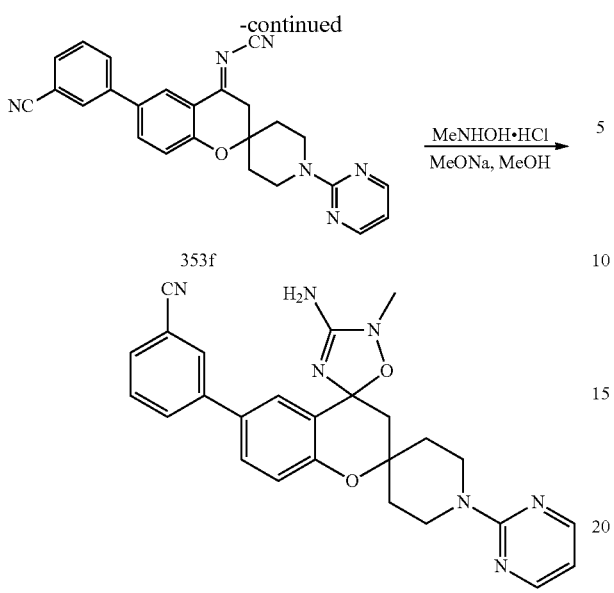

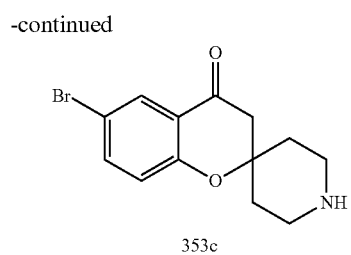

Experimental Data

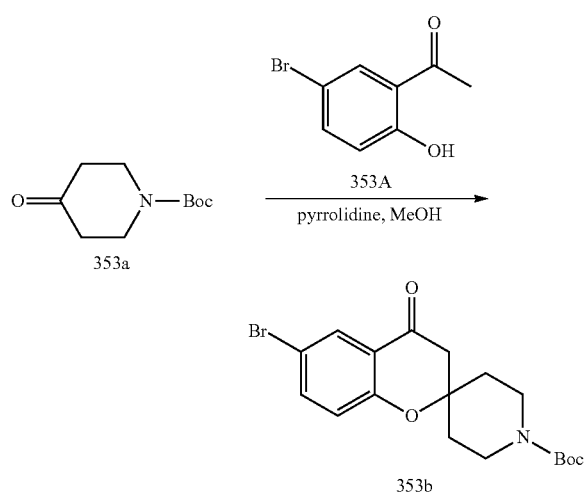

The mixture of compound 353a (27.8 g, 139 m mol), compound 353A, and pyrrolidine (9.43 g, 132 mmol) in MeOH (150 mL) was stirred at ambient temperature for 1 h, and refluxed overnight. The solvent was removed in vacuo, the residue was purified by column chromatography on silica gel with petroleum ether: EtOAc=20:1 to give the compound 353b (20 g, 72%) as a yellow solid. $^1$H-NMR (CDCl$_3$ 400 MHz): δ7.82 (s, 1H), 7.47 (d, 1H), 6.82 (d, 1H), 3.61 (m, 4H), 2.61 (s, 2H), 2.32 (m, 4H) 1.5 (s, 9H).

To a solution of compound 353b (10 g, 25.2 mmol) in anhydrous CH$_2$Cl$_2$ (40 mL) was added TFA 10 mL), and the mixture was stirred for 2 hours. TLC (petroleum ether:EtOAc=5:1) showed that the reaction was completed, and the mixture was neutralized with sat. NaHCO$_3$ solution (50 mL) until no CO$_2$ was evolved. The organic layer was washed with brine (100 mL), and concentrated to give the compound 353c as a yellow solid (6 g, 80%), which was used for the next step directly without purification.

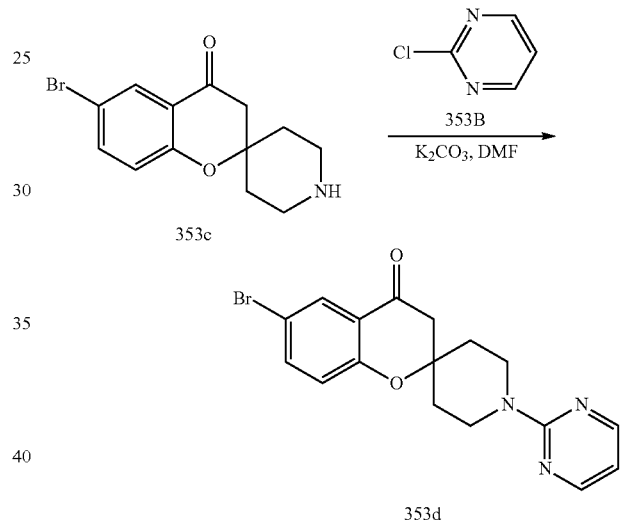

To a solution of compound 353c (2 g, 6.7 mmol) in anhydrous DMF (20 mL) was added K$_2$CO$_3$ (1.87 g, 13.4 mmol) and 353B (928 mg, 8.1 mmol). The reaction mixture was stirred overnight, quenched by sat. NH$_4$Cl solution, extracted with EtOAc (100 m×2), washed with brine, dried over Na$_2$SO$_4$, and concentrated to give the compound 353d as a yellow solid (1.1 g, 43%), which was used directly for the next step without purification. $^1$H-NMR (CDCl$_3$ 300 MHz): δ8.57 (m, 1H), 8.30 (m, 1H), 7.91 (m, 1H), 7.52 (m, 1H), 6.87 (d, 1H) 6.44 (m, 1H), 4.44 (m, 2H), 3.39 (m, 2H), 2.77 (s, 2H), 2.04 (d, 2H), 1.64 (m, 2H).

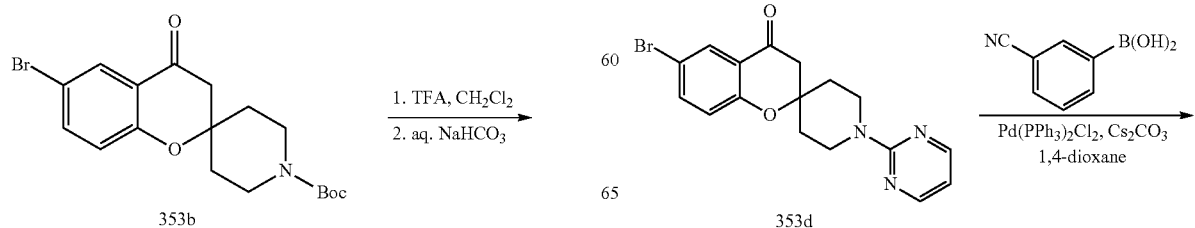

-continued

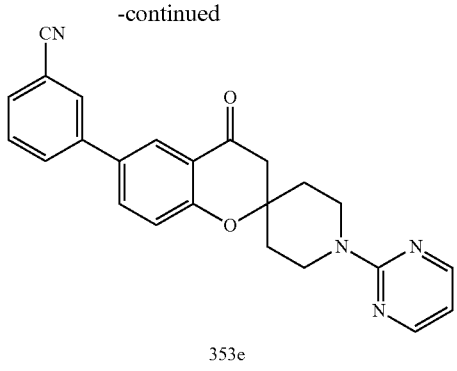

353e

Pd(PPh₃)₂Cl₂ (19.3 mg, 0.029 mmol) in a 100 mL flask under N₂ was treated sequentially with compound 353d (1.1 g, 2.9 mmol), Cs₂CO₃ (2 N, 5.3 mL), and the solution of 3-cyanophenylboronic acid (652 mg, 4.3 mmol) in 1,4-dioxane (26 mL). The mixture was refluxed for at 12° C. for 1 h, poured into water, extracted with EtOAc (100 m×2), washed with brine (100 mL), dried over Na₂SO₄, and concentrated, and the residue was purified by prep-TLC to give the compound 353e (100 mg, 10%) as a yellow solid. ¹H-NMR (CDCl₃ 400 MHz): δ8.38 (m, 2H), 8.10 (s, 1H), 7.86 (m, 1H), 7.83 (m, 1H), 7.75 (m, 1H), 7.64 (m, 1H), 7.57 (m, 1H), 7.15 (d, 1H), 6.51 (m, 1H), 4.51 (d, 2H), 3.51 (m, 2H), 2.80 (m, 2H), 2.14 (s, 2H), 1.73 (m, 2H).

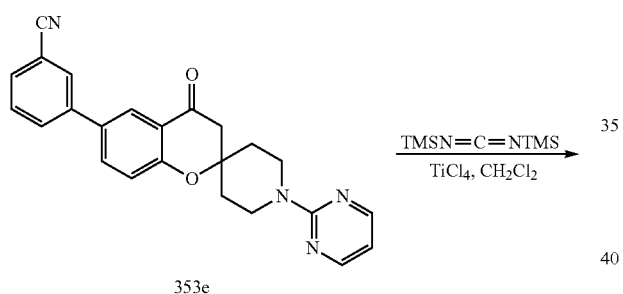

353e → 353f
TMSN=C=NTMS
TiCl₄, CH₂Cl₂

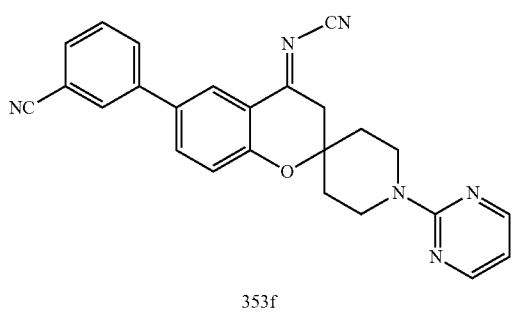

353f

To a solution of compound 353e (100 mg, 0.25 mmol) in anhydrous CH₂Cl₂ (2 mL) was added TiCl₄ (3.78 mL, 1 M in CH₂Cl₂) under N₂ atmosphere, and the mixture was stirred in microwave at 50° C. for 15 min TMSN=C=TMS (93 mg, 0.5 mmol) was added, and the mixture was stirred in microwave at 60° C. for 15 min, poured into ice-water (5 mL). The aqueous layer was extracted with CH₂Cl₂ (20 mL×2), the combined organic layers were washed with brine (50 mL), dried over Na₂SO₄ and concentrated to give the crude compound 353f (74 mg, crude) as a yellow solid, which was used directly for the next step without purification.

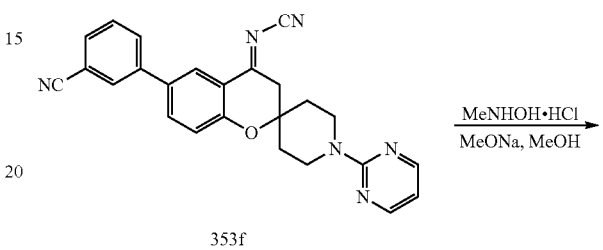

353f

MeNHOH·HCl
MeONa, MeOH

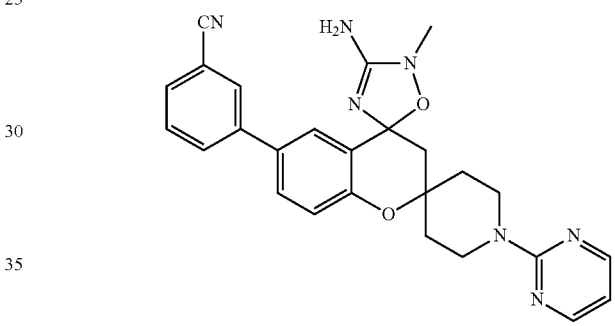

To a solution of MeNHOH.HCl (14.8 mg, 0.17 mmol) in MeOH (4 mL) was added MeONa (95 mg, 0.17 mmol, 10% in MeOH) and compound 353f (74 mg, 0.17 mmol). After being stirred for 10 minutes, the reaction was completed based on by LCMS, the solvent was removed in vacuo, the residue was purified by prep-TLC and prep-HPLC purification to afford compound 353 (10 mg, 12%) as a white solid. ¹H-NMR (CDCl₃ 400 MHz): δ8.25 (m, 2H), 7.68-7.92 (m, 4H), 7.61 (m, 1H), 7.53 (m, 1H), 7.05 (d, 1H), 6.51 (m, 1H), 4.2-4.4 (m, 2H), 3.52 (m, 1H), 3.30 (s, 3H), 2.72 (d, 2H), 2.14 (m, 2H), 1.8 (m, 2H), 1.7 (m, 1H); ESI MS: m/z 468 [M+H]⁺.

Example 333

Preparation of Compound 383

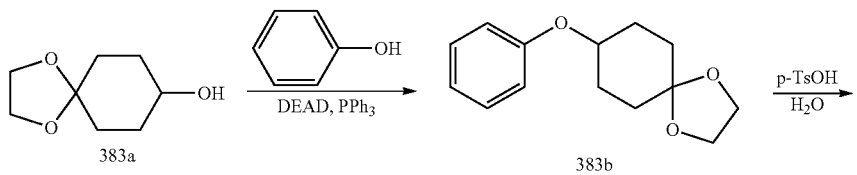

383a → 383b
DEAD, PPh₃
p-TsOH / H₂O

-continued
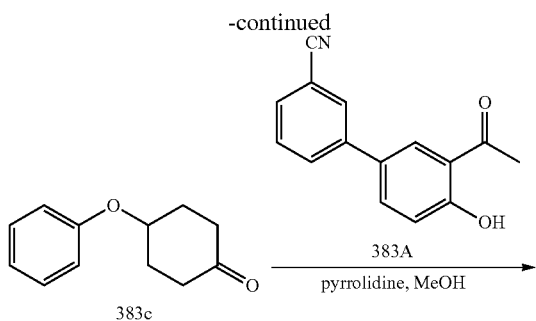
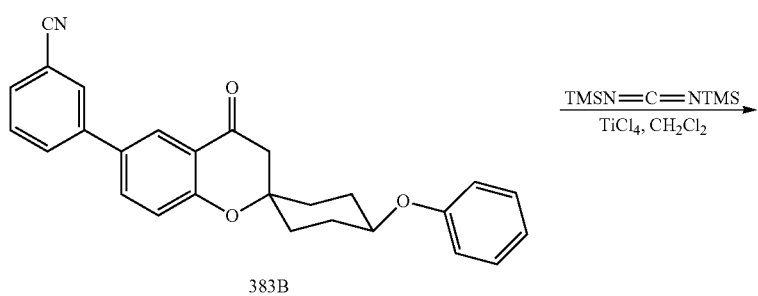
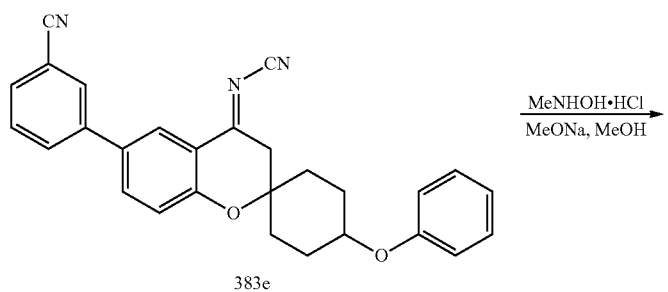
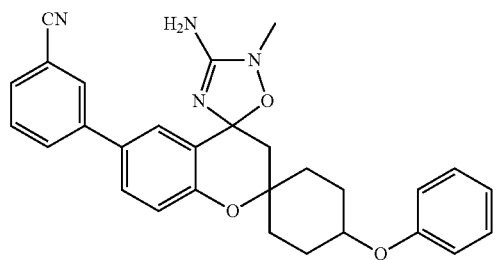

Experimental Data

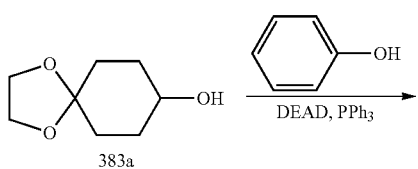

383a

To a solution of compound 383a (2 g, 12.65 mmol), phenol (1.07 g, 11.38 mmol), and PPh₃ (3.3 g, 12.65 mmol) in THF (15 mL) at 0° C. was added diethyl azodicarboxylate (2.2 g, 12.65 mmol). The reaction mixture was stirred at room temperature for 48 h, evaporated, and purified by column chromatography on silica gel (petroleum ether/EA=50/1) to compound 383b (1.16 g, 40%) as a solid. ¹H-NMR (CDCl₃ 400 MHz): δ7.33 (m, 2H), 6.93 (m, 3H), 4.45 (s, 1H), 4.00 (m, 3H), 1.95 (m, 5H), 1.66 (m, 2H), 1.33 (s, 1H).

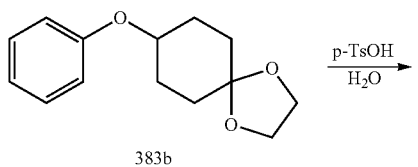

To a solution of compound 383b (1.158 g, 4.9 mmol) in H₂O (30 mL) was added a catalytic amount of p-TsOH (93.2 mg), and the mixture was refluxed for 1 h. The solution was extracted with EtOAc (30 mL×3), washed with brine (30 mL), dried over Na₂SO₄, and concentrated to give the compound 383c (1 g, 89%) as yellow liquid, which was used for the next step without purification. ¹H-NMR (CDCl₃ 400 MHz): δ7.33 (m, 2H), 6.93 (m, 3H), 4.65 (m, 1H), 2.65 (m, 2H), 2.13-2.35 (m, 4H), 2.02 (m, 1H), 1.85 (m, 1H).

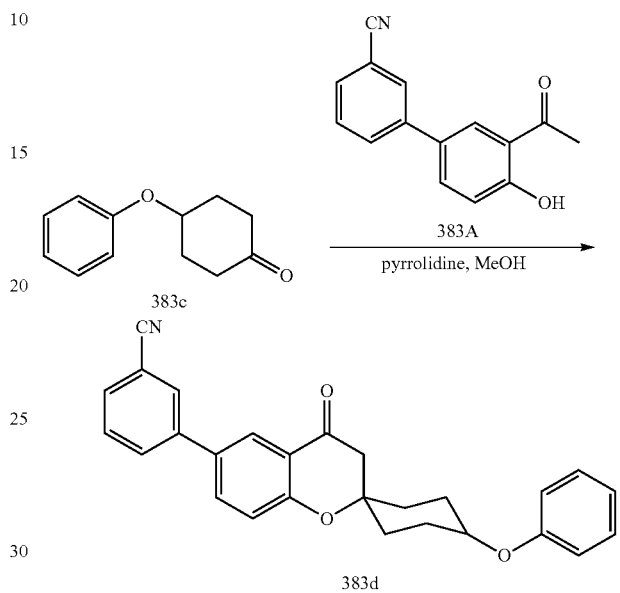

The mixture of compound 383c (400 mg, 2.1 mmol), compound 383A (398 mg, 1.7 mmol) and pyrrolidine (1 mL) in MeOH (5 mL) was refluxed overnight. The solvent was removed in vacuo, the residue was purified by TLC (petroleum ether:EA=3:1) to give the compound 383d as a yellow solid (96 mg, 11%). ¹H-NMR (CDCl₃ 400 MHz): δ8.15 (m, 1H), 7.5-7.45 (m, 5H), 7.33 (m, 1H), 7.21 (m, 1H), 6.9 (m, 4H), 4.32 (m, 1H), 2.80 (s, 2H), 2.28 (m, 2H), 1.98 (m, 4H), 1.62 (m, 2H).

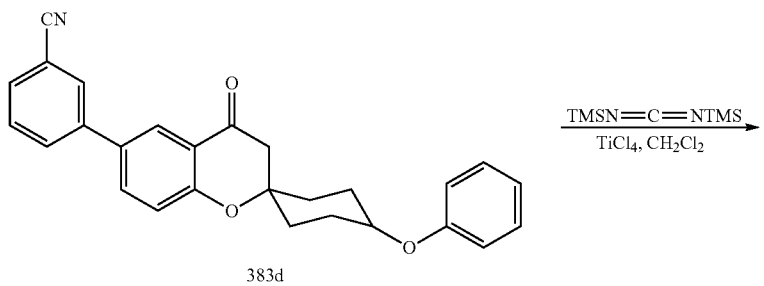

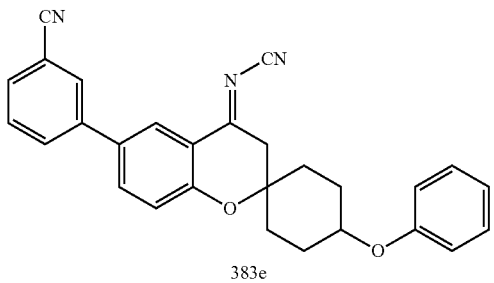

875

To a solution of compound 383d (96 mg, 0.25 mmol) in CH$_2$Cl$_2$ (5 mL) was added TiCl$_4$ (1 M in CH$_2$Cl$_2$, 0.5 mL, 0.5 mmol), and the mixture was stirred in microwave at 50° C. for 10 minutes. After being cooled to room temperature, N,N'-methanediylidenebis(1,1,1-trimethylsilanamine) (92.85 mg, 0.5 mmol) was added. The mixture was stirred in microwave at 60° C. for 10 minutes, and poured into ice-water. The mixture was extracted with CH$_2$Cl$_2$ (2×50 mL), washed with brine (100 mL), dried, and concentrated to give the compound 383e as a yellow solid (61 mg, 60%), which was used for the next step without purification.

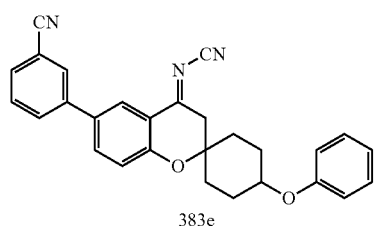

To a solution of methylhydroxylamine HCl salt (7 mg, 0.09 mmol) in anhydrous MeOH (4 mL) was added NaOMe (10% in MeOH, 5 drops) and compound 383e (35 mg, 0.09 mmol). After being stirred for 10 minutes, the solvent was removed in vacuum. The residue was dissolved in CH$_2$Cl$_2$ (25 mL). The mixture was filtered, and the solvent was removed, the residue was purified by preparative HPLC to give compound 383 as a yellow solid (2.0 mg, 5%). $^1$H-NMR (CD$_3$OD 400 MHz): δ7.88 (m, 3H), 7.5-7.7 (m, 3H), 7.18 (m, 2H), 7.03 (m, 1H), 6.82 (m, 3H), 4.30 (m, 1H), 3.53 (m, 1H), 3.28 (s, 3H), 2.63 (d, 1H), 2.55 (s, 2H), 2.10 (m, 1H), 1.95 (m, 2H), 1.78 (m, 2H), 1.56 (m, 1H); ESI MS: m/z 481 [M+H]$^+$.

Example 334

Preparation of Compound 375

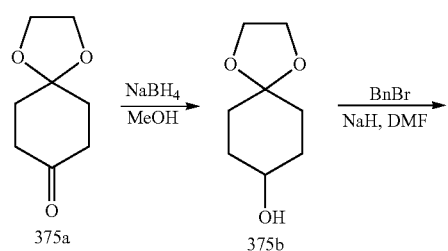

876

-continued

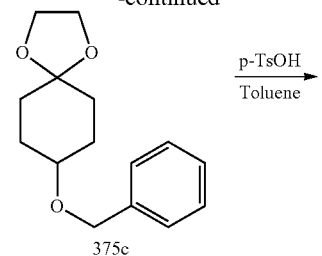

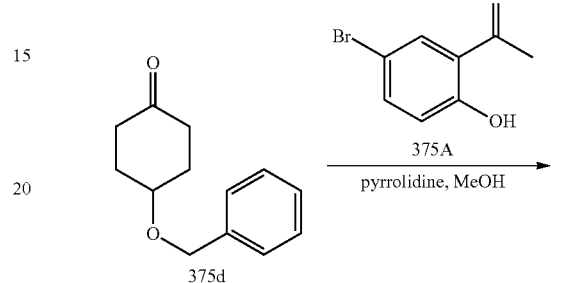

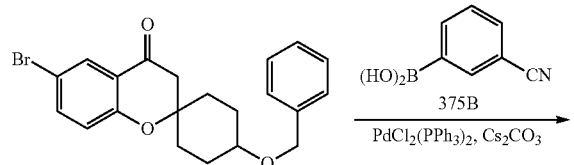

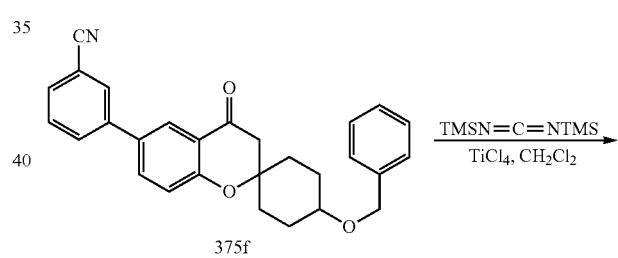

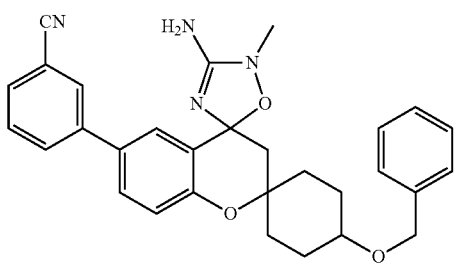

Experimental Data

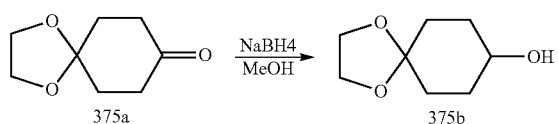

To a solution of compound 375a (30 g, 192.2 mmol) in anhydrous MeOH (650 mL) at 0° C. was added NaBH₄ (13.2 g, 345.96 mmol). The reaction mixture was stirred at room temperature for 1 hour, water was added to quench the reaction. The solvent was removed under reduced pressure. The residue was extracted with ethyl acetate (30 mL×3), washed with brine (30 mL), dried over Na₂SO₄ and concentrated to afford the compound 375b (30 g, 100%) as colorless liquid, which was used for the next step without purification. $^1$H-NMR (CDCl₃ 400 MHz): δ3.73 (m, 4H), 3.62 (s, 1H), 2.75 (s, 1H), 1.6-1.8 (m, 3H), 1.43 (m, 4H).

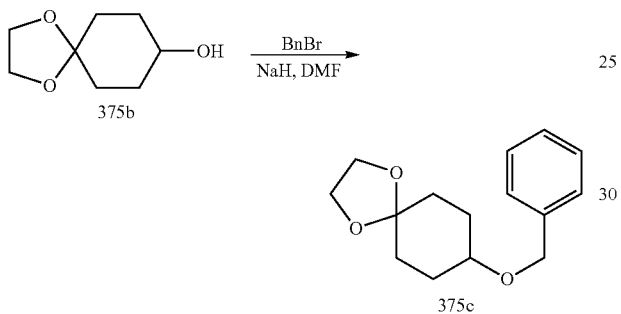

To a suspension of sodium hydride (1 g, 25.2 mmol) in DMF (20 mL) was added compound 375b (2 g, 12.6 mmol) at 0° C. The reaction mixture was stirred at 0° C. for 1.5 hours, followed by the addition of benzyl bromide (2.37 g, 15.2 mmol). The reaction mixture was stirred at room temperature overnight, quenched with saturated ammonium chloride solution, extracted with ethyl acetate (30 mL×2), washed with brine (30 mL), dried over sodium sulfate, filtered, and concentrated. The residue was purified on column chromatography on silica gel (petroleum ether/EA=20:1) to give the compound 375c (2.7 g, 87%) as colorless liquid. $^1$H-NMR (CDCl₃ 300 MHz): δ7.18-7.26 (m, 5H), 4.42 (s, 2H), 3.83 (m, 4H), 3.48 (s, 1H), 1.62-1.9 (m, 6H), 1.43 (m, 2H).

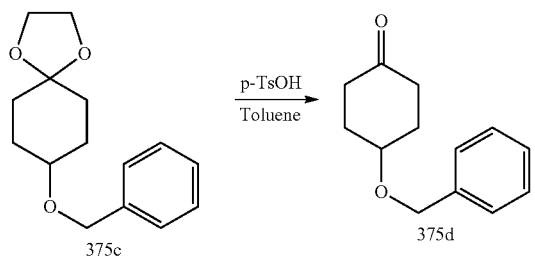 [SMILES: c1ccc(COC2CCC3(CC2)OCCO3)cc1 ; O=C1CCC(OCc2ccccc2)CC1]

To a solution of compound 375c (2.7 g, 10.9 mmol) in H₂O (50 mL) was added a catalytic amount of p-TsOH (207 mg), and the mixture was refluxed for 1 h. The solution was extracted with EtOAc (40 mL×3), and the organic phase was washed with brine (40 mL). The combine organic layers were dried over Na₂SO₄, the solvent was removed in vacuo to give the compound 375d (1.6 g, 75%) as yellow liquid, which was used for the next step without purification. $^1$H-NMR (CDCl₃ 400 MHz): δ7.25-7.4 (m, 5H), 4.65 (s, 1H), 3.85 (m, 1H), 2.62 (m, 2H), 2.22 (m, 2H), 1.95 (m, 2H).

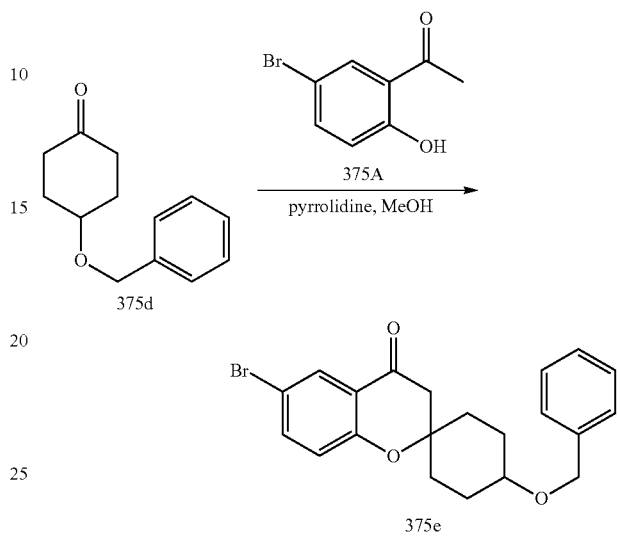

The mixture of compound 375d (5.17 g, 25.3 mmol), compound 375A (4.33 g, 20.3 mmol), and the solution of pyrrolidine (7 mL) in MeOH (30 mL) was refluxed overnight. The solvent was removed in vacuo, and the residue was purified by silica column chromatography (petroleum ether:EA=30:1) to give the compound 375e as a yellow solid (3.5 g, 35%). $^1$H-NMR (CDCl₃ 300 MHz): δ7.88 (m, 1H), 7.48 (m, 1H), 7.33 (m, 5H), 6.75 (d, 1H), 4.43 (s, 2H), 3.62 (s, 1H), 2.63 (s, 2H), 1.62-1.88 (m, 8H).

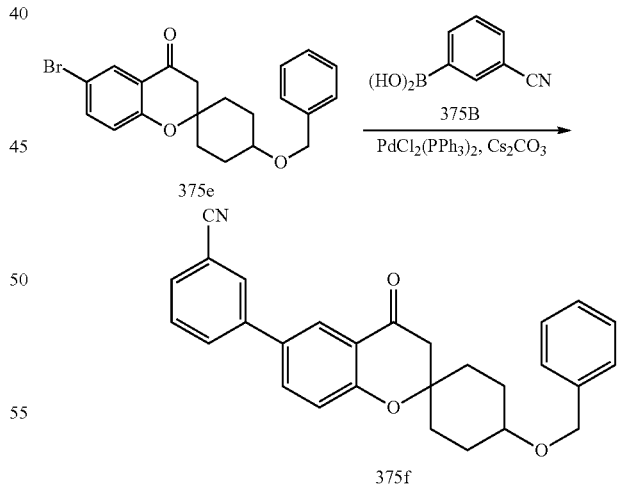

A mixture of compound 375e (500 mg, 1.24 mmol), 3-cyanophenylboronic acid (292.5 mg, 1.87 mmol), Cs₂CO₃ solution (2 M, 7.5 mL), and Pd(PPh₃)₂Cl₂ (62.5 mg) in 1,4-dioxane (20 mL) was stirred at 100° C. under N₂ for 45 minutes. The reaction mixture was concentrated in vacuum. The residue was purified by silica column chromatography (petroleum ether:EA=10:1) to give the compound 375f as a yellow solid (324 mg, 60%). $^1$H-NMR (CDCl₃ 400 MHz):

δ 8.0 (m, 1H), 7.6-7.7 (m, 2H), 7.6 (m, 1H), 7.52 (m, 1H), 7.48 (m, 1H), 7.23 (m, 4H), 7.2 (m, 1H), 6.70 (m, 1H), 4.43 (s, 2H), 3.63 (s, 1H), 2.6 (m, 2H), 1.6-1.9 (m, 8H).

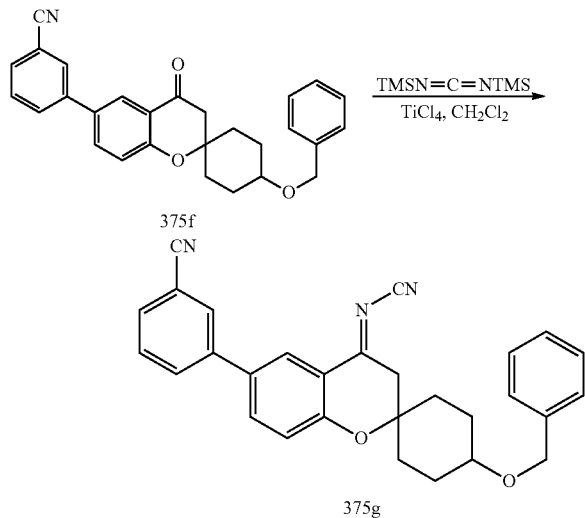

To a solution of compound 375f (100 mg, 0.24 mmol) in CH$_2$Cl$_2$ (3 mL) was added TiCl$_4$ (1 M in CH$_2$Cl$_2$, 0.48 mL, 0.48 mmol), and the mixture was stirred in microwave at 50° C. for 10 minutes. After being cooled to room temperature, N,N'-methanediylidenebis(1,1,1-trimethylsilanamine) (89.13 mg, 0.48 mmol) was added, the mixture was stirred at 60° C. for 10 minutes, poured into ice-water, and extracted with CH$_2$CL$_2$ (2×10 mL). The combined organic layer was washed with brine (10 mL), dried, and concentrated to give the compound 375g as a yellow solid (94 mg, 89%).

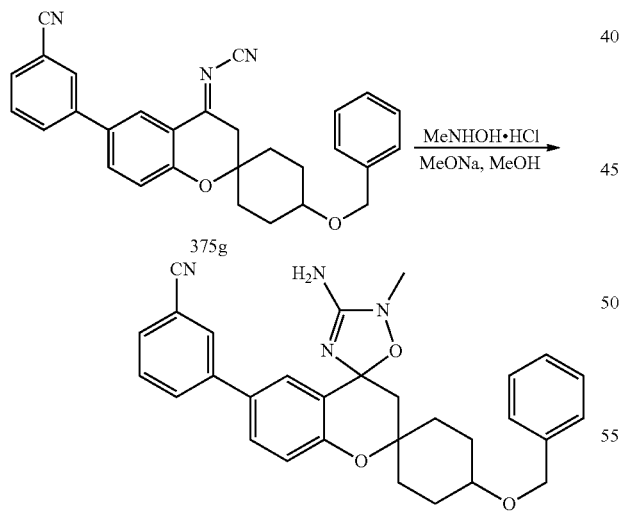

To a solution of methylhydroxylamine HCl salt (9.25 mg, 0.111 mmol) in anhydrous MeOH (5 mL) was added NaOMe (10% in MeOH, 10 drops) and compound 375g (50 mg, 0.111 mmol). After being stirred for 10 minutes, the solvent was removed, and the residue was dissolved in CH$_2$Cl$_2$ (25 mL). After filtration, the solvent was removed, and the residue was purified by preparative HPLC to give the compound 375 as a yellow solid (2.0 mg, 5%). $^1$H-NMR (CD$_3$OD 400 MHz): δ 7.75-7.95 (m, 3H), 7.6-7.7 (m, 3H), 7.13-7.42 (m, 5H), 6.92-7.1 (m, 1H), 4.45 (s, 2H), 3.63 (m, 1H), 3.45 (m, 3H), 2.55-2.78 (m, 2H), 2.00 (m, 1H), 1.95 (m, 2H), 1.7-2.0 (m, 5H), 1.56 (m, 2H); ESI MS: m/z 495 [M+H]$^+$.

Example 335

Biological Activities

Biological Assay Procedures

BACE Assay

Inhibitory activity of compounds was assessed by a fluorescence quench assay of BACE activity using commercially available substrate HiLyte Fluor™ 488-Glu-Val-Asn-Leu-Asp-Ala-Glu-Phe-Lys-(QXLT™ 520)-OH (AnaSpec, San Jose, Calif.) and truncated human beta-secretase (residues 1-458, His$_6$-tagged at the C-terminus) expressed in insect cells *D. melanogaster* S2 using a baculovirus expression system (Mallender et al., Characterization of recombinant, soluble beta-secretase from an insect cell expression system, Mol Pharmacol 59:619-26, 2001). The assay was performed at room temperature in 96-well white opaque Optiplates aque Optiplates (PerkinElmer, Waltham, Mass.) in a total volume of 200 μl of the incubation mixture containing 50 mM sodium acetate buffer, pH 4.5, 0.4 μM FRET substrate, 2.4 nM enzyme, 5% DMSO, and 0.05% Brij-35. The tested compounds were serially diluted in DMSO and pre-incubated with the substrate. The reaction was started by addition of enzyme, and the progress of the reaction was followed by measuring fluorescence with an excitation wavelength of 480 nm and an emission wavelength of 520 nm. Ten measurements were taken every 5-10 mM, and the intensity of fluorescence was regressed against time in order to derive velocities of reaction in all 96 wells. These velocities were used for calculating percent inhibition using an uninhibited control containing 5% DMSO and a fully inhibited control incubations performed in the absence of enzyme. IC$_{50}$ values were calculated by fitting percent inhibition vs inhibitor concentration into a four-parametric logistic model using XLFit software (IDBS, Guildford, UK).

Results

The in vitro enzyme activity studies were carried out for compounds of the invention and the data is shown below:

Compounds 1-130 and 178-458 have an IC$_{50}$ for BACE (fluorescence assay) ranging from 1 nM to less than 50 μM.

| Compound No. | IC$_{50}$ |
|---|---|
| 1 | ***** |
| 2 | **** |
| 2a | ***** |
| 2b | ***** |
| 3 | **** |
| 4 | **** |
| 5 | **** |
| 6 | **** |
| 7 | **** |
| 8a | **** |
| 8b | ** |
| 9 | **** |
| 10 | **** |
| 11 | **** |
| 12 | **** |
| 13 | **** |
| 14 | **** |
| 15 | *** |
| 16 | *** |
| 17 | *** |
| 18 | *** |

| Compound No. | IC$_{50}$ |
|---|---|
| 19 | *** |
| 19a | *** |
| 20 | *** |
| 21 | *** |
| 22 | ** |
| 23 | ** |
| 24 | ** |
| 25 | ** |
| 26 | ** |
| 27 | ** |
| 28 | ** |
| 29 | ** |
| 30 | ** |
| 31 | ** |
| 32 | ** |
| 33 | ** |
| 34 | ** |
| 35 | ** |
| 36 | ** |
| 37 | ** |
| 38 | ** |
| 39 | ** |
| 40 | ** |
| 41 | ** |
| 42 | * |
| 43 | * |
| 44 | # |
| 44a | * |
| 44b | * |
| 45 | * |
| 46 | * |
| 47 | * |
| 48 | * |
| 49 | * |
| 50 | * |
| 51 | * |
| 52 | * |
| 53 | # |
| 54 | # |
| 55a | # |
| 55b | # |
| 56 | # |
| 57 | # |
| 57a | # |
| 58 | # |
| 59 | # |
| 60 | # |
| 61 | # |
| 62 | # |
| 63 | # |
| 64 | # |
| 65 | # |
| 66 | # |
| 67 | # |
| 68 | # |
| 69 | # |
| 70 | # |
| 71 | # |
| 72 | ***** |
| 72a | ***** |
| 72b | **** |
| 72 | ***** |
| 73 | **** |
| 74 | **** |
| 75 | **** |
| 76 | **** |
| 77 | **** |
| 78 | *** |
| 79 | *** |
| 80 | ** |
| 81 | ** |
| 82 | ** |
| 83 | ** |
| 84 | # |
| 85 | ***** |
| 86 | ***** |
| 87 | **** |
| 88 | **** |
| 89a | **** |
| 89b | ** |
| 90 | **** |
| 91 | **** |
| 92 | **** |
| 93 | *** |
| 94 | *** |
| 95 | ** |
| 96 | ** |
| 97 | ** |
| 98 | ** |
| 99 | ** |
| 100 | ** |
| 101 | ** |
| 102 | ** |
| 103 | * |
| 104 | * |
| 105 | * |
| 106 | * |
| 107 | # |
| 108 | # |
| 109 | **** |
| 110 | **** |
| 111 | **** |
| 112 | *** |
| 113a | *** |
| 113b | *** |
| 114 | *** |
| 115 | *** |
| 116 | ** |
| 117 | ** |
| 118 | ** |
| 119 | ** |
| 120 | ** |
| 121 | ** |
| 122 | ** |
| 123 | * |
| 124 | * |
| 125 | * |
| 126 | * |
| 127a | * |
| 127b | * |
| 128 | # |
| 129 | # |
| 130 | # |
| 178-278 | ***** |
| 279-345 | **** |
| 346-373 | *** |
| 374-431 | ** |
| 432-447 | * |
| 448-458 | # |

\# represents IC$_{50}$ from less than 50 μM to 10 μM;
\* represents IC$_{50}$ from less than 10 μM to 5 μM;
** represents IC$_{50}$ from less than 5 μM to 1 μM;
*** represents IC$_{50}$ from less than 1 μM to 500 nM;
**** represents IC$_{50}$ from less than 500 nM to 100 nM;
***** represents IC$_{50}$ from less than 100 nM to 1 nM.

BACE Cell Assay

H4 neuroglioma cell line that stably expresses Amyloid Precursor Protein (APP) containing the KM-NL Swedish mutation (H4-APPsw) was generated. For the assay, cells are treated overnight in the presence of inhibitor and the culture media are subjected to ELISA analysis of soluble Amyloid Beta 1-40 (Aβ 1-40).

Materials
H4 neuroglioma cell line: ATCC, Cat #HTB-148
Dulbecco's Minimal Essential Medium (DMEM): Invitrogen, Cat #11995
Fetal bovine serum (FBS): Hyclone, Cat #SH30070.03)
Penicillin/streptomycin: Invitrogen, Cat#15140-122
Zeocin: Invitrogen, Cat #R25001
0.5% Trypsin/EDTA: Invitrogen, Cat #25300

96-well plate for compound serial dilution in DMSO
96-well deep well plate
96-well Black Polymer BTM β-D-L plate: Nunc, Cat #152037
96-well White polystyrene ½ area optiplate: Corning, Cat #3642
DMSO: Sigma, Cat #494429
Aβ 1-40 ELISA kit: Covance, Cat # sig38940
CellTiter Glo Viability Assay: Promega, Cat #G7571
Aβ 1-40 AlphaLISA kit: PerkinElmer, Cat #AL202F
Microscope
Wallac Victor$^2$ Multilabel HTS counter
PerkinElmer Fusion-Alpha FP-HT Multiplate reader
SpectraMax 384 plus plate reader
Generation and Maintenance of 114-APPsw Cell Line H4 neuroglioma cell line was cultured in DMEM with 10% FBS and 1% penicillin/streptomycin (Culture Medium) at 37° C., 5% $CO_2$. The culture plate (150 mm) with 50% confluence of H4 cells was transfected with 15 ug plasmid pcDNA3.1/Neo(+) containing a 2310-bp insert of APPsw at Hind3/Xba1 sites. 24 hrs after transfection, the cells were replaced into three new plates (150 mm) in fresh Culture Medium with 250 ug/ml Zeocin. The stably transfected cell colonies were isolated in about 2-3 weeks. The levels of APPsw expression were analyzed by immunoblotting and the production of Aβ 1-40 was detected by ELISA of culture supernatants. The selected clones are maintained in Culture Medium with 250 µg/ml Zeocin and routinely split in 3-4 days to maintain 20-80% confluence.

Assay Protocol

| Final Assay Conditions (96-well plate) | |
|---|---|
| H4-APPsw cells | 6 × 10$^3$ cells/well |
| DMEM | 200 µL |
| DMSO | 0.2% |

Day 1
Split Cells.

Split H4-APPsw cells in Culture Medium and culture overnight such that cells will be ~80% confluent next morning.

Day 2
Create Compound Dilution Plate.

After determining the desired final concentration of compound to be tested, create a 500× dilution plate. Add DMSO, but not inhibitor, to each well of Column 1. Use Column 2 for Control Compound (BACE inhibitor IV, EMD Bioscience, Cat #565788) serial dilution starting at 5 mM (final concentration of 2.5 µM). Add compounds of interest at 500× desired final concentration to wells A3-A10. Add DMSO, but not inhibitor, to each well of Columns 11 and 12. Dilute contents of Row A 1:3 in Row B, then continue through Rows C—H.

Create Media Plate.

To create a 2× solution of compound in media, add 996 µL Culture Medium to each well of a 96-well 2 ml deep well plate (Media Plate) in biosafety hood. Add 4 µL 5 mM control compound to Media Plate wells A1-D1 for determination of full inhibition. Add 4 µL from Compound Dilution Plate to corresponding wells of Medium Plate (do not add additional DMSO to wells A1-D1).

Add Media to Cell Plate.

With a multichannel pipettor, mix each well of Media Plate several times to insure homogeneity. Add 100 µL of mixture to Black polymer bottom P-D-L plates. Next, place Medium Plate and Cell Plate in the incubator.

Add Cells to Cell Plate.

Trypsinize and count H4-APPsw cells. Dilute cells 6×10$^5$ cells/ml in Culture Medium and remove Cell Plate from incubator. Vortex cells to homogeneity, then using a multichannel repeating pipettor, add 100 µL cell suspension to Cell Plate, adding cells from Row H to Row A. Place Cell Plate in incubator.

Change Media in Cell Plate. After 5 h, check Cell Plate by microscope to insure cells are attached. In culture hood, remove media from Cell Plate using multichannel repeating pipettor. Add 100 µl Culture Medium to each well. Remove Media Plate from incubator and mix with pipettor as previous. Add 100 µl from each well of Media Plate to corresponding well in Cell Plate. Place Cell Plate in incubator overnight.

Day 3
Perform ELISA to Determine Levels of Secreted Aβ 1-40.

After 16 h incubation, spin Cell Plate for 8 min at 1200 rpm. The primary reading of Aβ 1-40 levels is done using PerkinElmer AlphaLISA technology. Follow the manufacturer's protocol for performing AlphaLISA in a white ½ area Optiwell plate using Row 12 for peptide standard (1:2 dilutions, starting at 15 ng/ml). Data are acquired using PerkinElmer Fusion-Alpha FP-HT, Alpha protocol (Count Time 0.6 s, Count Time Ratio 30%:70%). To validate IC50 determinations, a second Aβ 1-40 ELISA was performed using a kit from Covance that uses different antibodies to Aβ 1-40 and a different detection method (absorbance at 490 nM) than the PerkinElmer kit.

Perform Viability Assay to Determine Compound Toxicity.

Remove remaining media from Cell Plate and add 100 µL CellTiter Glo reagent to cells. Incubate 9 min at room temperature and read luminescence counts on Wallac Victor$^2$ Multilabel HTS counter.

Data Reduction

Export data from Fusion using Columnar Report format into a separate file for each plate. Upload data into Activity Base using RIA-DOSE-RESPONSE protocol (Version 1). Data from at least eight doses were fitted to a four parameter logistical model using XLfit software to determine potency.

Results

The in vitro cell activity studies were carried out for compounds of the invention and the data is shown below:

| Compound No. | IC50 (nM) |
|---|---|
| 178-179 | ***** |
| 180 | **** |
| 181-184 | ***** |
| 185 | ***** |
| 186 | *** |
| 187 | ***** |
| 188 | **** |
| 189 | *** |
| 190 | ***** |
| 191 | **** |
| 192 | *** |
| 193-197 | ***** |
| 198 | ** |
| 199 | **** |
| 200 | ***** |
| 201 | ** |
| 202, 203 | ***** |
| 204 | ** |
| 205-207 | **** |
| 208, 209 | ** |
| 211 | **** |
| 212-214 | ***** |
| 215 | **** |
| 216 | ***** |
| 217 | **** |

| Compound No. | IC50 (nM) |
| --- | --- |
| 218 | ***** |
| 220 | **** |
| 221 | ** |
| 222, 223 | ***** |
| 224 | **** |
| 225 | *** |
| 226, 227 | ** |
| 228 | *** |
| 229 | **** |
| 230 | ***** |
| 231 | **** |
| 232 | *** |
| 233 | **** |
| 234, 235 | ** |
| 236, 237 | *** |
| 238, 239 | ** |
| 240 | * |
| 241 | **** |
| 242 | ** |
| 243, 244 | **** |
| 245, 247 | *** |
| 248 | **** |
| 249 | ** |
| 250, 251 | **** |
| 252 | ** |
| 253 | *** |
| 254-259 | **** |
| 260 | ** |
| 261 | *** |
| 262, 263 | **** |
| 264-266 | ** |
| 267 | **** |
| 269 | * |
| 270-273 | *** |
| 274 | ** |
| 275, 276 | *** |
| 277 | **** |
| 278 | * |
| 279 | ** |
| 280 | **** |
| 282 | ** |
| 283 | **** |
| 286-288 | **** |
| 290 | *** |
| 293-295 | ** |
| 297-299 | ** |
| 302 | **** |
| 303 | ** |
| 305 | * |
| 306 | ** |
| 308 | ** |
| 311 | *** |
| 313 | ** |
| 314 | *** |
| 316 | * |
| 317 | ** |
| 320 | ** |
| 322 | * |
| 323 | ** |
| 324 | * |
| 330 | ** |
| 331 | * |
| 333 | ** |
| 335 | * |
| 338 | ** |
| 345 | * |
| 348 | * |
| 349 | ** |
| 352 | ** |
| 353 | # |
| 355 | * |
| 373 | * |
| 379 | ** |
| 402 | # |
| 403 | * |
| 408 | * |
| 432 | # |

\# represents IC$_{50}$ from less than 50 μM to 10 μM;
\* represents IC$_{50}$ from less than 10 μM to 5 μM;
\*\* represents IC$_{50}$ from less than 5 μM to 1 μM;
\*\*\* represents IC$_{50}$ from less than 1 μM to 500 nM;
\*\*\*\* represents IC$_{50}$ from less than 500 nM to 100 nM;
\*\*\*\*\* represents IC$_{50}$ from less than 100 nM to 1 nM.

What is claimed is:

1. A method of treating a BACE mediated disorder in a subject comprising administering to the subject an effective amount of a compound represented by the following Structural Formula:

(I)

or a pharmaceutically acceptable salt thereof, wherein:
  $R_1$ is —H, ($C_1$-$C_6$)alkyl, aryl($C_1$-$C_6$)alkyl, or heteroaryl($C_1$-$C_6$)alkyl;
  each $R_2$ is independently selected from a) —H, —F, —Cl, —Br, and —CN, and b) ($C_1$-$C_6$)alkyl, ($C_2$-$C_6$)alkenyl, ($C_2$-$C_6$)alkynyl, ($C_3$-$C_8$)cycloalkyl, aryl, heteroaryl, phenoxy, or benzyloxy, each optionally substituted with 1 to 3 substituents selected from the group consisting of —F, —Cl, —Br, —CN, —OR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl;
  each $R_3$ and $R_4$ are independently —H, -halogen, —CN, —NO$_2$, —OR$_5$, —NR$_6$R$_7$, —S(O)$_t$R$_5$, —C(=O)OR$_5$, —C(=O)NR$_{12}$R$_{13}$, —C(=O)R$_5$, ($C_1$-$C_6$)alkyl, ($C_2$-$C_6$)alkenyl, ($C_2$-$C_6$)alkynyl, ($C_3$-$C_8$)cycloalkyl, aryl, or heteroaryl, wherein each ($C_1$-$C_6$)alkyl, ($C_2$-$C_6$)alkenyl, ($C_2$-$C_6$)alkynyl, ($C_3$-$C_8$)cycloalkyl, aryl, or heteroaryl is optionally substituted with 1 to 3 substituents independently selected from the group consisting of —F, —Cl, —Br, —CN, —OR$_5$, —NR$_6$R$_7$, —S(O)$_t$R$_5$, —NR$_{11}$S(=O)$_t$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, ($C_1$-$C_6$)alkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, an aryl group, and a heteroaryl group;
  X is —O—, —S—, —SO—, —SO$_2$—, —CH$_2$O— or —OCH$_2$—;
  each Y is independently —C(R$_8$R$_9$)—;
  W is —N(R$_{14}$)—, —S—, —O—;

Z is —C(=O)—, —C(=S)—, —C(=NR$_{15}$)—, —O—, —C(=O)C(R$_{16}$R$_{17}$)—, —C(=S)C(R$_{16}$R$_{17}$)—, —C(=NR$_{15}$)C(R$_{16}$R$_{17}$)—, —N(R$_{18}$)—, —(CR$_{16}$R$_{17}$)$_m$— or —O—(CR$_{16}$R$_{17}$)—;

R$_5$ is —H, (C$_1$-C$_6$)alkyl, halo(C$_1$-C$_6$)alkyl, (C$_2$-C$_6$)alkenyl, (C$_2$-C$_6$)alkynyl, (C$_1$-C$_3$)alkoxy(C$_1$-C$_6$)alkyl, (C$_3$-C$_8$)cycloalkyl, (C$_3$-C$_8$)cycloalkyl(C$_1$-C$_6$)alkyl, (C$_3$-C$_7$)cycloheteroalkyl, aryl, heteroaryl or benzyl, each of which is optionally substituted with 1 to 3 substituents independently selected from the group consisting of —F, —Cl, —Br, —CN, (C$_1$-C$_6$)alkyl, halo(C$_1$-C$_6$)alkyl, and (C$_1$-C$_3$)alkoxy(C$_1$-C$_6$)alkyl;

each R$_6$ and R$_7$ are independently selected from —H, (C$_1$-C$_6$)alkyl, hydroxy(C$_1$-C$_6$)alkyl, halo(C$_1$-C$_6$)alkyl, (C$_3$-C$_8$)cycloalkyl, and (C$_3$-C$_8$)cycloalkyl(C$_1$-C$_6$)alkyl, each optionally substituted with 1 to 3 substituents independently selected from the group consisting of —F, —Cl, —Br, —CN, (C$_1$-C$_6$)alkyl, halo(C$_1$-C$_6$)alkyl and (C$_1$-C$_3$)alkoxy(C$_1$-C$_6$)alkyl;

R$_8$ is selected from hydroxy(C$_1$-C$_6$)alkyl, halo(C$_1$-C$_6$)alkyl, (C$_2$-C$_6$)alkenyl, (C$_2$-C$_6$)alkynyl, (C$_3$-C$_{14}$)cycloalkyl, (C$_3$-C$_{13}$)cycloheteroalkyl, aryl or heteroaryl, each optionally substituted with 1 to 4 substituents independently selected from the group consisting of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl, heteroaryl, (C$_3$-C$_8$)cycloalkyl and (C$_3$-C$_7$)cycloheteroalkyl;

R$_9$— is selected from H, (C$_1$-C$_6$)alkyl, hydroxy(C$_1$-C$_6$)alkyl, halo(C$_1$-C$_6$)alkyl, (C$_2$-C$_6$)alkenyl, (C$_2$-C$_6$)alkynyl, (C$_3$-C$_{14}$)cycloalkyl, (C$_3$-C$_{13}$)cycloheteroalkyl, aryl or heteroaryl, each optionally substituted with 1 to 4 substituents independently selected from the group consisting of —F, —Cl, —Br, —CN, —OR$_5$—, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl, heteroaryl, (C$_3$-C$_8$)cycloalkyl and (C$_3$-C$_7$)cycloheteroalkyl; or R$_8$ and R$_9$, together with the carbon to which they are attached, form ring A, which is a 3-14 membered monocyclic, 9-14 membered bicyclic or 9-14 membered polycyclic ring, wherein ring A is optionally substituted with 1 to 4 substituents independently selected from the group consisting of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl, aryl and heteroaryl;

R$_{11}$ is —H, (C$_1$-C$_6$)alkyl or halo(C$_1$-C$_6$)alkyl;

each R$_{12}$ and R$_{13}$ are independently —H, (C$_1$-C$_6$)alkyl, (C$_1$-C$_3$)alkoxy(C$_1$-C$_6$)alkyl, hydroxy(C$_1$-C$_6$)alkyl, cyano(C$_1$-C$_6$)alkyl, amino(C$_1$-C$_6$)alkyl, (C$_1$-C$_3$)alkylamino(C$_1$-C$_6$)alkyl, or di(C$_1$-C$_3$)alkylamino(C$_1$-C$_6$)alkyl;

or R$_{12}$ and R$_{13}$, together with the nitrogen to which they are attached, form a 3-8 membered ring optionally substituted with 1 to 3 substituents independently selected from the group consisting, of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy and (C$_1$-C$_6$)alkoxy(C$_1$-C$_3$)alkyl, wherein the 3-8 membered ring optionally contains 1 to 3 additional heteroatoms, which are independently selected from O, N and S, wherein when the additional heteroatom is nitrogen, the nitrogens is substituted with —H, (C$_1$-C$_3$)alkyl or halo(C$_1$-C$_3$)alkyl, and when the additional heteroatom is sulfur, the sulfurs is optionally mono or di-oxygenated;

R$_{14}$ is —H, (C$_1$-C$_6$)alkyl, halo(C$_1$-C$_6$)alkyl, (C$_3$-C$_8$)cycloalkyl, cycloheteroalkyl(C$_1$-C$_3$)alkyl, (C$_3$-C$_8$)cycloalkyl(C$_1$-C$_3$)alkyl, aryl(C$_1$-C$_6$)alkyl, heteroaryl(C$_1$-C$_6$)alkyl, each optionally substituted with 1 to 3 substituents independently selected from the group consisting of —F, —Cl, —Br, —CN, (C$_1$-C$_6$)alkyl, halo (C$_1$-C$_6$)alkyl and (C$_1$-C$_3$)alkoxy;

R$_{15}$ is —H or (C$_1$-C$_6$)alkyl;

R$_{16}$ and R$_{17}$ are each independently —H or (C$_1$-C$_3$)alkyl;

R$_{18}$ is —H or (C$_1$-C$_3$)alkyl;

i is 0, 1 or 2;

p is 1 or 2;

m is 1 or 2; and n is 1 or 2.

2. The method of claim 1, wherein the disorder is selected from the group consisting of Alzheimer's disease, cognitive impairment, Down's Syndrome, HCHWA-D, cognitive decline, senile dementia, cerebral amyloid angiopathy, degenerative dementia, other neurodegenerative disorders, and glaucoma.

3. The method of claim 1, wherein the compound is represented by the following Structural Formula:

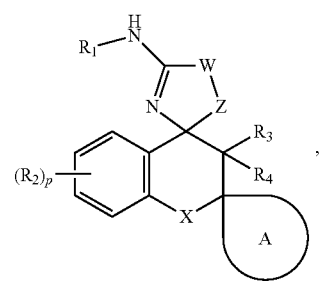

or a pharmaceutically acceptable salt thereof and ring A is a 5-7 membered monocyclic ring or a 9-14 membered bicyclic ring optionally substituted with 1 to 3 substituents independently selected from the group consisting of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$, (C$_1$-C$_6$)alkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy and (C$_1$-C$_6$)alkoxy(C$_1$-C$_3$)alkyl, wherein ring A contains 0 to 3 heteroatoms, which are selected from O, N, S; wherein when the heteroatom is nitrogen, the nitrogen is substituted with —H, (C$_1$-C$_6$)alkyl halo(C$_1$-C$_6$)alkyl or (C$_1$-C$_3$)alkylcarbonyl, and when the heteroatom is sulfur, the sulfur is optionally mono- or di-oxygenated.

4. The method of claim 3, wherein the compound is represented by any one of the following structural formulas:

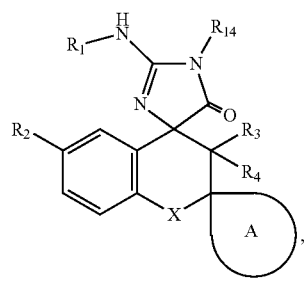
(IIIa)

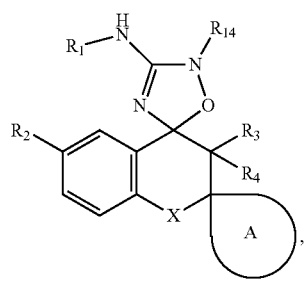
(IVa)

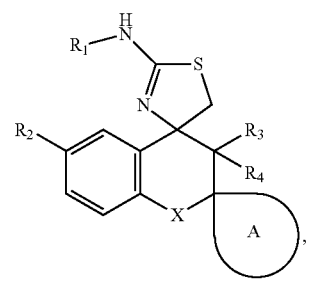
(Va)

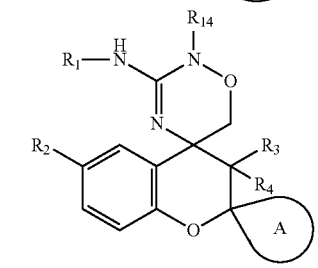
(VIa)

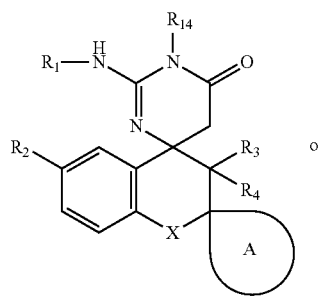
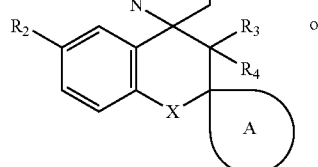
or

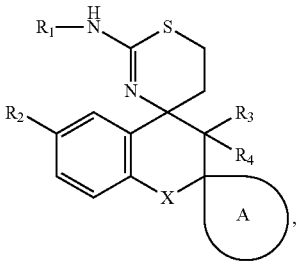
(VIIa)

or a pharmaceutically acceptable salt thereof.

5. The method of claim 4, wherein X is —O— and R$_2$ is —H, —Br, —F, (C$_1$-C$_6$)alkyl, (C$_3$-C$_8$)cycloalkyl, aryl, heteroaryl, phenoxy, or benzyloxy, each optionally substituted with 1 to 3 substituents independently selected from the group consisting of —F, —Cl, —Br, —CN, —OR$_5$, —NR$_6$R$_7$, S(O)$_t$R$_5$, —NR$_{11}$S(=O)$_t$R$_5$, —C(=O)OR$_5$, —C(=O)NR$_{12}$R$_{13}$, NR$_{11}$C(=O)R$_5$, —C(=S)NR$_{12}$R$_{13}$, —C(=O)R$_5$, (C$_1$-C$_6$)alkyl, (C$_3$-C$_8$)cycloalkyl, (C$_2$-C$_6$)alkenyl, halo(C$_1$-C$_6$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, (C$_1$-C$_3$)alkoxy, halo(C$_1$-C$_3$)alkoxy, (C$_1$-C$_6$)alkoxy(C$_1$-C$_3$)alkyl and a heteroaryl group.

6. The method of claim 5, wherein the compound is represented by any one of the following structural formulas:

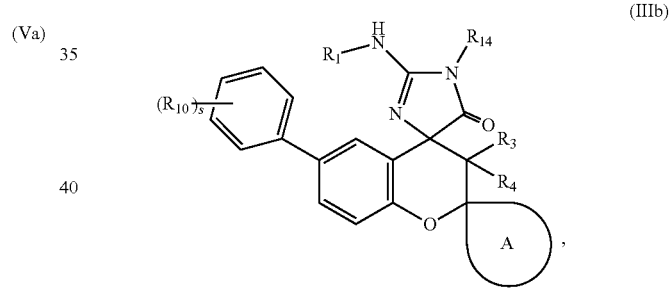
(IIIb)

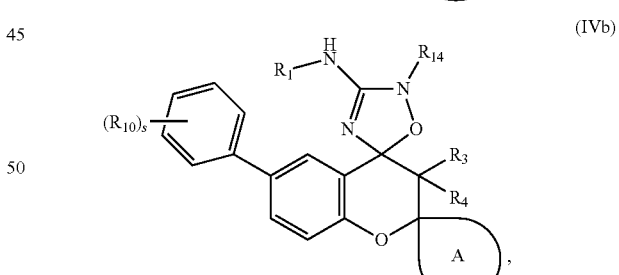
(IVb)

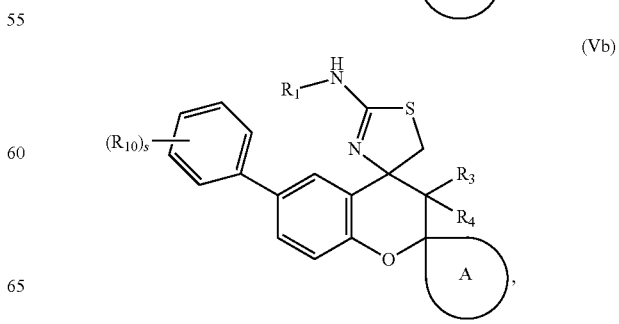
(Vb)

-continued

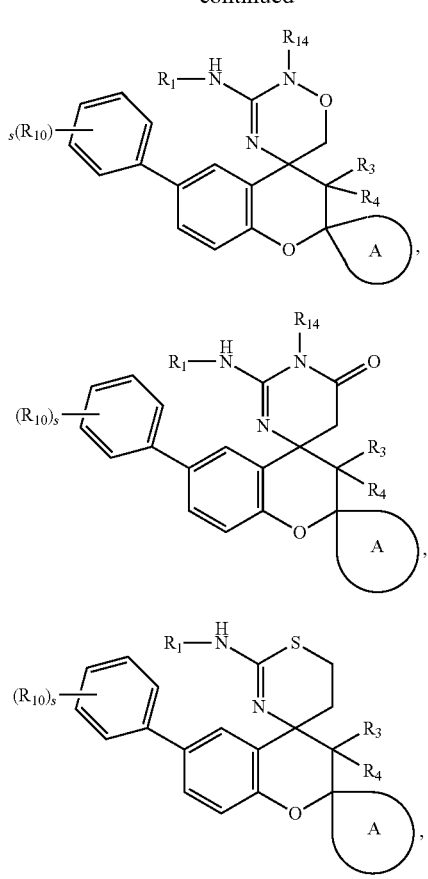

or a pharmaceutically acceptable salt thereof, wherein:
$R_{10}$ is selected from a group consisting of —F, —Cl, —Br, —CN, —$OR_5$, —$NR_6R_7$, —$S(O)_iR_5$, —$NR_{11}S(=O)_iR_5$, —$C(=O)OR_5$, —$C(=O)NR_{12}R_{13}$, —$NR_{11}C(=O)R_5$, —$C(=S)NR_{12}R_{13}$, —$C(=O)R_5$; ($C_1$-$C_3$)alkyl, halo($C_1$-$C_3$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, and ($C_1$-$C_6$)alkoxy($C_1$-$C_3$)alkyl; and
s is 0, 1, 2, or 3.

7. The method of claim 6, wherein ring A is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-H-indene, tetrahydronaphthalene, decahydronaphthalene, 5,6,7,8-tetrahydroquinoline, 5,6,7,8-tetrahydroisoquinoline, 2-oxabicyclo[2.2.2]octane, each optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy, 5-6 membered heteroaryl, phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxyl;
$R_{14}$ is methyl;
$R_1$ is —H; and
$R_3$ and $R_4$ are —H.

8. The method of claim 5, wherein $R_2$ is pyridinyl, thiophenyl, pyrrolyl, pyrimidinyl, thiozolyl or cyclohexyl, each optionally substituted with 1 to 3 substituents independently selected from the group consisting of —F, —Cl, —Br, —CN, —$OR_5$, —$SR_5$, —$NR_6R_7$, —$S(O)_iR_5$, —$NR_{11}S(=O)_iR_5$, —$C(=O)OR_5$, —$C(=O)NR_{12}R_{13}$, —$NR_{11}C(=O)R_5$, —$C(=S)NR_{12}R_{13}$, —$C(=O)R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl and a heteroaryl group.

9. The method of claim 8, wherein ring A is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-1H-indene, tetrahydronaphthalene, decahydronaphthalene, 5,6,7,8-tetrahydroquinoline, 5,6,7,8-tetrahydroisoquinoline, oxabicyclo[2.2.2]octane, each optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy 5-6 membered heteroaryl, phenyl, phenoxy and benzoxy, wherein the phenyl, phenoxy and benzoxy are each optionally substituted with —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy or halo($C_1$-$C_3$)alkoxyl;
$R_{14}$ is methyl;
$R_1$ is —H; and
$R_3$ and $R_4$ are —H.

10. The method of claim 1, wherein $R_8$ is hydroxy($C_1$-$C_6$)alkyl, halo($C_1$-$C_6$)alkyl, ($C_2$-$C_6$)alkenyl, ($C_2$-$C_6$)alkynyl, ($C_3$-$C_8$) cycloalkyl, ($C_3$-$C_7$)cycloheteroalkyl, aryl or heteroaryl, each optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy or ($C_3$-$C_8$) cycloheteroalkyl;
$R_9$ is —H, ($C_1$-$C_6$)alkyl, hydroxy($C_1$-$C_6$)alkyl, halo($C_1$-$C_6$)alkyl, ($C_2$-$C_6$)alkenyl, ($C_2$-$C_6$)alkynyl, ($C_3$-$C_8$) cycloalkyl, ($C_3$-$C_7$)cycloheteroalkyl, aryl or heteroaryl, each optionally substituted with 1 to 3 substituents independently selected from the group consisting of —F, —Cl, —Br, —CN, ($C_1$-$C_6$)alkyl, halo($C_1$-$C_6$)alkyl, hydroxy($C_1$-$C_6$)alkyl, ($C_1$-$C_3$)alkoxy, halo($C_1$-$C_3$)alkoxy or ($C_3$-$C_8$)cycloheteroalkyl.

11. The method of claim 10, wherein the compound is represented by any one of the following Structural Formulas:

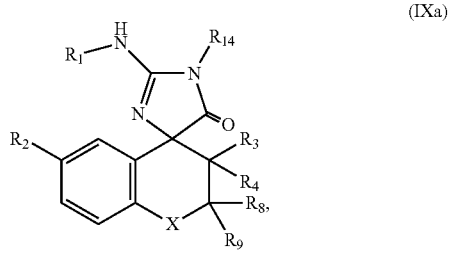

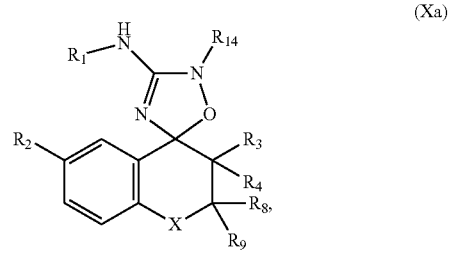

-continued

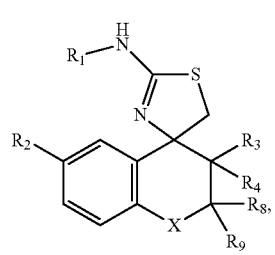
(XIa)

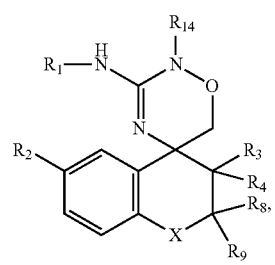
(XV)

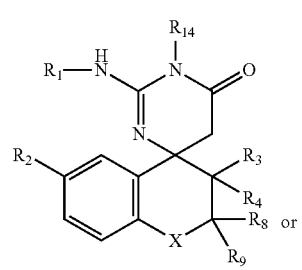
(XIIa)

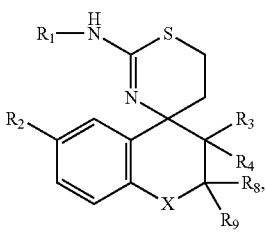
(XIIIa)

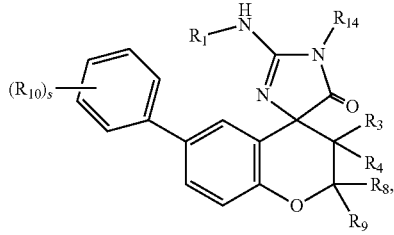
(IXb)

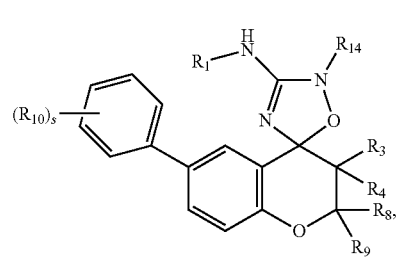
(Xb)

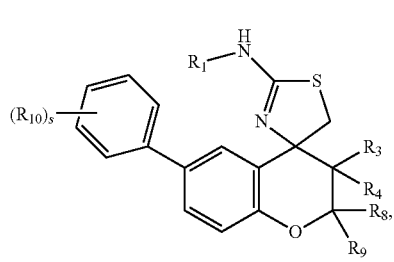
(XIb)

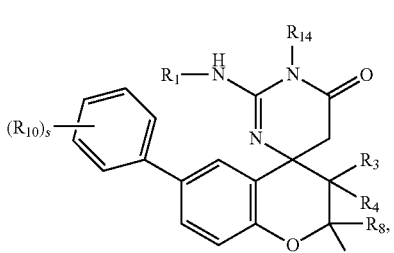
(XIIb)

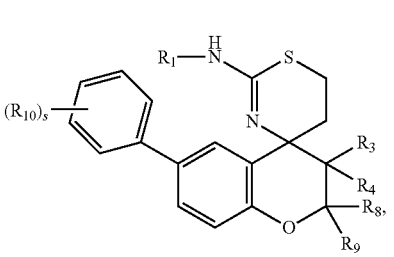
(XIIIb)

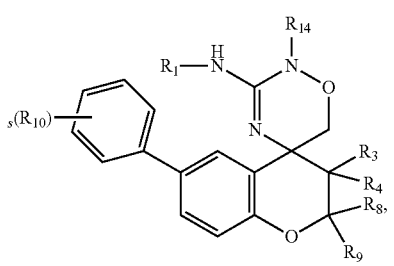
(XVb)

or a pharmaceutically acceptable salt thereof.

12. The method of claim 11, wherein X is —O—;
$R_2$ is —H, —Br, —F, ($C_1$-$C_6$)alkyl, ($C_3$-$C_8$)cycloalkyl, aryl, heteroaryl, phenoxy, or benzyloxy, each optionally substituted with 1 to 3 substituents independently selected from the group consisting of F, —Cl, —Br, —CN, —$OR_5$, —$NR_6R_7$, —S(O)$_iR_5$, —$NR_{11}$S(=O)$_iR_5$, —C(=O)$OR_5$, —C(=O)$NR_{12}R_{13}$, —$NR_{11}$C(=O)$R_5$, —C(=S)$NR_{12}R_{13}$, —C(=O)$R_5$, ($C_1$-$C_6$)alkyl, ($C_3$-$C_8$)cycloalkyl, ($C_2$-$C_6$)alkenyl, halo($C_1$-$C_6$)alkyl, ($C_1$-$C_3$)alkylsulfonylaminoalkyl, hydroxy($C_1$-$C_6$)alkyl, cyano($C_1$-$C_6$)alkyl, ($C_1$-$C_3$)alkylcarbonylamino($C_1$-$C_6$)alkyl, ($C_1$-$C_3$)alkoxy, halo($C_1$-$C_3$)alkoxy, ($C_1$-$C_6$)alkoxy($C_1$-$C_3$)alkyl, aryl and heteroaryl.

13. The method of claim 11, wherein the compound is represented by any one of the following Structural Formulas:

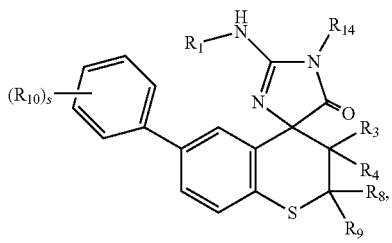
(IXc)

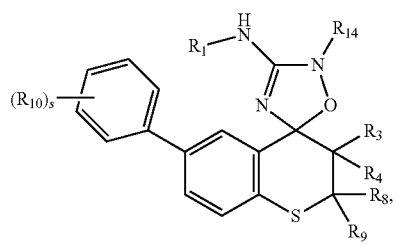
(Xc)

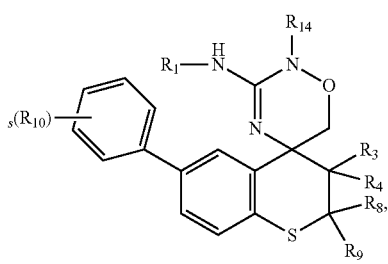
(XVc)

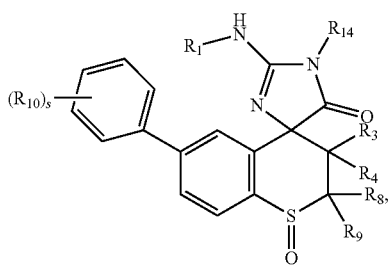
(IXd)

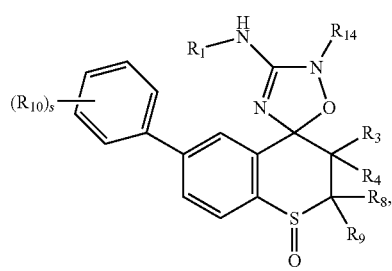
(Xd)

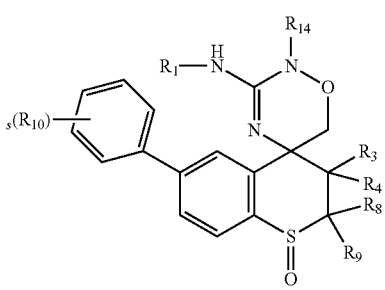
(XVd)

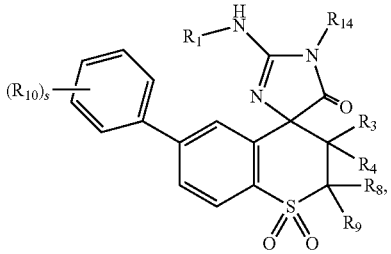
(IXe)

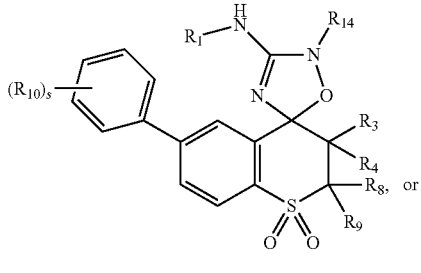
(Xe)

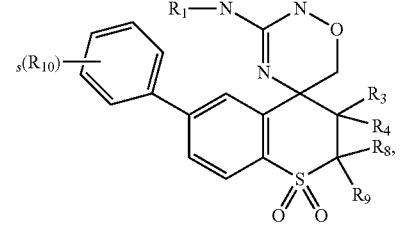
(XVe)

or a pharmaceutically acceptable salt thereof, wherein:
$R_{10}$ is selected from a group consisting of —F, —Cl, —Br, —CN, —OR$_5$, —NR$_6$R$_7$, —S(O)$_i$R$_5$, —NR$_{11}$S(=O)$_i$R$_5$, —C(=O)OR$_5$, —C(=O)NR$_{12}$R$_{13}$, —NR$_{11}$C(=O)R$_5$, —C(=S)NR$_{12}$R$_{13}$, —C(=O)R$_5$; (C$_1$-C$_3$)alkyl, halo(C$_1$-C$_3$)alkyl, (C$_1$-C$_3$)alkylsulfonylaminoalkyl, hydroxy(C$_1$-C$_6$)alkyl, cyano(C$_1$-C$_6$)alkyl, (C$_1$-C$_3$)alkylcarbonylamino(C$_1$-C$_6$)alkyl, and (C$_1$-C$_6$)alkoxy(C$_1$-C$_3$)alkyl; and
s is 0, 1, 2, or 3.

14. The method of claim 13, wherein R$_9$ is —H and R$_8$ is phenyl optionally substituted with 1 to 3 substitutents independently selected from the group consisting of —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy, halo(C$_1$-C$_3$)alkoxy, (C$_1$-C$_3$)alkylcarbonyl and (C$_1$-C$_3$)alkoxycarbonyl.

15. The method of claim 13, wherein R$_9$ is —H and R$_8$ is tetrahydrofuran, tetrahydropyran, cyclopentane, cyclohexane, cycloheptane, oxepane, 1,3-dioxane, piperidine, 6,7,8,9-tetrahydro-5H-benzo[7]annulene, 2,3-dihydro-4H-indene, tetrahydronaphthalene, decahydronaphthalene, 5,6,7,8-tetrahydroquinoline, 5,6,7,8-tetrahydroisoquinoline, 2-oxabicyclo[2.2.2]octane, each optionally substituted with 1 to 3 substituents independently selected from the group consisting —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy, halo(C$_1$-C$_3$)alkoxy 5-6 membered heteroaryl, phenyl, phenoxy and benzoxy, wherein the phenyl, phenoxy and benzoxy are each optionally substituted with —F, —Cl, —Br, —CN, (C$_1$-C$_6$)alkyl, halo(C$_1$-C$_6$)alkyl, hydroxy(C$_1$-C$_6$)alkyl, (C$_1$-C$_3$)alkoxy or halo(C$_1$-C$_3$)alkoxyl.

* * * * *

UNITED STATES PATENT AND TRADEMARK OFFICE
CERTIFICATE OF CORRECTION

PATENT NO. : 8,921,359 B2
APPLICATION NO. : 13/867590
DATED : December 30, 2014
INVENTOR(S) : Lawrence Wayne Dillard et al.

Page 1 of 1

It is certified that error appears in the above-identified patent and that said Letters Patent is hereby corrected as shown below:

IN THE CLAIMS:

In claim 1, at column 888, line number 18, delete "nitrogens" replace with --nitrogen--;

In claim 1, at column 888, line number 20, delete "sulfurs" replace with --sulfur--;

In claim 1, at column 888, line number 21, delete "mono" replace with --mono- --;

In claim 3, at column 889, line number 4, delete "$(C_1-C_6)$alkyl halo$(C_1-C_6)$alkyl" replace with --$(C_1-C_6)$alkyl, halo$(C_1-C_6)$alkyl--;

In claim 7, at column 891, line number 60, delete "halo$(C_1-C_3)$alkoxyl" replace with --halo$(C_1-C_3)$alkoxy--;

In claim 9, at column 892, line numbers 14 and 15, delete "oxabicyclo[2.2.2]octane" replace with --2-oxabicyclo[2.2.2]octane--;

In claim 9, at column 892, line numbers 18 and 19, delete "halo$(C_1-C_3)$alkoxy 5-6 membered heteroaryl," replace with --halo$(C_1-C_3)$alkoxy, 5-6 membered heteroaryl,--;

In claim 15, at column 896, line numbers 59 and 60, delete "halo$(C_1-C_3)$alkoxy 5-6 membered heteroaryl," replace with --halo$(C_1-C_3)$alkoxy, 5-6 membered heteroaryl,--; and In claim 15, at column 896, line number 64, delete "halo$(C_1-C_3)$alkoxyl" replace with --halo$(C_1-C_3)$alkoxy--.

Signed and Sealed this
Twenty-fifth Day of August, 2015

Michelle K. Lee
*Director of the United States Patent and Trademark Office*